(12) United States Patent
Singh et al.

(10) Patent No.: US 7,820,819 B2
(45) Date of Patent: *Oct. 26, 2010

(54) 2,4-PYRIMIDINEDIAMINE COMPOUNDS AND THEIR USES

(75) Inventors: Rajinder Singh, Belmont, CA (US); Ankush Argade, Foster City, CA (US); Donald Payan, Hillsborough, CA (US); Susan Molineaux, San Mateo, CA (US); Sacha J. Holland, San Francisco, CA (US); Jeffrey Clough, Redwood City, CA (US); Holger Keim, Menlo Park, CA (US); Somasekhar Bhamidipati, Foster City, CA (US); Catherine Sylvain, Burlingame, CA (US); Hui Li, Millbrae, CA (US); Alexander B. Rossi, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/539,049

(22) Filed: Oct. 5, 2006

(65) Prior Publication Data

US 2007/0293523 A1   Dec. 20, 2007

Related U.S. Application Data

(63) Continuation of application No. 10/355,543, filed on Jan. 31, 2003, now Pat. No. 7,557,210.

(60) Provisional application No. 60/353,333, filed on Feb. 1, 2002, provisional application No. 60/353,267, filed on Feb. 1, 2002, provisional application No. 60/399,673, filed on Jul. 29, 2002, provisional application No. 60/434,277, filed on Dec. 17, 2002.

(51) Int. Cl.
*C07D 239/02* (2006.01)
(52) U.S. Cl. ..................... 544/323; 514/275
(58) Field of Classification Search ............. 544/323, 544/324
See application file for complete search history.

(56) References Cited

U.S. PATENT DOCUMENTS

| | | | |
|---|---|---|---|
| 3,159,547 A | 12/1964 | Hollis et al. |
| 3,320,256 A | 5/1967 | Duschinsky et al. |
| 4,968,781 A | 11/1990 | Seitz et al. |
| 4,983,608 A | 1/1991 | Effland et al. |
| 5,147,876 A | 9/1992 | Mizuchi et al. |
| 5,179,204 A | 1/1993 | Effland et al. |
| 5,223,505 A | 6/1993 | Hargreaves et al. |
| 5,420,129 A | 5/1995 | Breu et al. |
| 5,521,184 A | 5/1996 | Zimmerman |
| 5,585,381 A | 12/1996 | Yanaka et al. |
| 5,840,893 A | 11/1998 | Bukrinsky et al. |
| 5,863,924 A | 1/1999 | Berger et al. |
| 5,958,935 A | 9/1999 | Davis et al. |
| 5,985,856 A | 11/1999 | Stella et al. |
| 6,004,985 A | 12/1999 | Kochanny et al. |
| 6,022,884 A | 2/2000 | Mantlo et al. |
| 6,048,866 A | 4/2000 | Hutchings et al. |
| 6,080,747 A | 6/2000 | Uckun et al. |
| 6,080,748 A | 6/2000 | Uckun et al. |
| 6,080,858 A | 6/2000 | Schumacher |
| 6,093,716 A | 7/2000 | Davis et al. |
| 6,127,376 A | 10/2000 | Davey et al. |
| 6,177,433 B1 | 1/2001 | Uckun et al. |
| 6,197,779 B1 | 3/2001 | Andries et al. |
| 6,200,977 B1 | 3/2001 | Cushing et al. |
| 6,235,746 B1 | 5/2001 | Davis et al. |
| 6,313,130 B1 | 11/2001 | Uckun et al. |
| 6,337,335 B1 | 1/2002 | Hutchings et al. |
| 6,342,503 B1 | 1/2002 | Aldrich et al. |
| 6,372,751 B1 | 4/2002 | Davey et al. |
| 6,432,963 B1 | 8/2002 | Hisamichi et al. |
| 6,440,986 B2 | 8/2002 | Andries et al. |
| 6,489,333 B2 | 12/2002 | Pitts et al. |
| 6,525,051 B2 | 2/2003 | Davey et al. |
| 6,528,513 B2 | 3/2003 | Cushing et al. |

(Continued)

FOREIGN PATENT DOCUMENTS

AU        748087 B2    8/1999

(Continued)

OTHER PUBLICATIONS

Kuz'menko et al., The 2-and 4-substituted 5-fluoropyrimidines, Khimiya Geterotsiklicheskikh Soedinenii (1973), (1), 117-19. See HCAPLUS Abstract.*

(Continued)

*Primary Examiner*—Daniel M Sullivan
*Assistant Examiner*—Yevegeny Valenrod
(74) *Attorney, Agent, or Firm*—Weaver Austin Villeneuve & Sampson LLP

(57) ABSTRACT

The present invention provides 2,4-pyrimidinediamine compounds that inhibit the IgE and/or IgG receptor signaling cascades that lead to the release of chemical mediators, intermediates and methods of synthesizing the compounds and methods of using the compounds in a variety of contexts, including in the treatment and prevention of diseases characterized by, caused by or associated with the release of chemical mediators via degranulation and other processes effected by activation of the IgE and/or IgG receptor signaling cascades.

17 Claims, 14 Drawing Sheets

U.S. PATENT DOCUMENTS

Figure 1:
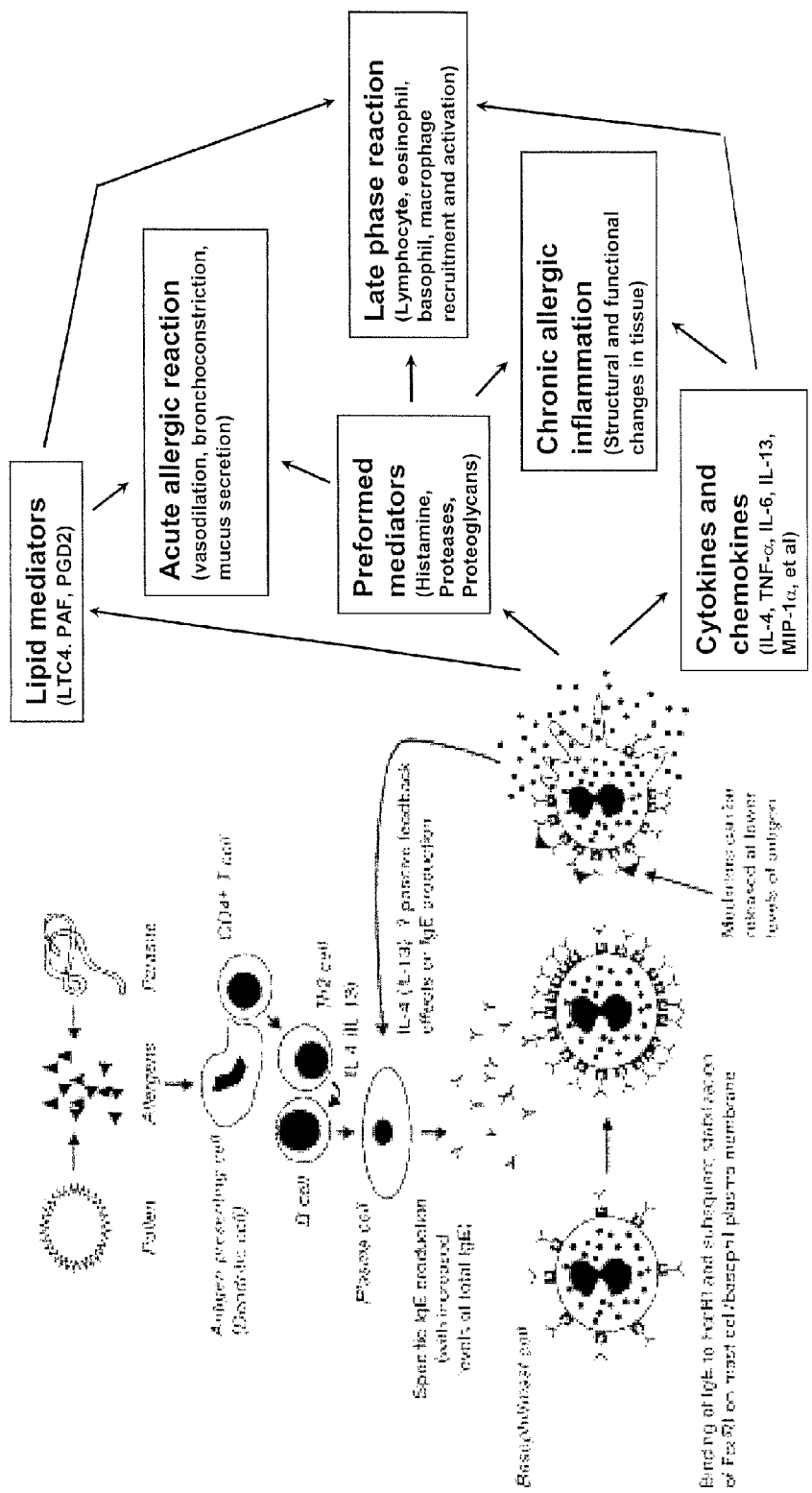

| | | | |
|---|---|---|---|
| 6,579,983 B1 | 6/2003 | Batchelor | |
| 6,586,594 B1 | 7/2003 | Butters et al. | |
| 6,593,326 B1 * | 7/2003 | Bradbury et al. | 514/235.8 |
| 6,635,651 B2 | 10/2003 | Uckun | |
| 6,649,608 B2 * | 11/2003 | Pease et al. | 514/227.8 |
| 6,710,052 B2 | 3/2004 | Pease et al. | |
| 6,762,179 B2 | 7/2004 | Cochran et al. | |
| 6,777,441 B2 | 8/2004 | Wang et al. | |
| 6,825,190 B2 | 11/2004 | Moon et al. | |
| 6,908,920 B2 | 6/2005 | Thomas et al. | |
| 6,939,874 B2 | 9/2005 | Harmange et al. | |
| 6,969,760 B2 | 11/2005 | Ihle et al. | |
| 6,998,391 B2 | 2/2006 | Lyons et al. | |
| 7,060,827 B2 | 6/2006 | Singh et al. | |
| 7,067,522 B2 * | 6/2006 | Pease et al. | 514/272 |
| 7,098,332 B2 | 8/2006 | Liu et al. | |
| 7,105,530 B2 | 9/2006 | Boloor et al. | |
| 7,115,617 B2 | 10/2006 | Buchanan et al. | |
| 7,122,542 B2 | 10/2006 | Singh et al. | |
| 7,122,552 B2 | 10/2006 | Ledford | |
| 7,135,550 B2 | 11/2006 | Come et al. | |
| 7,153,964 B2 * | 12/2006 | Pease et al. | 544/321 |
| 7,166,599 B2 | 1/2007 | Bornemann et al. | |
| 7,173,028 B2 | 2/2007 | Dahmann et al. | |
| 7,235,561 B2 | 6/2007 | Brumby et al. | |
| 7,259,161 B2 | 8/2007 | Bethiel et al. | |
| 7,288,547 B2 | 10/2007 | Lucking et al. | |
| 7,312,227 B2 | 12/2007 | Ledeboer et al. | |
| 7,329,671 B2 | 2/2008 | Singh et al. | |
| 7,329,672 B2 | 2/2008 | Singh et al. | |
| 7,332,484 B2 | 2/2008 | Singh et al. | |
| 2003/0134838 A1 | 7/2003 | Bornemann et al. | |
| 2003/0165873 A1 | 9/2003 | Come et al. | |
| 2004/0029902 A1 * | 2/2004 | Singh et al. | 514/275 |
| 2004/0102455 A1 | 5/2004 | Burns et al. | |
| 2004/0106615 A1 | 6/2004 | Cochran et al. | |
| 2004/0142947 A1 | 7/2004 | Cox et al. | |
| 2005/0004152 A1 | 1/2005 | Cochran et al. | |
| 2005/0026914 A1 | 2/2005 | Buchanan et al. | |
| 2005/0054732 A1 | 3/2005 | Meguro et al. | |
| 2005/0113398 A1 | 5/2005 | Argade et al. | |
| 2005/0176743 A1 | 8/2005 | Luecking et al. | |
| 2005/0192301 A1 | 9/2005 | Li et al. | |
| 2005/0209230 A1 | 9/2005 | Singh et al. | |
| 2005/0209246 A1 | 9/2005 | Ueda et al. | |
| 2005/0234049 A1 | 10/2005 | Singh et al. | |
| 2005/0272753 A1 | 12/2005 | Nagashima et al. | |
| 2006/0035891 A1 | 2/2006 | Li et al. | |
| 2006/0047135 A1 | 3/2006 | Chadwick et al. | |
| 2006/0058525 A1 | 3/2006 | Singh et al. | |
| 2006/0111378 A1 | 5/2006 | Cleve et al. | |
| 2006/0135543 A1 | 6/2006 | Singh et al. | |
| 2006/0167249 A1 | 7/2006 | Argade et al. | |
| 2006/0167254 A1 | 7/2006 | Cooper et al. | |
| 2006/0178407 A1 | 8/2006 | Argade et al. | |
| 2006/0211657 A1 | 9/2006 | Singh et al. | |
| 2006/0234983 A1 | 10/2006 | Singh et al. | |
| 2006/0270694 A1 | 11/2006 | Wong | |
| 2006/0293311 A1 * | 12/2006 | Li et al. | 514/223.2 |
| 2007/0004626 A1 | 1/2007 | Masuda et al. | |
| 2007/0060603 A1 | 3/2007 | Singh et al. | |
| 2007/0117775 A1 | 5/2007 | Payan | |
| 2007/0129360 A1 | 6/2007 | Bhamidipati et al. | |
| 2007/0129362 A1 | 6/2007 | Bhamidipati et al. | |
| 2007/0167439 A1 | 7/2007 | Singh et al. | |
| 2007/0191405 A1 | 8/2007 | Noronha et al. | |
| 2007/0197782 A1 | 8/2007 | Clough et al. | |
| 2007/0203162 A1 * | 8/2007 | Li et al. | 514/275 |
| 2007/0225321 A1 | 9/2007 | Singh et al. | |
| 2007/0225495 A1 | 9/2007 | Singh et al. | |
| 2007/0293520 A1 * | 12/2007 | Singh et al. | 514/275 |
| 2007/0293521 A1 * | 12/2007 | Singh et al. | 514/275 |
| 2007/0293522 A1 | 12/2007 | Singh et al. | |
| 2007/0293524 A1 * | 12/2007 | Singh et al. | 514/275 |
| 2007/0299095 A1 | 12/2007 | Singh et al. | |

FOREIGN PATENT DOCUMENTS

| | | |
|---|---|---|
| CA | 02463989 A1 | 4/2004 |
| CA | 2542492 | 4/2005 |
| DE | 4029650 A1 | 3/1991 |
| EP | 0 139 613 | 8/1984 |
| EP | 0 248 348 | 5/1987 |
| EP | 0 432 893 | 6/1991 |
| EP | 0 525 768 A1 | 2/1993 |
| EP | 1 056 742 B1 | 12/2000 |
| GB | 2373186 | 9/2002 |
| JP | 63008387 | 1/1988 |
| JP | 03/127790 A | 5/1991 |
| JP | 04178385 | 6/1992 |
| SU | 1499883 A1 | 10/1991 |
| WO | WO 90/12790 A1 | 11/1990 |
| WO | WO 91/18887 A1 | 12/1991 |
| WO | WO 95/19358 A1 | 7/1995 |
| WO | WO 97/19065 A1 | 5/1997 |
| WO | WO 98/33798 | 8/1998 |
| WO | WO 98/41512 A1 | 9/1998 |
| WO | WO 99/24874 A1 | 5/1999 |
| WO | WO 99/31073 | 6/1999 |
| WO | WO 99/33846 | 7/1999 |
| WO | WO 99/41253 A1 | 8/1999 |
| WO | WO 99/47529 | 9/1999 |
| WO | WO 99/50249 A2 | 10/1999 |
| WO | WO 99/50250 A1 | 10/1999 |
| WO | WO 99/50251 A1 | 10/1999 |
| WO | WO 99/61437 A1 | 12/1999 |
| WO | WO 00/00202 A1 | 1/2000 |
| WO | WO 00/10981 A1 | 3/2000 |
| WO | WO 00/12485 A1 | 3/2000 |
| WO | WO 00/27825 A1 | 5/2000 |
| WO | WO 00/27826 A1 | 5/2000 |
| WO | WO 00/33844 A1 | 6/2000 |
| WO | WO 00/39101 A1 | 7/2000 |
| WO | WO 00/51587 A2 | 9/2000 |
| WO | WO 00/58305 A1 | 10/2000 |
| WO | WO 00/59893 A1 | 10/2000 |
| WO | WO 00/63182 A2 | 10/2000 |
| WO | WO 00/76980 A1 | 12/2000 |
| WO | WO 00/78731 A1 | 12/2000 |
| WO | WO 01/09134 A1 | 2/2001 |
| WO | WO 01/22938 A1 | 4/2001 |
| WO | WO 01/23362 A2 | 4/2001 |
| WO | WO 01/23389 A2 | 4/2001 |
| WO | WO 01/30782 | 5/2001 |
| WO | WO 01/42246 A2 | 6/2001 |
| WO | WO 01/45641 A2 | 6/2001 |
| WO | WO 01/47897 A1 | 7/2001 |
| WO | WO 01/52852 | 7/2001 |
| WO | WO 01/60816 A1 | 8/2001 |
| WO | WO 01/64654 A1 | 9/2001 |
| WO | WO 01/64655 A1 | 9/2001 |
| WO | WO 01/64656 A1 | 9/2001 |
| WO | WO 01/72744 A1 | 10/2001 |
| WO | WO 01/85699 A2 | 11/2001 |
| WO | WO 01/85700 A2 | 11/2001 |
| WO | WO 02/00661 A1 | 1/2002 |
| WO | WO 02/04429 A1 | 1/2002 |
| WO | WO 02/16306 | 2/2002 |
| WO | WO 02/22601 A1 | 3/2002 |
| WO | WO 02/43735 A1 | 6/2002 |
| WO | WO 02/45652 A2 | 6/2002 |
| WO | WO 02/50066 A2 | 6/2002 |
| WO | WO 02/059110 A1 | 8/2002 |
| WO | WO 02/059112 A2 | 8/2002 |

| | | |
|---|---|---|
| WO | WO 02/060492 A1 | 8/2002 |
| WO | WO 02/062789 A1 | 8/2002 |
| WO | WO 02/064096 A2 | 8/2002 |
| WO | WO 02/066461 A1 | 8/2002 |
| WO | WO 02/066480 A2 | 8/2002 |
| WO | WO 02/066481 | 8/2002 |
| WO | WO 02/068409 | 9/2002 |
| WO | WO 02/096888 A1 | 12/2002 |
| WO | WO 02/096905 | 12/2002 |
| WO | WO 02/096909 A1 | 12/2002 |
| WO | WO 02/102313 A2 | 12/2002 |
| WO | WO 02/102800 A1 | 12/2002 |
| WO | WO 03/000186 A2 | 1/2003 |
| WO | WO 03/000695 | 1/2003 |
| WO | WO 03/002542 A1 | 1/2003 |
| WO | WO 03/002544 A1 | 1/2003 |
| WO | WO 03/016306 A1 | 2/2003 |
| WO | WO 03/018021 A1 | 3/2003 |
| WO | WO 03/018022 A1 | 3/2003 |
| WO | WO 03/026664 A1 | 4/2003 |
| WO | WO 03/026665 A1 | 4/2003 |
| WO | WO 03/026666 A1 | 4/2003 |
| WO | WO 03/030909 A1 | 4/2003 |
| WO | WO 03/032994 A2 | 4/2003 |
| WO | WO 03/032997 A1 | 4/2003 |
| WO | WO 03/040141 A1 | 5/2003 |
| WO | WO 03/045923 A1 | 6/2003 |
| WO | WO 03/048133 A1 | 6/2003 |
| WO | WO 03/048162 A1 | 6/2003 |
| WO | WO 03/055489 A1 | 7/2003 |
| WO | WO 03/062225 A1 | 7/2003 |
| WO | WO 03/063794 | 8/2003 |
| WO | WO 03/066601 A1 | 8/2003 |
| WO | WO 03/074515 | 9/2003 |
| WO | WO 03/076437 A1 | 9/2003 |
| WO | WO 03/078404 A1 | 9/2003 |
| WO | WO 03/080047 | 10/2003 |
| WO | WO 03/094920 A1 | 11/2003 |
| WO | WO 03/101989 A1 | 12/2003 |
| WO | WO 03/106416 A2 | 12/2003 |
| WO | WO 03/106451 | 12/2003 |
| WO | WO 2004/002964 A1 | 1/2004 |
| WO | WO 2004/014382 A1 | 2/2004 |
| WO | WO 2004/014384 | 2/2004 |
| WO | WO 2004/016597 A2 | 2/2004 |
| WO | WO 2004/039359 A2 | 5/2004 |
| WO | WO 2004/041789 A1 | 5/2004 |
| WO | WO 2004/041810 A1 | 5/2004 |
| WO | WO 2004/041814 A1 | 5/2004 |
| WO | WO 2004/043467 A1 | 5/2004 |
| WO | WO 2004/043953 A1 | 5/2004 |
| WO | WO 2004/046112 A2 | 6/2004 |
| WO | WO 2004/046118 A2 | 6/2004 |
| WO | WO 2004/047843 A1 | 6/2004 |
| WO | WO 2004/048343 A1 | 6/2004 |
| WO | WO 2004/050068 A1 | 6/2004 |
| WO | WO 2004/052359 | 6/2004 |
| WO | WO 2004/054617 A1 | 7/2004 |
| WO | WO 2004/056786 A2 | 7/2004 |
| WO | WO 2004/058749 A1 | 7/2004 |
| WO | WO 2004/058753 A2 | 7/2004 |
| WO | WO 2004/067516 | 8/2004 |
| WO | WO 2004/069812 A1 | 8/2004 |
| WO | WO 2004/074244 A2 | 9/2004 |
| WO | WO 2004/074261 A1 | 9/2004 |
| WO | WO 2004/074262 A1 | 9/2004 |
| WO | WO 2004/080980 A1 | 9/2004 |
| WO | WO 2004/099159 A1 | 11/2004 |
| WO | WO 2004/101549 A1 | 11/2004 |
| WO | WO 2004/101564 A1 | 11/2004 |
| WO | WO 2005/007621 A2 | 1/2005 |
| WO | WO 2005/007646 A1 | 1/2005 |
| WO | WO 2005/009980 A1 | 2/2005 |
| WO | WO 2005/012262 A1 | 2/2005 |
| WO | WO 2005/012294 | 2/2005 |
| WO | WO 2005/012304 A2 | 2/2005 |
| WO | WO 2005/012307 A1 | 2/2005 |
| WO | WO 2005/013996 | 2/2005 |
| WO | WO 2005/016893 A2 | 2/2005 |
| WO | WO 2005/016894 A1 | 2/2005 |
| WO | WO 2005/026130 A1 | 3/2005 |
| WO | WO 2005/026158 A1 | 3/2005 |
| WO | WO 2005/027848 A2 | 3/2005 |
| WO | WO 2005/028467 A1 | 3/2005 |
| WO | WO 2005/028479 A2 | 3/2005 |
| WO | WO 2005/037800 | 4/2005 |
| WO | WO 2005/051366 A2 | 6/2005 |
| WO | WO 2005/061458 A2 | 7/2005 |
| WO | WO 2005/066156 A1 | 7/2005 |
| WO | WO 2005/075468 A2 | 8/2005 |
| WO | WO 2005/080393 A1 | 9/2005 |
| WO | WO 2005/107760 A1 | 11/2005 |
| WO | WO 2005/118544 | 12/2005 |
| WO | WO 2006/021454 | 3/2006 |
| WO | WO 2006/026274 | 3/2006 |
| WO | WO 2006/034872 | 4/2006 |
| WO | WO 2006/074057 | 7/2006 |
| WO | WO 2006/078846 | 7/2006 |
| WO | WO 2006/133426 | 12/2006 |
| WO | WO 2007/006926 | 1/2007 |
| WO | WO 2007/014846 | 2/2007 |
| WO | WO 2007/032263 | 3/2007 |
| WO | WO 2007/053452 | 5/2007 |
| WO | WO 2007/076427 | 7/2007 |
| WO | WO 2007/085540 | 8/2007 |
| WO | WO 2007/085833 | 8/2007 |
| WO | WO 2007/098507 | 8/2007 |
| WO | WO 2008/014108 | 1/2008 |

OTHER PUBLICATIONS

U.S. Appl. No. 11/539,142, filed Oct. 5, 2006, Singh et al.
U.S. Appl. No. 11/539,074, filed Oct. 5, 2006, Singh et al.
U.S. Appl. No. 11/782,581, filed Jul. 24, 2007, Singh et al.
U.S. Appl. No. 11/875,772, filed Oct. 19, 2007, Li et al.
U.S. Appl. No. 11/943,506, filed Nov. 20, 2007, Bhamidipati et al.
U.S. Appl. No. 12/028,581, filed Feb. 8, 2008, Argade et al.
U.S. Appl. No. 12/030,031, filed Feb. 12, 2008, Li et al.
U.S. Appl. No. 12/030,069, filed Feb. 12, 2008, Argade et al.
U.S. Appl. No. 12/053,382, filed Mar. 21, 2008, Li et al.
U.S. Appl. No. 12/053,438, filed Mar. 21, 2008, Atuegbu et al.
Arutyunyan et al. 1970, "Reaction of uracils with phosphoric acid amides" *Izvestiya Akademii Nauk SSSR, Seriya Khimicheskaya* 4:904-909.
Banks 1944, "Arylaminoheterocycles. II. Arylaminopyrimidines" *Journal of American Chemical Society* 66:1131.
Biressi et al. 1966, "SU Alcune 5-Fluoro-6-Anilino-Amminopirimidine" *Bolletino Chimico Farmaceutico* 105(9):660-665.
Braselmann et al. 2006, "R406, an orally available spleen tyrosine kinase inhibitor blocks Fc receptor signaling and reduces immune complex-mediated inflammation" *J. Pharmacology and Experimental Therapeutics* 319(3):998-1008.
Breault et al. 2003, "Cyclin-Dependent Kinase 4 Inhibitors as a Treatment for Cancer. Part 2: Identification and Optimization of Substituted 2,4-Bis Anilino Pyrimidines" *Bioorg. Med. Chem. Lett.* 13(18):2961-2966.
Britkova et al. 1966, "Derivatives of Orotic Acid and its Analogs IV, Synthesis and Properties of Amino Acid Derivatives of the Lactone of 5-(Hydroxymethyl)pyrimidine-4-carboxylic Acid" *Khimiya Geterosiklichesikikh Soedinenii* 2(5):783-790 (as translated in *Chemistry of Heterocyclic Compounds*, 1968 The Faraday Press, pp. 606-611).
Brown 1954, "Improved Syntheses in the Pyrimidine Series. III. 5-Amino-4-(methylamino)pyrimidine" *J. Appl. Chem.* 4:72-75.

Cha et al. 2006, "A novel spleen tyrosine kinase inhibitor blocks c-Jun N-Terminal kinase-mediated gene expression in synoviocytes" *J. Pharmacology and Experimental Therapeutics* 317(2):571-578.
Chemical Abstracts 64:27547, compound 5177-26-4, 1954.
Chemical Abstracts 66:2531, compound 13150-23-7P, 1966.
Chemical Abstracts 67:64344, compound 15783-61-6P, 1996.
Chemical Abstracts 67:64344, compound 15783-79-6P, 1996.
Chemical Abstracts 71:81300, compound 19144-75-3P, 1967.
Chemical Abstracts 71:81300, compound 19144-76-4P, 1967.
Chemical Abstracts 72:111409, compound 26857-80-7P, 1969.
Chemical Abstracts 73:35322, compound 28458-89-1, 1944.
Chemical Abstracts 74:141685, compound 31796-90-4, 1970.
Chemical Abstracts 74:141685, compound 31796-91-5, 1970.
Chemical Abstracts 74:141685, compound 31796-99-3, 1970.
Chemical Abstracts 74:141685, compound 31797-00-9, 1970.
Chemical Abstracts 74:141685, compound 31797-01-0 1970.
Chemical Abstracts 74:141685, compound 31797-09-8, 1970.
Chemical Abstracts 74:3577, compound 29935-92-0, 1970.
Chemical Abstracts 74:3577, compound 29935-93-1, 1970.
Chemical Abstracts 74:3577 compound 29935-94-2, 1970.
Chemical Abstracts 74:3577, compound 29935-96-4, 1970.
Chemical Abstracts 74:3577, compound 29935-97-5, 1970.
Chemical Abstracts 74:3577, compound 29935-98-6, 1970.
Chemical Abstracts 74:3577, compound 29935-99-7, 1970.
Chemical Abstracts 74:51826, compound 31414-49-0, 1970.
Chemical Abstracts 74:51826, compound 31414-50-3, 1970.
Chemical Abstracts 75:5843 compound 30953-40-3P, 1970.
Chemical Abstracts 75:5843, compound 32090-58-7P, 1970.
Chemical Abstracts 75:5843 compound 32090-59-8P, 1971.
Chemical Abstracts 78:97592, compound 40423-75-4, 1971.
Chemical Abstracts 78:97592, compound 40423-76-5P, 1971.
Chemical Abstracts 78:97592, compound 40423-83-4P, 1971.
Chemical Abstracts 78:97592, compound 40423-84-5P, 1971.
Chemical Abstracts 78:97592, compound 40505-53-1P, 1971.
Chemical Abstracts 78:97592, compound 40864-28-6P, 1971.
Chemical Abstracts 79:39197, compound 29935-97-5, 1970.
Chemical Abstracts 83:126278, compound 40423-75-4, 1971.
Chemical Abstracts 86:89050, compound 61763-95-9, 1976.
Chemical Abstracts 86:89050, compound 61798-30-9, 1976.
Chemical Abstracts 88:151697, compound 66229-55-8P, 1978.
Cherkasov et al. 1970, "Aminolysis of 2,4-dichloro-5-nitro-6-aminopyrimidine" *Ukrainskii Khimicheskii Zhurnal (Russian Edition)* 36(7):694-696.
Chkhikvadze et al. 1967, "Preparation of 7-Substituted 5,6-Dihydropyrrolo[2,3-d] pyrimidines or its derivatives" *Khimiko-Farmatsevticheskii Zhurnal* 2:5-12.
Chkhikvadze et al. 1969, "5-Substituted pyrimidines. II. Synthesis of 5,6-dihydropyrrolo[2,3-d]pryimidines(5,7-diazaindolines)" *Khimiya Geterotsiklicheskikh Soedinenii* 1:138-144.
Coates et al. 1979, "Correlation analysis of pyrimidine folic acid antagonists as antibacterial agents, I." *Eur. J. Med. Chem. Chimica Therapeutica* 14(3):261-270.
Cook et al. 1978, "Fluorinated Pyrimidine Nucleosides. 2 reaction of 2,2'-anhydro-1-b-D-Arabinofuranosyl-2-fluorocytosine Hydrochloride with Nitrogen and Sulfur Nucleophiles" *J. Org. Chem.* 43 (21) :4200-4206.
Das et al. 2004, Roles of Conformational and Positional Adaptability in Structure-Based Design of TMC 125-R165335 (Etravirine) and Related Non-Nucleoside Reverse Transcriptase Inhibitors that are "Highly Potent and Effective Against Wild-Type and Drug-Resistant HIV-1Variants" *J. Med. Chem.* 47(10):2550-2560.
El-Kerdawy et al. 1986, "2,4-Bis(Substituted)-5-Nitropyrimidines of Expected Diuretic Action" *Egypt J. Chem.* 29(2):247-251.
Ghosh & Mukhehjee 1967, "2,4-Bis(arylamino)-5-methylpyrimidines as Antimicrobial Agents" *J. Med. Chem.* 10:974-975.
Ghosh 1981, "2,4-Bis(Arylamino)-6-Methyl Pyrimidines as Antimicrobial Agents" *J. Indian Chem. Soc.* 58:512-513.
Grigoreva et al. 1979, *Chemico-Pharm. J.* 13(3):5-10.
Grigoreva et al. 1980,*Chemico-Pharm. J.* 14(8):7-11.
Hare et al. 2004, "CORES: An Automated Method for Generating Three-Dimensional Models of Protein/Ligand Complexes" *J. Med. Chem.* 47(19):4731-4740.

Karn et al. 1983, *Khimiko-Farmatsevtsevtichesskii Zhurnal* 17(11):1281-1282, 1304-1307.
Karn et al. 1984, "Synthesis and Antiinflammatory Properties of O-Carboxyphenylamino Pyrimidines" *Kiev Scientific-Research Institute of Pharmacology and Toxicology Plenum Publishing Corporation*, pp. 777-779 (as translated from Karn et al. 1983, *Khimko-framatsevticheskii Zhurnal* 17(11):1304-1307).
Kokorin et al. 1976, "EPR study of the conformation of triazine series nitroxyl biradicals" *Izvestiya Akademii Nauk SSSR, Seriya Khimicheskaya* 9:1994-1999.
Ludovici et al. 2001, "Evolution of Anti-HIV Drug Candidates. Part 3: Diarylpyrimidine (DAPY) Analogues" *Bioorg. Med. Chem. Lett.* 11:2235-2239.
Lyne et al. 2004, "Identification of Compounds with Nanomolar Binding Affinity for Checkpoint Kinase-1 Using Knowledge-Based Virtual Screening" *J. Med. Chem.* 47(8):1962-1968.
Machon & Jasztold-Howorko 1976, "Synthesis of 2,4-Disubstituted 5-Aminopyrimidine-6-Carboxylic Acids Derivatives Part I." *Polish Journal of Pharmacology and Pharmacy* 28(1):61-67.
Mackie et al. 1952, "Influence of groups in the molecule 2,3-dihydro-3-keto-1,4-benzothiazine on its effect on liver fluke (*Fasciola hepatica*) in vitro". *British Journal of Pharmacology and Chemotherapy*, 7:219-22.
Mamaev & Sedova 1965, "Pyrimidines. III. Dehydrogenation of 4-phenylbenzo[h]quinazoline derivatives" *Khimiya Geterotsiklicheskikh Soedinenfi* 4:608-615.
Manesiotis et al. 2005, "Improved Imide Receptors by Imprinting Using Pyrimidine-Based Fluoroscent Reporter Monomers" *J. Org. Chem.* 70:2729-2738.
Mashkovsky 1993, *Meditsina* 1:8.
Mokhort 1970, "Search for Non-steroid Antiinflammatory Substances among Heterocyclic Anthranilic Acid Derivatives" *Farmatsevtichnii Zhurnal (Kiev)* 25(4):76.
Neunhoeffer et al. 1990, "1,4-Dioxino[2,3-b] pyridines and 1,4-oxathiino[2,3-b] pyridines" Chemische Berichte 123(12), 2453-2454.
Paegle et al. 1971, "Synthesis and Properties of N-(2-chloro-5-fluoro-4-pyrimidyl)- and N-(2-thylthio-5-fluoro-4pyrimidyl)amino Acids" *Khimiya Geterotsiklicheskikh Soedinenii* 7(2):258-261.
Polis 1970, "Mechanism of C-N Bond Breaking in Substituted Amines" *Khimiya Geterotsiklicheskikh Soedinenii* 4(571).
Popova et al. 1996A, "Study of Reactions of 2,4,6-Trifluoropyrimidines and 2- and 4-Aminodifluoropyrimidines with Ethylamine" *J. Org. Chem.* 32(5):749-755, as translated from *Zhurnal Organicheskoi Khimii* 32(5):781-787.
Popova et al. 1996B, "Synthesis and Properties of 2- and 4-Aminosubstituted Difluoropyrimidines" *J. Org. Chem.* 32(9):1424-1429, as translated from *Zhurnal Organicheskoi Khimii* 32(9):1418-1423.
Portnyagina & Danilenko 1971, "Guanidine derivatives of pyrimidine" *Khimiko-Farmatsevticheskii Zhurnal* 5(4):15-17.
Protsenko et al. 1966, "Derivatives of pyrimidine. III. Bis(ethylenimino)pyrimidines" *Ukrainskii Khimicheskii Zhurnal (Russian Edition)* 32(8):867-871.
Protsenko et al. 1970, "Reaction of ethyleniminopyrimidines with hydrogen chloride" *Ukrainskii Khimicheskii Zhurnal (Russian Edition)* 36(10):1043-1047.
Radinov et al. 1975, "Fiziologicheski Aktivnye Veshchestva" 7:68-72.
Rajinder et al. 2005, CAPLUS Abstract 124:219300.
Ryabukha & Mokhort 1970, "Relation between structure and pharmacological action in guanidine derivatives of pyrimidine" *Farmakologiya i Toksikologiya (Kiev)* 5:64-67.
Shridhar et al. 1985, "Synthesis and anthelmintic activity of some new 6- and 7-iosothiocyanato-2H-1,4-benzoxa(thia)zin-3(4H)-ones and benzoxa(thia)zin-3(4H)-thiones." Indian Journal of Chemistry, Section B: Organic Chemistry including Medicinal Chemistry, 24B(12):1263-7.
Singh et al. 2004, CAPLUS Abstract 140:199334.
Smirnov et al. 1969, "Products of the reaction of cyanuric trichloride with diiminoisoindoline" *Izvestiya Vysshikh Uchebnykh Zavedenii, Khimiya I Khimicheskaya Tekhnologiya* 12(10):1420-1423.

Strote et al. 1998, "Chemotherapy for Onchocerciassis: Results of in vitro Experiments with Promising New Compounds" *Tropical Medicine and International Health* 3(5):397-407.

Taylor et al. 1998, "1-Alkylcarbonyloxymethyl Prodrugs of 5-Fluorouracil (5-FU): Synthesis, Physicochemical Properties, and Topical Delivery of 5-FU" *J. Pharm. Sci.* 87:5-20.

Tret'Yakova et al. 1972, "Physiological activity of some amino- and chloropyrimidines" *Fiziologicheski Aktivnye Veschestva* 4:93-95.

Tret'Yakova et al. 1980, *Phys. Active Substances* 12:63-67.

Trinus et al. 1970, "Correlation Between the Chemical Structure and Pharmacological Activity of Nitrogen-Containing Heterocyclic Guanidine Derivatives" *Farmatsevtichinii Zhurnal (Kiev)* 25(6):66-68.

Tumkevicius et al. 1998, "Synthesis and Hypolipidemic Activity of 6-Alkyl (Aryl)Amino-2-Chloropyrimidine-4-Carboxylic Acid Esters" *Chemija Chemistry*, ISSN 0235-7216, pp. 90-92.

Vippagunta et al. 2001 "Crystalline Solids" *Advanced Drug Delivery Reviews* 48:3-26.

West 1988 "Solid State Chemistry and its Applications", Wiley, New York, pp. 358 & 365.

Wolff 1995 Burger's Medicinal Chemistry, 5th ed, vol. 1, John Wiley & Sons, pp. 975-977.

Zagulyaeva et al. 1978, "Relative reactivity of chlorine atoms in 2,4-dichloropyrimidine in reactions with ammonia and amines in isooctane and ethanol" *Zhurnal Organicheskoi* 14(2):409-13.

U.S. Appl. No. 12/175,441, filed Jul. 17, 2008, Singh et al.

U.S. Appl. No. 12/193,627, filed Aug. 18, 2008, Li et al.

U.S. Appl. No. 12/199,705, filed Aug. 27, 2008, Singh et al.

Anderson et al. 2003, "Imidazo[1,2a]pyridines: A potent and selective class of cyclin-dependent dinase inhibitors identified through structure-based hybridisation" *Bioorganic & Medicinal Chemistry Letters* 13(18):3021-3026.

Bamborough et al. 2007, "N-4-Pyrimidinyl-1H-indazol-4-amine inhibitors of Lck: Indazoles as phenol isosteres with improved pharmacokinetics" *Bioorganic & Medicinal Chemistry Letters* 17(15):4363-4368.

Bansal et al. 1981A, "N-hydroxymethyl derivatives of nitrogen heterocycles as possible prodrugs I: N-hydroxymethylation of uracils" *J. Pharm. Sci.* 70(8):850-854.

Bansal et al. 1981B, "N-hydroxymethyl derivatives of nitrogen heterocycles as possible prodrugs II: possible prodrugs of allopurinol, glutethimide, and phenobarbital" *J. Pharm. Sci.* 70(8):855-857.

Boloor et al. 2002, CAPLUS Abstract 137:140534.

Bundgaard 1985, "Design of prodrugs: Bioreversible derivatives for various functional groups and chemical entities" *Design of Prodrugs*, Elsevier Science Publishers B.V., Introduction, p. 1.

Bundgaard et al. 1989, "A novel solution-stable, water-soluble prodrug type for drugs containing a hydroxyl or an NH-acidic group." *J. Med. Chem.* 32(12):2503-2507.

Carreras et al. 1993, "Activated T cells in an animal model of allergic conjunctivitis" *Br. J. Ophthalmol* 77(8):509-514.

Cetkovic-Cvrlje 2004, "Therapeutic potential of Janus kinase 3 (JAK3) inhibitors." *Current Pharmaceutical Design* 10(15):1767-1784.

Chan et al. 2001 "Expression of interleukin-4 in the epidermis of transgenic mice results in a pruritic inflammatory skin disease: an experimental animal model to study atopic dermatitis" *J. Invest. Dermatol.* 117(4):977-983.

Changelian 2003, "Prevention of organ allograft rejection by a specific Janus kinase 3 inhibitor." *Science* 302(5646):875-878.

Claman et al. 1990, "Immunoglobulin dysregulation in murine graft-vs-host disease: a hyper-IgE syndrome" *Clin. Immunol. Tmmunopathol.* 56(1):46-53.

Clemens et al. 1997, "Evidence that serum NTx (collagen-type I N-telopeptides) can act as an immunochemical marker of bone resorption" *Clin. Chem.* 43(11):2058-2063.

Corral et al. 1998, "Dissociation between bone resorption and bone formation in osteopenic transgenic mice" *Proc. Natl. Acad. Sci. USA* 95(23):13835-13840.

Damasio 1996 "Alzheimer's Disease and Related Dementias" Cecil Textbook of Medicine, 20th Ed., 2:1992-6.

Demo et al. 1999, "Quantitative measurement of mast cell degranulation using a novel flow cytometric annexin-V binding assay" *Cytometry* 36(4):340-348.

Demoulin et al. 1996, "A single tyrosine of the interleukin-9 (IL-9) receptor is required for STAT activation, antiapoptotic activity, and growth regulation by IL-9." *Mol. Cell. Biol.* 16(9):4710-4716.

Dempster et al. 2001, "Effects of daily treatment with parathyroid hormone on bone microarchitecture and turnover in patients with osteoporosis: a paired biopsy study" *J. Bone Miner. Res.* 16(10):1846-1853.

Erion et al. 2004, "Design, synthesis, and characterization of a series of cytochrome P(450) 3A-activated prodrugs (HepDirect prodrugs) useful for targeting phosph(on)ate-based drugs to the liver" *J. Am. Chem. Soc.* 126(16):5154-5163.

Ettmayer et al. 2004, "Lessons learned from marketed and investigational prodrugs" *J. Med. Chem.* 47(10):2393-2404.

Foster 1995, "The pathophysiology of ocular allergy: current thinking" *Allergy* 50(21Suppl):6-9; discussion 34-38.

Fox et al. 1998, "A single amino acid substitution makes ERK2 susceptible to pyridinyl imidazole inhibitors of p38 MAP kinase" *Protein Science* 7(11):2249-2255.

Ghiron et al. 1995, "Effects of recombinant insulin-like growth factor-I and growth hormone on bone turnover in elderly women" *J. Bone Miner. Res.* 10(12):1844-1852.

Ghosh 1966, "2, 4-Bis(arylamino)pyrimidines as Antimicrobial Agents" *Journal of Medicinal Chemistry* 9:423-424.

Hakim et al. 1996, "A nine-amino acid peptide from IL-1beta augments antitumor immune responses induced by protein and DNA vaccines" *J. Immunol.* 157(12):5503-5511.

Halleen et al. 1999, "Intracellular fragmentation of bone resorption products by reactive oxygen species generated by osteoclastic tartrate-resistant acid phosphatase" *J. Biol. Chem.* 274(33):22907-22910.

Halleen et al. 2001, "Serum tartrate-resistant acid phosphatase 5b is a specific and sensitive marker of bone resorption" *Clin. Chem.* 47(3):597-600.

Hanks et al. 1995, "Protein kinases 6. The eukaryotic protein kinase superfamily: kinase (catalytic) domain structure and classification." *FASEB J.* 9(8):576-596.

Henrotin et al. 2001, "Strontium ranelate increases cartilage matrix formation" *J. Bone Miner. Res.* 16(2):299-308.

Janckila et al. 2003, "Disease-specific expression of tartrate-resistant acid phosphatase isoforms" *J. Bone Miner. Res.* 18(10):1916-1919.

Kagari et al. 2002, "The importance of IL-1 beta and TNF-alpha, and the noninvolvement of IL-6, in the development of monoclonal antibody-induced arthritis" *J. Immunol.* 169(3):1459-1466.

Kaneko et al. 1997, "Rescue by cytokines of apoptotic cell death induced by IL-2 deprivation of human antigen-specific T cell clones" *Clin. Exp. Immun.* 109(1):185-193.

Kawaguchi et al. 1994, "Nasal mast cells in experimentally induced allergic rhinitis in guinea-pigs" *Clin. Exp. Allergy* 24(3):238-244.

Kawakami et al. 2003, "A Ras activation pathway dependent on Syk phosphorylation of protein kinase C" *Proc. Natl. Acad. Sci. USA* 100(16):9470-9475.

Kaye 1964, "Substituted pyrido[2,3-b]pyrazines" *Journal of Medicinal Chemistry* 7(2), 240-241.

Khan et al. 1989, "Aqueous degradation of N-(hydroxymethyl)phthalimide in the presence of specific and general bases. Kinetic assessment of N-hydroxymethyl derivatives of nitrogen heterocycles as possible prodrugs" *J. Pharmaceutical and Biomedical Analysis* 7(6):685-691.

Kirken 2001, "Targeting Jak3 for immune suppression and allograft acceptance" *Transpl. Proc.* 33(7-8):3268-3270.

Kleinau et al. 2000, "Induction and suppression of collagen-induced arthritis is dependent on distinct fcgamma receptors" *J. Exp. Med.* 191:1611-1616.

Kluba and Zwierzak (1978) "Tertra-n-butylaminium Di-t-butyl Phosphate. A New Effective Phophorylating Agent for Alkyl Bromides" Synthesis 1978:770-771.

Konishi et al. 2002, "Platelets activated by collagen through immunoreceptor tyrosine-based activation motif play pivotal role in initiation and generation of neointimal hyperplasia after vascular injury" *Circulation* 105:912-916.

Krise et al. 1999, "Novel prodrug approach for tertiary amines: synthesis and preliminary evaluation of N-phosphonooxymethyl prodrugs" *J. Med. Chem.* 42(16):3094-3100.

Kudlacz et al. 2004, "The novel JAK-3 inhibitor CP-690550 is a potent immunosuppressive agent in various murine models." *Am. J. Transplant* 4(1):51-57.

Kunert et al. 2001, "Alteration in goblet cell numbers and mucin gene expression in a mouse model of allergic conjunctivitis" *Invest. Ophthalmol. Vis. Sci.* 42(11):2483-2489.

Kuno 2001, et al. "Constitutive kinase activation of the TEL-Syk fusion gene in myelodysplastic syndrome with t(9;12)(q22;p. 12)" *Blood* 97(4):1050-1055 (2001).

Lai et al. 2003, "Potent small molecule inhibitors of spleen tyrosine kinase (Syk)" *Bioorg. Med. Chem. Lett.* 13(18):3111-3114.

Lau et al. 2003, "Osteoblastic tartrate-resistant acid phosphatase: its potential role in the molecular mechanism of osteogenic action of fluoride" *J. Bone Miner. Res.* 18(10):1897-1900.

Layzer 1996 "Degenerative diseases of the Nervous System" Cecil Textbook of Medicine, 20th Ed., 1996, 2:2050-7.

Leonard et al. 2000, "Cytokine receptor signaling pathways." *J. Allergy Clin. Immunol.* 105(5):877-888.

Lin et al. 1998, "Heterogeneity of trabecular bone structure in the calcaneus using magnetic resonance imaging" *Osteoporos Int.* 8:16-24.

Lubec et al. 1996, "Evidence for McKusick's hypothesis of deficient collagen cross-linking in patients with homocystinuria" *Biochim. Biophys. Acta* 1315(3):159-162.

Macinnis et al. 2003, "Determinants of bone density in 30- to 65-year-old women: a co-twin study" *J. Bone Miner. Res.* 18(9):1650-1656.

Malaviya et al. 1999, "Targeting Janus kinase 3 in mast cells prevents immediate hypersensitivity reactions and anaphylaxis" *J. Biol. Chem.* 274(38):27028-27038.

Malaviya et al. 1999, "Genetic and biochemical evidence for a critical role of Janus kinase (JAK)-3 in mast cell-mediated type I hypersensitivity reactions" *Biochem. Biophys. Res. Commun.* 257(3):807-813.

Mantyla et al. 2002, "A novel synthetic route for the preparation of alkyl and benzyl chloromethyl phosphates" *Tet. Lett.* 43(21):3793-3794.

Maruyama et al. 1996, "Physical and functional association of cortactin with Syk in human leukemic cell line K562" *J. Biol. Chem.* 271(12):6631-6635.

Mawatari et al. 2000, "Effect of vitamin K2 on three-dimensional trabecular microarchitecture in ovariectomized rats" *J. Bone Miner. Res* 15(9):1810-1817.

McCoy et al. 2002, "The role of prostaglandin E2 receptors in the pathogenesis of rheumatoid arthritis" *J. Clin. Invest.* 110(5):651-658.

Meunier et al. 2002, "Strontium ranelate: dose-dependent effects in established postmenopausal vertebral osteoporosis—a 2-year randomized placebo controlled trial" *J. Clin. Endocrinol. Metab.* 87(5):2060-2066.

Mizuno et al. 2000, "Transgenic mice overexpressing soluble osteoclast differentiation factor (sODF) exhibit severe osteoporosis" *J. Bone Miner. Metab.* 20(6):337-344.

Mocsai et al. 2002, "Syk is required for integrin signaling in neutrophils" *Immunity* 16(4):547-558.

Monteiro & Van De Winkel 2003, "IgA Fc receptors" *Annu. Rev. Immunol.* 21:177-204.

Muller-Ladner et al. 2000, "Activation of the IL-4 STAT pathway in rheumatoid synovium." *J. Immunol.* 164(7):3894-3901.

Nakamura et al. 1996, "An epidermal growth factor receptor/Jak2 tyrosine kinase domain chimera induces tyrosine phosphorylation of Stat5 and transduces a growth signal in hematopoietic cells." *J. Biol. Chem.* 271(32):19483-19488.

Nakasato et al. 1999, "Clinical significance of immunoassays for type-5 tartrate-resistant acid phosphatase" *Clin. Chem.* 45(12):2150-2157.

Nomiyama et al. 2005, "Identification of genes differentially expressed in osteoclast-like cells" *J. Interferon. Cytokine. Res.* 25(4):227-231.

O'Keefe et al. 1987, Systemic mastocytosis in 16 dogs, *J. Vet. Intern. Med.* 1(2):75-80.

O'Shea et al. 2004, "A new modality for immunosuppression: targeting the JAK/STAT pathway." *Nature Reviews Drug Discovery* 3(7):555-564.

Ohmori et al. 1990, "Novel a-Amino-3-hydroxy-5-methylisozazole-4-propionate Receptor Antagonists: Synthesis and Structure-Activity Relationships of 6-(1H-Imidazol-1-yl)-7-nitro-2,3(1H,4H)-pyrido[2,3-b]pyrazinedione and Related compounds" *J. Med. Chem.* 39:1331-1338.

Peters et al. 1996, "Syk, activated by cross-linking the B-cell antigen receptor, localizes to the cytosol where it interacts with and phosphorylates alpha-tubulin on tyrosine" *J. Biol. Chem.* 271(9):4755-7462.

Petersen et al. 2000, "Identification of osteoblast/osteocyte factor 45 (OF45), a bone-specific cDNA encoding an RGD-containing protein that is highly expressed in osteoblasts and osteocytes" *J. Biol. Chem.* 275(46):36172-36180.

Reginster 2002, "Strontium ranelate in osteoporosis" *Curr. Pharm. Des.* 8(21):1907-1916.

Ringe et al. 1999, "Therapy of established postmenopausal osteoporosis with monofluorophosphate plus calcium: dose-related effects on bone density and fracture rate" *Osteop. Int.* 9(2):171-178.

Robins et al. 1994, "Direct, enzyme-linked immunoassay for urinary deoxypyridinoline as a specific marker for measuring bone resorption" *J. Bone Miner. Res.* 9(10):1643-1649.

Rosenquist et al. 1998, "Serum CrossLaps One Step ELISA. First application of monoclonal antibodies for measurement in serum of bone-related degradation products from C-terminal telopeptides of type I collagen" *Clin. Chem.* 44(11):2281-2289.

Ruzzene et al. 1996, "SH2 domains mediate the sequential phosphorylation of HS1 protein by p72syk and Src-related protein tyrosine kinases" *Biochemistry* 35(16):5327-5332.

Sada et al. 2001, "Structure and function of Syk protein-tyrosine kinase" *J. Biochem.* (Tokyo) 130(2):177-186.

Saiga et al. 1992, Clinical and cytologic aspects of ocular late-phase reaction in the guinea pig, *Ophthalmic Res.* 24(1):45-50.

Sammond et al. 2005, "Discovery of a novel and potent series of dianilinopyrimidineurea and urea isostere inhibitors of VEGFR2 tyrosine kinase" *Bioorganic & Medicinal Chemistry Letters* 15(15):3519-3523.

Seidel et al. 2000, "Pharmaceutical intervention in the JAK/STAT signaling pathway." *Oncogene* 19(21):2645-2656.

Seyedin et al. 1993, "Immunoassay for urinary pyridinoline: the new marker of bone resorption" *J. Bone Miner. Res.* 8(5):635-641.

Shiotani et al. 2002, "Regulation of osteoclast differentiation and function by receptor activator of NFkB ligand and osteoprotegerin" *Anat. Rec.* 268(2):137-146.

Shiraki et al. 2000, "Vitamin K2 (menatetrenone) effectively prevents fractures and sustains lumbar bone mineral density in osteoporosis" *J. Bone Miner. Res.* 15(3):515-521.

Silverman 1992, "Prodrugs and drug delivery systems", *The Organic Chemistry of Drug Design and Drug Action*, Academic Press, Inc., pp. 352-400.

Sudbeck et al. 1999, "Structure-based design of specific inhibitors of Janus kinase 3 as apoptosis-inducing antileukemic agents" *Clin. Cancer Res.* 5(6):1569-1582.

Sugimoto et al. 2000, "A new model of allergic rhinitis in rats by topical sensitization and evaluation of H(1)-receptor antagonists" *Immunopharmacology* 48(1):1-7.

Suto et al. 1999, "NC/Nga mice: a mouse model for atopic dermatitis" *Int. Arch. Allergy Immunol.* 120(Suppl 1):70-75.

Suzuki et al. 2000, "Role of common cytokine receptor gamma chain (gamma(c))- and Jak3-dependent signaling in the proliferation and survival of murine mast cells" *Blood* 96(6):2172-2180.

Svensson et al. 1998, "B cell-deficient mice do not develop type II collagen-induced arthritis (CIA)." *Clin. Exp. Immunol.* 111:521-526.

Szalai et al. 2000, "The Arthus reaction in rodents: species-specific requirement of complement" *J. Immunol.* 164(1):463-468.

Szelenyi et al. 2000, "Animal models of allergic rhinitis" *Arzneimittelforschung* 50(11):1037-1042.

Takahashi et al. 2002, "S 12911-2 inhibits osteoclastic bone resorption in vitro" *J. Bone Miner. Res.* 18(6):1082-1087.

Tamura et al. 1993, "New resorption assay with mouse osteoclast-like multinucleated cells formed in vitro" *J. Bone Miner. Res.* 8(8):953-960.

Terato et al. 1992, "Induction of arthritis with monoclonal antibodies to collagen" *J. Immunol.* 148(7):2103-2108.

Traxler 1997 "Protein Tyrosine Kinase inhibitors in cancer treatment" *Exp. Opin. Ther. Patents* 7(6):571-588.

Trieu et al. 2000, "A specific inhibitor of janus kinase-3 increases survival in a transgenic mouse model of amyotrophic lateral sclerosis" *Biochem Biophys. Res. Commun.* 267(1):22-25.

Tumas et al. 2001, "Anti-IgE efficacy in murine asthma models is dependent on the method of allergen sensitization" *J. Allergy Clin. Immunol.* 107(6):1025-1033.

Turner et al. 2000, "Tyrosine kinase SYK: essential functions for immunoreceptor signalling" *Immunology Today* 21:148-154.

Ueda et al. (2003) "Phosphonooxymethyl Prodrugs of the Broad Spectrum Antifungal Azole, Ravuconazole: Synthesis and Biological Porperties" Bioorganic & Medicinal Chemistry Letters 13:3669-3672.

Ulrich 2002, "Crystallization" *Kirk-Othmaer Encyclopedia of Chemical Technology*, John Wiley & Sons, Inc., Chapter 4: Crystal Characteristics.

Vonakis and Saini et al. 2005 "Basophils and Mast Cells in Chronic Idiopathis Urticaria" *Current Allergy and Asthma Reports* 5:270-276.

Wang et al. 1999, "G(s)alpha repression of adipogenesis via Syk" *J. Biol. Chem.* 274(45):32159-32166.

Watson & Gibbons 1998, "Collagen receptor signalling in platelets: extending the role of the ITAM" *Immunol. Today* 19:260-264.

Weinstein et al. 1997, "The effects of androgen deficiency on murine bone remodeling and bone mineral density are mediated via cells of the osteoblastic lineage" *Endocrinology* 138(9):4013-4021.

Wong et al. 2004, "Targeting Syk as a treatment for allergic and autoimmune disorders" *Expert Opin. Investig. Drugs* 13(7):743-762.

Yu 1997, "Constitutive activation of the Janus kinase-STAT pathway in T lymphoma overexpressing the Lck protein tyrosine kinase." *J Immunol.* 159(11):5206-5210.

Zwierzak and Kluba (1974) "Organophosphorus Esters-I t-Butyl as Protecting Group in Phosphorylation Via Nucleophilic Displacement" Tetrahedron 27:3163-3170.

U.S. Appl. No. 12/268,235, filed Nov. 10, 2008, Singh et al.

U.S. Appl. No. 12/268,218, filed Nov. 10, 2008, Singh et al.

U.S. Appl. No. 12/273,357, filed Nov. 18, 2008, Singh et al.

Catalog No. 0122-0021, 4-methyl-N-(4-t-butylphenyl)-6-(3,5-dimethylpyrazole)-2,pyrimidinamine, commercially available from Contact Services/Chemdiv, San Diego, CA, Feb. 28, 2002.

Catalog No. 0781-2697, N2,N4-Bis(4-hydroxy-2-methylphenyl)-6-methyl-5-nitro,2,4-pyrimidinediamine, commercially available from Contact Services/Chemdiv, San Diego, CA, Mar. 1, 2002.

Catalog No. 1079-1249, N2-(4-hydroxyphenyl)-N4-(4-methoxyphenyl)-6-methyl-2,4-diaminopyrimidine, commercially available from Contact Services/Chemdiv, San Diego, CA, Feb. 28, 2002.

Catalog No. 1142-0021, N2,N4-Bis(3-chlorophenyl)-5-fluoro-2,4-pyrimidinediamine, commercially available from Contact Services/Chemdiv, San Diego, CA, Mar. 1, 2002.

Catalog No. 1142-0024, N2,N4-Bis(2,5-dimethylphenyl)-5-fluoro-2,4-pyrimidinediamine, commercially available from Contact Services/Chemdiv, San Diego, CA, Mar. 1, 2002.

Catalog No. 1142-0026, N2,N4-Bis(4-ethoxyphenyl)-5-fluoro-2,4-pyrimidinediamine, commercially available from Contact Services/Chemdiv, San Diego, CA, Mar. 1, 2002.

Catalog No. 1142-0027, N2,N4-Bis(3,4-dimethylphenyl)-5-fluoro-2,4-pyrimidinediamine, commercially available from Contact Services/Chemdiv, San Diego, CA, Mar. 1, 2002.

Catalog No. 1142-0031, N2,N4-Bis(2-methoxyphenyl)-5-fluoro-2,4-pyrimidinediamine, commercially available from Contact Services/Chemdiv, San Diego, CA, Feb. 28, 2002.

Catalog No. 1142-0033, N2,N4-Bisphenyl-5-fluoro-2,4-pyrimidinediamine, commercially available from Contact Services/Chemdiv, San Diego, CA, Mar. 28, 2002.

Catalog No. 1142-0035, N2,N4-Bis(2,4-dimethylphenyl)-5-fluoro-2,4-pyrimidinediamine, commercially available from Contact Services/Chemdiv, San Diego, CA, Mar. 1, 2002.

Catalog No. 1142-0059, N2,N4-Bis(3-bromophenyl)-5-fluoro-2,4-pyrimidinediamine, commercially available from Contact Services/Chemdiv, San Diego, CA, Mar. 1, 2002.

Catalog No. 1690-0003, N2,N4-Bis(4-methoxyphenyl)-5-fluoro-2,4-pyrimidinediamine, commercially available from Contact Services/Chemdiv, San Diego, CA, Feb. 28, 2002.

Catalog No. 1690-0005, N2,N4-Bis(4-chlorophenyl)-5-fluoro-2,4-pyrimidinediamine, commercially available from Contact Services/Chemdiv, San Diego, CA, Mar. 1, 2002.

Catalog No. 1690-0007, N2,N4-Bis(2-chlorophenyl)-5-fluoro-2,4-pyrimidinediamine, commercially available from Contact Services/Chemdiv, San Diego, CA, Feb. 28, 2002.

Catalog No. 1690-0013, N2,N4-Bis(3-methylphenyl)-5-fluoro-2,4-pyrimidinediamine, commercially available from Contact Services/Chemdiv, San Diego, CA, Feb. 28, 2002.

Catalog No. GK 01237, 2,4-Pyrimidinediamine, 6-(4-chlorophenyl)-, commercially available from Maybridge, Cornwall, England, Jan. 18, 2005.

Catalog No. GK 01685 2,4-Pyrimidinediamine, 6-(1,1-dimethylethyl)-, commercially available from Maybridge, Cornwall, England, Jan. 18, 2005.

Catalog No. GK 01714, Benzenesulfonamide, N-[2-amino-6-(4-fluorophenyl)-4-pyrimidinyl]-4-(trifluoromethyl)-, commercially available from Maybridge, Cornwall, England, Jan. 18 2005.

Catalog No. KM 00680, 5-[(4-chlorophenyl)sulfonyl]pyrimidine-2,4-diamine,commercially available from Maybridge, Cornwall, England, Mar. 7, 2007.

Catalog No. RDR 02058, N4-(3-pyridylmethyl)-6-methylpyrimidine-2,4-diamine, commercially available from Maybridge, Cornwall, England, Mar. 7, 2002.

Catalog No. RDR 02059, N4-(3,4-dimethoxyphenethyl)-6-methylpyrimidine-2,4-diamine, commercially available from Maybridge, Cornwall, England, Mar. 7, 2007.

Catalog No. RJF 00403, N4-(2,4-difluorophenyl)-6-methyl-2,4-pyrimidinediamine hydrochloride, commercially available from Maybridge, Cornwall, England, Feb. 27, 2002.

\* cited by examiner

Mast Cell FceR1 Signaling Pathway

Inhibition of Phosphorylation of Proteins Downstream of Syk Kinase in Fcε Receptor Activated BMMC Cells The Disclosed Compounds Potently Inhibit the Activity of Syk Kinase Human Syk kinase
*In vitro* Fluorescence Polarization Kinase Assay

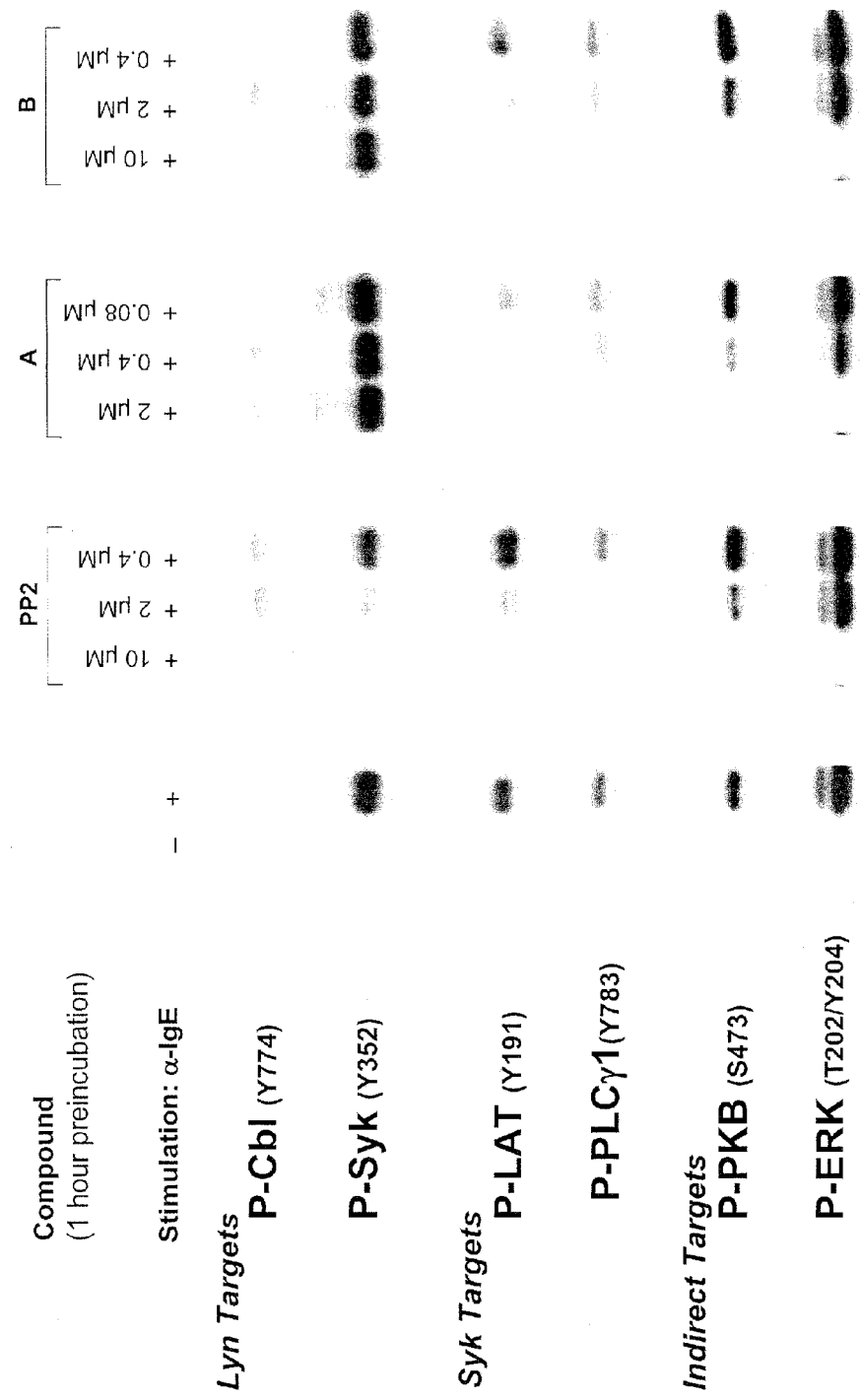

Inhibition of Phosphorylation of Proteins downstream of Syk in BMMC

Inhibition of Phosphorylation of Proteins downstream of Syk in BMMC

2,4-PYRIMIDINEDIAMINE COMPOUNDS AND THEIR USES

1. CROSS REFERENCE TO RELATED APPLICATIONS

This application is a continuation application of U.S. application Ser. No. 10/355,543 filed Jan. 31, 2003, which claims benefit under 35 U.S.C. §119(e) to application Ser. No. 60/353,333 filed Feb. 1, 2002; application Ser. No. 60/353,267 filed Feb. 1, 2002; application Ser. No. 60/399,673 filed Jul. 29, 2002; and application Ser. No. 60/434,277 filed Dec. 17, 2002.

2. FIELD OF THE INVENTION

The present invention relates generally to 2,4-pyrimidinediamine compounds, pharmaceutical compositions comprising the compounds, intermediates and synthetic methods of making the compounds and methods of using the compounds and compositions in a variety of contexts.

3. BACKGROUND OF THE INVENTION

Crosslinking of Fc receptors, such as the high affinity receptor for IgE (FcεRI) and/or the high affinity receptor for IgG (FcγRI) activates a signaling cascade in mast, basophil and other immune cells that results in the release of chemical mediators responsible for numerous adverse events. For example, such crosslinking leads to the release of preformed mediators of Type I (immediate) anaphylactic hypersensitivity reactions, such as histamine, from storage sites in granules via degranulation. It also leads to the synthesis and release of other mediators, including leukotrienes, prostaglandins and platelet-activating factors (PAFs), that play important roles in inflammatory reactions. Additional mediators that are synthesized and released upon crosslinking Fc receptors include cytokines and nitric oxide.

The signaling cascade(s) activated by crosslinking Fc receptors such as FcεRI and/or FcγRI comprises an array of cellular proteins. Among the most important intracellular signal propagators are the tyrosine kinases. And, an important tyrosine kinase involved in the signal transduction pathways associated with crosslinking the FcεRI and/or FcγRI receptors, as well as other signal transduction cascades, is Syk kinase (see Valent et al., 2002, *Intl. J. Hematol.* 75(4):257-362 for review).

As the mediators released as a result of FcεRI and FcγRI receptor cross-linking are responsible for, or play important roles in, the manifestation of numerous adverse events, the availability of compounds capable of inhibiting the signaling cascade(s) responsible for their release would be highly desirable. Moreover, owing to the critical role that Syk kinase plays these and other receptor signaling cascade(s), the availability of compounds capable of inhibiting Syk kinase would also be highly desirable.

4. SUMMARY OF THE INVENTION

In one aspect, the present invention provides novel 2,4-pyrimidinediamine compounds that, as will be discussed in more detail below, have myriad biological activities. The compounds generally comprise a 2,4-pyrimidinediamine "core" having the following structure and numbering convention:

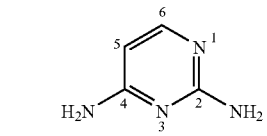

The compounds of the invention are substituted at the C2 nitrogen (N2) to form a secondary amine and are optionally further substituted at one or more of the following positions: the C4 nitrogen (N4), the C5 position and/or the C6 position. When substituted at N4, the substituent forms a secondary amine. The substituent at N2, as well as the optional substituents at the other positions, may range broadly in character and physico-chemical properties. For example, the substituent(s) may be a branched, straight-chained or cyclic alkyl, a branched, straight-chained or cyclic heteroalkyl, a mono- or polycyclic aryl a mono- or polycyclic heteroaryl or combinations of these groups. These substituent groups may be further substituted, as will be described in more detail below.

The N2 and/or N4 substituents may be attached directly to their respective nitrogen atoms, or they may be spaced away from their respective nitrogen atoms via linkers, which may be the same or different. The nature of the linkers can vary widely, and can include virtually any combination of atoms or groups useful for spacing one molecular moiety from another. For example, the linker may be an acyclic hydrocarbon bridge (e.g., a saturated or unsaturated alkyleno such as methano, ethano, etheno, propano, prop[1]eno, butano, but[1]eno, but[2]eno, buta[1,3]dieno, and the like), a monocyclic or polycyclic hydrocarbon bridge (e.g., [1,2]benzeno, [2,3]naphthaleno, and the like), a simple acyclic heteroatomic or heteroalkyldiyl bridge (e.g., —O—, —S—, —S—O—, —NH—, —PH—, —C(O)—, —C(O)NH—, —S(O)—, —S(O)₂—, —S(O)NH—, —S(O)₂NH—, —O—CH₂—, —CH₂—O—CH₂—, —O—CH=CH—CH₂—, and the like), a monocyclic or polycyclic heteroaryl bridge (e.g., [3,4] furano, pyridino, thiopheno, piperidino, piperazino, pyrazidino, pyrrolidino, and the like) or combinations of such bridges.

The substituents at the N2, N4, C5 and/or C6 positions, as well as the optional linkers, may be further substituted with one or more of the same or different substituent groups. The nature of these substituent groups may vary broadly. Non-limiting examples of suitable substituent groups include branched, straight-chain or cyclic alkyls, mono- or polycyclic aryls, branched, straight-chain or cyclic heteroalkyls, mono- or polycyclic heteroaryls, halos, branched, straight-chain or cyclic haloalkyls, hydroxyls, oxos, thioxos, branched, straight-chain or cyclic alkoxys, branched, straight-chain or cyclic haloalkoxys, trifluoromethoxys, mono- or polycyclic aryloxys, mono- or polycyclic heteroaryloxys, ethers, alcohols, sulfides, thioethers, sulfanyls (thiols), imines, azos, azides, amines (primary, secondary and tertiary), nitriles (any isomer), cyanates (any isomer), thiocyanates (any isomer), nitrosos, nitros, diazos, sulfoxides, sulfonyls, sulfonic acids, sulfamides, sulfonamides, sulfamic esters, aldehydes, ketones, carboxylic acids, esters, amides, amidines, formadines, amino acids, acetylenes, carbamates, lactones, lactams, glucosides, gluconurides, sulfones, ketals, acetals, thioketals, oximes, oxamic acids, oxamic esters, etc., and combinations of these groups. Substituent groups bearing reactive functionalities may be protected or unprotected, as is well-known in the art.

In one illustrative embodiment, the 2,4-pyrimidinediamine compounds of the invention are compounds according to structural formula (I):

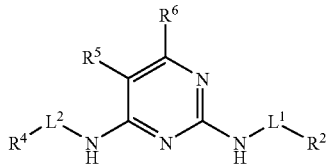

including salts, hydrates, solvates and N-oxides thereof, wherein:

$L^1$ and $L^2$ are each, independently of one another, selected from the group consisting of a direct bond and a linker;

$R^2$ is selected from the group consisting of (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups;

$R^4$ is selected from the group consisting of hydrogen, (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups;

$R^5$ is selected from the group consisting of $R^6$, (C1-C6) alkyl optionally substituted with one or more of the same or different $R^8$ groups, (C1-C4) alkanyl optionally substituted with one or more of the same or different $R^8$ groups, (C2-C4) alkenyl optionally substituted with one or more of the same or different $R^8$ groups and (C2-C4) alkynyl optionally substituted with one or more of the same or different $R^8$ groups;

each $R^6$ is independently selected from the group consisting of hydrogen, an electronegative group, —$OR^d$, —$SR^d$, (C1-C3) haloalkyloxy, (C1-C3) perhaloalkyloxy, —$NR^cR^c$, halogen, (C1-C3) haloalkyl, (C1-C3) perhaloalkyl, —$CF_3$, —$CH_2CF_3$, —$CF_2CF_3$, —CN, —NC, —OCN, —SCN, —NO, —$NO_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$OS(O)NR^cR^c$, —$OS(O)_2NR^cR^c$, —C(O)$R^d$, —C(O)O$R^d$, —C(O)NR^cR^c$, —C(NH)NR^cR^c$, —OC(O)$R^d$, —SC(O)$R^d$, —OC(O)O$R^d$, —SC(O)O$R^d$, —OC(O)NR^cR^c$, —SC(O)NR^cR^c$, —OC(NH)NR^cR^c$, —SC(NH)NR^cR^c$, —[NHC(O)]$_n$$R^d$, —[NHC(O)]$_n$O$R^d$, —[NHC(O)]$_n$NR^cR^c$ and —[NHC(NH)]$_n$NR^cR^c$, (C5-C10) aryl optionally substituted with one or more of the same or different $R^8$ groups, phenyl optionally substituted with one or more of the same or different $R^8$ groups, (C6-C16) arylalkyl optionally substituted with one or more of the same or different $R^8$ groups, 5-10 membered heteroaryl optionally substituted with one or more of the same or different $R^8$ groups and 6-16 membered heteroarylalkyl optionally substituted with one or more of the same or different $R^8$ groups;

$R^8$ is selected from the group consisting of $R^a$, $R^b$, $R^a$ substituted with one or more of the same or different $R^a$ or $R^b$, —$OR^a$ substituted with one or more of the same or different $R^a$ or $R^b$, —B(OR^a)$_2$, —B(NR^cR^c)$_2$, —(CH$_2$)$_m$—$R^b$, —(CHR^a)$_m$—$R^b$, —O(CH$_2$)$_m$—$R^b$, —S—(CH$_2$)$_m$—$R^b$, —O—CHR^aR^b$, —O—CR^a(R^b)$_2$, —O—(CHR^a)$_m$—$R^b$, —O—(CH$_2$)$_m$—CH[(CH$_2$)$_m$R^b$]$R^b$, —S—(CHR^a)$_m$—$R^b$, —C(O)NH—(CH$_2$)$_m$—$R^b$, —C(O)NH—(CHR^a)$_m$—$R^b$, —O—(CH$_2$)$_m$—C(O)NH—(CH$_2$)$_m$—$R^b$, —S—(CH$_2$)$_m$—C(O)NH—(CH$_2$)$_m$—$R^b$, —O—(CHR^a)$_m$—C(O)NH—(CHR^a)$_m$—$R^b$, —S—(CHR^a)$_m$—C(O)NH—(CHR^a)$_m$—$R^b$, —NH—(CH$_2$)$_m$—$R^b$, —NH(CHR^a)$_m$—$R^b$, —NH[(CH$_2$)$_m$R^b$], —N[(CH$_2$)$_m$R^b$]$_2$, —NH—C(O)—NH—(CH$_2$)$_m$—$R^b$, —NH—C(O)—(CH$_2$)$_m$—CHR^bR^b$ and —NH—(CH$_2$)$_m$—C(O)—NH—(CH$_2$)$_m$—$R^b$;

each $R^a$ is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each $R^b$ is a suitable group independently selected from the group consisting of =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —C(O)$R^d$, —C(O)O$R^d$, —C(O)NR^cR^c$, —C(NH)NR^cR^c$, —C(NR^a)NR^cR^c$, —C(NOH)$R^a$, —C(NOH)NR^cR^c$, —OC(O)$R^d$, —OC(O)O$R^d$, —OC(O)NR^cR^c$, —OC(NH)NR^cR^c$, —OC(NR^a)NR^cR^c$, —[NHC(O)]$_n$$R^d$, —[NR^aC(O)]$_n$$R^d$, —[NHC(O)]$_n$O$R^d$, —[NR^aC(O)]$_n$O$R^d$, —[NHC(O)]$_n$NR^cR^c$, —[NR^aC(O)]$_n$NR^cR^c$, —[NHC(NH)]$_n$NR^cR^c$ and —[NR^aC(NR^a)]$_n$NR^cR^c$;

each $R^c$ is independently a protecting group or $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different $R^a$ or suitable $R^b$ groups;

each $R^d$ is independently a protecting group or $R^a$;

each m is independently an integer from 1 to 3; and each n is independently an integer from 0 to 3.

In another aspect, the present invention provides prodrugs of the 2,4-pyrimidinediamine compounds. Such prodrugs may be active in their prodrug form, or may be inactive until converted under physiological or other conditions of use to an active drug form. In the prodrugs of the invention, one or more functional groups of the 2,4-pyrimidinediamine compounds are included in promoieties that cleave from the molecule under the conditions of use, typically by way of hydrolysis, enzymatic cleavage or some other cleavage mechanism, to yield the functional groups. For example, primary or secondary amino groups may be included in an amide promoiety that cleaves under conditions of use to generate the primary or secondary amino group. Thus, the prodrugs of the invention include special types of protecting groups, termed "progroups," masking one or more functional groups of the 2,4-pyrimidinediamine compounds that cleave under the conditions of use to yield an active 2,4-pyrimidinediamine drug compound. Functional groups within the 2,4-pyrimidinediamine compounds that may be masked with progroups for inclusion in a promoiety include, but are not limited to, amines (primary and secondary), hydroxyls, sulfanyls (thiols), carboxyls, carbonyls, phenols, catechols, diols, alkynes, phosphates, etc. Myriad progroups suitable for masking such functional groups to yield promoieties that are cleavable under the desired conditions of use are known in the art. All of these progroups, alone or in combinations, may be included in the prodrugs of the invention. Specific examples of promoieties that yield primary or secondary amine groups that can be included in the prodrugs of the invention include, but are not limited to, amides, carbamates, imines, ureas, phosphenyls, phosphoryls and sulfenyls. Specific examples of promoieties that yield sulfanyl groups that can be included in the prodrugs of the invention include, but are not limited to, thioethers, for example S-methyl derivatives (monothio, dithio, oxythio, aminothio acetals), silyl thioethers, thioesters, thiocarbonates, thiocarbamates, asymmetrical disulfides, etc. Specific examples of promoieties that cleave to yield hydroxyl groups that can be included in the prodrugs of the invention include, but are not limited to, sulfonates, esters and carbonates. Specific examples of promoieties that yield carboxyl groups that can be included in the prodrugs of the invention included, but are not limited to, esters (including silyl esters, oxamic acid esters and thioesters), amides and hydrazides.

In one illustrative embodiment, the prodrugs of the invention are compounds according to structural formula (I) in which the protecting group of $R^c$ and $R^d$ is a progroup.

Replacing the hydrogens attached to N2 and N4 in the 2,4-pyrimidinediamines of structural formula (I) with substituents adversely affects the activity of the compounds. However, as will be appreciated by skilled artisans, these nitrogens may be included in promoieties that, under conditions of use, cleave to yield 2,4-pyrimidinediamines according to structural formula (I). Thus, in another illustrative embodiment, the prodrugs of the invention are compounds according to structural formula (II):

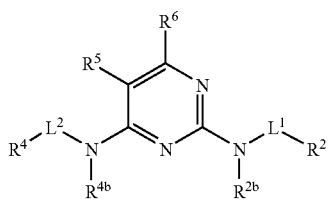

including salts, hydrates, solvates and N-oxides thereof, wherein:
$R^2$, $R^4$, $R^5$, $R^6$, $L^1$ and $L^2$ are as previously defined for structural formula (I); and
$R^{2b}$ and $R^{4b}$ are each, independently of one another, a progroup.

In another aspect, the present invention provides compositions comprising one or more compounds and/or prodrugs of the invention and an appropriate carrier, excipient or diluent. The exact nature of the carrier, excipient or diluent will depend upon the desired use for the composition, and may range from being suitable or acceptable for veterinary uses to being suitable or acceptable for human use.

In still another aspect, the present invention provides intermediates useful for synthesizing the 2,4-pyrimidinediamine compounds and prodrugs of the invention. In one embodiment, the intermediates are 4-pyrimidineamines according to structural formula (III):

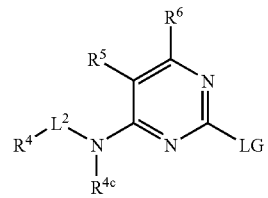

including salts, hydrates, solvates and N-oxides thereof, wherein $R^4$, $R^5$, $R^6$ and $L^2$ are as previously defined for structural formula (I); LG is a leaving group such as, for example, —S(O)₂Me, —SMe or halo (e.g., F, Cl, Br, I); and $R^{4c}$ is hydrogen or a progroup.

In another embodiment, the intermediates are 2-pyrimidineamines according to structural formula (IV):

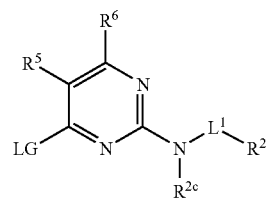

including salts, hydrates, solvates and N-oxides thereof, wherein $R^2$, $R^5$, $R^6$ and $L^1$ are as previously defined for structural formula (I); LG is a leaving group, such as, for example, —S(O)₂Me, —SMe or halo (e.g., F, Cl, Br, I) and $R^{2c}$ is hydrogen or a progroup.

In yet another embodiment, the intermediates are 4-amino- or 4-hydroxy-2-pyrimidineamines according to structural formula (V):

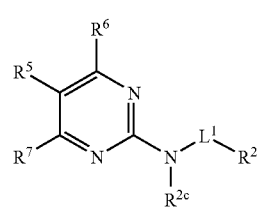

including salts, hydrates, solvates and N-oxides thereof, wherein $R^2$, $R^5$, $R^6$ and $L^1$ are as previously defined for structural formula (I), $R^7$ is an amino or hydroxyl group and $R^{2c}$ is hydrogen or a progroup.

In another embodiment, the intermediates are N4-substituted cytosines according to structural formula (VI):

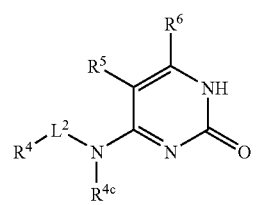

including salts, hydrates, solvates and N-oxides thereof, wherein $R^4$, $R^5$, $R^6$ and $L^2$ are as previously defined for structural formula (I) and $R^{4c}$ is hydrogen or a progroup.

In yet another aspect, the present invention provides methods of synthesizing the 2,4-pyrimidinediamine compounds and prodrugs of the invention. In one embodiment, the method involves reacting a 4-pyrimidineamine according to structural formula (III) with an amine of the formula $HR^{2c}N-L^1-R^2$, where $L^1$, $R^2$ and $R^{2c}$ are as previously defined for structural formula (IV) to yield a 2,4-pyrimidinediamine according to structural formula (I) or a prodrug according to structural formula (II).

In another embodiment, the method involves reacting a 2-pyrimidineamine according to structural formula (IV) with an amine of the formula $R^4-L^2-NHR^{4c}$ where $L^4$, $R^4$ and $R^{4c}$ are as previously defined for structural formula (III) to yield a 2,4-pyrimidinediamine according to structural formula (I) or a prodrug according to structural formula (II).

In yet another embodiment, the method involves reacting a 4-amino-2-pyrimidineamine according to structural formula (V) (in which $R^7$ is an amino group) with an amine of the formula $R^4-L^2-NHR^{4c}$, where $L^2$, $R^4$ and $R^{4c}$ are as defined for structural formula (III), to yield a 2,4-pyrimidinediamine according to structural formula (I) or a prodrug according to structural formula (II). Alternatively, the 4-amino-2-pyrimidineamine may be reacted with a compound of the formula $R^4-L^2-LG$, where $R^4$ and $L^2$ are as previously defined for structural formula (I) and LG is a leaving group.

In still another embodiment, the method involves halogenating a 4-hydroxy-2-pyrimidineamine according to structural formula (V) ($R^7$ is a hydroxyl group) to yield a 2-pyrimidineamine according to structural formula (IV) and reacting this pyrimidineamine with an appropriate amine, as described above.

In yet another embodiment, the method involves halogenating an N4-substituted cytosine according to structural formula (VI) to yield a 4-pyrimidineamine according to structural formula (III) and reacting this pyrimidineamine with an appropriate amine, as described above.

The 2,4-pyrimidinediamine compounds of the invention are potent inhibitors of degranulation of immune cells, such as mast, basophil, neutrophil and/or eosinophil cells. Thus, in still another aspect, the present invention provides methods of regulating, and in particular inhibiting, degranulation of such cells. The method generally involves contacting a cell that degranulates with an amount of a 2,4-pyrimidinediamine compound or prodrug of the invention, or an acceptable salt, hydrate, solvate, N-oxide and/or composition thereof, effective to regulate or inhibit degranulation of the cell. The method may be practiced in in vitro contexts or in in vivo contexts as a therapeutic approach towards the treatment or prevention of diseases characterized by, caused by or associated with cellular degranulation.

While not intending to be bound by any theory of operation, biochemical data confirm that the 2,4-pyrimidinediamine compounds exert their degranulation inhibitory effect, at least in part, by blocking or inhibiting the signal transduction cascade(s) initiated by crosslinking of the high affinity Fc receptors for IgE ("FcεRI") and/or IgG ("FcγRI"). Indeed, the 2,4-pyrimidinediamine compounds are potent inhibitors of both FcεRI-mediated and FcγRI-mediated degranulation. As a consequence, the 2,4-pyrimidine compounds may be used to inhibit these Fc receptor signalling cascades in any cell type expressing such FcεRI and/or FcγRI receptors including but not limited to macrophages, mast, basophil, neutrophil and/or eosinophil cells.

The methods also permit the regulation of, and in particular the inhibition of, downstream processes that result as a consequence of activating such Fc receptor signaling cascade(s). Such downstream processes include, but are not limited to, FcεRI-mediated and/or FcγRI-mediated degranulation, cytokine production and/or the production and/or release of lipid mediators such as leukotrienes and prostaglandins. The method generally involves contacting a cell expressing an Fc receptor, such as one of the cell types discussed above, with an amount of a 2,4-pyrimidinediamine compound or prodrug of the invention, or an acceptable salt, hydrate, solvent, N-oxide and/or composition thereof, effective to regulate or inhibit the Fc receptor signaling cascade and/or a downstream process effected by the activation of this signaling cascade. The method may be practiced in in vitro contexts or in in vivo contexts as a therapeutic approach towards the treatment or prevention of diseases characterized by, caused by or associated with the Fc receptor signaling cascade, such as diseases effected by the release of granule specific chemical mediators upon degranulation, the release and/or synthesis of cytokines and/or the release and/or synthesis of lipid mediators such as leukotrienes and prostaglandins.

In yet another aspect, the present invention provides methods of treating and/or preventing diseases characterized by, caused by or associated with the release of chemical mediators as a consequence of activating Fc receptor signaling cascades, such as FcεRI and/or FcγRI-signaling cascades. The methods may be practiced in animals in veterinary contexts or in humans. The methods generally involve administering to an animal subject or human an amount of a 2,4-pyrimidinediamine compound or prodrug of the invention, or an acceptable salt, hydrate, solvate, N-oxide and/or composition thereof, effective to treat or prevent the disease. As discussed previously, activation of the FcεRI or FcγRI receptor signaling cascade in certain immune cells leads to the release and/or synthesis of a variety of chemical substances that are pharmacological mediators of a wide variety of diseases. Any of these diseases may be treated or prevented according to the methods of the invention.

For example, in mast cells and basophil cells, activation of the FcεRI or FcγRI signaling cascade leads to the immediate (i.e., within 1-3 min. of receptor activation) release of preformed mediators of atopic and/or Type I hypersensitivity reactions (e.g., histamine, proteases such as tryptase, etc.) via the degranulation process. Such atopic or Type I hypersensitivity reactions include, but are not limited to, anaphylactic reactions to environmental and other allergens (e.g., pollens, insect and/or animal venoms, foods, drugs, contrast dyes, etc.), anaphylactoid reactions, hay fever, allergic conjunctivitis, allergic rhinitis, allergic asthma, atopic dermatitis, eczema, urticaria, mucosal disorders, tissue disorders and certain gastrointestinal disorders.

The immediate release of the preformed mediators via degranulation is followed by the release and/or synthesis of a variety of other chemical mediators, including, among other things, platelet activating factor (PAF), prostaglandins and leukotrienes (e.g., LTC4) and the de novo synthesis and release of cytokines such as TNFα, IL-4, IL-5, IL-6, IL-13, etc. The first of these two processes occurs approximately 3-30 min. following receptor activation; the latter approximately 30 min.-7 hrs. following receptor activation. These "late stage" mediators are thought to be in part responsible for the chronic symptoms of the above-listed atopic and Type I hypersensitivity reactions, and in addition are chemical mediators of inflammation and inflammatory diseases (e.g., osteoarthritis, inflammatory bowel disease, ulcerative colitis, Crohn's disease, idiopathic inflammatory bowel disease, irritable bowel syndrome, spastic colon, etc.), low grade scarring (e.g., scleroderma, increased fibrosis, keloids, post-surgical scars, pulmonary fibrosis, vascular spasms, migraine, reperfusion injury and post myocardial infarction), and sicca complex or syndrome. All of these diseases may be treated or prevented according to the methods of the invention.

Additional diseases which can be treated or prevented according to the methods of the invention include diseases associated with basophil cell and/or mast cell pathology. Examples of such diseases include, but are not limited to, diseases of the skin such as scleroderma, cardiac diseases such as post myocardial infarction, pulmonary diseases such as pulmonary muscle changes or remodeling and chronic obstructive pulmonary disease (COPD) and diseases of the gut such as inflammatory bowel syndrome (spastic colon).

The 2,4-pyrimidinediamine compounds of the invention are also potent inhibitors of the tyrosine kinase Syk kinase. Thus, in still another aspect, the present invention provides methods of regulating, and in particular inhibiting, Syk kinase activity. The method generally involves contacting a Syk kinase or a cell comprising a Syk kinase with an amount of a 2,4-pyrimidinediamine compound or prodrug of the invention, or an acceptable salt, hydrate, solvate, N-oxide and/or composition thereof, effective to regulate or inhibit Syk kinase activity. In one embodiment, the Syk kinase is an isolated or recombinant Syk kinase. In another embodiment, the Syk kinase is an endogenous or recombinant Syk kinase expressed by a cell, for example a mast cell or a basophil cell. The method may be practiced in in vitro contexts or in in vivo contexts as a therapeutic approach towards the treatment or prevention of diseases characterized by, caused by or associated with Syk kinase activity.

Figure 2:
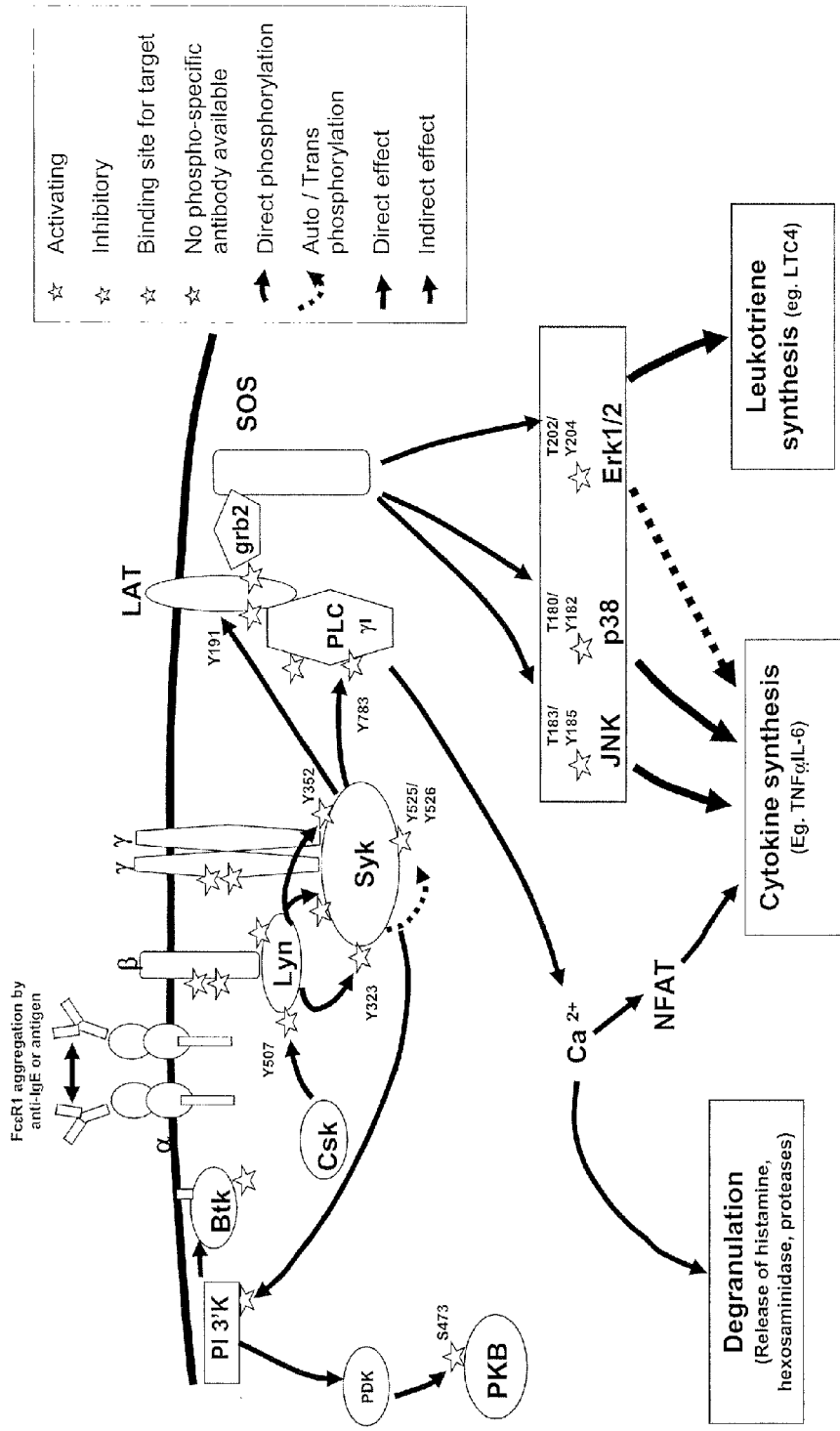

While not intending to be bound by any particular theory of operation, it is believed that the 2,4-pyrimidinediamine compounds of the invention inhibit cellular degranulation and/or the release of other chemical mediators primarily by inhibiting Syk kinase that gets activated through the gamma chain homodimer of FcεRI (see, e.g., FIG. 2). This gamma chain homodimer is shared by other Fc receptors, including FcγRI, FcγRIII and FcαRI. For all of these receptors, intracellular signal transduction is mediated by the common gamma chain homodimer. Binding and aggregation of those receptors results in the recruitment and activation of tyrosine kinases such as Syk kinase. As a consequence of these common signaling activities, the 2,4-pyrimidinediamine compounds described herein may be used to regulate, and in particular inhibit, the signaling cascades of Fc receptors having this gamma chain homodimer, such as FcεRI, FcγRI, FcγRIII and FcαRI, as well as the cellular responses elicited through these receptors.

Syk kinase is known to play a critical role in other signaling cascades. For example, Syk kinase is an effector of B-cell receptor (BCR) signaling (Turner et al, 2000, Immunology Today 21:148-154) and is an essential component of integrin beta(1), beta(2) and beta(3) signaling in neutrophils (Mocsai et al, 2002, Immunity 16:547-558). As the 2,4-pyrimidinediamine compounds described herein are potent inhibitors of Syk kinase, they can be used to regulate, and in particular inhibit, any signaling cascade where Syk plays a role, such as, fore example, the Fc receptor, BCR and integrin signaling cascades, as well as the cellular responses elicited through these signaling cascades. The particular cellular response regulated or inhibited will depend, in part, on the specific cell type and receptor signaling cascade, as is well known in the art. Non-limiting examples of cellular responses that may be regulated or inhibited with the 2,4-pyrimidinediamine compounds include a respiratory burst, cellular adhesion, cellular degranulation, cell spreading, cell migration, phagocytosis (e.g., in macrophages), calcium ion flux (e.g., in mast, basophil, neutrophil, eosinophil and B-cells), platelet aggregation, and cell maturation (e.g., in B-cells).

Thus, in another aspect, the present invention provides methods of regulating, and in particular inhibiting, signal transduction cascades in which Syk plays a role. The method generally involves contacting a Syk-dependent receptor or a cell expressing a Syk-dependent receptor with an amount of a 2,4-pyrimidinediamine compound or prodrug of the invention, or an acceptable salt, hydrate, solvate, N-oxide and/or composition thereof, effective to regulate or inhibit the signal transduction cascade. The methods may also be used to regulate, and in particular inhibit, downstream processes or cellular responses elicited by activation of the particular Syk-dependent signal transduction cascade. The methods may be practiced to regulate any signal trasduction cascade where Syk is not known or later discovered to play a role. The methods may be practiced in in vitro contexts or in in vivo contexts as a therapeutic approach towards the treatment or prevention of diseases characterized by, caused by or associated with activation of the Syk-dependent signal transduction cascade. Non-limited examples of such diseases include those previously discussed.

5. BRIEF DESCRIPTION OF THE FIGURES

Figure 3:
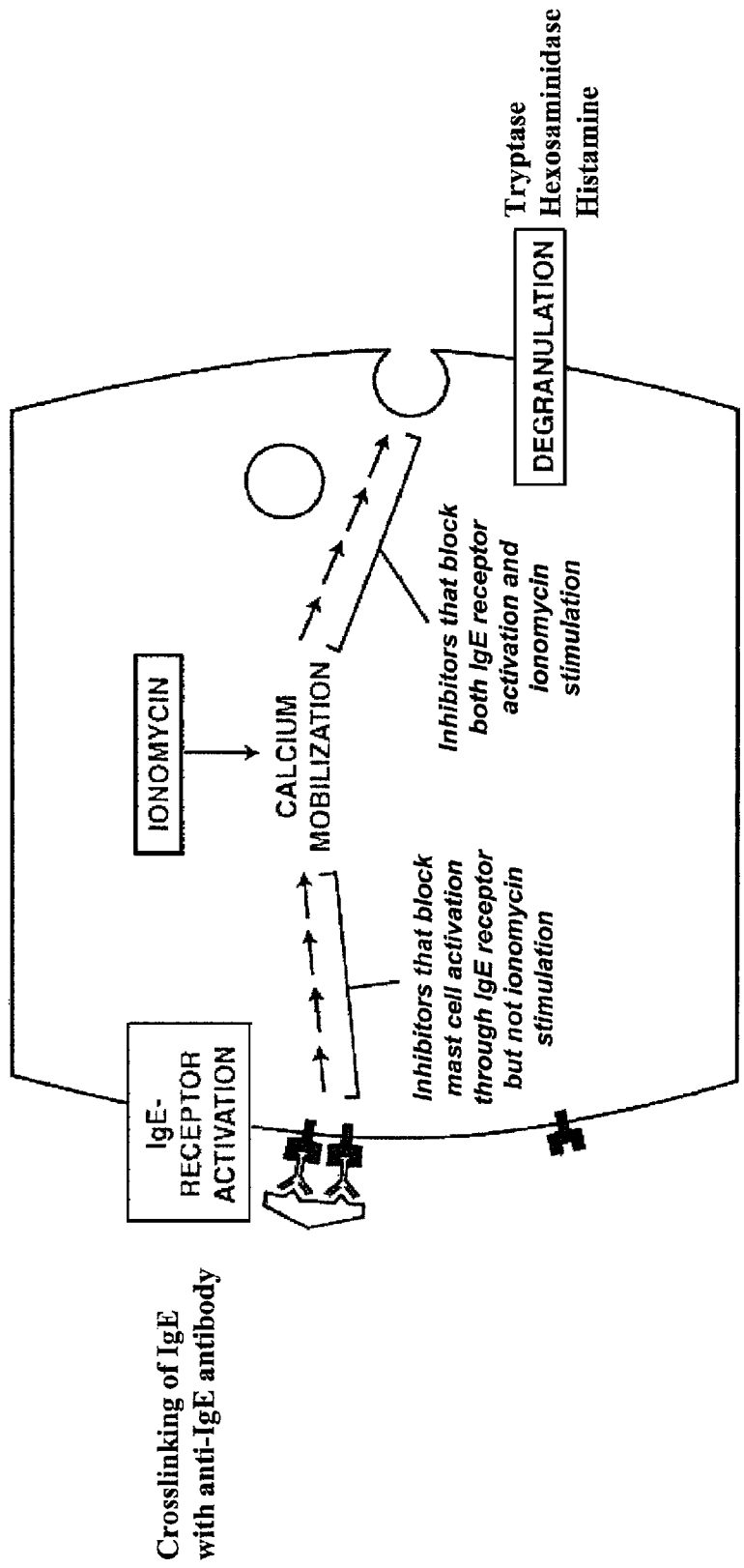
Figure 4:
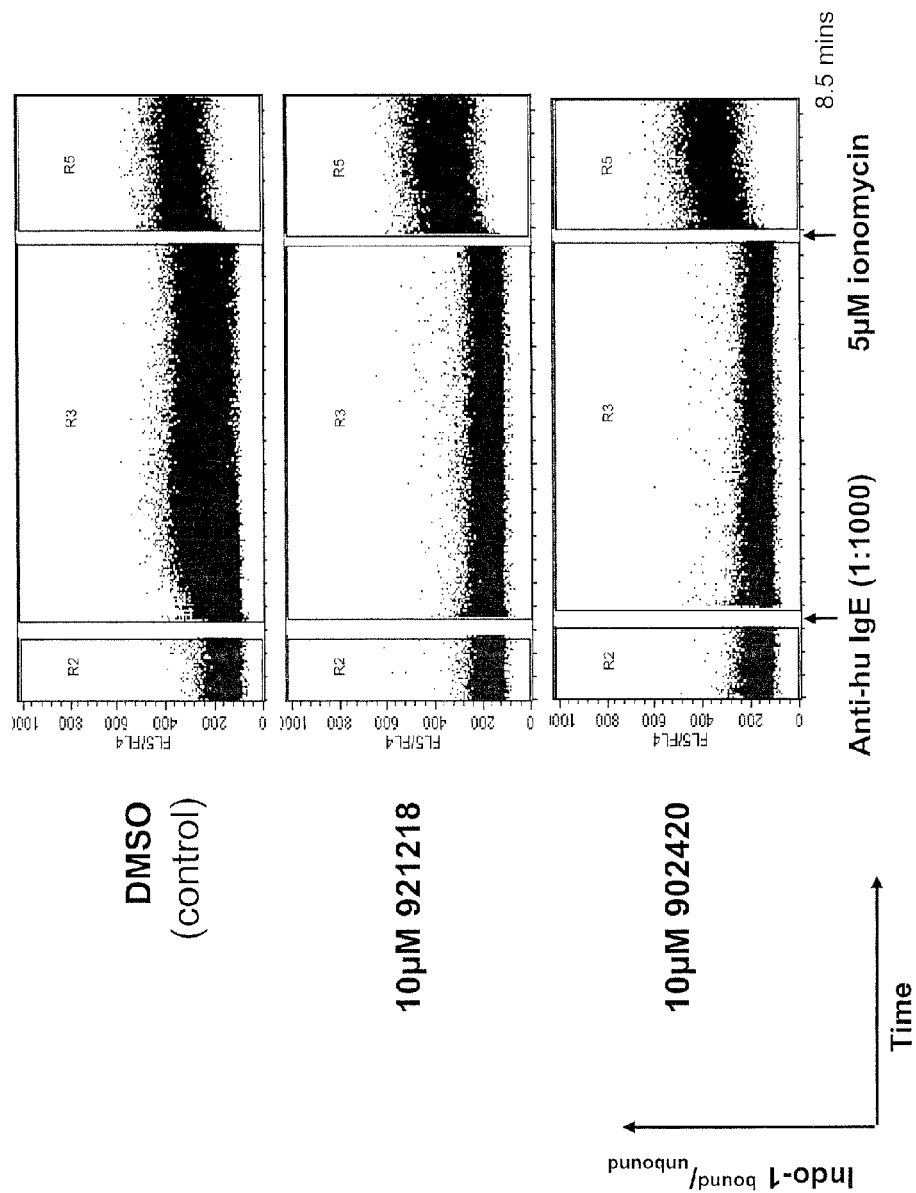
Figure 5:
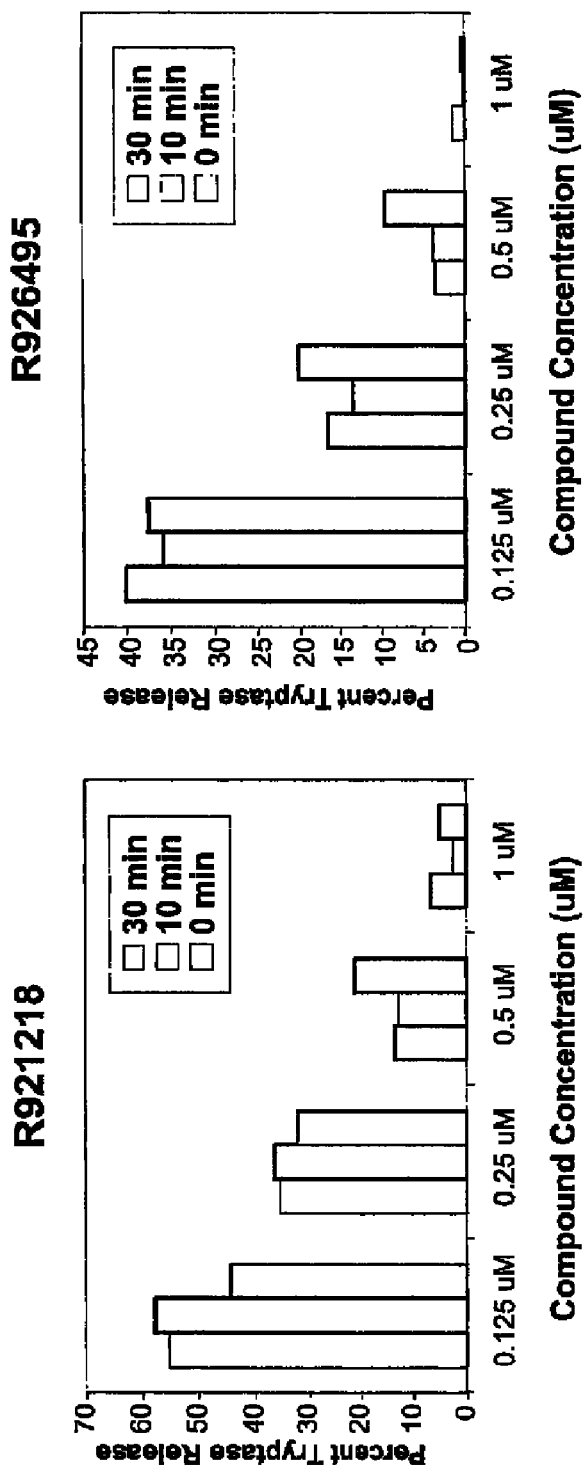
Figure 6:
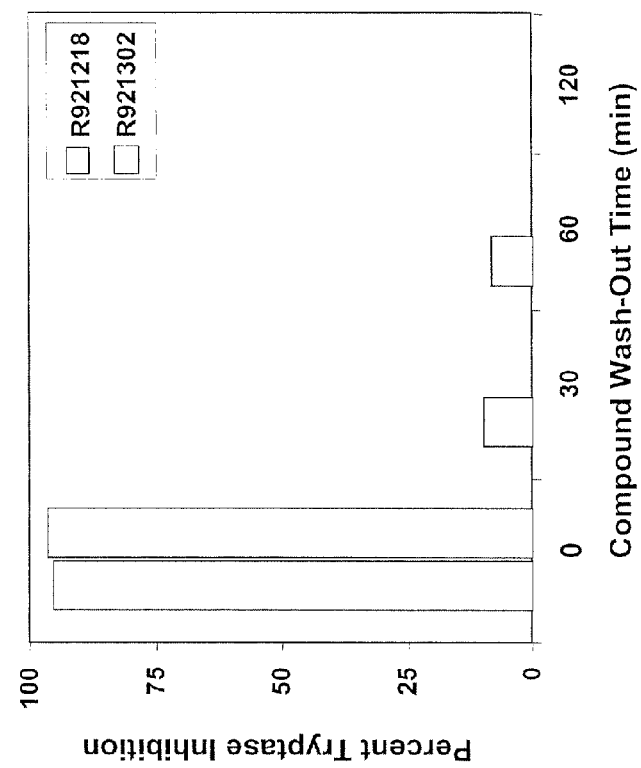
Figure 7:
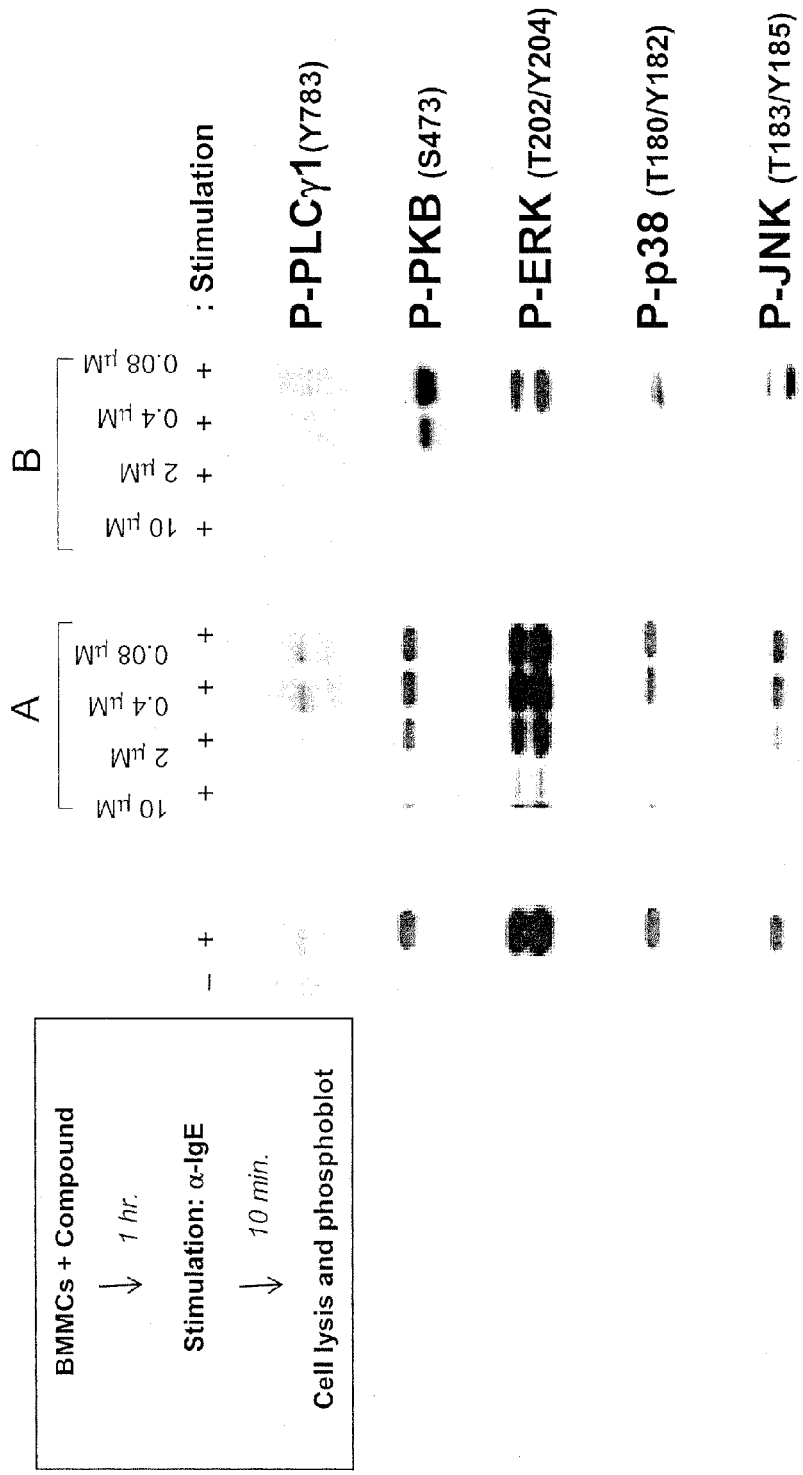
Figure 8:
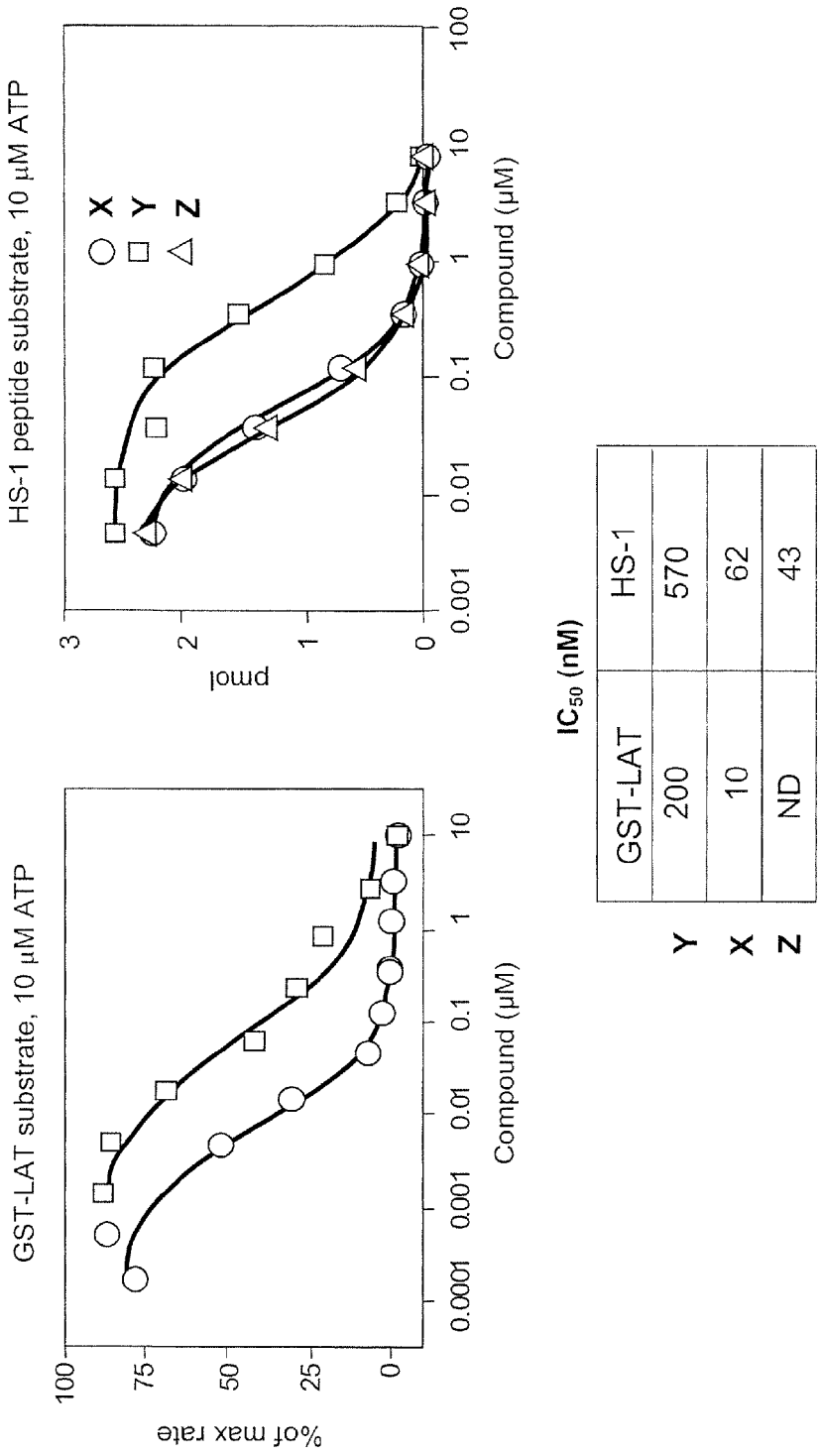
Figure 9:
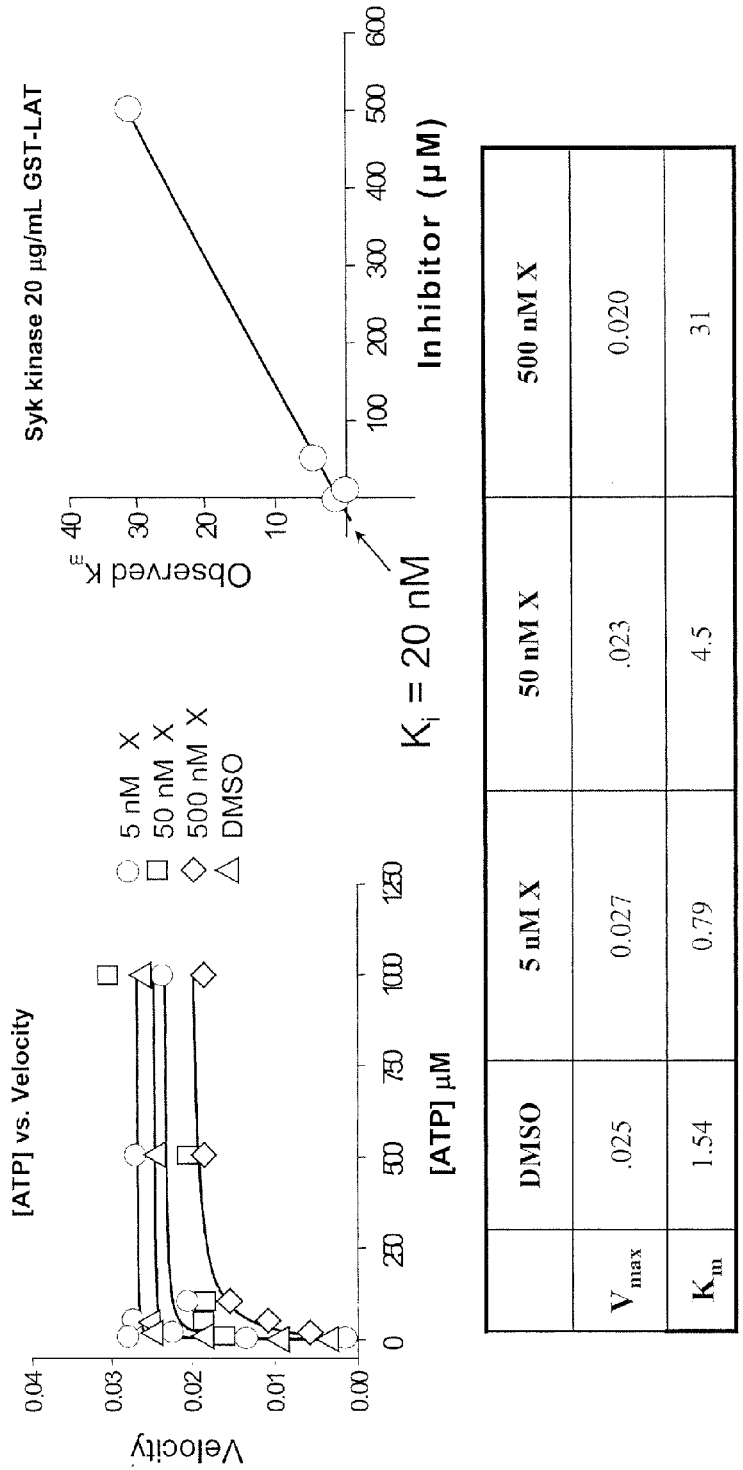
Figure 11A:
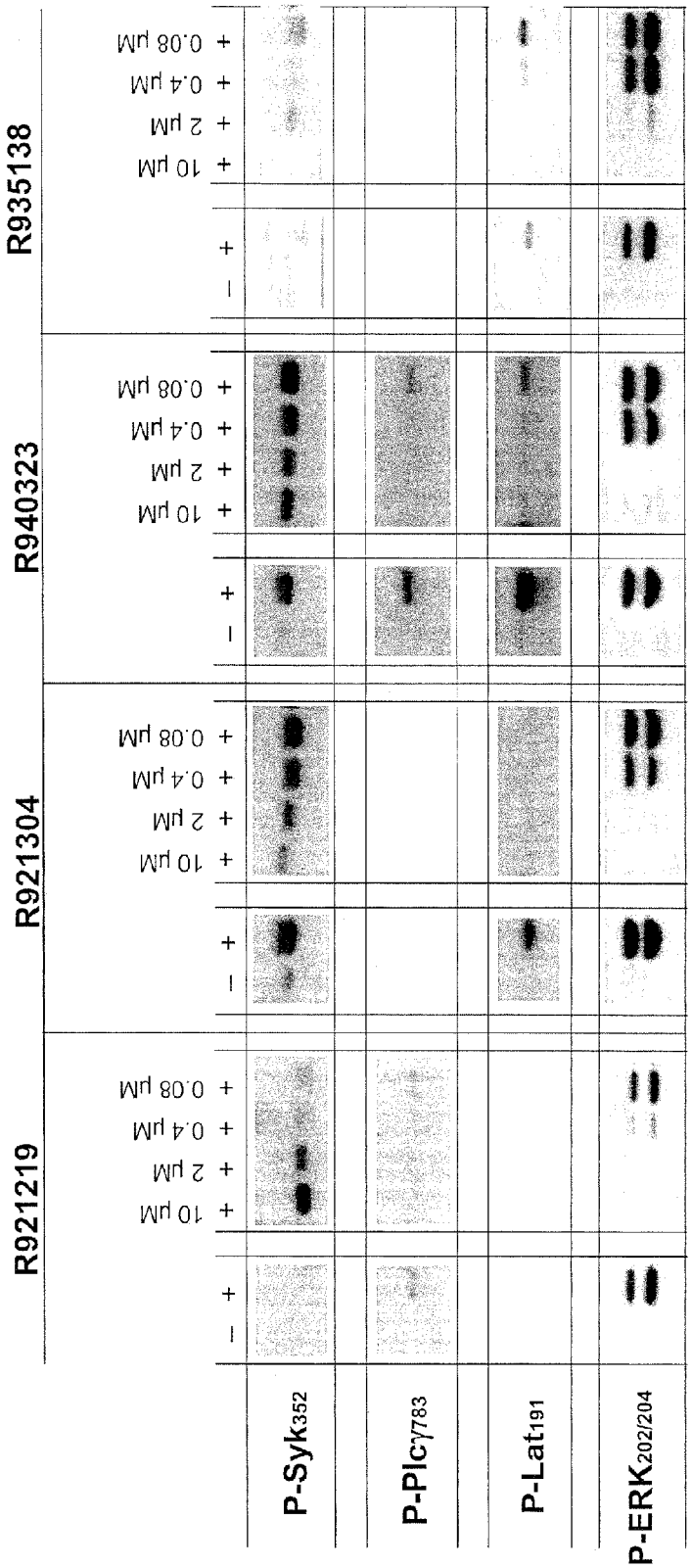
Figure 11B:
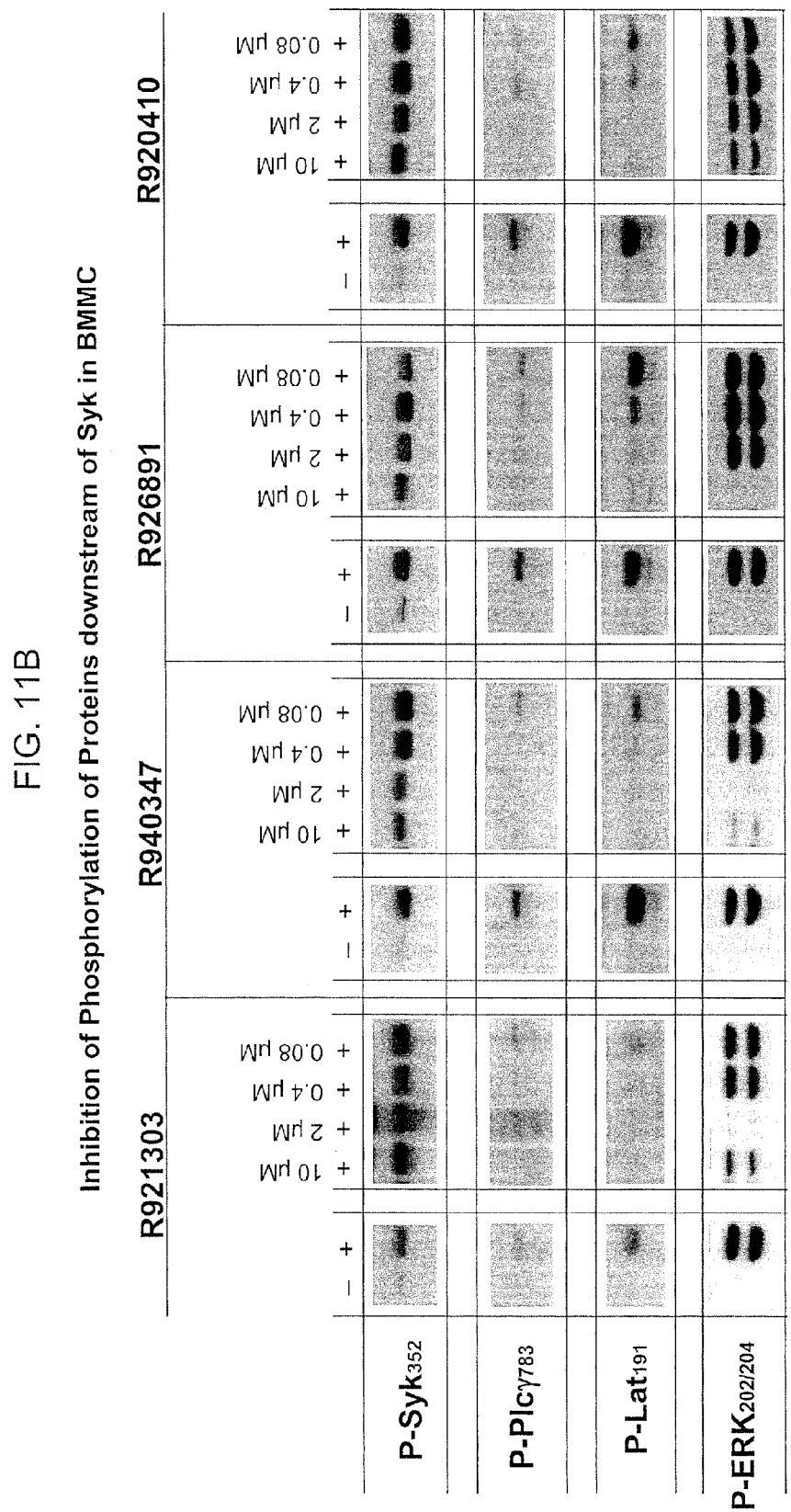
Figure 11C:
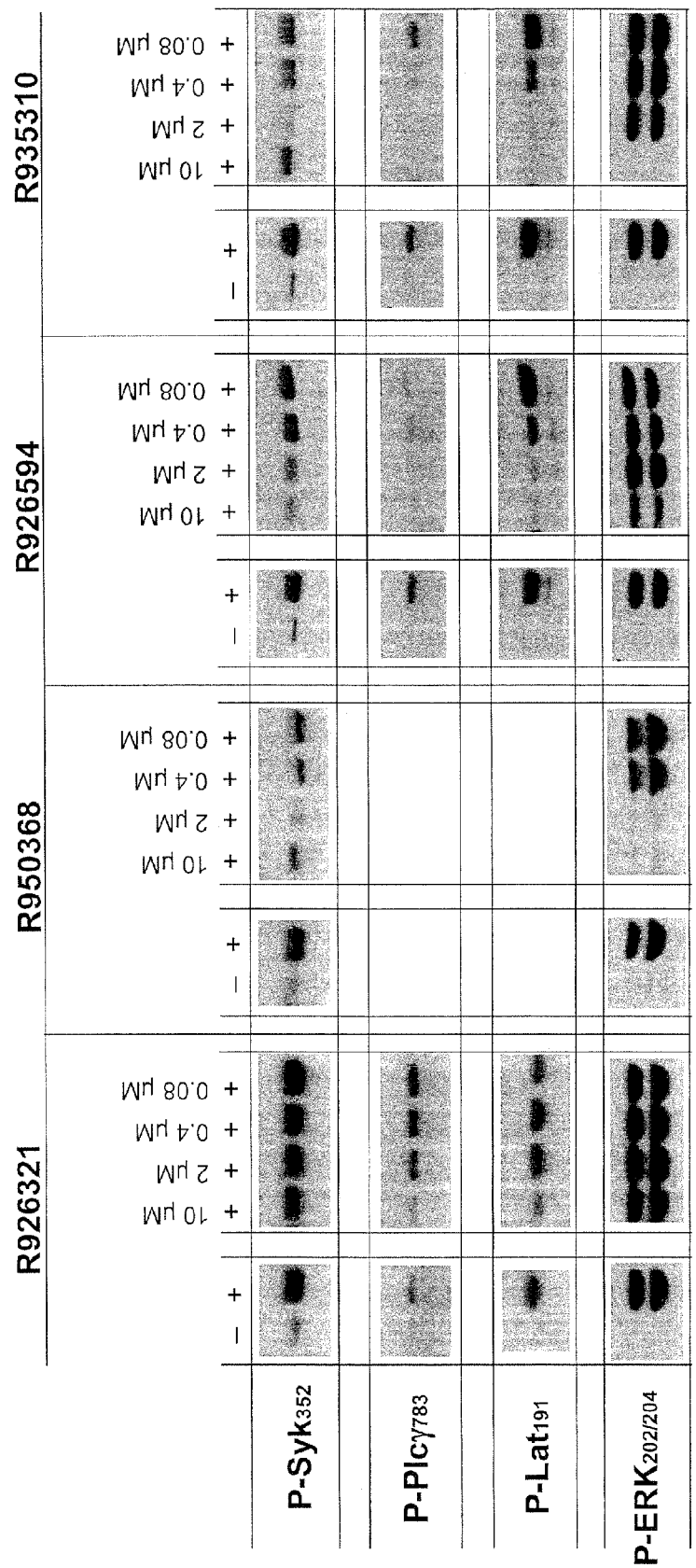
Figure 11D:
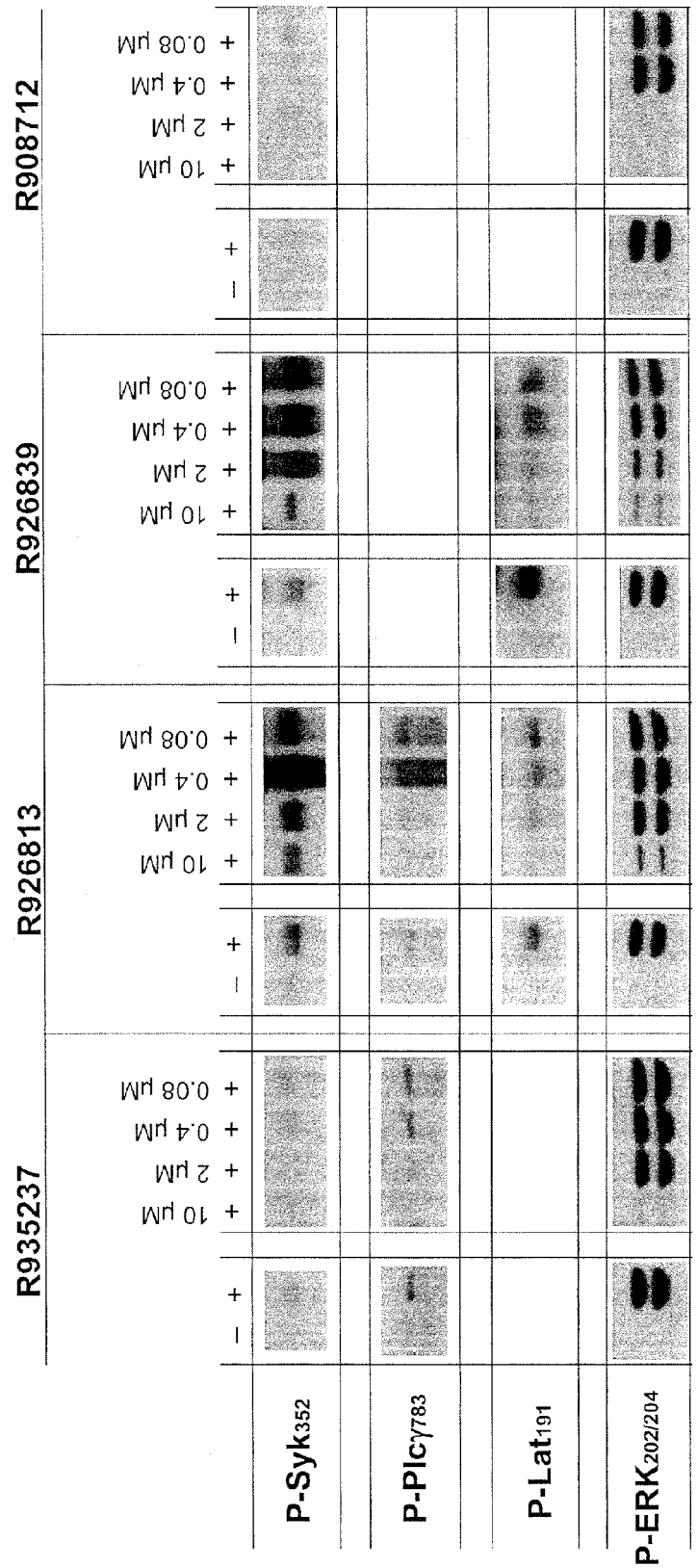

FIG. 1 provides a cartoon illustrating allergen-induced production of IgE and consequent release of preformed and other chemical mediators from mast cells;

FIG. 2 provides a cartoon illustrating the FcεRI signal transduction cascade leading to degranulation of mast and/or basophil cells;

FIG. 3 provides a cartoon illustrating the putative points of action of compounds that selectively inhibit upstream FcεRI-mediated degranulation and compounds that inhibit both FcεRI-mediated and ionomycin-induced degranulation;

FIG. 4 provides graphs illustrating the effects of certain 2,4-pyrimidinediamine compounds, DMSO (control) and ionomycin on $Ca^{2+}$ flux in CHMC cells;

FIG. 5 provides graphs illustrating the immediacy of the inhibitory activity of compounds R921218 and R926495;

FIG. 6 provides a graph illustrating the effect of washout on the inhibitory activity of compounds R921218 and R921302;

FIG. 7 provides data showing that varying concentrations of compounds R921218 (A) and R921219 (B) inhibit phosphorylation of various proteins downstream of Syk kinase in the IgE receptor signal transduction cascade in activated BMMC cells;

FIG. 8 provides data showing dose responsive inhibition of Syk kinase phosphorylation of an endogenous substrate (LAT) and a peptide substrate in the presence of increasing concentrations of compounds R921218 (X), R921219 (Y) and R921304 (Z);

FIG. 9 provides data showing that the inhibition of Syk kinase by compound R921219 is ATP competitive;

FIG. 10 provides data showing that varying concentrations of compounds R921219 (A) and R218218 (B) inhibit phosphorylation of proteins downstream of Syk kinase, but not LYN kinase, in the FcεRI signal transduction cascade in activated CHMC cells; also shown is inhibition of phosphorylation of proteins downstream of LYN kinase but not Syk kinase, in the presence of a known LYN kinase inhibitor (PP2); and FIGS. 11A-D provide data showing inhibition of phosphorylation of proteins downstream of Syk kinase in the FcεRI signal transduction cascade in BMMC cells.

6. DETAILED DESCRIPTION OF THE PREFERRED EMBODIMENTS

6.1 Definitions

As used herein, the following terms are intended to have the following meanings:

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C6) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are (C1-C6) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group is (C1-C6) alkyldiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Heteroalkyl," Heteroalkanyl," Heteroalkenyl," Heteroalkynyl," Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteroatoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O) NR'—, —S(O)$_2$NR'—, and the like, including combinations thereof, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O)NR'—, —S(O)$_2$NR'—, and the like, including combinations thereof, where each R' is independently hydrogen or (C1-C6) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are cyclopentadienyl, phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthyl, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are (C5-C15) aromatic rings, more preferably (C5-C10) aromatic rings. A particularly preferred biaryl group is biphenyl.

"Arylalkyl" by itself or as part of another substituent refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Specifically excluded from the definition of "parent heteroaromatic ring system" are benzene rings fused to cyclic polyalkylene glycols such as cyclic polyethylene glycols. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-15 membered heteroaromatic rings, more preferably 5-10 membered heteroaromatic rings.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR'", where R'" is a haloalkyl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated or alkylated such as benzyl and trityl ethers, as well as alkyl ethers, tetrahydropyranyl ethers, trialkylsilyl ethers (e.g., TMS or TIPPS groups) and allyl ethers.

"Prodrug" refers to a derivative of an active 2,4-pyrimidinediamine compound (drug) that requires a transformation under the conditions of use, such as within the body, to release the active 2,4-pyrimidinediamine drug. Prodrugs are frequently, but not necessarily, pharmacologically inactive until converted into the active drug. Prodrugs are typically obtained by masking a functional group in the 2,4-pyrimidinediamine drug believed to be in part required for activity with a progroup (defined below) to form a promoiety which undergoes a transformation, such as cleavage, under the specified conditions of use to release the functional group, and hence the active 2,4-pyrimidinediamine drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in the active 2,4-pyrimidinediamines compounds to yield prodrugs are well-known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active 2,4-pyrimidinediamine drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

"Fc Receptor" refers to a member of the family of cell surface molecules that binds the Fc portion (containing the specific constant region) of an immunoglobulin. Each Fc receptor binds immunoglobulins of a specific type. For example the Fcα receptor ("FcαR") binds IgA, the FcεR binds IgE and the FcγR binds IgG.

The FcαR family includes the polymeric Ig receptor involved in epithelial transport of IgA/IgM, the mycloid specific receptor R$^c$αRI (also called CD89), the Fcα/μR and at least two alternative IgA receptors (for a recent review see Monteiro & van de Winkel, 2003, Annu. Rev. Immunol, advanced e-publication. The FcαRI is expressed on neutrophils, eosinophils, monocytes/macrophages, dendritic cells and kupfer cells. The FcαRI includes one alpha chain and the FcR gamma homodimer that bears an activation motif (ITAM) in the cytoplasmic domain and phosphorylates Syk kinase.

The FcεR family includes two types, designated FcεRI and FcεRII (also known as CD23). FcεRI is a high affinity receptor (binds IgE with an affinity of about $10^{10}M^{-1}$) found on mast, basophil and eosinophil cells that anchors monomeric IgE to the cell surface. The FcεRI possesses one alpha chain, one beta chain and the gamma chain homodimer discussed above. The FcεRII is a low affinity receptor expressed on mononuclear phagocytes, B lymphocytes, eosinophils and platelets. The FcεRII comprises a single polypeptide chain and does not include the gamma chain homodimer.

The FcγR family includes three types, designated FcγRI (also known as CD64), FcγRII (also known as CD32) and FcγRIII (also known as CD16). FcγRI is a high affinity receptor (binds IgG1 with an affinity of $10^8M^{-1}$) found on mast, basophil, mononuclear, neutrophil, eosinophil, deudritic and phagocyte cells that anchors nomomeric IgG to the cell surface. The FcγRI includes one alpha chain and the gamma chain dimer shared by FcαRI and FcεRI.

The FcγRII is a low affinity receptor expressed on neutrophils, monocytes, eosinophils, platelets and B lymphocytes. The FcγRII includes one alpha chain, and does not include the gamma chain homodimer discussed above.

The FcγRIII is a low affinity (binds IgG1 with an affinity of $5 \times 10^5M^{-1}$) expressed on NK, eosinophil, macrophage, neutrophil and mast cells. It comprises one alpha chain and the gamma homodimer shared by FcαRI, FcεRI and FcγRI.

Skilled artisans will recognize that the subunit structure and binding properties of these various Fc receptors, cell types expressing them, are not completely characterized. The above discussion merely reflects the current state-of-the-art regarding these receptors (see, e.g., Immunobiology: The Immune System in Health & Disease, 5th Edition, Janeway et al., Eds, 2001, ISBN 0-8153-3642-x, FIG. 9.30 at pp. 371), and is not intended to be limiting with respect to the myriad receptor signaling cascades that can be regulated with the compounds described herein.

"Fc Receptor-Mediated Degranulation" or "Fc Receptor-Induced Degranulation" refers to degranulation that proceeds via an Fc receptor signal transduction cascade initiated by crosslinking of an Fc receptor.

"IgE-Induced Degranulation" or "FcεRI-Mediated Degranulation" refers to degranulation that proceeds via the IgE receptor signal transduction cascade initiated by crosslinking of FcεRI-bound IgE. The crosslinking may be induced by an IgE-specific allergen or other multivalent binding agent, such as an anti-IgE antibody. Referring to FIG. 2, in mast and/or basophil cells, the FcεRI signaling cascade leading to degranulation may be broken into two stages: upstream and downstream. The upstream stage includes all of the processes that occur prior to calcium ion mobilization (illustrated as "Ca$^{2+}$" in FIG. 2; see also FIG. 3). The downstream stage includes calcium ion mobilization and all processes downstream thereof. Compounds that inhibit FcεRI-mediated degranulation may act at any point along the FcεRI-mediated signal transduction cascade. Compounds that selectively inhibit upstream FcεRI-mediated degranulation act to inhibit that portion of the FcεRI signaling cascade upstream of the point at which calcium ion mobilization is induced. In cell-based assays, compounds that selectively inhibit upstream FcεRI-mediated degranulation inhibit degranulation of cells such as mast or basophil cells that are activated or stimulated with an IgE-specific allergen or binding agent (such as an anti-IgE antibody) but do not appreciably inhibit degranulation of cells that are activated or stimulated with degranulating agents that bypass the FcεRI signaling pathway, such as, for example the calcium ionophores ionomycin and A23187.

"IgG-Induced Degranulation" or "FcγRI-Mediated Degranulation" refers to degranulation that proceeds via the FcγRI signal transduction cascade initiated by crosslinking of FcγRI-bound IgG. The crosslinking may be induced by an IgG-specific allergen or another multivalent binding agent, such as an anti-IgG or fragment antibody. Like the FcεRI signaling cascade, in mast and basophil cells the FcγRI signaling cascade also leads to degranulation which may be broken into the same two stages: upstream and downstream. Similar to FcεRI-mediated degranulation, compounds that selectively inhibit upstream FcγRI-mediated degranulation act upstream of the point at which calcium ion mobilization is induced. In cell-based assays, compounds that selectively inhibit upstream FcγRI-mediated degranulation inhibit degranulation of cells such as mast or basophil cells that are activated or stimulated with an IgG-specific allergen or binding agent (such as an anti-IgG antibody or fragment) but do not appreciably inhibit degranulation of cells that are activated or stimulated with degranulating agents that bypass the FcγRI signaling pathway, such as, for example the calcium ionophores ionomycin and A23187.

"Ionophore-Induced Degranulation" or "Ionophore-Mediated Degranulation" refers to degranulation of a cell, such as a mast or basophil cell, that occurs upon exposure to a calcium ionophore such as, for example, ionomycin or A23187.

"Syk Kinsase" refers to the well-known 72 kDa non-receptor (cytoplasmic) spleen protein tyrosine kinase expressed in B-cells and other hematopoetic cells. Syk kinase includes two consensus Src-homology 2 (SH2) domains in tandem that bind to phosphorylated immunoreceptor tyrosine-based activation motifs ("ITAMs"), a "linker" domain and a catalytic domain (for a review of the structure and function of Syk kinase see Sada et al, 2001, J. Biochem. (Tokyo) 130:177-186); see also Turner et al., 2000, Immunology Today 21: 148-154). Syk kinase has been extensively studied as an effector of B-cell receptor (BCR) signaling (Turner et al., 2000, supra). Syk kinase is also critical for tyrosine phosphorylation of multiple proteins which regulate important pathways leading from immunoreceptors, such as Ca²⁺ mobilization and mitogen-activated protein kinase (MAPK) cascades (see, e.g., FIG. 2) and degranulation. Syk kinase also plays a critical role in integrin signaling in neutrophils (see, e.g., Mocsai et al. 2002, Immunity 16:547-558).

As used herein, Syk kinase includes kinases from any species of animal, including but not limited to, homosapiens, simian, bovine, porcine, rodent, etc., recognized as belonging to the Syk family. Specifically included are isoforms, splice variants, allelic variants, mutants, both naturally occurring and man-made. The amino acid sequences of such Syk kinases are well known and available from GENBANK. Specific examples of mRNAs encoding different isoforms of human Syk kinase can be found at GENBANK accession no. gi|21361552|ref|NM_003177.2|, gi|496899|emb|Z29630.1|HSSYKPTK[496899] and gi|15030258|gb|BC011399.1|BC011399[15030258], which are incorporated herein by reference.

Skilled artisans will appreciate that tyrosine kinases belonging to other families may have active sites or binding pockets that are similar in three-dimensional structure to that of Syk. As a consequence of this structural similarity, such kinases, referred to herein as "Syk mimics," are expected to catalyze phosphorylation of substrates phosphorylated by Syk. Thus, it will be appreciated that such Syk mimics, signal transduction cascades in which such Syk mimics play a role and biological responses effected by such Syk mimics and Syk mimic-dependent signaling cascades may be regulated, and in particular inhibited, with the 2,4-pyrimidinediamine compounds described herein.

"Syk-Dependent Signaling Cascade" refers to a signal transduction cascade in which Syk kinase plays a role. Non-limiting examples of such Syk-dependent signaling cascades include the FcαRI, FcεRI, FcγRI, FcγRIII, BCR and integrin signaling cascades.

6.2 The 2,4-Pyrimidinediamine Compounds

The compounds of the invention are generally 2,4-pyrimidinediamine compounds according to structural formula (I):

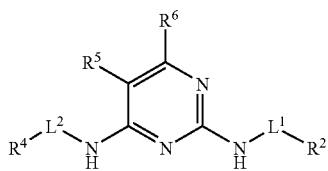

including salts, hydrates, solvates and N-oxides thereof, wherein:

$L^1$ and $L^2$ are each, independently of one another, selected from the group consisting of a direct bond and a linker;

$R^2$ is selected from the group consisting of (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups;

$R^4$ is selected from the group consisting of hydrogen, (C1-C6) alkyl optionally substituted with one or more of the same or different $R^8$ groups, (C3-C8) cycloalkyl optionally substituted with one or more of the same or different $R^8$ groups, cyclohexyl optionally substituted with one or more of the same or different $R^8$ groups, 3-8 membered cycloheteroalkyl optionally substituted with one or more of the same or different $R^8$ groups, (C5-C15) aryl optionally substituted with one or more of the same or different $R^8$ groups, phenyl optionally substituted with one or more of the same or different $R^8$ groups and 5-15 membered heteroaryl optionally substituted with one or more of the same or different $R^8$ groups;

$R^5$ is selected from the group consisting of $R^6$, (C1-C6) alkyl optionally substituted with one or more of the same or different $R^8$ groups, (C1-C4) alkanyl optionally substituted with one or more of the same or different $R^8$ groups, (C2-C4) alkenyl optionally substituted with one or more of the same or different $R^8$ groups and (C2-C4) alkynyl optionally substituted with one or more of the same or different $R^8$ groups;

each $R^6$ is independently selected from the group consisting of hydrogen, an electronegative group, $-OR^d$, $-SR^d$, (C1-C3) haloalkyloxy, (C1-C3) perhaloalkyloxy, $-NR^cR^c$, halogen, (C1-C3) haloalkyl, (C1-C3) perhaloalkyl, $-CF_3$, $-CH_2CF_3$, $-CF_2CF_3$, $-CN$, $-NC$, $-OCN$, $-SCN$, $-NO$, $-NO_2$, $-N_3$, $-S(O)R^d$, $-S(O)_2R^d$, $-S(O)_2OR^d$, $-S(O)NR^cR^c$, $-S(O)_2NR^cR^c$, $-OS(O)R^d$, $-OS(O)_2R^d$, $-OS(O)_2OR^d$, $-OS(O)NR^cR^c$, $-OS(O)_2NR^cR^c$, $-C(O)R^d$, $-C(O)OR^d$, $-C(O)NR^cR^c$, $-C(NH)NR^cR^c$, $-OC(O)R^d$, $-SC(O)R^d$, $-OC(O)OR^d$, $-SC(O)OR^d$, $-OC(O)NR^cR^c$, $-SC(O)NR^cR^c$, $-OC(NH)NR^cR^c$, $-SC(NH)NR^cR^c$, $-[NHC(O)]_nR^d$, $-[NHC(O)]_nOR^d$, $-[NHC(O)]_nNR^cR^c$ and $-[NHC(NH)]_nNR^cR^c$, (C5-C10) aryl optionally substituted with one or more of the same or different $R^8$ groups, phenyl optionally substituted with one or more of the same or different $R^8$ groups, (C6-C16) arylalkyl optionally substituted with one or more of the same or different $R^8$ groups, 5-10 membered heteroaryl optionally substituted with one or more of the same or different $R^8$ groups and 6-16 membered heteroarylalkyl optionally substituted with one or more of the same or different $R^8$ groups;

$R^8$ is selected from the group consisting of $R^a$, $R^b$, $R^a$ substituted with one or more of the same or different $R^a$ or $R^b$, $-OR^a$ substituted with one or more of the same or different $R^a$ or $R^b$, $-B(OR^a)_2$, $-B(NR^cR^c)_2$, $-(CH_2)_m-R^b$, $-(CHR^a)_m-R^b$, $-O-(CH_2)_m-R^b$, $-S-(CH_2)_m-R^b$, $-O-CHR^aR^b$, $-O-CR^a(R^b)_2$, $-O-(CHR^a)_m-R^b$, $-O-(CH_2)_m-CH[(CH_2)_mR^b]R^b$, $-S-(CHR^a)_m-R^b$, $-C(O)NH-(CH_2)_m-R^b$, $-C(O)NH-(CHR^a)_m-R^b$, $-O-(CH_2)_m-C(O)NH(CH_2)_m-R^b$, $-S-(CH_2)_m-C(O)NH-(CH_2)_m-R^b$, $-O-(CHR^a)_m-C(O)NH-(CHR^a)_m-R^b$, $-S-(CHR^a)_m-C(O)NH-(CHR^a)_m-R^b$, $-NH-(CH_2)_m-R^b$, $-NH-(CHR^a)_m-R^b$, $-NH[(CH_2)_mR^b]$, $-N[(CH_2)_mR^b]_2$, $-NH-C(O)-NH-(CH_2)_m-R^b$, $-NH-C(O)-(CH_2)_m-CHR^bR^b$ and $-NH-(CH_2)_m-C(O)-NH-(CH_2)_m-R^b$;

each $R^a$ is independently selected from the group consisting of hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl and 6-16 membered heteroarylalkyl;

each $R^b$ is a suitable group independently selected from the group consisting of $=O$, $-OR^d$, (C1-C3) haloalkyloxy, $-OCF_3$, $=S$, $-SR^d$, $=NR^d$, $=NOR^d$, $-NR^cR^c$, halogen, $-CF_3$, $-CN$, $-NC$, $-OCN$, $-SCN$, $-NO$, $-NO_2$, $=N_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$C(NR^a)NR^cR^c$, —$C(NOH)R^a$, —$C(NOH)NR^cR^c$, —$OC(O)R^d$, —$OC(O)OR^d$, —$OC(O)NR^cR^c$, —$OC(NH)NR^cR^c$, —$OC(NR^a)NR^cR^c$, —$[NHC(O)]_nR^d$, —$[NR^aC(O)]_nR^d$, —$[NHC(O)]_nOR^d$, —$[NR^aC(O)]_nOR^d$, —$[NHC(O)]_nNR^cR^c$, —$[NR^aC(O)]_nNR^cR^c$, —$[NHC(NH)]_nNR^cR^c$ and —$[NR^aC(NR^a)]_nNR^cR^c$;

each $R^c$ is independently $R^a$, or, alternatively, each $R^c$ is taken together with the nitrogen atom to which it is bonded to form a 5 to 8-membered cycloheteroalkyl or heteroaryl which may optionally include one or more of the same or different additional heteroatoms and which is optionally substituted with one or more of the same or different $R^a$ or suitable $R^b$ groups;

each $R^d$ is independently $R^a$;

each m is independently an integer from 1 to 3; and each n is independently an integer from 0 to 3.

In the compounds of structural formula (I), $L^1$ and $L^2$ represent, independently of one another, a direct bond or a linker. Thus, as will be appreciated by skilled artisans, the substituents $R^2$ and/or $R^4$ may be bonded either directly to their respective nitrogen atoms or, alternatively, spaced away from their respective nitrogen atoms by way of a linker. The identity of the linker is not critical and typical suitable linkers include, but are not limited to, (C1-C6) alkyldiyls, (C1-C6) alkanos and (C1-C6) heteroalkyldiyls, each of which may be optionally substituted with one or more of the same or different $R^8$ groups, where $R^8$ is as previously defined for structural formula (I). In a specific embodiment, $L^1$ and $L^2$ are each, independently of one another, selected from the group consisting of a direct bond, (C1-C3) alkyldiyl optionally substituted with one or more of the same or different $R^a$, suitable $R^b$ or $R^9$ groups and 1-3 membered heteroalkyldiyl optionally substituted with one or more of the same or different $R^a$, suitable $R^b$ or $R^9$ groups, wherein $R^9$ is selected from the group consisting of (C1-C3) alkyl, —$OR^a$, —$C(O)OR^a$, (C5-C10) aryl optionally substituted with one or more of the same or different halogens, phenyl optionally substituted with one or more of the same or different halogens, 5-10 membered heteroaryl optionally substituted with one or more of the same or different halogens and 6 membered heteroaryl optionally substituted with one or more of the same or different halogens; and $R^a$ and $R^b$ are as previously defined for structural formula (I). Specific $R^9$ groups that may be used to substitute $L^1$ and $L^2$ include —$OR^a$, —$C(O)OR^a$, phenyl, halophenyl and 4-halophenyl, wherein $R^a$ is as previously defined for structural formula (I).

In another specific embodiment, $L^1$ and $L^2$ are each, independently of one another, selected from the group consisting of methano, ethano and propano, each of which may be optionally monosubstituted with an $R^9$ group, where $R^9$ is as previously defined above.

In all of the above embodiments, specific $R^a$ groups that may be included in $R^9$ groups are selected from the group consisting of hydrogen, (C1-C6) alkyl, phenyl and benzyl.

In still another specific embodiment, $L^1$ and $L^2$ are each a direct bond such that the 2,4-pyrimidinediamine compounds of the invention are compounds according to structural formula (Ia):

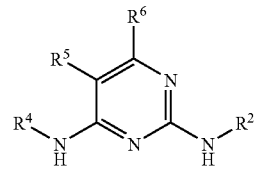

including salts, hydrates, solvates and N-oxides thereof, wherein $R^2$, $R^4$, $R^5$ and $R^6$ are as previously defined for structural formula (I). Additional specific embodiments of the 2,4-pyrimidinediamine compounds of the invention are described below.

In a first embodiment of the compounds of structural formulae (I) and (Ia), $R^2$, $R^4$, $R^5$, $R^6$, $L^1$ and $L^2$ are as previously defined for their respective structures (I) and (Ia), with the proviso that $R^2$ is not 3,4,5-trimethoxyphenyl, 3,4,5-tri (C1-C6) alkoxyphenyl or

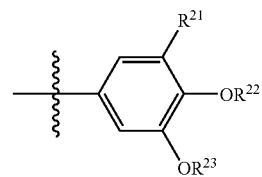

where $R^{21}$, $R^{22}$ and $R^{23}$ are as defined for $R^1$, $R^2$ and $R^3$, respectively of U.S. Pat. No. 6,235,746, the disclosure of which is incorporated by reference. In a specific embodiment of this first embodiment, $R^{21}$ is hydrogen, halo, straight-chain or branched (C1-C6) alkyl optionally substituted with one or more of the same or different $R^{25}$ groups, hydroxyl, (C1-C6) alkoxy optionally substituted with one or more of the same or different phenyl or $R^{25}$ groups, thiol (—SH), (C1-C6) alkylthio optionally substituted with one or more of the same or different phenyl or $R^{25}$ groups, amino (—$NH_2$), —$NHR^{26}$ or —$NR^{26}R^{26}$; $R^{22}$ and $R^{23}$ are each, independently of one another, a (C1-C6) straight-chain or branched alkyl optionally substituted with one or more of the same or different $R^{25}$ groups; $R^{25}$ is selected from the group consisting of halo, hydroxyl, (C1-C6) alkoxy, thiol, (C1-C6) alkylthio, (C1-C6) alkylamino and (C1-C6) dialkylamino; and each $R^{26}$ is independently a (C1-C6) alkyl optionally substituted with one or more of the same or different phenyl or $R^{25}$ groups or a —$C(O)R^{27}$, where $R^{27}$ is a (C1-C6) alkyl optionally substituted with one or more of the same or different phenyl or $R^{25}$ groups.

In another specific embodiment of this first embodiment, $R^{21}$ is methoxy optionally substituted with one or more of the same or different halo groups and/or $R^{22}$ and $R^{23}$ are each, independently of one another, a methyl or ethyl optionally substituted with one or more of the same or different halo groups.

In a second embodiment of the compounds of structural formulae (I) and (Ia), $R^2$, $R^4$, $R^5$ and $L^2$ are as previously described for their respective structures (I) and (Ia), $L^1$ is a direct bond and $R^6$ is hydrogen, with the proviso that $R^2$ is not 3,4,5-trimethoxyphenyl, 3,4,5-tri (C1-C6) alkoxyphenyl or

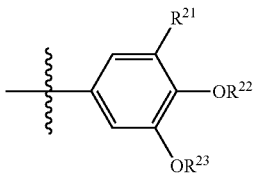

where $R^{21}$, $R^{22}$ and $R^{23}$ are as defined above, in connection with the first embodiment.

In a third embodiment, the 2,4-pyrimidinediamine compounds of structural formulae (I) and (Ia) exclude one or more of the following compounds:

N2,N4-bis(4-ethoxyphenyl)-5-fluoro-2,4-pyrimidinediamine (R070790);
N2,N4-bis(2-methoxyphenyl)-5-fluoro-2,4-pyrimidinediamine (R081166);
N2,N4-bis(4-methoxyphenyl)-5-fluoro-2,4-pyrimidinediamine (R088814);
N2,N4-bis(2-chlorophenyl)-5-fluoro-2,4-pyrimidinediamine (R088815);
N2,N4-bisphenyl-5-fluoro-2,4-pyrimidinediamine (R091880);
N2,N4-bis(3-methylphenyl)-5-fluoro-2,4-pyrimidinediamine (R092788);
N2,N4-bis(3-chlorophenyl)-5-fluoro-2,4-pyrimidinediamine (R067962);
N2,N4-bis(2,5-dimethylphenyl)-5-fluoro-2,4-pyrimidinediamine (R067963);
N2,N4-bis(3,4-dimethylphenyl)-5-fluoro-2,4-pyrimidinediamine (R067964);
N2,N4-bis(4-chlorophenyl)-5-fluoro-2,4-pyrimidinediamine (R0707153);
N2,N4-bis(2,4-dimethylphenyl)-5-fluoro-2,4-pyrimidinediamine (R070791);
N2,N4-bis(3-bromophenyl)-5-fluoro-2,4-pyrimidinediamine (R008958);
N2,N4-bis(phenyl)-5-fluoro-2,4-pyrimidinediamine;
N2,N4-bis(morpholino)-5-fluoro-2,4-pyrimidinediamine; and
N2,N4-bis[(3-chloro-4-methoxyphenyl)]-5-fluoro-2,4-pyrimidinediamine.

In a fourth embodiment, the compounds of structural formulae (I) and (Ia) exclude compounds according to the following structural formula (Ib):

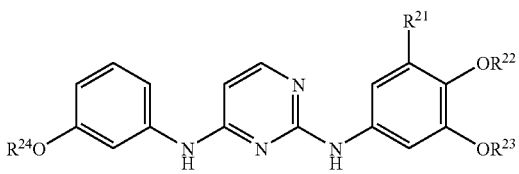

wherein $R^{24}$ is (C1-C6) alkyl; and $R^{21}$, $R^{22}$ and $R^{23}$ are as previously defined in connection with the first embodiment.

In a fifth embodiment, the compounds of structural formulae (I) and (Ia) exclude the compounds described in Examples 1-141 of U.S. Pat. No. 6,235,746, the disclosure of which is incorporated herein by reference.

In a sixth embodiment, the compounds of structural formulae (I) and (Ia) exclude compounds defined by formula (1) or formula 1(a) of this U.S. Pat. No. 6,235,746 (see, e.g., the disclosure at Col. 1, line 48 through Col. 7, line 49 and Col. 8, lines 9-36, which is incorporated by reference).

In a seventh embodiment, the compounds of structural formulae (I) and (Ia) exclude compounds in which $R^5$ is cyano or —C(O)NHR, where R is hydrogen or (C1-C6) alkyl, when $R^2$ is a substituted phenyl; $R^4$ is a substituted or unsubstituted (C1-C6) alkyl, $(C_3-C_8)$ cycloalkyl, 3-8 membered cycloheteralkyl or 5-15 membered heteroaryl; and $R^6$ is hydrogen.

In an eighth embodiment, the compounds of structural formulae (I) and (Ia) exclude the compounds defined by formulae (I) and (X) of WO 02/04429 or any compound disclosed in WO 02/04429, the disclosure of which is incorporated herein by reference.

In a ninth embodiment of the compounds of structural formulae (I) and (Ia), when $R^5$ is cyano or —C(O)NHR, where R is hydrogen or (C1-C6) alkyl; and $R^6$ is hydrogen, then $R^2$ is other than a substituted phenyl group.

In a tenth embodiment, the compounds of structural formulae (I) and (Ia) exclude compounds in which $R^2$ and $R^4$ are each independently a substituted or unsubstituted pyrrole or indole ring which is attached to the remainder of the molecule via its ring nitrogen atom.

In an eleventh embodiment, the compounds of structural formulae (I) and (Ia) exclude compounds defined by formulae (I) and (IV) of U.S. Pat. No. 4,983,608 or any compound disclosed in U.S. Pat. No. 4,983,608, the disclosure of which is incorporated herein by reference.

Those of skill in the art will appreciate that in the compounds of formulae (I) and (Ia), $R^2$ and $R^4$ may be the same or different, and may vary broadly. When $R^2$ and/or $R^4$ are optionally substituted rings, such as optionally substituted cycloalkyls, cycloheteroalkyls, aryls and heteroaryls, the ring may be attached to the remainder of the molecule through any available carbon or heteroatom. The optional substituents may be attached to any available carbon atoms and/or heteroatoms.

In a twelfth embodiment of the compounds of structural formulae (I) and (Ia), $R^2$ and/or $R^4$ is an optionally substituted phenyl or an optionally substituted (C5-C15) aryl, subject to the provisos that (1) when $R^6$ is hydrogen, then $R^2$ is not 3,4,5-trimethoxyphenyl or 3,4,5-tri (C1-C6) alkoxyphenyl; (2) when $R^2$ is a 3,4,5-trisubstituted phenyl, then the substituents at the 3- and 4-positions are not simultaneously methoxy or (C1-C6) alkoxy; or (3) when $R^6$ is hydrogen and $R^4$ is (C1-C6) alkyl, $(C_3-C_8)$ cycloalkyl, 3-8 membered cycloheteroalkyl or 5-15 membered heteroaryl, then $R^5$ is other than cyano. Alternatively, $R^2$ is subject to the provisos described in connection with the first or second embodiments. The optionally substituted aryl or phenyl group may be attached to the remainder of the molecule through any available carbon atom. Specific examples of optionally substituted phenyls include phenyls that are optionally mono-, di- or tri-substituted with the same or different $R^8$ groups, where $R^8$ is as previously defined for structural formula (I) and subject to the above provisos. When the phenyl is mono-substituted, the $R^8$ substituent may be positioned at either the ortho, meta or para position. When positioned at the ortho, meta or para position, $R^8$ is preferably selected from the group consisting of (C1-C10) alkyl, (C1-C10) branched alkyl, —$OR^a$ optionally substituted with one or more of the same or different $R^b$ groups, —O—C(O)$OR^a$, —O—$(CH_2)_m$—C(O)$OR^a$, —C(O)$OR^a$, —O—$(CH_2)_m$—$NR^cR^c$, —O—C(O)$NR^cR^c$, —O—$(CH_2)_m$—C(O)$NR^cR^c$, —O—C(NH)$NR^cR^c$, —O—$(CH_2)_m$—C(NH)$NR^cR^c$ and —NH—$(CH_2)_m$—$NR^cR^c$, where m, $R^a$ and $R^c$ are as previously defined for structural formula (I). In one embodiment of these compounds, —$NR^cR^c$ is a 5-6 membered heteroaryl which optionally includes one or more of the same or different additional heteroatoms. Specific examples of such 5-6 membered heteroaryls include, but are not limited to, oxadiazolyl, triazolyl, thiazolyl, oxazolyl, tetrazolyl and isoxazolyl.

In another embodiment of these compounds, —NR$^c$R$^c$ is a 5-6 membered saturated cycloheteroalkyl ring which optionally includes one or more of the same or different heteroatoms. Specific examples of such cycloheteroalkyls include, but are not limited to, pyrrolidinyl, pyrazolidinyl, imidazolidinyl, piperidinyl, piperazinyl and morpholinyl.

In still another embodiment of these compounds, each R$^a$ is independently a (C1-C6) alkyl and/or each —NR$^c$R$^c$ is —NHR$^a$, where R$^a$ is a (C1-C6) alkyl. In one specific embodiment, R$^8$ is —O—CH$_2$—C(O)NHCH$_3$. In another specific embodiment R$^8$ is —OH.

When the phenyl is di-substituted or tri-substituted, the R$^8$ substituents may be positioned at any combination of positions. For example, the R$^8$ substituents may be positioned at the 2,3-, 2,4-, 2,5-, 2,6-, 3,4-, 3,5-, 2,3,4-, 2,3,5-, 2,3,6-, 2,4,5-, 2,4,6-, 2,5,6- or 3,4,5-positions. In one embodiment of compounds including a disubstituted phenyl, the substituents are positioned other than 3,4. In another embodiment they are positioned 3,4. In one embodiment of compounds including a trisubstituted phenyl, the substituents are positioned other than 3,4,5 or, alternatively, no two of the substituents are positioned 3,4. In another embodiment, the substituents are positioned 3,4,5.

Specific examples of R$^8$ substituents in such di- and trisubstituted phenyls include the various R$^8$ substituents described above in connection with the ortho, meta and para substituted phenyls.

In another specific embodiment, R$^8$ substituents useful for substituting such di- and trisubstituted phenyls include (C1-C6) alkyl, (C1-C6) alkoxy, methoxy, halo, chloro, (C1-C6) perhaloalkyl, —CF$_3$, (C1-C6) perhaloalkoxy and —OCF$_3$. In a preferred embodiment, such R$^8$ substituents are positioned 3,4 or 3,5. Specific examples of preferred di-substituted phenyl rings include 3-chloro-4-methoxy-phenyl, 3-methoxy-4-chlorophenyl, 3-chloro-4-trifluoromethoxy-phenyl, 3-trifluoromethoxy-4-chloro-phenyl, 3,4-dichloro-phenyl, 3,4-dimethoxyphenyl and 3,5-dimethoxyphenyl, with the provisos that: (1) when R$^4$ is one of the above-identified phenyls, and R$^5$ and R$^6$ are each hydrogen, then R$^2$ is not 3,4,5-tri (C1-C6)alkoxyphenyl or 3,4,5-trimethoxyphenyl; (2) when R$^2$ is 3,4-dimethoxyphenyl and R$^5$ and R$^6$ are each hydrogen, then R$^4$ is not 3-(C1-C6)alkoxyphenyl, 3-methoxyphenyl, 3,4-di-(C1-C6) alkoxyphenyl or 3,4-dimethoxyphenyl; (3) when R$^4$ is 3-chloro-4-methoxyphenyl and R$^5$ is halo or fluoro, and optionally R$^6$ is hydrogen, then R$^2$ is not 3-chloro-4-(C1-C6)alkoxyphenyl or 3-chloro-4-methoxyphenyl; (4) when R$^4$ is 3,4-dichlorophenyl, R$^5$ is hydrogen, (C1-C6) alkyl, methyl, halo or chloro and optionally R$^6$ is hydrogen, then R$^2$ is not a phenyl mono substituted at the para position with a (C1-C6) alkoxy group which is optionally substituted with one or more of the same or different R$^b$, —OH or —NR$^c$R$^c$ groups, where R$^b$ and R$^c$ are as previously described for structural formula (I); and/or (5) R$^2$ and/or R$^4$ is not 3,4,5-tri (C1-C6)alkoxyphenyl or 3,4,5-trimethoxyphenyl, especially when R$^5$ and R$^6$ are each hydrogen.

In another embodiment of compounds including a trisubstituted phenyl, the trisubstituted phenyl has the formula:

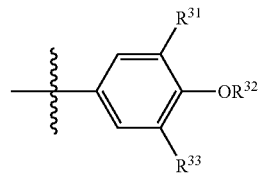

wherein: R$^{31}$ is methyl or (C1-C6) alkyl; R$^{32}$ is hydrogen, methyl or (C1-C6) alkyl; and R$^{33}$ is a halo group.

In a thirteenth embodiment of the compounds of structural formulae (I) and (Ia), R$^2$ and/or R$^4$ is an optionally substituted heteroaryl. Typical heteroaryl groups according to this thirteenth embodiment comprise from 5 to 15, and more typically from 5 to 111 ring atoms, and include one, two, three or four of the same or different heteroatoms or heteroatomic groups selected from the group consisting of N, NH, O, S, S(O) and S(O)$_2$. The optionally substituted heteroaryl may be attached to its respective C2 or C4 nitrogen atom or linker L$^1$ or L$^2$ through any available carbon atom or heteroatom, but is typically attached via a carbon atom. The optional substituents may be the same or different, and may be attached to any available carbon atom or heteroatom. In one embodiment of these compounds, R$^5$ is other than bromo, nitro, trifluoromethyl, cyano or —C(O)NHR, where R is hydrogen or (C1-C6) alkyl. In another embodiment of these compounds, when R$^2$ and R$^4$ are each a substituted or unsubstituted pyrrole or indole, then the ring is attached to the remainder of the molecule via a ring carbon atom. In still another embodiment of compounds including an optionally substituted heteroaryl group, the heteroaryl is unsubstituted or substituted with from one to four of the same or different R$^8$ groups, where R$^8$ is as previously defined for structural formula (I). Specific examples of such optionally substituted heteroaryls include, but are not limited to, the following heteroaryl groups:

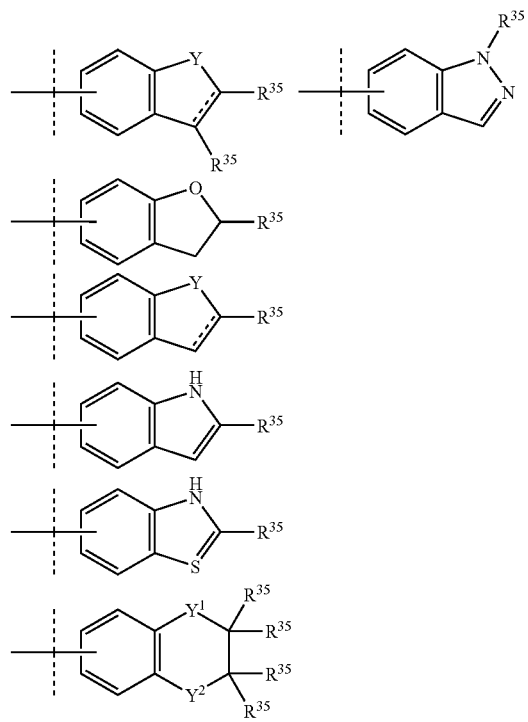

-continued
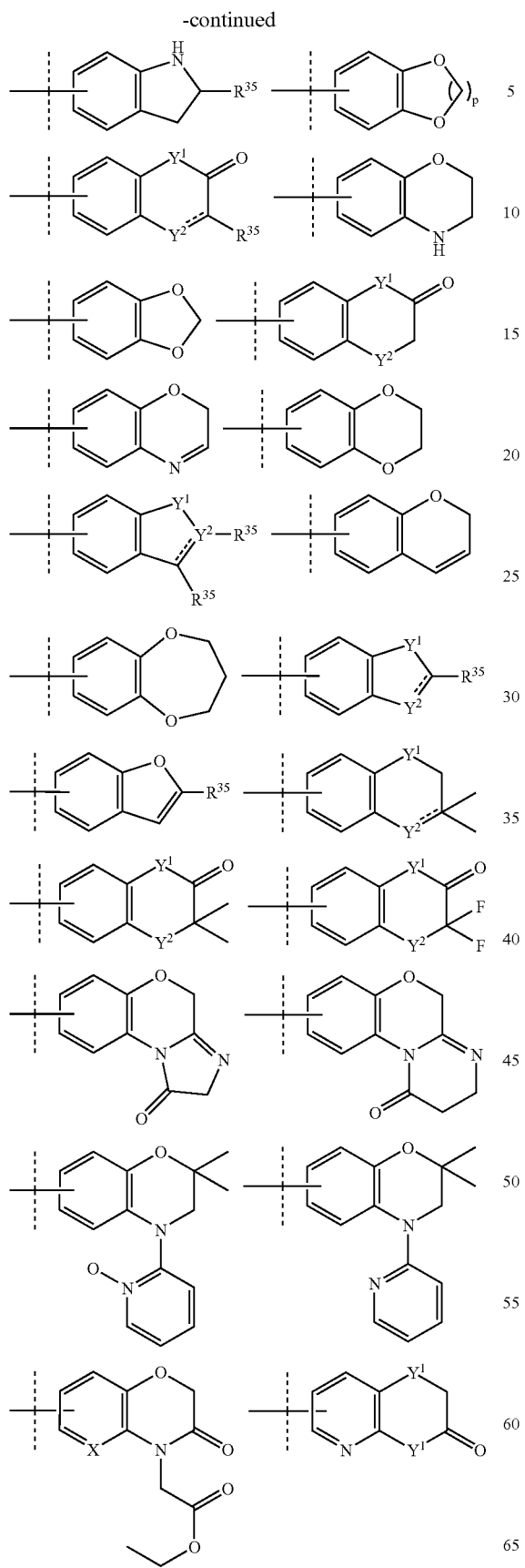
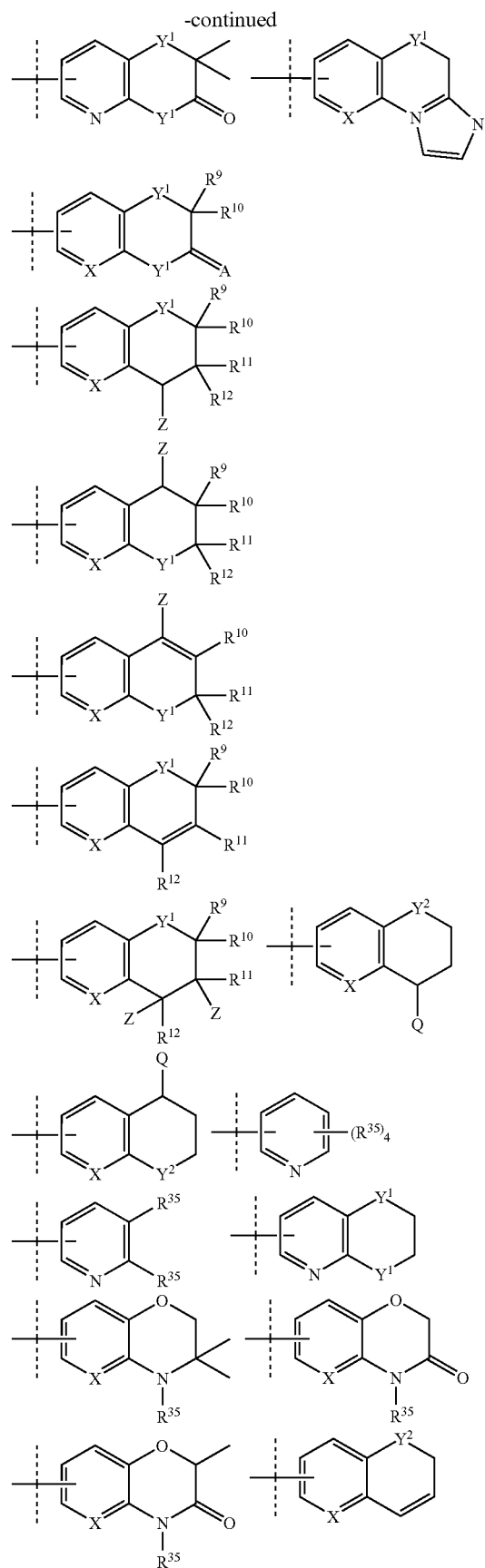

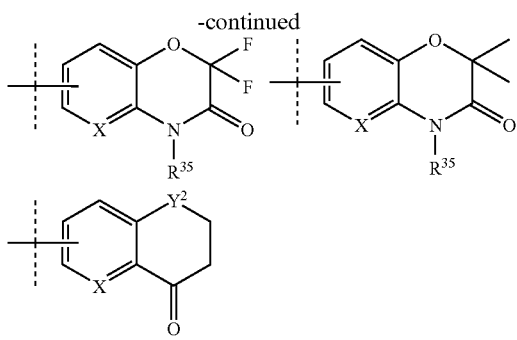

wherein:

p is an integer from one to three;

each ═ independently represents a single bond or a double bond;

$R^{35}$ is hydrogen or $R^8$, where $R^8$ is as previously defined for structural formula (I);

X is selected from the group consisting of CH, N and N—O;

each Y is independently selected from the group consisting of O, S and NH;

each $Y^1$ is independently selected from the group consisting of O, S, SO, $SO_2$, $SONR^{36}$, NH and $NR^{37}$;

each $Y^2$ is independently selected from the group consisting of CH, $CH_2$, O, S, N, NH and $NR^{37}$;

$R^{36}$ is hydrogen or alkyl;

$R^{37}$ is selected from the group consisting of hydrogen and a progroup, preferably hydrogen or a progroup selected from the group consisting of aryl, arylalkyl, heteroaryl, $R^a$, $R^b$—$CR^aR^b$—O—C(O)$R^8$, —$CR^aR^b$—O—PO(O$R^8$)$_2$, —$CH_2$—O—PO(O$R^8$)$_2$, —$CH_2$—PO(O$R^8$)$_2$, —C(O)—$CR^aR^b$—N(CH$_3$)$_2$, —$CR^aR^b$—O—C(O)—$CR^aR^b$—N(CH$_3$)$_2$, —C(O)$R^8$, —C(O)CF$_3$ and —C(O)—NR$^8$—C(O)$R^8$;

A is selected from the group consisting of O, NH and $NR^{38}$;

$R^{38}$ is selected from the group consisting of alkyl and aryl;

$R^9$, $R^{10}$, $R^{11}$ and $R^{12}$ are each, independently of one another, selected from the group consisting of alkyl, alkoxy, halogen, haloalkoxy, aminoalkyl and hydroxyalkyl, or, alternatively, $R^9$ and $R^{10}$ and/or $R^{11}$ and $R^{12}$ are taken together form a ketal;

each Z is selected from the group consisting of hydroxyl, alkoxy, aryloxy, ester, carbamate and sulfonyl;

Q is selected from the group consisting of —OH, O$R^8$, —N$R^cR^c$, —NHR$^{39}$—C(O)$R^8$, —NHR$^{39}$—C(O)O$R^8$, —NR$^{39}$—CHR$^{40}$—$R^b$, —NR$^{39}$—(CH$_2$)$_m$—$R^b$ and —NR$^{39}$—C(O)—CHR$^{40}$—N$R^cR^c$;

$R^{39}$ and $R^{40}$ are each, independently of one another, selected from the group consisting of hydrogen, alkyl, aryl, alkylaryl; arylalkyl and NHR$^8$; and $R^a$, $R^b$ and $R^c$ are as previously defined for structural formula (I). Preferred $R^b$ substituents for Q are selected from —C(O)O$R^8$, —O—C(O)$R^8$, —O—P(O)(O$R^8$)$_2$ and —P(O)(O$R^8$)$_2$.

In one embodiment of the above-depicted heteroaryls, as well as other 5-15 membered heteroaryls according to this embodiment of the invention, each $R^8$ is independently selected from the group consisting of $R^d$, —N$R^cR^c$, —(CH$_2$)$_m$—N$R^cR^c$, —C(O)N$R^cR^c$, —(CH$_2$)$_m$—C(O)N$R^cR^c$, —C(O)O$R^d$, —(CH$_2$)$_m$—C(O)O$R^d$ and —(CH$_2$)$_m$—O$R^d$, where m, $R^c$ and $R^d$ are as previously defined for structural formula (I).

In a specific embodiment, $R^d$ and/or $R^c$ is selected from the group consisting of $R^a$ and (C3-C8) cycloalkyl optionally substituted with one or more of the same or different hydroxyl, amino or carboxyl groups.

In another embodiment of the above-depicted heteroaryls, each $R^{35}$ is hydrogen or (C1-C6) ethyl or methyl.

In still another embodiment of the above-depicted heteroaryls, the aromatic ring connectivity is either at the 5 or 6 position. It should be understood that either $R^2$ or $R^4$ can utilize the heteroaryl groups discussed throughout this specification.

In a fourteenth embodiment of the compounds of structural formulae (I) and (Ia), $R^2$ and $R^4$ are each, independently of one another, an optionally substituted phenyl, aryl or heteroaryl, with the provisos that: (1) when $L^1$ is a direct bond and $R^6$ and optionally $R^5$ is hydrogen, then $R^2$ is other than 3,4,5-trimethoxyphenyl or 3,4,5-tri (C1-C6) alkoxyphenyl; (2) when $L^1$ and $L^2$ are each a direct bond, $R^6$ is hydrogen and $R^5$ is halo, then $R^2$ and $R^4$ are not each simultaneously 3,4,5-trimethoxyphenyl or 3,4,5-tri (C1-C6) alkoxyphenyl; (3) when $R^4$ is 3-methoxyphenyl or 3-(C1-C6) alkoxyphenyl and $R^2$ is a 3,4,5-trisubstituted phenyl, the substituents positioned at the 3 and 4 positions are not both simultaneously methoxy or (C1-C6) alkoxy; (4) when $R^2$ is a substituted phenyl and $R^6$ is hydrogen, then $R^5$ is other than cyano or —C(O)NHR, where R is hydrogen or (C1-C6) alkyl; and/or (5) when $R^2$ and $R^4$ are each independently a substituted or unsubstituted pyrrole or indole, then the pyrrole or indole is attached to the remainder of the molecule via a ring carbon atom. Alternatively, $R^2$ is subject to the provisos described in connection with the first or second embodiment.

In this fourteenth embodiment of the invention, the $R^2$ and $R^4$ substituents may be the same or different. Specific optionally substituted phenyl, aryl and/or heteroaryls include those illustrated above in connection with the twelfth and thirteenth embodiments.

In a fifteenth embodiment of the compounds of structural formulae (I) and (Ia), including the above-described first through fourteenth embodiments thereof, $R^6$ is hydrogen and $R^5$ is an electronegative group. As will be recognized by skilled artisans, electronegative groups are atoms or groups of atoms that have a relatively great tendency to attract electrons to themselves. Specific examples of electronegative groups according to this fourteenth embodiment include, but are not limited to, —CN, —NC, —NO$_2$, halo, bromo, chloro, fluoro, (C1-C3) haloalkyl, (C1-C3) perhaloalkyl, (C1-C3) fluoroalkyl, (C1-C3) perfluoroalkyl, —CF$_3$, (C1-C3) haloalkoxy, (C1-C3) perhaloalkoxy, (C1-C3) fluoroalkoxy, (C1-C3) perfluoroalkoxy, —OCF$_3$, —C(O)$R^a$, —C(O)O$R^3$, —C(O)CF$_3$ and —C(O)OCF$_3$. In a specific embodiment, the electronegative group is a halogen-containing electronegative group, such as —OCF$_3$, —CF$_3$, bromo, chloro or fluoro. In another specific embodiment, $R^5$ is fluoro, subject to the proviso that the compound is not any compound according to the third embodiment.

In a sixteenth embodiment, the compounds of structural formulae (I) and (Ia) are compounds according to structural formula (Ib):

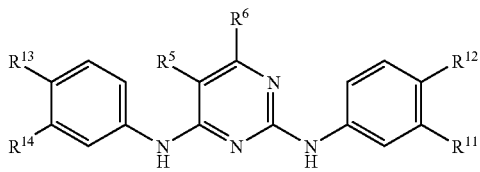

and salts, hydrates, solvates and N-oxides thereof, wherein $R^{11}$, $R^{12}$, $R^{13}$ and $R^{14}$ are each, independently of one another, selected from the group consisting of hydrogen, hydroxy, (C1-C6) alkoxy and —$NR^cR^c$; and $R^5$, $R^6$ and $R^c$ are as previously defined for structural formula (I), with the proviso that when $R^{13}$, $R^5$ and $R^6$ are each hydrogen, then $R^{11}$ and $R^{12}$ are not simultaneously methoxy, (C1-C6) alkoxy or (C1-C6) haloalkoxy In a seventeenth embodiment, the compounds of structural formulae (I) and (Ia) are compounds according to structural formula (Ic):

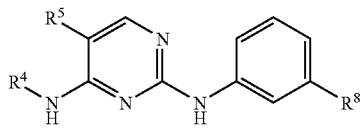

and salts, hydrates, solvates and N-oxides thereof, wherein:

$R^4$ is selected from the group consisting of 5-10 membered heteroaryl and 3-hydroxyphenyl;

$R^5$ is F or —$CF_3$; and $R^8$ is —$O(CH_2)_m$—$R^b$, where m and $R^b$ are as previously defined for structural formula (I). In a specific embodiment, $R^8$ is —O—$CH_2$—C(O)NH—$CH_3$ and/or $R^4$ is a heteroaryl according to the thirteenth embodiment.

In an eighteenth embodiment, the compounds of structural formulae (I) and (Ia) include any compound selected from TABLE 1 that inhibits an Fc receptor signal transduction cascade, a Syk kinase activity, a Syk-kinase dependent receptor signal transduction cascade or cell degranulation as measured in an in vitro assay, optionally subject to the proviso that the compound is not a compound excluded by the above-described third embodiment and/or other embodiments. In a specific embodiment, such compounds have an $IC_{50}$ of about 20 μM or less as measured in an in vitro degranulation assay, such as one of the degranulation assays described in the Examples section.

In a nineteenth embodiment, the compounds of structural formulae (I) and (Ia) include any compound selected from TABLE 1 that inhibits the $Fc\gamma R^1$ or $Fc\epsilon R^1$ receptor cascade with an $IC_{50}$ of about 20 μM or less as measured in an in vitro assay, such as one of the in vitro assays provided in the Examples section, optionally subject to the proviso that the compound is not a compound excluded by the above-described third embodiment and/or other embodiments.

Also specifically described are combinations of the above first through nineteenth specific embodiments.

Those of skill in the art will appreciate that the 2,4-pyrimidinediamine compounds described herein may include functional groups that can be masked with progroups to create prodrugs. Such prodrugs are usually, but need not be, pharmacologically inactive until converted into their active drug form. Indeed, many of the active 2,4-pyrimidinediamine compounds described in TABLE 1, infra, include promoieties that are hydrolyzable or otherwise cleavable under conditions of use. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, 2,4-pyrimidinediamines that include ester moieties may be considered prodrugs of their corresponding carboxylic acid, regardless of whether the ester form is pharmacologically active. Referring to TABLE 1, numerous ester-containing 2,4-pyrimidinediamines of the invention are active in their ester, "prodrug" form.

In the prodrugs of the invention, any available functional moiety may be masked with a progroup to yield a prodrug. Functional groups within the 2,4-pyrimidinediamine compounds that may be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, may be included in the prodrugs of the invention.

In one illustrative embodiment, the prodrugs of the invention are compounds according to structural formula (I) in which $R^c$ and $R^d$ may be, in addition to their previously-defined alternatives, a progroup.

Replacing the hydrogens attached to N2 and N4 in the 2,4-pyrimidinediamines of structural formula (I) with substituents adversely effects the activity of the compounds. However, as will be appreciated by skilled artisans, these nitrogens may be included in promoieties that, under conditions of use, cleave to yield 2,4-pyrimidinediamines according to structural formula (I). Thus, in another embodiment, the prodrugs of the invention are compounds according to structural formula (II):

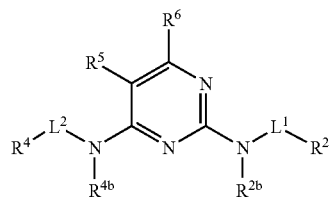

including salts, hydrates, solvates and N-oxides thereof, wherein:

$R^2$, $R^4$, $R^5$, $R^6$, $L^1$ and $L^2$ are as previously defined for structural formula (I); and $R^{2b}$ and $R^{4b}$ are each, independently of one another, a progroup. Specific examples of progroups according to this embodiment of the invention include, but are not limited to, (C1-C6) alkyl, —$C(O)CH_3$, —$C(O)NHR^{36}$ and —$S(O)_2R^{36}$, where $R^{36}$ is (C1-C6) alkyl, (C5-C15) aryl and (C3-C8) cycloalkyl.

In the prodrugs of structural formula (II), the various substituents may be as described for the various first through twentieth embodiments previously described for the compounds of structural formulae (I) and (Ia), or combinations of such embodiments.

Those of skill in the art will appreciate that many of the compounds and prodrugs of the invention, as well as the various compound species specifically described and/or illustrated herein, may exhibit the phenomena of tautomerism, conformational isomerism, geometric isomerism and/or optical isomerism. For example, the compounds and prodrugs of the invention may include one or more chiral centers and/or double bonds and as a consequence may exist as stereoisomers, such as double-bond isomers (i.e., geometric isomers), enantiomers and diastereomers and mixtures thereof, such as racemic mixtures. As another example, the compounds and prodrugs of the invention may exist in several tautomeric forms, including the enol form, the keto form and mixtures thereof. As the various compound names, formulae and compound drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds or prodrugs having one or more of the utilities described herein, as well as mixtures of these various different isomeric forms. In cases of limited rotation around the 2,4-pyrimidinediamine core structure, atrop isomers are also possible and are also specifically included in the compounds of the invention.

Moreover, skilled artisans will appreciate that when lists of alternative substituents include members which, owing to valency requirements or other reasons, cannot be used to substitute a particular group, the list is intended to be read in context to include those members of the list that are suitable for substituting the particular group. For example, skilled artisans will appreciate that while all of the listed alternatives for $R^b$ can be used to substitute an alkyl group, certain of the alternatives, such as =O, cannot be used to substitute a phenyl group. It is to be understood that only possible combinations of substituent-group pairs are intended.

The compounds and/or prodrugs of the invention may be identified by either their chemical structure or their chemical name. When the chemical structure and the chemical name conflict, the chemical structure is determinative of the identity of the specific compound.

Depending upon the nature of the various substituents, the 2,4-pyrimidinediamine compounds and prodrugs of the invention may be in the form of salts. Such salts include salts suitable for pharmaceutical uses ("pharmaceutically-acceptable salts"), salts suitable for veterinary uses, etc. Such salts may be derived from acids or bases, as is well-known in the art.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethanedisulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, etc.).

The 2,4-pyrimidinediamine compounds and of the invention, as well as the salts thereof, may also be in the form of hydrates, solvates and N-oxides, as are well-known in the art.

6.3 Methods of Synthesis

The compounds and prodrugs of the invention may be synthesized via a variety of different synthetic routes using commercially available starting materials and/or starting materials prepared by conventional synthetic methods. Suitable exemplary methods that may be routinely adapted to synthesize the 2,4-pyrimidinediamine compounds and prodrugs of the invention are found in U.S. Pat. No. 5,958,935, the disclosure of which is incorporated herein by reference. Specific examples describing the synthesis of numerous compounds and prodrugs of the invention, as well as intermediates therefor, are provided in the Examples section. All of the compounds of structural formulae (I), (Ia) and (II) may be prepared by routine adaptation of these methods.

A variety of exemplary synthetic routes that can be used to synthesize the 2,4-pyrimidinediamine compounds of the invention are described in Schemes (I)-(XI), below. In Schemes (I)-(XI), like-numbered compounds have similar structures. These methods may be routinely adapted to synthesize the prodrugs according to structural formula (II).

In one exemplary embodiment, the compounds can be synthesized from substituted or unsubstituted uracils or thiouracils as illustrated in Scheme (I), below:

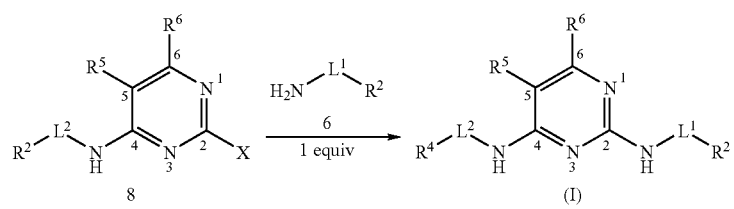

Scheme (I)

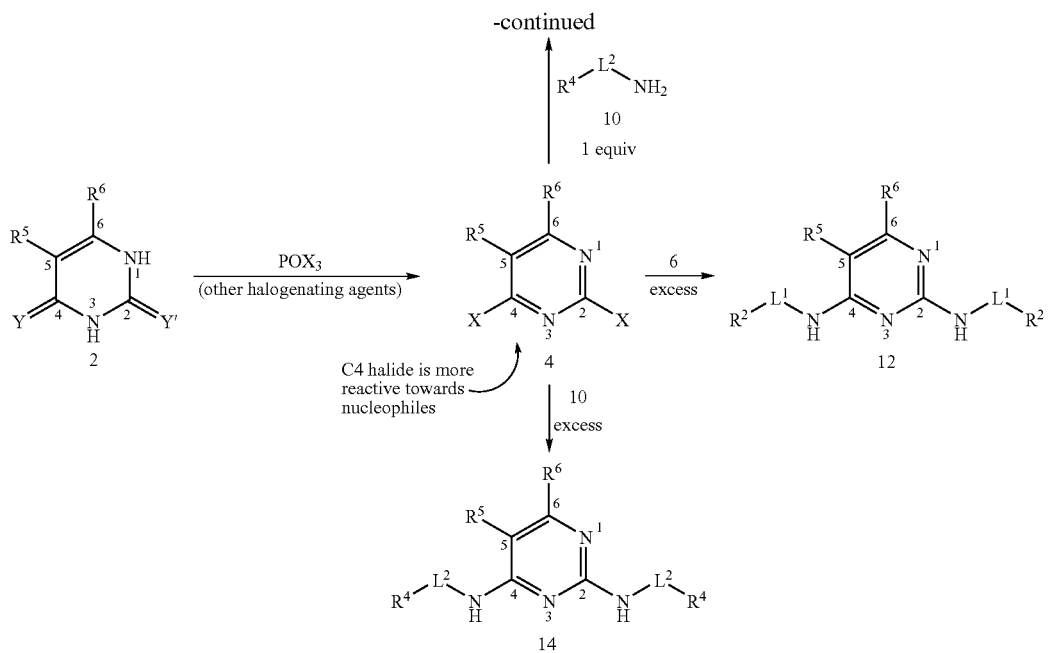

In Scheme (I), $R^2$, $R^4$, $R^5$, $R^6$, $L^1$ and $L^2$ are as previously defined for structural formula (I), X is a halogen (e.g., F, Cl, Br or I) and Y and Y' are each, independently of one another, selected from the group consisting of O and S. Referring to Scheme (I), uracil or thiouracil 2 is dihalogenated at the 2- and 4-positions using standard halogenating agent $POX_3$ (or other standard halogenating agent) under standard conditions to yield 2,4-bishalo pyrimidine 4. Depending upon the $R^5$ substituent, in pyrimidine 4, the halide at the C4 position is more reactive towards nucleophiles than the halide at the C2 position. This differential reactivity can be exploited to synthesize 2,4-pyrimidinediamines according structural formula (I) by first reacting 2,4-bishalopyrimidine 4 with one equivalent of amine 10, yielding 4N-substituted-2-halo-4-pyrimidineamine 8, followed by amine 6 to yield a 2,4-pyrimidinediamine according structural formula (I). 2N,4N-bis(substituted)-2,4-pyrimidinediamines 12 and 14 can be obtained by reacting 2,4-bishalopyrimidine 4 with excess 6 or 10, respectively.

In most situations, the C4 halide is more reactive towards nucleophiles, as illustrated in the Scheme. However, as will be recognized by skilled artisans, the identity of the $R^5$ substituent may alter this reactivity. For example, when $R^5$ is trifluoromethyl, a 50:50 mixture of 4N-substituted-4-pyrimidineamine 8 and the corresponding 2N-substituted-2-pyrimidineamine is obtained. Regardless of the identity of the $R^5$ substituent, the regioselectivity of the reaction can be controlled by adjusting the solvent and other synthetic conditions (such as temperature), as is well-known in the art.

The reactions depicted in Scheme (I) may proceed more quickly when the reaction mixtures are heated via microwave. When heating in this fashion, the following conditions may be used: heat to 175° C. in ethanol for 5-20 min. in a Smith Reactor (Personal Chemistry) in a sealed tube (at 20 bar pressure).

The uracil or thiouracil 2 starting materials may be purchased from commercial sources or prepared using standard techniques of organic chemistry. Commercially available uracils and thiouracils that can be used as starting materials in Scheme (I) include, by way of example and not limitation, uracil (Aldrich #13,078-8; CAS Registry 66-22-8); 2-thiouracil (Aldrich #11,558-4; CAS Registry 141-90-2); 2,4-dithiouracil (Aldrich #15,846-1; CAS Registry 2001-93-6); 5-acetouracil (Chem. Sources Int'l 2000; CAS Registry 6214-65-9); 5-azidouracil; 5-aminouracil (Aldrich #85,528-6; CAS Registry 932-52-5); 5-bromouracil (Aldrich #85,247-3; CAS Registry 51-20-7); 5-(trans-2-bromovinyl)-uracil (Aldrich #45,744-2; CAS Registry 69304-49-0); 5-(trans-2-chlorovinyl)-uracil (CAS Registry 81751-48-2); 5-(trans-2-carboxyvinyl)-uracil; uracil-5-carboxylic acid (2,4-dihydroxypyrimidine-5-carboxylic acid hydrate; Aldrich #27,770-3; CAS Registry 23945-44-0); 5-chlorouracil (Aldrich #22,458-8; CAS Registry 1820-81-1); 5-cyanouracil (Chem. Sources Int'l 2000; CAS Registry 4425-56-3); 5-ethyluracil (Aldrich #23,044-8; CAS Registry 4212-49-1); 5-ethenyluracil (CAS Registry 37107-81-6); 5-fluorouracil (Aldrich #85,847-1; CAS Registry 51-21-8); 5-iodouracil (Aldrich #85,785-8; CAS Registry 696-07-1); 5-methyluracil (thymine; Aldrich #13,199-7; CAS Registry 65-71-4); 5-nitrouracil (Aldrich #85,276-7; CAS Registry 611-08-5); uracil-5-sulfamic acid (Chem. Sources Int'l 2000; CAS Registry 5435-16-5); 5-(trifluoromethyl)-uracil (Aldrich #22,327-1; CAS Registry 54-20-6); 5-(2,2,2-trifluoroethyl)-uracil (CAS Registry 155143-31-6); 5-(pentafluoroethyl)-uracil (CAS Registry 60007-38-3); 6-aminouracil (Aldrich #A5060-6; CAS Registry 873-83-6) uracil-6-carboxylic acid (orotic acid; Aldrich #0-840-2; CAS Registry 50887-69-9); 6-methyluracil (Aldrich #D11,520-7; CAS Registry 626-48-2); uracil-5-amino-6-carboxylic acid (5-aminoorotic acid; Aldrich #19,121-3; CAS Registry #7164-43-4); 6-amino-5-nitrosouracil (6-amino-2,4-dihydroxy-5-nitrosopyrimidine; Aldrich #27,689-8; CAS Registry 5442-24-0); uracil-5-fluoro-6-carboxylic acid (5-fluoroorotic acid; Aldrich #42,513-3; CAS Registry 00000-00-0); and uracil-5-nitro-6-carboxylic acid (5-nitroorotic acid; Aldrich #18,528-0; CAS Registry 600779-49-9). Additional 5-, 6- and 5,6-substituted uracils and/or thiouracils are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

Amines 6 and 10 may be purchased from commercial sources or, alternatively, may be synthesized utilizing standard techniques. For example, suitable amines may be synthesized from nitro precursors using standard chemistry. Specific exemplary reactions are provided in the Examples section. See also Vogel, 1989, *Practical Organic Chemistry*, Addison Wesley Longman, Ltd. and John Wiley & Sons, Inc.

Skilled artisans will recognize that in some instances, amines 6 and 10 and/or substituents $R^5$ and/or $R^6$ on uracil or thiouracil 2 may include functional groups that require protection during synthesis. The exact identity of any protecting group(s) used will depend upon the identity of the functional group being protected, and will be apparent to these of skill in the art. Guidance for selecting appropriate protecting groups, as well as synthetic strategies for their attachment and removal, may be found, for example, in Greene & Wuts, *Protective Groups in Organic Synthesis,* 3d Edition, John Wiley & Sons, Inc., New York (1999) and the references cited therein (hereinafter "Greene & Wuts").

A specific embodiment of Scheme (I) utilizing 5-fluorouracil (Aldrich #32,937-1) as a starting material is illustrated in Scheme (Ia), below:

In Scheme (Ia), $R^2$, $R^4$, $L^1$ and $L^2$ are as previously defined for Scheme (I). According to Scheme (Ia), 5-fluorouracil 3 is halogenated with $POCl_3$ to yield 2,4-dichloro-5-fluoropyrimidine 5, which is then reacted with excess amine 6 or 10 to yield N2,N4-bis substituted 5-fluoro-2,4-pyrimidinediamine 11 or 13, respectively. Alternatively, asymmetric 2N,4N-disubstituted-5-fluoro-2,4-pyrimidinediamine 9 may be obtained by reacting 2,4-dichloro-5-fluoropyrimidine 5 with one equivalent of amine 10 (to yield 2-chloro-N4-substituted-5-fluoro-4-pyrimidineamine 7) followed by one or more equivalents of amine 6.

In another exemplary embodiment, the 2,4-pyrimidinediamine compounds of the invention may be synthesized from substituted or unsubstituted cytosines as illustrated in Schemes (IIa) and (IIb), below:

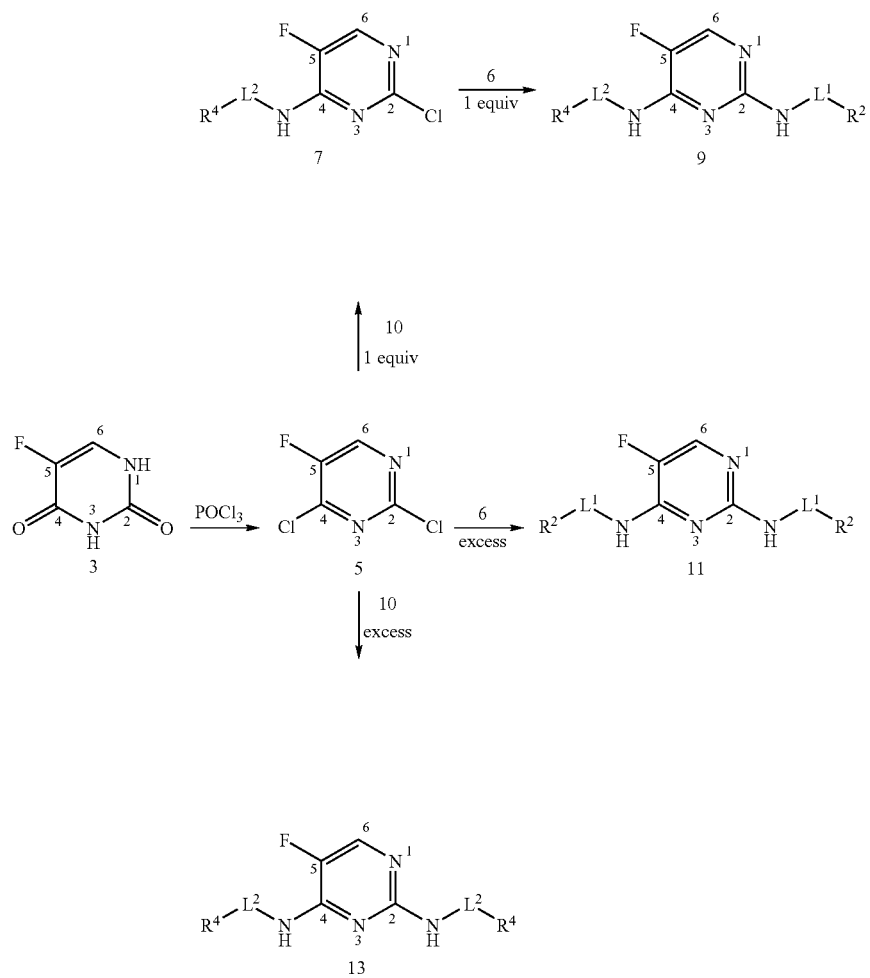

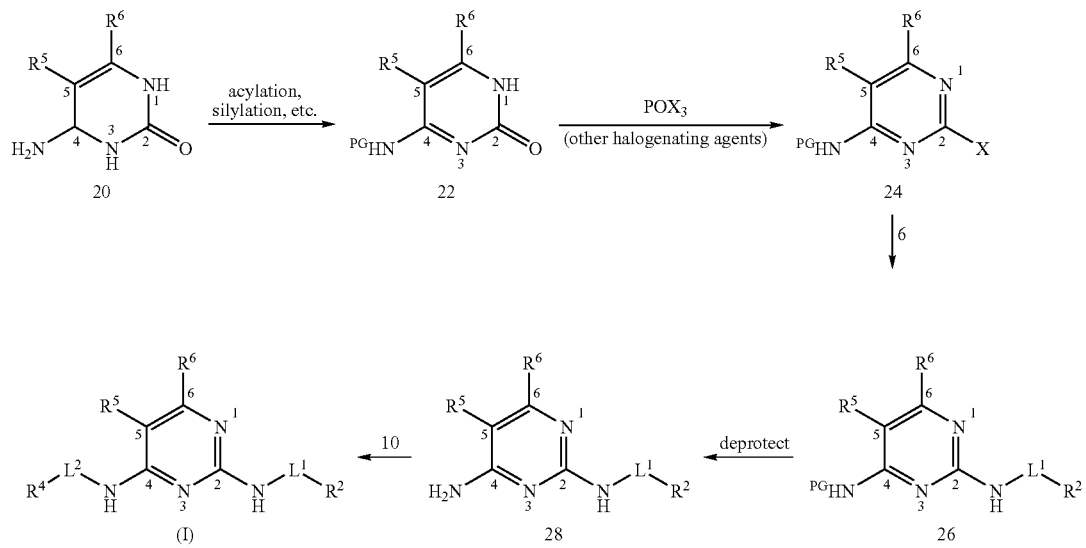

Scheme (IIa)

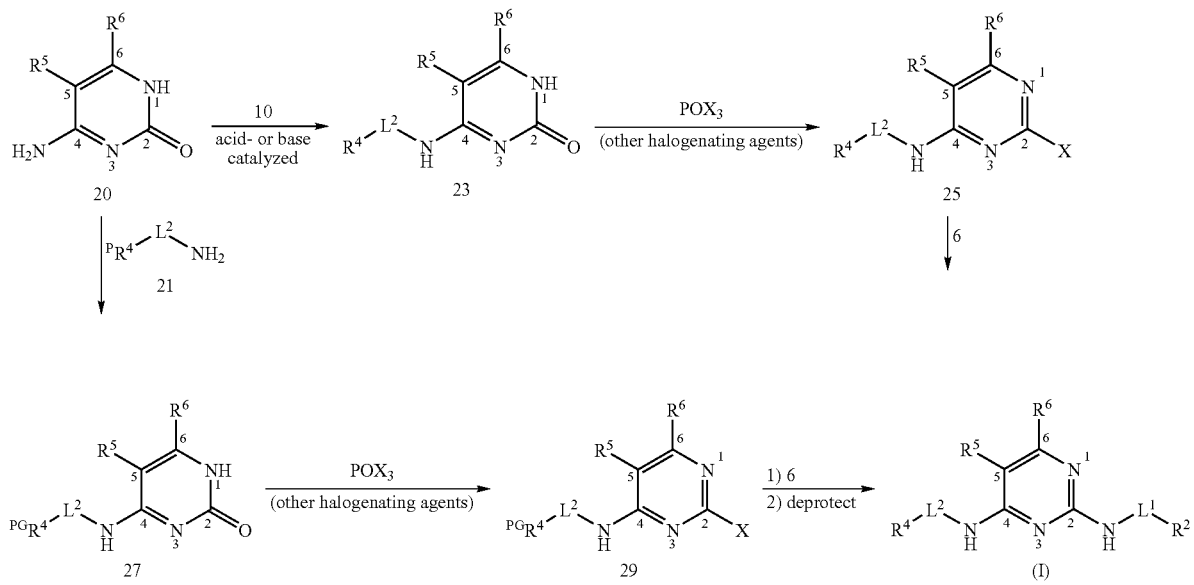

Scheme (IIb)

In Schemes (IIa) and (IIb), $R^2$, $R^4$, $R^5$, $R^6$, $L^1$, $L^2$ and X are as previously defined for Scheme (I) and PG represents a protecting group. Referring to Scheme (IIa), the C4 exocyclic amine of cytosine 20 is first protected with a suitable protecting group PG to yield N4-protected cytosine 22. For specific guidance regarding protecting groups useful in this context, see Vorbrüggen and Ruh-Pohlenz, 2001, *Handbook of Nucleoside Synthesis*, John Wiley & Sons, NY, pp. 1-631 ("Vorbrüggen"). Protected cytosine 22 is halogenated at the C2 position using a standard halogenation reagent under standard conditions to yield 2-chloro-4N-protected-4-pyrimidineamine 24. Reaction with amine 6 followed by deprotection of the C4 exocyclic amine and reaction with amine 10 yields a 2,4-pyrimidinediamine according to structural formula (I).

Alternatively, referring to Scheme (IIb), cytosine 20 may be reacted with amine 10 or protected amine 21 to yield N4-substituted cytosine 23 or 27, respectively. These substituted cytosines may then be halogenated as previously described, deprotected (in the case of N4-substituted cytosine 27) and reacted with amine 6 to yield a 2,4-pyrimidinediamine according to structural formula (I).

Commercially-available cytosines that may be used as starting materials in Schemes (IIa) and (IIb) include, but are not limited to, cytosine (Aldrich #14,201-8; CAS Registry 71-30-7); $N^4$-acetylcytosine (Aldrich #37,791-0; CAS Registry 14631-20-0); 5-fluorocytosine (Aldrich #27,159-4; CAS Registry 2022-85-7); and 5-(trifluoromethyl)-cytosine. Other suitable cytosines useful as starting materials in Schemes (IIa) are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

In still another exemplary embodiment, the 2,4-pyrimidinediamine compounds of the invention may be synthesized from substituted or unsubstituted 2-amino-4-pyrimidinols as illustrated in Scheme (III), below:

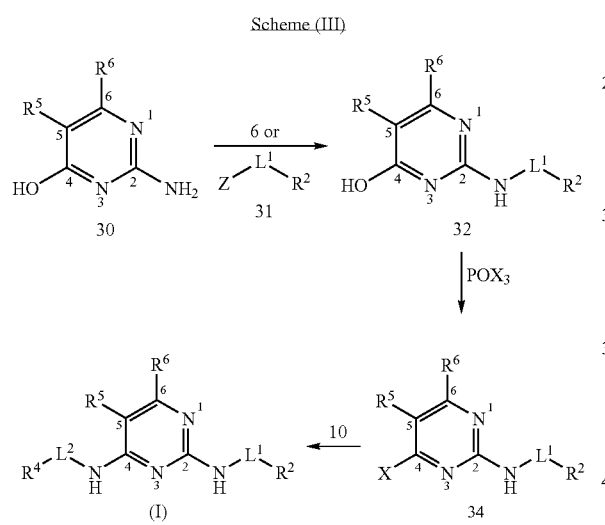

In Scheme (III), $R^2$, $R^4$, $R^5$, $R^6$, $L^1$, $L^2$ and X are as previously defined for Scheme (I) and Z is a leaving group as discussed in more detail in connection with Scheme IV, infra. Referring to Scheme (III), 2-amino-4-pyrimidinol 30 is reacted with amine 6 (or optionally protected amine 21) to yield N2-substituted-4-pyrimidinol 32, which is then halogenated as previously described to yield N2-substituted-4-halo-2-pyrimidineamine 34. Optional deprotection (for example if protected amine 21 was used in the first step) followed by reaction with amine 10 affords a 2,4-pyrimidinediamine according to structural formula (I). Alternatively, pyrimidinol 30 can be reacted with acylating agent 31.

Suitable commercially-available 2-amino-4-pyrimidinols 30 that can be used as starting materials in Scheme (III) include, but are not limited to, 2-amino-6-chloro-4-pyrimidinol hydrate (Aldrich #A4702-8; CAS Registry 00000-00-0) and 2-amino-6-hydroxy-4-pyrimidinol (Aldrich #A5040-1; CAS Registry 56-09-7). Other 2-amino-4-pyrimidinols 30 useful as starting materials in Scheme (III) are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

Alternatively, the 2,4-pyrimidinediamine compounds of the invention may be prepared from substituted or unsubstituted 4-amino-2-pyrimidinols as illustrated in Scheme (IV), below:

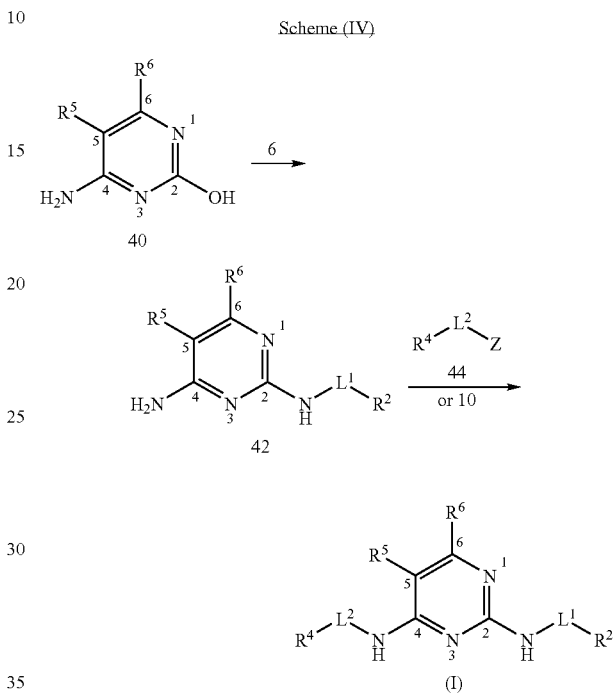

In Scheme (IV), $R^2$, $R^4$, $R^5$, $R^6$, $L^1$ and $L^2$ are as previously defined for Scheme (I) and Z represents a leaving group. Referring to Scheme (IV), the C2-hydroxyl of 4-amino-2-pyrimidinol 40 is more reactive towards nucleophiles than the C4-amino such that reaction with amine 6 yields N2-substituted-2,4-pyrimidinediamine 42. Subsequent reaction with compound 44, which includes a good leaving group Z, or amine 10 yields a 2,4-pyrimidinediamine according to structural formula (I). Compound 44 may include virtually any leaving group that can be displaced by the C4-amino of N2-substituted-2,4-pyrimidinediamine 42. Suitable leaving groups Z include, but are not limited to, halogens, methanesulfonyloxy (mesyloxy; "OMs"), trifluoromethanesulfonyloxy ("OTf") and p-toluenesulfonyloxy (tosyloxy; "OTs"), benzene sulfonyloxy ("besylate") and metanitro benzene sulfonyloxy ("nosylate"). Other suitable leaving groups will be apparent to those of skill in the art.

Substituted 4-amino-2-pyrimidinol starting materials may be obtained commercially or synthesized using standard techniques. Myriad textbook references teaching suitable synthetic methods are provided infra.

In still another exemplary embodiment, the 2,4-pyrimidinediamine compounds of the invention can be prepared from 2-chloro-4-aminopyrimidines or 2-amino-4-chloropyrimidines as illustrated in Scheme (V), below:

Scheme (V)

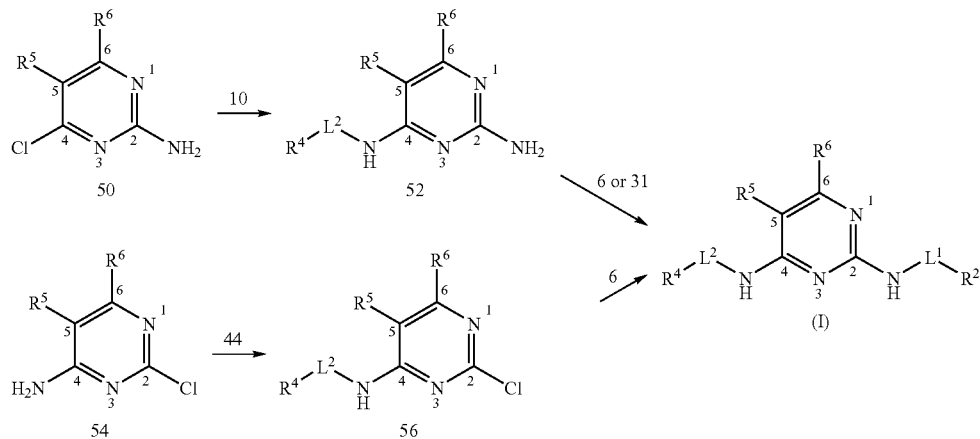

In Scheme (V), $R^2$, $R^4$, $R^5$, $R^6$, $L^1$, $L^2$ and X are as defined for Scheme (I) and Z is as defined for Scheme (IV). Referring to Scheme (V), 2-amino-4-chloropyrimidine 50 is reacted with amino 10 to yield 4N-substituted-2-pyrimidineamine 52 which, following reaction with compound 31 or amine 6, yields a 2,4-pyrimidinediamine according to structural formula (I). Alternatively, 2-chloro-4-amino-pyrimidine 54 may be reacted with compound 44 followed by amine 6 to yield a compound according to structural formula (I).

A variety of pyrimidines 50 and 54 suitable for use as starting materials in Scheme (V) are commercially available, including by way of example and not limitation, 2-amino-4,6-dichloropyrimidine (Aldrich #A4860-1; CAS Registry 56-05-3); 2-amino-4-chloro-6-methoxy-pyrimidine (Aldrich #51,864-6; CAS Registry 5734-64-5); 2-amino-4-chloro-6-methylpyrimidine (Aldrich #12,288-2; CAS Registry 5600-21-5); and 2-amino-4-chloro-6-methylthiopyrimidine (Aldrich #A4600-5; CAS Registry 1005-38-5). Additional pyrimidine starting materials are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

Alternatively, 4-chloro-2-pyrimidineamines 50 may be prepared as illustrated in Scheme (Va):

Scheme (Va)

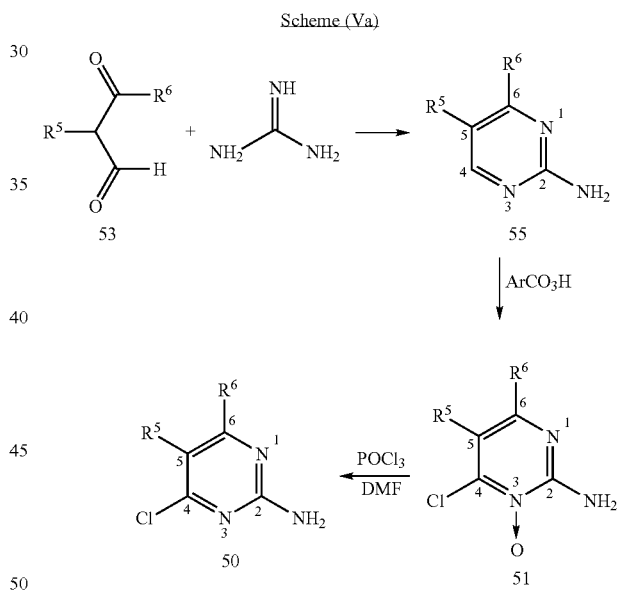

In Scheme (Va), $R^5$ and $R^6$ are as previously defined for structural formula (I). In Scheme (Va), dicarbonyl 53 is reacted with guanidine to yield 2-pyrimidineamine 51. Reaction with peracids like m-chloroperbenzoic acid, trifluoroperacetic acid or urea hydrogen peroxide complex yields N-oxide 55, which is then halogenated to give 4-chloro-2-pyrimidineamine 50. The corresponding 4-halo-2-pyrimidineamines may be obtained by using suitable halogenation reagents.

In yet another exemplary embodiment, the 2,4-pyrimidinediamine compounds of the invention can be prepared from substituted or unsubstituted uridines as illustrated in Scheme (VI), below:

Scheme (VI)

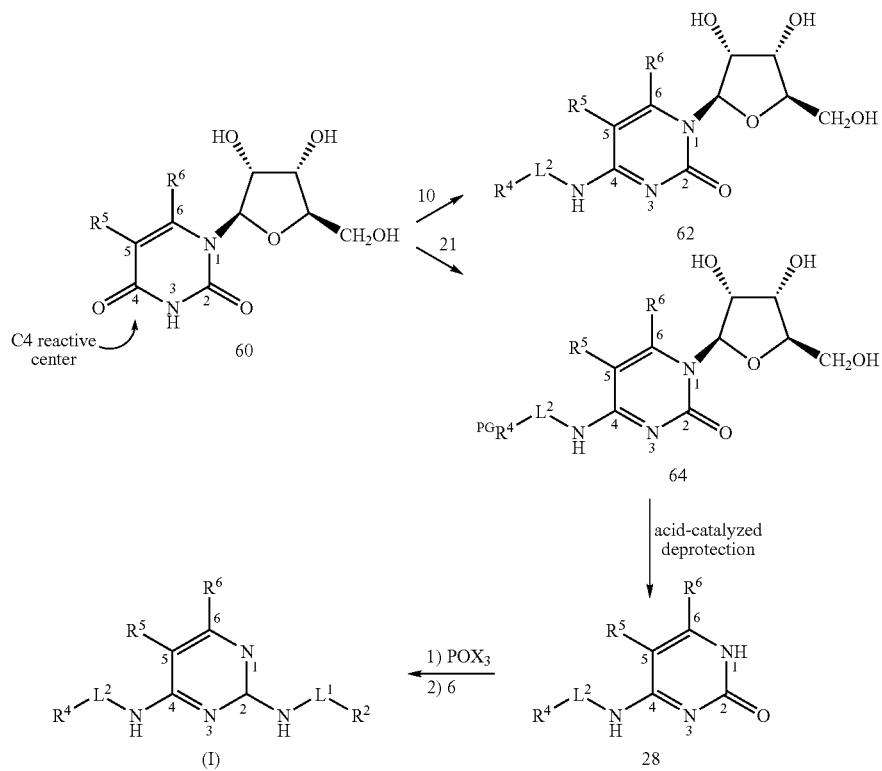

In Scheme (VI), $R^2$, $R^4$, $R^5$, $R^6$, $L^1$, $L^2$ and X are as previously defined for Scheme (I) and the superscript PG represents a protecting group, as discussed in connection with Scheme (IIb). According to Scheme (VI), uridine 60 has a C4 reactive center such that reaction with amine 10 or protected amine 21 yields N4-substituted cytidine 62 or 64, respectively. Acid-catalyzed deprotection of N4-substituted 62 or 64 (when "PG" represents an acid-labile protecting group) yields N4-substituted cytosine 28, which may be subsequently halogenated at the C2-position and reacted with amine 6 to yield a 2,4-pyrimidinediamine according to structural formula (I).

Cytidines may also be used as starting materials in an analogous manner, as illustrated in Scheme (VII), below:

Scheme (VII)

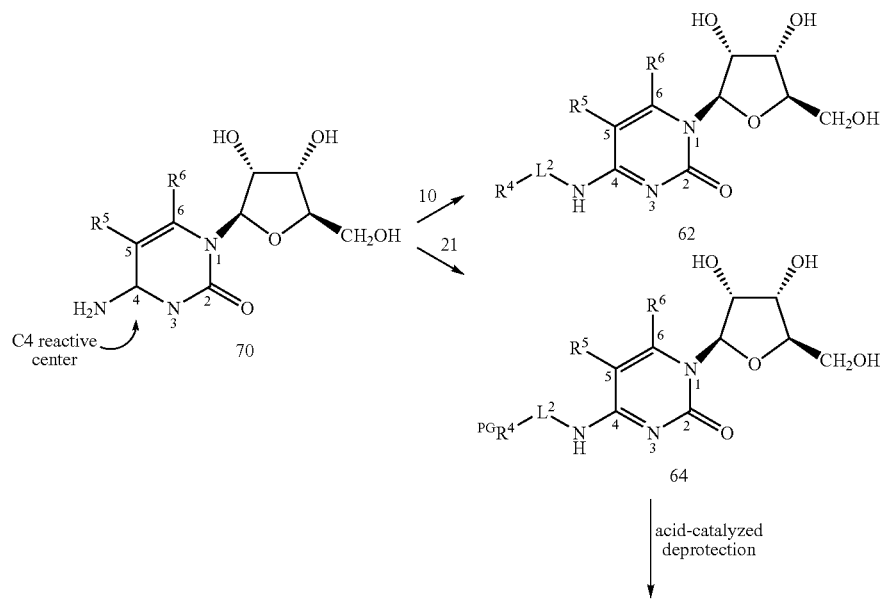

-continued

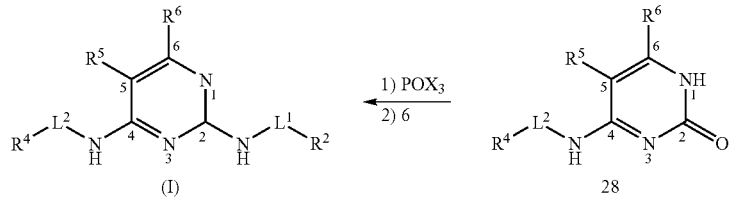

In Scheme (VII), $R^2$, $R^4$, $R^5$, $R^6$, $L^1$, $L^2$ and X are as previously defined in Scheme (I) and the superscript PG represents a protecting group as discussed above. Referring to Scheme (VII), like uridine 60, cytidine 70 has a C4 reactive center such that reaction with amine 10 or protected amine 21 yields N4-substituted cytidine 62 or 64, respectively. These cytidines 62 and 64 are then treated as previously described for Scheme (VI) to yield a 2,4-pyrimidinediamine according to structural formula (I).

Although Schemes (VI) and (VII) are exemplified with ribosylnucleosides, skilled artisans will appreciate that the corresponding 2'-deoxyribo and 2',3'-dideoxyribo nucleosides, as well as nucleosides including sugars or sugar analogs other than ribose, would also work.

Numerous uridines and cytidines useful as starting materials in Schemes (VI) and (VII) are known in the art, and include, by way of example and not limitation, 5-trifluoromethyl-2'-deoxycytidine (Chem. Sources #ABCR F07669; CAS Registry 66,384-66-5); 5-bromouridine (Chem. Sources Int'l 2000; CAS Registry 957-75-5); 5-iodo-2'-deoxyuridine (Aldrich #1-775-6; CAS Registry 54-42-2); 5-fluorouridine (Aldrich #32,937-1; CAS Registry 316-46-1); 5-iodouridine (Aldrich #85,259-7; CAS Registry 1024-99-3); 5-(trifluoromethyl)uridine (Chem. Sources Int'l 2000; CAS Registry 70-00-8); 5-trifluoromethyl-2'-deoxyuridine (Chem. Sources Int'l 2000; CAS Registry 70-00-8). Additional uridines and cytidines that can be used as starting materials in Schemes (VI) and (VII) are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

The 2,4-pyrimidinediamine compounds of the invention can also be synthesized from substituted pyrimidines, such as chloro-substituted pyrimidines, as illustrated in Schemes (VIII) and (IX), below:

Scheme (VIII)

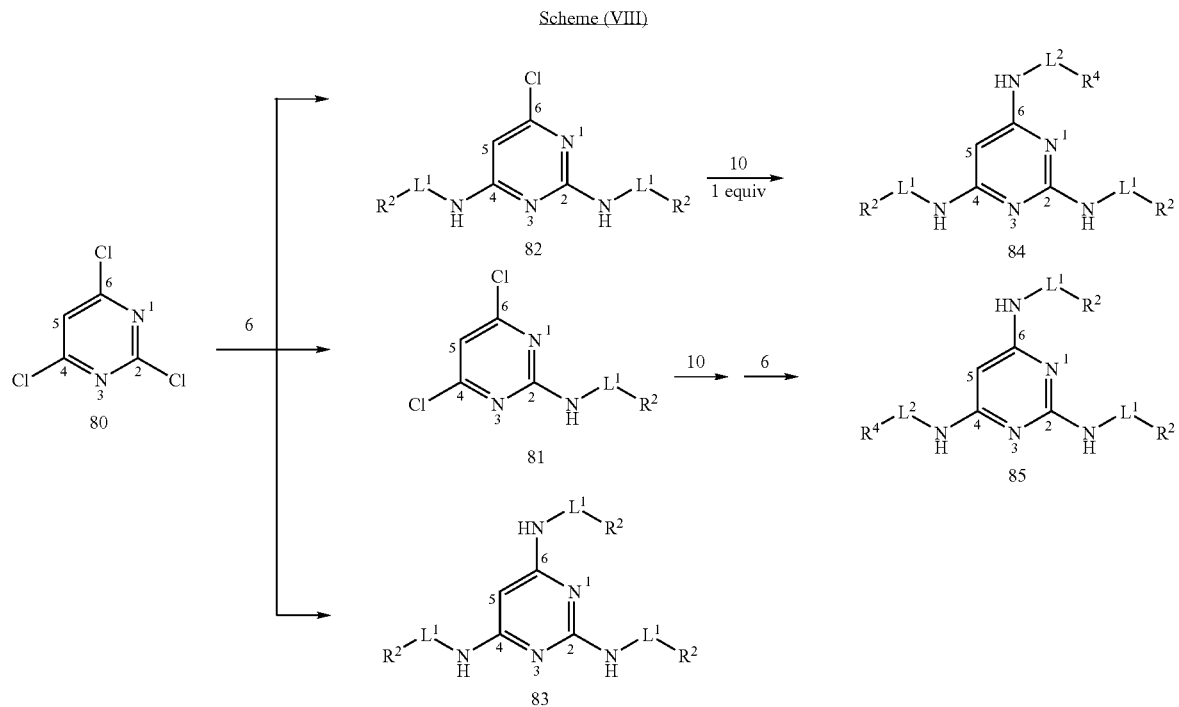

-continued
Scheme (IX)

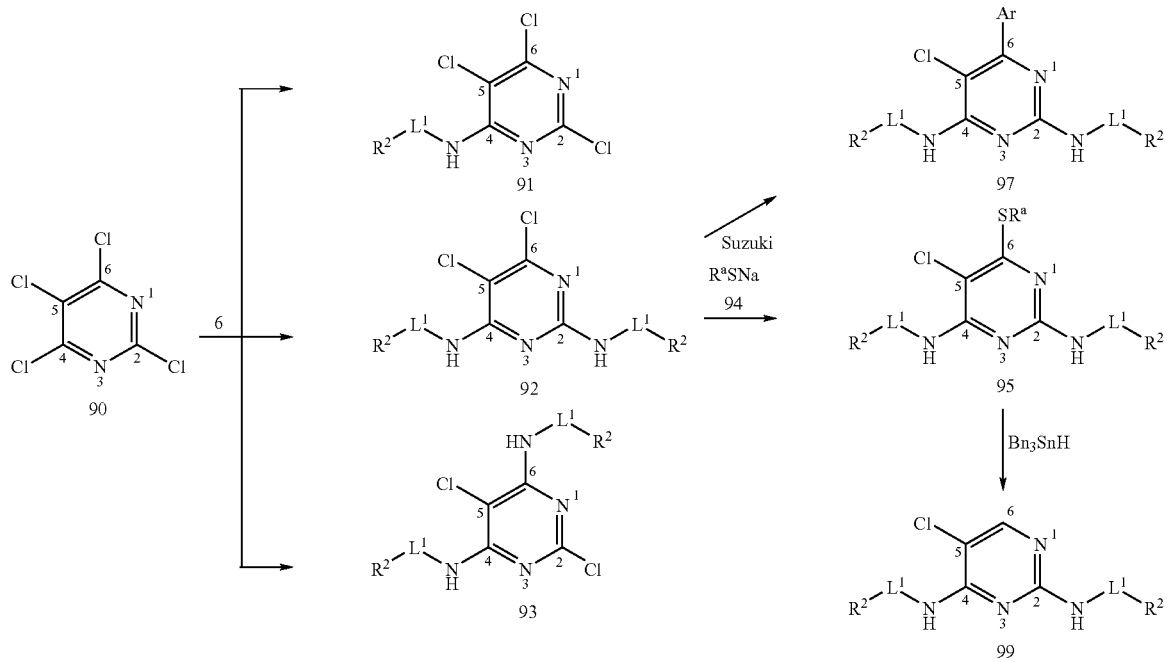

In Schemes (VIII) and (IX), $R^2$, $R^4$, $L^1$, $L^2$ and $R^a$ are as previously defined for structural formula (I) and "Ar" represents an aryl group. Referring to Scheme (VIII), reaction of 2,4,6-trichloropyrimidine 80 (Aldrich #T5,620-0; CAS#3764-01-0) with amine 6 yields a mixture of three compounds: substituted pyrimidine mono-, di- and triamines 81, 82 and 83, which can be separated and isolated using HPLC or other conventional techniques. Mono- and diamines 81 and 82 may be further reacted with amines 6 and/or 10 to yield N2,N4,N6-trisubstituted-2,4,6-pyrimidinetriamines 84 and 85, respectively.

N2,N4-bis-substituted-2,4-pyrimidinediamines can be prepared in a manner analogous to Scheme (VIII) by employing 2,4-dichloro-5-methylpyrimidine or 2,4-dichloro-pyrimidine as starting materials. In this instance, the mono-substituted pyrimidineamine corresponding to compound 81 is not obtained. Instead, the reaction proceeds to yield the N2,N4-bis-substituted-2,4-pyrimidinediamine directly.

Referring to Scheme (IX), 2,4,5,6-tetrachloropyrimidine 90 (Aldrich #24,671-9; CAS#1780-40-1) is reacted with excess amine 6 to yield a mixture of three compounds: 91, 92, and 93, which can be separated and isolated using HPLC or other conventional techniques. As illustrated, N2,N4-bis-substituted-5,6,-dichloro-2,4-pyrimidinediamine 92 may be further reacted at the C6 halide with, for example a nucleophilic agent 94 to yield compound 95. Alternatively, compound 92 can be converted into N2,N4-bis-substituted-5-chloro-6-aryl-2,4-pyrimidinediamine 97 via a Suzuki reaction. 2,4-Pyrimidinediamine 95 may be converted to 2,4-pyrimidinediamine 99 by reaction with $Bn_3SnH$.

As will be recognized by skilled artisans, 2,4-pyrimidinediamines according to the invention, synthesized via the exemplary methods described above or by other well-known means, may also be utilized as starting materials and/or intermediates to synthesize additional 2,4-pyrimidinediamine compounds of the invention. A specific example is illustrated in Scheme (X), below:

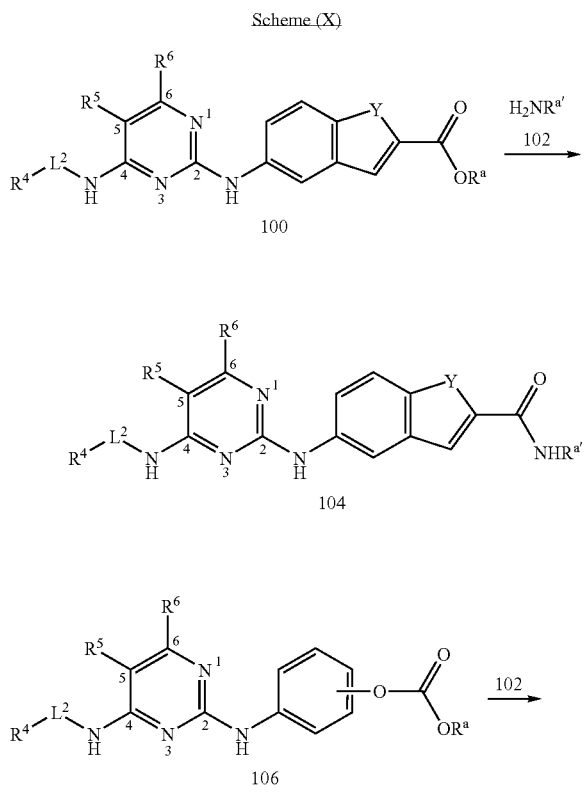

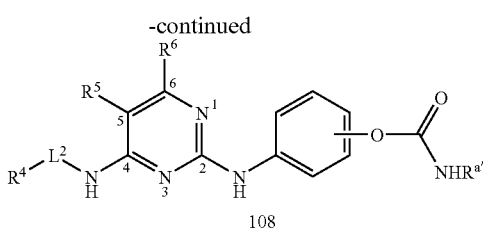

In Scheme (X), $R^4$, $R^5$, $R^6$, $L^2$ and $R^a$ are as previously defined for structural formula (I). Each $R^{a'}$ is independently an $R^a$, and may be the same or different from the illustrated $R^a$. Referring to Scheme (X), carboxylic acid or ester 100 may be converted to amide 104 by reaction with amine 102. In amine 102, $R^a$ may be the same or different than $R^a$ of acid or ester 100. Similarly, carbonate ester 106 may be converted to carbamate 108.

A second specific example is illustrated in Scheme (XI), below:

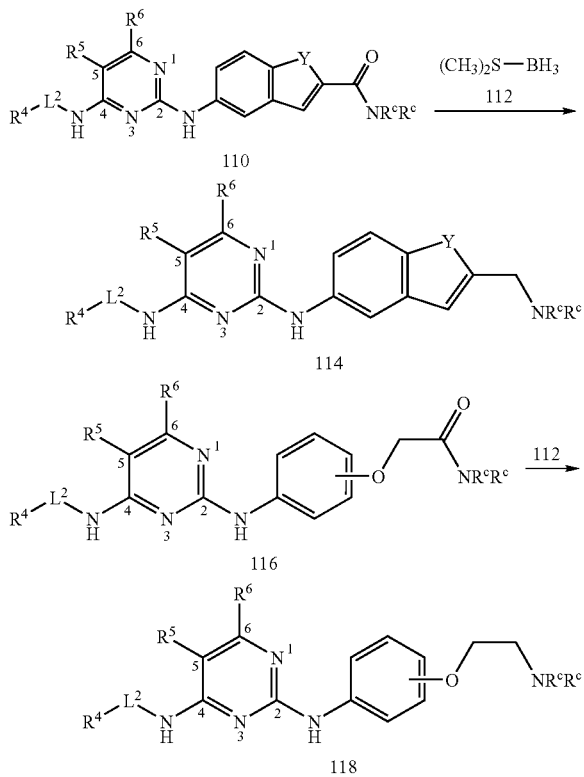

In Scheme (XI), $R^4$, $R^5$, $R^6$, $L^2$ and $R^c$ are as previously defined for structural formula (I). Referring to Scheme (XI), amide 110 or 116 may be converted to amine 114 or 118, respectively, by borane reduction with borane methylsulfide complex 112. Other suitable reactions for synthesizing 2,4-pyrimidinediamine compounds from 2,4-pyrimidinediamine starting materials will be apparent to those of skill in the art.

Although many of the synthetic schemes discussed above do not illustrate the use of protecting groups, skilled artisans will recognize that in some instances substituents $R^2$, $R^4$, $R^5$, $R^6$, $L^1$ and/or $L^2$ may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups and chemistries for their attachment and removal suitable for a particular application can be found, for example, in Greene & Wuts, supra.

Prodrugs according to structural formula (II) may be prepared by routine modification of the above-described methods. Alternatively, such prodrugs may be prepared by reacting a suitably protected 2,4-pyrimidinediamine of structural formula (I) with a suitable progroup. Conditions for carrying out such reactions and for deprotecting the product to yield a prodrug of formula (II) are well-known.

Myriad references teaching methods useful for synthesizing pyrimidines generally, as well as starting materials described in Schemes (I)-(IX), are known in the art. For specific guidance, the reader is referred to Brown, D. J., "The Pyrimidines", in *The Chemistry of Heterocyclic Compounds, Volume* 16 (Weissberger, A., Ed.), 1962, Interscience Publishers, (A Division of John Wiley & Sons), New York ("Brown I"); Brown, D. J., "The Pyrimidines", in *The Chemistry of Heterocyclic Compounds, Volume 16, Supplement I* (Weissberger, A. and Taylor, E. C., Ed.), 1970, Wiley-Interscience, (A Division of John Wiley & Sons), New York (Brown II"); Brown, D. J., "The Pyrimidines", in *The Chemistry of Heterocyclic Compounds, Volume* 16, *Supplement II* (Weissberger, A. and Taylor, E. C., Ed.), 1985, An Interscience Publication (John Wiley & Sons), New York ("Brown III"); Brown, D. J., "The Pyrimidines" in *The Chemistry of Heterocyclic Compounds, Volume* 52 (Weissberger, A. and Taylor, E. C., Ed.), 1994, John Wiley & Sons, Inc., New York, pp. 1-1509 (Brown IV"); Kenner, G. W. and Todd, A., in *Heterocyclic Compounds*, Volume 6, (Elderfield, R. C., Ed.), 1957, John Wiley, New York, Chapter 7 (pyrimidines); Paquette, L. A., *Principles of Modern Heterocyclic Chemistry*, 1968, W. A. Benjamin, Inc., New York, pp. 1-401 (uracil synthesis pp. 313, 315; pyrimidine synthesis pp. 313-316; amino pyrimidine synthesis pp. 315); Joule, J. A., Mills, K. and Smith, G. F., *Heterocyclic Chemistry*, $3^{rd}$ Edition, 1995, Chapman and Hall, London, UK, pp. 1-516; Vorbrüggen, H. and Ruh-Pohlenz, C., *Handbook of Nucleoside Synthesis*, John Wiley & Sons, New York, 2001, pp. 1-631 (protection of pyrimidines by acylation pp. 90-91; silylation of pyrimidines pp. 91-93); Joule, J. A., Mills, K. and Smith, G. F., *Heterocyclic Chemistry*, $4^{th}$ Edition, 2000, Blackwell Science, Ltd, Oxford, UK, pp. 1-589; and *Comprehensive Organic Synthesis*, Volumes 1-9 (Trost, B. M. and Fleming, I., Ed.), 1991, Pergamon Press, Oxford, UK.

6.4 Inhibition of Fc Receptor Signal Cascades

Active 2,4-pyrimidinediamine compounds of the invention inhibit Fc receptor signalling cascades that lead to, among other things, degranulation of cells. As a specific example, the compounds inhibit the FcεRI and/or FcγRI signal cascades that lead to degranulation of immune cells such as neutrophil, eosinophil, mast and/or basophil cells. Both mast and basophil cells play a central role in allergen-induced disorders, including, for example, allergic rhinitis and asthma. Referring to FIG. 1, upon exposure allergens, which may be, among other things, pollen or parasites, allergen-specific IgE antibodies are synthesized by B-cells activated by IL-4 (or IL-13) and other messengers to switch to IgE class specific antibody synthesis. These allergen-specific IgEs bind to the high affinity FcεRI. Upon binding of antigen, the FcεRI-bound IgEs are cross-linked and the IgE receptor signal transduction pathway is activated, which leads to degranulation of the cells and consequent release and/or synthesis of a host of chemical mediators, including histamine, proteases (e.g., tryptase and chymase), lipid mediators such as leukotrienes (e.g., LTC4), platelet-activating factor (PAF) and prostaglandins (e.g., PGD2) and a series of cytokines, including TNF-α, IL-4, IL-13, IL-5, IL-6, IL-8, GMCSF, VEGF and TGF-β. The release and/or synthesis of these mediators from mast and/or basophil cells accounts for the early and late stage responses induced by allergens, and is directly linked to downstream events that lead to a sustained inflammatory state.

The molecular events in the FcεRI signal transduction pathway that lead to release of preformed mediators via degranulation and release and/or synthesis of other chemical mediators are well-known and are illustrated in FIG. 2. Referring to FIG. 2, the FcεRI is a heterotetrameric receptor composed of an IgE-binding alpha-subunit, a beta subunit, and two gamma subunits (gamma homodimer). Cross-linking of FcεRI-bound IgE by multivalent binding agents (including, for example IgE-specific allergens or anti-IgE antibodies or fragments) induces the rapid association and activation of the Src-related kinase Lyn. Lyn phosphorylates immunoreceptor tyrosine-based activation motifs (ITAMS) on the intracellular beta and gamma subunits, which leads to the recruitment of additional Lyn to the beta subunit and Syk kinase to the gamma homodimer. These receptor-associated kinases, which are activated by intra- and intermolecular phosphorylation, phosphorylate other components of the pathway, such as the Btk kinase, LAT, and phospholipase C-gamma PLC-gamma). Activated PLC-gamma initiates pathways that lead to protein kinase C activation and $Ca^{2+}$ mobilization, both of which are required for degranulation. FcεRI cross-linking also activates the three major classes of mitogen activated protein (MAP) kinases, i.e. ERK1/2, JNK1/2, and p38. Activation of these pathways is important in the transcriptional regulation of proinflammatory mediators, such as TNF-α and IL-6, as well as the lipid mediator leukotriene CA (LTC4).

Although not illustrated, the FcγRI signaling cascade is believed to share some common elements with the FcεRI signaling cascade. Importantly, like FcεRI, the FcγRI includes a gamma homodimer that is phosphorylated and recruits Syk, and like FcεRI, activation of the FcγRI signaling cascade leads to, among other things, degranulation. Other Fc receptors that share the gamma homodimer, and which can be regulated by the active 2,4-pyrimidinediamine compounds include, but are not limited to, FcαRI and FcγRIII.

The ability of the 2,4-pyrimidinediamine compounds of the invention to inhibit Fc receptor signaling cascades may be simply determined or confirmed in in vitro assays. Suitable assays for confirming inhibition of FcεRI-mediated degranulation are provided in the Examples section. In one typical assay, cells capable of undergoing FcεRI-mediated degranulation, such as mast or basophil cells, are first grown in the presence of IL-4, Stem Cell Factor (SCF), IL-6 and IgE to increase expression of the FcεRI, exposed to a 2,4-pyrimidinediamine test compound of the invention and stimulated with anti-IgE antibodies (or, alternatively, an IgE-specific allergen). Following incubation, the amount of a chemical mediator or other chemical agent released and/or synthesized as a consequence of activating the FcεRI signaling cascade may be quantified using standard techniques and compared to the amount of the mediator or agent released from control cells (i.e., cells that are stimulated but that are not exposed to test compound). The concentration of test compound that yields a 50% reduction in the quantity of the mediator or agent measured as compared to control cells is the $IC_{50}$ of the test compound. The origin of the mast or basophil cells used in the assay will depend, in part, on the desired use for the compounds and will be apparent to those of skill in the art. For example, if the compounds will be used to treat or prevent a particular disease in humans, a convenient source of mast or basophil cells is a human or other animal which constitutes an accepted or known clinical model for the particular disease. Thus, depending upon the particular application, the mast or basophil cells may be derived from a wide variety of animal sources, ranging from, for example, lower mammals such as mice and rats, to dogs, sheep and other mammals commonly employed in clinical testing, to higher mammals such as monkeys, chimpanzees and apes, to humans. Specific examples of cells suitable for carrying out the in vitro assays include, but are not limited to, rodent or human basophil cells, rat basophil leukemia cell lines, primary mouse mast cells (such as bone marrow-derived mouse mast cells "BMMC") and primary human mast cells isolated from cord blood ("CHMC") or other tissues such as lung. Methods for isolating and culturing these cell types are well-known or are provided in the Examples section (see, e.g., Demo et al, 1999, Cytometry 36(4):340-348 and copending application Ser. No. 10/053,355, filed Nov. 8, 2001, the disclosures of which are incorporated herein by reference). Of course, other types of immune cells that degranulate upon activation of the FcεRI signaling cascade may also be used, including, for example, eosinophils.

As will be recognized by skilled artisans, the mediator or agent quantified is not critical. The only requirement is that it be a mediator or agent released and/or synthesized as a consequence of initiating or activating the Fc receptor signaling cascade. For example, referring to FIG. 1, activation of the FcεRI signaling cascade in mast and/or basophil cells leads to numerous downstream events. For example, activation of the FcεRI signal cascade leads to the immediate release (i.e., within 1-3 min. following receptor activation) of a variety of preformed chemical mediators and agents via degranulation. Thus, in one embodiment, the mediator or agent quantified may be specific to granules (i.e., present in granules but not in the cell cytoplasm generally). Examples of granule-specific mediators or agents that can be quantified to determine and/or confirm the activity of a 2,4-pyrimidinediamine compound of the invention include, but are not limited to, granule-specific enzymes such as hexosaminidase and tryptase and granule-specific components such as histamine and serotonin. Assays for quantifying such factors are well-known, and in many instances are commercially available. For example, tryptase and/or hexosaminidase release may be quantified by incubating the cells with cleavable substrates that fluoresce upon cleavage and quantifying the amount of fluorescence produced using conventional techniques. Such cleavable fluorogenic substrates are commercially available. For example, the fluorogenic substrates Z-Gly-Pro-Arg-AMC (Z=benzyloxycarbonyl; AMC=7-amino-4-methylcoumarin; BIOMOL Research Laboratories, Inc., Plymouth Meeting, Pa. 19462, Catalog No. P-142) and Z-Ala-Lys-Arg-AMC (Enzyme Systems Products, a division of ICN Biomedicals, Inc., Livermore, Calif. 94550, Catalog No. AMC-246) can be used to quantify the amount of tryptase released. The fluorogenic substrate 4-methylumbelliferyl-N-acetyl-β-D-glucosaminide (Sigma, St. Louis, Mo., Catalog #69585) can be used to quantify the amount of hexosaminidase released. Histamine release may be quantified using a commercially available enzyme-linked immunosorbent assay (ELISA) such as Immunotech histamine ELISA assay #IM2015 (Beckman-Coulter, Inc.). Specific methods of quantifying the release of tryptase, hexosaminidase and histamine are provided in the Examples section. Any of these assays may be used to determine or confirm the activity of the 2,4-pyrimidinediamine compounds of the invention.

Referring again to FIG. 1, degranulation is only one of several responses initiated by the FcεRI signaling cascade. In addition, activation of this signaling pathway leads to the de novo synthesis and release of cytokines and chemokines such as IL-4, IL-5, IL-6, TNF-α, IL-13 and MIP1-α), and release of lipid mediators such as leukotrienes (e.g., LTC4), platelet activating factor (PAF) and prostaglandins. Accordingly, the 2,4-pyrimidinediamine compounds of the invention may also be assessed for activity by quantifying the amount of one or more of these mediators released and/or synthesized by activated cells.

Unlike the granule-specific components discussed above, these "late stage" mediators are not released immediately following activation of the FcεRI signaling cascade. Accordingly, when quantifying these late stage mediators, care should be taken to insure that the activated cell culture is incubated for a time sufficient to result in the synthesis (if necessary) and release of the mediator being quantified. Generally, PAF and lipid mediators such as leukotriene C4 are released 3-30 min. following FcεRI activation. The cytokines and other late stage mediators are released approx. 4-8 hrs. following FcεRI activation. Incubation times suitable for a specific mediator will be apparent to those of skill in the art. Specific guidance and assays are provided in the Examples section.

The amount of a particular late stage mediator released may be quantified using any standard technique. In one embodiment, the amount(s) may be quantified using ELISA assays. ELISA assay kits suitable for quantifying the amount of TNFα, IL-4, IL-5, IL-6 and/or IL-13 released are available from, for example, Biosource International, Inc., Camarillo, Calif. 93012 (see, e.g., Catalog Nos. KHC3011, KHC0042, KHC0052, KHC0061 and KHC0132). ELISA assay kits suitable for quantifying the amount of leukotriene C4 (LTC4) released from cells are available from Cayman Chemical Co., Ann Arbor, Mich. 48108 (see, e.g., Catalog No. 520211).

Typically, active 2,4-pyrimidinediamine compounds of the invention will exhibit $IC_{50}$s with respect to FcεRI-mediated degranulation and/or mediator release or synthesis of about 20 μM or lower, as measured in an in vitro assay, such as one of the in vitro assays described above or in the Examples section. Of course, skilled artisans will appreciate that compounds which exhibit lower $IC_{50}$s, for example on the order of 10 μM, 1 μM, 100 nM, 10 nM, 1 nM, or even lower, are particularly useful.

Skilled artisans will also appreciate that the various mediators discussed above may induce different adverse effects or exhibit different potencies with respect to the same adverse effect. For example, the lipid mediator LTC4 is a potent vasoconstrictor—it is approximately 1000-fold more potent at inducing vasoconstriction than histamine. As another example, in addition to mediating atopic or Type I hypersensitivity reactions, cytokines can also cause tissue remodeling and cell proliferation. Thus, although compounds that inhibit release and/or synthesis of any one of the previously discussed chemical mediators are useful, skilled artisans will appreciate that compounds which inhibit the release and/or synthesis of a plurality, or even all, of the previously described mediators find particular use, as such compounds are useful for ameliorating or avoiding altogether a plurality, or even all, of the adverse effects induced by the particular mediators. For example, compounds which inhibit the release of all three types of mediators—granule-specific, lipid and cytokine—are useful for treating or preventing immediate Type I hypersensitivity reactions as well as the chronic symptoms associated therewith.

Compounds of the invention capable of inhibiting the release of more than one type of mediator (e.g., granule-specific or late stage) may be identified by determining the $IC_{50}$ with respect to a mediator representative of each class using the various in vitro assays described above (or other equivalent in vitro assays). Compounds of the invention which are capable of inhibiting the release of more than one mediator type will typically exhibit an $IC_{50}$ for each mediator type tested of less than about 20 μM. For example, a compound which exhibits an $IC_{50}$ of 1 μM with respect to histamine release ($IC_{50}^{histamine}$) and an $IC_{50}$ of 1 nM with respect to leukotriene LTC4 synthesis and/or release ($IC_{50}^{LTC4}$) inhibits both immediate (granule-specific) and late stage mediator release. As another specific example, a compound that exhibits an $IC_{50}^{tryptase}$ of 10 μM, an $IC_{50}^{LTC4}$ of 1 μM and an $IC_{50}^{IL-4}$ of 1 μM inhibits immediate (granule-specific), lipid and cytokine mediator release. Although the above specific examples utilize the $IC_{50}$s of one representative mediator of each class, skilled artisans will appreciate that the $IC_{50}$s of a plurality, or even all, mediators comprising one or more of the classes may be obtained. The quantity(ies) and identity(ies) of mediators for which $IC_{50}$ data should be ascertained for a particular compound and application will be apparent to those of skill in the art.

Similar assays may be utilized to confirm inhibition of signal transduction cascades initiated by other Fc receptors, such as FcαRI, FcγRI and/or FcγRIII signaling, with routine modification. For example, the ability of the compounds to inhibit FcγRI signal transduction may be confirmed in assays similar to those described above, with the exception that the FcγRI signaling cascade is activated, for example by incubating the cells with IgG and an IgG-specific allergen or antibody, instead of IgE and an IgE-specific allergen or antibody. Suitable cell types, activating agents and agents to quantify to confirm inhibition of other Fc receptors, such as Fc receptors that comprise a gamma homodimer, will be apparent to those of skill in the art.

One particularly useful class of compounds includes those 2,4-pyrimidinediamine compounds that inhibit the release of immediate granule-specific mediators and late stage mediators with approximately equivalent $IC_{50}$s. By approximately equivalent is meant that the $IC_{50}$s for each mediator type are within about a 10-fold range of one another. Another particularly useful class of compounds includes those 2,4-pyrimidinediamine compounds that inhibit the release of immediate granule-specific mediators, lipid mediators and cytokine mediators with approximately equivalent $IC_{50}$s. In a specific embodiment, such compounds inhibit the release of the following mediators with approximately equivalent $IC_{50}$s: histamine, tryptase, hexosaminidase, IL-4, IL-5, IL-6, IL-13, TNFα and LTC4. Such compounds are particularly useful for, among other things, ameliorating or avoiding altogether both the early and late stage responses associated with atopic or immediate Type I hypersensitivity reactions.

Ideally, the ability to inhibit the release of all desired types of mediators will reside in a single compound. However, mixtures of compounds can also be identified that achieve the same result. For example, a first compound which inhibits the release of granule specific mediators may be used in combination with a second compound which inhibits the release and/or synthesis of cytokine mediators.

In addition to the FcεRI or FcγRI degranulation pathways discussed above, degranulation of mast and/or basophil cells can be induced by other agents. For example, ionomycin, a calcium ionophore that bypasses the early FcεRI or FcγRI signal transduction machinery of the cell, directly induces a calcium flux that triggers degranulation. Referring again to FIG. 2, activated PLCγ initiates pathways that lead to, among other things, calcium ion mobilization and subsequent degranulation. As illustrated, this $Ca^{2+}$ mobilization is triggered late in the FcεRI signal transduction pathway. As mentioned above, and as illustrated in FIG. 3, ionomycin directly induces $Ca^{2+}$ mobilization and a $Ca^{2+}$ flux that leads to degranulation. Other ionophores that induce degranulation in this manner include A23187. The ability of granulation-inducing ionophores such as ionomycin to bypass the early stages of the FcεRI and/or FcγRI signaling cascades may be used as a counter screen to identify active compounds of the invention that specifically exert their degranulation-inhibitory activity by blocking or inhibiting the early FcεRI or FcγRI signaling cascades, as discussed above. Compounds which specifically inhibit such early FcεRI or FcγRI-mediated degranulation inhibit not only degranulation and subsequent rapid release of histamine, tryptase and other granule contents, but also inhibit the pro-inflammatory activation pathways causing the release of TNFα, IL-4, IL-13 and the lipid mediators such as LTC4. Thus, compounds which specifically inhibit such early FcεRI and/or FcγRI-mediated degranulation block or inhibit not only acute atopic or Type I hypersensitivity reactions, but also late responses involving multiple inflammatory mediators.

Compounds of the invention that specifically inhibit early FcεRI and/or FcγRI-mediated degranulation are those compounds that inhibit FcεRI and/or FcγRI-mediated degranulation (for example, have an $IC_{50}$ of less than about 20 µM with respect to the release of a granule-specific mediator or component as measured in an in vitro assay with cells stimulated with an IgE or IgG binding agent) but that do not appreciably inhibit ionophore-induced degranulation. In one embodiment, compounds are considered to not appreciably inhibit ionophore-induced degranulation if they exhibit an $IC_{50}$ of ionophore-induced degranulation of greater than about 20 µM, as measured in an in vitro assay. Of course, active compounds that exhibit even higher $IC_{50}$s of ionophore-induced degranulation, or that do not inhibit ionophore-induced degranulation at all, are particularly useful. In another embodiment, compounds are considered to not appreciably inhibit ionophore-induced degranulation if they exhibit a greater than 10-fold difference in their $IC_{50}$s of FcεRI and/or FcγRI-mediated degranulation and ionophore-induced degranulation, as measured in an in vitro assay. Assays suitable for determining the $IC_{50}$ of ionophore-induced degranulation include any of the previously-described degranulation assays, with the modification that the cells are stimulated or activated with a degranulation-inducing calcium ionophore such as ionomycin or A23187 (A.G. Scientific, San Diego, Calif.) instead of anti-IgE antibodies or an IgE-specific allergen. Specific assays for assessing the ability of a particular 2,4-pyrimidinediamine compound of the invention to inhibit ionophore-induced degranulation are provided in the Examples section.

As will be recognized by skilled artisans, compounds which exhibit a high degree of selectivity of FcεRI-mediated degranulation find particular use, as such compounds selectively target the FcεRI cascade and do not interfere with other degranulation mechanisms. Similarly, compounds which exhibit a high degree of selectivity of FcγRI-mediated degranulation find particular use, as such compounds selectively target the FcγRI cascade and do not interfere with other degranulation mechanisms. Compounds which exhibit a high degree of selectivity are generally 10-fold or more selective for FcεRI- or FcγRI-mediated degranulation over ionophore-induced degranulation, such as ionomycin-induced degranulation.

Biochemical and other data confirm that the 2,4-pyrimidinediamine compounds described herein are potent inhibitors of Syk kinase activity. For example, in experiments with an isolated Syk kinase, of twenty four 2,4-pyrimidinediamine compounds tested, all but two inhibited the Syk kinase catalyzed phosphorylation of a peptide substrate with IC50s in the submicromolar range. The remaining compounds inhibited phosphorylation in the micromolar range. In addition, of sixteen compounds tested in an in vitro assay with mast cells, all inhibited phosphorylation of Syk kinase substrates (e.g., PLC-gamma1, LAT) and proteins downstream of Syk kinase (e.g., JNK, p38, Erk1/2 and PKB, when tested), but not proteins upstream of Syk kinase in the cascade (e.g., Lyn). Phosphorylation of Lyn substrates was not inhibited by the 2,4-pyrimidinediamine compounds tested. Moreover, for the following compounds, a high correlation was observed between their inhibition of Syk kinase activity in biochemical assays ($IC_{50}$s in the range of 3 to 1850 nM) and their inhibition of $FcεR^1$-mediated degranulation in mast cells ($IC_{50}$s in the range of 30 to 1650 nM): R950373, R950368, R921302, R945371, R945370, R945369, R945365, R921304, R945144, R945140, R945071, R940358, R940353, R940352, R940351, R940350, R940347, R921303, R940338, R940323, R940290, R940277, R940276, R940275, R940269, R940255, R935393, R935372, R935366, R935310, R935309, R935307, R935304, R935302, R935293, R935237, R935198, R935196, R935194, R935193, R935191, R935190, R935138, R927050, R926968, R926956, R926931, R926891, R926839, R926834, R926816, R926813, R926791, R926782, R926780, R926757, R926753, R926745, R926715, R926508, R926505, R926502, R926501, R926500, R921218, R921147, R920410, R909268, R921219, R908712, R908702.

Accordingly, the activity of the 2,4-pyrimidinediamine compounds of the invention may also be confirmed in biochemical or cellular assays of Syk kinase activity. Referring again to FIG. 2, in the FcεRI signaling cascade in mast and/or basophil cells, Syk kinase phosphorylates LAT and PLC-gamma1, which leads to, among other things, degranulation. Any of these activities may be used to confirm the activity of the 2,4-pyrimidinediamine compounds of the invention. In one embodiment, the activity is confirmed by contacting an isolated Syk kinase, or an active fragment thereof with a 2,4-pyrimidinediamine compound in the presence of a Syk kinase substrate (e.g., a synthetic peptide or a protein that is known to be phosphorylated by Syk in a signaling cascade) and assessing whether the Syk kinase phosphorylated the substrate. Alternatively, the assay may be carried out with cells that express a Syk kinase. The cells may express the Syk kinase endogenously or they may be engineered to express a recombinant Syk kinase. The cells may optionally also express the Syk kinase substrate. Cells suitable for performing such confirmation assays, as well as methods of engineering suitable cells will be apparent to those of skill in the art. Specific examples of biochemical and cellular assays suitable for confirming the activity of the 2,4-pyrimidinediamine compounds are provided in the Examples section.

Generally, compounds that are Syk kinase inhibitors will exhibit an $IC_{50}$ with respect to a Syk kinase activity, such as the ability of Syk kinase to phosphorylate a synthetic or endogenous substrate, in an in vitro or cellular assay in the range of about 20 µM or less. Skilled artisans will appreciate that compounds that exhibit lower IC50s, such as in the range of 10 µM, 1 µM, 100 nM, 10 nM, 1 nM, or even lower, are particularly useful.

6.5 Uses and Compositions

As previously discussed, the active compounds of the invention inhibit Fc receptor signaling cascades, especially those Fc receptors including a gamma homodimer, such as the FcεRI and/or FcγRI signaling cascades, that lead to, among other things, the release and/or synthesis of chemical mediators from cells, either via degranulation or other processes. As also discussed, the active compounds are also potent inhibitors of Syk kinase. As a consequence of these activities, the active compounds of the invention may be used in a variety of in vitro, in vivo and ex vivo contexts to regulate or inhibit Syk kinase, signaling cascades in which Syk kinase plays a role, Fc receptor signaling cascades, and the biological responses effected by such signaling cascades. For example, in one embodiment, the compounds may be used to inhibit Syk kinase, either in vitro or in vivo, in virtually any cell type expressing Syk kinase. They may also be used to regulate signal transduction cascades in which Syk kinase plays a role. Such Syk-dependent signal transduction cascades include, but are not limited to, the FcεRI, FcγRI, FcγRIII, BCR and integrin signal transduction cascades. The compounds may also be used in vitro or in vivo to regulate, and in particular inhibit, cellular or biological responses effected by such Syk-dependent signal transduction cascades. Such cellular or biological responses include, but are not limited to, respiratory burst, cellular adhesion, cellular degranulation, cell spreading, cell migration, cell aggregation, phagocytosis, cytokine synthesis and release, cell maturation and $Ca^{2+}$ flux. Importantly, the compounds may be used to inhibit Syk kinase in vivo as a therapeutic approach towards the treatment or prevention of diseases mediated, either wholly or in part, by a Syk kinase activity. Non-limiting examples of Syk kinase mediated diseases that may be treated or prevented with the compounds are those discussed in more detail, below.

In another embodiment, the active compounds may be used to regulate or inhibit the Fc receptor signaling cascades and/or FcεRI- and/or FcγRI-mediated degranulation as a therapeutic approach towards the treatment or prevention of diseases characterized by, caused by and/or associated with the release or synthesis of chemical mediators of such Fc receptor signaling cascades or degranulation. Such treatments may be administered to animals in veterinary contexts or to humans. Diseases that are characterized by, caused by or associated with such mediator release, synthesis or degranulation, and that can therefore be treated or prevented with the active compounds include, by way of example and not limitation, atopy or anaphylactic hypersensitivity or allergic reactions, allergies (e.g., allergic conjunctivitis, allergic rhinitis, atopic asthma, atopic dermatitis and food allergies), low grade scarring (e.g., of scleroderma, increased fibrosis, keloids, post-surgical scars, pulmonary fibrosis, vascular spasms, migraine, reperfusion injury and post myocardial infarction), diseases associated with tissue destruction (e.g., of COPD, cardiobronchitis and post myocardial infarction), diseases associated with tissue inflammation (e.g., irritable bowel syndrome, spastic colon and inflammatory bowel disease), inflammation and scarring.

When used to treat or prevent such diseases, the active compounds may be administered singly, as mixtures of one or more active compounds or in mixture or combination with other agents useful for treating such diseases and/or the symptoms associated with such diseases. The active compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The active compounds may be administered per se in the form of prodrugs or as pharmaceutical compositions, comprising an active compound or prodrug.

Pharmaceutical compositions comprising the active compounds of the invention (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically.

The active compound or prodrug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the active compound(s) or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings. Compounds which are particularly suitable for oral administration include Compounds R940350, R935372, R935193, R927050 and R935391.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN®80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

Another specific example of an aqueous suspension suitable for administration of the compounds via inhalation, and in particular for such administration of Compound R921218, contains 1-20 mg/mL Compound or prodrug, 0.1-1% (v/v) Polysorbate 80 (TWEEN®80), 50 mM citrate and/or 0.9% sodium chloride.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851.

For prolonged delivery, the active compound(s) or prodrug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

6.6 Effective Dosages

The active compound(s) or prodrug(s) of the invention, or compositions thereof, will generally be used in an amount effective to achieve the intended result, for example in an amount effective to treat or prevent the particular disease being treated. The compound(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound may be administered to a patient at risk of developing one of the previously described diseases. For example, if it is unknown whether a patient is allergic to a particular drug, the compound may be administered prior to administration of the drug to avoid or ameliorate an allergic response to the drug. Alternatively, prophylactic administration may be applied to avoid the onset of symptoms in a patient diagnosed with the underlying disorder. For example, a compound may be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound may be administered to a healthy individual who is repeatedly exposed to an allergen known to induce allergies, such as latex, in an effort to prevent the individual from developing an allergy. Alternatively, a compound may be administered to a patient suffering from asthma prior to partaking in activities which trigger asthma attacks to lessen the severity of, or avoid altogether, an asthmatic episode.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an $IC_{50}$ of the particular compound as measured in as in vitro assay, such as the in vitro CHMC or BMMC and other in vitro assays described in the Examples section. Calculating dosages to achieve such circulating blood or serum concentrations taking into account the bioavailability of the particular compound is well within the capabilities of skilled artisans. For guidance, the reader is referred to Fingl & Woodbury, "General Principles," In: *Goodman and Gilman's The Pharmaceutical Basis of Therapeutics*, Chapter 1, pp. 1-46, latest edition, Pagamonon Press, and the references cited therein.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, 1995, Allergy 50(21Suppl):6-9, discussion 34-38 and Tumas et al., 2001, J. Allergy Clin. Immunol. 107(6): 1025-1033. Suitable animal models of allergic rhinitis are described in Szelenyi et al., 2000, Arzneimittelforschung 50(11):1037-42; Kawaguchi et al., 1994, Clin. Exp. Allergy 24(3):238-244 and Sugimoto et al., 2000, Immunopharmacology 48(1):1-7. Suitable animal models of allergic conjunctivitis are described in Carreras et al., 1993, Br. J. Ophthalmol. 77(8):509-514; Saiga et al., 1992, Ophthalmic Res. 24(1):45-50; and Kunert et al., 2001, Invest. Ophthalmol. Vis. Sci. 42(11):2483-2489. Suitable animal models of systemic mastocytosis are described in O'Keefe et al., 1987, J. Vet. Intern. Med. 1(2):75-80 and Bean-Knudsen et al, 1989, Vet. Pathol. 26(1):90-92. Suitable animal models of hyper IgE syndrome are described in Claman et al., 1990, Clin. Immunol. Immunopathol. 56(1):46-53. Suitable animal models of B-cell lymphoma are described in Hough et al., 1998, Proc. Natl. Acad. Sci. USA 95:13853-13858 and Hakim et al, 1996, J. Immunol. 157(12):5503-5511. Suitable animal models of atopic disorders such as atopic dermatitis, atopic eczema and atopic asthma are described in Chan et al., 2001, J. Invest. Dermatol. 117(4):977-983 and Suto et al., 1999, Int. Arch. Allergy Immunol. 120(Suppl 1):70-75. Ordinarily skilled artisans can routinely adapt such information to determine dosages suitable for human administration. Additional suitable animal models are described in the Examples section.

Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) effect is the therapeutic index. Compounds(s) that exhibit high therapeutic indices are preferred.

The invention having been described, the following examples are offered by way of illustration and not limitation.

7. EXAMPLES

7.1 Synthesis of Starting Materials and Intermediates Useful for Synthesizing the 2,4-Pyrimidinediamine Compounds According to Schemes (I)-(V)

A variety of starting materials and N4-monosubstituted-2-pyrimidineamines and N2-monosubstituted-4-pyrimidinediamines [mono Substitution Nucleophilic Aromatic Reaction (SNAR) products] useful for synthesizing the 2,4-pyrimidinediamine compounds of the invention according to Schemes (I)-(V) were prepared as described below. Conditions suitable for synthesizing the mono SNAR products are exemplified with 2-chloro-N4-(3,4-ethylenedioxyphenyl)-5-fluoro-4-pyrimidineamine (R926087).

7.1.1 2,4-Dichloro-5-fluoropyrimidine

To a dry reaction flask equipped with a stir bar and a reflux condenser was placed 5-fluorouracil (0.65 g, 5 mmol) followed by phosphorus oxychloride ($POCl_3$) (1.53 g, 10 mmol). The resultant mixture was heated at 110° C. for 8 hours under a nitrogen atmosphere. The reaction was cooled to room temperature, phosphorus pentachloride ($PCl_5$) (3.12 g, 15 mmol) was added and heated to 110° C. for a period of 12 hours. After cooling to room temperature, the mixture was poured into ice-water, saturated with sodium chloride and left for 1 hour at 0° C. to complete the decomposition of $POCl_3$ and $PCl_5$. The solid of 2,4-dichloro-5-fluoropyrimidine was collected by rapid filtration, dried using blotting paper and stored at low temperature. $^1H$ NMR ($CDCl_3$): δ8.47 (s, 1H); $^{13}C$ NMR ($CDCl_3$): δ 155.42, 151.87, 147.43 and 147.13; $^{19}F$ NMR ($CDCl_3$): −38149.

7.1.2 2,4-Dichloro-5-nitropyrimidine (Aldrich D6, 930-0)

A suspension of 5-nitrouracil (10 g, 63 mmol) in $POCl_3$ (100 mL) was refluxed for 5 h in the presence of N,N-dimethylaniline (10 mL), cooled to room temperature and poured on to crushed ice with vigorous stirring. The aqueous layer was extracted with ethyl acetate. The combined organic layers were dried over $MgSO_4$ and the solvent was evaporated under reduce pressure. The residue was purified by chromatography on silica gel (hexane/ethyl acetate; 1/1; v/v) to give the desired 2,4-dichloro-5-nitropyrimidine. LCMS: ret. time: 23.26 min.; purity: 95%; $^1$H NMR (CDCl$_3$): δ9.16 (1H, s).

7.1.3 2,4-Dichloro-5-cyanopyrimidine

In like manner to the preparation of 2,4-dichloro-5-nitropyrimidine, the reaction of 5-cyanouracil with POCl$_3$ and N,N-dimethylaniline gave 2,4-dichloro-5-cyanopyrimidine. LCMS: ret. time: 13.75 min.; purity: 95%.

7.1.4 2,4-Dichloro-5-trifluoromethylpyrimidine

In like manner to the preparation of 2,4-dichloro-5-nitropyrimidine, the reaction of 5-cyanouracil with POCl$_3$ and N,N-dimethylaniline gave 2,4-dichloro-5-cyanopyrimidine. $^1$H NMR (CD$_3$OD): δ9.07; LCMS: ret. time: 16.98 min. (fast method); purity: 70%.

7.1.5 2-Chloro-N4-(3,4-ethylenedioxyphenyl)-5-fluoro-4-pyrimidineamine (R926087)

The reaction flask equipped with a magnetic stirring bar and a rubber septum (to prevent loss of 2,4-dichloro-5-fluoropyrimidine and N$_2$ inlet was charged with 3,4-ethylenedioxyaniline (34 g, 225 mmol), MeOH (100 mL), H$_2$O (300 mL) and 2,4-dichloro-5-fluoropyrimidine (25 g, 150 mmol). The reaction mixture was stirred at room temperature for 1 h, diluted with H$_2$O (1.5 liter), acidified with 2N HCl (200 mL) and sonicated. The solid obtained was filtered, washed with H$_2$O and dried to obtain 33 g (78%) of the desired product, 2-chloro-N4-(3,4-ethylenedioxyphenyl)-5-fluoro-4-pyrimidineamine (R926087). $^1$H NMR (CDCl$_3$): δ 8.02 (1H, d, J=3 Hz), 7.25 (d, 1H, J=1.2 Hz), 6.98 (dd, 1H, J=2.4 and 8.1 Hz), 6.85 (d, 1H, J=5.7 Hz), 4.27 (m, 4H); $^{19}$F NMR (CDCl$_3$): −44570; LCMS: ret. time: 26.70 min.; purity 100%; MS (m/e): 283 (MH$^+$).

7.1.6 2-Chloro-N4-(3,4-ethylenedioxyphenyl)-5-nitro-4-pyrimidineamine (R940094)

In like manner to the preparation of 2-chloro-N4-(3,4-ethylenedioxyphenyl)-5-fluoro-4-pyrimidineamine, 2,4-dichloro-5-nitropyrimidine and 3,4-ethylenedioxyaniline were reacted to prepare 2-chloro-N4-(3,4-ethylenedioxyphenyl)-5-nitro-4-pyrimidineamine. LCMS: ret. time: 28.79 min.; purity: 90%; MS (m/e): 308 (M$^+$); $^1$HNMR (CDCl$_3$): δ 10.07 (1H, s), 9.15 (1H, s), 7.02-6.88 (3H, m), 4.29 (4H, s).

7.1.7 2-Chloro-N4-(3-hydroxyphenyl)-5-nitro-4-pyrimidineamine (R940097)

In like manner to the preparation of 2-chloro-N4-(3,4-ethylenedioxyphenyl)-5-fluoro-4-pyrimidineamine, 2,4-dichloro-5-nitropyrimidine and 3-hydroxyaniline were reacted to prepare 2-chloro-N4-(3-hydroxyphenyl)-5-nitro-4-pyrimidineamine. LCMS: ret. time: 24.21 min.; purity: 93%; MS (m/e): 267 (MH$^+$); $^1$HNMR (CDCl$_3$): δ 10.20 (1H, s), 9.19 (1H, s), 7.32 (1H, t, J=2.2 Hz), 7.28 (1H, d, J=7.8 Hz), 7.11 (1H, dd, J=7.8 and 1.8 Hz), 7.76 (1H, dd, J=8.4 and 2.4 Hz), 5.20 (1H, s).

7.1.8 2-Chloro-N4-(3-hydroxyphenyl)-5-fluoro-4-pyrimidineamine (R926111)

In like manner to the preparation of 2-chloro-N4-(3,4-ethylenedioxyphenyl)-5-fluoro-4-pyrimidineamine, 2,4-dichloro-5-fluoropyrimidine and 3-hydroxyaniline were reacted to prepare product 2-chloro-N4-(3-hydroxyphenyl)-5-fluoro-4-pyrimidineamine. $^1$H NMR (CD$_3$OD): δ 8.06 (bd, 1H), 7.26 (bd, 1H), 7.20-7.00 (m, 2H), 6.57 (d, 1H, J=7.2 Hz); $^{19}$F NMR (CD$_3$OD): −44374; LCMS: ret. time: 22.02; purity: 100%, MS (m/e): 240 (M$^+$).

7.1.9 2-Chloro-N4-(3,4-dimethoxyphenyl)-5-fluoro-4-pyrimidineamine (R926073)

In like manner to the preparation of 2-chloro-N4-(3,4-ethylenedioxyphenyl)-5-fluoro-4-pyrimidineamine, 2,4-dichloro-5-fluoropyrimidine and 3,4-dimethoxyaniline were reacted to prepare 2-chloro-N4-(3,4-dimethoxyphenyl)-5-fluoro-4-pyrimidineamine. $^1$H NMR (CDCl$_3$): δ 8.02 (d, 1H, J=2.7 Hz), 7.38 (d, 1H, J=2.4 Hz), 7.05 (dd, 1H, J=2.4 and 9.0 Hz), 6.89 (bs, 1H), 6.88 (d, 1H, J=9 Hz), 3.91 (s, 3H), 3.89 (s, 3H); $^{19}$F NMR (CDCl$_3$): −44593; LCMS: ret. time: 24.95 min.; purity: 98%; MS (m/e): 285 (MH$^+$).

7.1.10 2-Chloro-N4-(4-ethoxyphenyl)-5-fluoro-4-pyrimidineamine (R926066)

In like manner to the preparation of 2-chloro-N4-(3,4-ethylenedioxyphenyl)-5-fluoro-4-pyrimidineamine, 2,4-dichloro-5-fluoropyrimidine and 4-ethoxyaniline were reacted to prepare 2-chloro-N4-(4-ethoxyphenyl)-5-fluoro-4-pyrimidineamine. $^1$H NMR (CDCl$_3$): δ 8.01 (d, 1H, J=3 Hz), 7.49 (bdd, 2H, J=8.7 Hz), 6.92 (bdd, 2H, J=9.6 Hz), 4.03 (q, 2H, J=7.2 Hz), 1.42 (t, 3H, J=7.2 Hz); $^{19}$F NMR (CDCl$_3$): −44627; LCMS: ret. time: 29.50 min.; purity: 99%, MS (m/e): 268 (MH$^+$).

7.1.11 2-Chloro-N4-(4-chlorophenyl)-5-fluoro-4-pyrimidineamine (R926207)

In like manner to the preparation of 2-chloro-N4-(3,4-ethylenedioxyphenyl)-5-fluoro-4-pyrimidineamine, 2,4-dichloro-5-fluoropyrimidine and 4-chloroaniline were reacted to prepare 2-chloro-N4-(4-chlorophenyl)-5-fluoro-4-pyrimidineamine. $^1$H NMR (CDCl$_3$): δ 8.1 (bs, 1H), 8.60 (bdd, 2H), 8.36 (bdd, 2H), 6.90 (bs, 1H); $^{19}$F NMR (CDCl$_3$): −44407; LCMS: ret. time: 31.63 min.; purity: 85%; MS (m/e): 258 (MH$^+$).

7.1.12 2-Chloro-5-fluoro-N4-(3-hydroxy-4-methoxycarbonylmethyleneoxyphenyl)-4-pyrimidineamine (R926393)

In like manner to the preparation of 2-chloro-N4-(3,4-ethylenedioxyphenyl)-5-fluoro-4-pyrimidineamine, 2,4-dichloro-5-fluoropyrimidine and 3-hydroxy-4-methoxycarbonylmethylenoxyaniline were reacted to prepare 2-chloro-5-fluoro-N4-(3-hydroxy-4-methoxycarbonylmethyleneoxyphenyl)-4-pyrimidineamine. $^1$H NMR (CD$_3$OD): δ 8.03 (d, 1H, J=3.6 Hz), 7.35 (dd, 1H, J=2.4 Hz), 7.12 (dd, 1H, J=2.4 and 8.7 Hz), 6.82 (d, 1H, J=8.1 Hz), 4.86 (s, 2H), 3.81 (s, 3H).

7.1.13 N4-(4-tert-Butoxycarbonylmethyleneoxyphenyl)-2-chloro-5-fluoro-4-pyrimidineamine (R926573)

In like manner to the preparation of 2-chloro-N4-(3,4-ethylenedioxyphenyl)-5-fluoro-4-pyrimidineamine, 2,4-dichloro-5-fluoropyrimidine and tert-butyl 4-aminophenoxyacetate were reacted to prepare product N4-(4-tert-butoxycarbonylmethyleneoxyphenyl)-2-chloro-5-fluoro-4- pyrimidineamine $^1$H NMR (CDCl$_3$): δ 8.02 (d, 1H, J=2.7 Hz), 7.51 (d, 1H, J=8.7 Hz), 6.93 (d, 1H, J=8.7 Hz), 4.52 (s, 2H)), 1.49 (s, 9H); LCMS: ret. time: 29.50 min.; purity: 97%; MS (m/e): 354 (MH$^+$).

7.1.14 2-Chloro-5-fluoro-N4-(indol-5-yl)-4-pyrimidineamine (R926581)

In like manner to the preparation of 2-chloro-N4-(3,4-ethylenedioxyphenyl)-5-fluoro-4-pyrimidineamine, 2,4-dichloro-5-fluoropyrimidine and 5-aminoindole were reacted to prepare 2-chloro-5-fluoro-N4-(indol-5-yl)-4-pyrimidineamine. $^1$H NMR (CDCl$_3$+CD$_3$OD): δ 9.45 (bs, 1H), 8.00 (bs, 1H), 7.82 (bd, 1H), 7.75 (s, 1H), 7.38-7.10 (m, 3H), 6.40 (bs, 1H); LCMS: ret. time: 23.85 min.; purity: 100%; MS (m/e): 263 (MH$^+$).

7.1.15 2-Chloro-5-fluoro-N4-(4-methoxymethyl-coumarin-7-yl)-4-pyrimidineamine (R926618)

In like manner to the preparation of 2-chloro-N4-(3,4-ethylenedioxyphenyl)-5-fluoro-4-pyrimidineamine, 2,4-dichloro-5-fluoropyrimidine and 4-methoxymethyl-7-aminocoumarin were reacted to prepare 2-chloro-5-fluoro-N4-(4-methoxymethyl-coumarin-7-yl)-4-pyrimidineamine. $^1$H NMR (CD$_3$OD): δ 8.05 (d, 1H), 7.90 (s, 1H), 7.70 (dd, 1H, J=2.4 and 8.7 Hz), 7.53 (d, 1H, J=8.7 Hz), 6.42 (s, 1H), 4.61 (s, 2H), 3.49 (s, 3H); LCMS: ret. time: 26.38 min.; purity: 87%; MS (m/e): 336 (MH$^+$).

7.1.16 2-Chloro-N4-(2,5-dimethyl-4-hydroxyphenyl)-5-fluoro-4-pyrimidineamine (R926619)

In like manner to the preparation of 2-chloro-N4-(3,4-ethylenedioxyphenyl)-5-fluoro-4-pyrimidineamine, 2,4-dichloro-5-fluoropyrimidine and 2,5-dimethyl-4-hydroxyaniline were reacted to prepare 2-chloro-N4-(2,5-dimethyl-4-hydroxyphenyl)-5-fluoro-4-pyrimidineamine. LCMS: ret. time: 23.31 min.; purity: 96%; MS (m/e): 268 (MH$^+$).

7.1.17 2-Chloro-N4-(5-chloropyrid-2-yl)-5-fluoro-4-pyrimidineamine (R926061)

In like manner to the preparation of 2-chloro-N4-(3,4-ethylenedioxyphenyl)-5-fluoro-4-pyrimidineamine, 2,4-dichloro-5-fluoropyrimidine and 5-chloro-2-aminopyridine were reacted to prepare 2-chloro-N4-(5-chloropyrid-2-yl)-5-fluoro-4-pyrimidineamine. $^1$H NMR (CDCl$_3$): δ 8.40 (d, 1H, J=8.7 Hz), 8.28 (d, 1H, J=1.8 Hz), 8.17 (d, 1H, J=2.1 and 9 Hz); LCMS: ret. time: 28.58 min.; purity: 100%; MS (m/e): 259 (MH$^+$).

7.1.18 2-Chloro-5-fluoro-N4-(5-methylpyrid-2-yl))-4-pyrimidineamine (R926062)

In like manner to the preparation of 2-chloro-N4-(3,4-ethylenedioxyphenyl)-5-fluoro-4-pyrimidineamine, 2,4-dichloro-5-fluoropyrimidine and 5-methyl-2-aminopyridine were reacted to prepare 2-chloro-5-fluoro-N4-(5-methylpyrid-2-yl)-5-4-pyrimidineamine. $^1$H NMR (CDCl$_3$): δ 9.20 (s, 1H), 8.51 (s, 1H), 7.63 (d, 1H, J=5.7 Hz), 7.45 (dd, 1H, J=1.8 and 9.3 Hz), 2.43 (s, 3H); LCMS: ret. time: 21.29 min.; purity: 97%; MS (m/e): 239 (MH$^+$).

7.1.19 N4-[6-(1,4-Benzoxazinyl)]-N2-chloro-5-fluoro-4-pyrimidineamine

In like manner to 2-chloro-N4-(3,4-ethylenedioxyphenyl)-5-fluoro-4-pyrimidineamine, 2,4-dichloro-5-fluoropyrimidine and 6-amino-1,4-benzoxazine were reacted (in methanol or methanol:water) to yield N4-[6-(1,4-benzoxazinyl)]-N2-chloro-5-fluoro-4-pyrimidineamine. $^1$H NMR (DMSO-d6): δ 8.2 (d, 1H), 6.8 (m, 1H), 6.75 (m, 1H), 6.60 (m, 1H), 4.05 (m, 2H), 3.2 (m, 2H); LCMS: ret. time: 20.8 min.; purity: 95%; MS (m/e): 295 (MH$^+$).

7.1.20 N2-Chloro-N4-(2,3-dihydrobenzofuran-5-yl)-5-fluoro-4-pyrimidinediamine In like manner to 2-chloro-N4-(3,4-ethylenedioxyphenyl)-5-fluoro-4-pyrimidineamine, 2,4-dichloro-5-fluoropyrimidine and 5-amino-2,3-dihydrobenzofuran were reacted to yield N2-chloro-N4-(2,3-dihydrobenzofuran-5-yl)-5-fluoro-4-pyrimidinediamine. $^1$H NMR (DMSO-d6): δ 8.09 (d, 1H), 8.00 (m, 1H), 7.42 (m, 2H), 7.05 (m, 1H), 4.53 (m, 2H), 4.25 (s, 2H), 3.15 (m, 2H); LCMS: ret. time: 20.35 min.; purity: 90%; MS (m/e): 266 (MH$^+$).

7.1.21 2-Chloro-N4-(2-carboxy-4-chlorophenyl)-5-fluoro-4-pyrimidineamine (R940050)

In like manner to the preparation of 2-chloro-N4-(3,4-ethylenedioxyphenyl)-5-fluoro-4-pyrimidineamine, 2,4-dichloro-5-fluoropyrimidine and 2-carboxy-4-chloroaniline were reacted to prepare 2-chloro-N4-(2-carboxy-4-chlorophenyl)-5-fluoro-4-pyrimidineamine. LCMS: ret. time: 20.83 min.; purity: 98%; $^1$H NMR (CDCl$_3$): δ 8.64 (1H, d, J=4.8 Hz), 8.24 (1H, d, J=2.7 Hz), 7.76 (1H, dd, J=8.7 and 2.7 Hz), 7.70 (1H, dd, J=8.7 and J=0.9 Hz).

7.1.22 N-(2-Chloro-5-fluoro-4-pyrimidinyl)-L-tyrosine Methyl Ester (R940108)

In like manner to the preparation of 2-chloro-N4-(3,4-ethylenedioxyphenyl)-5-fluoro-4-pyrimidineamine, 2,4-dichloro-5-fluoropyrimidine and L-tyrosine methyl ester were reacted to prepare N-(2-chloro-5-fluoro-4-pyrimidinyl)-L-tyrosine Methyl Ester. LCMS: ret. time: 23.32 min.; purity: 83%; MS (m/e): 325 (M+); $^1$H NMR (CDCl$_3$): δ 7.90 (1H, d, J=2.7 Hz), 6.95 (2H, d, J=8.7 Hz), 6.75 (2H, d, J=8.7 Hz), 5.95 (1H, s), 5.72 (1H, d, J=7.5 Hz), 5.05 (1H, dt, J=7.5 and 5.3 Hz), 3.77 (3H, s), 3.16 (2H, m).

7.1.23 2-Chloro-N4-[3-(5-cyano-2-methyl-4-thiomethyl-6-pyrimidinyl)phenyl]-5-fluoro-4-pyrimidineamine (R940141)

In like manner to the preparation of 2-chloro-N4-(3,4-ethylenedioxyphenyl)-5-fluoro-4-pyrimidineamine, 2,4-dichloro-5-fluoropyrimidine and 3-(5-cyano-2-methyl-4-thiomethyl-6-pyrimidinyl)aniline were reacted to prepare 2-chloro-N4-[3-(5-cyano-2-methyl-4-thiomethyl-6-pyrimidinyl)phenyl]-5-fluoro-4-pyrimidineamine. LCMS: ret. time: 18.23 min.; purity: 84%; MS (m/e): 386 (M$^+$); $^1$H NMR (CDCl$_3$): δ 8.19 (1H, t, J=1.9 Hz), 8.11 (1H, d, J=3.1 Hz), 7.98 (1H, dd, J=8.1 and J=2.4 Hz), 7.82 (1H, dd, J=7.8 and 1.8 Hz), 7.57 (1H, t, J=7.8 Hz), 7.11 (1H, s), 2.79 (3H, s), 2.69 (3H, s).

7.1.24 N4-[4-(N-Benzylpiperazino)phenyl]-2-chloro-5-fluoro-4-pyrimidineamine (R945154)

In like manner to the preparation of 2-chloro-N4-(3,4-ethylenedioxyphenyl)-5-fluoro-4-pyrimidineamine, 4-(N-benzylpiperazino)aniline and 2,4-dichloro-5-fluoropyrimidine gave N4-[4-(N-benzylpiperazino)phenyl]-2-chloro-5-fluoro-4-pyrimidineamine. $^1$H NMR (CDCl$_3$): δ 2.81 (m, 4H), 3.37 (m, 6H), 6.85 (br, 1H), 6.93 (d, J=9.0 Hz, 2H), 7.40 (m, 5H), 7.50 (d, J=9.3 Hz, 2H), 8.02 (d, J=2.7 Hz, 1H); LCMS: ret. time: 20.56 min, purity: 97.75%; MS (m/e): 398.00 (MH$^+$).

7.1.25 2-Chloro-N4-(4-cyanomethyleneoxyphenyl)-5-fluoro-4-pyrimidineamine (R945069)

In a manner analogous to the preparation of N2,N4-bis(4-cyanomethyleneoxyphenyl)-5-fluoro-2,4-pyrimidinediamine, N4-(4-aminocarbonylmethyleneoxyphenyl)-2-chloro-5-fluoro-4-pyrimidineamine (178 mg, 0.6 mmol), trifluoroacetic anhydride (0.17 mL, 1.2 mmol) and pyridine (0.15 mL, 1.84 mmol) gave 2-chloro-N4-(4-cyanomethyleneoxyphenyl)-5-fluoro-4-pyrimidineamine (110 mg, 66%). $^1$H NMR (acetone-d$_6$): δ 5.22 (s, 2H), 7.24 (d, J=9.3 Hz, 2H), 7.62 (d, J=9.0 Hz, 2H), 8.94 (d, J=1.8 Hz, 1H); $^{19}$F NMR (acetone-d$_6$): −137.60; LCMS: ret. time: 26.19 min.; purity: 89.93%; MS (m/e): 279.06 (MH$^+$).

7.1.26 N4-(4-Acetoxyphenyl)-2-chloro-5-fluoro-4-pyrimidineamine (R940210)

In like manner to the preparation of 2-chloro-N4-(3,4-ethylenedioxyphenyl)-5-fluoro-4-pyrimidineamine, 2,4-dichloro-5-fluoropyrimidine and 4-acetoxyaniline were reacted to prepare N4-(4-acetoxyphenyl)-2-chloro-5-fluoro-4-pyrimidineamine. LCMS: ret. time: 25.97 min.; purity: 98%; MS (m/e): 281 (M$^+$); $^1$H NMR (CDCl$_3$): δ 8.07 (1H, d, J=2.7 Hz), 7.64 (2H, d, J=9 Hz), 7.12 (2H, d, J=9 Hz), 7.00 (1H, s), 2.31 (3H, s).

7.1.27 2-Chloro-5-fluoro-N4-(4-hydroxyphenyl)-4-pyrimidineamine (R940211)

In like manner to the preparation of 2-chloro-N4-(3,4-ethylenedioxyphenyl)-5-fluoro-4-pyrimidineamine, 2,4-dichloro-5-fluoropyrimidine and 4-hydroxyaniline were reacted to prepare 2-chloro-5-fluoro-N4-(4-hydroxyphenyl)-4-pyrimidineamine. LCMS: ret. time: 20.10 min.; purity: 98%; MS (m/e): 240 (MH$^+$); $^1$H NMR (CDCl$_3$): δ 8.02 (1H, d, J=2.7 Hz), 7.46 (2H, d, J=8.7 Hz), 6.86 (2H, d, J=9 Hz), 6.85 (1H, s), 4.94 (1H, s).

7.1.28 2-Chloro-N4-(2,3-dimethyl-4-hydroxyphenyl)-5-fluoro-4-pyrimidineamine (R940213)

In like manner to the preparation of 2-chloro-N4-(3,4-ethylenedioxyphenyl)-5-fluoro-4-pyrimidineamine, 2,4-dichloro-5-fluoropyrimidine and 2,3-dimethyl-4-hydroxyaniline were reacted to prepare 2-chloro-N4-(2,3-dimethyl-4-hydroxyphenyl)-5-fluoro-4-pyrimidineamine. LCMS: ret. time: 23.29 min.; purity: 93%; MS (m/e): 268 (MH$^+$); $^1$H NMR (CDCl$_3$): δ 8.00 (1H, d, J=2.7 Hz), 7.16 (1H, d, J=8.7 Hz), 6.68 (1H, d, J=8.7 Hz), 6.61 (1H, s), 4.87 (1H, s), 2.21 (3H, s), 2.16 (3H, s).

7.1.29 2-Chloro-N4-(3-chloro-4-hydroxy-5-methylphenyl)-5-fluoro-4-pyrimidineamine (R940230)

In like manner to the preparation of 2-chloro-N4-(3,4-ethylenedioxyphenyl)-5-fluoro-4-pyrimidineamine, 2,4-dichloro-5-fluoropyrimidine and 3-chloro-4-hydroxy-5-methylaniline were reacted to prepare 2-chloro-N4-(3-chloro-4-hydroxy-5-methylphenyl)-5-fluoro-4-pyrimidineamine. LCMS: ret. time: 26.26 min.; purity: 90%; $^1$H NMR (DMSO-d6): δ 9.94 (1H, s), 9.21 (1H, s), 8.37 (1H, d, 3.6 Hz), 7.68 (1H, s), 7.41 (1H, s), 2.30 (3H, s).

7.1.30 2-Chloro-5-fluoro-N4-[4-[3-(N-morpholino)propyl]oxyphenyl]-4-pyrimidineamine (R940247)

In like manner to the preparation of 2-chloro-N4-(3,4-ethylenedioxyphenyl)-5-fluoro-4-pyrimidineamine, 2,4-dichloro-5-fluoropyrimidine and 4-[3-(N-morpholino)propyl]oxyaniline were reacted to prepare 2-chloro-5-fluoro-N4-[4-[3-(N-morpholino)propyl]oxyphenyl]-4-pyrimidineamine. LCMS: ret. time: 17.15 min.; purity: 99%; MS (m/e): 367 (MH$^+$); $^1$H NMR (CDCl$_3$): δ 8.02 (1H, d, J=2.7 Hz), 7.49 (2H, d, J=8.7 Hz), 6.92 (2H, d, J=9 Hz), 6.85 (1H, s), 4.03 (2H, t, J=6.3 Hz), 3.73 (4H, t, J=4.6 Hz), 2.53 (2H, t, J=6.7 Hz), 2.47 (4H, m), 1.98 (2H, m).

7.1.31 N4-[2-[4-(N-Benzylpiperazino)ethyl]]-2-chloro-5-fluoro-4-pyrimidineamine (R940259)

In like manner to the preparation of 2-chloro-N4-(3,4-ethylenedioxyphenyl)-5-fluoro-4-pyrimidineamine 2,4-dichloro-5-fluoropyrimidine and 2-[4-(N-benzylpiperazino)ethylamine were reacted to prepare N4-[2-[4-(N-benzylpiperazino)ethyl]]-2-chloro-5-fluoro-4-pyrimidineamine. LCMS: ret. time: 21.11 min.; purity: 96%; MS (m/e): 349 (M$^+$); $^1$H NMR (CDCl$_3$): δ 7.88 (1H, d, J=2.6 Hz), 7.31-7.17 (4H, m), 7.14 (1H, d, J=1.7 Hz), 7.10 (1H, s), 3.76 (2H, m), 3.24 (2H, m), 2.90 (2H, m), 2.59 (2H, m), 2.34 (2H, m), 1.76 (4H, m).

7.1.32 N4-(3-tert-Butylphenyl)-2-chloro-5-fluoro-4-pyrimidineamine (R940268)

In like manner to the preparation of 2-chloro-N4-(3,4-ethylenedioxyphenyl)-5-fluoro-4-pyrimidineamine, 2,4-dichloro-5-fluoropyrimidine and 3-tert-butylaniline were reacted to prepare N4-(3-tert-butylphenyl)-2-chloro-5-fluoro-4-pyrimidineamine. LCMS: ret. time: 33.96 min.; purity: 98%; MS (m/e): 279 (M$^+$); $^1$H NMR (CDCl$_3$): δ 8.05 (1H, d, J=3 Hz), 7.62 (1H, t, J=1.3 Hz), 7.50 (1H, m), 7.34 (1H, t, J=7.8 Hz), 7.22 (1H, m), 6.96 (1H, s1), 1.34 (9H, s).

7.1.33 2-Chloro-5-fluoro-N4-[3-(hydroxymethyl)phenyl]-4-pyrimidineamine (R925756)

In a manner similar to the preparation of 2-chloro-N4-(3,4-ethylenedioxyphenyl)-5-fluoro-4-pyrimidineamine, 2,4-dichloro-5-fluoropyrimidine and 3-aminobenzylalcohol were reacted to yield 2-chloro-5-fluoro-N4-[3-(hydroxymethyl)phenyl]-4-pyrimidineamine. $^1$H NMR (CDCl$_3$): δ 8.45 (bs, 1H), 7.96 (d, 1H, J=2.9 Hz), 7.65 (d, 1H, J=8.2 Hz), 7.34 (s, 1H), 7.31 (t, 1H, J=8.2 Hz), 7.07 (d, 1H, J=8.2), 4.52 (s, 2H)); $^{19}$F NMR (CDCl$_3$): −44394 (s, 1F); LCMS: ret. time: 20.29 min.; purity: 100%; MS (m/e): 254 (MH$^+$).

7.1.34 2-Chloro-5-fluoro-N4-[4-(hydroxymethyl) phenyl]-4-pyrimidineamine (R925759)

In a manner similar to the preparation of 2-chloro-N4-(3, 4-ethylenedioxyphenyl)-5-fluoro-4-pyrimidineamine, 2,4-dichloro-5-fluoropyrimidine and 4-aminobenzylalcohol were reacted to yield 2-chloro-5-fluoro-N4-[4-(hydroxymethyl)phenyl]-4-pyrimidineamine. $^1$H NMR (CDCl$_3$): δ 8.08 (d, 1H, J=2.7 Hz), 7.62 (d, 2H, J=9.0 Hz), 7.40 (d, 2H, J=8.1 Hz), 6.99 (bs, 1H), 4.70 (s, 2H); $^{19}$F NMR (CDCl$_3$): −44570 (s, 1F); LCMS: ret. time: 19.57 min.; purity: 99%; MS (m/e): 254 (MH$^+$).

7.1.35 2-Chloro-N4-(3,3-dihydroisobenzofuranynl-1-one-6-yl)-5-fluoro-4-pyrimidineamine R940279

In like manner to the preparation of 2-chloro-N4-(3,4-ethylenedioxyphenyl)-5-fluoro-4-pyrimidineamine, 2,4-dichloro-5-fluoropyrimidine and 6-amino-3,3-dihydroisobenzofuran-1-one were reacted to give 2-chloro-N4-(3,3-dihydroisobenzofuranynl-1-one-6-yl)-5-fluoro-4-pyrimidineamine. LCMS: ret. time: 21.15 min.; purity: 94.7%; MS (m/e): 280 (MH$^+$).

7.1.36 2-Chloro-5-fluoro-N4-((2R)-hydroxy-(1S)-methyl-2-phenylethyl)-4-pyrimidineamine (R925762)

In a manner similar to the preparation of 2-chloro-N4-(3, 4-ethylenedioxyphenyl)-5-fluoro-4-pyrimidineamine, 2,4-dichloro-5-fluoropyrimidine and (1R,2S)-(−)-norephedrine were reacted to yield 2-chloro-5-fluoro-N4-(2R-hydroxy-1S-methyl-2-phenylethyl)-4-pyrimidineamine. $^1$H NMR (CDCl$_3$): δ 7.85 (d, 1H, J=3.0 Hz), 7.38 (m, 5H), 5.56 (d, 1H, J=7.5 Hz), 5.00 (d, 1H, J=3.0 Hz), 4.54 (m, 1H), 2.87 (bs, 1H), 1.10 (d, 1H, J=6.9 Hz); $^{19}$F NMR (CDCl$_3$): −44408.

7.1.37 N-(2-Chloro-6-ethoxycarbonyl-5-nitro-4-pyrimidinyl)glycine Ethyl Ester (R925850)

In a manner similar to the preparation of 2-chloro-N4-(3, 4-ethylenedioxyphenyl)-5-fluoro-4-pyrimidineamine, 2,4-dichloro-6-ethoxycarbonyl-5-nitropyrimidine and glycine ethyl ester hydrochloride salt were reacted to yield N-(2-chloro-6-ethoxycarbonyl-5-nitro-4-pyrimidinyl)glycine Ethyl Ester. $^1$H NMR (CDCl$_3$): δ 8.87 (bs, 1H), 4.48 (q, 2H, J=7.2 Hz), 4.39 (d, 2H, J=5.1 Hz), 1.40 (t, 3H, J=6.9 Hz), 1.33 (t, 3H, J=7.2 Hz); LCMS: ret. time: 28.27 min.; purity: 97%; MS (m/e): 332 (M$^+$).

7.1.38 2-Chloro-5-fluoro-N4-(2-hydroxy-2-phenylethyl)-4-pyrimidineamine (R925763)

In a manner similar to the preparation of 2-chloro-N4-(3, 4-ethylenedioxyphenyl)-5-fluoro-4-pyrimidineamine, 2,4-dichloro-5-fluoropyrimidine and 2-amino-1-phenylethanol were reacted to yield 2-chloro-5-fluoro-N4-(2-hydroxy-2-phenylethyl)-4-pyrimidineamine. $^1$H NMR (CDCl$_3$): δ 7.88 (d, 1H, J=3.0 Hz), 7.41-7.32 (m, 5H), 5.71 (bs, 1H), 4.97 (d, 1H, J=8.1 Hz), 3.98 (m, 1H), 3.56 (m, 1H), 2.57 (s, 1H); $^{19}$F NMR (CDCl$_3$): −45149; LCMS: ret. time: 22.27 min.; purity: 98%; MS (m/e): 263 (M$^+$).

7.1.39 2-Chloro-5-fluoro-N4-(furfuryl)-4-pyrimidineamine (R925764)

In a manner similar to the preparation of 2-chloro-N4-(3, 4-ethylenedioxyphenyl)-5-fluoro-4-pyrimidineamine, 2,4-dichloro-5-fluoropyrimidine and furfurylamine were reacted to yield 2-chloro-5-fluoro-N4-(furfuryl)-4-pyrimidineamine. $^1$H NMR (CDCl$_3$): δ 7.91 (d, 1H, J=1.8 Hz), 7.39 (d, 1H, J=1.2 Hz), 6.35 (m, 2H), 5.50 (bs, 1H), 4.69 (d, 2H, J=5.1 Hz); $^{19}$F NMR (CDCl$_3$): −45163; LCMS: ret. time: 24.52 min.; purity: 97%; MS (m/e): 228 (M$^+$).

7.1.40 R935010: (±)-2-Chloro-5-fluoro-N4-[1-(4-hydroxyphenyl)ethyl]-4-pyrimidineamine In like manner to the preparation of 2-chloro-N4-(3,4-ethylenedioxyphenyl)-5-fluoro-4-pyrimidineamine, 2,4-dichloro-5-fluoropyrimidine was reacted with 1-(4-hydroxyphenyl)ethylamine to provide (±)-2-chloro-5-fluoro-N4-[1-(4-hydroxyphenyl)ethyl]-4-pyrimidineamine. $^1$H NMR (CDCl$_3$): δ 7.88 (d, 1H, J=2.3 Hz), 7.50-7.47 (dd, 2H, J=1.7 and 8.7 Hz), 7.26-7.23 (dd, J=8.7 and 1.7 Hz), 5.35-5.28 (m, 2H), 1.59 (d, 3H, J=7.0 Hz).

7.1.41 R935011: (±)-N4-[1-(4-Bromophenyl)ethyl]-2-chloro-5-fluoro-4-pyrimidineamine In like manner to the preparation of 2-chloro-N4-(3,4-ethylenedioxyphenyl)-5-fluoro-4-pyrimidineamine, 2,4-dichloro-5-fluoropyrimidine was reacted with 1-(4-bromophenyl)ethylamine to provide (±)-N4-[1-(4-bromophenyl)ethyl]-2-chloro-5-fluoro-4-pyrimidineamine: $^1$H NMR (CDCl$_3$): δ 7.88 (d, 1H, J=2.3 Hz), 7.49 (d, 2H, J=8.7 Hz), 7.25 (d, 2H, J=8.7 Hz), 4.45-5.26 (m, 2H), 1.59 (d, 3H, J=7.0 Hz).

7.1.42 R935007: 2-chloro-5-fluoro-N4-[1-[(1S)-phenyl]ethyl]-4-pyrimidineamine In like manner to the preparation of of 2-chloro-N4-(3,4-ethylenedioxyphenyl)-5-fluoro-4-pyrimidineamine, 2,4-dichloro-5-fluoropyrimidine and 1-(1S)-phenyl ethylamine were reacted to produce 2-chloro-5-fluoro-N4-[1-[(1S)-phenyl]ethyl]-4-pyrimidineamine. $^1$H NMR (CDCl$_3$): δ 7.86 (d, 1H, J=2.9 Hz), 7.37 (d, 4H, J=4.7 Hz), 7.34-7.30 (m, 1H), 5.40-5.32 (m, 2H), 1.62 (d, 3H, J=6.4 Hz); LCMS: ret. time: 29.5 min.; purity: 98%; MS (m/e): 252 (MH$^+$).

7.1.43 R935008: 2-Chloro-5-fluoro-N4-[1-[(1R)-pheny]ethyl]-4-pyrimidineamine In like manner to the preparation of 2-chloro-N4-(3,4-ethylenedioxyphenyl)-5-fluoro-4-pyrimidineamine, 2,4-dichloro-5-fluoropyrimidine and 1-(1R)-phenyl ethylamine were reacted to produce 2-chloro-5-fluoro-N4-[1-[(1R)-phenyl]ethyl]-4-pyrimidineamine. $^1$H NMR (CDCl$_3$): δ 7.87 (d, 1H, J=2.9 Hz), 7.37 (d, 4H, J=4.1 Hz), 7.34-7.30 (m, 1H), 5.38-5.31 (m, 2H), 1.62 (d, 3H, J=6.4 Hz).

7.1.44 R935012: 2-Chloro-N4-[[di(3,5-di(trifluoromethyl)phenyl)]methyl]-5-fluoro-4-pyrimidineamine In like manner to the preparation of 2-chloro-N4-(3,4-ethylenedioxyphenyl)-5-fluoro-4-pyrimidineamine, 2,4-dichloro-5-fluoropyrimidine was reacted with di[3,5-di(trifluoromethyl)phenyl]methylamine to provide 2-chloro-N4-

[[di(3,5-di(trifluoromethyl)phenyl)]methyl]-5-fluoro-4-pyrimidineamine. $^1$H NMR (CDCl$_3$): δ 8.06 (d, 1H, J=2.3 Hz), 7.92 (s, 2H), 7.74 (s, 4H), 6.75 (d, 1H, J=7.6 Hz), 5.80 (d, 1H, J=7.0 Hz).

7.1.45 R935014: 2-Chloro-5-fluoro-N4-[1-[(1R)-4-methoxyphenyl]ethyl]-4-pyrimidineamine In like manner to the preparation of 2-chloro-N4-(3,4-ethylenedioxyphenyl)-5-fluoro-4-pyrimidineamine, 2,4-dichloro-5-fluoropyrimidine was reacted with (R)-(±)-1-(4-methoxyphenyl) ethylamine to provide 2-chloro-5-fluoro-N4-[1-[(1R)-4-methoxyphenyl]ethyl]-4-pyrimidineamine. $^1$H NMR (CDCl$_3$): δ 7.84 (d, 1H, J=2.3 Hz), 7.30 (d, 2H, J=8.8 Hz), 6.89 (d, 2H, J=8.8 Hz), 5.39-5.26 (m, 2H), 3.80 (s, 3H), 1.59 (d, 3H, J=6.4 Hz).

7.1.46 R935015: 2-Chloro-5-fluoro-N4-[1-[(1S)-4-methoxyphenyl]ethyl]-4-pyrimidineamine In like manner to the preparation of 2-chloro-5-fluoro-N4-(3,4-ethylenedioxyphenyl)-4-pyrimidineamine, 2,4-dichloro-5-fluoropyrimidine was reacted with (S)-(±)-1-(4-methoxyphenyl)ethylamine to provide 2-chloro-5-fluoro-N4-[1-[(1S)-4-methoxyphenyl]ethyl]-4-pyrimidineamine. $^1$H NMR (CDCl$_3$): δ 7.85 (d, 1H, J=2.3 Hz), 7.31 (d, 2H, J=8.8 Hz), 6.89 (d, 2H, J=8.8 Hz), 5.38-5.29 (m, 2H), 3.80 (s, 3H), 1.59 (d, 3H, J=7.7 Hz).

7.1.47 R935013: 2-Chloro-N-(fluoren-9-yl)-5-fluoro-4-pyrimidineamine

In like manner to the preparation of 2-chloro-N4-(3,4-ethylenedioxyphenyl)-5-fluoro 4-pyrimidineamine, 9-aminofluorene hydrochloride and 2,4-dichloro-5-fluoropyrimidine with added diisopropylethylamine were reacted to produce 2-chloro-N-(fluoren-9-yl)-5-fluoro-4-pyrimidineamine. $^1$H NMR (CDCl$_3$): δ 7.97 (d, 1H, J=2.3 Hz), 7.73 (d, 2H, J=7.6 Hz), 7.59(d, 2H, J=7.6 Hz), 7.44 (t, 2H, J=7.6 Hz), 7.32 (app t, 2H, J=7.6 Hz), 6.50 (d, 1H, J=8.8 Hz), 5.45 (d, 1H, J=8.4 Hz).

7.1.48 R935210: 2-Chloro-5-fluoro-N-[1-(methoxycarbonyl)methyl-indazoline-6-yl]-4-pyrimidineamine In like manner to the preparation of 2-chloro-N-(3,4-ethylenedioxyphenyl)-5-fluoro-4-pyrimidineamine, experiment, 2,4-dichloro-5-fluoropyrimidine was reacted with 4-(methoxycarbonylmethyleneoxy)aniline to produce 2-chloro-5-fluoro-N-[4-(methoxycarbonylmethyleneoxy)phenyl]-4-pyrimidineamine. $^1$H NMR (DMSO-d6): δ 10.17 (s, 1H), 8.33 (d, 1H, J=3.5 Hz), 8.05 (s, 1H), 7.91 (s, 1H), 7.74 (d, 1H, J=8.2 Hz), 7.40 (d, 1H, J=7.6 Hz), 5.31 (s, 2H), 3.66 (s, 3H).

7.1.49 R935200: 2-Chloro-5-fluoro-N-(1-methyl-indazoline-5-yl)-4-pyrimidineamine In like manner to the preparation of 2-chloro-N4-(3,4-ethylenedioxyphenyl)-5-fluoro-4-pyrimidineamine, 2,4-dichloro-5-fluoropyrimidine and 5-amino-1-methyl-indazoline were reacted to provide 2-chloro-5-fluoro-N-(1-methyl-indazoline-5-yl)-4-pyrimidineamine. $^1$H NMR (DMSO-d6): δ 10.01 (s, 1H), 8.27 (d, 1H, J=3.5 Hz), 8.04 (d, 1H, J=1.7 Hz), 7.98 (d, 1H, J=1.7 Hz), 7.64 (d, 1H, J=8.8 Hz), 7.56 (dd, 1H, J=1.7 and 8.8 Hz), 4.02 (s, 3H). LCMS: ret. time: 21.72 min.; purity: 99%; MS (m/e): 278 (MH$^+$).

7.1.50 R935017: N-(5-Bromo-2-chloropyrimidinyl)-4-fluorophenylethylamine

In like manner to the preparation of 2-chloro-N4-(3,4-ethylenedioxyphenyl)-5-fluoro 4-pyrimidineamine, 4-fluoro-α-methylbenzylamine and 5-bromo-2,4-dichloropyrimidine were reacted to produce N-(5-bromo-2-chloropyrimidinyl)-4-fluorophenylethylamine. $^1$H NMR (CDCl$_3$): δ 8.12 (s, 1H), 7.35-7.25 (dd, 2H, J=3.5 and 8.7 Hz), 7.05 (t, 1H, J=8.7 Hz), 5.63 (d, 1H, J=6.4 Hz), 5.36 (dq, 1H, 1H, J=6.4 and 7.0 Hz), 1.60 (d, 3H, J=7.0 Hz); LCMS: ret. time: 30.73 min.; purity: 94%; MS (m/e): 331 (MH$^+$).

7.1.51 R935009: (±)-N-(2-Chloro-5-fluoropyrimidinyl)-1-(4-fluorophenyl)ethylamine In like manner to the preparation of 2-chloro-N4-(3,4-ethylenedioxyphenyl)-5-fluoro 4-pyrimidineamine, 4-fluoro-α-methylbenzylamine and 2,4-dichloro-5-fluoropyrimidine were reacted to produce (±)-N-(2-chloro-5-fluoropyrimidinyl)-1-(4-fluorophenyl)ethylamine. $^1$H NMR (CDCl$_3$): δ 7.87 (d, 1H, J=2.3 Hz), 7.37-7.33 (dd, 2H, J=5.4 and 8.4 Hz), 7.04 (t, 2H, J=8.4 Hz), 5.35-5.31 (m, 2H), 1.60 (d, 3H, J=6.4 Hz); LCMS: ret. time: 32.90 min.; purity: 98%; MS (m/e): 270 (MH$^+$).

7.1.52 R935022: 5-Bromo-2-chloro-N4-[4-(N-methyl-2-methoxycarbonyl)ypyrrolyl)-4-pyrimidineamine In like manner to the preparation of 2-chloro-N4-(3,4-ethylenedioxyphenyl)-5-fluoro 4-pyrimidineamine, 5-bromo-2,4-dichloropyrimidine and N-methyl-2-carbomethoxy-4-aminopyrrole hydrochloride with added diisopropylethylamine were reacted to produce the desired product 5-bromo-2-chloro-N-(N-methyl-2-carbomethoxypyrrol-4-yl)-4-pyrimidineamine. $^1$H NMR (CDCl$_3$): δ 8.21 (s, 1H), 7.43 (d, 1H, J=1.8 Hz), 7.13 (br s, 1H), 6.84 (d, 1H, J=1.8 Hz), 3.95 (s, 3H), 3.82 (s, 3H); LCMS: ret. time: 26.96 min.; purity: 91%; MS (m/e): 346 (MH$^+$).

7.1.53 R935234: 2-Chloro-5-fluoro-N4-[4-(3-phenyl-1,2,4-oxadiazol-5-yl)methyleneoxyphenyl]-4-pyrimidineamine In like manner to the preparation of 2-chloro-N4-(3,4-ethylenedioxyphenyl)-5-fluoro-4-pyrimidineamine, 2,4-dichloro-5-fluoropyrimidine and 5-(4-aminophenoxymethyl)-3-phenyl-1,2,4-oxadiazole were reacted to produce 2-chloro-5-fluoro-N4-[4-(3-phenyl-1,2,4-oxadiazol-5-yl)methyleneoxyphenyl]-4-pyrimidineamine. $^1$H NMR (DMSO-d$_6$): δ 9.92 (s, 1H), 8.26 (d, 1H, J=3.5 Hz), 8.02-7.99 (m, 2H), 7.60-7.56 (m, 5H), 7.11 (d, 2H, J=8.8 Hz), 5.58 (s, 2H); LCMS: ret. time: 32.09 min.; purity: 96%; MS (m/e): 398 (MH$^+$)

7.1.54 R935235: 2-Chloro-5-fluoro-N4-[4-(3-methyl-1,2,4-oxadiazol-5-yl)methyleneoxyphenyl]-4-pyrimidineamine In like manner to the preparation of 2-chloro-N4-(3,4-ethylenedioxyphenyl)-5-fluoro-4-pyrimidineamine, 2,4-dichloro-5-fluoropyrimidine and 5-(4-aminophenoxymethyl)-3-methyl-1,2-4-oxadiazole were reacted to produce 2-chloro-5-fluoro-N4-[4-(3-methyl-1,2,4-oxadiazol-5-yl) methyleneoxyphenyl]-4-pyrimidineamine. $^1$H NMR (DMSO-d$_6$): δ 9.91 (s, 1H), 8.26 (d, 1H, J=3.5 Hz), 7.56 (d, 2H, J=8.8 Hz), 7.05 (d, 2H, J=8.8 Hz), 5.46 (s, 2H), 2.34 (s, 3H); LCMS: ret. time: 25.05 min.; purity: 98%; MS (m/e): 336 (MH$^+$).

7.1.55 R935236: 2-Chloro-5-fluoro-N4-[4-[(1-ethoxycarbonyl-1-methyl)ethyl]phenyl]-4-pyrimidineamine In like manner to the preparation of 2-chloro-N4-(3,4-ethylenedioxyphenyl)-5-fluoro-4-pyrimidineamine, 2,4-dichloro-5-fluoropyrimidine and 4-[1-ethoxycarbonyl-1-methyl)ethyl]aniline were reacted to produce 2-chloro-5-fluoro-N4-[4-[(1-ethoxycarbonyl-1-methyl)ethyl]phenyl]-4-pyrimidineamine. $^1$H NMR (DMSO-d$_6$): δ 9.99 (s, 1H), 8.30 (d, 1H, J=3.5 Hz), 7.60 (d, 2H, J=8.8 Hz), 7.30 (d, 2H, J=8.8 Hz), 4.04 (qt, 2H, J=7.0 Hz), 1.47 (s, 6H), 1.10 (t, 3H, J=7.0 Hz); LCMS: ret. time: 31.07 min.; purity: 97%; MS (m/e): 338 (MH$^+$)

7.1.56 2,4-Dichloro-5-ethoxycarbonylpyrimidine

A dry reaction flask equipped with a stirring bar and a reflux condenser was charged with 5-ethoxycarbonyluracil (1.84 g, 10 mmol), POCl$_3$ (10 mL) and N,N-dimethylaniline (1 mL) and heated at 90° C. for 2 h. The excess POCl$_3$ was removed under a reduced pressure and quenched with ice-water (100 g). The aqueous solution was extracted with ethyl ether (3×100 mL), washed with saturated aqueous NaHCO$_3$ solution and water (100 mL, each). After drying over sodium sulfate, the ethyl ether was removed and the residue was dried under a high vacuum to afford 2,4-dichloro-5-ethoxycarbonylpyrimidine. $^1$H NMR (CDCl$_3$): δ 9.00 (s, 1H), 4.45 (q, 2H, J=6.9 Hz), 1.42 (t, 3H, J=6.9 Hz).

7.1.57 N-(2-Chloro-5-ethoxycarbonyl-4-pyrimidinyl)-L-phenylalanine Ethyl Ester (R926518) and N-(4-Chloro-5-ethoxycarbonyl-2-pyrimidinyl)-L-phenylalanine Ethyl Ester (R926519)

A mixture of L-phenylalanine Ethyl Ester Hydrochloride (0.137 g, 0.6 mmol) 2,4-dichloro5-ethoxycarbonylpyrimidine (0.112 g, 0.5 mmol), triethylamine (0.7 mL, 0.6 mmol) in THF (4 mL) in a sealed tube was heated at 100° C. for 3 h. The reaction was diluted with H$_2$O (20 ML), extracted with CH$_2$Cl$_2$ (3×50 mL), washed with 2N HCl (10 mL), water (10 mL) and solvent was evaporated. The residue obtained was purified by preparative TLC using 15% EtOAc in hexanes to obtain two products mainly, N-(2-chloro-5-ethoxycarbonyl-4-pyrimidinyl)-L-phenylalanine Ethyl Ester (R926518). $^1$H NMR (CDCl$_3$): δ 8.72 (d, 1H, J=6.92 Hz), 8.66 (s, 1H), 7.32-7.17 (m, 5H), 5.05 (dq, 1H, J=1.2 and 5.7 Hz), 4.34 (q, 2H, J=6.9 Hz), 4.20 (q, 2H, J=5.1 Hz), 3.24 (dd, 1H, J=5.4 Hz), 3.16 (dd, 1H, J=7.5 Hz), 1.35 (t, 3H, J=7.2 Hz), 1.24 (t, 3H, J=7.2 Hz); LCMS: ret. time: 37.15 min.; purity: 99%; MS (m/e): 378 (MH$^+$) and N-(4-chloro-5-ethoxycarbonyl-2-pyrimidinyl)-L-phenylalanine Ethyl Ester (R926519). $^1$H NMR (CDCl$_3$): δ 8.83 (s, 1H), 7.28 (m, 3H), 7.18 (m, 2H), 6.00 (bt, 1H), 4.99 (bdq, 1H), 4.36 (q, 2H, J=7.8 Hz), 4.19 (q, 2H, J=6.9 Hz), 3.20 (q, 2H, J=6.9 Hz), 1.38 (t, 3H, J=4.5 Hz), 1.24 (t, 3H, J=6 Hz); LCMS: ret. time: 34.80 min.; purity: 88%; MS (m/e): 378 (M$^+$).

7.1.58 N-(2-Chloro-5-ethoxycarbonyl-4-pyrimidinyl)-L-valine Ethyl Ester (R926520) and N-(4-Chloro-5-ethoxycarbonyl-2-pyrimidinyl)-L-valine Ethyl Ester (R926521)

In like manner to the preparation of N-(2-chloro-5-ethoxycarbonyl-4-pyrimidinyl)-L-phenylalanine Ethyl Ester, 2,4-dichloro-5-ethoxycarbonylpyrimidine and L-valine Ethyl Ester were reacted to prepare N-(2-chloro-5-ethoxycarbonyl-4-pyrimidinyl)-L-valine Ethyl Ester (R926520). $^1$H NMR (CDCl$_3$): δ 8.80 (d, 1H, J=8.1 Hz), 8.68 (s, 1H), 4.77 (dd, 1H, J=4.8 Hz), 4.36 (q, 2H, J=7.2 Hz), 4.24 (q, 2H, J=6.6 Hz), 2.38 (m, 1H), 1.39 (t, 3H, J=6.9 Hz), 1.29 (t, 3H, J=7.2 Hz), 1.03 (d, 3H, J=3 Hz), 1.00 (d, 3H, J=2.7 Hz); LCMS: ret. time: 36.54 min.; purity: 89%; MS (m/e): 330 (MH$^+$) and N-(4-chloro-5-ethoxycarbonyl-2-pyrimidinyl)-L-valine Ethyl Ester (R926521). $^1$H NMR (CDCl$_3$): δ 8.82 (s, 1H), 6.02 (m, 1H), 4.69 (dd, 1H, J=4.8 and 4.5 Hz), 4.33 (q, 2H, J=7.5 Hz), 4.23 (q, 2H, J=7.5 Hz), 2.28 (sept, 1H), 1.34 (t, 3H, J=6.9 Hz), 1.28 (t, 3H, J=7 Hz), 1.00 (d, 6H, J=7.2 Hz); LCMS: ret. time: 33.53 min.; purity: 91%; MS (m/e): 330 (M$^+$).

7.1.59 N-(2-Chloro-5-ethoxycarbonyl-4-pyrimidinyl)-L-leucine Ethyl Ester (R926522)

In like manner to the preparation of N-(2-chloro-5-ethoxycarbonyl-4-pyrimidinyl)-L-phenylalanine Ethyl Ester, 2,4-dichloro-5-ethoxycarbonylpyrimidine and L-leucine Ethyl Ester were reacted to prepare N-(2-chloro-5-ethoxycarbonyl-4-pyrimidinyl)-L-leucine Ethyl Ester. $^1$H NMR (CDCl$_3$): δ 8.69 (s, 1H), 8.64 (d, 1H, 7.8 Hz), 4.84 (s, 1H), 4.38 (q, 2H, J=7.2 Hz), 3.75 (s, 3H), 1.73 (m, 2H), 1.39 (t, 3H, J=6.9 Hz), 0.97 (d, 3H, J=4.2 Hz), 0.95 (d, 3H, J=4.8 Hz); LCMS: ret. time: 36.09 min.; purity: 92%; MS (m/e): 330 (MH$^+$).

7.1.60 N-(2-Chloro-5-ethoxycarbonyl-4-pyrimidinyl)-L-alanine Ethyl Ester (R926523) and N-(4-Chloro-5-ethoxycarbonyl-2-pyrimidinyl)-L-alanine Ethyl Ester (R926524)

In like manner to the preparation of N-(2-chloro-ethoxycarbonyl-4-pyrimidinyl)-L-phenylalanine Ethyl Ester, 2,4-dichloro-5-ethoxycarbonylpyrimidine and L-valine Ethyl Ester were reacted to prepare N-(2-chloro-5-ethoxycarbonyl-4-pyrimidinyl)-L-alanine Ethyl Ester (R926523). $^1$H NMR (CDCl$_3$): δ 8.80 (bd, 1H), 8.68 (s, 1H), 4.79 (q, 1H, J=7.2 Hz), 4.35 (q, 2H, J=7.2 Hz), 4.24 (m, 2H), 1.53 (d, 3H, J=7.2 Hz), 1.38 (t, 3H, J=7.2 Hz), 1.29 (t, 3H, J=7.2 Hz); LCMS: ret. time: 31.89 min.; purity: 94%; MS (m/e): 303 (MH$^+$) and N-(4-chloro-5-ethoxycarbonyl-2-pyrimidinyl)-L-alanine Ethyl Ester (R926524). $^1$H NMR (CDCl$_3$): δ 8.80 (s, 1H), 6.01 (bs, 1H), 4.65 (bq, 1H), 4.35 (q, 2H), 4.20 (q, 2H), 1.55, t, 3H), 1.40 (t, 3H), 1.25 (t, 3H); LCMS: ret. time: 28.78 min.; purity: 84%; MS (m/e): 302 (M$^+$).

7.1.61 2-Chloro-N4-(4-n-butyloxyphenyl)-5-fluoro-4-pyrimidineamine

To a solution of 2,4-dichloro-5-fluoropyrimidine (0.5 g, 3.0 mmol) and 4-n-butoxyaniline (0.49 g, 3 mmol) in acetone/H$_2$O (1:9 mL) at room temperature was added concentrated HCl (0.1 mL). The mixture was heated at reflux for 1 h, cooled to room temperature, and made basic with 2 N NaOH (2 mL). The aqueous layer was extracted with EtOAc (2×50 mL) and the combined organic extracts were dried (Na$_2$SO$_4$), filtered, and concentrated in vacuo. The crude black solid was purified by chromatography (4:1 hexanes/EtOAc) to afford 2-chloro-N4-(4-n-butyloxyphenyl)-5-fluoro-4-pyrimidineamine (0.71 g, 80%) as a brown oil: $^1$H NMR (300 MHz, CDCl$_3$) δ 8.01 (d, J=2.7 Hz, 1H), 7.51-7.46 (m, 2H), 6.95-6.89 (m, 2H), 6.83 (bs, 1H), 3.99-3.95 (t, J=6.5 Hz, 2H), 1.82-1.57 (m, 2H), 1.53-1.43 (m, 2H), 0.98 (t, J=7.2 Hz, 3H).

7.1.62 2-Chloro-N4-(4-n-hexyloxyphenyl)-5-fluoro-4-pyridineamine

In like manner to the preparation of 2-chloro-N4-(4-n-butyloxyphenyl)-5-fluoro-4-pyrimidineamine, the reaction of 2,4-dichloro-5-fluoropyrimidine with 4-n-hexyloxyaniline gave 2-chloro-N4-(4-n-hexyloxyphenyl)-5-fluoro-4-pyridineamine. The crude product was purified by chromatography (4:1 CHCl$_3$/EtOAc) to afford (14) (0.74 g, 76%) as a red-brown oil that solidified upon standing: $^1$H NMR (300 MHz, CDCl$_3$) δ 8.01 (d, J=2.7 Hz, 1H), 7.50 (d, J=9.0 Hz, 2H), 6.92 (d, J=9.0 Hz, 2H), 6.84 (bs, 1H), 3.96 (t, J=6.5 Hz, 2H), 1.83-1.74 (m, 2H), 1.48-1.41 (m, 2H), 1.36-1.34 (m, 4H), 0.93-0.89 (m, 3H).

7.1.63 N4-(3-Benzyloxyphenyl)-2-chloro-4-pyrimidineamine

A mixture of 2,6-dichloropyrimidine (2.00 g, 13.4 mmol), 3-benzyloxoaniline (2.07 g, 13.4 mmol) and triethylamine (2.72 g, 26.8 mmol) in 1-butanol (20 mL) was stirred at 50° C. for 17 h. The reaction mixture was concentrated to remove most of the 1-butanol, the crude product was preadsorbed onto silica gel using chloroform and purified by flash chromatography (95:5 chloroform/methanol) to afford N4-(3-benzyloxyphenyl)-2-chloro-4-pyrimidineamine (1.70 g, 40%) as colorless oil: $^1$H NMR (300 MHz, DMSO-d$_6$) δ 10.2 (s, 1H), 8.16 (d, J=6.0 Hz, 1H), 7.48-7.24 (m, 7H), 7.12 (d, J=9.0 Hz, 1H), 6.78 (m, 2H), 5.11 (s, 2H); ESI MS m/z 312 [C$_{17}$H$_{14}$ClN$_3$O+H]+.

7.1.64 N4-[4-(tert-Butoxycarbonylmethyleneoxy)phenyl]-3-chloro-5-ethoxycarbonyl-4-pyrimidineamine (R926578)

In like manner to the preparation of N-(2-chloro-5-ethoxycarbonyl-4-pyrimidinyl)-L-phenylalanine Ethyl Ester, 5-carboxyethoxy-2,4-dichloropyrimidine and tert-butyl 4-aminophenoxyacetate were reacted to prepare N4-[4-(tert-butoxycarbonylmethyleneoxy)phenyl]-2-chloro-5-ethoxycarbonyl-2-chloro-4-pyrimidineamine. LCMS: MS (m/e): 407 (MH$^+$).

7.1.65 N4-(4-Ethoxyphenyl)-5-ethoxycarbonyl-2-trifluoromethyl-4-pyrimidineamine (R926059)

In like manner to the preparation of N-(2-chloro-5-ethoxycarbonyl-4-pyrimidinyl)-L-phenylalanine Ethyl Ester, 4-chloro-5-ethoxycarbonyl-2-trifluoromethylpyrimidine and 4-ethoxyaniline were reacted to prepare N4-(4-ethoxyphenyl)-5-ethoxycarbonyl-2-trifluoromethyl-4-pyrimidineamine. $^1$H NMR (CDCl$_3$): δ 10.39 (s, 1H), 9.02 (s, 1H), 7.59 (dd, 2H, J=2.1 and 7.2 Hz), 6.91 (dd, 2H, J=1.8 and 6.6 Hz), 4.44 (q, 2H, J=7.5 Hz), 4.06 (q, 2H, J=7.2 Hz), 1.44 (m, 6H); LCMS: ret. time: 38.49 min.; purity: 100%; MS (m/e): 356 (MH$^+$).

7.1.66 N2-(4-Ethoxyphenyl)-5-methoxycarbonyl-4-trifluoromethyl-2-pyrimidineamine (R926060)

In like manner to the preparation of N-(2-chloro-5-ethoxycarbonyl-4-pyrimidinyl)-L-phenylalanine Ethyl Ester, 2-chloro-5-methoxycarbonyl-4-trifluoromethylpyrimidine and 4-ethoxyaniline were reacted to prepare N2-(2-ethoxyphenyl)-5-methoxycarbonyl-4-trifluoromethyl-2-pyrimidineamine. $^1$H NMR (CDCl$_3$): δ 8.98 (s, 1H), 7.47 (m, 3H), 6.91 (dd, 2H, J=2.1 and 6.9 Hz), 4.05 (q, 2H, 6.9 Hz), 1.42 (t, 3H, J=6.8 Hz); $^{19}$F NMR (CDCl$_3$): −19105; LCMS: ret. time: 33.87 min; purity: 100%; MS (m/e): 342 (MH$^+$).

7.1.67 2-Chloro-5-fluoro-N4-[3-(1H-tetrazol-5-yl)phenyl]-4-pyrimidineamine (R926853)

A reaction mixture containing 2,4-dichloro-5-fluoro-pyrimidine (1.2 equivalents) and 3-(tetrazol-5-yl)aniline (1 equivalents) in methanol:water (1:1; v/v) was heated at 60° C. for 24 h. Upon dilution with water and acidification, the solid formed was filtered, washed with water, dried and analyzed to give 2-chloro-5-fluoro-N4-[3-(1H-tetrazol-5-yl)phenyl]-4-pyrimidineamine (R926853). Alternatively this reaction can be achieved by treating 2,4-dichloro-5-fluoropyrimidine (1 equivalent) with 3-(tetrazol-5-yl)aniline (3 equivalents) in methanol:water (1:1; v/v) at 60 oC for 2-3 hours or at room temperature for 24 h to give 2-chloro-5-fluoro-N4-[3-(1H-tetrazol-5-yl)phenyl]-4-pyrimidineamine. $^1$H NMR (DMSO-d6): δ 10.25 (s, 1H), 8.43 (s, 1H), 8.37 (d, 1H, J=3.6 Hz), 7.90 (dd, 1H, J=0.9 and 9 Hz), 7.75 (d, 1H, J=7.5 Hz), 7.61 (t, 1H, J=7.8 Hz); LCMS: purity: 90%; MS (m/e): 292 (MH$^+$).

7.1.68 2-Chloro-N4-(2,5-dimethoxy-4-chlorophenyl)-5-fluoro-4-pyrimidineamine (R926858)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 2,5-dimethoxy-4-chloroaniline gave 2-chloro-N4-(2,5-dimethoxy-4-chlorophenyl)-5-fluoro-4-pyrimidineamine. LCMS: purity: 97%; MS (m/e): 316 (M-2H) and 320 (M+2H).

7.1.69 2-Chloro-5-fluoro-N4-(3-methoxycarbonyl-5-trifluoromethylphenyl)-4-pyrimidineamine (R926861)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 3-methoxycarbonyl-5-trifluoromethylaniline gave 2-chloro-5-fluoro-N4-(3-methoxycarbonyl-5-trifluoromethylphenyl)-4-pyrimidineamine. $^1$H NMR (CD$_3$OD): δ 8.60 (s, 1H), 8.43 (s, 1H), 8.20 (d, 1H, J=3 Hz), 7.99 (s, 1H), 3.96 (s, 3H); $^{19}$F NMR (CD$_3$OD): −18332, −18374; and −44259; LCMS: purity: 91%; MS (m/e): 350 (MH$^+$).

7.1.70 2-Chloro-5-fluoro-N4-[3-(2-phenyl-1,3,4-oxadiazol-5-yl)phenyl]-4-pyrimidineamine (R926869)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 3-(2-phenyl-1,3,4-oxadiazol-5-yl)aniline gave 2-chloro-5-fluoro-N4-[3-(2-phenyl-1,3,4-oxadiazol-5-yl)phenyl]-4-pyrimidineamine. $^1$H NMR (DMSO-d6): δ 10.28 (s, 1H), 8.62 (s, 1H), 8.39 (d, 1H, J=3.3 Hz), 8.11 (m, 2H), 7.98 (bd, 1H, J=6.9 Hz), 7.88 (bd, 1H, J=8.4 Hz), 7.65 (m, 4H); LCMS: purity: 76%; MS (m/e): 76%.

7.1.71 2-Chloro-N4-[3-(2-ethoxycarbonylmethylene-1,3,4-oxadiazol-5-yl)phenyl)-5-fluoro-4-pyrimidineamine (R926873)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 3-(2-ethoxycarbonylmethylene-1,3,4-oxadiazol-5-yl)aniline gave 2-chloro-N4-[3-(2-ethoxycarbonylmethylene-1,3,4-oxadiazol-5-yl)phenyl]-5-fluoro-4-pyrimidineamine. $^1$H NMR (CD$_3$OD): δ 8.42 (t, 1H, J=1.8 Hz), 8.19 (d, 1H, J=3.3 Hz), 7.99 (dt, 1H, J=1.2 and 8.1 Hz), 7.82 (dt, 1H, J=1.2 and 8.1 Hz), 7.58 (t, 1H, J=9 Hz), 4.24 (q, 2H, J=3.9 Hz), 4.17 (s, 2H), 1.28 (t, 3H, J=7.2 Hz); LCMS: purity: 85%; MS (m/e): 379 (MH$^+$).

7.1.72 2-Chloro-5-fluoro-N4-(4-trifluoromethoxyphenyl)-4-pyrimidineamine (R926875)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 4-trifluoromethoxyaniline gave 2-chloro-5-fluoro-N4-(4-trifluoromethoxyphenyl)-4-pyrimidineamine. $^1$H NMR (CDCl$_3$): δ 8.11 (d, 1H, J=2.1 Hz), 7.68 (dd, 2H, J=2.4 and 7.6 Hz), 7.26 (dd, 2H, J=3 and 8.7 Hz), 7.0 (bs, 1H); 19F NMR (CD$_3$OD): 6-16517 and −44523; LCMS: purity: 94%; MS (m/e): 308 (MH$^+$).

7.1.73 2-Chloro-5-fluoro-N4-(4-trifluoromethylphenyl)-4-pyrimidineamine (R926876)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 4-trifluoromethylaniline gave 2-chloro-5-fluoro-N4-(4-trifluoromethylphenyl)-4-pyrimidineamine. $^1$H NMR (CDCl$_3$): δ 8.15 (d, 2.1 Hz), 7.80 (d, 2H, J=7.1 Hz), 7.66 (d, 2H, J=9 Hz), 7.10 (bs, 1H); $^{19}$F NMR (CDCl$_3$): −17682 and −44362; LCMS: purity: 91% and MS (m/z): 292 (MH$^+$).

7.1.74 2-Chloro-N4-(4-chloro-3-trifluoromethylphenyl)-5-fluoro-4-pyrimidineamine (R926877)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 4-chloro-3-trifluoromethylaniline gave 2-chloro-N4-(4-chloro-3-trifluoromethylphenyl)-5-fluoro-4-pyrimidineamine. $^1$H NMR (CDCl$_3$): δ 8.15 (d, 1H, J=2.1 Hz), 7.96 (d, 1H, J=3 Hz), 7.91 (dd, 1H, J=2.7 Hz and 8.7 Hz), 7.53 (d, 1H, J=8.1 Hz), 7.06 (bs, 1H); $^{19}$F NMR (CDCl$_3$): −17892 and −44402; LCMS: purity: 93%; MS (m/e): 326 (M$^+$).

7.1.75 2-Chloro-5-fluoro-N4-(6-methoxypyridin-3-yl)-4-pyrimidineamine (R926878)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 3-amino-6-methoxypyridine gave 2-chloro-5-fluoro-N4-(6-methoxypyridin-3-yl)-4-pyrimidineamine. $^1$H NMR (CD$_3$OD): δ 8.39 (d, 1H, J=3.0 Hz), 8.10 (d, 1H, J=3.6 Hz), 7.95 (dd, 1H, J=2.4 and 9 Hz), 8.30 (d, 1H, J=9 Hz), 3.91 (s, 3H); $^{19}$F NMR (CD$_3$OD): −44737; LCMS: purity: 97%; MS (m/e): 255 (M$^+$).

7.1.76 2-Chloro-N4-(3,4-difluorophenyl)-5-fluoro-4-pyrimidineamine (R926882)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 3,4-difluoroaniline gave 2-chloro-N4-(3,4-difluorophenyl)-5-fluoro-4-pyrimidineamine. $^1$H NMR (CDCl$_3$): δ 8.10 (d, 1H, J=2.1 Hz), 7.72 (m, 1H), 7.22 (m, 2H), 6.95 (bs, 1H); LCMS: purity: 93%; MS (m/e): 260 (M$^+$).

7.1.77 2-Chloro-N4-(3,4-Dichlorophenyl)-5-fluoro-4-pyrimidineamine (R926884)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 3,4-dichloroaniline gave 2-chloro-N4-(3,4-dichlorophenyl)-5-fluoro-4-pyrimidineamine. LCMS: purity: 95%; MS (m/e): 294 (M+2H).

7.1.78 2-Chloro-5-fluoro-N4-(6-methylpyridin-2-yl)-4-pyrimidineamine (R926888)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 2-amino-6-methylpyridine gave 2-chloro-5-fluoro-N4-(6-methylpyridin-2-yl)-4-pyrimidineamine. $^1$H NMR (CDCl$_3$): δ 8.23 (s, 1H), 8.19 (s, 1H), 8.12 (d, 1H, J=3 Hz), 7.55 (bs, 1H), 7.69 (t, 1H, J=7.4 Hz), 9.35 (d, 1H, J=7.5 Hz); 19F NMR (CDCl3): −44073; LCMS: purity: 96%; MS (m/e): 239 (M$^+$).

7.1.79 2-Chloro-N4-(2,6-Dimethoxypyridin-3-yl)-5-fluoro-4-pyrimidineamine (R926889)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 3-amino-2,6-dimethoxypyridine gave 2-chloro-N4-(2,6-dimethoxypyridin-3-yl)-5-fluoro-4-pyrimidineamine. $^1$H NMR (CDCl$_3$): δ 8.57 (d, 1H, J=8.7 Hz), 8.02 (d, 1H, J=2.7 Hz), 6.40 (d, 1H, J=8.1 Hz), 4.03 (s, 3H), 3.98 (s, 3H); $^{19}$F NMR (CDCl$_3$): −44640; LCMS: purity: 90%; MS (m/e): 285 (M$^+$).

7.1.80 2-Chloro-N4-(6-chloropyridin-3-yl)-5-fluoro-4-pyrimidineamine (R920400)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 3-amino-6-chloropyridine gave 2-chloro-N4-(6-chloropyridin-3-yl)-5-fluoro-4-pyrimidineamine. $^1$H NMR (CDCl$_3$): δ 8.53 (d, 1H, J=3 Hz), 8.25 (dd, 1H, J=3 and 9 Hz), 8.15 (d, 1H, J=2.4 Hz), 7.39 (d, 1H, J=8.7 Hz), 7.00 (bs, 1H); LCMS: purity: 98%; MS (m/e): 259 (M$^+$).

7.1.81 2-Chloro-5-fluoro-N4-(4-methylpyridin-2-yl)-4-pyrimidineamine (R920401)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 2-amino-4-methylpyridine gave 2-chloro-5-fluoro-N4-(4-methylpyridin-2-yl)-4-pyrimidineamine. $^1$H NMR (CDCl$_3$): δ 8.22 (s, 1H), 8.16 (d, 1H, J=8.4 Hz), 8.13 (d, 1H, J=2.4 Hz), 6.91 (d, 1H, J=5.4 Hz), 2.42 (s, 3H); LCMS: purity: 87%; MS (m/e): 239 (MH$^+$).

7.1.82 2-Chloro-5-fluoro-N4-(3-trifluoromethoxyphenyl)-4-pyrimidineamine (R920402)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 3-trifluoromethoxyaniline gave 2-chloro-5-fluoro-N4-(3-trifluoromethoxyphenyl)-4-pyrimidineamine. $^1$H NMR (CDCl$_3$): δ 8.12 (d, 1H, J=3 Hz), 7.68 (bs, 1H), 7.53 (dd, 1H, J=1.2 and 8.4 Hz), 7.41 9t, 1H, J=8.1 Hz), 7.04 (bdt, 2H); 19F NMR (CDCl$_3$): −16430 and −44463; LCMS: purity: 89%; MS (m/e): 308 (MH$^+$).

7.1.83 2-Chloro-N4-(3,4-Difluoromethylenedioxyphenyl)-5-fluoro-4-pyrimidineamine (R920403)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 3,4-difluoromethylenedioxyaniline gave 2-chloro-N4-(3,4-difluoromethylenedioxyphenyl)-5-fluoro-4-pyrimidineamine. $^1$H NMR (CDCl$_3$): δ 8.09 (d, 1H, J=3 Hz), 7.70 (d, 1H, J=2.4 Hz), 7.10 (dd, 1H, J=2.4 and 8.7 Hz), 7.06 (t, 1H, J=8.1 Hz), 6.97 (bs, 1H); $^{19}$F NMR (CDCl$_3$): −14175 and −44562; LCMS: purity: 95%; MS (m/e): 304 (MH$^+$).

7.1.84 2-Chloro-5-fluoro-N4-(quinolin-6-yl)-4-pyrimidineamine (R920409)

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 6-aminoquinoline gave 2-chloro-5-fluoro-N4-(quinolin-6-yl)-4-pyrimidineamine. $^1$H NMR (CDCl$_3$): δ 8.02 (dd, 1H, J=2.7 Hz), 8.00 (dd, 1H, J=2.4 Hz), 7.73 (d, 1H, J=9 Hz), 7.68 (dd, 1H, J=2.4 and 8.7 Hz), 7.28 (t, 1H, J=10.5 Hz), 6.42 (d, 1H, J=9.3 Hz); $^{19}$F NMR (CDCl$_3$): −44344; LCMS: purity: 91%; MS (m/e): 292 (M$^+$).

7.1.85 2-Chloro-N4-(3-chloro-4-trifluoromethoxyphenyl)-5-fluoro-4-pyrimidineamine In like manner to the preparation of 2-chloro-5-fluoro-N4-[3-(1H-tetrazol-5-yl)phenyl]-4-pyrimidineamine the reaction of 2,4-dichloro-5-fluoropyrimidine with 3-chloro-4-trifluoromethoxyaniline gave 2-chloro-N4-(3-chloro-4-trifluoromethoxyphenyl)-5-fluoro-4-pyrimidineamine. $^1$H NMR (CDCl$_3$): δ 8.15 (d, 1H, J=3.0 Hz), 7.86 (d, 1H, J=2.1 Hz), 7.61 (dd, 1H, J=2.1 and 8.7 Hz), 7.35 (dd, 1H, J=1.2 and 8.7 Hz), 6.98 (bs, 1H); LCMS: purity: 97%; MS (m/e): 342 (M+2H).

7.1.86 2-Chloro-N4-(4-chloro-3-methoxyphenyl)-5-fluoro-4-pyrimidineamine

In like manner to the preparation of 2-chloro-5-fluoro-N4-[3-(1H-tetrazol-5-yl)phenyl]-4-pyrimidineamine the reaction of 2,4-dichloro-5-fluoropyrimidine with 4-chloro-3-methoxyaniline gave 2-chloro-N4-(4-chloro-3-methoxyphenyl)-5-fluoro-4-aminopyrimidine. LCMS: purity: 88%; MS (m/e): 288 (MH$^+$).

7.1.87 2-Chloro-5-fluoro-N4-[2-(2-hydroxyethyleneoxy)pyridin-5-yl]-4-pyrimidinediamine In like manner to the preparation of 2-chloro-5-fluoro-N4-[3-(1H-tetrazol-5-yl)phenyl]-4-pyrimidineamine the reaction of 2,4-dichloro-5-fluoropyrimidine with 5-amino-2-(2-hydroxyethyloxy)pyridine gave 2-chloro-5-fluoro-N4-[2-(2-hydroxyethyleneoxy)pyridin-5-yl]-4-pyrimidinediamine. $^1$H NMR (CDCl$_3$): δ 8.28 (d, 1H, J=2.4 Hz), 8.08 (m, 1H), 7.99 (m, 1H), 7.00 (bs, 1H), 6.87 (bd, 1H), 4.47 (m, 2H), 3.97 (m, 2H).

7.1.88 2-Chloro-N4-[2-(2-chloro-5-fluoropyrimidin-4-yl)-1,2,3,4-tetrahydroisoquinolin-7-yl]-5-fluoro-4-pyrimidineamine (R926910)

In a like manner to the preparation of N2,N4-bis(3-hydroxyphenyl)-5-fluoro-2,4-pyrimidinediamine, 2,4-dichloro-5-fluoropyrimidine and 7-amino-1,2,3,4-tetrahydroisoquinoline were reacted to provide 2-chloro-N4-[2-(2-chloro-5-fluoropyrimidin-4-yl)-1,2,3,4-tetrahydroisoquinolin-7-yl]-5-fluoro-4-pyrimidineamine. $^1$H NMR (CDCl$_3$): δ 8.08 (d, 1H, J=3.0 Hz), 7.95 (d, 1H, J=6.0 Hz), 7.50-7.42 (m, 2H), 7.21 (d, 1H, J=8.4 Hz), 6.96-6.90 (m, 1H), 4.95 (s, 2H), 4.04 (t, 2H, J=5.7 Hz), 2.99 (t, 2H, J=5.7 Hz); $^{19}$F NMR (282 MHz, CDCl$_3$): −42555, −44573; LCMS: purity: 98%; MS (m/e): 410(MH$^+$).

7.1.89 2-Chloro-5-fluoro-N4-[2-(t-butoxycarbonyl)-1,2,3,4-tetrahydroisoquinolin-7-yl]-4-pyrimidineamine (R926911)

In a like manner to the preparation of 2-chloro-N4-(3,4-ethylenedioxyphenyl)-5-fluoro-4-pyrimidineamine, 2,4-dichloro-5-fluoropyrimidine and 7-amino-2-(t-butoxycarbonyl)-1,2,3,4-tetrahydroisoquinoline were reacted to provide 2-chloro-5-fluoro-N4-[2-(t-butoxycarbonyl)-1,2,3,4-tetrahydroisoquinolin-7-yl]-4-pyrimidineamine.

$^1$H NMR (CDCl$_3$): δ 8.03 (s, 1H), 7.50-7.26 (m, 2H), 7.19-7.11 (m, 2H), 4.57 (s, 2H), 3.64 (t, 2H, J=5.7 Hz), 2.80 (t, 2H, J=5.7 Hz), 1.48 (s, 9H); LCMS: purity: 89%; MS (m/e): 379(M$^+$).

7.1.90 2-Chloro-5-fluoro-N4-(1,2,3,4-tetrahydroisoquinolin-7-yl)-4-pyrimidineamine (R926912)

A solution of 2-chloro-5-fluoro-N4-[2-(t-butoxycarbonyl)-1,2,3,4-tetrahydroisoquinolin-7-yl]-4-pyrimidineamine in 40% trifluoroacetic acid/dichloromethane was stirred at rt for 30 min. Removal of the solvent left an oily residue which was suspended in water, made basic with NaHCO$_3$, and extracted with ethyl acetate. Purification by column chromatography over silica gel provided 2-chloro-5-fluoro-N4-(1,2,3,4-tetrahydroisoquinolin-7-yl)-4-pyrimidineamine. $^1$H NMR (CDCl$_3$): δ 8.04 (d, 1H, J=3.0 Hz), 7.37 (dd, 1H, J=2.4 and 8.4 Hz), 7.27 (d, 1H, J=1.5 Hz), 7.11 (d, 1H, J=8.4 Hz), 6.92 (s, 1H), 4.04 (s, 2H), 3.15 (t, 2H, J=6.0 Hz), 2.79 (t, 2H, J=6.0 Hz); $^{19}$F NMR (282 MHz, CDCl$_3$): −44648; LCMS: purity: 97%; MS (m/e): 279(MH$^+$).

7.1.91 2-Chloro-5-fluoro-N4-(4-methyl-3-trifluoromethylphenyl)-4-pyrimidineamine (R926920)

In a like manner to the preparation of 2-chloro-N4-(3,4-ethylenedioxyphenyl)-5-fluoro-4-pyrimidineamine, 2,4-dichloro-5-fluoropyrimidine and 4-methyl-3-trifluoromethylaniline were reacted to provide 2-chloro-5-fluoro-N4-(4- methyl-3-trifluoromethylphenyl)-4-pyrimidineamine. $^1$H NMR (CDCl$_3$): δ 8.10 (d, 1H, J=3.0 Hz), 7.85-7.78 (m, 2H), 7.33 (d, 1H, J=9.3 Hz), 6.96 (bs, 1H), 2.48 (d, 3H, J=1.2 Hz); $^{19}$F NMR (282 MHz, CDCl$_3$): −17641, −44541; LCMS: purity: 97%; MS (m/e): 306(MH$^+$).

7.1.92 2-Chloro-5-fluoro-N4-(4-fluoro-3-methylphenyl)-4-pyrimidineamine (R926921)

In a like manner to the preparation of 2-chloro-N4-(3,4-ethylenedioxyphenyl)-5-fluoro-4-pyrimidineamine, 2,4-dichloro-5-fluoropyrimidine and 4-fluoro-3-methylaniline were reacted to provide 2-chloro-5-fluoro-N4-(4-fluoro-3-methylphenyl)-4-pyrimidineamine. $^1$H NMR (CDCl$_3$): δ 8.06 (d, 1H, J=2.4 Hz), 7.48-7.43 (m, 1H), 7.39 (dd, 1H, J=2.7 and 6.3 Hz), 7.03 (t, 1H, J=9.0 Hz), 6.84 (bs, 1H), 2.30 (d, 1H, J=1.8 Hz); $^{19}$F NMR (282 MHz, CDCl$_3$): −34285, −44676; LCMS: purity: 95%; MS (m/e): 257(MH$^+$).

7.1.93 N4-[3-[(N-t-butoxycarbonyl)aminomethyl]-4-methylphenyl]-2-chloro-5-fluoro-4-pyrimidineamine (R926924)

In a like manner to the preparation of 2-chloro-N4-(3,4-ethylenedioxyphenyl)-5-fluoro-4-pyrimidineamine, 2,4-dichloro-5-fluoropyrimidine and 3-[(N-t-butoxycarbonyl)aminomethyl]-4-methylaniline were reacted to provide N4-[3-[(N-t-butoxycarbonyl)aminomethyl]-4-methylphenyl]-2-chloro-5-fluoro-4-pyrimidineamine.
$^1$H NMR (CDCl$_3$): δ 8.05 (d, 1H, J=3.0 Hz), 7.52 (d, 1H, J=9.3 Hz), 7.45 (s, 1H), 7.19 (d, 1H, J=8.1 Hz), 6.96-6.89 (m, 1H), 4.80 (bs, 1H), 2.31 (s, 2H), 1.46 (s, 9H); LCMS: purity: 97%; MS (m/e): 311 (M-(t-butyl)$^+$).

7.1.94 2-Chloro-N4-[3-[[4-(ethoxycarbonyl)piperidino]methyl]phenyl]-5-fluoro-4-pyrimidineamine In a like manner to the preparation of 2-chloro-N4-(3,4-ethylenedioxyphenyl)-5-fluoro-4-pyrimidineamine, 2,4-dichloro-5-fluoropyrimidine and ethyl 1-(3-aminobenzyl)piperidine-4-carboxylate were reacted to provide 2-chloro-N4-[3-[[4-(ethoxycarbonyl)piperidino]methyl]phenyl]-5-fluoro-4-pyrimidineamine. LCMS: purity: 97%; MS (m/e): 394(MH$^+$).

7.1.95 2-Chloro-N4-[3-[4-(ethoxycarbonyl)piperidino carbonyl]phenyl]-5-fluoro-4-pyrimidineamine In a like manner to the preparation of 2-chloro-N4-(3,4-ethylenedioxyphenyl)-5-fluoro-4-pyrimidineamine, 2,4-dichloro-5-fluoropyrimidine and 3-[[4-(ethoxycarbonyl)piperidino]carbonyl]aniline were reacted to provide 2-chloro-N4-[3-[[4-(ethoxycarbonyl)piperidino]carbonyl]phenyl]-5-fluoro-4-pyrimidineamine. LCMS: purity: 96%; MS (m/e): 407(M$^+$).

7.1.96 2-Chloro-5-fluoro-N4-(1,2,3,4-tetrahydro-1-hydroxynaphthalen-7-yl)-4-pyrimidineamine In a manner similar to the preparation of N4-(3,4-ethylenedioxy)-5-fluoro-N2-[2-(hydroxymethyl)benzofuran-5-yl]-2,4-pyrimidinediamine, 2-chloro-5-fluoro-N4-(1,2,3,4-tetrahydro-1-oxonaphthalen-7-yl)-4-pyrimidineamine was reduced with Dibal-H to yield 2-chloro-5-fluoro-N4-(1,2,3,4-tetrahydro-1-hydroxynaphthalen-7-yl)-4-pyrimidineamine.
$^1$H NMR (CDCl$_3$): δ 8.05 (d, 1H, J=3.0 Hz), 7.59 (d, 1H, J=2.4 Hz), 7.14 (d, 1H, J=8.1 Hz), 6.93 (bs, 1H), 4.82-4.78 (m, 1H), 2.82-2.71 (m, 2H), 2.08-1.74 (m, 5H); $^{19}$F NMR (282 MHz, CDCl$_3$): −44661; LCMS: purity: 94%; MS (m/e): 294(MH$^+$).

7.1.97 2-Chloro-5-fluoro-N4-(1,2,3,4-tetrahydro-1-oxonaphthalen-7-yl)-4-pyrimidineamine In a like manner to the preparation of 2-chloro-N4-(3,4-ethylenedioxyphenyl)-5-fluoro-4-pyrimidineamine, 2,4-dichloro-5-fluoropyrimidine and 7-amino-1-tetralone were reacted to provide 2-chloro-5-fluoro-N4-(1,2,3,4-tetrahydro-1-oxonaphthalen-7-yl)-4-pyrimidineamine. $^1$H NMR (DMSO-d$_6$): δ 10.08 (s, 1H), 8.31 (d, 1H, J=3.3 Hz), 8.15 (d, 1H, J=2.4 Hz), 7.82 (dd, 1H, J=2.4 and 8.1 Hz), 7.36 (d, 1H, J=8.1 Hz), 2.91 (t, 2H, J=6.0 Hz), 2.59 (t, 2H, J=6.0 Hz), 2.07-1.98 (m, 2H); LCMS: purity: 93%; MS (m/e): 294(MH$^+$).

7.1.98 2-Chloro-5-fluoro-N4-[3-(trifluoromethylthio)phenyl]-4-pyrimidineamine In a like manner to the preparation of 2-chloro-N4-(3,4-ethylenedioxyphenyl)-5-fluoro-4-pyrimidineamine, 2,4-dichloro-5-fluoropyrimidine and 3-(trifluoromethylthio) aniline were reacted to provide 2-chloro-5-fluoro-N4-[3-(trifluoromethylthio)phenyl]-4-pyrimidineamine. $^1$H NMR (CDCl$_3$): δ 8.13 (bs, 1H), 7.92 (bs, 1H), 7.89-7.84 (m, 1H), 7.48-7.45 (m, 2H), 7.04 (bs, 1H); LCMS: purity: 97%; MS (m/e): 325(MH$^+$).

7.1.99 2-Chloro-5-fluoro-N4-[(3-dihydroxyboryl)phenyl)]-4-pyrimidineamine

In a like manner to the preparation of 2-chloro-N4-(3,4-ethylenedioxyphenyl)-5-fluoro-4-pyrimidineamine, 2,4-dichloro-5-fluoropyrimidine and 3-aminobenzeneboronic acid were reacted to provide 2-chloro-5-fluoro-N4-[(3-dihydroxyboryl)phenyl)]-4-pyrimidineamine.

7.1.100 2-Chloro-5-fluoro-N4-[(1H)-indol-6-yl]-4-pyrimidineamine

In a like manner to the preparation of 2-chloro-N4-(3,4-ethylenedioxyphenyl)-5-fluoro-4-pyrimidineamine, 2,4-dichloro-5-fluoropyrimidine and 6-aminoindole were reacted to provide 2-chloro-5-fluoro-N4-[(1H)-indol-6-yl]-4-pyrimidineamine. LCMS: purity: 92%; MS (m/e): 263(MH$^+$).

7.1.101 2-Chloro-5-fluoro-N4-(2-hydroxy-4-methylphenyl)-4-pyrimidineamine

In a like manner to the preparation of 2-chloro-N4-(3,4-ethylenedioxyphenyl)-5-fluoro-4-pyrimidineamine, 2,4-dichloro-5-fluoropyrimidine and 3-hydroxy-4-methylaniline were reacted to provide 2-chloro-5-fluoro-N4-(2-hydroxy-4-methylphenyl)-4-pyrimidineamine. LCMS: purity: 97%; MS (m/e): 255(MH$^+$).

7.1.102 2-Chloro-5-fluoro-N4-[2-(methoxycarbonyl)-(1H)-indol-6-yl]-4-pyrimidineamine In a like manner to the preparation of 2-chloro-N4-(3,4-ethylenedioxyphenyl)-5-fluoro-4-pyrimidineamine, 2,4-dichloro-5-fluoropyrimidine and 6-amino-2-(methoxycarbonyl)-(1H)-indole were reacted to provide 2-chloro-5-fluoro- N4-[2-(methoxycarbonyl)-(1H)-indol-6-yl]-4-pyrimidineamine which was used without further purification. LCMS: purity: 65%; MS (m/e): 322(MH⁺).

7.1.103 N4-[3-(4-(2-Chloro-5-fluoropyrimidine)-N-aminomethylene)-phenyl]-2-chloro-5-fluoro-4-pyrimidineamine (R940298)

The reaction flask equipped with a magnetic stirring bar and a rubber septum (to prevent loss of 2,4-dichloro-5-fluoropyrimidine and $N_2$ inlet was charged 3-aminobenzylamine (0.22 g, 1.79 mmol), MeOH (1 mL), $H_2O$ (3 mL) and 2,4-dichloro-5-fluoropyrimidine (0.3 g, 1.79 mmol). The reaction mixture was stirred at 80° C. for 30 min., cool to room temperature, diluted with $H_2O$ (30 mL). Upon saturation with sodium chloride it was extracted with ethyl acetate (3×20 mL), dried over anhydrous sodium sulfate and the solvent was removed. The resulting residue was filtered through a pad of silica gel (200-400 mesh) using 1 to 3% MeOH in $CH_2Cl_2$ to obtain N4-[3-(4-(2-chloro-5-fluoropyrimidine)-N-methylaminomethylene)-phenyl]-2-chloro-5-fluoro-4-pyrimidineamine R940298. ¹H NMR (DMSO-d6): δ 10.09 (1H, s), 8.88 (1H, t, J=5.85 Hz), 8.40 (1H, d, J=3.6 Hz), 8.23 (1H, d, J=3.3 Hz), 7.74 (1H, s), 7.70 (1H, d, J=8.1 Hz), 7.44 (1H, t, J=7.8 Hz), 7.19 (1H, d, J=8.1 Hz), 4.69 (2H, d, J=5.7 Hz; purity 92%.

7.1.104 2-Chloro-5-fluoro-N4-(3-methyloxycarbonyl-4-methoxyphenyl)-4-pyrimidineamine (R940302)

The reaction flask equipped with a magnetic stirring bar and a rubber septum (to prevent loss of 2,4-dichloro-5-fluoropyrimidine and $N_2$ inlet was charged with 3-methyloxycarbonyl-4-methoxyaniline (0.88 g, 4.86 mmol), MeOH (3 mL), $H_2O$ (7 mL) and 2,4-dichloro-5-fluoropyrimidine (0.81 g, 4.86 mmol). The reaction mixture was stirred at 60° C. for 30 min., diluted with $H_2O$ (50 mL), acidified with 2N HCl (6 mL) and sonicated. The solid obtained was filtered, washed with $H_2O$ and dried to produce 2-chloro-5-fluoro-N4-(3-methyloxycarbonyl-4-methoxyphenyl)-4-pyrimidineamine R940302. ¹H NMR (DMSO-d6): δ 10.10 (1H, s), 8.39 (1H, d, J=3.6 Hz), 8.04 (1H, d, J=2.7 Hz), 7.98-7.93 (1H, m), 7.30 (1H, d, J=9 Hz), 3.92 (3H, s), 3.89 (3H, m); purity 96%; MS (m/e): 312 (MH⁺).

7.1.105 2-Chloro-5-fluoro-N4-(4-phahthlimide)-4-pyrimidineamine (R940303)

In like manner to the preparation of 2-chloro-5-fluoro-N4-(3-methyloxycarbonyl-4-methoxyphenyl)-4-pyrimidineamine, 2,4-dichloro-5-fluoropyrimidine and 4-aminophthalimide were reacted to produce 2-chloro-5-fluoro-N4-(4-phahthlimide)-4-pyrimidineamine R940303. ¹H NMR (DMSO-d6): δ 11.38 (1H, s), 10.60 (1H, s), 8.57 (1H, d, J=3.3 Hz), 8.39 (1H, d, J=1.8 Hz), 8.18 (1H, dd, J=8.4 Hz, J=2.1 Hz), 7.93 (1H, d, J=8.1 Hz); purity 90%; MS (m/e): 293 (MH⁺).

7.1.106 2-Chloro-5-fluoro-N4-(3-methylaminocarbonyl-4-methoxyphenyl)-4-pyrimidineamine (R940305)

In like manner to the preparation of 2-chloro-5-fluoro-N4-(3-methyloxycarbonyl-4-methoxyphenyl)-4-pyrimidineamine, 2,4-dichloro-5-fluoropyrimidine and 3-methylaminocarbonyl-4-methoxyaniline were reacted to produce 2-chloro-5-fluoro-N4-(3-methylaminocarbonyl-4-methoxyphenyl)-4-pyrimidineamine R940305. ¹H NMR (DMSO-d6): δ 9.91 (1H, s), 8.31 (1H, d, J=3.6 Hz), 8.11 (1H, d, J=2.7 Hz), 7.78 (1H, dd, J=9 Hz, J=2.7 Hz), 7.59 (1H, m), 6.87 (1H, d, J=9 Hz), 3.90 (3H, s), 2.96 (3H, d, J=4.5 Hz); purity 93%.

7.1.107 N2-Chloro-5-fluoro-N4-[3-(N-morpholinomethylene)-4-methoxyphenyl]-4-pyrimidineamine (R940313)

In like manner to the preparation of 2-chloro-5-fluoro-N4-(3-methyloxycarbonyl-4-methoxyphenyl)-4-pyrimidineamine, 2,4-dichloro-5-fluoropyrimidine and 3-(N-morpholinomethylene)-4-methoxyaniline were reacted to produce 2-chloro-5-fluoro-N4-[3-(N-morpholinomethylene)-4-methoxyphenyl]-4-pyrimidineamine R940313. ¹H NMR (DMSO-d6): δ 10.00 (1H, s), 8.35 (1H, d, J=3.3 Hz), 7.72 (1H, d, J=3 Hz), 7.58 (1H, d, J=9.3 Hz), 7.12 (1H, d, J=8.4 Hz), 3.89 (3H, s), 3.8-3.5 (6H, m), 2.58 (4H, m); purity 96%; MS (m/e): 352 (M).

7.1.108 N4-[3-(N-tert-Butoxycarbonyl-N-methylaminomethylene)-phenyl]-2-chloro-5-fluoro-4-pyrimidineamine (R940315)

In like manner to the preparation of 2-chloro-5-fluoro-N4-(3-methyloxycarbonyl-4-methoxyphenyl)-4-pyrimidineamine, 2,4-dichloro-5-fluoropyrimidine and 3-(N-tert-butoxycarbonyl-N-methylaminomethylene)-aniline were reacted to produce N4-[3-(N-tert-butoxycarbonyl-N-methylaminomethylene)-phenyl]-2-chloro-5-fluoro-4-pyrimidineamine R940315. ¹H NMR (DMSO-d6): δ 10.13 (1H, s), 8.42 (1H, d, J=3.6 Hz), 7.69 (1H, m), 7.64 (1H, s), 7.45 (1H, t, J=7.6 Hz), 7.09 (1H, d, J=7.8 Hz), 4.48 (2H, s), 2.90 (3H, s), 1.49 (9H, m); purity 92%; MS (m/e): 367 (MH⁺).

7.1.109 N4-(3-(N-tert-Butoxycarbonyl-N-isopropylaminomethylene)-4-methoxyphenyl)-2-chloro-5-fluoro-4-pyrimidineamine (R940320)

In like manner to the preparation of 2-chloro-5-fluoro-N4-(3-methyloxycarbonyl-4-methoxyphenyl)-4-pyrimidineamine, 2,4-dichloro-5-fluoropyrimidine and 3-(N-tert-butoxycarbonyl-N-iso-propylaminomethylene)-4-methoxy-aniline were reacted to produce N4-(3-(N-tert-butoxycarbonyl-N-iso-propylaminomethylene)-4-methoxyphenyl)-2-chloro-5-fluoro-4-pyrimidineamine R940320. ¹H NMR (DMSO-d6): δ 10.01 (1H, s), 8.34 (1H, d, J=3.6 Hz), 7.52 (2H, m), 7.08 (1H, d, J=8.7 Hz), 4.33 (3H, m), 3.90 (3H, s), 1.50-1.30 (9H, m), 1.18 (6H, d, J=6.9 Hz); purity 95%.

7.1.110 2-Chloro-N4-[(2,2-dimethyl-4H-benzo[1,4]oxazin-3-one)-6-yl]-5-fluoro-4-pyrimidineamine (R940322)

In like manner to the preparation of 2-chloro-5-fluoro-N4-(3-methyloxycarbonyl-4-methoxyphenyl)-4-pyrimidineamine, 2,4-dichloro-5-fluoropyrimidine and 6-amino-2,2-dimethyl-4H-benzo[1,4]oxazin-3-one were reacted to produce 2-chloro-N4-[(2,2-dimethyl-4H-benzo[1,4]oxazin-3-one)-6-yl]-5-fluoro-4-pyrimidineamine R940322. ¹H NMR (DMSO-d6): δ 10.89 (1H, s), 10.04 (1H, s), 8.38 (1H, d, J=3.6 Hz), 7.35 (2H, m), 7.04 (1H, d, J=8.4 Hz), 1.50 (6H, s); purity 91.4%; MS (m/e): 322 (M).

7.1.111 2-Chloro-N4-[3-dihydro-2,2-dimethyl-4-(2-(pyridyl-1-oxide)-benzo[1,4]oxazin-6-yl]-5-fluoro-4-pyrimidineamine (R940328)

In like manner to the preparation of 2-chloro-5-fluoro-N4-(3-methyloxycarbonyl-4-methoxyphenyl)-4-pyrimidineamine, 2,4-dichloro-5-fluoropyrimidine and 2-(6-amino-3-dihydro-2,2-dimethyl-benzo[1,4]oxazin-4-yl)pyridine 1-Oxide were reacted to produce 2-chloro-N4-[3-dihydro-2,2-dimethyl-4-(2-(pyridyl-1-oxide)-benzo[1,4]oxazin-6-yl]-5-fluoro-4-pyrimidineamine R940328. $^1$H NMR (DMSO-d6): δ 9.82 (1H, s), 8.39 (1H, dd, J=6.3 Hz, J=1.2 Hz), 8.30 (1H, d, J=3.6 Hz), 7.63 (1H, dd, J=8.4 Hz, J=2.4 Hz), 7.47 (1H, td, J=7.5 Hz, J=1.8 Hz), 7.34 (1H, m), 7.21 (1H, dd, J=8.7 Hz, J=2.4 Hz), 7.07 (1H, d, J=2.7 Hz), 6.91 (1H, d, J=8.7 Hz), 3.64 (2H, s), 1.41 (6H, s); purity 95.8%; MS (m/e): 402 (MH$^+$).

7.1.112 2-Chloro-N4-[3-dihydro-2,2-dimethyl-4-(2-pyridyl)-benzo[1,4]oxazin-6-yl]-5-fluoro-4-pyrimidineamine (R940336)

In like manner to the preparation of 2-chloro-5-fluoro-N4-(3-methyloxycarbonyl-4-methoxyphenyl)-4-pyrimidineamine, 2,4-dichloro-5-fluoropyrimidine and 6-amino-3-dihydro-2,2-dimethyl-4-(2-pyridyl)-benzo[1,4]oxazine were reacted to produce 2-chloro-N4-[3-dihydro-2,2-dimethyl-4-(2-pyridyl)-benzo[1,4]oxazin-6-yl]-5-fluoro-4-pyrimidineamine R940336. $^1$H NMR (DMSO-d6): δ 9.95 (1H, s), 8.38 (1H, dd, J=4.8 Hz, J=1.8 Hz), 8.33 (1H, d, J=3.6 Hz), 7.84 (1H, d, J=2.1 Hz), 7.79 (1H, ddd, J=15.6 Hz, J=7.2 Hz, J=2.1 Hz), 7.57 (1H, d, J=8.4 Hz), 7.19 (1H, dd, J=8.4 Hz, J=2.4 Hz), 7.01-6.95 (2H, m), 3.96 (2H, s), 1.32 (6H, s); purity 99.3%; MS (m/e): 386 (MH$^+$).

7.1.113 2-Chloro-N4-[(2,2-difluoro-4H-benzo[1,4]oxazin-3-one)-6-yl]-5-fluoro-4-pyrimidineamine (R940342)

In like manner to the preparation of 2-chloro-5-fluoro-N4-(3-methyloxycarbonyl-4-methoxyphenyl)-4-pyrimidineamine, 2,4-dichloro-5-fluoropyrimidine and 6-amino-2,2-difluoro-4H-benzo[1,4]oxazin-3-one were reacted to produce 2-chloro-N4-[(2,2-difluoro-4H-benzo[1,4]oxazin-3-one)-6-yl]-5-fluoro-4-pyrimidineamine R940342. $^1$H NMR (DMSO-d6): δ 12.24 (1H, s), 10.23 (1H, s), 8.45 (1H, dd, J=3.3 Hz, J=0.9 Hz), 7.66 (1H, dd, J=4.2 Hz, J=2.4 Hz), 7.55 (1H, dt, J=9 Hz, J=2.5 Hz), 7.43 (1H, d, J=9 Hz+); $^{19}$F NMR (DMSO-d6): δ −21582, −43415; purity 96.2%; MS (m/e): 331 (MH$^+$).

7.1.114 2-Chloro-N4-[(2,2-dimethyl-4H-5-pyrido[1,4]oxazin-3-one)-7-yl]-5-fluoro-4-pyrimidineamine (R940344)

In like manner to the preparation of 2-chloro-5-fluoro-N4-(3-methyloxycarbonyl-4-methoxyphenyl)-4-pyrimidineamine, 2,4-dichloro-5-fluoropyrimidine and 7-amino-2,2-dimethyl-4H-5-pyrido[1,4]oxazin-3-one were reacted to produce 2-chloro-N4-[(2,2-dimethyl-4H-5-pyrido[1,4]oxazin-3-one)-7-yl]-5-fluoro-4-pyrimidineamine R940344. $^1$H NMR (DMSO-d6): δ 11.32 (1H, s), 10.20 (1H, s), 8.45 (1H, d, J=3.6 Hz), 8.33 (1H, d, J=2.1 Hz), 7.84 (1H, d, J=2.1 Hz), 1.54 (6H, s); purity 90.8%; MS (m/e): 324 (MH$^+$).

7.1.115 N4-(4-Aminocarbonylmethyleneoxyphenyl)-2-chloro-5-fluoro-4-pyrimidineamine (R945028)

In a manner similar to the preparation of 2-chloro-N4-(3,4-ethylenedioxyphenyl)-5-fluoro-4-pyrimidineamine, 2,4-dichloro-5-fluoropyrimidine (250 mg, 1.50 mmol) and 4-aminocarbonylmethyleneoxyaniline (540 mg, 3.25 mmol) were reacted to yield N4-(4-aminocarbonylmethyleneoxyphenyl)-2-chloro-5-fluoro-4-pyrimidineamine. LCMS: ret. time: 18.34 min.; purity: 100%; MS (m/e): 298.47 (MH$^+$).

7.1.116 2-Chloro-5-fluoro-N4-[2H-pyrido[3,2-b]-1,4-oxazin-3(4H)-one-6-yl]-4-pyrimidineamine (R945298)

In a manner similar to the preparation of 2-chloro-N4-(3,4-ethylenedioxyphenyl)-5-fluoro-4-pyrimidineamine, 2,4-dichloro-5-fluoropyrimidine and 6-amino-2H-pyrido[3,2-b]-1,4-oxazin-3(4H)-one were reacted to yield 2-chloro-5-fluoro-N4-[2H-pyrido[3,2-b]-1,4-oxazin-3(4H)-one-6-yl]-4-pyrimidineamine. $^1$H NMR (DMSO-d$_6$): δ 4.63 (s, 2H), 7.34 (d, J=8.7 Hz, 1H), 7.44 (d, J=8.4 Hz, 1H), 8.33 (d, J=3.3 Hz, 1H), 10.14 (s, 1H, NH), 11.19 (s, 1H, NH); $^{19}$F NMR (282 MHz, DMSO-d$_6$): 6-152.35; LCMS: ret. time: 26.74 min.; purity: 85.90%; MS (m/e): 296.13 (MH$^+$).

7.1.117 N4-(1,4-Benzoxazin-6-yl)-N2-chloro-5-fluoropyrimidineamine

In like manner to 2-Chloro-N4-(3,4-ethylenedioxyphenyl)-5-fluoro-4-pyrimidineamine, 2,4-dichloro-5-fluoropyrimidine and 6-amino-1,4-benzoxazine were reacted to yield N4-(1,4-Benzoxazin-6-yl)-N2-chloro-5-fluoropyrimidineamine 1H DMSO 8.2 (d, 1H), 6.8 (m, 1H), 6.75 (m, 1H), 6.60 (m, 1H), 4.05 (m, 2H), 3.2 (m, 2H) purity 95% MS (m/e): 281(MH$^+$).

7.1.118 N4-(1,4-Benzoxazin-7-yl)]-N2-chloro-5-fluoropyrimidineamine

In like manner to 2-Chloro-N4-(3,4-ethylenedioxyphenyl)-5-fluoro-4-pyrimidineamine, 2,4-dichloro-5-fluoropyrimidine and 7-amino-1,4-benzoxazine were reacted to yield N4-(1,4-Benzoxazin-7-yl)]-N2-chloro-5-fluoropyrimidineamine 1H DMSO 8.2 (d, 1H), 6.8 (m, 1H), 6.75 (m, 1H), 6.60 (m, 1H), 4.05 (m, 2H), 3.2 (m, 2H) purity 94% MS (m/e): 281(MH$^+$).

7.1.119 N4-(1,4-Benzoxazin-3-on-6-yl)-N2-chloro-5-fluoropyrimidineamine

In like manner to 2-Chloro-N4-(3,4-ethylenedioxyphenyl)-5-fluoro-4-pyrimidineamine, 2,4-dichloro-5-fluoropyrimidine and 6-amino-1,4-benzoxazine-3-one were reacted to yield N4-(1,4-Benzoxazin-3-on-6-yl)-N2-chloro-5-fluoropyrimidineamine
1H DMSO 8.2 (d, 1H), 6.8 (m, 1H), 6.75 (m, 1H), 6.60 (m, 1H), 4.73 (s, 2H) purity 96% MS (m/e): 295 (MH$^+$)

7.1.120 N4-(1,4-Benzoxazin-3-on-7-yl)-N2-chloro-5-fluoropyrimidineamine

In like manner to 2-Chloro-N4-(3,4-ethylenedioxyphenyl)-5-fluoro-4-pyrimidineamine, 2,4-dichloro-5-fluoropyrimidine and 7-amino-1,4-benzoxazine-3-one were reacted to yield N4-(1,4-Benzoxazin-3-on-7-yl)-N2-chloro-5-fluoropyrimidineamine 1H DMSO 8.2 (d, 1H), 6.8 (m, 1H), 6.79 (m, 1H), 6.6 (m, 1H), 4.68 (s, 2H) purity 93% MS (m/e): 295 (MH⁺).

7.1.121 N2-Chloro-5-fluoro-N4-(N-methyl-1,4-benzoxazin-6-yl)-pyrimidineamine In like manner to 2-Chloro-N4-(3,4-ethylenedioxyphenyl)-5-fluoro-4-pyrimidineamine, 2,4-dichloro-5-fluoropyrimidine and 6-amino-4-N-methyl-1,4-benzoxazine were reacted to yield N2-Chloro-5-fluoro-N4-(N-methyl-1,4-benzoxazin-6-yl)-pyrimidineamine 1H DMSO 8.2 (d, 1H), 6.8 (m, 1H), 6.75 (m, 1H), 6.60 (m, 1H), 4.05 (m, 2H), 3.2 (m, 2H) 2.8 (s, 3H) purity 95% MS (m/e): 295 (MH⁺).

7.1.122 N2-Chloro-5-fluoro-N4-(N-methyl-1,4-benzoxazin-7-yl)-pyrimidineamine In like manner to 2-Chloro-N4-(3,4-ethylenedioxyphenyl)-5-fluoro-4-pyrimidineamine, 2,4-dichloro-5-fluoropyrimidine and 7-amino-4-N-methyl-1,4-benzoxazine were reacted to yield N2-Chloro-5-fluoro-N4-(N-methyl-1,4-benzoxazin-7-yl)-pyrimidineamine 1H DMSO 8.2 (d, 1H), 6.8 (m, 1H), 6.75 (m, 1H), 6.60 (m, 1H), 4.05 (m, 2H), 3.2 (m, 2H) 2.8 (s, 3H) purity 94% MS (m/e): 295 (MH⁺).

7.1.123 N2-Chloro-5-fluoro-N4-(N-methyl-1,4-benzoxazin-3-on-6-yl)-pyrimidineamine In like manner to 2-Chloro-N4-(3,4-ethylenedioxyphenyl)-5-fluoro-4-pyrimidineamine, 2,4-dichloro-5-fluoropyrimidine and 6-amino-4-N-methyl-1,4-benzoxazine-3-one were reacted to yield N2-Chloro-5-fluoro-N4-(N-methyl-1,4-benzoxazin-3-on-6-yl)-pyrimidineamine 1H DMSO 8.2 (d, 1H), 6.8 (m, 1H), 6.75 (m, 1H), 6.60 (m, 1H), 4.73 (s, 2H) 2.8 (s, 3H) purity 96% MS (m/e): 309 (MH⁺).

7.1.124 N2-Chloro-5-fluoro-N4-(N-methyl-1,4-benzoxazin-3-on-7-yl)-pyrimidineamine In like manner to 2-Chloro-N4-(3,4-ethylenedioxyphenyl)-5-fluoro-4-pyrimidineamine, 2,4-dichloro-5-fluoropyrimidine and 7-amino-4-N-methyl-1,4-benzoxazine-3-one were reacted to N2-Chloro-5-fluoro-N4-(N-methyl-1,4-benzoxazin-3-on-7-yl)-pyrimidineamine 1H DMSO 8.2 (d, 1H), 6.8 (m, 1H), 6.75 (m, 1H), 6.60 (m, 1H), 4.68 (s, 2H) 2.8 (s, 3H) purity 93% MS (m/e): 309 (MH⁺).

7.1.125 N2-chloro-N4-(3-ethylcarboxy-4H-imidazo[5,1-c]-1,4-benzoxazin-6-yl)-5-fluoropyrimidinediamine (R909258)

In like manner to 2-Chloro-N4-(3,4-ethylenedioxyphenyl)-5-fluoro-4-pyrimidineamine, 2,4-dichloro-5-fluoropyrimidine and ethyl 6-amino-3-carboxy-4H-imidazo[5,1-c]-1,4-benzoxazine were reacted to yield N2-chloro-N4-(3-ethylcarboxy-4H-imidazo[5,1-c]-1,4-benzoxazin-6-yl)-5-fluoropyrimidinediamine 1H (DMSO-d6) 8.42 (s, 1H), 8.30 (m, 1H), 8.05 (m, 1H), 7.43 (m, 1H), 5.53 (s, 2H), 4.25 (q, 2H J=6.5 Hz), 1.28 (t, 2H, J=6.5 Hz), purity 90% MS (m/e): 390 (MH⁺).

7.1.126 N2-Chloro-N4-(3,3-dimethyl-1,4-benzoxazin-6-yl)-5-fluoro-pyrimidineamine In like manner to 2-Chloro-N4-(3,4-ethylenedioxyphenyl)-5-fluoro-4-pyrimidineamine, 2,4-dichloro-5-fluoropyrimidine and 6-Amino-3,3-dimethyl-1,4-benzoxazine were reacted to yield N2-Chloro-N4-(3,3-dimethyl-1,4-benzoxazin-6-yl)-5-fluoro-pyrimidineamine 1H DMSO 8.18 (d, 1H), 6.8 (d, 1H), 6.67 (m, 2H), 3.76 (s, 2H), 1.05 (s, 6H) purity 99% MS (m/e): 309 (MH⁺)

7.1.127 2-Chloro-5-fluoro-N-[1-(methoxycarbonyl)methyl-indazoline-5-yl]-4-pyrimidineamine (R935241)

In like manner to the preparation of 2-chloro-N-(3,4-ethylenedioxyphenyl)-5-fluoro-4-pyrimidineamine, 2,4-dichloro-5-fluoropyrimidine was reacted with 5-amino-1-(methoxycarbonyl)methyl-indazoline to produce 2-chloro-5-fluoro-N-[1-(methoxycarbonyl)methyl-indazoline-5-yl]-4-pyrimidineamine. ¹H NMR (DMSO-d₆): δ 10.04 (s, 1H), 8.28 (d, 1H, J=3.5 Hz), 8.12 (s, 1H), 8.00 (dd, 1H, J=1.2 and 4.1 Hz), 7.64 (d, 1H, J=8.8 Hz), 7.58-7.54 (m, 1H), 5.39 (s, 2H), 3.66 (s, 3H).

7.1.128 2-Chloro-5-fluoro-N-[4H-imidazo[2,1-c][1,4]-benzoxazin-8-yl]-4-pyrimidineamine (R935257)

In like manner to the preparation of 2-chloro-N-(3,4-ethylenedioxyphenyl)-5-fluoro-4-pyrimidineamine, 2,4-dichloro-5-fluoropyrimidine was reacted with 8-amino-4H-imidazo[2,1-c][1,4]-benzoxazine to produce 2-chloro-5-fluoro-N-[4H-imidazo[2,1-c][1,4]-benzoxazin-8-yl]-4-pyrimidineamine. ¹H NMR (DMSO-d₆): ¹H NMR (DMSO-d₆): δ 10.08 (s, 1H), 8.31 (s, 1H), 7.91 (d, 1H, J=2.3 Hz), 7.74 (d, 1H, J=1.2 Hz), 7.37 (dd, 1H, J=2.3 and 8.8 Hz), 7.16 (d, 1H, J=8.8 Hz), 7.14 (d, 1H, J=1.2 Hz), 5.29 (s, 2H). LCMS: ret. time: 18.74 min.; purity: 99%; MS (m/e): 318 (MH⁺).

7.1.129 2-Chloro-5-fluoro-N-(indazoline-6-yl)-4-pyrimidineamine (R935260)

In like manner to the preparation of 2-chloro-N-(3,4-ethylenedioxyphenyl)-5-fluoro-4-pyrimidineamine, 2,4-dichloro-5-fluoropyrimidine was reacted with 6-aminoindazole to produce 2-chloro-5-fluoro-N-(indazoline-6-yl)-4-pyrimidineamine. ¹H NMR (CDCl₃): δ 13.03 (s, 1H), 10.07 (s, 1H), 8.32 (d, 1H, J=3.5 Hz), 8.07 (s, 1H), 7.99 (s, 1H), 7.71 (d, 1H, J=8.8 Hz), 7.34 (dd, 1H, J=1.7 and 8.8 Hz). LCMS: ret. time: 18.52 min.; purity: 99%; MS (m/e): 263 (MH⁺).

7.1.130 2-Chloro-5-fluoro-N-(indazoline-5-yl)-4-pyrimidineamine (R935265)

In like manner to the preparation of 2-chloro-N-(3,4-ethylenedioxyphenyl)-5-fluoro-4-pyrimidineamine, 2,4-dichloro-5-fluoropyrimidine was reacted with 5-aminoindazoline. ¹H NMR (CDCl₃): δ 9.99 (s, 1H), 8.26 (d, 1H, J=3.5 Hz), 8.07 (s, 1H), 7.99 (d, 1H, J=1.1 Hz), 7.53 (dd, 2H, J=1.7 and 8.8 Hz). LCMS: ret. time: 18.03 min.; purity: 97%; MS (m/e): 264 (MH⁺).

7.1.131 2-Chloro-5-fluoro-N-(1H-pyrrol-1-yl)-4-pyrimidineamine (R935275)

In like manner to the preparation of 2-chloro-N-(3,4-ethylenedioxyphenyl)-5-fluoro-4-pyrimidineamine, 2,4-dichloro-5-fluoropyrimidine was reacted with 1-aminopyrrole to produce 2-chloro-5-fluoro-N-(1H-pyrrol-1-yl)-4-pyrimidineamine. ¹H NMR (CDCl₃): δ 11.39 (s, 1H), 8.35 (d, 1H, J=3.5 Hz), 6.83 (t, 2H, J=2.3 Hz), 6.07 (t, 2H, J=2.3 Hz). LCMS: ret. time: 18.95 min.; purity: 97%; MS (m/e): 213 (MH⁺).

7.1.132 2-Chloro-5-fluoro-N4-[3-(1H-tetrazol-5-yl)phenyl]-4-pyrimidineamine (R926853)

A reaction mixture containing 2,4-dichloro-5-fluoro-pyrimidine (1.2 equivalents) and 3-(tetrazol-5-yl)aniline (1 equivalents) in methanol:water (1:1; v/v) was heated at 60° C. for 24 h. Upon dilution with water and acidification, the solid formed was fitered, washed with water, dried and analyzed to give 2-chloro-5-fluoro-N4-[3-(1H-tetrazol-5-yl)phenyl]-4-pyrimidineamine (R926853). Alternatively this reaction can be achieved by treating 2,4-dichloro-5-fluoropyrimidine (1 equivalent) with 3-(tetrazol-5-yl)aniline (3 equivalents) in methanol:water (1:1; v/v) at 60 oC for 2-3 hours or at room temperature for 24 h to give 2-chloro-5-fluoro-N4-[3-(1H-tetrazol-5-yl)phenyl]-4-pyrimidineamine. $^1$H NMR (DMSO-d6): δ 10.25 (s, 1H), 8.43 (s, 1H), 8.37 (d, 1H, J=3.6 Hz), 7.90 (dd, 1H, J=0.9 and 9 Hz), 7.75 (d, 1H, J=7.5 Hz), 7.61 (t, 1H, J=7.8 Hz); LCMS: purity: 90%; MS (m/e): 292 (MH$^+$).

7.1.133 2-Chloro-N4-(4-hydroxy-3,4-dihydro-2H-1-benzopyran-6-yl)-5-fluoro-2,4-pyrimidineamine (R950297)

A solution of 3,4-dihydro-4-hydroxy-6-amino-2H-1-benzopyran and 2,4-dichloro-5-fluoro-pyrimidine in MeOH was stirred for 2 hours at 70° C. The mixture was diluted with water and the resulting precipitate was filtered to give 2-chloro-N4-(4-hydroxy-3,4-dihydro-2H-1-benzopyran-6-yl)-5-fluoro-2,4-pyrimidineamine as a pale brown solid. LCMS: purity: 99.3%; MS (m/e): 296.1 (MH$^+$).

7.1.134 2-Chloro-N4-(4-methoxycarbonylethyleneoxyphenyl)-5-fluoro-2,4-pyrimidineamine (R950375)

A solution of 3-(p-aminophenyl)-propionic acid and 2,4-dichloro-5-fluoro-pyrimidine in MeOH was stirred for 2 hours at 70° C. The mixture was diluted with water and the resulting precipitate was filtered to give 2-chloro-N4-(4-methoxycarbonylethyleneoxyphenyl)-5-fluoro-2,4-pyrimidineamine as a pale brown solid. LCMS: purity: 93.3%; MS (m/e): 311.98 (M$^-$).

7.1.135 2-Chloro-N4-(3-carboxy-4-hydroxyphenyl)-5-fluoro-2,4-pyrimidineamine (R950298)

A solution of 3-carboxy-4-hydroxyaniline and 2,4-dichloro-5-fluoro-pyrimidine in MeOH was stirred for 2 hours at 70° C. The mixture was diluted with water and the resulting precipitate was filtered to give 2-chloro-N4-(3-carboxy-4-hydroxyphenyl)-5-fluoro-2,4-pyrimidineamine as a pale brown solid. LCMS: purity: 87.4%; MS (m/e): 284.1 (MH$^+$).

7.1.136 2-Chloro-N4-(4-trifluoromethyl-3-methoxycarbonylphenyl)-5-fluoro-2,4-pyrimidineamine (R950390)

A solution of 4-trifluoromethyl-3-methoxycarbonylaniline and 2,4-dichloro-5-fluoro-pyrimidine in MeOH was stirred for 2 hours at 70° C. The mixture was diluted with water and the resulting precipitate was filtered to give 2-chloro-N4-(4-trifluoromethyl-3-methoxycarbonylphenyl)-5-fluoro-2,4-pyrimidineamine as a pale brown solid. LCMS: purity: 96.4%; MS (m/e): 366.34 (MH$^+$).

7.1.137 2-Chloro-N4-(3-methylcarbonylphenyl)-5-fluoro-2,4-pyrimidineamine (R950369)

A solution of 3-methylcarbonylaniline and 2,4-dichloro-5-fluoro-pyrimidine in MeOH was stirred for 2 hours at 70° C. The mixture was diluted with water and the resulting precipitate was filtered to give 2-chloro-N4-(3-methylcarbonylphenyl)-5-fluoro-2,4-pyrimidineamine as a pale brown solid. LCMS: purity: 99.1%; MS (m/e): 266.12 (MH$^+$).

7.1.138 2-Chloro-N4-(3-phenylcarbonylphenyl)-5-fluoro-2,4-pyrimidineamine (R950370)

A solution of 3-phenylcarbonylaniline and 2,4-dichloro-5-fluoro-pyrimidine in MeOH was stirred for 2 hours at 70° C. The mixture was diluted with water and the resulting precipitate was filtered to give 2-chloro-N4-(3-phenylcarbonylphenyl)-5-fluoro-2,4-pyrimidineamine as a pale brown solid. LCMS: purity: 78.5%; MS (m/e): 328.16 (MH$^+$).

7.1.139 2-Chloro-N4-(3-nitrophenyl)-5-fluoro-2,4-pyrimidineamine

A solution of 3-nitroaniline and 2,4-dichloro-5-fluoro-pyrimidine in MeOH was stirred for 2 hours at 70° C. The mixture was diluted with water and the resulting precipitate was filtered to give 2-chloro-N4-(3-nitrophenyl)-5-fluoro-2,4-pyrimidineamine as a pale brown solid. $^1$H NMR (DMSO): δ 10.34 (s, 1H), 8.73 (d, 1H, J=2.4 Hz), 7.66-8.29 (m, 4H).

7.1.140 2-Chloro-N4-(3-hydroxymethylen-4-methoxyphenyl)-5-fluoro-4-aminopyridine (R950384)

A solution of 3-hydroxymethylen-4-methoxyaniline and 2,4-dichloro-5-fluoro-pyrimidine in MeOH was stirred for 2 hours at 70° C. The mixture was diluted with water and the resulting precipitate was filtered to give 2-chloro-N4-(3-hydroxymethylen-4-methoxyphenyl)-5-fluoro-4-aminopyridine as a pale brown solid. LCMS: purity: 91.8%; MS (m/e): 266.03 (MH$^-$).

7.1.141 2-Chloro-N4-(3-amino-4-ethoxyphenyl)-5-fluoro-4-aminopyridine (R950387)

A solution of 3-amino-4-ethoxyaniline and 2,4-dichloro-5-fluoro-pyrimidine in MeOH was stirred for 2 hours at 70° C. The mixture was diluted with water and the resulting precipitate was filtered to give 2-chloro-N4-(3-amino-4-ethoxyphenyl)-5-fluoro-4-aminopyridine as a pale brown solid. LCMS: purity: 93.2%; MS (m/e): 252.06 (MH$^-$).

7.2 Synthesis of Amines and Amine Precursors

7.2.1 5-Amino-2-(2-hydroxyethyleneoxy)pyridine

A methanolic solution (50 mL) of 2-(2-hydroxyethyleneoxy)-5-nitropyridine (0.5 g) was hydrogenated in the presence of Pd/C (10%; 0.05 g) using a balloon filled with hydrogen for 2 h. After the filtration through a pad of celite and washing with methanol the solution was concentrated to give the 5-amino-2-(2-hydroxyethyloxy)pyridine. $^1$H NMR (CDCl$_3$): δ 7.58 (d, 1H, J=3 Hz), 7.05 (dd, 1H, J=2.7 and 8.1 Hz), 6.64 (d, 1H, J=8.7 Hz), 4.36 (m, 2H), 3.89 (m, 2H).

7.2.2 4-Chloro-3-methoxyaniline

In like manner to the preparation of 5-amino-2-(2-hydroxyethyleneoxy)pyridine, the hydrogenation of 4-chloro- 3-methoxynitrobenzene gave 4-chloro-3-methoxyaniline. LCMS: purity: 98%; MS: 199 (M+acetonitrile).

7.2.3 2-[5-Amino-2-oxo-1,3-benzoxazol-3(2H)-yl]acetamide

In like manner to the preparation of 5-amino-2-(2-hydroxyethyleneoxy)pyridine, the hydrogenation of 2-[1,3-benzoxazol-2-oxo-5-nitro-3(2H)-yl]acetamide gave 2-[5-amino-2-oxo-1,3-benzoxazol-3(2H)-yl]acetamide. LCMS: purity: 96%; MS: 208 (MH+).

7.2.4 7-nitro-1,2,3,4-tetrahydroisoquinoline 7-nitro-1,2,3,4-tetrahydroisoquinoline was prepared by nitration of 1,2,3,4-tetrahydroisoquinoline according to the following reference: Grunewald, Gary L.; Dahanukar, Vilas H.; Caldwell, Timothy M.; Criscione, Kevin R.; Journal of Medicinal Chemistry (1997), 40(25), 3997-4005.

7.2.5 2-(t-Butoxycarbonyl)-7-nitro-1,2,3,4-tetrahydroisoquinoline

A mixture of 7-nitro-1,2,3,4-tetrahydroisoquinoline (0.55 g, 3.1 mmole), di-t-butyldicarbonate (0.70 g, 3.2 mmole), triethylamine (1.0 mL, 7.7 mmole) in dichloromethane (8 mL) was stirred at rt for 8 h. The reaction mixture was diluted with water (50 mL) and stirred for 1 h. The organic phase was separated and washed with brine. Concentration of the organic phase gave 2-(t-butoxycarbonyl)-7-nitro-1,2,3,4-tetrahydroisoquinoline. $^1$H NMR (CDCl$_3$): δ 8.03-7.95 (m, 2H), 7.28 (d, 1H, J=8.4 Hz), 4.66 (s, 2H), 3.68 (t, 2H, J=6.0 Hz), 2.92 (t, 2H, J=6.0 Hz), 1.49 (s, 9H).

7.2.6 2,3-Dihydro-6-nitro-4-benzypyranon 3-(p-Nitrophenyl)-propionic acid is dissolved in concentrated sulfuric acid and treated with P$_2$O$_5$. The mixture is stirred for 1 hr at room temperature and poured onto ice. Filtration gave 2,3-dihydro-6-nitro-4-benzypyranon as a white solid. $^1$H NMR (DMSO): δ 8.47 (d, J=3.0 Hz, 1H), 8.35 (dd, J=3.0, 9.0 Hz, 1H), 7.29 (d, J=9.0 Hz, 1H), 4.70 (t, J=7.2 Hz, 1H), 2.90 (t, J=7.2 Hz, 1H).

7.2.7 3,4-Dihydro-4-hydroxy-6-amino-2H-1-benzopyran

A mixture 2,3-dihydro-6-nitro-4-benzypyranon and Pd/C (10%) in MeOH was hydrogenated at 22° C. for 3 hours (40 psi). The mixture was filtered and concentrated to dryness to give 3,4-dihydro-4-hydroxy-6-amino-2H-1-benzopyran as a brown oil. $^1$H NMR (DMSO): δ 6.40-6.56 (m, 3H), 5.05 (bs, 1H), 4.45 (bs, 1H), 3.94-4.09 (m, 2H), 1.76-1.98 (m, 2H).

7.2.8 N4-(3,4-Ethylenedioxyphenyl)-5-ethoxycarbonyl-2,4-pyrimidinediamine (R950287)

A solution of 2-Chloro-5-ethoxycarbonyl-N4-(3,4-ethylenedioxyphenyl)-2,4-pyrimidineamine in EtOH was treated with a 25% aqueous solution of NH$_3$. The mixture was stirred for 30 min at 100° C. and purified by flash chromatography on silica gel to give N4-(3,4-ethylenedioxyphenyl)-5-ethoxycarbonyl-2,4-pyrimidinediamine as a white solid. LCMS: purity: 92.3%; MS (m/e): 317.28 (MH+, 100).

7.2.9 3-(N-morpholinocarbonyl)aniline

To a 0° C. solution of 3-nitrobenzoylchloride (0.50 g, 2.7 mmole) and pyridine (0.27 mL, 3.2 mmole) in anhydrous dichloromethane (15 mL) was added morpholine (0.28 mL, 3.2 mmole). The reaction mixture was allowed to warm to rt and was stirred for 20 h. The solvents were removed under vacuum and the residue suspended in ethyl acetate and washed with 1N HCl. The organic layer was washed with a saturated solution of NaHCO$_3$ and brine. Removal of the solvents under vacuum provided 1-(N-morpholinocarbonyl)-3-nitrobenzene which was used without further purification.

A mixture of 1-(N-morpholinocarbonyl)-3-nitrobenzene (0.64 g) and 10% Pd on activated carbon (60 mg) in degassed methanol (65 mL) was stirred under a balloon of H$_2$ for 2 h. The reaction mixture was filtered through Celite® filter aid and then concentrated under reduced pressure to provide 3-(N-morpholinocarbonyl)aniline in quantitative yield. $^1$H NMR(CDCl$_3$): δ 7.19-7.14 (m, 1H), 6.75-6.69 (m, 3H), 3.58-3.71 (m, 10H).

7.2.10 3-(N-propylcarbonyl)aniline

In like manner to the preparation of 3-(N-morpholinocarbonyl)aniline, 3-nitrobenzoylchloride and n-propylamine were reacted to prepare 1-[(N-propylamino)carbonyl]-3-nitrobenzene which underwent hydrogenation to provide 3-(N-propylcarbonyl)aniline. $^1$H NMR (CDCl$_3$): δ 7.18 (t, 1H, J=7.5 Hz), 7.13 (t, 1H, J=1.8 Hz), 7.05-7.01 (m, 1H), 6.78 (ddd, 1H, J=1.2, 2.4, and 7.5 Hz), 6.10 (bs, 1H), 3.58-3.53 (bs, 2H), 3.43-3.34 (m, 2H), 1.68-1.57 (m, 2H), 0.97 (t, 3H, J=7.2 Hz).

7.2.11 3-[4-(Ethoxycarbonyl)piperidinocarbonyl]aniline

In like manner to the preparation of 3-(N-morpholinocarbonyl)aniline, 3-nitrobenzoylchloride and ethyl isonipecotate were reacted to prepare 1-[4-(ethoxycarbonyl)piperidinocarbonyl]-3-nitrobenzene which underwent hydrogenation to provide 3-[4-(ethoxycarbonyl)piperidinocarbonyl]aniline.

7.2.12 3-(N-methylcarbonyl)aniline

In like manner to the preparation of 3-(N-morpholinocarbonyl)aniline, 3-nitrobenzoylchloride and methylamine hydrochloride were reacted to prepare 1-[(N-methylamino)carbonyl]-3-nitrobenzene which underwent hydrogenation to provide 3-(N-methylcarbonyl)aniline. $^1$H NMR (CDCl$_3$): δ 7.18 (t, 1H, J=7.5 Hz), 7.13 (t, 1H, J=1.8 Hz), 7.04-6.99 (m, 1H), 6.81-6.75 (m, 1H), 6.05 (bs, 1H), 3.84 (bs, 2H), 2.99 (d, 3H, J=4.8 Hz).

7.2.13 7-Amino-1-tetralone

In like manner to the preparation of ethyl 4-aminophenoxyacetate, hydrogenation of 7-nitro-1-tetralone was carried out to prepare 7-amino-1-tetralone. $^1$H NMR (CDCl$_3$): δ 7.32 (d, 1H, J=2.4 Hz), 7.05 (d, 1H, J=8.1 Hz), 6.82 (dd, 1H, J=2.4 and 8.1 Hz), 2.85 (t, 2H, J=6.6 Hz), 2.61 (t, 2H, J=6.6 Hz), 2.14-2.04 (m, 2H).

7.2.14 7-Amino-2-(t-butoxycarbonyl)-1,2,3,4-tetrahydroisoquinoline

In like manner to the preparation of ethyl 4-aminophenoxyacetate, hydrogenation of 2-(t-butoxycarbonyl)-7-nitro-1,2,3,4-tetrahydroisoquinoline was carried out to prepare 7-amino-2-(t-butoxycarbonyl)-1,2,3,4-tetrahydroisoquinoline. $^1$H NMR (CDCl$_3$): δ 6.92 (d, 1H, J=8.4 Hz), 6.52 (dd, 1H, J=2.4 and 8.4 Hz), 6.44 (bs, 1H), 4.47 (s, 2H), 3.63-3.48 (m, 2H), 2.71 (t, 2H, J=5.1 Hz), 1.45 (s, 9H).

7.2.15 7-Amino-1,2,3,4-tetrahydroisoquinoline

In like manner to the preparation of ethyl 4-aminophenoxyacetate, hydrogenation of 7-nitro-1,2,3,4-tetrahydroisoquinoline was carried out to prepare 7-amino-1,2,3,4-tetrahydroisoquinoline. $^1$H NMR (DMSO-$d_6$): δ 9.35 (bs, 1H), 6.82 (d, 1H, J=8.1 Hz), 6.45 (dd, 1H, J=2.4 and 8.4 Hz), 6.30 (d, 1H, J=2.4 Hz), 5.05 (s, 2H), 4.05 (s, 2H), 3.24 (t, 2H, J=6.6 Hz), 2.78 (t, 2H, J=6.6 Hz).

7.2.16 2-(3-aminophenoxy)-N,2-dimethylpropanamide

In like manner to the preparation of ethyl 4-aminophenoxyacetate, hydrogenation of N,2-dimethyl-2-(3-nitrophenoxy)propanamide was carried out to prepare 2-(3-aminophenoxy)-N,2-dimethylpropanamide. $^1$H NMR (CDCl$_3$): δ 7.03 (t, 1H, J=7.8 Hz), 6.71 (bs, 1H), 6.39 (dd, 1H, J=1.2 and 6.9 Hz), 6.29 (dd, 1H, J=2.4 and 9.6 Hz), 6.25-6.22 (m, 1H), 2.86 (d, 3H, J=4.2 Hz), 2.86 (d, 3H, J=4.2 Hz), 1.50 (s, 6H).

7.2.17 Ethyl 2-(3-aminophenoxy)-2-methylpropanate

In like manner to the preparation of ethyl 4-aminophenoxyacetate, hydrogenation of ethyl 2-methyl-2-(3-nitrophenoxy)propanate was carried out to prepare ethyl 2-(3-aminophenoxy)-2-methylpropanate. $^1$H NMR (CDCl$_3$): δ 6.99 (t, 2H, J=8.7 Hz), 6.32 (dt, 1H, J=1.2 and 7.2 Hz), 6.24-6.18 (m, 2H), 4.23 (q, 2H, J=7.2 Hz), 1.58 (s, 6H), 1.24 (t, 3H, J=6.9 Hz).

7.2.18 N-methyl-2-(5-amino-2-methylphenoxy)acetamide

In like manner to the preparation of ethyl 4-aminophenoxyacetate, hydrogenation of N-methyl-2-(2-methyl-5-nitrophenoxy)acetamide was carried out to prepare N-methyl-2-(5-amino-2-methylphenoxy)acetamide. $^1$H NMR (CD$_3$OD): δ 6.86 (d, 1H, J=7.5 Hz), 6.32-6.25 (m, 2H), 4.43 (s, 2H), 2.82 (s, 3H), 2.14 (s, 3H).

7.2.19 6-Amino-2-(methoxycarbonyl)-(1H)-indole

6-Amino-2-(methoxycarbonyl)-(1H)-indole was prepared according to the following references
1. Adams, Richard E.; Press, Jeffery B.; Deegan, Edward G.; Synthetic Communications (1991), 12 (5), 675-681.
2. Boger, Dale L.; Yun, Weiya; Han, Nianhe; Johnson, Douglas S.; Biiorganic & Medicinal Chemistry (1995), 3(6), 611-621

7.2.20 Preparation of 3-hydroxy-5-(methoxycarbonylmethyleneoxy)aniline and 3,5-bis(methoxycarbonylmethyleneoxy)aniline

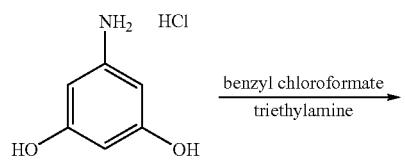

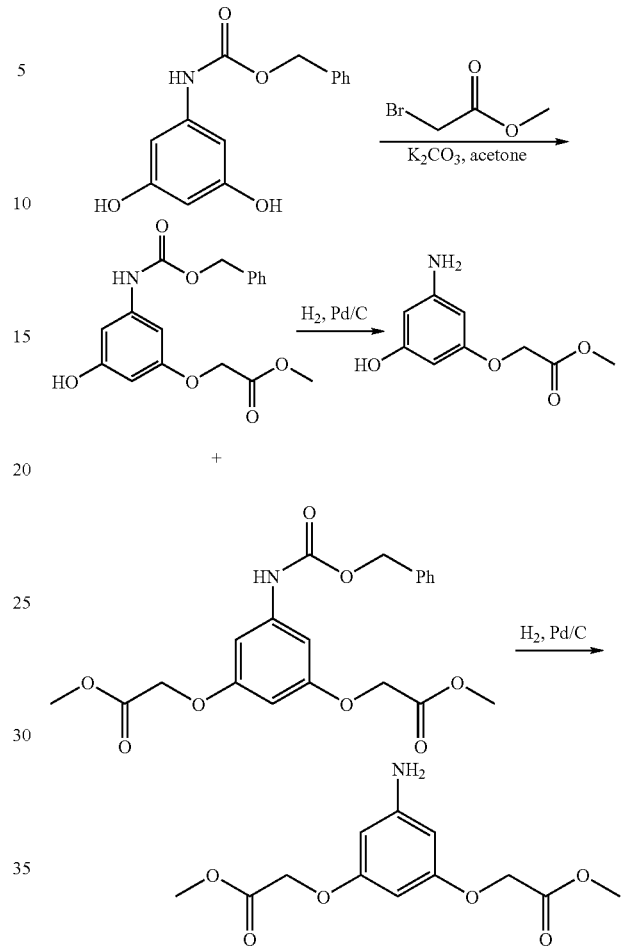

Benzyl N-(3,5-dihydroxyphenyl)carbamate

To a mixture of 5-aminobenzene-1,3-diol (0.60 g, 3.7 mmole) and sodium hydrogencarbonate (1.4 g, 16 mmole) in THF/water (15 mL, 1:1 v/v) was added dropwise benzyl chloroformate 1.6 mL, 11 mmole). After 3 h at rt, THF was removed under vacuum and the remaining aqueous layer was extracted with ethyl acetate. Purification by column chromatography over silica gel provided benzyl N-(3,5-dihydroxyphenyl)carbamate. $^1$H NMR (CD$_3$OD): δ 7.42-7.25 (m, 5H), 6.46 (d, 2H, J=2.4 Hz), 5.97-5.94 (m, 1H), 5.14 (s, 2H).

Benzyl N-[3-hydroxy-5-(methoxycarbonylmethyleneoxy) phenyl]carbamate and Benzyl N-[3,5-bis(methoxycarbonyl methyleneoxy)phenyl]carbamate In like manner to the preparation of ethyl 4-nitrophenoxyacetate, benzyl N-(3,5-dihydroxyphenyl)carbamate and methyl bromoacetate were reacted to give a mixture of benzyl N-[3-hydroxy-5-(methoxycarbonylmethyleneoxy)phenyl] carbamate $^1$H NMR (DMSO-$d_6$): δ 9.62 (s, 1H), 9.44 (s, 1H), 7.42-7.31 (m, 5H), 6.63 (s, 1H), 6.50 (t, 1H, J=2.4 Hz), 5.93 (t, 1H, J=2.4 Hz), 5.10 (s, 2H), 4.63 (s, 2H), 3.67 (s, 3H), and benzyl N-[3,5-bis(methoxycarbonylmethyleneoxy)phenyl] carbamate ¹H NMR (CDCl₃): δ 7.38-7.32 (m, 5H), 6.86 (s, 1H), 6.67 (d, 2H, J=1.8 Hz), 6.19 (t, 1H, J=2.4 Hz), 5.16 (s, 2H), 4.57 (s, 4H), 3.78 (s, 6H) which were separated by column chromatography over silica gel.

3-Hydroxy-5-(methoxycarbonylmethyleneoxy)aniline

In like manner to the preparation of ethyl 4-aminophenoxyacetate, hydrogenation of benzyl N-[3-hydroxy-5-(methoxycarbonylmethyleneoxy)phenyl]carbamate was carried out to prepare 3-hydroxy-5-(methoxycarbonylmethyleneoxy)aniline. ¹H NMR (CD₃OD): δ 5.87-5.80 (m, 2H), 5.78-5.72 (m, 1H), 4.56 (s, 2H), 3.76 (s, 3H).

3,5-Bis(methoxycarbonylmethyleneoxy)aniline

In like manner to the preparation of ethyl 4-aminophenoxyacetate, hydrogenation of benzyl N-[3,5-bis(methoxycarbonylmethyleneoxy)phenyl]carbamate was carried out to prepare 3,5-bis(methoxycarbonylmethyleneoxy)aniline. ¹H NMR (CD₃OD): δ 5.92 (d, 2H, J=2.4 Hz), 5.83 (t, 1H, J=2.4 Hz), 4.58 (s, 4H), 3.78 (s, 6H).

7.2.21 N4-(3,4-Ethylenedioxyphenyl)-5-ethoxycarbonyl-2,4-pyrimidinediamine (R950287)

A solution of 2-Chloro-5-ethoxycarbonyl-N4-(3,4-ethylenedioxyphenyl)-2,4-pyrimidineamine in EtOH was treated with a 25% aqueous solution of NH₃. The mixture was stirred for 30 min at 100° C. and purified by flash chromatography on silica gel to give N4-(3,4-ethylenedioxyphenyl)-5-ethoxycarbonyl-2,4-pyrimidinediamine as a white solid. LCMS: purity: 92.3%; MS (m/e): 317.28 (MH⁺, 100).

7.2.22 Ethyl 6-Nitro-3-carboxy-4H-imidazo[5,1-c]-1,4-benzoxazine

Was prepared according to J. of Heterocyclic Chemistry, 26, 205, (1989)

7.2.23 Ethyl 6-Amino-3-carboxy-4H-imidazo[5,1-c]-1,4-benzoxazine

Ethyl 6-Nitro-3-carboxy-4H-imidazo[5,1-c]-1,4-benzoxazine was reduced shaken in MeOH under 40 p.s.i. H2 with 20 weight percent of 10% Pd/C (Degussa) for 1 h then filtered and the solvent evaporated. The compound was purified directly by column chromatograph (EtOAc/hexane) to yield Ethyl 6-Amino-3-carboxy-4H-imidazo[5,1-c]-1,4-benzoxazine 1H (DMSO-d6) 8.41 (s, 1H), 6.98 (m, 1H), 6.82 (m, 1H), 6.43 (m, 1H), 5.28 ((s, 2H), 4.23 (q, 2H, J=6.2 Hz), 1.27 (t, 2H, J=6.2 Hz) purity 92% MS (m/e): 232 (MH⁺).

7.2.24 6-Amino-3,3-dimethyl-1,4-benzoxazine

A mixture of 15 g 2-Amino-4-nitrophenol and 40 g Boc₂O in 300 mL CHCl₃ was refluxed overnight filtered and the filtrate was evaporated to near dryness. The residue was triturated with hexanes, collected by suction filtration, and dried to yield 2-N-Boc-amino-4-nitrophenol. The 2-N-Boc-amino-4-nitrophenol was refluxed in acetone with 15.6 mL of 1-Chloro-2-methylpropene and 25 g potassium carbonate overnight. The reaction mixture was poured into ice-slush, the solid was collected by suction filtration and washed with water. The solid was dissolved in EtOAc and the organic was washed with 10% NaOH solution, water, then brine and dried over MgSO₄. The organic was filtered to remove the drying agent and evaporated to yield 18 g 1-(2-N-Boc-amino-4-nitrophenoxy)-2-methyl-2-propene. 7.8 g of 1-(2-N-Boc-amino-4-nitrophenoxy)-2-methyl-2-propene was stirred overnight in methanolic HCl in a round-bottom flask with a septum wired on, and then heated with a reflux condenser attached at 80° C. for 10 minutes. The reaction was cooled and the methanol was removed by rotary-evaporation. The residue was dissolved in 30 mL of 4N HCl, transferred to a new vessel to leave behind any undissolved solids and cooled to 0° C. 1.83 g of NaNO₂ in 5 mL water was added drop wise and the solution was neutralized with solid sodium bicarbonate. A solution of 1.64 g NaN₃ in 17 mL water was added slowly drop wise and the reaction was stirred 30 minutes. The precipitate was collected by suction filtration, washed well with water and dried on the funnel to yield 5.7 g 1-(2-Azido-4-nitrophenoxy)-2-methyl-2-propene. 7 g of 1-(2-Azido-4-nitrophenoxy)-2-methyl-2-propene was refluxed in 300 mL benzene overnight, cooled then evaporated. The crude product was recrystallized from EtOAc/Hexanes to yield 3-Methyl-6-nitro-azirino[2,1-c]-1,4-benzoxazine in two crops with a combined mass of 5.11 g of 3-Methyl-6-nitro-azirino[2,1-c]-1,4-benzoxazine was dissolved in 500 mL of MeOH/5% THF, 200 mg of 10% Pd/C (Degussa) was added and the resulting mixture was shaken under 30 p.s.i. H₂ atmosphere for 8 hours. The reaction mixture was filtered through a pad of celite and the solvent evaporated. The residue was dissolved in a minimum amount of DCM/THF/MeOH and loaded onto a 5 cm by 20 cm 3% MeOH/DCM SiO₂ column and the compound was eluted isocratically with a small amount of positive pressure. The appropriate fractions were combined and evaporated to yield 590 mg of 6-Amino-3,3-dimethyl-1, 4-benzoxazine.

1H (DMSO-d6) 6.30 (d, 1H), 5.75 (d, 1H), 5.65 (dd, 1H), 3.58 (s, 2H), 1.08 (s, 6H) purity 99% MS (m/e): 179 (MH⁺)

7.2.25 Ethyl 4-Aminophenoxyacetate

Ethyl 4-Nitrophenoxyacetate

A dry reaction flask equipped with a reflux condenser, N₂ inlet and a magnetic stirring bar was charged with 3-nitrophenol (76.45 g, 550 mmol), K₂CO₃ (76.45 g, 550 mmol) and dry acetone (500 mL) under N₂ atmosphere. To this at room temperature was added ethyl bromoacetate (55.44 mL, 500 mmol) over a period of 15 min. The reaction mixture was refluxed for 16 h, cooled and poured over ice-water (4 Kg). The resulting aqueous solution was extracted with CH₂Cl₂ (3×500 mL), dried over anhydrous Na₂SO₄ and solvent was removed to obtain 103 g (92%) of the desired ethyl 4-nitrophenoxyacetate.

¹H NMR (CDCl₃): δ 8.20 (d, 2H, J=8.2 Hz), 6.95 (d, 2H, J=8.1 Hz), 4.72 (s, 2H), 4.25 (q, 2H), 1.23 (t, 3H); LCMS: ret. time: 27.07 min.; purity: 100%; MS: 267 (M+acetonitrile).

Ethyl 4-Aminophenoxyacetate

A solution of ethyl 4-nitrophenoxyacetate (15 g) in EtOH (400 mL) was hydrogenated at 40 PSI for 40 minutes in the presence of 10% Pd/C (1.5 g, 10% by weight). After the filtration through a celite the solvent was removed under a reduced pressure to obtain ethyl 4-aminophenoxyacetate. ¹H NMR (CDCl₃): δ 6.77 (d, 2H, 8.1 Hz), 6.60 (d, 2H, J=8.0 Hz), 4.50 (s, 2H), 4.24 (q, 2H), 1.24 (t, 3H); LCMS: ret. time: 12.00 min.; purity: 100%; MS (m/e): 196 (MH+).

7.2.26 tert-Butyl 4-Aminophenoxyacetate tert-Butyl 4-Nitrophenoxyacetate

In like manner to the preparation of ethyl 4-nitrophenoxyacetate, 4-nitrophenol and tert-butyl bromoacetate were reacted to prepare tert-butyl 4-nitrophenoxyacetate. $^1$H NMR (CDCl$_3$): δ 8.2 (d, 2H, J=8.1 Hz), 6.95 (d, 2H, J=8.2 Hz), 4.60 (s, 2H), 1.42 (s, 9H).

tert-Butyl 4-Aminophenoxyacetate

In like manner to the preparation of ethyl 4-aminophenoxyacetate, hydrogenation of tert-butyl 4-nitrophenoxyacetate was carried out to prepare tert-butyl 4-aminophenoxyacetate. $^1$H NMR (CDCl$_3$): δ 6.74 (d, 2H, J=9 Hz), 6.62 (d, 2H, J=9 Hz), 4.42 (s, 2H), 1.42 (s, 9H); LCMS: ret. time: 16.35 min.; purity: 94%; MS (m/e): 224 (MH+).

7.2.27 Ethyl 3-Aminophenoxyacetate

Ethyl 3-Nitrophenoxyacetate

In like manner to the preparation of ethyl 4-nitrophenoxyacetate, 3-nitrophenol and ethyl bromoacetate were reacted to prepare ethyl 3-nitrophenoxyacetate. $^1$H NMR (CDCl$_3$): δ 7.88 (dt, 1H, J=1.2 and 8.7 Hz), 7.71 (t, 1H, J=2.4 Hz), 7.45 (t, 1H, J=8.4 Hz), 7.27 (dt, 1H, J=2.4 and 8.4 Hz), 4.70 (s, 2H), 4.29 (q, 2H, J=6.9 Hz), 1.30 (t, 3H, J=6.9 Hz); LCMS: ret. time: 27.28 min.; purity: 96%.

Ethyl 3-Aminophenoxyacetate

In like manner to the preparation of ethyl 4-aminophenoxyacetate, hydrogenation of ethyl 3-nitrophenoxyacetate was carried out to prepare ethyl 3-aminophenoxyacetate. $^1$H NMR (CDCl$_3$): δ 7.05 (t, 1H, J=7.2 Hz), 6.30 (m, 3H), 4.56 (s, 2H), 4.25 (q, 2H, J=7.2 Hz), 1.29 (t, 3H, J=6.9 Hz); LCMS: ret. time: 10.69 min.; purity: 96%; MS (m/e): 196 (MH+).

7.2.28 (±)-Ethyl 2-(4-Aminophenoxy)propionate

In like manner to the preparation of ethyl 4-aminophenoxyacetate, hydrogenation of ethyl (±)-2-(4-nitrophenoxy) propionate was carried out to prepare (±) ethyl 2-(4-aminophenoxy)propionate. $^1$H NMR (CDCl$_3$): δ 6.70 (d, 2H), 6.58 (d, 2H), 4.60 (m, 1H), 4.20 (q, 2H), 3.2 (bs, 2H), 1.45 (d, 3H), 1.22 (t, 3H).

7.2.29 N-Methyl 3-Aminophenoxyacetamide

N-Methyl 3-Nitrophenoxyacetamide

A mixture of ethyl 3-nitrophenoxyacetate (9.12 g, 40 mmol), methylamine hydrochloride (26.8 g, 400 mmol) and diisopropylethylamine (35.5 mL, 200 mL) in MeOH (100 mL) was stirred in a pressure vial at 90° C. for 6 h. The reaction was cooled to room temperature, diluted with water (1 liter), the solid formed was filtered, washed with water and dried to get the desired N-methyl 3-nitrophenoxyacetamide (8 g, 95%). $^1$H NMR CDCl$_3$): δ 7.91 (dd, 1H, J=1.8 and 8.1 Hz), 7.78 (t, 1H, J=2.4 Hz), 7.50 (t, 1H, J=8.7 Hz), 7.29 (dd, 1H, J=1.8 and 8.4 Hz), 6.50 (bs, 1H), 4.57 (s, 2H), 2.95 and 2.93 (2s, 3H); LCMS: ret. time: 17.54 min.; purity: 100%; MS (m/e): 211 (MH+).

N-Methyl 3-Aminophenoxyacetamide

In like manner to the preparation of ethyl 4-aminophenoxyacetate, the hydrogenation of N-methyl 3-nitrophenoxyacetamide (8 g, 39 mmol) was conducted to give the desired N-methyl 3-aminophenoxyacetamide (6 g, 86%). $^1$H NMR (CD$_3$OD): δ 6.99 (t, 1H, J=8.1 Hz), 6.37-6.25 (m, 3H), 4.41 (s, 2H), 2.80 (s, 3H); LCMS: ret. time: 19.80 min.; purity: 100%.

7.2.30 2-Methoxycarbonyl-5-aminobenzofuran (R926610)

2-Methoxycarbonyl-5-nitrobenzofuran (R926609)

To a suspension of 5-nitro-2-benzofurancarboxylic acid (5 g, 24.15 mmol) in CH$_2$Cl$_2$ (250 mL) at 0° C. was added DMF (0.100 mL) followed by (COCl)$_2$ (2M in CH$_2$Cl$_2$, 36.23 mL, 72.46 mL) over a period of 10 min. The reaction was stirred at 0° C. for 1 h and then at room temperature for 30 min. The reaction solvent was removed under a reduced pressure, dried under high vacuum and again suspended in CH$_2$Cl$_2$ (250 mL). The solution was cooled to 0° C., were added pyridine (4.8 mL, 48.03 mmol) followed by MeOH (10 mL, excess) and stirred overnight. The extractive work-up with CH$_2$Cl$_2$ gave the expected 2-methoxycarbonyl-5-nitrobenzofuran (R926609). $^1$H NMR (CDCl$_3$): δ 8.66 (d, 1H, J=2.4 Hz), 8.36 (dd, 1H, J=2.4 and 9.6 Hz), 7.71 (d, 1H, J=9.3 Hz), 7.65 (s, 1H), 4.01 (s, 3H); LCMS: ret. time: 26.94 min.

2-Methoxycarbonyl-5-aminobenzofuran (R926610)

In like manner to the preparation of ethyl 4-aminophenoxyacetate, the hydrogenation of 2-methoxycarbonyl-5-nitrobenzofuran (2 g) in MeOH gave 2-methoxycarbonyl-5-aminobenzofuran. $^1$H NMR (CDCl$_3$): δ 7.38 (bt, 2H), 6.90 (bd, 1H), 6.85 (bdd, 1H), 3.98 (s, 3H).

7.2.31 Methyl 2-(2-methyl-5-nitrophenoxy)acetate

In like manner to the preparation of ethyl 4-nitrophenoxyacetate, 2-methyl-5-nitrophenol and methyl bromoacetate were reacted to prepare methyl 2-(2-methyl-5-nitrophenoxy) acetate. $^1$H NMR (CD$_3$OD): δ 7.80 (dd, 1H, J=2.4 and 8.1 Hz), 7.65 (d, 1H, J=2.4 Hz), 7.38 (d, 1H, J=8.1 Hz), 4.90 (s, 2H), 3.80 (s, 3H), 2.36 (s, 3H).

7.2.32 Ethyl 2-methyl-2-(3-nitrophenoxy)propanate

A mixture of 3-nitrophenol (0.50 g, 3.6 mmole), ethyl bromodimethylacetate (0.64 g, 3.3 mmole), K$_2$CO$_3$ (1.3 g, 9.4 mmole), potassium iodide (catalytic) in absolute ethanol (8 mL) was heated at 70° C. for 18 h. The reaction mixture was cooled, poured into a saturated solution of NaHCO3, and extracted with dichloromethane. The product, ethyl 2-methyl-2-(3-nitrophenoxy)propanate, was obtained after purification by column chromatography over silica gel. $^1$H NMR (CDCl$_3$): δ 7.85 (dt, 1H, J=1.2 and 8.1 Hz), 7.68 (t, 1H, J=2.4 Hz), 7.40 (t, 1H, J=8.4 Hz), 7.19-7.13 (m, 1H), 4.26 (q, 2H, J=7.2 Hz), 1.64 (s, 6H), 1.26 (t, 3H, J=7.21),

7.2.33
N-Methyl-2-(2-methyl-5-nitrophenoxy)acetamide

In like manner to the preparation of N-methyl 3-nitrophenoxyacetamide, methyl 2-methyl-5-nitrophenoxyacetate and methylamine hydrochloride were reacted to prepare N-methyl-2-(2-methyl-5-nitrophenoxy)acetamide. $^1$H NMR (CD$_3$OD): δ 7.82 (dd, 1H, J=2.4 and 8.1 Hz), 7.69 (d, 1H, J=2.4 Hz), 7.40 (d, 1H, J=8.1 Hz), 4.66 (s, 2H), 2.83 (s, 3H), 2.40 (s, 3H).

7.2.34
N,2-Dimethyl-2-(3-nitrophenoxy)propanamide

In like manner to the preparation of ethyl 2-methyl-2-(3-nitrophenoxy)propanate, 3-nitrophenol and N,2-dimethyl-2-bromopropanamide (prepared according to the following reference: Guziec, Frank S., Jr.; Torres, Felix F. Journal of Organic Chemistry (1993), 58(6), 1604-6) were reacted to prepare N,2-dimethyl-2-(3-nitrophenoxy)propanamide. $^1$H NMR (CDCl$_3$): δ 7.94 (dt, 1H, J=1.2 and 8.1 Hz), 7.78 (t, 1H, J=2.4 Hz), 7.45 (t, 1H, J=8.4 Hz), 7.22 (ddd, 1H, J=1.2, 2.4, and 8.1 Hz), 6.61 (bs, 1H), 2.89 (d, 3H, J=5.1 Hz), 1.55 (s, 6H).

7.2.35 4-Amino-[(1H,1,2,3,4-tetrazolyl)methyleneoxy]benzene

4-Nitro-[(1H,1,2,3,4-tetrazol-5-yl)methyleneoxy]benzene

A mixture of 2-cyanomethoxy-4-nitrophenyl (5.8 g, 32.6 mmol), sodium azide (6.3 g, 98.0 mmol) and ammonium chloride (8.5 g, 163.3 mmol) was suspended in DMF (100 mL) containing acetic acid (1 mL) and the mixture heated at 70° C. After 17 h, the reaction was cooled to room temperature and 2 N aqueous hydrochloric acid (100 mL) was added. The solid which precipitated out of the reaction mixture was collected by filtration, washed with water (2×20 mL) then hexane (30 mL), affording compound 4-nitro-[(1H,1,2,3,4-tetrazol-5-yl)methyleneoxy]benzene (6.7 g, 99%) as an orange solid: $^1$H NMR (300 MHz, DMSO-d$_6$) δ 8.25 (d, J=9.2 Hz, 2H), 7.29 (d, J=9.1 Hz, 2H), 5.68 (s, 2H); ESI MS m/z 220 [C$_8$H$_7$N$_5$O$_3$—H]$^-$.

4-Amino-[(1H,1,2,3,4-tetrazolyl)methyleneoxy]benzene

A mixture of 4-nitro-[(1,2,3,4-tetrazol-5-yl)methyleneoxy]benzene (6.7 g, 30.4 mmol) and 5 wt % palladium on carbon (700 mg) suspended in ethanol/concentrated hydrochloric acid (14:1, 150 mL) was hydrogenated in a sealed vessel at 50 psi. The mixture was shaken until no further hydrogen uptake was observed, after which the reaction was filtered through diatomaceous earth with chloroform and the filtrate concentrated to afford crude product. Purification by flash chromatography (7:2.5:0.5 CHCl$_3$/CH$_3$OH/NH$_4$OH) afforded 4-amino-[(1H,1,2,3,4-tetrazolyl)methyleneoxy)] benzene as a brown solid: $^1$H NMR (300 MHz, DMSO-d$_6$) δ 6.76 (d, J=8.7 Hz, 2H), 6.52 (d, J=8.7 Hz, 2H), 5.07 (s, 2H); ESI MS m/z 190 [C$_8$H$_9$N$_5$O—H]$^-$.

7.2.36 4-Amino-[(1-methyl-1,2,3,4-tetrazol-5-yl)methyleneoxy]-benzene

4-Nitro-[(1-methyl-1,2,3,4-tetrazol-5-yl)methyleneoxy]-benzene and 4-Nitro-[(2-methyl-1,2,3,4-tetrazol-5-yl)methyleneoxy]benzene A mixture of 4-nitro-[(1H,1,2,3,4-tetrazolyl)methyleneoxy]benzene (10.00 g, 45.2 mmol), cesium carbonate (22.09 g, 67.8 mmol) and methyl iodide (7.70 g, 54.3 mmol) in DMF (200 mL) was stirred at room temperature for 24 h. The reaction mixture was concentrated to remove most of the DMF and the crude residue was partitioned between chloroform (100 mL) and water (50 mL). The organic phase was separated, washed with brine, dried (Na$_2$SO$_4$) and concentrated to afford crude product as a orange solid. Purification by flash chromatography (chloroform) afforded 4-nitro-[(1-methyl-1,2,3,4-tetrazol-5-yl)methyleneoxy]-benzene: $^1$H NMR (300 MHz, DMSO-d$_6$) δ 8.26 (d, J=9.2 Hz, 2H), 7.31 (d, J=9.2 Hz, 2H), 5.72 (s, 2H), 4.15 (s, 3H); and 4-nitro-(2-methyl-1,2,3,4-tetrazol-5-yl)methyleneoxy]benzene: $^1$H NMR (300 MHz, DMSO-d$_6$) δ 8.24 (d, J=9.3 Hz, 2H), 7.29 (d, J=9.3 Hz, 2H), 5.58 (s, 2H), 4.41 (s, 3H).

4-Amino-[(1-methyl-1,2,3,4-tetrazol-5-yl)methyleneoxy]-benzene

A mixture of 4-nitro-[(1-methyl-1,2,3,4-tetrazol-5-yl)methyleneoxy]-benzene (3.60 g, 15.3 mmol) and 5% Pd/C (0.40 g) in 14:1 ethanol/concentrated hydrochloric acid (75 mL) was shaken at room temperature in a atmosphere of hydrogen at 50 psi. After 4 h no further hydrogen uptake was observed. The reaction mixture was filtered through diatomaceous earth, the solids washed with a 6:3:1 chloroform/methanol/concentrated ammonium hydroxide solution and the filtrate concentrated to afford crude 4-amino-[(1-methyl-1,2,3,4-tetrazol-5-yl)methyleneoxy]-benzene, which was purified by flash chromatography (95:5 chloroform/methanol): $^1$H NMR (300 MHz, DMSO-d$_6$) δ 7.48 (br s, 2H), 6.79 (d, J=6.9 Hz, 2H), 6.55 (d, J=6.9 Hz, 2H), 5.36 (s, 2H), 4.10 (s, 3H).

7.2.37 4-Amino-[(2-methyl-1,2,3,4-tetrazol-5-yl)methyleneoxy]benzene

A mixture of 4-nitro-[(2-methyl-1,2,3,4-tetrazol-5-yl)methyleneoxy]benzene (3.60 g, 15.3 mmol) and 5% Pd/C (0.40 g) in 14:1 ethanol/concentrated hydrochloric acid (75 mL) was shaken at room temperature in a hydrogen atmosphere at 50 psi. After 3 h no further hydrogen uptake was observed. The reaction mixture was filtered through diatomaceous earth, the solids washed with a 6:3:1 chloroform/methanol/concentrated ammonium hydroxide solution and the filtrate concentrated to afford crude 4-amino-[(2-methyl-1,2,3,4-tetrazol-5-yl)methyleneoxy]benzene, which was purified by flash chromatography (95:5 chloroform/methanol): $^1$H NMR (300 MHz, DMSO-d$_6$) δ 6.80 (br s, 2H), 6.75 (d, J=9.0 Hz, 2H), 6.50 (d, J=9.0 Hz, 2H), 5.17 (s, 2H), 4.37 (s, 3H).

7.2.38 2-Ethoxycarbonyl-5-aminoindole (R926611)

In like manner to the preparation of ethyl 4-aminophenoxyacetate, the hydrogenation of 2-ethoxycarbonyl-5-nitroindole gave the 2-ethoxycarbonyl-5-aminoindol. LCMS: ret. time: 13.44 min.; purity: 93%; MS (m/e): 205 (MH$^+$).

7.2.39 5-[(4-Aminophenoxy)methyl]-3-phenyl-1,2,4-oaxadiazole

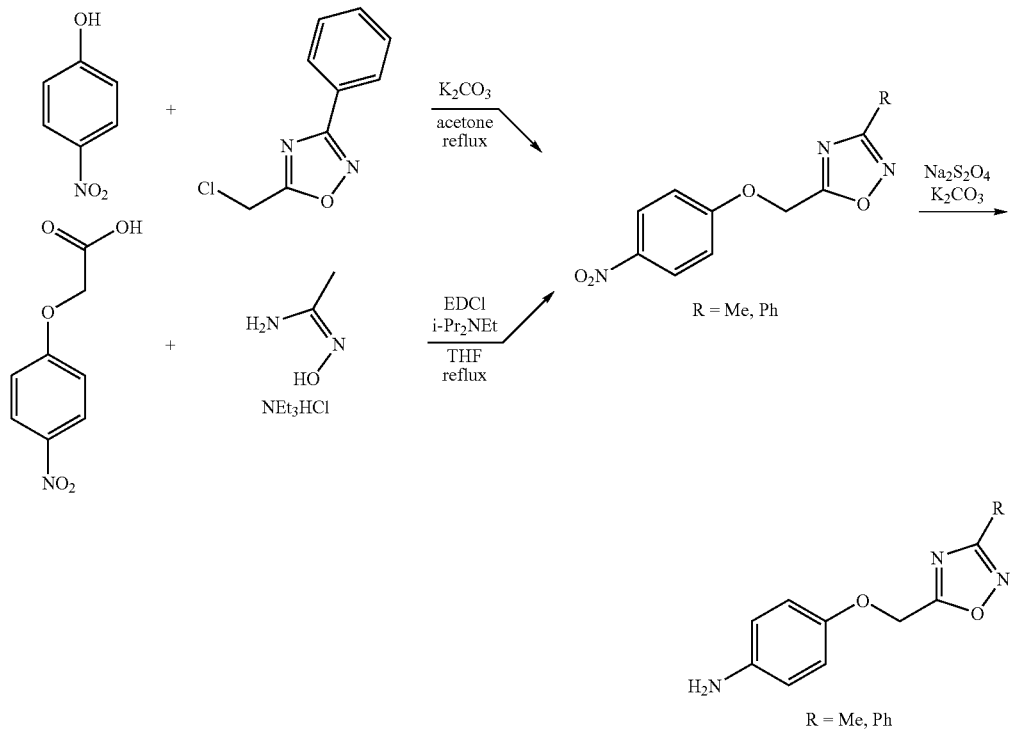

Preparation of 5-[4-(Nitrophenoxy)methyl]-3-phenyl-1,2,4-oxadiazole

4-Nitrophenol (0.36 g, 2.56 mmole), 5-(chloromethyl)-3-phenyl-1,2,4-oxadiazole (0.5 g, 2.56 mmole) and anhydrous $K_2CO_3$ (0.39 g, 2.82 mmole) were dissolved in anhydrous acetone (20 mL) and heated to reflux for 12 h. Reaction mixture was cooled and the solvent removed under vacuum. The crude solid formed was collected by filtration, washed with water and dried under vacuum to provide 5-[(4-nitrophenoxy)methyl]-3-phenyl-1,2,4-oxadiazole (0.70 g, 92%). $^1$H NMR (CDCl$_3$): δ 8.25 (d, 2H, J=8.8 Hz), 8.08 (dd, 2H, J=8.2 Hz), 7.52-7.49 (m, 3H), 7.13 (d, 2H, J=8.8 Hz), 5.45 (s, 2H).

Preparation of 5-[(4-Aminophenoxy)methyl]-3-phenyl-1,2,4-oxadiazole

The 5-[(4-nitrophenoxy)methyl]-3-phenyl-1,2,4-oxadiazole (0.5 g, 1.68 mmole) was dissolved in methanol:methylenechloride (1:1) (120 mL). Aqueous solution of (15 mL) sodium hydrosulfite (0.88 g, 5.05 mmole) and $K_2CO_3$ (0.70 g, 5.06 mmole) was added dropwise under nitrogen for 10 min. The contents were allowed to stir at room temperature. After consumption of starting material, reaction mixture was concentrated, diluted with water till the homogeneous layer formed. The aqueous layer was extracted with several times with ethylacetate and methylene chloride. The turbid organic layers were combined, dried with anhydrous $Na_2SO_4$ and concentrated. Purification of the solid concentrate by silica gel chromatography provided 5-[(4-aminophenoxy)methyl]-3-phenyl-1,2,4-oxadiazole (0.23 g, 51%). $^1$H NMR (CDCl$_3$): δ 8.11 (m, 2H), 7.52-7.46 (m, 3H), 6.87 (d, 2H, J=8.8 Hz), 6.64 (d, 2H, J=8.8 Hz), 5.26 (s, 2H), 3.49 (br s, 2H).

Preparation of 5-[(4-Nitrophenoxy)methyl]-3-methyl-1,2,4-oxadiazole

A mixture of 4-nitrophenoxy acetic acid (2.25 g, 11.4 mmole), acetamideoxime, triethylamine hydrochloride (3.85 g, 27.62 mmole), EDCI.HCl (4.37 g, 22.79 mmole) and diisopropylethylamine (7.42 g, 57.40 mmole) in anhydrous THF (250 ml) was refluxed for 18 h. The unhomogenous brown colored reaction mixture was quenched with water and extracted with EtOAc (3×300 mL). The combined organic layers washed successively with aqueous NaHCO$_3$, brine and dried over anhydrous Na$_2$SO$_4$. Removal of solvent and purified by chromatographic purification provided 5-[(4-nitrophenoxy)methyl]-3-methyl-1,2,4-oxadiazole (1.62 g, 60%). $^1$H NMR (CDCl$_3$): δ 8.24 (d, 2H, J=8.8 Hz), 7.08 (d, 2H, J=8.8 Hz), 5.36 (s, 2H), 2.44 (s, 3H).

Preparation of 5-[(4-Aminophenoxy)methyl]-3-methyl-1,2,4-oxadiazole

In like manner to the preparation of 5-[(4-aminophenoxy)methyl]-3-phenyl-1,2,4-oxadiazole, 5-(4-nitrophenoxymethyl)-3-methyl-1,2,4-oxadiazole was reacted with aqueous solution of sodium hydrosulfite and $K_2CO_3$ to prepare 5-[(4-aminophenox)ymethyl]-3-methyl-1,2,4-oxadiazole. $^1$H NMR (CDCl$_3$): δ 6.82 (d, 2H, J=8.8 Hz), 6.63 (d, 2H, J=8.8 Hz), 5.15 (s, 2H), 3.38 (br s, 2H), 2.41 (s, 3H).

7.2.40 Ethyl 2-(4-aminophenyl)-2-methylpropionate

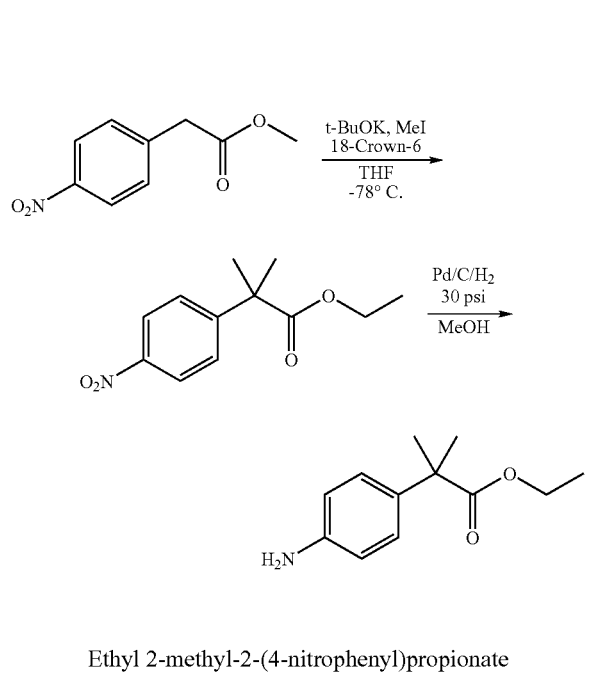

Ethyl 2-methyl-2-(4-nitrophenyl)propionate

A dry reaction flask charged with ethyl 4-nitrophenylacetate (5.0 g, 23.89 mmole), iodomethane (8.48 g, 3.72 mL, 59.74 mmole), 18-crown-6 (1.57 g, 5.93 mmole) in dry THF (200 mL) was cooled to −78° C. under nitrogen atmosphere. While stirring the contents, t-BuOK (5.90 g, 52.57 mmole) was added portionwise. The resulting violet precipitate was stirred at −78° C. for 2 h and allowed the contents to warm to room temperature. The reaction was stirred at room temperature for 6 h. At this time, once again the contents were cooled to −78° C. another portion of iodomethane, t-BuOK, and 18-crown-6 were added successively and stirred at the same temperature for 2 h. The reaction was allowed to warm to room temperature and stirred overnight. The reaction was quenched with saturated aq. NH$_4$Cl (75 mL), the resulting homogenous mixture extracted with ether (4×200 mL), dried over anhydrous Na$_2$SO$_4$, and concentrated. The concentrate was purified by silica gel column chromatography with 1% EtOAc/hexanes to provide ethyl 2-methyl-2-(4-nitrophenyl)propionate as a pale yellow oil (2.38, 42%). $^1$H NMR (CDCl$_3$): δ 8.17 (d, 2H, J=8.8 Hz), 7.49 (d, 2H, J=8.8 Hz), 4.12 (qt, 2H, J=7.0 Hz), 1.60 (s, 6H), 1.17 (t, 3H, J=7.0 Hz).

Ethyl-2-(4-aminophenyl)-2-methylpropionate

In like manner to the preparation of ethyl 4-aminophenoxyacetate, the hydrogenation of ethyl 2-methyl-2-(4-nitrophenyl)propionate provided ethyl-2-(4-aminophenyl)-2-methylpropionate. $^1$H NMR (CDCl$_3$): δ 7.16 (d, 2H, J=8.8 Hz), 6.63 (d, 2H, J=8.8 Hz), 4.09 (qt, 2H, J=7.0 Hz), 3.62 (br s, 2H), 1.52 (s, 6H), 1.17 (t, 3H, J=7.0 Hz).

7.2.41 Anilines Substituted with 1,3,4-oxadiazole Moieties

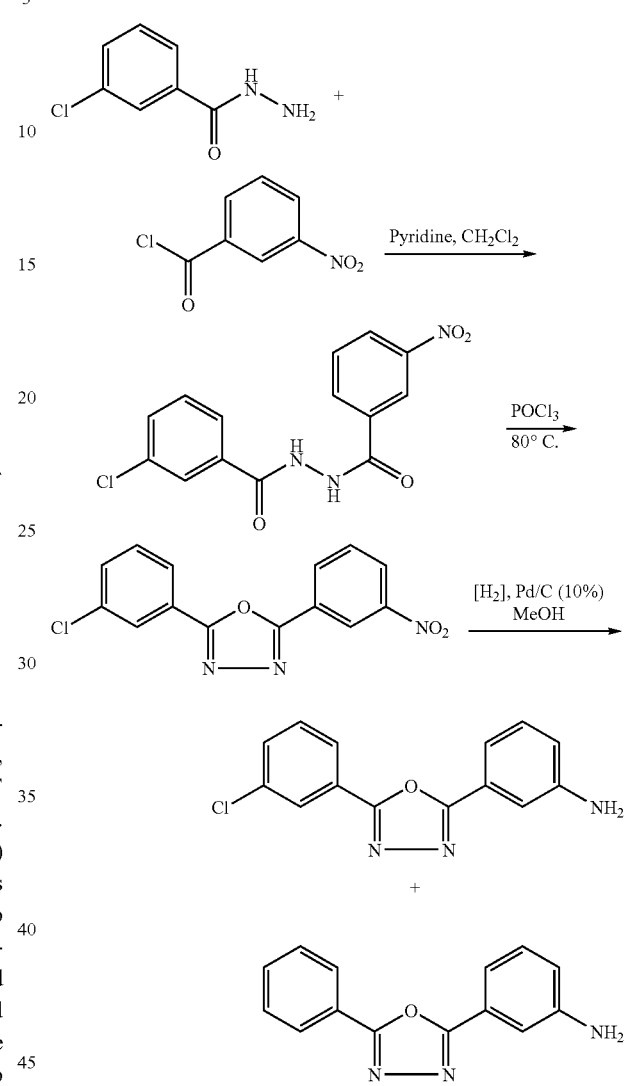

N'1-(3-Chlorobenzoyl)-3-nitrobenzene-1-carbohydrazide

To a solution of 3-chlorobenzohydrazide (1 equivalent) and pyridine (2 equivalents) in CH$_2$Cl$_2$ at 0° C. was added a CH$_2$Cl$_2$ solution of 3-nitrobenzoyl chloride (1 equivalents) and stirred at 0° C. for 1 h and then at room temperature for overnight. The resulting solution was concentrated and diluted with water, basified with NaHCO$_3$, the solid was filtered, washed with water, dried and analyzed to obtain N'1-(3-chlorobenzoyl)-3-nitrobenzene-1-carbohydrazide.
$^1$H NMR (DMSO-d6): δ 10.99 (s, 1H), 10.79 (s, 1H), 8.73 (bs, 1H), 8.43 (bdd, 1H, J=1.2 and 8.1 Hz), 8.33 (bdd, 1J, J=8.4 Hz), 7.95 (s, 1H), 7.87 (m, 2H), 7.67 (bdd, 1H, J=1.2 and 8.1 Hz), 7.57 (t, 1H, J=7.8 Hz); LCMS: purity: 85%; MS (m/e): 320 (MH$^+$).

[2-(3-Chlorophenyl)-1,3,4-oxadiazol-5-yl]-3-nitrobenzene

A suspension of N'1-(3-chlorobenzoyl)-3-nitrobenzene-1-carbohydrazide (0.321 g) in POCl₃ (3 mL) was stirred at 90° C. for 24 h. The resulting clear solution was quenched with ice-water, solid obtained was filtered washed with water, dried and analyzed to give [2-(3-chlorophenyl)-1,3,4-oxadiazol-5-yl]-3-nitrobenzene. $^1$H NMR (DMSO-d6): δ 8.86 (t, 1H, J=1.8 Hz), 8.59 (dt, 1H, J=1.8 and 8.4 Hz), 8.48 (m, 1H), 8.25 (t, 1H, J=1.8 Hz), 8.16 (dt, 1H, J=1.2 and 7.5 Hz), 7.93 (t, 1H, J=8.1 Hz), 7.75 (m, 1H), 7.66 (t, 1H, J=7.5 Hz); LCMS: purity: 86%; MS (m/e): 302 (MH⁺).

Reduction of [2-(3-chlorophenyl)-1,3,4-oxadiazol-5-yl]-3-nitrobenzene

The hydrogenation of [2-(3-chlorophenyl)-1,3,4-oxadiazol-5-yl]-3-nitrobenzene (0.2 g) using 10% Pd/C (0.04 g) in MeOH (200 mL) at 15 PSI for 1 h gave a mixture of two products viz. 3-amino-[2-(3-chlorophenyl)-1,3,4-oxadiazol-5-yl]benzene and 3-amino-(2-phenyl-1,3,4-oxadiazol-5-yl) benzene which were separated by silica gel column chromatography using n-hexanes then n-hexanes: 5-10% EtOAc as a solvent system. 3-Amino-[2-(3-chlorophenyl)-1,3,4-oxadiazol-5-yl]benzene: $^1$H NMR (DMSO-d6): δ 8.08 (m, 2H), 7.64 (m, 4H), 7.42 (m, 1H), 7.10 (m, 1H); LCMS: purity: 82%; MS (m/e): 272 (MH⁺). 3-Amino-(2-phenyl-1,3,4-oxadiazol-5-yl) benzene: $^1$H NMR (DMSO-d6): δ 8.13 (m, 1H), 7.54 (m, 5H), 7.30 (m, 1H), 6.86 (dd, 1H, J=1.5 and 8.1 Hz); LCMS: purity: 93%; MS (m/e): 238 (MH⁺).

N'1-(Ethoxycarbonylmethylenecabonyl)-3-nitrobenzene-1-carbohydrazide

In like manner to the preparation of N'1-(3-chlorobenzoyl)-3-nitrobenzene-1-carbohydrazide, the reaction of 3-nitrobenzoyl chloride with ethoxycarbonylmethlenecarbohydrazide gave N'1-(ethoxycarbonylmethylenecabonyl)-3-nitrobenzene-1-carbohydrazide. $^1$H NMR (CD₃OD): δ 8.74 (m, 1H), 8.44 (dd, 1H, 1.8 and 8.1 Hz), 8.25 (bd, 1H, J=8.4 Hz), 7.76 (t, 1H, J=8.4 Hz), 4.22 (q, 2H, J=6.9 Hz), 3.44 (bs, 2H), 1.29 (t, 3H, J=6.8 Hz); LCMS: purity: 93%; MS (m/e): 296 (MH⁺).

[2-(Ethoxycarbonylmethylene)-1,3,4-oxadiazol-5-yl]-3-nitrobenzene

In like manner to the preparation of [2-(3-chlorophenyl)-1,3,4-oxadiazol-5-yl]-3-nitrobenzene the reaction of POCl3 with N'1-(ethoxycarbonylmethylenecabonyl)-3-nitrobenzene-1-carbohydrazide gave [2-(ethoxycarbonylmethylene)-1,3,4-oxadiazol-5-yl]-3-nitrobenzene. $^1$H NMR (CDCl₃): δ 8.88 (t, 1H, J=1.8 Hz), 8.42 (m, 2H), 7.74 (t, 1H, J=7.5 Hz), 4.27 (q, 2H, J=7.2 Hz), 4.08 (s, 2H), 1.31 (t, 3H, J=7.2 Hz); LCMS: purity: 95%; MS (m/e): 278 (MH⁺).

7.2.42 Synthesis of (±)-5-Amino-(2,3-dihydro-2-methoxycarbonyl)benzofuran

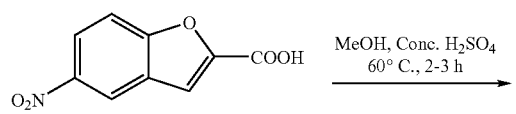

2-Methoxycarbonyl-5-nitrobenzofuran

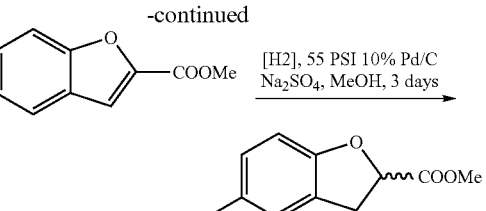

A mixture of 2-carboxy-5-nitrobenzofuran (2.0 g), MeOH (10 mL) and Concentrated H₂SO₄ (2.1 mL) was heated in a sealed tube at 60° C. for 3 h. Upon cooling to the room temperature it was quenched with ice-water and carefully basified with addition of NaHCO₃. The solid obtained was filtered, washed with water, dried and analyzed to give 2-methoxycarbonyl-5-nitrobenzofuran. $^1$H NMR (CDCl₃): δ 8.66 (d, 1H, J=2.4 Hz), 8.36 (dd, 1H, J=2.4 and 9.6 Hz), 7.71 (d, 1H, J=9.3 Hz), 7.65 (s, 1H), 4.01 (s, 3H); LCMS: purity: 97%; MS (m/e): 222 (MH⁺).

(±)-5-Amino-(2,3-dihydro-2-methoxycarbonyl)benzofuran

A suspension of 2-methoxycarbonyl-5-nitrobenzofuran (2.0 g), 10% Pd/C (2.0 g), Na₂SO₄ (2.0 g) in MeOH (500 mL) was hydrogenated at 55 PSI for 3 days. The resulting solution was filtered through a pad of celite, concentrated and chromatographed using n-hexanes then 10%, 20% EtOAc/n-hexanes to give (±)-5-amino-(2,3-dihydro-2-methoxycarbonyl) benzofuran. $^1$H NMR (CDCl₃): δ 6.69 (d, 1H, J=8.1 Hz), 6.56 (d, 1H, J=1.2 Hz), 6.48 (dd, 1H, J=1.8 and 7.5 Hz), 5.14 (dd, 1H, J=6.6 and 7.2 Hz), 3.79 (s, 3H), 3.47 (dd, 1H, J=10.5 and 10.8 Hz), 3.26 (dd, 1H, J=7.2 and 6.6 Hz); LCMS: purity: 100%; MS (m/e): 194 (MH⁺).

7.2.43 3-[1-Bis(ethoxycarbonyl)ethoxy]aniline

Preparation of Diethyl 2-methyl-2-(3-nitrophenoxy)malonate

Diethyl 2-bromo-2-methylmalonate (1.0 g, 3.95 mmole) was added to a stirred suspension of potassium fluoride (0.57 g, 9.8 mmole) in dry DMF (5 mL). After stirring for 20 min at room temperature, 3-nitrophenol (0.55 g, 3.95 mmole) was added. The resulting mixture was stirred at 60° C. for 6 h, cooled to room temperature, diluted with water (30 mL) and extracted with ethyl acetate (3×200 mL). The organic layer was washed with aq. 1N NaOH (2×75 mL), dried over anhydrous Na₂SO₄, filtered and evaporated in vacuo to provide diethyl 2-methyl-2-(3-nitrophenoxy)malonate (0.89 g, 80%). $^1$H NMR (CDCl₃): δ 7.92 (dd, 1H, J=2.3 and 8.2 Hz), 7.82 (t, 1H, J=2.3 Hz), 7.41 (t, 1H, J=8.2 Hz), 7.30 (dd, 1H, J=2.3 and 8.2 Hz), 4.28 (qt, 4H, J=7.0 Hz), 1.81 (s, 3H), 1.26 (t, 6H, J=7.0 Hz).

Preparation of 3-[1-Bis(ethoxycarbonyl)ethoxy]aniline

Diethyl 2-methyl-2-(3-nitrophenoxy)malonate (0.75 g, 2.40 mmole) was dissolved in toluene:ethanol (1:1, 100 mL), transferred to par shaker bottle containing Pd/C (0.15 g) and anhydrous Na₂SO₄ (5.0 g) in the presence of nitrogen atmosphere. The resulting mixture was treated with hydrogen (30 PSI) till the disappearance of diethyl 2-methyl-2-(3-nitrophenoxy)malonate (2 h). The mixture was filtered through celite covered with anhydrous Na$_2$SO$_4$ followed by washing the celite pad with EtOAc. The filtrated was concentrated and dried under vacuo to furnish 3-[1-bis(ethoxycarbonyl)ethoxy]aniline in quantitative yield $^1$H NMR (CDCl$_3$): δ 6.98 (t, 1H, J=8.2 Hz), 6.37-6.28 (m, 3H), 4.26 (qt, 4H, J=7.0 Hz), 3.65 (br s, 2H), 1.72 (s, 3H), 1.24 (t, 6H, J=7.0 Hz).

7.2.44 Preparation of 4-(4-aminophenoxymethyl)-2-methoxycarbonyl-furan

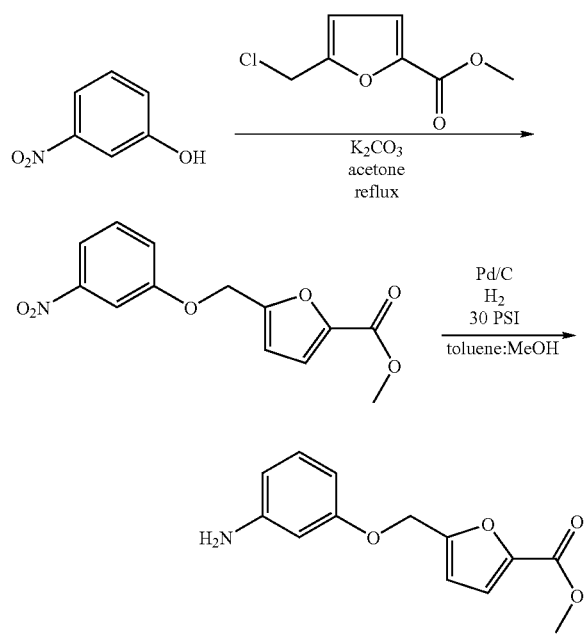

Preparation of 4-(4-nitrophenoxymethyl)-2-methoxycarbonyl-furan

3-Nitrophenol (1.0 g, 7.19 mmole), methyl 5-(chloromethyl)-2-furoate (1.38 g, 7.90 mmole) and anhydrous K$_2$CO$_3$ (1.19 g, 8.60 mmole) in acetone (30 mL) were refluxed for 8 h. The reaction mixture was cooled and diluted with water. The resultant white solid was filtered, washed with water and air dried overnight to give 1.81 g (90%) of the desired product. $^1$H NMR (CDCl$_3$): δ 7.86 (dd, 1H, J=2.3 and 8.2 Hz), 7.80 (t, 1H, J=2.3 Hz), 7.45 (t, 1H, J=8.2 Hz), 7.27 (dd, 1H, J=2.3 and 8.2 Hz), 7.17 (d, 1H, J=3.5 Hz), 6.58 (d, 1H, J=3.5 Hz), 5.13 (s, 2H), 3.90 (s, 3H).

Preparation of 4-(4-aminophenoxymethyl)-2-methoxycarbonyl-furan

In like manner to the reduction of diethyl 2-methyl-2-(3-nitrophenoxy)malonate, 4-(4-nitrophenoxymethyl)-2-methoxycarbonyl-furan was reduced to provide 4-(4-aminophenoxymethyl)-2-methoxycarbonyl-furan. $^1$H NMR (CDCl$_3$): δ 7.15 (d, 1H, J=3.5 Hz), 7.05 (t, 1H, J=8.2 Hz), 6.50 (d, 1H, J=3.5 Hz), 6.37-6.27 (m, 3H), 5.01 (s, 2H), 3.89 (s, 3H).

7.2.45 Preparation of 6-amino-1-(methoxycarbonyl)methylindazoline

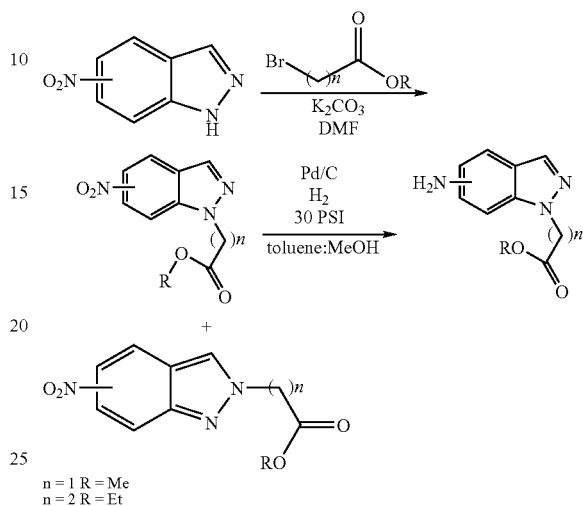

n = 1 R = Me
n = 2 R = Et

Preparation of 1-(methoxycarbonyl)methyl-6-nitroindazoline

To a solution of 6-nitroindazoline (2.0 g, 12.25 mmole) in dry DMF was added anhydrous K$_2$CO$_3$ (1.84 g, 13.31 mmole) and methyl 2-bromoacetate (2.04 g, 13.33 mmole). The resulting mixture was stirred at room temperature for 12 h. The reaction mixture was quenched with water and the resulting solid was collected by filtration, washed with excessive water, and air dried. The yellow solid collected was purified by silica gel column chromatography using gradient solvent system to furnish two products. The desired product (1.12 g, 41%) with high R$_f$ value on the TLC in 30% EtOAc:hexanes was collected.

In like manner to the reduction of diethyl 2-methyl-2-(3-nitrophenoxy)malonate, 1-(Methoxycarbonyl)methyl-6-nitro-indazoline was reduced to provide 6-amino-1-(methoxycarbonyl)methylindazoline. $^1$H NMR (CDCl$_3$): δ 7.73 (d, 1H, J=1.1 Hz), 7.35 (d, 1H, J=8.2 Hz), 6.49 (dd, 1H, J=1.8 and 8.8 Hz), 6.39 (s, 1H), 5.34 (br s, 2H), 5.10 (s, 2H), 3.64 (s, 3H).

Preparation of 1-(methoxycarbonyl)methyl-5-nitroindazoline

In like manner to the preparation of 1-(methoxycarbonyl)methyl-6-nitroindazoline, 1-(methoxycarbonyl)methyl-5-nitroindazoline was prepared by alkylation of 5-nitroindazoline with methyl 2-bromoacetate in presence of K$_2$CO$_3$. The desired product (1.34 g, 46%) with high R$_f$ value on the TLC in 30% EtOAc:hexanes was collected by silica gel column chromatographic purification. $^1$H NMR (CDCl$_3$): δ 8.75 (d, 1H, J=1.8 Hz), 8.30 (dd, 1H, J=2.3 and 8.2 Hz), 8.26 (s, 1H), 7.40 (d, 1H, J=8.2 Hz), 5.22 (s, 2H), 3.78 (s, 3H).

Preparation of 5-amino-1-(methoxycarbonyl)methylindazoline

In like manner to the reduction of diethyl 2-methyl-2-(3-nitrophenoxy)malonate, 1-(Methoxycarbonyl)methyl-5-nitro-indazoline was reduced to provide 5-amino-1-(methoxycarbonyl)methylindazoline. $^1$H NMR (CDCl$_3$): δ 7.84 (d, 1H, J=2.3 Hz), 7.15 (d, 1H, J=8.8 Hz), 6.95 (d, 1H, J=2.3 Hz), 6.88 (dd, 1H, J=2.3 and 8.8 Hz), 5.09 (s, 2H), 3.73 (s, 3H).

Preparation of
1-(2-ethoxycarbonylethyl)-6-nitroindazoline

In like manner to the preparation of 1-(methoxycarbonyl)methyl-6-nitroindazoline, 1-(ethoxycarbonyl)ethyl-6-nitroindazoline was prepared by alkylation of 6-nitroindazoline with ethyl 3-bromopropionate in presence of K$_2$CO$_3$. The desired product (58%) with high R$_f$ value on the TLC in 30% EtOAc:Hexanes was collected by silica gel column chromatographic purification. $^1$H NMR (CDCl$_3$): δ 8.49 (s, 1H), 8.12 (s, 1H), 8.01 (dd, 1H, J=1.7 and 8.8 Hz), 7.82 (d, 1H, J=8.8 Hz), 4.74 (t, 2H, J=6.4 Hz), 4.09 (qt, 2H, J=7.0 Hz), 3.03 (t, 2H, J=6.4 Hz), 1.18 (t, 3H, J=7.0 Hz).

Preparation of
6-amino-1-(2-ethoxycarbonylethyl)indazoline

In like manner to the reduction of diethyl 2-methyl-2-(3-nitrophenoxy)malonate, 1-(2-ethoxycarbonylethyl)-6-nitroindazoline was reduced to provide 6-amino-1-(2-ethoxycarbonylethyl)indazoline. $^1$H NMR (CDCl$_3$): δ 7.81 (s, 1H), 7.46 (d, 1H, J=8.8 Hz), 6.60 (app s, 1H), 6.55 (dd, 1H, J=2.3 and 8.8 Hz), 4.51 (t, 2H, J=7.0 Hz), 4.11 (qt, 2H, J=7.0 Hz), 3.52 (br s, 2H), 2.91 (t, 2H, J=7.0 Hz), 1.18 (t, 3H, J=7.0 Hz).

Preparation of
1-(2-ethoxycarbonylethyl)-5-nitroindazoline

In like manner to the preparation of 1-(methoxycarbonyl)methyl-5-nitroindazoline, 1-(ethoxycarbonyl)ethyl-5-nitroindazoline was prepared by alkylation of 5-nitroindazoline with ethyl 3-bromopropionate in presence of K$_2$CO$_3$. The desired product (43%) with high R$_f$ value on the TLC in 30% EtOAc:Hexanes was collected by silica gel column chromatographic purification. $^1$H NMR (CDCl$_3$): δ 8.70 (d, 1H, J=1.7 Hz), 8.27 (dd, 1H, J=2.3 and 8.8 Hz), 8.20 (d, 1H, J=1.7 Hz), 7.59 (d, 1H, J=8.8 Hz), 4.70 (t, 2H, J=6.4 Hz), 4.07 (qt, 2H, J=7.0 Hz), 3.01 (t, 2H, J=6.4 Hz), 1.16 (t, 3H, J=7.0 Hz).

Preparation of
5-amino-1-(2-ethoxycarbonylethyl)indazoline

In like manner to the reduction of diethyl 2-methyl-2-(3-nitrophenoxy)malonate, 1-(2-ethoxycarbonylethyl)-5-nitroindazoline was reduced to provide 5-amino-1-(2-ethoxycarbonylethyl)indazoline. $^1$H NMR (CDCl$_3$): δ 7.78 (s, 1H), 7.30 (d, 1H, J=8.8 Hz), 6.91 (d, 1H, J=2.3 Hz), 6.87 (dd, 1H, J=2.3 and 8.8 Hz), 4.59 (t, 2H, J=6.4 Hz), 4.08 (qt, 2H, J=7.0 Hz), 3.02 (br s, 2H), 2.92 (t, 2H, J=7.0 Hz), 1.16 (t, 3H, J=7.0 Hz).

Preparation of 5-amino-2-methylindazoline

In like manner to the reduction of diethyl 2-methyl-2-(3-nitrophenoxy)malonate, commercially available 2-methyl-5-nitrophenoxy)malonate, commercially available 2-methyl-5-nitroindazoline was reduced to provide 5-amino-2-methylindazoline. $^1$H NMR (CDCl$_3$): δ 7.61 (s, 1H), 7.53 (d, 1H, J=8.8 Hz), 6.81 (dd, 1H, J=2.3 and 8.8 Hz), 6.75 (d, 1H, J=2.3 Hz), 4.13 (s, 3H), 3.85 (br s, 2H).

7.2.46 Preparation of methyl
3-methoxy-4-[(6-nitroindazol-1-yl)methyl]benzoate

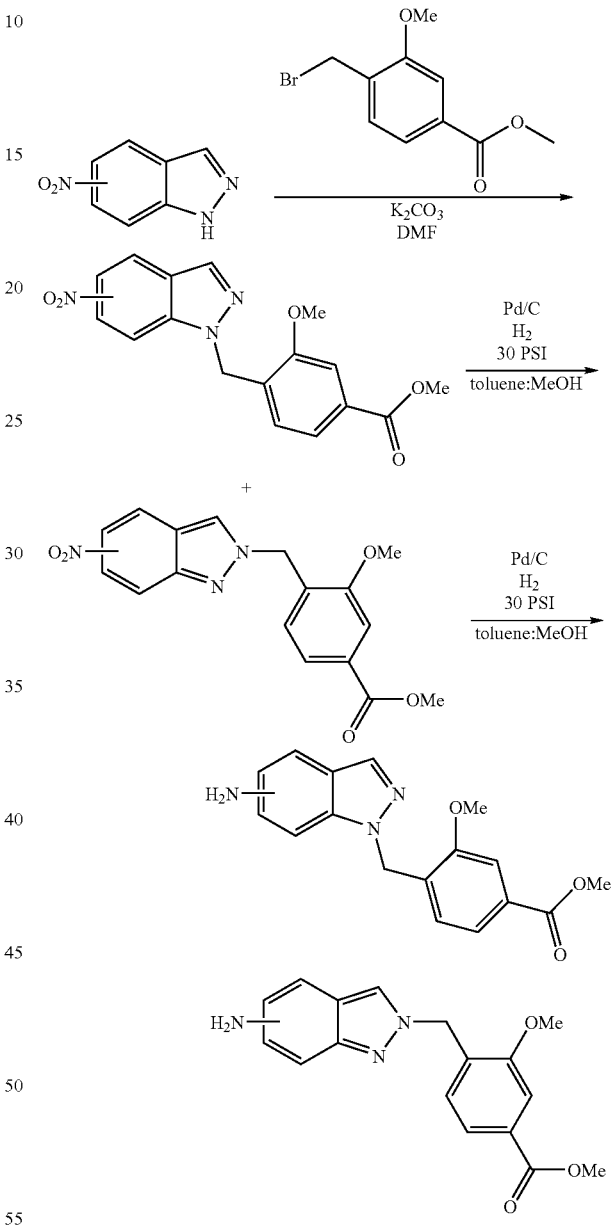

In like manner to the preparation of 1-(methoxycarbonyl)methyl-6-nitro-indazoline, methyl 3-methoxy-4-[(6-nitroindazol-1-yl)methyl]benzoate was prepared by alkylation of 6-nitroindazoline with methyl (4-bromomethyl)-3-methoxybenzoate in presence of K$_2$CO$_3$. The desired product (48%) with high R$_f$ value on the TLC in 30% EtOAc:hexanes was collected by silica gel column chromatographic purification. $^1$H NMR (CDCl$_3$): δ 8.50 (d, 1H, J=1.7 Hz), 8.14 (s, 1H), 8.00 (dd, 1H, J=1.8 and 8.8 Hz), 7.82 (d, 1H, J=8.8 Hz), 7.56 (s, 1H), 7.54 (d, 1H, J=1.8 Hz), 7.07 (d, 1H, J=8.2 Hz), 5.70 (s, 2H), 3.96 (s, 3H), 3.88 (s, 3H). Low R$_f$: Methyl 3-methoxy- 4-[(6-nitroindazol-2-yl)methyl]benzoate: ¹H NMR (CDCl₃): δ 8.68 (br s, 1H), 8.07 (s, 1H), 7.86 (dd, 1H, J=1.8 and 9.0 Hz), 7.72 (d, 1H, J=9.0 Hz), 7.61 (d, 1H, J=7.7 Hz), 7.58 (s, 1H), 7.19 (d, 1H, J=7.7 Hz), 5.69 (s, 2H), 3.93 (s, 3H), 3.90 (s, 3H).

Preparation of Methyl
4-[(6-aminoindazol-1-yl)methyl]benzoate

In like manner to the reduction of diethyl 2-methyl-2-(3-nitrophenoxy)malonate, methyl 3-methoxy-4-[(6-nitroindazol-1-yl)methyl]benzoate was reduced to provide methyl 4-[(6-aminoindazol-1-yl)methyl]benzoate. ¹H NMR (CDCl₃): δ 7.88 (s, 1H), 7.53 (d, 1H, J=8.8 Hz), 7.51 (d, 1H, J=8.8 Hz), 7.50 (d, 1H, J=1.7 Hz), 6.67 (d, 1H, J=8.8 Hz), 6.56 (dd, 1H, J=1.7 and 8.8 Hz), 6.45 (d, 1H, J=1.2 Hz), 5.50 (s, 2H), 3.94 (s, 3H), 3.87 (s, 3H), 3.79 (br s, 2H).

Preparation of Methyl
4-[(6-aminoindazol-2-yl)methyl]benzoate

In like manner to the reduction of diethyl 2-methyl-2-(3-nitrophenoxy)malonate, methyl 3-methoxy-4-[(6-nitroindazol-2-yl)methyl]benzoate was reduced to provide methyl 4-[(6-aminoindazol-2-yl)methyl]benzoate. ¹H NMR (CDCl₃): δ 7.78 (s, 1H), 7.56-7.53 (m, 2H), 7.43 (d, 1H, J=8.8 Hz), 6.98 (d, 1H, J=8.2 Hz), 6.81 (app s, 1H), 6.58 (dd, 1H, J=1.8 and 8.8 Hz), 5.53 (s, 2H), 3.91 (s, 3H), 3.89 (s, 3H).

7.2.47 Preparation of 6-amino-1-[2-methoxy-4-(o-toluylsulfonamidocarboxy)benzyl]indazoline

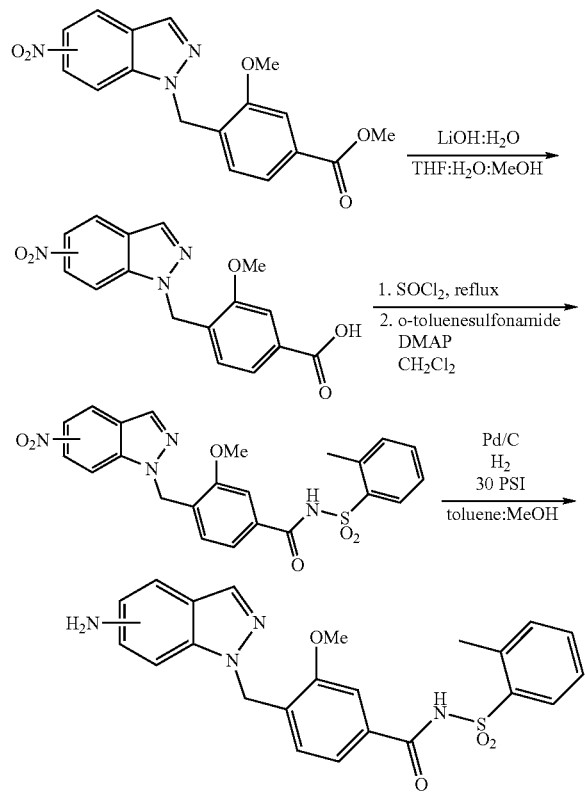

Preparation of 6-nitro-1-[2-methoxy-4-(o-toluylsulfonamidocarboxy)benzyl]indazoline Ester hydrolysis of methyl 3-methoxy-4-[(6-nitroindazol-1-yl)methyl]benzoate in presence of LiOH:H₂O produced the corresponding acid. The acid (1.65 g, 5.04 mmole) thus formed was converted to the acid chloride by reacting with SOCl₂ (3.68 mL, 50.45 mmole) at reflux temperature for 5 h. The reaction mixture was cooled to room temperature and concentrated under vacuo. To acid chloride concentrate dissolved in dry CH₂Cl₂ (75 mL), o-toluylbenzenesulfonamide (0.95 g, 5.54 mmole) and 4-(dimethylamino)-pyridine (0.67 g, 5.54 mmole) were added successively at room temperature and stirred for 12 h. The reaction mixture was concentrated, dissolved in EtOAc (700 mL) and successively treated with 2 N HCl (2×100 mL), water (150 mL) and brine (100 mL). Usual workup and purification by silica gel column chromatography provided the product (1.57 g, 64%). ¹H NMR (DMSO-d₆): δ 8.75 (s, 1H), 8.31 (s, 1H), 8.00 (d, 1H, J=8.8 Hz), 7.95-7.91 (m, 2H), 7.50 (d, 1H, J=1.2 Hz), 7.46-7.27 (m, 4H), 6.92 (d, 1H, J=7.6 Hz), 5.76 (s, 2H), 3.81 (s, 3H), 2.54 (s, 3H).

Preparation of 6-amino-1-[2-methoxy-4-(o-toluylsulfonamidocarboxy)benzyl]indazoline In like manner to the reduction of diethyl 2-methyl-2-(3-nitrophenoxy)malonate, 6-nitro-1-[2-methoxy-4-(o-toluylsulfonamidocarboxy)benzyl]indazoline was reduced to provide 6-amino-1-[2-methoxy-4-(o-toluylsulfonamidocarboxy)benzyl]indazoline. ¹H NMR (CDCl₃): δ 7.96 (dd, 1H, J=1.2 and 8.2 Hz), 7.76 (s, 1H), 7.51 (d, 1H, J=1.2 Hz), 7.49-7.44 (m, 1H), 7.37 (d, 2H, J=8.8 Hz), 7.34-7.32 (m, 1H), 7.30 (d, 1H, J=8.8 Hz), 6.51-6.47 (m, 2H), 6.35 (s, 1H), 5.35 (s, 2H), 3.89 (s, 3H), 2.54 (s, 3H).

Preparation of methyl
3-methoxy-4-[(5-nitroindazol-1-yl)methyl]benzoate

In like manner to the preparation of methyl 3-methoxy-4-[(6-nitroindazol-1-yl)methyl]benzoate, methyl 3-methoxy-4-[(5-nitroindazol-1-yl)methyl]benzoate was prepared by alkylation of 5-nitroindazoline with methyl (4-bromomethyl)-3-methoxybenzoate in presence of K₂CO₃. The desired product (47%) with high R_f value on the TLC in 30% EtOAc:Hexanes as eluent was collected by silica gel column chromatographic purification. ¹H NMR (CDCl₃): δ 8.73 (d, 1H, J=1.8 Hz), 8.26-8.22 (m, 2H), 7.56 (s, 1H), 7.54 (dd, 1H, J=1.8 and 8.2 Hz), 7.49 (d, 1H, J=9.4 Hz), 6.98 (d, 1H, J=8.2 Hz), 5.66 (s, 2H), 3.91 (s, 3H), 3.89 (s, 3H). Low R_f: Methyl 3-methoxy-4-[(5-nitroindazol-2-yl)methyl]benzoate.

Preparation of 5-nitro-1-[2-methoxy-4-(o-toluylsulfonamidocarboxy)benzyl]indazoline In like manner to the preparation of 6-nitro-1-[2-methoxy-4-(o-toluylsulfonamidocarboxy)benzyl]indazoline, 5-nitro-1-[2-methoxy-4-(o-toluylsulfonamidocarboxy)benzyl]indazoline was prepared from methyl 3-methoxy-4-[(5-nitroindazol-1-yl)methyl]benzoate. ¹H NMR (DMSO-d₆): δ 8.81 (d, 1H, J=2.3 Hz), 8.39 (s, 1H), 8.21 (dd, 1H, J=1.8 and 8.8 Hz), 7.87 (dd, 2H, J=3.6 and 8.8 Hz), 7.48 (d, 1H, J=1.2 Hz), 7.39 (d, 1H, J=1.2 and 8.2 Hz), 7.33-7.15 (m, 3H), 6.85 (d, 1H, J=8.2 Hz), 5.65 (s, 2H), 3.76 (s, 3H), 2.49 (s, 3H).

Preparation of 5-amino-1-[2-methoxy-4-(0-toluyl-sulfonamidocarboxy)benzyl]indazoline In like manner to the preparation of 6-amino-1-[2-methoxy-4-(o-toluylsulfonamidocarboxy)benzyl]indazoline, 5-amino-1-[2-methoxy-4-(o-toluylsulfonamidocarboxy)benzyl]indazoline was prepared by reduction of 5-nitro-1-[2-methoxy-4-(o-toluylsulfonamidocarboxy)benzyl]indazoline. $^1$H NMR (DMSO-d$_6$): δ 7.87 (dd, 1H, J=1.2 and 7.7 Hz), 7.73 (s, 1H), 7.50 (s, 1H), 7.35-7.14 (m, 5H), 6.78 (d, 1H, J=1.8 Hz), 6.75 (s, 1H), 6.53 (d, 1H, J=8.2 Hz), 5.44 (s, 2H), 3.82 (s, 3H), 2.50 (s, 3H).

7.2.48 Preparation of 8-amino-4H-imidazo[2,1-c][1,4]-benzoxazine

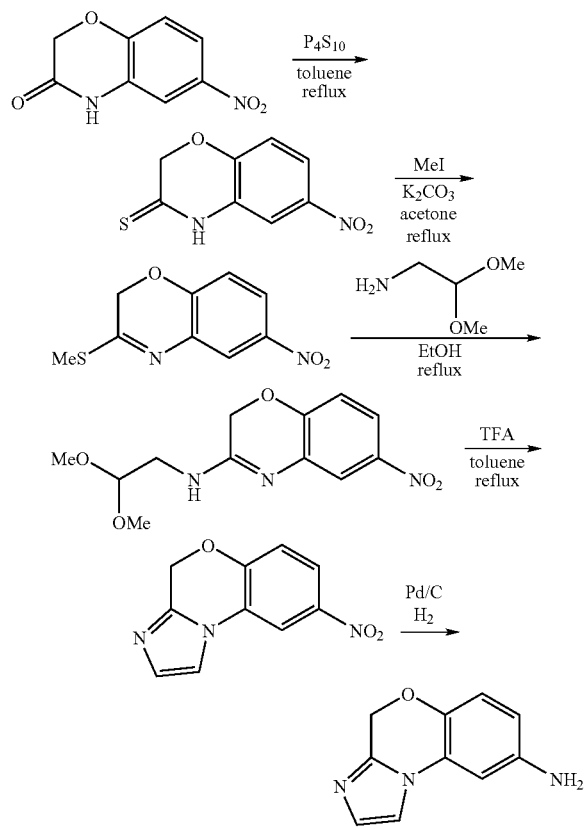

7.3 Synthesis of 2,4-Pyrimidinediamines

A variety of 2,4-pyrimidinediamines of the invention were synthesized from the above starting materials and intermediates and other commercially available reagents. Conditions suitable for synthesizing N2,N4-bis-substituted-2,4-pyrimidinediamine compounds ("general SNAr" reaction conditions; Substitution Nucleophilic Aromatic Reaction) are exemplified with N2,N4-bis(4-ethoxyphenyl)-2,4-pyrimidinediamine (R926069) and N2,N4-bis(3-hydroxyphenyl)-5-fluoro-2,4-pyrimidinediamine (R921218). Conditions suitable for synthesizing asymmetric N2,N4-disubstituted-2,4-pyrimidinediamines are exemplified by N4-(3,4-ethylenedioxyphenyl)-5-fluoro-N2-(3-hydroxyphenyl)-2,4-pyrimidinediamine (R926210).

7.3.1 N2,N4-Bis(4-ethoxyphenyl)-2,4-pyrimidinediamine (R926069)

To a solution of 2,4-dichloropyrimidine (0.015 g, 0.1 mmol) in EtOH (1 mL) was added 4-ethoxyaniline (0.034 g, 0.025 mmol) and heated in a sealed tube at 70-80° C. for 24 h. Upon cooling the reaction was diluted with H$_2$O (10 mL), acidified with 2N HCl, the solid obtained was filtered, washed with H$_2$O and dried to give N2,N4-bis(4-ethoxyphenyl)-2,4-pyrimidinediamine (R926069). $^1$H NMR (CD$_3$OD): δ 7.63 (d, 1H), 7.45 (d, 2H), J=9 Hz), 7.32 (d, 2H, J=9.3 Hz), 6.95 (d, 2H, J=6.9 Hz), 6.87 (d, 2H, J=8.7 Hz), 6.23 (d, 1H, J=7.2 Hz), 4.04 (m, 4H), 1.38 (m, 6H); LCMS: ret. time: 25.91 min.; purity: 99.5%; MS (m/e): 351 (MH$^+$).

7.3.2 N2,N4-Bis(3-hydroxyphenyl)-5-fluoro-2,4-pyrimidinediamine (R921218)

A mixture of 2,4-dichloro-5-fluoropyrimidine (0.0167 g, 0.1 mmol) and 3-aminophenol (0.033 g, 0.3 mmol) in MeOH:H$_2$O (1.8:0.2 mL; v/v) was shaken in a sealed tube at 100° C. for 24 h (or 80 oC for 3 days), cooled to room temperature, diluted with water (15 mL), acidified with 2N HCl (pH>2). Upon saturation with sodium chloride it was extracted with ethyl acetate (3×20 mL), dried over anhydrous sodium sulfate and solvent was removed. The resulting residue was filtered through a pad of silica gel (200-400 mesh) using CH$_2$Cl$_2$->1>10% MeOH in CH$_2$Cl$_2$ to obtain the desired N2,N4-bis(3-hydroxyphenyl)-5-fluoro-2,4-pyrimidinediamine (R921218). If the reaction scale is large enough, solid of the resulting product can be isolated by filtration. $^1$H NMR (CDCl$_3$): δ 7.73 (d, 1H, J=5.1 Hz), 7.12-6.90 (m, 6H), 6.64 (dd, 1H, J=1.8 and 8.1 Hz), 6.53 (dd, 1H, J=1.2 and 5.7 Hz); LCMS: ret. time: 16.12 min.; purity: 100%; MS (m/e): 313 (MH$^+$).

7.3.3 N2,N4-Bis(4-methoxyphenyl)-5-fluoro-2,4-pyrimidinediamine (R926017)

In like manner to the preparation of N2,N4-bis(3-hydroxyphenyl)-5-fluoro-2,4-pyrimidinediamine, 2,4-dichloro-5-fluoropyrimidine and 4-methoxyaniline were reacted to yield N2,N4-bis(4-methoxyphenyl)-5-fluoro-2,4-pyrimidinediamine. $^1$H NMR (CD$_3$OD): δ 7.67 (d, 1H, J=4.8 Hz), 7.43 (d, 2H, J=9.3 Hz), 7.67 (d, 2H, J=8.7 Hz), 6.87 (d, 2H, J=9.6 Hz), 6.83 (d, 2H, J=8.7 Hz), 3.83 (s, 3H), 3.81(s, 3H); LCMS: ret. time: 22.53 min.; purity: 100%; MS (m/e): 341 (MH$^+$).

7.3.4 N2,N4-Bis(3-fluoro-4-trifluoromethylphenyl)-5-fluoro-2,4-pyrimidinediamine (R926018)

In like manner to the preparation of N2,N4-bis(3-hydroxyphenyl)-5-fluoro-2,4-pyrimidinediamine, 2,4-dichloro-5-fluoropyrimidine and 3-fluoro-4-trifluoromethylaniline were reacted to yield N2,N4-bis(3-fluoro-4-trifluoromethylphenyl)-5-fluoro-2,4-pyrimidinediamine. $^1$H NMR (CDCl$_3$): δ 8.01 (d, 1H, J=3 Hz), 7.77 (m, 3H), 7.61 (dt, 1H, J=4.2 and 3 Hz), 7.20 (t, 1H, 8.7 Hz), 7.12 (t, 1H, J=9.3 Hz), 6.95 (s, 1H), 6.82 (s, 1H); $^{19}$F NMR (CDCl$_3$): 6-17505 (s, 3F), −17517 (s, 3F), −17525 (s, F), −17537 (s, F), −46835 (s, 1F); LCMS: ret. time: 32.39 min.; purity: 95%, MS (m/e): 453 (MH$^+$).

7.3.5 N2,N4-Bis(3,4-tetrafluoroethylendioxyphenyl)-5-fluoro-2,4-pyrimidinediamine (R926037)

In like manner to the preparation of N2,N4-bis(3-hydroxyphenyl)-5-fluoro-2,4-pyrimidinediamine, 2,4-dichloro-5-fluoropyrimidine and 3,4-tetrafluoroethylenedioxyaniline were reacted to yield N2,N4-bis(3,4-tetrafluoroethylenedioxyphenyl)-5-fluoro-2,4-pyrimidinediamine. $^1$H NMR (CDCl$_3$): δ 8.01 (d, 1H, J=3.0 Hz), 7.71 (d, 1H, J=2.4 Hz), 7.70 (1H, d, J=2.4 Hz), 7.18 (dd, 2H, J=2.4 and 6 Hz), 7.07 (d, 2H, J=1.8 Hz), 7.00 (1H, bs), 6.81 (d, 1H, J=2.7 Hz); $^{19}$F NMR (CDCl$_3$): −26029 (sept, 8F), −46791 (s, C5-F); LCMS: ret. time: 38.20 min.; purity: 85%; MS (m/e): 541 (MH$^+$).

7.3.6 N2,N4-Bis(3-trifluoromethoxyphenyl)-5-fluoro-2,4-pyrimidinediamine (R926038)

In like manner to the preparation of N2,N4-bis(3-hydroxyphenyl)-5-fluoro-2,4-pyrimidinediamine, 2,4-dichloro-5-fluoropyrimidine and 3-trifluoromethoxyaniline were reacted to yield N2,N4-bis(3-trifluoromethoxyphenyl)-5-fluoro-2,4-pyrimidinediamine. $^1$H NMR (CDCl$_3$): δ 8.03 (bd, 1H), 7.62 (bs, 2H), 7.48 (bd, 1H), 7.39 (t, 1H, J=8.1 Hz), 7.34 (m, 1H), 7.29 (t, 1H, J=7.5 Hz), 7.01 (m, 2H), 6.88 (m, 2H); $^{19}$F NMR (CDCl$_3$): −16447 (s, 3F), −16459 (s, 3F), −46738 (s, IF); LCMS: ret. time: 33.77 min.; purity: 93%; MS (m/e): 449 (MH$^+$).

7.3.7 N2,N4-Bis(4-chloro-3-trifluoromethylphenyl)-5-fluoro-2,4-pyrimidinediamine (R926039)

In like manner to the preparation of N2,N4-bis(3-hydroxyphenyl)-5-fluoro-2,4-pyrimidinediamine, 2,4-dichloro-5-fluoropyrimidine and 4-chloro-3-trifluoromethylaniline were reacted to yield N2,N4-bis(4-chloro-3-trifluoromethylphenyl)-5-fluoro-2,4-pyrimidinediamine. $^1$H NMR (CDCl$_3$): δ 8.05 (bs, 1H), 7.89 (bd, 1H), 7.77 (dd, 1H, J=2.4 and 9 Hz), 7.65 (dd, 1H, J=2.4 and 8.7 Hz), 7.49 (d, J=8.1 Hz), 7.40 (d, 1H, J=6.2 Hz), 7.03 (s, 1H), 6.91 (s, 1H); $^{19}$F NMR (CDCl$_3$): 6-17864 (s, 3F), −17894 (s, 3F), −46550 (s, 1F); LCMS: ret. time: 38.81 min.; purity: 75%; MS (m/e): 485 (MH$^+$).

7.3.8 N2,N4-Bis(3-ethoxyphenyl)-5-fluoro-2,4-pyrimidinediamine (R926064)

In like manner to the preparation of N2,N4-bis(3-hydroxyphenyl)-5-fluoro-2,4-pyrimidinediamine, 2,4-dichloro-5-fluoropyrimidine and 3-ethoxyaniline were reacted to yield N2,N4-bis(3-ethoxyphenyl)-5-fluoro-2,4-pyrimidinediamine. $^1$H NMR (CD$_3$OD): δ 7.96 (1H, d, J=4.8 Hz), 7.22 (m, 6H), 7.07 (t, 1H, J=1.8 Hz), 6.95 (dt, 1H, J=1.2 and 7.2 Hz), 6.77 (m, 2H), 3.88 (q, 4H, J=6.3 Hz), 1.33 (two t, 6H, J=6.3 Hz); $^{19}$F NMR (CDCl$_3$): −46175; LCMS: ret. time: 26.86 min.; purity: 97%; MS (m/e): 369 (MH$^+$).

7.3.9 N2,N4-Bis(3-hydroxy-4-methoxyphenyl)-5-fluoro-2,4-pyrimidinediamine (R926339)

In like manner to N2,N4-bis(3-hydroxyphenyl)-5-fluoro-2,4-pyrimidinediamine, 2,4-dichloro-5-fluoropyrimidine and 3-hydroxy-4-methoxyaniline were reacted to yield N2,N4-bis(3-hydroxy-4-methoxyphenyl)-5-fluoro-2,4-pyrimidinediamine. $^1$H NMR (CD$_3$OD): δ 7.82 (d, 1H J=4 Hz), 7.18 (m, 2H), 6.95 (m, 2H), 6.83 (m, 2H) 3.93 (s, 6H); LCMS: ret. time: 16.63 min.; purity: 97%; MS (m/e): 373 (MH$^+$).

7.3.10 N2,N4-Bis(4-ethoxycarbonylamino-3-hydroxyphenyl)-5-fluoro-2,4-pyrimidinediamine (R926340)

In like manner to N2,N4-bis(3-hydroxyphenyl)-5-fluoro-2,4-pyrimidinediamine, 2,4-dichloro-5-fluoropyrimidine and 4-ethoxycarbonylamino-3-hydroxyaniline were reacted to yield N2,N4-bis(4-ethoxycarbonylamino-3-hydroxyphenyl)-5-fluoro-2,4-pyrimidinediamine. $^1$H NMR (CD$_3$OD): δ 7.86 (d, 1H J=4 Hz), 7.67 (m, 2H), 7.20 (dd, 1H, J=8 Hz, J=4.1 Hz), 7.13 (d, 1H), 6.90 (m, 2H), 4.2(m, 4H), 1.32 (m, 6H); LCMS: ret. time: 20.92 min.; purity: 98%; MS (m/e): 487 (MH$^+$).

7.3.11 N2,N4-Bis(−3-hydroxy-4-methylphenyl)-5-fluoro-2,4-pyrimidinediaminediamine (R926341)

In like manner to N2,N4-bis(3-hydroxyphenyl)-5-fluoro-2,4-pyrimidinediamine, 2,4-dichloro-5-fluoropyrimidine and 3-hydroxy-4-methylaniline were reacted to yield N2,N4-bis(−3-hydroxy-4-methylphenyl)-5-fluoro-2,4-pyrimidinediamine. $^1$H NMR (CD$_3$OD): δ 7.83 (d, 1H J=4 Hz), 7.11 (m, 4H), 6.81 (m, 2H), 2.19 (m, 6H); LCMS: ret. time: 20.69 min.; purity: 98%; MS (m/e): 341 (MH$^+$).

7.3.12 N2,N4-Bis[4-(2-methoxyethyleneoxy)phenyl]-5-fluoro-2,4-pyrimidinediamine (R926342)

In like manner to N2,N4-bis(3-hydroxyphenyl)-5-fluoro-2,4-pyrimidinediamine, 2,4-dichloro-5-fluoropyrimidine and 4-(2-methoxyethyloxy)aniline were reacted to yield N2,N4-bis[4-(2-methoxyethyleneoxy)phenyl]-5-fluoro-2,4-pyrimidinediamine. $^1$H NMR (CD$_3$OD): δ 7.89 (d, 1H J=4 Hz), 7.54 (dd, 2H, J=6.8 and 2.7 Hz), 7.38 (dd, 2H, J=6.8 and 2.7 Hz), 6.87 (dd, 2H, J=6.8 and 2.7 Hz), 6.82 (dd, 2H, J=6.8 and 2.7 Hz) 4.6 (m, 4H), 4.11 (m, 4H), 3.35 (m, 6H); LCMS: ret. time: 21.76 min.; purity: 97%; MS (m/e): 429 (MH$^+$).

7.3.13 N2,N4-Bis(dihydrobenzofuran-5-yl)-5-fluoro-2,4-pyrimidinediaminediamine (R909237)

In like manner to N2,N4-bis(3-hydroxyphenyl)-5-fluoro-2,4-pyrimidinediamine, 2,4-dichloro-5-fluoropyrimidine and 5-amino-2,3-dihydrobenzofuran were reacted to yield N2,N4-bis(dihydrobenzofuran-5-yl)-5-fluoro-2,4-pyrimidinediaminediamine. $^1$H NMR (CD$_3$OD): δ 7.99 (d, 1H J=4 Hz), 7.22 (m, 4H), 6.81 (m, 2H), 4.55 (m, 4H), 3.22 (m, 4H); LCMS: ret. time: 23.80 min.; purity: 98%; MS (m/e): 438 (MH$^+$).

7.3.14 N2,N4-Bis(3-methoxyphenyl)-5-fluoro-2,4-pyrimidinediamine (R926065)

In like manner to the preparation of N2,N4-bis(3-hydroxyphenyl)-5-fluoro-2,4-pyrimidinediamine, 2,4-dichloro-5-fluoropyrimidine and 3-methoxyaniline were reacted to yield N2,N4-bis(3-methoxyphenyl)-5-fluoro-2,4-pyrimidinediamine. $^1$H NMR (CD$_3$OD): δ 7.96 (d, 1H, J=5.4 Hz), 7.24 (m, 6H), 7.06 (t, 1H, J=2.4 Hz), 7.00 (dt, 1H, J=1.2 Hz), 6.79 (m, 1H), 3.72 (s, 3H), 3.70 (s, 3H); $^{19}$F NMR (CD$_3$OD): 6-46112; LCMS: ret. time: 23.46 min.; purity: 99%; MS (m/e): 341 (MH$^+$).

7.3.15 N2,N4-Bis[4-(N,N-dimethylamino)phenyl]-5-fluoro-2,4-pyrimidinediamine (R926086)

In like manner to the preparation of N2,N4-bis(3-hydroxyphenyl)-5-fluoro-2,4-pyrimidinediamine, 2,4-dichloro-5-fluoropyrimidine and 4-N,N-dimethylaniline were reacted to yield N2,N4-bis[4-(N,N-dimethylamino)phenyl]-5-fluoro-2,4-pyrimidinediamine. $^1$H NMR (CDCl$_3$): δ 7.84 (d, 1H, J=3.6 Hz), 7.43 (d, 2H, J=8.7 Hz), 7.34 (d, 2H, J=8.7 Hz), 7.25 (s, 1H), 6.73 (m, 4H), 6.55 (s, 1H), 2.95 (s, 6H), 2.90 (s, 6H); $^{19}$F NMR (CDCl$_3$): −47770; LCMS: ret. time: 12.48 min.; purity: 99%; MS (m/e): 367 (MH$^+$).

7.3.16 N2,N4-Bis(3,4-ethylenedioxyphenyl)-5-fluoro-2,4-pyrimidinediamine (R926109)

In like manner to the preparation of N2,N4-bis(3-hydroxyphenyl)-5-fluoro-2,4-pyrimidinediamine, 2,4-dichloro-5-fluoropyrimidine and 3,4-ethylenedioxyaniline were reacted to yield N2,N4-bis(3,4-ethylenedioxyphenyl)-5-fluoro-2,4-pyrimidinediamine. $^1$H NMR (CDCl$_3$): δ 7.88 (d, 1H, J=3.6 Hz), 7.23 (d, 1H, J=2.3 Hz), 7.15 (d, 1H, J=2.4 Hz), 7.00 (dd, 1H, J=3 and 8.1 Hz), 6.98 (dd, 1H, J=3 and 8 Hz), 6.83 (d, 1H, J=8.7 Hz), 6.81 (d, 1H, J=8.7 Hz), 6.7(s, 1H), 6.58 (s, 1H), 4.23 (m, 4H), 4.24(m, 4H); $^{19}$F NMR (CDCl$_3$): δ −47445; LCMS: ret. time: 21.81 min.; purity: 96%; MS (m/e): 397 (MH$^+$).

7.3.17 N2,N4-Bis(3,4-dimethoxyphenyl)-5-fluoro-2,4-pyrimidinediamine (R926110)

In like manner to the preparation of N2,N4-bis(3-hydroxyphenyl)-5-fluoro-2,4-pyrimidinediamine, 2,4-dichloro-5-fluoropyrimidine and 3,4-dimethoxyaniline were reacted to yield N2,N4-bis(3,4-dimethoxyphenyl)-5-fluoro-2,4-pyrimidinediamine. $^1$H NMR (CDCl$_3$): δ 7.90 (d, 1H, J=1.8 Hz), 7.13 (d, 2H, J=4.8 Hz), 7.08 (d, 1H, J=8.7 Hz), 6.94 (d, 2H, J=10.5 Hz), 6.81 (d, 1H, J=8.7 Hz), 6.76 (d, 1H, J=8.7 Hz), 6.70 (s, 1H), 3.87 (s, 3H), 3.84 (s, 3H), 3.74 (s, 3H), 3.71 (s, 3H); $^{19}$F NMR (CDCl$_3$): 6-47433; LCMS: ret. time: 19.64 min.; purity: 95%; MS (m/e): 401 (MH$^+$).

7.3.18 N2,N4-Bis[4-(N-morpholino)phenyl]-5-fluoro-2,4-pyrimidinediamine (R926114)

In like manner to the preparation of N2,N4-bis(3-hydroxyphenyl)-5-fluoro-2,4-pyrimidinediamine, 2,4-dichloro-5-fluoropyrimidine and 4-N-morpholinylaniline were reacted to yield N2,N4-bis[4-N-morpholinyl)phenyl]-5-fluoro-2,4-pyrimidinediamine. $^1$H NMR (CD$_3$OD): δ 7.80 (s, 1H), 7.78 (s, 1H, partially exchanged), 7.76 (bs, 1H, partially exchanged), 7.53 (d, 2H, J=8.1 Hz), 7.39 (d, 2H, J=9 Hz), 6.93 (d, 2H, J=8.7 Hz), 6.86 (bd, 2H), 3.84 (m, 8H), 3.11 (m, 8H); $^{19}$F NMR (CD$_3$OD): 6-47697; LCMS: ret. time: 18.15 min.; purity: 99.55%; MS (m/e): 451 (MH$^+$).

7.3.19 N2,N4-Bis(4-chlorophenyl)-5-fluoro-2,4-pyrimidinediamine (R926206)

In like manner to the preparation of N2,N4-bis(3-hydroxyphenyl)-5-fluoro-2,4-pyrimidinediamine, 2,4-dichloro-5-fluoropyrimidine and 4-chloroaniline were reacted to yield N2,N4-bis(4-chlorophenyl)-5-fluoro-2,4-pyrimidinediamine. $^1$H NMR (CDCl$_3$+CD$_3$OD): δ 7.80 (d, 1H, J=4.2 Hz), 7.45 (d, 2H, J=8.7 Hz), 7.33 (d, 2H, J=9 Hz), 7.20 (d, 2H, J=8.7 Hz), 7.14 (d, 2H, J=9.6 Hz); LCMS: ret. time: 28.84 min.; purity: 87%; MS (m/e): 349 (MH$^+$).

7.3.20 N2,N4-Bis(3-chlorophenyl)-5-fluoro-2,4-pyrimidinediamine (R926209)

In like manner to the preparation of N2,N4-bis(3-hydroxyphenyl)-5-fluoro-2,4-pyrimidinediamine, 2,4-dichloro-5-fluoropyrimidine and 3-chloroaniline were reacted to yield N2,N4-bis(3-chlorophenyl)-5-fluoro-2,4-pyrimidinediamine. $^1$H NMR (CD$_3$OD): δ 8.08 (d, 1H, J=5.4 Hz), 7.70 (t, 1H, J=1.8 Hz), 7.57 (t, 1H, J=1.2 Hz), 7.54 (m, 1H), 7.35 (m, 4H), 7.28 (t, 1H, J=1.8 Hz), 7.24 (m, 1H), 7.22 (t, 1H, J=1.8 Hz); $^{19}$F NMR (CD$_3$OD): −43631; LCMS: ret. time: 28.99 min.; purity: 99%; MS (m/e): 349 (M$^+$).

7.3.21 N2,N4-Bis(4-tert-butylphenyl)-5-fluoro-2,4-pyrimidinediamine (R926222)

In like manner to the preparation of N2,N4-bis(3-hydroxyphenyl)-5-fluoro-2,4-pyrimidinediamine, 2,4-dichloro-5-fluoropyrimidine and 4-tert-butylaniline were reacted to yield N2,N4-bis(4-tert-butylphenyl)-5-fluoro-2,4-pyrimidinediamine. $^1$H NMR (CDCl$_3$): δ 7.77 (d, 1H, J=3.9 Hz), 7.47 (d, 2H, J=9 Hz), 7.38 (m, 4H), 7.30 (d, 2H, J=8.7 Hz), 1.34 (s, 9H), 1.32 (s, 9H); LCMS: ret. time: 34.09 min.; purity: 93%; MS: 393 (MH$^+$).

7.3.22 N2,N4-Bis(3-chloro-4-fluorophenyl)-5-fluoro-2,4-pyrimidinediamine (R926223)

In like manner to the preparation of N2,N4-bis(3-hydroxyphenyl)-5-fluoro-2,4-pyrimidinediamine, 2,4-dichloro-5-fluoropyrimidine and 3-chloro-4-fluoroaniline were reacted to yield N2,N4-bis(3-chloro-4-fluorophenyl)-5-fluoro-2,4-pyrimidinediamine. $^1$H NMR (CDCl$_3$+CD$_3$OD)): δ 7.81 (d, 1H), 7.60 (m, 1H), 7.58 (m, 1H), 7.38 (m, 1H), 7.19 (m, 1H), 7.0 (m, 2H); LCMS: ret. time: 28.98 min.; purity: 97%; MS (m/e): 385 (M$^+$).

7.3.23 N2,N4-Bis(4-fluorophenyl)-5-fluoro-2,4-pyrimidinediamine (R926224)

In like manner to the preparation of N2,N4-bis(3-hydroxyphenyl)-5-fluoro-2,4-pyrimidinediamine, 2,4-dichloro-5-fluoropyrimidine and 4-fluoroaniline were reacted to yield N2,N4-bis(4-fluorophenyl)-5-fluoro-2,4-pyrimidinediamine. $^1$H NMR (CDCl$_3$): δ 8.79 (d, 2H, J=5.4 Hz), 7.40 (m, 2H), 7.30 (m, 2H), 6.90 (m, 4H); $^{19}$NMR (CDCl$_3$): −32425 (s, 1F), −32940 (s, 1F), −45525 (s, 1F); LCMS: ret. time: 23.53 min.; purity: 100%; MS (m/e): 317 (MH$^+$).

7.3.24 N2,N4-Bis(4-methylphenyl)-5-fluoro-2,4-pyrimidinediamine (R926225)

In like manner to the preparation of N2,N4-bis(3-hydroxyphenyl)-5-fluoro-2,4-pyrimidinediamine, 2,4-dichloro-5-fluoropyrimidine and 4-methylaniline were reacted to yield N2,N4-bis(4-methylphenyl)-5-fluoro-2,4-pyrimidinediamine. $^1$H NMR (CDCl$_3$): δ 7.73 (d, 1H, J=4.2 Hz), 7.43 (d, 2H, J=8.1 Hz), 7.36 (d, 2H, J=8.4 Hz), 7.14 (d, 2H, J=8.4 Hz), 7.10 (d, 2H, J=8.1 Hz), 2.39 (s, 3H), 2.35 (s, 3H); LCMS: ret. time: 25.81 min.; purity: 99.65%; MS (m/e): 309 (MH$^+$).

7.3.25 N2,N4-Bis[(4-methoxycarbonylmethyleneoxy)phenyl]-5-fluoro-2,4-pyrimidinediamine (R926240)

In like manner to the preparation of N2,N4-bis(3-hydroxyphenyl)-5-fluoro-2,4-pyrimidinediamine, 2,4-dichloro-5-fluoropyrimidine and ethyl 4-aminophenoxyacetate were reacted to yield N2,N4-bis[(4-methoxycarbonylmethyleneoxy)phenyl]-5-fluoro-2,4-pyrimidinediamine. $^1$H NMR (CD$_3$OD): δ 7.8 (bs, 1H), 7.50 (d, 2H, J=9.3 Hz), 7.32 (d, 2H, J=8.41 Hz), 6.88 (m, 4H), 4.72 (s, 2H), 4.70 (s, 2H), 3.79 (s, 3H), 3.78 (s, 3H); $^{19}$F NMR (CDCl$_3$): −47570; LCMS: ret. time: 21.17 min.; purity: 95%; MS (m/e): 457 (MH$^+$).

7.3.26 (±)-N2,N4-Bis[4-methoxycarbonyl(α-methyl)methyleneoxyphenyl]-5-fluoro-2,4-pyrimidinediamine (R926254)

In like manner to the preparation of N2,N4-bis(3-hydroxyphenyl)-5-fluoro-2,4-pyrimidinediamine, 2,4-dichloro-5-fluoropyrimidine and (±)-ethyl 2-(4-aminophenoxy)propionate were reacted to yield (±)-N2,N4-bis[4-methoxycarbonyl(α-methyl)methyleneoxyphenyl]-5-fluoro-2,4-pyrimidinediamine. $^1$H NMR (CDCl$_3$): δ 7.89 (bs, 1H), 7.48 (dd, 2H, J=2.4 and 6.9 Hz), 7.40 (dd, 2H, J=1.8 and 6.9 Hz), 6.85 (m, 4H), 6.76 (s, 1H), 6.63 (s, 1H), 4.75 (hex, 2H, J=6.3 Hz), 3.77 (s, 3H), 3.76 (s, 3H), 1.62 (t, 6H, J=7.5 Hz); LCMS: ret. time: 23.76 min.; purity: 97%; MS (m/e): 485 (MH$^+$).

7.3.27 N2,N4-Bis[(3-methoxycarbonylmethyleneoxy)phenyl]-5-fluoro-2,4-pyrimidinediamine (R926255)

In like manner to the preparation of N2,N4-bis(3-hydroxyphenyl)-5-fluoro-2,4-pyrimidinediamine, 2,4-dichloro-5-fluoropyrimidine and ethyl 3-aminophenoxyacetate were reacted to yield N2,N4-bis[(3-methoxycarbonylmethyleneoxy)phenyl]-5-fluoro-2,4-pyrimidinediamine. $^1$H NMR (CDCl$_3$): δ 7.96 (d, 1H, J=2.4 Hz), 7.71 (t, 1H, J=2.4 Hz), 7.44 (m, 2H), 7.21 (m, 3H), 6.96 (dd, 1H, J=1.2 and 7.8 Hz), 6.86 (d, 1H, J=3 Hz), 6.53 (m, 1H), 4.64 (s, 2H), 4.60 (s, 2H), 3.79 (s, 6H); LCMS: ret. time: 21.72 min.; purity: 87%; MS (m/e): 457 (MH$^+$).

7.3.28 N2,N4-Bis(3-acetyloxyphenyl)-5-fluoro-2,4-pyrimidinediamine (R926387)

In like manner to the preparation of N2,N4-bis(3-hydroxyphenyl)-5-fluoro-2,4-pyrimidinediamine, 2,4-dichloro-5-fluoropyrimidine and 3-acetoxyaniline were reacted to yield N2,N4-bis[(3-acetoxyphenyl]-5-fluoro-2,4-pyrimidinediamine. Alternatively, N2,N4-bis[(3-acetoxyphenyl]-5-fluoro-2,4-pyrimidinediamine can be prepared by acetylation of N2,N4-bis(3-hydroxyphenyl)-5-fluoro-2,4-pyrimidinediamine with acetyl chloride in the presence of pyridine in CH$_2$Cl$_2$. $^1$H NMR (CDCl$_3$): δ 8.00 (bs, 1H), 7.51-7.25 (m, 8H), 2.32 (s, 3H), 2.28 (s, 3H); LCMS: ret. time: 22.14 min; purity: 100%; MS (m/e): 397 (MH$^+$).

7.3.29 N2,N4-Bis(3-benzyloxyphenyl)-5-fluoro-2,4-pyrimidinediamine (R926394)

In like manner to the preparation of N2,N4-bis(3-hydroxyphenyl)-5-fluoro-2,4-pyrimidinediamine, 2,4-dichloro-5-fluoropyrimidine and 3-benzyloxyaniline were reacted to yield N2,N4-bis(3-benzyloxyphenyl)-5-fluoro-2,4-pyrimidinediamine. $^1$H NMR (CDCl$_3$): δ 7.98 (bs, 1H), 7.42-6.99 (m, 16H), 6.75 (d, 1H, J=2.4 Hz), 6.71 (m, 1H), 6.60 (dd, 1H, J=2.4 and 8.4 Hz), 6.32 (m, 1H), 4.97 (s, 2H), 4.94 (s, 2H); LCMS: ret. time: 32.56 min.; purity: 98%; MS (m/e): 493 (MH$^+$).

7.3.30 N2,N4-Bis(2-phenylphenyl)-5-fluoro-2,4-pyrimidinediamine (R926398)

In like manner to the preparation of N2,N4-bis(3-hydroxyphenyl)-5-fluoro-2,4-pyrimidinediamine, 2,4-dichloro-5-fluoropyrimidine and 2-phenylaniline were reacted to yield N2,N4-bis[(2-phenylphenyl]-5-fluoro-2,4-pyrimidinediamine. $^1$H NMR (CDCl$_3$): δ 8.35 (m, 1H), 8.0 (s, 1H), 7.85 (s, 1H), 7.45-7.00 (m, 18H); LCMS: ret. time: 30.29 min.; purity: 68%; MS (m/e): 433 (MH$^+$).

7.3.31 (R926404) N2, N4-Bis(2-phenylphenyl)-5-methyl-2,4-pyrimidinediamine

In like manner to the preparation of 5-fluoro-N2,N4-bis(3-hydroxyphenyl)-2,4-pyrimidinediamine, 2-aminobiphenyl and 2,4-dichloro-5-methylpyrimidine were reacted to provide N2, N4-bis(2-phenylphenyl)-5-methyl-2,4-pyrimidinediamine. LCMS: ret. time: 30.47 min.; purity: 91%; MS (m/e): 429 (MH$^+$).

7.3.32 N2,N4-Bis[(4-methoxy-3-phenyl)phenyl]-5-fluoro-2,4-pyrimidinediamine (R926399)

In like manner to the preparation of N2,N4-bis(3-hydroxyphenyl)-5-fluoro-2,4-pyrimidinediamine, 2,4-dichloro-5-fluoropyrimidine and 4-methoxy-3-phenylaniline were reacted to yield N2,N4-bis[(4-methoxy-3-phenyl)phenyl]-5-fluoro-2,4-pyrimidinediamine.
$^1$H NMR (CD$_3$OD): δ 7.83 (d, 1H, J=4.2 Hz), 7.57 (bd, 1H, J=8.7 Hz), 7.48 (d, 1H, J=2.7 Hz), 7.47-7.22 (m, 12H), 6.85 (d, 1H, J=8.7 Hz), 6.78 (d, 1H, 9.3 Hz), 3.72 (s, 3H), 3.69 (s, 3H); LCMS: ret. time: 29.97 min.; purity: 92%; MS (m/e): 493 (MH$^+$).

7.3.33 N2,N4-Bis[(2-methoxy-5-phenyl)phenyl]-5-fluoro-2,4-pyrimidinediamine (R926400)

In like manner to the preparation of N2,N4-bis(3-hydroxyphenyl)-5-fluoro-2,4-pyrimidinediamine, 2,4-dichloro-5-fluoropyrimidine and 2-methoxy-5-phenylaniline were reacted to yield N2,N4-bis[(2-methoxy-5-phenyl)phenyl]-5-fluoro-2,4-pyrimidinediamine.
$^1$H NMR (CD$_3$OD): δ 8.03 (d, 1H, J=6.6 Hz), 7.76 (t, 1H, J=2.4 Hz), 7.28-7.10 (m, 13H), 7.07 (d, 1H, J=9 Hz), 7.01 (d, 1H, J=8.1 Hz), 3.91 (s, 3H), 3.86 (s, 3H); LCMS: ret. time: 18.58 min.; purity: 96%; MS (m/e): MH$^+$).

7.3.34 N2,N4-Bis[(2-methoxy-5-methyl-4-phenyl)phenyl]-5-fluoro-2,4-pyrimidinediamine (R926401)

In like manner to the preparation of N2,N4-bis(3-hydroxyphenyl)-5-fluoro-2,4-pyrimidinediamine, 2,4-dichloro-5-fluoropyrimidine and 2-methoxy-5-methyl-4-phenylaniline were reacted to yield N2,N4-bis[(2-methoxy-5-methyl-4-phenyl)phenyl]-5-fluoro-2,4-pyrimidinediamine. $^1$H NMR (CD$_3$OD): δ 8.00 (d, 1H, J=4.8 Hz), 7.73 (s, 1H), 7.66 (s, 1H), 7.43-7.24 (m, 9H), 6.91 (s, 1H), 6.82 (s, 1H), 3.86 (s, 3H), 3.85 (s, 3H), 2.14 (s, 3H), 1.99 (s, 3H); LCMS: ret. time: 19.98 min.; purity: 99%; MS (m/e): 521 (MH$^+$).

7.3.35 N2,N4-Bis[(2-methyl-5-phenyl)phenyl]-5-fluoro-2,4-pyrimidinediamine (R926402)

In like manner to the preparation of N2,N4-bis(3-hydroxyphenyl)-5-fluoro-2,4-pyrimidinediamine, 2,4-dichloro-5-fluoropyrimidine and 2-methyl-5-phenylaniline were reacted to yield N2,N4-bis[(2-methyl-5-phenyl)phenyl]-5-fluoro-2,4-pyrimidinediamine.
$^1$H NMR (CD$_3$OD): δ 7.84 (bd, 1H), 7.51-7.20 (m, 16H), 2.30 (s, 3H), 2.24 (s, 3H); LCMS: ret. time: 18.57 min.; purity: 87%; MS (m/e): 461 (MH$^+$).

7.3.36 N2,N4-Bis[(3-phenyl)phenyl]-5-fluoro-2,4-pyrimidinediamine (R926403)

In like manner to the preparation of N2,N4-bis(3-hydroxyphenyl)-5-fluoro-2,4-pyrimidinediamine, 2,4-dichloro-5-fluoropyrimidine and 3-phenylaniline were reacted to yield N2,N4-bis[(3-phenyl)phenyl]-5-fluoro-2,4-pyrimidinediamine. $^1$H NMR (CD$_3$OD): δ 8.02 (d, 1H, J=5.1 Hz), 7.82 (t, 1H, J=1.5 Hz), 7.67 (t, 1H, J=1.8 Hz), 7.58 (dd, 1H, J=1.2 and 7.2 Hz), 7.42-7.24 (m, 15H); LCMS: ret. time: 32.06 min.; purity: 94%; MS (m/e): 433 (MH$^+$).

7.3.37 N2,N4-Bis(4-hydroxyphenyl)-5-fluoro-2,4-pyrimidinediamine (R926405)

In like manner to the preparation of N2,N4-bis(3-hydroxyphenyl)-5-fluoro-2,4-pyrimidinediamine, 2,4-dichloro-5-fluoropyrimidine and 4-acetoxyaniline were reacted to yield N2,N4-bis[(4-hydroxyphenyl]-5-fluoro-2,4-pyrimidinediamine. After the work up it was observed that the acetoxy group was hydrolyzed to afford the N2,N4-bis(4-hydroxyphenyl)-5-fluoro-2,4-pyrimidinediamine instead of the corresponding acetate derivative. $^1$H NMR (CD$_3$OD): δ 7.74 (d, 1H, J=5.6 Hz), 7.43 (dd, 2H, J=2.1 and 6.6 Hz), 7.28 (dd, 2H, J=2.4 and 6.3 Hz), 6.74 (dd, 2H, J=2.4 and 6.3 Hz), 6.66 (dd, 2H, J=2.4 and 7.2 Hz); $^{19}$F NMR (CD$_3$OD): −48116 (d, 1F); LCMS: ret. time: 16.15 min; purity: 100%; MS (m/e): 313 (MH$^+$)

7.3.38 N2,N4'-Bis(4-hydroxy-3-methylphenyl)-5-fluoro-2,4-pyrimidinediamine (R926469)

In like manner to the preparation of N2,N4-bis(3-hydroxyphenyl)-5-fluoro-2,4-pyrimidinediamine, 2,4-dichloro-5-fluoropyrimidine and 4-hydroxy-3-methylaniline were reacted to yield N2,N4-bis[(4-hydroxy-3-methylphenyl]-5-fluoro-2,4-pyrimidinediamine.

$^1$H NMR (CD$_3$OD): δ 7.64 (d, 1H, J=3.6 Hz), 7.11 (t, 2H, J=9 Hz), 6.70-6.45 (m, 4H), 2.15 (s, 3H), 2.09 (s, 3H); $^{19}$F NMR (CD$_3$OD): −46278; LCMS: ret. time: 15.53; purity: 84%; MS (m/e): 341 (MH$^+$).

7.3.39 N2,N4-Bis[4-(tert-butoxycarbonylmethyleneoxy)phenyl]-5-fluoro-2,4-pyrimidinediamine (R926574)

In like manner to the preparation of N2,N4-bis(3-hydroxyphenyl)-5-fluoro-2,4-pyrimidinediamine, 2,4-dichloro-5-fluoropyrimidine and tert-butyl 4-aminophenoxyacetate were reacted to yield N2,N4-bis[4-(tert-butoxycarbonylmethyleneoxy)phenyl]-5-fluoro-2,4-pyrimidinediamine $^1$H NMR (CDCl$_3$): δ 7.88 (s, 1H), 7.48 (d, 2H, J=8.4 Hz), 7.40 (d, 2H, J=8.7 Hz), 6.86 (m, 4H), 4.52 (s, 2H), 4.48 (s, 2H), 1.49 (s, 9H), 1.48 (s, 9H); LCMS: ret. time: 28.48 min.; purity: 95%; MS (m/e): 541 (MH$^+$).

7.3.40 N2,N4-Bis(indol-5-yl)-5-fluoro-2,4-pyrimidinediamine (R926582)

In like manner to the preparation of N2,N4-bis(3-hydroxyphenyl)-5-fluoro-2,4-pyrimidinediamine, 2,4-dichloro-5-fluoropyrimidine and 5-aminoindole were reacted to yield N2,N4-bis(indol-5-yl)-5-fluoro-2,4-pyrimidinediamine. LCMS: ret. time: 20.26 min.; purity: 99%; MS (m/e): 359 (MH$^+$).

7.3.41 N2,N4-Bis(4-cyanomethylphenyl)-5-ethoxycarbonyl-2,4-pyrimidinediamine (R926319)

In like manner to N2,N4-bis(3-hydroxyphenyl)-5-ethoxycarbonyl-2,4-pyrimidinediamine, 2,4-dichloro-5-ethoxycarbonylpyrimidine and 4-cyanomethylaniline were reacted to yield N2,N4-bis(4-cyanomethylphenyl)-5-ethoxycarbonyl-2,4-pyrimidinediamine. $^1$H NMR (DMSO-d6): δ 8.72 (s, 1H), 7.64 (m, 4H), 7.32 (d, 2H, J=8.7 Hz), 7.21 (d, 2H, J=8.4 Hz), 4.3 (q, 2H, J=7.0 Hz), 3.97 (s, 2H), 3.89 (s, 2H), 1.32 (3H, J=7 Hz); LCMS: ret. time: 30.83 min.; purity: 90%; MS (m/e): 413 (MH$^+$).

7.3.42 N2,N4-Bis(3-indazol-6-yl)-5-ethoxycarbonyl-2,4-pyrimidinediamine (R926320)

In like manner to N2,N4-bis(3-hydroxyphenyl)-5-ethoxycarbonyl-2,4-pyrimidinediamine, 2,4-dichloro-5-ethoxycarbonylpyrimidine and 6-aminoindazole were reacted to yield N2,N4-bis(6-indazolyl)-5-ethoxycarbonyl-2,4-pyrimidinediamine. $^1$H NMR (DMSO-d6): δ 8.76 (s, 1H), 7.73 (d, 2H J=8.8), 7.54 (m, 4H), 7.36 (d, 2H, J=9.5 Hz), 4.3 (q, 2H, J=7.0 Hz), 1.34 (3H, J=7 Hz); LCMS: ret. time 27.59 min.; purity: 95%; MS (m/e): 415 (MH$^+$).

7.3.43 N2,N4-Bis(3-indazol-7-yl)-5-ethoxycarbonyl-2,4-pyrimidinediamine (R926321)

In like manner to N2,N4-bis(3-hydroxyphenyl)-5-ethoxycarbonyl-2,4-pyrimidinediamine, 2,4-dichloro-5-ethoxycarbonylpyrimidine and 7-aminoindazole were reacted to yield N2,N4-bis(7-indazolyl)-5-ethoxycarbonyl-2,4-pyrimidinediamine. $^1$H NMR (DMSO-d6): δ 8.70 (s, 1H), 7.54 (d, 2H J=8.4 Hz), 7.37 (m, 6H), 4.3 (q, 2H, J=7.0 Hz), 1.33 (3H, J=7 Hz); LCMS: ret. time 23.61 min.; purity: 94%; MS (m/e): 415 (MH$^+$).

7.3.44 N2,N4-Bis[6-(1,4-benzoxazine-3-onyl)]-5-ethoxycarbonyl-2,4-pyrimidinediamine (R926325)

In like manner to N2,N4-bis(3-hydroxyphenyl)-5-ethoxycarbonyl-2,4-pyrimidinediamine, 2,4-dichloro-5-ethoxycarbonylpyrimidine and 6-amino-1,4-benzoxazine-3-one were reacted to yield N2,N4-bis[6-(1,4-benzoxazine-3-onyl)]-5-ethoxycarbonyl-2,4-pyrimidinediamine. $^1$H NMR (DMSO-d6): δ 8.66 (s, 1H), 7.21 (dd, 2H J=8.8 and J=2.2 Hz), 6.89 (d, 2H J=8.4 Hz), 4.54 (s, 2H) 4.49 (s, 2H) 4.3 (q, 2H, J=7.0 Hz), 1.33 (3H, J=7 Hz); LCMS: ret. time 23.08 min.; purity: 88%; MS (m/e): 477 (MH$^+$).

7.3.45 N2,N4-Bis(4-ethoxycarbonylmethyleneaminophenyl)-5-ethoxycarbonyl-2,4-pyrimidinediamine (R926331)

In like manner to N2,N4-bis(3-hydroxyphenyl)-5-ethoxycarbonyl-2,4-pyrimidinediamine, 2,4-dichloro-5-ethoxycarbonylpyrimidine and 4-ethoxycarbonylmethyleneaminoaniline were reacted to yield N2,N4-bis(4-ethoxycarbonylaminophenyl)-5-ethoxycarbonyl-2,4-pyrimidinediamine. $^1$H NMR (CDCl$_3$): δ 8.72 (s, 1H), 7.70 (d, 2H J=8.8 Hz), 7.28 (d, 2H J=8.4 Hz), 7.05 (d, 2H, J=8.4 Hz) 6.82 (d, 2H J=8.4 Hz) 4.5 (m, 4H), 4.23 (m, 6H) 1.53 (m, 9H); LCMS: ret. time 18.08 min.; purity: 85%; MS (m/e): 537 (MH$^+$).

7.3.46 N2,N4-Bis(4-ethoxyphenyl)-6-methoxycarbonyl-2,4-pyrimidinediamine (R926058)

In a manner analogous to the preparation of N2,N4-bis(3-hydroxyphenyl)-5-fluoro-2,4-pyrimidinediamine, the reaction of 2,4-dichloro-6-methoxycarbonylpyrimidine with 4-ethoxyaniline gave N2,N4-bis(4-ethoxyphenyl)-6-methoxycarbonyl-2,4-pyrimidinediamine.
$^1$H NMR (CDCl$_3$): δ 7.42 (bs, 1H), 7.35 (bd, 4H), 6.85 (bs, 1H), 6.75 (bd, 4H), 3.97 (q, 4H, J=4.8 Hz), 3.92 (s, 3H), 1.36 (t, 6H, J=6.3 Hz); LCMS: ret. time: 27.47 min.; purity: 97%; MS (m/e): 409 (MH$^+$).

7.3.47 N2,N4-Bis(4-ethoxyphenyl)-5-methyl-2,4-pyrimidinediamine (R926068)

In a manner analogous to the preparation of N2,N4-bis(3-hydroxyphenyl)-5-fluoro-2,4-pyrimidinediamine, the reaction of 2,4-dichloro-5-methylpyrimidine with 4-ethoxyaniline gave N2,N4-bis(4-ethoxyphenyl)-5-methyl-2,4-pyrimidinediamine. $^1$H NMR (CD$_3$OD): δ 7.55 (s, 1H), 7.40 (d, 2H), 7.21 (d, 2H, J=8.7 Hz), 6.90 (dd, 4H, J=8.7 Hz), 4.04 (q, 4H, J=6.6 Hz), 2.17 (m, 6H); LCMS: ret. time: 26.51 min.; purity: 95%; MS (m/e): 365 (MH$^+$)

7.3.48 N2,N4-Bis(4-ethoxyphenyl)-6-chloro-2,4-pyrimidinediamine (R926072)

In a manner analogous to the preparation of N2,N4-bis(3-hydroxyphenyl)-5-fluoro-2,4-pyrimidinediamine, the reaction of 2,4,6-trichloropyrimidine with 4-ethoxyaniline gave N2,N4-bis(4-ethoxyphenyl)-6-chloro-2,4-pyrimidinediamine. $^1$H NMR (CDCl$_3$): δ 7.42 (d, 2H, J=9 Hz), 7.18 (d, 2H, J=8.7 Hz), 6.89 (d, 2H, J=6.3 Hz), 6.84 (d, 2H, J=8.7 Hz), 6.58 (bs, 1H), 4.02 (m, 4H), 1.43 (m, 6H); LCMS: ret. time: 83.21 min.; purity: 87%; MS (m/e): 385 (MH$^+$)

7.3.49 N2,N4-Bis(3,4-ethylenedioxyphenyl)-5-methyl-2,4-pyrimidinediamine (R926242)

In a manner analogous to the preparation of N2,N4-bis(3-hydroxyphenyl)-5-fluoro-2,4-pyrimidinediamine, the reaction of 2,4-dichloro-5-methylpyrimidine with 3,4-ethyleneoxyaniline gave N2,N4-bis(3,4-ethylenedioxyphenyl)-5-methyl-2,4-pyrimidinediamine. $^1$H NMR (CD$_3$OD): δ 7.75 (bs, 1H), 7.06 (d, 1H, J=2.4 Hz), 6.96 (d, 1H, J=2.1 Hz), 6.94 (d, 1H, J=2.1 Hz), 6.85-6.77 (m, 2H), 6.70 (d, 1H, J=9 Hz), 4.23 (s, 4H), 4.19 (s, 4H), 2.09 (s, 3H); LCMS: ret. time: 22.01 min.; purity: 100%; MS (m/e): 393 (MH$^+$).

7.3.50 N2,N4-Bis(3,4-ethylenedioxyphenyl)-2,4-pyrimidinediamine (R926243)

In a manner analogous to the preparation of N2,N4-bis(3-hydroxyphenyl)-5-fluoro-2,4-pyrimidinediamine, the reaction of 2,4-dichloropyrimidine with 3,4-ethyleneoxyaniline gave N2,N4-bis(3,4-ethylenedioxyphenyl)-2,4-pyrimidinediamine. $^1$H NMR (DMSO-d6): δ 10.95 (s, 1H), 10.50 (s, 1H), 7.84 (bd, 2H), 7.24 (bd, 2H), 6.79 (bd, 2H), 6.40 (bd, 2H), 4.24 (s, 8H); LCMS: ret. time: 21.68 min.; purity: 100%; MS (m/e): 379 (MH$^+$).

7.3.51 N2,N4-Bis(3-hydroxyphenyl)-5-methyl-2,4-pyrimidinediamine (R926248)

In a manner analogous to the preparation of N2,N4-bis(3-hydroxyphenyl)-5-fluoro-2,4-pyrimidinediamine, the reaction of 2,4-dichloro-5-methylpyrimidine with 3-hydroxyaniline gave N2,N4-bis(3-hydroxyphenyl)-5-methyl-2,4-pyrimidinediamine. LCMS: ret. time: 16.76 min.; purity: 100%, MS (m/e): 309 (MH$^+$).

7.3.52 N2,N4-Bis(3-hydroxyphenyl)-2,4-pyrimidinediamine (R926249)

In a manner analogous to the preparation of N2,N4-bis(3-hydroxyphenyl)-5-fluoro-2,4-pyrimidinediamine, the reaction of 2,4-dichloropyrimidine with 3-hydroxyaniline gave N2,N4-bis(3-hydroxyphenyl)-2,4-pyrimidinediamine. LCMS: ret. time: 16.21 min.; purity: 100%; MS (m/e): 295 (MH$^+$).

7.3.53 N2,N4-Bis[(4-methoxycarbonylmethyleneoxy)phenyl]-2,4-pyrimidinediamine (R926256)

In a manner analogous to the preparation of N2,N4-bis(3-hydroxyphenyl)-5-fluoro-2,4-pyrimidinediamine, the reaction of 2,4-dichloropyrimidine with methyl 4-aminophenoxyacetate gave N2,N4-bis[(4-methoxycarbonylmethyleneoxy)phenyl]-2,4-pyrimidinediamine. $^1$H NMR (DMSO-d6): δ 10.7 (bs, 1H), 10.28 (bs, 1H), 7.84 (d, 1H, J=6.9 Hz), 7.48 (bd, 2H), 7.35 (d, 2H, J=8.7 Hz), 6.95 (d, 2H, J=9 Hz), 6.90 (d, 2H, J=8.7 Hz), 6.35 (d, 1H, J=6.9 Hz), 4.81 (s, 2H), 4.79 (s, 2H), 3.69 (s, 3H), 3.68 (s, 3H); LCMS: ret. time: 21.27 min.; purity: 98%; MS (m/e): 439 (MH$^+$).

7.3.54 (±)-N2,N4-Bis[4-methoxycarbonyl(alpha-methyl)methyleneoxyphenyl]-2,4-pyrimidinediamine (R926257)

In a manner analogous to the preparation of N2,N4-bis(3-hydroxyphenyl)-5-fluoro-2,4-pyrimidinediamine, the reaction of 2,4-dichloropyrimidine with (±)-methyl 2-(4-aminophenoxy)propionate gave (±)-N2,N4-bis[4-methoxycarbonyl(alpha-methyl)methyleneoxyoxyphenyl]-2,4-pyrimidinediamine. LCMS: ret. time: 24.09 min.; purity: 90%; MS (m/e): 467 (MH$^+$).

7.3.55 N2,N4-Bis(4-methoxycarbonylmethyleneoxyphenyl)-5-methyl-2,4-pyrimidinediamine (R926258)

In a manner analogous to the preparation of N2,N4-bis(3-hydroxyphenyl)-5-fluoro-2,4-pyrimidinediamine, the reaction of 2,4-dichloro-5-methylpyrimidine with methyl-4-aminophenoxyacetate gave N2,N4-bis(4-methoxycarbonylmethyleneoxyphenyl)-5-methyl-2,4-pyrimidinediamine. $^1$H NMR (DMSO-d6): δ 10.21 (s, 1H), 9.65 (s, 1H), 7.78 (s, 1H), 7.42 (dd, 2H), J=2.7 and 8.7 Hz), 7.28 (dd, 2H, J=8.1 Hz), 6.94 (d, 2H, J=8.47 Hz), 6.85 (d, 2H, J=8.7 Hz), 4.82 (s, 2H), 4.77 (s, 2H), 3.69 (s, 3H), 3.68 (s, 3H), 2.12 (s, 3H); LCMS: ret. time: 21.76 min.; purity: 100%; MS (m/e): 453 (MH$^+$).

7.3.56 (±)-N2,N4-Bis[4-ethoxycarbonyl(alpha-methyl)methyleneoxyphenyl]-5-methyl-2,4-pyrimidinediamine (R926259)

In a manner analogous to the preparation of N2,N4-bis(3-hydroxyphenyl)-5-fluoro-2,4-pyrimidinediamine, the reaction of 2,4-dichloro-5-methylpyrimidine with (±)-ethyl 2-(4-aminophenoxy)propionate gave (±)-N2,N4-bis[4- ethoxycarbonyl(alpha-methyl)methyleneoxyphenyl]-5-methyl-2,4-pyrimidinediamine. $^1$H NMR (DMSO-d6): δ 9.9 (bs, 1H), 9.35 (bs, 1H), 7.79 (s, 1H), 7.43 (dd, 2H, J=3.6 and 8.7 Hz), 7.32 (d, 2H, J=7.5 Hz), 6.86 (d, 2H, J=9 Hz), 6.78 (d, 2H, J=8.7 Hz), 4.95 (q, 1H, J=7.2 Hz), 4.90 (q, 1H, J=7.2 Hz), 4.12 (2q, 4H, J=5.7 Hz), 2.10 (s, 3H), 1.51 (d, 3H, J=6.3 Hz), 1.47 (d, 3H, J=6.3 Hz), 1.16 (2t, 6H, J=5.7 Hz); LCMS: ret. time: 27.41 min.; purity: 96%; MS (m/e): 509 (MH$^+$).

7.3.57 N2,N4-Bis[2-(4-hydroxyphenyl)ethyl]-5-methyl-2,4-pyrimidinediamine (R926397)

In a manner analogous to the preparation of N2,N4-bis(3-hydroxyphenyl)-5-fluoro-2,4-pyrimidinediamine, the reaction of 2,4-dichloro-5-methylpyrimidine with 2-(4-hydroxyphenyl)ethylamine gave N2,N4-bis[2-(4-hydroxyphenyl)ethyl]-5-methyl-2,4-pyrimidinediamine. LCMS: ret. time: 19.94 min.; purity: 100%; MS (m/e): 365 (MH$^+$).

7.3.58 N2,N4-Bis-(3,4-dimethoxypenyl)-5-nitro-2,4-pyrimidinediamine (R940089)

In like manner to the preparation of N2,N4-bis(3-hydroxyphenyl)-5-fluoro-2,4-pyrimidinediamine, the reaction of 2,4-dichloro-5-nitropyrimidine with 3,4-dimethoxyaniline gave N2,N4-bis-(3,4-dimethoxyphenyl)-5-nitro-2,4-pyrimidinediamine. LCMS: ret. time: 28.30 min.; purity: 100%; MS (m/e): 428 (MH$^+$); $^1$H NMR (CDCl$_3$): δ 10.30 (1H, s), 9.14 (1H, s), 7.52 (1H, s), 7.08 (3H, m), 7.00 (1H, d, J=8.4 Hz), 6.84 (1H, d, J=8.4 Hz), 6.76 (1H, d, J=8.4 Hz), 3.90 (3H, s), 3.87 (3H, s), 3.68 (3H, s), 3.60 (3H, s).

7.3.59 N2,N4-Bis-(4-ethoxypenyl)-5-nitro-2,4-pyrimidinediamine (R940090)

In like manner to the preparation of N2,N4-bis(3-hydroxyphenyl)-5-fluoro-2,4-pyrimidinediamine, the reaction of 2,4-dichloro-5-nitropyrimidine with 4-ethoxyaniline gave N2,N4-bis-(4-ethoxyphenyl)-5-nitro-2,4-pyrimidinediamine. LCMS: ret. time: 35.91 min.; purity: 100%; MS (m/e): 396 (MH$^+$); $^1$H NMR (CDCl$_3$): δ 10.25 (1H, s), 9.11 (1H, s), 7.44 (2H, d, J=8.6 Hz), 7.37 (2H, d, J=9 Hz), 6.88 (2H, d, J=8.6 Hz), 6.80 (2H, d, J=8.6 Hz), 4.06 (2H, q, J=7.2 Hz), 4.02 (2H, q, J=7.2 Hz), 1.45 (3H, t, J=7.2 Hz), 1.42 (3H, t, J=7.2 Hz).

7.3.60 N2,N4-Bis-(3,4-ethylenedioxyphenyl)-5-nitro-2,4-pyrimidinediamine (R940095)

In like manner to the preparation of N2,N4-bis(3-hydroxyphenyl)-5-fluoro-2,4-pyrimidinediamine, the reaction of 2,4-dichloro-5-nitropyrimidine with 3,4-ethylenedioxyaniline gave N2,N4-bis-(3,4-ethylenedioxyphenyl)-5-nitro-2,4-pyrimidinediamine. LCMS: ret. time: 30.78 min.; purity: 100%; MS (m/e): 424 (MH$^+$); $^1$H NMR (CDCl$_3$): δ 10.21 (1H, s), 9.10 (1H, s), 7.40 (1H, s), 7.11-6.71 (6H, m), 4.29 (4H, s), 4.25 (4H, s).

7.3.61 N2,N4-Bis-[(4-ethoxycarbonylmethyleneoxy)phenyl]-5-nitro-2,4-pyrimidinediamine (R940096)

In like manner to the preparation of N2,N4-bis(3-hydroxyphenyl)-5-fluoro-2,4-pyrimidinediamine, the reaction of 2,4-dichloro-5-nitropyrimidine with ethyl-4-aminophenoxyacetate gave N2,N4-bis-[(4-ethoxycarbonylmethyleneoxy)phenyl]-5-nitro-2,4-pyrimidinediamine. LCMS: ret. time: 32.48 min.; purity: 94%; MS (m/e): 512 (MH$^+$);

1H NMR (CDCl$_3$): δ 10.22 (1H, s), 9.13 (1H, s), 7.50 (1H, s), 7.45 (2H, d, J=8.7 Hz), 7.38 (2H, d, J=8.7 Hz), 6.93 (2H, d, J=8.7 Hz), 6.83 (2H, d, J=8.7 Hz), 4.67 (2H, s), 4.63 (2H, s), 4.29 (2H, q, J=7.2 Hz, 4.28 (2H, q, J=7.2 Hz), 1.31 (3H, t, J=7.2 Hz), 1.30 (3H, t, J=7.2 Hz).

7.3.62 N2,N4-Bis-(2,2-difluoro-1,3-benzodioxol-5-yl)-5-nitro-2,4-pyrimidinediamine (R940100)

In like manner to the preparation of N2,N4-bis(3-hydroxyphenyl)-5-fluoro-2,4-pyrimidinediamine, the reaction of 2,4-dichloro-5-nitropyrimidine with 2,2-difluoro-5-amino-1,3-benzodioxole gave N2,N4-bis-(2,2-difluoro-1,3-benzodioxol-5-yl)-5-nitro-2,4-pyrimidinediamine. LCMS: ret. time: 38.15 min.; purity: 96%; MS (m/e): 467 (M$^+$); $^1$H NMR (CDCl$_3$): δ 10.76 (1H, s), 10.49 (1H, s), 9.20 (1H, s), 7.74 (2H, s), 7.56 (1H, d, J=11.4 Hz), 7.33 (2H, m), 7.20 (1H, m).

7.3.63 N2,N4-Bis-(3,5-dichloro-4-hydroxyphenyl)-5-fluoro-2,4-pyrimidinediamine (R940215)

In like manner to the preparation of N2,N4-bis(3-hydroxyphenyl)-5-fluoro-2,4-pyrimidinediamine, the reaction of 2,4-dichloro-5-fluoropyrimidine with 3,5-dichloro-4-hydroxyaniline gave N2,N4-bis-(3,5-dichloro-4-hydroxyphenyl)-5-fluoro-2,4-pyrimidinediamine. LCMS: ret. time: 21.26 min.; purity: 88%; MS (m/e): 450 (M$^+$); $^1$H NMR (DMSO-d6): δ 9.96 (1H, s), 9.59 (1H, s), 9.47 (1H, s), 9.37 (1H, s), 8.22 (1H, d, J=3.6 Hz), 7.79 (2H, s), 7.74 (2H, s).

7.3.64 N2,N4-Bis-(3-chloro-4-hydroxy-5-methylphenyl)-5-fluoro-2,4-pyrimidinediamine (R940216)

In like manner to the preparation of N2,N4-bis(3-hydroxyphenyl)-5-fluoro-2,4-pyrimidinediamine, the reaction of 2,4-dichloro-5-fluoropyrimidine with 3-chloro-4-hydroxy-5-methylaniline gave N2,N4-bis-(3-chloro-4-hydroxy-5-methylphenyl)-5-fluoro-2,4-pyrimidinediamine. LCMS: ret. time: 20.55 min.; purity: 99%; MS (m/e): 410 (MH$^+$);

$^1$H NMR (DMSO-d6): δ 9.23 (1H, s), 9.07 (1H, s), 8.99 (1H,s), 8.66 (1H, s), 8.13 (1H, d, J=3.6 Hz), 7.59 (2H, t, J=3.1 Hz), 7.50 (1H, d, J=2.3 Hz), 7.34 (1H, d, J=2.3 Hz), 2.27 (3H, s), 2.18 (3H, s).

7.3.65 N2,N4-Bis-(2,3-dimethyl-4-hydroxyphenyl)-5-fluoro-2,4-pyrimidinediamine (R940217)

In like manner to the preparation of N2,N4-bis(3-hydroxyphenyl)-5-fluoro-2,4-pyrimidinediamine, the reaction of 2,4-dichloro-5-fluoropyrimidine with 2,3-dimethyl-4-hydroxyaniline gave N2,N4-bis-(2,3-dimethyl-4-hydroxyphenyl)-5-fluoro-2,4-pyrimidinediamine. LCMS: ret. time: 19.07 min.; purity: 99%; MS (m/e): 369 (MH$^+$); $^1$H NMR (DMSO-d6): δ 9.21 (1H, s), 8.99 (1H, s), 8.63 (1H, s), 7.92 (1H, s), 7.84 (1H, d, J=3.6 Hz), 6.94 (1H, d, J=8.5 Hz), 6.85 (1H, d, J=8.5 Hz), 6.70 (1H, d, J=8.5 Hz), 6.58 (1H, d, J=8.5 Hz), 2.12 (3H, s), 2.06 (3H, s), 2.02 (3H, s), 1.94 (3H, s).

7.3.66 N2,N4-Bis-(4-Acetamidophenyl)-5-fluoro-2,4-pyrimidinediamine (R940222)

In like manner to the preparation of N2,N4-bis(3-hydroxyphenyl)-5-fluoro-2,4-pyrimidinediamine, the reaction of 2,4-dichloro-5-fluoropyrimidine with 4-acetamidoaniline gave N2,N4-bis-(4-acetamidophenyl)-5-fluoro-2,4-pyrimidinediamine. LCMS: ret. time: 14.82 min.; purity: 95%; MS (m/e): 395 (MH⁺); ¹H NMR (DMSO-d6): δ 10.33 (1H, s), 10.14 (1H, s), 10.07 (2H, s), 8.39 (1H, d, J=5.1 Hz), 7.64 (8H, m), 2.15 (3H, s), 2.13 (3H, s).

7.3.67 N2,N4-Bis(3-isopropylphenyl)-5-fluoro-2,4-pyrimidinediamine R940297

In like manner to the preparation of N2,N4-bis-(3-hydroxyphenyl)-5-fluoro-2,4-pyrimidinediamine, 2,4-dichloro-5-fluoropyrimidine and 3-isopropylaniline were reacted to give N2,N4-bis-(3-isopropylphenyl)-5-fluoro-2,4-pyrimidinediamine. LCMS: ret. time: 29.58 min.; Purity: 98%; MS (m/e): 365 (MH⁺); ¹H NMR (DMSO-d6): δ 10.5 (1H, s), 10.34 (1H, s), 8.41 (1H, d, J=5.1 Hz), 7.62 (1H, d, J=8.1 Hz), 7.53 (1H, s), 7.43 (1H, d, J=8.1 Hz), 7.37 (2H, m), 7.29 (1H, t, J=8.1 Hz), 7.19 (1H, d, J=7.8 Hz), 7.08 (1H, d, J=7.8 Hz), 2.88 (2H, m), 1.25 (6H, d, J=7.2 Hz), 1.201 (6H, d, J=7.2 Hz).

7.3.68 N2,N4-Bis(3,4,5-trimethoxyphenyl)-5-fluoro-2,4-pyrimidinediamine (R926688)

In a manner similar to the preparation of N2,N4-bis(3-hydroxyphenyl)-5-fluoro-2,4-pyrimidinediamine, 2,4-dichloro-5-fluoropyrimidine and 3,4,5-trimethoxyaniline were reacted to yield N2,N4-bis(3,4,5-trimethoxyphenyl)-5-fluoro-2,4-pyrimidinediamine. LCMS: ret. time: 19.55 min.; purity: 99%; MS (m/e): 461 (MH⁺).

7.3.69 N2,N4-Bis(2-methyl-5-phenylphenyl)-5-bromo-2,4-pyrimidinediamine R925800

In a manner similar to the preparation of N2,N4-bis(3-hydroxyphenyl)-5-fluoro-2,4-pyrimidinediamine, 5-bromo-2,4-dichloropyrimidine and 5-phenyl-ortho-toluidine were reacted to yield N2,N4-bis(2-methyl-5-phenylphenyl)-5-bromo-2,4-pyrimidinediamine. LCMS: ret. time: 19.54 min.; purity: 90%; MS (m/e): 422 (MH⁺).

7.3.70 N2,N4-Bis(2-methoxy-5-methyl-4-phenylphenyl)-5-bromo-2,4-pyrimidinediamine (R925801)

In a manner similar to the preparation of N2,N4-bis(3-hydroxyphenyl)-5-fluoro-2,4-pyrimidinediamine, 5-bromo-2,4-dichloropyrimidine 5-methyl-4-phenyl-ortho-anisidine were reacted to yield N2,N4-bis(2-methoxy-5-methyl-4-phenylphenyl)-5-bromo-2,4-pyrimidinediamine. LCMS: ret. time: 20.99 min.; purity: 85%; MS (m/e): 583 (MH⁺).

7.3.71 N2,N4-Bis(indol-6-yl)-5-fluoro-2,4-pyrimidinediamine (R926594)

In like manner to the preparation of N2,N4-bis(3-hydroxyphenyl)-5-fluoro-2,4-pyrimidinediamine, 2,4-dichloro-5-fluoropyrimidine and 6-aminoindole were reacted to yield N2,N4-bis(indol-6-yl)-5-fluoro-2,4-pyrimidinediamine. LCMS: ret. time: 22.39 min.; purity: 85%; MS (m/e): 359 (MH⁺).

7.3.72 N2,N4-Bis(2-methoxycarbonyl benzofuran-5-yl)-5-fluoro-2,4-pyrimidinediamine (R926604)

In like manner to the preparation of N2,N4-bis(3-hydroxyphenyl)-5-fluoro-2,4-pyrimidinediamine, 2,4-dichloro-5-fluoropyrimidine and 2-methoxycarbonyl-5-aminobenzofuran were reacted to yield N2,N4-bis(2-methoxycarbonyl benzofuran-5-yl))-5-fluoro-2,4-pyrimidinediamine. ¹H NMR (DMSO-d6): δ 10.3 (bs, 1H), 10.05 (bs, 1H), 8.25 (d, 1H, J=5.4 Hz), 8.06 (s, 1H), 7.94 (s, 1H), 7.77-7.49 (m, 5H), 7.36 (bs, 1H), 3.89 (s, 3H), 3.87 (s, 3H).

7.3.73 N2,N4-Bis[4-(methoxycarbonylmethyl)phenyl]-5-fluoro-2,4-pyrimidinediamine (R926605)

In like manner to the preparation of N2,N4-bis(3-hydroxyphenyl)-5-fluoro-2,4-pyrimidinediamine, 2,4-dichloro-5-fluoropyrimidine and ethyl 4-aminophenyl acetate were reacted to yield N2,N4-bis[4-(methoxycarbonylmethyl)phenyl]-5-fluoro-2,4-pyrimidinediamine. The cross esterification reaction of ethyl ester to obtain the corresponding methyl ester was observed. ¹H NMR (CDCl₃): δ 10.62 (s, 1H), 8.06 (s, 1H), 7.69 (d, 1H, J=4.5 Hz), 7.53 (d, 2H, J=8.1 Hz), 7.43 (d, 2H, J=8.7 Hz), 7.30 (d, 2H, J=8.4 Hz), 7.20 (d, 2H, J=8.4 Hz), 3.73 (s, 3H), 3.72 (s, 3H), 3.67 (s, 2H), 3.63 (s, 2H).

7.3.74 N2,N4-Bis(2-ethoxycarbonylindol-5-yl)-5-fluoro-2,4-pyrimidinediamine (R926616)

In like manner to the preparation of N2,N4-bis(3-hydroxyphenyl)-5-fluoro-2,4-pyrimidinediamine, 2,4-dichloro-5-fluoropyrimidine and 2-ethoxycarbonyl-5-indoleamine were reacted to yield N2,N4-bis(2-ethoxycarbonylindol-5-yl)-5-fluoro-2,4-pyrimidinediamine. ¹H NMR (DMSO-d6): δ 11.83 (s, 1H), 11.63 (s, 1H), 9.21 (s, 1H), 8.99 (s, 1H), 8.08 (s, 1H), 8.01 (m, 2H), 7.49-7.22 (m, 4H), 6.92 (s, 1H), 6.63 (s, 1H), 4.29 (q, 4H, J=7.2 Hz), 1.32 (m, 6H); LCMS: ret. time: 24.74 min.; purity: 99%; MS (m/e): 503 (MH⁺).

7.3.75 N2,N4-Bis(coumarin-6-yl)-5-fluoro-2,4-pyrimidinediamine (R926617)

In like manner to the preparation of N2,N4-bis(3-hydroxyphenyl)-5-fluoro-2,4-pyrimidinediamine, 2,4-dichloro-5-fluoropyrimidine and 6-aminocoumarin were reacted to yield N2,N4-bis(coumarin-6-yl)-5-fluoro-2,4-pyrimidinediamine. ¹H NMR (DMSO-d6): δ 8.17 (d, 2H, J=3.6 Hz), 7.97-7.74 (m, 5H), 7.40 (1H, d, J=8.7 Hz), 7.30 (d, 1H, J=9 Hz), 6.50 (d, 1H, J=10.2 Hz), 6.40 (d, 1H, J=9.3 Hz); LCMS: ret. time: 19.05 min.; purity: 94%; MS (m/e): 417 (MH⁺).

7.3.76 N2,N4-Bis(4-methoxymethyl)coumarin-7-yl)-5-fluoro-2,4-pyrimidinediamine (R926620)

In like manner to the preparation of N2,N4-bis(3-hydroxyphenyl)-5-fluoro-2,4-pyrimidinediamine, 2,4-dichloro-5-fluoropyrimidine and 7-amino-4-methoxymethylcoumarin were reacted to yield N2,N4-bis(coumarin-7-yl)-5-fluoro-2,4-pyrimidinediamine. ¹H NMR (DMSO-d6): δ 10.38 (s, 1H), 8.42 (d, 1H, J=3 Hz), 8.28 (m, 1H), 8.05-7.93 (m, 2H), 7.77-7.50 (m, 4H), 6.31 (s, 1H), 6.29 (s, 1H), 4.66 (s, 2H), 4.65 (s, 2H), 3.43 (s, 3H), 3.41 (s, 3H); LCMS: MS (m/e): 505 (MH⁺).

7.3.77 N2,N4-Bis(3-(hydroxymethyl)phenyl)-5-fluoro-2,4-pyrimidinediamine (R925757)

In a manner similar to the preparation of N2,N4-bis(3-hydroxyphenyl)-5-fluoro-2,4-pyrimidinediamine, 2,4-dichloro-5-fluoropyrimidine and 3-aminobenzylalcohol were reacted to yield N2,N4-bis(3-(hydroxymethyl)phenyl)-5-fluoro-2,4-pyrimidinediamine. ¹H NMR (CD₃OD): δ 7.90 (d, 1H, J=3.3 Hz), 7.71 (m, 1H), 7.61 (d, 1H, J=6.9 Hz), 7.50 (d, 1H, J=6.0), 7.47 (s, 1H), 7.31 (t, 1H, J=8.1 Hz), 7.22 (t, 1H, J=8.1 Hz), 7.10 (d, 1H, J=6.9), 6.97 (d, 1H, J=7.5 Hz), 4.63 (s, 4H); LCMS: ret. time: 15.36 min.; purity: 100%; MS (m/e): 342 (MH⁺).

7.3.78 N2,N4-Bis[(2R)-hydroxy-(1S)-methyl-2-phenylethyl]-5-fluoro-2,4-pyrimidinediamine (R925767)

In a manner similar to the preparation of N2,N4-bis(3-hydroxyphenyl)-5-fluoro-2,4-pyrimidinediamine, 2,4-dichloro-5-fluoropyrimidine and (1R,2S)-(−)-norephedrine were reacted to yield N2,N4-bis[(2R)-hydroxy-(1S)-methyl-2-phenylethyl]-5-fluoro-2,4-pyrimidinediamine. $^1$H NMR (acetone-d$_6$): δ 7.67 (s, 1H), 7.49-7.42 (m, 4H), 7.38-7.19 (m, 6H), 6.09 (d, 1H, J=9.0 Hz), 5.73 (d, 1H, J=7.5 Hz), 5.61 (d, 1H, J=9.3 Hz), 5.04 (d, 1H, J=3.6 Hz), 4.97 (d, 1H, J=2.7 Hz), 4.74 (bs, 1H), 4.48 (bs, 1H), 4.30-4.25 (m, 1H), 1.09 (d, 1H, J=6.9 Hz), 1.03 (d, 1H, J=6.6 Hz); LCMS: ret. time: 21.56 min.; purity: 98%; MS (m/e): 397(MH$^+$).

7.3.79 N2,N4-Bis(2-hydroxy-2-phenylethyl)-5-fluoro-2,4-pyrimidinediamine (R925768)

In a manner similar to the preparation of N2,N4-bis(3-hydroxyphenyl)-5-fluoro-2,4-pyrimidinediamine, 2,4-dichloro-5-fluoropyrimidine and 2-amino-1-phenylethanol were reacted to yield N2,N4-bis(2-hydroxy-2-phenylethyl)-5-fluoro-2,4-pyrimidinediamine. $^1$H NMR (acetone-d$_6$): δ 8.15 (s, 1H), 7.46-7.22 (m, 10H), 5.01 (dd, 1H), 4.91 (dd, 1H), 4.78 (dd, 1H), 3.86-3.18 (m, 5H); LCMS: ret. time: 19.64 min.; purity: 89%; MS (m/e): 369 (MH$^+$).

7.3.80 N2,N4-Bis(furfuryl)-5-fluoro-2,4-pyrimidinediamine (R925769)

In a manner similar to the preparation of N2,N4-bis(3-hydroxyphenyl)-5-fluoro-2,4-pyrimidinediamine, 2,4-dichloro-5-fluoropyrimidine and furfurylamine were reacted to yield N2,N4-bis(furfuryl)-5-fluoro-2,4-pyrimidinediamine. $^1$H NMR (CDCl$_3$): δ 7.72 (bs, 1H), 7.38 (dd, 2H, J=1.8 and 7.5 Hz), 6.34-6.30 (m, 2H), 6.22 (dd, 2H, J=2.4 and 9.9 Hz), 5.163 (bs, 2H), 4.63 (d, 2H, J=6.0), 4.54 (d, 2H, J=6.0); $^{19}$F NMR (CDCl$_3$): −48621; LCMS: ret. time: 97.27 min.; purity: 97%; MS (m/e): 289 (MH$^+$).

7.3.81 N2,N4-Bis(piperonyl)-5-fluoro-2,4-pyrimidineamine (R925770)

In a manner similar to the preparation of N2,N4-bis(3-hydroxyphenyl)-5-fluoro-2,4-pyrimidinediamine, 2,4-dichloro-5-fluoropyrimidine and piperonylamine were reacted to yield N2,N4-bis(piperonyl)-5-fluoro-2,4-pyrimidinediamine. $^1$H NMR (CDCl$_3$): δ 7.60 (bs, 1H), 6.78-6.69 (m, 6H), 5.93 (s, 2H), 5.91 (s, 2H), 4.51 (d, 2H, J=5.7 Hz), 4.43 (d, 2H, J=5.1 Hz); $^{19}$F NMR (CDCl$_3$): −45257; LCMS: ret. time: 22.06 min.; purity: 96%; MS (m/e): 397 (MH$^+$).

7.3.82 N2,N4-Dibenzyl-5-fluoro-2,4-pyrimidinediamine (R925772)

In a manner similar to the preparation of N2,N4-bis(3-hydroxyphenyl)-5-fluoro-2,4-pyrimidinediamine, 2,4-dichloro-5-fluoropyrimidine and benzylamine were reacted to yield N2,N4-bis(benzyl)-5-fluoro-2,4-pyrimidinediamine. $^1$H NMR (CDCl$_3$): δ 7.69 (bs, 1H), 7.35-7.24 (m, 10H), 5.63 (bs, 1H), 5.27 (bs, 1H), 4.61 (d, 2H, J=6.0 Hz), 4.55 (d, 2H, J=6.0 Hz); $^{19}$F NMR (CDCl$_3$): −48580; LCMS: ret. time: 23.73 min.; purity: 100%; MS (m/e): 309 (MH$^+$)

7.3.83 N2,N4-Bis(3,4-methylenedioxyphenyl)-5-fluoro-2,4-pyrimidinediamine (R925776)

In a manner similar to the preparation of N2,N4-bis(3-hydroxyphenyl)-5-fluoro-2,4-pyrimidinediamine, 2,4-dichloro-5-fluoropyrimidine and 3,4-methylenedioxyaniline were reacted to yield N2,N4-bis(3,4-methylenedioxyphenyl)-5-fluoro-2,4-pyrimidinediamine. $^1$H NMR (CDCl$_3$): δ 7.86 (bs, 1H), 7.27 (m, 1H), 7.19 (m, 1H), 6.89 (dd, 2H, J=2.1 and 8.1 Hz), 6.80 (dd, 2H, J=1.8 and 8.1 Hz), 6.73 (t, 2H, J=8.1 Hz), 5.97 (s, 2H), 5.92 (s, 2H); $^{19}$F NMR (CDCl$_3$): −47591; LCMS: ret. time: 21.74 min.; purity: 97%; MS (m/e): 369 (MH$^+$).

7.3.84 N2,N4-Bis[2-(4-hydroxyphenyl)ethyl]-5-fluoro-2,4-pyrimidinediamine (R925791)

In a manner similar to the preparation of N2,N4-bis(3-hydroxyphenyl)-5-fluoro-2,4-pyrimidinediamine, 2,4-dichloro-5-fluoropyrimidine and tyramine were reacted to yield N2,N4-bis[2-(4-hydroxyphenyl)ethyl]-5-fluoro-2,4-pyrimidinediamine. $^1$H NMR (DMSO-d6): δ 9.17 (bs, 1H), 8.22 (bs, 1H), 6.99 (d, 4H, J=8.1 Hz), 6.65 (d, 4H, J=8.1 Hz), 3.48-3.43 (m, 4H), 2.72 (t, 4H, J=7.7 Hz); LCMS: ret. time: 19.19 min.; purity: 100%; MS (m/e): 369 (MH$^+$).

7.3.85 N2,N4-Bis(4-cyanophenyl)-5-fluoro-2,4-pyrimidinediamine (R945057)

In like manner to the preparation of N2,N-4-bis(3-hydroxyphenyl)-5-fluoro-4-pyrimidineamine, 4-aminobenzonitrile and 2,4-dichloro-5-fluoropyrimidine gave N2,N4-bis(4-cyanophenyl)-5-fluoro-2,4-pyrimidinediamine. $^1$H NMR (DMSO-d6): δ 7.26 (d, J=8.7 Hz, 2H), 7.36 (d, J=9.0 Hz, 2H), 7.43 (d, J=8.7 Hz, 2H), 7.60 (d, J=8.7 Hz, 2H), 7.86 (d, J=3.6 Hz, 1H), 9.49 (br, 1H, NH), 9.51 (br, 1H, NH); $^{19}$F NMR (282 MHz, DMSO-d6): 6-161.48; LC: 27.15 min.; 100%; MS (m/e): 331.00 (MH$^+$).

7.3.86 N2,N4-Bis(4-ethylphenyl)-5-fluoro-2,4-pyrimidinediamine (R926234)

In a manner similar to the preparation of N2,N4-bis(3-hydroxyphenyl)-5-fluoro-2,4-pyrimidinediamine, 2,4-dichloro-5-fluoropyrimidine and 4-ethylaniline were reacted to yield N2,N4-bis(4-ethylphenyl)-5-fluoro-2,4-pyrimidinediamine. $^1$H NMR (CDCl$_3$): δ 8.83 (bs, 1H), 7.77 (d, 1H. J=3.9 Hz), 7.48 (d, 2H, J=8.7 Hz), 7.40 (d, 2H, J=8.7 Hz), 7.31 (bs, 1H), 7.18 (d, 2H, J=8.7 Hz), 7.11 (d, 2H, J=8.7 Hz), 2.68-2.61 (m, 4H), 1.28-1.21 (m, 6H); LCMS: ret. time: 29.17 min.; purity: 100%; MS (m/e): 337(MH$^+$).

7.3.87 N2,N4-Bis(3-chloro-4-hydroxyphenyl)-5-fluoro-2,4-pyrimidinediamine (R926675)

In a manner similar to the preparation of N2,N4-bis(3-hydroxyphenyl)-5-fluoro-2,4-pyrimidinediamine, 2,4-dichloro-5-fluoropyrimidine and 3-chloro-4-hydroxyaniline were reacted to yield N2,N4-bis(3-chloro-4-hydroxyphenyl)-5-fluoro-2,4-pyrimidinediamine. $^1$H NMR (CD$_3$OD): δ 7.83 (d, 1H, J=4.2 Hz), 7.59 (d, 1H, J=2.4 Hz), 7.53 (d, 1H, J=2.4 Hz), 7.40 (dd, 1H, J=2.4 and 8.7 Hz), 7.20 (dd, 1H, J=2.4 and 8.7 Hz), 6.89 (d, 1H, J=8.7 Hz), 6.81 (d, 1H, J=8.7 Hz); $^{19}$F NMR (CD$_3$OD): −47862; LCMS: ret. time: 17.89 min.; purity: 99%; MS (m/e): 382 (MH$^+$).

7.3.88 N2,N4-Bis[3-chloro-4-(ethoxycarbonylmethyleneoxy)phenyl]-5-fluoro-2,4-pyrimidinediamine (R926676)

In a manner similar to the preparation of N2,N4-bis(3-hydroxyphenyl)-5-fluoro-2,4-pyrimidinediamine, 2,4-dichloro-5-fluoropyrimidine and 3-chloro-4-(ethoxycarbonylmethyleneoxy)aniline were reacted to yield N2,N4-bis[3-chloro-4-(ethoxycarbonylmethyleneoxy)phenyl]-5-fluoro-2,4-pyrimidinediamine. $^1$H NMR (CDCl$_3$): δ 7.93 (bs, 1H), 7.67-7.65 (m, 2H), 7.41 (dd, 1H, J=3.0 and 9.3 Hz), 7.26 (dd, 1H, J=2.7 and 9.3 Hz), 6.92-6.85 (m, 3H), 6.69 (d, 1H, J=2.4 Hz), 4.71 (s, 2H), 4.66 (s, 2H), 4.32-4.23 (m, 4H), 1.33-1.27 (m, 6H); $^{19}$F NMR (CDCl$_3$): −47274; LCMS: ret. time: 27.51 min.; purity: 97%; MS (m/e): 553 (M$^+$).

7.3.89 N2,N4-Bis(3-fluoro-4-hydroxyphenyl)-5-fluoro-2,4-pyrimidinediamine (R926681)

In a manner similar to the preparation of N2,N4-bis(3-hydroxyphenyl)-5-fluoro-2,4-pyrimidinediamine, 2,4-dichloro-5-fluoropyrimidine and 3-fluoro-4-hydroxyaniline were reacted to yield N2,N4-bis(3-fluoro-4-hydroxyphenyl)-5-fluoro-2,4-pyrimidinediamine. $^1$H NMR (CDCl$_3$): δ 7.83 (d, 1H), 7.53 (dd, 1H), 7.42 (dd, 1H), 7.22 (dq, 1H), 7.03 (dq, 1H), 6.89 (d, 1H), 6.83 (s, 1H), 6.80 (s, 1H), 6.78 (d, 1H); $^{19}$F NMR (CDCl$_3$): −390060, −39165, −47835; LCMS: ret. time: 15.27 min.; purity: 95%; MS (m/e): 349 (MH$^+$).

7.3.90 N2,N4-Bis(3-acetamidophenyl)-5-fluoro-2,4-pyrimidinediamine (R926682)

In a manner similar to the preparation of N2,N4-bis(3-hydroxyphenyl)-5-fluoro-2,4-pyrimidinediamine, 2,4-dichloro-5-fluoropyrimidine and 3-aminoacetanilide were reacted to yield N2,N4-bis(3-acetamidophenyl)-5-fluoro-2,4-pyrimidinediamine. $^1$H NMR (DMSO-d6): δ 10.24 (bs, 1H), 10.03 (s, 1H), 9.94 (s, 1H), 8.20 (d, 1H, J=4.8 Hz), 7.91 (bs, 1H), 7.68 (bs, 1H), 7.43 (d, 1H, J=8.1 Hz), 7.35-7.30 (m, 2H), 7.24-7.19 (m, 2H), 7.11 (t, 1H, J=8.1 Hz), 2.03 (s, 3H), 2.01 (s, 3H); LCMS: ret. time: 15.10 min.; purity: 99%; MS (m/e): 395 (MH$^+$)

7.3.91 N2,N4-Bis(2-fluoro-4-hydroxyphenyl)-5-fluoro-2,4-pyrimidinediamine (R926683)

In a manner similar to the preparation of N2,N4-bis(3-hydroxyphenyl)-5-fluoro-2,4-pyrimidinediamine, 2,4-dichloro-5-fluoropyrimidine and 2-fluoro-4-hydroxyaniline were reacted to yield N2,N4-bis(2-fluoro-4-hydroxyphenyl)-5-fluoro-2,4-pyrimidinediamine. $^1$H NMR (DMSO-d6): δ 9.78 (s, 1H), 9.50 (s, 1H), 8.75 (s, 1H), 8.06 (s, 1H), 7.87 (d, 1H, J=4.2 Hz), 7.25-7.18 (m, 2H), 6.61 (dd, 1H, J=2.4 and 12.3 Hz), 6.56-6.47 (m, 2H), 6.39 (dd, 1H, J=1.8 and 8.7 Hz); LCMS: ret. time: 15.52 min.; purity: 99%; MS (m/e): 349 (MH$^+$).

7.3.92 N2,N4-Bis(4-isopropoxyphenyl)-5-fluoro-2,4-pyrimidinediamine (R926701)

In a manner similar to the preparation of N2,N4-bis(3-hydroxyphenyl)-5-fluoro-2,4-pyrimidinediamine, 2,4-dichloro-5-fluoropyrimidine and 4-isopropoxyaniline were reacted to yield N2,N4-bis(4-isopropoxy)phenyl)-5-fluoro-2,4-pyrimidinediamine. $^1$H NMR (CDCl$_3$): δ 7.89 (bs, 1H), 7.47 (d, 2H, J=8.7 Hz), 7.38 (d, 2H, J=9.0 Hz), 6.87 (d, 2H, J=9.0 Hz), 6.83 (d, 2H, J=8.7 Hz); LCMS: ret. time: 27.51 min.; purity: 98%; MS (m/e): 397 (MH$^+$).

7.3.93 N2,N4-Bis(3,4-ethylenedioxyphenyl)-5-bromo-2,4-pyrimidinediamine (R925771)

In a manner similar to the preparation of N2,N4-bis(3-hydroxyphenyl)-5-fluoro-2,4-pyrimidinediamine, 5-bromo-2,4-dichloropyrimidine and 3,4-ethylenedioxyaniline were reacted to yield N2,N4-bis(3,4-ethylenedioxyphenyl)-5-bromo-2,4-pyrimidinediamine. $^1$H NMR (CDCl$_3$): δ 8.07 (bs, 1H), 7.16 (d, 1H, J=3.0 Hz), 7.10 (d, 1H, J=2.7 Hz), 6.98-6.93 (m, 2H), 6.90-6.75 (m, 3H), 4.28-4.21 (m, 8H); LCMS: ret. time: 22.61 min.; purity: 100%; MS (m/e): 458 (MH$^+$).

7.3.94 N2,N4-Bis(3-hydroxyphenyl)-5-bromo-2,4-pyrimidinediamine (R925778)

In a manner similar to the preparation of N2,N4-bis(3-hydroxyphenyl)-5-fluoro-2,4-pyrimidinediamine, 5-bromo-2,4-dichloropyrimidine and 3-aminophenol were reacted to yield N2,N4-bis(3-hydroxyphenyl)-5-bromo-2,4-pyrimidinediamine. $^1$H NMR (DMSO-d6): δ 9.99 (bs, 1H), 9.34 (bs, 1H), 8.30 (s, 1H), 7.15 (t, 1H, J=8.4 Hz), 7.06-6.97 (m, 2H), 6.94-6.92 (m, 2H), 6.80 (bs, 1H), 6.62 (s, 1H, J=8.1 Hz), 6.43 (d, 1H, J=7.8 Hz); LCMS: ret. time: 18.48 min.; purity: 97%; MS (m/e): 374 (MH$^+$).

7.3.95 N2,N4-Bis[4-(ethoxycarbonylmethyleneoxy)phenyl]-5-bromo-2,4-pyrimidinediamine (R925779)

In a manner similar to the preparation of N2,N4-bis(3-hydroxyphenyl)-5-fluoro-2,4-pyrimidinediamine, 5-bromo-2,4-dichloropyrimidine and ethyl 4-aminophenoxyacetate were reacted to yield N2,N4-bis[4-(ethoxycarbonylmethyleneoxy)phenyl]-5-bromo-2,4-pyrimidinediamine. $^1$H NMR (DMSO-d6): δ 9.12 (s, 1H), 8.48 (s, 1H), 8.11 (s, 1H), 7.42 (d, 4H, J=8.7 Hz), 6.89 (d, 2H, J=9.0 Hz), 6.71 (d, 2H, J=9.3 Hz), 4.78 (s, 2H), 4.66 (s. 2H), 4.20-4.10 (m, 4H), 1.23-1.16 (m, 6H); LCMS: ret. time: 25.82 min.; purity: 94%; MS (m/e): 546 (MH$^+$).

7.3.96 N2,N4-Bis[2-(4-hydroxyphenyl)ethyl]-5-bromo-2,4-pyrimidinediamine (R925792)

In a manner similar to the preparation of N2,N4-bis(3-hydroxyphenyl)-5-fluoro-2,4-pyrimidinediamine, 5-bromo-2,4-dichloropyrimidine and tyramine were reacted to yield N2,N4-bis[2-(4-hydroxyphenyl)ethyl]-5-bromo-2,4-pyrimidinediamine. $^1$H NMR (DMSO-d6): δ 7.83 (s, 1H), 6.96 (d, 4H, J=8.1 Hz), 6.63 (d, 4H, J=8.1 Hz), 3.54-3.42 (m, 2H), 2.74-2.66 (m, 2H), 2.74-2.66 (m, 4H); ret. time: 20.10 min.; purity: 100%; MS (m/e): 430 (MH$^+$).

7.3.97 N2,N4-Bis(2-phenylphenyl)-5-bromo-2,4-pyrimidinediamine (R925798)

In a manner similar to the preparation of N2,N4-bis(3-hydroxyphenyl)-5-fluoro-2,4-pyrimidinediamine, 5-bromo-2,4-dichloropyrimidine and 2-aminobiphenyl were reacted to yield N2,N4-bis(2-phenylphenyl)-5-bromo-2,4-pyrimidinediamine. $^1$H NMR (CDCl$_3$): δ 8.34 (d, 1H, J=8.1 Hz), 8.27 (d, 1H, J=8.1 Hz), 8.00 (s, 1H), 7.51-7.18 (m, 17H), 6.95 (s, 1H); LCMS: ret. time: 18.87 min.; purity: 97%; MS (m/e): 495 (MH$^+$).

7.3.98 N2,N4-Bis(2-methoxy-5-phenylphenyl)-5-bromo-2,4-pyrimidinediamine (R925799)

In a manner similar to the preparation of N2,N4-bis(3-hydroxyphenyl)-5-fluoro-2,4-pyrimidinediamine, 5-bromo-2,4-dichloropyrimidine and 5-phenyl-ortho-anisidine were reacted to yield N2,N4-bis(2-methoxy-5-phenylphenyl)-5-bromo-2,4-pyrimidinediamine. $^1$H NMR (DMSO-d6): δ 8.26 (m, 2H), 8.05 (m, 2H), 7.39-7.21 (m, 12H), 7.17 (dd, 1H, J=2.4 and 8.1 Hz), 7.11 (d, 1H, J=8.7 Hz), 7.05 (d, 1H, J=9.0 Hz), 3.88 (s, 3H), 3.83 (s, 3H); LCMS: ret. time: 20.51 min.; purity: 98%; MS (m/e): 554 (MH$^+$).

7.3.99 N2,N4-Bis(4-methoxy-3-phenylphenyl)-5-bromo-2,4-pyrimidinediamine (R925802)

In a manner similar to the preparation of N2,N4-bis(3-hydroxyphenyl)-5-fluoro-2,4-pyrimidinediamine, with the addition of triethylamine, 5-bromo-2,4-dichloropyrimidine and 3-phenyl-para-anisidine hydrochloride were reacted to yield N2,N4-bis(4-methoxy-3-phenylphenyl)-5-bromo-2,4-pyrimidinediamine. $^1$H NMR (DMSO-d6): δ 8.26 (m, 2H), 8.06 (m, 2H), 7.38-7.25 (m, 12H), 7.18 (dd, 1H, J=2.4 and 8.1 Hz), 7.12 (d, 1H, J=8.7 Hz), 7.05 (d, 1H, 8.7 Hz), 3.89 (s, 3H), 3.83 (s, 3H); LCMS: ret. time: 36.77 min.; purity: 98%; MS (m/e): 554 (MH$^+$).

7.3.100 N2,N4-Bis(3-phenylphenyl)-5-bromo-2,4-pyrimidinediamine (R925803)

In a manner similar to the preparation of N2,N4-bis(3-hydroxyphenyl)-5-fluoro-2,4-pyrimidinediamine, 5-bromo-2,4-dichloropyrimidine and 3-aminobiphenyl were reacted to yield N2,N4-bis(3-phenylphenyl)-5-bromo-2,4-pyrimidinediamine. $^1$H NMR (DMSO-d6): δ 9.86 (bs, 1H), 9.20 (bs 1H), 8.33 (s, 1H), 7.79 (bs, 1H), 7.18 (bs, 1H), 7.61 (d, 1H), 7.56-7.51 (m, 2H), 7.48-7.23 (m, 11H), 7.17-7.04 (m, 2H); LCMS: ret. time: 19.52 min.; purity: 80%; MS (m/e): 494 (MH$^+$).

7.3.101 N2,N4-Bis(3,4-ethylenedioxyphenyl)-5-cyano-2,4-pyrimidinediamine (R925773)

In a manner similar to the preparation of N2,N4-bis(3-hydroxyphenyl)-5-fluoro-2,4-pyrimidinediamine, 2,4-dichloro-5-cyanopyrimidine and 3,4-ethylenedioxyaniline were reacted to yield N2,N4-bis(3,4-ethylenedioxyphenyl)-5-cyano-2,4-pyrimidinediamine. $^1$H NMR (DMSO-d6): δ 9.69 (bs, 1H), 9.28 (bs, 1H), 8.40 (s, 1H), 7.16-6.89 (m, 4H), 6.79 (d, 1H, J=9.0 Hz), 6.65 (bs, 1H), 4.22 (s, 4H), 4.16 (s, 4H); LCMS: ret. time: 24.42 min.; purity: 93%; MS (m/e): 404 (MH$^+$).

7.3.102 N2,N4-Bis(3-hydroxyphenyl)-5-cyano-2,4-pyrimidinediamine (R925774)

In a manner similar to the preparation of N2,N4-bis(3-hydroxyphenyl)-5-fluoro-2,4-pyrimidinediamine, 2,4-dichloro-5-cyanopyrimidine and 3-hydroxyaniline were reacted to yield N2,N4-bis(3-hydroxyphenyl-5-cyano-2,4-pyrimidinediamine. $^1$H NMR (DMSO-d6): δ 9.73 (bs, 1H), 9.40 (s, 1H), 9.33 (bs, 1H), 9.24 (s, 1H), 8.47 (s, 1H), 7.20 (d, 1H, J=7.5 Hz), 7.11 (t, 1H, J=7.5 Hz), 7.09-7.02 (m, 2H), 6.99-6.89 (m, 3H), 6.54 (d, 1H, J=7.2 Hz), 6.37 (dd, 1H, J=1.8 and 8.4 Hz); LCMS: ret. time: 19.71 min.; purity: 97%; MS (m/e): 320 (MH$^+$).

7.3.103 N2,N4-Bis[4-(ethoxycarbonylmethyleneoxy)phenyl]-5-cyano-2,4-pyrimidinediamine (R925775)

In a manner similar to the preparation of N2,N4-bis(3-hydroxyphenyl)-5-fluoro-2,4-pyrimidinediamine, 2,4-dichloro-5-cyanopyrimidine and ethyl 4-aminophenoxyacetate were reacted to yield N2,N4-bis[4-(ethoxycarbonylmethyleneoxy)phenyl]-5-cyano-2,4-pyrimidinediamine. $^1$H NMR (CD$_3$OD): δ 7.80 (s, 1H), 7.40 (d, 4H, J=8.7 Hz), 6.90 (4H, J=9.0 Hz), 6.82-6.75 (m, 2H), 4.60 (bs, 4H), 4.29-4.25 (m, 4H), 1.32-1.26 (m, 5H), LCMS: ret. time: 28.50 min.; purity: 100%; MS (m/e): 493 (MH$^+$).

7.3.104 R935192: N2, N4-Bis(1-methyl-indazolin-5-yl)-5-fluoro-2,4-pyrimidinediamine In like manner to the preparation of N2, N4-bis(3-hydroxyphenyl)-5-fluoro-2,4-pyrimidinediamine, 2-chloro-5-fluoropyrimidine and 1-methyl-5-aminoindazole were reacted to produce N2, N4-bis(1-methyl-indazolin-5-yl)-5-fluoro-2,4-pyrimidinediamine.

$^1$H NMR (DMSO-d6): δ 10.65 (s, 1H), 10.41 (s, 1H), 8.29 (d, 1H, J=5.3 Hz), 7.98 (s, 1H), 7.79 (d, 2H, J=9.4 Hz), 7.69-7.54 (m, 4H), 7.35 (dd, 1H, J=1.7 and 9.4 Hz), 4.03 (s, 3H), 4.01 (s, 3H). LCMS: ret. time: 16.86 min.; purity: 99%; MS (m/e): 389 (MH$^+$).

7.3.105 R935205: N2, N4-Bis[1-(methoxycarbonyl)methyl-indazoline-6-yl]-5-fluoro-2,4-pyrimidinediamine In like manner to the preparation of 5-fluoro-N2, N4-bis(3-hydroxyphenyl)-2,4-pyrimidinediamine, 2,4-dichloro-5-fluoropyrmidine and 6-amino-1-(methoxycarbonyl)methyl-indazoline were reacted to produce N2, N4-bis[1-(methoxycarbonyl)methyl-indazoline-6-yl]-5-fluoro-2,4-pyrimidinediamine. $^1$H NMR (DMSO-d6): δ 9.59 (s, 1H), 9.45 (s, 1H), 8.18 (d, 1H, J=3.5 Hz), 8.11 (s, 1H), 8.04 (s, 1H), 7.95 (s, 1H), 7.93 (s, 1H), 7.69 (d, 1H, J=8.8 Hz), 7.58 (d, 1H, J=8.8 Hz), 7.48 (dd, 1H, J=1.7 and 8.8 Hz), 7.32 (d, 1H, J=8.8 Hz), 5.17 (s, 2H), 4.88 (s, 1H), 3.58 (s, 3H), 3.58 (s, 3H). LCMS: ret. time: 17.80 min.; purity: 99%; MS (m/e): 505 (MH$^+$).

7.3.106 R935211: N2, N4-Bis[1-(methoxycarbonyl)methyl-indazoline-5-yl]-5-fluoro-2,4-pyrimidinediamine In like manner to the preparation of N4-(3,4-ethylenedioxyphenyl)-5-fluoro-N2-(3-hydroxyphenyl)-2,4-pyrimidinediamine, 2,4-dichloro-5-fluoropyrmidine and 6-amino-1-(methoxycarbonyl)methyl-indazoline was reacted to produce N2, N4-bis[1-(methoxycarbonyl)methyl-indazoline-6-yl]-5-fluoro-2,4-pyrimidinediamine. $^1$H NMR (DMSO-d6): δ 9.37 (s, 1H), 9.17 (s, 1H), 8.11-8.06 (m, 3H), 7.94 (s, 1H), 7.70 (s, 1H), 7.63 (s, 2H), 7.46 (s, 2H), 5.40 (s, 2H), 5.31 (s, 2H), 3.67 (s, 3H), 3.64 (s, 3H). LCMS: ret. time: 17.06 min.; purity: 96%; MS (m/e): 505 (MH$^+$).

7.3.107 R935188: N2,N4-Bis(indazolin-6-yl)-5-fluoro-2,4-pyrimidinediamine

In like manner to the preparation of 5-fluoro-N2, N4-bis(3-hydroxyphenyl)-2,4-pyrimidinediamine, 2,4-dichlro-5-fluoropyrimidine and 6-aminoindazoline were reacted to produce N2,N4-bis(indazolin-6-yl)-5-fluoro-2,4-pyrimidinediamine. $^1$H NMR (DMSO-d6): δ 9.80 (s, 1H), 9.65 (s, 1H), 8.20 (d, 1H, J=4.1 Hz), 8.01 (s, 1H), 7.96 (s, 1H), 7.93 (s, 1H), 7.89 (s, 1H), 7.69 (d, 1H, J=8.8 Hz), 7.57 (d, 1H, J=8.3 Hz), 7.54 (dd, 1H, J=1.7 and 8.8 Hz), 7.29 (dd, 1H, J=1.7 and 8.8 Hz); LCMS: ret. time: 15.17 min.; purity: 94%; MS (m/e): 361 (MH$^+$)

7.3.108 R935189: N2, N4-Bis(indazolin-5-yl)-5-fluoro-2,4-pyrimidinediamine

In like manner to the preparation of N2, N4-bis(3-hydroxyphenyl)-5-fluoro-2,4-pyrimidinediamine, 2,4-dichloro-5-fluoropyrimidine and 5-aminoindazole were reacted to produce N2, N4-bis(indazolin-5-yl)-5-fluoro-2,4-pyrimidinediamine. $^1$H NMR (DMSO-d6): δ 10.05 (s, 1H), 9.76 (s, 1H), 8.16 (d, 1H, J=4.7 Hz), 8.05 (s, 1H), 7.92 (s, 1H), 7.82 (s, 1H), 7.68 (s, 1H), 7.52-7.52 (m, 2H), 7.44 (d, 1H, J=8.8 Hz), 7.34 (dd, 1H, J=1.7 and 8.8 Hz); LCMS: ret. time: 14.33 min.; purity: 100%; MS (m/e): 361 (MH$^+$).

7.3.109 N2,N4-Bis(1-ethoxycarbonyl-2-methylpropyl)-5-cyano-2,4-pyrimidinediamine (R925814)

In a manner similar to the preparation of N2,N4-bis(3-hydroxyphenyl)-5-fluoro-2,4-pyrimidinediamine, 2,4-dichloro-5-cyanopyrimidine and valine ethyl ester were reacted to yield N2,N4-bis(1-ethoxycarbonyl-2-methylpropyl)-5-cyano-2,4-pyrimidinediamine. $^1$H NMR (CDCl$_3$): δ 8.15 (s, 1H), 6.10 (d, 1H, J=8.4 Hz), 5.67 (d, 1H, J=8.1 Hz), 4.66-4.62 (m, 1H), 4.50-4.46 (m, 1H), 4.25-4.13 (m, 4H), 2.27-2.14 (m, 2H), 1.31-1.24 (m, 6H), 1.00-0.94 (m, 12H); LCMS: ret. time: 30.41 min.; purity: 98%; MS (m/e): 392 (MH$^+$).

7.3.110 N2,N4-Bis(1-methoxycarbonyl-3-methylbutyl)-5-cyano-2,4-pyrimidinediamine (R925815)

In a manner similar to the preparation of N2,N4-bis(3-hydroxyphenyl)-5-fluoro-2,4-pyrimidinediamine, 2,4-dichloro-5-cyanopyrimidine and leucine methyl ester were reacted to yield N2,N4-bis(1-methoxycarbonyl-3-methylbutyl)-5-cyano-2,4-pyrimidinediamine. $^1$H NMR (CDCl$_3$): mixture of rotamers δ 8.15 (s, 1H), 6.10 and 5.49 (2d, 1H, J=8.1 Hz), 5.53 (d, 1H, J=8.4 Hz), 4.80-4.67 (m, 1H), 4.57-4.48 (m, 1H), 3.73 (s, 3H), 3.71 (s, 3H), 1.78-1.60 (m, 6H), 0.97-0.89 (m, 12H); LCMS: ret. time: 30.33 min.; purity: 91%; MS (m/e): 392 (MH$^+$).

7.3.111 N2,N4-Bis(methoxycarbonylbenzyl)-5-cyano-2,4-pyrimidinediamine (R925819)

In a manner similar to the preparation of N2,N4-bis(3-hydroxyphenyl)-5-fluoro-2,4-pyrimidinediamine, 2,4-dichloro-5-cyanopyrimidine and phenyl glycine methyl ester were reacted to yield N2,N4-bis(methoxycarbonylbenzyl)-5-cyano-2,4-pyrimidinediamine. $^1$H NMR (CDCl$_3$): mixture of rotamers δ 8.15 (s, 1H), 7.69-7.60 (m, 1H), 7.42-7.32 (m, 10H), 6.20 and 5.73 (2d, 1H, J=6.6 Hz), 6.14 and 5.65 (2d, 1H, J=6.3 Hz), 5.55 (d, 1H, J=6.3 Hz), 5.39 (t, 1H, J=7.2 Hz), 3.79 and 3.78 (2s, 3H), 3.67 and 3.65 (2s, 3H); LCMS: ret. time: 30.22 min.; purity: 91%; MS (m/e): 432 (MH$^+$).

7.3.112 N2,N4-Bis[4-(ethoxycarbonylmethyl)phenyl]-5-cyano-2,4-pyrimidinediamine (R926662)

In a manner similar to the preparation of N2,N4-bis(3-hydroxyphenyl)-5-fluoro-2,4-pyrimidinediamine, 2,4-dichloro-5-cyanopyrimidine and ethyl 4-aminophenylacetate were reacted to yield N2,N4-bis[4-(ethoxycarbonylmethyl)phenyl]-5-cyano-2,4-pyrimidinediamine. $^1$H NMR (CDCl$_3$): δ 8.29 (bs, 1H), 7.46 (2d, 4H, J=7.8 Hz), 7.28 (d, 2 h, J=8.1 Hz), 7.19 (d, 2H, J=8.1 Hz), 4.16 (2q, 4H, J=6.3 Hz), 3.64 (s, 2H), 3.59 (s, 2H), 1.30-1.23 (m, 6H); LCMS: ret. time: 29.29 min.; purity: 93%; MS (m/e): 461 (MH$^+$).

7.3.113 R935000: N2,N4-Bis(2-methoxy-5-phenylphenyl)-5-methyl-2,4-pyrimidinediamine In like manner to the preparation of 5-fluoro-N2,N4-bis(3-hydroxyphenyl)-2,4-pyrimidinediamine, 5-phenyl-2-anisidine and 2,4-dichloro-5-methylpyrimidine were reacted to provide N2,N4-bis(2-methoxy-5-phenylphenyl)-5-methyl-2,4-pyrimidinediamine. $^1$H NMR (CDCl$_3$+CD$_3$OD): δ 7.76 (d, 1H, J=2.3 Hz), 7.57 (s, 1H), 7.56 (s, 1H), 7.02-6.85 (m, 8H), 6.86-6.80 (m, 4H), 6.72 (d, 2H), 3.73 (s, 3H), 3.72 (s, 3H), 2.07 (s, 3H); LCMS: ret. time: 31.53 min.; purity: 97%; MS (m/e): 489 (MH$^+$).

7.3.114 R935001: N2,N4-Bis[(2-methyl-5-phenyl)phenyl]-5-methyl-2,4-pyrimidinediamine In like manner to the preparation of N2,N4-bis(3-hydroxyphenyl)-5-fluoro-2,4-pyrimidinediamine, 5-phenyl-2-toluidine and 2,4-dichloro-5-methylpyrimidine were reacted to produce N2,N4-bis[(2-methyl-5-phenyl)phenyl]-5-methyl-2,4-pyrimidinediamine. $^1$H NMR (CDCl$_3$): δ 7.59-7.55 (m, 1H), 7.45 (d, 2H, J=3.6 Hz), 7.26-7.17 (m, 6H), 7.09-6.98 (m, 8H), 2.36 (s, 3H), 2.22 (s, 3H), 2.21(s, 3H); LCMS: ret. time: 32.44 min.; purity: 90%; MS (m/e): 457 (MH$^+$).

7.3.115 R935002: N2,N4-Bis[(4-methoxy-3-phenyl)phenyl]-5-methyl-2,4-pyrimidinediamine In like manner to the preparation of N2,N4-bis(3-hydroxyphenyl)-5-fluoro-2,4-pyrimidinediamine, 3-phenyl-4-anisidine hydrochloride and 2,4-dichloro-5-methylpyrimidine with an added diisopropylethylamine were reacted to produce N2,N4-bis[(4-methoxy-3-phenyl)phenyl]-5-methyl-2,4-pyrimidinediamine. $^1$H NMR (CDCl$_3$): δ 8.15 (d, 1H, J=2.3 Hz), 7.76 (t, 1H, J=2.3 Hz), 7.71 (s, 1H), 7.59 (s, 1H), 7.16-7.03 (m, 8H), 6.98-6.81 (5H), 3.96 (s, 3H), 3.89 (s, 3H), 2.21 (s, 3H); LCMS: ret. time: 32.01 min.; purity: 90%; MS (m/e): 489 (MH$^+$).

7.3.116 R935003: N2,N4-Bis[(4-phenyl-2-methoxy-5-methyl)phenyl]-5-methyl-2,4-pyrimidinediamine In like manner to the preparation of N2,N4-bis(3-hydroxyphenyl)-5-fluoro-2,4-pyrimidinediamine, 5-methyl-4-phenyl-2-anisidine and 2,4-dichloro-5-methylpyrimidine were reacted to produce N2,N4-bis[(4-phenyl-2-methoxy-5-methyl)phenyl]-5-methyl-2,4-pyrimidinediamine. $^1$H NMR (CDCl$_3$): δ 9.25 (br s, 1H), 8.17 (s, 1H), 7.77 (t, 1H, J=6.4 Hz), 7.66 (s, 2H), 7.43-7.25 (m, 10H), 6.79 (s, 2H), 3.91 (s, 3H), 3.85 (s, 3H), 2.20 (s, 3H), 2.09 (s, 3H), 2.02 (s, 3H); LCMS: ret. time: 31.10 min.; purity: 100%; MS (m/e): 517 (MH$^+$).

7.3.117 R935004: N2,N4-Bis[[di-(4-methoxyphenyl)]methyl]-5-fluoro-2,4-pyrimidinediamine In like manner to the preparation of N2,N4-bis(3-hydroxyphenyl)-5-fluoro-2,4-pyrimidinediamine, 1,1-di(4-anisyl)methylamine and 2,4-dichloro-5-fluoropyrimidine were reacted to produce N2,N4-bis[[di-(4-methoxyphenyl)]methyl]-5-fluoro-2,4-pyrimidinediamine. $^1$H NMR (CDCl$_3$+ CD$_3$OD): δ 7.91 (d, 1H, J=2.3 Hz), 7.18 (d, 8H, J=9.0 Hz), 6.85 (d, 8H, J=9.0 Hz), 6.40 (d, 1H, J=8.2 Hz), 5.39 (d, 1H, J=7.1 Hz), 3.81 (s, 6H), 3.78 (s, 6H); LCMS: ret. time: 32.76 min.; purity: 95%; MS (m/e): 581 (MH$^+$).

7.3.118 R935005: N2,N4-Bis(diphenylmethyl)-5-fluoro-2,4-pyrimidinediamine

In like manner to the preparation of N2,N4-bis(3-hydroxyphenyl)-5-fluoro-2,4-pyrimidinediamine, 1,1-diphenyl methylamine and 2,4-dichloro-5-fluoropyrimidine were reacted to produce N2, N4-bis(diphenylmethyl)-5-fluoro-2,4-pyrimidinediamine. $^1$H NMR (CDCl$_3$): δ 7.91 (d, 1H, J=2.3 Hz), 7.39-7.25 (m, 20H), 6.51 (d, 1H, J=8.2 Hz), 5.77 (d, 1H, J=7.0 Hz); LCMS: ret. time: 33.46 min.; purity: 92%; MS (m/e): 461 (MH$^+$).

7.3.119 R935006: N2,N4-Bis[di-(4-chlorophenyl) methyl]-5-fluoro-2,4-pyrimidinediamine In like manner to the preparation of N2,N4-bis(3-hydroxyphenyl)-5-fluoro-2,4-pyrimidinediamine, benzhydrylamine and 2,4-dichloro-5-fluoropyrimidine were reacted to yield N2,N4-bis[di-(4-chlorophenyl)methyl]-5-fluoro-2,4-pyrimidinediamine. $^1$H NMR (CDCl$_3$+CD$_3$OD): δ 7.94 (d, 1H, J=2.3 Hz), 7.40-7.20 (m, 16H), 6.46 (d, 1H, J=8.2 Hz), 5.69 (d, 1H, J=7.0 Hz); LCMS: ret. time: 32.83 min.; purity: 90%; MS (m/e): 599 (MH$^+$).

7.3.120 R935016: N2,N4-Bis[1(R)-4-methoxyphenylethyl]-5-bromo-2,4-pyrimidineamine In like manner to the preparation of N2,N4-bis(3-hydroxyphenyl)-5-fluoro-2,4-pyrimidinediamine, (R)-(±)-1-(4-methoxyphenyl)ethylamine and 5-bromo-2,4-dichloropyrimidine were reacted to produce N2,N4-bis[1(R)-4-methoxyphenylethyl]-5-bromo-2,4-pyrimidineamine. $^1$H NMR (CDCl$_3$): δ 7.81 (s, 1H), 7.25 (d, 4H, J=8.4 Hz), 6.86 (app t, 4H, J=8.4 and 8.7 Hz), 5.27-5.20 m (2H), 5.09 (dq, 1H, J=6.4 and 7.0 Hz), 4.89 (dq, 1H, J=6.4 and 7.0 Hz), 3.80 (s, 3H), 3.79 (s, 3H), 1.40 (d, 6H, J=7.0 Hz).

7.3.121 R935075: N2, N4-Bis[3-(2-hydroxyethoxy) phenyl]-5-fluoro-2,4-pyrimidinediamine In like manner to the preparation of N2,N4-bis(3-hydroxyphenyl)-5-fluoro-2,4-pyrimidinediamine, 2,4-dichloro-5-fluoropyrimidine and 2-(3-aminophenoxy)ethanol were reacted to produce N2,N4-bis[3-(2-hydroxyethoxy)phenyl]-5-fluoro-2,4-pyrimidinediamine. $^1$H NMR (DMSO-d6): δ 9.50 (br s, 1H), 9.35 (br s, 1H), 8.13 (d, 1H, J=4.1 Hz), 7.44 (d, 1H, J=7.6 Hz), 7.26-7.19 (m, 4H), 7.10 (t, 1H, J=7.6 Hz), 6.65 (dd, 1H, J=2.3 and 8.2 Hz), 6.50 (dd, 1H, J=2.3 and 8.2 Hz), 5.0 (br s, 2H), 3.91 (t, 2H, J=5.2 Hz), 3.85 (t, 2H, J=5.2 Hz), 3.68 (qt, 2H, J=5.2 Hz), 3.66 (qt, 2H, J=5.2 Hz); LCMS: ret. time: 15.76 min.; purity: 97%; MS (m/e): 401 (MH$^+$).

7.3.122 R935076: N2,N4-Bis[3-(2-methoxyethyl) oxyphenyl]-5-fluoro-2,4-pyrimidinediamine In like manner to the preparation of N2,N4-bis(3-hydroxyphenyl)-5-fluoro-2,4-pyrimidinediamine, 2,4-dichloro-5-fluoropyrimidine and 3-(2-methoxyethoxy)aniline were reacted to produce N2,N4-bis[3-(2-methoxyethyl)oxyphenyl]-5-fluoro-2,4-pyrimidinediamine. $^1$H NMR (CDCl$_3$): δ 7.96 (d, 1H, J=2.9 Hz), 7.36 (t, 1H, J=1.7 Hz), 7.28 (t, 1H J=1.7 Hz), 7.25-7.06 (m, 4H), 6.98 (br s, 1H), 6.75 (d, 1H, J=2.3 Hz), 6.70 (dd, 1H, J=1.7 and 8.2 Hz), 6.58 (dd, 1H, J=1.7 and 8.2 Hz), 4.08-4.03 (m, 4H), 3.74-3.69 (m, 4H), 3.44 (s, 3H), 3.43 (s, 3H); LCMS: ret. time: 21.01 min.; purity: 97%; MS (m/e): 429 (MH$^+$).

7.3.123 R935077: N2,N4-Bis(5-hydroxy-2-isopropylphenyl)-5-fluoro-2,4-pyrimidinediamine In like manner to the preparation of N2,N4-bis(3-hydroxyphenyl)-5-fluoro-2,4-pyrimidinediamine, 3-amino-4-isopropylphenol and 2,4-dichloro-5-fluoropyrimidine were reacted to produce N2,N4-bis(5-hydroxy-2-isopropylphenyl)-5-fluoro-2,4-pyrimidinediamine. $^1$H NMR (CDCl$_3$): δ 7.93 (d, 1H, J=3.5 Hz), 7.79 (br s, 1H), 7.64 (br s, 1H), 7.13 (d, 1H, J=8.7 Hz), 7.06 (d, 1H, J=2.3 Hz), 7.05 (d, 1H, J=8.7 Hz), 6.89 (d, 1H, J=2.3 Hz), 6.66 (d, 1H, J=2.3 and 8.7 Hz), 6.57 (d, 1H, J=2.3 and 8.7 Hz), 2.96 (m, 2H), 1.25 (d, 6H, J=7.0 Hz), 1.13 (dd, 6H, J=7.0 Hz); LCMS: ret. time: 24.27 min.; purity: 97%; MS (m/e): 397 (MH$^+$).

7.3.124 R935114: N2,N4-Bis(3-methoxycarbonylmethylenephenyl)-5-fluoro-2,4-pyrimidinediamine In like manner to the preparation of N2,N4-bis(3-hydroxyphenyl)-5-fluoro-2,4-pyrimidinediamine, 2,4-dichloro-5-fluoropyrimidine and 3-(methoxycarbonylmethylene)aniline were reacted to produce the desired N2,N4-bis(3-methoxycarbonylmethylenephenyl)-5-fluoro-2,4-pyrimidinediamine. $^1$H NMR (DMSO-d6): δ 10.23 (br s, 1H), 10.05 (br s, 1H), 8.26 (d, 1H, J=4.6 Hz), 7.64 (d, 1H, J=8.2 Hz), 7.51 (br s, 1H), 7.46 (d, 1H, J=8.2 Hz), 7.33 (br s, 1H), 7.29 (t, 1H, J=7.6 Hz), 7.20 (t, 1H, J=7.6 Hz), 7.06 (d, 1H, J=7.6 Hz), 6.93 (d, 1H, J=7.6 Hz), 3.63 (s, 2H), 3.58 (s, 3H), 3.57 (s, 3H), 3.56 (s, 2H); LCMS: ret. time: 21.74 min.; purity: 92%; MS (m/e): 425 (MH$^+$).

7.3.125 R935162: N2, N4-Bis(3,4-propylenedioxyphenyl)-5-fluoro-2,4-pyrimidinediamine In like manner to the preparation of N2,N4-bis(3-hydroxyphenyl)-5-fluoro-2,4-pyrimidinediamine, 2,4-dichloro-5-fluoropyrimidine and (3,4-propylenedioxy)aniline were reacted to give N2,N4-bis(3,4-propylenedioxyphenyl)-5-fluoro-2,4-pyrimidinediamine. $^1$H NMR (DMSO-d6): δ 9.18 (s, 1H), 9.07 (s, 1H), 8.03 (d, 1H, J=3.5 Hz), 7.38 (dd, 1H, J=2.3 and 8.2 Hz), 7.35 (d, 1H, J=2.3 Hz), 7.33 (d, 1H, J=2.3 Hz), 7.18 (dd, 1H, J=2.3 and 8.8 Hz), 6.90 (d, 1H, J=8.8 Hz), 6.80 (d, 1H, J=8.2 Hz), 4.11-3.98 (m, 8H), 2.09-2.01 (m, 4H); LCMS: ret. time: 21.40 min.; purity: 97%; MS (m/e): 425 (MH$^+$).

7.3.126 R935163: N2,N4-Bis(3-chloro-4-fluoropheny)-2,4-pyrimidinediamine

In like manner to the preparation of N2,N4-bis(3-hydroxyphenyl)-5-fluoro-2,4-pyrimidinediamine, 2,4-dichloro-5-fluoropyrimidine and 3-chloro-4-fluoroaniline were reacted to produce N2, N4-bis(3-chloro-4-fluoropheny)-2,4-pyrimidinediamine. $^1$H NMR (DMSO-d6): δ 9.58 (s, 1H), 9.48 (s, 1H), 8.17 (d, 1H, J=4.1 Hz), 7.94-7.90 (m, 2H), 7.73-7.67 (m, 1H), 7.51-7.45 (m, 1H), 7.38 (t, 1H, J=8.8 Hz), 7.26 (t, 1H, J=8.8 Hz); LCMS: ret. time: 27.83 min.; purity: 99%; MS (m/e): 386 (MH$^+$).

7.3.127 N2,N4-Bis(3-hydroxyphenyl)-6-ethoxycarbonyl-5-nitro-2,4-pyrimidinediamine (R925849)

In a manner similar to the preparation of N2,N4-bis(3-hydroxyphenyl)-5-fluoro-2,4-pyrimidinediamine, 2,4-dichloro-6-ethoxycarbonyl-5-nitropyrimidine and 3-aminophenol were reacted to yield N2,N4-bis(3-hydroxyphenyl)-6-ethoxycarbonyl-5-nitro-2,4-pyrimidinediamine. $^1$H NMR (DMSO-d6): δ 10.56 (bs, 1H), 10.32 (bs, 1H), 9.54 (s, 1H), 9.32 (bs, 1H), 7.22-7.15 (m, 2H), 7.02-6.96 (m, 1H), 6.93-6.82 (m, 2H), 6.81-6.74 (m, 1H), 6.67 (d, 1H, J=9.3 Hz), 6.43 (d, 1H, J=8.1 Hz), 4.35 (q, 2H, J=6.9 Hz), 1.30 (t, 3H, J=6.9 Hz); LCMS: ret. time: 26.01 min.; purity: 96%; MS (m/e): 412 (MH$^+$).

7.3.128 N2,N4-Bis(3,4-ethylendioxyphenyl)-6-ethoxycarbonyl-5-nitro-2,4-pyrimidinediamine (R925852)

In a manner similar to the preparation of N2,N4-bis(3-hydroxyphenyl)-5-fluoro-2,4-pyrimidinediamine, 2,4-dichloro-6-ethoxycarbonyl-5-nitropyrimidine and 3,4-ethylenedioxyaniline were reacted to yield N2,N4-bis(3,4-ethylendioxyphenyl)-6-ethoxycarbonyl-5-nitro-2,4-pyrimidinediamine. $^1$H NMR (DMSO-d6): δ 10.52 (s, 1H), 10.28 (s, 1H), 7.07-7.01 (m, 2H), 6.96 (dd, 1H, J=1.8 and 8.7 Hz), 6.90-6.84 (m, 2H), 6.61 (d, 1H, J=8.7 Hz), 4.33 (q, 2H, J=6.9 Hz), 4.24 (s, 4H), 4.17 (s, 4H), 1.29 (t, 3H, J=6.9 Hz); LCMS: ret. time: 30.40 min.; purity: 100%; MS (m/e): 496 (MH$^+$).

7.3.129 N2,N4-Bis(ethoxycarbonylmethyl)-6-ethoxycarbonyl-5-nitro-2,4-pyrimidinediamine (R925864)

In a manner similar to the preparation of N2,N4-bis(3-hydroxyphenyl)-5-fluoro-2,4-pyrimidinediamine, with the addition of triethylamine, 2,4-dichloro-6-ethoxycarbonyl-5-nitropyrimidine and glycine ethyl ester hydrochloride were reacted to yield N2,N4-bis(ethoxycarbonylmethyl)-6-ethoxycarbonyl-5-nitro-2,4-pyrimidinediamine. $^1$H NMR (CDCl$_3$): mixture of rotamers δ 8.99 and 8.80 (2bs, 1H), 6.22 and 6.00 (2bs, 1H), 4.45 (t, 2H, J=7.2 Hz), 4.31-4.21 (m, 6H), 4.14 (d, 2H, J=5.1 Hz), 1.39 (t, 3H, J=7.2 Hz), 1.34-1.28 (m, 6H); LCMS: ret. time: 26.06 min.; purity: 99%; MS (m/e): 400 (MH$^+$).

7.3.130 N2,N4-Bis[2-(4-hydroxyphenyl)ethyl]-2,4-pyrimidinediamine (R925790)

In a manner similar to the preparation of N2,N4-bis(3-hydroxyphenyl)-5-fluoro-2,4-pyrimidinediamine, 2,4-dichloropyrimidine and tyramine were reacted to yield N2,N4-bis[2-(4-hydroxyphenyl)ethyl]-2,4-pyrimidinediamine. $^1$H NMR (DMSO-d6): δ 11.56 (bs, 1H), 9.23 (s, 1H), 8.89 (bs, 1H), 7.92 (bs, 1H), 7.60 (d, 1H, J=6.9 Hz), 6.99 (d, 4H, J=8.1 Hz), 6.65 (d, 4H, J=8.1 Hz), 6.00 (d, 1H, J=7.2 Hz), 3.59-3.42 (m, 4H), 2.76-2.67 (m, 4H); LCMS: ret. time: 17.93 min.; purity: 95%; MS (m/e): 351 (MH$^+$).

7.3.131 N2,N4-Bis(2-phenylphenyl)-2,4-pyrimidinediamine (R925804)

In a manner similar to the preparation of N2,N4-bis(3-hydroxyphenyl)-5-fluoro-2,4-pyrimidinediamine, 2,4-dichloropyrimidine and 2-aminobiphenyl were reacted to yield N2,N4-bis(2-phenylphenyl)-2,4-pyrimidinediamine. $^1$H NMR (CDCl$_3$): δ 8.36 (d, 1H, J=8.1 Hz), 7.97 (d, 1H, J=5.7 Hz), 7.80 (d, 1H, J=7.5 Hz), 7.50-7.21 (m, 15H), 7.12-7.05 (m, 1H), 6.91 (bs, 1H), 6.38 (bs, 1H), 6.07 (d, 1H, J=6.0 Hz); LCMS: ret. time: 29.94 min.; purity: 100%; MS (m/e): 415 (MH$^+$).

7.3.132 N2,N4-Bis(2-methoxy-5-phenylphenyl)-2,4-pyrimidinediamine (R925805)

In a manner similar to the preparation of N2,N4-bis(3-hydroxyphenyl)-5-fluoro-2,4-pyrimidinediamine, 2,4-dichloropyrimidine and 5-phenyl-ortho-anisidine were reacted to yield N2,N4-bis(2-methoxy-5-phenylphenyl)-2,4-pyrimidinediamine. $^1$H NMR (CD$_3$OD): δ 7.88-7.84 (m, 2H), 7.82 (d, 1H, J=6.9 Hz), 7.30-7.14 (m, 14H), 7.10 (dd, 2H, J=3.0 and 8.1 Hz), 6.48 (d, 1H, J=6.9 Hz), 3.93 (s, 3H), 3.92 (s, 3H); LCMS: ret. time: 30.09 min.; purity: 94%; MS (m/e): 476 (MH$^+$).

7.3.133 N2,N4-Bis(3-carboxy-4-hydroxyphenyl)-5-fluoro-2,4-pyrimidinediamine (R945041)

In a manner analogous to the preparation of N2,N4-bis(3-hydroxyphenyl)-5-fluoro-2,4-pyrimidinediamine, from 5-amino-2-hydroxybenzoic acid (458 mg, 3 mmol) and 2,4-dichloro-5-fluoropyrimidine (100 mg, 0.6 mmol) gave N2,N4-bis(3-carboxy-4-hydroxyphenyl)-5-fluoro-2,4-pyrimidinediamine (235 mg, 98%). $^1$H NMR (DMSO-d6): δ 6.76 (d, J=9.0 Hz, 1H), 6.88 (d, J=9.6 Hz, 1H), 7.75 (dd, J=3.0, 9.0 Hz, 1H), 7.90-7.94 (m, 3H), 8.02 (d, J=3.9 Hz, 1H), 9.04 (s, 1H, NH), 9.28 (s, 1H, NH); $^{19}$F NMR (282 MHz, DMSO-d6): δ -165.79; LC: 16.02 min, 86.82%; MS (m/z): 400.94 (MH$^+$).

7.3.134 N2,N4-Bis(4-methoxy-3-phenylphenyl)-2,4-pyrimidinediamine (R925806)

In a manner similar to the preparation of N2,N4-bis(3-hydroxyphenyl)-5-fluoro-2,4-pyrimidinediamine, with the addition of triethylamine, 2,4-dichloropyrimidine and 3-phenyl-para-anisidine hydrochloride were reacted to yield N2,N4-bis(4-methoxy-3-phenylphenyl)-2,4-pyrimidinediamine. $^1$H NMR (CD$_3$OD): δ 7.93 (d, 1H, J=2.4 Hz), 7.88 (d, 1H, J=2.4 Hz), 7.29 (dd, 1H, J=1.8 and 9.0 Hz), 7.26-7.18 (m, 13H), 7.10 (d, 2H, J=8.7 Hz), 6.46 (d, 1H, J=7.2 Hz), 3.93 (s, 3H), 3.92 (s, 3H); LCMS: ret. time: 29.99 min.; purity: 92%; MS (m/e): 476 (MH$^+$).

7.3.135 N2,N4-Bis(2-methyl-5-phenylphenyl)-2,4-pyrimidinediamine (R925807)

In a manner similar to the preparation of N2,N4-bis(3-hydroxyphenyl)-5-fluoro-2,4-pyrimidinediamine, 2,4-dichloropyrimidine and 5-phenyl-ortho-toluidine were reacted to yield N2,N4-bis(2-methyl-5-phenylphenyl)-2,4-pyrimidinediamine. $^1$H NMR (DMSO-d6): δ 10.45 (bs, 1H), 10.01 (bs, 1H), 7.86 (bs, 1H), 7.69-7.22 (m, 17H), 2.28 (s, 6H); LCMS: ret. time: 18.69 min.; purity: 98%; MS (m/e): 443 (MH$^+$).

7.3.136 N2,N4-Bis(2-methoxy-5-methyl-4-phenylphenyl)-2,4-pyrimidinediamine (R925808)

In a manner similar to the preparation of N2,N4-bis(3-hydroxyphenyl)-5-fluoro-2,4-pyrimidinediamine, 2,4-dichloropyrimidine and 5-methyl-4-phenyl-ortho-anisidine were reacted to yield N2,N4-bis(2-methoxy-5-methyl-4-phenylphenyl)-2,4-pyrimidinediamine. $^1$H NMR (DMSO-d6): δ 9.99 (bs, 1H), 9.22 (bs, 1H), 7.98 (d, 1H, J=6.3 Hz), 7.75 (s, 1H), 7.59 (s, 1H), 7.46-7.29 (m, 10H), 6.92 (s, 1H), 6.87 (s, 1H), 6.49 (d, 1H, J=5.4 Hz), 3.82 (s, 3H), 3.81 (s, 3H), 2.07 (s, 3H), 1.98 (s, 3H); LCMS: ret. time: 19.69 min.; purity: 93%; MS (m/e): 503 (MH$^+$).

7.3.137 N2,N4-Bis[4-(ethoxycarbonylmethyleneoxy)phenyl]-5-trifluoromethyl-2,4-pyrimidinediamine (R925862)

In a manner similar to the preparation of N2,N4-bis(3-hydroxyphenyl)-5-fluoro-2,4-pyrimidinediamine, 2,4-dichloro-5-trifluoromethylpyrimidine and ethyl 4-aminophenoxyacetate were reacted to yield N2,N4-bis[4-(ethoxycarbonylmethyleneoxy)phenyl]-5-trifluoromethyl-2,4-pyrimidinediamine. $^1$H NMR (DMSO-d6): δ 9.64 (bs, 1H), 8.80 (bs, 1H), 8.29 (s, 1H), 7.36 (d, 2H, J=8.1 Hz), 7.31 (d, 2H, J=9.3 Hz), 6.93 (d, 2H, J=8.7 Hz), 6.70 (d, 2H, J=9.0 Hz), 4.80 (s, 2H), 4.67 (s, 2H), 4.18 (q, 2H, J=6.9 Hz), 4.15 (q, 2H, J=6.9 Hz), 1.20 (t, 3H, J=6.9 Hz), 1.19 (t, 3H, J=6.9 Hz); $^{19}$F NMR (DMSO-d6): −16932; LCMS: ret. time: 26.33 min.; purity: 98%; MS (m/e): 535 (MH$^+$)

7.3.138 N2,N4-Bis(3-hydroxyphenyl)-5-trifluoromethyl-2,4-pyrimidinediamine (R925863)

In a manner similar to the preparation of N2,N4-bis(3-hydroxyphenyl)-5-fluoro-2,4-pyrimidinediamine, 2,4-dichloro-5-trifluoromethylpyrimidine and 3-aminophenol were reacted to yield N2,N4-bis(3-hydroxyphenyl)-5-trifluoromethyl-2,4-pyrimidinediamine. $^1$H NMR (DMSO-d6): δ 9.82 (bs, 1H), 8.88 (bs, 1H), 8.36 (s, 1H), 7.18-7.11 (m, 2H), 6.96 (m, 4H), 6.63 (dd, 1H, J=2.4 and 8.1 Hz), 6.38 (d, 1H, J=8.1 Hz); $^{19}$F NMR (DMSO-d6): −16979; LCMS: ret. time: 19.04 min.; purity: 95%; MS (m/e): 363 (MH$^+$).

7.3.139 N2,N4-Bis[4-(ethoxycarbonylmethyl)phenyl]-5-trifluoromethyl-2,4-pyrimidinediamine (R926663)

In a manner similar to the preparation of N2,N4-bis(3-hydroxyphenyl)-5-fluoro-2,4-pyrimidinediamine, 2,4-dichloro-5-trifluoromethylpyrimidine and ethyl 4-aminophenylacetate were reacted to yield N2,N4-bis[4-(ethoxycarbonylmethyl)phenyl]-5-trifluoromethyl-2,4-pyrimidinediamine. $^1$H NMR (CDCl$_3$): δ 8.31 (s, 1H), 7.46 (d, 2H, J=9.0 Hz), 7.45 (d, 2H, J=8.7 Hz), 7.30 (d, 2H, J=9.0 Hz), 7.18 (d, 2H, J=8.7 Hz), 7.16 (bs, 1H), 6.82 (bs, 1H), 4.16 (2q, 4H, J=7.8 Hz), 3.64 (s, 2H), 3.57 (s, 2H), 1.27 (t, 3H, J=7.8 Hz), 1.26 (t, 3H, J=7.8 Hz); $^{19}$F NMR (CDCl$_3$): −17223; LCMS: ret. time: 28.07 min.; purity: 99%; MS (m/e): 504 (MH$^+$).

7.3.140 N2,N4-Bis(2,5-dimethyl-4-hydroxyphenyl)-5-fluoro-2,4-pyrimidinediamine (R926623)

In like manner to the preparation of N2,N4-bis(3-hydroxyphenyl)-5-fluoro-2,4-pyrimidinediamine, 2,4-dichloro-5-fluoropyrimidine and 2,5-dimethyl-4-hydroxyaniline were reacted to yield N2,N4-bis(2,5-dimethyl-4-hydroxyphenyl)-5-fluoro-2,4-pyrimidinediamine. $^1$H NMR (CD$_3$OD): δ 7.63 (d, 1H, J=4.2 Hz), 7.05 (s, 1H), 6.97 (s, 1H), 6.64 (1H), 6.54 (s, 1H), 2.12 (s, 6H), 2.06 (s, 3H), 2.03 (s, 3H), 2.03 (s, 3H); $^{19}$F NMR (CD$_3$OD): −48488; LCMS: ret. time: 18.28; purity; 94%; MS (m/e): 369 (MH$^+$).

7.3.141 N2,N4-Bis(3-sodiumphenoxy)-5-fluoro-2,4-pyrimidinediamine (R926461)

The reaction of N2,N4-bis(3-hydroxyphenyl)-5-fluoro-2,4-pyrimidinediamine with 2 equivalents of sodium methoxide in methanol followed by removal of solvent gave the requisite compound, N2,N4-bis(3-sodiumphenoxy)-5-fluoro-2,4-pyrimidinediamine. $^1$H NMR (D$_2$O): δ 7.65 (bd, 1H), 7.00-6.90 (m, 2H), 6.71 (m, 2H), 6.55 (dd, 1H, J=1.2 and 6.3 Hz), 6.31 (bd, 1H, J=8.1 Hz), 6.23 (bd, 1H, J=8.7 Hz); $^{19}$F NMR (D$_2$O): −47016; LCMS: ret. time: 15.68 min.; purity: 99%; MS (m/e): 313 (MH$^+$).

7.3.142 N2,N4-Bis(3-cyanophenyl)-5-fluoro-2,4-pyrimidinediamine (R945051)

In a manner analogous to the preparation of N2,N4-bis(3-hydroxyphenyl)-5-fluoro-2,4-pyrimidinediamine, 3-aminobenzonitrile (177 mg, 1.5 mmol) and 2,4-dichloro-5-fluoropyrimidine (50 mg, 0.3 mmol) gave N2,N4-bis(3-cyanophenyl)-5-fluoro-2,4-pyrimidinediamine (75 mg, 76%). $^1$H NMR (acetone-d$_6$): δ 7.33 (dt, J=1.8, 7.8 Hz, 1H), 7.46-7.52 (m, 2H), 7.59 (t, J=7.8 Hz, 1H), 7.90 (ddd, J=0.9, 2.1 and 8.4 Hz, 1H), 8.09 (ddd, J=1.2, 2.4 and 8.4 Hz, 1H), 8.17 (d, J=3.3 Hz, 1H), 8.31 (m, 1H), 8.35 (t, J=2.1 Hz, 1H), 8.98 (br, 1H, NH), 9.02 (br, 1H, NH); $^{19}$F NMR (282 MHz, acetone-d$_6$): 6-165.80; LCMS: 24.64 min.; purity: 98.02%; MS (m/e): 331.01 (MH$^+$).

7.3.143 N2,N4-Bis(benzothiophen-3-ylmethyl)-5-fluoro-2,4-pyrimidinediamine (R945145)

Using procedure similar to the preparation of N2,N4-bis(3-hydroxyphenyl)-5-fluoro-2,4-pyrimidinediamine, benzothiophen-3-ylmethylamine and 2,4-dichloro-5-fluoropyrimidine gave N2,N4-bis(benzothiophen-3-ylmethyl)-5-fluoro-2,4-pyrimidinediamine. $^1$H NMR (CDCl$_3$): δ 4.82 (dd, J=0.9 and 5.7 Hz, 2H), 4.86 (dd, J=0.9 and 5.7 Hz, 2H), 5.14 (br, 2H), 7.31-7.40 (m, 6H), 7.75-7.89 (m, 5H); $^{19}$F NMR (282 MHz, CDCl$_3$): 6-172.12; LCMS: 27.79 min.; purity: 96.47%; MS (m/e): 420.92 (MH$^+$).

7.3.144 N2,N4-Bis[4-(N-benzylpiperazino)phenyl]-5-fluoro-2,4-pyrimidinediamine (R945152)

In a manner analogous to the preparation of N2,N4-bis(3-hydroxyphenyl)-5-fluoro-2,4-pyrimidinediamine, the reaction of 4-(N-benzylpiperazino)aniline (400 mg, 1.5 mmol) and 2,4-dichloro-5-fluoropyrimidine (50 mg, 0.3 mmol) resulted N2,N4-bis[4-(N-benzylpiperazino)phenyl]-5-fluoro-2,4-pyrimidinediamine (120 mg, 64%). $^1$H NMR (CDCl$_3$): δ 2.63 (p, J=2.4 Hz, 8H), 3.14 (t, J=4.8 Hz, 4H), 3.19 (t, J=4.8 Hz, 4H), 3.58 (s, 4H), 6.58 (d, 1H, NH), 6.67 (br, 1H, NH), 6.87 (d, J=9.3 Hz, 2H), 6.90 (d, J=9.0 Hz, 2H), 7.33-7.39 (m, 12H), 7.46 (d, J=9.0 Hz, 2H), 7.87 (d, J=3.3 Hz, 1H); $^{19}$F NMR (282 MHz, CDCl$_3$): 6-169.06; LCMS: 16.82 min.; purity: 96.88%; MS (m/e): 629.12 (MH$^+$).

7.3.145 N2,N4-Bis(3-hydroxy-2-methylphenyl)-5-fluoro-2,4-pyrimidinediamine (R945038)

In a manner analogous to the preparation of N2,N4-bis(3-hydroxyphenyl)-5-fluoro-2,4-pyrimidinediamine, the reaction of 3-hydroxy-2-methylaniline (369 mg, 3 mmol) and 2,4-dichloro-5-fluoropyrimidine (100 mg, 0.6 mmol) gave N2,N4-bis(3-hydroxy-2-methylphenyl)-5-fluoro-2,4-pyrimidinediamine (180 mg, 88%). $^1$H NMR (acetone-d$_6$): δ 2.14

(s, 3H), 2.22 (s, 3H), 6.61 (d, J=8.1 Hz, 1H), 6.78 (t, J=8.7 Hz, 1H), 6.87 (d, J=7.8 Hz, 1H), 6.99 (d, J=9.0 Hz, 1H), 7.08 (t, J=7.8 Hz, 1H), 7.13 (dd, J=3.9, 8.4 Hz, 1H), 8.24 (d, J=5.1 Hz, 1H), 8.32 (br, 1H, NH), 8.57 (br, 1H, NH); LCMS: ret. time: 16.51 min.; purity: 90.47%; MS (m/e): 341.07 (MH$^+$).

7.3.146 N2,N4-Bis(3-nitrophenyl)-5-fluoro-2,4-pyrimidinediamine (R950160)

2,4-Dichloro-5-fluoropyrimidine (4.7 g, 28.1 mmol) was dissolved in a mixture of MeOH (150 ml) and $H_2O$ (15 ml). 3-nitroaniline (15.5 g, 112 mmol) was added and the mixture was refluxed for 20 hours (100° C. oil-bath temperature). The mixture was cooled to 22° C. and filtered. The residue was washed carefully with 200 ml MeOH—$H_2O$ (1:1; v/v) and dried under vacuum to give 7.89 g (76%) of N2,N4-bis(3-nitrophenyl)-5-fluoro-2,4-pyrimidinediamine as yellow crystals. $^1$H NMR (DMSO-d6+$D_2O$): δ 8.63 (m, 2H), 8.21 (m, 1H), 8.08 (d, 1H, J=8.41 Hz), 7.88 (d, 1H, J=8.4 Hz), 7.79 (d, 1H, J=8.4 Hz), 7.70 (d, 1H, J=8.4 Hz), 7.57 (d, 1H, J=8.4 Hz), 7.45 (t, 1H, J=8.4 Hz); LCMS: purity: 100%; MS (m/e): 371.30 (M$^+$, 100).

7.3.147 N2,N4-Bis(3-aminophenyl)-5-fluoro-2,4-pyrimidinediamine (R921302)

N2,N4-Bis(3-nitrophenyl)-5-fluoro-2,4-pyrimidinediamine (4.0 g, 10.8 mmol) and Pd/C10% (1.2 g, 50% water content) were suspended in 300 ml EtOH-10% aqueous HCl (1:1) and hydrogenated in a Parr apparatus for 6 hours (22° C., 50 psi). The suspension was filtered over celite and carefully washed with 20 ml DMF-$H_2O$ (1:1; v/v) followed by 50 ml $H_2O$. The combined filtrates were concentrated under reduced pressure to give pale yellow oil, which was triturated with MeOH to give the product as fine white needles. The precipitate was filtered off and washed with MeOH followed by $Et_2O$. The remaining crystals were dried under vacuum to give 4.00 g of pure material (100%) as determined by LCMS. The free amine was obtained by adding 10 ml 1 N NaOH to a solution of Ig HCl-salt in 5 ml $H_2O$. The resulting precipitate was filtered, washed with $H_2O$ and dried under vacuum for 24 hours to give N2,N4-bis(3-aminophenyl)-5-fluoro-2,4-pyrimidinediamine (770 mg) as a white solid. $^1$H NMR (CD$_3$OD): δ 7.92 (d, 1H, J=3.6 Hz), 7.31 (t, 1H, J=2.1 Hz), 7.21 (t, 1H, J=2.4 Hz), 7.08, (t, 1H, J=8.1 Hz), 6.99 (t, 1H, J=8.1 Hz), 6.88 (m, 1H), 6.77 (m, 1H), 6.47 (m, 1H), 6.34 (m, 1H); LCMS: purity: 100%; MS (m/e): 311.07 (M$^+$, 100).

7.3.148 N2,N4-Bis(4-aminophenyl)-5-fluoro-2,4-pyrimidinediamine (R950122)

In like manner to the preparation of N2,N4-bis(3-nitrophenyl)-5-fluoro-2,4-pyrimidinediamine, 2,4-dichloro-5-fluoropyrimidine and 1,4-diaminobenzene were reacted to prepare N2,N4-bis(4-aminophenyl)-5-fluoro-2,4-pyrimidinediamine. LCMS: ret. time: 11.15 min.; purity: 100%; MS (m/e): 311.09 (MH$^+$).

7.3.149 N2,N4-Bis[3-(dimethylamino)phenyl]-5-fluoro-2,4-pyrimidinediamine (R950182)

2,4-Dichloro-5-fluoropyrimidine (50 mg, 0.30 mmol) was dissolved in a mixture of MeOH (0.3 ml) and $H_2O$ (0.03 ml). N,N-3-dimethyldiaminoaniline (163 mg, 1.2 mmol) was added and the mixture was refluxed for 24 hours (70° C. oil-bath temperature). The mixture was cooled to 22° C., concentrated to dryness under reduced pressure and subjected to column chromatography on silica gel (CHCl$_3$-Acetone, 2:1) to give N2,N4-bis[3-(dimethylamino)phenyl]-5-fluoro-2,4-pyrimidinediamine. LCMS purity: 99.0%; MS (m/e): 367.13 (M$^+$, 100).

7.3.150 N2,N4-Bis(3-amino-4-methylphenyl)-2,4-pyrimidinediamine (R950130)

2,4-Dichloropyrimidine (45 mg, 0.30 mmol) was dissolved in a mixture of MeOH (1 ml) and $H_2O$ (0.1 ml). 3-amino-4-methylaniline (146 mg, 1.2 mmol) was added and the mixture was refluxed for 20 hours (70° C. oil-bath temperature). The mixture was cooled to 22° C., concentrated to dryness under reduced pressure and subjected to column chromatography on silica gel (CHCl$_3$-Acetone, 2:1) to give N2,N4-bis(3-amino-4-methylphenyl)-2,4-pyrimidinediamine. $^1$H NMR (CD$_3$OD): δ 8.13 (s, 1H), 6.95 (d, 2H, J=7.5 Hz), 6.82 (d, 2H, J=1.8 Hz), 6.60 (dd, 2H, J=1.8, 7.5 Hz), 6.17 (s, 1H), 2.12 (s, 6H); LCMS purity: 97.3%; MS (m/e): 321.09 (M$^+$, 100).

7.3.151 N2,N4-Bis(3-amino-4-methylphenyl)-5-fluoro-2,4-pyrimidinediamine (R950129)

2,4-Dichloro-5-fluoropyrimidine (50 mg, 0.30 mmol) was dissolved in a mixture of MeOH (1 ml) and $H_2O$ (0.1 ml). 3-amino-4-methylaniline (146 mg, 1.2 mmol) was added and the mixture was refluxed for 20 hours (70° C. oil-bath temperature). The mixture was cooled to 22° C., concentrated to dryness under reduced pressure and subjected to column chromatography on silica gel (CHCl$_3$-Acetone, 2:1) to give N2,N4-bis(3-amino-4-methylphenyl)-5-fluoro-2,4-pyrimidinediamine. $^1$H NMR (CD$_3$OD): δ 8.11 (d, 1H, J=5.1 Hz), 7.98 (bs, 1H) (7.68 (dd, 1H, J=2.4, 8.1 Hz), 7.40-7.55 (m, 4H), 2.43 (s, 3H), 2.42 (s, 3H); LCMS: purity: 95.0%; MS (m/e): 338.66 (M$^+$, 70).

7.3.152 N2,N4-Bis[(4-methylsulfonylamino)phenyl]-5-fluoro-2,4-pyrimidinediamine (R950083)

2,4-Dichloro-5-fluoropyrimidine (50 mg, 0.30 mmol) was dissolved in a mixture of MeOH (1 ml) and $H_2O$ (0.1 ml). 4-methylsulfonylaminoaniline (335 mg, 1.8 mmol) was added and the mixture was refluxed for 24 hours (100° C. oil-bath temperature). The mixture was cooled to 22° C. and filtered. The residue was washed carefully with MeOH—$H_2O$ (1:1) and dried under vacuum to give N2,N4-bis[(4-methylsulfonylamino)phenyl]-5-fluoro-2,4-pyrimidinediamine. $^1$H NMR (CDCl$_3$): δ 8.86 (s, 1H), 8.65 (s, 1H), 8.53 (bs, 1H), 8.39 (bs, 1H), 7.32 (d, 1H, J=3.3 Hz), 7.12 (d, 1H, J=8.7 Hz), 6.98 (d, 1H, J=8.7 Hz), 6.62 (d, 1H, J=8.7 Hz), 6.52 (d, 1H, J=8.7 Hz), 2.32 (s, 3H), 2.27 (s, 3H); LCMS: purity: 96.8%; MS (m/e): 466.94 (M$^+$, 100).

7.3.153 N2,N4-Bis(4-benzyloxy-3-trifluoromethylphenyl)-5-fluoro-2,4-pyrimidinediamine (R950090)

2,4-Dichloro-5-fluoropyrimidine (50 mg, 0.30 mmol) was dissolved in a mixture of MeOH (1 ml) and $H_2O$ (0.1 ml). 4-benzyloxy-3-trifluoromethylaniline (481 mg, 1.8 mmol) was added and the mixture was refluxed for 2 days (70° C. oil-bath temperature). The mixture was cooled to 22° C., concentrated to dryness under reduced pressure and subjected to column chromatography on silica gel (CHCl$_3$-Acetone, 9:1) to give N2,N4-bis(4-benzyloxy-3-trifluoromethylphenyl)-5-fluoro-2,4-pyrimidinediamine. $^1$H NMR (CDCl$_3$): δ 8.51 (s, 1H), 8.05 (s, 1H), 7.38-7.64 (m, 5H), 6.94-7.14 (m, 11H), 6.44-6.73 (m, 4H), 4.84 (s, 2H), 4.79 (s, 2H); LCMS purity: 94.7%; MS (m/e): 628.93 (M$^+$, 100).

7.3.154 N2,N4-Bis(3-cyano-4-hydroxyphenyl)-5-fluoro-2,4-pyrimidinediamine (R950092)

2,4-Dichloro-5-fluoropyrimidine (50 mg, 0.30 mmol) was dissolved in a mixture of MeOH (1 ml) and H$_2$O (0.1 ml). 3-cyano-4-hydroxyaniline (241 mg, 1.8 mmol) was added and the mixture was refluxed for 2 days (70° C. oil-bath temperature). The mixture was cooled to 22° C., concentrated to dryness under reduced pressure and subjected to column chromatography on silica gel (CHCl$_3$-Acetone, 9:1) to give N2,N4-bis(4-hydroxy-3-cyanophenyl)-5-fluoro-2,4-pyrimidinediamine. $^1$H NMR (CDCl$_3$): δ 7.96 (d, 1H, J=3.5 Hz), 7.82 (d, 1H, J=3.0 Hz), 7.79 (d, 1H, J=3.0 Hz), 7.71 (dd, 1H, J=3.0, 8.8 Hz), 7.54 (dd, J=3.0, 8.8 Hz), 6.94 (d, 1H, J=8.8 Hz), 6.84 (d, 1H, J=8.8 Hz); LCMS: purity: 97.2%; MS (m/e): 362.98 (M$^+$, 100).

7.3.155 N2,N4-Bis[3-methylsulfonylamino)phenyl]-5-fluoro-2,4-pyrimidinediamine (R950100)

2,4-Dichloro-5-fluoropyrimidine (50 mg, 0.3 mmol) was dissolved in a mixture of MeOH (1 ml) and H$_2$O (0.1 ml). 3-methylsulfonylaminoaniline (300 mg, 1.5 mmol) was added and the mixture was refluxed for 24 hours (70° C. oil-bath temperature). The mixture was cooled to 22° C., concentrated to dryness under reduced pressure and subjected to column chromatography on silica gel (CHCl$_3$-Acetone, 9:1) to give N2,N4-bis[3-methylsulfonylamino)phenyl]-5-fluoro-2,4-pyrimidinediamine. $^1$H NMR (DMSO-d6+CD$_3$OD): δ 8.01 (d, 1H, J=3.5 Hz), 7.46-7.68 (m, 4H), 7.49 (t, 1H, J=8.2 Hz), 7.13 (t, 1H, J=8.2 Hz), 6.89 (dd, 1H, J=2.4, 8.2 Hz), 6.72 (m, 1H), 2.95 (s, 3H), 2.91 (s, 3H); LCMS: purity: 97.2%; MS (m/e): 466.89 (M$^+$, 100).

7.3.156 N2,N4-Bis[3-(tert-butoxycarbonylamino)phenyl]-5-fluoro-2,4-pyrimidinediamine (R950108)

2,4-Dichloro-5-fluoropyrimidine (75 mg, 0.45 mmol) was dissolved in a mixture of MeOH (2 ml) and H$_2$O (0.2 ml). 3-tert-butoxycarbonylaminoaniline (374 mg, 1.8 mmol) was added and the mixture was refluxed for 40 hours (70° C. oil-bath temperature). The mixture was cooled to 22° C., concentrated to dryness under reduced pressure and subjected to column chromatography on silica gel (CHCl$_3$-Acetone, 9:1) to give N2,N4-bis[3-(tert-butoxycarbonylamino)phenyl]-5-fluoro-2,4-pyrimidinediamine. $^1$H NMR (DMSO-d6+CD$_3$OD): δ 7.96 (d, 1H, J=4.1 Hz), 7.83 (m, 1H), 7.60 (m, 1H), 7.34-7.42 (m, 2H), 7.15-7.19 (m, 2H), 7.06 (t, 1H, J=8.2 Hz), 6.93 (d, 1H, J=8.2 Hz), 1.43 (s, 9H), 1.40 (s, 9H); LCMS: purity: 93.2%; MS (m/e): 511.06 (M$^+$, 100).

7.3.157 N2,N4-Bis[4-(tert-butoxycarbonylamino)phenyl]-5-fluoro-2,4-pyrimidinediamine (R950120)

2,4-Dichloro-5-fluoropyrimidine (75 mg, 0.45 mmol) was dissolved in a mixture of MeOH (2 ml) and H$_2$O (0.2 ml). 4-tert-butoxycarbonylaminoaniline (374 mg, 1.8 mmol) was added and the mixture was refluxed for 24 hours (70° C. oil-bath temperature). The mixture was cooled to 22° C., concentrated to dryness under reduced pressure and subjected to column chromatography on silica gel (CHCl$_3$-Acetone, 9:1) to give N2,N4-bis[4-(tert-butoxycarbonylamino)phenyl]-5-fluoro-2,4-pyrimidinediamine. $^1$H NMR (DMSO-d6+CD$_3$OD): δ 7.96 (d, 1H, J=3.5 Hz), 7.63 (d, 2H, J=8.8 Hz), 7.49 (d, 2H, J=8.8 Hz), 7.37 (d, 2H, J=8.8 Hz), 7.24 (d, 2H, J=8.8 Hz), 1.45 (s, 9H), 1.43 (s, 9H); LCMS: purity: 97.9%; MS (m/e): 511.04 (M$^+$, 100).

7.3.158 N2,N4-Bis[2-[2-(methylamino)ethyleneaminocarbonyl]-benzofurane-5-yl]-5-fluoro-2,4-pyrimidinediamine (R950170)

N2,N4-Bis[2-(ethoxycarbonyl)-benzofurane-5-yl]-5-fluoro-2,4-pyrimidinediamine (10 mg, 0.02 mmol) was dissolved in EtOH. To this was added N-methyl-1,2-aminoethane (0.1 ml: 0.1 ml) and the mixture was refluxed for 3 days (70° C. oil-bath temperature). The mixture was cooled to 22° C., diluted with water and filtered. The residue was subjected to column chromatography on silica gel (CHCl$_3$-Acetone, 2:1) to give N2,N4-bis[2-[2-(methylamino)ethyleneaminocarbonyl]-benzofurane-5-yl]-5-fluoro-2,4-pyrimidinediamine. $^1$H NMR (DMSO-d6+CD$_3$OD): δ 8.14 (s, 1H), 8.02 (s, 1H), 7.99 (d, 1H, J=2.4 Hz), 7.35-7.68 (m, 5H), 7.17 (s, 1H), 3.41 (m, 2H), 2.75 (m, 2H), 2.35 (s, 3H); LCMS: purity: 84.2%; MS (m/e): 561.08 (M$^+$, 100).

7.3.159 N2,N4-Bis[2-(2-hydroxyethyleneamoinocarbonyl)-benzofurane-5-yl]-5-fluoro-2,4-pyrimidinediamine (R950167)

In like manner to the preparation of N2,N4-bis[2-[2-(methylamino)ethyleneaminocarbonyl]-benzofurane-5-yl]-5-fluoro-2,4-pyrimidinediamine, N2,N4-bis[2-(ethoxycarbonyl)-benzofurane-5-yl]-5-fluoro-2,4-pyrimidinediamine and 2-aminoethanol were reacted to prepare N2,N4-bis[2-(2-hydroxyethyleneamoinocarbonyl)-benzofurane-5-yl]-5-fluoro-2,4-pyrimidinediamine. LCMS: ret. time: 14.22 min.; purity: 95.7%; MS (m/e): 535.01 (MH$^+$)

7.3.160 N2,N4-Bis[2-(2-aminoethyleneamoinocarbonyl)-benzofurane-5-yl]-5-fluoro-2,4-pyrimidinediamine (R950168)

In like manner to the preparation of N2,N4-bis[2-[2-(methylamino)ethyleneaminocarbonyl]-benzofurane-5-yl]-5-fluoro-2,4-pyrimidinediamine, N2,N4-bis[2-(ethoxycarbonyl)-benzofurane-5-yl]-5-fluoro-2,4-pyrimidinediamine and 1,2-diaminoethane were reacted to prepare N2,N4-bis[2-(2-aminoethyleneamoinocarbonyl)-benzofurane-5-yl]-5-fluoro-2,4-pyrimidinediamine. LCMS: ret. time: 13.15 min.; purity: 95.8%; MS (m/e): 532.99 (MH$^+$)

7.3.161 N2,N4-Bis[2-(2-(N-benzylamino)ethyleneamoinocarbonyl)-benzofurane-5-yl]-5-fluoro-2,4-pyrimidinediamine (R950169)

In like manner to the preparation of N2,N4-bis[2-[2-(methylamino)ethyleneaminocarbonyl]-benzofurane-5-yl]-5-fluoro-2,4-pyrimidinediamine, N2,N4-bis[2-(ethoxycarbonyl)-benzofurane-5-yl]-5-fluoro-2,4-pyrimidinediamine and N-benzyl-1,2-diaminoethane were reacted to prepare N2,N4-bis[2-(2-(N-benzylamino)ethyleneamoinocarbonyl)-benzofurane-5-yl]-5-fluoro-2,4-pyrimidinediamine. LCMS: ret. time: 13.15 min.; purity: 95.8%; MS (m/e): 713.10 (MH$^+$).

7.3.162 N2,N4-Bis[2-(N-morpholinocarbonyl)benzofurane-5-yl]-5-fluoro-2,4-pyrimidinediamine (R950172)

In like manner to the preparation of N2,N4-bis[2-[2-(methylamino)ethyleneaminocarbonyl]-benzofurane-5-yl]-5- fluoro-2,4-pyrimidinediamine, N2,N4-bis[2-(ethoxycarbonyl)-benzofurane-5-yl]-5-fluoro-2,4-pyrimidinediamine and morpholine were reacted to N2,N4-bis[2-(N-morpholinocarbonyl)benzofurane-5-yl]-5-fluoro-2,4-pyrimidinediamine.
$^1$H NMR (DMSO-d6+CD$_3$OD): δ 8.13 (d, 1H, J=2.7 Hz), 8.06 (d, 1H, J=2.4 Hz), 8.03 (d, 1H, J=3.6 Hz), 7.63 (dd, 1H, J=2.4, 8.8 Hz), 7.57 (d, 1H, J=9.3 Hz), 7.49 (dd, 1H, J=2.4, 8.4 Hz), 7.42 (d, 1H, J=8.8 Hz), 7.25 (s, 1H), 7.05 (s, 1H), 4.09 (m, 4H), 3.65 (m, 4H); LCMS: ret. time: 18.04 min.; purity: 83.2%; MS (m/e): 587.04 (MH$^+$).

7.3.163 N2,N4-Bis[2-(2-N-morpholinoethyleneaminocarbonyl)-benzofurane-5-yl]-5-fluoro-2,4-pyrimidinediamine (R950173)

In like manner to the preparation of N2,N4-bis[2-[2-(methylamino)ethyleneaminocarbonyl]-benzofurane-5-yl]-5-fluoro-2,4-pyrimidinediamine, N2,N4-bis[2-(ethoxycarbonyl)-benzofurane-5-yl]-5-fluoro-2,4-pyrimidinediamine and N-(2-aminoethyleneamino)morpholine were reacted to prepare N2,N4-bis[2-(2-N-morpholinoethyleneaminocarbonyl)-benzofurane-5-yl]-5-fluoro-2,4-pyrimidinediamine.
$^1$H NMR (DMSO-d6+CD$_3$OD): δ 8.16 (d, 1H, J=2.4 Hz), 8.03-8.05 (m, 2H), 7.71 (dd, 1H, J=1.8, 8.8 Hz), 7.56 (d, 1H, J=8.8 Hz), 7.42 (d, 1H, J=8.8 Hz), 7.36 (s, 1H), 7.19 (s, 1H), 4.19 (m, 4H), 3.38 (m, 4H), 3.16 (t, 2H, J=6.3 Hz), 2.28 (t, 2H, J=6.3 Hz); LCMS: ret. time: 12.85 min.; purity: 93.8%; MS (m/e): 673.35 (MH$^+$).

7.3.164 N2,N4-Bis(3-amino-4-nitrophenyl)-5-fluoro-2,4-pyrimidinediamine (R950135)

2,4-Dichloro-5-fluoropyrimidine (50 mg, 0.3 mmol) was dissolved in a mixture of MeOH (1 ml) and H$_2$O (0.1 ml). 3-amino-4-nitroaniline (184 mg, 1.2 mmol) was added and the mixture was refluxed for 3 days (70° C. oil-bath temperature). The mixture was cooled to 22° C., concentrated to dryness under reduced pressure and subjected to column chromatography on silica gel (CHCl$_3$-Acetone, 2:1) to give N2,N4-bis(3-amino-4-nitrophenyl)-5-fluoro-2,4-pyrimidinediamine. $^1$H NMR (DMSO-d6+CD$_3$OD): δ 8.21 (d, 1H, J=2.9 Hz), 7.89 (m, 3H), 7.56 (d, 1H, J=2.3 Hz), 7.01 (m, 1H), 6.81 (dd, 1H, J=2.3, 9.4 Hz); LCMS: purity: 91.1%; MS (m/e): 401.00 (M$^+$, 100).

7.3.165 N2,N4-Bis(3-amino-2,4-difluorophenyl)-5-fluoro-2,4-pyrimidinediamine (R950138)

In like manner to the preparation of N2,N4-bis(3-amino-4-nitrophenyl)-5-fluoro-2,4-pyrimidinediamine, 2,4-dichloro-5-fluoropyrimidine and 3-amino-2,4-difluoroaniline were reacted to prepare N2,N4-bis(3-amino-2,4-difluorophenyl)-5-fluoro-2,4-pyrimidinediamine. LCMS: ret. time: 16.98 min.; purity: 91.7%; MS (m/e): 382.97 (MH$^+$).

7.3.166 N2,N4-Bis(3-amino-4-ethoxyphenyl)-5-fluoro-2,4-pyrimidinediamine (R950139)

In like manner to the preparation of N2,N4-bis(3-amino-4-nitrophenyl)-5-fluoro-2,4-pyrimidinediamine, 2,4-dichloro-5-fluoropyrimidine and 3-amino-4-ethoxyaniline were reacted to prepare N2,N4-bis(3-amino-4-ethoxyphenyl)-5-fluoro-2,4-pyrimidinediamine. LCMS: ret. time: 14.29 min.; purity: 93.4%; MS (m/e): 399.09 (MH$^+$).

7.3.167 N2,N4-Bis(3-amino-5-methoxycarbonylphenyl)-5-fluoro-2,4-pyrimidinediamine (R950134)

In like manner to the preparation of N2,N4-bis(3-amino-4-nitrophenyl)-5-fluoro-2,4-pyrimidinediamine, 2,4-dichloro-5-fluoropyrimidine and 3-amino-5-methoxycarbonylaniline were reacted to prepare N2,N4-bis(3-amino-5-methoxycarbonylphenyl)-5-fluoro-2,4-pyrimidinediamine. LCMS: ret. time: 14.72 min.; purity: 93.8%; MS (m/e): 427.02 (MH$^+$).

7.3.168 N2,N4-Bis(3-amino-5-trifluoromethylphenyl)-5-fluoro-2,4-pyrimidinediamine (R950140)

In like manner to the preparation of N2,N4-bis(3-amino-4-nitrophenyl)-5-fluoro-2,4-pyrimidinediamine, 2,4-dichloro-5-fluoropyrimidine and 3-amino-5-trifluoromethylaniline were reacted to prepare N2,N4-bis(3-amino-5-trifluoromethylphenyl)-5-fluoro-2,4-pyrimidinediamine. LCMS: ret. time: 23.35 min.; purity: 100%; MS (m/e): 446.92 (MH$^+$).

7.3.169 N2,N4-Bis(3-amino-5-chlorophenyl)-5-fluoro-2,4-pyrimidinediamine (R950141)

In like manner to the preparation of N2,N4-bis(3-amino-4-nitrophenyl)-5-fluoro-2,4-pyrimidinediamine, 2,4-dichloro-5-fluoropyrimidine and 3-amino-5-chloroaniline were reacted to prepare N2,N4-bis(3-amino-5-chlorophenyl)-5-fluoro-2,4-pyrimidinediamine. LCMS: ret. time: 19.25 min.; purity: 99.3%; MS (m/e): 378.91 (MH$^+$).

7.3.170 N2,N4-Bis(4-hydroxy-3-trifluoromethylphenyl)-5-fluoro-2,4-pyrimidinediamine (R950093)

In like manner to the preparation of N2,N4-bis(3-amino-4-nitrophenyl)-5-fluoro-2,4-pyrimidinediamine, 2,4-dichloro-5-fluoropyrimidine and 4-hydroxy-3-trifluoromethylaniline were reacted to prepare N2,N4-bis(4-hydroxy-3-trifluoromethylphenyl)-5-fluoro-2,4-pyrimidinediamine. LCMS: ret. time: 22.06 min.; purity: 99.1%; MS (m/e): 448.88 (MH$^+$).

7.3.171 N2,N4-Bis(3-aminophenyl)-5-fluoro-2,4-pyrimidinediamine Hydrogen Chloride salt (R950107)

N2,N4-Bis(3-aminophenyl)-5-fluoro-2,4-pyrimidinediamine was treated with 2 equivalents of HCl in dioxane. The volatiles were removed under reduced pressure to give N2,N4-bis(3-aminophenyl)-5-fluoro-2,4-pyrimidinediamine hydrogen chloride salt. LCMS: ret. time: 9.74 min.; purity: 91.3%; MS (m/e): 311.06 (MH$^+$).

7.3.172 N2,N4-Bis(4-aminophenyl)-5-fluoro-2,4-pyrimidinediamine Hydrogen Chloride Salt (R950121)

N2,N4-Bis(4-aminophenyl)-5-fluoro-2,4-pyrimidinediamine was treated with 2 equivalents of HCl in dioxane. The volatiles were removed under reduced pressure to give N2,N4-bis(4-aminophenyl)-5-fluoro-2,4-pyrimidinediamine Hydrogen Chloride Salt. LCMS: ret. time: 11.15 min.; purity: 100%; MS (m/e): 311.09 (MH$^+$).

7.3.173 N2,N4-Bis(3-aminophenyl)-2,4-pyrimidinediamine (R950109)

In like manner to the preparation of N2,N4-bis(3-amino-4-nitrophenyl)-5-fluoro-2,4-pyrimidinediamine, 2,4-dichloropyrimidine and 3-aminoaniline were reacted to prepare N2,N4-bis(3-aminophenyl)-2,4-pyrimidinediamine. LCMS: ret. time: 8.90 min.; purity: 91%; MS (m/e): 293.06 (MH$^+$).

7.3.174 N2,N4-Bis(3-amino-2,4-difluorophenyl)-2,4-pyrimidinediamine (R950131)

In like manner to the preparation of N2,N4-bis(3-amino-4-nitrophenyl)-5-fluoro-2,4-pyrimidinediamine, 2,4-dichloropyrimidine and 3-amino-2,4-difluoroaniline were reacted to prepare N2,N4-bis(3-amino-2,4-difluorophenyl)-2,4-pyrimidinediamine. LCMS: ret. time: 16.62 min.; purity: 96.7%; MS (m/e): 364.99 (MH$^+$).

7.3.175 N2,N4-Bis(3-amino-4-ethoxyphenyl)-2,4-pyrimidinediamine (R950142)

In like manner to the preparation of N2,N4-bis(3-amino-4-nitrophenyl)-5-fluoro-2,4-pyrimidinediamine, 2,4-dichloropyrimidine and 3-amino-4-ethoxyaniline were reacted to prepare N2,N4-bis(3-amino-4-ethoxyphenyl)-2,4-pyrimidinediamine. LCMS: ret. time: 14.38 min.; purity: 99.7%; MS (m/e): 381.07 (MH$^+$).

7.3.176 N2,N4-Bis(3-amino-5-methoxycarbonylphenyl)-2,4-pyrimidinediamine (R950132)

In like manner to the preparation of N2,N4-bis(3-amino-4-nitrophenyl)-5-fluoro-2,4-pyrimidinediamine, 2,4-dichloropyrimidine and 3-amino-5-methoxycarbonylaniline were reacted to prepare N2,N4-bis(3-amino-5-methoxycarbonylphenyl)-2,4-pyrimidinediamine. LCMS: ret. time: 15.25 min.; purity: 93.6%; MS (m/e): 409.02 (MH$^+$).

7.3.177 N2,N4-Bis(3-amino-5-trifluoromethylphenyl)-2,4-pyrimidinediamine (R950143)

In like manner to the preparation of N2,N4-bis(3-amino-4-nitrophenyl)-5-fluoro-2,4-pyrimidinediamine, 2,4-dichloropyrimidine and 3-amino-5-trifluoromethylaniline were reacted to prepare N2,N4-bis(3-amino-5-trifluoromethylphenyl)-2,4-pyrimidinediamine. LCMS: ret. time: 23.23 min.; purity: 99.1%; MS (m/e): 428.95 (MH$^+$).

7.3.178 N2,N4-Bis(3-amino-5-chlorophenyl)-2,4-pyrimidinediamine (R950133)

In like manner to the preparation of N2,N4-bis(3-amino-4-nitrophenyl)-5-fluoro-2,4-pyrimidinediamine, 2,4-dichloropyrimidine and 3-amino-5-chloroaniline were reacted to prepare N2,N4-bis(3-amino-5-chlorophenyl)-2,4-pyrimidinediamine. LCMS: ret. time: 19.45 min.; purity: 100%; MS (m/e): 360.93 (MH$^+$).

7.3.179 N2,N4-Bis[3-amino-4-(N-phenylamino)-phenyl]-5-fluoro-2,4-pyrimidinediamine (R950125)

In like manner to the preparation of N2,N4-bis(3-amino-4-nitrophenyl)-5-fluoro-2,4-pyrimidinediamine, 2,4-dichloro-5-fluoropyrimidine and 3-amino-4-(N-phenylamino)-aniline were reacted to prepare N2,N4-bis[3-amino-4-(N-phenylamino)-phenyl]-5-fluoro-2,4-pyrimidinediamine. LCMS: ret. time: 23.67 min.; purity: 100%; MS (m/e): 476.36 (MH$^+$).

7.3.180 N2,N4-Bis[3-amino-4-(N-phenylamino)-phenyl]-2,4-pyrimidinediamine (R950123)

In like manner the preparation of N2,N4-bis(3-amino-4-nitrophenyl)-5-fluoro-2,4-pyrimidinediamine, 2,4-dichloropyrimidine and 3-amino-4-(N-phenylamino)-aniline were reacted to prepare N2,N4-bis[3-amino-4-(N-phenylamino)-phenyl]-2,4-pyrimidinediamine. LCMS: ret. time: 23.77 min.; purity: 77.8%; MS (m/e): 475.04 (MH$^+$).

7.3.181 N2,N4-Bis(5-amino-2-methylphenyl)-5-fluoro-2,4-pyrimidinediamine (R950157)

In like manner to the preparation of N2,N4-bis(3-amino-4-nitrophenyl)-5-fluoro-2,4-pyrimidinediamine, 2,4-dichloro-5-fluoropyrimidine and 5-amino-2-methylaniline were reacted to prepare N2,N4-bis(5-amino-2-methylphenyl)-5-fluoro-2,4-pyrimidinediamine. LCMS: ret. time: 10.61 min.; purity: 83.4%; MS (m/e): 339.13 (MH$^+$).

7.3.182 N2,N4-Bis(5-amino-2-fluorophenyl)-5-fluoro-2,4-pyrimidinediamine (R950158)

In like manner to the preparation of N2,N4-bis(3-amino-4-nitrophenyl)-5-fluoro-2,4-pyrimidinediamine, 2,4-dichloro-5-fluoropyrimidine and 5-amino-2-fluoroaniline were reacted to prepare N2,N4-bis(5-amino-2-fluorophenyl)-5-fluoro-2,4-pyrimidinediamine. LCMS: ret. time: 11.48 min.; purity: 95.6%; MS (m/e): 347.04 (MH$^+$).

7.3.183 N2,N4-Bis(3-amino-4-fluorophenyl)-5-fluoro-2,4-pyrimidinediamine (R950159)

In like manner to the preparation of N2,N4-bis(3-amino-4-nitrophenyl)-5-fluoro-2,4-pyrimidinediamine, 2,4-dichloro-5-fluoropyrimidine and 3-amino-4-fluoroaniline were reacted to prepare N2,N4-bis(3-amino-4-fluorophenyl)-5-fluoro-2,4-pyrimidinediamine. LCMS: ret. time: 18.74 min.; purity: 95.6%; MS (m/e): 347.29 (MH$^+$).

7.3.184 N2,N4-Bis(2-methyl-5-nitrophenyl)-5-fluoro-2,4-pyrimidinediamine (R950146)

2,4-Dichloro-5-fluoropyrimidine (33 mg, 0.2 mmol) was dissolved in a mixture of MeOH (1 ml) and H$_2$O (0.1 ml). 2-Methyl-5-nitroaniline (122 mg, 0.8 mmol) was added and the mixture was refluxed for 2 days (70° C. oil-bath temperature). The mixture was cooled to 22° C., concentrated to dryness under reduced pressure and subjected to column chromatography on silica gel (CHCl$_3$-Acetone, 9:1) to give N2,N4-bis(2-methyl-5-nitrophenyl)-5-fluoro-2,4-pyrimidinediamine. $^1$H NMR (DMSO-d6+CD$_3$OD): δ 8.31 (d, 1H, J=2.3 Hz), 8.20 (d, 1H, J=2.3 Hz), 8.06 (d, 1H, J=3.5 Hz), 7.91 (dd, 1H, J=2.3, 8.2 Hz), 7.65 (dd, 1H, J=2.9, 8.8 Hz), 7.41 (m, 1H), 7.28 (d, 1H, J=8.2 Hz), 2.28 (s, 3H), 2.24 (s, 3H); LCMS purity: 87.4%; MS (m/e): 399.20 (M$^+$, 100).

7.3.185 N2,N4-Bis(2-fluoro-5-nitrophenyl)-5-fluoro-2,4-pyrimidinediamine (R950147)

In like manner to the preparation of N2,N4-bis(2-methyl-5-nitrophenyl)-5-fluoro-2,4-pyrimidinediamine, 2,4-dichloro-5-fluoropyrimidine and 2-fluoro-5-nitroaniline were reacted to prepare N2,N4-bis(2-fluoro-5-nitrophenyl)-5-fluoro-2,4-pyrimidinediamine. LCMS: ret. time: 31.07 min.; purity: 93.6%; MS (m/e): 407.14 (MH$^+$).

7.3.186 N2,N4-Bis(4-fluoro-3-nitrophenyl)-5-fluoro-2,4-pyrimidinediamine (R950148)

In like manner to the preparation of N2,N4-bis(2-methyl-5-nitrophenyl)-5-fluoro-2,4-pyrimidinediamine, 2,4-dichloro-5-fluoropyrimidine and 4-fluoro-3-nitroaniline were reacted to prepare N2,N4-bis(4-fluoro-3-nitrophenyl)-5-fluoro-2,4-pyrimidinediamine. LCMS: ret. time: 27.17 min.; purity: 94.3%; MS (m/e): 406.96 (MH$^+$).

7.3.187 N2,N4-Bis(4-methyl-3-nitrophenyl)-5-fluoro-2,4-pyrimidinediamine (R950144)

In like manner to the preparation of N2,N4-bis(2-methyl-5-nitrophenyl)-5-fluoro-2,4-pyrimidinediamine, 2,4-dichloro-5-fluoropyrimidine and 4-methyl-3-nitroaniline were reacted to prepare N2,N4-bis(4-methyl-3-nitrophenyl)-5-fluoro-2,4-pyrimidinediamine. LCMS: ret. time: 27.40 min.; purity: 96.6%; MS (m/e): 399.00 (MH$^+$).

7.3.188 N2,N4-Bis(4-chloro-3-nitrophenyl)-5-fluoro-2,4-pyrimidinediamine (R950149)

In like manner to the preparation of N2,N4-bis(2-methyl-5-nitrophenyl)-5-fluoro-2,4-pyrimidinediamine, 2,4-dichloro-5-fluoropyrimidine and 4-chloro-3-nitroaniline were reacted to prepare N2,N4-bis(4-chloro-3-nitrophenyl)-5-fluoro-2,4-pyrimidinediamine. LCMS: ret. time: 35.63 min.; purity: 98.9%; MS (m/e): 439.09 (MH$^+$).

7.3.189 N2,N4-Bis(2-hydroxyethyleneamino-5-nitrophenyl)-5-fluoro-2,4-pyrimidinediamine (R950150)

In like manner to the preparation of N2,N4-bis(2-methyl-5-nitrophenyl)-5-fluoro-2,4-pyrimidinediamine, 2,4-dichloro-5-fluoropyrimidine and 2-hydroxyethyleneamino-5-nitroaniline were reacted to prepare N2,N4-bis(2-hydroxyethyleneamino-5-nitrophenyl)-5-fluoro-2,4-pyrimidinediamine. LCMS: ret. time: 17.90 min.; purity: 97.8%; MS (m/e): 489.19 (MH$^+$)

7.3.190 N2,N4-Bis(2-methoxy-5-nitrophenyl)-5-fluoro-2,4-pyrimidinediamine (R950151)

In like manner to the preparation of N2,N4-bis(2-methyl-5-nitrophenyl)-5-fluoro-2,4-pyrimidinediamine, 2,4-dichloro-5-fluoropyrimidine and 2-methoxy-5-nitroaniline were reacted to prepare N2,N4-bis(2-methoxy-5-nitrophenyl)-5-fluoro-2,4-pyrimidinediamine. LCMS: ret. time: 31.46 min.; purity: 95.9%; MS (m/e): 431.22 (MH$^+$).

7.3.191 N2,N4-Bis(4-fluoro-3-nitrophenyl)-2,4-pyrimidinediamine (R950152)

In like manner to the preparation of N2,N4-bis(2-methyl-5-nitrophenyl)-5-fluoro-2,4-pyrimidinediamine, 2,4-dichloropyrimidine and 4-fluoro-3-nitroaniline were reacted to prepare N2,N4-bis(4-fluoro-3-nitrophenyl)-2,4-pyrimidinediamine. LCMS: ret. time: 30.92 min.; purity: 94.4%; MS (m/e): 389.31 (MH$^+$).

7.3.192 N2,N4-Bis(4-methyl-3-nitrophenyl)-2,4-pyrimidinediamine (R950153)

In like manner to the preparation of N2,N4-bis(2-methyl-5-nitrophenyl)-5-fluoro-2,4-pyrimidinediamine, 2,4-dichloropyrimidine and 4-methyl-3-nitroaniline were reacted to prepare N2,N4-bis(4-methyl-3-nitrophenyl)-2,4-pyrimidinediamine. LCMS: ret. time: 31.22 min.; purity: 99.6%; MS (m/e): 381.35 (MH$^+$).

7.3.193 N2,N4-Bis(4-chloro-3-nitrophenyl)-2,4-pyrimidinediamine (R950154)

In like manner to the preparation of N2,N4-bis(2-methyl-5-nitrophenyl)-5-fluoro-2,4-pyrimidinediamine, 2,4-dichloropyrimidine and 4-chloro-3-nitroaniline were reacted to prepare N2,N4-bis(4-chloro-3-nitrophenyl)-2,4-pyrimidinediamine. LCMS: ret. time: 37.24 min.; purity: 99.1%; MS (m/e): 421.30 (MH$^+$).

7.3.194 N2,N4-Bis(2-hydroxy-5-nitrophenyl)-2,4-pyrimidinediamine (R950155)

In like manner to the preparation of N2,N4-bis(2-methyl-5-nitrophenyl)-5-fluoro-2,4-pyrimidinediamine, 2,4-dichloropyrimidine and 2-hydroxy-5-nitroaniline were reacted to prepare N2,N4-bis(2-hydroxy-5-nitrophenyl)-2,4-pyrimidinediamine. LCMS: ret. time: 23.26 min.; purity: 100%; MS (m/e): 385.33 (MH$^+$).

7.3.195 N2,N4-Bis(2-hydroxyethyleneamino-5-nitrophenyl)-2,4-pyrimidinediamine (R950156)

In like manner to the preparation of N2,N4-bis(2-methyl-5-nitrophenyl)-5-fluoro-2,4-pyrimidinediamine, 2,4-dichloropyrimidine and 2-hydroxyethyleneamino-5-nitroaniline were reacted to prepare N2,N4-bis(2-hydroxyethyleneamino-5-nitrophenyl)-2,4-pyrimidinediamine. LCMS: ret. time: 17.87 min.; purity: 97.2%; MS (m/e): 470.99 (MH$^+$).

7.3.196 N2,N4-Bis[3-(N-isopropyl)aminophenyl]-5-fluoro-2,4-pyrimidinediamine (R950166)

N2,N4-Bis(3-aminophenyl)-5-fluoro-2,4-pyrimidinediamine, acetone and sodiumcyanoborohydride were reacted together to give N2,N4-bis[3-(N-isopropyl)aminophenyl]-5-fluoro-2,4-pyrimidinediamine. LCMS: ret. time: 14.07 min.; purity: 90.3%; MS (m/e): 395.14 (MH$^+$).

7.3.197 N2,N4-Bis[3-N-(2-hydroxy-1-methylethyl)aminophenyl]-5-fluoro-2,4-pyrimidinediamine (R950171)

N2,N4-Bis(3-aminophenyl)-5-fluoro-2,4-pyrimidinediamine, 1-hydroxyacetone and sodiumcyanoborohydride were reacted to give N2,N4-bis[3-N-(2-hydroxy-1-methylethyl)aminophenyl]-5-fluoro-2,4-pyrimidinediamine. LCMS: ret. time: 11.97 min.; purity: 79.01%; MS (m/e): 427.12 (MH$^+$).

7.3.198 N2,N4-Bis(3-tert-butoxycarbonylmethyleneaminophenyl)-5-fluoro-2,4-pyrimidinediamine (R950177)

N2,N4-Bis(3-aminophenyl)-5-fluoro-2,4-pyrimidinediamine and tert-butyl bromoacetate were reacted together to give N2,N4-bis(3-tert-butoxycarbonylmethyleneaminophenyl)-5-fluoro-2,4-pyrimidinediamine. LCMS: ret. time: 29.34 min.; purity: 97.2%; MS (m/e): 427.07 (MH$^+$).

7.3.199 N4-(3-Aminophenyl)-N2-(3-tert-butoxycarbonylmethyleneaminophenyl)-5-fluoro-2,4-pyrimidinediamine (R950178)

In like manner to the preparation of N2,N4-bis(3-tert-butoxycarbonylmethyleneaminophenyl)-5-fluoro-2,4-pyrimidinediamine, N2,N4-bis(3-aminophenyl)-5-fluoro-2,4-pyrimidinediamine and tert-butyl bromoacetate were reacted together to give N4-(3-aminophenyl)-N2-(3-tert-butoxycarbonylmethyleneaminophenyl)-5-fluoro-2,4-pyrimidinediamine. LCMS: ret. time: 18.33 min.; purity: 94.5%; MS (m/e): 369.09 (MH$^+$).

7.3.200 N2-(3-Aminophenyl)-N4-(3-tert-butoxycarbonylmethyleneaminophenyl)-5-fluoro-2,4-pyrimidinediamine (R950179)

In like manner to the preparation of N2,N4-bis(3-tert-butoxycarbonylmethyleneaminophenyl)-5-fluoro-2,4-pyrimidinediamine, N2,N4-bis(3-aminophenyl)-5-fluoro-2,4-pyrimidinediamine and tert-butyl bromoacetate were reacted together to give N2-(3-aminophenyl)-N4-(3-tert-butoxycarbonylmethyleneaminophenyl)-5-fluoro-2,4-pyrimidinediamine. LCMS: ret. time: 18.82 min.; purity: 85.8%; MS (m/e): 369.11 (MH$^+$).

7.3.201 N2,N4-Bis(3-ethoxycarbonylmethyleneaminophenyl)-5-fluoro-2,4-pyrimidinediamine (R950184)

In like manner to the preparation of N2,N4-bis(3-tert-butoxycarbonylmethyleneaminophenyl)-5-fluoro-2,4-pyrimidinediamine, N2,N4-bis(3-aminophenyl)-5-fluoro-2,4-pyrimidinediamine and ethyl bromoacetate were reacted together to give N2,N4-bis(3-ethoxycarbonylmethyleneaminophenyl)-5-fluoro-2,4-pyrimidinediamine. LCMS: ret. time: 23.41 min.; purity: 96.3%; MS (m/e): 483.08 (MH$^+$).

7.3.202 N2,N4-Bis(3-ethoxycarbonylmethyleneaminophenyl)-N2-(ethoxycarbonylmethyl)-5-fluoro-2,4-pyrimidinediamine (R950183)

In like manner to the preparation of N2,N4-bis(3-tert-butoxycarbonylmethyleneaminophenyl)-5-fluoro-2,4-pyrimidinediamine, N2,N4-bis(3-aminophenyl)-5-fluoro-2,4-pyrimidinediamine and ethyl bromoacetate were reacted together to give N2,N4-bis(3-ethoxycarbonylmethyleneaminophenyl)-N2-(ethoxycarbonylmethyl)-5-fluoro-2,4-pyrimidinediamine. LCMS: ret. time: 25.65 min.; purity: 92.5%; MS (m/e): 569.08 (MH$^+$).

7.3.203 N2-(3-Aminophenyl)-N4-(3-hydroxyethyleneaminophenyl)-5-fluoro-2,4-pyrimidinediamine and N4-(3-Aminophenyl)-N2-(3-hydroxyethyleneaminophenyl)-5-fluoro-2,4-pyrimidinediamine (R950180)

In like manner to the preparation of N2,N4-bis(3-tert-butoxycarbonylmethyleneaminophenyl)-5-fluoro-2,4-pyrimidinediamine, N2,N4-bis(3-aminophenyl)-5-fluoro-2,4-pyrimidinediamine and 1-bromo-2-hydroxyethane were reacted together to give a unseparable mixture of N2-(3-aminophenyl)-N4-(3-hydroxyethyleneaminophenyl)-5-fluoro-2,4-pyrimidinediamine and N4-(3-aminophenyl)-N2-(3-hydroxyethyleneaminophenyl)-5-fluoro-2,4-pyrimidinediamine. LCMS: ret. time: 9.84 min.; purity: 89.5%; MS (m/e): 355.10 (MH$^+$).

7.3.204 N2,N4-Bis(3-hydroxyethyleneaminophenyl)-5-fluoro-2,4-pyrimidinediamine (R950181)

In like manner to the preparation of N2,N4-bis(3-tert-butoxycarbonylmethyleneaminophenyl)-5-fluoro-2,4-pyrimidinediamine, N2,N4-bis(3-aminophenyl)-5-fluoro-2,4-pyrimidinediamine and 1-bromo-2-hydroxyethane were reacted together to give N2,N4-bis(3-hydroxyethyleneaminophenyl)-5-fluoro-2,4-pyrimidinediamine. LCMS: ret. time: 11.46 min.; purity: 83.3%; MS (m/e): 399.12 (MH$^+$).

7.3.205 N2,N4-Bis[3-(N-benzyloxyethyleneamino)phenyl]-5-fluoro-2,4-pyrimidinediamine (R950174)

In like manner to the preparation of N2,N4-bis(3-tert-butoxycarbonylmethyleneaminophenyl)-5-fluoro-2,4-pyrimidinediamine, N2,N4-bis(3-aminophenyl)-5-fluoro-2,4-pyrimidinediamine and 1-benzyloxy-2-bromoethane were reacted together to give N2,N4-bis[3-(N-benzyloxyethyleneamino)phenyl]-5-fluoro-2,4-pyrimidinediamine. LCMS: ret. time: 32.92 min.; MS (m/e): 579.17 (MH$^+$).

7.3.206 N2-(3-Aminophenyl)-N4-[3-(N-benzyloxyethyleneamino)phenyl]-5-fluoro-2,4-pyrimidinediamine (R950175)

In like manner to the preparation of N2,N4-bis(3-tert-butoxycarbonylmethyleneaminophenyl)-5-fluoro-2,4-pyrimidinediamine, N2,N4-bis(3-aminophenyl)-5-fluoro-2,4-pyrimidinediamine and 1-benzyloxy-2-bromoethane were reacted together to give N2-(3-aminophenyl)-N4-[3-(N-benzyloxyethyleneamino)phenyl]-5-fluoro-2,4-pyrimidinediamine. LCMS: ret. time: 23.79 min.; MS (m/e): 445.11 (MH$^+$).

7.3.207 N4-(3-Aminophenyl)-N2-[3-(N-benzyloxyethyleneamino)phenyl]-5-fluoro-2,4-pyrimidinediamine (R950176)

In like manner to the preparation of N2,N4-bis(3-tert-butoxycarbonylmethyleneaminophenyl)-5-fluoro-2,4-pyrimidinediamine, N2,N4-bis(3-aminophenyl)-5-fluoro-2,4-pyrimidinediamine and 1-benzyloxy-2-bromoethane were reacted together to give N4-(3-aminophenyl)-N2-[3-(N-benzyloxyethyleneamino)phenyl]-5-fluoro-2,4-pyrimidinediamine. LCMS: ret. time: 23.64 min.; MS (m/e): 445.13 (MH$^+$).

7.3.208 N4-(3,4-Ethylenedioxyphenyl)-5-fluoro-N2-(3-hydroxyphenyl)-2,4-pyrimidinediamine (R926210)

To a solution of 2-chloro-N4-(3,4-ethylenedioxyphenyl)-5-fluoro-4-pyrimidineamine (0.028 g, 0.1 mmol) in MeOH: H$_2$O (1.8:0.2 mL) was added 3-hydroxyaniline (0.033 g, 0.3 mmol) and heated in a sealed tube at 100° C. for 24 h. The resulting reaction was diluted with H$_2$O (10 mL), acidified with 2N HCl (pH>2), saturated and the resulting solid was filtered to give the desired product, N4-(3,4-ethylenedioxyphenyl)-5-fluoro-N2-(3-hydroxyphenyl))-2,4-pyrimidinediamine (R926210). Purification can be done by filtration through a pad of silica gel using 1-5% MeOH in CH$_2$Cl$_2$ or by crystallization using an appropriate solvent system. $^1$H NMR (CDCl$_3$+CD$_3$OD): δ 7.76 (bs, 1H), 7.30 (d, 1H, J=2.4 Hz), 7.10 (m, 1H), 7.03 (t, 1H, J=8.1 Hz), 6.89 (dd, 2H, J=2.4 and 9 Hz), 6.78 (d, 1H, J=8.7 Hz), 6.42 (dd, 1H, J=2.4 and 9

Hz), 4.22 (m, 4H); $^{19}$F NMR (CDCl$_3$+CD$_3$OD): −47196; LCMS: ret. time: 19.55 min.; purity: 95%; MS (m/e): 355 (MH$^+$).

Note: When the substrate has ethyl, butyl, benzyl etc. ester functions and the reaction is carried out in methanol as a solvent, the cross esterification to produce methyl ester was observed.

7.3.209 N2-(3,4-Ethylenedioxyphenyl)-5-fluoro-N4-[3-(hydroxymethyl)phenyl]-2,4-pyrimidinediamine (R925758)

In a manner similar to the preparation of N4-(3,4-ethylenedioxyphenyl)-5-fluoro-N2-(3-hydroxyphenyl)-2,4-pyrimidinediamine, 2-chloro-5-fluoro-N4-[3-(hydroxymethyl)phenyl]-4-pyrimidineamine and 3,4-ethylenedioxyaniline were reacted to yield N2-(3,4-ethylenedioxyphenyl)-5-fluoro-N4-[3-(hydroxymethyl)phenyl]-2,4-pyrimidinediamine. $^1$H NMR (CDCl$_3$): δ 7.92 (d, 1H, J=3.0 Hz), 7.78 (bs, 1H), 7.41-7.31 (m, 3H), 7.12 (d, 1H, J=7.2 Hz), 6.94 (bs, 1H), 6.81-6.75 (m, 3H), 4.68 (s, 2H), 4.25 (s, 4H); $^{19}$F NMR (CDCl$_3$): −47438; LCMS: ret. time: 17.73 min.; purity: 100%; MS (m/e): 369 (MH$^+$)

7.3.210 N2-(3,4-Ethylenedioxyphenyl)-5-fluoro-N2-[4-(hydroxymethyl)phenyl]-2,4-pyrimidinediamine (R925760)

In a manner similar to the preparation of N4-(3,4-ethylenedioxyphenyl)-5-fluoro-N2-(3-hydroxyphenyl)-2,4-pyrimidinediamine, 2-chloro-5-fluoro-N4-[4-(hydroxymethyl)phenyl]-4-pyrimidineamine and 3,4-ethylenedioxyaniline were reacted to yield N2-(3,4-ethylenedioxyphenyl)-5-fluoro-N2-[4-(hydroxymethyl)phenyl]-2,4-pyrimidinediamine. $^1$H NMR (CDCl$_3$): δ 7.92 (bs, 1H), 7.62 (d, 2H, J=8.7 Hz), 7.36 (d, 2H, J=8.7 Hz), 7.19 (d, 1H, J=2.1), 6.87 (dd, 1H, J=2.7 and 8.7 Hz), 6.79 (d, 1H, J=8.7 Hz), 4.68 (s, 2H), 4.28-4.23 (m, 4H); $^{19}$F NMR (CDCl$_3$): −4.7466; LCMS: ret. time: 17.86 min.; purity: 93%; MS (m/e): 369 (MH$^+$).

7.3.211 N2-(3,4-Ethylenedioxyphenyl)-5-fluoro-N2-(2-hydroxy-2-phenylethyl)-2,4-pyrimidinediamine (R925765)

In a manner similar to the preparation of N4-(3,4-ethylenedioxyphenyl)-5-fluoro-N2-(3-hydroxyphenyl)-2,4-pyrimidinediamine, 2-chloro-5-fluoro-N4-(2-hydroxy-2-phenylethyl)-4-pyrimidineamine and 3,4-ethylenedioxyaniline were reacted to yield N2-(3,4-ethylenedioxyphenyl)-5-fluoro-N2-(2-hydroxy-2-phenylethyl)-2,4-pyrimidinediamine. $^1$H NMR (CDCl$_3$): δ 7.79 (s, 1H), 7.48 (m, 5H), 6.89-6.71 (m, 3H), 5.41-5.38, 4.97 (dd, 1H, J=3.6 and 7.5 Hz), 4.28-4.22 (m, 4H), 3.88 (ddd, 1H, J=4.2, 7.2, and 14.1), 3.64-3.55 (m, 1H); $^{19}$F NMR (CDCl$_3$): −47910; LCMS: ret. time: 20.47 min.; purity: 88%; MS (m/e): 383 (MH$^+$).

7.3.212 N2-(3,4-Ethylendioxyphenyl)-5-fluoro-N4-[(2R)-hydroxy-(1S)-methyl-2-phenylethyl]-2,4-pyrimidinediamine (R925766)

In a manner similar to the preparation of N4-(3,4-ethylenedioxyphenyl)-5-fluoro-N2-(3-hydroxyphenyl)-2,4-pyrimidinediamine, 2-chloro-5-fluoro-N4-[(2R)-hydroxy-(1S)-methyl-2-phenylethyl]-4-pyrimidineamine and 3,4-ethylenedioxyaniline were reacted to yield N2-(3,4-ethylendioxyphenyl)-5-fluoro-N4-[(2R)-hydroxy-(1S)-methyl-2-phenylethyl]-2,4-pyrimidinediamine. $^1$H NMR (CDCl$_3$): δ 7.80 (bs, 1H), 7.71 (bs, 1H), 7.36-7.23 (m, 6H), 6.91 (dd, 1H, J=3.0 and 9.0 Hz), 6.80 (d, 1H, J=9.0 Hz), 5.17 (d, 1H, J=8.1 Hz), 5.01 (d, 1H, J=3.0 Hz), 4.56-4.50 (m, 1H), 4.24 (s, 4H), 1.10 (d, 3H, J=6.3 Hz); $^{19}$F NMR (CDCl$_3$): −47840; LCMS: ret. time: 21.43 min.; purity: 99%; MS (m/e): 397 (MH$^+$).

7.3.213 N4-Cyclohexyl-N2-(3,4-ethylenedioxyphenyl)-5-fluoro-2,4-pyrimidinediamine (R925794)

In a manner similar to the preparation of N4-(3,4-ethylenedioxyphenyl)-5-fluoro-N2-(3-hydroxyphenyl)-2,4-pyrimidinediamine, 2-chloro-N4-cyclohexyl-5-fluoro-4-pyrimidineamine and 3,4-ethylenedioxyaniline were reacted to yield N4-cyclohexyl-N2-(3,4-ethylenedioxyphenyl)-5-fluoro-2,4-pyrimidinediamine. $^1$H NMR (CD$_3$OD): δ 7.62 (d, 1H, J=4.2 Hz), 7.31 (d, 1H, J=2.1 Hz), 6.86 (dd, 1H, J=2.4 and 8.7 Hz), 6.68 (d, 1H, J=8.7 Hz), 4.23-4.16 (m, 4H), 3.99-3.89 (m, 1H), 2.03 (dd, 2H, J=2.1 and 12.3 Hz), 1.80 (dt, 2H, J=3.0 and 13.5 Hz), 1.72-1.65 (m, 1H), 1.49-1.20 (m, 5H); $^{19}$F NMR (CD$_3$OD): −48332; LCMS: ret. time: 24.54 min.; purity: 95%; MS (m/e): 345 (MH$^+$).

7.3.214 N4-(4-Carboxycyclohexyl)-N2-(3,4-ethylenedioxyphenyl)-5-fluoro-2,4-pyrimidinediamine (R925795)

In a manner similar to the preparation of N4-(3,4-ethylenedioxyphenyl)-5-fluoro-N2-(3-hydroxyphenyl)-2,4-pyrimidinediamine, N4-(4-carboxycyclohexyl)-2-chloro-5-fluoro-4-pyrimidineamine and 3,4-ethylenedioxyaniline were reacted to yield N4-(4-carboxycyclohexyl)-N2-(3,4-ethylenedioxyphenyl)-5-fluoro-2,4-pyrimidinediamine. $^1$H NMR (CD$_3$OD): δ 7.62 (d, 1H, J=4.2 Hz), 7.31 (d, 1H, J=2.4 Hz), 6.84 (dd, 1H, J=2.4 and 8.7 Hz), 6.70 (d, 1H, J=8.7 Hz), 4.23-4.18 (m, 4H), 3.99-4.08 (m, 1H), 2.59 (t, 1H, J=3.9 Hz), 2.16-2.09 (m, 2H), 1.91-1.84 (m, 2H), 1.78-1.57 (m, 4H); $^{19}$F NMR (CD$_3$OD): −48152; LCMS: ret. time: 19.31 min.; purity: 96%; MS (m/e): 389 (MH$^+$).

7.3.215 N4-(3,4-Ethylenedioxyphenyl)-5-fluoro-N2-(3-hydroxyphenyl)-2,4-pyrimidinediamine (R925796)

In a manner similar to the preparation of N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)-4-pyrimidineamine and 3,4-ethylenedioxyaniline were reacted to yield N4-(3,4-ethylenedioxyphenyl)-5-fluoro-N2-(3-hydroxyphenyl)-2,4-pyrimidinediamine. $^1$H NMR (DMSO-d6): δ 9.30 (s, 1H), 9.12 (bs, 1H), 8.91 (bs, 1H), 8.02 (d, 1H, J=3.3 Hz), 7.35-7.30 (m, 1H), 7.24-7.21 (m, 1H), 7.12 (t, 1H, J=1.8 Hz), 7.09-7.04 (m, 2H), 6.67 (d, 1H, J=9.0), 6.46 (dd, 1H, J=1.8 and 8.4 Hz), 4.18-4.12 (m, 4H); $^{19}$F NMR (DMSO-d6): −46594; LCMS: ret. time: 18.43 min.; purity: 97%; MS (m/e): 355 (MH$^+$).

7.3.216 N2-Allyl-N4-(3,4-ethylenedioxyphenyl)-5-fluoro-2,4-pyrimidinediamine (R925823)

In a manner similar to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and allylamine were reacted to yield N2-allyl-N4-(3,4-ethylenedioxyphenyl)-5-fluoro-2,4-pyrimidinediamine. $^1$H NMR (CD$_3$OD): δ 7.71 (bs, 1H), 7.37 (d, 1H, J=2.4 Hz), 7.07 (dd, 1H, J=2.4 and 8.7 Hz), 6.75 (d, 1H, J=8.7 Hz), 5.98-5.85 (m, 1H), 5.19 (dq, 1H, J=1.8 and 16.8 Hz), 5.06 (dq, 1H, J=1.8 and 10.5 Hz), 4.24-4.18 (m, 4H), 3.92-3.68 (m, 2H); $^{19}F$ NMR (CD$_3$OD): –48552; LCMS: ret. time: 19.36 min.; purity: 95%; MS (m/e): 303 (MH$^+$).

7.3.217 N4-(3,4-Ethylenedioxyphenyl)-N2-(4-ethylphenyl)-5-fluoro-2,4-pyrimidinediamine (R926237)

In a manner similar to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 4-ethylaniline were reacted to yield N4-(3,4-ethylenedioxyphenyl)-N2-(4-ethylphenyl)-5-fluoro-2,4-pyrimidinediamine. $^1$H NMR (CDCl$_3$): δ 7.87 (bs, 1H), 7.42 (d, 2H, J=8.7 Hz), 7.26 (d, 1H, J=3.0 Hz), 7.13-7.08 (m, 3H), 6.95 (dd, 1H, J=2.4 and 8.7 Hz), 6.82 (d, 1H, J=9.0 Hz), 6.60 (bs, 1H), 4.23 (s, 4H), 2.59 (q, 2H, J=7.5 Hz), 1.20 (t, 3H, J=7.5 Hz); $^{19}F$ NMR (CDCl$_3$): –47549; LCMS: ret. time: 25.31 min.; purity: 99%; MS (m/e): 367 (MH$^+$).

7.3.218 N4-(3,4-Ethylenedioxyphenyl)-5-fluoro-N2-[2-(methoxycarbonyl)benzofuran-5-yl]-2,4-pyrimidinediamine (R926690)

In a manner similar to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 2-methoxycarbonyl-5-aminobenzofuran were reacted to yield N4-(3,4-ethylenedioxyphenyl)-5-fluoro-N2-[2-(methoxycarbonyl)benzofuran-5-yl]-2,4-pyrimidinediamine. $^1$H NMR (DMSO-d6): δ 9.68 (bs, 1H), 8.13-8.10 (m, 2H), 7.63-7.54 (m, 3H), 7.27 (bs, 1H), 7.10 (d, 1H, J=8.7 Hz), 6.80 (d, 1H, J=8.1 Hz), 4.21 (s, 4H), 3.88 (s, 3H); LCMS: ret. time: 23.22 min.; purity: 95%; MS (m/e): 437 (MH$^+$).

7.3.219 5-Fluoro-N2-(2-methoxycarbonylbenzofuran-5-yl)-N4-(4-isopropoxyphenyl)-2,4-pyrimidinediamine (R926704)

In a manner similar to the preparation of N4-(3,4-ethylenedioxyphenyl)-5-fluoro-N2-(3-hydroxyphenyl)-2,4-pyrimidinediamine, 2-chloro-5-fluoro-N4-[4-(isopropoxy)phenyl]-4-pyrimidineamine and 2-methoxycarbonyl-5-aminobenzofuran were reacted to yield 5-fluoro-N2-(2-methoxycarbonylbenzofuran-5-yl)-N4-(4-isopropoxyphenyl)-2,4-pyrimidinediamine. $^1$H NMR (CDCl$_3$): δ 8.04 (d, 1H, J=1.8 Hz), 7.49-7.41 (m, 4H), 7.35 (dd, 1H, J=2.4 and 8.7 Hz), 7.14 (bs, 1H), 6.90 (d, 2H, J=9.3 Hz), 6.70 (bs, 1H), 4.56 (2q, 1H, J=5.7 Hz), 3.98 (s, 3H), 1.37 (d, 6H, J=5.7 Hz); LCMS: ret. time: 25.52 min.; purity: 98%; MS (m/e): 437 (MH$^+$).

7.3.220 5-Fluoro-N4-(3-hydroxyphenyl)-N2-[4-(2-hydroxyethyl)oxyphenyl]-2,4-pyrimidinediamine (R926376)

In like manner to N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)]-4-pyrimidineamine and 4-(2-hydroxyethyloxy)aniline were reacted to yield 5-fluoro-N4-(3-hydroxyphenyl)-N2-[4-(2-hydroxyethyl)oxyphenyl]-2,4-pyrimidinediamine. $^1$H NMR (D$_2$O): δ 8.40 (d, 1H J=4 Hz), 7.57 (m, 6H), 7.12 (m, 2H), 6.90 (m, 2H), 4.40 (m, 4H) 2.2 (s, 3H); LCMS: ret. time: 13.61 min.; purity: 97%; MS (m/e): 357 (MH$^+$).

7.3.221 N2-[4-(2-N,N-Dimethylamino)ethoxyphenyl]-5-fluoro-N4-(3-hydroxyphenyl)-2,4-pyrimidinediamine (R909236)

In like manner to N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)]-4-pyrimidineamine and 4-(2-N,N-dimethylamino)ethoxyaniline were reacted to yield N2-[4-(2-N,N-dimethylamino)ethoxyphenyl]-5-fluoro-N4-(3-hydroxyphenyl)-2,4-pyrimidinediamine. $^1$H NMR (CD$_3$OD): δ 7.80 (d, 1H J=4 Hz), 7.47 (dd, 1H, J=6.8 Hz, 2.7 Hz), 7.44 (m, 1H), 7.05 (m, 1H), 6.85 (m, 1H), 6.78 (m, 2H), 4.16 (m, 2H), 3.03 (m, 2H), 2.55 (s, 6H); LCMS: ret. time: 12.74 min.; purity: 98%; MS (m/e): 384 (MH$^+$).

7.3.222 N2-(1,4-Benzoxazin-3-on-6-yl)-5-fluoro-N4-(3-hydroxyphenyl)-2,4-pyrimidinediamine (R909238)

In like manner to N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)]-4-pyrimidineamine and 6-amino-1,4-benzoxazin-3-one were reacted to yield N2-(1,4-benzoxazin-3-on-6-yl)-5-fluoro-N4-(3-hydroxyphenyl)-2,4-pyrimidinediamine. $^1$H NMR (DMSO-d6): δ 8.18 (d, 1H J=4 Hz), 7.17 (m, 3H), 7.09 (m, 1H), 7.06 (m, 1H), 6.58 (m, 1H) 4.52 (s, 3H); LCMS: ret. time: 17.18 min.; purity: 99%; MS (m/e): 368 (MH$^+$).

7.3.223 N2-(1,4-Benzoxazin-6-yl)-5-fluoro-N4-(3-hydroxyphenyl)-2,4-pyrimidinediamine (R909241)

In like manner to N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)]pyrimidineamine and 6-amino-1,4-benzoxazine were reacted to yield N2-(1,4-benzoxazin-6-yl)-5-fluoro-N4-(3-hydroxyphenyl)-2,4-pyrimidinediamine. $^1$H NMR (CD$_3$OD): δ ☐☐☐ (d, 1H, J=4 Hz), 7.15 (m, 3H), 6.68 (m, 2H), 6.52 (m, 2H), 6.52 (m, 1H), 4.18 (m, 2H), 3.37 (m, 2H); LCMS: ret. time 17.42 min.; purity: 95%; MS (m/e): 354 (MH$^+$).

7.3.224 N4-(1,4-Benzoxazin-6-yl)-N2-[3-ethoxyocarbonylmethyleneoxyphenyl]-5-fluoro-2,4-pyrimidinediamine (R909242)

In like manner to N4-(3,4-ethylenedioxyphenyl)-5-fluoro-N2-(3-hydroxyphenyl)-2,4-pyrimidinediamine, N4-(1,4-benzoxazin-6-yl)-N2-chloro-5-fluoro-4-pyrimidineamine and 3-ethoxyocarbonylmethyleneoxyaniline were reacted to yield N4-(1,4-benzoxazin-6-yl)-N2-(3-ethoxyocarbonylmethyleneoxyphenyl)-5-fluoro-2,4-pyrimidinediamine. $^1$H NMR (CD$_3$OD): δ ☐☐ (d, 1H, J=4 Hz), 7.15 (m, 4H), 6.84 (m, 2H), 6.62 (m, 1H), 4.65 (s, 2H), 4.15 (m, 4H), 3.28 (m, 2H), 1.19 (t, 3H. J=7 Hz); LCMS: ret. time 22.6 min.; purity: 94%; MS (m/e): 439 (MH$^+$).

7.3.225 N2-(1,4-Benzoxazin-6-yl)-5-fluoro-N4-(3-hydroxyphenyl)-2,4-pyrimidinediamine (R909243)

In like manner to N4-(3,4-ethylenedioxyphenyl)-5-fluoro-N2-(3-hydroxyphenyl)-2,4-pyrimidinediamine, N4-(1,4-benzoxazin-6-yl)-N2-chloro-5-fluoro-4-pyrimidineamine and 3-aminophenol were reacted to yield N4-(1,4-benzoxazin-6-yl)-5-fluoro-N2-(3-hydroxyphenyl)-2,4-pyrimidinediamine. $^1$H NMR (DMSO-d6): δ ☐☐☐ (d, 1H, J=4 Hz), 7.18 (m, 3H), 6.68 (m, 2H), 6.45 (m, 2H), 6.52 (m, 1H), 4.22 (m, 2H), 3.31 (m, 2H); LCMS: ret. time: 17.24; purity: 96%; MS (m/e): 354 (MH$^+$).

7.3.226 N4-(1,4-Benzoxazin-6-yl)-N2-(3,5-dimethoxyphenyl)-5-fluoro-2,4-pyrimidinediamine (R909245)

In like manner to N4-(3,4-ethylenedioxyphenyl)-5-fluoro-N2-(3-hydroxyphenyl)-2,4-pyrimidinediamine, N4-(1,4-benzoxazin-6-yl)-N2-chloro-5-fluoro-4-pyrimidineamine and 3,5-dimethoxyaniline were reacted to yield N4-(1,4-benzoxazin-6-yl)-N2-(3,5-dimethoxyphenyl)-5-fluoro-2,4-pyrimidinediamine. $^1$H NMR (DMSO-d6): δ ☐$_1$☐ (d, 1H, J=4 Hz), 6.80 (m, 4H), 6.60 (m, 1H), 6.05 (m, 1H), 4.02 (m, 2H), 3.65 (s, 6H), 3.31 (m, 2H); LCMS: ret. time: 22.38 min.; purity: 99%; MS (m/e): 398 (MH$^+$).

7.3.227 N4-(1,4-Benzoxazin-6-yl)-N2-(3-tert-butylphenyl)-5-fluoro-2,4-pyrimidinediamine (R909246)

In like manner to N4-(3,4-ethylenedioxyphenyl)-5-fluoro-N2-(3-hydroxyphenyl)-2,4-pyrimidinediamine, N4-(1,4-benzoxazin-6-yl)-N2-chloro-5-fluoro-4-pyrimidineamine and 3-tert-butylaniline were reacted to yield N4-(1,4-benzoxazin-6-yl)-N2-(3-tert-butylphenyl)-5-fluoro-2,4-pyrimidinediamine. $^1$H NMR (DMSO-d6): δ ☐☐ (d, 1H, J=4 Hz), 7.5 (m, 1H), 7.4 (m, 1H), 7.18 (m, 1H), 7.02 (m, 1H), 6.80 (m, 2H), 6.60 (m, 1H), 4.02 (m, 2H), 3.31 (m, 2H), 1.2 (s, 9H); LCMS: ret. time: 26.64 min.; purity: 99%; MS (m/e): 508 (MH$^+$).

7.3.228 N4-(1,4-Benzoxazin-6-yl)-5-fluoro-N2-[4-(2-hydroxyethyl)oxyphenyl]-2,4-pyrimidinediamine (R909248)

In like manner to N4-(3,4-ethylenedioxyphenyl)-5-fluoro-N2-(3-hydroxyphenyl)-2,4-pyrimidinediamine, N4-(1,4-benzoxazin-6-yl)-N2-chloro-5-fluoro-4-pyrimidineamine and 4-(2-hydroxyethyl)oxyaniline were reacted to yield N4-(1,4-benzoxazin-6-yl)-5-fluoro-N2-[4-(2-hydroxyethyl)oxyphenyl]-2,4-pyrimidinediamine. $^1$H NMR (DMSO-d6): δ ☐☐☐ (d, 1H, J=4 Hz), 7.52 (m, 1H), 7.4 (m, 3H), 6.90 (m, 2H), 6.68 (m, 1H), 4.56 (s, 2H), 4.02 (m, 2H), 3.75 (m, 2H), 3.31 (m, 4H); LCMS: ret. time: 26.67 min.; purity: 93%; MS(m/e): 399 (MH$^+$).

7.3.229 N2-(2,3-Dihydrobenzofuran-5-yl)-5-fluoro-N4-(3-hydroxyphenyl)-2,4-pyrimidinediamine (R909250)

In like manner to N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)]-4-pyrimidineamine and 5-amino-2,3-dihydrobenzofuran were reacted to yield N2-(2,3-dihydrobenzofuran-5-yl)-5-fluoro-N4-(3-hydroxyphenyl)-2,4-pyrimidinediamine. $^1$HNMR (DMSO-d6): δ 8.09 (d, 1H), 8.00 (m, 1H), 7.82 (m, 1H), 7.57 (m, 1H), 7.22 (m, 1H), 7.08 (m, 1H), 6.99 (m, 1H), 6.82 (m, 1H), 6.70 (m, 1H), 6.42 (m, 1H), 4.49 (m, 2H), 3.15 (m, 2H); LCMS: ret time: 19.39 min.; MS (m/e): 338 (MH$^+$).

7.3.230 N4-(1,4-Benzoxazin-6-yl)-N2-(3-chloro-4-hydroxy-5-methylphenyl)-5-fluoro-2,4-pyrimidinediamine (R909255)

In like manner to N4-(3,4-ethylenedioxyphenyl)-5-fluoro-N2-(3-hydroxyphenyl)-2,4-pyrimidinediamine, N4-(1,4-benzoxazin-6-yl)-N2-chloro-5-fluoro-4-pyrimidineamine and 3-chloro-4-hydroxy-5-methylaniline were reacted to yield N4-(1,4-benzoxazin-6-yl)-N2-(3-chloro-4-hydroxy-5-methylphenyl)-5-fluoro-2,4-pyrimidinediamine. $^1$H NMR (DMSO-d6): δ ☐☐☐ (d, 1H, J=4 Hz), 7.25 (m, 1H), 7.14 (m, 1H), 6.80 (m, 2H), 6.82 (m, 1H), 4.29 (s, 2H), 3.35 (m, 2H), 2.20 (s, 3H); LCMS: ret. time: 17.05 min.; purity: 99%; MS(m/e): 402 (MH$^+$).

7.3.231 5-Fluoro-N2-(2,3-dihydro-2-(methoxycarbonyl)benzofuran-5-yl)-N4-(4-isopropoxyphenyl)-2,4-pyrimidinediamine (R926706)

In a manner similar to the preparation of N4-(3,4-ethylenedioxyphenyl)-5-fluoro-N2-(3-hydroxyphenyl)-2,4-pyrimidinediamine, 2-chloro-5-fluoro-N4-(4-isopropoxyphenyl)-4-pyrimidineamine and 5-amino-2,3-dihydro-2-(methoxycarbonyl)benzofuran were reacted to yield 5-fluoro-N2-(2,3-dihydro-2-(methoxycarbonyl)benzofuran-5-yl)-N4-(4-isopropoxyphenyl)-2,4-pyrimidinediamine. $^1$H NMR (CDCl$_3$): δ 7.87 (d, 1H, J=3.0 Hz), 7.47-7.42 (m, 3H), 7.12 (dd, 1H, J=2.4 and 8.4 Hz), 6.87 (d, 2H, J=9.6 Hz), 6.80 (d, 1H, J=8.7 Hz), 6.63 (d, 1H, J=2.4 Hz), 5.21 (dd, 1H, J=6.3 and 10.5 Hz), 4.53 (2q, 1H, J=5.7 Hz), 3.80 (s, 3H), 3.52 (dd, 1H, J=10.5 and 15.9 Hz), 3.35 (dd, 1H, J=6.3 and 15.9 Hz), 1.34 (d, 6H, J=5.7 Hz); $^{19}$F NMR (CDCl$_3$): −47664; LCMS: ret. time: 23.78 min.; purity: 95%; MS (m/e): 439 (MH$^+$).

7.3.232 5-Fluoro-N4-(3-hydroxyphenyl)-N2-[4-[2-(N-morpholino)ethyleneoxy]phenyl]-2,4-pyrimidinediamine (R926699)

In a manner similar to the preparation of N4-(3,4-ethylenedioxyphenyl)-5-fluoro-N2-(3-hydroxyphenyl)-2,4-pyrimidinediamine, 2-chloro-N4-(3-hydroxyphenyl)-5-fluoro-4-pyrimidineamine and 4-[2-(N-morpholino)ethyleneoxy]aniline were reacted to yield 5-fluoro-N4-(3-hydroxyphenyl)-N2-[4-[2-(N-morpholino)ethyleneoxy]phenyl]-2,4-pyrimidinediamine. $^1$H NMR (DMSO-d6): δ 9.34 (s, 1H), 9.17 (bs, 1H), 8.95 (bs, 1H), 8.02 (d, 1H, J=3.3 Hz), 7.53 (d, 2H, J=9.0 Hz), 7.28-7.23 (m, 1H), 7.12-7.04 (m, 2H, 6.79 (d, 2H, J=9.0 Hz), 6.47 (dd, 1H, J=1.2 and 5.7 Hz), 4.00 (t, 2H, J=6.0 Hz), 3.56 (t, 4H, J=4.5 Hz), 2.64 (t, 2H, J=6.0 Hz), 2.44 (t, 4H, J=4.5 Hz); $^{19}$F NMR (DMSO-d6): −46715; LCMS: ret. time: 12.66 min.; purity: 95%; MS (m/e): 426 (MH$^+$).

7.3.233 N4-(3,4-Ethylenedioxyphenyl)-5-fluoro-N2-[4-[2-(N-morpholino)ethyleneoxy]phenyl]-2,4-pyrimidinediamine (R926709)

In a manner similar to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 4-[2-(N-morpholino)ethyleneoxy]aniline were reacted to yield N4-(3,4-ethylenedioxyphenyl)-5-fluoro-N2-[4-[2-(N-morpholino)ethyleneoxy]phenyl]-2,4-pyrimidinediamine. $^1$H NMR (CD$_3$OD): δ 7.80 (d, 1H, J=3.6 Hz), 7.72 (bs, 1H), 7.62 (bs, 1H), 7.41 (d, 1H, J=9.3 Hz), 7.24 (d, 1H, J=5.4 Hz), 7.05 (dd, 1H, J=2.4 and 8.7 Hz), 6.84 (d, 2H, J=8.7 Hz), 6.75 (d, 1H, J=9.0 Hz), 4.24 (bs, 4H), 4.11 (t, 2H, J=5.4 Hz), 3.74-3.69 (m, 4H), 2.80 (t, 2H, J=5.4 Hz), 2.62-2.58 (m, 4H); $^{19}F$ NMR (CD$_3$OD): –47912; LCMS: ret. time: 15.16 min.; purity: 91%; MS (m/e): 468 (MH$^+$).

7.3.234 5-Fluoro-N2-(3-hydroxyphenyl)-N4-[4-[2-(N-morpholino)ethyleneoxy]phenyl]-2,4-pyrimidinediamine (R926710)

In a manner similar to the preparation of N4-(3,4-ethylenedioxyphenyl)-5-fluoro-N2-(3-hydroxyphenyl)-2,4-pyrimidinediamine, 2-chloro-5-fluoro-N4-[4-[2-(N-morpholino)ethyleneoxy]phenyl]-4-pyrimidineamine and 3-aminophenol were reacted to yield 5-fluoro-N2-(3-hydroxyphenyl)-N4-[4-[2-(N-morpholino)ethyleneoxy]phenyl]-2,4-pyrimidinediamine. $^1H$ NMR (CD$_3$OD): δ 7.84 (d, 1H, J=4.2 Hz), 7.60 (d, 1H. J=9.3 Hz), 7.09 (t, 1H, J=2.4 Hz), 7.04-6.96 (m, 2H), 6.93 (d, 2H, J=9.3 Hz), 6.40 (dt, 1H, J=1.8 and 7.5 Hz), 4.15 (t, 2H, J=5.4 Hz), 3.75-3.70 (m, 4H), 2.81 (t, 2H, J=5.1 Hz), 2.63-2.59 (m, 4H); LCMS: ret. time: 14.16 min.; purity: 98%; MS (m/e): 426 (MH$^+$).

7.3.235 N2-(3,4-Ethylenedioxyphenyl)-5-fluoro-N4-[4-[2-(N-morpholino)ethyleneoxy]phenyl]-2,4-pyrimidinediamine (R926711)

In a manner similar to the preparation of N4-(3,4-ethylenedioxyphenyl)-5-fluoro-N2-(3-hydroxyphenyl)-2,4-pyrimidinediamine, 2-chloro-5-fluoro-N4-[4-[2-(N-morpholino)ethyleneoxy]phenyl]-4-pyrimidineamine and 3,4-ethylenedioxyaniline were reacted to yield N2-(3,4-ethylenedioxyphenyl)-5-fluoro-N4-[4-[2-(N-morpholino)ethyleneoxy]phenyl]-2,4-pyrimidinediamine. $^1H$ NMR (CD$_3$OD): δ 7.80 (d, 1H, J=4.2 Hz), 7.56 (d, 2H, J=8.7 Hz), 7.13 (d, 1H, J=2.4 Hz), 6.91 (d, 2H, J=9.6 Hz), 6.86 (dd, 1H, J=2.4 and 9.0 Hz), 6.67 (d, 1H, J=9.0 Hz), 4.23-4.18 (m, 4H), 4.14 (t, 3H, J=5.4 Hz), 3.74-3.70 (m, 4H), 2.82 (t, 3H, J=5.4 Hz), 2.64-2.59 (m, 4H); $^{19}F$ NMR (CDCl$_3$): –47914; LCMS: ret. time: 15.97 min.; purity: 94%; MS (m/e): 468 (MH$^+$).

7.3.236 N4-(3,4-Ethylenedioxyphenyl)-5-fluoro-N2-[4-(tetrahydro-(1H)-pyrrol-1-ylsulfonyl)phenyl]-2,4-pyrimidinediamine (R926716)

In a manner similar to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 4-(tetrahydro-(1H)-pyrrol-1-ylsulfonyl)aniline were reacted to yield N4-(3,4-ethylenedioxyphenyl)-5-fluoro-N2-[4-(tetrahydro-(1H)-pyrrol-1-ylsulfonyl)phenyl]-2,4-pyrimidinediamine. $^1H$ NMR (DMSO-d6): δ 10.11 (bs, 1H), 9.76 (bs, 1H), 8.19 (d, 1H, J=3.9 Hz), 7.82 (d, 2H, J=8.7 Hz), 7.62 (d, 2H, J=8.7 Hz), 7.27 (d, 1H, J=2.4 Hz), 7.08 (dd, 1H, J=2.4 and 8.7 Hz), 6.85 (d, 1H, J=8.7 Hz), 4.23 (s, 4H), 3.10-3.06 (m, 4H), 1.64-1.58 (m, 4H); LCMS: ret. time: 22.68 min.; purity: 93%; MS (m/e): 472 (MH$^+$).

7.3.237 N2-[3-[4-(2-Chloro-6-fluorobenzyl)piperazino]propyl]-N4-(3,4-ethylenedioxyphenyl)-5-fluoro-2,4-pyrimidinediamine (R926717)

In a manner similar to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 3-[4-(2-chloro-6-fluorobenzyl)piperazino]propylamine were reacted to yield N2-[3-[4-(2-chloro-6-fluorobenzyl)piperazino]propyl]-N4-(3,4-ethylenedioxyphenyl)-5-fluoro-2,4-pyrimidinediamine. $^1H$ NMR (CDCl$_3$): δ 7.79 (d, 1H, J=3.0 Hz), 7.37 (d, 1H, J=2.4 Hz), 7.19-7.15 (m, 2H), 7.00-6.93 (m, 2H), 6.81 (d, 1H, J=8.7 Hz), 6.56 (d, 1H, J=2.7 Hz), 5.48 (bs, 1H), 4.27-4.21 (m, 4H), 3.70 (d, 2H, J=1.8 Hz), 3.36 (q, 2H, J=6.3 Hz), 2.68-2.35 (m, 10H), 1.75 (q, 2H, J=6.3 Hz); $^{19}F$ NMR (CDCl$_3$): –31693, –48483; LCMS: ret. time: 18.20 min.; purity: 97%; MS (m/e): 532 (MH$^+$).

7.3.238 N2-(4-tert-Butylphenyl)-5-fluoro-N2-[2,3-dihydro-2-(methoxycarbonyl)benzofuran-5-yl]-2,4-pyrimidinediamine (R926719)

In a manner similar to the preparation of N4-(3,4-ethylenedioxyphenyl)-5-fluoro-N2-(3-hydroxyphenyl)-2,4-pyrimidinediamine, N4-(4-tert-butylphenyl]-2-chloro-5-fluoro-4-pyrimidineamine and 5-amino-2,3-dihydro-2-(methoxycarbonyl)benzofuran were reacted to yield N2-(4-tert-butylphenyl)-5-fluoro-N2-[2,3-dihydro-2-(methoxycarbonyl)benzofuran-5-yl]-2,4-pyrimidinediamine. $^1H$ NMR (DMSO-d6): δ 10.16 (bs, 1H), 9.84 (bs, 1H), 8.16 (d, 1H, J=5.4 Hz), 7.56 (d, 2H, J=8.1 Hz), 7.49 (s, 1H), 7.35 (d, 2H, J=8.7 Hz), 7.13 (dd, 1H, J=1.8 and 8.7 Hz), 6.78 (d, 1H, J=8.7 Hz), 5.35 (dd, 1H, J=6.6 and 10.5 Hz), 3.52 (dd, 1H, J=10.5 and 16.5 Hz), 3.20 (dd, 1H, J=6.6 and 16.5 Hz), 1.27 (s, 9H); LCMS: ret. time: 26.52 min.; purity: 96%; MS (m/e): 437 (MH$^+$).

7.3.239 N4-[(5-Chloro-1-benzothiophen-3-yl)methyl]-N2-(3,4-ethylenedioxyphenyl)-5-fluoro-2,4-pyrimidinediamine (R926721)

In a manner similar to the preparation of N4-(3,4-ethylenedioxyphenyl)-5-fluoro-N2-(3-hydroxyphenyl)-2,4-pyrimidinediamine, 2-chloro-N4-[(5-chloro-1-benzothiophen-3-yl)methyl]-5-fluoro-4-pyrimidineamine and 3,4-ethylenedioxyaniline were reacted to yield N4-[(5-chloro-1-benzothiophen-3-yl)methyl]-N2-(3,4-ethylenedioxyphenyl)-5-fluoro-2,4-pyrimidinediamine. $^1H$ NMR (DMSO-d6): δ 8.08 (d, 1H, J=1.8 Hz), 8.02 (d, 1H, J=8.7 Hz), 7.97 (d, 1H, J=4.8 Hz), 7.63 (s, 1H), 7.42 (dd, 1H, J=1.8 and 9.3 Hz), 7.07 (bs, 1H), 6.85 (dd, 1H, J=2.4 and 8.7 Hz), 6.56 (d, 1H, J=8.7 Hz), 4.77 (s, 1H), 4.75 (s, 1H), 4.14 (s, 4H); LCMS: ret. time: 25.89 min.; purity: 97%; MS (m/e): 444 (MH$^+$).

7.3.240 N4-[(5-Chloro-1-benzothiophen-3-yl)methyl]-5-fluoro-N2-(3-hydroxyphenyl)-2,4-pyrimidinediamine (R926722)

In a manner similar to the preparation of N4-(3,4-ethylenedioxyphenyl)-5-fluoro-N2-(3-hydroxyphenyl)-2,4-pyrimidinediamine, 2-chloro-N4-[(5-chloro-1-benzothiophen-3-yl)methyl]-5-fluoro-4-pyrimidineamine and 3-aminophenol were reacted to yield N4-[(5-chloro-1-benzothiophen-3-yl)methyl]-5-fluoro-N2-(3-hydroxyphenyl)-2,4-pyrimidinediamine. $^1H$ NMR (DMSO-d6): δ 9.47 (bs, 1H), 9.33 (bs, 1H), 8.78 (bs, 1), 8.11 (d, 1H, J=2.1 Hz), 8.02 (d, 1H, J=J=8.7 Hz), 7.98 (d, 1H, J=4.5 Hz), 7.69 (s, 1H), 7.41 (dd, 1H, J=1.8, 8.1 Hz), 7.07 (bs, 1H), 6.92 (d, 1H, J=8.4 Hz), 6.82 (t, 1H, J=8.1 Hz), 6.34 (d, 1H, J=6.9 Hz), 4.80 (s, 1H), 4.78 (s, 1H); LCMS: ret. time: 23.32 min.; purity: 93%; MS (m/e): 402 (MH$^+$).

7.3.241 N4-[2-[(2-Chloro-6-fluorobenzyl)thio]ethyl]-N2-(3,4-ethylenedioxy)-5-fluoro-2,4-pyrimidinediamine (R926723)

In a manner similar to the preparation of N4-(3,4-ethylenedioxyphenyl)-5-fluoro-N2-(3-hydroxyphenyl)-2,4-pyrimidinediamine, 2-chloro-N4-[2-[(2-chloro-6-fluorobenzyl)thio]ethyl]-5-fluoro-4-pyrimidineamine and 1,4-benzodioxan-6-amine were reacted to yield N4-[2-[(2-chloro-6-fluorobenzyl)thio]ethyl]-N2-(3,4-ethylenedioxy)-5-fluoro-2,4-pyrimidinediamine. $^1$H NMR (DMSO-d6): δ 9.09 (bs, 1H), 7.94 (bs, 1H), 7.87 (d, 1H, J=4.2 Hz), 7.34-7.30 (m, 2H), 7.24-7.18 (m, 2H), 7.01 (dd, 1H, J=2.4 and 8.7 Hz), 6.68 (d, 1H, J=8.7 Hz), 4.11 (s, 4H), 3.83 (d, 2H, J=1.2 Hz), 3.63-3.56 (m, 2H), 2.74 (t, 2H, J=7.5 Hz); LCMS: ret. time: 25.17 min.; purity: 92%; MS (m/e): 466 (MH$^+$).

7.3.242 N2-(2,3-Dihydro-1,4-benzodioxin-6-ylmethyl)-5-fluoro-N4-(3-hydroxyphenyl)-2,4-pyrimidinediamine (R945168)

In a manner analogous to the preparation of 2-chloro-N4-(3,4-ethylenedioxyphenyl)-5-fluoro-N2-(3-hydroxyphenyl)-2,4-pyrimidineamine, 2-chloro-5-fluoro-N4-(3-hydroxyphenyl)-4-pyrimidineamine and 2,3-dihydro-1,4-benzodioxin-6-ylmethylamine gave N2-(2,3-dihydro-1,4-benzodioxin-6-ylmethyl)-5-fluoro-N4-(3-hydroxyphenyl)-2,4-pyrimidinediamine. $^1$H NMR (CDCl$_3$) δ 4.24 (s, 4H), 4.45 (d, J=6.0 Hz, 2H), 6.55 (ddd, J=0.9, 2.4 and 8.4 Hz, 1H), 6.66 (d, 1H), 6.84 (m, 4H), 6.90 (m, 1H), 7.14 (t, J=8.1 Hz, 1H), 7.30 (m, 1H), 7.86 (d, J=3.3 Hz, 1H); $^{19}$F NMR (282 MHz, CDCl$_3$) 6-170.44; LCMS: ret. time: 18.33 min.; purity: 96.75%; MS (m/e): 369.03 (MH$^+$).

7.3.243 N4-[2-[(2-Chloro-6-fluorobenzyl)thio]ethyl]-5-fluoro-N2-(3-hydroxyphenyl)-2,4-pyrimidinediamine (R926724)

In a manner similar to the preparation of N4-(3,4-ethylenedioxyphenyl)-5-fluoro-N2-(3-hydroxyphenyl)-2,4-pyrimidinediamine, 2-chloro-N4-[2-[(2-chloro-6-fluorobenzyl)thio]ethyl]-5-fluoro-4-pyrimidineamine and 3-aminophenol were reacted to yield N4-[2-[(2-chloro-6-fluorobenzyl)thio]ethyl]-5-fluoro-N2-(3-hydroxyphenyl)-2,4-pyrimidinediamine. $^1$H NMR (methyl sulfoxide-d$_6$): δ 9.76 (bs, 1H), 9.42 (bs, 1H), 8.70 (bs, 1H), 8.02 (d, 1H, J=5.1 Hz), 7.33-7.30 (m, 2H), 7.24-7.18 (m, 1H), 7.08-6.96 (m, 2H), 6.42 (d, 1H, J=4.6 Hz), 3.82 (d, 2H, J=1.2 Hz), 3.68-3.61 (m, 2H), 2.77 (t, 2H, J=7.2 Hz); LCMS: ret. time: 23.00 min.; purity: 93%; MS (m/e): 424 (MH$^+$).

7.3.244 N4-(3,4-Ethylenedioxyphenyl)-5-fluoro-N2-(3-phenyl-5-methylisoxazol-4-yl)-2,4-pyrimidinediamine (R926743)

In a manner similar to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 5-methyl-3-phenyl-4-isoxazolamine were reacted to yield N4-(3,4-ethylenedioxyphenyl)-5-fluoro-N2-(3-phenyl-5-methylisoxazol-4-yl)-2,4-pyrimidinediamine. LCMS: ret. time: 20.90 min.; purity: 96%; MS (m/e): 420 (MH$^+$).

7.3.245 N4-(3,4-Ethylenedioxyphenyl)-5-fluoro-N2-(3,5-dimethylisoxazol-4-yl)-2,4-pyrimidinediamine (R926744)

In a manner similar to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 3,5-dimethyl-4-isoxazolamine were reacted to yield N4-(3,4-ethylenedioxyphenyl)-5-fluoro-N2-(3,5-dimethylisoxazol-4-yl)-2,4-pyrimidinediamine. LCMS: ret. time: 18.89 min.; purity: 98%; MS (m/e): 358 (MH$^+$).

7.3.246 N2-[2-(Ethoxycarbonylmethylenethio)pyridin-5-yl]-N4-(3,4-ethylenedioxyphenyl)-5-fluoro-2,4-pyrimidinediamine (R926727)

In a manner similar to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 5-amino-2-(ethoxycarbonylmethylenethio)pyridine were reacted to yield N2-[2-(ethoxycarbonylmethylenethio)pyridin-5-yl]-N4-(3,4-ethylenedioxyphenyl)-5-fluoro-2,4-pyrimidinediamine. $^1$H NMR (DMSO-d6): δ 9.30 (s, 1H), 9.22 (s, 1H), 8.62 (d, 1H, J=2.4 Hz), 8.06-8.01 (m, 2H), 7.25 (d, 1H, J=2.4 Hz), 7.18-7.14 (m, 2H), 6.80 (d, 1H, J=6.0 Hz), 4.22 (bs, 4H), 4.07 (q, 2H, J=6.9 Hz), 3.95 (s, 2H), 1.14 (t, 3H, J=6.9 Hz); LCMS: ret. time: 21.60 min.; purity: 97%; MS (m/e): 458 (MH$^+$).

7.3.247 N2-[2-(Ethoxycarbonylmethyleneoxy)pyridin-5-yl]-N4-(3,4-ethylenedioxyphenyl)-5-fluoro-2,4-pyrimidinediamine (R926740)

In a manner similar to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 5-amino-2-(ethoxycarbonylmethyleneoxy)pyridine were reacted to yield N2-[2-(ethoxycarbonylmethyleneoxy)pyridin-5-yl]-N4-(3,4-ethylenedioxyphenyl)-5-fluoro-2,4-pyrimidinediamine. $^1$H NMR (DMSO-d6): δ 9.54 (bs, 1H), 9.14 (bs, 1H), 8.05 (s, 1H), 7.88 (d, 1H, J=2.4 Hz), 7.54 (dd, 1H, J=2.7 and 10.2 Hz), 7.22 (d, 1H, J=1.8 Hz), 7.10 (dd, 1H, J=1.8 and 8.7 Hz), 6.75 (d, 1H, J=9.0 Hz), 6.40 (d, 1H, J=9.9 Hz), 4.55 (s, 2H), 4.20 (bs, 4H), 4.10 (q, 2H, J=7.2 Hz), 1.18 (t, 2H, J=7.2 Hz).

7.3.248 5-Bromo-N2-(3,4-ethylenedioxyphenyl)-N4-(3-hydroxyphenyl)-2,4-pyrimidinediamine (R925797)

In a manner similar to the preparation of N4-(3,4-ethylenedioxyphenyl)-5-fluoro-N2-(3-hydroxyphenyl)-2,4-pyrimidinediamine, 5-bromo-2-chloro-N4-(3-hydroxyphenyl)-4-pyrimidineamine and 3,4-ethylenedioxyaniline were reacted to yield 5-bromo-N2-(3,4-ethylenedioxyphenyl)-N4-(3-hydroxyphenyl)-2,4-pyrimidinediamine. $^1$H NMR (CDCl$_3$): δ 9.33 (s, 1H), 9.06 (s, 1H), 8.34 (s, 1H), 8.14 (s, 1H), 7.13-7.06-(m, 4H), 6.94 (bs, 1H), 6.61 (d, 1H, J=8.7 Hz), 6.54-6.50 (m, 1H), 4.17-4.13 (m, 4H); LCMS: ret. time: 20.01 min.; purity: 93%; MS (m/e): 416 (MH$^+$).

7.3.249 N2-Allyl-5-bromo-N4-(3-hydroxyphenyl)-2,4-pyrimidinediamine (R925822)

In a manner similar to the preparation of N4-(3,4-ethylenedioxyphenyl)-5-fluoro-N2-(3-hydroxyphenyl)-2,4-pyrimidinediamine, 5-bromo-2-chloro-N4-(3-hydroxyphenyl)-4-pyrimidineamine and allylamine were reacted to yield N2-allyl-5-bromo-N4-(3-hydroxyphenyl)-2,4-pyrimidinediamine. $^1$H NMR (CD$_3$OD): δ 8.08 (s, 1H), 7.21 (t, 1H, J=8.1 Hz), 7.02-6.97 (m, 2H), 6.71 (dd, 1H, J=2.4 and 8.7 Hz), 5.91-5.77 (m, 1H), 5.19-5.09 (m, 2H), 3.94-3.89 (m, 2H); LCMS: ret. time: 18.33 min.; purity: 99%; MS (m/e): 322 (MH$^+$).

7.3.250 5-Cyano-N2-(3,4-ethylenedioxyphenyl)-N4-(methoxycarbonylbenzyl)-2,4-pyrimidinediamine (R925820)

In a manner similar to the preparation of N4-(3,4-ethylenedioxyphenyl)-5-fluoro-N2-(3-hydroxyphenyl)-2,4-pyrimidinediamine, 2-chloro-5-cyano-N4-(methoxycarbonylbenzyl)-4-pyrimidineamine and 3,4-ethylenedioxyaniline were reacted to yield 5-cyano-N2-(3,4-ethylenedioxyphenyl)-N4-(methoxycarbonylbenzyl)-2,4-pyrimidinediamine. $^1$H NMR (CDCl$_3$): δ 8.23 (s, 1H), 7.41-7.32 (m, 5H), 7.01 (d, 1H, J=3.0 Hz), 6.86-6.71 (m, 3H), 6.54 (bs, 1H), 5.48 (d, 1H, J=6.3 Hz), 4.31 (bs, 4H), 3.68 (s, 3H); LCMS: ret. time: 25.53 min.; purity: 97%; MS (m/e): 418 (MH$^+$).

7.3.251 (R935172): N4-[4-[Ethoxycarbonyl(dimethyl)methyl]phenyl]-N2-(3,4-ethylenedioxyphenyl)-5-fluoro-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-N4-[4-[ethoxycarbonyl(dimethyl)methyl]phenyl]-5-fluoro-4-pyrimidineamine and 3,4-ethylenedioxyaniline were reacted to produce N4-[4-[ethoxycarbonyl(dimethyl)methyl]phenyl]-N2-(3,4-ethylenedioxyphenyl)-5-fluoro-2,4-pyrimidinediamine. $^1$H NMR (DMSO-d$_6$): δ 9.31 (s, 1H), 8.97 (s, 1H), 8.03 (d, 1H, J=3.5 Hz), 7.70 (d, 2H, J=8.8 Hz), 7.29 (d, 1H, J=2.3 Hz), 7.23 (d, 2H, J=8.8 Hz), 6.98 (dd, 1H, J=2.1 and 8.8 Hz), 6.66 (d, 1H, J=8.2 Hz), 4.19-4.15 (m, 4H), 4.07 (qt, 2H, J=7.0 Hz), 1.48 (s, 6H), 1.10 (t, 3H, J=7.0 Hz). LCMS: ret. time: 24.51 min.; purity: 100%; MS (m/e): 453 (MH$^+$).

7.3.252 (R935173): N2-(3,4-Ethylenedioxyphenyl)-5-fluoro-N4-[4-(2-hydroxy-1,1-dimethylethyl)phenyl]-2,4-pyrimidinediamine In like manner to the preparation of N2-(3,4-ethylenedioxyphenyl)-5-fluoro-N4-[4(2-hydroxy-1,1-dimethylethyl)phenyl]-pyrimidine-2,4-diamine, N4-[4-[ethoxycarbonyl(dimethyl)methyl]phenyl]-N2-(3,4-ethylenedioxyphenyl)-5-fluoro-2,4-pyrimidinediamine was reduced with DIBALH to give N2-(3,4-ethylenedioxyphenyl)-5-fluoro-N4-[4-(2-hydroxy-1,1-dimethylethyl)phenyl]-2,4-pyrimidinediamine. $^1$H NMR (DMSO-d$_6$): δ 9.23 (s, 1H), 8.94 (s, 1H), 8.01 (d, 1H, J=3.5 Hz), 7.63 (d, 2H, J=8.8 Hz), 7.31-7.27 (m, 3H), 6.98 (dd, 1H, J=2.9 and 8.8 Hz), 6.65 (d, 1H, J=8.8 Hz), 4.65 (t, 1H, J=5.3 Hz), 4.17-4.16 (m, 4H), 3.39 (d, 2H, J=5.2 Hz), 1.20 (s, 6H). 8.9 Hz), LCMS: ret. time: 19.52 min.; purity: 100%; MS (m/e): 411 (MH$^+$).

7.3.253 R935182: 5-Fluoro-N2-[4-(methoxycarbonylmethyleneoxy)phenyl]-N4-(3,4-propylenedioxyphenyl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N4-(3,4-propylenedioxyphenyl)-4-pyrimidineamine and 4-(methoxycarbonylmethyleneoxy)aniline were reacted to produce 5-fluoro-N2-[4-(methoxycarbonylmethyleneoxy)phenyl]-N4-(3,4-propylenedioxyphenyl)-2,4-pyrimidinediamine. $^1$H NMR (DMSO-d6): δ 9.16 (s, 1H), 9.01 (s, 1H), 8.10 (d, 1H, J=4.1 Hz), 7.51 (d, 2H, J=8.8 Hz), 7.37 (d, 1H, J=2.9 Hz), 7.32 (dd, 1H, J=2.9 and 8.8 Hz), 6.98 (d, 1H, J=8.3 Hz), 6.80 (d, 2H, J=8.3 Hz), 4.70 (s, 2H), 4.12-4.05 (app qt, 4H, J=5.3 Hz), 3.68 (s, 3H), 2.07 (q, 2H, J=5.3 Hz); LCMS: ret. time: 20.51 min.; purity: 97%; MS (m/e): 441 (MH$^+$).

7.3.254 R935185: 5-Fluoro-N2-[3-(methoxycarbonylmethyleneoxy)phenyl]-N4-(3,4-propylenedioxyphenyl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N4-(3,4-propylenedioxyphenyl)-4-pyrimidineamine and 3-(methoxycarbonylmethyleneoxy)aniline were reacted to produce 5-fluoro-N2-[3-(methoxycarbonylmethyleneoxy)phenyl]-N4-(3,4-propylenedioxyphenyl)-2,4-pyrimidinediamine. $^1$H NMR (DMSO-d6): δ 9.22 (s, 1H), 9.18 (s, 1H), 8.07 (d, 1H, J=3.5 Hz), 7.41-7.35 (m, 2H), 7.32-7.28 (m, 2H), 7.09 (t, 1H, J=8.2 Hz), 6.90 (d, 1H, J=8.2 Hz), 6.43 (dd, 1H, J=2.3 and 8.8 Hz), 4.65 (s, 2H), 4.11-4.04 (app q, 4H, J=5.3 Hz), 3.67 (s, 3H), 2.06 (q, 2H, J=5.3 Hz); LCMS: ret. time: 20.57 min.; purity: 97%; MS (m/e): 441 (MH$^+$).

7.3.255 R935187: N4-[3-(1-Bis(ethoxycarbonyl)ethoxy)phenyl]-5-fluoro-N2-[4-isopropoxyphenyl]-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(4-isopropoxyphenyl)-4-pyrimidineamine and 3-[1-bis(ethoxycarbonyl)ethoxy]aniline were reacted to provide N4-[3-(1-bis(ethyloxycarbonyl)ethoxy)phenyl]-5-fluoro-N2-[4-isopropoxyphenyl]-2,4-pyrimidinediamine. $^1$H NMR (DMSO-d6): δ 10.08 (s, 1H), 9.98 (s, 1H), 8.19 (d, 1H, J=4.7 Hz), 7.55 (d, 2H, J=8.8 Hz), 7.25 (d, 1H, J=8.8 Hz), 7.15 (d 1H, J=8.3 Hz), 7.13 (d, 1H, J=8.3 Hz), 6.91 (d, 2H, J=8.8 Hz), 6.51 (dd, 1H, J=1.7 and 8.3 Hz), 4.56 (q, 1H, J=5.8 Hz), 4.19 (qt, 4H, J=7.0 Hz), 1.61 (s, 3H), 1.23 (d, 6H, J=5.8 Hz), 1.14 (t, 6H, J=7.0 Hz); LCMS: ret. time: 15.23 min.; purity: 94%; MS (m/e): 527 (MH$^+$).

7.3.256 R935190: N4-(3,4-Ethylenedioxyphenyl)-5-fluoro-N2-(indazolin-6-yl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-N-(3,4-ethylenedioxyphenyl)-5-fluoro-4-pyrimidineamine and 6-aminoindazole were reacted to produce N4-(3,4-ethylenedioxyphenyl)-5-fluoro-N2-(indazolin-6-yl)-2,4-pyrimidinediamine. $^1$H NMR (DMSO-d6): δ 9.69 (s, 1H), 9.62 (s, 1H), 8.14 (d, 1H, J=4.7 Hz), 7.93 (s, 1H), 7.92 (s, 1H), 7.60 (d, 1H, J=8.8 Hz), 7.33-7.31 (m 1H), 7.24 (dd, 2H, J=1.7 and 8.8 Hz), 6.79 (d, J=8.8 Hz), 4.20 (s, 4H); LCMS: ret. time: 17.66 min.; purity: 99%; MS (m/e): 379 (MH$^+$)

7.3.257 R935191: 5-Fluoro-N4-(3-hydroxyphenyl)-N2-(indazolin-6-yl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine and 5-aminoindazole were reacted to give 5-fluoro N4-(3-hydroxyphenyl)-N2-(indazolin-6-yl)-2,4-pyrimidinediamine. $^1$H NMR (DMSO-d6): δ 9.74 (s, 1H), 9.66 (s, 1H), 8.18 (d, 1H, J=4.1 Hz), 7.95 (s, 1H), 7.93 (s, 1H), 7.59 (d, 1H, J=8.8 Hz), 7.33-7.26 (m, 2H), 7.12-7.07 (m, 2H), 6.52 (dd, 1H, J=2.3 and 8.2 Hz); LCMS: ret. time: 15.27 min.; purity: 99%; MS (m/e): 337 (MH$^+$)

7.3.258 R935193: N4-(3,4-Ethylenedioxyphenyl)-5-fluoro-N2-(1-methyl-indazolin-5-yl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(3,4-ethylenedioxyphenyl)-4-pyrimidineamime and 1-methyl-5-aminoindazole were reacted to give N4-(3,4-ethylenedioxyphenyl)-5-fluoro-N2-(1-methyl-indazoline-5-yl)-2,4-pyrimidinediamine. $^1$H NMR (DMSO-d6): δ 10.42 (s, 2H), 8.25 (d, 1H, J=5.2 Hz), 7.92 (s, 1H), 7.86 (app s, 1H), 7.61 (d, 1H, J=8.8 Hz), 7.38 (dd, 1H, J=2.3 and 9.3 Hz), 7.21 (d, 1H, J=2.3 Hz), 7.09 (dd, 1H, J=2.3 and 8.8 Hz), 6.79 (d, 1H, J=8.8 Hz), 4.20 (s, 4H), 4.02 (s, 3H); LCMS: ret. time: 19.09 min.; purity: 99%; MS (m/e): 393 (MH$^+$).

7.3.259 R935194: 5-Fluoro-N4-(3-hydroxyphenyl)-N2-(1-methy-indazoline-5-yl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine was reacted with 1-methyl-5-aminoindazole to produce 5-fluoro-N4-(3-hydroxyphenyl)-N2-(1-methy-indazoline-5-yl)-2,4-pyrimidinediamine. $^1$H NMR (DMSO-d6): δ 10.56 (s, 1H), 10.49 (s, 1H), 8.29 (d, 1H, J=5.2 Hz), 7.98 (d, 1H, J=1.7 Hz), 7.92 (s, 1H), 7.59 (d, 1H, J=8.8 Hz), 7.36 (dd, 1H, J=1.7 and 8.8 Hz), 7.10 (brm, 3H), 6.66 (td, 1H, J=1.7 and 7.0 Hz), 4.01 (s, 3H). LCMS: ret. time: 16.62 min.; purity: 98%; MS (m/e): 351 (MH$^+$).

7.3.260 R935197: 5-Fluoro-N2-(indazoline-5-yl)-N4-(4-isopropoxyphenyl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(4-isopropoxyphenyl)-4-pyrimidineamine was reacted with 5-aminoindazoline to produce 5-fluoro-N2-(indazoline-5-yl)-N4-(4-isopropoxyphenyl)-2,4-pyrimidinediamine. $^1$H NMR (DMSO-d6): δ 9.96 (s, 1H), 9.76 (s, 1H), 8.12 (d, 1H, J=4.6 Hz), 7.94 (s, 1H), 7.92 (s, 1H), 7.53 (d, 2H, J=9.8 Hz), 7.46 (d, 1H, J=8.8 Hz), 7.34 (dd, 1H, J=1.7 and 9.8 Hz), 6.83 (d, 2H, J=9.8 Hz), 4.55 (q, 1H, J=5.8 Hz), 1.24 (d, 6H, J=5.8 Hz). LCMS: ret. time: 18.96 min.; purity: 100%; MS (m/e): 379 (MH$^+$).

7.3.261 R935198: N4-(3,4-Ethylenedioxyphenyl)-5-fluoro-N2-(indazoline-5-yl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(3,4-ethylenedioxyphenyl)-4-pyrimidineamine and 5-aminoindazole were reacted to give N4-(3,4-ethylenedioxyphenyl)-5-fluoro-N2-(indazoline-5-yl)-2,4-pyrimidinediamine. $^1$H NMR (DMSO-d6): δ 9.91 (s, 1H), 9.82 (s, 1H), 8.13 (d, 1H, J=4.6 Hz), 7.94 (app s, 2H), 7.47 (d, 1H, J=8.8 Hz), 7.36 (dd, 1H, J=1.7 and 8.8 Hz), 7.23 (d, 1H, J=2.3 Hz), 7.13(dd, 1H, J=2.3 and 8.8 Hz), 6.76 (d, 1H, J=8.8 Hz), 4.20 (s, 4H); LCMS: ret. time: 16.17 min.; purity: 99%; MS (m/e): 379 (MH$^+$).

7.3.262 R935199: 5-Fluoro-N4-(3-hydroxyphenyl)-N2-(indazoline-5-yl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamime and 5-aminoindazole were reacted to give 5-fluoro-N4-(3-hydroxyphenyl)-N2-(indazoline-5-yl)-2,4-pyrimidinediamine. $^1$H NMR (DMSO-d6): δ 9.78 (s, 1H), 9.68 (s, 1H), 9.49 (br s, 1H), 8.13 (d, 1H, J=4.6 Hz), 8.06 (s, 1H), 7.93 (s, 1H), 7.50 (d, 1H, J=8.8 Hz), 7.38 (dd, 1H, J=1.7 and 8.8 Hz), 7.17 (d, 1H, J=8.2 Hz), 7.11-7.06 (m, 2H), 6.57 (dd, 1H, J=1.1 and 8.2 Hz). LCMS: ret. time: 13.79 min.; purity: 96%; MS (m/e): 337 (MH$^+$).

7.3.263 R935203: 5-Fluoro-N2-(4-isopropoxyphenyl)-N4-(1-methyl-indazoline-5-yl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(1-methyl-indazoline-5-yl)-4-pyrimidineamine and 4-isopropoxyaniline were reacted to produce 5-fluoro-N2-(4-isopropoxyphenyl)-N4-(1-methyl-indazoline-5-yl)-2,4-pyrimidinediamine. $^1$H NMR (DMSO-d6): δ 10.57 (s, 1H), 10.12 (s, 1H), 8.24 (d, 1H, J=5.3 Hz), 8.04 (s, 1H), 7.95 (s, 1H), 7.63 (d, 1H, J=9.3 Hz), 7.55 (dd, 1H, J=1.7 and 8.8 Hz), 7.30 (d, 2H, J=9.4 Hz), 6.82 (d, 2H, J=8.8 Hz), 4.53 (q, 1H, J=6.4 Hz), 4.02 (s, 3H), 1.22 (d, 6H, J=6.4 Hz). LCMS: ret. time: 20.56 min.; purity: 99%; MS (m/e): 393 (MH$^+$).

7.3.264 R935204: 5-Fluoro-N2-(3-hydroxyphenyl)-N4-(1-methyl-indazoline-5-yl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(1-methyl-indazoline-5-yl)-4-pyrimidineamine and 3-aminophenol were reacted to produce 5-fluoro-N2-(3-hydroxyphenyl)-N4-(1-methyl-indazoline-5-yl)-2,4-pyrimidinediamine. LCMS: ret. time: 15.55 min.; purity: 98%; MS (m/e): 351 (MH$^+$).

7.3.265 R935207: N4-(3,4-ethylenedioxyphenyl)-5-fluoro-N2-[3-(2-methoxycarbonyl-fur-4-yl)methyleneoxyphenyl]-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-N-(3,4-ethylenedioxyphenyl)-5-fluoro-4-pyrimidineamine was reacted with 4-(4-aminophenoxymethyl)-2-methoxycarbonyl-furan to give N4-(3,4-ethylenedioxyphenyl)-5-fluoro-N2-[3-(2-methoxycarbonyl-fur-4-yl)methyleneoxyphenyl]-2,4-pyrimidinediamine. $^1$H NMR (DMSO-d6): δ 9.48 (s, 1H), 9.41 (s, 1H), 8.08 (d, 1H, J=3.4 Hz), 7.37-7.10 (m, 6H), 6.74 (d, 2H, J=8.2 Hz), 6.61 (d, 1H, J=8.2 Hz), 5.00 (s, 2H), 4.19 (br s, 4H), 3.79 (s, 3H). LCMS: ret. time: 22.85 min.; purity: 97%; MS (m/e): 493 (MH$^+$).

7.3.266 R935208: N4-(3,4-ethylenedioxyphenyl)-5-fluoro-N2-[1-(methoxycarbonyl)methyl-indazoline-6-yl]-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(3,4-ethylenedioxyphenyl)-4-pyrimidineamine was reacted with 6-amino-1-(methoxycarbonyl)methyl-indazoline to produce N4-(3,4-ethylenedioxyphenyl)-5-fluoro-N2-[1-(methoxycarbonyl)methyl-indazoline-6-yl]-2,4-pyrimidinediamine. $^1$H NMR (DMSO-d6): δ 9.39 (s, 1H), 9.19 (s, 1H), 8.08 (d, 1H, J=3.5 Hz), 7.95 (s, 1H), 7.91 (s, 1H), 7.56 (d, 1H, J=8.2 Hz), 7.32 (d, 2H, J=8.9 Hz), 7.22 (dd, 1H, J=2.9 and 8.2 Hz), 6.78 (d, 1H, J=8.8 Hz), 5.06 (s, 2H), 4.21 (s, 4H), 3.61 (s, 3H). LCMS: ret. time: 19.39 min.; purity: 93%; MS (m/e): 451 (MH$^+$).

7.3.267 R935209: 5-Fluoro-N2-[4-(methoxycarbonylmethyleneoxy)phenyl]-N4-(1-methyl-indazoline-5-yl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(1-methyl-indazoline-5-yl)-4-pyrimidineamine and 4-(methoxycarbonylmethyleneoxy)aniline were reacted to provide 5-fluoro-N2-[4-(methoxycarbonylmethyleneoxy)phenyl]-N4-(1-methyl-indazoline-5-yl)-2,4-pyrimidinediamine. $^1$H NMR (DMSO-d6): δ 9.31 (s, 1H), 8.99 (s, 1H), 8.17 (s, 1H), 8.02 (d, 1H, J=3.5 Hz), 7.92 (s, 1H), 7.59 (s, 2H), 7.50 (d, 2H, J=8.8 Hz), 6.73 (d, 2H, J=8.8 Hz), 4.69 (s, 2H), 4.03 (s, 3H), 3.68 (s, 3H). LCMS: ret. time: 17.60 min.; purity: 99%; MS (m/e): 423 (MH$^+$).

7.3.268 R935214: 5-Fluoro-N2-(3,5-dimethoxyphenyl)-N4-(1-methyl-indazoline-5-yl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(1-methyl-indazoline-5-yl)-4-pyrimidineamine and 3,5-dimethoxyaniline were reacted to produce 5-fluoro-N2-(3,5-dimethoxyphenyl)-N4-(1-methyl-indazoline-5-yl)-2,4-pyrimidinediamine. $^1$HNMR (DMSO-d6): δ 9.34 (s, 1H), 9.09 (s, 1H), 8.20 (d, 1H, J=5.3 Hz), 8.07 (d, 1H, J=3.5 Hz), 7.90 (s, 1H), 7.63-7.55 (m, 2H), 6.89 (d, 2H, J=1.7 Hz), 6.02 (t, 1H, J=2.3 Hz), 4.02 (s, 3H), 3.54 (s, 6H). LCMS: ret. time: 18.81 min.; purity: 97%; MS (m/e): 395 (MH$^+$).

7.3.269 R935215: 5-Fluoro-N4-(3-hydroxyphenyl)-N2-[1-(methoxycarbonyl)methyl-indazoline-6-yl]-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine was reacted with 6-amino-1-(methoxycarbonyl)methyl-indazoline to produce 5-fluoro-N4-(3-hydroxyphenyl)-N2-[1-(methoxycarbonyl)methyl-indazoline-6-yl]-2,4-pyrimidinediamine. LCMS: ret. time: 16.08 min.; purity: 90%; MS (m/e): 408 (MH$^+$).

7.3.270 R935218: 5-Fluoro-N2-(4-isopropoxyphenyl)-N4-[1-(methoxycarbonyl)methyl-indazoline-6-yl]-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-[1-(methoxycarbonyl)methyl-indazoline-6-yl]-4-pyrimidineamine was reacted with 4-isopropoxyaniline to provide 5-fluoro-N2-(4-isopropoxyphenyl)-N4-[1-(methoxycarbonyl)methyl-indazoline-6-yl]-2,4-pyrimidinediamine. $^1$H NMR (DMSO-d6): δ 9.47 (s, 1H), 8.99 (s, 1H), 8.10 (s, 1H), 8.07 (d, 1H, J=4.1 Hz), 8.02 (s, 1H), 7.68 (d, 1H, J=8.8 Hz), 7.50-7.46 (m, 3H), 6.74 (d, 2H, 8.8 Hz), 5.26 (s, 2H), 4.47 (q, 1H, J=5.8 Hz), 3.62 (s, 3H), 1.21 (d, 6H, J=5.8 Hz). LCMS: ret. time: 21.76 min.; purity: 97%; MS (m/e): 451 (MH$^+$).

7.3.271 R935219: N2-(3,4-Ethylenedioxyphenyl)-5-fluoro-N4-[1-(methoxycarbonyl)methyl-indazoline-6-yl]-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-[1-(methoxycarbonyl)methyl-indazoline-6-yl]-4-pyrimidineamine was reacted with 3,4-ethylenedioxyaniline to provide N2-(3,4-ethylenedioxyphenyl)-5-fluoro-N4-[1-(methoxycarbonyl)methyl-indazoline-6-yl]-2,4-pyrimidinediamine. $^1$H NMR (DMSO-d6): δ 9.48 (s, 1H), 9.01 (s, 1H), 8.10 (s, 1H), 8.09 (d, 1H, J=3.5 Hz), 8.01 (s, 1H), 7.68 (d, 1H, J=8.8 Hz), 7.48-7.43 (m, 1H), 7.29 (d, 1H, J=2.3 Hz), 6.99 (d, 1H, J=2.3 and 8.2 Hz), 6.67 (dd, 1H, J=2.3 and 8.8 Hz), 5.27 (s, 2H), 4.15 (s, 4H), 3.62 (s, 3H). LCMS: ret. time: 18.99 min.; purity: 93%; MS (m/e): 451 (MH$^+$).

7.3.272 R935220: 5-Fluoro-N2-(3-hydroxyphenyl)-N4-[1-(methoxycarbonyl)methyl-indazoline-6-yl]-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-[1-(methoxycarbonyl)methyl-indazoline-6-yl]-4-pyrimidineamine was reacted with 3-aminophenol to provide 5-fluoro-N2-(3-hydroxyphenyl)-N4-[1-(methoxycarbonyl)methyl-indazoline-6-yl]-2,4-pyrimidinediamine. $^1$H NMR (DMSO-d6): δ 9.51 (s, 1H), 9.19 (s, 1H), 9.10 (s, 1H), 8.21 (s, 1H), 8.12 (d, 1H, J=3.5 Hz), 8.02 (s, 1H), 7.68 (d, 1H, J=8.8 Hz), 7.49-7.45 (m 1H), 7.16 (s, 1H), 7.09 (d, 1H, J=7.6 Hz), 6.95 (app t, 1H, J=7.6 and 8.2 Hz), 6.31 (dd, 1H, J=1.7 and 7.6 Hz), 5.29 (s, 2H), 3.62 (s, 3H). LCMS: ret. time: 16.16 min.; purity: 97%; MS (m/e): 409 (MH$^+$).

7.3.273 N4-(3,4-Ethylenedioxyphenyl)-N2-(3-furanylmethylene)-5-fluoro-2,4-pyrimidinediamine (R950203)

In like manner to the preparation of N4-(3-aminophenyl)-N2-[2-(methoxycarbonyl)-benzofurane-5-yl]-5-fluoro-2,4-pyrimidinediamine, 2-chloro-N4-(3,4-ethylenedioxyphenyl)-5-fluoro-4-pyrimidineamine and 3-aminomethylenefurane were reacted to give N4-(3,4-ethylenedioxyphenyl)-N2-(3-furanylmethylene)-5-fluoro-2,4-pyrimidinediamine. LCMS: ret. time: 19.99 min.; purity: 88.4%; MS (m/e): 343.07 (MH$^+$).

7.3.274 N4-(3,4-Ethylenedioxyphenyl)-5-fluoro-N2-[(4-methoxyphenyloxy)ethyl]-2,4-pyrimidinediamine (R950204)

In like manner to the preparation of N4-(3-aminophenyl)-N2-[2-(methoxycarbonyl)-benzofurane-5-yl]-5-fluoro-2,4-pyrimidinediamine, 2-chloro-N4-(3,4-ethylenedioxyphenyl)-5-fluoro-4-pyrimidineamine and 2-(4-methoxyphenyloxy)ethyl amine were reacted to give N4-(3,4-ethylenedioxyphenyl)-5-fluoro-N2-[(4-methoxyphenyloxy)ethyl]-2,4-pyrimidinediamine. LCMS: ret. time: 22.74 min.; purity: 91.9%; MS (m/e): 413.05 (MH$^+$).

7.3.275 N2-[2,3-Dihydrobenzo[b]furan-5-ylmethyl]-N4-(3,4-ethylenedioxyphenyl)-5-fluoro-2,4-pyrimidinediamine (R950205)

In like manner to the preparation of N4-(3-aminophenyl)-N2-[2-(methoxycarbonyl)-benzofurane-5-yl]-5-fluoro-2,4-pyrimidinediamine, 2-chloro-N4-(3,4-ethylenedioxyphenyl)-5-fluoro-4-pyrimidineamine and 2,3-dihydrobenzo[b]furan-5-ylmethylamine were reacted to give N2-[2,3-dihydrobenzo[b]furan-5-ylmethyl]-N4-(3,4-ethylenedioxyphenyl)-5-fluoro-2,4-pyrimidinediamine. LCMS: ret. time: 21.43 min.; purity: 97.5%; MS (m/e): 395.05 (MH$^+$).

7.3.276 N2-(2,3-Dihydro-1,4-benzodioxin-2-ylmethyl)-N4-(3,4-ethylenedioxyphenyl)-5-fluoro-2,4-pyrimidinediamine (R950206)

In like manner to the preparation of N4-(3-aminophenyl)-N2-[2-(methoxycarbonyl)-benzofurane-5-yl]-5-fluoro-2,4-pyrimidinediamine, 2-chloro-N4-(3,4-ethylenedioxyphenyl)-5-fluoro-4-pyrimidineamine and 2,3-dihydro-1,4-benzodioxin-2-ylmethylamine were reacted to give N2-(2,3-dihydro-1,4-benzodioxin-2-ylmethyl)-N4-(3,4-ethylenedioxyphenyl)-5-fluoro-2,4-pyrimidinediamine. LCMS: ret. time: 22.49 min.; purity: 87.6%; MS (m/e): 411.01 (MH$^+$).

7.3.277 N4-(3,4-Ethylenedioxyphenyl)-5-fluoro-N2-[2-(methylthio)-1,3-benzothiaz-6-yl]-2,4-pyrimidinediamine (R950201)

In like manner to the preparation of N4-(3-aminophenyl)-N2-[2-(methoxycarbonyl)-benzofurane-5-yl]-5-fluoro-2,4-pyrimidinediamine, 2-chloro-N4-(3,4-ethylenedioxyphenyl)-5-fluoro-4-pyrimidineamine and 2-(methylthio)-1,3-benzothiazol-6-amine were reacted to give N4-(3,4-ethylenedioxyphenyl)-5-fluoro-N2-[2-(methylthio)-1,3-benzothiaz-6-yl]-2,4-pyrimidinediamine. LCMS: ret. time: 22.67 min.; purity: 76.9%; MS (m/e): 441.91 (MH$^+$).

7.3.278 N2-[2,3-Dihydrobenzo[b]furan-5-ylmethyl]-5-fluoro-N4-(3-hydroxyphenyl)-2,4-pyrimidinediamine (R950213)

In like manner to the preparation of N4-(3-aminophenyl)-N2-[2-(methoxycarbonyl)-benzofurane-5-yl]-5-fluoro-2,4-pyrimidinediamine, 2-chloro-5-fluoro-N4-(3-hydroxyphenyl)-4-pyrimidineamine and 2,3-dihydrobenzo[b]furan-5-ylmethylamine were reacted to N2-[2,3-dihydrobenzo[b]furan-5-ylmethyl]-5-fluoro-N4-(3-hydroxyphenyl)-2,4-pyrimidinediamine. LCMS: ret. time: 17.80 min.; purity: 99.2%; MS (m/e): 353.08 (MH$^+$).

7.3.279 N2-(2,3-Dihydro-1,4-benzodioxin-2-ylmethyl)-5-fluoro-N4-(3-hydroxyphenyl)-2,4-pyrimidinediamine (R950214)

In like manner to the preparation of N4-(3-aminophenyl)-N2-[2-(methoxycarbonyl)-benzofurane-5-yl]-5-fluoro-2,4-pyrimidinediamine, 2-chloro-5-fluoro-N4-(3-hydroxyphenyl)-4-pyrimidineamine and 2,3-dihydro-1,4-benzodioxin-2-ylmethylamine were reacted to give N2-(2,3-dihydro-1,4-benzodioxin-2-ylmethyl)-5-fluoro-N4-(3-hydroxyphenyl)-2,4-pyrimidinediamine. LCMS: ret. time: 19.26 min.; purity: 96.2%; MS (m/e): 369.08 (MH$^+$).

7.3.280 5-Fluoro-N4-(3-hydroxyphenyl)-N2-[2-(methylthio)-1,3-benzothiaz-6-yl]-2,4-pyrimidinediamine (R950212)

In like manner to the preparation of N4-(3-aminophenyl)-N2-[2-(methoxycarbonyl)-benzofurane-5-yl]-5-fluoro-2,4-pyrimidinediamine, 2-chloro-5-fluoro-N4-(3-hydroxyphenyl)-4-pyrimidineamine and 2-(methylthio)-1,3-benzothiazol-6-amine were reacted to give 5-fluoro-N4-(3-hydroxyphenyl)-N2-[2-(methylthio)-1,3-benzothiaz-6-yl]-2,4-pyrimidinediamine. LCMS: ret. time: 19.83 min.; purity: 98.9%; MS (m/e): 399.98 (MH$^+$).

7.3.281 N2-(3-Aminophenyl)-5-fluoro-N4-(3-hydroxyphenyl)-2,4-pyrimidinediamine (R950227)

In like manner to the preparation of N4-(3-aminophenyl)-N2-[2-(methoxycarbonyl)-benzofurane-5-yl]-5-fluoro-2,4-pyrimidinediamine, 2-chloro-5-fluoro-N4-(3-hydroxyphenyl)-4-pyrimidineamine and 1,3-diaminobenzene were reacted to give N2-(3-aminophenyl)-5-fluoro-N4-(3-hydroxyphenyl)-2,4-pyrimidinediamine. LCMS: ret. time: 11.89 min.; purity: 97.6%; MS (m/e): 312.05 (MH$^+$).

7.3.282 N2-(1,4-Benzoxazin-6-yl)]-5-fluoro-N4-(3-nitrophenyl)-2,4-pyrimidinediamine (R950253)

In like manner to the preparation of N4-(3-aminophenyl)-N2-[2-(methoxycarbonyl)-benzofurane-5-yl]-5-fluoro-2,4-pyrimidinediamine, 2-chloro-5-fluoro-N4-(3-hydroxyphenyl)-4-pyrimidineamine and 6-amino-1,4-benzoxazine were reacted to give N2-(1,4-benzoxazin-6-yl)]-5-fluoro-N4-(3-nitrophenyl)-2,4-pyrimidinediamine. LCMS: ret. time: 18.52 min.; purity: 99.5%; MS (m/e): 382.93 (MH$^+$).

7.3.283 N2-(Ethoxycarbonylmethyleneaminophenyl)-5-fluoro-N4-(3-hydroxyphenyl)-2,4-pyrimidinediamine (R950215)

In like manner to the preparation of N4-(3-aminophenyl)-N2-[2-(methoxycarbonyl)-benzofurane-5-yl]-5-fluoro-2,4-pyrimidinediamine, 2-chloro-5-fluoro-N4-(3-hydroxyphenyl)-4-pyrimidineamine and 3-ethoxycarbonylmethyleneaminophenylaniline were reacted to N2-(ethoxycarbonylmethyleneaminophenyl)-5-fluoro-N4-(3-hydroxyphenyl)-2,4-pyrimidinediamine. LCMS: ret. time: 18.90 min.; purity: 83.4%; MS (m/e): 398.06 (MH$^+$).

7.3.284 N2-(Ethoxycarbonylmethyleneaminophenyl)-5-fluoro-N4-[3-(2-hydroxyethylamino)phenyl]-2,4-pyrimidinediamine (R950229)

In like manner to the preparation of N4-(3-aminophenyl)-N2-[2-(methoxycarbonyl)-benzofurane-5-yl]-5-fluoro-2,4-pyrimidinediamine, 2-chloro-5-fluoro-N4-(3-hydroxyphenyl)-4-pyrimidineamine and 3-ethoxycarbonylmethyleneaminophenylaniline were reacted to N2-(ethoxycarbonylmethyleneaminophenyl)-5-fluoro-N4-[3-(2-hydroxyethylamino)phenyl]-2,4-pyrimidinediamine. LCMS: ret. time: 16.37 min.; purity: 78.3%; MS (m/e): 441.03 (MH+).

7.3.285 5-Cyano-N2-(3-hydroxyphenyl)-N4-(methoxycarbonylbenzyl)-2,4-pyrimidinediamine (R925821)

In a manner similar to the preparation of N4-(3,4-ethylenedioxyphenyl)-5-fluoro-N2-(3-hydroxyphenyl)-2,4-pyrimidinediamine, 2-chloro-5-cyano-N4-(methoxycarbonylbenzyl)-4-pyrimidineamine and 3-hydroxyaniline were reacted to yield 5-cyano-N2-(3-hydroxyphenyl)-N4-(methoxycarbonylbenzyl)-2,4-pyrimidinediamine. $^1$H NMR (CD$_3$OD): δ 8.27 (s, 1H), 7.38-7.28 (m, 5H), 7.19-7.07 (m, 2H), 6.98-6.91 (m, 2H), 6.64 (d, 1H, J=6.6 Hz), 3.55 (s, 3H); LCMS: ret. time: 24.18 min.; purity: 98%; MS (m/e): 376 (MH+)

7.3.286 5-Fluoro-N4-[2-fluoro-4-(methoxymethyleneoxy)phenyl]-N2-(3-hydroxyphenyl)-2,4-pyrimidinediamine (R926680)

In a manner similar to the preparation of N4-(3,4-ethylenedioxyphenyl)-5-fluoro-N2-(3-hydroxyphenyl)-2,4-pyrimidinediamine, 2-chloro-5-fluoro-N4-(2-fluoro-4-methoxymethyleneoxyphenyl)-4-pyrimidineamine and 3-hydroxyaniline were reacted to yield 5-fluoro-N4-(2-fluoro-4-methoxymethyleneoxyphenyl)-N2-(3-hydroxyphenyl)-2,4-pyrimidinediamine.

7.3.287 N4-(3,4-Ethylenedioxyphenyl)-5-fluoro-N2-[(1H)-indol-5-yl]-2,4-pyrimidinediamine (R926748)

In a manner similar to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 5-aminoindole were reacted to yield N4-(3,4-ethylenedioxyphenyl)-5-fluoro-N2-[(1H)-indol-5-yl]-2,4-pyrimidinediamine. LCMS: ret. time: 20.37 min.; purity: 97%; MS (m/e): 378 (MH+).

7.3.288 5-Fluoro-N4-(3-hydroxyphenyl)-N2-[(1H)-indol-5-yl]-2,4-pyrimidinediamine (R926749)

In a manner similar to the preparation of N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)-4-pyrimidineamine and 5-aminoindole were reacted to yield 5-fluoro-N4-(3-hydroxyphenyl)-N2-[(1H)-indol-5-yl]-2,4-pyrimidinediamine. LCMS: ret. time: 17.31 min.; purity: 94%; MS (m/e): 366 (MH+).

7.3.289 N4-(3,4-Ethylenedioxyphenyl)-5-fluoro-N2-[(1H)-indol-6-yl]-2,4-pyrimidinediamine (R926750)

In a manner similar to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 6-aminoindole were reacted to yield N4-(3,4-ethylenedioxyphenyl)-5-fluoro-N2-[(1H)-indol-6-yl]-2,4-pyrimidinediamine. LCMS: ret. time: 20.80 min.; purity: 91%; MS (m/e): 378 (MH+).

7.3.290 5-Fluoro-N4-(3-hydroxyphenyl)-N2-[(1H)-indol-6-yl]-2,4-pyrimidinediamine (R926751)

In a manner similar to the preparation of N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)-4-pyrimidineamine and 6-aminoindole were reacted to yield 5-fluoro-N4-(3-hydroxyphenyl)-N2-[(1H)-indol-6-yl]-2,4-pyrimidinediamine. LCMS: ret. time: 18.13 min.; purity: 96%; MS (m/e): 336 (MH+).

7.3.291 N4-[4-(Aminocarbonylmethyleneoxy)phenyl]-5-fluoro-N2-(3-hydroxyphenyl)-2,4-pyrimidinediamine (R945063)

In a manner analogous to the preparation of N4-(3,4-ethylenedioxyphenyl)-5-fluoro-N2-(3-hydroxyphenyl)-2,4-pyrimidinediamine, the reaction of 3-hydroxyaniline (110 mg, 1 mmol) and N4-[4-(aminocarbonylmethyleneoxy)phenyl]-2-chloro-5-fluoro-4-pyrimidineamine (80 mg, 0.27 mmol) gave N4-[4-(aminocarbonylmethyleneoxy)phenyl]-5-fluoro-N2-(3-hydroxyphenyl)-2,4-pyrimidinediamine (75 mg, 76%). $^1$H NMR (acetone-d$_6$): δ 4.51 (s, 2H), 6.64 (dm, J=8.4 Hz, 1H), 7.06-7.14 (m, 5H), 7.70 (dd, J=2.4 and 9.0 Hz, 2H), 8.27 (d, J=6.0 Hz, 1H); $^{19}$F NMR (282 MHz, acetone-d$_6$): 6-164.00; LCMS: ret. time: 14.66 min.; purity: 88.63%; MS (m/e): 370.00 (MH+).

7.3.292 N4-[4-(Cyanomethyleneoxy)phenyl]-5-fluoro-N2-(3-hydroxyphenyl)-2,4-pyrimidinediamine (R945071)

In a manner analogous to the preparation of N4-(3,4-ethylenedioxyphenyl)-5-fluoro-N2-(3-hydroxyphenyl)-2,4-pyrimidinediamine, 3-hydroxyaniline (94 mg, 0.86 mmol) and 2-chloro-N4-[4-(cyanomethyleneoxy)phenyl]-5-fluoro-4-pyrimidineamine (80 mg, 0.29 mmol) gave N4-[4-(cyanomethyleneoxy)phenyl]-5-fluoro-N2-(3-hydroxyphenyl)-2,4-pyrimidinediamine (65 mg, 64%) as a off-white solid. $^1$H NMR (acetone-d$_6$): δ 5.16 (s, 2H), 6.64 (ddd, J=1.8, 2.4 and 7.5 Hz, 1H), 7.03 (t, J=2.1 Hz, 1H), 7.08-7.16 (m, 2H), 7.19 (d, J=9.3 Hz, 2H), 7.77 (d, J=9.3 Hz, 2H), 8.30 (d, J=5.4 Hz, 1H), 10.04 (s, 1H, NH), 11.33 (s, 1H, NH); $^{19}$F NMR (282 MHz, acetone-d$_6$): 6-163.52; LCMS: ret. time: 17.08 min.; purity: 100%; MS (m/e): 352.13 (MH+).

7.3.293 N4-(3-Cyanophenyl)-5-fluoro-N2-(3-hydroxyphenyl)-2,4-pyrimidinediamine (R945109)

In a manner analogous to the preparation of N4-(3,4-ethylenedioxyphenyl)-5-fluoro-N2-(3-hydroxyphenyl)-2,4-pyrimidinediamine, 3-aminobenzonitrile (142 mg, 1.2 mmol) and 2,4-dichloro-5-fluoropyrimidine (100 mg, 0.6 mmol) gave 2-chloro-N4-(3-cyanophenyl)-5-fluoro-4-pyrimidineamine (128 mg, 86%) as a white solid. The reaction of 2-chloro-N4-(3-cyanophenyl)-5-fluoro-4-pyrimidineamine (50 mg, 0.2 mmol) and 3-aminophenol (66 mg, 0.6 mmol) gave N4-(3-cyanophenyl)-5-fluoro-N2-(3-hydroxyphenyl)-2,4-pyrimidinediamine (40 mg, 62%). $^1$H NMR (acetone-d$_6$): δ 6.48 (ddd, J=0.9, 2.4 and 7.8 Hz, 1H), 7.10 (t, J=8.1 Hz, 1H), 7.18 (ddd, J=1.2, 2.1 and 8.1 Hz, 1H), 7.33 (t, J=2.1 Hz, 1H), 7.45 (dt, J=1.2 and 7.8 Hz, 1H), 7.54 (t, J=8.1 Hz, 1H), 8.08 (d, J=3.3 Hz, 1H), 8.14 (ddd, J=1.5, 2.7 and 8.4 Hz, 1H), 8.39 (t, J=2.1 Hz, 1H), 8.58 (s, 1H, NH), 8.84 (s, 1H, NH); $^{19}$F NMR (282 MHz, acetone-d$_6$): 6-167.41; LCMS: ret. time: 17.75 min.; purity: 92.39%; MS (m/e): 322.59 (MH$^+$).

7.3.294 N4-(3-Cyanophenyl)-5-fluoro-N2-(4-methoxycarbonylmethyleneoxyphenyl)-2,4-pyrimidinediamine (R945110)

In like manner to the preparation of N4-(3,4-ethylenedioxyphenyl)-5-fluoro-N2-(3-hydroxyphenyl)-2,4-pyrimidinediamine, 2-chloro-N4-(3-cyanophenyl)-5-fluoro-4-pyrimidineamine (50 mg, 0.2 mmol) and 4-(methoxycarbonylmethyleneoxy)aniline (109 mg, 0.6 mmol) gave N4-(3-cyanophenyl)-5-fluoro-N2-(4-methoxycarbonylmethyleneoxyphenyl)-2,4-pyrimidinediamine (30 mg, 38%). $^1$H NMR (acetone-d$_6$): δ 3.74 (s, 3H), 4.72 (s, 2H), 6.93 (d, J=9.0 Hz, 2H), 7.46 (dt, J=1.5 and 7.5 Hz, 1H), 7.54 (t, J=7.8 Hz, 1H), 7.60 (dd, J=1.8 and 9.0 Hz, 2H), 8.03-8.07 (m, 2H), 8.43 (m, 1H), 8.48 (br, 1H, NH), 8.80 (br, 1H, NH); $^{19}$F NMR (282 MHz, acetone-d$_6$): 6-168.2; LCMS: ret. time: 20.24 min.; purity: 94.79%; MS (m/e): 393.98 (MH$^+$).

7.3.295 5-Fluoro-N4-(3-hydroxyphenyl)-N2-[2-(indol-3-yl)ethyl]-2,4-pyrimidinediamine (R945117)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine (50 mg, 0.21 mmol) and tryptamine (100 mg, 0.62 mmol) gave 5-fluoro-N4-(3-hydroxyphenyl)-N2-[2-(indol-3-yl)ethyl]-2,4-pyrimidinediamine (40 mg, 53%). $^1$H NMR (CD$_3$OD): δ 3.01 (t, J=7.2 Hz, 2H), 3.61 (t, J=7.2 Hz, 2H), 6.51 (ddd, J=0.9, 2.1 and 8.1 Hz, 1H), 6.96 (td, J=0.9 and 7.2 Hz, 1H), 7.03-7.09 (m, 3H), 7.22 (d, J=7.5 Hz, 1H), 7.28-7.32 (m, 2H), 7.53 (d, J=7.8 Hz, 1H), 7.72 (d, J=4.5 Hz, 1H); $^{19}$F NMR (282 MHz, CD$_3$OD): 6-171.72; LCMS: ret. time: 20.17 min.; 95.66%; MS (m/e): 364.05 (MH$^+$).

7.3.296 5-Fluoro-N4-(3-hydroxyphenyl)-N2-(3-methoxycarbonylmethyleneoxyphenyl)-2,4-pyrimidinediamine (R945118)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine (80 mg, 0.33 mmol) and 3-methoxycarbonylmethyleneoxyaniline (180 mg, 0.99 mmol) gave 5-fluoro-N4-(3-hydroxyphenyl)-N2-(3-methoxycarbonylmethyleneoxyphenyl)-2,4-pyrimidinediamine (130 mg). $^1$H NMR (acetone-d$_6$): δ 3.74 (s, 3H), 4.64 (s, 2H), 6.71 (m, 1H), 6.80 (m, 1H), 7.23-7.32 (m, 6H), 8.32 (d, J=5.1 Hz, 1H); LCMS: ret. time: 18.37 min.; purity: 100%; MS (m/e): 384.70 (MH$^+$).

7.3.297 N4-(3,4-Ethylenedioxyphenyl)-5-fluoro-N2-(3-methoxycarbonylmethyleneoxyphenyl)-2,4-pyrimidinediamine (R945124)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine (80 mg, 0.28 mmol) and 3-methoxycarbonylmethyleneoxyaniline (154 mg, 0.85 mmol) gave N4-(3,4-ethylenedioxyphenyl)-5-fluoro-N2-(3-methoxycarbonylmethyleneoxyphenyl)-2,4-pyrimidinediamine (90 mg, 74%). $^1$H NMR (CDCl$_3$): δ 3.80 (s, 3H), 4.27 (q, J=0.9 Hz, 4H), 4.58 (s, 2H), 6.54 (ddd, J=0.9, 2.7 and 8.1 Hz, 1H), 6.65 (d, J=2.7 Hz, 1H), 6.86 (d, J=8.7 Hz, 1H), 6.98 (dd, J=2.4 and 8.4 Hz, 1H), 6.98 (br, 1H), 7.09 (ddd, J=1.2, 2.1 and 8.1 Hz, 1H), 7.18 (t, J=8.1 Hz, 1H), 7.24 (d, J=2.4 Hz, 1H), 7.32 (t, J=2.1 Hz, 1H), 7.92 (d, J=3.3 Hz, 1H); $^{19}$F NMR (282 MHz, CDCl$_3$): 6-167.52; LCMS: ret. time: 21.64 min.; purity: 98.07%; MS (m/e): 426.99 (MH$^+$).

7.3.298 5-Fluoro-N4-(4-isopropoxyphenyl)-N2-(3-methoxycarbonylmethyleneoxyphenyl)-2,4-pyrimidinediamine (R945125)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(4-isopropoxyphenyl)-4-pyrimidineamine (80 mg, 0.28 mmol) and methyl 3-aminophenoxyacete (154 mg, 0.85 mmol) gave 5-fluoro-N4-(4-isopropoxyphenyl)-N2-(3-methoxycarbonylmethyleneoxyphenyl)-2,4-pyrimidinediamine (80 mg, 66%). $^1$H NMR (CDCl$_3$) δ 1.33 (s, 3H), 1.35 (s, 3H), 3.80 (s, 3H), 4.52 (p, J=6.0 Hz, 1H), 4.55 (s, 2H), 6.53 (ddd, J=0.9, 2.4 and 8.1 Hz, 1H), 6.69 (d, J=2.4 Hz, 1H), 6.90 (d, J=9.0 Hz, 2H), 7.04-7.08 (m, 2H), 7.16 (t, J=8.1 Hz, 1H), 7.32 (t, J=2.1 Hz, 1H), 7.47 (d, J=8.7 Hz, 2H), 7.92 (d, J=3.0 Hz, 1H); $^{19}$F NMR (282 MHz, CDCl$_3$): 6-167.64; LCMS: ret. time: 24.70 min.; purity: 100%; MS (m/e): 427.00 (MH$^+$).

7.3.299 N2-[4-(Aminocarbonylmethyleneoxy)phenyl]-5-fluoro-N4-(3-hydroxyphenyl)-2,4-pyrimidinediamine (R945064)

In a manner analogous to the preparation of N4-(3,4-ethylenedioxyphenyl)-N2-(3-hydroxyphenyl))-5-fluoro-2,4-pyrimidinediamine, 4-(aminocarbonylmethyleneoxy)aniline (198 mg, 1.2 mmol) and 2-chloro-5-fluoro-N4-(3-hydroxyphenyl)-4-pyrimidineamine (95 mg, 0.4 mmol) gave N2-[4-(aminocarbonylmethyleneoxy)phenyl]-5-fluoro-N4-(3-hydroxyphenyl)-2,4-pyrimidinediamine (60 mg, 41%). $^1$H NMR (CD$_3$OD): δ 4.55 (s, 2H), 6.75 (dm, J=7.5 Hz, 1H), 7.08 (d, J=9.3 Hz, 2H), 7.18 (m, 2H), 7.22 (d, J=8.7 Hz, 1H), 7.46 (d, J=9.0 Hz, 2H), 8.09 (d, 1H); LCMS: ret. time: 14.38 min.; purity: 100%; MS (m/e): 370.00 (MH$^+$).

7.3.300 5-Fluoro-N2-(3-hydroxyphenyl)-N4-[3-(5-methyl-1,2,4-oxadiazol-3-yl)methyleneoxyphenyl]-2,4-pyrimidinediamine (R945132)

In a manner analogous to the preparation of N4-(3,4-ethylenedioxyphenyl)-5-fluoro-N2-(3-hydroxyphenyl)-2,4-pyrimidinediamine, the reaction of 3-(5-methyl-1,2,4-oxadiazol-3-yl)methyleneoxyaniline (490 mg, 2.4 mmol) and 2,4-dichloro-5-fluoropyrimidine (200 mg, 1.2 mmol) gave 2-chloro-5-fluoro-N4-[3-(5-methyl-1,2,4-oxadiazol-3-yl)methyleneoxyphenyl]-4-pyrimidineamine. The reaction of 2-chloro-5-fluoro-N4-[3-(5-methyl-1,2,4-oxadiazol-3-yl)methyleneoxyphenyl]-4-pyrimidineamine (40 mg, 0.12 mmol) and 3-aminophenol (40 mg, 0.36 mmol) gave 5-fluoro-N2-(3-hydroxyphenyl)-N4-[3-(5-methyl-1,2,4-oxadiazol-3-yl)methyleneoxyphenyl]-2,4-pyrimidinediamine (30 mg, 62%). $^1$H NMR (CDCl$_3$): δ 2.61 (s, 3H), 5.21 (s, 2H), 6.50 (ddd, J=0.9, 2.4 and 7.8 Hz, 1H), 6.76 (ddd, J=0.6, 2.4 and 9.0 Hz, 1H), 6.80-6.85 (m, 3H), 7.12 (t, J=8.1 Hz, 1H), 7.23 (t, J=7.8 Hz, 1H), 7.50-7.52 (m, 2H), 7.94 (d, J=3.3 Hz, 1H), 7.98 (t, J=2.4 Hz, 1H); $^{19}$F NMR (282 MHz, CDCl$_3$): 6-167.19; LCMS: ret. time: 18.88 min.; purity: 100%; MS (m/e): 408.97 (MH$^+$).

7.3.301 N2-[4-(Aminocarbonylmethoxy)phenyl]-5-fluoro-N4-[3-(5-methyl-1,2,4-oxadiazol-3-yl)methyleneoxyphenyl]-2,4-pyrimidinediamine (R945133)

In a manner analogous to the preparation of N4-(3,4-ethylenedioxyphenyl)-5-fluoro-N2-(3-hydroxyphenyl)-2,4-pyrimidinediamine, the reaction of 2-chloro-5-fluoro-N4-[3-(5-methyl-1,2,4-oxadiazol-3-yl)methyleneoxyphenyl]-4-pyrimidineamine (30 mg, 0.09 mmol) and 4-(aminocarbonylmethyleneoxy)aniline (45 mg, 0.27 mmol) gave N2-[4-(aminocarbonylmethyleneoxy)phenyl]-5-fluoro-N4-[3-(5-methyl-1,2,4-oxadiazol-3-yl)methyleneoxyphenyl]-2,4-pyrimidinediamine (10 mg, 24%). $^1$H NMR (acetone-$d_6$): δ 2.62 (s, 3H), 4.43 (s, 2H), 5.19 (s, 2H), 6.77 (ddd, J=1.2, 2.4 and 8.1 Hz, 1H), 6.94 (d, J=9.0 Hz, 2H), 7.25 (t, J=8.1 Hz, 1H), 7.34 (ddd, J=0.9, 1.8, 9.0 Hz, 1H), 7.68 (d, J=9.0 Hz, 2H), 7.81 (t, J=2.1 Hz, 1H), 7.99 (d, J=3.6 Hz, 1H), 8.45 (br, 1H, NH), 8.57 (br, 1H, NH); $^{19}$F NMR (282 MHz, acetone-$d_6$): 6-168.20; LCMS: ret. time: 16.80 min.; purity: 84.91%; MS (m/e): 466.05 (MH$^+$).

7.3.302 N4-(3,4-Ethylenedioxyphenyl)-5-fluoro-N2-[3-(5-methyl-1,2,4-oxadiazol-3-yl)methyleneoxyphenyl]-2,4-pyrimidinediamine (R945128)

In a manner analogous to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine (40 mg, 0.14 mmol) and 3-(5-methyl-1,2,4-oxadiazol-3-yl)methyleneoxyaniline (87 mg, 0.42 mmol) gave N4-(3,4-ethylenedioxyphenyl)-5-fluoro-N2-[3-(5-methyl-1,2,4-oxadiazol-3-yl)methyleneoxyphenyl]-2,4-pyrimidinediamine (30 mg, 47%). $^1$H NMR (CDCl$_3$): δ 2.62 (s, 3H), 4.26 (q, J=2.1 Hz, 4H), 5.09 (s, 2H), 6.63-6.67 (m, 2H), 6.85 (d, J=8.4 Hz, 1H), 6.95-6.99 (m, 2H), 7.09 (dt, J=0.9 and 6.9 Hz, 1H), 7.19 (t, J=8.4 Hz, 1H), 7.23 (d, J=2.4 Hz, 1H), 7.42 (t, J=2.4 Hz, 1H), 7.92 (d, J=3.0 Hz, 1H); $^{19}$F NMR (282 MHz, CDCl$_3$): 6-167.47; LCMS: ret. time: 21.26 min.; purity: 96.72%; MS (m/e): 451.01 (MH$^+$).

7.3.303 5-Fluoro-N4-(4-isopropoxyphenyl)-N2-[3-(5-methyl-1,2,4-oxadiazol-3-yl)methyleneoxyphenyl]-2,4-pyrimidinediamine (R945129)

In a manner analogous to the preparation of N4-(3,4-ethylenedioxyphenyl)-5-fluoro-N2-(3-hydroxyphenyl)-2,4-pyrimidinediamine, the reaction of 2-chloro-5-fluoro-N4-(4-isopropoxyphenyl)-4-pyrimidineamine (40 mg, 0.14 mmol) and 3-(5-methyl-1,2,4-oxadiazol-3-yl)methyleneoxyaniline (87 mg, 0.42 mmol) gave 5-fluoro-N4-(4-isopropoxyphenyl)-N2-[3-(5-methyl-1,2,4-oxadiazol-3-yl)methyleneoxyphenyl]-2,4-pyrimidinediamine (40 mg, 63%). $^1$H NMR (CDCl$_3$): δ 1.32 (s, 3H), 1.34 (s, 3H), 2.61 (s, 3H), 4.52 (p, J=6.0 Hz, 1H), 5.08 (s, 2H), 6.64 (ddd, J=1.2, 2.7 and 8.1 Hz, 1H), 6.70 (d, J=2.4 Hz, 1H), 6.89 (d, J=9.0 Hz, 2H), 7.07-7.11 (m, 2H), 7.16 (t, J=8.1 Hz, 1H), 7.38 (t, J=2.1 Hz, 1H), 7.46 (d, J=9.0 Hz, 2H), 7.91 (d, J=3.3 Hz, 1H); $^{19}$F NMR (282 MHz, CDCl$_3$): 6-167.55; LCMS: ret. time: 24.49 min.; 96.15%; MS (m/e): 451.08 (MH$^+$).

7.3.304 N2-(3,4-Ethylenedioxyphenyl)-5-fluoro-N4-[3-(5-methyl-1,2,4-oxadiazol-3-yl)methyleneoxyphenyl]-2,4-pyrimidinediamine (R945137)

In a manner analogous to the preparation of N4-(3,4-ethylenedioxyphenyl)-5-fluoro-N2-(3-hydroxyphenyl)-2,4-pyrimidinediamine, 2-chloro-5-fluoro-N4-[3-(5-methyl-1,2,4-oxadiazol-3-yl)methyleneoxyphenyl]-4-pyrimidineamine (40 mg, 0.12 mmol) and 3,4-ethylenedioxyaniline (55 mg, 0.36 mmol) reacted to give N2-(3,4-ethylenedioxyphenyl)-5-fluoro-N4-[3-(5-methyl-1,2,4-oxadiazol-3-yl)methyleneoxyphenyl]-2,4-pyrimidinediamine. $^1$H NMR (CDCl$_3$): δ 2.60 (s, 3H), 4.24 (q, J=2.7 Hz, 4H), 5.21 (s, 2H), 6.74-6.78 (m, 2H), 6.81 (d, J=8.4 Hz, 1H), 6.90 (dd, J=1.2, 7.8 Hz, 1H), 7.01 (dd, J=2.4 and 8.4 Hz, 1H), 7.22 (t, J=8.4 Hz, 1H), 7.30 (d, J=2.4 Hz, 1H), 7.48 (br, 1H), 7.94 (d, J=3.3 Hz, 1H), 7.98 (br, 1H); $^{19}$F NMR (282 MHz, CDCl$_3$) 6-168.23; LCMS: ret. time: 21.20 min.; purity: 91.09%; MS (m/e): 450.99 (MH$^+$).

7.3.305 5-Fluoro-N2-(4-isopropoxyphenyl)-N4-[3-(5-methyl-1,2,4-oxadiazol-3-yl)methyleneoxyphenyl]-2,4-pyrimidinediamine (R945138)

In a manner analogous to the preparation of N4-(3,4-ethylenedioxyphenyl)-5-fluoro-N2-(3-hydroxyphenyl)-2,4-pyrimidinediamine, the reaction of 2-chloro-5-fluoro-N4-[3-(5-methyl-1,2,4-oxadiazol-3-yl)methyleneoxyphenyl]-4-pyrimidineamine (40 mg, 0.12 mmol) and 4-isopropoxyaniline (55 mg, 0.36 mmol) gave 5-fluoro-N2-(4-isopropoxyphenyl)-N4-[3-(5-methyl-1,2,4-oxadiazol-3-yl)methyleneoxyphenyl]-2,4-pyrimidinediamine. $^1$H NMR (CDCl$_3$): δ 1.31 (s, 3H), 1.33 (s, 3H), 2.60 (s, 3H), 4.48 (p, J=6.0 Hz, 1H), 5.20 (s, 2H), 6.74-6.78 (m, 2H), 6.87 (d, J=9.0 Hz, 2H), 6.92 (dd, J=1.2 and 8.4 Hz, 1H), 7.22 (t, J=8.4 Hz, 1H), 7.50 (m, 3H), 7.94 (d, J=3.0 Hz, 2H); $^{19}$F NMR (282 MHz, CDCl$_3$): 6-168.46; LCMS: ret. time: 24.95 min.; purity: 73.74%; MS (m/e): 451.06 (MH$^+$).

7.3.306 N4-(3,5-Dimethyl-4-hydroxyphenyl)-5-fluoro-N2-(3-methoxycarbonylmethyleneoxyphenyl)-2,4-pyrimidinediamine (R945139)

Using general hydrogenation conditions, 2,6-dimethyl-4-nitrophenol was reduced to 4-amino-2,6-dimethylphenol. In a manner analogous to the preparation of N4-(3,4-ethylenedioxyphenyl)-5-fluoro-N2-(3-hydroxyphenyl)-2,4-pyrimidinediamine, the reaction of 4-amino-2,6-dimethylphenol (823 mg, 6 mmol) and 2,4-dichloro-5-fluoropyrimidine (500 mg, 3 mmol) gave 2-chloro-N4-(3,5-dimethyl-4-hydroxyphenyl)-5-fluoro-4-pyrimidineamine. Compound 2-chloro-N4-(3,5-dimethyl-4-hydroxyphenyl)-5-fluoro-4-pyrimidineamine (500 mg, 1.87 mmol) and 3-(methoxycarbonylmethyleneoxy)aniline (500 mg, 2.76 mmol) reacted to give N4-(3,5-dimethyl-4-hydroxyphenyl)-5-fluoro-N2-(3-methoxycarbonylmethyleneoxyphenyl)-2,4-pyrimidinediamine (500 mg, 65%). $^1$H NMR (CD$_3$OD): δ 2.16 (s, 6H), 3.76 (s, 3H), 4.51 (s, 2H), 6.79 (ddd, J=0.9, 2.4 and 8.1 Hz, 1H), 7.01-7.06 (m, 2H), 7.15 (s, 2H), 7.26 (t, J=8.1 Hz, 1H), 7.93 (d, J=5.7 Hz, 1H); $^{19}$F NMR (282 MHz, CD$_3$OD): 6-163.31; LCMS: ret. time: 20.44 min.; purity: 84.25%; MS (m/e): 413.03 (MH$^+$).

7.3.307 N4-(Benzothiophen-3-ylmethyl)-5-fluoro-N2-(3-hydroxyphenyl)-2,4-pyrimidinediamine (R945146)

In a manner analogous to the preparation of N4-(3,4-ethylenedioxyphenyl)-5-fluoro-N2-(3-hydroxyphenyl)-2,4-pyrimidinediamine, the reaction of benzothiophen-3-ylmethylamine (244 mg, 1.5 mmol) and 2,4-dichloro-5-fluoropyrimidine (50 mg, 0.3 mmol) gave N4-(benzothiophen-3-ylmethyl)-2-chloro-5-fluoro-4-pyrimidineamine. The reaction of N4-(benzothiophen-3- ylmethyl)-2-chloro-5-fluoro-4-pyrimidineamine and 3-aminophenol (200 mg, 1.83 mmol) gave N4-(benzothiophen-3-ylmethyl)-5-fluoro-N2-(3-hydroxyphenyl)-2,4-pyrimidinediamine. (40 mg, 36%). $^1$H NMR (CDCl$_3$): δ 4.45 (br, 1H), 4.95 (dd, J=1.2 and 5.4 Hz, 2H), 5.33 (br, 1H), 6.40 (ddd, J=1.2, 2.4 and 8.1 Hz, 1H), 6.85 (ddd, J=0.9, 2.1 and 8.1 Hz, 1H), 6.91 (br, 1H), 7.05 (t, J=8.1 Hz, 1H), 7.26 (m, 1H), 7.39-7.47 (m, 3H), 7.81 (dd, J=1.2 and 5.1 Hz, 1H), 7.84 (d, J=3.3 Hz, 1H), 7.92 (m, 1H); $^{19}$F NMR (282 MHz, CDCl$_3$): 6-168.89; LCMS: ret. time: 21.91 min.; purity: 99.34%; MS (m/e): 366.96 (MH$^+$).

7.3.308 5-Fluoro-N2-(3-hydroxyphenyl)-N4-(3-pyridylmethyl)-2,4-pyrimidinediamine (R945147)

In a manner analogous to the preparation of N4-(3,4-ethylenedioxyphenyl)-5-fluoro-N2-(3-hydroxyphenyl)-2,4-pyrimidinediamine, 3-pyridylmethylamine (162 mg, 1.5 mmol) and 2,4-dichloro-5-fluoropyrimidine (50 mg, 0.3 mmol) were reacted to give 2-chloro-5-fluoro-N4-(3-pyridylmethyl)-4-pyrimidineamine. Then 2-chloro-5-fluoro-N4-(3-pyridylmethyl)-4-pyrimidineamine and 3-aminophenol (200 mg, 1.83 mmol) reacted to give 5-fluoro-N2-(3-hydroxyphenyl)-N4-(3-pyridylmethyl)-2,4-pyrimidinediamine (40 mg, 43%). $^1$H NMR (CD$_3$OD): δ 4.71 (s, 2H), 6.38 (ddd, J=0.9, 2.4 and 8.1 Hz, 1H), 6.88 (ddd, J=0.9, 2.1 and 8.1 Hz, 1H), 7.00 (t, J=8.1 Hz, 1H), 7.14 (t, J=2.4 Hz, 1H), 7.37 (dd, J=4.8 and 7.8 Hz, 1H), 7.73 (d, J=3.6 Hz, 1H), 7.87 (dt, J=2.1 and 7.5 Hz, 1H), 8.39 (dd, J=1.2 and 7.8 Hz, 1H), 8.57 (d, J=2.1 Hz, 1H); $^{19}$F NMR (282 MHz, CD$_3$OD): 6-170.99; LCMS: ret. time: 8.82 min.; purity: 92.90%; MS (m/e): 312.05 (MH$^+$).

7.3.309 N4-(3-Chloro-4-hydroxy-5-methylphenyl)-5-fluoro-N2-(3-methoxycarbonylmethyleneoxyphenyl)-2,4-pyrimidinediamine (R945148)

In a manner analogous to the preparation of N4-(3,4-ethylenedioxyphenyl)-5-fluoro-N2-(3-hydroxyphenyl)-2,4-pyrimidinediamine, 4-amino-2-chloro-6-methylphenol and 2,4-dichloro-5-fluoropyrimidine resulted 2-chloro-N4-(3-chloro-4-hydroxy-5-methylphenyl)-5-fluoro-4-pyrimidineamine. The reaction of 2-chloro-N4-(3-chloro-4-hydroxy-5-methylphenyl)-5-fluoro-4-pyrimidineamine and 3-methoxycarbonylmethyleneoxyaniline (1.95 g, 11 mmol) gave N4-(3-chloro-4-hydroxy-5-methylphenyl)-5-fluoro-N2-(3-methoxycarbonylmethyleneoxyphenyl)-2,4-pyrimidinediamine (850 mg, 55%). $^1$H NMR (CD$_3$OD): δ 2.22 (s, 3H), 3.76 (s, 3H), 4.52 (s, 2H), 6.50 (dt, J=2.7 and 6.3 Hz, 1H), 7.09-7.14 (m, 2H), 7.24 (t, J=1.8 Hz, 1H), 7.30 (t, J=1.2 Hz, 1H), 7.49 (d, J=2.4 Hz, 1H), 7.88 (d, J=3.9 Hz, 1H); $^{19}$F NMR (282 MHz, CD$_3$OD): 6-168.70; LCMS: ret. time: 20.63 min.; purity: 98.56%; MS (m/e): 432.96 (MH$^+$).

7.3.310 N4-[(2,5-Dimethyl-3-furyl)methyl]-5-fluoro-N2-(3-hydroxyphenyl)-2,4-pyrimidinediamine (R945151)

In a manner analogous to the preparation of N4-(3,4-ethylenedioxyphenyl)-5-fluoro-N2-(3-hydroxyphenyl)-2,4-pyrimidinediamine, the reaction of (2,5-dimethyl-3-furyl)methylamine (188 mg, 1.5 mmol) and 2,4-dichloro-5-fluoropyrimidine (50 mg, 0.3 mmol) gave 2-chloro-N4-[(2,5-dimethyl-3-furyl)methyl]-5-fluoro-4-pyrimidineamine. The reaction of 2-chloro-N4-[(2,5-dimethyl-3-furyl)methyl]-5-fluoro-4-pyrimidineamine and 3-aminophenol (200 mg, 1.83 mmol) gave N4-[(2,5-dimethyl-3-furyl)methyl]-5-fluoro-N2-(3-hydroxyphenyl)-2,4-pyrimidinediamine (50 mg, 51%). $^1$H NMR (CDCl$_3$): δ 2.22 (s, 3H), 2.23 (s, 3H), 4.39 (d, J=5.1 Hz, 2H), 5.24 (br, 1H), 5.90 (s, 1H), 6.52 (d, J=6.6 Hz, 1H), 6.99 (d, J=8.1 Hz, 1H), 7.13 (t, J=8.1 Hz, 1H), 7.29 (s, 1H), 7.71 (m, 2H); $^{19}$F NMR (282 MHz, CDCl$_3$): 6-167.84; LCMS: ret. time: 19.83 min.; purity: 96.32%; MS (m/e): 329.05 (MH$^+$).

7.3.311 N4-(3,5-Dimethyl-4-methoxyphenyl)-5-fluoro-N2-(3-methoxycarbonylmethyleneoxyphenyl)-2,4-pyrimidinediamine (R945153)

In a manner analogous to the preparation of N2,N4-bis[3-methoxy-4-(methoxycarbonyl)phenyl]-5-fluoro-2,4-pyrimidinediamine, the reaction of 2,6-dimethyl-4-nitrophenol (1.67 g, 10 mmol), potassium carbonate (13 g, 0.1 mol) and iodomethane (2.5 mL, 50 mmol) gave 2,6-dimethyl-1-methoxy-4-nitrobenzene. Hydrogenation of 2,6-dimethyl-1-methoxy-4-nitrobenzene gave 3,5-dimethyl-4-methoxyaniline.

In a manner analogous to the preparation of N4-(3,4-ethylenedioxyphenyl)-N2-(3-hydroxyphenyl)-5-fluoro-2,4-pyrimidinediamine, the reaction of 3,5-dimethyl-4-methoxyaniline (400 mg, 2.6 mmol) and 2,4-dichloro-5-fluoropyrimidine (200 mg, 1.2 mmol) gave 2-chloro-N4-(3,5-dimethyl-4-methoxyphenyl)-5-fluoro-4-pyrimidineamine. The reaction of 2-chloro-N4-(3,5-dimethyl-4-methoxyphenyl)-5-fluoro-4-pyrimidineamine a n d 3-(methoxycarbonylmethyleneoxy)aniline (650 mg, 3.6 mmol) gave N4-(3,5-dimethyl-4-methoxyphenyl)-5-fluoro-N2-(3-methoxycarbonylmethyleneoxyphenyl)-2,4-pyrimidinediamine (180 mg, 35%). $^1$H NMR (CD$_3$OD): δ 2.20 (s, 6H), 3.70 (s, 3H), 3.74 (s, 3H), 4.52 (s, 2H), 6.76 (ddd, J=0.9, 2.4 and 8.4 Hz, 1H), 7.03-7.08 (m, 2H), 7.24 (m, 3H), 7.96 (d, J=5.4 Hz, 1H); $^{19}$F NMR (282 MHz, CD$_3$OD): 6-162.92; LCMS: ret. time: 23.13 min.; purity: 100%; MS (m/e): 427.04 (MH$^+$).

7.3.312 N4-[4-(N-Benzylpiperazino)phenyl]-N2-(3,4-ethylenedioxyphenyl)-5-fluoro-2,4-pyrimidinediamine (R945155)

In like manner to the preparation of N4-(3,4-ethylenedioxyphenyl)-N2-(3-hydroxyphenyl)-5-fluoro-2,4-pyrimidineamine, the reaction of N4-[4-(N-benzylpiperazino)phenyl]-2-chloro-5-fluoro-4-pyrimidineamine (50 mg, 0.12 mmol) and 3,4-ethylenedioxyaniline (0.045 mL, 0.36 mmol) gave N4-[4-(N-benzylpiperazino)phenyl)]—N2-(3,4-ethylenedioxyphenyl)-5-fluoro-2,4-pyrimidinediamine (40 mg, 63%). $^1$H NMR (CDCl$_3$): δ 2.64 (t, J=4.8 Hz, 4H), 3.20 (t, J=4.8 Hz, 4H), 3.59 (s, 2H), 4.24 (m, 4H), 6.61 (d, 1H, NH), 6.68 (br, 1H, NH), 6.76 (d, J=8.7 Hz, 1H), 6.88 (dd, J=2.4 and 8.7 Hz, 1H), 6.93 (d, J=8.7 Hz, 2H), 7.19 (d, J=2.4 Hz, 1H), 7.28-7.36 (m, 5H), 7.47 (d, J=8.7 Hz, 2H), 7.87 (d, J=3.3 Hz, 1H); $^{19}$F NMR (282 MHz, CDCl$_3$): 6-168.66; LCMS: ret. time: 18.05 min.; purity: 100%; MS (m/e): 513.10 (MH$^+$).

7.3.313 N2-[(2,5-Dimethyl-3-furyl)methyl]-5-fluoro-N4-(3-hydroxyphenyl)-2,4-pyrimidinediamine (R945162)

In a manner analogous to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine (50 mg, 0.21 mmol) and (2,5-dimethyl-3-furyl)methylamine (80 mg, 0.63 mmol) gave N2-[(2,5-dimethyl-3-furyl)methyl]-5-fluoro-N4-(3-hydroxyphenyl)-2,4-pyrimidinediamine (40 mg, 59%). $^1$H NMR (acetone-d$_6$): δ 2.14 (s, 6H), 4.37 (d, J=4.2 Hz, 2H), 5.96 (s, 1H), 6.77 (d, J=6.6 Hz, 1H), 7.23-7.28 (m, 2H), 7.44 (s, 1H), 8.11 (d, J=4.8 Hz, 1H), 9.05 (br, 1H), 9.75 (br, 1H); $^{19}$F NMR (282 MHz, acetone-d$_6$): 6-165.77; LCMS: ret. time: 19.23 min.; purity: 94.89%; MS (m/e): 329.08 (MH$^+$).

7.3.314 N2-[4-(N-Benzylpiperazino)phenyl]-N4-(3,4-ethylenedioxyphenyl)-5-fluoro-2,4-pyrimidinediamine (R945163)

In a manner analogous to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine (50 mg, 0.18 mmol) and 4-(4-benzylpiperazino)aniline (142 mg, 0.53 mmol) resulted N2-[4-(N-benzylpiperazino)phenyl]-N4-(3,4-ethylenedioxyphenyl)-5-fluoro-2,4-pyrimidinediamine (30 mg, 33%). $^1$H NMR (CDCl$_3$): δ 2.63 (t, J=4.8 Hz, 4H), 3.16 (t, J=4.8 Hz, 4H), 3.58 (s, 2H), 4.27 (m, 4H), 6.56 (d, 1H, NH), 6.70 (br, 1H, NH), 6.82 (d, J=8.7 Hz, 1H), 6.89 (d, J=9.0 Hz, 2H), 6.96 (dd, J=2.7 and 8.7 Hz, 1H), 7.28 (d, J=2.7 Hz, 1H), 7.30-7.36 (m, 5H), 7.39 (d, J=8.7 Hz, 2H), 7.88 (d, J=3.3 Hz, 1H); $^{19}$F NMR (282 MHz, CDCl$_3$): 6-168.94; LCMS: ret. time: 18.12 min.; purity: 98.42%; MS (m/e): 512.95 (MH$^+$).

7.3.315 N2-(Benzothiophen-3-ylmethyl)-5-fluoro-N4-(3-hydroxyphenyl)-2,4-pyrimidinediamine (R945164)

In a manner analogous to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine (50 mg, 0.21 mmol) and benzothiophen-3-ylmethylamine (100 mg, 0.61 mmol) gave N2-(benzothiophen-3-ylmethyl)-5-fluoro-N4-(3-hydroxyphenyl)-2,4-pyrimidinediamine (40 mg, 53%). $^1$H NMR (CDCl$_3$): δ 4.82 (d, J=6.0 Hz, 2H), 6.45 (dd, J=8.1 Hz, 1H), 6.70 (m, 1H), 6.80 (d, J=8.4 Hz, 1H), 7.03 (t, J=8.1 Hz, 1H), 7.22 (m, 1H), 7.34 (s, 1H), 7.39-7.46 (m, 2H), 7.82 (m, 1H), 7.89-7.92 (m, 2H); $^{19}$F NMR (282 MHz, CDCl$_3$): 6-170.02; LCMS: ret. time: 21.29 min.; purity: 92.97%; MS (m/e): 367.03 (MH$^+$).

7.3.316 5-Fluoro-N4-(3-hydroxyphenyl)-N2-(3-pyridylmethyl)-2,4-pyrimidinediamine (R945165)

In a manner analogous to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine (50 mg, 0.21 mmol) and 3-pyridylmethylamine (68 mg, 0.63 mmol) gave 5-fluoro-N4-(3-hydroxyphenyl)-N2-(3-pyridylmethyl)-2,4-pyrimidinediamine (40 mg, 62%). $^1$H NMR (CDCl$_3$): δ 4.40 (d, J=6.3 Hz, 2H), 5.60 (br, 1H), 6.62-6.70 (m, 3H), 7.05 (br, 1H), 7.14 (t, J=8.1 Hz, 1H), 7.30 (dd, J=5.1 and 7.8 Hz, 1H), 7.73 (d, J=7.5 Hz, 1H), 7.80 (d, J=3.3 Hz, 1H), 8.49 (d, J=4.5 Hz, 1H), 8.66 (s, 1H); $^{19}$F NMR (282 MHz, CDCl$_3$): 6-169.52; LCMS: ret. time: 9.41 min.; purity: 99.25%; MS (m/e): 312.01 (MH$^+$).

7.3.317 5-Fluoro-N4-(3-hydroxyphenyl)-N2-(2-pyridylmethyl)-2,4-pyrimidinediamine (R945166)

In a manner analogous to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine (50 mg, 0.21 mmol) and 2-pyridylmethylamine (68 mg, 0.63 mmol) gave 5-fluoro-N4-(3-hydroxyphenyl)-N2-(2-pyridylmethyl)-2,4-pyrimidinediamine (40 mg, 62%). $^1$H NMR (CDCl$_3$): δ 4.73 (d, J=6.3 Hz, 2H), 5.85 (t, J=6.0 Hz, 1H, NH), 6.48 (d, J=6.9 Hz, 1H), 6.61 (dd, J=2.7 and 8.1 Hz, 1H), 6.67 (s, 1H), 7.13 (t, J=8.1 Hz, 1H), 7.21 (dd, J=5.1 and 7.5 Hz, 1H), 7.49 (d, J=7.5 Hz, 1H), 7.69 (td, J=1.8 and 7.8 Hz, 1H), 7.85 (d, J=3.6 Hz, 1H), 8.38 (br, 1H), 8.56 (dd, J=1.2 and 3.9 Hz, 1H); $^{19}$F NMR (282 MHz, CDCl$_3$): 6-170.49; LCMS: ret. time: 10.10 min.; purity: 100%; MS (m/e): 312.08 (MH$^+$).

7.3.318 N4-(3,5-Dimethoxyphenyl)-N2-(3-hydroxyphenyl)-5-fluoro-2,4-pyrimidinediamine (R926802)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,5-dimethoxyphenyl)-5-fluoro-4-pyrimidineamine with 3-hydroxyaniline gave N4-(3,5-dimethoxyphenyl)-N2-(3-hydroxyphenyl)-5-fluoro-2,4-pyrimidinediamine. LCMS: ret. time: 18.98 min.; purity: 90%; MS (m/e): 357 (MH$^+$).

7.3.319 N4-(3,5-Dimethoxyphenyl)-N2-(2-ethoxycarbonylindol-7-yl)-5-fluoro-2,4-pyrimidinediamine (R926803)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,5-dimethoxyphenyl)-5-fluoro-4-pyrimidineamine with 2-ethoxycarbonyl-7-aminoindole gave N4-(3,5-dimethoxyphenyl)-N2-(2-ethoxycarbonylindol-7-yl)-5-fluoro-2,4-pyrimidinediamine. LCMS: ret. time: 24.21 min.; purity: 91%; MS (m/e): 452 (MH$^+$).

7.3.320 N2-(3,4-Dimethoxyphenyl)-N4-(4-ethoxyphenyl)-5-fluoro-2,4-pyrimidinediamine (R926108)

In like manner to the preparation of N4-(3,4-ethylenedioxyphenyl)-5-fluoro-N2-(3-hydroxyphenyl)-2,4-pyrimidinediamine, the reaction of 2-chloro-N4-(4-ethoxyphenyl)-5-fluoro-4-pyrimidineamine with 3,4-dimethoxyaniline gave N2-(3,4-dimethoxyphenyl)-N4-(4-ethoxyphenyl)-5-fluoro-2,4-pyrimidinediamine. $^1$H NMR (CDCl$_3$): δ 7.89 (d, 1H, J=3 Hz), 7.45 (bd, 2H, J=9 Hz), 7.20 (d, 1H, J=2.4 Hz), 6.96-6.77 (m, 5H), 6.63 (bs, 1H), 4.03 (q, 2H, J=7.2 Hz), 3.86 (s, 3H), 3.72 (s, 3H), 1.42 (t, 3H, J=7.2 Hz); $^{19}$F NMR (CDCl3): −47473.

7.3.321 N4-(4-Ethoxyphenyl)-N2-(3-hydroxyphenyl)-5-fluoro-2,4-pyrimidinediamine (R926146)

In like manner to the preparation of N4-(3,4-ethylenedioxyphenyl)-5-fluoro-N2-(3-hydroxyphenyl)-2,4-pyrimidinediamine, the reaction of 2-chloro-N4-(4-ethoxyphenyl)-5-fluoro-4-pyrimidineamine with 3-hydroxyaniline gave N4-(4-ethoxyphenyl)-N2-(3-hydroxyphenyl)-5-fluoro-2,4-pyrimidinediamine. $^1$H NMR (CD$_3$OD): δ 7.79 (d, 1H, J=4.2 Hz), 7.54 (dd, 2H, J=2.4 and 7.2 Hz), 7.05-6.97 (m, 3H), 6.87 (dd, 2H, J=2.4 and 4.2 Hz), 6.41 (m, 1H), 4.02 (q, 2H, J=6.6 Hz), 1.38 (t, 3H, J=6.9 Hz); $^{19}$F NMR (CD$_3$OD): −47444; LCMS: ret. time: 21.15 min.; purity: 98%; MS (m/e): 341 (MH$^+$).

7.3.322 N4-(4-Ethoxyphenyl)-N2-(3,4-ethylenedioxyphenyl)-5-fluoro-2,4-pyrimidinediamine (R926213)

In like manner to the preparation of N4-(3,4-ethylenedioxyphenyl)-5-fluoro-N2-(3-hydroxyphenyl)-2,4-pyrimidinediamine, the reaction of 2-chloro-N4-(4-ethoxyphenyl)-5-fluoro-4-pyrimidineamine with 3,4-ethylenedioxyaniline gave N4-(4-ethoxyphenyl)-N2-(3,4-ethylenedioxyphenyl)-5-fluoro-2,4-pyrimidinediamine. $^1$H NMR (CDCl$_3$): δ 7.87 (d, 1H, J=3 Hz), 7.47 (dd, 2H, J=2.4 and 5.1 Hz), 7.18 (d, 1H, J=2.4 Hz), 6.91-6.85 (m, 3H), 6.79-6.73 (m, 2H), 6.64 (bs, 1H), 4.25 (bs, 4H), 4.05 (q, 2H, J=6.9 Hz), 1.43 (t, 3H, J=7.2 Hz); $^{19}$F NMR (CDCl$_3$): −47467; LCMS: ret. time: 24.32 min.; purity: 90%; MS (m/e): 383 (MH$^+$).

7.3.323 N4-(3,4-Dimethoxyphenyl)-N2-(4-ethoxyphenyl)-5-fluoro-2,4-pyrimidinediamine (R926145)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-dimethoxyphenyl)-5-fluoro-4-pyrimidineamine with 4-ethoxyaniline gave N4-(3,4-dimethoxyphenyl)-N2-(4-ethoxyphenyl)-5-fluoro-2,4-pyrimidinediamine. $^1$H NMR (CDCl$_3$): δ 7.90 (bs, 1H), 7.37 (dd, 2H, J=2.4 and 6.3 Hz), 7.21 (d, 1H, J=2.4 Hz), 7.03 (dd, 1H, J=2.4 and 8.1 Hz), 6.86-6.80 (m, 4H), 6.65 (bs, 1H), 4.00 (q, 2H, J=7.2 Hz), 3.89 (s, 3H), 3.75 (s, 3H), 1.39 (t, 3H, J=6.9 Hz); $^{19}$F NMR (CDCl$_3$): −47501; LCMS: ret. time: 22.69 min.; purity: 98%; MS (m/e): 385 (MH$^+$).

7.3.324 N4-(3,4-Dimethoxyphenyl)-5-fluoro-N2-(3-hydroxyphenyl)-2,4-pyrimidinediamine (R926147)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-dimethoxyphenyl)-5-fluoro-4-pyrimidineamine with 3-hydroxyaniline gave N4-(3,4-dimethoxyphenyl)-5-fluoro-N2-(3-hydroxyphenyl)-2,4-pyrimidinediamine. $^1$H NMR (CD$_3$OD): δ 7.77 (d, 1H, J=3.3 Hz), 7.15 (d, 1H, J=2.4 Hz), 7.05 (dd, 1H, J=2.4 and 8.4 Hz), 7.00-6.90 (m, 4H), 6.80 (d, 1H, J=8.1 Hz), 6.40 (m, 1H), 4.05 (q, 2H), 3.80 (s, 3H), 3.75 (s, 3H), 1.20 (t, 3H); $^{19}$F NMR (CD$_3$OD): −47223; LCMS: ret. time: 17.94 min.; purity: 99%; MS (m/e): 357 (MH$^+$).

7.3.325 N2-(3,4-Dimethoxyphenyl)-5-fluoro-N4-(3-hydroxyphenyl)-2,4-pyrimidinediamine (R926113)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with 3,4-dimethoxyaniline gave N2-(3,4-dimethoxyphenyl)-5-fluoro-N4-(3-hydroxyphenyl)-2,4-pyrimidinediamine. $^1$H NMR (CDCl$_3$): δ 7.90 (d, 1H, J=6.6 Hz), 7.59 (bs, 1H), 7.30 (s, 1H), 7.20-7.10 (m, 2H), 7.00-6.75 (m, 4H), 6.59 (bd, 1H, J=7.8 Hz), 3.87 (s, 3H), 3.84 (s, 3H); $^{19}$F NMR (CDCl$_3$): −47229; LCMS: ret. time: 17.77 min.; purity: 78%; MS (m/e): 357 (MH$^+$).

7.3.326 N2-(4-Ethoxycarbonylmethyleneoxyphenyl)-5-fluoro-N4-(3-hydroxyphenyl)-2,4-pyrimidinediamine (R926395)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with ethyl-4-aminophenoxyacetate gave N2-(4-ethoxycarbonylmethyleneoxyphenyl)-5-fluoro-N4-(3-hydroxyphenyl)-2,4-pyrimidinediamine. $^1$H NMR (CD$_3$OD): δ 7.90 (d, 1H, J=5.1 Hz), 7.35 (dd, 2H, J=2.1 and 7.2 Hz), 7.13 (t, 1H, J=7.2 Hz), 7.10 9d, 1H, J=6.6 Hz), 6.96 (dd, 2H, J=2.4 and 7.2 Hz), 6.67 (m, 1H), 4.72 (s, 2H), 4.25 (q, 2H, J=7.2 Hz), 1.29 (t, 3H, J=7.2 Hz); $^{19}$F NMR (CD$_3$OD): −21885; LCMS: ret. time: 20.18 min.; purity: 92%; MS (m/e): 399 (MH$^+$).

7.3.327 5-Bromo-N2-(4-ethoxycarbonylmethyleneoxyphenyl)-N4-(3-hydroxyphenyl)-2,4-pyrimidinediamine (R926396)

In like manner to the preparation of N4-(3,4-ethylenedioxyphenyl)-5-fluoro-N2-(3-hydroxyphenyl)-2,4-pyrimidinediamine, the reaction of 2-chloro-N4-(3-hydroxyphenyl)-4-pyrimidineamine with ethyl 4-aminophenoxyacetate gave 5-bromo-N2-(4-ethoxycarbonylmethyleneoxyphenyl)-N4-(3-hydroxyphenyl)-2,4-pyrimidinediamine. LCMS: ret. time: 21.64 min.; purity: 92%; MS (m/e): 459 (MH$^+$).

7.3.328 N2-(4-Ethoxyphenyl)-N4-(3,4-ethylenedioxyphenyl)-5-fluoro-2,4-pyrimidinediamine (R926211)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 4-ethoxyaniline were reacted to yield N2-(4-ethoxyphenyl)-N4-(3,4-ethylenedioxyphenyl)-5-fluoro-2,4-pyrimidinediamine. $^1$H NMR (CDCl$_3$): δ 7.88 (bs, 1H), 7.40 (bd, 2H, J=8.7 Hz), 7.27 (bd, 2H, J=6.3 Hz), 6.95 (dd, 1H, J=3 and 9 Hz), 6.86-6.77 (m, 3H), 6.58 (s, 1H), 4.28 (bs, 4H), 4.01 (q, 2H, J=6.9 Hz), 1.40 (t, 3H, J=6.9 Hz); LCMS: ret. time: 24.46 min.; purity: 90%; MS (m/e): 383 (MH$^+$).

7.3.329 N2-(3,4-Dimethoxyphenyl)-N4-(3,4-ethylenedioxyphenyl)-5-fluoro-2,4-pyrimidinediamine (R926212)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 3,4-dimethoxyaniline were reacted to yield N2-(3,4-dimethoxyphenyl)-N4-(3,4-ethylenedioxyphenyl)-5-fluoro-2,4-pyrimidinediamine. LCMS: ret. time: 20.98 min.; purity: 74%; MS (m/e): 399 (MH$^+$).

7.3.330 N2-(3-Chloro-4-fluorophenyl)-N4-(3,4-ethylenedioxyphenyl)-5-fluoro-2,4-pyrimidinediamine (R926218)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 3-chloro-4-fluoroaniline were reacted to yield N2-(3-chloro-4-fluorophenyl)-N4-(3,4-ethylenedioxyphenyl)-5-fluoro-2,4-pyrimidinediamine. $^1$H NMR (CD$_3$OD): δ 7.75 (bd, 1H), 7.70 (bd, 1H), 7.18 (m, 1H), 7.10 (m, 1H), 6.90 (m, 2H), 6.75 (m, 1H), 4.20 (bs, 4H); LCMS: ret. time: 25.04 min.; purity: 99%; MS (m/e): 392 (MH$^+$).

7.3.331 N2-(4-tert-Butylphenyl)-N4-(3,4-ethylenedioxyphenyl)-5-fluoro-2,4-pyrimidinediamine (R926219)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 4-tert-butylaniline were reacted to yield N2-(4-tert-butylphenyl)-N4-(3,4-ethylenedioxyphenyl)-5-fluoro-2,4-pyrimidinediamine. $^1$H NMR (CDCl$_3$): δ 7.85 (d, 1H, J=3.6 Hz), 7.44 (bdd, 2H, J=6.3 Hz), 7.35-7.31 (m, 3H), 6.93 (dd, 1H, J=2.7 and 8.7 Hz), 6.83 (d, 1H, J=9 Hz), 6.80 (bs, 1H), 4.23 (s, 4H), 1.28 (s, 9H); LCMS: ret. time: 27.67 min.; purity: 98%; MS (m/e): 395 (MH$^+$).

7.3.332 N4-(3,4-Ethylenedioxyphenyl)-N2-(4-fluorophenyl)-5-fluoro-2,4-pyrimidinediamine (R926220)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 4-fluoroaniline were reacted to yield N4-(3,4-ethylenedioxyphenyl)-N2-(4-fluorophenyl)-5-fluoro-2,4-pyrimidinediamine. $^1$H NMR (CDCl$_3$): δ 7.92 (bs, 1H), 7.80 (bs, 1H), 7.60 (bd, 2H), 6.90 (m, 2H), 6.80 (bs, 1H), 6.65 (bs, 1H), 4.25 (s, 4H); LCMS: ret. time: 22.87 min.; purity: 97%; MS (m/e): 357 (MH$^+$).

7.3.333 N4-(3,4-Ethylenedioxyphenyl)-N2-(3-fluorophenyl)-5-fluoro-2,4-pyrimidinediamine (R926221)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 3-fluoroaniline were reacted to yield N4-(3,4-ethylenedioxyphenyl)-N2-(3-fluorophenyl)-5-fluoro-2,4-pyrimidinediamine. $^1$H NMR (CDCl$_3$): δ 7.76 (d, 1H, J=5.6 Hz), 7.39 (m, 2H), 7.14 (d, 1H, J=2.4 Hz), 6.94-6.85 (m, 3H), 6.75 (d, 1H, J=9 Hz), 4.21 (s, 4H); LCMS: ret. time: 22.60 min.; purity: 100%; MS (m/e): 357 (MH$^+$).

7.3.334 N4-(3,4-Ethylenedioxyphenyl)-5-fluoro-N2-(2-methoxyethyl)-2,4-pyrimidinediamine (R926229)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 2-methoxyethylamine were reacted to yield N4-(3,4-ethylenedioxyphenyl)-5-fluoro-N2-(2-methoxyethyl)-2,4-pyrimidinediamine. $^1$H NMR (CDCl$_3$): δ 7.81 (bs, 1H), 7.33 (d, 1H, J=2.4 Hz), 6.93 (dd, 1H, J=2.4 Hz and 9 Hz), 6.81 (d, 1H, J=9 Hz), 6.53 (s, 1H), 4.25 (bs, 2H), 3.54 (bs, 2H), 3.36 (s, 3H); LCMS: ret. time: 18.01 min.; purity: 100%; MS (m/e): 321 (MH$^+$).

7.3.335 N4-(3,4-Ethylenedioxyphenyl)-5-fluoro-N2-(4-methoxybenzyl)-2,4-pyrimidinediamine (R926230)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 4-methoxybenzylamine were reacted to yield N4-(3,4-ethylenedioxyphenyl)-5-fluoro-N2-(4-methoxybenzyl)-2,4-pyrimidinediamine. $^1$H NMR (CDCl$_3$): δ 7.81 (d, 1H, J=2.7 Hz), 7.27 (m, 3H), 6.86 (m, 3H), 6.52 (s, 1H), 5.14 (s, 1H), 4.46 (d, 2H, J=5.4 Hz), 4.24 (s, 4H), 3.78 (s, 3H); LCMS: ret. time: 23.06 min.; purity: 94%; MS (m/e): 383 (MH$^+$).

7.3.336 N2-(2,2-Difluorobenzodioxol-5-yl)-N4-(3,4-ethylenedioxyphenyl)-5-fluoro-2,4-pyrimidinediamine (R926386)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 2,2-difluoro-5-aminobenzodioxole were reacted to yield N2-(2,2-difluorobenzodioxol-5-yl)-N4-(3,4-ethylenedioxyphenyl)-5-fluoro-2,4-pyrimidinediamine. $^1$H NMR (CDCl$_3$): δ 9.39 (s, 1H), 9.24 (s, 1H), 8.06 (d, 1H, J=5.6 Hz), 7.87 (d, 1H, J=1.8 Hz), 7.27-7.19 (m, 3H), 7.08 (dd, 1H, J=2.4 and 8.7 Hz), 6.80 (d, 1H, J=9 Hz), 4.21 (bs, 4H); $^{19}$F NMR (CDCl$_3$): −14012 and −46487; LCMS: ret. time: 25.32 min; purity: 100%; MS (m/e): 419 (MH$^+$)

7.3.337 N2-(2-Ethoxycarbonylindol-5-yl)-N4-(3,4-ethylenedioxyphenyl)-5-fluoro-2,4-pyrimidinediamine (R926476)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 2-ethoxycarbonyl-5-aminoindole were reacted to yield N2-(2-ethoxycarbonylindol-5-yl)-N4-(3,4-ethylenedioxyphenyl)-5-fluoro-2,4-pyrimidinediamine. $^1$H NMR (CDCl$_3$): δ 7.84 (d, 1H, J=5.4 Hz), 7.76 (d, 1H, J=3.6 Hz), 7.50 (d, 1H, J=9 Hz), 7.23-7.15 (m, 3H), 7.03 (bd, 1H, J=8.7 Hz), 6.78 (d, 1H, J=8.7 Hz), 4.38 (q, 2H, J=7.2 Hz), 4.22 (s, 4H), 1.41 (t, 3H, J=6.9 Hz); LCMS: ret. time: 23.58 min; purity: 100%; MS (m/e): 451 (MH$^+$).

7.3.338 N2-(4-Cyanomethyleneoxyphenyl)-N4-(3,4-ethylenedioxyphenyl)-5-fluoro-2,4-pyrimidinediamine (R926480)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 4-cyanomethyleneoxyaniline were reacted to yield N2-(4-cyanomethyleneoxyphenyl)-N4-(3,4-ethylenedioxyphenyl)-5-fluoro-2,4-pyrimidinediamine. $^1$H NMR (CDCl$_3$): δ 7.87 (d, 1H, J=3.6 Hz), 7.52 (d, 1H, J=8.7 Hz), 7.38 (bs, 1H), 7.28 (d, 1H, J=2.4 Hz), 6.96-6.86 (m, 3H), 6.65 (bd, 1H), 4.73 (s, 2H), 4.29 (m, 4H); $^{19}$F NMR (CDCl$_3$): −47416; LCMS: ret. time: 20.49 min.; purity: 100%; MS (m/e): 394 (MH$^+$).

7.3.339 N2-(3-Ethoxycarbonylmethyleneoxyphenyl)-N4-(3,4-ethylenedioxyphenyl)-5-fluoro-2,4-pyrimidinediamine (R926482)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and ethyl-3-aminophenoxyacetate were reacted to yield N2-(3-ethoxycarbonylmethyleneoxyphenyl)-N4-(3,4-ethylenedioxyphenyl)-5-fluoro-2,4-pyrimidinediamine. $^1$H NMR (CDCl$_3$): δ 10.53 (s, 1H), 8.18 (s, 1H), 7.67 (d, 1H, J=4.8 Hz), 7.19-7.02 (m, 5H), 6.86 (d, 1H, 9 Hz), 6.71 (dd, 1H, J=1.8 and 9 Hz), 4.51 (s, 2H), 4.25 (m, 6H), 1.29 (t, 3H, J=7.5 Hz); ¹⁹F NMR (CDCl₃): –45640; LCMS: ret. time: 22.71 min.; purity: 99%; MS (m/e): 441 (MH⁺).

7.3.340 N2-(3-Ethoxycarbonylphenyl)-N4-(3,4-ethylenedioxyphenyl)-5-fluoro-2,4-pyrimidinediamine (R925745)

In like manner to preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 3-ethoxycarbonylaniline gave N2-(3-ethoxycarbonylphenyl)-N4-(3,4-ethylenedioxyphenyl)-5-fluoro-2,4-pyrimidinediamine. ¹H NMR (CDCl₃): δ 8.04 (bs, 1H), 7.94 (bs, 1H), 7.90 (bd, 1H), 7.68 (bd, 1H, J=7.5 Hz), 7.35 (t, 1H, J=8.1 Hz), 7.28 (d, 1H, J=2.4 Hz), 7.07 (s, 1H), 6.93 (dd, 1H, J=3 and 8.7 Hz), 6.83 (d, 1H, J=9 Hz), 6.64 (bs, 1H), 4.36 (q, 2H, J=7.2 Hz), 4.26 9s, 4H), 1.35 (t, 3H, J=7.5 Hz); ¹⁹F NMR (CDCl₃): –47247; LCMS: ret. time: 15.88; purity: 100%; MS (m/e): 411 (MH⁺).

7.3.341 N4-(3,4-Ethylenedioxyphenyl)-5-fluoro-N2-(2-hydroxyethyl)-2,4-pyrimidinediamine (R925746)

In like manner to preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 2-hydroxyethylamine gave N4-(3,4-ethylenedioxyphenyl)-5-fluoro-N2-(2-hydroxyethyl)-2,4-pyrimidinediamine. ¹H NMR (CD₃OD): δ 7.7 (bs, 1H), 7.32 (d, 1H, J=2.4 Hz), 7.05 (dd, 1H, J=2.4 and 9 Hz), 6.75 (d, 1H, J=8.9 Hz), 4.21 (s, 4H), 3.67 (t, 2H, J=5.7 Hz), 3.38 (t, 2H, J=5.4 Hz); ¹⁹F NMR (CD₃OD): –48518; LCMD: ret. time: 15.54 min.; purity: 100%; MS (m/e): 307 (MH⁺).

7.3.342 N2-(4-Ethoxycarbonylmethyleneoxyphenyl)-N4-(3,4-ethylenedioxyphenyl)-5-fluoro-2,4-pyrimidinediamine (R925747)

In like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and ethyl-4-aminophenoxyacetate gave N2-(4-ethoxycarbonylmethyleneoxyphenyl)-N4-(3,4-ethylenedioxyphenyl)-5-fluoro-2,4-pyrimidinediamine. ¹H NMR (CDCl₃): δ 7.88 (bs, 1H), 7.42 (dd, 2H, J=2.4 and 6.9 Hz), 7.28 (d, 1H, J=3 Hz), 6.95-6.81 (m, 4H), 6.59 (s, 1H), 4.59 (s, 4H), 4.28 (q, 2H, J=6.2 Hz), 1.30 (t, 3H, J=6.1 Hz); 19F NMR (CDCl3): –47570; LCMS: ret. time: 22.74 min.; purity: 100%; MS (m/e): 441 (MH⁺).

7.3.343 N2-(3-Chloro-4-hydroxy-5-methylphenyl)-5-fluoro-N4-(3-hydroxyphenyl)-2,4-pyrimidinediamine (R940233)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with 3-chloro-4-hydroxy-5-methylaniline gave N2-(3-chloro-4-hydroxy-5-methylphenyl)-5-fluoro-N4-(3-hydroxyphenyl)-2,4-pyrimidinediamine. LCMS: retn, time: 19.20 min.; purity: 94%; MS (m/e): 360 (M⁺); ¹H NMR (CDCl₃): δ 7.93 (1H, d, J=3.1 Hz), 7.54 (1H, d, J=2.6 Hz), 7.30 (1H, t, J=2.1 Hz), 7.21 (1H, t, J=7.9 Hz), 7.02 (3H, m), 6.78 (1H, s), 6.61 (1H, dd, J=7.9 Hz, J=2.1 Hz), 2.26 (3H, s).

7.3.344 N4-(3-Chloro-4-hydroxy-5-methylphenyl)-5-fluoro-N2-(3-hydroxyphenyl)-2,4-pyrimidinediamine (R940235)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-chloro-4-hydroxy-5-methylphenyl)-4-pyrimidineamine with 3-hydroxyaniline gave N4-(3-chloro-4-hydroxy-5-methylphenyl)-5-fluoro-N2-(3-hydroxyphenyl)-2,4-pyrimidinediamine. LCMS: retn, time: 18.20 min.; purity: 94%; MS (m/e): 360 (M⁺); 1☐☐☐☐ (DMSO-d6): δ 9.26 (1H, s), 9.23 (1H, s), 9.16 (1H, s), 8.89 (1H, s), 8.14 (1H, d, J=4.5 Hz), 7.66 (1H, d, J=2.1 Hz), 7.60 (1H, d, J=2.1 Hz), 7.29 (1H, d, J=8.4 Hz), 7.11 (1H, s), 7.06 (1H, t, J=8.4 Hz), 6.41 (1H, d, J=8.4 Hz), 2.30 (3H, s).

7.3.345 N2-(3,4-Dimethoxyphenyl)-5-fluoro-N4-[4-[3-(N-morpholinyl)propyl]oxyphenyl]-2,4-pyrimidinediamine (R940250)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-[4-[3-(N-morpholinyl)propyl]oxyphenyl]-4-pyrimidineamine with 3,4-dimethoxyaniline gave N2-(3,4-dimethoxyphenyl)-5-fluoro-N4-[4-[3-(N-morpholinyl)propyl]oxyphenyl]-2,4-pyrimidinediamine. LCMS: retn, time: 14.72 min.; purity: 94%; MS (m/e): 484 (MH⁺); ¹H NMR (CDCl₃): δ 7.89 (1H, d, J=3.3 Hz), 7.47 (2H, d, J=9 Hz), 7.22 (1H, d, J=2.2 Hz), 6.93-6.76 (5H, m), 6.64 (1H, d, J=2.2 Hz), 4.01 (2H, t, J=5.6 Hz), 3.86 (3H, s), 3.72 (3H, s), 3.71 (4H, m), 2.58-2.44 (6H, m), 1.97 (2H, m).

7.3.346 N2-(3-Chloro-4-hydroxy-5-methylphenyl)-5-fluoro-N4-[4-[3-(N-morpholinyl)propyl]oxyphenyl]-2,4-pyrimidinediamine (R940251)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-[4-[3-(N-morpholinyl)propyl]oxyphenyl]-4-pyrimidineamine with 2-chloro-4-hydroxy-5-methylaniline gave N2-(2-chloro-4-hydroxy-5-methylphenyl)-5-fluoro-N4-[4-[3-(N-morpholinyl)propyl]oxyphenyl]-2,4-pyrimidinediamine. LCMS: retn, time: 15.19 min.; purity: 94%; MS (m/e): 488 (MH⁺); ¹H NMR (CDCl₃): δ 7.89 (1H, d, J=3.3 Hz), 7.52 (1H, d, J=2.5 Hz), 7.44 (2H, d, 8.7 Hz), 6.97 (1H, d, J=2.5 Hz), 6.91 (2H, d, 9 Hz), 6.71 (1H, s), 6.64 (1H, 2.5 Hz), 4.03 (2H, t, J=6.03 Hz), 3.74 (4H, t, J=4.65 Hz), 2.60-2.43 (6H, m), 2.23 (3H, s), 1.49 (2H, m).

7.3.347 N4-(3,5-Dimethyl-4-hydroxyphenyl)-N2-(3-ethoxycarbonylmethyleneoxyphenyl)-5-fluoro-2,4-pyrimidinediamine (R940253)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,5-dimethyl-4-hydroxyphenyl)-5-fluoro-4-pyrimidineamine with ethyl 3-aminophenoxyacetate gave N4-(3,5-dimethyl-4-hydroxyphenyl)-N2-(3-ethoxycarbonylmethyleneoxyphenyl)-5-fluoro-2,4-pyrimidinediamine. LCMS: retn, time: 21.79 min.; purity: 91%; MS (m/e): 427 (MH⁺); 1H NMR (DMSO-d6): δ 9.80 (1H, s), 8.30 (1H, s), 8.23 (1H, d, J=4.5 Hz), 7.37-7.17 (5H, m), 6.66 (1H, d, J=9 Hz), 4.73 (2H, s), 4.25 (2H, q, J=7.2 Hz), 2.23 (6H, s), 1.29 (3H, t, J=7.0 Hz).

7.3.348 N2-(3-tert-Butylphenyl)-N4-(3-ethoxycarbonylmethyleneoxyphenyl)-5-fluoro-4-pyrimidinediamine (R940266)

In like manner to the preparation of N4-(3,4-ethylenedioxyphenyl)-5-fluoro-N2-(3-hydroxyphenyl)-2,4-pyrimidinediamine, the reaction of 2-chloro-N4-(3-ethoxycarbonylmethyleneoxyphenyl)-5-fluoro-4-pyrimidineamine with 3-tert-butylaniline gave N2-(3-tert-butylphenyl)-N4-(3-ethoxycarbonylmethyleneoxyphenyl)-5-fluoro-4-pyrimidinediamine. LCMS: retn, time: 28.17 min.; purity: 96%; MS (m/e): 439 (M$^+$), 440 (MH$^+$); $^1$H NMR (DMSO-d6): δ 9.40 (1H, s), 9.19 (1H, s), 8.21 (1H, d, J=3.6 Hz), 7.78 (1H, d, J=8.5 Hz) 7.60 (2H, m), 7.48 (1H, t, J=2 Hz), 7.31 (1H, t, J=8.5 Hz), 7.25 (1H, t, J=8.5 Hz), 7.02 (1H, d, J=8.5 Hz), 6.70 (1H, dd, J=8.5 and 2 Hz), 4.79 (2H, s), 4.26 (2H, q, J=7.2 Hz), 1.33 (9H, s), 1.29 (3H, t, J=7.2 Hz).

7.3.349 5-Fluoro-N4-(3-isopropylphenyl)-N2-(2-methoxycarbonylbenzofur-5-yl)-2,4-pyrimidinediamine and 5-fluoro-N2-(2-ethoxoxycarbonylbenzofur-5-yl)-N4-(3-isopropylphenyl)-2,4-pyrimidinediamine R940284

In like manner to the preparation of N4-(3,4-ethylenedioxyphenyl)-5-fluoro-N2-(3-hyroxyphenyl)-2,4-pyrimidinediamine, 2-chloro-5-fluoro-N4-(3-isopropylphenyl)-4-pyrimidineamine and ethyl 3-aminophenoxyacetate were reacted to give the mixture of 5-fluoro-N4-(3-isopropylphenyl)-N2-(2-methoxycarbonylbenzofur-5-yl)-2,4-pyrimidinediamine and 5-fluoro-N2-(2-ethoxoxycarbonylbenzofur-5-yl)-N4-(3-isopropylphenyl)-2,4-pyrimidinediamine. (R=CO$_2$Me). LCMS: retn, time: 25.41 min.; purity: 60.61%; MS (m/e): 411 (MH$^+$); 1H NMR (DMSO-d6): δ 9.38 (1H, s), 9.29 (1H, s), 8.20 (1H, d, J=3.9 Hz), 7.85 (1H, d, J=9.3 Hz), 7.58 (1H, t, J=1.6 Hz), 7.43-7.33 (3H, m), 7.18 (1H, t, J=8.2 Hz), 7.05 (1H, d, J=7.8 Hz), 6.53 (1H, dd, J=8.4 Hz, J=2.1 Hz), 4.72 (2H, s), 3.79 (3H, s), 2.95 (1H, quint, J=7.2 Hz), 1.26 (6H, d, J=7.2 Hz) (R=CO$_2$Et) LCMS: retn, time: 26.99 min.; purity: 39%; MS (m/e): 425 (MH$^+$); 1H NMR (DMSO-d6): δ 9.38 (1H, s), 9.29 (1H, s), 8.20 (1H, d, J=3.9 Hz), 7.85 (1H, d, J=9.3 Hz), 7.58 (1H, t, J=1.6 Hz), 7.43-7.33 (3H, m), 7.18 (1H, t, J=8.2 Hz), 7.05 (1H, d, J=7.8 Hz), 6.53 (1H, dd, J=8.4 and 2.1 Hz), 4.71 (2H, s), 4.25 (2H, q, J=7.2 Hz), 2.95 (1H, quint, J=7.2 Hz), 1.31 (3H, t, J=7.2 Hz), 1.26 (6H, d, J=7.2 Hz).

7.3.350 N4-(3-tert-Butylphenyl)-5-fluoro-N2-(2-methoxycarbonylbenzofur-5-yl)-2,4-pyrimidinediamine R940281

In like manner to the preparation of N4-(3,4-ethylenedioxyphenyl)-5-fluoro-N2-(3-hyroxyphenyl)-2,4-pyrimidinediamine, N4-(3-tert-butylphenyl)-2-chloro-5-fluoro-4-pyrimidineamine and 2-methoxycarbonyl-5-aminobenzofuran were reacted to give N4-(3-tert-butylphenyl)-5-fluoro-N2-(2-methoxycarbonylbenzofur-5-yl)-2,4-pyrimidinediamine. LCMS: retn, time: 26.76 min.; purity: 97%; MS (m/e): 435 (MH$^+$); 1H NMR (DMSO-d6): δ 9.41 (2H, s1), 8.27 (1H, s), 8.21 (1H, d, J 3.9 Hz), 7.98 (1H, m), 7.77-7.60 (3H, m), 7.37 (1H, t, J 8.1 Hz), 7.22 (1H, d, J 8.1 Hz), 3.98 (3H, s), 1.34 (9H, s).

7.3.351 5-fluoro-N4-(3-isopropylphenyl)-N2-(2-methoxycarbonylbenzofur-5-yl)-2,4-pyrimidinediamine R940283

In like manner to the preparation of N4-(3,4-ethylenedioxyphenyl)-5-fluoro-N2-(3-hyroxyphenyl)-2,4-pyrimidinediamine, 2-chloro-5-fluoro-N4-(3-isopropylphenyl)-4-pyrimidineamine and 2-methoxycarbonyl-5-aminobenzofuran were reacted to give 5-fluoro-N4-(3-isopropylphenyl)-N2-(2-methoxycarbonylbenzofur-5-yl)-2,4-pyrimidinediamine. LCMS: retn, time: 26.05 min.; purity: 99%; MS (m/e): 420 (M$^+$), 422 (MH$^+$); $^1$H NMR (DMSO-d6): δ 10.00 (1H, s), 9.95 (1H, s), 8.31 (1H, d, J=4.8 Hz), 8.11 (1H, s), 7.74 (3H, m), 7.35 (1H, s), 7.35 (1H, t, J=7.2 Hz), 7.12 (1H, d, J=7.2 Hz), 3.99 (3H, s), 2.83 (1H, sept, J=6.9 Hz), 1.20 (6H, d, J=6.9 Hz).

7.3.352 N2-(1,1-Dihydroisobenzofuran-1-one-6-yl)-N4-(3,4-ethylenedioxyphenyl)-5-fluoro-2,4-pyrimidinediamine (R926786)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine with 6-amino-1,1-dihydroisobenzofuran-1-one gave N2-(1,1-dihydroisobenzofuran-1-one-6-yl)-N4-(3,4-ethylenedioxyphenyl)-5-fluoro-2,4-pyrimidinediamine. $^1$H NMR (DMSO-d6): δ 10.20 (s, 1H), 9.85 (s, 1H), 8.22 (d, 1H, J=4.8 Hz), 8.10 (d, 1H, J=1.2 Hz), 7.86 (dd, 1H, J=2.4 and 8.7 Hz), 7.54 (d, 1H, J=8.4 Hz), 7.22 (d, 1H, J=2.4 Hz), 7.13 (dd, 1H, J=2.1 and 9 Hz), 6.81 (d, 1H, J=8.7 Hz), 5.34 (s, 2H), 4.20 (s, 4H); LCMS: ret. time: 17.40 min.; purity: 83%; MS (m/e): 395 (MH$^+$).

7.3.353 N2-[3-(3-Acetamidophenoxy)propyl]-N4-(3,4-ethylenedioxyphenyl)-5-fluoro-2,4-pyrimidinediamine (R926787)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine with 3-N-acetamidophenoxy-3-propylamine gave N2-[3-(3-acetamidophenoxy)propyl]-N4-(3,4-ethylenedioxyphenyl)-5-fluoro-2,4-pyrimidinediamine. $^1$H NMR (DMSO-d6): δ 10.45 (bs, 1H), 10.07 (s, 1H), 8.42 (s, 1H), 8.20 (s, 1H), 7.37 (d, 1H, J=3 Hz), 7.31 (s, 1H), 7.20-7.05 (m, 3H), 6.83 (d, 1H, J=9 Hz), 6.53 (d, 1H, J=6.6 Hz), 4.18 (s, 4H), 3.95 (t, 2H, J=6 Hz), 2.48 (m, 2H), 2.07 (s, 3H), 1.96 (t, 3H, J=7.8 Hz); LCMS: ret. time: 19.58 min.; purity: 99%; MS (m/e): 454 (MH$^+$).

7.3.354 N2-[4-(4,5-Dichloro-1H-imidazol-1-yl)phenyl]-N4-(3,4-ethylenedioxyphenyl)-5-fluoro-2,4-pyrimidinediamine (R926788)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine with 4,5-dichloro-1H-imidazoleamine gave N2-[4-(4,5-dichloro-1H-imidazol-1-yl)phenyl]-N4-(3,4-ethylenedioxyphenyl)-5-fluoro-2,4-pyrimidinediamine. $^1$H NMR (DMSO-d6): δ 10.10 (s, 1H), 9.85 (s, 1H), 8.20 (d, 1H, J=4.2 Hz), 8.01 (s, 1H), 7.78 (d, 1H, J=8.7 Hz), 7.36 (d, 1H, J=9 Hz), 7.25 (d, 1H, J=3 Hz), 7.14 (dd, 1H, J=2.1 and 9 Hz), 6.85 (d, 1H, J=8.7 Hz); LCMS: ret. time: 23.59 min.; purity: 95%; MS (m/e): 474 (MH$^+$).

7.3.355 N2-(2,4-Dimethoxyphenyl)-N4-(3,4-ethylenedioxyphenyl)-5-fluoro-2,4-pyrimidinediamine (R926789)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine with 2,4-dimethoxyaniline gave N2-(2,4-dimethoxyphenyl)-N4-(3,4-ethylenedioxyphenyl)-5-fluoro-2,4-pyrimidinediamine. $^1$H NMR (DMSO-d6): δ 10.35 (s, 1H), 8.14 (bd, 1H), 7.38 (d, 1H, J=9 Hz), 7.23 (s, 1H), 7.09 (d, 1H, J=8.7 Hz), 6.79 (d, 1H, J=8.7 Hz), 6.66 (d, 1H, J=2.4 Hz), 6.49 (dd, 1H, J=2.4 and 9 Hz), 4.22 (s, 4H), 3.77 (s, 6H); LCMS: ret. time: 20.93 min.; purity: 98%; MS (m/e): 399 (MH$^+$).

7.3.356 N4-(3,4-Ethylenedioxyphenyl)-5-fluoro-N2-(4-isopropylphenyl)-2,4-pyrimidinediamine (R926790)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine with 4-isopropylaniline gave N4-(3,4-ethylenedioxyphenyl)-5-fluoro-N2-(4-isopropylphenyl)-2,4-pyrimidinediamine. $^1$H NMR (DMSO-d6): δ 10.30 (s, 1H), 10.50 (s, 1H), 8.22 (d, 1H, J=5.4 Hz), 7.37 (d, 1H, J=8.4 Hz), 7.26 (d, 1H, J=3 Hz), 7.18 (s, 1H), 7.15 (s, 1H), 7.06 (dd, 1H, J=3.3 and 8.7 Hz), 6.81 (d, 1H, J=8.7 Hz), 4.23 (s, 4H), 2.85 (sept., 1H, J=7.2 Hz), 1.17 (d, 6H, J=6.9 Hz); LCMS: ret. time: 24.91 min.; purity: 95%; MS (m/e): 381 (MH$^+$).

7.3.357 N2-(3,5-Dimethoxyphenyl)-N4-(3,4-ethylenedioxyphenyl)-5-fluoro-2,4-pyrimidinediamine (R926791)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine with 3,4-dimethoxyaniline gave N2-(3,5-dimethoxyphenyl)-N4-(3,4-ethylenedioxyphenyl)-5-fluoro-2,4-pyrimidinediamine. $^1$H NMR (DMSO-d6): δ 10.08 (s, 1H), 9.99 (s, 1H), 8.19 (m, 1H), 7.21 (d, 1H, J=2.4 Hz), 7.14 (dd, 1H, J=2.1 and 8.7 Hz), 6.79 (d, 1H, J=9 Hz), 6.72 (s, 1H), 6.20 (d, 1H, J=1.8 Hz), 4.21 (s, 4H); LCMS: ret. time: 21.19 min.; purity: 93%; MS (m/e): 399 (MH$^+$).

7.3.358 N2-(2,5-Dimethyl-4-hydroxyphenyl)-N4-(3,4-ethylenedioxyphenyl)-5-fluoro-2,4-pyrimidinediamine (R926792)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine with 2,5-dimethyl-4-hydroxyaniline gave N2-(2,5-dimethyl-4-hydroxyphenyl)-N4-(3,4-ethylenedioxyphenyl)-5-fluoro-2,4-pyrimidinediamine. $^1$H NMR (CD$_3$OD): δ 7.69 (d, 1H, J=3.9 Hz), 7.16 (d, 1H, J=2.4 Hz), 7.05 (d, 1H, J=2.4 Hz), 7.02 (d, 1H, J=1.2 Hz), 6.66 (s, 1H), 6.63 (s, 1H), 6.62 (s, 1H), 4.19 (s, 4H), 2.12 (s, 3H), 2.10 (s, 3H); LCMS: ret. time: 19.80 min.; purity: 90%; MS (m/e): 383 (MH$^+$).

7.3.359 N4-(3,4-Ethylenedioxyphenyl)-5-fluoro-N2-(5-methyl-3-phenyl-4-oxazolyl)-2,4-pyrimidinediamine (R926793)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine with 5-methyl-3-phenyl-4-oxazolylamine gave N4-(3,4-ethylenedioxyphenyl)-5-fluoro-N2-(5-methyl-3-phenyl-4-oxazolyl)-2,4-pyrimidinediamine. $^1$H NMR (CD$_3$OD): δ 7.80-7.65 (m, 2H), 7.45 (bd, 1H), 7.20 (m, 1H), 7.00 (m, 1H), 6.65 (bd, 1H), 4.20 (s, 4H), 2.35 (s, 3H); LCMS: ret. time: 20.61 min.; purity: 78%; MS (m/e): 420 (MH$^+$).

7.3.360 N4-(3,5-Dimethoxyphenyl)-N2-(3-ethoxycarbonylmethyleneoxyphenyl)-5-fluoro-2,4-pyrimidinediamine (R926795)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,5-dimethoxyphenyl)-5-fluoro-4-pyrimidineamine with ethyl-3-aminophenoxyacetate gave N4-(3,5-dimethoxyphenyl)-N2-(3-ethoxycarbonylmethyleneoxyphenyl)-5-fluoro-2,4-pyrimidinediamine. LCMS: ret. time: 21.02 min.; purity: 84%; MS (m/e): 429 (MH$^+$).

7.3.361 N4-(3,4-Ethylenedioxyphenyl)-N2-(3-ethoxycarbonylmethyleneoxyphenyl)-5-ethoxycarbonyl-2,4-pyrimidinediamine (R926797)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-dimethoxyphenyl)-5-ethoxycarbonyl-4-pyrimidineamine with ethyl-3-aminophenoxyacetate gave N4-(3,4-ethylenedioxyphenyl)-N2-(3-ethoxycarbonylmethyleneoxyphenyl)-5-ethoxycarbonyl-2,4-pyrimidinediamine. LCMS: ret. time: 27.60 min.; purity: 82%; MS (m/e): 495 (MH$^+$).

7.3.362 N4-(3-Hydroxyphenyl)-N2-(3-ethoxycarbonylmethyleneoxyphenyl)-5-ethoxycarbonyl-2,4-pyrimidinediamine (R926798)

In like manner to the preparation of N4-(3,4-ethylenedioxyphenyl)-5-fluoro-N2-(3-hydroxyphenyl)-2,4-pyrimidinediamine, the reaction of 2-chloro-5-ethoxycarbonyl-N4-(3-hydroxyphenyl)-4-pyrimidineamine with ethyl-3-aminophenoxyacetate gave N4-(3-hydroxyphenyl)-N2-(3-ethoxycarbonylmethyleneoxyphenyl)-5-ethoxycarbonyl-2,4-pyrimidinediamine. LCMS: ret. time: 24.78 min.; purity: 85%; MS (m/e): 453 (MH$^+$).

7.3.363 5-Fluoro-N4-(3-hydroxyphenyl)-N2-(2-methoxycarbonylbenzofuran-5-yl)-2,4-pyrimidinediamine (R926614)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with 2-methoxycarbonyl-5-aminobenzofuran gave 5-fluoro-N4-(3-hydroxyphenyl)-N2-(2-methoxycarbonylbenzofuran-5-yl)-2,4-pyrimidinediamine. $^1$H NMR (CD$_3$OD): δ 9.42 (s, 1H), 9.33 (s, 1H), 9.23 (s, 1H), 8.26 (s, 1H), 8.09 (d, 1H, J=3.6 Hz), 7.59 (m, 3H), 7.13 (m, 3H), 6.53 (d, 1H, J=7.5 Hz), 3.87 (s, 3H), 3.87 (s, 3H).

7.3.364 N2-(2-Ethoxycarbonylindol-5-yl)-5-fluoro-N4-(3-hydroxyphenyl)-2,4-pyrimidinediamine (R926615)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with 2-ethoxycarbony-5-aminoindole gave N2-(2-ethoxycarbonylindol-5-yl)-5-fluoro-N4-(3-hydroxyphenyl)-2,4-pyrimidinediamine. $^1$H NMR (CD$_3$OD): δ 7.95 (d, 1H), 7.84 (d, 1H, J=3.9 Hz), 7.34 (s, 1H), 7.33 (d, 1H, J=1.8 Hz), 7.22-7.19 (m, 2H), 7.11-7.05 (m, 2H), 6.55 (m, 1H), 4.62 (s, 2H), 4.38 (q, 1H, J=6.9 Hz), 1.40 9t, 3H, J=7.5 Hz).

7.3.365 N2-[4-(4,5-Dichloro-1H-imidazol-1-yl)phenyl]-5-fluoro-N4-(3-hydroxyphenyl)-2,4-pyrimidinediamine (R926777)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with (4,5-dichloro-1H-imidazol-1-yl)-4-aniline gave N2-[4-(4,5-dichloro-1H-imidazol-1-yl)phenyl]-5-fluoro-N4-(3-hydroxyphenyl)-2,4-pyrimidinediamine. LCMS: ret. time: 22.09 min.; purity: 98%; MS (m/e): 431 (MH$^+$).

7.3.366 5-Fluoro-N4-(3-hydroxyphenyl)-N2-(4-isopropylphenyl)-2,4-pyrimidinediamine (R926778)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with 4-isopropylaniline gave 5-fluoro-N4-(3-hydroxyphenyl)-N2-(4-isopropylphenyl)-2,4-pyrimidinediamine. LCMS: ret. time: 23.08 min.; purity: 99%; MS (m/e): 439 (MH$^+$).

7.3.367 5-Fluoro N4-(3-hydroxyphenyl)-N2-(5-methyl-4-oxazolyl-2-phenyl)-2,4-pyrimidinediamine (R926779)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with 5-methyl-4-oxazolyl-2-phenyl-1-amine gave 5-fluoro N4-(3-hydroxyphenyl)-N2-(5-methyl-4-oxazolylphenyl)-2,4-pyrimidinediamine. LCMS: ret. time: 23.08 min.; purity: 99%; MS (m/e): 439 (MH$^+$). LCMS: ret. time: 19.17 min.; purity: 81%; MS (m/e): 378 (MH$^+$).

7.3.368 N2-(3,5-Dimethoxyphenyl)-5-fluoro-N4-(3-hydroxyphenyl)-2,4-pyrimidinediamine (R926780)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with 3,5-dimethoxyaniline gave N2-(3,5-dimethoxyphenyl)-5-fluoro-N4-(3-hydroxyphenyl)-2,4-pyrimidinediamine. LCMS: ret. time: 19.61 min.; purity: 97%; MS (m/e): 357 (MH$^+$).

7.3.369 N4-(4-tert-Butoxycarbonylmethyleneoxyphenyl)-5-fluoro-N2-(4-methoxycarbonylmethyleneoxyphenyl-2,4-pyrimidinediamine (R926572)

In like manner to the preparation of N4-(3,4-ethylenedioxyphenyl)-5-fluoro-N2-(3-hydroxyphenyl)-2,4-pyrimidinediamine, the reaction of N4-(4-tert-butoxycarbonylmethyleneoxyphenyl)-2-chloro-5-fluoro-4-pyrimidineamine with methyl 4-aminophenoxyacetate gave N4-(4-tert-butoxycarbonylmethyleneoxyphenyl)-5-fluoro-N2-(4-methoxycarbonylmethyleneoxyphenyl-2,4-pyrimidinediamine. $^1$H NMR (CDCl$_3$): δ 7.49 (d, 2H, J=8.7 Hz), 7.40 (d, 2H, J=9.3 Hz), 6.89 (d, 2H, J=9.3 Hz), 6.85 (d, 2H, J=8.7 Hz), 4.62 (s, 2H), 4.52 (s, 2H), 3.81 (s, 3H), 1.49 (s, 9H); LCMS: ret. time: 24.68 min.; purity: 100%; MS (m/e): 499 (MH$^+$).

7.3.370 5-Fluoro-N4-(3-isopropoxyphenyl)-N2-(2-methoxycarbonylbenzofuran-5-yl)-2,4-pyrimidinediamine (R926487)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-isopropoxyphenyl)-4-pyrimidinediamineamine with 2-methoxycarbonyl-5-aminobenzofuran gave 5-fluoro-N4-(3-isopropoxyphenyl)-N2-(2-methoxycarbonylbenzofuran-5-yl)-2,4-pyrimidinediamine. $^1$H NMR (CDCl$_3$): δ 8.09 (d, 1H, J=2.4 Hz), 7.96 (d, 1H, J=3 Hz), 7.52 (s, 1H), 7.48 (t, 1H, J=1.8 Hz), 7.40 (dd, 1H, J=6.3 Hz), 7.24 9m, 2H), 7.10 (m, 1H), 6.97 (bs, 1H), 6.74 (d, 1H, J=2.4 Hz), 6.68 (dd, 1H, J=2.1 and 6.9 Hz), 4.49 (sept., 1H, J=5.7 Hz), 3.98 (s, 3H), 1.30 (d, 6H, J=5.7 Hz); LCMS: ret. time: 25.86 min.; purity: 94%; MS (m/e): 437 (MH$^+$).

7.3.371 N4-(4-tert-Butylphenyl)-N2-(2-ethoxycarbonylindol-5-yl)-5-fluoro-2,4-pyrimidinediamine (R926474)

In like manner to the preparation of N4-(3,4-ethylenedioxyphenyl)-5-fluoro-N2-(3-hydroxyphenyl)-2,4-pyrimidinediamine, the reaction of N4-(tert-butylcarbonylmethyleneoxyphenyl)-2-chloro-5-fluoro-4-pyrimidineamine with 2-ethoxycarbony-5-aminoindole gave N4-(4-tert-butylphenyl)-N2-(2-ethoxycarbonylindol-5-yl)-5-fluoro-2,4-pyrimidinediamine. $^1$H NMR (CDCl$_3$): δ 8.05 (d, 1H, J=1.8 Hz), 7.85 (d, 1H, J=3.9 Hz), 7.58 (d, 2H, J=9 Hz), 7.36-7.10 (m, 4H), 7.03 (s, 1H), 6.95 (bd, 1H), 6.84 (dd, 1H, J=7.2 Hz), 4.36 (q, 2H, J=7.2 Hz), 1.40 (t, 3H, J=7.5 Hz), 1.33 (s, 9H); LCMS: ret. time: 28.67 min.; purity: 100%; MS (m/e): 449 (MH$^+$).

7.3.372 N4-(4-tert-Butylphenyl)-5-fluoro-N2-(2-methoxycarbonylbenzofuran-5-yl)-2,4-pyrimidinediamine (R926477)

In like manner to the preparation of N4-(3,4-ethylenedioxyphenyl)-5-fluoro-N2-(3-hydroxyphenyl)-2,4-pyrimidinediamine, the reaction of N4-(tert-butylcarbonylmethyleneoxyphenyl)-2-chloro-5-fluoro-4-pyrimidineamine with 2-methoxycarbonyl-5-aminobenzofuran gave N4-(4-tert-butylphenyl)-5-fluoro-N2-(2-methoxycarbonylbenzofuran-5-yl)-2,4-pyrimidinediamine. $^1$H NMR (CDCl$_3$): δ 8.6 (s, 1H), 8.09)d, 1H, J=1.8 Hz), 7.86 (d, 1H, J=3.3 Hz), 7.54-7.36 (m, 6H), 6.90 (m, 1H) 3.97 (s, 3H), 1.36 (s, 9H), $^{19}$F NMR (CDCl$_3$): −47188; LCMS: ret. time: 29.69 min.; purity: 84%; MS (m/e): 393 (M-41).

7.3.373 N2-(3,4-Ethylenedioxyphenyl)-N4-(2-methoxycarbonylbenzofuran-5-yl)-5-fluoro-2,4-pyrimidinediamine (R926485)

In like manner to the preparation of N4-(3,4-ethylenedioxyphenyl)-5-fluoro-N2-(3-hydroxyphenyl)-2,4-pyrimidinediamine, the reaction of 2-chloro-N2-(3,4-ethylenedioxyphenyl)-5-fluoro-2,4-pyrimidineamine with 2-methoxycarbonyl-5-aminobenzofuran gave N2-(3,4-ethylenedioxyphenyl)-N4-(2-methoxycarbonylbenzofuran-5-yl)-5-fluoro-2,4-pyrimidinediamine. $^1$H NMR (CDCl$_3$): δ 8.07 (s, 1H), 7.76 (s, 1H), 7.44 (m, 3H), 7.13 (m, 1H), 6.68 (m, 2H0, 4.18 (s, 4H), 3.95 (s, 3H); LCMS: ret. time: 26.63 min.; purity: 100%; MS (m/e): 437 (MH$^+$).

7.3.374 N4-(3-Ethoxycarbonylmethyleneoxyphenyl)-N2-(3,4-ethylenedioxyphenyl)-5-fluoro-2,4-pyrimidinediamine (R926774)

In like manner to the preparation of N4-(3,4-ethylenedioxyphenyl)-5-fluoro-N2-(3-hydroxyphenyl)-2,4-pyrimidinediamine, the reaction of 2-chloro-N4-(3-ethoxycarbonylmethyleneoxyphenyl)-5-fluoro-2,4-pyrimidineamine with 3,4-ethylenedioxyaniline gave N4-(3-ethoxycarbonylmethyleneoxyphenyl)-N2-(3,4-ethylenedioxyphenyl)-5-fluoro-2,4-pyrimidinediamine. $^1$H NMR (CDCl$_3$): δ 7.92 (d, 1H, J=3.6 Hz), 7.67 (s, 1H), 7.40 (s, 1H), 7.28-7.21 (m, 2H), 7.01-6.96 (m, 2H), 6.80 (m, 2H), 6.68 (bd, 1H, 1H), 4.61 (s, 2H), 4.25 (m, 6H), 1.25 (t, 3H, J=6.9 Hz); LCMS: ret. time: 22.03 min.; purity: 84%; MS (m/e): 441 (MH$^+$).

7.3.375 N4-(3-Ethoxycarbonylmethyleneoxyphenyl)-5-fluoro-N2-(3-hydroxyphenyl)-2,4-pyrimidinediamine (R926775)

In like manner to the preparation of N4-(3,4-ethylenedioxyphenyl)-5-fluoro-N2-(3-hydroxyphenyl)-2,4-pyrimidinediamine, the reaction of 2-chloro-N4-(3-ethoxycarbonylmethyleneoxyphenyl)-5-fluoro-2,4-pyrimidineamine with 3-hydroxyaniline gave N4-(3-ethoxycarbonylmethyleneoxyphenyl)-5-fluoro-N2-(3-hydroxyphenyl)-2,4-pyrimidinediamine. LCMS: ret. time: 19.50 min.; purity: 84%; MS (m/e): 399 (MH$^+$).

7.3.376 N4-(4-Aminocarbonylmethyleneoxyphenyl)-N2-(3,4-ethylenedioxyphenyl)-5-fluoro-2,4-pyrimidinediamine (R945171)

In a manner analogous to the preparation of N4-(3,4-ethylenedioxyphenyl)-5-fluoro-N4-(3-hydroxyphenyl)-2,4-pyrimidinediamine, 2-chloro-N4-(4-aminocarbonylmethyleneoxyphenyl)-5-fluoro-4-pyrimidineamine and 3,4-ethylenedioxyaniline gave N4-(4-aminocarbonylmethyleneoxyphenyl)-N2-(3,4-ethylenedioxyphenyl)-5-fluoro-2,4-pyrimidinediamine. $^1$H NMR (acetone-d$_6$): δ δ 4.24-4.31 (m, 4H), 4.51 (s, 2H), 6.77 (d, J=8.7 Hz, 1H), 6.95 (dm, J=8.7 Hz, 1H), 7.06 (d, J=9.3 Hz, 2H), 7.28 (m, 1H), 7.71 (d, J=9.0 Hz, 2H), 8.15 (m, 1H); LCMS: 15.23 min, 97.05%; MS (m/e): 412.01 (MH$^+$).

7.3.377 (R935019): 5-Fluoro-N2-(3-hydroxyphenyl)-N4-[di-(4-chlorophenyl)methyl]-2,4-pyrimidinediamine In like manner to the preparation of N4-(3,4-ethylenedioxyphenyl)-5-fluoro-N2-(3-hydroxyphenyl)-4-pyrimidinediamine, 3-aminophenol and N-(2-chloro-5-fluoro-pyrimidinyl)-1,1-di(4-chlorophenyl)methylamine produced 5-fluoro-N2-(3-hydroxyphenyl)-N4-[di-(4-chlorophenyl)methyl]-2,4-pyrimidinediamine. LCMS: ret. time: 25.59 min.; purity: 91%; MS (m/e): 421 (MH$^+$—Cl).

7.3.378 (R935020): N4-(Fluoren-9-yl)-5-fluoro-N2-(3-hydroxyphenyl)-2,4-pyrimidinediamine In like manner to the preparation of N4-(3,4-ethylenedioxyphenyl)-5-fluoro-N2-(3-hydroxyphenyl)-4-pyrimidinediamine, 2-chloro-N-(fluoren-9-yl)-5-fluoro-4-pyrimidineamine and 3-aminophenol were reacted to produce N4-(fluoren-9-yl)-5-fluoro-N2-(3-hydroxyphenyl)-2,4-pyrimidinediamine. $^1$H NMR (CDCl$_3$): δ 7.85 (d, 1H, J=2.9 Hz), 7.74 (d, 2H, J=7.6 Hz), 7.64 (d, 2H, J=7.6 Hz), 7.41-7.28 (m, 6H), 7.14-7.05 (m, 2H), 6.56 (d, 1H, J=8.8 Hz), 5.28 (d, 1H, J=8.8 Hz); LCMS: ret. time: 23.27 min.; purity: 89%; MS (m/e): 385 (MH$^+$).

7.3.379 (R935021): (±)-5-Fluoro-N4-[1-(4-fluorophenyl)ethyl]-N2-(3-hydroxyphenyl)-2,4-pyrimidinediamine In like manner to the preparation of N4-(3,4-ethylenedioxyphenyl)-5-fluoro-N2-(3-hydroxyphenyl)-4-pyrimidinediamine, 3-aminophenol and (±)-N-(2-chloro-5-fluoropyrimidinyl)-1-(4-fluorophenyl)ethylamine were reacted to produce the desired (±)-5-fluoro-N4-[1-(4-fluorophenyl)ethyl]-N2-(3-hydroxyphenyl)-2,4-pyrimidinediamine. $^1$H NMR (CDCl$_3$): δ 7.79 (d, 1H, J=3.3 Hz), 7.38-7.34 (dd, 2H, J=5.2 and 8.5 Hz), 7.14 (t, 1H, J=4.5 Hz), 7.09 (d, 1H, J=8.5 Hz), 7.03 (d, 1H, J=8.5 Hz), 6.84 (br s, 1H), 6.84-6.78 (ddd, 1H, J=0.8, 2.0, and 8.2 Hz), 6.46-6.42 (ddd, 1H, J=0.8, 2.0 and 8.2 Hz), 5.26 (overlapped dq, 1H, J=7.1 and 7.9 Hz), 5.18 (d, 1H, J=7.1 Hz), 1.59 (d, 3H, J=7.1 Hz); LCMS: ret. time: 21.52 min.; purity: 92%; MS (m/e): 343 (MH$^+$).

7.3.380 (R935023): (±)-5-Bromo-N4-[1-(4-fluorophenyl)ethyl]-N2-(3-hydroxyphenyl)-2,4-pyrimidinediamine In like manner to the preparation of N4-(3,4-ethylenedioxyphenyl)-5-fluoro-N2-(3-hydroxyphenyl)-4-pyrimidinediamine, 3-aminophenol and (±)-5-bromo-2-chloro-N4-[1-(4-fluorophenyl)ethyl]-4-pyrimidineamine were reacted to produce (±)-5-bromo-N4-[1-(4-fluorophenyl)ethyl]-N2-(3-hydroxyphenyl)-2,4-pyrimidinediamine. $^1$H NMR (CDCl$_3$): δ 7.97 (s, 1H), 7.36-7.31 (m, 2H), 7.17 (s, 1H), 7.09-7.01 (m, 4H), 6.82 (dd, 1H, J=2.2 and 8.2 Hz), 6.46 (d, 1H, J=2.2 and 8.2 Hz), 5.50 (br d, 1H, J=7.0), 5.27 (overlapped dq, 1H, J=7.1 and 7.9 Hz), 1.58 (d, 3H, J=7.0 Hz); LCMS: ret. time: 22.64 min.; purity: 94%; MS (m/e): 404 (MH$^+$)

7.3.381 (R935025): 5-Bromo-N2-(3-hydroxyphenyl)-N4-(N-methyl-2-carbomethoxypyrrol-4-yl)-2,4-pyrimidinediamine In like manner to the preparation of N4-(3,4-ethylenedioxyphenyl)-5-fluoro-N2-(3-hydroxyphenyl)-4-pyrimidinediamine, 3-aminophenol and 5-bromo-2-chloro-N-(N-methyl-2-carbomethoxypyrrol-4-yl)-4-pyrimidineamine were reacted to give 5-bromo-N2-(3-hydroxyphenyl)-N4-(N-methyl-5-carbomethoxypyrrol-4-yl)-2,4-pyrimidinediamine. $^1$H NMR (CDCl$_3$+CD$_3$OD): δ 7.92 (s, 1H), 7.58 (d, 1H, J=8.0 Hz), 7.09 (d, 1H, J=8.5 Hz), 7.04 (d, 1H, J=8.5 Hz), 6.90 (d, 1H, J=4.5 Hz), 6.81 (d, 1H, J=1.8 Hz), 6.5 (m, 1H), 3.82 (s, 3H), 3.75 (s, 3H): LCMS: ret. time: 19.73 min.; purity: 90%; MS (m/e): 419 (MH$^+$)

7.3.382 (R935029): 4-Amino-5-bromo-N2-(3-hydroxyphenyl)-2-pyrimidineamine

In like manner to the preparation of N4-(3,4-ethylenedioxyphenyl)-5-fluoro-N2-(3-hydroxyphenyl)-4-pyrimidinediamine, 4-amino-5-bromo-2-chloropyrimidine and 3-aminophenol were reacted to give 4-amino-5-bromo-N2-(3-hydroxyphenyl)-2-pyrimidineamine. $^1$H NMR (DMSO-d6): δ 10.33 (br s, 1H), 8.27 (s, 1H), 7.14-6.06 (m, 2H), 7.01 (d, 1H, J=1.7 Hz), 6.54 (td, 1H, J=1.7 Hz and 7.0 Hz).

7.3.383 R935134: 5-Fluoro-N4-(3-hydroxyphenyl)-N2-[4-(3-phenyl-1,2,4-oxadiazol-5-yl)methyleneoxyphenyl]-2,4-pyrimidinediamine The reaction of 2-chloro-5-fluoro-N4-(3-hydroxyphenyl)-4-pyrimidineamine and 5-(4-aminophenoxymethyl)-3-phenyl-1,2,4-oxadiazole were reacted in microwave at 180° C. for 10-20 minutes at 20 bar. Upon concentration and addition of 2N HCl provided 5-fluoro-N4-(3-hydroxyphenyl)-N2-[4-(3-phenyl-1,2,4-oxadiazol-5-yl)methyleneoxyphenyl]-2,4-pyrimidinediamine. $^1$H NMR (DMSO-d6): δ 10.21 (br s, 1H), 9.91 (br s, 1H), 8.18 (d, 1H, J=5.2 Hz), 8.03-7.99 (m, 2H), 7.61-7.53 (m, 3H), 7.46 (br d, 2H, J=7.9 Hz), 7.14-7.01 (m, 5H), 6.54 (app d, 1H, J=7.96 Hz), 5.56 (s, 2H); LCMS: ret. time: 24.61 min.; purity: 100%; MS (m/e): 471 (MH$^+$).

7.3.384 R935135: 5-Fluoro-N4-(4-isopropoxyphenyl)-N2-[4-(3-phenyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(4-isopropoxyphenyl)-4-pyrimidineamine and 5-(4-aminophenoxymethyl)-3-phenyl-1,2,4-oxadiazole were reacted to provide 5-fluoro-N4-(4-isopropyloxyphenyl)-N2-[4-(3-phenyl-1,2,4-oxadiazol-5-yl)methyleneoxyphenyl]-2,4-pyrimidinediamine as fine flakes of the solid. $^1$H NMR (DMSO-d6): δ 10.21 (br s, 1H), 9.93 (br s, 1H), 8.17 (d, 1H, J=5.2 Hz), 8.02-7.98 (m, 2H), 7.60-7.49 (m, 5H), 7.42 (app d, 2H, J=7.0 Hz), 7.04 (d, 2H, J=9.4 Hz), 6.89 (app d, 2H, J=9.4 Hz), 5.56 (s, 2H), 4.58 (septet, 1H, J=6.4 Hz), 1.23 (app d, 6H, J=6.4 Hz); LCMS: ret. time: 26.90 min.; purity: 97%; MS (m/e): 513 (MH$^+$).

7.3.385 R935136: N4-(3,4-Ethylenedioxyphenyl)-5-fluoro-N2-[4-(3-phenyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(3,4-ethylenedioxy)phenyl-4-pyrimidineamine and 5-(4-aminophenoxymethyl)-3-phenyl-1,2,4-oxadiazole were reacted provide N4-(3,4-ethylenedioxyphenyl)-5-fluoro-N2-[4-(3-phenyl-1,2,4-oxadiazol-5-yl)methyleneoxyphenyl]-2,4-pyrimidinediamine as fine flakes of the solid. $^1$H NMR (DMSO-d6): δ 10.18 (br s, 1H), 9.12 (br s, 1H), 8.14 (d, 1H, 4.7 Hz), 8.02-7.97 (m, 2H), 7.65-7.52 (m, 3H), 7.44 (d, 2H, J=8.8 Hz), 7.25-7.23 (m, 1H), 7.15-7.08 (m, 1H), 7.03 (d, 2H, J=8.8 Hz), 6.81 (d, 1H, J=8.8 Hz), 5.56 (s, 2H), 4.24-4.20 (m, 4H); LCMS: ret. time: 26.90 min.; purity: 97%; MS (m/e): 513 (MH$^+$).

7.3.386 R935137: 5-Fluoro-N4-(2-methoxycarbonylbenzofura-5-yl)-N2-[4-(3-phenyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(2-methoxycarbonylbenzofurfa-5-yl)-4-pyrimidineamine and 5-(4-aminophenoxymethyl)-3-phenyl-1,2-4-oxadiazole were reacted to provide 5-fluoro-N4-(2-methoxycarbonylbenzofura-5-yl)-N2-[4-(3-phenyl-1,2,4-oxadiazol-5-yl)methyleneoxyphenyl]-2,4-pyrimidinediamine. $^1$H NMR (DMSO-d6): δ 10.21 (br s, 1H), 9.79 (br s, 1H), 8.19 (d, 1H, J=4.7 Hz), 8.09 (br s, 1H), 7.99 (dd, 2H, J=2.3 and 8.2 Hz), 7.76-7.67 (m, 2H), 7.59-7.52 (m, 4H), 7.44 (d, 2H, J=8.8 Hz), 7.02 (d, 2H, J=8.8 Hz), 5.55 (s, 2H), 3.85 (s, 3H); LCMS: ret. time: 27.61 min.; purity: 92%; MS (m/e): 553 (MH$^+$).

7.3.387 R935138: 5-Fluoro-N2-(3-hydroxyphenyl)-N4-[4-(3-phenyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[4-(3-phenyl-1,2,4-oxadiazol-5-yl)methyleneoxyphenyl]-4-pyrimidineamine and 3-aminophenol were reacted to provide 5-fluoro-N2-(3-hydroxyphenyl)-N4-[4-(3-phenyl-1,2,4-oxadiazol-5-yl)methyleneoxyphenyl]-2,4-pyrimidinediamine as fine flakes of the solid. $^1$H NMR (DMSO-d6): δ 8.12 (d, 1H, J=4.7 Hz), 8.03-7.99 (m, 2H), 7.69 (dd, 2H, J=3.5 and 8.8 Hz), 7.61-7.53 (m, 3H), 7.06 (d, 2H, J=9.9 Hz), 6.98 (m, 3H), 6.38 (br s, 1H), 5.58 (s, 2H). LCMS: ret. time: 24.83 min.; purity: 96%; MS (m/e): 471 (MH$^+$).

7.3.388 R935139: 5-Fluoro-N2-(4-isopropoxyphenyl)-N4-[4-(3-phenyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[4-(3-phenyl-1,2,4-oxadiazol-5-yl)methyleneoxyphenyl]-4-pyrimidineamine and 4-isopropoxyaniline were reacted to provide 5-fluoro-N2-(4-isopropoxyphenyl)-N4-[4-(3-phenyl-1,2,4-oxadiazol-5-yl)methyleneoxyphenyl]-2,4-pyrimidinediamine as fine flakes of the solid. $^1$H NMR (DMSO-d6): δ 10.21 (br s, 1H), 9.78 (br s, 1H), 8.13 (d, 1H, J=4.7 Hz), 8.02-7.98 (m 2H), 7.65-7.53 (m, 5H), 7.34 (d, 2H, J=7.6 Hz), 7.07 (d, 2H, J=9.3 Hz), 6.86 (d, 2H, J=8.8 Hz), 5.59 (s, 2H), 4.54 (sept, 1H, J=5.8 Hz), 1.22 (d, 6H, J=5.8 Hz); LCMS: ret. time: 29.64 min.; purity: 97%; MS (m/e): 513 (MH$^+$).

7.3.389 R935140: N2-(3,4-Ethylenedioxyphenyl)-5-fluoro-N4-[4-(3-phenyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[4-(3-phenyl-1,2,4-oxadiazol-5-yl)methyleneoxyphenyl]-4-pyrimidineamine and 3,4-ethylenedioxyaniline were reacted to provide N2-(3,4-ethylenedioxyphenyl)-5-fluoro-N4-[4-(3-phenyl-1,2,4-oxadiazol-5-yl)methyleneoxyphenyl]-2,4- pyrimidinediamine. $^1$H NMR (DMSO-d6): δ 10.31 (br s, 1H), 9.59 (br s, 1H), 8.11 (d, 1H, J=4.7 Hz), 8.03-7.99 (m, 2H), 7.68-7.49 (m, 5H), 7.14-7.08 (m, 1H), 7.06 (d, 2H, J=8.8 Hz), 6.90 (d, 1H, J=8.8 Hz), 6.76 (d, 1H, J=8.8 Hz), 5.59 (s, 2H), 4.22-4.17 (m, 4H); LCMS: ret. time: 21.35 min.; purity: 95%; MS (m/e): 513 (MH$^+$).

7.3.390 R935141: 5-Fluoro-N4-(3-hydroxyphenyl)-N2-[4-(3-methyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl) methyleneoxyphenyl]-2,4-pyrimidinediamine, 2-chloro-5-fluoro-N4-(3-hydroxyphenyl)-4-pyrimidineamine and 5-(4-aminophenoxymethyl)-3-methyl-1,2,4-oxadiazole were reacted to provide 5-fluoro-N4-(3-hydroxyphenyl)-N2-[4-(3-methyl-1,2,4-oxadiazol-5-yl)methyleneoxyphenyl]-2,4-pyrimidinediamine as fine flakes of the solid. $^1$H NMR (DMSO-d6): δ 10.91 (br s, 1H), 9.91 (br s, 1H), 8.18 (d, 1H, J=4.7 Hz), 7.43 (d, 2H, J=8.8 Hz), 7.15-7.04 (m, 3H), 6.96 (d, 2H, J=8.8 Hz), 6.58 (app d, 1H, J=7.6 Hz), 5.43 (s, 2H), 2.34 (s, 3H); LCMS: ret. time: 18.68 min.; purity: 95%; MS (m/e): 409 (MH$^+$).

7.3.391 R935142: 5-Fluoro-N4-(4-isopropoxyphenyl)-N2-[4-(3-methyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(4-isopropoxyphenyl)-4-pyrimidineamine and 5-(4-aminophenoxymethyl)-3-methyl-1,2,4-oxadiazole were reacted to provide 5-fluoro-N4-(4-isopropoxyphenyl)-N2-[4-(3-methyl-1,2,4-oxadiazol-5-yl)methyleneoxyphenyl]-2,4-pyrimidinediamine as fine flakes of the solid. $^1$H NMR (DMSO-d6): δ 8.16 (d, 1H, J=5.2 Hz), 7.52 (dd, 2H, J=3.5 Hz and 9.3 Hz), 7.40 (d, 2H, J=8.8 Hz), 6.98 (d, 2H, J=8.8 Hz), 6.88 (d, 2H, J=9.3 Hz), 5.44 (s, 2H), 4.58 (sept, 1H, J=5.8 Hz), 2.34 (s, 3H), 1.24 (d, 6H, J=5.8 Hz); LCMS: ret. time: 24.47 min.; purity: 93%; MS (m/e): 451 (MH$^+$).

7.3.392 R935143: N4-(3,4-Ethylenedioxyphenyl)-5-fluoro-N2-[4-(3-methyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(3,4-ethylenedioxy)phenyl-4-pyrimidineamine and 5-(4-aminophenoxymethyl)-3-methyl-1,2,4-oxadiazole were reacted to provide N4-(3,4-ethylenedioxyphenyl)-5-fluoro-N2-[4-(3-methyl-1,2,4-oxadiazol-5-yl)methyleneoxyphenyl]-2,4-pyrimidinediamine as fine flakes of the solid. $^1$H NMR (DMSO-d6): δ 9.12 (br s, 1H), 9.04 (br s, 1H), 7.99 (d, 1H, J=3.5 Hz), 7.55 (d, 2H, J=1.7 and 8.8 Hz), 7.30 (d, 1H, J=2.9 Hz), 7.17 (td, 1H, J=2.9 and 8.8 Hz), 6.88 (d, 2H, J=8.8 Hz), 6.77 (d, 1H, J=8.8 Hz), 5.38 (s, 2H), 4.24-4.20 (m, 4H), 2.34 (s, 3H); LCMS: ret. time: 21.34 min.; purity: 97%; MS (m/e): 451 (MH$^+$).

7.3.393 R935144: 5-Fluoro-N2-(4-isopropoxyphenyl)-N4-[4-(3-methyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[4-(3-methyl-1,2,4-oxadiazol-5-yl)methyleneoxyphenyl]-4-pyrimidineamine and 4-isopropoxyaniline were reacted to provide 5-fluoro-N2-(4-isopropoxyphenyl)-N4-[4-(3-methyl-1,2,4-oxadiazol-5-yl)methyleneoxyphenyl]-2,4-pyrimidinediamine as fine flakes of the solid. $^1$H NMR (DMSO-d6): δ 10.11 (br s, 1H), 9.72 (br s, 1H), 8.12 (s, 1H, J=5.3 Hz), 7.61 (dd, 2H, J=8.8 Hz), 7.34 (d, 2H, J=7.3 Hz), 7.01 (d, 2H, J=8.8 Hz), 6.84 (d, 2H, J=8.8 Hz), 5.47 (s, 2H), 4.54 (septet, 1H, J=5.8 Hz), 2.34 (s, 3H), 1.23 (d, 6H, J=6.4 Hz); LCMS: ret. time: 24.31 min.; purity: 96%; MS (m/e): 451 (MH$^+$).

7.3.394 R935145: N2-(3,4-Ethylenedioxyphenyl)-5-fluoro-N4-[4-(3-methyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[4-(3-methyl-1,2,4-oxadiazol-5-yl)methyleneoxyphenyl]-4-pyrimidineamine and 3,4-ethylenedioxyaniline were reacted to provide N2-(3,4-ethylenedioxyphenyl)-5-fluoro-N4-[4-(3-methyl-1,2,4-oxadiazol-5-yl)methyleneoxyphenyl]-5-fluoro-2,4-pyrimidinediamine. $^1$H NMR (DMSO-d6): δ 10.81 (br s, 1H), 9.67 (br s, 1H), 8.13 (d, 1H, J=4.7 Hz), 7.63 (dd, 2H, J=4.1 and 8.8 Hz), 7.07 (m, 1H), 7.00 (d, 2H, J=8.8 Hz), 6.89 (d, 1H, J=8.8 Hz), 6.76 (d, 1H, J=8.8 Hz), 5.46 (s, 2H), 4.22-4.18 (m, 4H), 2.34 (s, 3H); LCMS: ret. time: 21.54 min.; purity: 97%; MS (m/e): 451 (MH$^+$).

7.3.395 R935146: 5-Fluoro-N2-(2-methoxycarbonylbenzofura-5-yl)-N4-[4-(3-methyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[4-(3-methyl-1,2,4-oxadiazol-5-yl)methyleneoxyphenyl]-4-pyrimidineamine and 2-methoxycarbonyl-5-aminobenzofuran were reacted to provide 5-fluoro-N2-(2-methoxycarbonylbenzofura-5-yl)-N4-[4-(3-methyl-1,2,4-oxadiazol-5-yl)methyleneoxyphenyl]-2,4-pyrimidinediamine. $^1$H NMR (DMSO-d6): δ 8.14 (d, 1H, J=4.7 Hz), 8.02 (s, 1H), 7.63-7.56 (m, 5H), 7.02 (d, 2H, J=8.8 Hz), 5.47 (s, 2H), 3.85 (s, 3H), 2.34 (s, 3H); LCMS: ret. time: 22.46 min.; purity: 97%; MS (m/e): 491 (MH$^+$).

7.3.396 R935147: 5-Fluoro-N2-(3-hydroxyphenyl)-N4-[4-(3-methyl-1,2,4-oxadiazol-5-yl)methyleneoxyphenyl]-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[4-(3-methyl-1,2,4-oxadiazol-5-yl)methyleneoxyphenyl]-4-pyrimidineamine and 3-hydroxyaniline were reacted to provide 5-fluoro-N2-(3-hydroxyphenyl)-N4-[4-(3-methyl-1,2,4-oxadiazol-5-yl)methyleneoxyphenyl]-2,4-pyrimidinediamine as fine flakes of the product. $^1$H NMR (DMSO-d6): δ 8.11 (d, 1H, J=4.6 Hz), 7.66 (d, 2H, J=5.8 Hz), 7.06-6.97 (m, 5H), 6.42-40 (m, 1H), 5.46 (s, 2H), 2.35 (s, 3H); LCMS: ret. time: 19.00 min.; purity: 95%; MS (m/e): 409 (MH$^+$).

7.3.397 R935148: N2-(3,4-Ethylenedioxyphenyl)-N4-[4-[(1-ethoxycarbonyl-1-methyl)ethyl]phenyl]-5-fluoro-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-Chloro-[4-[ethoxycarbonyl(dimethyl)methyl]phenyl]-5-fluoro-2,4-pyrimidine amine and 3,4-ethylenedioxyaniline were reacted to produce N2-(3,4-ethylenedioxyphenyl)-N4-[4-[(1-ethoxycarbonyl-1-methyl)ethyl]phenyl]-5-fluoro-2,4-pyrimidinediamine. $^1$H NMR (DMSO-d6): δ 9.31 (s, 1H), 8.97 (s, 1H), 8.03 (d, 1H, J=3.5 Hz), 7.70 (d, 2H, J=8.8 Hz), 7.29 (d, 1H, J=2.3 Hz), 7.23 (d, 2H, J=8.8 Hz), 6.98 (dd, 1H, J=2.1 and 8.8 Hz), 6.66 (d, 1H, 8.2 Hz); 4.19-4.15 (m, 4H), 4.07 (qt, 2H, J=7.0 Hz), 1.48 (s, 6H), 1.10 (t, 3H, J=7.0 Hz); LCMS: ret. time: 24.51 min.; purity: 100%; MS (m/e): 453 (MH$^+$).

7.3.398 R935150: N2-[4-[(1-Ethoxycarbonyl-1-methyl)ethyl]phenyl]-5-fluoro-N4-(4-isopropoxyphenyl)-2,4-pyrimidinediamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine (or it can be be prepared similar to the preparation of N4-(3,4-ethylenedioxyphenyl)-5-fluoro-N2-(3-hydroxyphenyl)-2,4-pyrimidinediamine), 2-chloro-5-fluoro-N4-(4-isopropoxyphenyl)-4-pyrimidineamine and 4-[ethoxycarbonyl(dimethyl)methyl]aniline were reacted to produce N2-[4-[(1-ethoxycarbonyl-1-methyl)ethyl]phenyl]-5-fluoro-N4-(4-isopropoxyphenyl)-2,4-pyrimidinediamine. $^1$H NMR (DMSO-d6): δ 9.18 (br s, 1H), 9.11 (br s, 1H), 8.01 (d, 1H, J=3.5 Hz), 7.56 (d, 2H, J=8.8 Hz), 7.54 (d, 2H, J=8.8 Hz), 7.09 (d, 2H, J=8.8 Hz), 6.86 (d, 2H, J=8.8 Hz), 4.56 (sept, 1H, J=5.8 Hz), 4.02 (qt, 2H, J=7.0 Hz), 1.43 (s, 6H), 1.26 (d, 6H, J=7.0 Hz), 1.09 (t, 3H, J=7.0 Hz); LCMS: ret. time: 28.49 min.; purity: 98%; MS (m/e): 453 (MH$^+$).

7.3.399 R935179: N2-[4-(2,3-Dihydroxypropoxy)phenyl]-N4-(3,4-ethylenedioxypheny)-5-fluoro-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(3,4-ethylenedioxyphenyl)-4-pyrimidineamine and 4-(2,3-dihydroxypropoxy)aniline were reacted to produce N2-[4-(2,3-dihydroxypropoxy)phenyl]-N4-(3,4-ethylenedioxyphenyl)-5-fluoro-2,4-pyrimidinediamine. $^1$H NMR (DMSO-d6): δ 9.09 (s, 1H), 8.95 (s, 1H), 7.98 (d, 1H, J=3.5 Hz), 7.51 (d, 2H, J=8.8 Hz), 7.32 (d, 1H, J=2.3 Hz), 7.17 (dd, 1H, J=2.3 and 8.8 Hz), 6.77 (dd, 3H, J=8.8 Hz), 4.90 (d, 1H, J=5.3 Hz), 4.64 (t, 1H, J=5.8 Hz), 4.23-4.19 (m, 4H), 3.91-3.89 (m, 1H), 3.80-3.73 (m, 2H), 3.41 (t, 2H, J=5.3 Hz); LCMS: ret. time: 15.04 min.; purity: 96%; MS (m/e): 429 (MH$^+$).

7.3.400 R935180: N2-[4-(2,3-Dihydroxypropoxy)phenyl]-5-fluoro-N4-(3-hydroxyphenyl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine and 4-(2,3-dihydroxypropoxy)aniline were reacted to produce N2-[4-(2,3-dihydroxypropoxy)phenyl]-5-fluoro-N4-(3-hydroxyphenyl)-2,4-pyrimidinediamine. $^1$H NMR (DMSO-d6): δ 9.38 (s, 1H), 9.18 (s, 1H), 8.98 (s, 1H), 8.12 (d, 1H, J=3.5 Hz), 7.58 (d, 2H, J=8.8 Hz), 7.22 (d, 1H, J=2.3 Hz), 7.12 (dd, 2H, J=2.3 and 8.8 Hz), 6.79 (d, 2H, J=8.8 Hz), 6.45 (d, 1H, J=8.8 Hz), 4.91 (d, 1H, J=5.3 Hz), 4.65 (t, 1H, J=5.8 Hz), 3.92-3.89 (m, 1H), 3.79-3.74 (m, 2H), 3.44 (t, 2H, J=5.3 Hz); LCMS: ret. time: 12.79 min.; purity: 89%; MS (m/e): 387 (MH$^+$).

7.3.401 R935175: N2-[4-(2,3-Dihydroxypropoxy)phenyl]-5-fluoro-N4-(4-isopropoxyphenyl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N-(4-isoproxyphenyl)-4-pyrimidineamine and 4-(2,3-dihydroxypropoxy)aniline were reacted to produce N2-[4-(2,3-dihydroxypropoxy)phenyl]-5-fluoro-N4-(4-isopropoxyphenyl)-2,4-pyrimidinediamine: $^1$H NMR (DMSO-d6): δ 9.12 (s, 1H), 8.91 (s, 1H), 7.97 (d, 1H, J=3.5 Hz), 7.58 (d, 2H, J=8.8 Hz), 7.49 (d, 2H, J=8.8 Hz), 6.85 (d, 2H, J=8.8 Hz), 6.76 (d, 2H, J=8.8 Hz); 4.89 (d, 1H, J=4.7 Hz), 4.63 (t, 1H, J=5.2 Hz), 4.56 (septet, 1H, J=5.8 Hz), 3.90-3.89 (m, 1H), 3.76-3.73 (m, 2H), 3.41 (t, 2H, J=5.3 Hz), 1.25 (d, 6H, J=5.8 Hz); LCMS: ret. time: 17.48 min.; purity: 98%; MS (m/e): 429 (MH$^+$).

7.3.402 R935169: N4-[4-[(1-Ethoxycarbonyl-1-methyl)ethyl]phenyl]-5-fluoro-N2-(3-hydroxyphenyl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-N4-[4-[(1-ethoxycarbonyl-1-methyl)ethyl]phenyl]-5-fluoro-4-pyrimidineamine and 3-aminophenol were reacted to produce N4-[4-[(1-ethoxycarbonyl-1-methyl)ethyl]phenyl]-5-fluoro-N2-(3-hydroxyphenyl)-2,4-pyrimidinediamine. $^1$H NMR (DMSO-d6): δ 7.87 (d, 1H, J=3.5 Hz), 7.56 (d, 2H, J=8.8 Hz), 7.35 (d, 2H, J=8.8 Hz), 7.25-7.23 (m, 1H), 7.08 (t, 1H, J=8.2 Hz), 6.91 (d, 1H, J=2.3 Hz), 6.83 (d, 1H, J=7.6 Hz), 6.50 (dd, 1H, J=1.7 and 8.2 Hz), 4.13 (qt, 2H, J=7.0 Hz), 1.58 (s, 6H), 1.19 (t, 3H, J=7.0 Hz); LCMS: ret. time: 22.97 min.; purity: 98%; MS (m/e): 411 (MH$^+$)

7.3.403 R935164: 5-Fluoro-N4-(4-isopropoxyphenyl)-N2-[(N-methyl-2-methoxycarbonyl)pyrrol-4-yl]-2,4-pyrimidinediamine In like manner to the preparation of N4-(3,4-ethylenedioxyphenyl)-5-fluoro-N2-(3-hydroxyphenyl)-2,4-pyrimidinediamine, 2,4-dichloro-5-fluoropyrimidine, 2-chloro-5-fluoro-N-(4-isopropoxyphenyl)-4-pyrimidineamine and N-methyl-2-methoxycarbonyl-4-aminopyrrole hydrochloride with added diisopropylethylamine were reacted to produce the desired product 5-fluoro-N4-(4-isopropoxyphenyl)-N2-[(N-methyl-2-carbomethoxy)pyrrol-4-yl]-2,4-pyrimidinediamine. $^1$H NMR (CDCl$_3$): δ 7.87 (br s, 1H), 7.44 (d, 2H, J=8.8 Hz), 7.08 (br s, 1H), 6.99-6.85 (m, 3H), 6.70 (d, 1H, J=2.3 Hz), 6.63 (d, 1H, J=1.7 Hz), 4.52 (septet, 1H, J=5.8 Hz), 3.80 (s, 3H), 3.79 (s, 3H), 1.34 (d, 6H, J=5.8 Hz); LCMS: ret. time: 23.89 min.; purity: 99%; MS (m/e): 400 (MH⁺).

7.3.404 R935165: 5-Fluoro-N2-(4-isopropoxyphenyl)-N4-[(N-methyl-2-carbomethoxy)pyrrole-4-yl]-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N4-(N-methyl-2-carbomethoxypyrrol-4-yl)-4-pyrimidineamine and 4-isopropoxyaniline were reacted to produce 5-fluoro-N2-(4-isopropoxyphenyl)-N4-[(N-methyl-5-carbomethoxy)pyrrol-4-yl]-2,4-pyrimidinediamine. ¹H NMR (CDCl₃): δ 7.84 (d, 1H, J=2.3 Hz), 7.36 (d, 2H, J=8.8 Hz), 7.22 (d, 1H, J=1.1 Hz), 6.87 (d, 2H, J=8.8 Hz), 6.84 (s, 1H), 6.77 (d, 1H, J=1.7 Hz), 6.61 (br s, 1H), 4.49 (septet, 1H, J=5.8 Hz), 3.82 (d, 3H), 3.81 (s, 3H), 1.33 (d, 6H, J=5.8 Hz); LCMS: ret. time: 23.36 min.; purity: 96%; MS (m/e): 400 (MH⁺).

7.3.405 R935166: N2-(3,4-Ethylenedioxyphenyl)-5-fluoro-N4-[(N-methyl-2-methoxycarbonyl)pyrrol-4-yl]-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-5-fluoro-N4-(N-methyl-2-methoxycarbonylpyrrol-2-yl)-4-pyrimidineamine and 3,4-ethylenedioxyaniline were reacted to produce 5-fluoro-N2-(3,4-ethylenedioxyphenyl)-N4-[(N-methyl-2-carbomethoxy)pyrrol-4-yl]-2,4-pyrimidinediamine. ¹H NMR (CDCl₃): δ 7.84 (d, 1H, J=3.5 Hz), 7.34 (s, 1H), 7.21 (s, 1H), 6.82 (d, 2H, J=8.8 Hz), 6.76 (d, 2H, J=8.8 Hz), 6.58 (s, 1H), 4.27-4.18 (m, 4H), 3.90 (s, 3H), 3.81 (s, 3H); LCMS: ret. time: 20.02 min.; purity: 93%; MS (m/e): 400 (MH⁺).

7.3.406 R935167: N4-[4-[(1-Ethoxycarbonyl-1-methyl)ethyl]phenyl]-5-fluoro-N2-(4-isopropoxyphenyl)-2,4-pyrimidinediamine In like manner to the preparation of N4-(3,4-ethylenedioxyphenyl)-5-fluoro-N2-(3-hydroxyphenyl)-2,4-pyrimidinediamine, 2-chloro-N4-[4-[1-ethoxycarbonyl-1-methyl)ethyl]phenyl]-5-fluoro-4-pyrimidineamine and 4-isopropoxyaniline were reacted to produce N4-[4-[(1-ethoxycarbonyl-1-methyl)ethyl]phenyl]-5-fluoro-N2-(4-isopropoxyphenyl)-2,4-pyrimidinediamine. ¹H NMR (DMSO-d6): δ 9.29 (s, 1H), 8.95 (s, 1H), 8.02 (d, 1H, J=4.1 Hz), 7.68 (d, 2H, J=8.8 Hz), 7.46 (d, 2H, J=8.8 Hz), 7.22 (d, 2H, J=8.8 Hz), 6.75 (d, 2H, J=8.8 Hz), 4.48 (septet, 1H, J=5.8 Hz), 4.04 (qt, 2H, J=7.0 Hz), 1.47 (s, 6H), 1.22 (d, 6H, J=5.8 Hz), 1.10 (t, 3H, J=7.0 Hz); LCMS: ret. time: 28.11 min.; purity: 99%; MS (m/e): 453 (MH⁺).

7.3.407 R935159: 5-Fluoro-N4-(4-isopropoxyphenyl)-N2-(4-methoxycarbonylmethyleneoxyphenyl)-2,4-pyrimidinediamine In like manner to the preparation of N4-(3,4-ethylenedioxyphenyl)-5-fluoro-N4-[3-hydroxyphenyl]-pyrimidine-2,4-diamine, 2-chloro-5-fluoro-N4-(4-isopropoxyphenyl)-4-pyrimidineamine and methl 4-aminophenoxyacetate were reacted to produce 5-fluoro-N4-(4-isopropoxyphenyl)-N2-(4-methoxycarbonylmethyleneoxyphenyl)-2,4-pyrimidinediamine. ¹H NMR (CDCl₃): δ 7.88 (d, 1H, J=3.5 Hz), 7.46 (d, 2H, J=8.8 Hz), 7.42 (d, 2H, J=8.8 Hz), 6.88 (d, 2H, J=9.3 Hz), 6.85 (d, 2H, J=9.3 Hz), 6.78 (br s, 1H), 6.63 (br d, 1H, J=2.3 Hz), 4.61 (s, 2H), 4.53 (septet, 1H, J=6.4 Hz), 3.81 (s, 3H), 1.35 (d, 6H, J=6.4 Hz); LCMS: ret. time: 23.19 min.; purity: 97%; MS (m/e): 427 (MH⁺).

7.3.408 R935157: N4-[4-[(1-Ethoxycarbonyl-1-methyl)ethyl]phenyl]-5-fluoro-N2-(4-methoxycarbonylmethyleneoxyphenyl)-2,4-pyrimidinediamine In like manner to the preparation of N4-(3,4-ethylenedioxyphenyl)-5-fluoro-N4-[3-hydroxyphenyl]-pyrimidine-2,4-diamine, 2-chloro-N4-[4-[1-ethoxycarbonyl-1-methyl)ethyl]phenyl]-5-fluoro-4-pyrimidineamine was reacted with 4-(methoxycarbonylmethyleneoxy)aniline to produce N4-[4-[(1-ethoxycarbonyl-1-methyl)ethyl]phenyl]-5-fluoro-N2-(4-methoxycarbonylmethyleneoxyphenyl)-2,4-pyrimidinediamine. ¹H NMR (CDCl₃): δ 7.92 (s, 1H), 7.55 (d, 2H, J=8.7 Hz), 7.43 (d, 2H, J=9.3 Hz), 7.33 (d, 2H, J=8.7 Hz), 6.87 (d, 2H, J=9.3 Hz), 6.79 (s, 1H), 6.73 (d, 1H, J=2.3 Hz), 4.62 (s, 2H), 4.13 (qt, 2H, J=7.0 Hz), 3.81 (s, 3H), 1.59 (s, 6H), 1.20 (t, 3H, 7.0 Hz); LCMS: ret. time: 25.20 min.; purity: 97%; MS (m/e): 483 (MH⁺).

7.3.409 R935152: N2-[4-[(1-Ethoxycarbonyl-1-methyl)ethyl]phenyl]-5-fluoro-N4-(3-hydroxyphenyl)-2,4-pyrimidinediamine In like manner to the preparation of N2-[4-(1-ethoxycarbonyl-1-methyl)ethyl)phenyl]-5-fluoro-N4-(4-isopropoxyphenyl)-2,4-pyrimidinediamine, 2-chloro-5-fluoro-N4-(3-hydroxyphenyl)-4-pyrimidineamine and 4-[1-ethoxycarbonyl-1-methyl)ethyl]aniline were reacted to give N2-[4-[(1-ethoxycarbonyl-1-methyl)ethyl]phenyl]-5-fluoro-N4-(3-hydroxyphenyl)-2,4-pyrimidinediamine. ¹H NMR (CDCl₃): δ 7.89 (d, 1H, J=2.9 Hz), 7.24-7.10 (m, 5H), 6.93 (d, 1H, J=7.6 Hz), 6.68 (d, 2H, J=8.2 Hz), 4.08 (qt, 2H, J=7.0 Hz), 1.52 (s, 3H), 1.49 (s, 3H), 1.16 (t, 3H, J=7.0 Hz); LCMS: ret. time: 22.15 min.; purity: 96%; MS (m/e): 411 (MH⁺).

7.3.410 N2-(3-tert-Butylphenyl)-5-fluoro-N4-(3-hydroxyphenyl)-2,4-pyrimidinediamine (R940257)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with 3-tert-buthylaniline gave N2-(3-tert-butylphenyl)-5-fluoro-N4-(3-hydroxyphenyl)-2,4-pyrimidinediamine. LCMS: ret. time: 23.82 min.; purity: 100%; MS (m/e): 353 (MH⁺); ¹H NMR (CDCl₃): δ 7.96 (1H, d, J=3 Hz), 7.61 (1H, ddd, J=7.5, 2.2 and 0.9 Hz), 7.49 (1H, t, J=2.5 Hz), 7.27 (1H, m), 7.18 (1H, t, J=8.1 Hz), 7.99 (1H, m), 6.94 (1H, s), 6.91 (1H, dd, J=7.5 and 2.5 Hz), 6.80 (1H, d, J=7.5 Hz), 6.72 (2H, m), 6.58 (1H, ddd, J=7.5, 2.5 and 0.9 Hz), 6.52 (1H, ddd, J=7.5, 2.5 and 0.9 Hz), 1.28 (9H, s).

7.3.411 N4-(3-Chloro-4-hydroxy-5-methylphenyl)-5-fluoro-N2-(3-methoxycarbonylmethyleneoxyphenyl)-2,4-pyrimidinediamine and N4-(3-chloro-4-hydroxy-5-methylphenyl)-N2-(3-ethoxycarbonylmethyleneoxyphenyl)-5-fluoro-2,4-pyrimidinediamine (R940258)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-chloro-4-hydroxy-5-methylphenyl)-4-pyrimidineamine with ethyl 3-aminophenoxyacetate gave a mixture of N4-(3-chloro-4-hydroxy-5-methylphenyl)-5-fluoro-N2-(3-methoxycarbonylmethyleneoxyphenyl)-2,4-pyrimidinediamine and N4-(3-chloro-4-hydroxy-5-methylphenyl)-N2-(3-ethoxycarbonylmethyleneoxyphenyl)-5-fluoro-2,4-pyrimidinediamine. LCMS: ret. time: 20.34 min. (CO$_2$Me); purity: 17%; MS (m/e): 432 (M$^+$); LCMS: ret. time: 21.83 min; purity 78%; MS (m/e): 446 (M$^+$).

7.3.412 N2-(3-tert-Butylphenyl)-N4-(3,4-dimethoxyphenyl)-5-fluoro-2,4-pyrimidinediamine (R940260)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3,4-dimethoxyphenyl)-4-pyrimidineamine with ethyl 3-tert-buthylaniline gave N2-(3-tert-butylphenyl)-N4-(3,4-dimethoxyphenyl)-5-fluoro-2,4-pyrimidinediamine. LCMS: ret. time: 24.87 min.; purity: 99%; MS (m/e): 397 (MH$^+$); $^1$H NMR (CDCl$_3$): δ 7.92 (1H, d, J=3.4 Hz), 7.50 (1H, d, J=8 Hz), 7.28 (1H, t, J=2.3 Hz), 7.21 (1H, d, J=8 Hz), 718 (1H, m), 7.08-7.01 (2H, m), 6.99 (1H, s), 6.84 (2H, d, J=9.2 Hz), 6.65 (1H, s), 3.89 (3H, s), 3.72 (3H, s), 1.26 (9H, s).

7.3.413 N2-[2-(N-Benzylpiperazino)ethyl]-5-fluoro-N4-(3-hydroxyphenyl)-2,4-pyrimidinediamine (R940261)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with 4-(N-benzylpiperazino)ethylamine gave N2-[2-(N-benzylpiperazino)ethyl]-5-fluoro-N4-(3-hydroxyphenyl)-2,4-pyrimidinediamine. LCMS: ret. time: 17.15 min.; purity: 90%; MS (m/e): 422 (M$^+$), 423 (MH$^+$); $^1$H NMR (CDCl$_3$): δ 8.42 (1H, s), 7.82 (1H, d, J=3.9 Hz), 7.32-7.08 (6H, m), 6.73 (1H, s), 6.61 (1H, dd, J=8.1 and 2.1 Hz), 6.51 (1H, d, J=7.5 Hz), 5.18 (1H, s), 3.59 (2H, m), 3.02 (2H, m), 2.71-2.41 (3H, m), 2.10-1.16 (5H, m).

7.3.414 N2-[2-(N-Benzylpiperazino)ethyl]-N4-(3,4-dimethoxyphenyl)-5-fluoro-2,4-pyrimidinediamine (R940262)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3,4-dimethoxyphenyl)-4-pyrimidineamine with 4-(N-benzylpiperazino)ethylamine gave N2-[2-(N-benzylpiperazino)ethyl]-N4-(3,4-dimethoxyphenyl)-5-fluoro-2,4-pyrimidinediamine. LCMS: ret. time: 17.48 min.; purity: 99%; MS (m/e): 466 (M$^+$), 467 (MH$^+$); $^1$H NMR (CDCl$_3$): δ 7.82 (1H, d, J=3.9 Hz), 7.44 (1H, s), 7.33-7.10 (6H, m), 7.04 (1H, dd, J=8.9 and 2.5 Hz), 6.84 (1H, d, J=8.9 Hz), 6.58 (1H, s), 5.40 (1H, s), 3.91 (3H, s), 3.87 (3H, s), 3.41 (2H, m), 2.87 (2H, m), 2.51 (3H, m), 1.80 (2H, m), 1.60 (4H, m), 1.30 (1H, m).

7.3.415 N2-[4-(N-Benzylpiperidino)]-N4-(3,4-dimethoxyphenyl)-5-fluoro-2,4-pyrimidinediamine (R940263)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3,4-dimethoxyphenyl)-4-pyrimidineamine with N-benzyl-4-aminopiperidine gave N2-[4-(N-benzylpiperidino)]-N4-(3,4-dimethoxyphenyl)-5-fluoro-2,4-pyrimidinediamine. LCMS: ret. time: 15.52 min.; purity: 99%; MS (m/e): 438 (MH$^+$); $^1$H NMR(CDCl$_3$): δ 7.81 (1H, d, 3.3 Hz), 7.35-7.18 (5H, m), 7.10 (1H, dd, J=8.7 and 2.6 Hz), 6.84 (1H, d, J=8.7 Hz), 6.56 (1H, s), 4.73 (1H, d, J=6.9 Hz), 3.89 (6H, s), 3.75 (1H, m), 3.51 (2H, m), 2.81 (2H, m), 2.15 (2H, m), 2.00 (2H, m), 1.66-1.44 (4H, m).

7.3.416 N2-[4-(N-Benzylpiperidino)]-5-fluoro-N4-(3-hydroxyphenyl)-2,4-pyrimidinediamine (R940264)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with N-benzyl-4-aminopiperidine gave N2-[4-(N-benzylpiperidino)]-5-fluoro-N4-(3-hydroxyphenyl)-2,4-pyrimidinediamine. LCMS: ret. time: 14.00 min.; purity: 96%; MS (m/e): 394 (M$^+$), 395 (MH$^+$); $^1$H NMR(CDCl$_3$): δ 7.81 (1H, d, J=3.6 Hz), 7.40-7.28 (5H, m), 7.21-7.14 (2H, m), 6.69 (1H, m), 6.62 (1H, m), 6.59 (1H, m), 5.20 (1H, s), 3.65 (2H, s), 3.50 (1H, s), 3.03 (1H, m), 2.83 (1H, m), 2.13 (1H, m), 1.95-1.70 (1H, m), 1.58 (4H, m).

7.3.417 N4-(3-tert-Butylphenyl)-N2-(3-ethoxycarbonylmethyleneoxyphenyl)-5-fluoro-2,4-pyrimidinediamine (R940270)

In like manner to the preparation of N4-(3,4-ethylenedioxyphenyl)-5-fluoro-N2-(3-hydroxyphenyl)-2,4-pyrimidinediamine, the reaction of N4-(3-tert-butylphenyl)-2-chloro-5-fluoro-4-pyrimidineamine with ethyl 3-aminophenoxyacetate gave N4-(3-tert-butylphenyl)-N2-(3-ethoxycarbonylmethyleneoxyphenyl)-5-fluoro-2,4-pyrimidinediamine. LCMS: ret. time: 27.30 min.; purity: 98%; MS (m/e): 439 (MH$^+$); $^1$H NMR (DMSO-d6): δ 9.50 (1H, s), 9.33 (1H, s), 8.11 (1H, dd, J=4.2 and 1.8 Hz), 7.81 (1H, d, J=7.2 Hz), 7.49 (1H, t, 2.4 Hz), 7.30-7.28 (3H, m), 7.14-7.03 (2H, m), 6.46 (1H, d, J=7.8 Hz), 4.57 (2H, s), 4.13 (2H, q, J=7.2 Hz), 1.23 (9H, s), 1.18 (3H, t, J=7.2 Hz).

7.3.418 N4-(3-tert-Butylphenyl)-N2-(3-chloro-4-hydroxy-5-methylphenyl)-5-fluoro-2,4-pyrimidinediamine (R940271)

In like manner to the preparation of N4-(3,4-ethylenedioxyphenyl)-5-fluoro-N2-(3-hydroxyphenyl)-2,4-pyrimidinediamine, the reaction of N4-(3-tert-butylphenyl)-2-chloro-5-fluoro-4-pyrimidineamine with 3-chloro-4-hydroxy-5-methylaniline gave N4-(3-tert-butylphenyl)-N2-(3-chloro-4-hydroxy-5-methylphenyl)-5-fluoro-2,4-pyrimidinediamine. LCMS: ret. time: 25.46 min.; purity: 100%; MS (m/e): 400 (M$^+$); $^1$H NMR (DMSO-d6): δ 9.63 (1H, s), 9.30 (1H, s), 8.82 (1H, s), 8.20 (1H, d, J=3.9 Hz), 7.92 (1H, d, J=8.8 Hz), 7.58 (2H, m), 7.40-7.20 (3H, m) 2.22 (3H, s), 1.35 (9H, s).

7.3.419 N2-(3-tert-Butylcarbonylaminophenyl)-N4-(3-hydroxyphenyl)-5-fluoro-2,4-pyrimidinediamine (R940275)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with 3-butylcarbonylaminoaniline gave N2-(3-tert-butylcarbonylaminophenyl)-N4-(3-hydroxyphenyl)-5-fluoro-2,4-pyrimidinediamine. LCMS: ret. time: 20.19 min.; purity: 91%; MS (m/e): 396 (MH$^+$); 1H NMR (DMSO-d6): δ 9.42 (1H, s), 9.28 (1H, s), 9.21 (1H, s), 9.18

(1H, s), 8.17 (1H, d, J=3.9 Hz), 7.90 (1H, s), 7.55 (1H, dt, J=6.9 and 2.1 Hz), 7.51 (1H, dd, J=7.8 and 1.5 Hz), 7.26-7.13 (4H, m), 6.57 (1H, dd, J=7.5 and 1.5 Hz), 1.30 (9H, s).

7.3.420 N4-(3,3-Dihydroisobenzofuranyl-1-one-6-yl)-5-fluoro-N2-(2-methoxycarbonylbenzofur-5-yl)-2,4-pyrimidinediamine R940294

In like manner to the preparation of N4-(3,4-ethylenedioxyphenyl)-5-fluoro-N2-(3-hyroxyphenyl)-2,4-pyrimidinediamine, 2-chloro-N4-(3,3-dihydroisobenzofuranyl-1-one-6-yl)-5-fluoro-4-pyrimidineamine and 2-methoxycarbonyl-5-aminobenzofuran were reacted to give N4-(3,3-dihydroisobenzofuranyl-1-one-6-yl)-5-fluoro-N2-(2-methoxycarbonylbenzofur-5-yl)-2,4-pyrimidinediamine. LCMS: ret. time: 21.34 min.; purity: 97%; MS (m/e): 434 ($M^+$); 1H NMR (DMSO-d6): δ 9.90 (1H, s), 9.61 (1H, s), 8.4-8.12 (4H, m), 7.35-7.67 (4H, m), 5.50 (2H, s), 3.98 (3H, s).

7.3.421 N2-[3-Ethoxycarbonylmethyleneoxyphenyl]-N4-(3,3-dihydroisobenzofuranyl-1-one-6-yl)-5-fluoro-2,4-pyrimidinediamine R940285

In like manner to the preparation of N4-(3,4-ethylenedioxyphenyl)-5-fluoro-N2-(3-hyroxyphenyl)-2,4-pyrimidinediamine, 2-chloro-N4-(3,3-dihydroisobenzofuranyl-1-one-6-yl)-5-fluoro-4-pyrimidineamine and ethyl 3-aminophenoxyacetate were reacted to give N2-(3-ethoxycarbonylmethyleneoxyphenyl)-N4-(3,3-dihydroisobenzofuranyl-1-one-6-yl)-5-fluoro-2,4-pyrimidinediamine. LCMS: ret. time: 20.55 min.; purity: 76%; MS (m/e): 438 ($M^+$), 440 ($MH^+$); 1H NMR (DMSO-d6): δ 9.70 (1H, s), 9.30 (1H, s), 8.23-8.06 (1H, m), 8.05 (1H, s), 7.63 (1H, d, J=8.1 Hz), 7.30 (1H, s), 7.22 (1H, m), 7.08 (1H, t, J=8.1 Hz), 6.43 (1H, d, J=8.1 Hz), 5.37 (1H, s), 5.37 (2H, s), 4.60 (2H, s), 4.13 (2H, q, J=7.2 Hz), 1.18 (3H, t, J=7.2 Hz).

7.3.422 N2-(3,5-Dimethoxyphenyl)-N4-(3-ethoxycarbonylmethyleneoxyphenyl)-5-fluoro-2,4-pyrimidinediamine (R926804)

In like manner to the preparation of N4-(3,4-ethylenedioxyphenyl)-5-fluoro-N2-(3-hydroxyphenyl)-2,4-pyrimidinediamine, the reaction of 2-chloro-N4-(3-ethoxycarbonylmethyleneoxyphenyl)-5-fluoro-4-pyrimidineamine with 3,5-dimethoxyaniline gave N2-(3,5-dimethoxyphenyl)-N4-(3-ethoxycarbonylmethyleneoxyphenyl)-5-fluoro-2,4-pyrimidinediamine. LCMS: ret. time: 24.12 min.; purity: 86%; MS (m/e): 443 ($MH^+$).

7.3.423 N4-(3,4-Ethylenedioxyphenyl)-5-fluoro-N2-(3-trifluoromethylphenyl)]-2,4-pyrimidinediamine (R926805)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine with 3-trifluoromethylaniline gave N4-(3,4-ethylenedioxyphenyl)-5-fluoro-N2-(3-trifluoromethylphenyl)-2,4-pyrimidinediamine. LCMS: ret. time: 25.88 min.; purity: 89%; MS (m/e): 407 ($MH^+$).

7.3.424 N2-(2-Ethoxycarbonylindol-7-yl)-N4-(3,4-ethylenedioxyphenyl)-5-fluoro-2,4-pyridinediamine (R926808)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine with 2-ethoxycarbonyl-7-aminoindole gave N2-(2-ethoxycarbonylindol-7-yl)-N4-(3,4-ethylenedioxyphenyl)-5-fluoro-2,4-pyridinediamine. LCMS: ret. time: 24.11 min.; purity: 88%, MS (m/e): 450 ($MH^+$).

7.3.425 N4-[4-(4,5-Dichloro-1H-imidazol-1-yl)phenyl]-5-fluoro-N2-(3-ethoxycarbonylmethyleneoxyphenyl)-2,4-pyrimidinediamine (R926809)

In like manner to the preparation of N4-(3,4-ethylenedioxyphenyl)-5-fluoro-N2-(3-hydroxyphenyl)-2,4-pyrimidinediamine, the reaction of N-4-[4-(4,5-dichloro-1H-imidazol-1-yl)phenyl]-2-chloro-5-fluoro-4-pyrimidineamine with ethyl-3-aminophenoxyacetate gave N4-[4-(4,5-dichloro-1H-imidazol-1-ylphenyl)]-5-fluoro-N2-(3-ethoxycarbonylmethyleneoxyphenyl)-2,4-pyrimidinediamine. LCMS: ret. time: 25.22 min, purity: 77%; MS (m/e): 519 ($MH^+$).

7.3.426 N4-(3,4-Ethylenedioxyphenyl)-5-fluoro-N2-[3-(1,3-oxazol-5-yl)phenyl]-2,4-pyrimidinediamine (R926813)

In like manner to the preparation of N4-(3,4-ethylenedioxyphenyl)-5-fluoro-N2-(3-hydroxyphenyl)-2,4-pyrimidinediamine, the reaction of 2-chloro-N4-(3,4-ethylenedioxyphenyl)-5-fluoro-4-pyrimidineamine with 3-(1,3-oxazol-5-yl) aniline gave N4-(3,4-ethylenedioxyphenyl)-5-fluoro-N2-[3-(1,3-oxazol-5-yl)phenyl]-2,4-pyrimidinediamine. LCMS: ret. time: 20.25 min.; purity: 81%, MS (m/e): 406 ($MH^+$).

7.3.427 N2-(2-Ethoxycarbonylindol-7-yl)-5-fluoro-N4-(3-hydroxyphenyl)-2,4-pyridinediamine (R926814)

In like manner to the preparation of N4-(3,4-ethylenedioxyphenyl)-5-fluoro-N2-(3-hydroxyphenyl)-2,4-pyrimidinediamine, the reaction of 2-chloro-5-fluoro-N4-(3-hydroxyphenyl)-4-pyrimidineamine with 2-ethoxycarbonyl-7-aminoindol gave N2-(2-ethoxycarbonylindol-7-yl)-5-fluoro N4-(3-hydroxyphenyl)-2,4-pyridinediamine. LCMS: ret. time: 25.94 min.; purity: 91%.

7.3.428 N2-(3-Aminophenyl)-N4-(3,4-ethylenedioxyphenyl)-5-fluoro-2,4-pyrimidinediamine (R950207)

N4-(3,4-Ethylenedioxyphenyl)-2-chloro-5-fluoro-4-pyrimidineamine (50 mg, 0.18 mmol) was dissolved in dry MeOH (1 ml), to it was added 3-aminoaniline (163 mg, 1.2 mmol) and the mixture was refluxed for 4 days (70° C. oil-bath temperature). The mixture was cooled to 22° C., concentrated to dryness under reduced pressure and subjected to column chromatography on silica gel ($CHCl_3$-Acetone, 9:1) to give N2-(3-aminophenyl)-N4-(3,4-ethylenedioxyphenyl)-5-fluoro-2,4-pyrimidinediamine. $^1$H NMR ($CD_3OD$): δ 7.66 (d, 1H, J=3.6 Hz), 7.18 (d, 1H, J=2.1 Hz), 7.09 (t, 1H, J=2.1 Hz), 6.80-6.90, (m, 1H), 6.69 (d, 1H, J=8.1 Hz), 6.57 (m, 1H), 6.20 (m, 1H), 6.60 (m, 1H), 4.10 (m, 4H); LCMS purity: 90.7%; MS (m/e): 354.13 ($M^+$, 100).

7.3.429 N4-(3,4-Ethylenedioxyphenyl)-N2-(3-ethoxycarbonylmethyleneaminophenyl)-5-fluoro-2,4-pyrimidinediamine (R950186)

In like manner to the preparation of N2-(3-aminophenyl)-N4-(3,4-ethylenedioxyphenyl)-5-fluoro-2,4-pyrimidinediamine, N4-(3,4-ethylenedioxyphenyl)-2-chloro-5-fluoro-4-pyrimidineamine and 3-ethoxycarbonylmethyleneaminophenylaniline were reacted to prepare N4-(3,4-ethylenedioxyphenyl)-N2-(3-ethoxycarbonylmethyleneaminophenyl)-5-fluoro-2,4-pyrimidinediamine. LCMS: ret. time: 23.29 min.; purity: 95.7%; MS (m/e): 440.41 (MH$^+$).

7.3.430 N4-(3,5-Dichloro-4-hydroxyphenyl)-N2-(3-ethoxycarbonylmethyleneoxyphenyl)-5-fluoro-2,4-pyrimidinediamine (R950185)

In like manner to the preparation of N2-(3-aminophenyl)-N4-(3,4-ethylenedioxyphenyl)-5-fluoro-2,4-pyrimidinediamine, 2-chloro-N4-(3,5-dichlorophenyl-4-hydroxy)-5-fluoro-4-pyrimidineamine and ethyl 3-aminophenoxyacetate were reacted to prepare N4-(3,5-dichloro-4-hydroxyphenyl)-N2-(3-ethoxycarbonylmethyleneoxyphenyl)-5-fluoro-2,4-pyrimidinediamine. LCMS: ret. time: 22.51 min.; purity: 96.1%; MS (m/e): 466.88 (MH$^+$).

7.3.431 N4-(3-Aminophenyl)-5-fluoro-N2-(2-methoxycarbonylbenzofurane-5-yl)-2,4-pyrimidinediamine (R950162)

A mixture of N4-(3-aminophenyl)-2-chloro-5-fluoro-4-pyrimidineamine (10 mg, 0.06 mmol) and 2-methoxycarbonyl-5-aminobenzofuran (36 mg, 0.18 mmol) in dry MeOH (0.5 ml) was refluxed for 2 days (100° C. oil-bath temperature). The mixture was cooled to 22° C., concentrated to dryness under reduced pressure and subjected to column chromatography on silica gel (CHCl$_3$:Acetone, 9:1) to give N4-(3-aminophenyl)-5-fluoro-N2-(2-methoxycarbonylbenzofurane-5-yl)-2,4-pyrimidinediamine. $^1$H NMR (DMSO-d6): δ 8.24 (s, 1H), 7.96 (dd, 1H, J=1.7, 3.5 Hz), 7.46-7.59 (m, 3H), 6.93-6.99 (m, 2H), 6.84 (d, 1H, J=8.2 Hz), 6.35 (m, 1H), 3.84 (s, 3H); LCMS purity: 97.8%; MS (ES) m/e 394.02 (M$^+$, 70).

7.3.432 N4-(3-Aminophenyl)-5-fluoro-N2-(3-hydroxyphenyl)-2,4-pyrimidinediamine (R950163)

In like manner to the preparation of N4-(3-aminophenyl)-5-fluoro-N2-(2-methoxycarbonylbenzofurane-5-yl)-5-fluoro-2,4-pyrimidinediamine, N4-(3-aminophenyl)-2-chloro-5-fluoro-4-pyrimidineamine and 3-hydroxyaniline were reacted to prepare N4-(3-aminophenyl)-5-fluoro-N2-(3-hydroxyphenyl)-2,4-pyrimidinediamine. $^1$H NMR (DMSO-d6): δ 7.94 (d, 1H, J=4.1 Hz), 7.20 (m, 2H), 6.89-7.00 (m, 4H), 6.30 (m, 2H); LCMS: ret. time: 11.92 min.; purity: 95.0%; MS (m/e): 312.09 (MH$^+$).

7.3.433 N4-(3-Aminophenyl)-5-fluoro-N2-(3-isopropoxyphenyl)-2,4-pyrimidinediamine (R950164)

In like manner to the preparation of N4-(3-aminophenyl)-5-fluoro-N2-(2-methoxycarbonylbenzofurane-5-yl)-5-fluoro-2,4-pyrimidinediamine, N4-(3-aminophenyl)-2-chloro-5-fluoro-4-pyrimidineamine and 3-isopropoxyaniline were reacted to prepare N4-(3-aminophenyl)-5-fluoro-N2-(3-isopropoxyphenyl)-2,4-pyrimidinediamine. LCMS: ret. time: 17.52 min.; purity: 98.9%; MS (m/e): 354.13 (MH$^+$).

7.3.434 N4-(3-Aminophenyl)-5-fluoro-N2-(4-isopropoxyphenyl)-2,4-pyrimidinediamine (R950165)

In like manner to the preparation of N4-(3-aminophenyl)-5-fluoro-N2-(2-methoxycarbonylbenzofurane-5-yl)-5-fluoro-2,4-pyrimidinediamine, N4-(3-aminophenyl)-2-chloro-5-fluoro-4-pyrimidineamine and 4-isopropoxyaniline were reacted to prepare N4-(3-aminophenyl)-5-fluoro-N2-(4-isopropoxyphenyl)-2,4-pyrimidinediamine. $^1$H NMR (DMSO-D6-MeOD, 300 MHz): δ 7.90 (d, 1H, J=4.1 Hz), 7.47 (m, 2H), 7.03 (t, 1H, J=1.7 Hz), 6.60-6.95 (m, 5H), 6.29 (m, 1H), 4.43 (septett, 1H, J=6.0 Hz), 1.18 (d, 6H, J=6.0 Hz); LCMS: ret. time: 17.11 min.; purity: 88.4%; MS (m/e): 354.09 (MH$^+$).

7.3.435 N2-(3-Furylmethylene)-5-fluoro-N4-(3-hydroxyphenyl)-2,4-pyrimidinediamine (R950210)

In like manner to the preparation of N4-(3-aminophenyl)-5-fluoro-N2-(2-methoxycarbonylbenzofurane-5-yl)-5-fluoro-2,4-pyrimidinediamine, 2-chloro-5-fluoro-N4-(3-hydroxyphenyl)-4-pyrimidineamine and 3-furylmathylamine were reacted to prepare N2-(3-furylmethylene)-5-fluoro-N4-(3-hydroxyphenyl)-2,4-pyrimidinediamine. LCMS: ret. time: 16.03 min.; purity: 93.5%; MS (m/e): 301.10 (MH$^+$).

7.3.436 5-Fluoro-N4-(3-hydroxyphenyl)-N2-(4-methoxyphenyloxyethyleneamino)-2,4-pyrimidinediamine (R950211)

In like manner to the preparation of N4-(3-aminophenyl)-5-fluoro-N2-(2-methoxycarbonylbenzofurane-5-yl)-5-fluoro-2,4-pyrimidinediamine, 2-chloro-5-fluoro-N4-(3-hydroxyphenyl)-4-pyrimidineamine and 2-(4-methoxyphenyl)ethylamine were reacted to prepare 5-fluoro-N4-(3-hydroxyphenyl)-N2-(4-methoxyphenyloxyethyleneamino)-2,4-pyrimidinediamine. LCMS: ret. time: 18.88 min.; purity: 97.6%; MS (m/e): 371.09 (MH$^+$).

7.3.437 N4-(3-Aminophenyl)-N2-[[N3-[N4-(3-aminophenyl)]-5-fluoro-2,4-pyrimidinediamine]aminophenyl]-5-fluoro-2,4-pyrimidinediamine (R950137)

2,4-Dichloro-5-fluoropyrimidine and 3-aminoaniline were reacted to prepare N4-(3-aminophenyl)-N2-[[N3-[N4-(3-aminophenyl)]-5-fluoro-2,4-pyrimidinediamine]aminophenyl]-5-fluoro-2,4-pyrimidinediamine. LCMS: ret. time: 13.10 min.; purity: 96.4%; MS (m/e): 513.01 (MH$^+$).

7.3.438 N4-(3,4-Ethylenedioxyphenyl)-5-fluoro-N2-[3-(hydroxyethyleneamino)phenyl]-2,4-pyrimidinediamine (R950208)

N2-(3-Aminophenyl)-N4-(3,4-ethylenedioxyphenyl)-5-fluoro-2,4-pyrimidinediamine and 2-bromoethanol were reacted together to give N4-(3,4-ethylenedioxyphenyl)-N2-[3-(hydroxyethylamino)phenyl]-5-fluoro-2,4-pyrimidinediamine. LCMS: ret. time: 15.44 min.; purity: 98.6%; MS (m/e): 398.05 (MH$^+$).

7.3.439 N2-[3-Bis(hydroxyethyl)aminophenyl]-N4-(3,4-ethylenedioxyphenyl)-5-fluoro-2,4-pyrimidinediamine (R950209)

N2-(3-Aminophenyl)-N4-(3,4-ethylenedioxyphenyl)-5-fluoro-2,4-pyrimidinediamine and 2-bromoethanol were reacted together to give N2-[3-bis(hydroxyethyl)aminophenyl]-N4-(3,4-ethylenedioxyphenyl)-5-fluoro-2,4-pyrimidinediamine. LCMS: ret. time: 15.64 min.; purity: 97.8%; MS (m/e): 442.06 (MH$^+$).

7.3.440 6-Ethoxycarbonyl-N4-(ethoxycarbonylmethyl)-N2-(4-ethoxycarbonylmethyleneoxyphenyl)-5-nitro-2,4-pyrimidinediamine (R925858)

In a manner similar to the preparation of N4-(3,4-ethylenedioxyphenyl)-5-fluoro-N2-[3-hydroxyphenyl)-2,4-pyrimidinediamine, N-(2-chloro-6-ethoxycarbonyl-5-nitro-4-pyrimidinyl)glycine ethyl ester and ethyl 4-aminophenoxyacetate were reacted to yield 6-ethoxycarbonyl-N4-(ethoxycarbonylmethyl)-N2-(4-ethoxycarbonylmethyleneoxyphenyl)-5-nitro-2,4-pyrimidinediamine. $^1$H NMR (CDCl$_3$): δ 9.00 (bs, 1H), 7.49 (bs, 1H), 7.41 (d, 2H, J=9.0 Hz), 6.89 (d, 2H, J=9.0 Hz), 4.62 (s, 2H), 4.46 (q, 2H, J=7.2 Hz), 4.31-4.19 (m, 6H), 1.40 (t, 3H, J=7.2 Hz), 1.33-1.25 (m, 6H); LCMS: ret. time: 30.00 min.; purity: 98%; MS (m/e): 492 (MH$^+$).

7.3.441 N4-Benzyloxy-5-ethoxycarbonyl-N2-(3,4-ethylenedioxyphenyl)-2,4-pyrimidinediamine (R925837)

In a manner similar to the preparation of N4-(3,4-ethylenedioxyphenyl)-5-fluoro-N2-(3-hydroxyphenyl)-2,4-pyrimidinediamine, N4-benzyloxy-2-chloro-5-ethoxycarbonyl-4-pyrimidineamine and 1,4-benzodioxan-6-amine were reacted to yield N4-benzyloxy-5-ethoxycarbonyl-N2-(3,4-ethylenedioxyphenyl)-2,4-pyrimidinediamine. $^1$H NMR (DMSO-d6): δ 8.55 (s, 1H), 7.49-7.44 (m, 3H), 7.39-7.34 (m, 4H), 7.30-7.22 (m, 1H), 6.67 (d, 1H, J=8.4 Hz), 4.98 (s, 2H), 4.23-4.17 (m, 6H), 1.26 (t, 3H, J=7.2 Hz); LCMS: ret. time: 26.14 min.; purity: 95%; MS (m/e): 423 (MH$^+$).

7.3.442 N4-Benzyloxy-5-ethoxycarbonyl-N2-(3-hydroxyphenyl)-2,4-pyrimidinediamine (R925824)

In a manner similar to the preparation of N4-(3,4-ethylenedioxyphenyl)-5-fluoro-N2-(3-hydroxyphenyl)-2,4-pyrimidinediamine, N4-benzyloxy-2-chloro-5-ethoxycarbonyl-4-pyrimidineamine and 3-hydroxyaniline were reacted to yield N4-benzyloxy-5-ethoxycarbonyl-N2-(3-hydroxyphenyl)-2,4-pyrimidinediamine. LCMS: ret. time: 24.28 min.; purity: 88%; MS (m/e): 381 (MH$^+$).

7.3.443 N2,N4-Bis[4-(aminocarbonylmethyleneoxy)phenyl]-5-fluoro-2,4-pyrimidinediamine (R945025)

A mixture of 4-nitrophenol (7.65 g, 55 mmol), 2-bromoacetamide (6.90 g, 50 mmol) and K$_2$CO$_3$ (13.8 g, 0.1 mol) in acetone (50 mL) was stirred at room temperature for 24 h.

The reaction mixture was diluted with water, and acetone was removed under reduced pressure. The formed light-yellow precipitate was collected by filtration, washed with water and dried to give 1-aminocarbonylmethyleneoxy-4-nitrobenzene (8.28 g, 84%).

Hydrogenation of 1-aminocarbonylmethyleneoxy-4-nitrobenzene (3 g, 15 mmol) in methanol (50 mL) catalyzed by 10% Pd—C (500 mg) and Na$_2$SO$_4$ (500 mg) at 50 psi for 2 h gave 4-(aminocarbonylmethyleneoxy)aniline (2.59 g, quant.).

4-(Aminocarbonylmethyleneoxy)aniline (500 mg, 3 mmol) and 2,4-dichloro-5-fluoropyrimidine (200 mg, 1.2 mmol) were dissolved in methanol (10 mL) and water (1 mL) and was stirred at 70° C. for 24 h. Then methanol was removed under reduced pressure. The remaining aqueous solution was acidified with 1 N HCl (80 mL). The formed white precipitate was collected by filtration to give N2,N4-bis[4-(aminocarbonylmethyleneoxy)phenyl]-5-fluoro-2,4-pyrimidinediamine (370 mg, 72%). $^1$H NMR (acetone-d$_6$): δ 4.46 (s, 2H), 4.50 (s, 2H), 6.81 (br, NH, 2H), 6.91 (d, J=9.0 Hz, 2H), 6.98 (d, J=9.0 Hz, 2H), 7.20 (br, 2H, NH), 7.63 (d, J=9.3 Hz, 2H), 7.72 (d, J=8.7 Hz, 2H), 7.93 (d, J=3.6 Hz, 1H), 8.27 (br, 1H, NH), 8.44 (br, 1H, NH); LCMS: ret. time: 13.91 min.; purity: 100%; MS (m/e): 427.02 (MH$^+$).

7.3.444 N2,N4-Bis[4-(cyanomethyleneoxy)phenyl]-5-fluoro-2,4-pyrimidinediamine (R945032)

To a solution of N2,N4-bis[4-(aminocarbonylmethyleneoxy)phenyl]-5-fluoro-2,4-pyrimidinediamine (200 mg, 0.47 mmol) in THF (10 mL) was added trifluoroacetic anhydride (0.33 mL, 2.35 mmol) and pyridine (0.38 mL, 4.7 mmol) at room temperature and was stirred at room temperature overnight. The mixture was diluted with ethyl acetate (80 mL) and 1 N HCl (80 mL). The organic layer was washed with 1 N HCl (2×60 mL), water (2×60 mL) and brine (60 mL). The ethyl acetate layer was dried and evaporated. The residue was recrystallized from ethyl acetate and hexanes to give N2,N4-bis[4-(cyanomethyleneoxy)phenyl]-5-fluoro-2,4-pyrimidinediamine (159 mg, 87%) as a white solid. $^1$H NMR (acetone-d$_6$): δ 5.09 (s, 2H), 5.16 (s, 2H), 7.08 (d, J=9.3 Hz, 2H), 7.17 (d, J=9.0 Hz, 2H), 7.63 (d, J=9.0 Hz, 2H), 7.77 (d, J=9.3 Hz, 2H), 8.17 (d, J=4.8 Hz, 1H), 9.55 (br, 1H, NH), 11.00 (br, 1H, NH); LCMS: 21.47 min.; 96.11%; MS (m/e): 391.20 (MH$^+$).

7.3.445 N2,N4-Bis[4-(1H-1,2,3,4-tetrazol-5-yl)methyleneoxyphenyl]-5-fluoro-2,4-pyrimidinediamine (R945033)

To a solution of N2,N4-bis[4-(cyanomethyleneoxy)phenyl]-5-fluoro-2,4-pyrimidinediamine (100 mg, 0.26 mmol) in DMF (10 mL) was added NH$_4$Cl (136 mg, 2.54 mmol), sodium azide (100 mg, 1.54 mmol), and one drop of acetic acid and was stirred at 70° C. overnight. Then it was titrated with ethyl acetate (80 mL) to give precipitation. The precipitate was collected by filtration, washed with 1 N HCl and water to give N2,N4-bis[4-(1H-1,2,3,4-tetrazol-5-yl)methyleneoxyphenyl]-5-fluoro-2,4-pyrimidinediamine (66 mg, 54%) as a white solid. $^1$H NMR (CD$_3$OD): δ 5.31 (s, 2H), 5.34 (s, 2H), 6.93 (d, J=9.0 Hz, 2H), 7.00 (d, J=9.3 Hz, 2H), 7.04 (d, J=9.0 Hz, 2H), 7.57 (d, J=9.0 Hz, 2H), 7.81 (d, J=4.2 Hz, 1H); LCMS: 16.54 min.; purity: 88.34%; MS (m/e): 477.02 (MH$^+$).

7.3.446 N2,N4-Bis(4-methoxycarbonylphenyl)-5-fluoro-2,4-pyrimidinediamine (R945034)

A mixture of 4-Aminobenzoic acid (410 mg, 3 mmol) and 2,4-dichloro-5-fluoropyrimidine (100 mg, 0.6 mmol) in methanol (10 mL) and water (1 mL) was stirred at 100° C. for 24 h to yield N2,N4-bis(4-carboxyphenyl)-5-fluoro-2,4-pyrimidinediamine after methanol was removal. This residue was redissolved in DMF (10 mL) and to it was added potassium carbonate (1.65 g, 12 mmol) and iodomethane (0.37 mL, 6 mmol), stirred at room temperature overnight, and then diluted with 1 N HCl (80 mL) and ethyl acetate (80 mL). The ethyl acetate layer was washed with 1N HCl (60 mL) and water (60 mL). The organic layer was separated, dried, evaporated and the resulting residue was recrystallized from ethyl acetate/hexanes to give N2,N4-bis(4-methoxycarbonylphenyl)-5-fluoro-2,4-pyrimidinediamine (150 mg, 63%). $^1$H NMR (acetone-$d_6$): δ 3.85 (s, 3H), 3.88 (s, 3H), 7.88-7.97 (m, 4H), 7.98-8.05 (m, 4H), 8.18 (d, J=3.0 Hz, 1H), 9.00 (br, 1H, NH), 9.04 (br, 1H, NH); LCMS: ret. time: 27.07 min.; purity: 95.54%; MS (m/e): 397.04 (MH$^+$).

7.3.447 N2,N4-Bis(3-methoxycarbonylphenyl)-5-fluoro-2,4-pyrimidinediamine (R945035)

In a manner analogous to the preparation of N2,N4-bis(4-methoxycarbonylphenyl)-5-fluoro-2,4-pyrimidinediamine, the reaction of 3-aminobenzoic acid (410 mg, 3 mmol) and 2,4-dichloro-5-fluoropyrimidine (100 mg, 0.6 mmol) gave N2,N4-bis(3-methoxycarbonylphenyl)-5-fluoro-2,4-pyrimidinediamine (180 mg, 76%) as a white solid. $^1$H NMR (acetone-$d_6$): δ 3.81 (s, 3H), 3.83 (s, 3H), 7.37 (t, J=8.1 Hz, 1H), 7.47 (t, J=8.1 Hz, 1H), 7.60 (d, J=7.8 Hz, 1H), 7.75 (d, J=7.5 Hz, 1H), 8.02 (d, J=6.3 Hz, 1H), 8.10 (d, J=3.6 Hz, 1H), 8.24 (d, J=8.4 Hz, 1H), 8.36 (d, J=11.4 Hz, 2H), 8.74 (br, 1H, NH), 8.82 (br, 1H, NH); LCMS: ret. time: 22.77 min.; purity: 91.04%; MS (m/e): 397.00 (MH$^+$).

7.3.448 N2,N4-Bis(3-carboxyphenyl)-5-fluoro-2,4-pyrimidinediamine (R945036)

A solution of N2,N4-bis(3-methoxycarbonylphenyl)-5-fluoro-2,4-pyrimidinediamine (100 mg, 0.25 mmol) and NaOH (140 mg, 3.5 mmol) in THF:$H_2O$ (5 mL, each) was stirred at room temperature overnight. The reaction mixture was diluted with water (60 mL) and ethyl acetate (60 mL). The aqueous layer was separated, acidified with 1N HCl solution to pH 3. The formed precipitate was collected by filtration and recrystallized from methanol to give N2,N4-bis(3-carboxyphenyl)-5-fluoro-2,4-pyrimidinediamine (54 mg, 58%) as a white solid. $^1$H NMR (CD$_3$OD): δ 7.31 (t, J=8.1 Hz, 1H), 7.42 (t, J=8.1 Hz, 1H), 7.61 (dm, J=7.8 Hz, 1H), 7.76 (dm, J=8.4 Hz, 1H), 7.89 (dm, J=7.2 Hz, 1H), 7.98 (d, J=3.6 Hz, 1H), 8.01 (m, 1H), 8.20 (m, 1H), 8.37 (m, 1H); LCMS: ret. time: 15.77 min.; purity: 98.84%; MS (m/e): 369.03 (MH$^+$).

7.3.449 N2,N4-Bis(4-carboxyphenyl)-5-fluoro-2,4-pyrimidinediamine (R945037)

In a manner analogous to the preparation of N2,N4-bis(3-carboxyphenyl)-5-fluoro-2,4-pyrimidinediamine, N2,N4-bis(4-methoxycarbonylphenyl)-5-fluoro-2,4-pyrimidinediamine (100 mg, 0.25 mmol) and NaOH (200 mg, 5 mmol) gave N2,N4-bis(4-carboxyphenyl)-5-fluoro-2,4-pyrimidinediamine (55 mg, 59%) as a white solid. $^1$H NMR (CD$_3$OD): δ 7.77 (d, J=8.7 Hz, 2H), 7.92 (d, J=8.7 Hz, 2H), 7.94 (d, J=8.4 Hz, 2H), 8.02 (d, J=8.7 Hz, 2H), 8.07 (d, J=3.6 Hz, 1H); LCMS: ret. time: 16.34 min.; purity: 100%; MS (m/e): 368.87 (MH$^+$).

7.3.450 N2,N4-Bis(3-isopropylaminocarbonyloxyphenyl)-5-fluoro-2,4-pyrimidinediamine (R926412)

The reaction of 1 equivalent of N2,N4-bis(3-hydroxyphenyl)-5-fluoro-2,4-pyrimidinediamine with 3 equivalents of isopropyl isocyanate in the presence of pyridine in CH$_2$Cl$_2$ at room temperature for 24 h followed by extractive work up using CH$_2$Cl$_2$ gave the desired N2,N4-bis(3-isopropylaminocarbonyloxyphenyl)-5-fluoro-2,4-pyrimidinediamine. $^1$H NMR (CDCl$_3$+CD$_3$OD): δ 7.82 (d, 1H, J=3.6 Hz), 7.66 (bd, 1H), 7.48 (bd, 1H), 7.15-7.02 (m, 2H), 6.76-6.76 (m, 2H), 6.56 (bd, 1H, J=8.1 Hz), 6.45 (dd, 1H, J=1.8 and 8.4 Hz), 4.70 (m, 2H), 1.05 (d, 12H, J=6.3 Hz); $^{19}$F NMR (CDCl$_3$+CD$_3$OD): −47206; LCMS: ret. time: 15.40 min.; purity: 90%.

7.3.451 N2,N4-Bis[4-(ethylaminocarbonylamino)phenyl]-5-fluoro-2,4-pyrimidinediamine (R945040)

A mixture of 1,4-diaminobenzene (4 g, 37 mmol), ethyl isocyanate (1 mL, 12.6 mmol) and potassium carbonate (8.72 g, 63 mmol) in THF (20 mL) was stirred at room temperature overnight. The reaction mixture was partitioned in 1N HCl solution (80 mL) and ethyl acetate (80 mL). The aqueous layer was extracted with ethyl acetate (4×80 mL). The combined organic layers was dried, evaporated, recrystallized from MeOH/CH$_2$Cl$_2$/hexanes to give 4-(ethylaminocarbonylamino)aniline (1.4 g, 62%) as a beige solid.

In a manner analogous to the preparation of N2,N4-bis(3-hydroxyphenyl)-5-fluoro-2,4-pyrimidinediamine, 4-(ethylaminocarbonylamino)aniline (537 mg, 3 mmol) and 2,4-dichloro-5-fluoropyrimidine (100 mg, 0.6 mmol) gave N2,N4-bis[4-(ethylaminocarbonylamino)phenyl]-5-fluoro-2,4-pyrimidinediamine (180 mg, 66%) as a white solid. $^1$H NMR (CD$_3$OD): δ 1.16 (t, J=7.2 Hz, 6H), 3.24 (q, J=7.2 Hz, 4H), 7.29 (d, J=9.0 Hz, 2H), 7.40 (t, J=9.0 Hz, 4H), 7.55 (d, J=9.0 Hz, 2H), 7.87 (s, 1H, NH), 7.89 (s, 1H, NH); LCMS: ret. time: 16.93 min.; purity: 93.43%; MS (m/e): 453.03 (MH$^+$).

7.3.452 N2,N4-Bis[3-(ethylaminocarbonylamino)phenyl]-5-fluoro-2,4-pyrimidinediamine (R945045)

In a manner analogous to the preparation of N2,N4-bis[4-(ethylaminocarbonylamino)phenyl]-5-fluoro-2,4-pyrimidinediamine, the reaction of 1,3-diaminobenzene (2 g, 18.5 mmol), ethyl isocyanate (0.5 mL, 6.3 mmol) and potassium carbonate (4.36 g, 31.5 mmol) gave 3-(ethylaminocarbonylamino)aniline (940 mg, 83%). The reaction of 3-(ethylaminocarbonylamino)aniline (537 mg, 3 mmol) and 2,4-dichloro-5-fluoropyrimidine (100 mg, 0.6 mmol) gave N2,N4-bis[3-(ethylaminocarbonylamino)phenyl]-5-fluoro-2,4-pyrimidinediamine (180 mg, 66%) as a white solid. $^1$H NMR (CD$_3$OD): δ 1.14 (t, J=6.9 Hz, 3H), 1.15 (t, J=7.5 Hz, 3H), 3.21 (q, J=7.2 Hz, 2H), 3.22 (q, J=7.5 Hz, 2H), 7.06 (ddd, J=0.9, 2.1, 7.8 Hz, 1H), 7.10-7.28 (m, 5H), 7.53 (t, J=2.1 Hz, 1H), 7.80 (m, 1H), 7.92 (d, J=5.7 Hz, 1H); LCMS: ret. time: 17.17 min.; purity: 89.63%; MS (m/e): 453.38 (MH$^+$).

7.3.453 N2,N4-Bis(4-hydroxy-3-methoxycarbonylphenyl)-5-fluoro-2,4-pyrimidinediamine (R945043)

A solution of N2,N4-bis(3-carboxy-4-hydroxyphenyl)-5-fluoro-2,4-pyrimidinediamine (70 mg, 0.17 mmol) and thionyl chloride (0.04 mL, 0.55 mmol) in MeOH (10 mL) was refluxed overnight. Methanol was removed in vacuo. The residue was diluted with EtOAc (60 mL) and sodium hydrogen carbonate solution (60 mL). The EtOAc layer was washed with NaHCO$_3$ aqueous solution (60 mL) and water (60 mL). The organic layer was dried, evaporated and crystallized from MeOH/Et$_2$O to give N2,N4-bis(4-hydroxy-3-methoxycarbonylphenyl)-5-fluoro-2,4-pyrimidinediamine (58 mg, 77%). $^1$H NMR (DMSO-d6): δ 3.69 (s, 3H), 3.71 (s, 3H), 6.81 (d, J=9.3 Hz, 1H), 6.92 (d, J=9.0 Hz, 1H), 7.64 (dd, J=2.7, 9.0 Hz, 1H), 7.84 (dd, J=2.1 and 8.4 Hz, 1H), 8.03-8.07 (m, 3H), 9.14 (s, 1H, NH), 9.34 (s, 1H, NH), 10.16 (s, 1H, OH), 10.29 (s, 1H, OH); $^{19}$F NMR (282 MHz, DMSO-d6): 6-165.60; LCMS: ret. time: 22.24 min.; purity: 100%; MS (m/e): 428.98 (MH$^+$).

7.3.454 N2,N4-Bis[4-(2-methyl-1,2,3,4-tetrazol-5-yl)methyleneoxyphenyl]-5-fluoro-2,4-pyrimidinediamine (R945046)

5-Fluoro-N2,N4-[4-(1-methyl-1,2,3,4-tetrazol-5-yl)methyleneoxyphenyl], [4-(2-methyl-1,2,3,4-tetrazol-5-yl)methyleneoxyphenyl]-2,4-pyrimidinediamine (R945047)

N2,N4-Bis[4-(1-methyl-1,2,3,4-tetrazol-5-yl)methyleneoxyphenyl]-5-fluoro-2,4-pyrimidinediamine (R945048)

Compound N2,N4-bis[4-(1H-1,2,3,4-tetrazol-5-yl)methyleneoxyphenyl]-5-fluoro-2,4-pyrimidinediamine (30 mg, 0.063 mmol), iodomethane (0.024 mL, 0.38 mmol) and K$_2$CO$_3$ (88 mg, 0.64 mmol) in DMF (5 mL) was stirred at room temperature overnight. Then it was diluted with ethyl acetate (50 mL) and water (50 mL). The organic layer was washed with water (50 mL) and brine (50 mL). After separation, the ethyl acetate layer was dried, evaporated and purified by flash column chromatography (EtOAc/hexanes=2/1, 1/1, EtOAc) to give a mixture of following compounds: N2,N4-bis[4-(2-methyl-1,2,3,4-tetrazol-5-yl)methyleneoxyphenyl]-5-fluoro-2,4-pyrimidinediamine R945046 (6 mg, 19%), $^1$H NMR (CDCl$_3$): δ 4.37 (s, 3H), 4.38 (s, 3H), 5.33 (s, 2H), 5.36 (s, 2H), 6.65 (d, J=3.0 Hz, 1H), 6.76 (s, 1H), 6.98 (d, J=9.0 Hz, 2H), 7.04 (d, J=9.3 Hz, 2H), 7.42 (d, J=9.0 Hz, 2H), 7.51 (d, J=9.0 Hz, 2H), 7.90 (br, 1H); $^{19}$F NMR (282 MHz, CDCl$_3$): 6-168.52; LCMS: ret. time: 20.44 min.; purity: 94.92%; MS (m/e): 505.02 (MH$^+$); 5-fluoro-N2,N4-[4-(1-methyl-1,2,3,4-tetrazol-5-yl)methyleneoxyphenyl],[4-(2-methyl-1,2,3,4-tetrazol-5-yl)methyleneoxyphenyl]-2,4-pyrimidinediamine R945047 (8 mg, 25%), $^1$H NMR (CDCl$_3$): δ 4.18 (s, 3H), 4.20 (s, 3H), 4.36 (s, 3H), 4.37 (s, 3H), 5.34 (s, 2H), 5.37 (s, 2H), 5.42 (s, 2H), 5.46 (s, 2H), 6.69 (br, 2H), 6.80 (s, 1H), 6.83 (s, 1H), 6.91 (d, J=9.3 Hz, 2H), 6.98 (d, J=9.0 Hz, 2H), 6.99 (d, J=9.3 Hz, 2H), 7.04 (d, J=9.0 Hz, 2H), 7.41 (d, J=9.9 Hz, 2H), 7.44 (d, J=9.3 Hz, 2H), 7.50 (d, J=9.0 Hz, 2H), 7.54 (d, J=9.0 Hz, 2H), 7.91 (br, 2H); $^{19}$F NMR (282 MHz, CDCl$_3$): 6-168.39, −168.16; LCMS: ret. time: 19.42 min.; purity: 91.18%; MS (m/e): 504.99 (MH$^+$), and N2,N4-bis[4-(1-methyl-1,2,3,4-tetrazol-5-yl)methyleneoxyphenyl]-5-fluoro-2,4-pyrimidinediamine R945048 (6 mg, 19%), $^1$H NMR (CD$_3$OD+CDCl$_3$): δ 4.20 (s, 3H), 4.22 (s, 3H), 5.50 (s, 2H), 5.55 (s, 2H), 6.95 (d, J=9.0 Hz, 2H), 7.02 (d, J=9.3 Hz, 2H), 7.52 (d, J=9.0 Hz, 2H), 7.66 (d, J=9.3 Hz, 2H), 7.84 (d, J=3.6 Hz, 1H); $^{19}$F NMR (282 MHz, CD$_3$OD+CDCl$_3$): 6-163.12; LCMS: ret. time: 18.32 min.; purity: 83.41%; MS (m/e): 504.99 (MH$^+$).

7.3.455 N4-(4-Aminocarbonylmethyleneoxyphenyl)-5-fluoro-N2-(4-methoxycarbonylmethyleneoxyphenyl)-2,4-pyrimidinediamine (R945052)

In like manner to the preparation of 2-chloro-N4-(3,4-ethylenedioxyphenyl)-5-fluoro-4-pyrimidineamine, 4-(aminocarbonylmethyleneoxy)aniline (398 mg, 2.4 mmol) and 2,4-dichloro-5-fluoropyrimidine (200 mg, 1.2 mmol) gave N4-(4-aminocarbonylmethyleneoxyphenyl)-2-chloro-5-fluoro-4-pyrimidineamine (270 mg, 76%). In like manner to the preparation of N2,N4-bis(3-hydroxyphenyl)-5-fluoro-2,4-pyrimidinediamine, the reaction of methyl 4-aminophenoxyacetate (183 mg, 1 mmol) and N4-(4-aminocarbonylmethyleneoxyphenyl)-2-chloro-5-fluoro-4-pyrimidineamine (100 mg, 0.34 mmol) gave N4-(4-aminocarbonylmethyleneoxyphenyl)-5-fluoro-N2-(4-methoxycarbonylmethyleneoxyphenyl)-2,4-pyrimidinediamine (120 mg, 80%). $^1$H NMR (acetone-d$_6$): δ 3.25 (s, 3H), 3.98 (s, 2H), 4.33 (s, 2H), 6.45 (d, J=8.7 Hz, 2H), 6.49 (d, J=9.3 Hz, 2H), 6.93 (d, J=8.7 Hz, 2H), 7.13 (d, J=9.0 Hz, 2H), 7.71 (d, J=5.1 Hz, 1H), 9.46 (br, 1H, NH), 9.78 (br, 1H, NH); LCMS: ret. time: 16.65 min.; purity: 100%; MS (m/e): 442.01 (MH$^+$).

7.3.456 N4-(4-Cyanomethyleneoxyphenyl])5-fluoro-N2-(4-methoxycarbonylmethyleneoxyphenyl)-2,4-pyrimidinediamine (R945053)

In a manner analogous to the preparation of N2,N4-bis(4-cyanomethyleneoxyphenyl)-5-fluoro-2,4-pyrimidinediamine, the reaction of N4-(4-aminocarbonylmethyleneoxyphenyl)-5-fluoro-N2-(4-methoxycarbonylmethyleneoxyphenyl)-2,4-pyrimidinediamine (80 mg, 0.18 mmol), trifluoroacetic anhydride (0.13 mL, 0.92 mmol) and pyridine (0.15 mL, 1.84 mmol) gave N4-(4-cyanomethyleneoxyphenyl)-5-fluoro-N2-(4-methoxycarbonylmethyleneoxyphenyl)-2,4-pyrimidinediamine (52 mg, 68%) as a white solid. $^1$H NMR (DMSO-d6): δ 3.24 (s, 3H), 4.26 (s, 2H), 4.71 (s, 2H), 6.36 (d, J=9.3 Hz, 2H), 6.59 (d, J=9.0 Hz, 2H), 7.06 (d, J=9.0 Hz, 2H), 7.28 (d, J=9.0 Hz, 2H), 7.58 (d, J=3.6 Hz, 1H), 8.59 (br, 1H, NH), 8.85 (br, 1H, NH); $^{19}$F NMR (282 MHz, DMSO-d6): 6-166.26; LCMS: ret. time: 21.37 min.; purity: 100%; MS (m/e): 424.01 (MH$^+$).

7.3.457 N2,N4-Bis[3-hydroxy-4-(methoxycarbonyl)phenyl]-5-fluoro-2,4-pyrimidinediamine (R945056)

A solution of 4-amino-2-hydroxybenzoic acid (1 g, 6.5 mmol) in MeOH (15 mL) and concentrated sulfonic acid (1 mL) was refluxed overnight. The reaction mixture was quenched with NaHCO$_3$ aqueous solution (60 mL) and EtOAc (60 mL). The organic layer was separated, dried, evaporated to give 3-hydroxy-4-methoxycarbonylaniline.

In a manner analogous to the preparation of N2,N4-bis(3-hydroxyphenyl)-5-fluoro-2,4-pyrimidinediamine, 3-hydroxy-4-methoxycarbonylaniline (500 mg, 3 mmol) and 2,4-dichloropyrimidine (100 mg, 0.6 mmol) gave N2,N4-bis-[3-hydroxy-4-(methoxycarbonyl)phenyl]-5-fluoro-2,4-pyrimidinediamine (105 mg, 41%). $^1$H NMR (DMSO-d6): δ 3.90 (s, 3H), 3.93 (s, 3H), 7.31 (dd, J=2.4, 9.0 Hz, 1H), 7.56 (dd, J=2.1, 8.7 Hz, 1H), 7.63 (d, J=2.1 Hz, 1H), 7.67 (d, J=2.1 Hz, 1H), 7.67 (d, J=9.0 Hz, 1H), 7.79 (d, J=9.0 Hz, 1H), 8.28 (d, J=3.6 Hz, 1H), 9.72 (s, 1H, NH), 9.82 (s, 1H, NH), 10.77 (s, 1H, OH), 10.80 (s, 1H, OH); $^{19}$F NMR (282 MHz, DMSO-d6): 6-161.74; LCMS: ret. time: 31.47 min.; purity: 96.03%; MS (m/e): 428.99 (MH$^+$).

7.3.458 N2-(4-Aminocarbonylmethyleneoxyphenyl)-5-fluoro-N4-(4-methoxycarbonylmethyleneoxyphenyl)-2,4-pyrimidinediamine (R945060)

In a manner analogous to the preparation of N4-(4-aminocarbonylmethyleneoxyphenyl)-5-fluoro-N2-(4-methoxycarbonylmethyleneoxyphenyl)-2,4-pyrimidinediamine, 2-chloro-5-fluoro-N4-(4-methoxycarbonylmethyleneoxyphenyl)-4-pyrimidineamine (150 mg, 0.48 mmol) and 4-(aminocarbonylmethyleneoxy)aniline (240 mg, 1.44 mmol) gave N2-(4-aminocarbonylmethyleneoxyphenyl)-5-fluoro-N4-(4-methoxycarbonylmethyleneoxyphenyl)-2,4-pyrimidinediamine (145 mg, 68%). $^1$H NMR (DMSO-d6): δ 3.70 (s, 3H), 4.40 (s, 2H), 4.81 (s, 2H), 6.91 (d, J=8.4 Hz, 2H), 6.93 (d, J=8.4 Hz, 2H), 7.36 (d, J=8.4 Hz, 2H), 7.54 (d, J=8.7 Hz, 2H), 8.21 (d, J=4.8 Hz, 1H), 10.13 (br, 1H, NH), 10.39 (br, 1H, NH); $^{19}$F NMR (282 MHz, DMSO-d6): 6-162.26; LCMS: ret. time: 15.37 min.; purity: 78.49%; MS (m/e): 442.07 (MH$^+$).

7.3.459 N2,N4-Bis(3-hydroxy-4-carboxyphenyl)-5-fluoro-2,4-pyrimidinediamine (R945061)

In a manner analogous to the preparation of N2,N4-bis(3-carboxyphenyl)-5-fluoro-2,4-pyrimidinediamine, the reaction of N2,N4-bis[3-hydroxy-4-(methoxycarbonyl)phenyl]-5-fluoro-2,4-pyrimidinediamine (70 mg, 0.16 mmol) and NaOH (100 mg, 2.5 mmol) gave N2,N4-bis(3-hydroxy-4-carboxyphenyl)-5-fluoro-2,4-pyrimidinediamine (50 mg, 77%) as a white solid. $^1$H NMR (DMSO-d6): δ 7.21 (dd, J=1.5 and 8.7 Hz, 1H), 7.46-7.52 (m, 3H), 7.63 (d, J=8.7 Hz, 1H), 7.72 (d, J=8.7 Hz, 1H), 8.28 (d, J=3.3 Hz, 1H), 9.71 (s, 1H, NH), 9.79 (s, 1H, NH), 11.34 (br, 2H); $^{19}$F NMR (282 MHz, DMSO-d6): 6-161.10; LCMS: ret. time: 20.76 min.; purity: 84.65%; MS (m/e): 400.95 (MH$^+$).

7.3.460 N2-(4-Cyanomethyleneoxyphenyl)-5-fluoro-N4-(4-methoxycarbonylmethyleneoxyphenyl)-2,4-pyrimidinediamine (R945062)

In a manner analogous to the preparation of N2,N4-bis(4-cyanomethyleneoxyphenyl)-5-fluoro-2,4-pyrimidinediamine, N2-(4-aminocarbonylmethyleneoxyphenyl)-5-fluoro-N4-(4-methoxycarbonylmethyleneoxyphenyl)-2,4-pyrimidinediamine (100 mg, 0.23 mmol), trifluoroacetic anhydride (0.16 mL, 1.13 mmol) and pyridine (0.18 mL, 2.21 mmol) gave N2-(4-cyanomethyleneoxyphenyl)-5-fluoro-N4-(4-methoxycarbonylmethyleneoxyphenyl)-2,4-pyrimidinediamine (66 mg, 69%) as a white solid. $^1$H NMR (acetone-d6): δ 3.75 (s, 3H), 4.67 (s, 2H), 4.89 (s, 2H), 6.88 (d, J=9.0 Hz, 2H), 6.90 (d, J=9.3 Hz, 2H), 7.48 (d, J=9.0 Hz, 2H), 7.54 (d, J=9.0 Hz, 2H), 7.84 (d, J=4.2 Hz, 1H), 9.17 (br, 1H, NH), 10.59 (br, 1H, NH); $^{19}$F NMR (282 MHz, acetone-d6): 6-164.65; LCMS: ret. time: 20.69 min.; purity: 94.35%; MS (m/e): 424.02 (MH$^+$).

7.3.461 N2,N4-Bis(3-methoxy-4-methoxycarbonylphenyl)-5-fluoro-2,4-pyrimidinediamine (R945065)

In a manner analogous to the preparation of N2,N4-bis[4-(2-methyl-1,2,3,4-tetrazol-5-yl)methyleneoxyphenyl]-5-fluoro-2,4-pyrimidinediamine, 2-methoxy-4-nitrobenzoic acid (1 g, 5 mmol), potassium carbonate (1.4 g, 10 mmol) and iodomethane (0.47 mL, 7.5 mmol) gave methyl 2-methoxy-4-nitrobenzoate (820 mg, 77%) as a white solid.

The hydrogenation of methyl 2-methoxy-4-nitrobenzoate (700 mg, 3.3 mmol) in methanol (10 mL) catalyzed by 5% Pd—C (100 mg) and Na$_2$SO$_4$ (100 mg) at 50 psi for 1 h gave methyl 4-amino-2-methoxybenzoate (600 mg, quant.) as a white solid.

In a manner analogous to the preparation of N2,N4-bis(3-hydroxyphenyl)-2,4-pyrimidinediamine, methyl 4-amino-2-methoxybenzoate (542 mg, 3 mmol) and 2,4-dichloro-5-fluoropyrimidine (100 mg, 0.6 mmol) gave N2,N4-bis(3-methoxy-4-methoxycarbonylphenyl)-5-fluoro-2,4-pyrimidinediamine (180 mg, 66%) as a white solid. $^1$H NMR (acetone-d6): δ 3.76 (s, 3H), 3.77 (s, 3H), 3.81 (s, 6H), 7.36 (dd, J=1.8, 8.7 Hz, 1H), 7.57 (s, 1H), 7.58 (dd, J=2.1 and 7.2 Hz, 1H), 7.69 (d, J=2.1 Hz, 1H), 7.73 (d, J=8.4 Hz, 1H), 7.75 (d, J=9.0 Hz, 1H), 8.17 (d, J=3.3 Hz, 1H), 8.89 (s, 2H, NH); $^{19}$F NMR (282 MHz, acetone-d6): 6-165.18; LCMS: ret. time: 23.17 min.; purity: 100%; MS (m/e): 456.96 (MH$^+$).

7.3.462 N2,N4-Bis(4-methoxy-3-methoxycarbonylphenyl)-5-fluoro-2,4-pyrimidinediamine (R945066)

In a manner analogous to the preparation of N2,N4-bis(3-methoxy-4-methoxycarbonyl)phenyl)-5-fluoro-2,4-pyrimidinediamine, 2-hydroxy-5-nitrobenzoic acid (1 g, 5.5 mmol), potassium carbonate (3 g, 22 mmol) and iodomethane (1 mL, 16 mmol) gave methyl 2-hydroxy-5-nitrobenzoate (880 mg, 77%).

The hydrogenation of methyl 2-hydroxy-5-nitrobenzoate (700 mg, 3.3 mmol) using 10% Pd—C (100 mg) and Na$_2$SO$_4$ (100 mg) in MeOH at 50 psi gave methyl 5-amino-2-methoxybenzoate (600 mg).

In a manner analogous to the preparation of N2,N4-bis(3-hydroxyphenyl)-2,4-pyrimidinediamine, methyl 5-amino-2-methoxybenzoate (542 mg, 3 mmol) and 2,4-dichloro-5-fluoropyrimidine (100 mg, 0.6 mmol) gave N2,N4-bis(4-methoxy-3-methoxycarbonylphenyl)-5-fluoro-2,4-pyrimidinediamine (170 mg, 62%) as a pink solid. $^1$H NMR (acetone-d6): δ 3.76 (s, 3H), 3.77 (s, 3H), 3.88 (s, 3H), 3.93 (s, 3H), 7.08 (dd, J=0.8, 9.0 Hz, 1H), 7.18 (d, J=9.0 Hz, 1H), 7.66 (dd, J=3.0 and 8.7 Hz, 1H), 7.78 (dd, J=1.5 and 3.0 Hz, 1H), 7.86 (dt, J=2.7 and 9.0 Hz, 1H), 7.98 (t, J=2.7 Hz, 1H), 8.32 (d, J=5.1 Hz, 1H); $^{19}$F NMR (282 MHz, acetone-d6): 6-163.88; LCMS: ret. time: 19.07 min.; purity: 98.17%; MS (m/e): 456.94 (MH$^+$).

7.3.463 N2,N4-Bis(3-carboxy-4-methoxyphenyl)-5-fluoro-2,4-pyrimidinediamine (R945067)

In a manner analogous to the preparation of N2,N4-bis(3-carboxyphenyl)-5-fluoro-2,4-pyrimidinediamine, N2,N4-bis[4-methoxy-3-(methoxycarbonyl)phenyl]-5-fluoro-2,4-pyrimidinediamine (80 mg, 0.18 mmol) and NaOH (200 mg, 5 mmol) gave N2,N4-bis(3-carboxy-4-methoxyphenyl)-5-fluoro-2,4-pyrimidinediamine (80 mg). $^1$H NMR (DMSO-d6): δ 3.75 (s, 3H), 3.80 (s, 3H), 6.94 (d, J=9.6 Hz, 1H), 7.05 (d, J=9.3 Hz, 1H), 7.78-7.80 (m, 3H), 7.94 (dd, J=9.3 Hz, 1H), 8.04 (d, J=3.6 Hz, 1H), 9.10 (s, 1H, NH), 9.30 (s, 1H, NH); $^{19}$F NMR (282 MHz, DMSO-d6): 6-165.56; LCMS: ret. time: 14.65 min.; purity: 100%; MS (m/e): 428.83 (MH$^+$).

7.3.464 N2,N4-Bis(4-carboxy-3-methoxyphenyl)-5-fluoro-2,4-pyrimidinediamine (R945068)

In a manner analogous to the preparation of N2,N4-bis(3-carboxyphenyl)-5-fluoro-2,4-pyrimidinediamine, N2,N4-bis(3-methoxy-4-methoxycarbonylphenyl)-5-fluoro-2,4-pyrimidinediamine (30 mg, 0.06 mmol) and NaOH (200 mg, 5 mmol) gave N2,N4-bis(4-carboxy-3-methoxyphenyl)-5-fluoro-2,4-pyrimidinediamine (18 mg, 64%) as a white solid. $^1$H NMR (DMSO-d6): δ 3.66 (s, 3H), 3.73 (s, 3H), 7.37 (d, J=8.4 Hz, 1H), 7.47 (s, 1H), 7.49 (s, 1H), 7.61-7.71 (m, 3H), 8.25 (d, J=3.6 Hz, 1H), 9.65 (s, 1H, NH), 9.70 (s, 1H, NH); $^{19}$F NMR (282 MHz, DMSO-d6): 6-162.11; LCMS: ret. time: 17.25 min.; purity: 100%; MS (m/e): 429.04 (MH$^+$).

7.3.465 N2-(4-Cyanomethyleneoxyphenyl)-5-fluoro-N4-(3-hydroxyphenyl)-2,4-pyrimidinediamine (R945070)

In a manner analogous to the preparation of N2,N4-bis(4-cyanomethyleneoxyphenyl)-5-fluoro-2,4-pyrimidinediamine, N2-(4-(aminocarbonylmethyleneoxyphenyl)-5-fluoro-N4-(3-hydroxyphenyl)-2,4-pyrimidinediamine (60 mg, 0.16 mmol), trifluoroacetic anhydride (0.11 mL, 0.8 mmol) and pyridine (0.13 mL, 1.6 mmol) gave N2-(4-cyanomethyleneoxyphenyl)-5-fluoro-N4-(3-hydroxyphenyl)-2,4-pyrimidinediamine (30 mg, 53%). $^1$H NMR (acetone-$d_6$): δ 5.04 (s, 2H), 6.60 (ddd, J=0.9, 2.4 and 8.1 Hz, 1H), 7.02 (d, J=9.3 Hz, 2H), 7.15 (t, J=8.1 Hz, 1H), 7.31 (ddd, J=1.2, 2.1 and 8.1 Hz, 1H), 7.38 (t, J=2.1 Hz, 1H), 7.78 (d, J=9.3 Hz, 2H), 7.98 (d, J=3.6 Hz, 1H), 8.34 (s, 1H, NH), 8.42 (s, 1H, NH); $^{19}$F NMR (282 MHz, acetone-$d_6$): 6-168.06; LCMS: ret. time: 18.17 min.; purity: 97.47%; MS (m/e): 352.05 (MH$^+$).

7.3.466 N4-(4-Cyanomethyleneoxyphenyl)-N2-(3,4-ethylenedioxyphenyl)-5-fluoro-2,4-pyrimidinediamine (R945172)

In a manner analogous to the preparation of N2,N4-bis(4-cyanomethyleneoxyphenyl)-5-fluoro-2,4-pyrimidinediamine, N4-(4-aminocarbonylmethyleneoxyphenyl)-N2-(3,4-ethylenedioxyphenyl)-5-fluoro-2,4-pyrimidinediamine, trifluoroacetic anhydride and pyridine in THF gave N4-(4-cyanomethyleneoxyphenyl)-N2-(3,4-ethylenedioxyphenyl)-5-fluoro-2,4-pyrimidinediamine. $^1$H NMR (CDCl$_3$): δ 4.27 (m, 4H), 4.82 (s, 2H), 6.70 (dd, J=2.4 and 8.4 Hz, 1H), 6.75 (d, J=2.4 Hz, 1H), 6.86 (d, J=8.4 Hz, 1H), 7.02 (d, J=9.0 Hz, 2H), 7.32 (d, J=9.0 Hz, 2H), 8.64 (d, J=1.8 Hz, 1H); $^{19}$F NMR (282 MHz, CDCl$_3$): 6-135.58; LCMS: ret. time: 19.92 min.; purity: 98.02%; MS (m/e): 393.98 (MH$^+$).

7.3.467 N2,N4-Bis[4-[2-methoxyimino(amino)ethyleneoxy]phenyl]-5-fluoro-2,4-pyrimidinediamine (R945096)

N2,N4-Bis(4-cyanomethyleneoxyphenyl)-5-fluoro-2,4-pyrimidinediamine (50 mg, 0.13 mmol), methoxyamine HCl salt (54 mg, 0.65 mmol) and sodium bicarbonate (54 mg, 0.65 mmol) were dissolved in methanol (5 mL). The reaction solution was stirred at 70° C. for 7 days. Then methanol was removed under reduced pressure. The residue was partitioned in EtOAc (60 ml) and water (60 mL). The ethyl acetate layer was washed with water (2×60 mL), dried, evaporated and purified by flash column chromatography (EtOAc/hexanes; 1:1; EtOAc) to give N2,N4-bis[4-[2-methoxyimino(amino)ethyleneoxy]phenyl]-5-fluoro-2,4-pyrimidinediamine (30 mg, 48%). $^1$H NMR (acetone-$d_6$): δ 3.70 (s, 3H), 3.71 (s, 3H), 4.44 (s, 2H), 4.49 (s, 2H), 5.43 (br, 2H), 5.47 (br, 2H), 6.93 (d, J=9.0 Hz, 2H), 7.00 (d, J=9.0 Hz, 2H), 7.62 (d, J=9.0 Hz, 2H), 7.71 (d, J=9.0 Hz, 2H), 7.93 (d, J=3.6 Hz, 1H), 8.26 (br, 1H, NH), 8.40 (br, 1H, NH); $^{19}$F NMR (282 MHz, acetone-$d_6$): 6-169.08; LCMS: ret. time: 14.41 min.; purity: 100%; MS (m/e): 484.97 (MH$^+$)

7.3.468 N2-(4-Carboxymethyleneoxyphenyl)-N4-(4-cyanomethyleneoxyphenyl)-5-fluoro-2,4-pyrimidinediamine (R945097)

In a manner analogous to the preparation of N2,N4-bis(3-carboxyphenyl)-5-fluoro-2,4-pyrimidinediamine, N4-(4-cyanomethyleneoxyphenyl)-5-fluoro-N2-(4-methoxycarbonylmethyleneoxyphenyl)-2,4-pyrimidinediamine (10 mg, 0.024 mmol) and LiOH (2 mg, 0.048 mmol) gave N2-(4-carboxymethyleneoxyphenyl)-N4-(4-cyanomethyleneoxyphenyl)-5-fluoro-2,4-pyrimidinediamine (5 mg, 52%) as a white solid. $^1$H NMR (CD$_3$OD): δ 4.60 (s, 2H), 4.99 (s, 2H), 6.88 (d, J=9.0 Hz, 2H), 7.02 (d, J=9.0 Hz, 2H), 7.39 (d, J=8.7 Hz, 2H), 7.65 (d, J=9.0 Hz, 2H), 7.84 (d, J=3.9 Hz, 1H); $^{19}$F NMR (282 MHz, CD$_3$OD): 6-168.81; LCMS: ret. time: 17.95 min.; purity: 86.04%; MS (m/e): 409.99 (MH$^+$).

7.3.469 5-Fluoro-N4-(3-hydroxyphenyl)-N2-[3-(5-methyl-1,2,4-oxadiazol-3-yl)methyleneoxyphenyl]-2,4-pyrimidinediamine (R945127)

A mixture of 3-nitrophenol (4 g, 29 mmol), bromoacetonitrile (2.5 mL, 36 mmol) and K$_2$CO$_3$ (8 g, 58 mmol) in acetone (20 mL) was stirred at room temperature overnight. The reaction mixture was diluted with water (80 mL) and acetone was removed under reduced pressure. The light-yellow precipitate was collected by filtration, washed with water and dried to give 1-cyanomethyleneoxy-3-nitrobenzene.

1-Cyanomethyleneoxy-3-nitrobenzene (2 g, 11 mmol) was dissolved in methanol (20 mL) and to the solution was added hydroxyamine HCl salt (1 g, 14 mmol) and triethylamine (3 mL, 22 mmol). The reaction mixture was refluxed for 2 h and the solvent was removed under reduced pressure. The residue was redissolved in THF (30 mL). To the solution was added acetyl chloride (4 mL, 56 mmol) and pyridine (9 mL, 0.11 mol). The reaction mixture was stirred at room temperature overnight, then added THF (10 mL), water (10 mL) and NaOH (3 g, 75 mmol). The reaction solution was refluxed overnight, diluted with water (80 mL). The aqueous solution was extracted with EtOAc (3×60 mL). After separation, the combined EtOAc layers was dried, evaporated to give 1-(5-methyl-1,2,4-oxadiazol-3-yl)methyleneoxy-3-nitrobenzene.

1-(5-Methyl-1,2,4-oxadiazol-3-yl)methyleneoxy-3-nitrobenzene was dissolved in THF (10 mL) and water (10 mL) and to it were added sodium bisulfite (1 g, 5.7 mmol) and sodium bicarbonate (1 g, 12 mmol). The resulting mixture was stirred at room temperature for 30 min, then diluted with EtOAc (80 mL) and water (80 mL). The aqueous solution was extracted with EtOAc (80 mL). The organic layers were combined, dried, evaporated to give 3-(5-methyl-1,2,4-oxadiazol-3-yl)methyleneoxyaniline (500 mg, 22% in four steps).

The reaction of 2-chloro-5-fluoro-N4-(3-hydroxyphenyl)-4-pyrimidineamine (40 mg, 0.17 mmol) and 3-(5-methyl-1,2,4-oxadiazol-3-yl)methyleneoxyaniline (102 mg, 0.50 mmol) gave 5-fluoro-N4-(3-hydroxyphenyl)-N2-[3-(5-methyl-1,2,4-oxadiazol-3-yl)methyleneoxyphenyl]-2,4-pyrimidinediamine (35 mg, 51%). $^1$H NMR (CDCl$_3$): δ 2.61 (s, 3H), 5.09 (s, 2H), 6.58-6.62 (m, 2H), 6.76 (dt, J=1.2, 8.1 Hz, 1H), 6.84 (dt, J=1.2 and 7.8 Hz, 1H), 6.92 (d, J=3.0 Hz, 1H), 7.139 (t, J=8.1 Hz, 1H), 7.145 (t, J=8.1 Hz, 1H), 7.25 (m, 1H), 7.54 (dt, J=2.1, 8.7 Hz, 2H), 7.88 (d, J=3.3 Hz, 1H); $^{19}$F NMR (282 MHz, CDCl$_3$): −166.52; LCMS: ret. time: 19.33 min.; purity: 84.80%; MS (m/e): 409.35 (MH$^+$).

7.3.470 5-Fluoro-N2-(3-hydroxyphenyl)-N4-[3-(3-methyl-1,2,4-oxadiazol-5-yl)methyleneoxyphenyl]-2,4-pyrimidinediamine (R945130)

1-Methoxycarbonylmethyleneoxy-3-nitrobenzene (2 g, 9.5 mmol) was dissolved in THF (10 mL) and water (10 mL). To the solution was added NaOH (1 g, 25 mmol). The reaction mixture was stirred at room temperature overnight. The solution was diluted with water (60 mL) and EtOAc (60 mL). After extraction, the aqueous layer was separated, acidified with 1N HCl to pH 3. The formed white precipitate was collected by filtration, washed with water, dried to give 1-carboxymethyleneoxy-3-nitrobenzene.

Acetonitrile (2.25 mL, 43 mmol) was dissolved in methanol (10 mL) and to the solution was added hydroxyamine HCl salt (2 g, 29 mmol) and triethylamine (8 mL, 57 mmol). The reaction mixture was refluxed for 2 days and the solvent was removed under reduced pressure to give acetamide oxime as white solid.

Acetamide oxime (0.75 g, 10 mmol), 1-carboxymethyleneoxy-3-nitrobenzene (1 g, 5 mmol), EDC HCl (1.45 g, 7.5 mmol) and diisopropylethylamine (2.65 mL, 15 mmol) were dissolved in THF (15 mL) and refluxed for 4 h. The reaction mixture was diluted with EtOAc (60 mL) and water (60 mL). The EtOAc layer was washed with sodium bicarbonate aqueous solution (2×60 mL), 1N HCl (2×60 mL) and water (60 mL). After separation, the EtOAc layer was dried, evaporated to give 1-(3-methyl-1,2,4-oxadiazol-5-yl)methyleneoxy-3-nitrobenzene.

Sodium bisulfite (1.5 g, 8.6 mmol), sodium bicarbonate (1.5 g, 18 mmol) and 1-(3-methyl-1,2,4-oxadiazol-5-yl)methyleneoxy-3-nitrobenzene (1 g, 4 mmol) were dissolved in THF (15 mL) and water (15 mL). It was stirred at room temperature for 20 min, diluted with EtOAc (60 mL) and water (60 mL). The aqueous solution was extracted with EtOAc (2×60 mL). The organic layers were combined, dried, evaporated to give 3-(3-methyl-1,2,4-oxadiazol-5-yl)methyleneoxyaniline.

In a manner analogous to the preparation of N4-(3,4-ethylenedioxyphenyl)-5-fluoro-N2-(3-hydroxyphenyl)-2,4-pyrimidinediamine, the reaction of 3-(3-methyl-1,2,4-oxadiazol-5-yl)methyleneoxyaniline (369 mg, 1.8 mmol) and 2,4-dichloro-5-fluoropyrimidine (150 mg, 0.9 mmol) gave 2-chloro-5-fluoro-N4-[3-(3-methyl-1,2,4-oxadiazol-5-yl)methyleneoxyphenyl]-4-pyrimidineamine. The reaction of 2-chloro-5-fluoro-N4-[3-(3-methyl-1,2,4-oxadiazol-5-yl)methyleneoxyphenyl]-4-pyrimidineamine (20 mg, 0.06 mmol) and 3-hydroxyaniline (20 mg, 0.18 mmol) gave 5-fluoro-N2-(3-hydroxyphenyl)-N4-[3-(3-methyl-1,2,4-oxadiazol-5-yl)methyleneoxyphenyl]-2,4-pyrimidinediamine (10 mg, 42%). $^1$H NMR (CDCl$_3$): δ 2.42 (s, 3H), 5.28 (s, 2H), 6.49 (ddd, J=0.9, 2.7 and 8.4 Hz, 1H), 6.73 (ddd, J=0.9, 2.7 and 8.4 Hz, 1H), 6.81-6.84 (m, 2H), 6.88 (ddd, J=0.6, 2.1 and 8.1 Hz, 1H), 7.13 (t, J=8.1 Hz, 1H), 7.26 (t, J=8.1 Hz, 1H), 7.40 (br, 1H), 7.49 (t, J=2.1 Hz, 1H), 7.94-7.97 (m, 2H); $^{19}$F NMR (282 MHz, CDCl$_3$): 6-167.11; LCMS: ret. time: 18.80 min.; purity: 92.01%; MS (m/e): 409.01 (MH$^+$).

7.3.471 5-Fluoro-N4-(2-methoxycarbonylbenzofuran-5-yl)-N2-[3-(5-methyl-1,2,4-oxadiazol-3-yl)methyleneoxyphenyl]-2,4-pyrimidinediamine (R945131)

In a manner analogous to the preparation of N4-(3,4-ethylenedioxyphenyl)-5-fluoro-N2-(3-hydroxyphenyl)-2,4-pyrimidinediamine, the reaction of N4-(2-carboxybenzofuran-5-yl)-2-chloro-5-fluoro-4-pyrimidineamine (50 mg, 0.16 mmol) and 3-(5-methyl-1,2,4-oxadiazol-3-yl)methyleneoxyaniline (100 mg, 0.49 mmol) gave N4-(2-carboxybenzofuran-5-yl)-5-fluoro-N2-[3-(5-methyl-1,2,4-oxadiazol-3-yl)methyleneoxyphenyl]-2,4-pyrimidinediamine.

In a manner analogous to the preparation of N2,N4-bis[4-(2-methyl-1,2,3,4-tetrazol-5-yl)methyleneoxyphenyl]-5-fluoro-2,4-pyrimidinediamine, the reaction of N4-(2-carboxybenzofuran-5-yl)-5-fluoro-N2-[3-(5-methyl-1,2,4-oxadiazol-3-yl)methyleneoxyphenyl]-2,4-pyrimidinediamine, potassium carbonate (100 mg, 0.7 mmol) and iodomethane (0.03 mL, 0.5 mmol) gave 5-fluoro-N4-(2-methoxycarbonylbenzofuran-5-yl)-N2-[3-(5-methyl-1,2,4-oxadiazol-3-yl)methyleneoxyphenyl]-2,4-pyrimidinediamine (40 mg, 50%). $^1$H NMR (acetone-d$_6$): δ 2.63 (s, 3H), 3.94 (s, 3H), 5.04 (s, 2H), 6.65 (ddd, J=0.9, 2.4 and 7.8 Hz, 1H), 7.16 (t, J=7.8 Hz, 1H), 7.24 (ddd, J=1.2, 1.8 and 8.1 Hz, 1H), 7.58 (d, J=1.2 Hz, 1H), 7.64 (d, J=9.3 Hz, 1H), 7.67 (t, J=2.1 Hz, 1H), 7.88 (dd, J=2.1 and 9.0 Hz, 1H), 8.04 (d, J=3.6 Hz, 1H), 8.26 (d, J=1.8 Hz, 1H), 8.47 (br, 1H, NH), 8.71 (br, 1H, NH); $^{19}$F NMR (282 MHz, acetone-d$_6$): 6-167.73; LCMS: ret. time: 22.55 min.; purity: 85.43%; MS (m/e): 490.97 (MH$^+$).

7.3.472 N4-(2-Carboxybenzofuran-5-yl)-5-fluoro-N2-[3-(5-methyl-1,2,4-oxadiazol-3-yl)methyleneoxyphenyl]-2,4-pyrimidinediamine (R945134)

In a manner analogous to the preparation of N2,N4-bis(3-carboxyphenyl)-5-fluoro-2,4-pyrimidinediamine, the reaction of 5-fluoro-N4-(2-methoxycarbonylbenzofuran-5-yl)-N2-[3-(5-methyl-1,2,4-oxadiazol-3-yl)methyleneoxyphenyl]-2,4-pyrimidinediamine (20 mg, 0.04 mmol) and NaOH (10 mg, 0.25 mmol) gave N4-(2-carboxybenzofuran-5-yl)-5-fluoro-N2-[3-(5-methyl-1,2,4-oxadiazol-3-yl)methyleneoxyphenyl]-2,4-pyrimidinediamine. $^1$H NMR (acetone-d$_6$): δ 2.63 (s, 3H), 5.04 (s, 2H), 6.64 (d, J=8.1 Hz, 1H), 7.17 (t, J=8.1 Hz, 1H), 7.26 (d, J=7.8 Hz, 1H), 7.56 (s, 1H), 7.62 (d, J=9.3 Hz, 1H), 7.67 (t, 1H), 7.86 (dd, J=1.8 and 9.0 Hz, 1H), 8.04 (d, J=3.3 Hz, 1H), 8.26 (d, 1H), 8.48 (br, 1H, NH), 8.71 (br, 1H, NH); LCMS: ret. time: 18.00 min.; purity: 75.13%; MS (m/e): 476.70 (MH$^+$).

7.3.473 N4-(2-Aminocarbonylbenzofuran-5-yl)-5-fluoro-N2-[3-(5-methyl-1,2,4-oxadiazol-3-yl)methyleneoxyphenyl]-2,4-pyrimidinediamine (R945135)

A mixture of 5-fluoro-N4-(2-methoxycarbonylbenzofuran-5-yl)-N2-[3-(5-methyl-1,2,4-oxadiazol-3-yl)methyleneoxyphenyl]-2,4-pyrimidinediamine (20 mg, 0.04 mmol) and concentrated NH$_4$OH (5 mL) in methanol (5 mL) was stirred at room temperature overnight. The solvent was evaporated to give N4-[2-(aminocarbonyl)benzofuran-5-yl]-5-fluoro-N2-[3-(5-methyl-1,2,4-oxadiazol-3-yl)methyleneoxyphenyl]-2,4-pyrimidinediamine. $^1$H NMR (acetone-d$_6$): δ 2.61 (s, 3H), 5.04 (s, 2H), 6.64 (ddd, J=0.9, 2.4 and 8.1 Hz, 1H), 7.16 (t, J=8.1 Hz, 1H), 7.27 (ddd, J=0.9, 1.8 and 8.4 Hz, 1H), 7.44 (d, J=0.6 Hz, 1H), 7.55 (dd, J=0.6 and 8.1 Hz, 1H), 7.64 (t, J=2.4 Hz, 1H), 7.79 (dd, J=2.4 and 9.0 Hz, 1H), 8.03 (d, J=3.6 Hz, 1H), 8.24 (d, J=2.4 Hz, 1H), 8.48 (br, 1H, NH), 8.68 (br, 1H, NH); $^{19}$F NMR (282 MHz, acetone-d$_6$): 6-167.80; LCMS: ret. time: 17.43 min.; purity: 100%; MS (m/e): 475.62 (MH$^+$)

7.3.474 5-Fluoro-N4-(3-hydroxyphenyl)-N2-[4-(2-methoxyimino(amino)ethyleneoxy)phenyl]-2,4-pyrimidinediamine (R945167)

In a manner analogous to the preparation of N2,N4-bis[4-(2-methoxyimino(amino)ethyleneoxy)phenyl]-5-fluoro-2,4-pyrimidinediamine, the reaction of N2-(4-cyanomethyleneoxyphenyl)-5-fluoro-N4-(3-hydroxyphenyl)-2,4-pyrimidinediamine (50 mg, 0.14 mmol), methoxyamine HCl salt (0.71 mmol) and triethylamine (0.2 mL, 1.4 mmol) gave 5-fluoro-N4-(3-hydroxyphenyl)-N2-[4-(2-methoxyimino(amino)ethyleneoxy)phenyl]-2,4-pyrimidinediamine (40 mg, 70%). $^1$H NMR (CDCl$_3$): δ 3.82 (s, 3H), 4.50 (s, 2H), 4.87 (br, 2H, NH), 6.60 (ddd, J=0.9, 2.4 and 8.1 Hz, 1H), 6.79-6.84 (m, 2H), 6.86 (d, J=8.7 Hz, 2H), 7.00 (s, 1H), 7.14 (t, J=8.1 Hz, 1H), 7.34 (d, J=9.0 Hz, 2H), 7.47 (t, J=2.1 Hz, 1H), 7.87 (d, J=3.3 Hz, 1H); $^{19}$F NMR (282 MHz, CDCl$_3$): δ-167.67; LCMS: ret. time: 13.69 min.; purity: 92.51%; MS (m/e): 399.01 (MH$^+$).

7.3.475 N2-(3,4-Ethylenedioxyphenyl)-5-fluoro-N4-[4-methoxyimino(amino)ethyleneoxyphenyl]-2,4-pyrimidinediamine (R945175)

In a manner analogous to the preparation of N2,N4-bis[4-(2-methoxyimino(amino)ethyleneoxyphenyl)]-5-fluoro-2,4-pyrimidinediamine, N4-(4-cyanomethyleneoxyphenyl)-N2-(3,4-ethylenedioxyphenyl)-5-fluoro-2,4-pyrimidinediamine, methoxyamine hydrochloride salt and triethylamine gave N2-(3,4-ethylenedioxyphenyl)-5-fluoro-N4-[4-methoxyimino(amino)ethyleneoxyphenyl]-2,4-pyrimidinediamine. $^1$H NMR (acetone-d$_6$): δ 3.70 (s, 3H), 4.21-4.28 (m, 4H), 4.48 (s, 2H), 5.46 (br, 2H), 6.71 (d, J=8.7 Hz, 1H), 6.99 (d, J=9.0 Hz, 2H), 7.06 (dd, J=2.4 and 8.7 Hz, 1H), 7.42 (d, J=2.4 Hz, 1H), 7.72 (d, J=9.3 Hz, 2H), 7.93 (d, J=3.3 Hz, 1H), 8.22 (br, 1H, NH), 8.40 (br, 1H, NH); $^{19}$F NMR (282 MHz, acetone-d$_6$): δ-169.05; LCMS: ret. time: 16.49 min.; purity: 96.47%; MS (m/e): 440.96 (MH$^+$).

7.3.476 N4-(3,4-Ethylenedioxyphenyl)-5-fluoro-N2-[3-(N-methylamino)carbonylmethyleneoxyphenyl]-2,4-pyrimidinediamine (R926495)

A mixture of N2-(3-ethoxy/or methoxycarbonylmethyleneoxyphenyl)-N4-(3,4-ethylenedioxyphenyl)-5-fluoro-2,4-pyrimidinediamine (19.8 g, 45 mmol), methylamine hydrochloride (30.63 g, 450 mmol) and diisopropylethylamine (78.07 mL, 450 mmol) in MeOH (450 mL) was stirred in a pressure bottle at 100° C. for 8 h (followed by TLC). The reaction was cooled to room temperature, diluted with H$_2$O (6 lit), the solid obtained was filtered, washed with H$_2$O and dried to obtain 18 g of N4-(3,4-ethylenedioxyphenyl)-5-fluoro-N2-[3-(N-methylaminocarbonylmethyleneoxyphenyl)]-2,4-pyrimidinediamine. Alternatively, the reaction of equimolar amount of 2-chloro-N4-(3,4-ethylenedioxyphenyl)-5-fluoro-4-aminopyridine with 3-(N-methylamino)carbonylmethyleneoxyaniline in MeOH in a pressure tube at 110° C. for 24 h and or in EtOH using microwave at 175° C. for 10-20 min followed by aqueous work up gave N4-(3,4-ethylenedioxyphenyl)-5-fluoro-N2-[3-(N-methylamino)carbonylmethyleneoxyphenyl]-2,4-pyrimidinediamine. $^1$H NMR (CD$_3$OD): δ 7.90 (s, 1H), 7.89 (bs, 1H), 7.38 (d, 1H, J=2.4 Hz), 7.28 (d, 1H, J=2.4 Hz), 7.17-7.09 (m, 2H), 6.79 (d, 1H, J=9 Hz), 6.57 (m, 1H), 4.38 (s, 2H), 4.24 (s, 4H), 2.81 (s, 3H); LCMS: ret. time: 18.20 min.; purity: 98%; MS (m/e): 426 (MH$^+$).

7.3.477 N4-(1,4-Benzoxazin-6-yl)-5-fluoro-N2-[3-(N-methylamino)carbonylmethyleneoxyphenyl]-2,4-pyrimidinediamine (R921219)

In like manner to N4-(3,4-ethylendioxyphenyl)-5-fluoro-N2-[3-(N-methylamino)carbonylmethyleneoxyphenyl]-2,4-pyrimidinediamine, N4-(1,4-benzoxazin-6-yl)-N2-(3-ethoxyocarbonylmethyleneoxyphenyl)-5-fluoro-pyrimidinediamine and methylamine hydrochloride were reacted to yield N4-(1,4-benzoxazin-6-yl)-5-fluoro-N2-[3-(N-methylamino)carbonylmethyleneoxyphenyl]-2,4-pyrimidinediamine. $^1$H NMR (CD$_3$OD): δ 7.8 (d, 1H), 7.4 (m, 1H), 7.05 (m, 2H), 7.0 (s, 1H), 6.8 (dd, 1H), 6.66 (d, 1H), 6.56 (dd, 1H), 4.35 (s, 2H), 4.18 (m, 2H), 3.25 (m, 2H), 2.8 (s, 3H); LCMS: ret time: 18.0 min. purity: 97%; MS (m/e): 425 (MH$^+$).

7.3.478 N4-(3,4-Ethylendioxyphenyl)-5-fluoro-N2-[4-(N-2-hydroxyethylamino)carbonylmethyleneoxyphenyl]-2,4-pyrimidinediamine (R909239)

In like manner to N4-(3,4-ethylendioxyphenyl)-5-fluoro-N2-[3-(N-methylamino)carbonylmethyleneoxyphenyl]-2,4-pyrimidinediamine, N4-(3,4-ethylendioxyphenyl)-5-fluoro-N2-(4-ethoxycarbonylmethyleneoxyphenyl)-2,4-pyrimidinediamine and 2-hydroxyethylamine were reacted to yield N4-(3,4-ethylendioxyphenyl)-5-fluoro-N2-[4-(N-2-hydroxyethylamino) carbonylmethyleneoxyphenyl]-2,4-pyrimidinediamine. $^1$H NMR (D$_2$O): δ 8.02 (d, 1H, J=4 Hz), 7.40 (m, 2H), 7.28 (m, 1H), 7.05 (m, 5H), 4.83 (s, 2H), 4.5 (m, 2H), 4.23 (m, 2H), 4.03 (m, 2H), 3.87 (m, 2H); LCMS: ret. time: 17.17 min.; purity: 94%; MS (m/e): 456 (MH$^+$).

7.3.479 N4-(3,4-Ethylendioxyphenyl)-5-fluoro-[4-(N-methylamino)carbonylmethyleneoxyphenyl]-2,4-pyrimidinediamine (R909240)

In like manner to N4-(3,4-ethylendioxyphenyl)-5-fluoro-N2-[3-(N-methylamino)carbonylmethyleneoxyphenyl]-2,4-pyrimidinediamine, 2-chloro-N4-(3,4-ethylenedioxyphenyl)-5-fluoro-4-pyrimideaneamine and 4-(N-methylamino) carbonylmethyleneoxyaniline were reacted to yield N4-(3,4-ethylendioxyphenyl)-5-fluoro-[4-(N-methylamino) carbonylmethyleneoxyphenyl]-2,4-pyrimidinediamine. $^1$H NMR (D$_2$O): δ 8.02 (d, 1H, J=4 Hz), 7.40 (m, 2H), 7.28 (m, 1H), 7.05 (m, 5H), 4.83 (s, 2H), 4.5 (m, 2H), 4.23 (m, 2H), 3.87 (s, 3H); LCMS: ret. time: 18.43 min.; purity: 94%; MS (m/e): 426 (MH$^+$).

7.3.480 N4-(1,4-Benzoxazin-6-yl)-5-fluoro-N2-[3-(N-2-hydroxypropylamino)carbonylmethyleneoxyphenyl]-2,4-pyrimidinediamine (R909251)

In like manner to N4-(3,4-ethylendioxyphenyl)-5-fluoro-N2-[3-(N-methylamino)carbonylmethyleneoxyphenyl]-2,4-pyrimidinediamine, N4-(1,4-benzoxazin-6-yl)-N2-(3-ethoxyocarbonylmethyleneoxyphenyl)-5-fluoro-2,4-pyrimidinediamine and 2-hydroxypropylamine were reacted to yield N4-(1,4-benzoxazin-6-yl)-5-fluoro-N2-[3-(N-2-hydroxypropylamino)carbonylmethyleneoxyphenyl]-2,4-pyrimidinediamine. $^1$H NMR (DMSO-d6): δ □□□ (d, 1H, J=4 Hz), 7.25 (m, 2H), 7.04 (m, 1H), 6.82 (m, 2H), 6.58 (m, 1H), 6.45 (m, 1H) 4.36 (s, 2H), 4.02 (m, 2H), 3.75 (m, 1H), 3.31 (m, 2H), 3.00 (m, 2H), 1.00 (m, 3H); LCMS: ret. time: 17.33 min.; purity: 97%; MS(m/e): 469 (MH$^+$).

7.3.481 N4-(1,4-Benzoxazin-6-yl)-5-fluoro-N2-[3-(N-3-hydroxypropylamino)carbonylmethyleneoxyphenyl]-2,4-pyrimidinediamine (R909252)

In like manner to N4-(3,4-ethylendioxyphenyl)-5-fluoro-N2-[3-(N-methylamino)carbonylmethyleneoxyphenyl]-2,4-pyrimidinediamine, N4-(1,4-benzoxazin-6-yl)-N2-[3-ethoxyocarbonylmethyleneoxyphenyl]-5-fluoro-2,4-pyrimidinediamine and 3-hydroxypropylamine were reacted to yield N4-(1,4-benzoxazin-6-yl)-5-fluoro-N2-[3-(N-3-hydroxypropylamino)carbonylmethyleneoxyphenyl]-2,4-pyrimidinediamine. $^1$H NMR (DMSO-d6): δ □□□ (d, 1H, J=4 Hz), 7.39 (m, 2H), 7.04 (m, 1H), 6.87 (m, 2H), 6.55 (m, 1H), 6.41 (m, 1H), 4.29 (s, 2H), 4.02 (m, 2H), 3.35 (m, 2H), 3.31 (m, 2H), 3.09 (m, 2H), 1.50 (m, 3H); LCMS: ret. time: 17.11 min.; purity: 94%; MS (m/e): 469 (MH+).

7.3.482 N4-(1,4-Benzoxazin-6-yl)-N2-[3-(N-isopropylamino)carbonylmethyleneoxyphenyl]-5-fluoro-2,4-pyrimidinediamine (R909254)

In like manner to N4-(3,4-ethylendioxyphenyl)-5-fluoro-N2-[3-(N-methylamino)carbonylmethyleneoxyphenyl]-2,4-pyrimidinediamine, N4-(1,4-benzoxazin-6-yl)]-N2-(3-ethoxyocarbonylmethyleneoxyphenyl)-5-fluoro-pyrimidinediamine and isopropylamine were reacted to yield N4-(1,4-benzoxazin-6-yl)-5-fluoro-N2-[3-(N-isopropylamino)carbonylmethyleneoxyphenyl]-2,4-pyrimidinediamine. $^1$H NMR (DMSO-d6): δ☐☐☐ (d, 1H, J=4 Hz), 7.25 (m, 1H), 7.14 (m, 1H), 7.02 (m, 1H), 6.85 (m, 3H), 6.63 (m, 1H), 4.39 (s, 2H), 4.12 (m, 2H), 4.05 (m, 1H), 3.38 (m, 2H), 1.20 (m, 6H); LCMS: ret. time: 20.83 min.; purity: 96%; MS (m/e): 453 (MH+).

7.3.483 5-Fluoro-N4-(4-isopropoxyphenyl)-N2-[2-(N-pyrrolidino)carbonylbenzofuran-5-yl]-2,4-pyrimidinediamine (R926703)

In a manner similar to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N2-(2-methoxycarbonylbenzofuran-5-yl)-N4-(4-isopropoxyphenyl)-2,4-pyrimidinediamine and pyrrolidine were reacted to yield 5-fluoro-N4-(4-isopropoxyphenyl)-N2-[2-(N-pyrrolidino)carbonylbenzofuran-5-yl]-2,4-pyrimidinediamine. $^1$H NMR (CDCl$_3$): δ 7.83 (s, 1H), 7.79 (d, 1H, J=5.4 Hz), 7.42 (bs, 1H), 7.39 (d, 2H, J=8.7 Hz), 7.28-7.24 (m, 2H), 6.81 (d, 2H, J=8.7 Hz), 4.52 (2q, 1H, J=6.0 Hz), 3.92 (t, 2H, J=6.9 Hz), 3.67 (t, 2H, J=6.9 Hz), 2.05-1.90 (m, 4H), 1.32 (d, 6H, J=6.6 Hz); $^{19}$F NMR (CDCl$_3$): −24000; LCMS: ret. time: 23.49 min.; purity: 97%; MS (m/e): 476 (MH+).

7.3.484 N4-(3,4-Ethylenedioxyphenyl)-5-fluoro-N2-[4-(N-methylamino)carbonylmethyleneoxyphenyl]-2,4-pyrimidinediamine (R926708)

In a manner similar to the preparation of N4-(3,4-ethylendioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-(4-methoxycarbonylmethyleneoxyphenyl)-2,4-pyrimidinediamine and methylamine hydrochloride were reacted to yield N4-(3,4-ethylenedioxyphenyl)-5-fluoro-N2-[4-(N-methylamino)carbonylmethyleneoxyphenyl]-2,4-pyrimidinediamine. $^1$H NMR (DMSO-d6): δ 10.10 (bs, 1H), 9.88 (bs, 1H), 8.15 (t, 1H, J=4.5 Hz), 8.05 (bs, 1H), 7.40 (d, 2H, J=8.7Hz), 7.23 (d, 1H, J=2.1 Hz), 7.11 (dd, 1H, J=2.4 and 8.7 Hz), 6.89 (d, 2H, J=8.7 Hz), 6.81 (d, 1H, J=8.7 Hz), 4.42 (s, 2H), 4.23 (s, 4H), 2.64 (d, 3H, J=4.5 Hz); LCMS: ret. time: 17.60 min.; purity: 96%; MS (m/e): 426 (MH+).

7.3.485 N4-(4-tert-Butylphenyl)-5-fluoro-N2-[2-(N-methylamino)carbonylbenzofuran-5-yl]-2,4-pyrimidinediamine (R926494)

In like manner to the preparation of N4-(ethylenedioxyphenyl)-5-fluoro-N2-[3-(N-methylamino)carbonylmethyleneoxyphenyl]-2,4-pyrimidinediamine, the reaction of N4-(4-tert-butylphenyl)-5-fluoro-N2-(2-methoxycarbonyl benzofuran-5-yl)-2,4-pyrimidinediamine with methylamine hydrochloride gave N4-(4-tert-butylphenyl)-5-fluoro-N2-[2-(N-methylamino)carbonylbenzofuran-5-yl]-2,4-pyrimidinediamine. $^1$H NMR (CD$_3$OD): δ 8.04 (d, 1H, J=2.4 Hz), 7.88 (d, 1H, 4.2 Hz), 7.58-7.30 (m, 7H), 2.94 (s, 3H), 1.33 (s, 9H); LCMS: ret. time: 22.86 min.; purity: 94%; MS (m/e): 434 (MH+).

7.3.486 N4-(4-tert-Butylphenyl)-5-fluoro-N2-[4-(N-methylamino)carbonylmethyleneoxyphenyl]-2,4-pyrimidinediamine (R926712)

In a manner similar to the preparation of N4-(3,4-ethylendioxyphenyl)-5-fluoro-N2-[3-(N-methylamino)carbonylmethyleneoxyphenyl]-2,4-pyrimidinediamine, N4-[4-(tert-butyl)phenyl]-5-fluoro-N2-(4-methoxycarbonylmethyleneoxyphenyl)-2,4-pyrimidinediamine and methylamine hydrochloride were reacted to yield N4-(4-tert-butylphenyl)-5-fluoro-N2-[4-(N-methylamino)carbonylmethyleneoxyphenyl]-2,4-pyrimidinediamine. $^1$H NMR (CD$_3$OD): δ 7.92 (d, 1H, J=5.4 Hz), 7.53 (d, 2H, J=8.7 Hz), 7.40 (d, 2H, J=8.7 Hz), 7.34 (d, 2H, J=8.7 Hz), 7.03 (d, 2H, J=8.7 Hz), 4.52 (s, 2H), 2.82 (s, 3H), 1.35 (s, 9H); $^{19}$F NMR (CD$_3$OD): −46174; LCMS: ret. time: 23.34 min.; purity: 94%; MS (m/e): 424 (MH+).

7.3.487 N4-(3-tert-Buthylpheny)-5-fluoro-N2-[3-(N-2-hydroxyethylamino)carbonylmethyleneoxyphenyl]-2,4-pyrimidinediamine R940295

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3-tert-butylphenyl)-5-fluoro-N2-(3-methoxycarbonylmethyleneoxyphenyl)-2,4-pyrimidinediamine and 2-hydroxyethylamine were reacted to give N4-(3-tert-butylpheny)-5-fluoro-N2-[3-(N-2-hydroxyethylamino)carbonylmethyleneoxyphenyl]-2,4-pyrimidinediamine. LCMS: ret. time: 21.34 min.; purity: 97%; MS (m/e): 453 (M+); 454 (MH+); $^1$H NMR (CDCl$_3$): δ 10.34 (1H, s), 7.76 (1H, m), 7.52 (1H, m), 7.4-7.1 (5H, m), 6.98 (1H, m), 6.7 (1H, m), 4.36 (2H, s), 3.77 (2H, t, J 5 Hz), 3.51 (2H, m), 1.27 (9H, s).

7.3.488 N2,N4-Bis[4-(N-pyrrolidino)carbonylmethyleneoxyphenyl]-5-ethoxycarbonyl-2,4-pyrimidinediamine (R926562)

In like manner of the preparation of N4-(3,4-ethylenedioxyphenyl)-5-fluoro-N2-[3-(N-methylamino)carbonylmethyleneoxyphenyl]-2,4-pyrimidinediamine, the reaction of N2,N4-bis(4-ethoxycarbonylmethyleneoxyphenyl)-5-ethoxycarbonyl-2,4-pyrimidinediamine with pyrrolidine gave N2,N4-bis[4-(N-pyrrolidino)carbonylmethyleneoxyphenyl]-5-ethoxycarbonyl-2,4-pyrimidinediamine. $^1$H NMR (DMSO-d6): δ 10.17 (s, 1H), 8.73 (bs, 1H), 7.50(bd, 2H, J=9.0 Hz), 7.43 (d, 2H, J=2.4 and 6.9 Hz), 6.91 (m, 4H), 4.64 (s, 2H), 4.62 (s, 2H), 4.34 (q, 2H, J=7.2 Hz), 3.53 (m, 8H), 1.95 (m, 4H), 1.86 (m, 4H), 1.38 (t, 3H, J=6.9 Hz); LCMS: ret. time: 22.54 min.; purity: 100%; MS (m/e): 590 (MH+).

7.3.489 N2,N4-Bis(4-N-pyrrolidinocarbonylmethyleneoxyphenyl)-5-fluoro-2,4-pyrimidinediamine (R926563)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of N2,N4-bis(4-methoxycarbonylmethyleneoxyphenyl)-5-fluoro-2,4-pyrimidinediamine with pyrrolidine gave N2,N4-bis[4-(N-pyrrolidino)carbonylmethyleneoxyphenyl]-5-fluoro-2,4-pyrimidinediamine. $^1$H NMR (CDCl$_3$): δ 7.90 (s, 1H), 7.50 (bd, 2H, J=7.8 Hz), 7.41 (bd, 2H, J=7.2 Hz), 6.93 (m, 4H), 6.73 (s, 1H), 6.64 (s, 1H), 4.65 (s, 1H), 4.65 (s, 1H), 3.54 (m, 8H), 1.96 (m, 4H), 1.87 (m, 4H).

7.3.490 N4-(3-tert-Butylpheny)-N2-[3-(N-1,3-dihydroxypropyl-2-amino)carbonylmethyleneoxyphenyl]-5-fluoro-2,4-pyrimidinediamine (R940296)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3-tert-butylphenyl)-5-fluoro-N2-(3-methoxycarbonylmethyleneoxyphenyl]-2,4-pyrimidinediamine and 2-amino-1,3-propanediol were reacted to give N4-(3-tert-butylpheny)-N2-[-3-(1,3-dihydroxypropyl-2-amino)carbonylmethyleneoxyphenyl]-5-fluoro-2,4-pyrimidinediamine. LCMS: ret. time: 20.26 min.; purity: 97.67%; MS (m/e): 484 (M$^+$); 485 (MH$^+$); 1H NMR (DMSO-d6): δ 9.75 (1H, s), 9.57 (1H, s), 8.25 (1H, m), 7.92 (1H, m), 7.62 (2H, m), 7.37 (3H, m), 7.23 (1H, m), 6.66 (1H, m), 4.46 (2H, s), 3.87 (1H, m), 3.55 (4H, m), 1.36 (9H, s).

7.3.491 N2-[3-(N-2,3-Dihydroxypropylamino)carbonylmethyleneoxyphenyl]-5-fluoro-N4-(3-isopropylphenyl)-2,4-pyrimidinediamine R940290

In like manner to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N4-(3-isopropylphenyl)-N2-(3-methoxycarbonylmethyleneoxyphenyl)-2,4-pyrimidinediamine and 3-amino-1,2-propanediol were reacted to give N2-[3-(N-2,3-dihydroxypropylamino)carbonylmethyleneoxyphenyl)-5-fluoro-N4-(3-isopropylphenyl)-2,4-pyrimidinediamine. LCMS: ret. time: 20.04 min.; purity: 98%; MS (m/e): 470 (MH$^+$); $^1$H NMR (DMSO-d6): δ 9.54 (1H, s), 9.41 (1H, s), 8.22 (1H, m), 7.95 (1H, m), 7.85 (1H, d, J=10 Hz), 7.58 (1H, s), 7.43-7.32 (3H, m), 7.25 (1H, t, J=7.75 Hz), 7.06 (1H, d, J=7.75 Hz), 6.64 (1H, d, J=10 Hz), 4.47 (2H, s), 3.38 (4H, m), 3.16 (1H, m), 2.96 (1H, m), 1.28 (6H, d, J=6.9 Hz).

7.3.492 5-Fluoro-N4-(3-isopropylphenyl)-N2-[3-(N-methylamino)carbonylmethyleneoxyphenyl]-2,4-pyrimidinediamine R940288

In like manner to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N4-(3-isopropylphenyl)-N2-(3-methoxycarbonylmethyleneoxyphenyl)-2,4-pyrimidinediamine and methylamine hydrochloride were reacted to give 5-fluoro-N4-(3-isopropylphenyl)-N2-[3-(N-methylamino)carbonylmethyleneoxy)phenyl]-2,4-pyrimidinediamine. LCMS: ret. time: 23.43 min.; purity: 99%; MS (m/e): 409 (M$^+$), 411 (MH$^+$); $^1$H NMR (DMSO-d6): δ 9.90 (1H, s), 9.74 (1H, s), 8.28 (1H, d, J=4.8 Hz), 8.06 (1H, m), 7.78 (1H, d, J=7.2 Hz), 7.58 (1H, s), 7.4-7.3 (3H, m), 7.24 (1H, t, J=8.4 Hz), 7.00 (1H, d, J=7.25 Hz), 6.70 (1H, d, J=7.25 Hz), 4.44 (2H, s), 2.93 (1H, sept, J=6.9 Hz), 2.74 (3H, d, J=4.8 Hz), 1.27 (6H, d, J=6.9 Hz).

7.3.493 5-Fluoro-N4-(3-hydroxyphenyl)-N2-[2-(N-dimethylamino)carbonylbenzofuran-5-yl]-2,4-pyrimidinediamine (R926718)

In a manner similar to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N4-(3-hydroxyphenyl)-N2-(2-methoxycarbonylbenzofuran-5-yl)-2,4-pyrimidinediamine and dimethylamine were reacted to yield 5-fluoro-N4-(3-hydroxyphenyl)-N2-[2-(N-dimethylamino)carbonylbenzofuran-5-yl)-2,4-pyrimidinediamine. $^1$H NMR (CDCl$_3$): δ 8.06 (d, 1H, J=2.1 Hz), 7.91 (d, 1H, J=3.6 Hz), 7.57 (t, 1H, J=2.4 Hz), 7.37 (d, 1H, J=9.0 Hz), 7.28 (s, 1H), 7.19 (t, 1H, J=7.8), 7.06 (s, 1H), 6.82-6.76 (m, 2H), 6.71 (dd, 1H, J=2.4 and 7.8 Hz), 3.31 (s, 3H), 3.09 (s, 3H); $^{19}$F NMR (CDCl$_3$): –47292; LCMS: ret. time: 17.29 min.; purity: 92%; MS (m/e): 408 (MH$^+$).

7.3.494 N4-(3-Chloro-4-hydroxy-5-methylphenyl)-5-fluoro-N2-[3-(N-piperazino)carbonylmethyleneoxyphenyl]-2,4-pyrimidinediamine (R945149)

In a manner analogous to the preparation of N4-(3,4-ethylenedioxyphenyl)-5-fluoro-N2-[3-(N-methylamino)carbonylmethyleneoxyphenyl]-2,4-pyrimidinediamine, the reaction of N4-(3-chloro-4-hydroxy-5-methylphenyl)-5-fluoro-N2-(3-methoxycarbonylmethyleneoxyphenyl)-2,4-pyrimidinediamine (700 mg, 1.6 mmol) and piperazine (4 g, 46 mmol) gave N4-(3-chloro-4-hydroxy-5-methylphenyl)-5-fluoro-N2-[3-(N-piperazino)carbonylmethyleneoxyphenyl]-2,4-pyrimidinediamine (520 mg, 66%). $^1$H NMR (CD$_3$OD): δ δ 2.22 (s, 3H), 2.75 (t, J=5.4 Hz, 4H), 3.40 (t, J=4.8 Hz, 2H), 3.54 (t, J=5.1 Hz, 2H), 4.62 (s, 2H), 6.57 (ddd, J=1.5, 2.7 and 7.5 Hz, 1H), 7.09 (dt, J=1.5 and 8.1 Hz, 1H), 7.14 (t, J=7.8 Hz, 1H), 7.28 (t, J=2.1 Hz, 1H), 7.31 (dd, J=0.9 and 2.7 Hz, 1H), 7.50 (d, J=2.7 Hz, 1H), 7.88 (d, J=3.9 Hz, 1H); $^{19}$F NMR (282 MHz, CD$_3$OD): δ –168.63; LCMS: ret. time: 14.99 min.; 93.88%; MS (m/e): 486.96 (MH$^+$).

7.3.495 N4-(4-tert-Butylphenyl)-5-fluoro-N2-[2-(N-methylamino)carbonylbenzofuran-5-yl]-2,4-pyrimidinediamine (R926713)

In a manner similar to the preparation of N4-(3,4-ethylenedioxyphenyl)-5-fluoro-N2-[3-(N-methylamino)carbonylmethyleneoxyphenyl]-2,4-pyrimidinediamine, N4-(4-tert-butylphenyl)-5-fluoro-N2-(2-methoxycarbonylbenzofuran-5-yl)-2,4-pyrimidinediamine and methylamine hydrochloride were reacted to yield N4-(4-tert-butylphenyl)-5-fluoro-N2-[2-(N-methylaminocarbonylbenzofuran-5-yl]-2,4-pyrimidinediamine. $^1$H NMR (CD$_3$OD): δ 8.05 (d, 1H, J=2.4 Hz), 7.88 (d, 1H, J=4.2 Hz), 7.57 (d, 2H, J=8.7 Hz), 7.51-7.41 (m, 2H), 7.34-7.31 (m, 3H), 2.94 (s, 3H), 1.33 (s, 9H); $^{19}$F NMR (CD$_3$OD): –47682; LCMS: ret. time: 23.02 min.; purity: 90%; MS (m/e): 434 (MH$^+$).

7.3.496 N4-(3,5-Dimethoxyphenyl)-5-fluoro-N2-[3-(N-methylamino)carbonylmethyleneoxyphenyl]-2,4-pyrimidinediamine (R926796)

In like manner to the preparation of N4-(ethylenedioxyphenyl)-5-fluoro-N2-[3-(N-methylamino)carbonylmethyleneoxyphenyl]-2,4-pyrimidinediamine, the reaction of N4-(3,5-dimethoxyphenyl)-N2-(3-ethoxycarbonylmethyleneoxyphenyl)-5-fluoro-2,4-pyrimidinediamine with methylamine hydrochloride gave N4-(3,5-dimethoxyphenyl)-5-fluoro-N2-[3-(N-methylamino)

carbonylmethyleneoxyphenyl]-2,4-pyrimidinediamine. $^1$H NMR (CD$_3$OD): δ 7.92 (d, 1H, J=4.2 Hz), 7.42 (t, 1H, J=1.8 Hz), 7.12 (m, 2H), 6.91 (d, 1H, J=2.4 Hz), 6.59 (m, 1H), 6.22 (t, 1H, J=1.8 Hz), 4.35 (s, 2H), 3.69 (s, 6H), 2.81 (s, 3H); LCMS: ret. time: 18.35 min.; purity: 93%; MS (m/e): 428 (MH$^+$).

7.3.497 5-Ethoxycarbonyl-N4-(3,4-ethylenedioxyphenyl)-N2-[3-(N-methylamino)carbonylmethyleneoxyphenyl]-2,4-pyrimidinediamine (R926800)

In like manner to the preparation of N4-(ethylenedioxyphenyl)-5-fluoro-N2-[3-(N-methylamino)carbonylmethyleneoxyphenyl]-2,4-pyrimidinediamine, the reaction of 5-ethoxycarbonyl-N2-(3-ethoxycarbonylmethyleneoxyphenyl)-N4-(3,4-ethylenedioxyphenyl)-2,4-pyridinediamine with methylamine hydrochloride gave 5-ethoxycarbonyl-N4-(3,4-ethylenedioxyphenyl)-N2-[3-(N-methylamino)carbonylmethyleneoxyphenyl]-2,4-pyrimidinediamine. $^1$H NMR (DMSO-d6): δ 10.05 (s, 1H), 9.34 (s, 1H), 8.69 (s, 1H), 7.95 (d, 1H, J=4.8 Hz), 7.34 (dd, 1H, J=1.2 and 7.8 Hz), 7.25 (bs, 2H), 7.13 (t, 1H, J=8.1 Hz), 7.00 (bd, 1H, J=9 Hz), 6.81 (d, 1H, J=8.7 Hz), 6.59 (dd, 1H, J=1.5 and 8.4 Hz), 4.32 (s, 2H), 4.30 (q, 2H, J=7.2 Hz), 4.21 (s, 4H), 2.63 and 2.62 (2s, 3H), 1.31 (t, 3H, J=7.2 Hz); LCMS: ret. time: 24.12 min.; purity: 91%; MS (m/e): 481 (MH$^+$).

7.3.498 N4-(3,5-Dimethoxyphenyl)-5-ethoxycarbonyl-N2-[3-(N-methylamino)carbonylmethyleneoxyphenyl]-2,4-pyrimidinediamine (R926801)

In like manner to the preparation of N4-(ethylenedioxyphenyl)-5-fluoro-N2-[3-(N-methylaminocarbonylmethyleneoxyphenyl)]-2,4-pyrimidinediamine, the reaction of N4-(3,5-dimethoxyphenyl)-5-ethoxycarbonyl-N2-(3-ethoxycarbonylmethyleneoxyphenyl)-2,4-pyridinediamine with methylamine hydrochloride gave N4-(3,5-dimethoxyphenyl)-5-ethoxycarbonyl-N2-[3-(N-methylamino)carbonylmethyleneoxyphenyl]-2,4-pyrimidinediamine. $^1$H NMR (DMSO-d6): δ 10.20 (s, 1H), 9.96 (s, 1H), 8.73 (s, 1H), 7.90 (bs, 1H), 7.36 (d, 1H, J=8.7 Hz), 7.28 (bs, 1H), 7.12 (t, 1H, J=7.5 Hz), 6.84 (s, 2H), 6.59 (dd, 1H, J=1.8 and 8.1 Hz), 6.25 (t, 1H, J=2.4 Hz), 4.31 (m, 4H), 3.67 (s, 6H), 2.63 and 2.62 (2s, 3H), 1.31 (t, 3H, J=7.2 Hz); LCMS: ret. time: 25.50 min.; purity: 96%; MS (m/e): 482 (MH$^+$).

7.3.499 N4-(4-tert-Butylphenyl)-5-fluoro-N2-[3-(N-methylamino)carbonylmethyleneoxyphenyl]-2,4-pyrimidinediamine (R926714)

In a manner similar to the preparation of N4-(3,4-ethylenedioxyphenyl)-5-fluoro-N2-[3-(N-methylamino)carbonylmethyleneoxyphenyl]-2,4-pyrimidinediamine, N4-(4-tert-butylphenyl)-5-fluoro-N2-(3-methoxycarbonylmethyleneoxyphenyl)-2,4-pyrimidinediamine and methylamine hydrochloride were reacted to yield N4-(4-tert-butylphenyl)-5-fluoro-N2-[3-(N-methylamino)carbonylmethyleneoxyphenyl)-2,4-pyrimidinediamine. $^1$H NMR (CD$_3$OD): δ 7.90 (d, 1H, J=3.3 Hz), 7.61 (d, 2H, J=8.7 Hz), 7.40-7.33 (m, 3H), 7.14-7.11 (m, 2H), 6.62-6.57 (m, 1H), 4.36 (s, 2H), 2.79 (s, 3H), 1.31 (s, 9H); $^{19}$F NMR (CD$_3$OD): −47514; LCMS: ret. time: 23.70 min.; purity: 93%; MS (m/e): 424 (MH$^+$).

7.3.500 N4-(3-Hydroxyphenyl)-5-trifluoromethyl-N2-[3-(N-methylamino)carbonylmethyleneoxyphenyl]-2,4-pyrimidinediamine (R926742)

In a manner similar to the preparation of N4-(3,4-ethylenedioxyphenyl)-5-fluoro-N2-[3-(N-methylamino)carbonylmethyleneoxyphenyl]-2,4-pyrimidinediamine, N4-(3-hydroxyphenyl)-5-trifluoromethyl-N2-(3-methoxycarbonylmethyleneoxyphenyl)-2,4-pyrimidinediamine and methylamine hydrochloride were reacted to yield N4-(3-hydroxyphenyl)-5-trifluoromethyl-N2-[3-(N-methylamino)carbonylmethyleneoxyphenyl]-2,4-pyrimidinediamine. LCMS: ret. time: 19.11 min.; purity: 99%; MS (m/e): 434 (MH$^+$).

7.3.501 5-Fluoro-N4-[(1H)-indol-6-yl]-N2-[3-(N-methylamino)carbonylmethyleneoxyphenyl]-2,4-pyrimidinediamine (R926745)

In a manner similar to the preparation of N4-(3,4-ethylenedioxyphenyl)-5-fluoro-N2-[3-(N-methylamino)carbonylmethyleneoxyphenyl]-2,4-pyrimidinediamine, 2-chloro-5-fluoro-N4-[(1H)-indol-6-yl]-4-pyrimidineamine and 3-(N-methylamino)carbonylmethyleneoxyaniline were reacted to yield 5-fluoro-N4-[(1H)-indol-6-yl]-N2-[3-(N-methylamino)carbonylmethyleneoxyphenyl]-2,4-pyrimidinediamine. LCMS: ret. time: 17.41 min.; purity: 93%; MS (m/e): 407(MH$^+$).

7.3.502 N4-(3,5-Dimethyl-4-methoxyphenyl)-5-fluoro-N2-[3-(N-piperazino)carbonylmethyleneoxyphenyl]-2,4-pyrimidinediamine (R945156)

In a manner analogous to the preparation of N4-(3,4-ethylenedioxyphenyl)-5-fluoro-N2-[3-(N-methylamino)carbonylmethyleneoxyphenyl]-2,4-pyrimidinediamine, the reaction of N4-(3,5-dimethyl-4-methoxyphenyl)-5-fluoro-N2-(3-methoxycarbonylmethyleneoxyphenyl)-2,4-pyrimidinediamine and piperazine gave N4-(3,5-dimethyl-4-methoxyphenyl)-5-fluoro-N2-[3-(N-piperazino)carbonylmethyleneoxyphenyl]-2,4-pyrimidinediamine. $^1$H NMR (CD$_3$OD): δ 2.23 (s, 6H), 3.24 (m, 4H), 3.71 (s, 3H), 3.72-3.81 (m, 4H), 4.75 (s, 2H), 6.81 (dt, J=1.2 and 8.1 Hz, 1H), 7.10-7.13 (m, 2H), 7.24 (d, J=8.7 Hz, 1H), 7.29 (s, 2H), 7.98 (d, J=4.8 Hz, 1H); $^{19}$F NMR (282 MHz, CD$_3$OD): 6-163.88; LCMS: ret. time: 15.94 min.; purity: 100%; MS (m/e): 481.12 (MH$^+$).

7.3.503 N4-(3-tert-Butylphenyl)-5-fluoro-N2-[2-(N-methylamino)carbonylbenzofur-5-yl]-2,4-pyrimidinediamine R940291

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3-tert-butylphenyl)-5-fluoro-N2-(2-methoxycarbonylbenzofur-5-yl)-2,4-pyrimidinediamine and methylamine hydrochloride were reacted to give N4-(3-tert-butylphenyl)-5-fluoro-N2-[2-(N-methylamino)carbonylbenzofur-5-yl]-2,4-pyrimidinediamine. LCMS: ret. time: 23.05 min.; purity: 100%; MS (m/e): 434 (MH$^+$); $^1$□□□ (DMSO-d6): δ 9.6 (1H, s), 9.57 (1H, s), 8.75 (1H, m), 8.25 (1H, s), 8.15 (1H, s), 7.93 (1H, d, J=8.5 Hz), 7.47 (3H, m), 7.44 (1H, s), 7.36 (1H, t, J=8.5 Hz), 7.25 (1H, d, J=8.5 Hz), 2.89 (3H, d, J=4.5 Hz), 1.33 (9H, s).

7.3.504 N4-(3,4-Ethylenedioxyphenyl)-5-fluoro-N2-[3-(2-hydroxyethylamino)carbonylmethyleneoxyphenyl]-2,4-pyrimidinediamine (R926505)

In like manner to preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-(3-methoxycarbonylmethyleneoxy)phenyl]-2,4-pyrimidinediamine and 2-hydroxyethylamine gave N4-(3,4-ethylenedioxyphenyl)-5-fluoro-N2-[3-(2-hydroxyethylamino)carbonylmethyleneoxyphenyl]-2,4-pyrimidinediamine. $^1$H NMR (CD$_3$OD): δ 7.87 (d, 1H, J=3.6 Hz), 7.37 (t, 1H, J=1.8 Hz), 7.24 (d, 1H, J=2.4 Hz), 7.13 (m, 2H), 7.08 (dd, 1H, J=2.1 and 8.1 Hz), 6.77 (m, 1H), 4.38 (s, 2H), 4.22 (s, 3H), 3.63 (t, 2H), 3.40 (t, 2H, J=6 Hz); LCMS: ret. time: 16.72 min.; purity: 98%; MS (m/e): 456 (MH$^+$).

7.3.505 5-Fluoro-N4-(3-hydroxyphenyl)-N2-[3-(N-2,3-dihydroxypropylamino)carbonylmethyleneoxyphenyl]-2,4-pyrimidinediamine (R926746)

In a manner similar to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N4-(3-hydroxyphenyl)-N2-(3-methoxycarbonylmethyleneoxyphenyl)-2,4-pyrimidinediamine and 3-amino-1,2-propanediol were reacted to yield 5-fluoro-N4-(3-hydroxyphenyl)-N2-[3-(N-2,3-dihydroxypropylamino)carbonylmethyleneoxyphenyl]-2,4-pyrimidinediamine. LCMS: ret. time: 12.84 min.; purity: 96%; MS (m/e): 444 (MH$^+$).

7.3.506 5-Fluoro-N2-[2-(2-hydroxy-1,1-dimethylethylamino)carbonylbenzofuran-5-yl]-N4-(3-hydroxyphenyl)-2,4-pyrimidinediamine (R926715)

In a manner similar to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N4-(3-hydroxyphenyl)-N2-(2-methoxycarbonylbenzofuran-5-yl)-2,4-pyrimidinediamine and 2-amino-2-methylpropanol were reacted to yield 5-fluoro-N2-[2-(2-hydroxy-1,1-dimethylethylamino)carbonylbenzofuran-5-yl]-N4-(3-hydroxyphenyl)-2,4-pyrimidinediamine. $^1$H NMR (DMSO-d6): δ 9.41 (s, 1H), 9.28 (s, 1H), 9.22 (s, 1H), 8.18 (t, 1H, J=2.4, Hz), 8.09 (d, 1H, J=3.6 Hz), 7.56 (dd, 1H, J=2.4 and 8.7 Hz), 7.47 (d, 1H, J=8.7 Hz), 7.32 (s, 1H), 7.26-7.21 (m, 1H), 7.13-7.07 (m, 2H), 6.53 (d, 1H, J=8.7 Hz), 5.05 (t, 1H, J=5.7 Hz), 3.46 (d, 2H, J=5.7 Hz), 1.32 (s, 6H); LCMS: ret. time: 17.93 min.; purity: 97%; MS (m/e): 452 (MH$^+$).

7.3.507 5-Fluoro-N4-(4-isopropoxyphenyl)-N2-[3-(N-methylamino)carbonylmethyleneoxyphenyl]-2,4-pyrimidinediamine (R926730)

In a manner similar to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N2-(3-methoxycarbonylmethyleneoxyphenyl)-N4-(4-isopropoxyphenyl)-2,4-pyrimidinediamine and methylamine hydrochloride were reacted to yield 5-fluoro-N4-(4-isopropoxyphenyl)-N2-[3-(N-methylamino)carbonylmethyleneoxyphenyl]-2,4-pyrimidinediamine. $^1$H NMR (CDCl$_3$): δ 7.93 (d, 1H, J=3.0 Hz), 7.47 (d, 2H, J=9.3 Hz), 7.42 (t, 1H, J=1.8 Hz), 7.17 (t, 1H, J=8.1 Hz), 7.10 (bs, 1H), 7.00 (dd, 1H, J=1.8 and 9.3 Hz), 6.89 (d, 2H, J=9.3 Hz), 6.80 (d, 1H, J=1.8 Hz), 6.58 (bs, 1H), 6.50 (dd, 1H, J=1.5 and 8.1 Hz), 4.51 (2q, 1H, J=5.7 Hz), 4.44 (s, 2H), 2.88 (d, 3H, J=4.5 Hz), 1.33 (d, 6H, J=5.7 Hz); $^{19}$F NMR (CDCl$_3$): −47198; LCMS: ret. time: 19.66 min.; purity: 97%; MS (m/e): 426 (MH$^+$).

7.3.508 5-Fluoro-N4-(3-hydroxyphenyl)-N2-[4-(N-methylamino)carbonylmethyleneoxyphenyl]-2,4-pyrimidinediamine (R945170)

In a manner analogous to the preparation of N4-(3,4-ethylenedioxyphenyl)-5-fluoro-N2-[3-(N-methylamino)methyleneoxyphenyl]-2,4-pyrimidinediamine, the reaction of N2-(4-cyanomethyleneoxyphenyl)-5-fluoro-N4-(3-hydroxyphenyl)-2,4-pyrimidinediamine and methylamine hydrochloride gave 5-fluoro-N4-(3-hydroxyphenyl)-N2-[4-(N-methylamino)carbonylmethyleneoxyphenyl]-2,4-pyrimidinediamine. $^1$H NMR (CDCl$_3$): δ 2.91 (d, J=5.1 Hz, 3H), 4.48 (s, 2H), 6.61 (ddd, J=0.9, 2.7 and 8.1 Hz, 1H), 6.63 (br, 1H), 6.76 (d, J=3.0 Hz, 1H), 6.84-6.89 (m, 4H), 7.18 (t, J=8.1 Hz, 1H), 7.44 (d, J=8.7 Hz, 2H), 7.51 (t, J=2.1 Hz, 1H), 7.92 (d, 1H); $^{19}$F NMR (282 MHz, CDCl$_3$): 6-167.70; LCMS: ret. time: 14.32 min.; purity: 100%; MS (m/e): 383.98 (MH$^+$).

7.3.509 5-Fluoro-N4-(3-isopropoxyphenyl)-N2-[2-(N-morpholino)carbonylbenzofuran-5-yl]-2,4-pyrimidinediamine (R926489)

In like manner to the preparation of N4-(ethylenedioxyphenyl)-5-fluoro-N2-[3-(N-methylamino)carbonylmethyleneoxyphenyl]-2,4-pyrimidinediamine, the reaction of 5-fluoro-N4-(3-isopropoxyphenyl)-N2-(2-methoxycarbonylbenzofuran-5-yl)-2,4-pyrimidineamine with morpholine gave 5-fluoro-N4-(3-isopropoxyphenyl)-N2-[2-(N-morpholino)carbonylbenzofuran-5-yl]-2,4-pyrimidinediamine. $^1$H NMR (CDCl$_3$): δ 8.01 (d, 1H, J=1.2 Hz), 7.95 (bs, 1H), 7.43-7.38 (m, 2H), 7.29 (s, 1H), 7.25-7.11 (m, 4H), 6.97 (bs, 1H), 6.73 (m, 1H), 6.67 (bdd, 1H), 4.48 (sept, 1H, J=5.7 Hz), 3.87 (m, 4H), 3.79 (m, 4H), 1.30 (d, 6H, J=5.7 Hz), LCMS: ret. time: 22.12 min.; purity: 98%; MS (m/e): 492 (MH$^+$).

7.3.510 5-Fluoro-N4-(3-hydroxyphenyl)-N2-[3-(N-piperazino)carbonylmethyleneoxyphenyl]-2,4-pyrimidinediamine (R926772)

In like manner to the preparation of N4-(ethylenedioxyphenyl)-5-fluoro-N2-[3-(N-methylamino)carbonylmethyleneoxyphenyl]-2,4-pyrimidinediamine, the reaction of 5-fluoro-N2-(3-ethoxycarbonylmethyleneoxyphenyl)-N4-(3-hydroxyphenyl)-2,4-pyrimidinediamine with piperazine gave 5-fluoro-N4-(3-hydroxyphenyl)-N2-[3-(N-piperazino)carbonylmethyleneoxyphenyl]-2,4-pyrimidinediamine. $^1$H NMR (CD$_3$OD): δ 7.91 (d, 1H, J=3.6 Hz), 7.42 (t, 1H, J=2.4 Hz), 7.20-7.07 (m, 5H), 6.55 (m, 2H), 4.63 (s, 2H), 3.54 (t, 2H, J=6 Hz), 3.40 (t, 2H, J=5.1 Hz), 2.76 (t, 4H, J=5.4 Hz); LCMS: ret. time: 12.98 min.; purity: 92%; MS (m/e): 439 (MH$^+$).

7.3.511 5-Fluoro-N4-(3-hydroxyphenyl)-N2-[3-(N-2-hydroxyethylamino)carbonylmethyleneoxyphenyl]-2,4-pyrimidinediamine (R926506)

In like manner to the preparation of N4-(ethylenedioxyphenyl)-5-fluoro-N2-[3-(N-methylamino)carbonylmethyleneoxyphenyl]-2,4-pyrimidinediamine, the reaction of 5-fluoro-N4-(3-hydroxyphenyl)-N2-(3-methoxycarbonylmethyleneoxyphenyl)-2,4-pyrimidinediamine with 2-hydroxyethylamine gave 5-fluoro-N4-(3-hydroxyphenyl)-N2-[3-(N-2-hydroxyethylamino)carbonylmethyleneoxyphenyl]-2,4-pyrimidinediamine. LCMS: ret. time: 14.95 min.; purity: 96%; MS (m/e): 414 (MH$^+$).

7.3.512 5-Fluoro-N4-(3-hydroxyphenyl)-N2-[3-(N-methylamino)carbonylmethyleneoxyphenyl]-2,4-pyrimidinediamine (R926508)

In like manner to the preparation of N4-(ethylenedioxyphenyl)-5-fluoro-N2-[3-(N-methylamino)carbonylmethyleneoxyphenyl]-2,4-pyrimidinediamine, the reaction of 5-fluoro-N4-(3-hydroxyphenyl)-N2-(3-ethoxy or methoxycarbonylmethyleneoxyphenyl)-2,4-pyrimidinediamine with methylamine hydrochloride gave 5-fluoro-N4-(3-hydroxyphenyl)-N2-[3-(N-methylamino)carbonylmethyleneoxyphenyl]-2,4-pyrimidinediamine. $^1$H NMR (DMSO-d6): δ 9.64 (bs, 1H), 9.58 (bs, 1H), 8.15 (d, 1H, J=4.2 Hz), 7.95 (bd, 1H), 7.25 (bd, 2H, J=6.6 Hz), 7.16-7.07 (m, 4H), 6.53 (m, 2H), 4.35 (s, 2H), 2.64 and 2.62 (2s, 3H); LCMS: ret. time: 15.66 min.; purity: 98%; MS (m/e): 384 (MH$^+$).

7.3.513 5-Fluoro-N4-[3,4-(1,1,2,2-tetrafluoroethylendioxy)phenyl]-N2-[3-(N-methylamino)carbonylmethyleneoxyphenyl]-2,4-pyrimidinediamine (R926732)

In a manner similar to the preparation of N4-(3,4-ethylenedioxyphenyl)-5-fluoro-N2-[3-(N-methylamino)carbonylmethyleneoxyphenyl]-2,4-pyrimidinediamine, 2-chloro-5-fluoro-N4-[3,4-(1,1,2,2-tetrafluoroethylendioxy)phenyl]-4-pyrimidineamine and methylamine hydrochloride were reacted to yield 5-fluoro-N4-[3,4-(1,1,2,2-tetrafluoroethylendioxy)phenyl]-N2-[3-(N-methylamino)carbonylmethyleneoxyphenyl]-2,4-pyrimidinediamine. $^1$H NMR (DMSO-d6): δ 9.65 (s, 1H), 9.37 (s, 1H), 8.16 (d, 1H, J=3.6 Hz), 8.14 (d, 1H, J=2.4 Hz), 7.97 (d, 1H, J=4.8 Hz), 7.65 (dd, 1H, J=2.4 and 8.7 Hz), 7.41 (d, 1H, J=9.3 Hz), 7.34 (t, 1H, J=2.4 Hz), 7.27 (d, 1H, J=8.1 Hz), 7.13 (t, 1H, J=8.1 Hz), 6.51 (dd, 1H, J=2.1 and 7.5 Hz), 4.36 (s, 2H), 2.63 (d, 3H, J=4.8 Hz); $^{19}$F NMR (DMSO-d6): −25765 (pent, 2F), −25830 (pent, 2F), −46309; LCMS: ret. time: 24.85 min.; purity: 95%; MS (m/e): 497 (MH$^+$).

7.3.514 N4-(3,5-Dimethyl-4-hydroxyphenyl)-5-fluoro-N2-[3-(N-morpholino)carbonylmethyleneoxyphenyl]-2,4-pyrimidinediamine (R940254)

In like manner to the preparation of N4-(ethylenedioxyphenyl)-5-fluoro-N2-[3-(N-methylamino)carbonylmethyleneoxyphenyl]-2,4-pyrimidinediamine, the reaction of N4-(3,5-dimethyl-4-hydroxyphenyl)-N2-(3-ethoxycarbonylmethyleneoxyphenyl)-5-fluoro-2,4-pyrimidinediamine with morpholine gave N4-(3,5-dimethyl-4-hydroxyphenyl)-5-fluoro-N2-(N-morpholinocarbonylmethyleneoxyphenyl)-2,4-pyrimidinediamine. LCMS: ret. time: 18.38 min.; purity: 92%; MS (m/e): 468 (MH$^+$); 1 (DMSO-d6): δ 9.20 (1H, s), 9.10 (1H, s), 8.15 (1H, s), 8.11 (1H, d, J=3.9 Hz), 7.43 (1H, d, J=8.1 Hz), 7.32 (3H, m), 7.14 (1H, t, J=8.1 Hz), 6.54 (1H, dd, J=8.1 and 2.0 Hz), 4.77 (2H, s), 3.64 (4H, m), 3.54-3.45 (4H, m), 2.24 (6H, s).

7.3.515 N4-(3-tert-Butylphenyl)-N2-[3-(N-methylamino)carbonylmethyleneoxyphenyl]-5-fluoro-2,4-pyrimidinediamine (R940276)

In like manner to the preparation of N4-(ethylenedioxyphenyl)-5-fluoro-N2-[3-(N-methylamino)carbonylmethyleneoxyphenyl]-2,4-pyrimidinediamine, the reaction of N4-(3-tert-butylphenyl)-N2-(3-ethoxycarbonylmethyleneoxyphenyl)-5-fluoro-2,4-pyrimidinediamine with methylamine hydrochloride gave N4-(3-tert-butylphenyl)-N2-[3-(N-methylamino)carbonylmethyleneoxyphenyl]-5-fluoro-2,4-pyrimidinediamine. LCMS: ret. time: 22.90 min.; purity: 99%; MS (m/e): 424 (MH$^+$); 1 (DMSO-d6): δ 9.46 (1H, s), 9.34 (1H, s), 8.08 (1H, d, J=3.9 Hz), 7.90 (1H, m), 7.30 (1H, d, J=8.1 Hz), 7.46 (1H, m), 7.26 (1H, m), 7.20 (2H, m), 7.10-7.03 (2H, m), 6.47 (1H, d, J=8.1 Hz), 4.26 (2H, s), 2.59 (3H, d, J=4.5 Hz), 1.20 (9H, s).

7.3.516 N4-(3-tert-Butylphenyl)-N2-[3-(N-2,3-dihydroxypropylamino)carbonylmethyleneoxyphenyl]-5-fluoro-2,4-pyrimidinediamine (R940277)

In like manner to the preparation of N4-(ethylenedioxyphenyl)-5-fluoro-N2-[3-(N-methylamino)carbonylmethyleneoxyphenyl]-2,4-pyrimidinediamine, the reaction of N4-(3-tert-butylphenyl)-N2-(3-ethoxycarbonylmethyleneoxyphenyl)-5-fluoro-2,4-pyrimidinediamine with 2,3-dihydroxypropylamine gave N4-(3-tert-butylphenyl)-N2-[3-(N-2,3-dihydroxypropylamino)carbonylmethyleneoxyphenyl]-5-fluoro-2,4-pyrimidinediamine. LCMS: retn. time: 20.46 min.; purity: 100%; MS (m/e): 484 (MH$^+$); 1 (DMSO-d6): δ 9.38 (1H, s), 9.29 (1H, s), 8.20 (1H, d, J=3.9 Hz), 8.00 (1H, d, J=8.3 Hz), 7.93 (1H, t, J=5.5 Hz), 7.60 (1H, m), 7.47 (1H, m), 7.41-7.17 (4H, m), 6.59 (1H, dd, J=8.3 and 2 Hz), 3.43 (2H, s), 3.39 (4H, m), 3.16 (1H, m), 1.36 (9H, s).

7.3.517 N4-(3,3-Dihydroisobenzofuran-1-one-6-yl)-N2-[3-(N-2,3-dihydroxypropylamino)carbonylmethyleneoxyphenyl]-5-fluoro-2,4-pyrimidinediamine R940293

In like manner to the preparation of N4-(3,4-ethylenedioxyphenyl)-5-fluoro-N2-[3-(N-methylamino)carbonylmethyleneoxyphenyl]-2,4-pyrimidinediamine, N2-[3-(ethoxycarbonylmethyleneoxy)phenyl]-N4-(3,3-dihydroisobenzofuran-1-one-6-yl)-5-fluoro-2,4-pyrimidinediamine and 3-amino-1,2-propanediol were reacted to N4-(3,3-dihydroisobenzofuran-1-one-6-yl)-N2-[3-(N-2,3-dihydroxypropylamino)carbonylmethyleneoxyphenyl]-5-fluoro-2,4-pyrimidinediamine. LCMS: ret. time: 13.92 min.; purity: 92%; MS (m/e): 483 (M$^+$); 1 (DMSO-d6): δ 9.80 (1H, s), 9.46 (1H, s), 8.37-8.27 (2H, m), 8.21 (1H, s), 7.96 (1H, t, J=4.6 Hz), 7.24 (1H, d, J=9 Hz), 7.44 (1H, s), 7.37 (1H, d, J=9 Hz), 7.23 (1H, t, J=8 Hz), 6.60 (1H, dd, J=7 and 3.75 Hz) 5.49 (2H, s), 4.46 (2H, s), 3.38 (4H, m), 3.2-3.1 (1H, m).

7.3.518 N4-(3,4-Dimethoxyphenyl)-5-fluoro-N2-[3-(N-methylamino)carbonylmethyleneoxyphenyl]-2,4-pyrimidinediamine (R926733)

In a manner similar to the preparation of N4-(3,4-ethylenedioxyphenyl)-5-fluoro-N2-[3-(N-methylamino)carbonylmethyleneoxyphenyl]-2,4-pyrimidinediamine, N4-(3,4-dimethoxyphenyl)-5-fluoro-N2-(3-methoxycarbonyl methyleneoxyphenyl)-2,4-pyrimidine diamine and methylaminehydrochloride were reacted to yield N4-(3,4-dimethoxyphenyl)-5-fluoro-N2-[3-(N-methylamino)carbonylmethyleneoxyphenyl]-2,4-pyrimidinediamine. $^1$H NMR (CDCl$_3$): δ 7.95 (d, 1H, J=3.6 Hz), 7.45 (t, 1H, J=1.8 Hz), 7.21-7.17 (m, 2H), 7.05 (dd, 1H, J=2.7 and 8.7 Hz), 6.96-6.90 (m, 2H), 6.87 (d, 1H, J=9.0 Hz), 6.72 (d, 1H, J=2.4 Hz), 6.67-6.58 (m, 1H), 6.52 (dd, 1H, J=3.6 and 8.1 Hz), 4.39 (s, 2H), 3.89 (s, 3H), 3.78 (s, 3H), 2.90 (d, 3H, J=4.8 Hz); LCMS: ret. time: 17.09 min.; purity: 98%; MS (m/e): 428 (MH$^+$).

7.3.519 N2-[3-(N-2,3-Dihydroxypropylamino) carbonylmethyleneoxyphenyl]-N4-(3,4-dimethoxyphenyl)-5-fluoro-2,4-pyrimidinediamine (R926734)

In a manner similar to the preparation of N4-(3,4-ethylenedioxyphenyl)-5-fluoro-N2-[3-(N-methylamino)carbonylmethyleneoxyphenyl]-2,4-pyrimidinediamine, N4-(3,4-dimethoxyphenyl)-5-fluoro-N2-(3-methoxycarbonylmethyleneoxyphenyl)-2,4-pyrimidinediamine and 3-amino-1,2-propanediol were reacted to yield N2-[3-(N-2,3-dihydroxypropylamino)carbonylmethyleneoxyphenyl]-N4-(3,4-dimethoxyphenyl)-5-fluoro-2,4-pyrimidinediamine. $^1$H NMR (DMSO-d6): δ 8.05 (d, 1H, J=4.2 Hz), 7.38-7.34 (m, 2H), 7.31-7.26 (m, 2H), 7.07 (t, 1H, J=8.4 Hz), 6.89 (d, 1H, J=8.7 Hz), 6.46 (dd, 1H, J=2.4 and 8.4 Hz), 4.36 (s, 2H), 3.72 (s, 3H), 3.68 (s, 3H), 3.32-3.24 (m, 3H), 3.03 (dd, 1H, J=6.9 and 13.5 Hz); $^{19}$F NMR (DMSO-d6): −46574; LCMS: ret. time: 14.85 min.; purity: 94%; MS (m/e): 488 (MH$^+$).

7.3.520 5-Fluoro-N4-(3-methoxyphenyl)-N2-[3-(N-methylamino)carbonylmethyleneoxyphenyl]-2,4-pyrimidinediamine (R926738)

In a manner similar to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N4-(3-methoxyphenyl)-N2-(4-methoxycarbonylmethyleneoxyphenyl)-2,4-pyrimidinediamine and methylamine hydrochloride were reacted to yield 5-fluoro-N4-(3-methoxyphenyl)-N2-[3-(N-methylamino)carbonylmethyleneoxyphenyl]-2,4-pyrimidinediamine. LCMS: ret. time: 18.40 min.; purity: 98%; MS (m/e): 398 (MH$^+$).

7.3.521 N2-[3-(N-2,3-Dihydroxypropylamino) carbonylmethyleneoxyphenyl]-5-fluoro-N4-(3-methoxyphenyl)-2,4-pyrimidinediamine (R926739)

In a manner similar to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N2-(3-methoxycarbonylmethyleneoxyphenyl)-N4-(3-methoxyphenyl)-2,4-pyrimidinediamine and 3-amino-1,2-propanediol were reacted to yield N2-[3-(N-2,3-dihydroxypropylamino)carbonylmethyleneoxyphenyl]-5-fluoro-N4-(3-methoxyphenyl)-2,4-pyrimidinediamine. LCMS: ret. time: 16.66 min.; purity: 99%; MS (m/e): 458 (MH$^+$).

7.3.522 N4-(3,5-Dimethyl-4-hydroxyphenyl)-5-fluoro-N2-[3-(N-piperazino)carbonylmethyleneoxyphenyl]-2,4-pyrimidinediamine (R945140)

In a manner analogous to the preparation of N4-(3,4-ethylenedioxyphenyl)-5-fluoro-N2-[3-(N-methylamino)carbonylmethyleneoxyphenyl]-2,4-pyrimidinediamine, the reaction of N4-(3,5-dimethyl-4-hydroxyphenyl)-5-fluoro-N2-(3-methoxycarbonylmethyleneoxyphenyl)-2,4-pyrimidinediamine and piperazine gave N4-(3,5-dimethyl-4-hydroxyphenyl)-5-fluoro-N2-[3-(N-piperazino)carbonylmethyleneoxyphenyl]-2,4-pyrimidinediamine. $^1$H NMR (CD$_3$OD): δ 2.18 (s, 6H), 2.72 (q, J=5.1 Hz, 4H), 3.32 (t, 2H), 3.52 (t, J=5.1 Hz, 2H), 4.55 (s, 2H), 6.56 (ddd, J=1.2, 2.4 and 8.1 Hz, 1H), 7.03 (ddd, J=1.2, 1.8 and 8.1 Hz, 1H), 7.11 (t, J=8.1 Hz, 1H), 7.20 (s, 2H), 7.35 (t, J=2.1 Hz, 1H), 7.84 (d, J=3.9 Hz, 1H); $^{19}$F NMR (282 MHz, CD$_3$OD): 6-168.78; LCMS: ret. time: 14.32 min.; purity: 88.37%; MS (m/e): 467.06 (MH$^+$).

7.3.523 5-Fluoro-N4-(3-hydroxyphenyl)-N2-[2-(N-morpholino)carbonylbenzofuran-5-yl]-2,4-pyrimidinediamine (R926488)

In like manner to the preparation of N4-(ethylenedioxyphenyl)-5-fluoro-N2-[3-(N-methylamino)carbonylmethyleneoxyphenyl]-2,4-pyrimidinediamine, the reaction of 5-fluoro-N4-(3-hydroxyphenyl)-N2-(2-methoxycarbonylbenzofuran-5-yl)-2,4-pyrimidinediamine with morpholine gave 5-fluoro-N4-(3-hydroxyphenyl)-N2-[2-(N-morpholino)carbonylbenzofuran-5-yl]-2,4-pyrimidinediamine. $^1$H NMR (CD$_3$OD): δ 8.19 (t, 1H, J=1.5 Hz), 7.90 (d, 1H, J=3.9 Hz), 7.44 (d, 2H, J=0.9 hz), 7.28 (s, 1H), 7.21 (t, 1H, J=2.4 Hz), 7.15 (t, 1H, J=7.5 Hz), 7.08 (m, 1H), 7.61 (bd, 1H, J=6.9 Hz), 3.8 (m, 4H), 3.65 (m, 4H); LCMS: ret. time: 17.21 min.; purity: 83%; MS (m/e): 450 (MH$^+$).

7.3.524 5-Fluoro-N4-(3-hydroxyphenyl)-N2-[2-(N-methylamino)carbonylbenzofuran-5-yl]-2,4-pyrimidinediamine (R926493)

In like manner to the preparation of N4-(ethylenedioxyphenyl)-5-fluoro-N2-[3-(N-methylamino)carbonylmethyleneoxyphenyl]-2,4-pyrimidinediamine, the reaction of 5-fluoro-N4-(3-hydroxyphenyl)-N2-(2-methoxycarbonylbenzofuran-5-yl)-2,4-pyrimidinediamine with methylamine hydrochloride gave 5-fluoro-N4-(3-hydroxyphenyl)-N2-[2-(N-methylamino)carbonylbenzofuran-5-yl]-2,4-pyrimidinediamine. $^1$H NMR (CD$_3$OD): δ 8.71 (d, 1H, J=4.8 Hz), 8.00-7.92 (m, 2H), 7.56-7.52 (m, 1H), 7.44-7.39 (m, 2H), 7.12 (m, 2H), 6.69 (bdd, 1H), 2.96 and 2.94 (2s, 3H).

7.3.525 5-Fluoro-N4-(3-hydroxyphenyl)-N2-[2-(N-2-hydroxyethylamino)carbonylbenzofuran-5-yl]-2,4-pyrimidinediamine (R926497)

In like manner to the preparation of N4-(ethylenedioxyphenyl)-5-fluoro-N2-[3-(N-methylamino)carbonylmethyleneoxyphenyl]-2,4-pyrimidinediamine, the reaction of 5-fluoro-N4-(3-hydroxyphenyl)-N2-(2-methoxycarbonylbenzofuran-5-yl)-2,4-pyrimidinediamine with 2-hydroxyethylamine gave 5-fluoro-N4-(3-hydroxyphenyl)-N2-[2-(N-2-hydroxyethylamino)carbonylbenzofuran-5-yl]-2,4-pyrimidinediamine. $^1$H NMR (CDCl$_3$): δ 8.18 (d, 1H, J=1.8 Hz), 7.80 (bs, 1H), 7.60 (m, 1H), 7.34-7.16 (m, 3H), 7.10 9t, 1H, 8.4 Hz), 6.85 (bdd, 1H), 6.62 (dd, 1H, J=1.5 and 8.1 Hz), 3.70 (t, 2H, J=4.8 Hz), 3.52 (t, 2H, J=4.0 Hz); LCMS: ret. time: 14.49 min.; purity: 97%; MS (m/e): 424 (MH$^+$).

7.3.526 5-Fluoro-N4-(3-hydroxyphenyl)-N2-[2-(N-piperazino)carbonylbenzofuran-5-yl]-2,4-pyrimidinediamine (R926500)

In like manner to the preparation of N4-(ethylenedioxyphenyl)-5-fluoro-N2-[3-(N-methylamino)carbonylmethyleneoxyphenyl]-2,4-pyrimidinediamine, the reaction of 5-fluoro-N4-(3-hydroxyphenyl)-N2-(2-methoxycarbonylbenzofuran-5-yl)-2,4-pyrimidinediamine with piperazine gave 5-fluoro-N4-(3-hydroxyphenyl)-N2-[2-(N-piperazino)carbonylbenzofuran-5-yl]-2,4-pyrimidinediamine. $^1$H NMR (CD$_3$OD): δ 8.19 (t, 1H, J=1.2 Hz), 7.90 (d, 1H, J=3.9 Hz), 7.43 (d, 2H, J=1.2 Hz), 7.25-7.06 (m, 4H), 6.59 (m, 1H), 3.80 (m, 4H), 2.95 (m, 4H); LCMS: ret. time: 12.97 min.; purity: 79%; MS (m/e): 449 (MH$^+$).

7.3.527 5-Cyano-N4-(3-hydroxyphenyl)-N2-[4-(N-methylamino)carbonylmethyleneoxyphenyl]-2,4-pyrimidinediamine (R925844)

In a manner similar to the preparation of N4-(3,4-ethylenedioxyphenyl)-5-fluoro-N2-[3-N-methylaminocarbonylmethyleneoxyphenyl]-2,4-pyrimidinediamine, the reaction of 5-cyano-N2-(4-ethoxycarbonylmethyleneoxyphenyl)-N4-(3-hydroxyphenyl)-2,4-pyrimidinediamine with methylamine hydrochloride gave 5-cyano-N4-(3-hydroxyphenyl)-N2-[4-(N-methylamino)carbonylmethyleneoxyphenyl]-2,4-pyrimidinediamine. LCMS: ret. time: 18.83 min.; purity: 96%; MS (m/e): 391 (MH$^+$).

7.3.528 5-Cyano-N4-[4-(N-cyclopropylmethylamino)carbonylmethyleneoxyphenyl]-N2-(3-hydroxyphenyl)-2,4-pyrimidinediamine (R925845)

In a manner similar to the preparation of N4-(3,4-ethylenedioxyphenyl)-5-fluoro-N2-[3-(N-methylamino)carbonylmethyleneoxyphenyl]-2,4-pyrimidinediamine, 5-cyano-N2-(4-ethoxycarbonylmethyleneoxyphenyl)-N4-(3-hydroxyphenyl)-2,4-pyrimidinediamine reacted with cyclopropylmethylamine to give 5-cyano-N4-[4-(N-cyclopropylmethylamino) carbonylmethyleneoxyphenyl]-N2-(3-hydroxyphenyl)-2,4-pyrimidinediamine. LCMS: ret. time: 22.47 min.; purity: 100%; MS (m/e): 431 (MH$^+$).

7.3.529 5-Cyano-N4-(3-hydroxyphenyl)-N2-[4-(N-2,3-dihydroxypropylamino)carbonylmethyleneoxyphenyl]-2,4-pyrimidinediamine (R925846)

In a manner similar to the preparation of N4-(3,4-ethylenedioxyphenyl)-5-fluoro-N2-[3-(N-methylamino)carbonylmethyleneoxyphenyl]-2,4-pyrimidinediamine, 5-cyano-N2-(4-ethoxycarbonylmethyleneoxyphenyl)-N4-(3-hydroxyphenyl)-2,4-pyrimidinediamine reacted with 2,3-dihydroxypropylamine to give 5-cyano-N4-(3-hydroxyphenyl)-N2-[4-(N-2,3-dihydroxypropylamino)carbonylmethyleneoxyphenyl]-2,4-pyrimidinediamine. LCMS: ret. time: 15.84 min.; purity: 100%; MS (m/e): 451 (MH$^+$).

7.3.530 5-Fluoro-N2-[3-(N-methylamino)carbonylmethyleneoxyphenyl]-N4-(3-trifluoromethylphenyl)-2,4-pyrimidinediamine In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of N2-(3-ethoxycarbonylmethyleneoxyphenyl)-5-fluoro-N4-(3-trifluoromethylphenyl)-2,4-pyrimidineamine with methylamine hydrochloride gave 5-fluoro-N2-[3-(N-methylamino)carbonylmethyleneoxyphenyl)]-N4-(3-trifluoromethylphenyl)-2,4-pyrimidinediamine. LCMS: ret. time: 21.98 min., purity: 86%, MS (m/e): 436 (MH$^+$).

7.3.531 N4-[4-(4,5-Dichloro-1H-imidazol-1-ylphenyl)]-5-fluoro-N2-[3-(N-methylamino)carbonylmethyleneoxyphenyl]-2,4-pyrimidinediamine (R926812)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of N-4-[4-(4,5-dichloro-1H-imidazol-1-ylphenyl)]-5-fluoro-N2-(3-ethoxycarbonylmethyleneoxyphenyl)-2,4-pyrimidinediamine with methylamine hydrochloride gave N4-[4-(4,5-dichloro-1H-imidazol-1-ylphenyl)]-5-fluoro N2-(3-[N-methylamino)carbonylmethyleneoxyphenyl]-2,4-pyrimidinediamine. LCMS: ret. time: 21.02 min., purity: 100%, MS (m/e): 502 (MH$^+$).

7.3.532 N4-(3,4-Ethylenedioxyphenyl)-5-fluoro-N2-[2-(N-methylaminocarbonyllindol-7-yl)-2,4-pyridinediamine (R926815)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of N2-(3-ethoxycarbonylmethyleneoxyphenyl)-5-fluoro-N4-(3-trifluorophenyl)-2,4-pyrimidineamine with methylamine hydrochloride gave N4-(3,4-ethylenedioxyphenyl)-5-fluoro-N2-[2-(N-methylaminocarbonyllindol-7-yl)-2,4-pyridinediamine. LCMS: ret. time: 17.97 min., purity: 97%, MS (m/e): 435 (MH$^+$).

7.3.533 N4-(3,4-Ethylenedioxyphenyl)-5-fluoro-N2-[3-(N-morpholino)carbonylmethyleneoxyphenyl]-2,4-pyrimidinediamine (R926484)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of N2-(3-ethoxycarbonylmethyleneoxyphenyl)-N4-(3,4-ethylenedioxyphenyl)-5-fluoro-2,4-pyrimidinediamine and morpholine gave N4-(3,4-ethylenedioxyphenyl)-5-fluoro-N2-[3-(N-morpholino)carbonylmethyleneoxyphenyl]-2,4-pyrimidinediamine. $^1$H NMR (CDCl$_3$): δ 7.94 (bs, 1H), 7.35 (t, 1H, J=2.4 Hz), 7.24 (m, 1H), 7.19 (t, 1H, J=8.1 Hz), 7.10 (bdd, 1H, J=6.9 Hz), 6.95 (m, 2H), 6.85 (d, 1H, J=8.1 Hz), 6.94 (s, 1H), 6.58 (dd, 1H, J=1.8 and 2.8 Hz), 4.64 (s, 2H), 4.27 9s, 4H), 3.62 (m, 4H), 3.55 (m, 4H); LCMS: ret. time: 18.45 min.; purity: 100%; MS (m/e): 482 (MH$^+$).

7.3.534 N4-(3,4-Ethylenedioxyphenyl)-5-fluoro-N2-[2-(N-morpholino)carbonylbenzofuran-5-yl]-2,4-pyrimidinediamine (R926492)

In like manner to preparation of N4-(3,4-ethylenedioxyphenyl)-5-fluoro-N2-[3-(N-methylamino)carbonylmethyleneoxyphenyl]-2,4-pyrimidinediamine, the reaction of N4-(3,4-ethylenedioxyphenyl)-5-fluoro-N2-(2-methoxycarbonylbenzofuron-5-yl)-2,4-pyrimidinediamine with morpholine gave N4-(3,4-ethylenedioxyphenyl)-5-fluoro-N2-[2-(N-morpholino)carbonylbenzofuron-5-yl]-2,4-pyrimidinediamine. $^1$H NMR (DMSO-d6): δ 9.27 (s, 1H), 9.17 (s, 1H), 8.14 (d, 1H, J=2.4 Hz), 8.05 (d, 1H, J=5.6 Hz), 7.58-7.46 (m, 2H), 7.27 (m, 1H), 7.15 (dd, 1H, J=2.4 and 9 Hz), 6.80 9m, 1H), 4.24 (s, 4H), 3.80-3.45 (m, 8H); LCMS: ret. time: 19.97 min.; purity: 76%; MS (m/e): 492 (MH+).

7.3.535 N4-(3,4-Ethylenedioxyphenyl)-5-fluoro-N2-[2-(N-methylamino)carbonylbenzofuran-5-yl]-2,4-pyrimidinediamine (R926496)

In like manner to preparation of N4-(3,4-ethylenedioxyphenyl)-5-fluoro-N2-[3-(N-methylamino)carbonylmethyleneoxyphenyl]-2,4-pyrimidinediamine, the reaction of N4-(3,4-ethylenedioxyphenyl)-5-fluoro-N2-(2-methoxycarbonylbenzofuran-5-yl)-2,4-pyrimidinediamine and methylamine hydrochloride gave N4-(3,4-ethylenedioxyphenyl)-5-fluoro-N2-[2-(N-methylamino)carbonylbenzofuran-5-yl]-2,4-pyrimidinediamine. $^1$H NMR (CD$_3$OD): δ 8.06 (s, 1H), 7.85 (d, 1H, J=3.3 Hz), 7.42 (d, 2H, J=1.2 Hz), 7.35 (s, 1H), 7.29 (d, 1H, J=2.4 Hz), 6.99 (dd, 1H, J=3.3 and 8.7 Hz), 6.78 (d, 1H, J=8.7 Hz), 4.24 (s, 4H), 2.94 (s, 3H); LCMS: ret. time: 18.05 min.; purity: 99%; MS (m/e): 436 (MH+).

7.3.536 N4-(3,4-Ethylenedioxyphenyl)-5-fluoro-N2-[2-(N-2-hydroxyethylamino)carbonylbenzofuran-5-yl]-2,4-pyrimidinediamine (R926498)

In like manner to preparation of N4-(3,4-ethylenedioxyphenyl)-5-fluoro-N2-[3-(N-methylamino)carbonylmethyleneoxyphenyl]-2,4-pyrimidinediamine, the reaction of N4-(3,4-ethylenedioxyphenyl)-5-fluoro-N2-(2-methoxycarbonylbenzofuran-5-yl)-2,4-pyrimidinediamine with 2-hydroxyethylamine yielded N4-(3,4-ethylenedioxyphenyl)-5-fluoro-N2-[2-(N-2-hydroxyethylamino)carbonylbenzofuran-5-yl]-2,4-pyrimidinediamine. $^1$H NMR (CD$_3$OD): δ 8.07 (d, 1H, J=1.2 Hz), 7.86 (d, 1H, J=3.9 Hz), 7.43 (d, 2H, J=1.5 Hz), 7.38 (s, 1H), 7.29 (d, 1H, J=2.4 Hz), 6.98 (dd, 1H, J=2.1 and 9 Hz), 6.78 (d, 1H, J=8.7 Hz), 4.23 (s, 4H), 3.72 (t, 2H, J=5.7 Hz), 3.53 (t, 2H, J=6.0 Hz); LCMS: ret. time: 16.21 min.; purity: 97%; MS (m/e): 466 (MH+).

7.3.537 N4-(3,4-Ethylenedioxyphenyl)-5-fluoro-N2-[2-(N-piperazino)carbonylbenzofuran-5-yl]-2,4-pyrimidinediamine (R926499)

In like manner to preparation of N4-(3,4-ethylenedioxyphenyl)-5-fluoro-N2-[3-(N-methylamino)carbonylmethyleneoxyphenyl]-2,4-pyrimidinediamine, the reaction of N4-(3,4-ethylenedioxyphenyl)-5-fluoro-N2-(2-methoxycarbonylbenzofuran-5-yl)-2,4-pyrimidinediamine and piperazine yielded N4-(3,4-ethylenedioxyphenyl)-5-fluoro-N2-[2-(N-piperazino)carbonylbenzofuran-5-yl]-2,4-pyrimidinediamine. $^1$H NMR (DMSO-d6): δ 9.26 (s, 1H), 9.16 (s, 1H), 8.12 (d, 1H, J=1.8 Hz), 8.04 (d, 1H, J=3.6 Hz), 7.49 (d, 2H), 7.30 (d, 1H, J=2.4 Hz), 7.20 (s, 1H), 7.15 (bdd, 1H, J=3 Hz), 6.79 (d, 1H, J=8.7 Hz), 4.22 (s, 4H), 2.48 (s, 3H); LCMS: ret. time: 14.61 min.; purity: 94%; MS (m/e): 491 (MH+).

7.3.538 N4-(3,4-Ethylenedioxyphenyl)-5-fluoro-N2-[3-(N-piperazino)carbonylmethyleneoxyphenyl]-2,4-pyrimidinediamine (R926503)

In like manner to preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-(3-methoxycarbony methyleneoxyphenyl)-2,4-pyrimidinediamine and piperazine were reacted to yield N4-(3,4-ethylenedioxyphenyl)-5-fluoro-N2-[3-(N-piperazino)carbonylmethyleneoxyphenyl]-2,4-pyrimidinediamine. $^1$H NMR (CD$_3$OD): δ 9.14 (bs, 2H), 8.04 (d, 3.6 Hz), 7.32-7.20 (m, 4H), 7.06 (t, 1H, J=8.1 Hz), 6.79 (d, d, 1H, J=9 Hz), 6.43 (bd, 1H, J=9.9 Hz), 4.64 (s, 2H), 4.20 (bs, 4H), 3.29 (m, 4H), 2.59 (m, 4H); LCMS: ret. time: 14.92 min.; purity: 99%; MS (m/e): 481 (MH+).

7.3.539 N4-(3,4-Ethylenedioxyphenyl)-5-fluoro-N2-[3-(N-2-hydroxy-1,1-dimethylethylamino)carboxymethyleneoxyphenyl]-2,4-pyrimidinediamine (R926764)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-(3-methoxycarbonylmethyleneoxyphenyl)-2,4-pyrimidinediamine and 2-amino-2-methylpropanol gave N4-(3,4-ethylenedioxyphenyl)-5-fluoro-N2-[3-(N-2-hydroxy-1,1-dimethylethylamino)carboxymethyleneoxy]phenyl]-2,4-pyrimidinediamine. $^1$H NMR (CDCl$_3$): δ 7.95 (d, 1H, J=2.7 Hz), 7.47 (t, 1H, J=2.4 Hz), 7.20 (t, 1H, J=8.1 Hz), 7.03 (dd, 1H, J=1.2 and 8.1 Hz), 6.98 (dd, 1H, J=3 and 8.2 Hz), 6.93 (s, 1H), 6.84 (d, 1H, J=8.7 Hz), 6.66 (d, 1H, J=3 Hz), 6.57 (bs, 1H), 6.53 (m, 1H), 4.65 (m, 1H), 4.39 (s, 2H), 4.28 (s, 4H), 3.63 (d, 2H, J=5.7 Hz), 1.31 (s, 6H); LCMS: ret. time: 19.19 min.; purity: 89%; MS (m/e): 484 (MH+).

7.3.540 N2-[3-(N-Cyclohexylamino)carbonylmethyleneoxyphenyl]-N4-(3,4-ethylenedioxyphenyl)-5-fluoro-2,4-pyrimidinediamine (R926765)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-[3-methoxycarbonylmethyleneoxyphenyl)-2,4-pyrimidinediamine and cyclohexylamine gave N2-[3-(N-cyclohexylamino)carbonyl methyleneoxyphenyl]-N4-(3,4-ethylenedioxyphenyl)-5-fluoro-2,4-pyrimidinediamine. $^1$H NMR (CDCl$_3$): δ 7.94 (d, 1H, J=3.3 Hz), 7.41 (t, 1H, J=2.4 Hz), 7.28 (d, 1H, J=2.4 Hz), 7.20 (t, 1H, J=7.5 Hz), 7.04 (dd, 1H, J=1.2 and 8.1 Hz), 6.95 (m, 2H), 6.85 (d, 1H, J=8.7 Hz), 6.68 (d, 1H, J=3.0 Hz), 6.53 (dd, 1H, J=2.4 and 8.4 Hz), 6.45 (bd, 1H, J=8.1 Hz), 4.43 (s, 2H), 4.24 (s, 4H), 3.85 (m, 1H), 1.90 (m, 2H), 1.75-1.55 (m, 2H), 1.45-1.05 (m, 6H); LCMS: ret. time: 23.70 min.; purity: 97%; MS (m/e): 494 (MH+).

7.3.541 N4-(3,4-Ethylenedioxyphenyl)-5-fluoro-N2-[3-[N-methyl-N-(2-hydroxyethyl)amino]carbonylmethyleneoxyphenyl]-2,4-pyrimidinediamine (R926766)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-[3-methoxycarbonylmethyleneoxyphenyl)-2,4-pyrimidinediamine and N-methyl-N-2-hydroxyethylamine gave N4-(3,4-ethylenedioxyphenyl)-5-fluoro-N2-[3-[N-methyl-N-(2-hydroxyethyl)amino]carbonylmethyleneoxyphenyl]-2,4-pyrimidinediamine. $^1$H NMR (CDCl$_3$): δ 7.93 (d, 1H, J=3 Hz), 7.92 (bs, 1H), 7.35 (t, 1H, J=2.4 Hz), 7.18 (m, 1H), 7.06 (dd, 1H, J=1.2 and 8.7 Hz), 6.97 (t, 1H, J=2.4 Hz), 6.94 (m, 1H), 6.85 (d, 1H, J=8.7 Hz), 6.70 (bd, 1H), 6.59 (dd, 1H, J=1.8 and 8.1 Hz), 4.66 (s, 2H), 4.28 (s, 4H), 3.79 (t, 2H, J=5.4 Hz), 3.56 (t, 3H, J=5.4 Hz), 3.10 (s, 3H); LCMS: ret. time: 16.64 min.; purity: 97%; MS (m/e): 470 (MH$^+$).

7.3.542 N4-(3,4-Ethylenedioxyphenyl)-5-fluoro-N2-[2-(N-homopiperazino)carbonylbenzofuran-5-yl]-2,4-pyrimidinediamine (R926767)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-(2-methoxycarbonylbenzofuran-5-yl)-2,4-pyrimidinediamine and homopiperazine gave N4-(3,4-ethylenedioxyphenyl)-5-fluoro-N2-(2-homopiperazinocarbonylbenzofuran-5-yl)-2,4-pyrimidinediamine. $^1$H NMR (DMSO-d6): δ 9.27 (s, 1H), 9.17 (d, 1H, J=1.2 Hz), 8.14 (s, 1H), 8.05 (d, 1H, J=3.6 Hz), 7.54-7.46 (m, 2H), 7.30 (d, 1H, J=2.4 Hz), 7.24 (s, 1H), 7.17 (dd, 1H, J=2.4 and 8.7 Hz), 6.80 (d, 1H, J=8.7 Hz), 4.22 (s, 4H), 3.79 (m, 2H), 3.65 (m, 2H), 3.01 (m, 2H), 2.89 (m, 2H), 1.90 (m, 1H), 1.80 (m, 1H); $^{19}$F NMR (DMSO-d6): −46687; LCMS: ret. time: 14.99 min.; purity: 77%; MS (m/e): 505 (MH$^+$).

7.3.543 N4-(3,4-Ethylenedioxyphenyl)-N2-[3-(N,N-dimethylamino)carbonylmethyleneoxyphenyl]-5-fluoro-2,4-pyrimidinediamine (R925755)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-(3-methoxycarbonylmethyleneoxyphenyl)-2,4-pyrimidinediamine and N,N-dimethylamine hydrochloride gave N4-(3,4-ethylenedioxyphenyl)-N2-[3-(N,N-dimethylamino)carbonylmethyleneoxyphenyl]-5-fluoro-2,4-pyrimidinediamine. $^1$H NMR (DMSO-d6): δ 9.16 (d, 1H, J=1.2 Hz), 9.15 (s, 1H), 8.04 (d, 1H), J=5.6 Hz), 7.30-7.21 (m, 4H), 7.06 (t, 1H, J=9 Hz), 6.78 (d, 1H, J=9 Hz), 6.43 (m, 1H), 4.65 (s, 2H), 4.21 (s, 4H), 2.94 (s, 3H), 2.82 (s, 3H); LCMS: ret. time: 18.70 min.; purity: 83%; MS (m/e): 440 (MH$^+$).

7.3.544 N2-[3-[N,N-Bis-(2-hydroxyethylamino)]carbonylmethyleneoxyphenyl]-N4-(3,4-ethylenedioxyphenyl)-5-fluoro-2,4-pyrimidinediamine (R926781)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-(3-methoxycarbonylmethyleneoxyphenyl)-2,4-pyrimidinediamine and N,N-bis(hydroxyethyl)amine gave N2-[3-[N,N-bis-(2-hydroxyethylamino)]carbonylmethyleneoxyphenyl]-N4-(3,4-ethylenedioxyphenyl)-5-fluoro-2,4-pyrimidinediamine. $^1$H NMR (CD$_3$OD): δ 7.86 (d, 1H, J=3.6 Hz), 7.25 (m, 2H), 7.17-7.03 (m, 3H), 6.78 (d, 1H, J=9 Hz), 6.58 (bd, 1H), 4.80 (s, 2H), 4.23 (s, 4H), 3.71 (t, 4H, J=4.8 Hz), 3.53 (t, 2H, J=6 Hz), 3.49 (t, 3H, J=5.4 Hz); LCMS: ret. time: 16.25 min.; purity: 94%; MS (m/e): 500 (MH$^+$).

7.3.545 N2-[3-(N-2,3-Dihydroxypropylamino) carbonylmethyleneoxyphenyl]-N4-(3,4-ethylenedioxyphenyl)-5-fluoro-2,4-pyrimidinediamine (R926782)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-[3-methoxycarbonylmethyleneoxyphenyl)-2,4-pyrimidinediamine and 2,3-dihydroxypropylamine gave N2-[3-(N-2,3-dihydroxypropylamino)carbonylmethyleneoxyphenyl]-N4-(3,4-ethylenedioxyphenyl)-5-fluoro-2,4-pyrimidinediamine. $^1$H NMR (CD$_3$OD): δ 7.86 (d, 1H, J=4.2 Hz), 7.37 (t, 1H, J=1.8 Hz), 7.24 (d, 1H, J=2.4 Hz), 7.14 (m, 2H), 7.09 (dd, 1H, J=2.4 and 9 Hz), 6.78 (d, 1H, J=8.7 Hz), 6.59 (m, 1H), 4.39 (s, 2H), 4.22 (s, 4H), 3.73 (m, 1H), 3.48 (m, 4H); $^{19}$F NMR (CD$_3$OD): −47575; LCMS: ret. time: 15.97; purity: 98%; MS (m/e): 486 (MH$^+$).

7.3.546 N2-[2-(N-2,3-Dihydroxypropylamino)carbonylbenzofuran-5-yl]-N4-(3,4-ethylenedioxyphenyl)-5-fluoro-2,4-pyrimidinediamine (R926783)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-(2-methoxycarbonylbenzofuran-5-yl)-2,4-pyrimidinediamine and 2,3-dihydroxypropylamine gave N2-[2-(N-2,3-dihydroxypropylamino)carbonylbenzofuran-5-yl]-N4-(3,4-ethylenedioxyphenyl)-5-fluoro-2,4-pyrimidinediamine. $^1$H NMR (CD$_3$OD): δ 7.86 (d, 1H, J=4.2 Hz), 7.35 (t, 1H, J=1.2 Hz), 7.24 (d, 1H, J=3 Hz), 7.15 (m, 2H), 7.07 (dd, 1H, J=2.1 and 8.7 Hz), 6.78 (d, 1H, J=8.7 Hz), 6.59 (m, 1H), 4.40 9s, 1H), 4.23 (s, 4H), 4.03 (t, 1H, J=5.7 Hz), 3.67 (d, 2H, 3.6 Hz), 3.65 (d, 2H, J=4.2 Hz); $^{19}$F NMR (CD$_3$OD): −47578; LCMS: ret. time: 15.72 min.; purity: 99%; MS (m/e): 486 (MH$^+$).

7.3.547 N2-[3-(N-1,3-Dihydroxy-2-propylamino) carbonylmethyleneoxyphenyl]-N4-(3,4-ethylenedioxyphenyl)-5-fluoro-2,4-pyrimidinediamine (R926784)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-(3-methoxycarbonylmethylenedioxyphenyl)-2,4-pyrimidinediamine and 2-amino-1,3-propanediol gave N2-[3-(N-1,3-dihydroxy-2-propylamino)carbonylmethyleneoxyphenyl]-N4-(3,4-ethylenedioxyphenyl)-5-fluoro-2,4-pyrimidinediamine. $^1$H NMR (CD$_3$OD): δ 8.08 (bd, 1H), 7.86 (bs, 1H), 7.44 (s, 2H), 7.39 (s, 1H), 7.29 (d, 1H, J=2.4 Hz), 6.97 (dd, 1H, J=2.4 and 8.7 Hz), 6.78 (d, 1H, J==8.7 Hz), 4.24 (s, 4H), 3.84 (m, 1H), 3.56 (m, 2H), 3.44 (m, 2H); LCMS: ret. time: 16.63 min.; purity: 97%; MS (m/e): 496 (MH$^+$).

7.3.548 N2-[2-(N-1,3-Dihydroxy-2-propylamino) carbonylbenzofuran-5-yl]-N4-(3,4-ethylenedioxyphenyl)-5-fluoro-2,4-pyrimidinediamine (R926785)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-(2-methoxycarbonylbenzofuran-5-yl)-2,4-pyrimidinediamine and 2-amino-1,3-propanediol gave N2-[2-(N-1,3-dihydroxy-2-propylamino)carbonylbenzofuran-5-yl]-N4-(3,4-ethylenedioxyphenyl)-5-fluoro-2,4-pyrimidinediamine. $^1$H NMR (CD$_3$OD): δ 8.08 (t, 1H, J=1.8 Hz), 7.86 (d, 1H, J=3.9 Hz), 7.45 (s, 2H), 7.41 (s, 1H), 7.29 (d, 1H, J=2.4 Hz), 6.97 (dd, 1H, J=3 and 8.7 Hz), 6.77 (d, 1H, J=8.7 Hz), 4.24 (s, 4H), 4.19 (t, 1H, J=5.7 Hz), 3.75 (d, 4H, J=5.4 Hz); $^{19}$F NMR (CD$_3$OD): −47745; LCMS: ret. time: 15.09 min., purity: 97%; MS (m/e): 496 (MH$^+$).

7.3.549 N4-(3-Chloro-4-hydroxy-5-methylphenyl)-5-fluoro-N2-[3-(N-morpholino)carbonylmethyleneoxyphenyl]-2,4-pyrimidinediamine (R940265)

In like manner to the preparation of N4-(ethylenedioxyphenyl)-5-fluoro-N2-[3-(N-methylamino)carbonylmethyleneoxyphenyl]-2,4-pyrimidinediamine, the reaction of N4-(3-chloro-4-hydroxy-5-methylphenyl)-N2-(3-ethoxycarbonylmethyleneoxyphenyl)-5-fluoro-2,4-pyrimidinediamine with morpholine gave N4-(3-chloro-4-hydroxy-5-methylphenyl)-5-fluoro-N2-[3-(N-morpholino)carbonylmethyleneoxyphenyl]-2,4-pyrimidinediamine. LCMS: ret. time: 18.66 min.; purity: 92%; MS (m/e): 487 (M$^+$), 489 (MH$^+$); $^1$H NMR (DMSO-d6): 9.28 (2H, s), 9.01 (1H, s), 8.17 (1H, d, J=3.6 Hz), 7.65 (1H, d, J=2.4 Hz), 7.5 (1H, d, J=2.7 Hz), 7.42 (1H, d, J=6.6 Hz), 7.29 (1H, s), 7.18 (1H, t, J=8.1 Hz), 6.57 (1H, dd, J=6.6 and 2.2 Hz), 4.79 (2H, s), 3.67 (4H, m), 3.52 (4H, m), 2.29 (3H, s).

7.3.550 N4-(3,5-Dichloro-4-hydroxyphenyl)-5-fluoro-N2-[3-(N-morpholino)carbonylmethyleneoxyphenyl]-2,4-pyrimidinediamine (R950187)

N4-(3,5-Dichlorophenyl-4-hydroxy)-N2-(3-ethoxycarbonylmethyleneoxyphenyl)-5-fluoro-2,4-pyrimidinediamine (0.5 g, 1.1 mmol) was dissolved in EtOH:morpholine (4 ml: 4 ml) and the mixture was refluxed for 1 day (100° C. oil-bath temperature). The mixture was cooled to 22° C., diluted with water and brine, filtered, and dried under reduced pressure to give N4-(3,5-dichloro-4-hydroxyphenyl)-5-fluoro-N2-[3-(N-morpholino)carbonylmethyleneoxyphenyl]-2,4-pyrimidinediamine. $^1$H NMR (DMSO-d6): δ 9.35 (s, 1H), 9.22 (s, 1H), 8.09 (d, 1H, J=3.6 Hz), 7.94 (m, 1H), 7.75 (m, 1H), 7.27 (m, 1H), 7.18 (m, 1H), 7.12 (t, 1H, J=8.4 Hz), 6.44 (m, 1H), 4.64 (s, 2H), 3.39 (m, 4H), 2.68 (m, 4H); LCMS purity: 92.6%; MS (m/e): 507.89 (M$^+$, 100).

7.3.551 N4-(3,5-Dichloro-4-hydroxyphenyl)-5-fluoro-N2-[3-(N-piperazino)carbonylmethyleneoxyphenyl]-2,4-pyrimidinediamine (R950188)

In like manner to the preparation of N4-(3,5-dichloro-4-hydroxyphenyl)-5-fluoro-N2-[3-(N-morpholino)carbonylmethyleneoxyphenyl]-2,4-pyrimidinediamine, N4-(3,5-dichloro-4-hydroxyphenyl)-N2-(3-ethoxycarbonylmethyleneoxyphenyl)-5-fluoro-2,4-pyrimidinediamine and piperazine were reacted to prepare N4-(3,5-dichloro-4-hydroxyphenyl)-5-fluoro-N2-[3-(N-piperazino)carbonylmethyleneoxyphenyl]-2,4-pyrimidinediamine. LCMS: ret. time: 15.26 min.; purity: 88.5%; MS (m/e): 506.89 (MH$^+$).

7.3.552 N2-(3,4-Ethylenedioxyphenyl)-5-fluoro-N4-[3-(N-methylamino)carbonylmethyeleneoxyphenyl]-2,4-pyrimidinediamine (R926776)

In like manner to the preparation of N4-(ethylenedioxyphenyl)-5-fluoro-N2-[3-(N-methylamino)carbonylmethyleneoxyphenyl]-2,4-pyrimidinediamine, the reaction of N4-(3-ethoxycarbonylmethyleneoxyphenyl)-N2-(3,4-ethylenedioxyphenyl)-5-fluoro-2,4-pyrimidinediamine with methylamine hydrochloride gave N2-(3,4-ethylenedioxyphenyl)-5-fluoro-N4-[3-(N-methylamino)carbonylmethyeleneoxyphenyl]-2,4-pyrimidinediamine. LCMS: ret. time: 16.94 min.; purity: 73%; MS (m/e): 426 (MH$^+$).

7.3.553 N2-(3,4-Ethylenedioxyphenyl)-5-fluoro-N4-(4-methylaminocarbonylmethyleneoxyphenyl)-2,4-pyrimidinediamine (R945173)

In a manner analogous to the preparation of 5-fluoro-N4-(3-hydroxyphenyl)-N2-(4-methylaminocarbonylmethyleneoxyphenyl)-2,4-pyrimidinediamine, N4-(4-cyanomethyleneoxyphenyl)-N2-(3,4-ethylenedioxyphenyl)-5-fluoro-2,4-pyrimidinediamine and methylamine hydrochloride salt gave N2-(3,4-ethylenedioxyphenyl)-5-fluoro-N4-(4-methylaminocarbonylmethyleneoxyphenyl)-2,4-pyrimidinediamine. $^1$H NMR (acetone-d$_6$): δ 2.80 (d, 3H), 4.21-4.28 (m, 4H), 4.47 (s, 2H), 6.71 (d, J=8.7 Hz, 1H), 6.96 (d, J=9.0 Hz, 2H), 7.06 (dd, J=2.7 and 9.0 Hz, 1H), 7.41 (d, J=2.4 Hz, 1H), 7.74 (d, J=9.0 Hz, 2H), 7.93 (d, J=3.6 Hz, 1H), 8.20 (br, 1H, NH), 8.41 (br, 1H, NH); $^{19}$F NMR (282 MHz, acetone-d$_6$): δ −169.05; LCMS: ret. time: 17.47 min.; purity: 98.99%; MS (m/e): 425.89 (MH$^+$).

7.3.554 N2-[4-(2-N,N-Dimethylaminoethyl)oxyphenyl]-5-fluoro-N4-[3-(N-methylamino)carbonylmethyleneoxyphenyl]-2,4-pyrimidinediamine (R909253)

In like manner to N4-(3,4-ethylenedioxyphenyl)-5-fluoro-N2-(3-hydroxyphenyl)-2,4-pyrimidinediamine, N2-chloro-5-fluoro-N4-[3-(N-methylamino)carbonylmethyleneoxyphenyl]-4-pyrimidineamine and 4-(2-N,N-dimethylaminoethyl)oxyaniline were reacted to yield N2-[4-(2-N,N-dimethylaminoethyl)oxyphenyl]-5-fluoro-N4-[3-(N-methylamino)carbonylmethyleneoxyphenyl]-2,4-pyrimidinediamine. $^1$H NMR (CD$_3$OD): δ 8.0 (d, 1H J=4 Hz), 7.42 (m, 2H), 7.24 (m, 2H), 7.05 (m, 2H), 6.85 (m, 1H), 4.39 (s, 2H), 4.30 (m, 2H), 3.66 (m, 2H), 3.04 (s, 6H), 2.83 (s, 3H); LCMS: ret. time: 14.0 min.; purity: 96%; MS (m/e): 455 (MH$^+$).

7.3.555 N2-(1,4-Benzoxazin-6-yl)-5-fluoro-N4-[3-(N-methylamino)carbonylmethyleneoxyphenyl]-2,4-pyrimidinediamine (R909247)

In like manner to N4-(3,4-ethylenedioxyphenyl)-5-fluoro-N2-(3-hydroxyphenyl)-2,4-pyrimidinediamine, N2-chloro-5-fluoro-N4-[3-(N-methylamino)carbonylmethyleneoxyphenyl]-4-pyrimidineamine and 6-amino-1,4-benzoxazine were reacted to yield N2-(1,4-benzoxazin-6-yl)-5-fluoro-N4-[3-(N-methylamino)carbonylmethyleneoxyphenyl]-2,4-pyrimidinediamine. $^1$H (DMSO-d6): δ 8.0 (d, 1H), 7.6 (m, 1H), 7.42 (m, 1H), 7.20 (m, 1H), 6.95 (m, 1H), 6.76 (m, 1H), 6.56 (m, 1H), 4.43 (s, 2H), 4.05 (m, 2H), 3.25 (s, 3H), 3.13 (m, 2H); LCMS: ret time: 17.67 min.; MS (m/e): 425 (MH$^+$).

7.3.556 N2-(4-Dihydrobenzofuranyl)-5-fluoro-N4-[3-(N-methylamino)carbonylmethyleneoxyphenyl]-2,4-pyrimidinediamine (R909249)

In like manner to N4-(3,4-ethylenedioxyphenyl)-5-fluoro-N2-(3-hydroxyphenyl)-2,4-pyrimidinediamine, N2-chloro-5-fluoro-N4-[3-(N-methylamino)carbonylmethyleneoxyphenyl]-4-pyrimidineamine and 5-amino-2,3-dihydrobenzofuran were reacted to yield N2-(4-dihydrobenzofuranyl)-5-fluoro-N4-[3-(N-methylamino)carbonylmethyleneoxyphenyl]-2,4-pyrimidinediamine. $^1$H NMR (DMSO-d6): δ 8.09 (d, 1H), 8.00 (m, 1H), 7.42 (m, 2H), 7.05 (m, 1H), 6.96 (m, 1H), 6.76 (m, 1H), 6.58 (m, 1H), 4.53 (m, 2H), 4.25 (s, 2H), 3.15 (m, 2H), 2.70 (m, 3H); LCMS: ret time: 19.24 min; MS (m/e): 410 (MH⁺).

7.3.557 N2-(3-tert-Butylphenyl)-N4-[3-(N-methylamino)carbonylmethyleneoxyphenyl]-5-fluoro-2,4-pyrimidinediamine (R940267)

In like manner to the preparation of N4-(ethylenedioxyphenyl)-5-fluoro-N2-[3-(N-methylamino)carbonylmethyleneoxyphenyl]-2,4-pyrimidinediamine, the reaction of N2-(3-tert-butylphenyl)-N4-(3-ethoxycarbonylmethyleneoxyphenyl)-5-fluoro-2,4-pyrimidinediamine with methylamine hydrochloride gave N2-(3-tert-butylphenyl)-N4-[3-(N-methylamino)carbonylmethyleneoxyphenyl]-5-fluoro-2,4-pyrimidinediamine. LCMS: ret. time: 22.22 min.; purity: 97%; MS (m/e): 424 (MH⁺); ¹H NMR (CDCl₃): δ 7.98 (2H, m), 7.76 (2H, m), 7.56 (1H, t, J=1.3 Hz), 7.28-7.22 (1H, m), 7.04 (1H, d, J=7.8 Hz), 6.90 (1H, dd, J=9 Hz, J=1.3 Hz), 6.80 (1H, 2.6 Hz), 6.66 (1H, dd, J=9 and 2.6 Hz), 6.46 (1H, s), 4.53 (2H, s), 2.88 (3H, d, J=5.1 Hz), 1.31 (9H, s).

7.3.558 N2-(3,4-Ethylenedioxyphenyl)-5-fluoro-N4-[2-(N-methylamino)carbonylbenzofuran-5-yl]-2,4-pyrimidinediamine (R926491)

In like manner to the preparation of N4-(ethylenedioxyphenyl)-5-fluoro-N2-[3-(N-methylamino)carbonylmethyleneoxyphenyl]-2,4-pyrimidinediamine, the reaction of N2-(3,4-ethylenedioxyphenyl)-N4-(2-methoxycarbonylbenzofuran-5-yl)-5-fluoro-2,4-pyrimidinediamine with methylamine hydrochloride gave N2-(3,4-ethylenedioxyphenyl)-5-fluoro-N4-[2-(N-methylamino)carbonylbenzofuran-5-yl]-2,4-pyrimidinediamine. ¹H NMR (CD₃OD): δ 8.10 (s, 1H), 7.94 (d, 1H, J=5.1 Hz), 7.59 (s, 2H), 7.44 (s, 1H), 6.96 (d, 1H, J=2.4 Hz), 6.82 (d, 1H, J=8.4 Hz), 6.76 (dd, 1H, J=3.6 and 8.1 Hz), 4.22 (s, 2H), 4.21 (s, 2H), 2.95 (s, 3H); LCMS: ret. time: 17.76 min.; purity: 97%; MS (m/e): 436 (MH⁺).

7.3.559 N2-(3,5-Dimethoxyphenyl)-N4-[3-(N-methylamino)carbonylmethyleneoxyphenyl)-5-fluoro-2,4-pyrimidinediamine (R926810)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of N2-(3,5-dimethoxyphenyl)-N4-(3-ethoxycarbonylmethyleneoxyphenyl)-5-fluoro-2,4-pyrimidinediamine with methylamine hydrochloride gave N2-(3,5-dimethoxyphenyl)-N4-[3-(N-methylamino)carbonylmethyleneoxyphenyl)-5-fluoro-2,4-pyrimidinediamine. ¹H NMR (CD₃OD): δ 7.93 (d, 1H, J=3.9 Hz), 7.72 (t, 1H, J=1.8 Hz), 7.27-7.19 9m, 2H), 6.88 (d, 2H, J=2.4 Hz), 6.72 (m, 1H), 6.01 (t, 1H, J=2.4 Hz), 4.44 (s, 2H), 3.67 (s, 6H), 2.80 (s, 3H).

7.3.560 5-Bromo-N2-(3,4-ethylenedioxyphenyl)-N4-[4-(N-methylamino)carbonylmethyleneoxyphenyl]-2,4-pyrimidinediamine (R925851)

In a manner similar to the preparation of N4-(3,4-ethylenedioxyphenyl)-5-fluoro-N2-[3-(N-methylamino)carbonylmethyleneoxyphenyl]-2,4-pyrimidinediamine, 5-bromo-N2-(3,4-ethylenedioxyphenyl)-N4-(4-methoxycarbonylmethyleneoxyphenyl)-2,4-pyrimidinediamine and methylamine hydrochloride were reacted to yield 5-bromo-N2-(3,4-ethylenedioxyphenyl)-N4-[4-(N-methylamino)carbonylmethyleneoxyphenyl]-2,4-pyrimidinediamine. ¹H NMR (CD₃OD): δ 8.01 (s, 1H), 7.48 (d, 2H, J=8.7 Hz), 7.09 (d, 1H, J=3.0 Hz), 7.08 (d, 2H, J=8.7 Hz), 6.81 (dd, 1H, J=8.7 Hz), 6.64 (d, 1H, J=8.7 Hz), 4.52 (s, 2H), 4.20 (bs, 4H), 2.83 (s, 3H); LCMS: ret. time: 19.13 min.; purity: 94%; MS (m/e): 487 (MH⁺).

7.3.561 N2-(3-Hydroxyphenyl)-5-trifluoromethyl-N4-[3-(N-methylamino)carbonylmethyleneoxyphenyl]-2,4-pyrimidinediamine (R926741)

In a manner similar to the preparation of N4-(3,4-ethylenedioxyphenyl)-5-fluoro-N2-[3-(N-methylamino)carbonylmethyleneoxyphenyl]-2,4-pyrimidinediamine, N2-(3-hydroxyphenyl)-5-trifluoromethyl-N4-(3-N-methoxycarbonylmethyleneoxyphenyl)-2,4-pyrimidinediamine and methylamine hydrochloride were reacted to yield N2-(3-hydroxyphenyl)-5-trifluoromethyl-N4-[3-(N-methylamino)carbonylmethyleneoxyphenyl]-2,4-pyrimidinediamine. LCMS: ret. time: 18.52 min.; purity: 96%; MS (m/e): 434 (MH⁺).

7.3.562 N2,N4-Bis[4-(N-n-butylamino)carbonylmethyleneoxyphenyl]-5-cyano-2,4-pyrimidinediamine (R925860)

In a manner similar to the preparation of N4-(3,4-ethylenedioxyphenyl)-5-fluoro-N2-[3-(N-methylamino)carbonylmethyleneoxyphenyl]-2,4-pyrimidinediamine, N2,N4-bis(4-ethoxycarbonylmethyleneoxyphenyl)-5-cyano-2,4-pyrimidinediamine and n-butylamine were reacted to yield N2,N4-bis[4-(N-n-butylamino)carbonylmethyleneoxyphenyl]-5-cyano-2,4-pyrimidinediamine. ¹H NMR (DMSO-d6): δ 9.77 (bs, 1H), 9.38 (bs, 1H), 8.42 (s, 1H), 8.09 (t, 1H, J=5.4 Hz), 8.02 (t, 1H, J=5.7 Hz), 7.48-7.34 (m, 4H), 6.93 (d, 2H, J=9.3 Hz), 6.82-6.72 (m, 2H), 4.47 (s, 2H), 4.38 (s, 2H), 3.14-3.06 (m, 4H), 1.42-1.33 (m, 4H), 1.28-1.18 (m, 4H), 0.83 (t, 6H, J=6.9 Hz); LCMS: ret. time: 26.40 min.; purity: 97%; MS (m/e): 546 (MH⁺).

7.3.563 N2,N4-Bis[4-(N-isopropylamino)carbonylmethyleneoxyphenyl]-5-cyano-2,4-pyrimidinediamine (R925861)

In a manner similar to the preparation of N4-(3,4-ethylenedioxyphenyl)-5-fluoro-N2-[3-(N-methylamino)carbonylmethyleneoxyphenyl]-2,4-pyrimidinediamine, N2,N4-bis(4-ethoxycarbonylmethyleneoxyphenyl)-5-cyano-2,4-pyrimidinediamine and isopropylamine were reacted to yield N2,N4-bis[4-(N-isopropylamino)carbonylmethyleneoxyphenyl]-5-cyano-2,4-pyrimidinediamine. ¹H NMR (DMSO-d6): δ 8.41 (s, 1H), 7.90 (d, 1H, J=7.5 Hz), 7.81 (d, 1H, J=7.5 Hz), 7.50-7.36 (m, 4H), 6.93 (d, 2H, J=8.7 Hz), 6.84-6.75 (m, 2H), 4.45 (s, 2H), 4.36 (s, 2H), 3.99-3.87 (m, 2H), 1.08 (d, 6H, J=3.0 Hz), 1.06 (d, 6H, J=2.4 Hz); LCMS: ret. time: 23.45 min.; purity: 89%; MS (m/e): 518 (MH⁺).

7.3.564 N2,N4-Bis[4-(N-n-propylamino)carbonylmethyleneoxyphenyl]-5-cyano-2,4-pyrimidinediamine (R925853)

In a manner similar to the preparation of N4-(3,4-ethylenedioxyphenyl)-5-fluoro-N2-[3-(N-methylamino)carbonylmethyleneoxyphenyl]-2,4-pyrimidinediamine, N2,N4-bis(4-ethoxycarbonylmethyleneoxyphenyl)-5-cyano-2,4-pyrimidinediamine and n-propyl amine were reacted to yield N2,N4-bis[4-(N-n-propylamino)carbonylmethyleneoxyphenyl]-5-cyano-2,4-pyrimidinediamine. $^1$H NMR (DMSO-d6): δ 9.78 (bs, 1H), 9.38 (bs, 1H), 8.41 (s, 1H), 8.07 (dt, 2H, J=6.0 and 22.5 Hz), 7.48-7.36 (m, 4H), 6.93 (d, 2H, J=8.7 Hz), 6.78 (d, 2H, J=8.1 Hz), 4.48 (s, 2H), 4.39 (s, 2H), 3.07 (2q, 4H, J=7.2 Hz), 1.47-1.38 (m, 4H), 0.90-0.77 (m, 6H); LCMS: ret. time: 23.67 min.; purity: 94%; MS (m/e): 519 (MH$^+$).

7.3.565 N2,N4-Bis[4-(N-morphonlino)carbonylmethyleneoxyphenyl]-5-cyano-2,4-pyrimidinediamine (R925854)

In a manner similar to the preparation of N4-(3,4-ethylenedioxyphenyl)-5-fluoro-N2-[3-(N-methylamino)carbonylmethyleneoxyphenyl]-2,4-pyrimidinediamine, N2,N4-bis(4-ethoxycarbonylmethyleneoxyphenyl)-5-cyano-2,4-pyrimidinediamine and morpholine were reacted to yield N2,N4-bis[4-(N-morphonlino)carbonylmethyleneoxyphenyl]-5-cyano-2,4-pyrimidinediamine. $^1$H NMR (DMSO-d6): δ 9.78 (bs, 1H), 9.31 (bs, 1H), 8.41 (s, 1H), 7.43 (d, 4H, J=8.1 Hz), 6.89 (d, 2H, J=9.3 Hz), 6.75 (d, 2H, J=8.4 Hz), 4.84 (s, 2H), 4.74 (s, 2H), 3.76 (t, 4H, J=5.1 Hz), 3.62-3.50 (m, 4H), 3.49-3.38 (m, 4H), 3.08-3.01 (m, 4H); LCMS: ret. time: 19.25 min.; purity: 89%; MS (m/e): 574 MH$^+$).

7.3.566 N2,N4-Bis[4-(N-piperidino)carbonylmethyleneoxyphenyl]-5-cyano-2,4-pyrimidinediamine (R925855)

In a manner similar to the preparation of N4-(3,4-ethylenedioxyphenyl)-5-fluoro-N2-[3-(N-methylamino)carbonylmethyleneoxyphenyl]-2,4-pyrimidinediamine, N2,N4-bis(4-ethoxycarbonylmethyleneoxyphenyl)-5-cyano-2,4-pyrimidinediamine and piperidine were reacted to yield N2,N4-bis[4-(N-piperidino)carbonylmethyleneoxyphenyl]-5-cyano-2,4-pyrimidinediamine. $^1$H NMR (acetone-d$_6$): δ 8.86 (bs, 1H), 8.48 (bs, 1H), 8.34 (s, 1H), 7.61-7.50 (m, 4H), 6.98 (d, 2H, J=8.7 Hz), 6.90 (d, 2H, J=9.3 Hz), 4.84 (s, 2H), 4.75 (s, 2H), 3.59-3.48 (m, 8H), 1.68-1.44 (m, 12H); LCMS: ret. time: 24.76 min.; purity: 98%; MS (m/e): 571 (MH$^+$).

7.3.567 N2,N4-Bis[4-(N-cyclopropylmethylamino)carbonylmethyleneoxyphenyl]-5-cyano-2,4-pyrimidinediamine (R925859)

In a manner similar to the preparation of N4-(3,4-ethylenedioxyphenyl)-5-fluoro-N2-[3-(N-methylamino)carbonylmethyleneoxyphenyl]-2,4-pyrimidinediamine, N2,N4-bis(4-ethoxycarbonylmethyleneoxyphenyl)-5-cyano-2,4-pyrimidinediamine and cyclopropylmethylamine were reacted to yield N2,N4-bis[4-(N-cyclopropylmethylamino)carbonylmethyleneoxyphenyl]-5-cyano-2,4-pyrimidinediamine. $^1$H NMR (DMSO-d6): δ 9.78 (bs, 1H), 9.36 (bs, 1H), 8.41 (s, 1H), 8.18 (t, 1H, J=5.1 Hz), 8.10 (t, 1H, J=5.1 Hz), 7.52-7.38 (m, 4H), 6.94 (d, 2H, J=8.7 Hz), 6.84-6.76 (m, 2H), 4.48 (s, 2H), 4.40 (s, 2H), 3.00 (q, 4H, J=6.3 Hz), 0.97-0.88 (m, 2H), 0.40-0.33 (m, 4H), 0.18-0.03 (m, 4H); $^{19}$F NMR (CDCl$_3$): LCMS: ret. time: 24.58 min.; purity: 100%; MS (m/e): 543 (MH$^+$)

7.3.568 N4-(3-Aminophenyl)-N2-(1,4-benzoxazin-6-yl)-5-fluoro-2,4-pyrimidinediamine (R950254)

N4-(3-Nitrophenyl)-N2-[(2H) 1,4-benzoxazin-3(4H)-one-6-yl]-5-fluoro-2,4-pyrimidinediamine (940 mg, 2.5 mmol) and Pd/C10% (300 mg, 50% water content) were suspended in EtOH (7 mL) and 10% aqueous HCl (5 mL) and hydrogenated in a Parr apparatus for 3 hours (22° C., 60 psi). The suspension was filtered over celite and neutralized by addition of K$_2$CO$_3$. The solvents were removed and the resulting black slurry was suspended in MeOH. Silica gel (4 g) was added and the volatiles were removed under reduced pressure. The residue was subjected to column chromatography on silica gel (CHCl$_3$-Acetone, 2:1) to give 186 mg of N4-(3-aminophenyl)-N2-(1,4-benzoxazin-6-yl)-5-fluoro-2,4-pyrimidinediamine as brownish solid. $^1$H NMR (DMSO-d6): δ 8.92 (s, 1H), 8.64 (s, 1H), 7.95 (d, 1H, J=3.6 Hz), 7.11 (s, 1H), 6.84-6.95 (m, 3H), 6.66 (dd, 1H, J=2.4, 9.0 Hz), 6.46 (d, 1H, J=8.1 Hz), 6.28 (d, 1H, J=8.1 Hz), 5.62 (s, 1H), 4.98 (s, 2H), 4.03 (m, 2H), 3.31 (m, 2H); LCMS purity: 98.4%; MS (m/e): 352.7 (M$^+$, 100).

7.3.569 N4-(3,4-Ethylenedioxyphenyl)-5-fluoro-N2-[3-(N-2-morpholinoethyleneamino)carbonylmethyleneaminophenyl]-2,4-pyrimidinediamine (R950200)

N2-(3-Ethoxycarbonylmethyleneaminophenyl)-N4-(3,4-ethylenedioxyphenyl)-5-fluoro-2,4-pyrimidinediamine (50 mg, 0.11 mmol) was dissolved in EtOH:4-(2-aminoethyl)morpholine (0.5 ml: 0.5 ml) and the mixture was refluxed for 3 hours (100° C. oil-bath temperature). The mixture was cooled to 22° C., diluted with water and washed with EtOAc. The organic phase was dried over MgSO$_4$, concentrated under educed pressure, and the residue was subjected to column chromatography on silica gel (CHCl$_3$:Acetone, 2:1) to give N4-(3,4-ethylenedioxyphenyl)-5-fluoro-N2-[3-(N-2-morpholinoethyleneamino) carbonylmethyleneaminophenyl]-2,4-pyrimidinediamine. $^1$H NMR (DMSO-d6+ CD$_3$OD): δ 7.92 (d, 1H, J=4.1 Hz), 7.31 (d, 1H, J=2.3 Hz), 7.20 (dd, 1H, J=2.7, 8.8 Hz), 6.87-6.99 (m, 2H), 6.74 (d, 1H, J=8.8 Hz), 6.09 (m, 1H), 4.19 (m, 4H), 3.38 (m, 4H), 3.16 (t, 2H, J=6.3 Hz), 2.28 (t, 2H, J=6.3 Hz); LCMS purity: 99.2%; MS (m/e): 524.01 (M$^+$, 100).

7.3.570 N4-(3,4-Ethylenedioxyphenyl)-N2-[3-N-methylamino)carbonylmethyleneaminophenyl]-5-fluoro-2,4-pyrimidinediamine (R950191)

In like manner to the preparation of N4-(3,4-ethylenedioxyphenyl)-5-fluoro-N2-[3-(N-morpholinoethyleneamino) carbonylmethyleneaminophenyl]-2,4-pyrimidinediamine, N2-(3-ethoxycarbonylmethyleneaminophenyl)-N4-(3,4-ethylenedioxyphenyl)-5-fluoro-2,4-pyrimidinediamine and methylamine were reacted to prepare N4-(3,4-ethylenedioxyphenyl)-N2-[3-(N-methylamino)carbonylmethyleneaminophenyl]-5-fluoro-2,4-pyrimidinediamine. LCMS: ret. time: 17.32 min.; purity: 99.3%; MS (m/e): 425.04 (MH$^+$).

7.3.571 N2-[3-(N-Amino)carbonylmethyleneaminophenyl]-N4-(3,4-ethylenedioxyphenyl)-5-fluoro-2,4-pyrimidinediamine (R950192)

In like manner to the preparation of N4-(3,4-ethylenedioxyphenyl)-5-fluoro-N2-[3-(N-morpholinoethyleneamino) carbonylmethyleneaminophenyl]-2,4-pyrimidinediamine, N2-(3-ethoxycarbonylmethyleneaminophenyl)-N4-(3,4-ethylenedioxyphenyl)-5-fluoro-2,4-pyrimidinediamine and aqueous ammonia were reacted to prepare N2-[3-(N-amino) carbonylmethyleneaminophenyl]-N4-(3,4-ethylenedioxyphenyl)-5-fluoro-2,4-pyrimidinediamine. LCMS: ret. time: 16.59 min.; purity: 98.8%; MS (m/e): 411.02 (MH$^+$).

7.3.572 N4-(3,4-Ethylenedioxyphenyl)-5-fluoro-N2-[3-(N-morpholino)carbonylmethyleneaminophenyl]-2,4-pyrimidinediamine (R950193)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-N4-(3,4-ethylenedioxyphenyl)-5-fluoro-2,4-pyrimidinediamine and morpholine were reacted to prepare N4-(3,4-ethylenedioxyphenyl)-5-fluoro-N2-[3-(N-morpholino)carbonylmethyleneaminophenyl]-2,4-pyrimidinediamine. LCMS: ret. time: 18.70 min.; purity: 85.8%; MS (m/e): 481.05 (MH$^+$).

7.3.573 N4-(3,4-Ethylenedioxyphenyl)-5-fluoro-N2-[3-(N-(N-methyl)-piperazino)carbonylmethyleneaminophenyl]-2,4-pyrimidinediamine (R950194)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-N4-(3,4-ethylenedioxyphenyl)-5-fluoro-2,4-pyrimidinediamine and N-methylpiperazine were reacted to prepare N4-(3,4-ethylenedioxyphenyl)-5-fluoro-N2-[3-(N-(N-methyl)piperazino)carbonylmethyleneaminophenyl]-2,4-pyrimidinediamine. LCMS: ret. time: 15.75 min.; purity: 99.1%; MS (m/e): 494.06 (MH$^+$).

7.3.574 N4-(3,4-Ethylenedioxyphenyl)-5-fluoro-N2-[3-(N-2-hydroxyethyleneamino)carbonylmethyleneaminophenyl]-5-fluoro-2,4-pyrimidinediamine (R950195)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-N4-(3,4-ethylenedioxyphenyl)-5-fluoro-2,4-pyrimidinediamine and 2-aminoethanol were reacted to prepare N4-(3,4-ethylenedioxyphenyl)-5-fluoro-N2-[3-(N-2-hydroxyethyleneamino)carbonylmethyleneaminophenyl]-5-fluoro-2,4-pyrimidinediamine. LCMS: ret. time: 16.23 min.; purity: 97.3%; MS (m/e): 455.02 (MH$^+$).

7.3.575 N4-(3,4-Ethylenedioxyphenyl)-5-fluoro-N2-[3-(N-methylamino)ethyleneaminocarbonylmethyleneaminophenyl]-2,4-pyrimidinediamine (R950196)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-N4-(3,4-ethylenedioxyphenyl)-5-fluoro-2,4-pyrimidinediamine and N-methyl-ethylen-1,2-diamine were reacted to prepare N4-(3,4-ethylenedioxyphenyl)-5-fluoro-N2-[3-(N-methylamino)ethyleneaminocarbonylmethyleneaminophenyl]-2,4-pyrimidinediamine. LCMS: ret. time: 15.34 min.; purity: 98.2%; MS (m/e): 468.06 (MH$^+$).

7.3.576 N4-(3,4-Ethylenedioxyphenyl)-5-fluoro-N2-[3-(N-piperazino)carbonylmethyleneaminophenyl]-5-fluoro-2,4-pyrimidinediamine (R950197)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-N4-(3,4-ethylenedioxyphenyl)-5-fluoro-2,4-pyrimidinediamine and piperazine were reacted to prepare N4-(3,4-ethylenedioxyphenyl)-5-fluoro-N2-[3-(N-piperazino)carbonylmethyleneaminophenyl]-5-fluoro-2,4-pyrimidinediamine. LCMS: ret. time: 15.38 min.; purity: 93.2%; MS (m/e): 479.99 (MH$^+$).

7.3.577 N2-[3-(N-Benzylamino)ethyleneaminocarbonylmethyleneaminophenyl]-N4-(3,4-ethylenedioxyphenyl)-5-fluoro-2,4-pyrimidinediamine (R950198)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-N4-(3,4-ethylenedioxyphenyl)-5-fluoro-2,4-pyrimidinediamine and N-benzyl-ethylen-1,2-diamine were reacted to prepare N2-[3-(N-benzylamino)ethyleneaminocarbonylmethyleneaminophenyl]-N4-(3,4-ethylenedioxyphenyl)-5-fluoro-2,4-pyrimidinediamine. LCMS: ret. time: 17.70 min.; purity: 92.5%; MS (m/e): 544.04 (MH$^+$).

7.3.578 N2-[3-(N,N'-Bis(2-N-hydroxyethyl)amino)carbonylmethyleneaminophenyl]-N4-(3,4-ethylenedioxyphenyl)-5-fluoro-2,4-pyrimidinediamine (R950199)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-N4-(3,4-ethylenedioxyphenyl)-5-fluoro-2,4-pyrimidinediamine and N,N'-bis(2-hydroxyethylene)amine were reacted to N2-[3-(N,N'-bis(2-N-hydroxyethyl)amino)carbonylmethyleneaminophenyl]-N4-(3,4-ethylenedioxyphenyl)-5-fluoro-2,4-pyrimidinediamine. LCMS: ret. time: 15.81 min.; purity: 99.4%; MS (m/e): 499.01 (MH$^+$).

7.3.579 5-Fluoro-N4-(3-hydroxyphenyl)-N2-[3-(N-methylamino)carbonylmethyleneaminophenyl]-2,4-pyrimidinediamine (R950217)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-5-fluoro-N4-(3-hydroxyphenyl)-2,4-pyrimidinediamine and methylamine were reacted to prepare 5-fluoro-N4-(3-hydroxyphenyl)-N2-[3-(N-methylamino)carbonylmethyleneaminophenyl]-2,4-pyrimidinediamine. LCMS: ret. time: 14.41 min.; purity: 93.0%; MS (m/e): 383.02 (MH$^+$).

7.3.580 N2-(3-Aminocarbonylmethyleneaminophenyl)-5-fluoro-N4-(3-hydroxyphenyl)-2,4-pyrimidinediamine (R950219)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-5-fluoro-N4-(3-hydroxyphenyl)-2,4-pyrimidinediamine and aqueous ammonia were reacted to prepare N2-(3-aminocarbonylmethyleneaminophenyl)-5-fluoro-N4-(3-hydroxyphenyl)-2,4-pyrimidinediamine. LCMS: ret. time: 14.23 min.; purity: 95.0%; MS (m/e): 369.03 (MH$^+$).

7.3.581 N2-[3-(N,N-Dimethylamino)carbonylmethyleneaminophenyl]-5-fluoro-N4-(3-hydroxyphenyl)-2,4-pyrimidinediamine (R950220)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-5-fluoro-N4-(3-hydroxyphenyl)-2,4-pyrimidinediamine and dimethylamine were reacted to prepare N2-[3-(N,N-dimethylamino)carbonylmethyleneaminophenyl]-5-fluoro-N4-(3-hydroxyphenyl)-2,4-pyrimidinediamine. LCMS: ret. time: 16.59 min.; purity: 96.5%; MS (m/e): 397.06 (MH$^+$).

7.3.582 5-Fluoro-N4-(3-hydroxyphenyl)-N2-[3-(N-morpholino)carbonylmethyleneaminophenyl]-2,4-pyrimidinediamine (R950221)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-5-fluoro-N4-(3-hydroxyphenyl)-2,4-pyrimidinediamine and morpholine were reacted to prepare 5-fluoro-N4-(3-hydroxyphenyl)-N2-[3-(N-morpholino)carbonylmethyleneaminophenyl]-2,4-pyrimidinediamine. LCMS: ret. time: 16.29 min.; purity: 91.5%; MS (m/e): 439.03 (MH$^+$).

7.3.583 5-Fluoro-N4-(3-hydroxyphenyl)-N2-[3-(N-piperazino)carbonylmethyleneaminophenyl]-2,4-pyrimidinediamine (R950222)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-5-fluoro-N4-(3-hydroxyphenyl)-2,4-pyrimidinediamine and piperazine were reacted to prepare 5-fluoro-N4-(3-hydroxyphenyl)-N2-[3-(N-piperazino)carbonylmethyleneaminophenyl]-2,4-pyrimidinediamine. LCMS: ret. time: 13.04 min.; purity: 89.9%; MS (m/e): 438.06 (MH$^+$).

7.3.584 5-Fluoro-N4-(3-hydroxyphenyl)-N2-[3-[N—(N-methyl)piperazino]carbonylmethyleneaminophenyl]-2,4-pyrimidinediamine (R950223)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-5-fluoro-N4-(3-hydroxyphenyl)-2,4-pyrimidinediamine and N-methylpiperazine were reacted to prepare 5-fluoro-N4-(3-hydroxyphenyl)-N2-[3-[N—(N-methyl)piperazino]carbonylmethyleneaminophenyl]-2,4-pyrimidinediamine. LCMS: ret. time: 12.06 min.; purity: 98.7%; MS (m/e): 452.06 (MH$^+$).

7.3.585 5-Fluoro-N4-(3-hydroxyphenyl)-N2-[3-(N-2-hydroxyethylamino)carbonylmethyleneaminophenyl]-2,4-pyrimidinediamine (R950224)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-5-fluoro-N4-(3-hydroxyphenyl)-2,4-pyrimidinediamine and 2-aminoethanol were reacted to prepare 5-fluoro-N4-(3-hydroxyphenyl)-N2-[3-(N-2-hydroxyethylamino)carbonylmethyleneaminophenyl]-2,4-pyrimidinediamine. LCMS: ret. time: 13.28 min.; purity: 97.3%; MS (m/e): 413.04 (MH$^+$).

7.3.586 5-Fluoro-N4-(3-hydroxyphenyl)-N2-[3-[(N-methylamino)ethylamino]carbonylmethyleneaminophenyl]-2,4-pyrimidinediamine (R950225)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-5-fluoro-N4-(3-hydroxyphenyl)-2,4-pyrimidinediamine and N-methyl-ethylen-1,2-diamine were reacted to prepare 5-fluoro-N4-(3-hydroxyphenyl)-N2-[3-[(N-methylamino)ethylamino]carbonylmethyleneaminophenyl]-2,4-pyrimidinediamine. LCMS: ret. time: 12.31 min.; purity: 94.7%; MS (m/e): 426.01 (MH$^+$).

7.3.587 5-Fluoro-N4-(3-hydroxyphenyl)-N2-[3-[(N-2-morpholinoethylamino)carbonylmethyleneaminophenyl]-2,4-pyrimidinediamine (R950226)

In like manner to the preparation of N4-(3,4-ethylenedioxyphenyl)-5-fluoro-N2-[3-(N-morpholinoethyleneamino)carbonylmethyleneaminophenyl]-2,4-pyrimidinediamine, N2-(3-ethoxycarbonylmethyleneaminophenyl)-5-fluoro-N4-(3-hydroxyphenyl)-2,4-pyrimidinediamine and N-morpholinylethylamine were reacted to prepare 5-fluoro-N4-(3-hydroxyphenyl)-N2-[3-(N-2-morpholinoethylamino)carbonylmethyleneaminophenyl]-2,4-pyrimidinediamine. LCMS: ret. time: 12.66 min.; MS (m/e): 482.39 (MH$^+$).

7.3.588 R935184: 5-Fluoro-N2-[4-(N-methylamino)carbonylmethyleneoxyphenyl]-N4-(3,4-propylenedioxyphenyl)-2,4-pyrimidinediamine In like manner to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N2-[4-(methoxycarbonylmethyleneoxy)phenyl]-N4-(3,4-propylenedioxyphenyl)-2,4-pyrimidinediamine was reacted with Me$_2$NH.HCl and i-Pr$_2$NEt in methanol to produce 5-fluoro-N2-[4-(N-methylamino)carbonylmethyleneoxyphenyl]-N4-(3,4-propylenedioxyphenyl)-2,4-pyrimidinediamine. LCMS: ret. time: 6.91 min.; purity: 98%; MS (m/e): 440 (MH$^+$).

7.3.589 R935196: N2-[3-(1-Bis(N-methylaminocarbonyl)ethoxy)phenyl]-5-fluoro-N4-(4-isopropoxyphenyl)-2,4-pyrimidineamine In like manner to the preparation of N4-(3,4-ethylenedioxyphenyl)-5-fluoro-N2-[3-(N-methylamino)carbonylmethyleneoxyphenyl]-2,4-pyrimidinediamine, N4-[3-(1-bis(ethyloxycarbonyl)ethoxy)phenyl]-5-fluoro-N2-[4-isopropoxyphenyl)-2,4-pyrimidinediamine was reacted with Me$_2$NH.HCl and i-Pr$_2$NEt in presence of methanol to produce N2-[3-(1-bis(N-methylaminocarbonyl)ethoxy)phenyl]-5-fluoro-N4-(4-isopropoxyphenyl)-2,4-pyrimidineamine.
$^1$H NMR (DMSO-d6): δ 9.18 (s, 1H), 9.15 (s, 1H), 8.07 (app qt, 2H, J=4.7 Hz), 8.01 (d, 1H, J=3.5 Hz), 7.65-7.62 (m 2H), 7.36 (br s, 1H), 7.28 (dd, 1H, J=1.1 and 8.2 Hz), 7.03 (t, 1H, J=8.2 Hz), 6.87 (d, 2H, J=8.8 Hz), 6.35 (dd, 1H, J=1.1 and 8.8 Hz), 4.54 (q, 1H, J=6.4 Hz), 2.62 (d, 6H, J=4.7 Hz), 1.49 (s, 3H), 1.23 (d, 6H, J=5.8 Hz). LCMS: ret. time: 19.40 min.; purity: 94%; MS (m/e): 497 (MH⁺).

7.3.590 R935202: 5-Fluoro-N2-[3-(N-methylamino)carbonylmethyleneoxyphenyl]-N4-(3,4-propylenedioxyphenyl)-2,4-pyrimidinediamine In like manner to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N2-[3-(methoxycarbonylmethyleneoxy)phenyl]-N4-(3,4-propylenedioxyphenyl)-2,4-pyrimidinediamine was reacted with Me₂NH.HCl to give 5-fluoro-N2-[3-(N-methylamino)carbonylmethyleneoxyphenyl]-N4-(3,4-propylenedioxyphenyl)-2,4-pyrimidinediamine. ¹H NMR (DMSO-d6): δ 9.21 (s, 1H), 9.19 (s, 1H), 8.06 (d, 1H, J=4.1 Hz), 7.94 (q, 1H, J=3.5 Hz), 7.42-7.38 (m, 2H), 7.30 (d, 2H, J=7.6 Hz), 7.12 (t, 1H, J=7.6 Hz), 6.89 (d, 1H, J=8.2 Hz), 6.47 (dd, 1H, J=2.3 and 8.8 Hz), 4.33 (s, 2H), 4.11-4.03 (m, 4H), 2.63 (d, 3H, J=4.7 Hz)), 2.08-2.03 (m, 2H). LCMS: ret. time: 17.33 min.; purity: 98%; MS (m/e): 440 (MH⁺).

7.3.591 R935206: N2, N4-Bis[1-(N-methylaminocarbonyl)methyl-indazoline-6-yl]-5-fluoro-2,4-pyrimidinediamine In like manner to the preparation of N4-(3,4-ethylenedioxyphenyl)-5-fluoro-N2-[3-(N-methylamino)carbonylmethyleneoxyphenyl]-2,4-pyrimidinediamine, N2, N4-Bis[1-(methoxycarbonyl)methyl-indazoline-6-yl]-5-fluoro-2,4-pyrimidinediamine and was reacted with Me₂NH.HCl and i-PrN₂Et in presence of methanol to produce N2, N4-bis[1-(N-methylaminocarbonyl)methyl-indazoline-6-yl]-5-fluoro-2,4-pyrimidinediamine. ¹H NMR (DMSO-d6): δ 9.56 (s, 1H), 9.40 (s, 1H), 8.17 (d, 1H, J=3.5 Hz), 8.12 (s, 1H), 7.99 (s, 1H), 7.96 (s, 2H), 7.90 (s, 2H), 7.66 (d, 1H, J=8.8 Hz), 7.56 (d, 1H, J=8.8 Hz), 7.49 (dd, 1H, J=1.7 and 8.8 Hz), 7.34 (dd, 1H, J=1.7 and 8.8 Hz), 4.90 (s, 2H), 4.66 (s, 2H), 2.56 (d, 6H, J=4.11 Hz). LCMS: ret. time: 13.85 min.; purity: 98%; MS (m/e): 503 (MH⁺).

7.3.592 R935212: N4-(3,4-ethylenedioxyphenyl)-5-fluoro-N2-[1-(N-methylaminocarbonyl)methyl-indazoline-6-yl]-2,4-pyrimidinediamine In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-[1-(methoxycarbonyl)methyl-indazoline-6-yl]-2,4-pyrimidinediamine and Me₂NH.HCl was reacted to produce N4-(3,4-ethylenedioxyphenyl)-5-fluoro-N2-[1-(N-methylaminocarbonyl)methyl-indazoline-6-yl]-2,4-pyrimidinediamine. ¹H NMR (DMSO-d6): δ 9.35 (s, 1H), 9.17 (s, 1H), 8.07 (d, 1H, J=4.8 Hz), 7.92 (s, 1H), 7.89 (s, 1H), 7.66 (q, 1H, J=4.7 Hz), 7.54 (d, 1H, J=8.8 Hz), 7.35-7.24 (m, 3H), 6.76 (d, 1H, J=8.8 Hz), 4.77 (s, 2H), 4.20 (s, 4H), 2.57 (d, 3H, J=4.7 Hz). LCMS: ret. time: 15.82 min.; purity: 94%; MS (m/e): 450 (MH⁺).

7.3.593 R935213: N4-(3,4-ethylenedioxyphenyl)-5-fluoro-N2-[3-(2-(N-methylamino)carbonyl-fur-4-yl)methyleneoxyphenyl]-2,4-pyrimidinediamine In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-[3-(2-methoxycarbonyl-fur-4-yl)methyleneoxyphenyl]-2,4-pyrimidinediamine was reacted with Me₂NH.HCl and i-Pr₂NEt. to give N4-(3,4-ethylenedioxyphenyl)-5-fluoro-N2-[3-(2-(N-methylamino)carbonyl-fur-4-yl)methyleneoxyphenyl]-2,4-pyrimidinediamine. ¹H NMR (DMSO-d6): δ 9.17 (s, 2H), 8.30 (q, 1H, J=4.7 Hz), 8.05 (d, 1H, J=3.5 Hz), 7.42 (s, 1H), 7.29-7.19 (m, 2H), 7.09 (t, 1H, J=8.2 Hz), 7.02 (d, 1H, J=2.9 Hz), 6.76 (d, 1H, J=8.8 Hz), 6.67 (d, 1H, J=2.9 Hz), 6.54 (dd, 1H, J=1.7 and 8.2 Hz), 4.94 (s, 2H), 4.21-4.18 (m, 4H), 2.70 (d, 3H, J=4.7 Hz). LCMS: ret. time: 18.85 min.; purity: 91%; MS (m/e): 492 (MH⁺).

7.3.594 R935216: 5-Fluoro-N2-[4-(N-methylamino)carbonylmethyleneoxyphenyl]-N4-(1-methyl-indazoline-5-yl)-2,4-pyrimidinediamine In like manner to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N2-[4-(methoxycarbonylmethyleneoxy)phenyl]-N4-(1-methyl-indazoline-5-yl)-2,4-pyrimidinediamine and Me₂NH.HCl were reacted to provide 5-fluoro-N2-[4-(N-methylamino)carbonylmethyleneoxy)phenyl]-N4-(1-methyl-indazoline-5-yl)-2,4-pyrimidinediamine ¹H NMR (DMSO-d6): δ 9.31 (s, 1H), 9.00 (s, 1H), 8.17 (s, 1H), 8.02 (d, 1H, J=3.5 Hz), 7.99 (m, 1H), 7.93 (s, 1H), 7.59 (m, 2H), 7.52 (d, 2H, J=8.8 Hz), 6.78 (d, 2H, J=8.8 Hz), 4.36 (s, 2H), 4.03 (s, 3H), 2.63 (d, 3H, J=4.7 Hz). LCMS: ret. time: 14.81 min.; purity: 99%; MS (m/e): 422 (MH⁺).

7.3.595 R935217: N2, N4-Bis[1-(N-methylaminocarbonyl)methyl-indazoline-5-yl]-5-fluoro-2,4-pyrimidinediamine In like manner to the preparation of N4-(3,4-ethylenedioxyphenyl)-5-fluoro-N2-[3-(N-methylamino)carbonylmethyleneoxyphenyl]-2,4-pyrimidinediamine, N2, N4-bis[1-(methoxycarbonyl)methyl-indazoline-6-yl]-5-fluoro-2,4-pyrimidinediamine and Me₂NH.HCl were reacted to produce N2, N4-bis[1-(N-methylaminocarbonyl)methyl-indazoline-5-yl]-5-fluoro-2,4-pyrimidinediamine. ¹H NMR (DMSO-d6): δ 9.35 (s, 1H), 9.15 (s, 1H), 8.09-8.06 (m, 2H), 7.97-7.96 (m, 2H), 7.91 (s, 1H), 7.70 (s, 1H), 7.69 (s, 1H), 7.64-7.55 (m, 2H), 7.48-7.40 (m, 2H), 5.06 (s, 2H), 4.97 (s, 2H), 2.62 (d, 3H, J=4.7 Hz), 2.61 (d, 3H, J=4.7 Hz). LCMS: ret. time: 12.54 min.; purity: 95%; MS (m/e): 503 (MH⁺).

7.3.596 N4-(3,4-Ethylenedioxyphenyl)-5-fluoro-N2-[3-[2-(N-morpholino)ethyleneoxy]phenyl]-2,4-pyrimidinediamine (R926486)

A dry reaction vial equipped with a rubber septum was charged with N4-(3,4-ethylenedioxyphenyl)-5-fluoro-N2-[3-(N-morpholino)carbonylmethyleneoxyphenyl]-2,4-pyrimidinediamine (0.019 g, 0.04 mmol) and THF (1 mL). To this was added boranemethyl sulfide complex (0.044 mL, 0.088 mmol) and stirred at room temperature for 2 h. The amount of boranemethyl sulfide complex was evaporated and the reaction was quenched with MeOH (CAUTION: vigorous evolution of hydrogen gas occurs during the addition of MeOH), heated for 30 min. The solvent was removed and again the residue was suspended in MeOH, extracted with EtOAc, EtOAc was evaporated and the residue was purified by preparative TLC to obtain N4-(3,4-ethylenedioxyphenyl)-5-fluoro-N2-[3-[2-(N-morpholino)ethyleneoxy]phenyl]-2,4-pyrimidinediamine. ¹H NMR (CDCl₃): δ 8.20 (s, 1H), 8.01 (d, 1H, J=6 Hz), 7.26-7.05 (m, 3H), 7.05-6.97 (m, 3H), 6.82

(d, 1H, J=9.3 Hz), 6.67 (dd, 1H, J=1.8 and 8.1 Hz), 4.44 (t, 2H), 4.27 (s, 4H), 4.14 (m, 2H), 3.76 (m, 2H), 3.22 (t, 2H, J=5.4 Hz), 3.05 (m, 2H), 2.88 (m, 2H).

7.3.597 N4-(3,4-Ethylenedioxyphenyl)-5-fluoro-N2-[2-(N-morpholinomethylene)benzofuran-5-yl]-2,4-pyrimidinediamine (R926490)

In like manner to the preparation of N4-(3,4-ethylenedioxyphenyl)-5-fluoro-N2-[3-[2-(N-morpholino)ethyleneoxy]phenyl]-2,4-pyrimidinediamine, the reaction of N4-(3,4-ethylenedioxyphenyl)-5-fluoro-N2-[2-(N-morpholino)carbonylbenzofuran-5-yl]-2,4-pyrimidinediamine with boranemethyl sulfide complex gave N4-(3,4-ethylenedioxyphenyl)-5-fluoro-N2-[2-(N-morpholinomethylene)benzofuran-5-yl]-2,4-pyrimidinediamine. $^1$H NMR (CD$_3$OD): δ 8.65 (d, 2H, J=2.1 Hz), 8.30 (dd, 2H, J=2.1 and 9.6 Hz), 7.73 (d, 2H, J=9.3 Hz), 7.49 (bs, 2H), 7.32 (m, 1H), 6.74 (m, 1H), 4.24 (s, 4H), 3.97 (s, 2H), 3.78 (m, 4H), 3.56 (m, 4H).

7.3.598 N4-(3,4-Ethylenedioxyphenyl)-5-fluoro-N2-[3-[2-(N-methylamino)ethyleneoxy]phenyl]-2,4-pyrimidinediamine (R926510)

In like manner to the preparation of N4-(3,4-ethylenedioxyphenyl)-5-fluoro-N2-[3-[2-(N-morpholino)ethyleneoxy]phenyl]-2,4-pyrimidinediamine, N4-(3,4-ethylenedioxyphenyl)-5-fluoro-N2-[3-(N-methylamino)carbonylmethyleneoxyphenyl]-2,4-pyrimidinediamine and boranemethyl sulfide complex gave N4-(3,4-ethylenedioxyphenyl)-5-fluoro-N2-[3-[2-(N-methylamino)ethyleneoxy]phenyl]-2,4-pyrimidinediamine. $^1$H NMR (CD$_3$OD): δ 8.00 (d, 1H, J=5.2 Hz), 7.50-7.30 (m, 2H), 7.16-6.80 (m, 5H), 4.28 (m, 1H), 4.27 (bs, 4H), 4.22 (m, 1H), 3.44 (m, 2H), 2.79 (d, 3H, J=3 Hz); LCMS: ret. time: 15.64 min.; purity: 96%; MS (m/e): 412 (MH$^+$).

7.3.599 5-Fluoro-N4-(3-hydroxyphenyl)-N2-[2-(N-piperazinomethylene)benzofuran-5-yl]-2,4-pyrimidinediamine (R926770)

In like manner to the preparation of N4-(3,4-ethylenedioxyphenyl)-5-fluoro-N2-[3-[2-(N-morpholino)ethyleneoxy]phenyl]-2,4-pyrimidinediamine, the reaction of 5-fluoro-N4-(3-hydroxyphenyl)-N2-[2-(N-piperazino)carbonylbenzofuran-5-yl]-2,4-pyrimidinediamine with boranemethyl sulfide complex gave 5-fluoro-N4-(3-hydroxyphenyl)-N2-[2-(N-piperazinomethylene)benzofuran-5-yl]-2,4-pyrimidinediamine. LCMS: ret. time: 12.06 min.; purity: 75%; MS (m/e): 435 (MH$^+$).

7.3.600 N4-(3,5-Dimethyl-4-hydroxyphenyl)-5-fluoro-N2-[3-[2-(N-morpholino)ethyleneoxy]phenyl]-2,4-pyrimidinediamine (R940255)

In like manner to the preparation of N4-(3,4-ethylenedioxyphenyl)-5-fluoro-N2-[3-[2-(N-morpholino)ethyleneoxy]phenyl]-2,4-pyrimidinediamine, the reaction of N4-(3,5-dimethyl-4-hydroxyphenyl)-5-fluoro-N2-[3-(N-morpholino)carbonylmethyleneoxyphenyl]-2,4-pyrimidinediamine with boranemethyl sulfide complex gave N4-(3,5-dimethyl-4-hydroxyphenyl)-5-fluoro-N2-[3-[2-(N-morpholino)ethyleneoxy]phenyl]-2,4-pyrimidinediamine. LCMS: ret. time: 15.94 min.; purity: 99%; MS (m/e): 454 (MH$^+$); $^1$H NMR (DMSO-d6): δ 9.16 (1H, s), 9.07 (1H, s), 8.15 (1H, s), 8.11 (1H, d, J=3.9 Hz), 7.40-7.30 (4H, m), 7.13 (1H, t, 8.1 Hz), 6.55 (1H, dd, J=8.1 Hz, 3.2 Hz), 4.01 (2H, t, J=5.7 Hz), 3.65 (4H, t, J=4.2 Hz), 2.72 (2H, t, J=5.7 Hz), 2.515 (4H, t, J=4.5 Hz), 2.24 (6H, s).

7.3.601 N4-(3,5-Dimethyl-4-hydroxyphenyl)-5-fluoro-N2-[3-[2-(N-piperazino)ethoxy]phenyl]-2,4-pyrimidinediamine bis Hydrogen Chloride Salt (R945142)

In like manner to the preparation of N4-(3,4-ethylenedioxyphenyl)-5-fluoro-N2-[3-[2-(N-morpholino)ethyleneoxy]phenyl]-2,4-pyrimidinediamine, N4-(3,5-dimethyl-4-hydroxyphenyl)-5-fluoro-N2-[3-(N-piperazino)carbonylmethyleneoxyphenyl]-2,4-pyrimidinediamine was treated with boranemethyl sulfide complex to give N4-(3,5-dimethyl-4-hydroxyphenyl)-5-fluoro-N2-[3-[2-(N-piperazino)ethyloxy]phenyl]-2,4-pyrimidinediamine, which was then treated with 4N HCl in dioxane (3 mL) followed crystallization from MeOH/EtOAc to give N4-(3,5-dimethyl-4-hydroxyphenyl)-5-fluoro-N2-[3-[2-(N-piperazino)ethoxy]phenyl]-2,4-pyrimidinediamine bis Hydrogen Chloride Salt. $^1$H NMR (CD$_3$OD): δ 2.17 (s, 6H), 3.66 (m, 10H), 4.26 (t, J=4.5 Hz, 2H), 6.93 (dd, J=1.5, 7.2 Hz, 1H), 7.10-7.13 (m, 2H), 7.17 (s, 2H), 7.31 (t, J=8.4 Hz, 1H), 7.98 (d, J=6.0 Hz, 1H); $^{19}$F NMR (282 MHz, CD$_3$OD): 6-162.93; LCMS: ret. time: 13.25 min.; purity: 96.08%; MS (m/e): 453.09 (MH$^+$).

7.3.602 N4-(3,4-Ethylenedioxyphenyl)-5-fluoro-N2-[4-(2-hydroxyethyloxy)phenyl]-2,4-pyrimidinediamine (R945144)

In like manner to the preparation of N4-(3,4-ethylenedioxyphenyl)-5-fluoro-N2-[3-[2-(N-morpholino)ethyleneoxy]phenyl]-2,4-pyrimidinediamine, the reaction of N2-(4-carboxymethyleneoxyphenyl)-N4-(3,4-ethylendioxyphenyl)-5-fluoro-2,4-pyrimidinediamine and boranemethyl sulfide complex gave N4-(3,4-ethylenedioxyphenyl)-5-fluoro-N2-[4-(2-hydroxyethoxy)phenyl]-2,4-pyrimidinediamine. $^1$H NMR (acetone-d$_6$): δ 3.86 (t, J=4.8 Hz, 2H), 4.04 (t, J=4.8 Hz, 2H), 4.28 (m, 4H), 6.78 (d, J=9.0 Hz, 1H), 6.86 (d, J=9.0 Hz, 2H), 7.18 (dd, J=2.7, 8.7 Hz, 1H), 7.47 (d, J=2.7 Hz, 1H), 7.63 (d, J=9.0 Hz, 2H), 7.91 (d, J=3.6 Hz, 1H), 8.29 (br, 1H, NH), 8.31 (br, 1H, NH); $^{19}$F NMR (282 MHz, acetone-d$_6$): 6-169.18; LCMS: ret. time: 17.41 min.; purity: 98.36%; MS (m/e): 399.01 (MH$^+$).

7.3.603 N4-(3-Chloro-4-hydroxy-5-methylphenyl)-5-fluoro-N2-[3-[2-(N-piperazino)ethoxy]phenyl]-2,4-pyrimidinediamine Dihydrochloride Salt (R945150)

In like manner to the preparation of N4-(3,4-ethylenedioxyphenyl)-5-fluoro-N2-[3-[2-(N-morpholino)ethyleneoxy]phenyl]-2,4-pyrimidinediamine, N4-(3-chloro-4-hydroxy-5-methylphenyl)-5-fluoro-N2-[3-(N-piperazino)carbonylmethyleneoxyphenyl]-2,4-pyrimidinediamine was treated with boranemethyl sulfide complex to give N4-(3-chloro-4-hydroxy-5-methylphenyl)-5-fluoro-N2-[3-[2-(N-piperazino)ethyloxy]phenyl]-2,4-pyrimidinediamine, which was then treated with 4N HCl in dioxane (3 mL) followed crystallization from MeOH/EtOAc to give N4-(3-chloro-4-hydroxy-5-methylphenyl)-5-fluoro-N2-[3-[2-(N-piperazino)ethoxy]phenyl]-2,4-pyrimidinediamine bis Hydrogen Chloride Salt. $^1$H NMR (CD$_3$OD): δ 2.21 (s, 3H), 3.72 (m, 10H), 4.35 (t, J=4.5 Hz, 2H), 6.95 (dt, J=1.5 and 9.0 Hz, 1H), 7.11-7.14 (m, 2H), 7.26 (dd, J=0.9 and 2.7 Hz, 1H), 7.34 (t, J=8.4 Hz, 1H), 7.50 (d, J=2.4 Hz, 1H), 8.03 (d, J=5.4 Hz, 1H); $^{19}$F NMR (282 MHz, CD$_3$OD): 6-162.74; LCMS: ret. time: 14.50 min.; purity: 94.75%; MS (m/e): 472.98 (MH$^+$).

7.3.604 N4-(3,5-Dimethyl-4-methoxyphenyl)-5-fluoro-N2-[3-[2-(N-piperazino)ethoxy]phenyl]-2,4-pyrimidinediamine Dihydrochloride Salt (R945157)

In like manner to the preparation of N4-(3,4-ethylenedioxyphenyl)-5-fluoro-N2-[3-[2-(N-morpholino)ethyleneoxy]phenyl]-2,4-pyrimidinediamine, N4-(3,5-dimethyl-4-methoxyphenyl)-5-fluoro-N2-[3-(N-piperazino)carbonylmethyleneoxyphenyl]-2,4-pyrimidinediamine was treated with boranemethyl sulfide complex to give N4-(3,5-dimethyl-4-methoxyphenyl)-5-fluoro-N2-[3-[2-(N-piperazino)ethyloxy]phenyl]-2,4-pyrimidinediamine, which was then treated with 4N HCl in dioxane (3 mL) followed crystallization from MeOH/EtOAc to give N4-(3,5-dimethyl-4-methoxyphenyl)-5-fluoro-N2-[3-[2-(N-piperazino)ethoxy]phenyl]-2,4-pyrimidinediamine bis Hydrogen Chloride Salt. $^1$H NMR (CD$_3$OD): δ 2.23 (s, 6H), 3.66 (m, 10H), 3.72 (s, 3H), 4.31 (t, J=4.5 Hz, 2H), 6.95 (dd, J=1.8 and 8.4 Hz, 1H), 7.09-7.15 (m, 2H), 7.27 (s, 2H), 7.32 (t, J=8.1 Hz, 1H), 8.01 (d, J=5.4 Hz, 1H); $^{19}$F NMR (282 MHz, CD$_3$OD): 6-162.71; LCMS: ret. time: 16.41 min.; purity: 97.50%; MS (m/e): 467.12 (MH$^+$).

7.3.605 N4-(3,4-Ethylenedioxyphenyl)-5-fluoro-N2-[2-(N-piperazino)carbonylbenzofuran-5-yl]-2,4-pyrimidinediamine Hydrogen Chloride Salt (R926501)

The reaction of equivalent amount of N4-(3,4-ethylenedioxyphenyl)-5-fluoro-N2-[2-(N-piperazino)carbonylbenzofuran-5-yl]-2,4-pyrimidinediamine with hydrogen chloride (4M, dioxane) in methanol at 0° C. followed by dilution with dry ethyl ether or ethyl acetate gave the precipitate. The resulting precipitate was isolated by filtration (and/or using centrifuse technique) to give N4-(3,4-ethylenedioxyphenyl)-5-fluoro-N2-[2-(N-piperazino)carbonylbenzofuran-5-yl]-2,4-pyrimidinediamine Hydrogen Chloride Salt. $^1$H NMR (CD$_3$OD): δ 7.97 (d, 1H, J=5.4 Hz), 7.92 (d, 1H, J=1.8 Hz), 7.62 (d, 1H, J=8.2 Hz), 7.48 (s, 1H), 7.43 (dd, 1H, J=J=2.4 and 8.7 Hz), 7.17 (d, 1H, J=2.4 Hz), 6.98 (dd, 1H, J=2.4 and 8.7 Hz), 6.77 (d, 1H, J=8.7 Hz), 4.13 (m, 4H), 4.22 (s, 4H), 3.38 (t, 4H, J=5.7 Hz); LCMS: ret. time: 15.12 min; purity: 89%; MS (m/e): 491 (MH$^+$).

7.3.606 N4-(3,4-Ethylenedioxyphenyl)-5-fluoro-N2-[3-(N-piperazino)carbonylmethyleneoxyphenyl]-2,4-pyrimidinediamine Hydrogen Chloride Salt (R926504)

In like manner to the preparation of N4-(3,4-ethylenedioxyphenyl)-5-fluoro-N2-[2-(N-piperazino)carbonylbenzofuran-5-yl]-2,4-pyrimidinediamine Hydrogen Chloride Salt, the reaction of N4-(3,4-ethylenedioxyphenyl)-5-fluoro-N2-[3-(N-piperazino)carbonylmethyleneoxyphenyl]-2,4-pyrimidinediamine and hydrogen chloride gave N4-(3,4-ethylenedioxyphenyl)-5-fluoro-N2-[3-(N-piperazino)carbonylmethyleneoxyphenyl]-2,4-pyrimidinediamine Hydrogen Chloride Salt. $^1$H NMR (DMSO-d6): δ 9.6 (bs, 1H), 9.04 (bs, 1H), 8.12 (d, 1H, J=3.6 Hz), 7.25-7.00 (m, 5H), 7.81 (d, 1H, J=8.7 Hz), 6.54 (d, 1H, J=8.4 Hz), 4.74 (s, 2H), 4.22 (s, 4H), 3.64 (m, 4H), 3.11 (m, 4H); LCMS: ret. time: 15.34 min.; purity: 100%; MS (m/e): 481 (MH$^+$).

7.3.607 N4-(3,4-Ethylenedioxyphenyl)-5-fluoro-N2-[3-(2-N-methylaminoethyl)phenyl]-2,4-pyrimidinediamine Hydrogen Chloride Salt (R926509)

In like manner to the preparation of N4-(3,4-ethylenedioxyphenyl)-5-fluoro-N2-[2-(N-piperazino)carbonylbenzofuran-5-yl]-2,4-pyrimidinediamine Hydrogen Chloride Salt, the reaction of N4-(3,4-ethylenedioxyphenyl)-5-fluoro-N2-[3-[2-(N-methylamino)ethyloxy]phenyl]-2,4-pyrimidinediamine with hydrogen chloride (4M, dioxane) gave N4-(3,4-ethylenedioxyphenyl)-5-fluoro-N2-[3-[2-(N-methylamino)ethyloxy]phenyl]-2,4-pyrimidinediamine Hydrogen Chloride Salt. LCMS: ret. time: 15.88 min.; purity: 92%; MS (m/e): 412 (MH$^+$).

7.3.608 N4-(3,4-Ethylenedioxyphenyl)-5-fluoro-N2-[3-[2-(N-morpholino)ethyloxy]phenyl]-2,4-pyrimidinediamine Hydrogen Chloride Salt (R926511)

In like manner to the preparation of N4-(3,4-ethylenedioxyphenyl)-5-fluoro-N2-[2-(N-piperazino)carbonylbenzofuran-5-yl]-2,4-pyrimidinediamine Hydrogen Chloride Salt, the reaction of N4-(3,4-ethylenedioxyphenyl)-5-fluoro-N2-[3-[2-(N-morpholino)ethyloxy]phenyl]-2,4-pyrimidinediamine and hydrogen chloride gave N4-(3,4-ethylenedioxyphenyl)-5-fluoro-N2-[3-[2-(N-morpholino)ethyloxy]phenyl]-2,4-pyrimidinediamine Hydrogen Chloride Salt. $^1$H NMR (CD$_3$OD): δ 7.98 (d, 1H, J=5.4 Hz), 7.34 (t, 1H, 8.4 Hz), 7.16-6.81 (m, 6H), 4.42 (m, 1H), 4.40 (m, 2H), 4.25 (m, 5H), 4.10 (m, 2H), 3.90 (bs, 2H), 3.60 (m, 4H); LCMS: ret. time: 16.39 min.; purity: 100%; MS (m/e): 468 (MH$^+$)

7.3.609 N4-(3,4-Ethylenedioxyphenyl)-5-fluoro-N2-[2-(N-homopiperazino)carbonylbenzofuran-5-yl]-2,4-pyrimidinediamine Hydrogen Chloride Salt (R926768)

In like manner to the preparation of N4-(3,4-ethylenedioxyphenyl)-5-fluoro-N2-[2-(N-piperazino)carbonylbenzofuran-5-yl]-2,4-pyrimidinediamine Hydrogen Chloride Salt, the reaction of N4-(3,4-ethylenedioxyphenyl)-5-fluoro-N2-[2-(N-homopiperazino)carbonylbenzofuran-5-yl]-2,4-pyrimidinediamine with hydrogen chloride treatment gave N4-(3,4-ethylenedioxyphenyl)-5-fluoro-N2-[2-(N-homopiperazino)carbonylbenzofuran-5-yl]-2,4-pyrimidinediamine Hydrogen Chloride Salt. $^1$H NMR (DMSO-d6): δ 9.98 (bs, 1H), 9.05 (bs, 1H), 8.18 (d, 1H, J=4.8 Hz), 8.01 (s, 1H), 7.58 (d, 1H, J=8.7 Hz), 7.50 (bd, 1H), 7.35 (s, 1H), 7.24 (d, 1H, J=2.4 Hz), 7.11 (dd, 1H, J=3 and 9 Hz), 6.80 (d, 1H, J=8.7 Hz), 4.22 (s, 4H), 4.20-3.60 (m, 8H), 3.20 (m, 2H); LCMS: ret. time: 14.91 min.; purity: 86%; MS (m/e): 505 (MH$^+$).

7.3.610 5-Fluoro-N4-(3-hydroxyphenyl)-N2-[2-(N-piperazino)carbonylbenzofuran-5-yl]-2,4-pyrimidinediamine Hydrogen Chloride Salt R926502)

In like manner to the preparation of N4-(3,4-ethylenedioxyphenyl)-5-fluoro-N2-[2-(N-piperazino)carbonylbenzofuran-5-yl]-2,4-pyrimidinediamine Hydrogen Chloride Salt, 5-fluoro-N4-(3-hydroxyphenyl)-N2-[2-(N-piperazino)carbonylbenzofuran-5-yl]-2,4-pyrimidinediamine upon treatment with hydrogen chloride (4M, dioxane) gave 5-fluoro-N4-(3-hydroxyphenyl)-N2-[2-(N-piperazino)carbonylbenzofuran-5-yl]-2,4-pyrimidinediamine Hydrogen Chloride Salt. $^1$H NMR (CDC$_3$OD): δ 8.00 (s, 1H), 7.89 (s, 1H), 7.98 (s, 1H), 7.60 (d, 1H, J=8.7 Hz), 7.45 (m, 3H), 7.16 (t, 1H, J=8.1 Hz), 7.10 (m, 1H), 7.02 (dd, 1H, J=1.2 and 7.2 Hz), 6.70 (dd, 1H, J=2.4 and 8.4 Hz), 4.13 (m, 4H), 3.37 (t, 4H, J=5.4 Hz), 3.38 (t, 4H, J=5.7 Hz); LCMS: ret. time: 13.40 min; purity: 79%; MS (m/e): 450 (MH$^+$).

7.3.611 5-Fluoro-N4-(3-hydroxyphenyl)-N2-[2-(N-piperazinomethylene)benzofuran-5-yl]-2,4-pyrimidinediamine Dihydrochloride Salt (R926769)

In like manner to the preparation of N4-(3,4-ethylenedioxyphenyl)-5-fluoro-N2-[2-(N-piperazino)carbonylbenzofuran-5-yl]-2,4-pyrimidinediamine Hydrogen Chloride Salt, the reaction of 5-fluoro-N4-(3-hydroxyphenyl)-N2-[2-(N-piperazinomethylene)benzofuran-5-yl]-2,4-pyrimidinediamine with hydrogen chloride (4M, dioxane) gave 5-fluoro-N4-(3-hydroxyphenyl)-N2-[2-(N-piperazinomethylene)benzofuran-5-yl]-2,4-pyrimidinediamine Dihydrochloride Salt. $^1$H NMR (CD$_3$OD): δ 8.00 (d, 1H), 7.85 (bd, 1H), 7.75 (m, 3H), 7.60 (m, 2H), 7.40-7.15 (m, 4H), 7.05 (s, 1H), 7.00-6.800 (m, 3H), 4.65 (dd, 2H), 3.60 (m, 8H).

7.3.612 5-Fluoro-N4-(3-hydroxyphenyl)-N2-[3-(N-piperazino)carbonylmethyleneoxyphenyl]-2,4-pyrimidinediamine Hydrogen Chloride Salt (R926773)

In like manner to the preparation of N4-(3,4-ethylenedioxyphenyl)-5-fluoro-N2-[2-(N-piperazino)carbonylbenzofuran-5-yl]-2,4-pyrimidinediamine Hydrogen Chloride Salt, 5-fluoro-N4-(3-hydroxyphenyl)-N2-[3-(N-piperazino)carbonylmethyleneoxyphenyl]-2,4-pyrimidinediamine and hydrogen chloride (4M, dioxane) gave 5-fluoro-N4-(3-hydroxyphenyl)-N2-[3-(N-piperazino)carbonylmethyleneoxyphenyl]-2,4-pyrimidinediamine Hydrogen Chloride Salt. $^1$H NMR (CD$_3$OD): δ 7.99 (d, 1H, J=5.1 Hz), 7.29 (t, 1H, J=8.1 Hz), 7.21-7.05 (m, 5H), 6.83 (dd, 1H, J=2.4 and 8.7 Hz), 6.77 (bd, 1H), 4.79 (s, 2H), 3.83 (m, 2H), 3.78 (m, 2H), 3.25 (m, 2H); LCMS: ret. time: 12.27 min.; purity: 91%; MS (m/e): 439 (MH$^+$).

7.3.613 N2-[3-[2-(N, N-Dimethylamino)ethyloxy]phenyl]-N4-(3,4-Ethylenedioxyphenyl)-5-fluoro-2,4-pyrimidinediamine Hydrogen Chloride Salt (R926771)

In like manner to the preparation of N4-(3,4-ethylenedioxyphenyl)-5-fluoro-N2-[2-(N-piperazino)carbonylbenzofuran-5-yl]-2,4-pyrimidinediamine Hydrogen Chloride Salt, the treatment of N4-(3,4-ethylenedioxyphenyl)-N2-[3-[2-(N,N-dimethylamino)ethyloxy]phenyl]-5-fluoro-2,4-pyrimidinediamine with equivalent amount of hydrogen chloride (4M, dioxane) gave N4-(3,4-ethylenedioxyphenyl)-N2-[3-[2-(N,N-dimethylamino)ethyloxy]phenyl]-5-fluoro-2,4-pyrimidinediamine Hydrogen Chloride Salt. LCMS: ret. time: 15.37 min.; purity: 93%; MS (m/e): 426 (MH$^+$).

7.3.614 N4-(3,5-Dimethyl-4-hydroxyphenyl)-5-fluoro-N2-[3-[2-(N-morpholino)ethyloxy]phenyl]-2,4-pyrimidinediamine Hydrogen Chloride Salt (R940256)

In like manner to the preparation of N4-(3,4-ethylenedioxyphenyl)-5-fluoro-N2-[2-(N-piperazino)carbonylbenzofuran-5-yl]-2,4-pyrimidinediamine Hydrogen Chloride Salt, the reaction of N4-(3,5-dimethyl-4-hydroxyphenyl)-5-fluoro-N2-[3-[2-(N-morpholino)ethyloxy]phenyl]-2,4-pyrimidinediamine with hydrogen chloride (4M, dioxane) gave N4-(3,5-dimethyl-4-hydroxyphenyl)-5-fluoro-N2-[3-[2-(N-morpholino)ethyloxy]phenyl]-2,4-pyrimidinediamine Hydrogen Chloride Salt. LCMS: ret. time: 15.78 min.; purity: 98%; MS (M/e): 454 (MH$^+$); 1 ☐☐☐ (DMSO-d6): δ 10.60 (1H, s), 9.58 (1H, s), 8.29 (1H, s), 8.20 (1H, s), 7.43 (1H, d, J=9 Hz), 7.38-7.30 (3H, m), 7.24 (1H, t, J=9 Hz), 6.70 (1H, d, J=9 Hz), 4.35 (2H, m), 4.05 (2H, m), 3.84 (4H, m), 3.65-3.50 (2H, m), 3.26 (2H, m), 2.25 (6H, s).

7.3.615 N4-(3-Chloro-4-hydroxy-5-methylphenyl)-5-fluoro-N2-[3-[2-(N-morpholino)ethyloxy]phenyl]-2,4-pyrimidinediamine Hydrogen Chloride Salt (R940269)

In like manner to the preparation of N4-(3,4-ethylenedioxyphenyl)-5-fluoro-N2-[2-(N-piperazino)carbonylbenzofuran-5-yl]-2,4-pyrimidinediamine Hydrogen Chloride Salt, the reaction of N4-(3-chloro-4-hydroxy-5-methylphenyl)-5-fluoro-N2-[3-[2-(N-morpholino)ethyloxy]phenyl]-2,4-pyrimidinediamine with hydrogen chloride (4M, dioxane) gave N4-(3-chloro-4-hydroxy-5-methylphenyl)-5-fluoro-N2-[3-[2-(N-morpholino)ethyloxy]phenyl]-2,4-pyrimidinediamine Hydrogen Chloride Salt. LCMS: ret. time: 14.74 min.; purity: 96%; MS (m/e): 474 (M$^+$), 475 (MH$^+$); $^1$☐☐☐ (DMSO-d6): δ 10.03 (1H, s), 9.35 (2H, s), 9.06 (1H, s), 8.17 (1H, d, J=3.9 Hz), 7.67 (1H, m), 7.52 (1H, m), 7.46 (1H, d, J=8.7 Hz), 7.39 (1H, s), 7.24 (1H, t, J=8.1 Hz), 6.66 (1H, d, J=8.1 Hz), 4.33 (1H, m), 4.07 (1H, d, J=13 Hz), 3.79 (1H, t, J=12.5 Hz), 3.56 (4H, m), 3.49 (4H, m), 3.29 (1H, t, J=12.5 Hz), 2.29 (3H, s).

7.3.616 N4-(3,4-Ethylenedioxyphenyl)-5-fluoro-N2-[3-(N-methylamino)carbonylmethyleneoxyphenyl]-2,4-pyrimidinediamine Hydrogen Chloride Salt (R926816)

In like manner to the preparation of N4-(3,4-ethylenedioxyphenyl)-5-fluoro-N2-[2-(N-piperazino)carbonylbenzofuran-5-yl]-2,4-pyrimidinediamine Hydrogen Chloride Salt, the treatment of N4-(3,4-ethylenedioxyphenyl)-5-fluoro-N2-[3-(N-methylamino)carbonylmethyleneoxyphenyl]-2,4-pyrimidinediamine with equivalent amount of hydrohen chloride (4M, dioxane) gave the N4-(3,4-ethylenedioxyphenyl)-5-fluoro-N2-[3-(N-methylamino)carbonylmethyleneoxyphenyl]-2,4-pyrimidinediamine Hydrogen Chloride salt. LCMS: ret. time: 17.04 min., purity: 96%, MS (m/e): 426 (MH$^+$).

7.3.617 N4-(3,4-Ethylenedioxy)-5-fluoro-N2-[2-(hydroxymethyl)benzofuran-5-yl]-2,4-pyrimidinediamine (R926696)

A dry reaction flask charged with N4-(3,4-Ethylenedioxyphenyl)-5-fluoro-N2-(2-methoxycarbonylbenzofuran-5-yl)-2,4-pyrimidinediamine was reacted with diisobutylaluminum hydride (DIBALH) (5 equivalents) in CH$_2$Cl$_2$ at −78° C. (reaction was monitored by TLC) followed by treatment with Rochell's salt to yield N4-(3,4-ethylenedioxy)-5-fluoro-N2-[2-(hydroxymethyl)benzofuran-5-yl]-2,4-pyrimidinediamine. $^1$H NMR (DMSO-d6): δ 9.11 (s, 1H), 8.02 (d, 1H, J=3.3 Hz), 7.96 (t, 1H, J=1.8 Hz), 7.40-7.30 (m, 3H), 7.19 (dt, 1H, J=3.6 and 8.1 Hz), 6.78 (d, 1H, J=8.7 Hz), 6.59 (s, 1H), 4.52 (d, 2H, J=5.1 Hz), 4.22 (s, 4H); $^{19}$F NMR (DMSO-d6): −46802; LCMS: ret. time: 19.14 min.; purity: 95%; MS (m/e): 409 (MH$^+$).

7.3.618 5-Fluoro-N4-(3-hydroxyphenyl)-N2-[2-(hydroxymethyl)-(1H)-indol-5-yl]-2,4-pyrimidinediamine (R926700)

In a manner similar to the preparation of N4-(3,4-ethylenedioxy)-5-fluoro-N2-[2-(hydroxymethyl)benzofuran-5-yl]-2,4-pyrimidinediamine, 5-fluoro-N4-(3-hydroxyphenyl)-N2-

[2-(methoxycarbonyl)-(1H)-indol-5-yl]-2,4-pyrimidine diamine was reduced with DIBALH to yield 5-fluoro-N4-(3-hydroxyphenyl)-N2-[2-(hydroxymethyl)-(1H)-indol-5-yl]-2,4-pyrimidinediamine. $^1$H NMR (CD$_3$OD): δ 7.81 (d, 1H, J=4.2 Hz), 7.23 (d, 1H, J=1.8 Hz), 7.28-7.23 (m, 2H), 7.19 (t, 1H, J=2.4 Hz), 7.12 (dd, 1H, J=1.8 and 9.0 Hz), 7.07 (t, 1H, J=8.4 Hz), 6.52 (ddd, 1H, J=1.2 and 8.1 Hz), 6.30 (s, 1H), 4.71 (s, 2H); $^{19}$F NMR (CD$_3$OD): −47971; LCMS: ret. time: 15.36 min.; purity: 100%; MS (m/e): 366 (MH$^+$).

7.3.619 5-Fluoro-N2-[2-(hydroxymethyl)benzofuran-5-yl]-N4-[4-(isopropoxy)phenyl]-2,4-pyrimidinediamine (R926705)

In a manner similar to the preparation of N4-(3,4-ethylenedioxy)-5-fluoro-N2-[2-(hydroxymethyl)benzofuran-5-yl]-2,4-pyrimidinediamine, 5-fluoro-N2-(2-methoxycarbonylbenzofuran-5-yl)-N4-(4-isopropoxyphenyl)-2,4-pyrimidinediamine was reduced with DIBALH to yield 5-fluoro-N2-[2-(hydroxymethyl)benzofuran-5-yl]-N4-(4-isopropoxyphenyl)-2,4-pyrimidinediamine. $^1$H NMR (CD$_3$OD): δ 7.83 (d, 1H, J=3.3 Hz), 7.81 (s, 1H), 7.50 (d, 2H, J=9.0 Hz), 7.29 (d, 1H, J=9.0 Hz), 7.22 (dd, 1H, J=2.4 and 8.7 Hz), 6.84 (d, 2H, J=8.7 Hz), 6.56 (d, 1H, J=1.2 Hz), 4.64 (s, 2H), 4.56 (2q, 1H, J=5.7 Hz), 1.31 (d, 6H, J=6.0 Hz); $^{19}$F NMR (CD$_3$OD): −47926; LCMS: ret. time: 21.03 min.; purity: 99%; MS (m/e): 409 (MH$^+$).

7.3.620 5-Fluoro-N2-[2-(hydroxymethyl)benzofuran-5-yl]-N4-(3-hydroxyphenyl)-2,4-pyrimidinediamine (R926707)

In a manner similar to the preparation of N4-(3,4-ethylenedioxy)-5-fluoro-N2-[2-(hydroxymethyl)benzofuran-5-yl]-2,4-pyrimidinediamine, 5-fluoro-N4-(3-hydroxyphenyl)-N2-[2-(methoxycarbonyl)benzofuran-5-yl]-2,4-pyrimidinediamine was reduced with DIBALH to yield 5-fluoro-N2-[2-(hydroxymethyl)benzofuran-5-yl]-N4-(3-hydroxyphenyl)-2,4-pyrimidinediamine. $^1$H NMR (DMSO-d6): δ 9.37 (s, 1H), 9.17 (s, 1H), 9.12 (s, 1H), 8.06 (d, 1H, J=3.9 Hz), 8.01 (d, 1H, J=1.8 Hz), 7.41-7.35 (m, 2H), 7.26 (d, 1H, J=8.1 Hz), 7.11-7.05 (m, 2H), 6.60 (s, 1H), 6.51 (dd, 1H, J=2.4 and 8.4 Hz), 5.41 (t, 1H, J=6.0 Hz), 4.51 (d, 2H, J=5.7 Hz); LCMS: ret. time: 16.21 min.; purity: 95%; MS (m/e): 367 (MH$^+$).

7.3.621 N4-(4-tert-Butyl)phenyl)-5-fluoro-N2-[3-(2-hydroxyethyleneoxy)phenyl]-2,4-pyrimidinediamine (R926728)

In a manner similar to the preparation of N4-(3,4-ethylenedioxy)-5-fluoro-N2-[2-(hydroxymethyl)benzofuran-5-yl]-2,4-pyrimidinediamine, N4-(4-tert-butylphenyl)-5-fluoro-N2-(3-methoxycarbonylmethyleneoxyphenyl)-2,4-pyrimidinediamine was reduced with DIBAL to yield N4-(4-tert-butylphenyl)-5-fluoro-N2-[3-(2-hydroxyethyleneoxy) phenyl]-2,4-pyrimidinediamine. $^1$H NMR (CDCl$_3$): δ 7.94 (d, 1H, J=3.0 Hz), 7.54 (d, 2H, J=9.0 Hz), 7.37 (d, 2H, J=8.4 Hz), 7.29-7.35 (m, 1H), 7.19-7.14 (m, 2H), 7.06 (d, 1H, J=8.1 Hz), 6.82 (d, 1H, J=2.7 Hz), 6.57 (dd, 1H, J=2.4 and 8.1 Hz), 4.04-4.00 (m, 2H), 3.93-3.89 (m, 2H), 1.33 (s, 9H); $^{19}$F NMR (CDCl$_3$): −47214; LCMS: ret. time: 22.39 min.; purity: 94%; MS (m/e): 397 (MH$^+$).

7.3.622 5-(Hydroxymethyl)-N2-[3-(2-hydroxyethyleneoxy)phenyl]-N4-(3-hydroxyphenyl)-2,4-pyrimidinediamine (R926735)

In a manner similar to the preparation of N4-(3,4-ethylenedioxy)-5-fluoro-N2-[2-(hydroxymethyl)benzofuran-5-yl]-2,4-pyrimidinediamine, N4-(3-hydroxyphenyl)-5-methoxycarbonyl-N2-[3-(methoxycarbonylmethyleneoxy)phenyl]-2,4-pyrimidinediamine was reduced with DIBALH to yield 5-(hydroxymethyl)-N2-[3-(2-hydroxyethyleneoxy)phenyl]-N4-(3-hydroxyphenyl)-2,4-pyrimidinediamine. $^1$H NMR (CD$_3$OD): δ 7.87 (s, 1H), 7.35 (t, 1H, J=1.5 Hz), 7.15-7.08 (m, 5H), 6.57-6.50 (m, 2H), 4.56 (s, 2H), 3.92-3.86 (m, 2H), 3.84-3.79 (m, 2H); LCMS: ret. time: 14.11 min.; purity: 89%; MS (m/e): 369 (MH$^+$).

7.3.623 5-Fluoro-N2-[3-(2-hydroxyethyleneoxy)phenyl]-N4-(3-isopropylphenyl)-2,4-pyrimidinediamine R940289

In like manner to the preparation of N4-(3,4-ethylenedioxyphenyl)-5-fluoro-N2-[3-[2-(N-morpholino)ethyleneoxy]phenyl]-2,4-pyrimidinediamine, 5-fluoro-N4-(3-isopropylphenyl)-N2-(3-methoxycarbonylmethyleneoxyphenyl)-2,4-pyrimidinediamine reacted with DIBALH to give 5-fluoro-N2-[3-(2-hydroxyethyleneoxy)phenyl]-N4-(3-isopropylphenyl)-2,4-pyrimidinediamine. LCMS: ret. time: 23.03 min.; purity: 93%; MS (m/e): 382 (M$^+$), 384 (MH$^+$); $^1$H NMR (DMSO-d6): δ 9.36 (1H, s), 9.24 (1H, s), 8.20 (1H, d, J=4.2 Hz), 7.85 (1H, d, J=8.5 Hz), 7.57 (1H, s), 7.41 (1H, s), 7.33 (1H, t, J=8.5 Hz), 7.17 (1H, t, J=8.5 Hz), 7.05 (1H, d, J=8.5 Hz), 6.56 (1H, dd, J=8.5 Hz, J=2 Hz) 4.94 (1H, t, J=12 Hz), 3.94 (2H, t, J=4.7 Hz), 3.76 (2H, m), 2.95 (1H, sept, J=6.9 Hz), 1.28 (6H, dd, J=6.9 Hz, J=0.6 Hz).

7.3.624 N4-(3-tert-Butylphenyl)-5-fluoro-N2-[(2-hydroxymethylene)benzofur-5-yl]-2,4-pyrimidinediamine R940287

In like manner to the preparation of N4-(3,4-ethylenedioxyphenyl)-5-fluoro-N2-[3-[2-(N-morpholino)ethyleneoxy]phenyl]-2,4-pyrimidinediamine, N4-(3-tert-butylphenyl)-5-fluoro-N2-(2-methoxycarbonylbenzofur-5-yl)-2,4-pyrimidinediamine reacted with DIBALH to give N4-(3-tert-butylphenyl)-5-fluoro-N2-[2-(hydroxymethylene)benzofur-5-yl]-2,4-pyrimidinediamine. LCMS: retn, time: 23.15 min.; purity: 99%; MS (m/e): 407 (MH$^+$); $^1$H NMR (DMSO-d6): δ 9.34 (1H, s), 9.22 (1H, s), 8.18 (1H, d, J=3.9 Hz), 8.04 (1H, s), 8.00 (1H, d, J=8.7 Hz), 7.60 (1H, t, J=2.1 Hz), 7.47 (2H, m), 7.34 (1H, t, J=7.8 Hz), 7.21 (1H, d, J=8.7 Hz), 6.69 (1H, s), 5.54 (1H, t, J=5.8 Hz), 4.63 (2H, d, J=5.8 Hz), 1.35 (9H, s).

7.3.625 5-Fluoro-N4-(3-isopropylphenyl)-N2-[(2-hydroxymethylene]benzofur-5-yl]-2,4-pyrimidinediamine R940286

In like manner to the preparation of N4-(3,4-ethylenedioxyphenyl)-5-fluoro-N2-[3-[2-(N-morpholino)ethyleneoxy]phenyl]-2,4-pyrimidinediamine, 5-fluoro-N4-(3-isopropylphenyl)-N2-(2-methoxycarbonylbenzofur-5-yl)-2,4-pyrimidinediamine reacted with DIBALH to give 5-fluoro-N4-(3-isopropylphenyl)-N2-[(2-hydroxymethylene)benzofur-5-yl]-2,4-pyrimidinediamine. LCMS: ret. time: 21.93 min.; purity: 99%; MS (m/e): 393 (MH$^+$); $^1$H NMR (DMSO-d6): δ 9.33 (1H, s), 9.23 (1H, s), 8.18 (1H, d, J=3.9 Hz), 8.03 (1H, s), 7.86 (1H, d, J=7.1 Hz), 7.57 (1H, s), 7.49

(2H, m), 7.33 (1H, t, J=7.1 Hz), 7.05 (1H, d, J=7.1 Hz), 6.69 (1H, s), 5.54 (1H, t, J=5.7 Hz), 4.63 (2H, d, J=5.7 Hz), 2.90 (1H, sept, J=6.9 Hz), 1.26 (6H, d, J=6.9 Hz).

7.3.626 N4-(3-tert-Butylphenyl)-5-fluoro-N2-[3-(2-hydroxyethyleneoxy)phenyl]-2,4-pyrimidinediamine R940282

In like manner to the preparation of N4-(3,4-ethylenedioxyphenyl)-5-fluoro-N2-[3-[2-(N-morpholino)ethyleneoxy]phenyl]-2,4-pyrimidinediamine, N4-(3-tert-butylphenyl)-5-fluoro-N2-(3-methoxycarbonylmethyleneoxyphenyl)-2,4-pyrimidinediamine reacted with DIBALH to give N4-(3-tert-butylphenyl)-5-fluoro-N2-[3-(2-hydroxyethyleneoxy)phenyl]-2,4-pyrimidinediamine.

LCMS: ret. time: 21.63 min.; Purity: 98%; MS (m/e): 396 (M$^+$).

7.3.627 N4-[3,4-Bis(hydroxymethyl)phenyl]-5-fluoro-N2-[3-(2-hydroxyethyleneoxy)phenyl]-2,4-pyrimidinediamine (R940292)

In like manner to the preparation of N4-(3,4-ethylenedioxyphenyl)-5-fluoro-N2-[3-[2-(N-morpholino)ethyleneoxy]phenyl]-2,4-pyrimidinediamine, N2-(3-ethoxycarbonylmethyleneoxyphenyl)-N4-[6-(3,3-dihydroisobenzofuranyl-1-one)]-5-fluoro-2,4-pyrimidinediamine reacted with DIBALH to give N4-[3,4-bis(hydroxymethyl)phenyl]-5-fluoro-N2-[3-(2-hydroxyethyleneoxy)phenyl]-2,4-pyrimidinediamine. LCMS: retn, time: 13.06 min.; purity: 100%; MS (m/e): 400 (M$^+$).

7.3.628 (R935149): N2-(3,4-Ethylenedioxyphenyl)-N4-[4-(2-hydroxy-1,1-dimethylethyl)phenyl]-5-fluoro-2,4-pyrimidinediamine 2-Chloro-5-fluoro-N4-[4-[ethoxycarbonyl(dimethyl)methyl]phenyl]-N2-(3,4-ethylenedioxyphenyl)-2,4-pyrimidinediamine was reduced with 10 eq. DIBALH (1.0 M in toluene) at 0° C. in dichloromethane. Reaction was quenched with methanol, diluted with ethylacetate followed by the addition of aqueous Rochelle's salt solution, stirred at room temperature for 30 minutes followed by the addition of anhydrous sodium sulfate. The solution was filtered through Celite, concentrated and purified the concentrated by silica gel column chromatography to furnish the N2-(3,4-ethylenedioxyphenyl)-N4-[4-(2-hydroxy-1,1-dimethylethyl)phenyl]-5-fluoro-2,4-pyrimidinediamine. $^1$H NMR (DMSO-d6): δ 10.01 (br s, 1H), 9.6 (br s, 1H), 8.13 (d, 1H, J=4.7 Hz), 7.58 (d, 2H, J=8.2 Hz), 7.31 (d, 2H, J=8.8 Hz), 7.18 (d, 1H, J=2.3 Hz), 6.88 (dd, 1H, J=2.3 and 8.8 Hz), 6.73 (d, 1H, J=8.8 Hz), 4.21-4.19 (m, 4H), 3.56 (br s, 2H), 1.20 (s, 6H); LCMS: ret. time: 20.34 min.; purity: 98%; MS (m/e): 411 (MH$^+$).

7.3.629 (R935151): 5-Fluoro-N2-[4-(2-hydroxy-1,1-dimethylethyl)phenyl]-N4-(4-isopropoxyphenyl)-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, N2-[4-[(1-ethoxycarbonyl-1-methyl)ethyl]phenyl]-5-fluoro-N4-(4-isopropoxyphenyl)-2,4-pyrimidinediamine was reduced with DIBALH to provide 5-fluoro-N2-[4-(2-hydroxy-1,1-dimethylethyl)phenyl]-N4-(4-isopropoxyphenyl)-2,4-pyrimidinediamine. $^1$H NMR (CDCl$_3$): δ 7.89 (d, 1H, J=2.9 Hz), 7.46 (d, 3H, J=8.8 Hz), 7.27 (d, 2H, J=8.2 Hz), 6.89 (d, 2H, J=9.3 Hz), 6.68-6.65 (m, 1H), 4.53 (septet, 1H, J=5.8 Hz), 3.57 (s, 2H), 1.36 (d, 6H, J=5.8 Hz), 1.31 (s, 6H); LCMS: ret. time: 23.43 min.; purity: 99%; MS (m/e): 411 (MH$^+$).

7.3.630 (R935153): 5-Fluoro-N2-[4-(2-hydroxy-1,1-dimethylethyl)phenyl]-N4-(3-hydroxyphenyl)-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, N2-[4-[ethoxycarbonyl(dimethyl)methyl]phenyl]-5-fluoro-N4-(3-hydroxyphenyl)-2,4-pyrimidinediamine was reduced with DIBALH to provide 5-fluoro-N2-[4-(2-hydroxy-1,1-dimethylethyl)phenyl]-N4-(3-hydroxyphenyl)-2,4-pyrimidinediamine. $^1$H NMR (CDCl$_3$): δ 7.89 (d, 1H, J=2.9 Hz), 7.57 (s, 1H), 7.41 (d, 2H, J=8.8 Hz), 7.29 (d, 2H, J=8.2 Hz), 7.16 (d, 1H, J=8.2 Hz), 7.10 (d, 1H, J=8.8 Hz), 6.80-6.55 (m, 2H), 5.58 (s, 2H), 1.30 (s, 6H); LCMS: ret. time: 18.01 min.; purity: 98%; MS (m/e): 369 (MH$^+$).

7.3.631 (R935154): N4-(3,4-Ethylenedioxyphenyl)-5-fluoro-N2-[3-(2-hydroxyethoxy)phenyl]-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, N4-(3,4-ethylenedioxyphenyl)-5-fluoro-N2-(3-methoxycarbonylmethyleneoxyoxyphenyl)-2,4-pyrimidine diamine was reduced with DIBALH to provide N4-(3,4-ethylenedioxyphenyl)-5-fluoro-N2-[3-(2-hydroxyethoxy)phenyl]-2,4-pyrimidinediamine. $^1$H NMR (CDCl$_3$): δ 7.88 (d, 1H, J=3.8 Hz), 7.34 (t, 1H, J=2.3 Hz), 7.19 (dd, 1H, J=2.3 and 8.2 Hz), 7.14 (d, 1H, J=7.6 Hz), 7.01-6.97 (m, 2H), 6.84 (d, 1H, J=8.8 Hz), 6.53 (dd, 1H, J=1.7 and 7.6 Hz), 4.26 (s, 4H), 3.98 (t, 2H, J=4.1 Hz), 3.89 (t, 2H, J=4.1 Hz); LCMS: ret. time: 18.36 min.; purity: 99%; MS (m/e): 399 (MH$^+$).

7.3.632 (R935155): 5-Fluoro-N2-[4-(2-hydroxyethoxy)phenyl]-N4-(3-hydroxyphenyl)-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, 5-fluoro-N4-(3-hydroxyphenyl)-N2-[4-(methoxycarbonylmethyleneoxy)phenyl]-2,4-pyrimidinediamine was reduced to 5-fluoro-N2-[4-(2-hydroxyethoxy)phenyl]-N4-(3-hydroxyphenyl)-2,4-pyrimidinediamine with DIBALH. $^1$H NMR (CDCl$_3$): δ 7.73 (d, 1H, J=3.5 Hz), 7.33 (d, 2H, J=8.8 Hz), 7.15 (br s, 1H), 7.04 (app t, 2H, J=8.2 and 7.6 Hz), 6.78 (d, 2H, J=8.8 Hz), 6.49 (d, 1H, J=7.6 Hz), 3.95 (t, 2H, J=4.7 Hz), 3.80 (t, 2H, J=4.7 Hz); LCMS: ret. time: 14.49 min.; purity: 98%; MS (m/e): 357 (MH$^+$).

7.3.633 (R935156): 5-Fluoro-N2-[3-(2-hydroxyethoxy)phenyl]-N4-(4-isopropoxyphenyl)-2,4-pyrimidinediamine In like manner to the preparation of N2-(3,4-ethylenedioxyphenyl)-5-fluoro-N4-[4(2-hydroxy-1,1-dimethylethyl)phenyl]-2,4-pyrimidinediamine, 5-fluoro-N4-(4-isopropoxyphenyl)-N2-(3-methoxycarbonylmethyleneoxyphenyl)-2,4-pyrimidinediamine was reduced with DIBALH to provide 5-fluoro-N2-[3-(2-hydroxyethoxy)phenyl]-N4-(4-isopropoxyphenyl)-2,4-pyrimidinediamine. $^1$H NMR (CDCl$_3$): δ 7.90 (d, 1H, J=3.5 Hz), 7.45 (d, 2H, J=8.8 Hz), 7.34 (t, 1H, J=2.3 Hz), 7.13 (t, 1H, J=8.2 Hz), 6.93 (m, 3H), 7.76 (d, 1H, J=2.3 Hz), 6.52 (dd, 1H, J=2.3 and 8.2 Hz), 4.52 (septet, 1H, J=5.7 Hz), 3.95-3.85 (m, 4H), 1.34 (d, 6H, J=5.7 Hz); LCMS: ret. time: 21.17 min.; purity: 98%; MS (m/e): 399 (MH$^+$).

7.3.634 (R935158): 5-Fluoro-N4-[4-(2-hydroxy-1,1-dimethylethyl)phenyl]-N2-[4-(2-hydroxyethoxy)phenyl]-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, N4-[4-[1-ethoxycarbonyl 1-methyl)ethyl]phenyl]-5-fluoro-N2-(4-methoxycarbonylmethyleneoxyphenyl)-2,4-pyrimidinediamine was reduced with DIBALH to give 5-fluoro-N4-[4-(2-hydroxy-1,1-dimethylethyl)phenyl]-N2-[4-(2-hydroxyethoxy)phenyl]-2,4-pyrimidinediamine. $^1$H NMR (CDCl$_3$): δ 7.83 (d, 1H, J=3.5 Hz), 7.49 (d, 2H, J=8.8 Hz), 7.35 (d, 2H, J=8.8 Hz), 7.31 (d, 2H, J=8.8 Hz), 6.82 (d, 2H, J=8.8 Hz), 4.03 (t, 2H, J=4.7 Hz), 3.89 (t, 2H, J=4.7 Hz), 3.56 (s, 2H), 1.30 (s, 6H); LCMS: ret. time: 16.86 min.; purity: 96%; MS (m/e): 413 (MH$^+$).

7.3.635 (R935160): 5-Fluoro-N2-[4-(2-hydroxyethoxy)phenyl]-N4-(4-isopropoxyphenyl)-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, 5-fluoro-N4-(4-isopropoxyphenyl)-N2-(4-methoxycarbonylmethyleneoxyphenyl)-2,4-pyrimidinediamine was reduced with DIBALH to give 5-fluoro-N2-[4-(2-hydroxyethoxy)phenyl]-N4-(4-isopropoxyphenyl)-2,4-pyrimidinediamine. $^1$H NMR (DMSO-d6): δ 9.12 (s, 1H), 8.92 (s, 1H), 7.98 (d, 1H, J=3.5 Hz), 7.59 (d, 2H, J=8.8 Hz), 7.49 (d, 2H, J=9.3 Hz), 6.86 (d, 2H, J=8.8 Hz), 6.76 (d, 2H, J=9.3 Hz), 4.82 (t, 1H, J=4.9 Hz), 4.55 (septet, 1H, J=6.4 Hz), 3.89 (t, 2H, J=5.3 Hz), 3.67 (app q, 2H, J=5.3 and 4.9 Hz), 1.24 (d, 6H, J=6.4 Hz); LCMS: ret. time: 19.56 min.; purity: 100%; MS (m/e): 399 (MH$^+$).

7.3.636 (R935161): 5-Fluoro-N4-[4-(2-hydroxy-1,1-dimethylethyl)phenyl]-N2-[3-(2-hydroxyethoxy)phenyl]-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, N4-[4-(1-ethoxycarbonyl-1-methyl)ethyl]phenyl]-5-fluoro-N2-(3-methoxycarbonylmethylphenyl)-2,4-pyrimidinediamine was reduced with DIBALH to give 5-fluoro-N4-[4-(2-hydroxy-1,1-dimethylethyl)phenyl]-N2-[3-(2-hydroxyethoxy)phenyl]-2,4-pyrimidinediamine. $^1$H NMR (DMSO-d6): δ 9.27 (s, 1H), 9.11 (s, 1H), 8.07 (d, 1H, J=3.5 Hz), 7.67 (d, 2H, J=8.8 Hz), 7.38-7.24 (m, 4H), 7.06 (t, 1H, J=8.2 Hz), 6.46 (dd, 1H, J=8.2 Hz), 4.83 (t, 1H, J=5.3 Hz), 4.66 (t, 1H, J=5.3 Hz), 3.88 (t, 2H, J=5.3 Hz), 3.67 (t, 1H, J=5.3 Hz), 3.66 (t, 1H, J=5.3 Hz), 3.38 (d, 2H, J=5.3 Hz), 1.20 (s, 6H); LCMS: ret. time: 17.17 min.; purity: 96%; MS (m/e): 413 (MH$^+$).

7.3.637 (R935168): 5-Fluoro-N4-[4-(2-hydroxy-1,1-dimethylethyl)phenyl]-N2-(4-isopropoxyphenyl)-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, N4-[4-(1-ethoxycarbonyl-1-methyl)ethylphenyl]-5-fluoro-N2-(4-isopropoxyphenyl)-2,4-pyrimidinediamine was reduced with DIBALH to produce 5-fluoro-N4-[4-(2-hydroxy-1,1-dimethylethyl)phenyl]-N2-(4-isopropoxyphenyl)-2,4-pyrimidinediamine. $^1$H NMR (DMSO-d6): δ 9.21 (s, 1H), 8.93 (s, 1H), 8.00 (d, 1H, J=4.1 Hz), 7.62 (d, 2H, J=8.8 Hz), 7.48 (d, 2H, J=8.8 Hz), 7.27 (d, 2H, J=8.8 Hz), 6.75 (d, 2H, J=8.8 Hz), 4.65 (t, 1H, J=5.3 Hz), 4.47 (septet, 1H, J=5.8 Hz), 3.38 (d, 2H, J=5.3 Hz), 1.22 (d, 6H, J=5.8 Hz), 1.20 (s, 6H); LCMS: ret. time: 22.97 min.; purity: 99%; MS (m/e): 411 (MH$^+$).

7.3.638 (R935170): 5-Fluoro-N4-[3-(2-hydroxyethoxy)phenyl]-N2-(3-hydroxyphenyl)-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, 5-fluoro-N2-(3-hydroxyphenyl)-N4-(3-methoxycarbonylmethyleneoxyphenyl)-2,4-pyrimidinediamine was reduced with DIBALH to produce 5-fluoro-N4-[3-(2-hydroxyethoxy)phenyl]-N2-(3-hydroxyphenyl)-2,4-pyrimidinediamine. $^1$H NMR (DMSO-d6): δ 9.23 (s, 1H), 9.14 (s, 1H), 9.06 (s, 1H), 8.07 (d, 1H, J=4.1 Hz), 7.51 (dd, 1H, J=1.7 and 7.6 Hz), 7.30 (app t, 1H, J=2.3 and 1.7 Hz), 7.19 (t, 1H, J=8.2 Hz), 7.13 (br s, 1H), 7.11 (m, 1H), 6.96 (t, 1H, J=7.6 Hz), 6.61 (dd, 1H, J=2.3 and 8.2 Hz), 6.28 (dd, 1H, J=2.3 Hz and 8.2 Hz), 4.84 (t, 1H, J=5.8 Hz), 3.92 (t, 2H, J=5.2 Hz), 3.68 (app qt, 2H, J=5.2 Hz); LCMS: ret. time: 14.71 min.; purity: 96%; MS (m/e): 357 (MH$^+$).

7.3.639 (R935171): 5-Fluoro-N2-[4-(2-hydroxy-1,1-dimethylethyl)phenyl]-N4-(3-hydroxyphenyl)-2,4-pyrimidinediamine In like manner to the preparation of N2-(3,4-ethylenedioxyphenyl)-5-fluoro-N4-[4-(2-hydroxy-1,1-dimethylethyl)phenyl]-pyrimidine-2,4-diamine, N4-[4-(1-ethoxycarbonyl-1-methyl)ethyl]phenyl]-5-fluoro-N2-(3-hydoxyphenyl)-2,4-pyrimidinediamine was reduced with DIBALH to give 5-fluoro-N2-[4-(2-hydroxy-1,1-dimethylethyl)phenyl]-N4-(3-hydroxyphenyl)-2,4-pyrimidinediamine. $^1$H NMR (DMSO-d6): δ 9.24 (s, 1H), 9.13 (s, 1H), 9.01 (s, 1H), 8.04 (d, 1H, J=3.5 Hz), 7.68 (d, 2H, J=8.8 Hz), 7.29 (d, 2H, J=8.8 Hz), 7.16 (br s, 1H), 7.07 (m, 1H), 6.94 (t, 1H, 8.8 Hz), 6.30 (m, 1H), 4.64 (t, 1H, J=5.8 Hz), 3.38 (d, 2H, J=5.3 Hz), 1.20 (s, 6H); LCMS: ret. time: 17.36 min.; purity: 100%; MS (m/e): 369 (MH$^+$)

7.3.640 (R935174): 5-Fluoro-N2-[4-(2-hydroxyethoxy)phenyl]-N4-(2-hydroxymethylbenzofur-5-yl)-2,4-pyrimidinediamine In like manner to the preparation of N2-(3,4-ethylenedioxyphenyl)-5-fluoro-N4-[4(2-hydroxy-1,1-dimethylethyl)phenyl]-2,4-pyrimidinediamine, N2-(2-carbomethoxybenzofur-5-yl)-5-fluoro-N4-(4-methoxycarbonylmethyleneoxyphenyl)-2,4-pyrimidinediamine was reduced with DIBALH to provide 5-fluoro-N2[4-(2-hydroxyethoxy)phenyl]-N2-(2-hydroxymethylbenzofur-5-yl)-2,4-pyrimidinediamine. $^1$H NMR (DMSO-d6): δ 9.26 (s, 1H), 8.94 (s, 1H), 8.01 (d, 1H, J=4.1H), 7.99 (s, 1H), 7.52-7.45 (m, 4H), 6.72 (d, 2H, J=9.3 Hz), 6.66 (s, 1H), 5.46 (t, 1H, J=5.3 Hz), 4.82 (t, 1H, J=5.8 Hz), 4.55 (d, 2H, J=5.8 Hz), 3.89 (t, 2H, J=5.3 Hz), 3.67 (app qt, 2H, J=5.3 Hz); LCMS: ret. time: 14.97 min.; purity: 91%; MS (m/e): 411 (MH$^+$).

7.3.641 (R935176): N2-(3,4-Ethylenedioxyphenyl)-5-fluoro-N4-[3-(2-hydroxyethoxy)phenyl]-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, N2-(3,4-ethylenedioxyphenyl)-5-fluoro-N4-(3-methoxycarbonylmethyleneoxypheny)-2,4-pyrimidinediamine was reduced with DIBALH to provide N2-(3,4-ethylenedioxyphenyl)-5-fluoro-N4-[3-(2-hydroxyethoxy)phenyl]-2,4-pyrimidinediamine. $^1$H NMR (DMSO-d6): δ 9.22 (s, 1H), 8.98 (s, 1H), 8.05 (d, 1H, J=3.5 Hz), 7.47 (dd, 1H, J=1.1 and 8.2 Hz), 7.27 (t, 1H, J=1.7 Hz), 7.23 (d, 1H, J=2.3 Hz), 7.18 (t, 1H, J=8.2 Hz), 7.05 (dd, 1H, J=2.3 and 8.8 Hz), 6.68 (d, 1H, J=8.2 Hz), 6.61 (dd, 1H, J=1.7 and 8.8 Hz), 4.85 (t, 1H, J=5.3 Hz), 4.18-4.14 (m, 4H), 3.91 (t, 2H, J=5.3 Hz), 3.68 (qt, 2H, J=5.3 Hz); LCMS: ret. time: 17.35 min.; purity: 92%; MS (m/e): 399 (MH$^+$).

7.3.642 (R935177): 5-Fluoro-N2-[4-(2-hydroxy-1,1,dimethylethyl)phenyl]-N4-(2-hydroxymethylbenzofur-5-yl)-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, N4-(2-carbomethoxybenzofur-5-yl)-N2-[4-(1-ethoxycarbonyl-1-methyl)ethylphenyl]-5-fluoro-2,4-pyrimidinediamine was reduced with DIBALH to produce 5-fluoro-N2-[4-(2-hydroxy-1,1,dimethylethyl)phenyl]-N4-(2-hydroxymethylbenzofur-5-yl)-2,4-pyrimidinediamine. LCMS: ret. time: 18.17 min.; purity: 94%; MS (m/e): 423 (MH$^+$).

7.3.643 (R935178): 5-Fluoro-N2-[3-(2-hydroxyethyloxy)phenyl]-N4-(2-hydroxymethylbenzofur-5-yl)-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, N4-(2-carbomethoxybenzofur-5-yl)-5-fluoro-N2-(3-methoxycarbonylmethyleneoxyphenyl)-2,4-pyrimidinediamine was reduced with DIBALH to provide 5-fluoro-N2-[3-(2-hydroxyethyloxy)phenyl]-N4-(2-hydroxymethylbenzofur-5-yl)-2,4-pyrimidinediamine. $^1$H NMR (DMSO-d6): δ 9.93 (s, 1H), 9.12 (s, 1H), 8.07 (d, 1H, J=3.6 Hz), 8.01 (d, 1H, J=2.3 Hz), 7.55-7.46 (m, 2H), 7.29 (br s, 1H), 7.23 (d, 1H, J=8.2 Hz), 7.03 (t, 1H, J=8.2 Hz), 6.68 (s, 1H), 6.44 (dd, 1H, J=2.3 and 8.2 Hz), 5.47 (t, 1H, J=5.8 Hz), 4.80 (t, 1H, J=5.3 Hz), 4.55 (d, 2H, J=5.3 Hz), 3.81 (qt, 2H, J=5.3 Hz), 3.63 (qt, 2H, J=5.3 Hz); LCMS: ret. time: 15.41 min.; purity: 88%; MS (m/e): 411 (MH$^+$).

7.3.644 (R935181): N4-(3,5-Dimethoxyphenyl)-5-fluoro-N2-[3-(2-hydroxyethoxy)phenyl]-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, N4-(3,5-dimethoxyphenyl)-5-fluoro-N2-(3-methoxycarbonylmethyleneoxyphenyl)-2,4-pyrimidineamine was reduced with DIBALH to give N4-(3,5-dimethoxyphenyl)-5-fluoro-N2-[3-(2-hydroxyethoxy)phenyl]-2,4-pyrimidinediamine: $^1$H NMR (DMSO-d6): δ 9.24 (s, 1H), 9.18 (s, 1H), 8.11 (d, 1H, J=3.5 Hz), 7.31-7.26 (m, 2H), 7.05 (d, 1H, J=8.2 Hz), 6.99 (d, 1H, J=2.3 Hz), 6.43 (dd, 1H, J=2.3 Hz, 8.2 Hz), 6.20 (t, 1H, J=2.3 Hz), 4.80 (t, 1H, J=5.8 Hz), 3.83 (t, 2H, J=5.3 Hz), 3.67 (s, 6H), 3.66-3.60 (m, 2H); LCMS: ret. time: 18.78 min.; purity: 95%; MS (m/e): 400 (MH$^+$).

7.3.645 (R935183): 5-Fluoro-N2-[4-(2-hydroxyethoxy)phenyl]-N4-(3,4-propylenedioxyphenyl)-2,4-pyrimidinediamine In like manner to the preparation of N2-(3,4-ethylenedioxyphenyl)-5-fluoro-N4-[4-(2-hydroxy-1,1-dimethylethyl)phenyl]-2,4-pyrimidinediamine, 5-fluoro-N2-[4-(methoxycarbonylmethyleneoxy)phenyl]-N4-(3,4-propylenedioxyphenyl)-2,4-pyrimidinediamine was reduced with DIBAL-H to provide 5-fluoro-N2-[4-(2-hydroxyethoxy)phenyl]-N4-(3,4-propylenedioxyphenyl)-2,4-pyrimidinediamine. H NMR (DMSO-d6): δ 9.15 (s, 1H), 8.97 (s, 1H), 8.00 (d, 1H, J=3.5 Hz), 7.49 (d, 2H; J=8.8 Hz), 7.40-7.31 (m 2H), 6.88 (d, 1H, J=8.8 Hz), 6.80 (d, 2H, J=8.8 Hz), 4.82 (t, 1H, J=5.3 Hz), 4.12-4.04 (m 4H), 3.90 (t, 2H, J=5.2 Hz), 3.70-3.65 (app qt, 2H, J=5.3 Hz), 2.07 (q, 2H, J=5.3 Hz); LCMS: ret. time: 17.05 min.; purity: 96%; MS (m/e): 413 (MH$^+$).

7.3.646 (R935186): 5-Fluoro-N2-[4-(2-hydroxyethoxy)phenyl]-N4-(3,4-propylenedioxyphenyl)-2,4-pyrimidinediamine In like manner to the preparation of N2-(3,4-ethylenedioxyphenyl)-5-fluoro-N4-[4(2-hydroxy-1,1-dimethylethyl)phenyl]-2,4-pyrimidinediamine, 5-fluoro-N2-[3-(methoxycarbonylmethyleneoxy)phenyl]-N4-(3,4-propylenedioxyphenyl)-2,4-pyrimidinediamine was reduced with DIBALH to provide 5-fluoro-N2-[3-(2-hydroxyethoxy)phenyl]-N4-(3,4-propylenedioxyphenyl)-2,4-pyrimidinediamine. $^1$H NMR (DMSO-d6): δ 9.21 (s, 1H), 9.14 (s, 1H), 8.07 (d, 1H, J=3.5 Hz), 7.42-7.36 (m, 2H), 7.29-7.24 (m, 2H), 7.07 (t, 1H, J=8.2 Hz), 6.90 (d, 1H, J=8.8 Hz), 6.45 (dd, 1H, J=1.7 and 8.3 Hz), 4.82 (t, 1H, J=5.3 Hz), 4.12-4.04 (app q, 2H, J=5.3 Hz), 3.86 (t, 2H, J=5.3 Hz), 3.67 (app qt, 2H, J=5.3 Hz), 2.07 (q, 2H, J=5.3 Hz); LCMS: ret. time: 17.95 min.; purity: 96%; MS (m/e): 413 (MH$^+$).

7.3.647 N4-(4-tert-Butylphenyl)-5-fluoro-N2-[2,3-dihydro-2-(carboxy)benzofuran-5-yl]-2,4-pyrimidinediamine (R926720)

The reaction of N2-(4-tert-butylphenyl)-5-fluoro-N2-[2,3-dihydro-2-(methoxycarbonyl)benzofuran-5-yl]-2,4-pyrimidinediamine and lithium hydroxide (LiOH) in THF:H$_2$O at room temperature gave N4-(4-tert-butylphenyl)-5-fluoro-N2-[2,3-dihydro-2-(carboxy)benzofuran-5-yl]-2,4-pyrimidinediamine. $^1$H NMR (DMSO-d6): δ 10.01 (bs, 1H), 9.69 (bs, 1H), 8.13 (d, 1H, J=4.8 Hz), 7.57 (d, 2H, J=8.7 Hz), 7.50 (s, 1H), 7.35 (d, 2H, J=8.1 Hz), 7.13 (d, 1H, J=8.7 Hz), 6.75 (d, 1H, J=9.0 Hz), 5.21 (dd, 1H, J=6.3 and 10.5 Hz), 3.49 (dd, 1H, J=10.5 and 16.5 Hz), 3.17 (dd, 1H, J=6.6 and 16.5 Hz), 1.27 (s, 9H); LCMS: ret. time: 22.53 min.; purity: 93%; MS (m/e): 423 (MH$^+$).

7.3.648 N4-(4-tert-Butylphenyl)-N2-(3-carboxymethyleneoxyphenyl)-5-fluor-2,4-pyrimidinediamine (R926726)

In a manner similar to the preparation of N4-(4-tert-butylphenyl)-5-fluoro-N2-[2,3-dihydro-2-(carboxy)benzofuran-5-yl]-2,4-pyrimidinediamine, N4-(4-tert-butylphenyl)-5-fluoro-N2-(3-methoxycarbonylmethyleneoxyphenyl)-2,4-pyrimidinediamine and lithium hydroxide were reacted to yield N4-(4-tert-butylphenyl)-5-fluoro-N2-(3-carboxymethyleneoxyphenyl)-2,4-pyrimidinediamine. $^1$H NMR (DMSO-d6): δ 12.88 (bs, 1H), 9.29 (s, 1H), 9.16 (s, 1H), 8.07 (d, 1H, J=3.3 Hz), 7.68 (d, 2H, J=8.7 Hz), 7.35-7.31 (m, 3H), 7.26 (d, 1H, J=8.4 Hz), 7.06 (t, 1H, J=8.4 Hz), 6.41 (dd, 1H, J=2.4 and 8.4 Hz), 4.54 (s, 2H), 1.27 (s, 9H); $^{19}$F NMR (DMSO-d6): −46463; LCMS: ret. time: 22.94 min.; purity: 97%; MS (m/e): 411 (MH$^+$).

7.3.649 5-Fluoro-N2-[3-(carboxymethyleneoxy)phenyl]-N4-[4-(isopropoxy)phenyl]-2,4-pyrimidinediamine (R926731)

In a manner similar to the preparation of N4-(4-tert-butylphenyl)-5-fluoro-N2-[2,3-dihydro-2-(carboxy)benzofuran-5-yl]-2,4-pyrimidinediamine, 5-fluoro-N2-(3-methoxycarbonylmethyleneoxyphenyl)-N4-(4-isopropoxyphenyl)-2,4-pyrimidinediamine and lithium hydroxide were reacted to yield 5-fluoro-N2-(3-carboxymethyleneoxyphenyl)-N4-(4-isopropoxyphenyl)-2,4-pyrimidinediamine. $^1$H NMR (DMSO-d6): δ 6.19 (bs, 1H), 9.01 (s, 1H), 8.02 (d, 1H, J=3.9 Hz), 7.63 (d, 2H, J=9.3 Hz), 7.19-7.14 (m, 2H), 6.96 (t, 1H, J=8.7 Hz), 6.87 (d, 2H, J=9.6 Hz), 6.28 (dd, 1H, J=2.45 and 9.0 Hz), 4.56 (2q, 1H, J=6.6 Hz), 3.94 (s, 2H), 1.24 (d, 6H, J=6.6 Hz); LCMS: ret. time: 20.13 min.; purity: 100%; MS (m/e): 413 (MH$^+$).

7.3.650 N2,N4-Bis(4-carboxymethyleneoxy)phenyl-5-fluoro-2,4-pyrimidinediamine (R926560)

In a manner similar to the preparation of N4-(4-tert-butylphenyl)-5-fluoro-N2-[2,3-dihydro-2-(carboxy)benzofuran-5-yl]-2,4-pyrimidinediamine, the hydrolysis of N2,N4-bis(4-methoxycarbonylmethyleneoxyphenyl)-5-fluoro-2,4-pyrimidinediamine with LiOH gave N2,N4-bis(4-carboxymethyleneoxy)phenyl-5-fluoro-2,4-pyrimidinediamine $^1$H NMR (CD$_3$OD): δ 7.86 (bs, 1H), 7.55 (d, 2H, J=9.0 Hz), 7.32 (bd, 2H, J=9.3 Hz), 6.95 (m, 4H), 4.66 (s, 2H), $^{19}$F NMR (CDCl$_3$): −21852; LCMS: ret. time: 15.16 min.; purity: 77%; MS (m/e): 429 (MH$^+$).

7.3.651 N2-(3-Carboxymethyleneoxyphenyl)-N4-(3,4-ethylenedioxyphenyl)-5-fluoro-2,4-pyrimidinediamine (R926483)

In a manner similar to the preparation of N4-(4-tert-butylphenyl)-5-fluoro-N2-[2,3-dihydro-2-(carboxy)benzofuran-5-yl]-2,4-pyrimidinediamine, the reaction of N2-(3-ethoxycarbonylmethyleneoxyphenyl)-N4-(3,4-ethylenedioxyphenyl)-5-fluoro-2,4-pyrimidinediamine with LiOH gave N2-(3-carboxymethyleneoxyphenyl)-N4-(3,4-ethylenedioxyphenyl)-5-fluoro-2,4-pyrimidinediamine. $^1$H NMR (DMSO-d6): δ 12.90 (s, 1H), 9.20 (s, 2H), 8.05 (d, 1H, J=1.2 Hz), 7.32-7.21 (m, 3H), 7.08 (t, 1H, J=8.1 Hz), 6.80 (d, 1H, J=8.4 Hz), 6.40 (dd, 1H, J=1.8 and 8.2 Hz), 4.53 (s, 2H), 4.20 (s, 4H); LCMS: ret. time: 18.26 min.; purity: 100%; MS (m/e): 413 (MH$^+$).

7.3.652 N2-(3-Carboxymethyleneoxyphenyl)-5-fluoro-N4-(3-hydroxyphenyl)-2,4-pyrimidinediamine (R945126)

In a manner similar to the preparation of N4-(4-tert-butylphenyl)-5-fluoro-N2-[2,3-dihydro-2-(carboxy)benzofuran-5-yl]-2,4-pyrimidinediamine, the reaction of 5-fluoro-N4-(3-hydroxyphenyl)-N2-(3-(methoxycarbonylmethyleneoxyphenyl)-2,4-pyrimidinediamine with LiOH gave N2-(3-carboxymethyleneoxyphenyl)-5-fluoro-N4-(3-hydroxyphenyl)-2,4-pyrimidinediamine $^1$H NMR (DMSO-d6): δ 4.55 (s, 2H), 6.43 (dd, J=2.1, 8.1 Hz, 1H), 6.48 (dd, J=2.1 and 7.2 Hz, 1H), 7.06-7.13 (m, 3H), 7.28-7.34 (m, 3H), 8.09 (d, J=3.6 Hz, 1H), 9.22 (br, 1H), 9.28 (br, 1H), 9.34 (br, 1H); $^{19}$F NMR (282 MHz, DMSO-d6): 6-163.85; LCMS: ret. time: 15.88 min.; purity: 100%; MS (m/e): 370.63 (MH$^+$).

7.3.653 N2-(4-Carboxymethyleneoxyphenyl)-N4-(3,4-ethylenedioxyphenyl)-5-fluoro-2,4-pyrimidinediamine (R926238)

In a manner similar to the preparation of N4-(4-tert-butylphenyl)-5-fluoro-N2-[2,3-dihydro-2-(carboxy)benzofuran-5-yl]-2,4-pyrimidinediamine, the reaction of N2-(4-ethoxycarbonylmethyleneoxyphenyl)-N4-(3,4-ethylenedioxyphenyl)-5-fluoro-2,4-pyrimidinediamine with LiOH gave N2-(carboxymethyleneoxyphenyl)-N4-(3,4-ethylenedioxyphenyl)-5-fluoro-2,4-pyrimidinediamine. $^1$H NMR (DMSO-d6): δ 8.16 (d, 1H, J=4.8 Hz), 7.37 (bd, 2H, J=9 Hz), 7.25 9d, 1H, J=3 Hz), 7.08 (m, 1H), 6.83 (m, 3H), 4.64 (s, 2H), 4.23 (s, 4H); LCMS: ret. time: 19.15 min.; purity: 100%; MS (m/e): 413 (MH$^+$).

7.3.654 N2-(4-Carboxymethyleneoxyphenyl)-5-Fluoro-N4-(3-hydroxyphenyl)-2,4-pyrimidinediamine (R926564)

In a manner similar to the preparation of N4-(4-tert-butylphenyl)-5-fluoro-N2-[2,3-dihydro-2-(carboxy)benzofuran-5-yl]-2,4-pyrimidinediamine, 5-fluoro-N2-(4-ethoxycarbonylmethyleneoxyphenyl)-N4-(3-hydroxyphenyl)-2,4-pyrimidinediamine upon treatment with LiOH gave 5-fluoro-N2-(4-carboxymethyleneoxyphenyl)-N4-(3-hydroxyphenyl)-2,4-pyrimidinediamine. $^1$H NMR (CD$_3$OD): δ 7.89 (d, 1H, J=5.1 Hz), 7.34 (dd, 2H, J=2.1 and 9.3 Hz), 7.19-7.08 (m, 2H), 6.98 (dd, 2H, J=2.4 and 8.4 Hz), 6.69 (m, 1H), 4.68 (s, 2H); $^{19}$F NMR (CD$_3$OD): −21860; LCMS: ret. time: 15.69 min.; purity: 99%; MS (m/e): 371 (MH$^+$)

7.3.655 N2-(2-Carboxybenzofuran-5-yl)-5-fluoro-N4-(3-hydroxyphenyl)-2,4-pyrimidinediamine (R926478)

In a manner similar to the preparation of N4-(4-tert-butylphenyl)-5-fluoro-N2-[2,3-dihydro-2-(carboxy)benzofuran-5-yl]-2,4-pyrimidinediamine, 5-fluoro-N4-(3-hydroxyphenyl)-N2-(2-methoxycarbonylbenzofuran-5-yl)-4-pyrimidinediamine upon LiOH treatment gave N2-(2-carboxybenzofuran-5-yl)-5-fluoro-N4-(3-hydroxyphenyl)-2,4-pyrimidinediamine. $^1$H NMR (CD$_3$OD): δ 7.97 (bd, 2H), 7.60-7.44 (m, 4H), 7.20-7.05 (m, 3H), 6.69 (bd, 1H); $^{19}$F NMR (CD$_3$OD): −21844; LCMS: ret. time: 16.77 min.; purity: 100%; MS (m/e): 381 (MH$^+$).

7.3.656 N2-(2-Carboxyindol-5-yl)-5-fluoro-N4-(3-hydroxyphenyl)-2,4-pyrimidinediamine (R926479)

In a manner similar to the preparation of N4-(4-tert-butylphenyl)-5-fluoro-N2-[2,3-dihydro-2-(carboxy)benzofuran-5-yl]-2,4-pyrimidinediamine, N2-(2-ethoxycarbonylindol-5-yl)-5-fluoro-N4-(3-hydroxyphenyl)-2,4-pyrimidinediamine upon LiOH treatment gave N2-(2-carboxyindol-5-yl)-5-fluoro-N4-(3-hydroxyphenyl)-2,4-pyrimidinediamine. $^1$H NMR (CD$_3$OD): δ 7.83 (m, 1H), 7.73 (s, 1H), 7.50 (bd, 1H, J=8.7 Hz), 7.30-7.11 (m, 5H), 6.68 (bd, 1H); LCMS: ret. time: 16.50 min.; purity: 97%; MS (m/e): 380 (MH$^+$).

7.3.657 N4-(4-tert-Butylphenyl)-N2-(2-carboxybenzofuran-5-yl)-5-fluoro-2,4-pyrimidinediamine (R926481)

In a manner similar to the preparation of N4-(4-tert-butylphenyl)-5-fluoro-N2-[2,3-dihydro-2-(carboxy)benzofuran-5-yl]-2,4-pyrimidinediamine, LiOH treatment with N4-(4-tert-butylphenyl)-5-fluoro-N2-(2-methoxycarbonylbenzofuran-5-yl)-2,4-pyrimidinediamine gave N4-(4-tert-butylphenyl)-N2-(2-carboxybenzofuran-5-yl)-5-fluoro-2,4-pyrimidinediamine. $^1$H NMR (CD$_3$OD): δ 9.3 (bd, 2H), 8.25 (s, 1H), 8.10 (s, 1H), 7.65-7.30 (m, 5H), 1.25 (s, 9H); $^{19}$F NMR (CD$_3$OD): −21844; LCMS: ret. time: 23.32 min.; purity: 100%; MS (m/e): 421 (MH$^+$).

7.3.658 N4-(3-tert-Butylphenyl)-N2-[3-carboxymethyleneoxyphenyl]-5-fluoro-2,4-pyrimidinediamine R940280

In a manner similar to the preparation of N4-(4-tert-butylphenyl)-5-fluoro-N2-[2,3-dihydro-2-(carboxy)benzofuran-5-yl]-2,4-pyrimidinediamine, N4-(3-tert-butylphenyl)-5-fluoro-N2-(3-methoxycarbonylmethyleneoxyphenyl)-2,4-pyrimidinediamine was reacted with LiOH to give N4-(3-tert-butylphenyl)-N2-(3-carboxymethyleneoxyphenyl)-5-fluoro 2,4-pyrimidinediamine. LCMS: ret. time: 23.61 min.; purity: 99%; MS (m/e): 410 (M$^+$), 412 (MH$^+$); $^1$H NMR (DMSO-d6): δ 9.45 (1H, s), 9.33 (1H, s), 8.21 (1H, d, J=3.9 Hz), 7.98 (1H, d, J=6.6 Hz), 7.60 (1H, t, J=2 Hz), 7.44-7.34 (3H, m), 7.24-7.15 (2H, m), 6.54 (1H, d, J=7.8 Hz), 4.68 (2H, s), 1.36 (9H, s).

7.3.659 N2-(3-Carboxymethyleneaminophenyl)-N4-(3,4-ethylenedioxyphenyl)-5-fluoro-2,4-pyrimidinediamine (R950190)

The reaction of N2-(3-ethoxycarbonylmethyleneaminophenyl)-N4-(3,4-ethylenedioxyphenyl)-5-fluoro-2,4-pyrimidinediamine (0.1 g) and LiOH (10 equivalents) in MeOH:water (1:1, v/v) for 1 h at room temperature followed by treatment with aqueous HCl gave the solid. The resulting solid was filtered, washed with water and dried to give N2-(3-carboxymethyleneaminophenyl)-N4-(3,4-ethylenedioxyphenyl)-5-fluoro-2,4-pyrimidinediamine. LCMS: ret. time: 18.23 min.; purity: 87.6%; MS (m/e): 412.01 (MH$^+$).

7.3.660 N2-(Carboxymethyleneaminophenyl)-5-fluoro-N4-[3-(2-hydroxyethyloxy)phenyl]-2,4-pyrimidinediamine (R950230)

In a manner similar to the preparation of N2-(3-carboxymethyleneaminophenyl)-N4-(3,4-ethylenedioxyphenyl)-5-fluoro-2,4-pyrimidinediamine, the hydrolysis of N2-(ethoxycarbonylmethyleneaminophenyl)-5-fluoro-N4-[3-(2-hydroxyethylenoxy)phenyl]-2,4-pyrimidinediamine with LiOH gave N2-(carboxymethyleneaminophenyl)-5-fluoro-N4-[3-(2-hydroxyethyloxy)phenyl]-2,4-pyrimidinediamine. LCMS: ret. time: 12.15 min.; purity: 78.3%; MS (m/e): 413.01 (MH$^+$).

7.3.661 5-Fluoro-N4-[3-(2-hydroxyethylamino)phenyl]-N2-[3-[N-(2-hydroxyethylamino)]carbonylmethyleneaminophenyl]-2,4-pyrimidinediamine (R950231)

A mixture of N2-(carboxymethyleneaminophenyl)-5-fluoro-N4-[3-(2-hydroxyethylamino)phenyl]-2,4-pyrimidinediamine (10 mg), 2-aminoethanol (10 equiv.) and PyBroP (2 equiv.) was stirred in 0.5 ml DMF for 24 hours at room temperature. The mixture was diluted with water, extracted with EtOAc and the organic phase was dried over MgSO$_4$. The solvent was removed under reduced pressure and the residue was subjected to column chromatography on silica gel (CHCl$_3$:Acetone, 2:1) to give 5-fluoro-N4-[3-(2-hydroxyethylamino)phenyl]-N2-[3-[N-(2-hydroxyethylamino)]carbonylmethyleneaminophenyl]-2,4-pyrimidinediamine. LCMS: ret. time: 12.98 min.; purity: 92.6%; MS (m/e): 455.97 (MH$^+$).

7.3.662 N2-[3-(N-2-Aminoethylamino)carbonylmethyleneaminophenyl]-5-fluoro-N4-[3-(2-hydroxyethylenoxy)phenyl]-2,4-pyrimidinediamine (R950232)

In like manner to the preparation of N4-[3-(2-hydroxyethylamino)phenyl]-N2-[3-[N-(2-hydroxyethylamino)]carbonylmethyleneaminophenyl]-5-fluoro-2,4-pyrimidinediamine, N2-(carboxymethyleneaminophenyl)-5-fluoro-N4-[3-(2-hydroxyethylamino)phenyl]-2,4-pyrimidinediamine and 1,2-ethylenediamine were reacted to afford N2-[3-(N-2-aminoethylamino)carbonylmethyleneaminophenyl]-5-fluoro-N4-[3-(2-hydroxyethylenoxy)phenyl]-2,4-pyrimidinediamine. LCMS: ret. time: 11.31 min.; purity: 93.6%; MS (m/e): 454.94 (MH$^+$).

7.3.663 5-Fluoro-N4-[3-(2-hydroxyethylamino)phenyl]-N2-[3-(N-methylamino)carbonylmethyleneaminophenyl]-2,4-pyrimidinediamine (R950233)

In like manner to the preparation of N4-[3-(2-hydroxyethylamino)phenyl]-N2-[3-[N-(2-hydroxyethylamino)]carbonylmethyleneaminophenyl]-5-fluoro-2,4-pyrimidinediamine, N2-(carboxymethyleneaminophenyl)-5-fluoro-N4-[3-(2-hydroxyethylamino)phenyl]-2,4-pyrimidinediamine and methylamine were reacted to give 5-fluoro-N4-[3-(2-hydroxyethylamino)phenyl]-N2-[3-(N-methylamino)carbonylmethyleneaminophenyl]-2,4-pyrimidinediamine. LCMS: ret. time: 14.93 min.; purity: 92.9%; MS (m/e): 426.27 (MH$^+$).

7.3.664 5-Fluoro-N4-[3-(2-hydroxyethylamino)phenyl]-N2-[3-[N-(2-methylamino)ethylamino]carbonylmethyleneaminophenyl]-2,4-pyrimidinediamine (R950234)

In like manner to the preparation of N4-[3-(2-hydroxyethylamino)phenyl]-N2-[3-[N-(2-hydroxyethylamino)]carbonylmethyleneaminophenyl]-5-fluoro-2,4-pyrimidinediamine, N2-(carboxymethyleneaminophenyl)-5-fluoro-N4-[3-(2-hydroxyethylamino)phenyl]-2,4-pyrimidinediamine and N-methylethylenediamine were reacted to give 5-fluoro-N4-[3-(2-hydroxyethylamino)phenyl]-N2-[3-[N-(2-methylamino)ethylamino]carbonylmethyleneaminophenyl]-2,4-pyrimidinediamine. LCMS: ret. time: 11.39 min.; purity: 97.7%; MS (m/e): 468.96 (MH$^+$).

7.3.665 N2-[3-[N-(2-N-Benzylamino)ethylamino]carbonylmethyleneaminophenyl]-5-fluoro-N4-[3-(2-hydroxyethylamino)phenyl]-2,4-pyrimidinediamine (R950235)

In like manner to the preparation of N4-[3-(2-hydroxyethylamino)phenyl]-N2-[3-[N-(2-hydroxyethylamino)]carbonylmethyleneaminophenyl]-5-fluoro-2,4-pyrimidinediamine, N2-(carboxymethyleneaminophenyl)-5-fluoro-N4-[3-(2-hydroxyethylamino)phenyl]-2,4-pyrimidinediamine and N-benzylethylenediamine were reacted to give N2-[3-[N-(2-N-benzylamino)ethylamino]carbonylmethyleneaminophenyl]-5-fluoro-N4-[3-(2-hydroxyethylamino)phenyl]-2,4-pyrimidinediamine. LCMS: ret. time: 14.39 min.; purity: 97.3%; MS (m/e): 545.01 (MH$^+$).

7.3.666 5-Fluoro-N4-[3-(2-hydroxyethylamino)phenyl]-N2-[3-(N-morpholino)carbonylmethyleneaminophenyl]-2,4-pyrimidinediamine (R950236)

In like manner to the preparation of N4-[3-(2-hydroxyethylamino)phenyl]-N2-[3-[N-(2-hydroxyethylamino)]carbonylmethyleneaminophenyl]-5-fluoro-2,4-pyrimidinediamine, N2-(carboxymethyleneaminophenyl)-5-fluoro-N4-[3-(2-hydroxyethylamino)phenyl]-2,4-pyrimidinediamine and morpholine were reacted to afford 5-fluoro-N4-[3-(2-hydroxyethylamino)phenyl]-N2-[3-(N-morpholino)carbonylmethyleneaminophenyl]-2,4-pyrimidinediamine. LCMS: ret. time: 15.24 min.; purity: 94.6xx %; MS (m/e): 482.40 (MH$^+$).

7.3.667 N2-[3-(3-N,N-Dimethylaminopropyl)aminocarbonylmethyleneaminophenyl]-5-fluoro-N4-[3-(2-hydroxyethylamino)phenyl]-2,4-pyrimidinediamine (R950237)

In like manner to the preparation of N4-[3-(2-hydroxyethylamino)phenyl]-N2-[3-[N-(2-hydroxyethylamino)]carbonylmethyleneaminophenyl]-5-fluoro-2,4-pyrimidinediamine, N2-(carboxymethyleneaminophenyl)-5-fluoro-N4-[3-(2-hydroxyethylamino)phenyl]-2,4-pyrimidinediamine and N,N-dimethylpropanediamine were reacted to give N2-[3-(3-N,N-Dimethylaminopropyl)aminocarbonylmethyleneaminophenyl]-5-fluoro-N4-[3-(2-hydroxyethylamino)phenyl]-2,4-pyrimidinediamine. LCMS: ret. time: 13.33 min.; purity: 91.4%; MS (m/e): 497.47 (MH$^+$).

7.3.668 N2-[3-[N-(2,3-Dihydroxypropyl)amino]carbonylmethyleneaminophenyl]-5-fluoro-N4-[3-(2-hydroxyethylamino)phenyl]-2,4-pyrimidinediamine (R950238)

In like manner to the preparation of N4-[3-(2-hydroxyethylamino)phenyl]-N2-[3-[N-(2-hydroxyethylamino)]carbonylmethyleneaminophenyl]-5-fluoro-2,4-pyrimidinediamine, N2-(carboxymethyleneaminophenyl)-5-fluoro-N4-[3-(2-hydroxyethylamino)phenyl]-2,4-pyrimidinediamine and 1-amino-2,3-propanediol were reacted to give N2-[3-[N-(2,3-dihydroxypropyl)amino]carbonylmethyleneaminophenyl]-5-fluoro-N4-[3-(2-hydroxyethylamino)phenyl]-2,4-pyrimidinediamine. LCMS: ret. time: 12.86 min.; purity: 90.0%; MS (m/e): 486.40 (MH$^+$).

7.3.669 5-Fluoro-N4-[3-(2-hydroxyethylamino)phenyl]-N2-[3-(N-morpholinoethyleneamino)carbonylmethyleneaminophenyl]-2,4-pyrimidinediamine (R950239)

In like manner to the preparation of N4-[3-(2-hydroxyethylamino)phenyl]-N2-[3-[N-(2-hydroxyethylamino)]carbonylmethyleneaminophenyl]-5-fluoro-2,4-pyrimidinediamine, N2-(carboxymethyleneaminophenyl)-5-fluoro-N4-[3-(2-hydroxyethylamino)phenyl]-2,4-pyrimidinediamine and 4-(2-aminoethyl)morpholine were reacted to give 5-fluoro-N4-[3-(2-hydroxyethylamino)phenyl]-N2-[3-(N-morpholinoethyleneamino) carbonylmethyleneaminophenyl]-2,4-pyrimidinediamine. LCMS: ret. time: 13.52 min.; purity: 92.4%; MS (m/e): 525.47 (MH$^+$).

7.3.670 2,4-Bis[N-(L)-tyrosine methyl ester]-5-ethoxycarbonylpyrimidine (R926514) and 5-Ethoxycarbonyl-2-methoxy-4-[N-(L)-tyrosine methyl ester]pyrimidine (R926513)

A mixture of tyrosine methyl ester (58 mg, 0.3 mmol), 2,4-dichloro-5-ethoxycarbonylpyrimidine (44 mg, 0.1 mmol) in MeOH (2 mL) was heated in a sealed tube at 100° C. for a period of overnight, diluted with H$_2$O (20 mL), acidified with 2N HCl and extracted with ethyl acetate (3×25 mL). The solvent was evaporated and the residue was purified by preparative TLC using 30% EtOAc/Hexanes to obtain a mixture of 2,4-bis[N-(L)-tyrosine methyl ester]-5-ethoxycarbonylpyrimidine (R926514). $^1$H NMR (CDCl$_3$): δ 8.60 (1H, J=6.6 Hz), 8.36 (s, 1H), 7.05 (d, 2H, J=8.7 Hz), 6.84 (d, 2H, J=8.1 Hz), 6.74 (d, 2H, J=9 Hz), 6.54 (d, 2H, J=9 Hz), 4.82 (t, 2H, J=6 Hz), 4.25 (q, 2H, J=6.3 Hz), 3.73 (s, 3H), 3.72 (s, 3H), 3.06 (m, 4H), 1.31 (t, 3H, J=7.2 Hz) and 5-ethoxycarbonyl-2-methoxy-4-[N-(L)-tyrosine methyl ester]pyrimidine (R926513): $^1$H NMR (CDCl$_3$): δ 8.78 (s, 1H), 8.65 (d, 1H, J=6.9 Hz), 7.02 (dd, 2H, J=2.1 and 6.3 Hz), 6.77 (dd, 2H, J=2.4 and 6.6 Hz), 4.93 (q, 1H, J=1.5 and 6.9 Hz), 4.30 (q, 2H, J=8.1 Hz), 3.90 (s, 3H), 3.70 (s, 3H), 3.17 (dd, 1H, J=5.4 Hz), 3.06 (dd, 1H, J=7.5 and 7.8 Hz), 1.33 (t, 3H, J=6.9 Hz); LCMS: ret. time: 22.58 min.; purity: 99%; MS (m/e): 376 (M$^+$).

7.3.671 N2,N4-Bis(3,4-ethylenedioxyphenyl)-5-ethoxycarbonyl-2,4-pyrimidinediamine (R926252)

In like manner to the preparation of N2,N4-bis[N-(L)-tyrosine methyl ester]-5-ethoxycarbonylpyrimidine, the reaction of 2,4-dichloro-5-ethoxycarbonylpyrimidine with 3,4-ethylenedioxyaniline gave N2,N4-bis(3,4-ethylenedioxyphenyl)-5-ethoxycarbonyl-2,4-pyrimidinediamine. $^1$H NMR (DMSO-d6): δ 10.01 (s, 1H), 9.65 (bs, 1H), 8.62 (s, 1H), 7.18 (bs, 2H), 7.04 (dd, 1H, J=1.8 and 8.7 Hz), 6.93 (d, 1H, J=7.5 Hz), 6.76 (d, 1H, J=8.7 Hz), 6.65 (d, 1H, J=8.7 Hz), 4.28 (q, 2H, J=6.9 Hz), 1.31 (t, 3H, J=7.2 Hz); LCMS: ret. time: 27.25 min.; purity: 100%; MS (m/e): 451 (MH$^+$).

7.3.672 N2,N4-Bis(4-methoxycarbonylmethyleneoxyphenyl)-5-ethoxycarbonyl-2,4-pyrimidinediamine (R926253)

In like manner to the preparation of N2,N4-bis[N-(L)-tyrosine methyl ester]-5-ethoxycarbonylpyrimidine, the reaction of 2,4-dichloro-5-ethoxycarbonylpyrimidine with ethyl 4-aminophenoxyacetate gave N2,N4-bis(4-methoxycarbonylmethyleneoxyphenyl)-5-ethoxycarbonyl-2,4-pyrimidinediamine (R926253). $^1$H NMR (CD$_3$OD): δ 8.60 (bs, 1H), 7.4 (bs, 1H), 7.33 (d, 4H, J=9 Hz), 6.94 (bd, 4H), 4.76 (s, 2H), 4.75 (s, 2H), 4.44 (q, 2H, J=6.9 Hz), 3.79 (s, 3H), 1.40 (t, 3H, J=6.9 Hz); LCMS: ret. time: 25.83 min.; purity: 89%; MS (m/e): 511 (MH$^+$).

7.3.673 2,4-Bis[N-(L)-phenylalaninyl ethyl ester]-5-ethoxycarbonylpyrimidine (R926526)

In like manner to the preparation of N2,N4-bis[N-(L)-tyrosine methyl ester]-5-ethoxycarbonylpyrimidine, the reaction of 2,4-dichloro-5-ethoxycarbonylpyrimidine with ethyl (L)-phenylalanine ethyl ester in MeOH or EtOAc gave 2,4-bis[N-(L)-phenylalanine ethyl ester]-5-ethoxycarbonylpyrimidine. $^1$H NMR (CDCl$_3$): δ 8.55 (d, 1H, J=7.2 Hz), 8.51 (s, 1H), 7.35-7.10 (m, 10H), 5.88 (d, 1H, J=J=6 Hz), 4.88 (ddd, 1H, J=6.3 Hz), 4.80 (ddd, 1H, J=6.3 Hz), 4.23 (q, 2H, J=7.2 Hz), 4.12 (q, 4H, J=7.2 Hz), 3.65 (t, 2H, J=6 Hz), 3.56 (t, 2H, J=6.0 Hz), 1.30 (t, 2H, J=6 Hz), 1.30 (t, 3H, J=7.2 Hz), 1.20 (m, 6H); LCMS: ret. time: 32.22 min.; purity: 89%; MS (m/e): 535 (MH$^+$).

7.3.674 2,4-Bis[N-(L)-valinyl ethyl ester]-5-ethoxycarbonylpyrimidine (R926527)

In like manner to the preparation of N2,N4-bis[N-(L)-tyrosine methyl ester]-5-ethoxycarbonylpyrimidine, the reaction of 2,4-dichloro-5-ethoxycarbonylpyrimidine with ethyl (L)-valine ethyl ester in MeOH or EtOAc gave 2,4-bis[N-(L)-valinyl ethyl ester]-5-ethoxycarbonylpyrimidine. $^1$H NMR (CDCl$_3$): δ 8.59 (d, 1H, J=7.8 Hz), 8.56 (s, 1H), 5.69 (d, 1H, J=8.7 Hz), 4.62 (m, 1H), 4.51 (m, 1H), 4.25 (q, 2H, J=7.5 Hz), 4.20 (m, 4H), 2.20 (m, 2H), 1.34 (t, 3H, J=7.8 Hz), 1.27 (t, 6H, J=7.5 Hz), 1.00 (m, 12H); LCMS: ret. time: 29.27 min.; purity: 97%; MS (m/e): 439 (MH$^+$).

7.3.675 5-Ethoxycarbonyl-N2-(3-hydroxyphenyl)-4-[N-(L)-phenylalanine ethyl ester]-2-pyrimidineamine (R926528)

The reaction of 2-chloro-N4-(3-hydroxyphenyl)-5-ethoxycarbonylpyrimidineamine with 3 equivalents of (L)-N-phenylalanine ethyl ester in methanol at 80-100° C. for 24 h followed by dilution with water and acidification with 2N HCl have the acidic solution. The resulting solution was extracted with EtOAc and the residue was purified by silica gel column chromatography to afford 4-[N-(L)-phenylalanine ethyl ester]-N2-(3-hydroxyphenyl)-5-ethoxycarbonyl-2-pyrimidineamine. $^1$H NMR (CDCl$_3$): δ 9.4 (bs, 1H), 9.13 (d, 1H, J=6 Hz), 8.45 (bs, 1H), 7.59 (s, 1H), 7.34-7.25 (m, 5H), 7.15 (t, 1H, J=8.1 Hz), 6.73 (bd, 1H, J=7.5 Hz), 6.67 (dd, 1H, J=1.8 and 7.8 Hz), 4.86 (dt, 1H, J=3 and 5.1 Hz), 4.32 (q, 2H, J=6.3 Hz), 4.19 (q, 2H, J=7.2 Hz), 3.30 (dd, 1H, J=4.8 and 8.7 Hz), 3.18 (dd, 1H, J=5.1 and 8.7 Hz), 1.36 (t, 3H, J=6.9 Hz), 1.65 (t, 3H, J=7.2 Hz); LCMS: ret. time: 27.49 min.; purity: 91%; MS (m/e): 451 (MH$^+$).

7.3.676 N2-(3,4-Ethylenedioxyphenyl)-5-ethoxycarbonyl-4-[N-(L)-phenyl glycinyl ethyl ester)-2-pyrimidineamine (R926536)

In like manner to the preparation of 4-[N-(L)-phenylalanine ethyl ester]-N2-(3-hydroxyphenyl)-5-ethoxycarbonyl-2-pyrimidineamine, the reaction of 2-chloro-5-ethoxycarbonyl-4-[N-(L)-phenyl glycinyl ethyl ester)pyrimidine with 3,4-ethylenedioxyaniline in MeOH or EtOAc gave N2-(3,4-ethylenedioxyphenyl)-5-ethoxycarbonyl-4-[N-(L)-phenyl glycinyl ethyl ester]-2-pyrimidineamine. $^1$H NMR (CDCl$_3$): δ 9.15 (s, 1H), 8.9 (s, 1H), 8.61 (s, 1H), 7.48 (m, 2H), 7.38 (m, 3H), 7.16 (bs, 1H), 6.80 (m, 2H0, 5.75 (d, 1H), 4.24 (m, 6H), 3.66 (s, 3H), 1.35 (t, 3H); LCMS: ret. time: 28.16 min.; purity: 85%; MS (m/e): 465 (MH$^+$).

7.3.677 N4-(4-tert-Butoxycarbonylmethyleneoxyphenyl)-5-ethoxycarbonyl-N2-(4-methoxycarbonylmethyleneoxyphenyl)-2,4-pyrimidinediamine (R926579)

In like manner to the preparation of 4-[N-(L)-phenylalanine ethyl ester]-N2-(3-hydroxyphenyl)-5-ethoxycarbonyl-2-pyrimidineamine, the reaction of N4-(4-tert-butoxycarbonylmethyleneoxyphenyl)-2-chloro-5-ethoxycarbonyl-4-pyrimidineamine with methyl 4-aminophenoxyacetate gave N4-(4-tert-butoxycarbonylmethyleneoxyphenyl)-5-ethoxycarbonyl-N2-(4-methoxycarbonylmethyleneoxyphenyl)-2,4-pyrimidinediamine. $^1$H NMR (CDCl$_3$): δ 10.17 (s, 1H), 8.73 (s, 1H), 8.45 (bs, 1H), 7.49 (d, 2H, J=8.7 Hz), 7.43 (d, 2H, J=8.7 Hz), 7.33 (bs, 1H), 6.87 (d, 2H, J=6 Hz), 6.84 (d, 2H, J=5.7 Hz), 4.63 (s, 2H), 4.53 (s, 2H), 4.33 (q, 2H, J=6.9 Hz), 3.81 (s, 3H), 1.49 (s, 9H), 1.39 (t, 3H, J=7.5 Hz); LCMS: ret. time: 27.93 min.; purity: 96%; MS (m/e): 553 (MH$^+$).

7.3.678 N4-(4-tert-Butoxycarbonylmethyleneoxyphenyl)-N2-(4-methoxycarbonylmethyleneoxyphenyl)-5-methoxycarbonyl-2,4-pyrimidinediamine (R926580)

In like manner to the preparation of 4-[N-(L)-phenylalanine ethyl ester]-N2-(3-hydroxyphenyl)-5-ethoxycarbonyl-2-pyrimidineamine, the reaction of N4-(4-tert-butoxycarbonylmethyleneoxyphenyl)-2-chloro-5-ethoxycarbonyl-4-pyrimidineamine with methyl 4-aminophenoxyacetate gave N4-(4-tert-butoxycarbonylmethyleneoxyphenyl)-5-methoxycarbonyl-N2-(4-methoxycarbonylmethyleneoxyphenyl)-2,4-pyrimidinediamine. 5-methyl ester was obtained due to the cross esterification reaction in MeOH. $^1$H NMR (CDCl$_3$): δ 10.13 (s, 1H), 8.73 (s, 1H), 8.45 (bs, 1H), 7.49 (d, 2H, J=8.7 Hz), 7.43 (d, 2H, J=8.7 Hz), 7.33 (bs, 1H), 6.87 (m, 4H), 4.63 (s, 2H), 4.53 (s, 2H), 4.33 (q, 2H, J=6.9 Hz), 3.88 (s, 3H), 3.81 (s, 3H), 1.49 (s, 9H); LCMS: ret. time: 27.43 min.; purity: 100%; MS (m/e): 539 (MH$^+$).

7.3.679 N4-(4-Carboxymethyleneoxyphenyl)-5-ethoxycarbonyl-N2-(4-methoxycarbonylmethyleneoxyphenyl)-2,4-pyrimidinediamine (R926583)

The treatment of N4-(4-tert-butoxycarbonylmethyleneoxyphenyl)-5-ethoxycarbonyl-N2-(4-methoxycarbonylmethyleneoxyphenyl)-2,4-pyrimidinediamine with trifluoroacetic acid in THF:H$_2$O at room temperature afforded N4-(4-carboxymethyleneoxyphenyl)-5-ethoxycarbonyl-N2-(4-methoxycarbonylmethyleneoxyphenyl)-2,4-pyrimidinediamine. $^1$H NMR (DMSO-d6): δ 10.03 (s, 1H), 8.65 (s, 1H), 7.49 (bd, 4H, J=8.7 Hz), 6.89 (d, 2H, J=9.3 Hz), 6.81 (d, 2H, J=8.1 Hz), 4.70 (s, 2H), 4.65 (s, 2H), 4.33 (q, 2H, J=6.9 Hz), 3.81 (s, 3H), 1.49 (s, 9H), 1.39 (t, 3H, J=7.5 Hz); LCMS: ret. time: 22.28 min.; purity: 73%; MS (m/e): 497 (MH$^+$).

7.3.680 N2-(4-Carboxymethyleneoxyphenyl)-5-ethoxycarbonyl-N4-(4-methoxycarbonylmethyleneoxyphenyl)-2,4-pyrimidinediamine (R926584)

The treatment of N2-(4-tert-butoxycarbonylmethyleneoxyphenyl)-5-ethoxycarbonyl-N4-(4-methoxycarbonylmethyleneoxyphenyl)-2,4-pyrimidinediamine with trifluoroacetic acid in THF:$H_2O$ at room temperature afforded N2-(4-carboxymethyleneoxyphenyl)-5-ethoxycarbonyl-N4-(4-methoxycarbonylmethyleneoxyphenyl)-2,4-pyrimidinediamine. $^1$H NMR (DMSO-d6): δ 10.01 (s, 1H), 8.64 (s, 1H), 7.45 (bd, 4H, J=7.2 Hz), 6.90 (d, 2H, J=8.7 Hz), 6.75 (d, 2H, J=8.4 Hz), 4.80 (s, 2H), 4.38 (s, 2H), 4.26 (q, 2H, J=7.2 Hz), 3.70 (s, 3H), 1.30 (t, 3H, J=7.2 Hz); LCMS: ret. time: 22.37 min.; purity: 100%; MS (m/e): 497 (MH$^+$).

7.3.681 5-Carboxy-N2-(3-hydroxyphenyl)-N4-[N-(L)-phenylglycine)-2-pyrimidineamine (R926535)

The LiOH hydrolysis of N2-(3-hydroxyphenyl)-5-ethoxycarbonyl-4-[N-(L)-phenyl glycine ethyl ester]-2-pyrimidineamine afforded 5-carboxy-N2-(3-hydroxyphenyl)-N4-[N-(L)-phenylglycine)-2-pyrimidineamine. $^1$H NMR (CD$_3$OD): δ 8.89 (s, 1H), 8.50 (s, 1H), 7.43 (m, 2H), 7.33 (m, 3H), 7.14 (m, 2H), 6.98 (m, 2H), 6.62 (m, 1H), 5.71 (s, 1H); LCMS: ret. time: 17.75 min.; purity: 73%; MS (m/e): 382 (MH$^+$).

7.3.682 5-Amino-6-ethoxycarbonyl-N2,N4-bis(3-hydroxyphenyl)-2,4-pyrimidinediamine (R925856)

A suspension of 6-ethoxycarbonyl-N2,N4-bis(3-hydroxyphenyl)-5-nitro-2,4-pyrimidinediamine and 10% Pd/C (10% by weight) in ethanol was prepared and reacted in a Parr bottle under hydrogen gas (20 PSI) for 1 h. The reaction mixture was filtered through Celite. Purification by column chromatography gave 5-amino-6-ethoxycarbonyl-N2,N4-bis(3-hydroxyphenyl)-2,4-pyrimidinediamine. $^1$H NMR (CD$_3$OD): δ 7.30 (bs, 1H), 7.18-7.10 (m, 3H), 7.00 (t, 2H, J=8.1 Hz), 6.59-6.54 (m, 1H), 6.33 (dd, 1H, J=2.1 and 11.1 Hz), 4.39 (q, 2H, J=6.9 Hz), 1.43 (t, 3H, J=6.9 Hz); LCMS: ret. time: 19.24 min.; purity: 100%; MS (m/e): 382 (MH$^+$).

7.3.683 5-Amino-6-ethoxycarbonyl-N2,N4-bis(3,4-ethylenedioxyphenyl)-2,4-pyrimidinediamine (R925857)

In a manner similar to the preparation of 5-amino-6-ethoxycarbonyl-N2,N4-bis(3-hydroxyphenyl)-2,4-pyrimidinediamine, 6-ethoxycarbonyl-N2,N4-bis(3,4-ethylenedioxyphenyl)-5-nitro-2,4-pyrimidinediamine, hydrogen, and 10% Pd/C were reacted to yield 5-amino-6-ethoxycarbonyl-N2,N4-bis(3,4-ethylenedioxyphenyl)-2,4-pyrimidinediamine. $^1$H NMR (CD$_3$OD): δ 7.16 (d, 1H, J=2.4 Hz), 7.07 (d, 1H, J=2.4 Hz), 7.04 (dd, 1H, J=2.4 and 9.0 Hz), 6.84-6.79 (m, 2H), 6.70 (d, 1H, J=9.0), 4.43 (q, 2H, J=7.8 Hz), 4.25 (s, 4H), 4.21 (bs, 4H), 1.43 (t, 3H, J=7.8 Hz); LCMS: ret. time: 23.70 min.; purity: 100%; MS (m/e): 466 (MH$^+$).

7.3.684 5-Amino-N2,N4-bis(ethoxycarbonylmethyl)-6-ethoxycarbonyl-2,4-pyrimidinediamine (R925865)

In a manner similar to the preparation of 5-amino-6-ethoxycarbonyl-N2,N4-bis(3-hydroxyphenyl)-2,4-pyrimidinediamine, 6-ethoxycarbonyl-N2,N4-bis(ethoxycarbonylmethyl)-5-nitro-2,4-pyrimidinediamine, hydrogen, and 10% Pd/C were reacted to yield 5-amino-N2,N4-bis(ethoxycarbonylmethyl)-6-ethoxycarbonyl-2,4-pyrimidinediamine. $^1$H NMR (CDCl$_3$): δ 6.25 (bs, 2H), 4.38 (q, 2H, J=6.9 Hz), 4.23-4.14 (m, 6H), 4.05 (bs, 2H), 1.39 (t, 3H, J=6.9 Hz), 1.30-1.22 (m, 6H); LCMS: ret. time: 17.67 min.; purity: 95%; MS (m/e): 370 (MH$^+$).

7.3.685 5-Amino-N2,N4-bis(4-ethoxycarbonylmethyleneoxyphenyl)-6-ethoxycarbonyl-2,4-pyrimidinediamine (R926567)

Hydrogenation of N2,N4-bis(4-ethoxycarbonylmethyleneoxyphenyl)-6-ethoxycarbonyl-5-nitro-2,4-pyrimidinediamine using Pd/C in MeOH at 40 PSI gave 5-amino-N2,N4-bis(4-ethoxycarbonylmethyleneoxyphenyl)-6-ethoxycarbonyl-2,4-pyrimidinediamine. $^1$H NMR (CDCl$_3$): δ 7.47 (d, 2H, J=8.7 Hz), 7.41 (d, 2H, J=8.7 Hz), 6.88 (d, 2H, J=8.1 Hz), 6.81 (d, 2H, J=8.7 Hz), 4.63 (s, 2H), 4.59 (s, 2H), 4.41 (q, 2H, J=7.5 Hz), 4.29 (m, 4H), 1.44 (t, 3H), 1.31 (m, 6H); LCMS: ret. time: 26.15 min.; purity: 97%; MS (m/e): 554 (MH$^+$).

7.3.686 N2,N4-Bis(4-ethoxycarbonylmethyleneoxyphenyl)-6-ethoxycarbonyl-5-(phenylaminocarbonylamino)-2,4-pyrimidinediamine (R926571)

A dry reaction flask equipped with a rubber septum and a N$_2$ inlet was charged with 5-amino-N2,N4-bis(4-ethoxycarbonylmethyleneoxyphenyl)-6-ethoxycarbonyl-2,4-pyrimidinediamine, equimolar amount of pyridine and phenyl isocyanate at room temperature. The reaction was allowed to stirred at room temperature for overnight and the resulting reaction was poured over n-hexane to precipitate the desired product, N2,N4-bis(4-ethoxycarbonylmethyleneoxyphenyl)-6-ethoxycarbonyl-5-(phenylaminocarbonylamino)-2,4-pyrimidinediamine. $^1$H NMR (CDCl$_3$): δ 7.92 (s, 1H), 7.47 (s, 1H), 7.35 (bt, 5H, J=8.4 Hz), 7.25 (bt, 2H, J=7.5 Hz), 7.03 (m, 2H), 6.81 (d, 2H, J=8.7 Hz), 6.76 (d, 2H, J=8.7 Hz), 4.60 (s, 2H), 4.58 (s, 2H), 4.29 (m, 6H), 1.45 (m, 9H); LCMS: ret. time: 27.75 min.; purity: 91%; MS (m/e): 673 (MH$^+$).

7.3.687 5-Allylaminocarbonylamino-N2,N4-bis(4-ethoxycarbonylmethyleneoxyphenyl)-6-ethoxycarbonyl)-2,4-pyrimidinediamine (R926585)

In like manner to the preparation of N2,N4-bis(4-ethoxycarbonylmethyleneoxyphenyl)-6-ethoxycarbonyl-5-(phenylaminocarbonylamino)-2,4-pyrimidinediamine, the reaction of 5-amino-N2,N4-bis(4-ethoxycarbonylmethyleneoxyphenyl)-6-ethoxycarbonyl-2,4-pyrimidinediamine with allyl isocyanate gave 5-allylaminocarbonylamino-N2,N4-bis(4-ethoxycarbonylmethyleneoxyphenyl)-6-ethoxycarbonyl)-2,4-pyrimidinediamine. LCMS: ret. time: 25.60 min.; purity: 91%; MS (m/e): 637 (MH$^+$).

7.3.688 N2,N4-Bis(4-ethoxycarbonylmethyleneoxyphenyl)-6-ethoxycarbonyl-5-(ethoxycarbonylaminocarbonylamino)-2,4-5-pyrimidinetriamine (R926586)

In like manner to the preparation of N2,N4-bis(4-ethoxycarbonylmethyleneoxyphenyl)-6-ethoxycarbonyl-5-(phenylaminocarbonylamino)-2,4-pyrimidinediamine, the reaction of 5-amino-N2,N4-bis(4-ethoxycarbonylmethyleneoxyphenyl)-6-ethoxycarbonyl-2,4-pyrimidinediamine with ethoxycarbonyl isocyanate gave N2,N4-bis(4-ethoxycarbonylmethyleneoxyphenyl)-6-ethoxycarbonyl-5-(ethoxycarbonylaminocarbonylamino)-2,4-pyrimidinediamine. LCMS: ret. time: 26.79 min.; purity: 88%; MS (m/e): 669 (MH+).

7.3.689 N2,N4-Bis(4-ethoxycarbonylmethyleneoxyphenyl)-6-ethoxycarbonyl-5-(ethoxycarbonylmethylene aminocarbonylamino)-2,4-pyrimidinediamine (R926587)

In like manner to the preparation of N2,N4-bis(4-ethoxycarbonylmethyleneoxyphenyl)-6-ethoxycarbonyl-5-(phenylaminocarbonylamino)-2,4-pyrimidinediamine, the reaction of 5-amino-N2,N4-bis(4-ethoxycarbonylmethyleneoxyphenyl)-6-ethoxycarbonyl-2,4-pyrimidinediamine with ethylacetyl isocyanate gave N2,N4-bis(4-ethoxycarbonylmethyleneoxyphenyl)-6-ethoxycarbonyl-5-(ethoxycarbonylmethyleneaminocarbonylamino)-2,4-pyrimidinediamine. LCMS: ret. time: 25.76 min.; purity: 96%; MS (m/e): 683 (MH+).

7.3.690 N2,N4-Bis(4-ethoxycarbonylmethyleneoxyphenyl)-6-ethoxycarbonyl-5-(cyclopentylaminocarbonylamino)-2,4-pyrimidinediamine (R926588)

In like manner to the preparation of N2,N4-bis(4-ethoxycarbonylmethyleneoxyphenyl)-6-ethoxycarbonyl-5-(phenylaminocarbonylamino)-2,4-pyrimidinediamine, the reaction of 5-amino-N2,N4-bis(4-ethoxycarbonylmethyleneoxyphenyl)-6-ethoxycarbonyl-2,4-pyrimidinediamine with cyclopentyl isocyanate gave N2,N4-bis(4-ethoxycarbonylmethyleneoxyphenyl)-6-ethoxycarbonyl-5-(cyclopentylaminocarbonylamino)-2,4-pyrimidinediamine. LCMS: ret. time: 27.36 min.; purity: 83%; MS (m/e): 665 (MH+).

7.3.691 N2,N4-Bis(4-ethoxycarbonylmethyleneoxyphenyl)-6-ethoxycarbonyl-5-(chloroacetylaminocarbonylamino)-2,4-pyrimidinediamine (R926589)

In like manner to the preparation of N2,N4-bis(ethoxycarbonylmethyleneoxyphenyl)-6-ethoxycarbonyl-5-(N-phenyl-formyl-amino)-2,4-pyrimidinediamine, the reaction of N5-amino-N2,N4-bis(ethoxycarbonylmethyleneoxyphenyl)-6-ethoxycarbonyl-2,4-pyrimidinediamine with chloroacetylformyl isocyanate gave N2,N4-bis(4-ethoxycarbonylmethyleneoxyphenyl)-6-ethoxycarbonyl-5-(chloroacetylaminocarbonylamino)-2,4-pyrimidinediamine. LCMS: ret. time: 26.60 min.; purity: 100%; MS (m/e): 580 (MH+).

7.3.692 (R920669): N2,N4-Bis(3,4-ethylenedioxyphenyl)-5-trifluoro-2,4-pyridinediamine A mixture of 2,4-dichloro-5-trifluoromethylpyrimidine (416 mg, 1.9 mmol), 3,4-ethylenedioxyaniline (0.5 mL, 4.1 mmol), and concentrated HCl (0.1 mL) in 1:9 acetone/$H_2O$ (10 mL) was heated to reflux. After 1 h, the reaction was complete as determined by TLC. The mixture was cooled to room temperature and EtOAc (30 mL) was added. The organic layer was washed with 2 N HCl (2×15 mL), water (15 mL), and dried ($Na_2SO_4$). The organic layer was filtered through a silica gel pad, washing the filter cake with EtOAc, and concentrated. The material was purified by chromatography (silica gel, 95:5 dichloromethane/ethyl acetate) to afford N2,N4-bis(3,4-ethylenedioxyphenyl)-5-trifluoro-2,4-pyridinediamine (380 mg, 44%): $R_f$ 0.27 (silica gel, 9.5:0.5 dichloromethane/ethyl acetate); mp 141-143° C.; $^1H$ NMR (300 MHz, $CDCl_3$) δ 8.25 (s, 1H), 7.07 (m, 2H), 6.99 (bs, 1H), 6.93-6.84 (m, 3H), 6.77-6.74 (m, 1H), 6.67 (bs, 1H), 4.29-4.24 (m, 8H); $^{13}C$ NMR (75 MHz, $CDCl_3$) δ 161.2, 157.9, 155.8, 143.7, 132.6, 131.1, 117.5, 117.3, 114.4, 113.2, 110.3, 64.7, 64.5; IR (ATR) 3446 $cm^{-1}$; ESI MS m/z 447 $[C_{21}H_{17}F_3N_4O_4+H]+$; HPLC (Method C)>99% (AUC), $t_R$=8.5 min. Anal. Calcd for $C_{21}H_{17}F_3N_4O_4$: C, 56.50; H, 3.84; N, 12.55. Found: C, 56.46; H, 4.41; N, 12.57.

7.3.693 (R920668): N4-(3,4-Ethylenedioxyphenyl)-5-fluoro-N2-(3-pyridyl)-2,4-pyrimidinediamine A mixture of 2-chloro-N4-(3,4-ethylenedioxyphenyl)-5-fluoro-4-pyrimidineamine (280 mg, 1 mmol), 3-aminopyridine (113 mg, 1.2 mmol), sodium t-butoxide (134 mg, 1.4 mmol), binap (38 mg, 0.06 mmol), and palladium(II)acetate (14 mg, 0.06 mmol) in 9 mL of toluene was purged with $N_2$ (3 cycles of alternating $N_2$ and vacuum). The mixture was heated to 80° C. (oil-bath temperature). After 24 h, the mixture was cooled to room temperature and EtOAc (30 mL) and of water (10 mL) was added. After stirring 15 min, the precipitate was collected by filtration. A $^1H$ NMR spectrum and ESI mass spectrum of the solid (150 mg) indicated the product (TLC analysis of the organic layer of the filtrate detected only starting materials). The crude product was slurried in 2 N HCl and the mixture was filtered. The filtrate was neutralized with 10% aqueous NaOH and concentrated. The material was slurried with MeOH and the solids removed by filtration. The concentrated material was slurried in $CH_3CN$ and TFA was added to afford a solution. N,N-diisopropylethylamine was added to the solution and the solid was collected by filtration, washing with $CH_3CN$ followed by $Et_2O$ to afford N4-(3,4-ethylenedioxyphenyl)-5-fluoro-N2-(3-pyridyl)-2,4-pyrimidinediamine (55 mg, 14%): $R_f$ 0.42 (silica gel, 4:1:0.1:0.1 dichloromethane/ethyl acetate/methanol/concentrated ammonium hydroxide); mp 251-253° C.; $^1H$ NMR (300 MHz, DMSO-$d_6$) δ 9.38 (s, 1H), 9.26 (s, 1H), 8.74 (s, 1H), 8.20-8.17 (m, 1H), 8.09-8.08 (m, 2H), 7.29-7.28 (m, 1H), 7.23-7.17 (m, 2H), 6.83-6.80 (m, 1H), 4.24 (m, 4H); $^{13}C$ NMR (75 MHz, DMSO-$d_6$) δ 155.2, 149.8, 142.9, 141.6, 140.5, 140.0, 139.8, 139.7, 137.5, 132.1, 124.8, 123.0, 116.4, 115.1, 110.9, 64.1, 64.0; IR (ATR) 3264, 3195 $cm^{-1}$; APCI MS m/z 340 $[C_{17}H_{14}FN_5O_2+H]+$. Anal. Calcd for $C_{17}H_{14}FN_5O_2.0.5H_2O$: C, 58.70; H, 4.20; N, 20.13. Found: C, 58.71; H, 4.20; N, 19.51.

7.3.694 (R920664): N4-(3,4-Ethylenedioxyphenyl)-5-fluoro-N2-(4-n-hexyloxyphenyl)-2,4-pyrimidindiamine To a magnetically stirred solution of 2-chloro-N4-(3,4-ethylenedioxyphenyl)-5-fluoro-4-pyrimidineamine (0.25 g, 0.89 mmol) in ethylene glycol (3.0 mL) under nitrogen at room temperature was added N,N-diisopropylethylamine (0.12 g, 0.89 mmol) followed by 4-hexyloxyaniline (0.27 g, 1.4 mmol). The reaction mixture was heated to 170° C. for 5.5 h, cooled to room temperature and partitioned between water (20 mL) and chloroform (20 mL). The aqueous layer was extracted with chloroform (20 mL) and the combined organic layers were dried ($Na_2SO_4$), filtered and concentrated in vacuo. The crude brown solid was purified by chromatography (silica gel, 2:1 hexanes/ethyl acetate) to afford N4-(3,4-ethylenedioxyphenyl)-5-fluoro-N2-(4-n-hexyloxyphenyl)-2,4-pyrimidinediamine (0.09 g, 23%) as a white solid: $R_f$ 0.53 (silica gel, 4:1 chloroform/ethyl acetate); mp 115-117° C.; $^1H$ NMR (500 MHz, $CDCl_3$) δ 7.90 (d, J=3.2 Hz, 1H), 7.40 (d, J=8.9 Hz, 2H), 7.29 (d, J=2.5 Hz, 2H), 6.98 (d, J=8.8 Hz, 1H), 6.88-6.82 (m, 3H), 6.61 (s, 1H), 4.29 (d, J=3.1 Hz, 4H), 3.94 (t, J=6.6, 6.7 Hz, 2H), 1.77 (m, 2H), 1.47 (m, 2H), 1.35 (m, 4H), 0.92 (m, 3H); $^{13}$C NMR (75 MHz, CDCl$_3$) δ 156.3, 155.1, 150.3, 143.6, 142.7, 140.3, 140.07, 139.4, 133.0, 131.7, 121.9, 117.3, 115.0, 114.7, 110.8, 68.6, 64.6, 31.8, 29.5, 25.9, 22.8, 14.2; IR (ATR) 3357 cm$^{-1}$; ESI MS m/z 439 [C$_{24}$H$_{27}$FN$_4$O$_3$+H]$^+$; HPLC (Method B) 98.5% (AUC), $t_R$=7.9 min. Anal. Calcd for C$_{24}$H$_{27}$FN$_4$O$_3$: C, 65.74; H, 6.21; N, 12.78. Found: C, 65.34; H, 6.19; N, 12.96.

7.3.695 (R920666): N2-(4-n-Butyloxyphenyl)-N4-(3,4-ethylenedioxyphenyl)-5-fluoro-2,4-pyridinediamine To a magnetically stirred solution of 2-chloro-N4-(3,4-ethylenedioxyphenyl)-5-fluoro-4-pyrimidineamine (0.25 g, 0.89 mmol) in ethylene glycol (3.0 mL) under nitrogen at room temperature was added N,N-diisopropylethylamine (0.12 g, 0.89 mmol) followed by 4-butoxyaniline (0.18 g, 1.1 mmol). The reaction mixture was heated to 185° C. for 5 h, cooled to room temperature, and partitioned between water (20 mL) and ethyl acetate (20 mL). The aqueous layer was extracted with ethyl acetate (20 mL) and the combined organic layers were dried (Na$_2$SO$_4$), filtered and concentrated in vacuo. The crude brown solid was purified by chromatography (silica gel, 2:1 hexanes/ethyl acetate) to afford N2-(4-n-Butyloxyphenyl)-N4-(3,4-ethylenedioxyphenyl)-5-fluoro-2,4-pyridinediamine (0.18 g, 49%) as a tan solid: R$_f$ 0.66 (silica gel, 4:1 chloroform/ethyl acetate); mp 133-135° C.; $^1$H NMR (300 MHz, CDCl$_3$) δ 7.89 (d, J=3.2 Hz, 1H), 7.39 (d, J=8.9 Hz, 2H), 7.28 (d, J=2.5 Hz, 1H), 6.95 (dd, J=8.7, 2.5 Hz, 1H) 6.90-6.81 (m, 4H), 6.60 (d, J=2.4 Hz, 1H), 4.27 (s, 4H), 3.94 (t, J=6.5 Hz, 2H), 1.80-1.71 (m, 2H), 1.55-1.42 (m, 2H), 0.97 (t, J=7.3 Hz, 3H); $^{13}$C NMR (75 MHz, CDCl$_3$) δ 156.3, 155.1, 150.4, 143.6, 142.7, 140.3, 140.0, 139.4, 133.0, 131.7, 121.9, 117.3, 115.0, 114.7, 110.8, 68.2, 64.7, 64.5, 31.6, 19.4, 14.0; IR (ATR) 3356 cm$^{-1}$; ESI MS m/z 411 [C$_{22}$H$_{23}$FN$_4$O$_3$+H]$^+$; HPLC (Method A)>99% (AUC), $t_R$=17.3 min. Anal. Calcd for C$_{22}$H$_{23}$FN$_4$O$_3$: C, 64.38; H, 5.65; N, 13.65. Found: C, 62.64; H, 5.59; N, 13.15.

7.3.696 (R920670): N4-(4-ethyloxyphenyl)-N2-(3,4-ethylenedioxyphenyl)-5-fluoro-2,4-pyrimidinediamine To a solution of 2-chloro-N4-(4-ethyloxyphenyl)-5-fluoro-4-pyrimidineamine (0.25 g, 0.93 mmol) in ethylene glycol (3 mL) under nitrogen at room temperature was added i-Pr$_2$EtN, 0.93 mmol) followed by 3,4-ethylenedioxyaniline (0.17 g, 1.12 mmol). The reaction mixture was heated to 200° C. for 5 h and then cooled to room temperature. The mixture was partitioned between H$_2$O (20 mL) and EtOAc (20 mL) and the aqueous layer was extracted with EtOAc (20 mL). The combined organic layers were dried (Na$_2$SO$_4$), filtered, and concentrated in vacuo. The crude brown solid was purified by chromatography (2:1 CHCl$_3$/EtOAc) to afford N4-(4-ethyloxyphenyl)-N2-(3,4-ethylenedioxyphenyl)-5-fluoro-2,4-pyrimidinediamine (0.21 g, 60%) as a tan solid: R$_f$ 0.42 (4:1 CHCl$_3$/EtOAc); mp 163.8-167.2° C. (DSC); $^1$H NMR (300 MHz, CDCl$_3$) δ 7.89 (d, J=2.8 Hz, 1H), 7.50-7.45 (m, 2H), 7.17 (d, J=2.5 Hz, 1H), 6.92-6.86 (m, 3H), 6.80-6.75 (m, 2H), 6.64 (bs, 1H), 4.26-4.21 (m, 4H), 4.03 (q, J=7.0, 2H), 1.42 (t, J=6.9 Hz, 3H); $^{13}$C NMR (75 MHz, CDCl$_3$) δ 156.1, 150.6, 143.6, 142.8, 140.3, 140.0, 139.5, 139.3, 134.0, 130.8, 123.2, 117.2, 115.1, 113.6, 109.4, 64.6, 64.0, 15.1; IR (ATR) 3403 cm$^{-1}$; ESI MS m/z 383 [C$_{20}$H$_{19}$FN$_4$O$_3$+H]+; HPLC (Method A) 98.1% (AUC), $t_R$=12.0 min. Anal. Calcd for C$_{20}$H$_{19}$FN$_4$O$_3$: C, 62.82; H, 5.01; N, 14.65. Found: C, 62.06; H, 5.01; N, 14.35.

7.3.697 (R920671): N4-(4-n-Butyloxyphenyl)-N2-(3,4-ethylenedioxyphenyl)-5-fluoro-2,4-pyridinediamine In like manner to the preparation of N4-(4-ethyloxyphenyl)-N2-(3,4-ethylenedioxyphenyl)-5-fluoro-2,4-pyrimidinediamine, the reaction of 2-chloro-N4-(4-n-butyloxyphenyl)-5-fluoro-4-pyrimidineamine with 3,4-ethylenedioxyaniline gave N4-(4-n-butyloxyphenyl)-N2-(3,4-ethylenedioxyphenyl)-5-fluoro-2,4-pyridinediamine. The crude product was purified by chromatography (2:1 CHCl$_3$/EtOAc); (0.17 g, 52%) as a tan solid: R$_f$ 0.51 (4:1 CHCl$_3$/EtOAc); mp 149.6-151.4° C. (DSC); $^1$H NMR (300 MHz, CDCl$_3$) δ 7.88 (d, J=3.4 Hz, 1H), 7.47 (d, J=8.8 Hz, 2H), 7.18 (d, J=2.4 Hz, 1H), 6.91-6.86 (m, 3H), 6.78-6.75 (m, 2H), 6.62 (bs, 1H), 4.26-4.22 (m, 4H), 3.96 (t, J=6.5 Hz, 2H), 1.82-1.73 (m, 2H), 1.56-1.44 (m, 2H), 0.98 (t, J=7.4 Hz, 3H); $^{13}$C NMR (75 MHz, CDCl$_3$) δ 156.1, 150.8, 143.6, 142.8, 140.2, 139.9, 139.5, 139.2, 133.9, 130.7, 123.1, 117.1, 115.0, 113.5, 109.4, 68.2, 64.6, 31.6, 19.4, 14.0; IR (ATR) 3365 cm$^{-1}$; ESI MS m/z 411 [C$_{22}$H$_{23}$FN$_4$O$_3$+H]+; HPLC (Method A) 99.0% (AUC), $t_R$=13.2 min. Anal. Calcd for C$_{22}$H$_{23}$FN$_4$O$_3$: C, 64.38; H, 5.65; N, 13.65. Found: C, 63.63; H, 5.60; N, 13.38.

7.3.698 (R920672): N4-(4-n-Hexyloxyphenyl)-N2-(3,4-ethylenedioxyphenyl)-5-fluoro-2,4-pyridinediamine In like manner to the preparation of N4-(4-ethyloxyphenyl)-N2-(3,4-ethylenedioxyphenyl)-5-fluoro-2,4-pyrimidinediamine, the reaction of 2-chloro-N4-(4-n-hexyloxyphenyl)-5-fluoro-4-pyrimidineamine with 3,4-ethylenedioxyaniline gave N4-(4-n-hexyloxyphenyl)-N2-(3,4-ethylenedioxyphenyl)-5-fluoro-2,4-pyridinediamine. The crude product was purified by chromatography (2:1 CHCl$_3$/EtOAc) (0.22 g, 69%) as a tan solid: R$_f$ 0.54 (4:1 CHCl$_3$/EtOAc); mp 124.0-125.2° C. (DSC); $^1$H NMR (300 MHz, CDCl$_3$) δ 7.88 (d, J=3.2 Hz, 1H), 7.47 (d, J=8.9 Hz, 2H), 7.18 (d, J=2.4 Hz, 1H), 6.91-6.86 (m, 3H), 6.78-6.74 (m, 2H), 6.62 (d, J=1.8 Hz, 1H), 4.26-4.22 (m, 4H), 3.96 (t, J=6.5, 2H), 1.83-1.74 (m, 2H), 1.51-1.42 (m, 2H), 1.36-1.32 (m, 4H), 0.93-0.89 (t, J=6.7 Hz, 3H); $^{13}$C NMR (75 MHz, CDCl$_3$) δ 156.1, 150.5, 143.5, 143.0, 142.8, 140.2, 139.9, 139.5, 139.2, 133.9, 130.7, 123.1, 117.1, 115.0, 113.5, 109.3, 68.5, 64.7, 64.5, 31.8, 29.5, 25.9, 22.8, 14.2; IR (ATR) 3378 cm$^{-1}$; ESI MS m/z 439 [C$_{24}$H$_{27}$FN$_4$O$_3$+H]+; HPLC (Method A)>99% (AUC), $t_R$=14.6 min. Anal. Calcd for C$_{24}$H$_{27}$FN$_4$O$_3$: C, 65.74; H, 6.21; N, 12.78. Found: C, 65.52; H, 6.23; N, 12.66.

7.3.699 (R920818): 5-Fluoro-N4-(3-hydroxyphenyl)-N2-[4-(1,2,3,4-tetrazol-5-yl)methyleneoxyphenyl]-2,4-pyrimidinediamine To a mixture of 4-amino-[(1,2,3,4-tetrazol-5-yl)methyleneoxy]benzene (1.2 g, 6.2 mmol), 1-propanol (40 mL) and trifluoroacetic acid (1 mL) was added 2-chloro-5-fluoro-N4-(3-hydroxyphenyl)-4-pyridineamine (1.5 g, 6.2 mmol). The mixture was heated at 110° C. for 17 h and then cooled to room temperature. The purple solid that formed was collected by filtration, washing with 1-propanol (30 mL) to afford 5-Fluoro-N4-(3-hydroxyphenyl)-N2-[4-(1,2,3,4-tetrazol-5-yl)methyleneoxyphenyl]-2,4-pyrimidinediamine (1.6 g, 65%) as an off-white solid: R$_f$ 0.55 (6:3:1 CHCl$_3$/CH$_3$OH/

NH$_4$OH); mp (DSC) 191.2-193.7° C., 257.2-260.0° C., 344.7-345.2° C.; $^1$H NMR (300 MHz, DMSO-d$_6$) δ 9.39 (s, 1H), 9.21 (s, 1H), 9.10 (s, 1H), 8.04 (d, J=3.8 Hz, 1H), 7.59 (d, J=9.1 Hz, 2H), 7.38 (s, 1H), 7.23 (t, J=8.1 Hz, 1H), 7.17 (d, J=1.8 Hz, 1H), 7.05 (t, J=8.1 Hz, 1H), 6.93 (d, J=9.1 Hz, 2H), 6.50 (dd, J=1.8, 8.1 Hz, 1H), 5.40 (s, 2H); $^{13}$C NMR (75 MHz, DMSO-d$_6$) δ 157.3, 155.3, 153.5, 151.9, 149.8, 149.7, 141.0 (d, J$_{C-F}$=150.0 Hz), 139.7, 138.7, 135.0, 128.9, 120.2, 114.8, 110.3, 108.7, 59.6; IR (ATR) 3338, 2923, 2581, 1724, 1661, 1580, 1557 cm$^{-1}$; ESI MS m/z 395 [C$_{18}$H$_{15}$FN$_8$O$_2$+H]+; HPLC (Method A) 96.5% (AUC), t$_R$=6.9 min.

7.3.700 (R920819): N4-(3-Hydroxyphenyl)-N2-[4-(1H,1,2,3,4-tetrazol-5-yl)methyleneoxyphenyl]-2,4-pyrimidinediamine To a mixture of 4-amino-[(1H,1,2,3,4-tetrazolyl)methyleneoxy]benzene (0.1 g, 0.5 mmol), 1-propanol (2 mL) and trifluoroacetic acid (0.2 mL) was added 2-chloro-N4-(3-hydroxyphenyl)-4-pyrimidineamine (0.1 g, 0.5 mmol). The mixture was heated at 110° C. for 17 h and then cooled to room temperature. The purple solid that formed was collected by filtration, washing with 1-propanol (5 mL) to afford N4-(3-hydroxyphenyl)-N2-[4-(1H,1,2,3,4-tetrazol-5-yl)methyleneoxyphenyl]-2,4-pyrimidinediamine (59.4 mg, 30%) as an off-white solid: R$_f$ 0.51 (6:3:1 CHCl$_3$/CH$_3$OH/NH$_4$OH); mp 292-295° C. dec; $^1$H NMR (300 MHz, DMSO-d$_6$) δ 9.34 (s, 2H), 9.13 (s, 1H), 7.95 (d, J=5.8 Hz, 1H), 7.64 (d, J=8.9 Hz, 2H), 7.39 (s, 1H), 7.19 (t, J=8.1 Hz, 1H), 7.05 (t, J=8.1 Hz, 1H), 6.96 (d, J=8.9 Hz, 2H), 6.43 (dd, J=1.4, 8.1 Hz, 1H), 6.20 (d, J=5.8 Hz, 1H), 5.40 (s, 2H); $^{13}$C NMR (75 MHz, DMSO-d$_6$) δ 160.4, 158.5, 157.5, 154.0, 153.7, 152.2, 140.6, 134.4, 129.1, 120.9, 114.7, 111.0, 109.5, 107.2, 98.4, 59.6; IR (ATR) 3321, 2920, 2581, 1649, 1605, 1487 cm$^{-1}$; ESI MS m/z 377 [C$_{18}$H$_{16}$N$_8$O$_2$+H]+; HPLC (Method A) 97.6% (AUC), t$_R$=7.6 min.

7.3.701 (R920820): N4-(3-Hydroxyphenyl)-5-methyl-N2-[4-(1H,1,2,3,4-tetrazol-5-yl)methyleneoxyphenyl]-2,4-pyrimidinediamine To a mixture of 4-amino-[(1H,1,2,3,4-tetrazolyl)methyleneoxy]benzene (0.2 g, 0.9 mmol), 1-propanol (4 mL) and trifluoroacetic acid (0.2 mL) was added 2-chloro-N4-(3-hydroxyphenyl)-5-methyl-4-pyrimidineamine (0.2 g, 0.9 mmol). The mixture was heated at 110° C. for 17 h and then cooled to room temperature. The purple solid that formed was collected by filtration, washing with 1-propanol (10 mL) to afford N4-(3-hydroxyphenyl)-5-methyl-N2-[4-(1H, 1,2,3,4-tetrazol-5-yl)methyleneoxyphenyl]-2,4-pyrimidinediamine (0.3 g, 89%) as an off-white solid: R$_f$ 0.44 (6:3:1 CHCl$_3$/CH$_3$OH/NH$_4$OH); mp (DSC) 255.3-262.4° C.; $^1$H NMR (300 MHz, DMSO-d$_6$) δ 10.32 (s, 1H), 9.65 (s, 2H), 7.85 (s, 1H), 7.38 (d, J=10.5 Hz, 2H), 7.17 (s, 1H), 7.12 (t, J=7.9 Hz, 1H), 7.06 (s, 1H), 6.90 (d, J=10.5 Hz, 2H), 6.68 (d, J=7.9 Hz, 1H), 5.45 (s, 2H), 2.14 (s, 3H); $^{13}$C NMR (75 MHz, DMSO-d$_6$) δ 161.6, 157.9, 154.5, 153.7, 151.2, 140.4, 138.2, 130.1, 129.4, 123.3, 115.9, 115.4, 113.5, 112.4, 107.5, 59.8, 13.7; IR (ATR) 3214, 3051, 2157, 1632, 1596, 1547 cm$^{-1}$; ESI MS m/z 391 [C$_{19}$H$_{18}$N$_8$O$_2$+H]+; HPLC (Method A)>99% (AUC), t$_R$=7.9 min.

7.3.702 N4-(3-Benzyloxyphenyl)-N2-[4-(1-methyl-1,2,3,4-tetrazol-5-yl)methyleneoxyphenyl]-2,4-pyrimidineamine [NEED R NO.]

A mixture of N4-(3-benzyloxyphenyl)-2-chloro-4-pyrimidineamine (0.25 g, 0.82 mmol), 4-amino-(1-methyl-1,2,3,4-tetrazol-5-yl)methyleneoxy]-benzene (0.17 g, 0.82 mmol) and trifluoroacetic acid (0.2 mL) in 1-propanol (10 mL) was heated to 110° C. for 24 h. The reaction was concentrated to remove most of the 1-propanol, the crude product was preadsorbed onto silica gel using 95:5 methylene chloride/methanol and purified by flash chromatography (95:5 methylene chloride/methanol) to give N4-(3-benzyloxyphenyl)-N2-[4-(1-methyl-1,2,3,4-tetrazol-5-yl)methyleneoxyphenyl]-2,4-pyrimidineamine as a tan solid (0.20 g, 52%): $^1$H NMR (300 MHz, DMSO-d$_6$) δ 8.00 (br s, 1H), 7.86 (d, J=6.1 Hz, 1H), 7.53-7.20 (m, 13H), 7.14 (d, J=9.0 Hz, 2H), 6.93 (d, J=6.1 Hz, 1H), 6.13 (d, J=6.1 Hz, 1H), 5.27 (s, 2H), 4.04 (s, 3H); ESI MS m/z 481 [C$_{26}$H$_{24}$N$_8$O$_2$+H]+

7.3.703 (R920917): N4-(3-hydroxyphenyl)-N2-[4-(1-methyl-1,2,3,4-tetrazol-5-yl)methyleneoxyphenyl]-2,4-pyrimidineamine A mixture of N4-(3-benzyloxyphenyl)-N2-[4-(1-methyl-1,2,3,4-tetrazol-5-yl)methyleneoxyphenyl]-2,4-pyrimidineamine (0.20 g, 0.42 mmol) and 5% Pd/C (0.10 g) in 14:1 ethanol/concentrated hydrochloric acid (40 mL) was at room temperature was shaken in a hydrogen atmosphere at 50 psi. After 3 h no further hydrogen uptake was observed. The reaction mixture was filtered through diatomaceous earth, the solids washed with 95:5 methylene chloride/methanol and the filtrate concentrated to afford N4-(3-hydroxyphenyl)-N2-[4-(1-methyl-1,2,3,4-tetrazol-5-yl)methyleneoxyphenyl]-2,4-pyrimidineamine (0.16 g, 95%) as a tan solid: R$_f$ 0.23 (95:5 methylene chloride/methanol); mp (DSC) 207.1-212.8, 287.4-295.7° C.; $^1$H NMR (300 MHz, DMSO-d$_6$) δ 10.87 (br s, 1H), 10.81 (br s, 1H), 9.62 (br s, 1H), 8.08-8.06 (m, 1H), 7.72 (d, J=9.0 Hz, 2H), 7.24 (br s, 1H), 7.20-7.00 (m, 3H), 6.61 (m, 2H), 6.46, (d, J=6.0 Hz, 1H), 5.38 (s, 2H), 4.40 (s, 3H); $^{13}$C NMR (75 MHz, DMSO-d$_6$) δ 161.3, 160.1, 157.0, 154.3, 151.6, 141.7, 137.6, 129.1, 128.6, 123.4, 114.4, 111.9, 111.5, 108.3, 98.6, 59.6, 38.0; IR (ATR) 2975, 1639, 1602, 1521 cm$^{-1}$; ESI MS m/z 391 [C$_{19}$H$_{18}$N$_8$O$_2$+H]+; HPLC (Method A) 94.9% (AUC), t$_R$=8.19 min.

7.3.704 N4-(3-Benzyloxyphenyl)-N2-[4-(2-methyl-1,2,3,4-tetrazol-5-yl)methyleneoxyphenyl]-2,4-pyrimidineamine [NEED R NO.]

A mixture of N4-(3-benzyloxyphenyl)-2-chloro-4-pyrimidineamine (0.52 g, 1.69 mmol), 4-amino-(2-methyl-1,2,3,4-tetrazol-5-yl)methyleneoxy]benzene (0.34 g, 1.69 mmol) and trifluoroacetic acid (0.4 mL) in 1-propanol (10 mL) was heated to 110° C. for 24 h. The reaction was concentrated to remove most of the 1-propanol. The crude product was preadsorbed onto silica gel using 95:5 methylene chloride/methanol and purified by flash chromatography (95:5 methylene chloride/methanol) affording the requisite product N4-(3-benzyloxyphenyl)-N2-[4-(2-methyl-1,2,3,4-tetrazol-5-yl)methyleneoxyphenyl)-2,4-pyrimidineamine as a tan solid (0.41 g, 51%): $^1$H NMR (300 MHz, DMSO-d$_6$) δ 7.85 (d, J=6.1 Hz, 1H), 7.49-7.04 (m, 14H), 6.93 (d, J=9.0 Hz, 2H), 6.60-6.72 (m, 1H), 6.11 (d, J=6.1 Hz, 1H), 5.14 (s, 2H), 4.34 (s, 3H); ESI MS m/z 481 [C$_{26}$H$_{24}$N$_8$O$_2$+H]$^+$

7.3.705 (R920910): N4-(3-Hydroxyphenyl)-N2-[4-(2-methyl-1,2,3,4-tetrazol-5-yl)methyleneoxyphenyl]-2,4-pyrimidineamine A mixture of N4-(3-benzyloxyphenyl)-N2-[4-(2-methyl-1,2,3,4-tetrazol-5-yl)methyleneoxyphenyl]-2,4-pyrimidineamine (0.40 g, 0.42 mmol) and 5% Pd/C (0.10 g) in 14:1 ethanol/concentrated hydrochloric acid (40 mL) at room temperature was shaken in an atmosphere of hydrogen at 50 psi. After 3 h no further hydrogen uptake was observed. The reaction mixture was filtered through diatomaceous earth, the solids washed with 95:5 methylene chloride/methanol and the filtrate concentrated to afford N4-(3-hydroxyphenyl)-N2-[4-(2-methyl-1,2,3,4-tetrazol-5-yl)methyleneoxyphenyl]-2,4-pyrimidineamine (0.29 mg, 89%) as a beige solid: $R_f$ 0.43 (95:5 methylene chloride/methanol); mp 140-152° C.; $^1$H NMR (300 MHz, DMSO-$d_6$) δ 10.24 (br s, 1H), 9.98 (br s, 1H), 9.52 (br s, 1H), 7.94 (d, J=6.6 Hz, 2H), 7.54 (d, J=8.8 Hz, 2H), 7.43 (s, 1H), 7.26 (s, 1H), 7.18-7.01 (m, 3H), 6.53, (d, J=7.5 Hz, 1H), 6.37, (d, J=6.6 Hz, 1H), 5.52 (s, 2H), 4.13 (s, 3H); $^{13}$C NMR (75 MHz, DMSO-$d_6$) δ 160.2, 157.2, 154.5, 153.0, 151.2, 146.8, 139.9, 131.8, 128.7, 122.3, 114.7, 111.4, 110.5, 107.5, 99.5, 59.5, 33.3; IR (ATR) 3042, 1578, 1504, 1459 cm$^{-1}$; ESI MS m/z 391 [$C_{19}H_{18}N_8O_2$+H]+; HPLC (Method A) 95.8% (AUC), $t_R$=8.82 min.

7.3.706 (R920861): 5-Fluoro-N4-(3-hydroxyphenyl)-N2-[4-(1-methyl-1,2,3,4-tetrazol-5-yl)methyleneoxyphenyl]-2,4-pyrimidineamine A mixture of 2-chloro-5-fluoro-N4-(3-hydroxyphenyl)-4-pyrimidineamine (0.22 g, 0.93 mmol, 4-amino-[(1-methyl-1,2,3,4-tetrazol-5-yl)methyleneoxy]-benzene (0.19 g, 0.93 mmol) and trifluoroacetic acid (0.2 mL) in 1-propanol (8 mL) was heated to 110° C. for 24 h. The reaction was concentrated to remove most of the 1-propanol. The crude product was preadsorbed onto silica gel using 95:5 methylene chloride/methanol and purified by flash chromatography (95:5 methylene chloride/methanol) affording the requisite product 5-fluoro-N4-(3-hydroxyphenyl)-N2-[4-(1-methyl-1,2,3,4-tetrazol-5-yl)methyleneoxyphenyl]-2,4-pyrimidineamine as a purple solid (0.18 g, 49%): $R_f$ 0.47 (95:5 methylene chloride/methanol); mp 219-224° C.; $^1$H NMR (300 MHz, DMSO-$d_6$) δ 9.36 (s, 1H), 9.18 (s, 1H), 9.06 (s, 1H), 8.05 (d, J=6.0 Hz, 1H), 7.60 (d, J=9.0 Hz, 2H), 7.27 (d, J=9.0 Hz, 1H), 7.09 (t, J=8.0 Hz, 2H), 6.94 (d, J=9.0 Hz, 2H), 6.49 (dd, J=8.0, 2.1 Hz, 1H), 5.45 (s, 2H), 4.11 (s, 3H); $^{13}$C NMR (75 MHz, DMSO-$d_6$) δ 157.4, 155.5, 151.7, 151.6, 149.6, 149.5, 142.0, 142.0, 139.3 (d, $J_{C-F}$=127.5 Hz), 135.3, 128.9, 120.1, 114.9, 112.3, 110.3, 108.5, 58.5, 33.9; IR (ATR) 3278, 1586, 1542, 1508 cm$^{-1}$; ESI MS m/z 409 [$C_{19}H_{17}FN_8O_2$+H]+; HPLC (Method A) 98.2% (AUC), $t_R$=7.69 min. Anal. Calcd for $C_{19}H_{17}FN_8O_2$ 0.5H$_2$O: C, 54.74; H, 4.23; N, 26.88. Found: C, 54.55; H, 4.02; N, 26.62.

7.3.707 (R920860): 5-Fluoro-N4-(3-hydroxyphenyl)-N2-[4-(1-methyl-1,2,3,4-tetrazol-5-yl)methyleneoxyphenyl]-2,4-pyrimidineamine A mixture of 2-chloro-5-fluoro-N4-(3-hydroxyphenyl)-4-pyrimidineamine (0.31 g, 1.28 mmol), 4-amino-[(2-methyl-1,2,3,4-tetrazol-5-yl)methyleneoxy]-benzene (0.26 g, 1.28 mmol) and trifluoroacetic acid (0.2 mL) in 1-propanol (8 mL) was heated at 110° C. for 24 h. The reaction was concentrated to remove most of the 1-propanol. The crude product was preadsorbed onto silica gel using 95:5 methylene chloride/methanol and purified by flash chromatography (95:5 methylene chloride/methanol) to give 5-fluoro-N4-(3-hydroxyphenyl)-N2-[4-(2-methyl-1,2,3,4-tetrazol-5-yl)methyleneoxyphenyl]-2,4-pyrimidineamine as a purple solid (0.20 g, 37%): $R_f$ 0.63 (95:5 methylene chloride/methanol); mp 220-224° C.; $^1$H NMR (300 MHz, DMSO-$d_6$) δ 9.36 (s, 1H), 9.17 (s, 1H), 9.02 (s, 1H), 8.05 (d, J=2.8 Hz, 1H), 7.57 (d, J=9.1 Hz, 2H), 7.27 (d, J=8.0 Hz, 1H), 7.10 (dt, J=2.8, 8.0 Hz, 2H), 6.91 (d, J=9.1 Hz, 2H), 6.49 (dd, J=8.0, 2.8 Hz, 1H), 5.29 (s, 2H), 4.39 (s, 3H); $^{13}$C NMR (75 MHz, DMSO-$d_6$) δ 162.2, 157.4, 155.5, 152.1, 149.6, 149.5, 140.9 (d, $J_{C-F}$=142.0 Hz), 140.5, 140.2, 138.7, 134.8, 128.9, 120.2, 114.5, 112.2, 110.2, 108.5, 60.5, 38.5; IR (ATR) 3274, 1587, 1507 cm$^{-1}$; ESI MS m/z 409 [$C_{19}H_{17}FN_8O_2$+H]+; HPLC (Method A) 97.2% (AUC), $t_R$=8.04 min. Anal. Calcd for $C_{19}H_{17}FN_8O_2$: C, 55.88; H, 4.20; N, 27.44. Found: C, 55.56; H, 4.10; N, 27.17.

7.3.708 (R920894): N4-(3-Hydroxyphenyl)-5-methyl-N2-[4-(1-methyl-1,2,3,4-tetrazol-5-yl)methyleneoxyphenyl]-2,4-pyrimidineamine A mixture of 2-chloro-N4-(3-hydroxyphenyl)-5-methyl-4-pyrimidineamine (0.20 g, 0.85 mmol, 4-amino-(1-methyl-1,2,3,4-tetrazol-5-yl)methyleneoxy]-benzene (0.17 g, 0.85 mmol) and trifluoroacetic acid (0.2 mL) in 1-propanol (8 mL) was heated at 110° C. for 24 h. The reaction was concentrated to remove most of the 1-propanol. The crude product was preadsorbed onto silica gel using 95:5 methylene chloride/methanol and purified by flash chromatography (95:5 methylene chloride/methanol) to give N4-(3-hydroxyphenyl)-5-methyl-N2-[4-(1-methyl-1,2,3,4-tetrazol-5-yl)methyleneoxyphenyl]-2,4-pyrimidineamine as a purple solid (0.18 g, 52%): $R_f$ 0.61 (95:5 methylene chloride/methanol); mp 209-211° C.; $^1$H NMR (300 MHz, DMSO-$d_6$) δ 9.30 (s, 1H), 8.82 (s, 1H), 8.13 (s, 1H), 7.83 (s, 1H), 7.60 (d, J=9.0 Hz, 2H), 7.18-7.05 (m, 3H), 6.89 (d, J=9.0 Hz, 2H), 6.48 (t, J=7.1 Hz, 1H), 5.27 (s, 2H), 4.39 (s, 3H), 2.08 (s, 3H); $^{13}$C NMR (75 MHz, DMSO-$d_6$) δ 161.7, 158.6, 157.5, 156.7, 154.7, 151.2, 140.2, 134.6, 134.6, 128.1, 119.3, 114.0, 112.6, 109.4, 108.9, 104.7, 59.8, 38.0, 12.9; IR (ATR) 3003, 1602, 1581, 1531, 1507 cm$^1$; ESI MS m/z 405 [$C_{20}H_{20}N_8O_2$+H]+; HPLC (Method A) 96.8% (AUC), $t_R$=8.23 min.

7.3.709 (R920893): N4-(3-Hydroxyphenyl)-5-methyl-N2-[4-(2-methyl-1,2,3,4-tetrazol-5-yl)methyleneoxyphenyl]-2,4-pyrimidineamine A mixture of 2-chloro-N4-(3-hydroxyphenyl)-5-methyl-4-pyrimidineamine (0.20 g, 0.85 mmol), 4-amino-(2-methyl-1,2,3,4-tetrazol-5-yl)methyleneoxy]-benzene (0.17 g, 0.85 mmol) and trifluoroacetic acid (0.2 mL) in 1-propanol (8 mL) was heated at 110° C. for 24 h. The reaction was concentrated to remove most of the 1-propanol. The crude product was preadsorbed onto silica gel using 95:5 methylene chloride/methanol and purified by flash chromatography (95:5 methylene chloride/methanol) to give N4-(3-Hydroxyphenyl)-5-methyl-N2-[4-(2-methyl-1,2,3,4-tetrazol-5-yl)methyleneoxyphenyl]-2,4-pyrimidineamine as a purple solid (0.14 g, 42%): $R_f$ 0.44 (95:5 methylene chloride/methanol); mp 219-221° C.; $^1$H NMR (300 MHz, DMSO-$d_6$) δ 9.32 (s, 1H), 8.85 (s, 1H), 8.13 (s, 1H), 7.85 (s, 1H), 7.64 (d, J=9.0 Hz, 2H), 7.20-7.07 (m, 3H), 6.91 (d, J=9.0 Hz, 2H), 6.50 (dd, J=8.0, 1.2 Hz, 1H), 5.45 (s, 2H), 4.12 (s, 3H), 2.09 (s, 3H); $^{13}$C NMR (75 MHz, DMSO-$d_6$) δ 158.0, 157.0, 156.1, 154.3, 150.6, 150.0, 139.6, 134.6, 127.5, 118.6, 113.7, 112.0, 108.8, 108.2, 104.2, 57.4, 32.7, 12.3; IR (ATR) 3428, 1595, 1567, 1509 cm$^{-1}$; ESI MS m/z 405 [$C_{20}H_{20}N_8O_2$+H]+; HPLC (Method A) 98.5% (AUC), $t_R$=7.89 min. Anal. Calcd for $C_{20}H_{20}N_8O_2$. H$_2$O: C, 57.00; H, 5.02; N, 26.59. Found: C, 56.86; H, 4.92; N, 26.50.

7.3.710 N2,N4-Bis(4-ethoxycarbonylmethyleneoxyphenyl)-5-(1,2,3,4-tetrazol-5-yl)-2,4-pyrimidinediamine (R925810)

In a manner similar to experiment #, N2,N4-bis(4-ethoxycarbonylmethyleneoxyphenyl)-5-cyano-2,4-pyrimidinediamine and sodium azide were reacted to yield N2,N4-bis(4-ethoxycarbonylmethyleneoxyphenyl)-5-(1,2,3,4-tetrazol-5-yl)-2,4-pyrimidinediamine. LCMS: ret. time: 25.8 min.; purity: 95%; MS: 535 (MH$^+$).

7.3.711 N2-[4-(N-Cyclopropylmethylamino) carbonylmethyleneoxyphenyl]-5-ethoxycarbonyl-N4-(3-hydroxyphenyl)-2,4-pyrimidinediamine (R925838)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of 5-ethoxycarbonyl-N4-(3-hydroxyphenyl)-N2-(methoxycarbonylmethyleneoxyphenyl)-2,4-pyridinediamine with cyclopropylmethylamine gave N2-[4-(N-cyclopropylmethylamino)carbonylmethyleneoxyphenyl]-5-ethoxycarbonyl-N4-(3-hydroxyphenyl)-2,4-pyrimidinediamine. LCMS: MS (m/e): 478 (MH$^+$).

7.3.712 5-Ethoxycarbonyl-N4-(3-hydroxyphenyl)-N2-[4-(N-methylamino)carbonylmethyleneoxyphenyl]-2,4-pyrimidinediamine (R925839)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of 5-ethoxycarbonyl-N4-(3-hydroxyphenyl)-N2-(methoxycarbonylmethyleneoxyphenyl)-2,4-pyridinediamine with methylamine hydrochloride gave 5-ethoxycarbonyl-N4-(3-hydroxyphenyl)-N2-[4-(N-methylamino)carbonylmethyleneoxyphenyl]-2,4-pyrimidinediamine. LCMS: MS (m/e): 438 (MH$^+$).

7.3.713 N2-[4-(N-2,3-Dihydroxypropylamino) carbonylmethyleneoxyphenyl]-5-ethoxycarbonyl-N4-(3-hydroxyphenyl)-2,4-pyrimidinediamine (R925840)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of 5-ethoxycarbonyl-N4-(3-hydroxyphenyl)-N2-(methoxycarbonylmethyleneoxyphenyl)-2,4-pyridinediamine with 3-amino-1,2-propanediol gave N2-[4-(N-2,3-dihydroxypropylamino)carbonylmethyleneoxyphenyl]-5-ethoxycarbonyl-N4-(3-hydroxyphenyl)-2,4-pyrimidinediamine. LCMS: MS (m/e): 498 (MH$^+$).

7.3.714 N2,N4-Bis[4-[N-(3-methoxybenzylamino) carbonylmethyleneoxy]phenyl]-5-bromo-2,4-pyrimidinediamine (R925841)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of N2,N4-bis[4-ethoxycarbonylmethyleneoxyphenyl]-5-bromo-2,4-pyrimidinediamine with 3-methoxybenzylamine gave N2,N4-bis[4-[N-(3-methoxybenzylamino) carbonylmethyleneoxy]phenyl]-5-bromo-2,4-pyrimidinediamine. LCMS: ret. time: 25.94 min.; purity: 95%; MS (m/e): 727 (MH$^+$).

7.3.715 5-Bromo-N4-[4-[(N-cyclopropylmethylamino) carbonylmethyleneoxyphenyl]-N2-(3-hydroxyphenyl)-2,4-pyrimidinediamine (R925842)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of 5-bromo-N4-(4-ethoxycarbonylmethyleneoxyphenyl)-N2-(3-hydroxyphenyl)-2,4-pyrimidinediamine with cyclopropylmethylamine gave 5-bromo-N4-[4-(N-cyclopropylmethylamino)carbonylmethyleneoxyphenyl]-N2-(3-hydroxyphenyl)-2,4-pyrimidinediamine. LCMS: ret. time: 20.63 min.; purity: 100%; MS (m/e): 485 (MH$^+$).

7.3.716 5-Bromo-N2-(3-hydroxyphenyl)-N4-[4-(N-3-methoxybenzylamino)carbonylmethyleneoxyphenyl]-2,4-pyrimidinediamine (R925843)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of 5-bromo-N4-(4-ethoxycarbonylmethyleneoxyphenyl)-N2-(3-hydroxyphenyl)-2,4-pyrimidinediamine with 3-methoxybenzylamine gave 5-bromo-N2-(3-hydroxyphenyl)-N4-[4-(N-3-methoxybenzylamino) carbonylmethyleneoxyphenyl]-2,4-pyrimidinediamine. LCMS: ret. time: 22.34 min.; purity: 90%; MS (m/e): 551 (MH$^+$).

7.3.717 N4-(3,4-Ethylenedioxyphenyl)-5-fluoro-N2-(2-carboxybenzofuran-5-yl)-2,4-pyrimidinediamine (R926698)

In a manner similar to the preparation of N4-(4-tert-butylphenyl)-5-fluoro-N2-(2,3-dihydro-2-carboxybenzofuran-5-yl)-2,4-pyrimidinediamine, N4-(3,4-ethylenedioxyphenyl)-5-fluoro-N2-(2-methoxycarbonylbenzofuran-5-yl)-2,4-pyrimidinediamine and LiOH were reacted to yield N4-(3,4-ethylenedioxyphenyl)-5-fluoro-N2-(2-carboxybenzofuran-5-yl)-2,4-pyrimidinediamine.

7.3.718 N2,N4-Bis(4-trifluoromethylphenyl)-5-fluoro-2,4-pyrimidinediamine (R926016)

In a manner similar to the preparation of N2-N4-bis(3-hydroxyphenyl)-5-fluoro-2,4-pyrimidineamine, the reaction of 2,4-dichloro-5-fluoropyrimidine with 4-trifluoromethylaniline gave N2,N4-bis(4-trifluoromethylphenyl)-5-fluoro-2,4-pyrimidinediamine. $^1$H NMR (CDCl$_3$): δ 8.06 (bs, 1H), 7.75 (d, 2H, J=9 Hz), 7.67 (d, 2H, J=9 Hz), 7.63 (d, 2H, J=9 Hz), 7.54 (d, 2H, J=9 Hz), 7.19 (bs, 1H), 6.96 (s, 1H); $^{19}$F NMR (CDCl$_3$): 6-17598 (s, 3F), −17676 (s, 3F), −46549 (s, 1F); HPLC: 85% pure.

7.3.719 N2-(3,4-Ethylenedioxyphenyl)-N4-(3,4-methylenedioxyphenylhydrazinyl)-5-fluoro-2-pyrimidineamine (R926406)

In a manner similar to the preparation of N2-(3-hydroxyphenyl)-N4-(3,4-ethylenedioxyphenyl)-5-fluoro-2,4-pyrimidineamine, the reaction of 2-chloro-5-fluoro N4-(3,4-methylenedioxyphenylhydrazinyl)-4-pyrimidineamine with 3,4-ethylenedioxyaniline gave N2-(3,4-ethylenedioxyphenyl)-5-fluoro-N4-(3,4-methylenedioxyphenylhydrazinyl)-2-pyrimidineamine. $^1$H NMR (CD$_3$OD): δ 7.82 (d, 1H, J=3.6 Hz), 7.52 (dd, 1H, J=1.8 and 7.5 Hz), 7.40 (d, 1H, J=1.2 Hz), 7.14 (d, 1H, J=2.4 Hz), 6.92 (d, 1H, J=8.4 Hz), 6.85 (dd, 1H, J=2.1 and 8.7 Hz), 6.45 (d, 1H, J=9 Hz), 6.06 (s, 2H), 4.10 (s, 4H); LCMS: ret. time: 12.14 min.; purity: 88%; MS (m/e): 426 (MH$^+$).

7.3.720 N2,N4-Bis(4-ethoxycarbonylmethylenedioxyphenyl)-6-ethoxycarbonyl-5-nitro-2,4-pyrimidinediamine (R926566)

To a solution of 2,4-dichloro-5-nitropyrimidine (0.264 g, 1 mmol) in EtOAc (10 mL) at 0° C. was added diisopropylethyl amine (0.200 mL) followed by ethyl 4-aminophenoxy acetate (0.585 g, 3 mmol) and then shaken at room temperature for 2 h. The reaction was quenched with water and extracted with EtOAc. The EtOAc extract was washed with 2N HCl and water. The solvent was evaporated and the residue was purified by crystallization using EtOAc/hexanes to afford N2,N4-bis(4-ethoxycarbonylmethylenedioxyphenyl)-6-ethoxycarbonyl-5-nitro-2,4-pyrimidinediamine (R926566). $^1$H NMR (CDCl$_3$): 10.32 (s, 1H), 7.42 (s, 1H), 7.40 (d, 2H, J=8.7 Hz), 7.32 (d, 2H, J=8.7 Hz), 6.93 (d, 2H, J=8.7 Hz), 6.82 (d, 2H, J=8.7 Hz), 4.67 (s, 2H), 4.62 (s, 2H), 4.47 (q, 2H, J=7.5 Hz), 4.30 (m, 4H), 1.42 (t, 3H, J=6.9 Hz), 1.31 (m, 6H); LCMS: ret. time: 32.10 min.; purity: 100%; MS (m/e): 584 (MH$^+$).

7.3.721 N2,N4-Bis[2-(methylthio)-1,3-benzothiaz-6-yl]-5-fluoro-2,4-pyrimidinediamine (R950202)

In like manner to the preparation of N2,N4-bis(3-hydroxyphenyl)-5-fluoro-2,4-pyrimidinediamine, the reaction of 2,4-dichloro-5-fluoropyrimidine and 2-(methylthio)-1,3-benzothiazol-6-amine were reacted to prepare N2,N4-bis[2-(methylthio)-1,3-benzothiaz-6-yl]-5-fluoro-2,4-pyrimidinediamine. LCMS: ret. time: 24.98 min.; purity: 84.6%; MS (m/e): 486.80 (MH$^+$).

7.3.722 N4-[3-(2-Hydroxyethyleamino)phenyl]-N2-[3-(N-(N-methyl)-piperazino)carbonylmethyleneaminophenyl]-5-fluoro-2,4-pyrimidinediamine (R950240)

In like manner to the preparation of N4-(3,4-ethylenedioxyphenyl)-5-fluoro-N2-[3-(N-methylamino)carbonylmethyleneoxyphenyl]-2,4-pyrimidinediamine, N2-(carboxymethyleneaminophenyl)-5-fluoro-N4-[3-(2-hydroxyethylamino)phenyl]-2,4-pyrimidinediamine and N-methylpiperazine were reacted to give N4-[3-(2-hydroxyethylenoxy)phenyl]-N2-[3-(N-(N-methyl)-piperazino)carbonylmethyleneaminophenyl]-5-fluoro-2,4-pyrimidinediamine. LCMS: ret. time: 13.36 min.; purity: 97.6%; MS (m/e): 495.42 (MH$^+$).

7.3.723 N4-[3-(2-Hydroxyethyleamino)phenyl]-N2-[3-(N-piperazino)-carbonylmethyleneaminophenyl]-5-fluoro-2,4-pyrimidinediamine (R950241)

In like manner to the preparation of N4-(3,4-ethylenedioxyphenyl)-5-fluoro-N2-[3-(N-methylamino)carbonylmethyleneoxyphenyl]-2,4-pyrimidinediamine, N2-(carboxymethyleneaminophenyl)-5-fluoro-N4-[3-(2-hydroxyethyleneamino)phenyl]-2,4-pyrimidinediamine and piperazine were reacted to give N4-[3-(2-hydroxyethyleneamino)phenyl]-N2-[3-(N-piperazino)-carbonylmethyleneaminophenyl]-5-fluoro-2,4-pyrimidinediamine. LCMS: ret. time: 13.21 min.; purity: 100%; MS (m/e): 481.40 (MH$^+$).

7.3.724 (±)-N4-(3-Aminophenyl)-5-fluoro-N2-(3-(3-carboxy-3-D,L-N-phtaloylamino)propylenecarbonylaminophenyl)-2,4-pyrimidinediamine (R950251)

N2,N4-Bis(4-aminophenyl)-5-fluoro-2,4-pyrimidinediamine and N-phtaloyl-DL-glutamic anhydride were reacted in DMF to give N4-(3-aminophenyl)-5-fluoro-N2-(3-(3-carboxy-3-D,L-N-phtaloylamino)propylenecarbonylaminophenyl)-2,4-pyrimidinediamine. LCMS: ret. time: 19.41 min.; purity: 95.7%; MS (m/e): 569.98 (MH$^+$).

7.3.725 (±)-N4-(3-Aminophenyl)-5-fluoro-N2-[3-(3-carboxy-3-amino)propylenecarbonylaminophenyl]-2,4-pyrimidinediamine (R950255)

(±)-N4-(3-Aminophenyl)-5-fluoro-N2-[3-(3-carboxy-3-D,L-N-phtaloylamino)propylenecarbonylaminophenyl]-2,4-pyrimidinediamine was reacted with hydrazine to give N4-(3-aminophenyl)-5-fluoro-N2-[3-(3-carboxy-3-amino)propylenecarbonylaminophenyl]-2,4-pyrimidinediamine. LCMS: ret. time: 11.98 min.; purity: 90.1%; MS (m/e): 440.3 (MH$^+$).

7.3.726 5-Methoxycarbonyl-N2,N4-bis[4-(N-pyrrolidino) carbonylmethyleneoxyphenyl)-2,4-pyrimidinediamine (R926559)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of 5-ethoxycarbonyl-N2,N4-bis(4-methoxycarbonylmethyleneoxyphenyl)-2,4-pyrimidinediamine with pyrrolidine gave 5-methoxycarbonyl-N2,N4-bis[4-(N-pyrrolidino) methoxycarbonylmethyleneoxyphenyl)-2,4-pyrimidinediamine. The ethyl ester at 5-position was exchanged to methyl ester in methanol as a solvent. MS (m/e): 575 (MH$^+$).

7.3.727 N2,N4-Bis(4-ethoxycarbonylmethyleneoxyphenyl)-5-fluoro-2,4-pyridinediamine (R925565)

In like manner to the preparation of N2,N4-bis(3-hydroxyphenyl)-5-fluoro-2,4-pyrimidinediamine, the reaction of 2,4-dichloro-5-fluoropyrimidine with ethyl 4-aminophenoxyacetate gave N2,N4-bis(4-ethoxycarbonylmethyleneoxyphenyl)-5-fluoro-2,4-pyridinediamine. MS (m/e): 485 (MH$^+$).

7.3.728 N2-(3-Ethoxycarbonylmethyleneoxyphenyl)-5-ethoxycarbonyl-N4-(3,4-tetrafluoroethylenedioxyphenyl)-2,4-pyrimidinediamine (R926799)

In a manner similar to the preparation of N2-(3-hydroxyphenyl)-N4-(3,4-ethylenedioxyphenyl)-5-fluoro-2,4-pyrimidineamine, the reaction of ethyl 3-aminophenoxyacetate with 2-chloro-5-ethoxycarbonyl-N4-(3,4-tetrafluoroethylenedioxyphenyl)-4-pyrimidineamine gave N2-(3-ethoxycarbonylmethyleneoxyphenyl)-5-ethoxycarbonyl-N4-(3,4-tetrafluoroethylenedioxyphenyl)-2,4-pyrimidinediamine. MS (m/e): 567 (MH$^+$).

7.3.729 N4-(3,4-Ethylenedioxyphenyl)-5-fluoro-N2-[3-[N-2-(D)-(±)-biotinylethylamino]carbonylmethyleneoxyphenyl]-2,4-pyrimidinediamine (R926811)

To a solution of D-(±)-biotin and N4-(3,4-ethylenedioxyphenyl)-5-fluoro-N2-[3-(N-2-hydroxyethylamino)carbonylmethyleneoxyphenyl]-2,4-pyrimidinediamine in DMF at −20° C. was added diisopropylethylamine and the mixture was shaken for 10 minutes. To this mixture was added benzotriazole-1-yl-oxy-tris(dimethylamino)-phosphonium-hexafluorophosphate (BOP) and shaken at room temperature for 24 h. The reaction was quenched with water and extracted with ethyl acetate. The ethyl acetate extract was washed with aqueous solution of NaHCO3 and finally with water. The residue obtained after the removal of solvent was purified by preparative TLC to obtain the desired N4-(3,4-ethylenedioxyphenyl)-5-fluoro-N2-[3-[N-2-(D)-(±)-biotinylethylamino]carbonylmethyleneoxyphenyl]-2,4-pyrimidinediamine. LCMS: ret. time: 19.29 min.; purity: 99%; MS (m/e): 682 (M$^+$).

7.3.730 5-Fluoro-N4-(3-hydroxyphenyl)-N2[2-(N-methyl-N-2-hydroxyethyl)carbonylbenzofuran-5-yl)-2,4-pyrimidinediamine (R926725)

In like manner to the preparation of N4-(3,4-ethylenedioxyphenyl)-5-fluoro-N2-[3-(N-methylamino)carbonylmethyleneoxyphenyl]-2,4-pyrimidinediamine, the reaction of 5-fluoro-N4-(3-hydroxyphenyl)-N2[2-methoxycarbonylbenzofuran-5-yl)-2,4-pyrimidinediamine with 2-(N-methyl) ethanolamine gave 5-fluoro-N4-(3-hydroxyphenyl)-N2[2-(N-methyl-N-2-hydroxyethyl)carbonylbenzofuran-5-yl)-2,4-pyrimidinediamine. LCMS: ret. time: 14.87 min.; purity: 98%; MS: 438 (MH$^+$).

7.3.731 N2,N4-Bis(3-ethoxycarbonylphenyl)-5-fluoro-2,4-pyrimidinediamine (R926228)

In like manner to the preparation of N2,N4-bis(3-hydroxyphenyl)-5-fluoro-2,4-pyrimidinediamine, the reaction of 2,4-dichloro-5-fluoropyrimidine and 3-ethoxycarbonylaniline gave N2,N4-bis(3-ethoxycarbonylphenyl)-5-fluoro-2,4-pyrimidinediamine. LCMS: ret. time: 26.55 min.; purity: 100%; MS (m/e): 425 (MH$^+$).

7.3.732 N2-(3-chloro-4-methylbenzyl)-N4-(3,4-ethylenedioxyphenyl)-5-fluoro-2,4-pyrimidinediamine (R908696)

In a manner similar to the preparation of N2-(3-hydroxyphenyl)-N4-(3,4-ethylenedioxyphenyl)-5-fluoro-2,4-pyrimidineamine, the reaction of 2-chloro-N4-ethylenedioxyphenyl)-5-fluoro-4-pyrimidineamine with 3-chloro-4-methylbenzylamine gave N2-(3-chloro-4-methylbenzyl)-N4-(3,4-ethylenedioxyphenyl)-5-fluoro-2,4-pyrimidinediamine. LCMS: ret. time: 25.38 min.; purity: 99%; MS (m/e): 401 (MH$^+$).

7.3.733 (±)-N4-(3,4-Ethylenedioxyphenyl)-5-fluoro-N2-(2-phenylethyl)-2,4-pyrimidinediamine (R908697)

In a manner similar to the preparation of N2-(3-hydroxyphenyl)-N4-(3,4-ethylenedioxyphenyl)-5-fluoro-2,4-pyrimidineamine, the reaction of 2-chloro-N4-ethylenedioxyphenyl)-5-fluoro-4-pyrimidineamine with (±)-2-aminoethylbenzene gave (±)-N4-(3,4-ethylenedioxyphenyl)-5-fluoro-N2-(2-phenylethyl)-2,4-pyrimidinediamine. LCMS: ret. time: 23.48 min.; purity: 99%; MS (m/e): 367 (MH$^+$).

7.3.734 N2-(3-Ethoxycarbonylphenyl)-N4-(3,4-ethylenedioxyphenyl)-5-fluoro-2,4-pyrimidinediamine (R925745)

In like manner to preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 3-ethoxycarbonylaniline gave N2-(3-ethoxycarbonylphenyl)-N4-(3,4-ethylenedioxyphenyl)-5-fluoro-2,4-pyrimidinediamine. $^1$H NMR (CDCl$_3$): δ 8.04 (bs, 1H), 7.94 (bs, 1H), 7.90 (bd, 1H), 7.68 (bd, 1H, J=7.5 Hz), 7.35 (t, 1H, J=8.1 Hz), 7.28 (d, 1H, J=2.4 Hz), 7.07 (s, 1H), 6.93 (dd, 1H, J=3 and 8.7 Hz), 6.83 (d, 1H, J=9 Hz), 6.64 (bs, 1H), 4.36 (q, 2H, J=7.2 Hz), 4.26 9s, 4H), 1.35 (t, 3H, J=7.5 Hz); $^{19}$F NMR (CDCl$_3$): −47247; LCMS: ret. time: 15.88; purity: 100%; MS (m/e): 411 (MH$^+$).

7.3.735 N4-(3,4-Difluorophenyl)-5-fluoro-N2-[3-(N-methylamino)carbonylmethyleneoxyphenyl]-2,4-pyrimidinediamine (R920394)

A solution of N-methyl 3-aminophenoxyacetamide (1 equivalent) and 2-chloro-N4-(3,4-difluorophenyl)-5-fluoro-4-pyrimidineamine (1.2 equivalents) in MeOH was shaken in a sealed tube at 100° C. for 24 hours for 24 h. Upon cooling to the room temperature, it was diluted with ethyl acetate. The resulting solid was filtered and washed with a mixture of ethyl acetate:n-hexanes (1:1; v/v) to obtain N4-(3,4-difluorophenyl)-5-fluoro-N2-[3-(N-methylamino)carbonylmethyleneoxyphenyl]-2,4-pyrimidinediamine. $^1$H NMR (DMSO-d6): δ 10.05 (bs, 1H), 9.83 (bs, 1H), 8.23 (d, 1H, J=2.7 Hz), 7.98 (m, 2H), 7.52 (m, 1H), 7.39 9m, 1H), 7.20 (m, 3H), 6.60 (m, 1H), 4.37 (s, 2H0, 2.63 (d, 3H, J=3.3 Hz); LCMS: purity: 94%; MS (m/e): 404 (MH$^+$).

7.3.736 N4-(4-Chlorophenyl)-5-fluoro-N2-[3-(N-methylamino) carbonylmethyleneoxyphenyl]-2,4-pyrimidinediamine (R920396)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(4-chlorophenyl)-5-fluoro-4-pyrimidineamine gave N4-(4-chlorophenyl)-5-fluoro-N2-[3-(N-methylamino)carbonylmethyleneoxyphenyl]-2,4-pyrimidinediamine. $^1$H NMR (DMSO-d6): δ 10.21 (bs, 1H), 10.00 (bs, 1H), 8.26 (d, 1H, J=4.8 Hz), 8.00 (bd, 1H, J=4.2 Hz), 7.77 (dd, 2H, J=2.1 and 7.6 Hz), 7.37 (dd, 2H, J=2.1 and 7.6 Hz), 7.17 9m, 3H), 8.63 (dd, 1H, J=1.8 and 8.1 Hz), 4.37 (s, 2H), 2.64 (d, 3H, 4.5 Hz); LCMS: purity: 92%; MS (m/e): 402 (MH$^+$).

7.3.736.1 N4-(3,4-Dichlorophenyl)-5-fluoro-N2-[3-(N-methylamino) carbonylmethyleneoxyphenyl]-2,4-pyrimidinediamine (R920397)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(3,4-dichlorophenyl)-5-fluoro-4-pyrimidineamine gave N4-(3,4-dichlorophenyl)-5-fluoro-N2-[3-(N-methylamino)carbonylmethyleneoxyphenyl]-2,4-pyrimidinediamine. $^1$H NMR (DMSO-d6): δ 10.02 (bs, 1H), 9.76 (bs, 1H), 8.24 (d, 1H, J=4.2 Hz), 8.08 (m, 1H), 7.97 (bd, 1H, J=4.8 Hz), 7.77 (m, 1H), 7.55 (d, 1H, J=8.7 Hz), 7.18 (m, 3H), 6.58 (m, 1H), 4.36 (s, 1H), 2.63 (d, 1H, J=2.7 Hz); LCMS: purity: 91%; MS: 434 (MH$^+$).

7.3.737 5-Fluoro-N4-(5-methylpyridin-2-yl)-N2-[3-(N-methylamino) carbonylmethyleneoxyphenyl]-2,4-pyrimidinediamine (R920398)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(5-methylpyridin-2-yl)-4-pyrimidineamine gave 5-fluoro-N4-(5-methylpyridin-2-yl)-N2-[3-(N-methylamino)carbonylmethyleneoxyphenyl]-2,4-pyrimidinediamine. $^1$H NMR (DMSO-d6): δ 11.35 (bs, 1H), 10.70 (bs, 1H), 8.58 (s, 1H), 8.42 (d, 1H, J=3.0 Hz), 8.12 (bd, 1H, J=9.3 Hz), 8.03 (bd, 1H, J=4.2 Hz), 7.82 (d, 1H, J=8.7 Hz), 7.56 (s, 1H), 7.30 (bdd, 1H, J=8.1 Hz), 7.19 (t, 1H, J=8.1 Hz), 6.55 (dd, 1H, J=1.8 and 8.1 Hz), 4.41 (s, 2H), 2.63 (d, 3H, J=3.6 Hz), 2.36 (s, 3H); LCMS: purity: 99%; MS (m/e): 382 (M$^+$).

7.3.738 5-Fluoro-N4-(6-methylpyridin-2-yl)-N2-[3-(N-methylamino) carbonylmethyleneoxyphenyl]-2,4-pyrimidinediamine (R920399)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(6-methylpyridin-2-yl)-4-pyrimidineamine gave 5-fluoro-N4-(6-methylpyridin-2-yl)-N2-[3-(N-methylamino)carbonylmethyleneoxyphenyl]-2,4-pyrimidinediamine. $^1$H NMR (DMSO-d6): δ 10.00 (bs, 1H), 9.60 (bs, 1H), 8.25 (s, 1H), 7.95 (m, 3H), 7.30 (s, 1H), 7.10 (m, 3H), 6.55 (d, 1H, J=7.2 Hz), 4.40 (s, 2H), 2.62 (d, 3H, J=3.6 Hz), 2.45 (s, 3H); LCMS: purity: 92%; MS (m/e): 383 (MH$^+$).

7.3.739 N4-(5-Chloropyridin-2-yl)-5-fluoro-N2-[3-(N-methylamino) carbonylmethyleneoxyphenyl)-2,4-pyrimidinediamine (R920405)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(5-chloropyridin-2-yl)-5-fluoro-4-pyrimidineamine gave N4-(5-chloropyridin-2-yl)-5-fluoro-N2-[3-(N-methylamino)carbonylmethyleneoxyphenyl]-2,4-pyrimidinediamine. $^1$H NMR (DMSO-d6): δ 10.04 (bs, 1H), 9.53 (bs, 1H), 8.40 (d, 1H, J=2.4 Hz), 8.22 (m, 2H), 7.88 (bd, 1H, J=4.5 Hz), 7.86 (dd, 1H, J=2.4 and 8.7 Hz), 7.40 (d, 1H, J=1.8 Hz), 7.19 (m, 2H), 6.51 (bdd, 1H, J=1.2 and 9 Hz), 4.38 (s, 2H), 2.64 (d, 3H, J=3.3 Hz); LCMS: purity: 95%; MS (m/e): 403 (MH$^+$).

7.3.740 N4-(6-Chloropyridin-3-yl)-5-fluoro-N2-[3-(N-methylamino) carbonylmethyleneoxyphenyl)-2,4-pyrimidinediamine (R920406)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(6-chloropyridin-3-yl)-5-fluoro-4-pyrimidineamine gave N4-(6-chloropyridin-3-yl)-5-fluoro-N2-[3-(N-methylamino)carbonylmethyleneoxyphenyl]-2,4-pyrimidinediamine. $^1$H NMR (DMSO-d6): δ 9.72 (s, 1H), 9.38 (s, 1H), 8.93 (t, 1H, J=3.0 Hz), 8.28 (m, 1H), 8.18 (d, 1H, J=3.6 Hz), 7.95 (m, 1H), 7.45 (d, 1H, J=8.7 Hz), 7.39 (m, 1H), 7.21 (m, 1H), 7.14 (t, 1H, J=4.8 Hz), 6.50 (bdd, 1H, J=7.8 Hz), 4.4 (s, 2H), 2.63 (d, 3H); LCMS: purity: 100%; MS (m/e): 403 (MH$^+$).

7.3.741 5-Fluoro-N2-[3-(N-methylamino)carbonylmethyleneoxyphenyl]-N4-(4-methylpyridin-2-yl)-2,4-pyrimidinediamine (R927016)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(4-methylpyridin-2-yl)-4-pyrimidineamine gave 5-fluoro-N2-[3-(N-methylamino)carbonylmethyleneoxyphenyl]-N4-(4-methylpyridin-2-yl)-2,4-pyrimidinediamine. LCMS: purity: 95%; MS (m/e): 383 (MH$^+$).

7.3.742 5-Fluoro-N2-[3-(N-methylamino)carbonylmethyleneoxyphenyl]-N4-(3-trifluoromethoxyphenyl)-2,4-pyrimidinediamine (R920407)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(3-trifluoromethylphenyl)-4-pyrimidineamine gave 5-fluoro-N2-[3-(N-methylamino)carbonylmethyleneoxyphenyl]-N4-(3-trifluoromethoxyphenyl)-2,4-pyrimidinediamine. $^1$H NMR (DMSO-d6): δ 9.835 (bs, 1H), 9.54 (bs, 1H), 8.20 (d, 1H, J=3.6 Hz), 7.94 (m, 2H), 7.78 (bs, 1H), 7.43 (t, 1H, J=8.4 Hz), 7.25 (m, 2H), 7.15 (t, 1H, J=7.5 Hz), 7.03 (bd, 1H, J=9.3 Hz), 6.55 (bd, 1H, J=7.5 Hz), 4.36 (s, 2H), 2.63 (d, 3H, J=4.5 Hz); LCMS: purity: 91%; MS (m/e): 452 (MH$^+$).

7.3.743 N4-(3,4-Difluoromethylenedioxyphenyl)-5-fluoro-N2-[3-(N-methylamino)carbonylmethyleneoxyphenyl]-2,4-pyrimidinediamine (R920408)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(3,4-difluoromethylenedioxyphenyl)-5-fluoro-4-pyrimidineamine gave N4-(3,4-difluoromethylenedioxyphenyl)-5-fluoro-N2-[3-(N-methylamino)carbonylmethyleneoxyphenyl]-2,4-pyrimidinediamine. $^1$H NMR (DMSO-d6): δ 9.91 (bs, 1H), 9.64 (bs, 1H), 8.19 (d, 1H, J=3.9 Hz), 8.03 (s, 1H), 7.96 (bd, 1H, J=4.8 Hz), 7.46 (m, 1H), 7.36 (d, 1H, J=8.7 Hz), 7.27 (bs, 1H), 7.17 (m, 2H), 6.57 (bdd, 1H, J=7.2 Hz), 4.36 (s, 1H), 2.62 (d, 3H, J=4.5 Hz); LCMS: purity: 96%; MS (m/e): 448 (MH$^+$).

7.3.744 N4-(3-Chloro-4-trifluoromethoxyphenyl)-5-fluoro-N2-[3-(N-methylamino)carbonylmethyleneoxyphenyl]-2,4-pyrimidinediamine (R920410)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(3-chloro-4-trifluoromethoxyphenyl)-5-fluoro-4-pyrimidineamine gave N4-(3-chloro-4-trifluoromethoxyphenyl)-5-fluoro-N2-[3-(N-methylamino)carbonylmethyleneoxyphenyl]-2,4-pyrimidinediamine. $^1$H NMR (CD$_3$OD): δ 8.08 (d, 1H, J=5.4 Hz), 7.99 (d, 1H, J=3.6 Hz), 7.67 (dd, 1H, J=2.4 and 9.0 Hz), 7.40 (m, 3H), 7.06 (m, 2H), 6.92 (dd, 1H, J=2.4 and 8.4 Hz), 4.44 (s, 2H), 2.80 (s, 3H); $^{19}$F NMR (CD$_3$OD): −16973 and −45983; LCMS: purity: 96%; MS (m/e): 486 (MH$^+$).

7.3.745 N4-(4-Ethoxyphenyl)-5-fluoro-N2-[3-(N-methylamino) carbonylmethyleneoxyphenyl]-2,4-pyrimidinediamine (R926827)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(4-ethoxyphenyl)-5-fluoro-4-pyrimidineamine gave N4-(4-ethoxyphenyl)-5-fluoro-N2-[3-(N-methylamino)carbonylmethyleneoxyphenyl]-2,4-pyrimidinediamine. LCMS: purity: 96%; MS: 412 (MH$^+$).

7.3.746 N4-(3,4-Ethylenedioxyphenyl)-5-fluoro-N2-[4-methoxy-3-(N-methylamino)carbonylmethyleneoxyphenyl]-2,4-pyrimidinediamine (R926828)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-amino-6-methoxyphenoxyacetamide with 2-chloro-N4-(3,4-ethylenedioxyphenyl)-5-fluoro-4-pyrimidineamine gave N4-(3,4-ethylenedioxyphenyl)-5-fluoro-N2-[4-methoxy-3-(N-methylamino)carbonylmethyleneoxyphenyl]-2,4-pyrimidinediamine. $^1$H NMR (CD$_3$OD): δ 7.83 (s, 1H), 7.80 (d, 1H, J=4.2 Hz), 7.30 (d, 1H, 2.4 Hz), 7.23 (d, 1H, J=2.4 Hz), 7.06 (m, 2H), 6.90 (d, 1H, J=5.7 Hz), 6.73 (d, 1H, J=5.2 Hz), 4.32 (s, 2H), 4.22 (s, 4H), 3.86 (s, 3H), 2.83 (s, 3H); LCMS: purity: 97%; MS (m/e): 455 (MH$^+$).

7.3.747 5-Fluoro-N4-(3-hydroxyphenyl)-N2-[4-methoxy-3-(N-methylamino)carbonylmethyleneoxyphenyl]-2,4-pyrimidinediamine (R926829)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-amino-4-methoxyphenoxyacetamide with 2-chloro-5-fluoro-N4-(3-hydroxyphenyl)-4-pyrimidineamine gave 5-fluoro-N4-(3-hydroxyphenyl)-N2-[4-methoxy-3-(N-methylamino)carbonylmethyleneoxyphenyl]-2,4-pyrimidinediamine. $^1$H NMR (CD$_3$OD): δ 7.86 (d, 1H, J=4.2 Hz), 7.35 (d, 1H, J=2.4 Hz), 7.19 (m, 1H), 7.12 (m, 3H), 6.93 (d, 1H, J=8.7 Hz), 6.52 (m, 1H), 4.37 (s, 2H), 3.85 (s, 3H), 2.82 (s, 3H); $^{19}$F NMR (CD$_3$OD): −47650; LCMS: purity: 100%; MS: 414 (MH$^+$).

7.3.748 N4-(3-Chlorophenyl)-5-fluoro-N2-[3-(N-methylamino)carbonylmethyleneoxyphenyl]-2,4-pyrimidinediamine (R926832)

In like manner to preparation of N4-(3,4-difluorophenyl)-5-fluoro-N2-[3-(N-methylamino)carbonylmethyleneoxyphenyl]-2,4-pyrimidinediamine the reaction of 3 N-methyl 3-aminophenoxyacetamide with 2-chloro-N4-(3-chlorophenyl)-5-fluoro-4-pyrimidineamine gave N4-(3-chlorophenyl)-5-fluoro-N2-[3-(N-methylamino)carbonylmethyleneoxyphenyl]-2,4-pyrimidinediamine. $^1$H NMR (DMSO-d6): δ 10.12 (s, 1H), 9.93 (s, 1H), 8.27 (d, 1H, J=4.2 Hz), 7.98 (d, 1H, J=4.9 Hz), 7.85 (s, 1H), 7.73 (d, 1H, J=8.1 Hz), 7.35 (t, 1H, J=8.4 Hz), 7.19 (m, 3H), 6.62 (m, 1H), 4.36 (s, 2H), 2.63 (d, 3H, J=4.2 Hz); LCMS: purity: 95%; MS: 402 (MH$^+$).

7.3.749 5-Fluoro-N4-(3-methoxy-5-trifluoromethylphenyl)-N2-[3-(N-methylamino)carbonylmethyleneoxyphenyl]-2,4-pyrimidinediamine (R926833)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(3-methoxy-5-trifluoromethylphenyl)-4-pyrimidineamine gave 5-fluoro-N4-(3-methoxy-5-trifluoromethylphenyl)-N2-[3-(N-methylamino)carbonylmethyleneoxyphenyl]-2,4-pyrimidinediamine. LCMS: purity: 95%; MS (m/e): 466 (MH$^+$).

7.3.750 5-Fluoro-N4-(3-hydroxy-4-methoxyphenyl)-N2-[3-(N-methylamino) carbonylmethyleneoxyphenyl]-2,4-pyrimidinediamine (R926834)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(3-hydroxy-4-methoxyphenyl)-4-pyrimidineamine gave 5-fluoro-N4-(3-hydroxy-4-methoxyphenyl)-N2-[3-(N-methylamino)carbonylmethyleneoxyphenyl]-2,4-pyrimidinediamine. $^1$H NMR (DMSO-d6): δ 9.70 (bs, 2H), 8.12 (d, 1H, J=4.8 Hz), 7.96 (m, 1H), 7.12 (m, 5H), 6.85 (d, 1H, J=8.7 Hz), 6.57 (bd, 1H, J=8.1 Hz), 4.35 (s, 2H), 3.74 (s, 3H), 2.63 (d, 3H, J=4.5 Hz); LCMS: purity: 99%; MS (m/e): 414 (MH$^+$).

7.3.751 5-Fluoro-N4-(4-methoxy-3-trifluoromethylphenyl)-N2-[3-(N-methylamino)carbonylmethyleneoxyphenyl]-2,4-pyrimidinediamine (R926835)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(4-methoxy-3-trifluoromethylphenyl)-4-pyrimidineamine gave 5-fluoro-N4-(4-methoxy-3-trifluoromethylphenyl)-N2-[3-(N-methylamino)carbonylmethyleneoxyphenyl]-2,4-pyrimidinediamine. $^1$H NMR (DMSO-d6): δ 9.9 Bs, 1H), 9.62 (bs, 1H), 8.17 (d, 1H, J=4.2 Hz), 8.04 (bdd, 1H, J=7.2 Hz), 7.82 (t, 1H, 2.7 Hz), 7.18 (m, 3H), 7.11 (t, 1H, J=8.1 Hz), 6.55 (bd, 1H, J=6.9 Hz); 4.33 (s, 2H), 3.86 (s, 3H), 2.61 (d, 3H, J=4.0 Hz); LCMS: purity: 93%; MS: 466 (MH$^+$).

7.3.752 5-Fluoro-N4-(4-fluoro-3-trifluoromethylphenyl)-N2-[3-(N-methylamino)carbonylmethyleneoxyphenyl]-2,4-pyrimidinediamine (R926838)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(4-fluoro-3-trifluoromethylphenyl)-4-pyrimidineamine gave 5-fluoro-N4-(4-fluoro-3-trifluoromethylphenyl)-N2-[3-(N-methylamino)carbonylmethyleneoxyphenyl]-2,4-pyrimidinediamine. $^1$H NMR (DMSO-d6): δ 9.80 (s, 1H), 9.44 (s, 1H), 8.25 (m, 1H), 8.18 (d, 1H, J=3.9 Hz), 8.00 (m, 1H), 7.97 (m, 1H), 7.47 (t, 1H, J=9.6 Hz), 7.26 (s, 1H), 7.21 (m, 1H), 7.11 (t, 1H, J=8.4 Hz), 6.51 (bd, 1H, J=9.9 Hz), 4.34 (s, 2H), 2.62 (d, 3H, J=4.8 Hz); LCMS: purity: 88%; MS: 454 (MH$^+$).

7.3.753 N4-(3-Chloro-4-methylphenyl)-5-fluoro-N2-[3-(N-methylamino)carbonylmethyleneoxyphenyl]-2,4-pyrimidinediamine (R926839)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(3-chloro-4-methylphenyl)-4-pyrimidineamine gave N4-(3-chloro-4-methylphenyl)-5-fluoro-N2-[3-(N-methylamino)carbonylmethyleneoxyphenyl]-2,4-pyrimidinediamine. $^1$H NMR (DMSO-d6): δ 9.69 (s, 1H), 9.52 (s, 1H), 8.16 (d, 1H, J=4.2 Hz), 7.96 (bs, 1H), 7.81 (d, 1H, J=2.1 Hz), 7.67 (bd, 1H, J=8.4 Hz), 7.26 (m, 3H), 7.15 (t, 1H, J=8.1 Hz), 6.54 (bd, 1H, J=7.2 Hz), 4.34 (s, 2H), 2.63 (d, 3H, J=4.2 Hz), 2.27 (s, 3H); LCMS: purity: 80%; MS (m/e): 415 (M$^+$).

7.3.754 N4-(2-Chloro-5-methylphenyl)-5-fluoro-N2-[3-(N-methylamino) carbonylmethyleneoxyphenyl]-2,4-pyrimidinediamine (R926840)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(2-chloro-5-methylphenyl)-4-pyrimidineamine gave N4-(2-chloro-5-methylphenyl)-5-fluoro-N2-[3-(N-methylamino)carbonylmethyleneoxyphenyl]-2,4-pyrimidinediamine. $^1$H NMR (DMSO-d6): δ 9.80 (bs, 2H), 8.21 (d, 1H, J=4.8 Hz), 7.92 (d, 1H, J=4.8 Hz), 7.46 (m, 1H), 7.31 (m, 2H), 7.04 (m, 2H), 6.53 (bd, 1H, J=8.1 Hz), 4.30 (s, 1H), 2.18 (s, 3H); LCMS: purity: 93%; MS (m/e): 416 (MH$^+$).

7.3.755 N4-(3,4-Ethylenedioxyphenyl)-5-fluoro-N2-[3-(N-isopropylamino) carbonylmethyleneoxyphenyl]-2,4-pyrimidinediamine (R926830)

The reaction of N4-(3,4-ethylenedioxyphenyl)-5-fluoro-N2-(ethoxycarbonylmethyleneoxyphenyl)-2,4-pyrimidinediamine with isopropylamine (5 equivalents) in the presence of diisopropylethylamine (5 equivalents) in MeOH in a sealed tube at 80° C. for 24 hours gave N4-(3,4-ethylenedioxyphenyl)-5-fluoro-N2-[3-(N-isopropylamino)carbonylmethyleneoxyphenyl]-2,4-pyrimidinediamine. $^1$H NMR (DMSO-d6): δ 9.15 (s, 1H), 8.04 (d, 1H, J=4.2 Hz), 7.77 (d, 1H, J=7.5 Hz), 7.28 (m, 4H), 7.08 (t, 1H, J=8.1 Hz), 6.78 (d, 1H, J=8.7 Hz), 6.45 (dd, 1H, J=1.8 and 7.8 Hz), 4.30 (s, 2H), 4.20 (s, 4H), 3.92 (m, 1H), 1.06 (d, 6H, J=6.6 Hz); LCMS: purity: 95%; MS (m/e): 454 (MH$^+$).

7.3.756 N2-[3-(N-Cyclopropylamino)carbonylmethyleneoxyphenyl]-N4-(3,4-ethylenedioxyphenyl)-5-fluoro-2,4-pyrimidinediamine (R926848)

In like manner to the preparation of N4-(3,4-ethylenedioxyphenyl)-5-fluoro-N2-[3-(N-isopropylamino)carbonylmethyleneoxyphenyl]-2,4-pyrimidinediamine, the reaction of N4-(3,4-ethylenedioxyphenyl)-5-fluoro-N2-(ethoxycarbonylmethyleneoxyphenyl)-2,4-pyrimidinediamine with cyclopropylamine gave 5-fluoro-N4-(3,4-ethylenedioxyphenyl)-N2-[3-(N-cyclopropylamino)carbonylmethyleneoxyphenyl]-2,4-pyrimidinediamine. $^1$H NMR (DMSO-d6): δ 9.17 (bs, 2H), 8.05 (m, 2H), 7.27 (m, 4H), 7.08 (t, 1H, J=8.1 Hz), 7.67 (d, 1H, J=8.7 Hz), 6.42 (dd, 1H, J=2.4 and 8.1 Hz), 4.3 (s, 2H), 4.2 (bs, 4H), 2.65 (m, 1H), 0.6 (m, 2H), 0.45 (m, 2H); LCMS: purity: 91%; MS (m/e): 452 (MH$^+$).

7.3.757 N4-(4-Cyano-3-methylphenyl)-5-fluoro-N2-[3-(N-methylamino) carbonylmethyleneoxyphenyl]-2,4-pyrimidinediamine (R926851)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(4-cyano-3-methylphenyl)-4-pyrimidineamine gave N4-(4-cyano-3-methylphenyl)-5-fluoro-N2-[3-(N-methylamino)carbonylmethyleneoxyphenyl]-2,4-pyrimidinediamine. $^1$H NMR (DMSO-d6): δ 9.7 (s, 1H), 9.40 (s, 1H), 8.2 (s, 1H), 8.00-7.50 (m, 3H), 7.40-7.00 (m, 3H), 6.50 (bm, 1H), 4.35 (s, 2H), 2.60 (s, 3H), 2.35 (s, 3H); LCMS: purity: 91%; MS (m/e): 407 (MH$^+$).

7.3.758 5-Fluoro-N2-[3-(N-methylamino)carbonylmethyleneoxyphenyl]-N4-[3-(tetrazol-5-yl)phenyl]-2,4-pyrimidinediamine (R926855)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-[3-(1H-tetrazol-5-yl)phenyl]-4-pyrimidineamine gave 5-fluoro-N2-[3-(N-methylamino)carbonylmethyleneoxyphenyl]-N4-[3-(tetrazol-5-yl)phenyl]-2,4-pyrimidinediamine. $^1$H NMR (DMSO-d6): δ 10.04 (bs, 1H), 9.65 (bs, 1H), 8.35 (s, 1H), 8.23 (d, 1H, J=3.9 Hz), 8.00 (bd, 1H, J=6.6 Hz), 7.91 (bd, J=3.6 Hz), 7.77 (d, 1H, J=8.1 Hz), 7.57 (t, 1H, J=8.1 Hz), 7.23 (m, 2H), 6.95 (t, 1H, J=8.4 Hz), 6.46 (bdd, 1H, J=1.8 and 8.1 Hz), 4.22 (s, 2H), 2.62 (d, 3H, 4.2 Hz); LCMS: purity: 83%; MS (m/e): 436 (MH$^+$).

7.3.759 5-Fluoro-N2-[3-(N-methylamino)carbonylmethyleneoxyphenyl]-N4-(N-methylphthalimido-4-yl)-2,4-pyrimidinediamine (R926856)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(N-methylphthalimido-4-yl)-4-pyrimidineamine gave 5-fluoro-N2-[3-(N-methylamino)carbonylmethyleneoxyphenyl]-N4-(N-methylphthalimido-4-yl)-2,4-pyrimidinediamine. $^1$H NMR (DMSO-d6): δ 9.95 (s, 1H), 9.44 (s, 1H), 8.29 (m, 1H), 8.25 (m, 1H), 8.18 (d, 1H, J=1.8 Hz), 7.88 (bd, 1H, J=4.5 Hz), 7.75 (d, 1H, J=6.6 Hz), 7.38 (bs, 1H), 7.22 (bd, 1H, J=8.1 Hz), 7.14 (t, 1H, J=7.8 Hz), 6.50 (dd, 1H, J=1.8 and 9.0 Hz), 4.28 (s, 2H), 2.99 (s, 3H), 2.60 (d, 3H, J=4.5 Hz); LCMS: purity: 92%; MS (m/e): 451 (MH$^+$).

7.3.760 N4-(2,5-Dimethoxy-4-chlorophenyl)-5-fluoro-N2-[3-(N-methylamino)carbonylmethyleneoxyphenyl]-2,4-pyrimidinediamine (R926859)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with N4-(2,5-dimethoxy-4-chlorophenyl)-2-chloro-5-fluoro-4-pyrimidineamine gave N4-(2,5-dimethoxy-4-chlorophenyl)-5-fluoro-N2-[3-(N-methylamino)carbonylmethyleneoxyphenyl]-2,4-pyrimidinediamine. $^1$H NMR (CD$_3$OD): δ 8.05 (d, 1H, J=5.4 Hz), 7.29 (s, 1H), 7.24 (t, 1H, J=8.1 Hz), 7.18 (s, 1H), 7.02 (t, 1H, J=2.1 Hz), 6.92 (dd, 1H, J=1.8 and 8.1 Hz), 6.83 (dd, 1H,

7.3.761 5-Fluoro-N2-[3-(N-methylamino)carbonyl-methyleneoxyphenyl]-N4-(3-methoxycarbonyl-5-trifluoromethylphenyl)-2,4-pyrimidinediamine (R926862)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(3-methoxycarbonyl-5-trifluoromethylphenyl)-4-pyrimidineamine gave 5-fluoro-N2-[3-(N-methylamino)carbonyl-methyleneoxyphenyl]-N4-(3-methoxycarbonyl-5-trifluoromethylphenyl)-2,4-pyrimidinediamine. $^1$H NMR (DMSO-d6): δ 9.95 (s, 1H), 9.41 (s, 1H), 8.57 (s, 1H), 8.33 (s, 1H), 8.23 (d, 1H, J=3 Hz), 7.83 (s and d, 2H), 7.22 (m, 2H), 7.02(t, 1H, J=8.7 Hz), 6.48 (1H, J=2.4 and 7.5 Hz), 4.27 (s, 2H), 3.80 (s, 3H), 2.60 (d, 3H, J=4.8 Hz); $^{19}$F NMR (DMSO-d6): −17446; LCMS: purity: 94%; MS (m/z): 494 (MH$^+$).

7.3.762 5-Fluoro-N2-[3-(N-methylamino)carbonyl-methyleneoxyphenyl]-N4-[3-(2-phenyl-1,3,4-oxadiazol-5-yl)phenyl]-2,4-pyrimidinediamine (R926870)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-[3-(2-phenyl-1,3,4-oxadiazol-5-yl)phenyl]-4-pyrimidineamine gave 5-fluoro-N2-[3-(N-methylamino)carbonylmethyleneoxyphenyl]-N4-[3-(2-phenyl-1,3,4-oxadiazol-5-yl)phenyl]-2,4-pyrimidinediamine. LCMS: purity: 86%; MS (m/e): 512 (MH$^+$).

7.3.763 N4-[3-(2-(3-Chlorophenyl)-1,3,4-oxadiazol-5-yl)phenyl]-5-fluoro-N2-[3-(N-methylamino)carbonylmethyleneoxyphenyl]-2,4-pyrimidinediamine (R926871)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-[3-(2-(3-chlorophenyl)-1,3,4-oxadiazol-5-yl)phenyl]-4-pyrimidineamine gave N4-[3-(2-(3-chlorophenyl)-1,3,4-oxadiazol-5-yl)phenyl]-5-fluoro-N2-[3-(N-methylamino)carbonylmethyleneoxyphenyl]-2,4-pyrimidinediamine. LCMS: purity: 100%; MS (m/e): 546 (MH$^+$).

7.3.764 5-Fluoro-N2-[3-(N-methylamino)carbonyl-methyleneoxyphenyl]-N4-[4-trifluoromethoxyphenyl]-2,4-pyrimidinediamine (R926879)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(4-trifluoromethoxyphenyl)-4-pyrimidineamine gave 5-fluoro-N2-[3-(N-methylamino)carbonylmethyleneoxyphenyl]-N4-[4-trifluoromethoxyphenyl]-2,4-pyrimidinediamine. $^1$H NMR (DMSO-d6): δ 10.05 (bs, 1H), 9.74 (bd, 1H, J=1.5 Hz), 8.22 (d, 1H, J=4.2 Hz), 7.99 (bd, 1H, J=4.5 Hz), 7.86 (m, 2H), 7.32 (d, 2H, J=8.1 Hz), 7.26 (s, 1H), 7.16 (m, 2H), 6.58 (m, 1H), 4.36 (s, 2H), 2.65 (bd, 3H); LCMS: purity: 92%; MS (m/e): 452 (MH$^+$).

7.3.765 5-Fluoro-N2-[3-(N-methylamino)carbonyl-methyleneoxyphenyl]-N4-[4-trifluoromethylphenyl]-2,4-pyrimidinediamine (R926880)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(4-trifluoromethylphenyl)-4-pyrimidineamine gave 5-fluoro-N2-[3-(N-methylamino)carbonylmethyleneoxyphenyl]-N4-[4-trifluoromethylphenyl]-2,4-pyrimidinediamine. $^1$H NMR (DMSO-d6): δ 10.10 (bs, 1H), 9.72 (d, 1H, J=1.2 Hz), 8.26 (d, 1H, J=4.2 Hz), 8.00 (m, 3H), 7.65 (d, 2H, J=8.1 Hz), 7.31 (bs, 1H), 7.17 (d, 2H, J=5.4 Hz), 6.59 (m, 1H), 4.36 (s, 2H), 2.62 (d, 3H, J=4.8 Hz); LCMS: purity: 92%; MS (m/e): 436 (MH$^+$).

7.3.766 N4-(4-Chloro-3-trifluoromethylphenyl)-5-fluoro-N2-[3-(N-methylamino)carbonylmethyl-eneoxyphenyl]-2,4-pyrimidinediamine (R926881)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(4-chloro-3-trifluoromethylphenyl)-5-fluoro-4-pyrimidineamine gave N4-(4-chloro-3-trifluoromethylphenyl)-5-fluoro-N2-[3-(N-methylamino)carbonylmethyleneoxyphenyl)-2,4-pyrimidinediamine. $^1$H NMR (DMSO-d6): δ 10.20 (bs, 1H), 9.81 (bs, 1H), 8.28 (d, 1H, J=3.9 Hz), 8.23 (bdd, 1H, J=8.7 Hz), 8.11 (d, 1H, J=2.4 Hz), 7.98 (bd, 1H, J=4.5 Hz), 7.65 (d, 1H, J=8.7 Hz), 7.17 (m, 3H), 6.59 (m, 1H), 4.35 (s, 2H), 2.63 (d, 3H, J=4.2 Hz); LCMS: purity: 87%; MS (m/e): 470 (MH$^+$).

7.3.767 5-Fluoro-N2-[3-(N-methylamino)carbonyl-methyleneoxyphenyl]-N4-(quinolin-6-yl)-2,4-pyrimidinediamine (R926883)

In like manner to preparation of N4-(3,4-difluorophenyl)-5-fluoro-N2-[3-(N-methylamino)carbonylmethyleneoxyphenyl]-2,4-pyrimidinediamine the reaction of 3 N-methyl 3-aminophenoxyacetamide with 2-chloro-5-fluoro-N4-(quinolin-6-yl)-4-pyrimidineamine gave 5-fluoro-N2-[3-(N-methylamino)carbonylmethyleneoxyphenyl)-N4-(quinolin-6-yl)-2,4-pyrimidinediamine. $^1$H NMR (DMSO-d6): δ 10.17 (bs, 1H), 9.83 (s, 1H), 8.24 (d, 1H, J=4.8 Hz), 8.17 (m, 1H), 7.94 (m, 2H), 7.86 (m, 1H), 7.39 (d, 1H, J=9.3 Hz), 7.25 (s, 1H), 7.16 (m, 2H), 6.60 (m, 1H), 6.50 (d, 1H, J=9.6 Hz), 4.32 (s, 2H), 2.60 (d, 3H, J=3.6 Hz); LCMS: purity: 98%; MS 9 m/e): 436 (MH$^+$).

7.3.768 5-Fluoro-N4-(2-methoxypyridin-5-yl)-N2-[3-(N-methylamino)carbonylmethyleneoxyphenyl)-2,4-pyrimidinediamine (R926886)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-(2-methoxypyridin-5-yl)-4-pyrimidineamine gave 5-fluoro-N4-(2-methoxypyridin-5-yl)-N2-[3-(N-methylamino)carbonylmethyleneoxyphenyl)-2,4-pyrimidinediamine. $^1$H NMR (DMSO-d 6): δ 9.36 (bs, 1H), 9.19 (s, 1H), 8.59 (d, 1H, J=3 Hz), 8.05 (m, 3H), 7.38 (m, 1H), 7.24 (bd, 1H, J=8.1 Hz), 7.08 (t, 1H, J=8.4 Hz), 6.79 (d, 1H, J=8.7 Hz), 6.46 (dd, 1H, J=2.4 and 7.8 Hz), 4.34 (s, 2H), 3.82 (s, 3H), 2.63 (d, 3H, J=4.5 Hz); LCMS: purity: 95%; MS (m/e): 399 (MH$^+$).

7.3.769 5-Fluoro-N4-[2-(2-hydroxyethyleneoxy) pyridin-5-yl]-N2-[3-(N-methylamino)carbonylmethyleneoxyphenyl]-2,4-pyrimidinediamine (R927023)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-5-fluoro-N4-[2-(2-hydroxyethyleneoxy) pyridin-5-yl]-4-pyrimidineamine gave 5-fluoro-N4-[2-(2-hydroxyethyleneoxy)pyridin-5-yl]-N2-[3-(N-methylamino)carbonylmethyleneoxyphenyl]-2,4-pyrimidinediamine. $^1$H NMR (DMSO-d6): δ 9.65 (bs, 1H), 9.45 (bs, 1H), 8.55 (s, 1H), 8.12 (d, 1H, J=3.6 Hz), 7.99 (m, 2H), 7.28 (m, 1H), 7.19 (m, 2H), 7.11 (t, 1H, J=8.4 Hz), 6.81 (d, 1H, J=8.7 Hz), 6.52 (m, 2H), 4.35 (s, 2H), 4.23 (t, 2H, J=5.1 Hz), 3.69 (t, 2H, J=4.5 Hz), 2.63 (d, 3H, J=2.7 Hz); LCMS: purity: 95%; MS (m/e): 429 (MH$^+$).

7.3.770 N4-(2,6-Dimethoxypyridin-3-yl)-5-fluoro-N2-[3-(N-methylamino)carbonylmethyleneoxyphenyl]-2,4-pyrimidinediamine (R920404)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(2,6-dimethoxypyridin-3-yl]-5-fluoro-4-pyrimidineamine gave N4-(2,6-dimethoxypyridin-3-yl)-5-fluoro-N2-[3-(N-methylamino)carbonylmethyleneoxyphenyl)-2,4-pyrimidinediamine. $^1$H NMR (DMSO-d6): δ 9.05 (d, 1H, J=1.8 Hz), 8.62 (s, 1H), 8.01 (d, 1H, J=3.6 Hz), 7.91 (bd, 1H, J=4.8 Hz), 7.77 (m, 1H), 7.18 (m, 2H), 6.96 (t, 1H, J=8.1 Hz), 6.40 (d, 2H, J=8.1 Hz), 4.29 (s, 2H), 3.86 (s, 3H), 3.85 (s, 3H), 2.63 (d, 3H, J=4.5 Hz); LCMS: purity: 86%; MS (m/e): 429 (MH$^+$).

7.3.771 N4-(4-Chloro-3-methoxyphenyl))-5-fluoro-N2-[3-(N-methylamino)carbonylmethyleneoxyphenyl]-2,4-pyrimidinediamine (R927042)

In like manner to preparation of N4-(3,4-difluorophenyl)-5-fluoro-N2-[3-(N-methylamino)carbonylmethyleneoxyphenyl]-2,4-pyrimidinediamine the reaction of N-methyl 3-aminophenoxyacetamide with 2-chloro-N4-(4-chloro-3-methoxyphenyl)-5-fluoro-4-pyrimidineamine gave N4-(4-chloro-3-methoxyphenyl)-5-fluoro-N2-[3-(N-methylamino) carbonylmethyleneoxyphenyl]-2,4-pyrimidinediamine. $^1$H NMR (DMSO-d6): δ 9.89 (bs, 1H), 9.66 (bs, 1H), 8.20 (d, 1H, J=4.2 Hz), 7.95 (bd, 1H), 7.48 (m, 2H), 7.33 (d, 1H, J=9.1 Hz), 7.26 (bs, 1H), 7.17 (m, 2H), 6.57 (bd, 1H, J=7.8 Hz), 4.34 (s, 2H), 3.72 (s, 3H), 2.62 (d, 3H); LCMS: purity: 97%; MS (m/e): 432 (MH$^+$).

7.3.772 N4-(3-Chloro-4-trifluoromethoxyphenyl)-5-fluoro-N2-(3-hydroxyphenyl)-2,4-pyrimidinediamine (R920411)

A solution of 2-chloro-N4-(3-chloro-4-trifluoromethoxyphenyl)-5-fluoro-4-pyrimidineamine (1.1 equivalents) and 3-hydroxyaniline (1 equivalent) in a sealed tube was heated at 100° C. for 24 hours. The resulting solution was diluted with EtOAc and the solid obtained was filtered, washed with a mixture of EtOAc:n-hexanes (1:1; v/v), dried and analyzed to give N4-(3-chloro-4-trifluoromethoxyphenyl)-5-fluoro-N2-(3-hydroxyphenyl)-2,4-pyrimidineamine. $^1$H NMR (CD$_3$OD): δ 8.02 (d, 1H, J=5.1 Hz), 7.98 (d, 1H, J=3.0 Hz), 7.72 (dd, 1H, J=3.0 and 9.3 Hz), 7.42 (dd, 1H, J=1.2 and 9.0 Hz), 7.22 (t, 1H, J=8.4 Hz), 6.85 (m, 2H), 6.73 (dd, 1H, J=2.4 and 8.7 Hz); 19F NMR (CD$_3$OD): −16967 and −46027; LCMS: purity: 97%; MS (m/e): 415 (MH$^+$).

7.3.773 5-Fluoro-N2-(3-hydroxyphenyl)-N4-[3-(3-phenyl-1,3,4-oxadiazol-5-yl)phenyl]-2,4-pyrimidinediamine (R926866)

In like manner to the preparation of N4-(3-chloro-4-trifluoromethoxyphenyl)-5-fluoro-N2-(3-hydroxyphenyl)-2,4-pyrimidineamine, the reaction of 3-hydroxyaniline with 2-chloro-5-fluoro-N4-[3-(2-phenyl-1,3,4-oxadiazol-5-yl)phenyl]-4-pyrimidineamine gave 5-fluoro-N2-(3-hydroxyphenyl)-N4-[3-(2-phenyl-1,3,4-oxadiazol-5-yl)phenyl]-2,4-pyrimidinediamine. $^1$H NMR (CD$_3$OD): δ 7.72 (bs, 1H), 7.96 (bd, 3H), 7.85 (m, 2H), 7.56 (m, 4H), 7.14 (d, 1H, J=2.1 Hz), 6.91 (m, 2H), 6.28 (dd, 1H, J=1.8 and 6.9 Hz); LCMS: purity: 80%; MS (m/e): 441 (MH$^+$).

7.3.774 N4-(3,4-Difluoromethylenedioxyphenyl)-5-fluoro-N2-(3-hydroxyphenyl)-2,4-pyrimidinediamine (R926794)

In like manner to the preparation of N4-(3-chloro-4-trifluoromethoxyphenyl)-5-fluoro-N2-(3-hydroxyphenyl)-2,4-pyrimidineamine, the reaction of 3-hydroxyaniline with 2-chloro-N4-(3,4-difluoromethylenedioxyphenyl)-5-fluoro-4-pyrimidineamine gave N4-(3,4-difluoromethylenedioxyphenyl)-5-fluoro-N2-(3-hydroxyphenyl)-2,4-pyrimidinediamine. LCMS: purity: 85%; MS (m/e): 377 (MH$^+$).

7.3.775 5-Fluoro-N2-(3-hydroxyphenyl)-N4-(3-trifluoromethoxyphenyl)-2,4-pyrimidinediamine (R926885)

In like manner to the preparation of N4-(3-chloro-4-trifluoromethoxyphenyl)-5-fluoro-N2-(3-hydroxyphenyl)-2,4-pyrimidineamine, the reaction of 3-hydroxyaniline with 2-chloro-5-fluoro-N4-(3-trifluoromethoxyphenyl)-4-pyrimidineamine gave 5-fluoro-N2-(3-hydroxyphenyl)-N4-(3-trifluoromethoxyphenyl)-2,4-pyrimidinediamine. $^1$H NMR (DMSO-d6): δ 9.99 (bs, 1H), 9.61 (bs, 1H), 8.21 (d, 1H, J=4.2 Hz), 7.93 (bd, 1H, J=7.5 Hz), 7.78 (s, 1H), 7.43 (t, 1H, J=8.4 Hz), 7.03 (m, 4H), 6.43 (m, 1H); $^{19}$F NMR (DMSO-d6): −16097; LCMS: purity: 85%; MS (m/e): 381 (MH$^+$).

7.3.776 N4-(2,6-Dimethoxypyridin-3-yl)-5-fluoro-N2-(3-hydroxyphenyl)-2,4-pyrimidinediamine (R926887)

In like manner to the preparation of N4-(3-chloro-4-trifluoromethoxyphenyl)-5-fluoro-N2-(3-hydroxyphenyl)-2,4-pyrimidineamine, the reaction of 3-hydroxyaniline with 2-chloro-N4-(2,6-dimethoxypyridin-3-yl)-5-fluoro-4-pyrimidineamine gave N4-(2,6-dimethoxypyridin-3-yl)-5-fluoro-N2-(3-hydroxyphenyl)-2,4-pyrimidinediamine. $^1$H NMR (DMSO-d6): δ 9.98 (bs, 2H), 8.20 (d, 1H, J=5.4 Hz), 7.72 9m, 1H), 6.90 (t, 1H, J=7.8 Hz), 6.81 (m, 2H), 6.42 (m, 2H), 3.88 (s, 3H), 3.86 (s, 3H); LCMS: purity: 94%; MS (m/e): 358 (MH$^+$).

7.3.777 5-Fluoro-N2-(3-hydroxyphenyl)-N4-(5-methylpyridin-2-yl)-2,4-pyrimidinediamine (R927017)

In like manner to the preparation of N4-(3-chloro-4-trifluoromethoxyphenyl)-5-fluoro-N2-(3-hydroxyphenyl)-2,4-pyrimidineamine, the reaction of 3-hydroxyaniline with 2-chloro-5-fluoro-N4-(5-methylpyridin-2-yl)-4-pyrimidineamine gave 5-fluoro-N2-(3-hydroxyphenyl)-N4-(5-methylpyridin-2-yl)-2,4-pyrimidinediamine. ¹H NMR (DMSO-d6): δ 11.39 (bs, 1H), 10.59 (bs, 1H), 8.58 (s, 1H0, 8.41 (d, 1H, J=3 Hz), 8.12 (d, 1H, J=8.7 Hz), 7.82 (d, 1H, J=8.7 Hz), 7.29 (s, 1H), 7.16 (d, 1H, J=9 Hz), 7.05 (t, 1H, J=8.4 Hz), 6.38 (dd, 1H, 1.2 and 6.9 Hz); LCMS: purity: 99%; MS (m/e): 312 (MH⁺).

7.3.778 N4-(6-Chloropyridin-3-yl)-5-fluoro-N2-(3-hydroxyphenyl)-2,4-pyrimidinediamine (R927018)

In like manner to the preparation of N4-(3-chloro-4-trifluoromethoxyphenyl)-5-fluoro-N2-(3-hydroxyphenyl)-2,4-pyrimidineamine, the reaction of 3-hydroxyaniline with 2-chloro-N4-(6-chloropyridin-3-yl)-5-fluoro-4-pyrimidineamine gave N4-(6-chloropyridin-3-yl)-5-fluoro-N2-(3-hydroxyphenyl)-2,4-pyrimidinediamine. ¹H NMR (DMSO-d6): δ 10.10 (bs, 1H), 9.64 (bs, 1H), 8.85 (m, 1H), 8.30 (m, 2H), 8.22 (d, 1H, J=4.2 Hz), 7.43 (d, 1H, J=8.7 Hz), 7.01 (m, 3H), 6.42 (bd, 1H, J=8.4 Hz); LCMS: purity: 93%; MS (m/e): 332 (MH⁺).

7.3.779 5-Fluoro-N2-(3-hydroxyphenyl)-N4-(quinolin-6-yl)-2,4-pyrimidinediamine (R927019)

In like manner to the preparation of N4-(3-chloro-4-trifluoromethoxyphenyl)-5-fluoro-N2-(3-hydroxyphenyl)-2,4-pyrimidineamine, the reaction of 3-hydroxyaniline with 2-chloro-5-fluoro-N4-(quinolin-6-yl)-4-pyrimidineamine gave 5-fluoro-N2-(3-hydroxyphenyl)-N4-(quinolin-6-yl)-2,4-pyrimidinediamine. ¹H NMR (DMSO-d6): δ 10.50 (s, 1H), 10.14 (s, 1H), 8.29 (d, 1H, J=4.8 Hz), 8.14 (d, 1H, J=1.8 Hz), 7.96 (d, 1H, J=9.3 Hz), 7.83 (dd, 1H, J=2.4 and 9.0 Hz), 7.40 (d, 1H, J=8.7 Hz), 7.04 (t, 1H, J=8.1 Hz), 6.93 (m, 2H), 6.52 (m, 2H); LCMS: purity: 93%; MS (m/e): 365 (MH⁺).

7.3.780 N4-(5-Chloropyridin-2-yl)-5-fluoro-N2-(3-hydroxyphenyl)-2,4-pyrimidinediamine (R927020)

In like manner to the preparation of N4-(3-chloro-4-trifluoromethoxyphenyl)-5-fluoro-N2-(3-hydroxyphenyl)-2,4-pyrimidineamine, the reaction of 3-hydroxyaniline with 2-chloro-N4-(5-chloropyridin-2-yl)-5-fluoro-4-pyrimidineamine gave N4-(5-chloropyridin-2-yl)-5-fluoro-N2-(3-hydroxyphenyl)-2,4-pyrimidinediamine. ¹H NMR (DMSO-d6): δ 10.80 (bs, 1H), 9.77 (bs, 1H), 8.45 (bd, 1H), 8.26 (d, 1H, J=3.9 Hz), 8.15 (d, 1H, J=8.7 Hz), 7.85 (dd, 1H, J=2.4 and 8.7 Hz), 7.06 (m, 3H), 6.43 (bd, 1H, J=7.2 Hz); LCMS: purity: 97%; MS (m/e): 332 (MH⁺).

7.3.781 N4-(4-Chloro-2,5-dimethoxyphenyl)-5-fluoro-N2-(3-hydroxyphenyl)-2,4-primidinediamine (R926860)

In like manner to the preparation of N4-(3-chloro-4-trifluoromethoxyphenyl)-5-fluoro-N2-(3-hydroxyphenyl)-2,4-pyrimidineamine, the reaction of 3-hydroxyaniline with 2-chloro-N4-(4-chloro-2,5-dimethoxyphenyl)-5-fluoro-4-pyrimidineamine gave N4-(4-chloro-2,5-dimethoxyphenyl)-5-fluoro-N2-(3-hydroxyphenyl)-2,4-primidinediamine. ¹H NMR (CD₃OD): δ 7.96 (d, 1H, J=4.8 Hz), 7.66 (s, 1H), 7.13 (s, 1H), 7.07 (t, 1H, J=8.7 Hz), 8.86 (m, 2H), 6.57 (dd, 1H, J=3.2 and 8.1 Hz), 3.48 (s, 3H), 3.66 (s, 3H); ¹⁹F NMR (CD₃OD): −46968.

7.3.782 N4-(4-Chlorophenyl)-5-fluoro-N2-(2-methoxycarbonylbenzofuran-5-yl)-2,4-pyrimidinediamine (R927026)

In like manner to the preparation of N4-(3-chloro-4-trifluoromethoxyphenyl)-5-fluoro-N2-(3-hydroxyphenyl)-2,4-pyrimidineamine, the reaction of 5-amino-2-methoxycarbonylbenzofuran with 2-chloro-N4-(4-chlorophenyl)-5-fluoro-4-pyrimidineamine gave N4-(4-chlorophenyl)-5-fluoro-N2-(2-methoxycarbonylbenzofuran-5-yl)-2,4-pyrimidinediamine. ¹HNMR (DMSO-d6): δ 10.28 (bs, 1H), 10.18 (bs, 1H), 8.25 (d, 1H, J=4.5 Hz), 7.96 (bs, 1H), 7.84 (m, 1H), 7.67 (m, 3H), 7.57 (m, 1H), 7.37 (bd, 2H, J=9.0 Hz), 3.88 (s, 3H); LCMS: purity: 96%; MS (m/e): 413 (MH⁺).

7.3.783 N4-(3,4-Dichlorophenyl)-5-fluoro-N2-(2-methoxycarbonylbenzofuran-5-yl)-2,4-pyrimidinediamine (R927027)

In like manner to the preparation of N4-(3-chloro-4-trifluoromethoxyphenyl)-5-fluoro-N2-(3-hydroxyphenyl)-2,4-pyrimidineamine, the reaction of 5-amino-2-methoxycarbonylbenzofuran with 2-chloro-N4-(3,4-dichlorophenyl)-5-fluoro-4-pyrimidineamine gave N4-(3,4-dichlorophenyl)-5-fluoro-N2-(2-methoxycarbonylbenzofuran-5-yl)-2,4-pyrimidinediamine. ¹H NMR (DMSO-d6): δ 9.70 (bs, 1H), 9.50 (bs, 1H), 8.20 (d, 1H, J=4.5 Hz), 8.09 (m, 1H), 7.80 (m, 3H), 7.62 (m, 2H), 7.53 (m, 1H), 7.38 (m, 1H), 3.88 (s, 3H); LCMS: purity: 94%; MS (m/e): 448 (MH⁺).

7.3.784 5-Fluoro-N4-(3-hydroxyphenyl)-N2-(3-methoxycarbonyl-5-trifluoromethylphenyl)-2,4-pyrimidinediamine (R926863)

In like manner to the preparation of N4-(3-chloro-4-trifluoromethoxyphenyl)-5-fluoro-N2-(3-hydroxyphenyl)-2,4-pyrimidineamine, the reaction of 2-chloro-5-fluoro-N4-(3-hydroxyphenyl)-4-pyrimidineamine with 3-methoxycarbonyl-5-trifluoromethylaniline gave 5-fluoro-N4-(3-hydroxyphenyl)-N2-(3-methoxycarbonyl-5-trifluoromethylphenyl)-2,4-pyrimidinediamine. ¹H NMR (DMSO-d6): δ 9.98 (s, 1H), 9.52 (s, 1H), 8.53 (s, 1H), 8.38 (s, 1H), 8.20 (d, 1H, J=4.2 Hz), 7.69 (s, 1H), 7.27 (d, 1H, J=8.1 Hz), 7.14 (s, 1H), 7.05 (t, 1H, 7.8 Hz), 6.49 (dd, 1H, J=1.8 and 8.4 Hz), 3.80 (s, 3H); LCMS: purity: 82%; MS (m/e): 423 (MH⁺).

7.3.785 N2-(4-Chloro-2,5-dimethoxyphenyl)-5-fluoro-N4-(3-hydroxyphenyl)-2,4-pyrimidinediamine (R926857)

In like manner to the preparation of N4-(3-chloro-4-trifluoromethoxyphenyl)-5-fluoro-N2-(3-hydroxyphenyl)-2,4-pyrimidineamine, the reaction of 2-chloro-5-fluoro-N4-(3-hydroxyphenyl)-4-pyrimidineamine with 4-chloro-2,5-dimethoxyaniline gave N2-(4-chloro-2,5-dimethoxyphenyl)-5-fluoro-N4-(3-hydroxyphenyl)-2,4-pyrimidinediamine. ¹H NMR (CD₃OD): δ 8.04 (d, 1H, J=5.4 Hz), 7.46 (s, 1H), 7.17 (m, 2H), 7.03 (m, 2H), 6.72 (dd, 1H, J=1.8 and 7.8 Hz), 3.85 (s, 3H), 3.52 (s, 3H); LCMS: purity: 98%; MS (m/e): 390 (MH⁺).

7.3.786 N2-(3-Bromo-5-trifluorophenyl)-5-fluoro-N4-(3-hydroxyphenyl)-2,4-pyrimidinediamine (R926846)

In like manner to the preparation of N4-(3-chloro-4-trifluoromethoxyphenyl)-5-fluoro-N2-(3-hydroxyphenyl)-2,4- pyrimidineamine, the reaction of 2-chloro-5-fluoro-N4-(3-hydroxyphenyl)-4-pyrimidineamine with 3-bromo-5-trifluoromethylaniline gave N2-(3-bromo-5-trifluorophenyl)-5-fluoro-N4-(3-hydroxyphenyl)-2,4-pyrimidinediamine. $^1$H NMR (DMSO-d6): δ 9.70 (s, 1H), 9.36 (s, 1H), 9.34 (s, 1H), 8.31 (s, 1H), 8.18 (d, 1H, J=3.6 Hz), 8.02 (s, 1H), 7.35 (s, 1H), 7.28 (bd, 1H, J=7.2 Hz), 7.11 (t, 1H, J=8.4 Hz), 7.02 (m, 1H), 6.49 (dd, 1H, J=1.8 and 7.8 Hz); LCMS: purity: 94%; MS (m/e): 442 (MH$^+$).

7.3.787 5-Fluoro-N4-(3-hydroxyphenyl)-N2-[3-(1H-pyrazol-3-yl)phenyl]-2,4-pyrimidinediamine (R926841)

In like manner to the preparation of N4-(3-chloro-4-trifluoromethoxyphenyl)-5-fluoro-N2-(3-hydroxyphenyl)-2,4-pyrimidineamine, the reaction of 2-chloro-5-fluoro-N4-(3-hydroxyphenyl)-4-pyrimidineamine with 3-(1H-pyrazol-3-yl)aniline gave 5-fluoro-N4-(3-hydroxyphenyl)-N2-[3-(1H-pyrazol-3-yl)phenyl]-2,4-pyrimidinediamine. LCMS: purity: 84%; MS 363 (MH$^+$)

7.3.788 5-Fluoro-N4-(3-hydroxyphenyl)-N2-[3-(tetrazol-5-yl)phenyl]-2,4-pyrimidinediamine (R926842)

In like manner to the preparation of N4-(3-chloro-4-trifluoromethoxyphenyl)-5-fluoro-N2-(3-hydroxyphenyl)-2,4-pyrimidineamine, the reaction of 2-chloro-5-fluoro-N4-(3-hydroxyphenyl)-4-pyrimidineamine with 3-(tetrazol-5-yl)aniline gave 5-fluoro-N4-(3-hydroxyphenyl)-N2-[3-(tetrazol-5-yl)phenyl]-2,4-pyrimidinediamine. $^1$H NMR (DMSO-d6): δ 10.05 (bs, 1H), 9.80 (bs, 1H), 8.27 (s, 1H), 8.23 (d, 1H, J=3.3 Hz), 7.86 (d, 1H, J=8.1 Hz) 7.65 (d, 1H, J=6.9 Hz), 7.44 (t, 1H, J=7.5 Hz), 7.19 (m, 2H), 6.93 (t, 1H, J=7.5 Hz), 6.49 (dd, 1H, J=2.4 and 8.1 Hz); LCMS: purity: 89%; MS (m/e): 364 (MH$^+$).

7.3.789 5-Fluoro-N4-(3-hydroxyphenyl)-N2-[3-(1,3-oxazol-5-yl)phenyl]-2,4-pyrimidinediamine (R926831)

In like manner to the preparation of N4-(3-chloro-4-trifluoromethoxyphenyl)-5-fluoro-N2-(3-hydroxyphenyl)-2,4-pyrimidineamine, the reaction of 2-chloro-5-fluoro-N4-(3-hydroxyphenyl)-4-pyrimidineamine with 3-(1,3-oxazol-5-yl)aniline gave 5-fluoro-N4-(3-hydroxyphenyl)-N2-(3-(1,3-oxazol-5-yl)phenyl]-2,4-pyrimidinediamine. LCMS: purity: 76%; MS (m/e): 364 (MH$^+$).

7.3.790 N2-(3-Chloro-4-trifluoromethylphenyl)-5-fluoro-N4-(3-hydroxyphenyl)-2,4-pyrimidinedimine (R926844)

In like manner to the preparation of N4-(3-chloro-4-trifluoromethoxyphenyl)-5-fluoro-N2-(3-hydroxyphenyl)-2,4-pyrimidineamine, the reaction of 2-chloro-5-fluoro-N4-(3-hydroxyphenyl)-4-pyrimidineamine with 3-chloro-4-trifluoromethoxyaniline gave N2-(3-chloro-4-trifluoromethylphenyl)-5-fluoro-N4-(3-hydroxyphenyl)-2,4-pyrimidinedimine. $^1$H NMR (DMSO-d6): δ 9.70 (bs, 1H), 9.48 (bs, 1H), 8.15 (bd, 1H, J=3.6 Hz), 8.06 (s, 1H), 7.62 (dd, 1H, J=2.4 and 9.3 Hz), 7.37 (d, 1H, J=9.0 Hz), 7.20 9m, 1H), 7.11 (m, 3H), 6.53 (bd, 1H, J=8.1 Hz); LCMS: purity: 93%; MS (m/e): 414 (MH$^+$).

7.3.791 5-Fluoro-N4-(3,4-ethylenedioxyphenyl)-N2-[3-(tetrazol-5-yl)phenyl]-2,4-pyrimidinediamine (R926843)

In like manner to the preparation of N4-(3-chloro-4-trifluoromethoxyphenyl)-5-fluoro-N2-(3-hydroxyphenyl)-2,4-pyrimidineamine, the reaction of 2-chloro-5-fluoro-N4-(3,4-ethylenedioxyphenyl)-4-pyrimidineamine with 3-(tetrazol-5-yl)aniline gave 5-fluoro-N4-(3,4-ethylenedioxyphenyl)-N2-[3-(tetrazol-5-yl)phenyl]-2,4-pyrimidinediamine. $^1$H NMR (DMSO-d6): δ 9.91 (s, 1H), 9.74 (s, 1H), 8.29 (s, 1H), 8.18 (d, 1H, J=4.5 Hz), 7.76 (bdd, 1H, J=1.5 and 8.1 Hz), 7.64 (d, 1H, J=8.1 Hz), 7.46 (t, 1H, J=8.1 Hz), 7.29 (m, 1H), 7.13 (dd, 1H, J=2.4 and 8.7 Hz), 6.64 (d, 1H, J=8.7 Hz), 4.11 (m, 4H); LCMS: purity: 91%; MS (m/e): 407 (MH$^+$).

7.3.792 N4-(3,4-Ethylenedioxyphenyl)-5-fluoro-N2-(4-methoxy-2-methylphenyl)-2,4-pyrimidinediamine (R926845)

In like manner to the preparation of N4-(3-chloro-4-trifluoromethoxyphenyl)-5-fluoro-N2-(3-hydroxyphenyl)-2,4-pyrimidineamine, the reaction of 2-chloro-5-fluoro-N4-(3,4-ethylenedioxyphenyl)-4-pyrimidineamine with 4-methoxy-2-methylaniline gave N4-(3,4-ethylenedioxyphenyl)-5-fluoro-N2-(4-methoxy-2-methylphenyl)-2,4-pyrimidinediamine. $^1$H NMR (DMSO-d6): δ 10.30 (bs, 1H), 9.10 (bs, 1H), 8.22 (d, 1H, J=5.1 Hz), 7.55 (m, 1H), 7.15 (m, 1H), 7.07 (m, 1H), 6.92 (m, 2H), 6.82 (d, 1H, J=8.7 Hz), 4.22 (bs, 4H), 3.80 (s, 3H), 2.15 (s, 3H); LCMS: purity: 94%; MS (m/e): 383 (MH$^+$).

7.3.793 N2-[5-(N-Aminocarbonylmethylene-2-oxo-1,3-oxazol-3(2H)-yl)phenyl]-N4-(3,4-ethylenedioxyphenyl)-5-fluoro-2,4-pyrmidinediamine (R926847)

In like manner to the preparation of N4-(3-chloro-4-trifluoromethoxyphenyl)-5-fluoro-N2-(3-hydroxyphenyl)-2,4-pyrimidineamine, the reaction of 2-chloro-5-fluoro-N4-(3,4-ethylenedioxyphenyl)-4-pyrimidineamine with 2-[5-amino-2-oxo-1,3-benzoxazol-3(2H)-yl)acetamide gave N2-[5-(N-aminocarbonylmethylene-2-oxo-1,3-oxazol-3(2H)-yl)phenyl]-N4-(3,4-ethylenedioxyphenyl)-5-fluoro-2,4-pyrmidinediamine. $^1$H NMR (CD$_3$OD): δ 7.95 (d, 1H, J=8.4 Hz), 7.32 (dd, 1H, J=2.4 and 8.1 Hz), 7.24 (d, 1H, J=2.4 Hz), 7.19 (m, 2H), 6.95 (dd, 1H, J=2.7 and 9 Hz), 6.80 (d, 1H, J=9 Hz), 4.51 (s, 2H), 4.21 (m, 4H).

7.3.794 N2-[3-(2-Ethoxycarbonylmethylene-1,3,4-oxadiazol-5-yl)phenyl-5-fluoro-N4-(3-hydroxyphenyl)-2,4-pyrimidinediamine (R926874)

In like manner to the preparation of N4-(3-chloro-4-trifluoromethoxyphenyl)-5-fluoro-N2-(3-hydroxyphenyl)-2,4-pyrimidineamine, the reaction of 2-chloro-5-fluoro-N4-(3-hydroxyphenyl)-4-pyrimidineamine with 3-(2-ethoxycarbonylmethylene-1,3,4-oxadiazol-5-yl)aniline gave N2-[3-(2-ethoxycarbonylmethylene-1,3,4-oxadiazol-5-yl)phenyl-5-fluoro-N4-(3-hydroxyphenyl)-2,4-pyrimidinediamine. $^1$H NMR (DMSO-d6): δ 9.52 (s, 1H), 9.31 (s, 1H), 9.28 (s, 1H), 8.30 (s, 1H), 8.12 (d, 1H, J=3.6 Hz), 8.00 (m, 1H), 7.49 (d, 1H, J=7.5 Hz), 7.42 (d, 1H, J=8.4 Hz), 7.30 (m, 1H), 7.12 (bs, 1H), 7.03 (t, 1H, J=8.1 Hz), 6.46 (m, 1H), 4.21 (s, 2H), 4.15 (q, 2H, J=6.9 Hz), 1.19 (t, 3H, J=7.2 Hz); LCMS: purity: 90%; MS (m/e): 451 (MH$^+$).

7.3.795 N2,N4-Bis(3-boronylphenyl)-5-fluoro-2,4-pyrimidinediamine (R926836)

A mixture of 2,4-dichloro-5-fluoro-pyrimidine (1 equivalents) and 3-aminophenylboronic acid (3 equivalents) in MeOH was heated in a sealed tube at 100° C. for 24 hours. The resulting mixture was cooled to room temperature, acidified with 2N HCl and the solid obtained was filtered, washed with water, dried and analyzed to give N2,N4-sis(3-boronylphenyl)-5-fluoro-2,4-pyrimidinediamine. $^1$H NMR (DMSO-d6): δ 10.40 (s, 1H), 10.07 (s, 1H), 8.25 (d, 8.4 Hz), 7.85 (s, 1H), 7.73 (d, 1H, J=7.5 Hz), 7.63 (bt, 3H), 7.48 (d, 1H, J=6.9 Hz), 7.30 (t, 1H, J=8.4 Hz), 7.12 (t, 1H, J=2.5 Hz); LCMS: purity: 85%; MS (m/e): 368 (MH$^+$).

7.3.796 N2-(3-Boronylphenyl)-N4-(3,4-ethylenedioxyphenyl)-5-fluoro-2,4-pyrimidinediamine (R926837)

In like manner to the preparation of N4-(3-chloro-4-trifluoromethoxyphenyl)-5-fluoro-N2-(3-hydroxyphenyl)-2,4-pyrimidineamine, the reaction of 2-chloro-5-fluoro-N4-(3,4-ethylenedioxyphenyl)-4-pyrimidineamine with 3-aminophenylboronic acid gave N2-(3-boronylphenyl)-N4-(3,4-ethylenedioxyphenyl)-5-fluoro-2,4-pyrimidinediamine. LCMS: purity: 99%; MS (m/e): 383 (MH$^+$).

7.3.797 (±)-N4-(3,4-Difluorophenyl)-N2-(2,3-dihydro-2-methoxycarbonylbenzofuran-5-yl)-5-fluoro-2,4-pyrimidinediamine (R927030)

A mixture of equivalent amount of 2-chloro-N4-(3,4-difluorophenyl)-5-fluoro-4-pyrimidineamine and (±)-5-amino-2,3-dihydro-2-methoxycarbonylbenzofuran in MeOH was shaken in a sealed tube at 80° C. for 48 h, cooled to room temperature and diluted with a mixture of n-hexanes:EtOAc (1:1; v/v). The resulting solid formed was filtered, washed with a mixture of EtOAc:n-hexanes (1:1; v/v), dried and analyzed to give (±)-N4-(3,4-difluorophenyl)-N2-(2,3-dihydro-2-methoxycarbonylbenzofuran-5-yl)-5-fluoro-2,4-pyrimidinediamine. $^1$H NMR (DMSO-d6): δ 10.21 (bs, 1H), 9.80 (bs, 1H), 8.20 (d, 1H, J=4.8 Hz), 7.94 (bs, 1H), 7.43 (m, 3H0, 7.15 (bd, 1H, J=8.4 Hz), 6.81 (d, 1H, J=8.1 Hz), 5.35 (dd, 1H, J=6.0 and 6.3 Hz), 3.69 (s, 3H), 3.52 (dd, 1H, J=10.5), 3.22 (dd, 1H, J=9.0 and 6.0 Hz); LCMS: purity: 99%; MS (m/e): 417 (MH$^+$).

7.3.798 (±)-N4-(4-Chlorophenyl)-N2-(2,3-dihydro-2-methoxycarbonylbenzofuran-5-yl)-5-fluoro-2,4-pyrimidinediamine (R927024)

In like manner to the preparation of (±)-N4-(3,4-difluorophenyl)-N2-(2,3-dihydro-2-methoxycarbonylbenzofuran-5-yl)-5-fluoro-2,4-pyrimidinediamine, the reaction of (±)-5-amino-2,3-dihydro-2-methoxycarbonylbenzofuran with 2-chloro-N4-(4-chlorophenyl)-5-fluoro-4-pyrimidineamine gave (±)-N4-(4-chlorophenyl)-N2-(2,3-dihydro-2-methoxycarbonylbenzofuran-5-yl)-5-fluoro-2,4-pyrimidinediamine. $^1$H NMR (DMSO-d6): δ 10.29 (bs, 1H), 9.89 (bs, 1H), 8.21 (d, 1H, J=4.8 Hz), 7.69 (m, 2H), 7.38 (m, 3H), 7.13 (bd, 1H, J=8.1 Hz), 6.83 (d, 1H, J=8.4 Hz), 5.36 (dd, 1H, J=6.3 and 5.7 Hz), 3.70 (s, 3H), 3.52 (dd, 1H, J=10.5 Hz), 3.20 (dd, 1H, J=5.4 and 5.7 Hz); LCMS: purity: 98%; MS (m/e): 415 (MH$^+$).

7.3.799 (±)-N4-(3,4-Dichlorophenyl)-N2-(2,3-dihydro-2-methoxycarbonylbenzofuran-5-yl)-5-fluoro-2,4-pyrimidinediamine (R927031)

In like manner to the preparation of (±)-N4-(3,4-difluorophenyl)-N2-(2,3-dihydro-2-methoxycarbonylbenzofuran-5-yl)-5-fluoro-2,4-pyrimidinediamine, the reaction of (±)-5-amino-2,3-dihydro-2-methoxycarbonylbenzofuran with 2-chloro-N4-(3,4-dichlorophenyl)-5-fluoro-4-pyrimidineamine gave (±)-N4-(3,4-dichlorophenyl)-N2-(2,3-dihydro-2-methoxycarbonylbenzofuran-5-yl)-5-fluoro-2,4-pyrimidinediamine. $^1$H NMR (DMSO-d6): δ 10.13 (bs, 1H), 9.70 (bs, 1H), 8.21 (d, 1H, J=4.8 Hz), 8.04 (d, 1H, J=2.4 Hz), 7.68 (m, 1H), 7.54 (d, 1H, J=9.0 Hz), 7.37 (bs, 1H), 7.19 (m, 1H), 6.80 (d, 1H, J=8.7 Hz), 5.35 (dd, 1H, J=6.6 Hz), 3.69 (s, 3H), 3.53 (dd, 1H, J=10.5 and 11.1 Hz), 3.21 (dd, 1H, J=6.0 Hz); LCMS: purity: 100%; MS (m/e): 450 (MH$^+$).

7.3.800 (±)-N2-(2,3-Dihydro-2-methoxycarbonylbenzofuran-5-yl)-N4-(2,6-dimethoxypyridin-3-yl)-5-fluoro-2,4-pyrimidinediamine (R927032)

In like manner to the preparation of (±)-N4-(3,4-difluorophenyl)-N2-(2,3-dihydro-2-methoxycarbonylbenzofuran-5-yl)-5-fluoro-2,4-pyrimidinediamine, the reaction of (±)-5-amino-2,3-dihydro-2-methoxycarbonylbenzofuran with 2-chloro-N4-(2,6-dimethoxypyridin-3-yl)-5-fluoro-4-pyrimidineamine gave (±)-N2-(2,3-dihydro-2-methoxycarbonylbenzofuran-5-yl)-N4-(2,6-dimethoxypyridin-3-yl)-5-fluoro-2,4-pyrimidinediamine. $^1$H NMR (DMSO-d6): δ 10.03 (bs, 2H), 8.18 (d, 1H, J=4.8 Hz), 7.68 (bd, 1H, J=8.1 Hz), 7.27 (bs, 1H), 6.98 (bd, 1H, J=8.1 Hz), 6.69 (d, 1H, J=8.7 Hz), 6.44 (d, 1H, J=8.1 Hz), 5.33 (dd, 1H, J=5.7 Hz), 3.88 (s, 3H), 3.86 (s, 3H), 3.69 (s, 3H), 3.42 (dd, 1H, J=10.8 and 11.1 Hz), 3.10 (dd, 1H, J=6.3 and 6.6 Hz); LCMS: purity: 99%; MS (m/e): 442 (MH$^+$).

7.3.801 (±)-N2-(2,3-Dihydro-2-methoxycarbonylbenzofuran-5-yl)-5-fluoro-N4-[2-(2-hydroxyethyleneoxy)pyridin-5-yl]-5-fluoro-2,4-pyrimidinediamine (R927025)

In like manner to the preparation of (±)-N4-(3,4-difluorophenyl)-N2-(2,3-dihydro-2-methoxycarbonylbenzofuran-5-yl)-5-fluoro-2,4-pyrimidinediamine, the reaction of (±)-5-amino-2,3-dihydro-2-methoxycarbonylbenzofuran with 2-chloro-5-fluoro-N4-[2-(2-hydroxyethyleneoxy)pyridin-5-yl]-4-pyrimidineamine gave (±)-N2-(2,3-dihydro-2-methoxycarbonylbenzofuran-5-yl)-5-fluoro-N4-[2-(2-hydroxyethyleneoxy)pyridin-5-yl]-2,4-pyrimidinediamine. $^1$H NMR (DMSO-d6): δ 10.10 (bs, 1H), 9.70 (bs, 1H), 8.46 (m, 1H), 8.13 (d, 1H, J=4.8 Hz), 7.92 (m, 1H), 7.41 (bs, 1H), 7.12 (bdd, 1H, J=8.4 Hz), 6.79 (m, 2H), 5.35 (dd, 1H, J=5.7 and 6.0 Hz), 4.24 (t, 2H, J=5.1 Hz), 3.70 (s, 3H), 3.69 (t, 2H, J=5.1 Hz), 3.52 (dd, 1H, J=11.1 Hz), 3.24 (dd, 1H, J=6.6 Hz); LCMS: purity: 92%; MS (m/e): 442 (MH$^+$).

7.3.802 (±)-N2-(2,3-Dihydro-2-methoxycarbonylbenzofuran-5-yl)-5-fluoro-N4-(3-trifluorophenyl)-2,4-pyrimidinediamine (R927028)

In like manner to the preparation of (±)-N4-(3,4-difluorophenyl)-N2-(2,3-dihydro-2-methoxycarbonylbenzofuran-5-yl)-5-fluoro-2,4-pyrimidinediamine, the reaction of (±)-5-amino-2,3-dihydro-2-methoxycarbonylbenzofuran with 2-chloro-5-fluoro-N4-(3-trifluorophenyl)-4-pyrimidineamine gave (±)-N2-(2,3-dihydro-2-methoxycarbonylbenzofuran-5-yl)-5-fluoro-N4-(3-trifluorophenyl)-2,4-pyrimidinediamine. $^1$H NMR (DMSO-d6): δ 10.32 (bs, 1H), 9.90 (bs, 1H), 8.23 (d, 1H, J=4.8 Hz), 7.80 (bd, 1H, J=6.9 Hz), 7.73 (bs, 1H), 7.43 (t, 1H, J=8.1 Hz), 7.36 (bs, 1H), 7.16 (m, 2H), 6.79 (d, 1H, J=8.1 Hz), 5.33 (dd, 1H, J=6.0 and 6.6 Hz), 3.69 (s, 3H), 3.51 (dd, 1H, J=10.5 Hz), 3.20 (dd, 1H, J=6.0 Hz); LCMS: purity: 98%; MS (m/e): 465 (MH$^+$).

7.3.803 (±)-N2-(2,3-Dihydro-2-methoxycarbonylbenzofuran-5-yl)-N4-(3,4-difluoromethylenedioxyphenyl)-5-fluoro-2,4-pyrimidinediamine (R927029)

In like manner to the preparation of (±)-N4-(3,4-difluorophenyl)-N2-(2,3-dihydro-2-methoxycarbonylbenzofuran-5-yl)-5-fluoro-2,4-pyrimidinediamine, the reaction of (±)-5-amino-2,3-dihydro-2-methoxycarbonylbenzofuran with 2-chloro-N4-(3,4-difluoromethylenedioxyphenyl)-5-fluoro-4-pyrimidineamine gave (±)-N2-(2,3-dihydro-2-methoxycarbonylbenzofuran-5-yl)-N4-(3,4-difluoromethylenedioxyphenyl)-5-fluoro-2,4-pyrimidinediamine. $^1$H NMR (DMSO-d6): δ 10.36 (bs, 1H), 9.93 (bs, 1H), 8.22 (d, 1H, J=4.8 Hz), 7.91 (bs, 1H), 7.38 (m, 3H), 7.15 9bd, 1H, J=8.7 Hz), 6.79 (d, 1H, J=6.0 Hz), 5.33 (dd, 1H, J=6.3 and 6.6 Hz), 3.69 (s, 3H), 3.50 (dd, 1H, J=10.5 and 10.8 Hz), 3.22 (dd, 1H, J=6.0 Hz); LCMS: purity: 100%; MS (m/e): 461 (MH$^+$).

Esters were transformed to amides allowing to the scheme illustrated below:

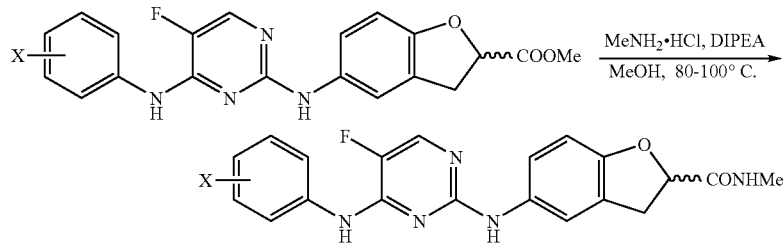

7.3.804 (±)-N4-(3,4-Difluorophenyl)-5-fluoro-N2-[2,3-dihydro-2-(N-methylamino)carbonylbenzofuran-5-yl]-2,4-pyrimidinediamine (R927035)

A mixture of (±)-N4-(3,4-difluorophenyl)-N2-(2,3-dihydro-2-methoxycarbonylbenzofuran-5-yl)-5-fluoro-2,4-pyrimidinediamine, methylamine Hydrogen Chloride (5 equivalents) and diisopropylethylamine (5 equivalents) in MeOH was shaken in a sealed tube at 80° C. for 24 h. The resulting solution was diluted with water and the precipitate obtained was filtered, washed with water, dried and analyzed to afford (±)-N4-(3,4-difluorophenyl)-5-fluoro-N2-[2,3-dihydro-2-(N-methylamino)carbonylbenzofuran-5-yl]-2,4-pyrimidinediamine. $^1$H NMR (DMSO-d6): δ 9.46 (s, 1H), 9.07 (s, 1H), 8.05 (m, 3H), 7.48 (m, 2H), 7.35 (m, 1H), 7.22 (m, 1H), 6.72 (d, 1H, J=8.1 Hz), 5.07 (dd, 1H, J=6.6 and 6.3 Hz), 3.40 (dd, 1H), 3.15 (dd, 1H), 2.60 (d, 3H, J=4.5 Hz); LCMS: purity: 98%; MS (m/e): 416 (MH$^+$).

7.3.805 (±)-N4-(4-Chlorophenyl)-N2-[2,3-dihydro-2-(N-methylamino)carbonylbenzofuran-5-yl]-5-fluoro-2,4-pyrimidinediamine (R927036)

In like manner to the preparation of (±)-N4-(3,4-difluorophenyl)-5-fluoro-N2-[2-(N-methylamino)carbonyl-2,3-dihydrobenzofuran-5-yl]-2,4-pyrimidinediamine, the reaction of methyl amine Hydrogen Chloride with (±)-N4-(4-chlorophenyl)-N2-(2,3-dihydro-2-methoxycarbonylbenzofuran-5-yl)-5-fluoro-2,4-pyrimidinediamine gave (±)-N4-(4-chlorophenyl)-N2-[2,3-dihydro-2-(N-methylamino)carbonylbenzofuran-5-yl]-5-fluoro-2,4-pyrimidinediamine. $^1$H NMR (DMSO-d6): δ 9.40 (s, 1H), 9.02 (s, 1H), 8.05 (m, 2H), 7.84 (dd, 2H, J=2.7 and 9.3 Hz), 7.51 (bs, 1H), 7.32 (bd, 2H, J=8.7 Hz), 7.23 (bd, 1H, J=8.7 Hz), 6.72 (d, 1H, J=8.7 Hz), 5.07 (dd, 1H, J=6.0 and 6.3 Hz), 3.39 (dd, 1H), 3.17 (dd, 1H), 2.60 (d, 3H, J=4.8 Hz); LCMS: purity: 99%; MS (m/e): 414 (MH$^+$).

7.3.806 (±)-N4-(3,4-Dichlorophenyl)-N2-[2,3-dihydro-2-(N-methylamino)carbonylbenzofuran-5-yl]-5-fluoro-2,4-pyrimidinediamine (R927037)

In like manner to the preparation of (±)-N4-(3,4-difluorophenyl)-5-fluoro-N2-[2-(N-methylamino)carbonyl-2,3-dihydrobenzofuran-5-yl]-2,4-pyrimidinediamine, the reaction of methyl amine Hydrogen Chloride with (±)-N4-(3,4-dichlorophenyl)-N2-(2,3-dihydro-2-methoxycarbonylbenzofuran-5-yl)-5-fluoro-2,4-pyrimidinediamine gave (±)-N4-(3,4-dichlorophenyl)-N2-[2,3-dihydro-2-(N-methylamino)carbonylbenzofuran-5-yl]-5-fluoro-2,4-pyrimidinediamine. $^1$H NMR (DMSO-d6): δ 9.52 (s, 1H), 9.09 (s, 1H), 8.08 (m, 3H), 7.76 (bd, 1H, J=9.3 Hz), 7.50 (d, 1H, J=9.0 Hz), 7.43 (bs, 1H), 7.24 (bd, 1H, J=8.7 Hz), 6.73 (d, 1H, J=8.1 Hz), 5.07 (dd, 1H, J=6.3 and 6.6 Hz), 3.39 (dd, 1H, J=10.5 Hz), 3.15 (dd, 1H, J=6.3 Hz), 2.60 (d, 3H, J=4.8 Hz); LCMS: purity: 99%; MS (m/e): 450 (MH$^+$).

7.3.807 (±)-N4-(2,6-Dimethoxypyridin-3-yl)-N2-[2,3-dihydro-2-(N-methylamino)carbonylbenzofuran-5-yl]-5-fluoro-2,4-pyrimidinediamine (R927038)

In like manner to the preparation of (±)-N4-(3,4-difluorophenyl)-5-fluoro-N2-[2-(N-methylamino)carbonyl-2,3-dihydrobenzofuran-5-yl]-2,4-pyrimidinediamine, the reaction of methyl amine Hydrogen Chloride with (±)-N4-(2,6-dimethoxypyridin-3-yl)-N2-(2,3-dihydro-2-methoxycarbonylbenzofuran-5-yl)-5-fluoro-2,4-pyrimidinediamine gave (±)-N4-(2,6-dimethoxypyridin-3-yl)-N2-[2,3-dihydro-2-(N-methylamino)carbonylbenzofuran-5-yl]-5-fluoro-2,4-pyrimidinediamine. $^1$H NMR (CD$_3$OD): δ 7.98 (d, 1H, J=8.1 Hz), 7.81 (d, 1H, J=3.6 Hz), 7.39 (bd, 1H, J=2.4 Hz), 7.06 (dd, 1H, J=2.4 and 8.7 Hz), 6.72 (d, 1H, J=8.1 Hz), 6.31 (d, 1H, J=8.7 Hz), 5.07 (dd, 1H, J=6.3 Hz), 3.96 (s, 3H), 3.93 (s, 3H), 3.46 (dd, 1H, J=7.8 and 10.5 Hz), 3.19 (dd, 1H, J=5.7 and 6.3 Hz), 2.77 (d, 3H, J=4.8 Hz); LCMS: purity: 98%; MS (m/e): 441 (MH$^+$).

7.3.808 (±)-N2-[2,3-Dihydro-(N-methylamino)carbonylbenzofuran-5-yl]-5-fluoro-N4-[2-(2-hydroxyethyleneoxy)pyridin-5-yl]-2,4-pyrimidinediamine (R927039)

In like manner to the preparation of (±)-N4-(3,4-difluorophenyl)-5-fluoro-N2-[2-(N-methylamino)carbonyl-2,3-dihydrobenzofuran-5-yl]-2,4-pyrimidinediamine, the reaction of methyl amine Hydrogen Chloride with (±)-N2-(2,3-dihydro-2-methoxycarbonylbenzofuran-5-yl)-5-fluoro-N4-[2-(2-hydroxyethyleneoxy)pyridin-5-yl]-2,4-pyrimidinediamine gave (±)-5-fluoro-N4-[2-(2-hydroxyethyleneoxy)pyridin-5-yl]-N2-[2-(N-methylamino)carbonyl-2,3-dihydrobenzofuran-5-yl]-2,4-pyrimidinediamine. $^1$H NMR (DMSO-d6): δ 9.26 (s, 1H), 8.99 (s, 1H), 8.50 (bd, 1H, J=3.0 Hz), 8.02 (bd, 2H, J=3.6 Hz), 7.94 (dd, 2H, J=2.7 and 5.1 Hz), 7.52 (bs, 1H), 7.20 (bd, 1H, J=8.7 Hz), 6.78 (d, 1H, J=8.7 Hz), 6.67 (d, 1H, J=8.7 Hz), 5.05 (dd, 1H, J=6.3 and 6.6 Hz), 4.80 (t, 1H), 4.23 (t, 2H, J=5.1 Hz), 3.69(q, 2H, J=5.4 Hz), 3.40 (dd, 1H), 3.15 (dd, 1H, J=6.3 and 9.9 Hz), 2.60 (d, 3H, J=4.5 Hz); LCMS: purity: 86%; MS (m/e): 441 (MH$^+$).

7.3.809 (±)-N2-[2,3-Dihydro-(N-methylamino)carbonylbenzofuran-5-yl]-5-fluoro-N4-(3-trifluoromethoxyphenyl)-2,4-pyrimidinediamine (R927040)

In like manner to the preparation of (±)-N4-(3,4-difluorophenyl)-5-fluoro-N2-[2-(N-methylamino) carbonyl-2,3-dihydrobenzofuran-5-yl]-2,4-pyrimidinediamine, the reaction of methyl amine Hydrogen Chloride with (±)-N2-(2,3-dihydro-2-methoxycarbonylbenzofuran-5-yl)-5-fluoro-N4-(3-trifluoromethoxyphenyl)-2,4-pyrimidinediamine gave (±)-N2-[2,3-dihydro-(N-methylamino)carbonylbenzofuran-5-yl]-5-fluoro-N4-(3-trifluoromethoxyphenyl)-2,4-pyrimidinediamine. LCMS: purity: 94%; MS (m/e): 464 (MH$^+$).

7.3.810 (±)-N2-[2,3-Dihydro-(N-methylamino)carbonylbenzofuran-5-yl]-N4-(3,4-difluoromethyleneoxyphenyl)-5-fluoro-2,4-pyrimidinediamine (R927041)

In like manner to the preparation of (±)-N4-(3,4-difluorophenyl)-5-fluoro-N2-[2-(N-methylamino)carbonyl-2,3-dihydrobenzofuran-5-yl]-2,4-pyrimidinediamine, the reaction of methyl amine Hydrogen Chloride with (±)-N2-(2,3-dihydro-2-methoxycarbonylbenzofuran-5-yl)-5-fluoro-N4-(3-trifluoromethoxyphenyl)-2,4-pyrimidinediamine gave (±)-N2-[2,3-dihydro-(N-methylamino)carbonylbenzofuran-5-yl]-N4-(3,4-difluoromethyleneoxyphenyl)-5-fluoro-2,4-pyrimidinediamine. 1H NMR (DMSO-d6): d 9.46 (s, 1H), 9.05 (s, 1H), 8.05 (m, 3H), 7.43 (m, 2H), 7.31 (d, 1H, J=8.7 Hz), 7.23 (bd, 1H, J=7.5 Hz), 6.70 (d, 1H, J=9.0 Hz), 5.04 (dd, 1H, J=6.6 Hz), 3.40 (dd, 1H), 3.14 (dd, 1H, J=5.7 and 6.6 Hz), 2.60 (d, 3H, J=3.9 Hz); LCMS: purity: 94%; MS (m/e): 460 (MH$^+$).

7.3.811 N2-(4-Carboxymethyleneoxyphenyl)-N4-(3,4-ethylenedioxyphenyl)-5-fluoro-2,4-pyrimidinediamine (R926238)

The reaction of N2-(4-ethoxycarbonylmethyleneoxyphenyl)-N4-(3,4-ethylenedioxyphenyl)-5-fluoro-2,4-pyrimidinediamine with LiOH in THF:H$_2$O at room temperature gave N2-(carboxymethyleneoxyphenyl)-N4-(3,4-ethylenedioxyphenyl)-5-fluoro-2,4-pyrimidinediamine. $^1$H NMR (DMSO-d6): δ 8.16 (d, 1H, J=4.8 Hz), 7.37 (bd, 2H, J=9 Hz), 7.25 9d, 1H, J=3 Hz), 7.08 (m, 1H), 6.83 (m, 3H), 4.64 (s, 2H), 4.23 (s, 4H); LCMS: ret. time: 19.15 min.; purity: 100%; MS (m/e): 413 (MH$^+$).

7.3.812 N4-(1,4-Benzoxazin-6-yl)-5-fluoro-N2-[3-(N-methylamino)carbonylmethyleneoxyphenyl]-2,4-pyrimidinediamine Hydrogen Chloride Salt (R920395)

To a solution of N4-(1,4-benzoxazin-6-yl)-5-fluoro-N2-[3-(N-methylamino)carbonylmethyleneoxyphenyl]-2,4-pyrimidinediamine (1 equivalent) in MeOH at 0° C. was added HCl (4M, dioxane, 1.1 equivalents) dropwise and shaken for 5 minutes. The resulting solution was diluted with EtOAc and the solid obtained was filtered washed with EtOAc, dried and analyzed to give N4-(1,4-benzoxazin-6-yl)-5-fluoro-N2-[3-(N-methylamino)carbonylmethyleneoxyphenyl]-2,4-pyrimidinediamine Hydrogen Chloride Salt. $^1$H NMR (DMSO-d6): δ 9.80 (bs, 2H), 8.12 (d, 1H, J=4.8 Hz), 7.89 (bd, 1H, J=4.5 Hz), 7.18 (m, 3H), 8.24 (m, 2H), 6.60 (bd, 2H, J=8.1 Hz), 4.36 (s, 2H), 4.10 (t, 2H, J=3.9 Hz), 3.27 (t, 2H, J=3.9 Hz), 2.62 (d, 3H, J=4.5 Hz); LCMS: purity: 98%, MS (m/e): 425 (MH$^+$).

7.3.813 N4-(3,4-Ethylenedioxyphenyl)-5-fluoro-N2-[3-(N-methylamino)carbonylmethyleneoxyphenyl]-2,4-pyrimidinediamine Trifluoro Acetic Acid Salt (R926826)

In like manner to the synthesis of N4-(1,4-benzoxazin-6-yl)-5-fluoro-N2-[3-(N-methylamino)carbonylmethyleneoxyphenyl]-2,4-pyrimidinediamine Hydrogen Chloride Salt the reaction of N4-(3,4-ethylenedioxyphenyl)-5-fluoro-N2-[3-(N-methylamino)carbonylmethyleneoxyphenyl]-2,4-pyrimidinediamine with trifluoroacetic acid gave N4-(3,4-Ethylenedioxyphenyl)-5-fluoro-N2-[3-(N-methylamino)carbonylmethyleneoxyphenyl]-2,4-pyrimidinediamine Trifluoro Acetic Acid Salt. $^1$H NMR (DMSO-d6): δ 9.40 (bs, 1H), 9.36 (bs, 1H), 8.07 (d, 1H, J=4.2 Hz), 7.94 (bd, 1H), 7.22 (m, 4H), 7.11 (t, 1H, J=7.5 Hz), 6.79 (d, 1H, J=8.7 Hz), 6.51 (bd, 1H, J=7.5 Hz), 4.33 (s, 2H), 4.21 (bs, 4H), 2.63 (d, 3H, 3.3 Hz).

7.3.814 5-Fluoro-N4-[(1H)-indol-6-yl]-N2-[4-methoxy-3-[(N-methylamino)carbonylmethyleneoxy]phenyl]-2,4-pyrimidinediamine (R926752)

In a like manner to the preparation of N4-(3,4-ethylenedioxyphenyl)-5-fluoro-N2-(3-hydroxyphenyl)-2,4-pyrimidinediamine, 2-chloro-5-fluoro-N4-[(1H)indol-6-yl]-4-pyrimidineamine and 4-methoxy-3-[(N-methylamino)carbonylmethyleneoxy]aniline were reacted to produce 5-fluoro-N4-[(1H)-indol-6-yl]-N2-[4-methoxy-3-[(N-methylamino)carbonylmethyleneoxy]phenyl]-2,4-pyrimidinediamine. $^1$H NMR (CD$_3$OD): δ 7.83 (d, 1H, J=3.6 Hz), 7.73 (d, 1H, J=0.9 Hz), 7.49 (d, 1H, J=8.1 Hz), 7.39 (d, 1H, J=3.0 Hz), 7.20 (d, 1H, J=3.6 Hz), 7.15 (dd, 1H, J=1.8 and 8.1 Hz), 7.05 (dd, 1H, J=2.1 and 8.7 Hz), 6.81 (d, 1H, J=8.7 Hz), 6.41 (d, 1H, J=4.2 Hz), 4.09 (s, 2H), 3.81 (s, 3H), 2.76 (s, 3H); LCMS: purity: 100%; MS (m/e): 437(MH$^+$).

7.3.815 5-Fluoro-N4-(3-hydroxy-4-methylphenyl)-N2-[3-[(N-methylamino)carbonylmethyleneoxy]phenyl]-2,4-pyrimidinediamine (R926753)

In a like manner to the preparation of N4-(3,4-ethylenedioxyphenyl)-5-fluoro-N2-(3-hydroxyphenyl)-2,4-pyrimidinediamine, 2-chloro-5-fluoro-N4-(2-hydroxy-4-methylphenyl)-4-pyrimidineamine and 3-[(N-methylamino)carbonylmethyleneoxy]aniline were reacted to produce 5-fluoro-N4-(3-hydroxy-4-methylphenyl)-N2-[3-[(N-methylamino)carbonylmethyleneoxy]phenyl]-2,4-pyrimidinediamine. $^1$H NMR (DMSO-d$_6$): δ 9.95 (bs, 1H), 9.83 (bs, 1H), 9.38 (bs, 1H), 8.17 (d, 1H, J=4.4 Hz), 7.97 (d, 1H, J=4.8 Hz), 7.24-7.17 (m, 2H), 7.16 (d, 1H, J=8.4 Hz), 7.10 (dd, 1H, J=1.8 and 8.4 Hz), 7.03 (d, 1H, J=2.4 Hz), 7.00 (d, 1H, J=9.0 Hz), 6.61 (d, 1H, J=8.7 Hz), 4.34 (s, 2H), 2.63 (d, 3H, J=4.5 Hz), 2.08 (s, 3H); LCMS: purity: 96%; MS (m/e): 398(MH$^+$).

7.3.816 5-Fluoro-N4-(3-dihydroxyborylphenyl)-N2-[3-[(N-methylamino)carbonylmethyleneoxy]phenyl]-2,4-pyrimidinediamine (R926754)

In a like manner to the preparation of N4-(3,4-ethylenedioxyphenyl)-5-fluoro-N2-(3-hydroxyphenyl)-2,4-pyrimidinediamine, 2-chloro-5-fluoro-N4-(3-dihydroxyborylphenyl)-4-pyrimidineamine and 3-[(N-methylamino)carbonylmethyleneoxy]aniline were reacted to produce 5-fluoro-N4-(3-dihydroxyborylphenyl)-N2-[3-[(N-methylamino)carbonylmethyleneoxy]phenyl]-2,4-pyrimidinediamine. $^1$H NMR (DMSO-d$_6$): δ 9.38 (bs, 1H), 9.22 (bs, 1H), 8.08 (d, 1H, J=3.6 Hz), 8.06-7.81 (m, 4H), 7.51 (d, 1H, J=8.1 Hz), 7.33-7.28 (m, 3H), 7.06 (t, 1H, J=8.1 Hz), 6.44 (dd, 1H, J=2.4 and 7.5 Hz), 4.33 (s, 2H), 2.63 (d, 3H, J=4.8 Hz); LCMS: purity: 95%; MS (m/e): 412(MH$^+$).

7.3.817 5-Fluoro-N4-(3-dihydroxyborylphenyl)-N2-(3-hydroxyphenyl)-2,4-pyrimidinediamine (R926755)

In a like manner to the preparation of N4-(3,4-ethylenedioxyphenyl)-5-fluoro-N2-(3-hydroxyphenyl)-2,4-pyrimidinediamine, 2-chloro-5-fluoro-N4-(3-dihydroxyborylphenyl)-4-pyrimidineamine and 3-hydroxyaniline were reacted to produce 5-Fluoro-N4-(3-dihydroxyborylphenyl)-N2-(3-hydroxyphenyl)-2,4-pyrimidinediamine. $^1$H NMR (DMSO-d$_6$): δ 9.68 (bs, 1H), 9.35 (bs, 1H), 9.22 (bs, 1H), 8.10 (d, 1H, J=3.9 Hz), 7.88-7.80 (m, 2H), 7.54 (d, 1H, J=7.2 Hz), 7.31 (t, 1H, J=7.2 Hz), 7.08 (d, 1H, J=8.4 Hz), 6.98-6.93 (m, 2H), 6.35 (d, 1H, J=8.4 Hz); LCMS: purity: 96%; MS (m/e): 341 (MH$^+$).

7.3.818 N2-(3,4-Ethylenedioxyphenyl)-5-fluoro-N4-(3-hydroxyborylphenyl)-2,4-pyrimidinediamine (R926756)

In a like manner to the preparation of N4-(3,4-ethylenedioxyphenyl)-5-fluoro-N2-(3-hydroxyphenyl)-2,4-pyrimidinediamine, 2-chloro-5-fluoro-N4-(3-dihydroxyborylphenyl)-4-pyrimidineamine and 3,4-ethylenedioxyaniline were reacted to produce N2-(3,4-ethylenedioxyphenyl)-5-fluoro-N4-(3-hydroxyborylphenyl)-2,4-pyrimidinediamine. $^1$H NMR (DMSO-d$_6$): δ 9.46 (bs, 1H), 9.11 (bs, 1H), 8.05 (d, 1H, J=4.2 Hz), 7.95 (bs, 1H), 7.88 (s, 1H), 7.78 (d, 1H, J=7.5 Hz), 7.52 (d, 1H, J=7.5 Hz), 7.29 (t, 1H, J=7.5 Hz), 7.16 (s, 1H), 7.02 (d, 1H, J=8.7 Hz), 6.65 (d, 1H, J=8.7 Hz), 3.40 (s, 4H); LCMS: purity: 98%; MS (m/e): 383(MH$^+$).

7.3.819 5-Fluoro-N4-(3-hydroxyphenyl)-N2-[4-methyl-3-[(N-methylamino)carbonylmethyleneoxy]phenyl]-2,4-pyrimidinediamine (R926757)

In a like manner to the preparation of N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)-4-pyrimidineamine and 4-methyl-3-[(N-methylamino)carbonylmethyleneoxy]aniline were reacted to produce 5-fluoro-N4-(3-hydroxyphenyl)-N2-[4-methyl-3-[(N-methylamino)carbonylmethyleneoxy]phenyl]-2,4-pyrimidinediamine. $^1$H NMR (DMSO-d$_6$): δ 9.32 (s, 1H), 9.17 (s, 1H), 9.04 (s, 1H), 8.04 (d, 1H, J=4.2 Hz), 7.76 (d, 1H, J=4.8 Hz), 7.32 (td, 2H, J=1.8 and 8.1 Hz), 7.13-7.04 (m, 3H), 6.95 (d, 1H, J=8.4 Hz), 6.46 (dd, 1H, J=1.8 and 8.4 Hz), 4.31 (s, 2H), 2.65 (d, 3H, J=4.8 Hz), 2.14 (s, 3H); LCMS: purity: 99%; MS (m/e): 398(MH$^+$).

7.3.820 N4-(3,4-Ethylenedioxyphenyl)-5-fluoro-N2-[4-methyl-3-[(N-methylamino)carbonylmethyleneoxy]phenyl]-2,4-pyrimidinediamine (R926758)

In a like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 4-methyl-3-[(N-methylamino)carbonylmethyleneoxy]aniline were reacted to produce N4-(3,4-ethylenedioxyphenyl)-5-fluoro-N2-[4-methyl-3-[(N-methylamino)carbonylmethyleneoxy]phenyl]-2,4-pyrimidinediamine. $^1$H NMR (DMSO-d$_6$): δ 9.13 (bs, 1H), 9.05 (s, 1H), 8.01 (d, 1H, J=4.2 Hz), 7.76 (d, 1H, J=4.8 Hz), 7.32 (d, 1H, J=2.4 Hz), 7.27 (dd, 1H, J=2.4 and 8.1 Hz), 7.21 (dd, 1H, J=2.4 and 8.7 Hz), 7.13 (d, 1H, J=1.8 Hz), 6.95 (d, 1H, J=8.1 Hz), 6.76 (d, 1H, J=8.7 Hz), 4.28 (s, 2H), 4.20 (s, 4H), 2.65 (d, 3H, J=4.8 Hz), 2.15 (s, 3H); LCMS: purity: 97%; MS (m/e): 440(MH$^+$).

7.3.821 5-Fluoro-N4-(3-hydroxy-4-methylphenyl)-N2-[4-methyl-3-[(N-methylamino)carbonylmethyleneoxy]phenyl]-2,4-pyrimidinediamine (R926759)

In a like manner to the preparation of N4-(3,4-ethylenedioxyphenyl)-5-fluoro-N2-(3-hydroxyphenyl)-2,4-pyrimidinediamine, 2-chloro-5-fluoro-N4-(2-hydroxy-4-methylphenyl)-4-pyrimidineamine and 4-methyl-3-[(N-methylamino)carbonylmethyleneoxy]aniline were reacted to produce 5-fluoro-N4-(3-hydroxy-4-methylphenyl)-N2-[4-methyl-3-[(N-methylamino)carbonylmethyleneoxy]phenyl]-2,4-pyrimidinediamine. $^1$H NMR (DMSO-d$_6$): δ 10.09 (bs, 1H), 9.96 (bs, 1H), 9.44 (bs, 1H), 8.16 (d, 1H, J=4.8 Hz), 7.81 (d, 1H, J=4.8 Hz), 7.13-6.94 (m, 6H), 4.29 (s, 2H), 2.64 (d, 3H, J=4.5 Hz), 2.17 (s, 3H), 2.07 (s, 3H); LCMS: purity: 99%; MS (m/e): 412(MH$^+$).

7.3.822 5-Fluoro-N2,N4-bis[4-methyl-3-[(N-methylamino)carbonylmethyleneoxy]phenyl]-2,4-pyrimidinediamine (R926760)

In a like manner to the preparation of N2,N4-bis(3-hydroxyphenyl)-5-fluoro-2,4-pyrimidinediamine, 2,4-dichloro-5-fluoropyrimidine and 4-methyl-3-[(N-methylamino)carbonylmethyleneoxy]aniline were reacted to provide 5-fluoro-N2,N4-bis[4-methyl-3-[(N-methylamino)carbonylmethyleneoxy]phenyl]-2,4-pyrimidinediamine. $^1$H NMR (DMSO-d$_6$): δ 9.30 (s, 1H), 9.02 (s, 1H), 8.06 (d, 1H, J=3.6 Hz), 7.94 (d, 1H, J=4.5 Hz), 7.80 (d, 1H, J=4.2 Hz), 7.58 (bs, 1H), 7.31-7.22 (m, 3H), 7.05 (d, 1H, J=9.0 Hz), 6.97

(d, 1H, J=7.5 Hz), 4.41 (s, 2H), 4.27 (s, 2H), 2.66 (d, 3H, J=4.2 Hz), 2.63 (d, 3H, J=4.2 Hz), 2.18 (s, 3H), 2.14 (s, 3H); LCMS: purity: 100%; MS (m/e): 483(MH$^+$).

7.3.823 5-Fluoro-N4-(3-hydroxyphenyl)-N2-(3,4,5-trimethoxyphenyl)-2,4-pyrimidinediamine (R926761)

In a like manner to the preparation of N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)-4-pyrimidineamine and 3,4,5-trimethoxyaniline were reacted to produce 5-fluoro-N4-(3-hydroxyphenyl)-N2-(3,4,5-trimethoxyphenyl)-2,4-pyrimidinediamine. $^1$H NMR (DMSO-d$_6$): δ 9.33 (s, 1H), 9.17 (s, 1H), 8.99 (s, 1H), 8.06 (d, 1H, J=3.3 Hz), 7.27 (d, 1H, J=7.5 Hz), 7.08-7.02 (m, 4H), 6.46 (dd, 1H, J=1.8 and 7.8 Hz), 3.60 (s, 6H), 3.57 (s, 3H); LCMS: purity: 99%; MS (m/e): 387(MH$^+$).

7.3.824 N4-(3,4-Ethylenedioxyphenyl)-5-fluoro-N2-(3,4,5-trimethoxyphenyl)-2,4-pyrimidinediamine (R926762)

In a like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 3,4,5-trimethoxyaniline were reacted to produce N4-(3,4-ethylenedioxyphenyl)-5-fluoro-N2-(3,4,5-trimethoxyphenyl)-2,4-pyrimidinediamine $^1$H NMR (DMSO-d$_6$): δ 8.08 (d, 1H, J=4.8 Hz), 7.29 (d, 1H, J=2.4 Hz), 7.15 (dd, 1H, J=3.0 and 9.0 Hz), 6.91 (s, 1H), 6.76 (d, 1H, J=8.7 Hz), 4.20 (s, 4H), 3.61 (s, 6H), 3.59 (s, 3H); LCMS: purity: 97%; MS (m/e): 429(MH$^+$).

7.3.825 N4-(3,4-Ethylenedioxyphenyl)-5-fluoro-N2-(3,5-dichloro-4-hydroxyphenyl)-2,4-pyrimidinediamine (R926763)

In a like manner to the preparation of N4-(3,4-ethylenedioxyphenyl)-5-fluoro-N2-(3-hydroxyphenyl)-2,4-pyrimidinediamine, 2-chloro-N4-(3,4-ethylenedioxyphenyl)-5-fluoro-4-pyrimidineamine and 3,5-dichloro-4-hydroxyaniline were reacted to produce N4-(3,4-ethylenedioxyphenyl)-5-fluoro-N2-(3,5-dichloro-4-hydroxyphenyl)-2,4-pyrimidinediamine. $^1$H NMR (DMSO-d$_6$): δ 9.50 (bs, 1H), 9.26 (bd, 2H, J=7.5 Hz), 8.06 (d, 1H, J=3.9 Hz), 7.65 (s, 2H), 7.18-7.13 (m, 2H), 6.80 (d, 1H, J=9.0 Hz), 4.20 (s, 4H); LCMS: purity: 100%; MS (m/e): 424 (MH$^+$).

7.3.826 5-Fluoro-N2-(3,5-dichloro-4-hydroxyphenyl)-N4-(3-hydroxyphenyl)-2,4-pyrimidinediamine (R926890)

In a like manner to the preparation of N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)-4-pyrimidineamine and 3,5-dichloro-4-hydroxyaniline were reacted to produce 5-Fluoro-N2-(3,5-dichloro-4-hydroxyphenyl)-N4-(3-hydroxyphenyl)-2,4-pyrimidinediamine. $^1$H NMR (DMSO-d$_6$): δ 9.47 (bs, 1H), 9.35 (bs, 1H), 9.22 (bs, 2H), 8.09 (d, 1H, J=3.6 Hz), 7.70 (s, 2H), 7.31 (dd, 1H, J=1.2 and 9.3 Hz), 7.10 (t, 1H, J=7.5 Hz), 7.00 (bs, 1H), 6.48 (dd, 1H, J=1.2 and 6.9 Hz); LCMS: purity: 93%; MS (m/e): 382 (MH$^+$).

7.3.827 N4-(3-Chloro-4-methoxyphenyl)-5-fluoro-N2-[3-[(N-methylamino)carbonylmethyleneoxy]phenyl]-2,4-pyrimidinediamine (R926891)

In a like manner to the preparation of N4-(3,4-ethylenedioxyphenyl)-5-fluoro-N2-(3-hydroxyphenyl)-2,4-pyrimidinediamine, 2-chloro-N4-(3-chloro-4-methoxyphenyl)-5-fluoro-4-pyrimidineamine and 3-[(N-methylamino)carbonylmethyleneoxy]aniline were reacted to produce N4-(3-chloro-4-methoxyphenyl)-5-fluoro-N2-[3-[(N-methylamino)carbonylmethyleneoxy]phenyl]-2,4-pyrimidinediamine. $^1$H NMR (DMSO-d$_6$): δ 9.85 (bs, 1H), 9.70 (bs, 1H), 8.17 (d, 1H, J=4.8 Hz), 7.98 (d, 1H, J=3.9 Hz), 7.79 (d, 1H, J=2.4 Hz), 7.65 (dd, 1H, J=3.0 and 9.3 Hz), 7.24-7.09 (m, 4H), 6.57 (d, 1H, J=5.7 Hz), 4.34 (s, 2H), 3.82 (s, 3H), 2.62 (d, 3H, J=4.8 Hz); LCMS: purity: 95%; MS (m/e): 433(MH$^+$)

7.3.828 5-Fluoro-N4-(3-fluoro-4-methoxyphenyl)-N2-[3-[(N-methylamino)carbonylmethyleneoxy]phenyl]-2,4-pyrimidinediamine (R926892)

In a like manner to the preparation of N4-(3,4-ethylenedioxyphenyl)-5-fluoro-N2-(3-hydroxyphenyl)-2,4-pyrimidinediamine, 2-chloro-5-fluoro-N4-(3-fluoro-4-methoxyphenyl)-4-pyrimidineamine and 3-[(N-methylamino)carbonylmethyleneoxy]aniline were reacted to produce 5-fluoro-N4-(3-fluoro-4-methoxyphenyl)-N2-[3-[(N-methylamino)carbonylmethyleneoxy]phenyl]-2,4-pyrimidinediamine. $^1$H NMR (DMSO-d$_6$): δ 9.68 (bs, 1H), 9.53 (bs, 1H), 8.13 (d, 1H, J=4.2 Hz), 7.97 (d, 1H, J=4.8 Hz), 7.76 (dd, 1H, J=2.4 and 13.5 Hz), 7.47 (d, 1H, J=7.5 Hz), 7.27-7.08 (m, 4H), 6.54 (d, 1H, J=8.4 Hz), 4.35 (s, 2H), 3.80 (s, 3H), 2.63 (d, 3H, J=4.8 Hz); LCMS: purity: 94%; MS (m/e): 416 (MH$^+$).

7.3.829 N4-(3,4-Ethylenedioxyphenyl)-5-fluoro-N4-(3-hydroxy-5-methylphenyl)-2,4-pyrimidinediamine (R926893)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(3,4-ethylenedioxyphenyl)-5-fluoro-4-pyrimidineamine, 4-amino-m-cresol hydrogenchloride salt, and diisopropylethylamine were reacted to provide N4-(3,4-ethylenedioxyphenyl)-5-fluoro-N4-(3-hydroxy-5-methylphenyl)-2,4-pyrimidinediamine. $^1$H NMR (DMSO-d$_6$): δ 9.06 (s, 1H), 8.94 (s, 1H), 8.11 (s, 1H), 7.86 (d, 1H, J=3.9 Hz), 7.21-7.15 (m, 2H), 7.03 (d, 1H, J=8.1 Hz), 6.59 (bd, 2H, J=8.7 Hz), 6.52 (dd, 1H, J=3.0 and 8.1 Hz), 4.17 (s, 4H), 2.05 (s, 3H); LCMS: purity: 99%; MS (m/e): 369(MH$^+$).

7.3.830 N4-(3,4-Ethylenedioxyphenyl)-5-fluoro-N2-(3-fluoro-5-trifluoromethylphenyl)-2,4-pyrimidinediamine (R926894)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(3,4-ethylenedioxyphenyl)-5-fluoro-4-pyrimidineamine and 3-amino-5-fluorobenzotrifluoride were reacted to provide N4-(3,4-ethylenedioxyphenyl)-5-fluoro-N2-(3-fluoro-5-trifluoromethylphenyl)-2,4-pyrimidinediamine. $^1$H NMR (DMSO-d$_6$): δ 9.75 (s, 1H), 9.32 (d, 1H, J=1.2 Hz), 8.13 (d, 1H, J=3.6 Hz), 7.99 (d, 1H, J=12.3 Hz), 7.77 (s, 1H), 7.21 (d, 1H, J=2.4 Hz), 7.13 (dd, 1H, J=2.1 and 8.7 Hz), 7.03 (d, 1H, J=9.0 Hz), 6.80 (d, 1H, J=8.7 Hz), 4.21 (s, 4H); LCMS: purity: 97%; MS (m/e): 425(MH$^+$).

7.3.831 N4-(3,4-Ethylenedioxyphenyl)-5-fluoro-N2-(3-methyl-5-trifluoromethylphenyl)-2,4-pyrimidinediamine (R926895)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(3,4-ethylenedioxyphenyl)-5-fluoro-4-pyrimidineamine and 3-amino-5-methylbenzotrifluoride were reacted to provide N4-(3,4-ethylenedioxyphenyl)-5-fluoro-N2-(3-methyl-5-trifluoromethylphenyl)-2,4-pyrimidinediamine. $^1$H NMR (DMSO-d$_6$): δ 9.57 (bs, 1H), 9.39 (bs, 1H), 8.12 (d, 1H, J=3.6 Hz), 7.77 (s, 2H), 7.25-7.13 (m, 2H), 7.02 (s, 1H), 6.79 (d, 1H, J=9.0 Hz), 4.20 (s, 4H), 2.27 (s, 3H); LCMS: purity: 100%; MS (m/e): 421 (MH$^+$).

7.3.832 N4-(3,4-Ethylenedioxyphenyl)-5-fluoro-N2-(5-methoxy-2-methylphenyl)-2,4-pyrimidinediamine (R926896)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(3,4-ethylenedioxyphenyl)-5-fluoro-4-pyrimidineamine and 5-methoxy-2-methylaniline were reacted to provide N4-(3,4-ethylenedioxyphenyl)-5-fluoro-N2-(5-methoxy-2-methylphenyl)-2,4-pyrimidinediamine. $^1$H NMR (CDCl$_3$): δ 7.91 (bs, 1H), 7.61 (d, 1H, J=2.1 Hz), 7.17 (d, 1H, J=3.0 Hz), 7.05 (d, 1H, J=9.3 Hz), 7.03 (dd, 1H, J=3.0 and 8.7 Hz), 6.82 (d, 1H, J=8.1 Hz), 6.68-6.60 (m, 2H), 6.55 (dd, 1H, J=2.1 and 8.1 Hz), 4.26 (s, 4H), 3.70 (s, 3H), 2.22 (s, 3H); $^{19}$F NMR (282 MHz, CDCl$_3$): −47450; LCMS: purity: 99%; MS (m/e): 383 (MH$^+$).

7.3.833 N4-(3,4-Ethylenedioxyphenyl)-5-fluoro-N2-(2-fluoro-5-methylphenyl)-2,4-pyrimidinediamine (R926897)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(3,4-ethylenedioxyphenyl)-5-fluoro-4-pyrimidineamine and 2-fluoro-5-methylaniline were reacted to provide N4-(3,4-ethylenedioxyphenyl)-5-fluoro-N2-(2-fluoro-5-methylphenyl)-2,4-pyrimidinediamine. $^1$H NMR (CDCl$_3$): δ 8.11 (dd, 1H, J=1.8 and 8.1 Hz), 7.94 (d, 1H, J=2.7 Hz), 7.08-6.84 (m, 4H), 6.74-6.67 (m, 1H), 6.64-6.59 (m, 1H), 4.27 (s, 4H), 2.28 (s, 3H); $^{19}$F NMR (282 MHz, CDCl$_3$): −38659, −47267; LCMS: purity: 100%; MS (m/e): 371(MH$^+$).

7.3.834 N4-(3,4-Ethylenedioxyphenyl)-5-fluoro-N2-(3,5-difluorophenyl)-2,4-pyrimidinediamine (R926898)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(3,4-ethylenedioxyphenyl)-5-fluoro-4-pyrimidineamine and 3,5-difluoroaniline were reacted to provide N4-(3,4-ethylenedioxyphenyl)-5-fluoro-N2-(3,5-difluorophenyl)-2,4-pyrimidinediamine. $^1$H NMR (CDCl$_3$): δ 7.94 (d, 1H, J=3.3 Hz), 7.20-7.11 (m, 3H), 7.02 (s, 1H), 6.92-6.90 (m, 2H), 6.65 (s, 1H), 6.39 (tt, 1H, J=2.4 and 9.0 Hz), 4.31 (s, 4H); $^{19}$F NMR (282 MHz, CDCl$_3$): −31142, −47002; LCMS: purity: 97%; MS (m/e): 375(MH$^+$).

7.3.835 N4-(3,4-Ethylenedioxyphenyl)-5-fluoro-N2-(4-trifluoromethylthiophenyl)-2,4-pyrimidinediamine (R926899)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(3,4-ethylenedioxyphenyl)-5-fluoro-4-pyrimidineamine and 4-(trifluoromethylthio)aniline were reacted to provide N4-(3,4-ethylenedioxyphenyl)-5-fluoro-N2-(4-trifluoromethylthiophenyl)-2,4-pyrimidinediamine. $^1$H NMR (DMSO-d$_6$): δ 9.73 (s, 1H), 9.47 (s, 1H), 8.13 (d, 1H, J=3.6 Hz), 7.79 (d, 2H, J=9.0 Hz), 7.51 (d, 2H, J=9.0 Hz), 7.28 (d, 1H, J=2.1 Hz), 7.12 (dd, 1H, J=2.4 and 9.0 Hz), 6.83 (d, 1H, J=8.7 Hz), 4.23 (s, 4H); $^{19}$F NMR (282 MHz DMSO-d$_6$): −12306; LCMS: purity: 97%; MS (m/e): 439(MH$^+$).

7.3.836 N4-[3-(Benzothiazol-2-yl)-4-chlorophenyl]-5-fluoro-N2-[3-[(N-methylamino)carbonylmethyleneoxy]phenyl]-2,4-pyrimidinediamine (R926900)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, N4-[3-(Benzothiazol-2-yl)-4-chlorophenyl]-2-chloro-5-fluoro-4-pyrimidineamine and 3-[(N-methylamino)carbonylmethyleneoxy]aniline were reacted to provide N4-[3-(benzothiazol-2-yl)-4-chlorophenyl]-5-fluoro-N2-[3-[(N-methylamino)carbonylmethyleneoxy]phenyl]-2,4-pyrimidinediamine. $^1$H NMR (DMSO-d$_6$): δ 9.77 (s, 1H), 9.30 (s, 1H), 8.49 (d, 1H, J=3.0 Hz), 8.25 (dd, 1H, J=3.0 and 9.0), 8.21-8.16 (m, 2H), 8.06 (d, 1H, J=7.8 Hz), 7.92 (d, 1H, J=4.8 Hz), 7.63-7.48 (m, 3H), 7.30 (t, 1H, J=1.8 Hz), 7.22 (dd, 1H, J=1.8 and 7.5 Hz), 6.95 (t, 1H, J=8.1 Hz), 6.32 (dd, 1H, J=1.2 and 8.1 Hz), 4.29 (s, 2H), 2.62 (d, 1H, J=4.8 Hz); LCMS: purity: 100%; MS (m/e): 536(MH$^+$).

7.3.837 5-Fluoro-N2-[3-[(N-methylamino)carbonylmethyleneoxy]phenyl]-N4-(3-methoxy-4-methylphenyl)-2,4-pyrimidinediamine (R926902)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-Chloro-5-fluoro-N4-(3-methoxy-4-methylphenyl)-4-pyrimidineamine and 3-methoxy-4-methylaniline were reacted to provide 5-fluoro-N2-[3-[(N-methylamino)carbonylmethyleneoxy]phenyl]-N4-(3-methoxy-4-methylphenyl)-2,4-pyrimidinediamine. $^1$H NMR (DMSO-d$_6$): δ 9.78 (bs, 1H), 9.63 (bs, 1H), 8.15 (d, 1H, J=4.5 Hz), 7.94 (d, 1H, J=4.5 Hz), 7.94 (d, 1H, J=4.5 Hz), 7.30 (dd, 1H, J=1.8 and 8.4 Hz), 7.25-7.04 (m, 5H), 6.57 (d, 1H, J=8.1 Hz), 4.31 (s, 2H), 3.66 (s, 3H), 2.62 (d, 1H, J=4.8 Hz), 2.09 (s, 3H); LCMS: purity: 95%; MS (m/e): 412(MH$^+$)

7.3.838 5-Fluoro-N4-(3-hydroxyphenyl)-N2-[2-(methoxycarbonyl)-(1H)-indol-6-yl])-2,4-pyrimidinediamine (R926903)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(3-hydroxyphenyl)-4-pyrimidineamine and 6-amino-2-(methoxycarbonyl)-(1H)-indole were reacted to provide 5-fluoro-N4-(3-hydroxyphenyl)-N2-[2-(methoxycarbonyl)-(1H)-indol-6-yl])-2,4-pyrimidinediamine. $^1$H NMR (DMSO-d$_6$): δ 11.53 (s, 1H), 9.37 (s, 1H), 9.18 (d, 2H, J=9.9

Hz), 8.08 (d, 1H, J=3.6 Hz), 7.96 (bs, 1H), 7.46 (d, 1H, J=9.0 Hz), 7.39-7.35 (m, 2H), 7.16 (t, 1H, J=2.4 Hz), 7.10-7.04 (m, 2H), 6.48 (dd, 1H, J=2.4 and 7.5 Hz), 3.82 (s, 3H); LCMS: purity: 95%; MS (m/e): 394(MH$^+$).

7.3.839 5-Fluoro-N2-[3-[(N-methylamino)carbonylmethyleneoxy]phenyl]-N4-[2-(methoxycarbonyl)-(1H)-indol-6-yl]-2,4-pyrimidinediamine (R926904)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro N4-[2-(methoxycarbonyl)-(1H)-indol-6-yl])-4-pyrimidineamine and 3-[(N-methylamino)carbonylmethyleneoxy]aniline were reacted to provide 5-fluoro-N2-[3-[(N-methylamino)carbonylmethyleneoxy]phenyl]-N4-[2-(methoxycarbonyl)-(1H)-indol-6-yl]-2,4-pyrimidinediamine. $^1$H NMR (CDCl$_3$): δ 9.05 (bs, 1H), 8.35 (s, 1H), 8.00 (bs, 1H), 7.66-7.62 (m, 2H), 7.27-7.17 (m, 3H), 7.01-6.90 (m, 3H), 6.64 (dd, 1H, J=2.4 and 8.1 Hz), 6.40 (bs, 1H), 4.49 (s, 2H), 3.94 (s, 3H), 2.75 (d, 3H, J=5.1 Hz); LCMS: purity: 86%; MS (m/e): 465(MH$^+$).

7.3.840 N4-[3-[[4-(Ethoxycarbonyl)piperidino]methyl]phenyl]-5-fluoro-N2-[3-[(N-methylamino)carbonylmethyleneoxy]phenyl-2,4-pyrimidinediamine (R926905)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[3-[[4-(ethoxycarbonyl)piperidino]methyl]phenyl]-4-pyrimidineamine and 3-[(N-methylamino)carbonylmethyleneoxy]aniline were reacted to provide 5-fluoro-N4-[3-[[4-(ethoxycarbonyl)piperidino]methyl]phenyl]-N2-[3-[(N-methylamino)carbonylmethyleneoxy]phenyl-2,4-pyrimidinediamine. $^1$H NMR (DMSO-d$_6$): 9.33 (s, 1H), 9.20 (s, 1H), 8.09 (d, 1H, J=4.2 Hz), 7.93 (d, 1H, J=4.8 Hz), 7.82 (d, 1H, J=8.1 Hz), 7.55 (s, 1H), 7.35 (t, 1H, J=2.4 Hz), 7.29-7.22 (m, 2H), 7.09 (t, 1H, J=8.1 Hz), 6.96 (d, 1H, J=7.8 Hz), 6.47 (dd, 1H, J=2.4 and 8.1 Hz), 4.32 (s, 2H), 4.02 (q, 2H, J=6.9 Hz), 3.39 (s, 2H), 2.73 (bd, 2H, J=11.1 Hz), 2.63 (d, 3H, J=4.5 Hz), 2.30-2.20 (m, 1H), 1.94 (t, 2H, J=11.1 Hz), 1.74 (d, 2H, J=9.9 Hz), 1.60-1.50 (m, 2H), 1.14 (t, 3H, J=6.9 Hz); LCMS: purity: 99%; MS (m/e): 537(M-CH$_2$$^+$).

7.3.841 N2-[3-(Ethoxycarbonyl-1,1-dimethylmethyleneoxy)phenyl]-5-fluoro-N4-(3-hydroxyphenyl)-2,4-pyrimidinediamine (R926906)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(3-hydroxyphenyl)-4-pyrimidineamine and 3-(ethoxycarbonyl-1,1-dimethylmethyleneoxy)aniline were reacted to provide N2-[3-(ethoxycarbonyl-1,1-dimethylmethyleneoxy)phenyl]-5-fluoro-N4-(3-hydroxyphenyl)-2,4-pyrimidinediamine. $^1$H NMR (CD$_3$OD): δ 7.91 (d, 1H, J=4.8 Hz), 7.20-7.03 (m, 6H), 6.67 (td, 1H, J=2.1 and 7.5 Hz), 6.57-6.53 (m, 1H), 4.19 (q, 2H, J=6.9 Hz), 1.53 (s, 6H), 1.20 (t, 3H, J=6.9 Hz); $^{19}$F NMR (282 MHz, CD$_3$OD): −46120; LCMS: purity: 91%; MS (m/e): 427(MH$^+$).

7.3.842 N2-[3-(Ethoxycarbonyl-1,1-dimethylmethyleneoxy)phenyl]-N4-(3,4-ethylenedioxyphenyl)-5-fluoro-2,4-pyrimidinediamine (R926907)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(3,4-ethylenedioxyphenyl)-5-fluoro-4-pyrimidineamine and 3-(ethoxycarbonyl-1,1-dimethylmethyleneoxy)aniline were reacted to provide N2-[3-(ethoxycarbonyl-1,1-dimethylmethyleneoxy)phenyl]-N4-(3,4-ethylenedioxyphenyl)-5-fluoro-2,4-pyrimidinediamine. $^1$H NMR (CDCl$_3$): δ 7.92 (d, 1H, J=3.0 Hz), 7.21-7.08 (m, 4H), 7.00 (dd, 1H, J=2.4 and 8.4 Hz), 6.93 (bs, 1H), 6.86 (d, 1H, J=8.7 Hz), 6.99 (d, 1H, J=2.4 Hz), 6.45 (ddd, 1H, J=1.2, 1.2, and 7.8 Hz), 4.27 (s, 4H), 4.23 (q, 2H, J=6.9 Hz), 1.60 (s, 6H), 1.23 (t, 3H, J=6.9 Hz); $^{19}$F NMR (282 MHz, CDCl$_3$): −47216; LCMS: purity: 85%; MS (m/e): 469(MH$^+$).

7.3.843 N2-[3-(Ethoxycarbonyl-1,1-dimethylmethyleneoxy)phenyl]-5-fluoro-N4-(3-hydroxy-4-methylphenyl)-2,4-pyrimidinediamine (R926908)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(2-hydroxy-4-methylphenyl)-4-pyrimidineamine and 3-(ethoxycarbonyl-1,1-dimethylmethyleneoxy)aniline were reacted to provide N2-[3-(ethoxycarbonyl-1,1-dimethylmethyleneoxy)phenyl]-5-fluoro-N4-(3-hydroxy-4-methylphenyl)-2,4-pyrimidinediamine. $^1$H NMR (CDCl$_3$): δ 7.86 (bs, 1H), 7.80 (bs, 1H), 7.53 (s, 1H), 7.16-6.86 (m, 4H), 6.54 (d, 2H, J=7.5 Hz), 4.21 (q, 2H, J=6.9 Hz), 3.48 (s, 2H), 2.20 (s, 3H), 1.60 (s, 6H), 1.22 (t, 3H, J=6.9 Hz); $^{19}$F NMR (282 MHz, CDCl$_3$): −46808; LCMS: purity: 96%; MS (m/e): 441(MH$^+$).

7.3.844 N2-[3-(Ethoxycarbonyl-1,1-dimethylmethyleneoxy)phenyl]-5-fluoro-N4-[(1H)-indol-6-yl]-2,4-pyrimidinediamine (R926909)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[(1H)indol-6-yl]-4-pyrimidineamine and 3-(ethoxycarbonyl-1,1-dimethylmethyleneoxy)aniline were reacted to provide N2-[3-(Ethoxycarbonyl-1,1-dimethylmethyleneoxy)phenyl]-5-fluoro-N4-[(1H)-indol-6-yl]-2,4-pyrimidinediamine. $^1$H NMR (CDCl$_3$): δ 9.43 (bs, 1H), 8.64 (s, 1H), 7.92 (d, 1H, J=3.6 Hz), 7.66 (t, 1H, J=2.4 Hz), 7.54 (d, 1H, J=8.4 Hz), 7.44 (s, 1H), 7.19 (t, 1H, J=3.0 Hz), 7.15 (d, 1H, J=8.1 Hz), 6.96 (d, 1H, J=3.0 Hz), 6.80 (dd, 1H, J=1.8 and 7.5 Hz), 6.77 (dd, 1H, J=1.8 and 8.1 Hz), 6.52 (dd, 1H, J=1.8 and 7.5 Hz), 6.49-6.46 (m, 1H), 4.32 (q, 2H, J=7.2 Hz), 1.57 (s, 6H), 1.31 (t, 3H, J=7.2 Hz); $^{19}$F NMR (282 MHz, CDCl$_3$): −47190; LCMS: purity: 93%; MS (m/e): 450(MH$^+$).

7.3.845 5-Fluoro-N4-(3-hydroxyphenyl)-N2-[3-[(N-methylamino)carbonyl-1,1-dimethylmethyleneoxy]phenyl]-2,4-pyrimidinediamine (R926913)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(3-hydroxyphenyl)-4-pyrimidineamine and 3-(N-methylamino)carbonyl-1,1-dimethylmethyleneoxy)aniline were reacted to provide 5-fluoro-N4-(3-hydroxyphenyl)-N2-[3-[(N-methylamino)carbonyl-1,1-dimethylmethyleneoxy]

phenyl]-2,4-pyrimidinediamine. $^1$H NMR (DMSO-d$_6$): δ 9.35 (s, 1H), 9.20 (s, 1H), 9.17 (s, 1H), 8.07 (d, 1H, J=3.3 Hz), 7.93 (d, 1H, J=3.9 Hz), 7.40-7.29 (m, 3H), 7.13-7.02 (m, 3H), 6.47 (d, 1H, J=7.5 Hz), 6.33 (d, 1H, J=7.5 Hz), 2.60 (s, 3H), 1.37 (s, 6H); LCMS: purity: 97%; MS (m/e): 412(MH$^+$).

7.3.846 5-Fluoro-N4-(1,2,3,4-tetrahydroisoquin-7-yl)-N2-[3-[(N-methylamino)carbonylmethyleneoxy]phenyl]-2,4-pyrimidinediamine (R926914)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[2-(t-butoxycarbonyl)-1,2,3,4-tetrahydroisoquinolin-7-yl]-4-pyrimidineamine and 3-[(N-methylamino)carbonylmethyleneoxy]aniline were reacted to provide 5-fluoro-N4-(1,2,3,4-tetrahydroisoquin-7-yl)-N2-[3-[(N-methylamino)carbonylmethyleneoxy]phenyl]-2,4-pyrimidinediamine. $^1$H NMR (DMSO-d$_6$): δ 7.90 (d, 1H, J=3.3 Hz), 7.47 (d, 1H, J=2.4 Hz), 7.42-7.37 (m, 2H), 7.16 (t, 1H, J=8.4 Hz), 7.10-7.04 (m, 2H), 6.50 (ddd, 1H, J=1.2, 2.4, and 8.1 Hz), 4.26 (s, 2H), 3.93 (s, 2H), 3.12 (t, 2H, J=6.3 Hz), 2.84-2.76 (m, 5H); $^{19}$F NMR (282 MHz, CD$_3$OD): −47489; LCMS: purity: 87%; MS (m/e): 423(MH$^+$).

7.3.847 N4-(3,4-Ethylenedioxyphenyl)-5-fluoro-N2-[3-[(N-methylamino)carbonyl-1,1-dimethylmethyleneoxy]phenyl]-2,4-pyrimidinediamine (R926915)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-(3,4-ethylenedioxyphenyl)-5-fluoro-4-pyrimidineamine and 3-(N-methylamino)carbonyl-1,1-dimethylmethyleneoxy)aniline were reacted to provide N4-(3,4-Ethylenedioxyphenyl)-5-fluoro-N2-[3-[(N-methylamino)carbonyl-1,1-dimethylmethyleneoxy]phenyl]-2,4-pyrimidinediamine. $^1$H NMR (CD$_3$OD): δ 7.26 (t, 1H, J=7.5 Hz), 7.19 (d, 1H, J=9.3 Hz), 7.13 (d, 1H, J=2.4 Hz), 7.06 (dd, 1H, J=2.4 and 8.7 Hz), 7.04-7.03 (m, 1H), 6.83 (d, 1H, J=9.0 Hz), 6.75 (d, 1H, J=7.2 Hz), 4.25 (s, 4H), 2.76 (s, 3H), 1.43 (s, 6H); LCMS: purity: 97%; MS (m/e): 454(MH$^+$).

7.3.848 5-Fluoro-N4-[3-[(N-allylamino)carbonyloxy]phenyl]-N2-[3-[(N-methylamino)carbonylmethyleneoxy]phenyl]-2,4-pyrimidinediamine (R926917)

A mixture of 5-fluoro-N4-(3-hydroxyphenyl)-N2-[3-(N-methylamino)carbonyl methyleneoxyphenyl]-2,4-pyrimidinediamine (20 mg, 0.052 mmol), allyl isocyanate (13 mg, 0.16 mmol), and 2-(N,N-dimethylamino)pyridine (18 mg, 0.15 mmol) in anhydrous THF (1 mL) were heated at 60° C. in a sealed vial for 2 days. The reaction was diluted with ethyl acetate and washed with 1N HCl and brine. Concentration gave an oily residue which was purified by preparative TLC (5% methanol/dichloromethane) to give the product 5-fluoro-N4-[3-[(N-allylamino)carbonyloxy]phenyl]-N2-[3-[(N-methylamino)carbonylmethyleneoxy]phenyl]-2,4-pyrimidinediamine. $^1$H NMR (CD$_3$OD): δ 7.93 (d, 1H, J=3.6 Hz), 7.62-7.55 (m, 2H), 7.32 (s, 1H), 7.30 (t, 1H, J=8.1 Hz), 7.19-7.15 (m, 2H), 6.82 (dd, 1H, J=2.4 and 8.1 Hz), 6.61 (m, 1H), 5.96-5.82 (m, 1H), 5.24 (dd, 1H, J=1.8 and 16.8 Hz), 5.13 (dd, 1H, J=1.8 and 11.7 Hz), 4.41 (s, 2H), 3.79 (d, 1H, J=5.4 Hz), 2.80 (s, 3H); $^{19}$F NMR (282 MHz, CD$_3$OD): −47357; LCMS: purity: 99%; MS (m/e): 468(MH$^+$).

7.3.849 5-Fluoro-N2-[3-[(N-methylamino)carbonylmethyleneoxy]phenyl]-N4-[3-[[(N-isopropylamino)carbonyl]-N-isopropylamino) carbonyloxy]phenyl]-2,4-pyrimidinediamine (R926916)

In a like manner to the preparation of 5-fluoro-N4-[3-[(N-allylamino)carbonyloxy]phenyl]-N2-[3-[(N-methylamino)carbonylmethyleneoxy]phenyl]-2,4-pyrimidinediamine and isopropyl isocyanate were reacted to provide 5-fluoro-N2-[3-[(N-methylamino)carbonylmethyleneoxy]phenyl]-N4-[3-[[(N-isopropylamino)carbonyl]-N-isopropylamino)carbonyloxy]phenyl]-2,4-pyrimidinediamine. $^1$H NMR (DMSO-d$_6$): δ 9.40 (bs, 1H), 9.27 (bs, 1H), 8.12 (d, 1H, J=3.6 Hz), 7.94 (d, 1H, J=3.9 Hz), 7.78 (d, 1H, J=8.7 Hz), 7.64 (d, 1H, J=7.5 Hz), 7.46 (s, 1H), 7.36-7.26 (m, 3H), 7.12 (t, 1H, J=8.1 Hz), 6.81-6.74 (m, 1H), 6.47 (dd, 1H, J=2.4 and 8.1 Hz), 5.43 (d, 1H, J=3.9 Hz), 4.36 (s, 2H), 3.65-3.55 (m, 2H), 3.14 (s, 2H), 2.63 (d, 3H, J=3.9 Hz), 1.10 (d, 6H, J=7.2 Hz), 0.97 (d, 6H, J=6.6 Hz).

7.3.850 N4-[3-[[N-(Ethoxycarbonylmethyl)amino]carbonyloxy]phenyl]-5-fluoro-N2-[3-[(N-methylamino)carbonylmethyleneoxy]phenyl]-2,4-pyrimidinediamine (R926918)

In a like manner to the preparation of 5-fluoro-N4-[3-[(N-allylamino)carbonyloxy]phenyl]-N2-[3-[(N-methylamino)carbonylmethyleneoxy]phenyl]-2,4-pyrimidinediamine and ethyl isocyanatoacetate were reacted to provide N4-[3-[[N-(ethoxycarbonylmethyl)amino]carbonyloxy]phenyl]-5-fluoro-N2-[3-[(N-methylamino)carbonylmethyleneoxy]phenyl]-2,4-pyrimidinediamine. $^1$H NMR (CD$_3$OD): δ 7.94 (d, 1H, J=3.3 Hz), 7.69 (t, 1H, J=1.8 Hz), 7.56 (ddd, 1H, J=1.2, 1.2, and 8.1 Hz), 7.35 (m, 1H), 7.31 (t, 1H, J=8.1 Hz), 7.18 (d, 1H, J=2.4 Hz), 7.17 (d, 1H, J=1.2 Hz), 6.84 (dd, 1H, J=2.4 and 8.1 Hz), 6.63-6.58 (m, 1H), 4.42 (s, 2H), 4.20 (q, 2H, J=7.2 Hz), 3.93 (s, 2H), 2.80 (s, 3H), 1.27 (t, 3H, J=7.2 Hz); $^{19}$F NMR (282 MHz, CD$_3$OD): −47371; LCMS: purity: 89%; MS (m/e): 513(MH$^+$).

7.3.851 N4-[3-[(N-(Ethylamino)carbonyloxy]phenyl]-5-fluoro-N2-[3-[(N-methylamino)carbonylmethyleneoxy]phenyl]-2,4-pyrimidinediamine (R926919)

In a like manner to the preparation of 5-fluoro-N4-[3-[(N-allylamino)carbonyloxy]phenyl]-N2-[3-[(N-methylamino)carbonylmethyleneoxy]phenyl]-2,4-pyrimidinediamine and ethyl isocyanate were reacted to provide N4-[3-[(N-(ethylamino)carbonyloxy]phenyl]-5-fluoro-N2-[3-[(N-methylamino)carbonylmethyleneoxy]phenyl]-2,4-pyrimidinediamine. $^1$H NMR (CD$_3$OD): δ 7.94 (d, 1H, J=3.3 Hz), 6.84-6.79 (m, 2H), 7.61-7.55 (m, 2H), 6.62-6.56 (m, 2H), 7.33-7.27 (m, 1H), 7.19-7.17 (m, 1H), 4.41 (s, 2H), 3.23 (q, 2H, J=7.2 Hz), 2.80 (s, 3H), 1.17 (t, 3H, J=7.2 Hz); $^{19}$F NMR (282 MHz, CD$_3$OD): −47378; LCMS: purity: 100%; MS (m/e): 455(MH$^+$).

7.3.852 5-Fluoro-N2-[3-[(N-methylamino)carbonylmethyleneoxy]phenyl]-N4-(4-methyl-3-trifluoromethylphenyl)-2,4-pyrimidinediamine (R926922)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(4-methyl-3-trifluoromethylphenyl)-4-pyrimidineamine and 3-[(N-methylamino)carbonylmethyleneoxy]aniline were reacted to provide 5-fluoro-N2-[3-[(N-methylamino)carbonylmethyleneoxy]phenyl]-N4-(4-methyl-3-trifluoromethylphenyl)-2,4-pyrimidinediamine. $^1$H NMR (DMSO-$d_6$): δ 9.79 (bs, 1H), 9.48 (bs, 1H), 8.17 (d, 1H, J=4.2 Hz), 8.10 (d, 1H, J=6.3 Hz), 7.96 (d, 1H, J=4.8 Hz), 7.89 (d, 1H, J=2.1 Hz), 7.38 (d, 1H, J=9.0 Hz), 7.26-7.20 (m, 2H), 7.11 (t, 1H, J=8.4 Hz), 6.53 (d, 1H, J=8.4 Hz), 4.33 (s, 2H), 2.62 (d, 3H, J=4.8 Hz), 2.39 (s, 3H); LCMS: purity: 94%; MS (m/e): 450(MH$^+$).

7.3.853 5-Fluoro-N4-(4-fluoro-3-methylphenyl)-N2-[3-[(N-methylamino)carbonylmethyleneoxy]phenyl]-2,4-pyrimidinediamine (R926923)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(4-fluoro-3-methylphenyl)-4-pyrimidineamine and 3-[(N-methylamino)carbonylmethyleneoxy]aniline were reacted to provide 5-Fluoro-N4-(4-fluoro-3-methylphenyl)-N2-[3-[(N-methylamino)carbonylmethyleneoxy]phenyl]-2,4-pyrimidinediamine. $^1$H NMR (DMSO-$d_6$): δ 9.67 (bs, 1H), 9.51 (bs, 1H), 8.14 (d, 1H, J=4.8 Hz), 7.95 (d, 1H, J=4.2 Hz), 7.64 (dd, 1H, J=2.7 and 6.9 Hz), 7.57-7.50 (m, 1H), 7.23-7.06 (m, 4H), 6.55 (d, 1H, J=7.5 Hz), 4.33 (s, 2H), 2.63 (d, 3H, J=4.8 Hz), 2.19 (s, 3H); LCMS: purity: 94%; MS (m/e): 400(MH$^+$).

7.3.854 5-Fluoro-N2-[3-[(N-methylamino)carbonylmethyleneoxy]phenyl]-N4-(3-trifluoromethylthiophenyl)-2,4-pyrimidinediamine (R926925)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(3-trifluoromethylthiophenyl)-4-pyrimidineamine and 3-[(N-methylamino)carbonylmethyleneoxy]aniline were reacted to provide 5-fluoro-N2-[3-[(N-methylamino)carbonylmethyleneoxy]phenyl]-N4-(3-trifluoromethylthiophenyl)-2,4-pyrimidinediamine. $^1$H NMR (DMSO-$d_6$): δ 9.83 (bs, 1H), 9.49 (bs, 1H), 8.21-8.15 (m, 2H), 8.01 (s, 1H), 7.94 (bs, 1H), 7.49 (t, 1H, J=7.8 Hz), 7.38 (d, 1H, J=7.8 Hz), 7.29 (s, 1H), 7.22 (d, 1H, J=7.5 Hz), 7.14 (t, 1H, J=8.4 Hz), 6.54 (d, 1H, J=9.9 Hz), 4.34 (s, 2H), 2.62 (d, 3H, J=4.8 Hz); LCMS: purity: 98%; MS (m/e): 468(MH$^+$).

7.3.855 N2-[3,5-Bis(methoxycarbonylmethyleneoxy)phenyl]-5-fluoro-N4-(3-hydroxyphenyl)-2,4-pyrimidinediamine (R926926)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(3-hydroxyphenyl)-4-pyrimidineamine and 3,5-bis(methoxycarbonylmethyleneoxy)aniline were reacted to provide N2-[3,5-bis(methoxycarbonylmethyleneoxy)phenyl]-5-fluoro-N4-(3-hydroxyphenyl)-2,4-pyrimidinediamine. $^1$H NMR (CD$_3$OD): δ 7.92 (d, 1H, J=4.2 Hz), 7.20-7.10 (m, 3H), 6.92 (d, 2H, J=2.4 Hz), 6.52 (ddd, 1H, J=1.8, 1.8, and 7.5 Hz), 6.12 (t, 1H, J=2.4 Hz), 4.55 (s, 4H), 3.77 (s, 6H); $^{19}$F NMR (282 MHz, CD$_3$OD): −47342; LCMS: purity: 92%; MS (m/e): 473(MH$^+$)

7.3.856 5-Fluoro-N2-[3-hydroxy-5-(methoxycarbonylmethyleneoxy)phenyl]-N4-(3-hydroxyphenyl)-2,4-pyrimidinediamine (R926927)

In a like manner to the preparation of N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)-4-pyrimidineamine and 3-hydroxy-5-(methoxycarbonylmethyleneoxy)aniline were reacted to produce 5-fluoro-N2-[3-hydroxy-5-(methoxycarbonylmethyleneoxy)phenyl]-N4-(3-hydroxyphenyl)-2,4-pyrimidinediamine. $^1$H NMR (DMSO-$d_6$): δ 8.13 (d, 1H, J=4.8 Hz), 7.37-7.33 (m, 1H), 7.11 (t, 1H, J=8.4 Hz), 7.07-7.05 (m, 1H), 6.73-6.65 (m, 2H), 6.51 (dd, 1H, J=2.1 and 8.1 Hz), 5.97 ((s, 1H), 4.59 (s, 2H), 3.67 (s, 3H); LCMS: purity: 93%; MS (m/e): 401(MH$^+$).

7.3.857 N2-[3-[(N-Ethylamino)carbonyloxy]phenyl]-5-fluoro-N4-(3-hydroxyphenyl)-2,4-pyrimidinediamine (R926928)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(3-hydroxyphenyl)-4-pyrimidineamine and 3-[(N-ethylamino)carbonyloxy]aniline were reacted to provide N2-[3-[(N-ethylamino)carbonyloxy]phenyl]-5-fluoro-N4-(3-hydroxyphenyl)-2,4-pyrimidinediamine. $^1$H NMR (CDCl$_3$): δ 7.92 (d, 1H, J=3.0 Hz), 7.67-7.55 (m, 2H), 7.24 (t, 1H, J=7.5 Hz), 7.16 (t, 1H, J=7.5 Hz), 7.07-6.98 (m, 2H), 6.84-6.79 (m, 2H), 6.67 (m, 2H), 6.60 (d, 1H, J=7.5 Hz), 5.22-5.14 (m, 1H), 3.36-3.27 (m, 2H), 2.95 (s, 1H), 2.88 (s, 1H), 1.20 (t, 3H, J=7.5 Hz); $^{19}$F NMR (282 MHz, CDCl$_3$): −47012; LCMS: purity: 99%; MS (m/e): 384(MH$^+$).

7.3.858 5-Fluoro-N2-[3-hydroxy-5-[(N-methylamino) carbonylmethyleneoxy]phenyl]-N4-(3-hydroxyphenyl)-2,4-pyrimidinediamine (R926929)

A solution of 5-fluoro-N2-[3-hydroxy-5-(methoxycarbonylmethyleneoxy)phenyl]-N4-(3-hydroxyphenyl)-2,4-pyrimidinediamine (56 mg, 0.13 mmol), methylamine hydrochloride (90 mg, 1.3 mmol), and diisopropylethylamine (0.12 mL, 0.70 mmol) in methanol (2 mL) was heated at 100° C. for 8 h. The cooled reaction mixture was poured into 1N HCl (20 mL) saturated with NaCl, and extracted with ethyl acetate. Purification by preparative TLC (5% methanol/dichloromethane) gave the product, 5-fluoro-N2-[3-hydroxy-5-[(N-methylamino)carbonylmethyleneoxy]phenyl]-N4-(3-hydroxyphenyl)-2,4-pyrimidinediamine. $^1$H NMR (DMSO-$d_6$): δ 9.29 (bs, 1H), 9.16 (s, 1H), 9.01 (s, 1H), 8.06 (d, 1H, J=3.3 Hz), 7.87 (d, 1H, J=4.8 Hz), 7.42 (dd, 1H, J=1.5 and 8.1 Hz), 7.13-7.05 (m, 2H), 6.89-6.81 (m, 2H), 6.45 (dd, 1H, J=2.4 and 8.4 Hz), 5.92 (t, 1H, J=2.4 Hz), 4.28 (s, 2H), 3.30(bs, 1H), 2.63 (s, 3H); LCMS: purity: 94%; MS (m/e): 400(MH$^+$).

7.3.859 N2-[3,5-Bis[(N-methylamino)carbonylmethyleneoxy]phenyl]-5-fluoro-N4-(3-hydroxyphenyl)-2,4-pyrimidinediamine (R926930)

In a like manner to the preparation of 5-fluoro-N2-[3-hydroxy-5-[(N-methylamino)carbonylmethyleneoxy]phenyl]-N4-(3-hydroxyphenyl)-2,4-pyrimidinediamine, N2-[3,5-bis(methoxycarbonylmethyleneoxy)phenyl]-5-fluoro-N4-(3-hydroxyphenyl)-2,4-pyrimidinediamine, methylamine hydrochloride, and diisopropylethylamine were reacted to give N2-[3,5-Bis[(N-methylamino)carbonylmethyleneoxy]

phenyl]-5-fluoro-N4-(3-hydroxyphenyl)-2,4-pyrimidinediamine. $^1$H NMR (CD$_3$OD): δ 7.91 (bs, 1H), 7.25 (t, 1H, J=1.8 Hz), 7.14-7.11 (m, 1H), 6.98 (s, 1H), 6.97 (s, 1H), 6.55-6.50 (m, 1H), 6.26-6.23 (m, 1H), 4.39 (s, 4H), 2.81 (s, 6H); $^{19}$F NMR (282 MHz, CD$_3$OD): −47307; LCMS: purity: 99%; MS (m/e): 471=(MH$^+$)

7.3.860 5-Fluoro-N4-[(1H)-indol-5-yl]-N2-[3-[(N-methylamino) carbonylmethyleneoxy]phenyl]-2,4-pyrimidinediamine (R926931)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[(1H)-indol-5-yl]-4-pyrimidineamine and 3-[(N-methylamino)carbonylmethyleneoxy]aniline were reacted to provide 5-fluoro-N4-[(1H)-indol-5-yl]-N2-[3-[(N-methylamino)carbonylmethyleneoxy]phenyl]-2,4-pyrimidinediamine. $^1$H NMR (DMSO-d$_6$): δ 11.09 (bs, 1H), 9.93 (bs, 1H), 9.67 (bs, 1H), 8.12 (d, 1H, J=4.81 Hz), 7.94-7.82 (m, 2H), 7.37-7.22 (m, 4H), 7.13 (bs, 1H), 7.07 (t, 1H, J=8.1 Hz), 6.58 (d, 1H, J=7.8 Hz), 6.37 (s, 1H), 4.32 (s, 2H), 2.61 (d, 3H, J=4.2 Hz); LCMS: purity: 92%; MS (m/e): 407(MH$^+$).

7.3.861 5-Fluoro-N2-(3-hydroxyphenyl)-N4-[(1H)-indol-5-yl]-2,4-pyrimidinediamine (R926932)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[(1H)-indol-5-yl]-4-pyrimidineamine and 3-hydroxyaniline were reacted to provide 5-fluoro-N2-(3-hydroxyphenyl)-N4-[(1H)-indol-5-yl]-2,4-pyrimidinediamine. $^1$H NMR (DMSO-d$_6$): δ 11.13 (s, 1H), 10.25 (bs, 1H), 9.87 (bs, 1H), 9.43 (bs, 1H), 8.16 (d, 1H, J=5.1 Hz), 7.89 (d, 1H, J=0.09 Hz), 7.39-7.27 (m, 3H), 7.03-6.94 (m, 2H), 6.83 (s, 1H), 6.48 (d, 1H, J=7.5 Hz), 6.40 (t, 1H, J=2.1 Hz); LCMS: purity: 92%; MS (m/e): 336(MH$^+$).

7.3.862 5-Fluoro-N4-[(1H)-indol-6-yl]-N2-[3-[(N-methylamino)carbonyl]phenyl]-2,4-pyrimidinediamine (R926933)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[(1H)indol-6-yl]-4-pyrimidineamine and 3-[(N-methylamino)carbonyl]aniline were reacted to provide 5-fluoro-N4-[(1H)indol-6-yl]-N2-[3-[(N-methylamino)carbonyl]phenyl]-2,4-pyrimidinediamine. $^1$H NMR (CD$_3$OD): δ 7.99 (t, 1H, J=1.8 Hz), 7.89 (d, 1H, J=3.6 Hz), 7.78-7.76 (m, 1H), 7.70 (ddd, 1H, J=1.2, 2.4, and 8.4 Hz), 7.50 (d, 1H, J=9.0 Hz), 7.31 (td, 1H, J=1.2 and 7.5 Hz), 7.23-7.17 (m, 3H), 6.43 (dd, 1H, J=1.2 and 3.6 Hz), 2.73 (s, 3H); $^{19}$F NMR (282 MHz, CD$_3$OD): −47513; LCMS: purity: 99%; MS (m/e): 377(MH$^+$).

7.3.863 5-Fluoro-N4-[(1H)-indol-6-yl]-N2-[3-(N-morpholinocarbonyl)phenyl]-2,4-pyrimidinediamine (R926934)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[(1H)indol-6-yl]-4-pyrimidineamine and 3-(N-morpholinocarbonyl)aniline were reacted to provide 5-fluoro-N4-[(1H)indol-6-yl]-N2-[3-(N-morpholinocarbonyl)phenyl]-2,4-pyrimidinediamine. $^1$H NMR (CD$_3$OD): δ 7.96 (d, 1H, J=4.8 Hz), 7.73 (t, 1H, J=2.4 Hz), 7.66 (d, 1H, J=1.2 Hz), 7.52 (d, 1H, J=8.1 Hz), 7.49 (ddd, 1H, J=0.09, 2.1, and 8.1 Hz), 7.33-7.26 (m, 2H), 7.19 (dd, 1H, J=1.8 and 8.7 Hz), 7.12-7.06 (m, 1H), 6.45 (dd, 1H, J=1.3 and 3.0 Hz), 3.62-3.15 (m, 8H); $^{19}$F NMR (282 MHz, CD$_3$OD): −46545; LCMS: purity: 91%; MS (m/e): 433(MH$^+$).

7.3.864 N2-[3-[[4-(Ethoxycarbonyl)piperidino]carbonyl]phenyl]-5-fluoro-N4-[(1H)-indol-6-yl]-2,4-pyrimidinediamine (R926935)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-[(1H)indol-6-yl]-4-pyrimidineamine and 3-[4-(ethoxycarbonyl)piperidino]aniline were reacted to provide N2-[3-[[4-(ethoxycarbonyl)piperidino]carbonyl]phenyl]-5-fluoro-N4-[(1H)-indol-6-yl]-2,4-pyrimidinediamine. $^1$H NMR (CD$_3$OD): δ 7.99 (d, 1H, J=5.1 Hz), 7.64-7.58 (m, 2H), 7.52 (d, 1H, J=8.7 Hz), 7.48 (ddd, 1H, J=1.2, 2.4, and 8.1 Hz), 7.34-7.27 (m, 2H), 7.19-7.13 (m, 2H), 6.46 (dd, 1H, J=1.2 and 4.2 Hz), 4.40-4.27 (m, 1H), 4.13 (q, 2H, J=6.9 Hz), 3.56-3.41 (m, 1H), 2.95-2.82 (m, 2H), 2.58-2.47 (m, 1H), 1.98-1.82 (m, 1H), 1.75-7.60 (m, 1H), 1.58-1.39 (m, 2H), 1.24 (t, 3H, J=6.9 Hz); $^{19}$F NMR (282 MHz, CD$_3$OD): −46101; LCMS: purity: 90%; MS (m/e): 503(MH$^+$).

7.3.865 5-Fluoro-N4-(3-hydroxyphenyl)-N2-[3-[(N-methylamino)carbonyl]phenyl]-2,4-pyrimidinediamine (R926936)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(3-hydroxyphenyl)-4-pyrimidineamine and 3-[(N-methylamino)carbonyl]aniline were reacted to provide 5-fluoro-N4-(3-hydroxyphenyl)-N2-[3-[(N-methylamino)carbonyl]phenyl]-2,4-pyrimidinediamine. $^1$H NMR (CD$_3$OD): δ 8.01 (d, 1H, J=5.4 Hz), 7.84 (t, 1H, J=1.8 Hz), 7.68-7.61 (m, 2H), 7.45 (t, 1H, J=8.4 Hz), 7.16-7.03 (m, 3H), 6.68 (td, 1H, J=1.2 and 8.7 Hz), 2.90 (s, 3H); LCMS: purity: 95%; MS (m/e): 354(MH$^+$)

7.3.866 5-Fluoro-N4-(3-hydroxyphenyl)-N2-[3-[(N-propylamino)carbonyl]phenyl]-2,4-pyrimidinediamine (R926937)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(3-hydroxyphenyl)-4-pyrimidineamine and 3-[(N-propylamino)carbonyl]aniline were reacted to provide 5-fluoro-N4-(3-hydroxyphenyl)-N2-[3-[(N-propylamino)carbonyl]phenyl]-2,4-pyrimidinediamine. $^1$H NMR (CD$_3$OD): δ 8.00 (d, 1H, J=5.4 Hz), 7.84 (t, 1H, J=1.8 Hz), 7.69-7.59 (m, 2H), 7.44 (t, 1H, J=7.5 Hz), 7.16-7.05 (m, 3H), 6.67 (td, 1H, J=2.4 and 7.2 Hz), 3.34-3.29 (m, 2H), 1.65-1.56 (m, 2H), 0.96 (t, 3H, J=7.5 Hz); $^{19}$F NMR (282 MHz, CD$_3$OD): −46049; LCMS: purity: 94%; MS (m/e): 382(MH$^+$)

7.3.867 5-Fluoro-N4-(3-hydroxyphenyl)-N2-[3-(N-morphonlinocarbonyl)phenyl]-2,4-pyrimidinediamine (R926938)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(3-hydroxyphenyl)-4-pyrimidineamine and 3-(N-morpholinocarbonyl)aniline were reacted to provide 5-fluoro-N4-(3-hydroxyphenyl)-N2-[3-(N-morphonlinocarbonyl)phenyl]-2,4-pyrimidinediamine. $^1$H NMR (CD$_3$OD): δ 7.93 (d, 1H, J=3.6 Hz), 7.84 (t, 1H, J=1.8 Hz), 7.62 (ddd, 1H, J=1.2, 2.4, and 8.1 Hz), 7.32 (t, 1H, J=8.4 Hz), 7.19-7.10 (m, 3H), 6.96 (dd, 1H, J=1.2 and 7.8 Hz), 6.56 (ddd, 1H, J=1.2, 3.0, and 6.9 Hz), 3.78-3.34 (m, 8H); $^{19}$F NMR (282 MHz, CD$_3$OD): −47323; LCMS: purity: 100%; MS (m/e): 410(MH$^+$).

7.3.868 N2-[3-[[4-(Ethoxycarbonyl)piperidino]carbonyl]phenyl]-5-fluoro-N4-(3-hydroxyphenyl)-2,4-pyrimidinediamine (R926939)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(3-hydroxyphenyl)-4-pyrimidineamine and 3-[[4-(ethoxycarbonyl)piperidino]carbonyl]aniline were reacted to provide N2-[3-[[4-(ethoxycarbonyl)piperidino]carbonyl]phenyl]-5-fluoro-N4-(3-hydroxyphenyl)-2,4-pyrimidinediamine. $^1$H NMR (CD$_3$OD): δ 7.92 (d, 1H, J=3.6 Hz), 7.82 (s, 1H), 7.62 (td, 1H, J=1.2 and 8.4 Hz), 7.30 (t, 1H, J=8.4 Hz), 7.19-7.09 (m, 3H), 6.93 (d, 1H, J=7.5 Hz), 6.55 (td, 1H, J=1.2 and 7.5 Hz), 4.43 (bd, 1H, J=12.3 Hz), 4.13 (q, 2H, J=6.9 Hz), 3.7 (bd, 1H, J=11.7 Hz), 3.10-2.92 (m, 2H), 2.67-2.55 (m, 1H), 2.06-1.50 (m, 4H), 1.24 (t, H, J=6.9 Hz); $^{19}$F NMR (282 MHz, CD$_3$OD): −47299; LCMS: purity: 99%; MS (m/e): 480(MH$^+$).

7.3.869 N4-[3-[[4-(Ethoxycarbonyl)piperidino]carbonyl]phenyl]-5-fluoro-N2-(3-hydroxyphenyl)-2,4-pyrimidinediamine (R926940)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-[3-[[4-(ethoxycarbonyl)piperidino]carbonyl]phenyl]-5-fluoro-4-pyrimidineamine and 3-hydroxyaniline were reacted to provide N4-[3-[[4-(ethoxycarbonyl)piperidino]carbonyl]phenyl]-5-fluoro-N2-(3-hydroxyphenyl)-2,4-pyrimidinediamine. $^1$H NMR (CD$_3$OD): δ 7.93 (d, 1H, J=3.6 Hz), 7.89 (t, 1H, J=1.8 Hz), 7.83 (td, 1H, J=1.2 and 8.4 Hz), 7.41 (t, 1H, J=7.8 Hz), 7.11-6.95 (m, 4H), 6.41 (td, 1H, J=1.8 and 7.2 Hz), 4.44 (bd, 1H, J=12.9 Hz), 4.10 (q, 2H, J=7.2 Hz), 3.73 (bd, 1H, J=12.3 Hz), 3.18-2.98 (m, 2H), 2.67-2.55 (m, 1H), 2.05-1.53 (m, 4H), 1.23 (t, 3H, J=7.2 Hz); $^{19}$F NMR (282 MHz, CD$_3$OD): −47483; LCMS: purity: 99%; MS (m/e): 480(MH$^+$).

7.3.870 N4-[3-[[4-(Ethoxycarbonyl)piperidino]carbonyl]phenyl]-5-fluoro-N2-[3-[(N-methylamino)carbonylmethyleneoxy]phenyl]-2,4-pyrimidinediamine (R926941)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-N4-[3-[[4-(ethoxycarbonyl)piperidino]carbonyl]phenyl]-5-fluoro-4-pyrimidineamine and 3-[(N-methylamino)carbonylmethyleneoxy]aniline were reacted to provide N4-[3-[[4-(ethoxycarbonyl)piperidino]carbonyl]phenyl]-5-fluoro-N2-[3-[(N-methylamino)carbonylmethyleneoxy]phenyl]-2,4-pyrimidinediamine. $^1$H NMR (CD$_3$OD): δ 7.95 (d, 1H, J=3.3 Hz), 7.90 (t, 1H, J=1.8 Hz), 7.80 (ddd, 1H, J=0.09, 2.1, 8.1 Hz), 7.39 (t, 1H, J=7.5 Hz), 7.31 (t, 1H, J=1.2 Hz), 7.17-7.06 (m, 3H), 6.60-6.54 (m, 1H), 4.48-4.38 (m, 3H), 4.10 (q, 2H, J=6.9 Hz), 3.78-3.65 (m, 1H), 3.17-2.95 (m, 2H), 2.79 (s, 3H), 2.65-2.53 (m, 1H), 2.01-1.52 (m, 4H), 1.22 (t, 3H, J=6.9 Hz); $^{19}$F NMR (282 MHz, CD$_3$OD): −47309; LCMS: purity: 99%; MS (m/e): 551(MH$^+$).

7.3.871 Reaction of 3-hydroxyaniline and 2-chloro-5-fluoro-N4-(1,2,3,4-tetrahydro-1-hydroxynaphthalen-7-yl)-4-pyrimidineamine In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(1,2,3,4-tetrahydro-1-hydroxynaphthalen-7-yl)-4-pyrimidineamine and 3-hydroxyaniline were reacted to provide two products, R926942 and R926943.

7.3.872 N4-(1-Ethoxy-1,2,3,4-tetrahydronaphthalen-7-yl)-5-fluoro-N2-(3-hydroxyphenyl)-2,4-pyrimidinediamine (R926942)

$^1$H NMR (DMSO-d$_6$): δ 9.23 (bs, 1H), 9.14 (bs, 1H), 8.97 (bs, 1H), 8.04 (d, 1H, J=3.6 Hz), 7.71 (dd, 1H, J=2.4 and 7.5 Hz), 7.56 (bs, 1H), 7.14-6.98 (m, 3H), 6.93 (t, 1H, J=8.1 Hz), 6.29 (bd, 1H, J=7.2 Hz), 4.35 (bs, 1H), 3.59-3.36 (m, 2H), 2.69-2.60 (m, 2H), 1.89-1.78 (m, 2H), 1.72-1.56 (m, 2H), 1.08 (t, 3H, J=6.9 Hz); LCMS: purity: 96%; MS (m/e): 395 (MH$^+$).

7.3.873 5-Fluoro-N4-(3,4-dihydronaphthalen-7-yl)-N2-(3-hydroxyphenyl)-2,4-pyrimidinediamine (R926943)

$^1$H NMR (DMSO-d$_6$): δ 9.19 (bs, 2H), 9.01 (s, 1H), 8.04 (d, 1H, J=3.6 Hz), 7.56-7.46 (m, 2H), 7.16-7.03 (m, 3H), 6.94 (t, 1H, J=8.1 Hz), 6.46 (d, 1H, J=9.6 Hz), 6.03 (dd, 1H, J=1.8 and 8.1 Hz), 6.09-6.01 (m, 1H), 2.69 (t, 2H, J=8.4 Hz), 2.28-2.20 (m, 2H); $^{19}$F NMR (282 MHz, DMSO-d$_6$): −46541; LCMS: purity: 98%; MS (m/e): 349(MH$^+$).

7.3.874 5-Fluoro-N4-(3,4-dihydronaphthalen-7-yl)-N2-[3-[(N-methylamino)carbonylmethyleneoxy]phenyl]-2,4-pyrimidinediamine (R926944)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(1,2,3,4-tetrahydro-1-hydroxynaphthalen-7-yl)-4-pyrimidineamine and 3-[(N-methylamino)carbonylmethyleneoxy]aniline were reacted to provide 5-fluoro-N4-(3,4-dihydronaphthalen-7-yl)-N2-[3-[(N-methylamino)carbonylmethyleneoxy]phenyl]-2,4-pyrimidinediamine. $^1$H NMR (DMSO-d$_6$): δ 8.07 (d, 1H, J=3.9 Hz), 7.53-7.45 (m, 2H), 7.32-7.29 (m, 2H), 7.11-7.01 (m, 2H), 6.49-6.40 (m, 2H), 6.08-6.00 (m, 1H), 4.32 (s, 2H), 2.69 (t, 2H, J=8.4 Hz), 2.62 (s, 3H); LCMS: purity: 99%; MS (m/e): 420(MH$^+$).

7.3.875 N4-(3-Chloro-4-methoxyphenyl)-5-fluoro-N2-(3-hydroxyphenyl)-2,4-pyrimidinediamine (R926945)

In a like manner to the preparation of N4-(3,4-ethylenedioxyphenyl)-5-fluoro-N2-(3-hydroxyphenyl)-2,4-pyrimidinediamine, 2-chloro-N4-(3-chloro-4-methoxyphenyl)-5-fluoro-4-pyrimidineamine and 3-hydroxyaniline were reacted to produce N4-(3-chloro-4-methoxyphenyl)-5-fluoro-N2-(3-hydroxyphenyl)-2,4-pyrimidinediamine. $^1$H NMR (CD$_3$OD): δ 7.91 (d, 1H, J=5.4 Hz), 7.71 (d, 1H, J=2.4 Hz), 7.58 (dd, 1H, J=3.0 and 9.0 Hz), 7.15 (t, 1H, J=8.4 Hz), 7.06 (d, 1H, J=8.7 Hz), 6.92 (td, 1H, J=1.8 and 9.9 Hz), 6.88 (t, 1H, J=1.8 Hz), 6.61 (ddd, 1H, J=1.2, 2.4, and 8.1 Hz), 3.89 (s, 3H); $^{19}$F NMR (282 MHz, CD$_3$OD): −46612; LCMS: purity: 98%; MS (m/e): 362(MH$^+$).

7.3.876 N2,N4-Bis(3-chloro-4-methoxyphenyl)-5-fluoro-2,4-pyrimidinediamine (R926946)

In a like manner to the preparation of N2,N4-bis(3-hydroxyphenyl)-5-fluoro-2,4-pyrimidinediamine, 2,4-dichloro-5-fluoropyrimidine and 3-chloro-4-methoxyaniline were reacted to provide N2,N4-Bis(3-chloro-4-methoxyphenyl)-5-fluoro-2,4-pyrimidinediamine. $^1$H NMR (DMSO-d$_6$): δ 9.90 (bs, 1H), 9.68 (bs, 1H), 8.16 (d, 1H, J=4.8 Hz), 7.72 (d, 1H, J=2.4 Hz), 7.65 (d, 1H, J=2.1 Hz), 7.58 (dd, 1H, J=2.4 and 9.0 Hz), 7.38 (dd, 1H, J=2.7 and 9.3 Hz), 7.12 (d, 1H, J=8.7 Hz), 7.12 (d, 1H, J=8.7 Hz), 7.05 (d, 1H, J=8.7 Hz), 3.83 (s, 3H), 3.79 (s, 3H); LCMS: purity: 99%; MS (m/e): 410(MH$^+$).

7.3.877 5-Fluoro-N4-(1,2,3,4-tetrahydro-1-oxonaphthalen-7-yl)-N2-[3-[(N-methylamino)carbonylmethyleneoxy]phenyl]-2,4-pyrimidinediamine (R926947)

In like manner to the preparation of 5-fluoro-N4-(3-hydroxyphenyl)-N2-[4-(3-phenyl-1,2,4-oxadiazol-5-yl)methyleneoxyphenyl]-2,4-pyrimidinediamine, 2-chloro-5-fluoro-N4-(1,2,3,4-tetrahydro-1-oxo-naphthalen-7-yl)-4-pyrimidineamine and 3-[(N-methylamino)carbonylmethyleneoxy]aniline were reacted to provide 5-fluoro-N4-(1,2,3,4-tetrahydro-1-oxo-naphthalen-7-yl)-N2-[3-[(N-methylamino)carbonylmethyleneoxy]phenyl]-2,4-pyrimidinediamine. $^1$H NMR (DMSO-d$_6$): δ 9.89 (bs, 1H), 9.55 (bs, 1H), 8.17 (d, 1H, J=4.2 Hz), 8.04-7.93 (m, 3H), 7.32 (d, 1H, J=8.7 Hz), 7.25-7.16 (m, 2H), 7.09 (t, 1H, J=7.5 Hz), 6.52 (dd, 1H, J=2.4 and 8.1 Hz), 4.28 (s, 2H), 2.90 (t, 2H, J=6.0 Hz), 2.63 (d, 3H, J=4.8 Hz), 2.59 (t, 2H, J=6.6 Hz), 2.02 (t, 2H, J=6.6 Hz); LCMS: purity: 93%; MS (m/e): 436(MH$^+$).

7.3.878 5-Fluoro-N4-(1,2,3,4-tetrahydro-1-hydroxyiminonaphthalen-7-yl)-N2-[3-[(N-methylamino)carbonylmethyleneoxy]phenyl]-2,4-pyrimidinediamine (R926948)

A solution of 5-fluoro-N4-(1,2,3,4-tetrahydro-1-oxo-naphthalen-7-yl)-N2-[3-[(N-methylamino)carbonylmethyleneoxy]phenyl]-2,4-pyrimidinediamine (42 mg, 0.095 mmole) and hydroxylamine hydrochloride (8.5 mg, 0.12 mmole) in DMF (1 mL) was heated at 60° C. for 12 h. The reaction mixture was cooled to rt and then poured into brine (20 mL). A brown solid was collected by suction filtration and further purified by reverse phase chromatography to provide 5-fluoro-N4-(1,2,3,4-tetrahydro-1-hydroxyiminonaphthalen-7-yl)-N2-[3-[(N-methylamino)carbonylmethyleneoxy]phenyl]-2,4-pyrimidinediamine. $^1$H NMR (DMSO-d$_6$): δ 8.13-8.05 (m, 2H), 7.99-7.92 (m, 2H), 7.77-7.72 (m, 1H), 7.33-7.21 (m, 2H), 7.14 (d, 1H, J=8.7 Hz), 7.10-7.02 (m, 1H), 6.47 (dd, 1H, J=2.4 and 7.5 Hz), 4.30 (s, 2H), 2.90 (t, 1H, J=6.0 Hz), 2.70-2.40 (m, 6H), 2.07-1.98 (m, 1H), 1.74 (t, 1H, J=6.6 Hz); LCMS: purity: 96%; MS (m/e): 451(MH$^+$).

7.3.879 5-Fluoro-N4-(1,2,3,4-tetrahydro-1-hydroxynaphthalen-7-yl)-N2-[3-[(N-methylamino)carbonylmethyleneoxy]phenyl]-2,4-pyrimidinediamine (R926949)

To a 0° C. suspension of 5-fluoro-N4-(1,2,3,4-tetrahydro-1-oxo-naphthalen-7-yl)-N2-[3-[(N-methylamino)carbonylmethyleneoxy]phenyl]-2,4-pyrimidinediamine (50 mg, 0.11 mmol) in anhydrous THF (2.0 mL) was added lithiumborohydride (5 mg, 0.23 mmole). The reaction mixture was warmed to rt, stirred for 8 h, and then quenched with methanol. The reaction mixture was poured into water and then extracted with ethyl acetate. Purification by preparative TLC (5% methanol/dichloromethane) provided 5-fluoro-N4-(1,2,3,4-tetrahydro-1-hydroxynaphthalen-7-yl)-N2-[3-[(N-methylamino)carbonylmethyleneoxy]phenyl]-2,4-pyrimidinediamine. LCMS: purity: 96%; MS (m/e): 438(MH$^+$).

7.3.880 N4-(3-Chloro-4-methoxyphenyl)-5-fluoro-N2-[2-(methoxycarbonyl) benzofuran-5-yl]-2,4-pyrimidinediamine (R926950)

In a like manner to the preparation of N4-(3,4-ethylenedioxyphenyl)-5-fluoro-N2-(3-hydroxyphenyl)-2,4-pyrimidinediamine, 2-chloro-N4-(3-chloro-4-methoxyphenyl)-5-fluoro-4-pyrimidineamine and 5-amino-2-(methoxycarbonyl)benzofuran were reacted to produce N4-(3-chloro-4-methoxyphenyl)-5-fluoro-N2-[2-(methoxycarbonyl)benzofuran-5-yl]-2,4-pyrimidinediamine. $^1$H NMR (DMSO-d$_6$): δ 9.34 (bs, 2H), 8.10-8.07 (m, 2H), 7.78 (t, 1H, J=2.7 Hz), 7.66-7.53 (m, 4H), 7.12 (d, 1H, J=9.3 Hz), 3.87 (s, 3H), 3.85 (s, 3H); LCMS: purity: 99%; MS (m/e): 443(MH$^+$).

7.3.881 N4-(3-Chloro-4-methoxyphenyl)-5-fluoro-N2-[2,3-dihydro-2-(methoxycarbonyl)benzofuran-5-yl]-2,4-pyrimidinediamine (R926951)

In a like manner to the preparation of N4-(3,4-ethylenedioxyphenyl)-5-fluoro-N2-(3-hydroxyphenyl)-2,4-pyrimidinediamine, 2-chloro-N4-(3-chloro-4-methoxyphenyl)-5-fluoro-4-pyrimidineamine and 5-amino-2,3-dihydro-2-(methoxycarbonyl)benzofuran were reacted to produce N4-(3-chloro-4-methoxyphenyl)-5-fluoro-N2-[2,3-dihydro-2-(methoxycarbonyl)benzofuran-5-yl]-2,4-pyrimidinediamine. $^1$H NMR (DMSO-d$_6$): δ 10.31 (bs, 1H), 10.04 (bs, 1H), 8.21 (d, 1H, J=4.8 Hz), 7.75 (t, 1H, J=3.0 Hz), 7.54 (td, 1H, J=3.0 and 9.0 Hz), 7.34 (s, 1H), 7.20-7.15 (m, 2H), 6.80 (d, 1H, J=8.1 Hz), 5.38-5.31 (m, 1H), 3.85 (s, 3H), 3.69 (s, 3H), 3.49 (dd, 1H, J=11.1 and 16.5 Hz); LCMS: purity: 99%; MS (m/e): 446(MH$^+$).

7.3.882 N4-(3-Chloro-4-trifluoromethoxyphenyl)-5-fluoro-N2-[2,3-dihydro-2-(methoxycarbonyl)benzofuran-5-yl]-2,4-pyrimidinediamine (R926953)

In a like manner to the preparation of N4-(3,4-ethylenedioxyphenyl)-5-fluoro-N2-(3-hydroxyphenyl)-2,4-pyrimidinediamine, 2-chloro-N4-(3-chloro-4-trifluoromethoxyphenyl)-5-fluoro-4-pyrimidineamine and 5-amino-2,3-dihydro-2-(methoxycarbonyl)benzofuran were reacted to produce N4-(3-chloro-4-trifluoromethoxyphenyl)-5-fluoro- N2-[2,3-dihydro-2-(methoxycarbonyl)benzofuran-5-yl]-2,4-pyrimidinediamine. $^1$H NMR (DMSO-d$_6$): δ 9.99 (bs, 1H), 9.49 (bs, 1H), 8.18 (d, 1H, J=4.5 Hz), 8.08 (t, 1H, J=2.4 Hz), 7.81-7.74 (m, 1H), 7.49 (d, 1H, J=8.1 Hz), 7.42 (s, 1H), 7.20 (d, 1H, J=8.1 Hz), 6.78 (d, 1H, J=8.7 Hz), 5.36 (m, 1H), 3.80-3.47 (m, 4H), 3.20 (dd, 1H, J=6.0 and 16.5 Hz); LCMS: purity: 100%; MS (m/e): 500(MH$^+$).

7.3.883 N4-(3-Chloro-4-trifluoromethoxyphenyl)-5-fluoro-N2-[2,3-dihydro-2-[(N-methylamino)carbonyl]benzofuran-5-yl]-2,4-pyrimidinediamine (R926954)

In a like manner to the preparation of N4-(3,5-dichloro-4-hydroxyphenyl)-5-fluoro-N2-[3-(N-morpholino)carbonylmethyleneoxyphenyl]-2,4-pyrimidinediamine, 2-chloro-N4-(3-chloro-4-trifluoromethoxyphenyl)-5-fluoro-4-pyrimidineamine, methylamine hydrogen chloride salt, and diisopropylethylamine were reacted to provide N4-(3-chloro-4-trifluoromethoxyphenyl)-5-fluoro-N2-[2,3-dihydro-2-[(N-methylamino)carbonyl]benzofuran-5-yl]-2,4-pyrimidinediamine. $^1$H NMR (DMSO-d$_6$): δ 9.59 (s, 1H), 9.10 (s, 2H), 8.13-8.10 (m, 1H), 8.08-7.98 (m, 1H), 7.82 (d, 1H, J=8.1 Hz), 7.48-7.42 (m, 2H), 7.24 (d, 1H, J=8.7 Hz), 6.72 (d, 1H, J=8.7 Hz), 5.06 (dd, 1H, J=5.4 and 9.3 Hz), 3.39 (dd, 1H, J=10.5 and 15.6 Hz), 3.15 (dd, 1H, J=6.3 and 15.9 Hz), 2.59 (d, 3H, J=4.5 Hz); LCMS: purity: 95%; MS (m/e): 499(MH$^+$).

7.3.884 N4-(3-Chloro-4-methoxyphenyl)-5-fluoro-N2-[2,3-dihydro-2-[(N-methylamino)carbonyl]benzofuran-5-yl]-2,4-pyrimidinediamine (R926955)

In a like manner to the preparation of N4-(3,5-dichloro-4-hydroxyphenyl)-5-fluoro-N2-[3-(N-morpholino)carbonylmethyleneoxyphenyl]-2,4-pyrimidinediamine, 2-chloro-N4-(3-chloro-4-methoxyphenyl)-5-fluoro-4-pyrimidineamine, methylamine hydrochloride, and diisopropylethylamine were reacted to provide N4-(3-chloro-4-methoxyphenyl)-5-fluoro-N2-[2,3-dihydro-2-[(N-methylamino)carbonyl]benzofuran-5-yl]-2,4-pyrimidinediamine. $^1$H NMR (DMSO-d$_6$): δ 9.24 (s, 1H), 8.99 (s, 2H), 8.02 (d, 1H, J=3.0 Hz), 7.80-7.75 (m, 1H), 7.63 (d, 1H, J=9.0 Hz), 7.47 (s, 1H), 7.23 (d, 1H, J=8.1 Hz), 7.07 (d, 1H, J=8.7 Hz), 6.69 (d, 1H, J=8.1 Hz), 5.05 (dd, 1H, J=2.1 and 9.9 Hz), 3.37 (dd, 1H, J=10.5 and 15.9 Hz), 3.13 (dd, 1H, J=6.0 and 15.9 Hz), 2.59 (d, 3H, J=4.5 Hz); LCMS: purity: 95%; MS (m/e): 445(MH$^+$).

7.3.885 5-Fluoro-N2-[2,3-dihydro-2-[(N-methylamino)carbonyl]benzofuran-5-yl]-N4-(4-isopropoxyphenyl)-2,4-pyrimidinediamine (R926956)

In a like manner to the preparation of N4-(3,5-dichloro-4-hydroxyphenyl)-5-fluoro-N2-[3-(N-morpholino)carbonylmethyleneoxyphenyl]-2,4-pyrimidinediamine, 2-chloro-5-fluoro-N4-(4-isopropoxyphenyl)-4-pyrimidineamine, methylamine hydrochloride, and diisopropylethylamine were reacted to provide 5-fluoro-N2-[2,3-dihydro-2-[(N-methylamino)carbonyl]benzofuran-5-yl]-N4-(4-isopropoxyphenyl)-2,4-pyrimidinediamine. $^1$H NMR (DMSO-d$_6$): δ 9.11 (s, 1H), 8.92 (s, 1H), 8.06-7.98 (m, 1H), 7.97 (d, 1H, J=4.2 Hz), 7.60-7.52 (m, 3H), 7.20 (d, 1H, J=8.1 Hz), 6.85 (d, 2H, J=8.7 Hz), 6.67 (d, 1H, J=9.0 Hz), 5.04 (dd, 1H, J=5.7 and 9.9 Hz), 4.56 (quintet, 1H, J=6.6 Hz), 3.36 (dd, 1H, J=10.5 and 16.5 Hz), 3.10 (dd, 1H, J=5.7 and 15.3 Hz), 2.59 (d, 1H, J=4.5 Hz), 1.24 (d, 6H, J=6.6 Hz); LCMS: purity: 96%; MS (m/e): 438(MH$^+$).

7.3.886 N2,N4-Bis(3-phenylphenyl)-2,4-pyrimidinediamine (R925809)

In a like manner to the preparation of N2,N4-bis(3-hydroxyphenyl)-5-fluoro-2,4-pyrimidinediamine, 2,4-dichloro-5-fluoropyrimidine and 3-aminobiphenyl were reacted to provide N2,N4-Bis(3-phenylphenyl)-2,4-pyrimidinediamine. LCMS: purity: 98%; MS (m/e): 415(MH$^+$).

7.3.887 2-Dimethylamine-5-fluoro-N4-(thyrosinyl methyl ester) pyrimidine (R940110)

A solution of 2,4-dichloro-5-fluoropyrimidine (0.03 g, 0.18 mmol) and L-tyrosine methyl ester (0.14 g, 0.7 mmol) in DMF was heated at 100° C. for 3 days. The reaction mixture was cool to room temperature and diluted with H$_2$O (10 mL). Upon saturation with sodium chloride it was extracted with ethyl acetate (3×15 mL), dried over anhydrous sodium sulfate and the solvent was removed. The resulting residue was filtered through a pad of silica gel (200-400 mesh, hexanes/EtOAc 2/8) to obtain 2-dimethylamine-5-fluoro-N4-(thyrosinyl methyl ester) pyrimidine R940110. $^1$H NMR (CDCl$_3$): δ 7.76 (1H, d, J=3.2 Hz), 7.00 (2H, d, J=7.5 Hz), 6.76 (2H, d, J=7.5 Hz), 5.20 (1H, d, J=7.5 Hz), 4.90 (1H, q, J=5.0 Hz), 3.71 (3H, s), 3.14 (2H, m), 3.08 (6H, s); purity: 98%; MS (m/e): 335 (M+H).

7.3.888 5-Fluoro-N2-[3-(methylaminocarbonylmethyleneoxy)phenyl]-N4-(3-aminocarbonylphenyl)-2,4-pyrimidinediamine (R940299)

To a solution of 2-chloro-5-fluoro-N4-(3-aminocarbonylphenyl)-4-pyrimidineamine (0.050 g, 0.18 mmol) in (2 mL) was added 3-(methylaminocarbonylmethyleneoxy)aniline (0.1 g, 0.5 mmol). The mixture was heated in a sealed tube at 100° C. for 24 h. The resulting reaction was diluted with H$_2$O (10 mL), acidified with 2N HCl (pH>2), saturated with sodium chloride and the resulting solid was filtered to give the desired product 5-fluoro-N2-[3-(methylaminocarbonylmethyleneoxy)phenyl]-N4-(3-aminocarbonylphenyl)-2,4-pyrimidinediamine R940299. Purification can be done by filtration through a pad of silica gel using 1-5% MeOH in CH$_2$Cl$_2$ or by crystallization using an appropriate solvent system. Alternatively, the reaction of equimolar amount of 2-chloro-5-fluoro-N4-(3-aminocarbonylphenyl)-4-pyrimidineamine and 3-(methylaminocarbonylmethyleneoxy) aniline in MeOH in a pressure tube at 110° C. for 24 h or, in EtOH using microwave at 175° C. for 30-60 min followed by aqueous work up, also gave the desired product. $^1$H NMR (DMSO-d6): δ 9.79 (1H, s), 9.49 (1H, s), 8.26 (1H, d, J=3.9 Hz), 8.15 (1H, t, J=1.8 Hz), 8.10-8.02 (3H, m), 7.68 (1H, d, J=7.5 Hz), 7.51 (1H, t, J=7.9 Hz), 7.48 (1H, s), 7.38 (2H, m), 7.20 (1H, t, J=8.4 Hz), 6.60 (1H, d, J=9.3 Hz), 4.45 (2H, s), 2.74 (3H, d, J=4.8 Hz); purity: 95%; MS (m/e): 411 (MH+).

7.3.889 5-Fluoro-N2-[3-(methylaminocarbonylmethyleneoxy)phenyl]-N4-(3-methyloxycarbonyl-4-methoxyphenyl)-2,4-pyrimidinediamine (R940300)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-5-fluoro- N4-(3-methyloxycarbonyl-4-methoxyphenyl)-4-pyrimidineamine and 3-(methylaminocarbonylmethyleneoxy)aniline were reacted to yield 5-fluoro-N2-[3-(methylaminocarbonylmethyleneoxy)phenyl]-N4-(3-methyloxycarbonyl-4-methoxyphenyl)-2,4-pyrimidinediamine R940300. $^1$H NMR (DMSO-d6): δ 9.66 (1H, s), 9.45 (1H, s), 8.21 (1H, d, J=3.9 Hz), 8.06 (2H, m), 8.01 (1H, t, J=2.7 Hz), 7.35 (2H, m), 7.23 (1H, d, J=9 Hz), 7.18 (1H, t, J=8.1 Hz), 6.60 (1H, d, J=7.8 Hz), 4.45 (2H, s), 3.91 (3H, s), 3.84 (3H, s), 2.74 (3H, d, J=3.6 Hz); purity: 93%; MS (m/e): 456 (MH+).

7.3.890 5-Fluoro-N4-(3-hydroxyphenyl)-N2-(3-methyloxycarbonyl-4-methoxyphenyl)-2,4-pyrimidinediamine (R940301)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-5-fluoro-N4-(3-hydroxyphenyl)-4-pyrimidineamine and 3-methyloxycarbonyl-4-methoxyaniline were reacted to yield 5-fluoro-N4-(3-hydroxyphenyl)-N2-(3-methyloxycarbonyl-4-methoxyphenyl)-2,4-pyrimidinediamine R940301. $^1$H NMR (DMSO-d6): δ 9.93 (1H, s), 9.79 (1H, s), 9.54 (1H, s), 8.26 (1H, s, J=4.5 Hz), 7.92 (1H, s), 7.81 (1H, dd, J=9.3 Hz, J=2.7 Hz), 7.32 (1H, d, J=8.1 Hz), 7.20-7.13 (3H, m), 6.64 (1H, d, J=8.1 Hz), 3.89 (3H, s), 3.84 (3H, s); purity: 97%; MS (m/e): 385 (MH+).

7.3.891 5-Fluoro-N4-(3-methylaminocarbonyl-4-methoxyphenyl)-N2-methyl-2,4-pyrimidinediamine (R940304)

A mixture of 2-chloro-5-fluoro-N4-(3-methyloxycarbonyl-4-methoxyphenyl)-4-pyrimidineamine (0.15 g, 0.4 mmol), methylamine hydrochloride (0.324 g, 48 mmol) and diisopropylethylamine (0.84 mL, 48 mmol) in MeOH (2 mL) was heated in a sealed tube at 100° C. for 24 h (followed by TLC). The reaction was cooled to room temperature and diluted with H$_2$O (20 mL). The solid was filtered, washed with H$_2$O and dried to obtain 5-fluoro-N4-(3-methylaminocarbonyl-4-methoxyphenyl)-N2-methyl-2,4-pyrimidinediamine R940304. $^1$H NMR (DMSO-d6): δ 10.65 (1H, s), 8.48 (1H, s), 8.29 (2H, m), 7.93 (1H, m), 7.28 (1H, d, J=9 Hz), 4.00 (3H, s), 2.94 (3H, s), 2.90 (3H, d, J=4.5 Hz); purity: 90%; MS (m/e): 306 (MH+);

7.3.892 5-Fluoro-N2-[3-(methylaminocarbonylmethyleneoxy)phenyl]-N4-(3-methylaminocarbonyl-4-methoxyphenyl)-2,4-pyrimidinediamine (R940306)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-5-fluoro-N4-(3-methylaminocarbonyl-4-methoxyphenyl)-4-pyrimidineamine and 3-(methylaminocarbonylmethyleneoxy)aniline were reacted to yield 5-fluoro-N2-[3-(methylaminocarbonylmethyleneoxy)phenyl]-N4-(3-methylaminocarbonyl-4-methoxyphenyl)-2,4-pyrimidinediamine R940306. $^1$H NMR (DMSO-d6): δ 9.28 (1H, s), 9.21 (1H, s), 8.12 (1H, d, J=3.9 Hz), 8.06 (1H, d, J=2.7 Hz), 7.99 (1H, m), 7.89 (1H, dd, J=9.3 Hz, J=2.7 Hz), 7.52 (1H, q, J=4.9 Hz), 7.41 (1H, t, J=2.1 Hz), 7.37 (1H, d, J=7.5 Hz), 7.10 (1H, t, J=8.1 Hz), 6.83 (1H, d, J=9 Hz), 6.53 (1H, dd, J=8.1 Hz, J=1.8 Hz), 4.40 (2H, s), 3.82 (3H, s), 2.96 (3H, d, J=5.1 Hz), 2.73 (3H, d, J=4.5 Hz); purity: 93%; MS (m/e): 455 (MH+).

7.3.893 (R)-N2-[3-(dihydroxypropylaminocarbonylmethyleneoxy)-phenyl]-5-fluoro-N4-(3-isopropylphenyl)-2,4-pyrimidinediamine (R940307)

In like manner to the preparation of 5-fluoro-N4-(3-methylaminocarbonyl-4-methoxyphenyl)-N2-methyl-2,4-pyrimidinediamine, 5-fluoro-N4-(3-isopropylphenyl)-N2-(3-methoxycarbonylmethyleneoxyphenyl)-2,4-pyrimidinediamine and (R)-3-amino-1,2-propanediol were reacted to give (R)-N2-[3-(N-2,3-dihydroxypropylamino)carbonylmethyleneoxyphenyl]-5-fluoro-N4-(3-isopropylphenyl)-2,4-pyrimidinediamine R940307. $^1$H NMR (DMSO-d6): δ 9.96 (1H, s), 9.80 (1H, s), 8.29 (1H, d, J=4.5 Hz), 7.98 (1H, t, J=5.5 Hz), 7.77 (1H, d, J=7.2 Hz), 7.57 (1H, s), 7.37 (1H, t, J=7.8 Hz), 7.30-7.22 (3H, m), 7.12 (1H, d, J=7.8 Hz), 6.70 (1H, d, J=7.5 Hz), 4.47 (2H, s), 3.62 (1H, m), 3.38 (3H, m), 3.15 (1H, m), 2.94 (1H, quint, J=6.9 Hz), 1.27 (6H, d, 6.9 Hz); purity: 99%; MS (m/e): 469 (M), 470 (MH+).

7.3.894 N4-(3-tert-Butylpheny)-5-fluoro-N2-[3-(1,1-dimethyl-2-hydroxyethylaminocarbonylmethyleneoxy)-phenyl]-2,4-pyrimidinediamine (R940308)

In like manner to the preparation of 5-fluoro-N4-(3-methylaminocarbonyl-4-methoxyphenyl)-N2-methyl-2,4-pyrimidinediamine, N4-(3-tert-butylphenyl)-5-fluoro-N2-(3-methoxycarbonylmethyleneoxyphenyl)-2,4-pyrimidinediamine and 2-amino-2-methyl-1-propanol were reacted to give N4-(3-tert-butylpheny)-5-fluoro-N2-[3-(1,1-dimethyl-2-hydroxyethylaminocarbonylmethyleneoxy)-phenyl]-2,4-pyrimidinediamine R940308. $^1$H NMR (DMSO-d6): δ 9.38 (1H, s), 9.28 (1H, s), 8.20 (1H, d, J=3.9 Hz), 7.99 (1H, d, J=7.5 Hz), 7.60 (1H, t, J=2.1 Hz), 7.46 (1H, s), 7.37 (2H, t, J=7.9 Hz), 7.30 (1H, s), 7.19 (2H, t, J=7.9 Hz), 6.56 (1H, dd, J=7.5 Hz, J=1.5 Hz), 5.06 (1H, t, J=5.7 Hz), 4.37 (2H, s), 3.40 (2H, m), 1.36 (9H, s), 1.32 (6H, s); purity: 93%; MS (m/e): 482 (MH+).

7.3.895 N4-(3-Aminomethylenephenyl)-5-fluoro-N2-[3-(methylaminocarbonylmethyleneoxy)phenyl]-2,4-pyrimidinediamine (R940309)

A mixture of N4-[3-(N-tert-butoxycarbonyl-N-aminomethylene)-phenyl]-2-chloro-5-fluoro-4-pyrimidineamine and 3-(methylaminocarbonylmethyleneoxy)aniline in MeOH was heated in a sealed tube at 100° C. for 12 h. The reaction was cool to room temperature and the solvent was removed under reduce pressure. The resulting residue was filtered through a pad of silica gel (200-400 mesh, EtOAc/MeOH (2M NH$_3$) 95:5) to obtain the desired product N4-(3-aminomethylenephenyl)-5-fluoro-N2-[3-(methylaminocarbonylmethyleneoxy)phenyl]-2,4-pyrimidinediamine R940309. $^1$H NMR (DMSO-d6): δ 9.41 (1H, s), 9.23 (1H, s), 8.20 (1H, d, J=3.9 Hz), 8.00 (1H, m), 7.78 (1H, s), 7.72 (1H, d, J=7.2 Hz), 7.46 (1H, s), 7.42-7.33 (2H, m), 7.21 (1H, t, J=7.8 Hz), 7.14 (1H, d, J=7.8 Hz), 6.59 (1H, dd, J=8.1 Hz, J=2.4 Hz), 4.42 (2H, s), 3.79 (2H, s), 2.74 (3H, d, J=4.8 Hz); purity: 98%; MS (m/e): 397 (MH+).

7.3.896 N4-[3-(2-(N4-(3-aminomethylenephenyl)-5-fluoro-4-pyrimidineamine)-N-methylaminomethylene)-phenyl]-5-fluoro-N2-[3-(methylaminocarbonylmethyleneoxy)phenyl]-2,4-pyrimidineamine (R940311)

A mixture of N4-[3-(N-methylaminomethylene)-phenyl]-2-chloro-5-fluoro-4-pyrimidineamine (0.05 g, 0.18 mmol)

and 3-(methylaminocarbonylmethyleneoxy)aniline (0.04 g, 0.22 mmol) in EtOH (0.5 mL), was heated at 175° C. for 35 min using microwave. An aqueous work up gave the desired N4-[3-(2-(N4-(3-aminomethylenephenyl)-5-fluoro-4-pyrimidineamine)-N-methylaminomethylene)-phenyl]-5-fluoro-N2-[3-(methylaminocarbonylmethyleneoxy)phenyl]-2,4-pyrimidineamine R940311. $^1$H NMR (DMSO-d6): δ 9.48 (1H, s), 9.31 (1H, s), 9.26 (1H, s), 8.20 (1H, d, J=3.6 Hz), 8.10-8.05 (4H, m), 7.62 (1H, s), 7.49 (2H, m), 7.41 (1H, t, J=8.1 Hz), 7.36 (2H, m), 7.22 (1H, t, J=8.4 Hz), 7.17 (1H, t, J=8.4 Hz), 7.06 (1H, d, J=7.5 Hz), 6.59 (1H, dd, J=8.4 Hz, J=2.4 Hz), 6.54 (1H, dd, J=7.8 Hz, J=2.4 Hz), 4.93 (2H, s), 4.46 (2H, s), 4.45 (2H, s), 3.28 (3H, d, J=3 Hz), 2.73 (6H, m); purity: 98%; MS (m/e): 684 (M), 685 (MH+).

7.3.897 5-Fluoro-N2-[3-(methylaminocarbonylmethyleneoxy)phenyl]-N4-(3-isopropylaminocarbonyl-4-methoxyphenyl)-2,4-pyrimidinediamine (R940312)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-5-fluoro-N4-(3-N-iso-propylaminomethylene-4-methoxyphenyl)-4-pyrimidineamine and 3-(methylaminocarbonylmethyleneoxy)aniline were reacted to produce 5-fluoro-N2-[3-(methylaminocarbonylmethyleneoxy)phenyl]-N4-(3-iso-propylaminocarbonyl-4-methoxyphenyl)-2,4-pyrimidinediamine R940312. $^1$H NMR (DMSO-d6): δ 10.09 (1H, s), 9.88 (1H, s), 8.25 (1H, d, J=4.8 Hz), 8.07 (1H, d, J=2.7 Hz), 8.05 (1H, m), 7.81 (1H, dd, J=9 Hz, J=2.7 Hz), 7.63 (1H, s), 7.25 (2H, m), 7.17 (1H, t, J=8.25 Hz), 6.91 (1H, d, J=9 Hz), 6.68 (1H, d, J=8.1 Hz), 4.42 (2H, s), 3.85 (1H, m), 3.81 (3H, s), 2.72 (3H, d, J=4.2 Hz), 1.30 (6H, d, J=6 Hz); purity: 97%; MS (m/e): 483 (MH+).

7.3.898 5-Fluoro-N2-[3-(methylaminocarbonylmethyleneoxy)phenyl]-N4-[3-(N-morpholinomethylene)-4-methoxyphenyl]-2,4-pyrimidinediamine (R940314)

In like manner to the preparation of 5-fluoro-N2-[3-(methylaminocarbonylmethyleneoxy)phenyl]-N4-(3-aminocarbonylphenyl)-2,4-pyrimidinediamine, N2-chloro-5-fluoro-N4-[3-(N-morpholinomethylene)-4-methoxyphenyl]-4-pyrimidineamine and 3-(methylaminocarbonylmethyleneoxy)aniline were reacted to produce 5-fluoro-N2-[3-(methylaminocarbonylmethyleneoxy)phenyl]-N4-[3-(N-morpholinomethylene)-4-methoxyphenyl]-2,4-pyrimidinediamine R940314. $^1$H NMR (DMSO-d6): δ 9.33 (1H, s), 9.21 (1H, s), 8.15 (1H, d, J=3.6 Hz), 8.04 (1H, d, J=4.8 Hz), 7.82 (1H, dd, J=9 Hz, J=2.7 Hz), 7.57 (1H, d, J=3 Hz), 7.47 (1H, t, J=1.95 Hz), 7.34 (1H, m), 7.18 (1H, t, J=8.1 Hz), 7.04 (1H, d, J=9 Hz), 6.56 (1H, dd, J=8.4 Hz, J=2.1 Hz), 4.40 (2H, s), 3.86 (3H, s), 3.63 (4H, t, J=4.5 Hz), 3.53 (2H, s), 2.74 (3H, d, J=4.5 Hz), 2.46 (4H, m); purity: 97%; MS (m/e): 497 (MH+).

7.3.899 N2-(3-Chloro-4-hydroxy-5-methylphenyl)-5-fluoro-N4-[3-(N-morpholinomethylene)-4-methoxyphenyl]-2,4-pyrimidinediamine (R940316)

In like manner to the preparation of 5-fluoro-N2-[3-(methylaminocarbonylmethyleneoxy)phenyl]-N4-(3-aminocarbonylphenyl)-2,4-pyrimidinediamine, N2-chloro-5-fluoro-N4-[3-(N-morpholinomethylene)-4-methoxyphenyl]-4-pyrimidineamine and 4-amino-2-chloro-6-methylphenol were reacted to produce N2-(3-chloro-4-hydroxy-5-methylphenyl)-5-fluoro-N4-[3-(N-morpholinomethylene)-4-methoxyphenyl]-2,4-pyrimidinediamine R940316. $^1$H NMR (DMSO-d6): δ 9.28 (1H, s), 9.01 (1H, s), 8.65 (1H, s), 8.11 (1H, d, J=3.9 Hz), 7.76 (1H, dd, J=9 Hz, J=3 Hz), 7.61 (1H, d, J=2.4 Hz), 7.50 (1H, d, J=2.7 Hz), 7.30 (1H, d, J=2.1 Hz), 7.04 (1H, d, J=8.7 Hz), 3.87 (3H, s), 3.63 (4H, t, J=4.3 Hz), 3.52 (2H, s), 2.45 (4H, m), 2.17 (3H, s); purity: 97%; MS (m/e): 474 (MH+).

7.3.900 N4-(3-N-methylaminomethylenephenyl)-5-fluoro-N2-[3-(methylaminocarbonylmethyleneoxy)phenyl]-2,4-pyrimidinediamine (R940317)

In like manner to the preparation of 5-fluoro-N2-[3-(methylaminocarbonylmethyleneoxy)phenyl]-N4-(3-aminocarbonylphenyl)-2,4-pyrimidinediamine, N4-[3-(N-tert-butoxycarbonyl-N-methylaminomethylene)-phenyl]-2-chloro-5-fluoro-4-pyrimidineamine and 3-(methylaminocarbonylmethyleneoxy)aniline were reacted to produce N4-(3-N-methylaminomethylenephenyl)-5-fluoro-N2-[3-(methylaminocarbonylmethyleneoxy)phenyl]-2,4-pyrimidinediamine R940317. $^1$H NMR (DMSO-d6): δ 9.41 (1H, s), 9.31 (1H, s), 9.29 (1H, s), 8.20 (1H, d, J=3 Hz), 8.05 (1H, m), 7.80 (1H, d, J=7.8 Hz), 7.74 (1H, s), 7.45-7.35 (3H, m), 7.21 (1H, t, J=8.1 Hz), 7.13 (1H, d, J=7.5 Hz), 6.59 (1H, d, J=9.6 Hz), 4.43 (2H, s), 3.71 (2H, s), 2.75 (3H, d, J=4.2 Hz), 2.35 (3H, s); purity: 83.9%; MS (m/e): 411 (MH+).

7.3.901 N2-(3-Chloro-4-hydroxy-5-methylphenyl)-5-fluoro-N4-[3-(N-piperazinomethylene)-4-methoxyphenyl]-2,4-pyrimidinediamine (R940318)

In like manner to the preparation of 5-fluoro-N2-[3-(methylaminocarbonylmethyleneoxy)phenyl]-N4-(3-aminocarbonylphenyl)-2,4-pyrimidinediamine, N4-[3-(N-piperazinomethylene)-4-methoxyphenyl]-2-chloro-5-fluoro-4-pyrimidineamine and 4-amino-2-chloro-6-methylphenol were reacted to produce N2-(3-chloro-4-hydroxy-5-methylphenyl)-5-fluoro-N4-[3-(N-piperazinomethylene)-4-methoxyphenyl]-2,4-pyrimidinediamine R940318. $^1$H NMR (DMSO-d6): δ 9.27 (1H, s), 9.00 (1H, s), 8.10 (1H, d, J=3.6 Hz), 7.75 (1H, dd, J=8.7 Hz, J=2.7 Hz), 7.61 (1H, d, J=2.4 Hz), 7.49 (1H, d, J=2.4 Hz), 7.31 (1H, d, J=2.4 Hz), 7.03 (1H, d, J=9 Hz), 3.86 (3H, s), 3.49 (2H, s), 2.75 (4H, t, J=4.65 Hz), 2.39 (4H, m), 2.17 (3H, s); purity: 95%; MS (m/e): 473 (MH+).

7.3.902 N4-(3-(N-tert-Butoxycarbonyl-N-iso-propylaminomethylene)-4-methoxyphenyl)-5-fluoro-N2-[3-(methylaminocarbonyl methyleneoxy)phenyl]-2,4-pyrimidinediamine (R940319)

In like manner to the preparation of 5-fluoro-N2-[3-(methylaminocarbonylmethyleneoxy)phenyl]-N4-(3-aminocarbonylphenyl)-2,4-pyrimidinediamine, N4-(3-(N-tert-butoxycarbonyl-N-iso-propylaminomethylene)-4-methoxyphenyl)-2-chloro-5-fluoro-4-pyrimidineamine and 3-(methylaminocarbonylmethyleneoxy)aniline were reacted to produce N4-(3-(N-tert-butoxycarbonyl-N-iso-propylaminomethylene)-4-methoxyphenyl)-5-fluoro-N2-[3-(methylaminocarbonylmethyleneoxy)phenyl]-2,4-pyrimidinediamine R940319. $^1$H NMR (DMSO-d6): δ 9.44 (1H, s), 8.95 (1H, s), 8.15 (1H, d, J=3.6 Hz), 8.06 (1H, m), 7.83 (1H, m), 7.74 (1H, m), 7.56 (1H, m), 7.37 (1H, m), 7.20 (1H, t, J=7.9 Hz), 7.02 (1H, d, J=9.3 Hz), 6.57 (1H, d, J=7.8 Hz), 4.44 (2H, s), 4.42 (2H, m), 4.33 (2H, s), 3.89 (3H, s), 2.74 (3H, d, J=4.8 Hz), 1.52-1.30 (9H, m), 1.16 (6H, d, J=6.9 Hz); purity: 98%; MS (m/e): 569 (MH+).

7.3.903 N4-(3-N,N-Dimethylaminomethylene-4-methoxyphenyl)-5-fluoro-N2-[3-(methylaminocarbonylmethyleneoxy)phenyl]-2,4-pyrimidinediamine (R940321)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-(3-N,N-dimethylaminomethylene-4-methoxyphenyl)-5-fluoro-4-pyrimidineamine and 3-(methylaminocarbonylmethyleneoxy)aniline were reacted to produce N4-(3-N,N-dimethylaminomethylene-4-methoxyphenyl)-5-fluoro-N2-[3-(methylaminocarbonylmethyleneoxy)phenyl]-2,4-pyrimidinediamine R940321. $^1$H NMR (DMSO-d6): δ 9.32 (1H, s), 9.23 (1H, s), 8.14 (1H, d, J=3.9 Hz), 8.05 (1H, m), 7.83 (1H, dd, J=8.7 Hz, J=2.4 Hz), 7.55 (1H, d, J=2.4 Hz), 7.45 (1H, s), 7.36 (1H, d, J=8.4 Hz), 7.18 (1H, t, J=8.1 Hz), 7.03 (1H, d, J=9 Hz), 6.56 (1H, dd, J=7.2 Hz, J=1.5 Hz), 4.41 (2H, s), 3.86 (3H, s), 2.73 (3H, d, J=4.5 Hz), 2.24 (6H, s); purity: 91.8%; MS (m/e): 455 (MH+).

7.3.904 N4-[(2,2-Dimethyl-4H-benzo[1,4]oxazin-3-one)-6-yl]-5-fluoro-N2-[3-(methylaminocarbonylmethyleneoxy)phenyl]-2,4-pyrimidinediamine (R940323)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[(2,2-dimethyl-4H-benzo[1,4]oxazin-3-one)-6-yl]-5-fluoro-4-pyrimidineamine and 3-(methylaminocarbonylmethyleneoxy)aniline were reacted to produce N4-[(2,2-dimethyl-4H-benzo[1,4]oxazin-3-one)-6-yl]-5-fluoro-N2-[3-(methylaminocarbonylmethyleneoxy)phenyl]-2,4-pyrimidinediamine R940323. $^1$H NMR (DMSO-d6): δ 10.70 (1H, s), 9.45 (1H, s), 9.19 (1H, s), 8.17 (1H, d, J=3.9 Hz), 8.05 (1H, m), 7.43-7.34 (4H, m), 7.17 (1H, t, J=8.25 Hz), 6.98 (1H, d, J=8.4 Hz), 6.56 (1H, dd, J=7.8 Hz, J=2.1 Hz), 4.25 (2H, s), 2.74 (3H, d, J=4.5 Hz), 1.5 (6H, s); purity: 98.7%; MS (m/e): 467 (MH+).

7.3.905 N4-[3-Dihydro-2,2-dimethyl-4-(2-pyridyl)-benzo[1,4]oxazin-6-yl]-5-fluoro-N2-[3-(methylaminocarbonylmethyleneoxy)phenyl]-2,4-pyrimidinediamine (R940337)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[3-dihydro-2,2-dimethyl-4-(2-pyridyl)-benzo[1,4]oxazin-6-yl]-5-fluoro-4-pyrimidineamine and 3-(methylaminocarbonylmethyleneoxy)aniline were reacted to produce N4-[3-dihydro-2,2-dimethyl-4-(2-pyridyl)-benzo[1,4]oxazin-6-yl]-5-fluoro-N2-[3-(methylaminocarbonylmethyleneoxy)phenyl]-2,4-pyrimidinediamine R940337. $^1$H NMR (DMSO-d6): δ 9.28 (1H, s), 9.20 (1H, s), 8.34 (1H, dd, J=4.8 Hz, J=1.2 Hz), 8.14 (1H, d, J=3.8 Hz), 8.03 (1H, m), 7.64-7.60 (2H, m), 7.51-7.46 (3H, m), 7.37 (1H, d, J=8.4 Hz), 7.17 (1H, t, J=8.1 Hz), 6.94-6.91 (2H, m), 6.55 (1H, dd, J=8.4 Hz, J=3 Hz), 4.42 (2H, s), 3.93 (2H, s), 2.74 (3H, d, J=4.5 Hz), 1.32 (6H, s); purity: 98.2%; MS (m/e): 530 (MH+);

7.3.906 N4-[(2,2-Dimethyl-4H-benzo[1,4]oxazin-3-one)-6-yl]-5-fluoro-N2-(1-methylindazolin-5-yl)-2,4-pyrimidinediamine (R940338)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[(2,2-dimethyl-4H-benzo[1,4]oxazin-3-one)-6-yl]-5-fluoro-4-pyrimidineamine and 5-amino-1-methyl-1-indazole were reacted to produce N4-[(2,2-dimethyl-4H-benzo[1,4]oxazin-3-one)-6-yl]-5-fluoro-N2-(1-methylindazolin-5-yl)-2,4-pyrimidinediamine R940338. $^1$H NMR (DMSO-d6): δ 10.73 (1H, s), 9.39 (1H, s), 9.17 (1H, s), 8.21 (1H, s), 8.16 (1H, d, J=3.9 Hz), 7.87 (1H, s), 7.56 (2H, m), 7.41 (1H, m), 7.32 (1H, s), 7.00 (1H, d, J=8.4 Hz), 4.07 (3H, s), 1.51 (6H, s); purity: 99.2%; MS (m/e): 434 (MH+).

7.3.907 N4-[(2,2-Difluoro-4H-benzo[1,4]oxazin-3-one)-6-yl]-5-fluoro-N2-[3-(methylaminocarbonylmethyleneoxy)phenyl]-2,4-pyrimidinediamine (R921303)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[(2,2-difluoro-4H-benzo[1,4]oxazin-3-one)-6-yl]-5-fluoro-4-pyrimidineamine and 3-(methylaminocarbonylmethyleneoxy)aniline were reacted to produce N4-[(2,2-difluoro-4H-benzo[1,4]oxazin-3-one)-6-yl]-5-fluoro-N2-[3-(methylaminocarbonylmethyleneoxy)phenyl]-2,4-pyrimidinediamine R921303. $^1$H NMR (DMSO-d6): δ 12.05 (1H, s), 9.67 (1H, s), 9.27 (1H, s), 8.24 (1H, d, J=3.6 Hz), 8.05 (1H, m), 7.73-7.68 (1H, m), 7.56 (1H, t, J=2.7 Hz), 7.50 (1H, s), 7.36 (2H, d, J=8.7 Hz), 7.19 (1H, t, J=8.2 Hz), 6.58 (1H, dd, J=8.4 Hz, J=2.4 Hz), 4.34 (2H, s), 2.74 (3H, d, J=4.5 Hz); $^{19}$F NMR (DMSO-d6): 6-21643, −46385; purity: 100%; MS (m/e): 475 (MH+).

7.3.908 N4-[(2,2-Dimethyl-4H-5-pyrido[1,4]oxazin-3-one)-7-yl]-5-fluoro-N2-[3-(methylaminocarbonylmethyleneoxy)phenyl]-2,4-pyrimidinediamine (R940345)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[(2,2-dimethyl-4H-5-pyrido[1,4]oxazin-3-one)-7-yl]-5-fluoro-4-pyrimidineamine and 3-(methylaminocarbonylmethyleneoxy)aniline were reacted to produce N4-[(2,2-dimethyl-4H-5-pyrido[1,4]oxazin-3-one)-7-yl]-5-fluoro-N2-[3-(methylaminocarbonylmethyleneoxy)phenyl]-2,4-pyrimidinediamine R940345. $^1$H NMR (DMSO-d6): δ 11.23 (1H, s), 9.69 (1H, s), 9.54 (1H, s), 8.50 (1H, s), 8.25 (1H, d, J=3.3 Hz), 8.06 (1H, m), 7.96 (1H, t, J=2.5 Hz), 7.41-7.36 (2H, m), 7.24 (1H, t, J=8.25 Hz), 6.34 (1H, d, J=8.7 Hz), 4.47 (2H, s), 2.74 (3H, d, J=3.3 Hz), 1.53 (6H, s); purity: 98.4%; MS (m/e): 468 (MH+).

7.3.909 N4-[(2,2-Dimethyl-4H-benzo[1,4]oxazin-3-one)-6-yl]-5-fluoro-N2-(3-hydroxyphenyl)-2,4-pyrimidinediamine (R940346)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[(2,2-dimethyl-4H-benzo[1,4]oxazin-3-one)-6-yl]-5-fluoro-4-pyrimidineamine and 3-aminophenol were reacted to produce N4-[(2,2-dimethyl-4H-benzo[1,4]oxazin-3-one)-6-yl]-5-fluoro-N2-(3-hydroxyphenyl)-2,4-pyrimidinediamine R940346. $^1$H NMR (DMSO-d6): δ 10.75 (1H, s), 8.25 (1H, d, J=4.5 Hz), 7.42-7.37 (1H, m), 7.34 (1H, s), 7.10 (3H, m), 7.00 (1H, d, J=8.4 Hz), 6.53 (1H, m), 1.50 (6H, s); purity: 97.5%; MS (m/e): 396 (MH+).

7.3.910 N4-[(2,2-Dimethyl-4H-5-pyrido[1,4]oxazin-3-one)-6-yl]-5-fluoro-N2-[3-(methylaminocarbonylmethyleneoxy)phenyl]-2,4-pyrimidinediamine (R940347)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[(2,2-dimethyl-4H-5-pyrido[1,4]oxazin-3-one)-6-yl]-5-fluoro-4-pyrimidineamine and 3-(methylaminocarbonylmethyleneoxy)aniline were reacted to produce N4-[(2,2-dimethyl-4H-5-pyrido[1,4]oxazin-3-one)-6-yl]-5-fluoro-N2-[3-(methylaminocarbonylmethyleneoxy)phenyl]-2,4-pyrimidinediamine R940347. $^1$H NMR (DMSO-d6): δ 11.20 (1H, s), 9.46 (1H, s), 8.26 (1H, d, J=3.6 Hz), 8.06 (1H, s), 7.71 (1H, m), 7.49 (1H, d, J=8.4 Hz), 7.45 (1H, s), 7.38 (1H, d, J=9 Hz), 7.21 (1H, t, J=8.1 Hz), 6.61 (1H, d, J=8.7 Hz), 4.47 (2H, s), 2.74 (3H, s), 1.52 (6H, s); purity: 100%; MS (m/e): 468 (MH+).

7.3.911 N4-[3-Dihydro-2,2-dimethyl-4-(2-pyridyl)-benzo[1,4]oxazin-6-yl]-5-fluoro-N2-(3-hydroxyphenyl)-2,4-pyrimidinediamine (R940348)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[3-dihydro-2,2-dimethyl-4-(2-pyridyl)-benzo[1,4]oxazin-6-yl]-5-fluoro-4-pyrimidineamine and 3-aminophenol were reacted to produce N4-[3-dihydro-2,2-dimethyl-4-(2-pyridyl)-benzo[1,4]oxazin-6-yl]-5-fluoro-N2-(3-hydroxyphenyl)-2,4-pyrimidinediamine R940348. $^1$H NMR (DMSO-d6): δ 9.25 (1H, s), 9.23 (1H, s), 9.02 (1H, s), 8.34 (1H, d, J=4.5 Hz), 8.11 (1H, d, J=3.3 Hz), 7.62 (2H, m), 7.52 (2H, m), 7.22 (1H, s), 7.19 (1H, d, J=7.5 Hz), 7.03 (1H, t, J=7.9 Hz), 6.93 (2H, m), 6.38 (1H, d, J=7.8 Hz), 3.93 (2H, s), 1.32 (6H, s); purity: 96.5%.

7.3.912 N4-[(2,2-Difluoro-4H-benzo[1,4]oxazin-3-one)-6-yl]-5-fluoro-N2-(3-hydroxyphenyl)-2,4-pyrimidinediamine (R940349)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[(2,2-difluoro-4H-benzo[1,4]oxazin-3-one)-6-yl]-5-fluoro-4-pyrimidineamine and 3-aminophenol were reacted to produce N4-[(2,2-difluoro-4H-benzo[1,4]oxazin-3-one)-6-yl]-5-fluoro-N2-(3-hydroxyphenyl)-2,4-pyrimidinediamine R940349. $^1$H NMR (DMSO-d6): δ 12.03 (1H, s), 9.63 (1H, s), 9.26 (1H, s), 9.09 (1H, s), 8.21 (1H, d, J=3.6 Hz), 7.70 (1H, dd, J=9 Hz, J=2.4 Hz), 7.59 (1H, d, J=2.7 Hz), 7.34 (1H, d, J=9.3 Hz), 7.26 (1H, s), 7.16 (1H, d, J=7.8 Hz), 7.04 (1H, t, J=8.2 Hz), 6.41 (1H, d, J=10.2 Hz); $^{19}$F NMR (DMSO-d6): 6-21646, −46516; purity: 95.8%; MS (m/e): 404 (MH+);

7.3.913 N2,N4-[(2,2-Dimethyl-4H-benzo[1,4]oxazin-3-one)-6-yl]-5-fluoro-2,4-pyrimidinediamine (R940350)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[(2,2-dimethyl-4H-5-benzo[1,4]oxazin-3-one)-6-yl]-5-fluoro-4-pyrimidineamine and 6-amino-2,2-dimethyl-4-benzo[1,4]oxazin-3-one were reacted to produce N2,N4-[(2,2-dimethyl-4H-benzo[1,4]oxazin-3-one)-6-yl]-5-fluoro-2,4-pyrimidinediamine R940350. $^1$H NMR (DMSO-d6): δ 10.68 (1H, s), 10.62 (1H, s), 9.38 (1H, s), 9.04 (1H, s), 8.11 (1H, d, J=3.6 Hz), 7.46 (1H, dd, J=8.1 Hz, J=1.8 Hz), 7.33-7.26 (3H, m), 6.95 (1H, d, J=8.7 Hz), 6.84 (1H, d, J=8.4 Hz), 1.49 (6H, s), 1.45 (6H, s); purity: 95.4%; MS (m/e): 479 (MH+).

7.3.914 N2-[(2,2-Difluoro-4H-benzo[1,4]oxazin-3-one)-6-yl]-N4-[(2,2-dimethyl-4H-benzo[1,4]oxazin-3-one)-6-yl]-5-fluoro-2,4-pyrimidinediamine (R940351)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[(2,2-dimethyl-4H-5-pyrido[1,4]oxazin-3-one)-6-yl]-5-fluoro-4-pyrimidineamine and 6-amino-2,2-difluoro-4H-benzo[1,4]oxazin-3-one were reacted to produce N2-[(2,2-difluoro-4H-benzo[1,4]oxazin-3-one)-6-yl]-N4-[(2,2-dimethyl-4H-benzo[1,4]oxazin-3-one)-6-yl]-5-fluoro-2,4-pyrimidinediamine R940351. $^1$H NMR (DMSO-d6): δ 11.99 (1H, s), 10.74 (1H, s), 9.64 (1H, s), 9.50 (1H, s), 8.19 (1H, d, J=3.9 Hz), 7.50 (2H, m), 7.43 (1H, dd, J=8.4 Hz, J=1.8 Hz), 7.32 (1H, s), 7.20 (1H, d, J=9.3 Hz), 6.98 (1H, d, J=8.7 Hz), 1.49 (6H, s); purity: 94.77%; MS (m/e): 487 (MH+).

7.3.915 N2,N4-[(2,2-Difluoro-4H-benzo[1,4]oxazin-3-one)-6-yl]-5-fluoro-2,4-pyrimidinediamine (R940352)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[(2,2-difluoro-4H-benzo[1,4]oxazin-3-one)-6-yl]-5-fluoro-4-pyrimidineamine and 6-amino-2,2-difluoro-4H-benzo[1,4]oxazin-3-one were reacted to produce N2,N4-[(2,2-difluoro-4H-benzo[1,4]oxazin-3-one)-6-yl]-5-fluoro-2,4-pyrimidinediamine R940352. $^1$H NMR (DMSO-d6): δ 12.08 (1H, s), 12.00 (1H, s), 9.72 (1H, s), 9.44 (1H, s), 8.23 (1H, d, J=3.6 Hz), 7.73 (1H, dd, J=11.1 Hz, J=1.5 Hz), 7.6 (1H, s), 7.56 (1H, s), 7.51 (1H, dd, J=9.6 Hz, J=2.4 Hz), 7.35 (1H, d, J=9 Hz), 7.24 (1H, d, J=8.7 Hz); $^{19}$F NMR (DMSO-d6): 6-21670, −21722, −4651; purity: 100%; MS (m/e): 495 (MH+).

7.3.916 N4-[(2,2-Difluoro-4H-benzo[1,4]oxazin-3-one)-6-yl]-5-fluoro-N2-(2-methoxycarbonylbenzofur-5-yl)-2,4-pyrimidinediamine (R940353)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[(2,2-difluoro-4H-benzo[1,4]oxazin-3-one)-6-yl]-5-fluoro-4-pyrimidineamine and methyl 5-aminobenzofuran-2-carboxylate were reacted to produce N4-[(2,2-difluoro-4H-benzo[1,4]oxazin-3-one)-6-yl]-5-fluoro-N2-(2-methoxycarbonylbenzofur-5-yl)-2,4-pyrimidinediamine R940353. $^1$H NMR (DMSO-d6): δ 12.05 (1H, s), 9.69 (1H, s), 9.43 (1H, s), 8.28 (1H, s), 8.25 (1H, d, J=3.6 Hz), 7.40-7.64 (4H, m), 7.54 (1H, s), 7.38 (1H, d, J=9 Hz), 3.97 (3H, s); $^{19}$F NMR (DMSO-d6): 6-21707, −46489; purity: 97.77%; MS (m/e): 486 (MH+).

7.3.917 N4-[(2,2-Dimethyl-4H-benzo[1,4]oxazin-3-one)-6-yl]-5-fluoro-N2-(2-methoxycarbonylbenzofur-5-yl)-2,4-pyrimidinediamine (R940354)

In like manner to the preparation of 5-fluoro-N2-[3-(methylaminocarbonylmethyleneoxy)phenyl]-N4-(3-aminocarbonylphenyl)-2,4-pyrimidinediamine, 2-chloro-N4-[(2,2-dimethyl-4H-benzo[1,4]oxazin-3-one)-6-yl]-5-fluoro-4-pyrimidineamine and methyl 5-aminobenzofuran-2-carboxylate were reacted to produce N4-[(2,2-dimethyl-4H-benzo[1,4]oxazin-3-one)-6-yl]-5-fluoro-N2-(2-methoxycarbonylbenzofur-5-yl)-2,4-pyrimidinediamine R940354. $^1$H NMR (DMSO-d6): δ 10.75 (1H, s), 9.67 (1H, s), 9.53 (1H, s), 8.25 (1H, s), 8.21 (1H, d, J=4.2 Hz), 7.66 (2H, s), 7.59 (1H, s), 7.31 (1H, d, J=8.7 Hz), 7.26 (1H, s), 7.03 (1H, d, J=8.1 Hz), 3.97 (3H, s), 1.52 (6H, s); purity: 95.58%; MS (m/e): 478 (MH+).

7.3.918 N2,N4-Bis(3-N-acetylaminophenyl)-5-fluoro-N2,N4-pyrimidinediacetylamine (R950244)

N2,N4-Bis(3-aminophenyl)-5-fluoro-2,4-pyrimidinediamine, dimethylaminopyridine (DMAP) and acetic anhydride were refluxed in pyridine for 1 hour. The mixture was cooled to room temperature, concentrated, and the residue was subjected to column chromatography on silica gel (CHCl$_3$:Acetone, 2:1) to give N2,N4-bis(3-N-acetylaminophenyl)-5-fluoro-N2,N4-pyrimidinediacetylamine. $^1$H NMR (MeOD, 300 MHz): δ 8.65 (d, 1H, J=2.4 Hz), 7.15-7.58 (m, 8H), 2.24 (s, 3H), 2.22 (s, 3H), 2.14 (s, 3H), 2.09 (s, 3H); LCMS: ret. time: 17.03 min.; purity: 87.0%; MS (m/e): 478.89 (MH+).

7.3.919 N4-(3-N,N-Diacetylaminophenyl)-N2-(3-N-acetylamipheny)-5-fluoro-N2,N4-pyrimidinediacetylamine (R950245)

N2,N4-Bis(3-aminophenyl)-5-fluoro-2,4-pyrimidinediamine, dimethylaminopyridine (DMAP) and acetic anhydride were refluxed in pyridine for 1 hour. The mixture was cooled to room temperature, concentrated, and the residue was subjected to column chromatography on silica gel (CHCl$_3$:Acetone, 2:1) to give N4-(3-N,N-diacetylaminophenyl)-N2-(3-N-acetylamipheny)-5-fluoro-N2,N4-pyrimidinediacetylamine. $^1$H NMR (MeOD, 300 MHz): δ 8.65 (d, 1H, J=2.4 Hz), 7.03-7.66 (m, 8H), 2.21 (s, 6H), 2.14 (s, 3H), 2.12 (s, 3H), 2.08 (s, 3H); LCMS: ret. time: 19.27 min.; purity: 92.6%; MS (m/e): 521.01 (MH+).

7.3.920 N4-(3-N-Acetylaminophenyl)-N2-(3-N,N-diacetylaminopheny)-5-fluoro-N2,N4-pyrimidinediacetylamine (R950246)

N2,N4-Bis(3-aminophenyl)-5-fluoro-2,4-pyrimidinediamine, dimethylaminopyridine (DMAP) and acetic anhydride were refluxed in pyridine for 1 hour. The mixture was cooled to room temperature, concentrated, and the residue was subjected to column chromatography on silica gel (CHCl$_3$:Acetone, 2:1) to give N4-[3-N-acetylaminophenyl]-N2-(3-N,N-diacetylaminopheny)-5-fluoro-N2,N4-pyrimidinediacetylamine. $^1$H NMR (MeOD, 300 MHz): δ 8.66 (d, 1H, J=2.4 Hz), 6.88-7.57 (m, 8H), 2.22 (s, 6H), 2.11 (s, 3H), 2.10 (s, 3H), 2.09 (s, 3H); LCMS: ret. time: 18.89 min.; purity: 83.0%; MS (m/e): 520.97 (MH+).

7.3.921 N2,N4-Bis(3-N,N-diacetylaminophenyl)-5-fluoro-N2,N4-pyrimidinediacetylamine (R950247)

N2,N4-Bis(3-aminophenyl)-5-fluoro-2,4-pyrimidinediamine, dimethylaminopyridine (DMAP) and acetic anhydride were refluxed in pyridine for 1 hour. The mixture was cooled to room temperature, concentrated, and the residue was subjected to column chromatography on silica gel (CHCl$_3$:Acetone, 2:1) to give N2,N4-bis(3-N,N-diacetylaminophenyl)-5-fluoro-N2,N4-pyrimidinediacetylamine. $^1$H NMR (MeOD, 300 MHz): δ 8.58 (d, 1H, J=2.4 Hz), 6.75-7.53 (m, 8H), 2.04 (s, 3H), 2.03 (s, 3H), 2.01 (s, 6H), 1.99 (s, 6H); LCMS: ret. time: 21.51 min.; purity: 91.8%; MS (m/e): 563.00 (MH+).

7.3.922 N4-(3-Nitrophenyl)-5-fluoro-N2-[3-(N-methylamino)carbonylmethyleneoxyphenyl]-2,4-pyrimidinediamine (R950261)

A mixture of equimolar amounts of 2-chloro-N4-(3-nitrophenyl)-5-fluoro-4-aminopyridine and 3-(N-methylamino)carbonylmethyleneoxyaniline in MeOH in a pressure tube at 110° C. for 24 h or in EtOH using microwave at 175° C. for 10-20 min followed by aqueous work up gave N4-(3-nitrophenyl)-5-fluoro-N2-[3-(N-methylamino)carbonylmethyleneoxyphenyl]-2,4-pyrimidinediamine. LCMS: purity: 92.7%; MS (m/e): 412.94 (MH+).

7.3.923 N4-(3-Aminophenyl)-5-fluoro-N2-[3-(N-methylamino)carbonylmethyleneoxyphenyl]-2,4-pyrimidinediamine HCl salt (R950262)

N4-(3-Nitrophenyl)-5-fluoro-N2-[3-(N-methylamino)carbonylmethyleneoxyphenyl]-2,4-pyrimidinediamine and Pd/C10% (50% water content) were suspended in EtOH-10% aqueous HCl (1:1) and hydrogenated in a Parr apparatus for 2 hours (22° C., 50 psi). The suspension was filtered over celite and carefully washed with MeOH. The combined filtrates were concentrated under reduced pressure to give the HCl salt of N4-(3-aminophenyl)-5-fluoro-N2-[3-(N-methylamino)carbonylmethyleneoxyphenyl]-2,4-pyrimidinediamine as a white solid. LCMS: purity: 92.7%; MS (m/e): 383.07 (M-Cl+, 100).

7.3.924 N4-(3-Aminophenyl)-5-fluoro-N2-[3-(N-methylamino)carbonylmethyleneoxyphenyl]-2,4-pyrimidinediamine (R950263)

The HCl salt of N4-(3-aminophenyl)-5-fluoro-N2-[3-(N-methylamino)carbonylmethyleneoxyphenyl]-2,4-pyrimidinediamine was neutralized with aqueous sodium carbonate solution and extracted with EtOAc. The organic phase was dried and concentrated to give N4-(3-aminophenyl)-5-fluoro-N2-[3-(N-methylamino)carbonylmethyleneoxyphenyl]-2,4-pyrimidinediamine as a pale yellow solid. $^1$H NMR (DMSO): δ 10.00 (s, 1H), 9.92 (s, 1H), 8.07 (d, 1H, J=2.4 Hz), 8.15 (bs, 2H), 7.91-8.07 (m, 3H), 7.08-7.21 (m, 5H), 6.56 (d, 1H, J=7.2 Hz), 4.32 (s, 2H), 2.72 (d, 3H, J 4.8 Hz); LCMS: purity: 92.7%; MS (m/e): 383.17 (MH+, 100).

7.3.925 N4-(3-Bis-N-methylaminophenyl)-5-fluoro-N2-[3-(N-methylamino)carbonylmethyleneoxyphenyl]-2,4-pyrimidinediamine (R950264)

A solution of N4-(3-aminophenyl)-5-fluoro-N2-[3-(N-methylamino)carbonylmethyleneoxyphenyl]-2,4-pyrimidinediamine in DME-DMF (1:1) was treated with 10 equivalents of MeI and sodium bicarbonate. The mixture was stirred for 1.5 hours at 70° C. and purified by flash chromatography on silica gel to give N4-(3-bis-N-methylaminophenyl)-5-fluoro-N2-[3-(N-methylamino)carbonylmethyleneoxyphenyl]-2,4-pyrimidinediamine as a white solid. LCMS: purity: 90.2%; MS (m/e): 411.04 (MH$^+$, 100).

7.3.926 N4-(3-N-Hydroxyethylaminophenyl)-5-fluoro-N2-[3-(N-methylamino)carbonylmethyleneoxyphenyl]-2,4-pyrimidinediamine (R950265)

A solution of N4-(3-aminophenyl)-5-fluoro-N2-[3-(N-methylamino)carbonylmethyleneoxyphenyl]-2,4-pyrimidinediamine in DME-DMF (1:1) was treated with 10 equivalents of 2-bromoethanol and sodium bicarbonate. The mixture was stirred for 16 hours at 70° C. and purified by flash chromatography on silica gel to give N4-(3-N-hydroxyethylaminophenyl)-5-fluoro. LCMS: purity: 90.2%; MS (m/e): 427.33 (MH$^+$, 100).

7.3.927 N4-(3-Bis(N-hydroxyethyl)aminophenyl)-5-fluoro-N2-[3-(N-methylamino)carbonylmethyleneoxyphenyl]-2,4-pyrimidinediamine (R950266)

A solution of N4-(3-aminophenyl)-5-fluoro-N2-[3-(N-methylamino)carbonylmethyleneoxyphenyl]-2,4-pyrimidinediamine in DME-DMF (1:1) was treated with 10 equivalents of 2-bromoethanol and sodium bicarbonate. The mixture was stirred for 16 hours at 70° C. and purified by flash chromatography on silica gel to give N4-(3-bis(N-hydroxyethyl)aminophenyl)-5-fluoro-N2-[3-(N-methylamino)carbonylmethyleneoxyphenyl]-2,4-pyrimidinediamine as a white solid. LCMS: purity: 94.2%; MS (m/e): 471.46 (MH$^+$, 100).

7.3.928 N4-(3-N-Methylaminophenyl)-5-fluoro-N2-[3-(N-methylamino)carbonylmethyleneoxyphenyl]-2,4-pyrimidinediamine (R950267)

A solution of N4-(3-aminophenyl)-5-fluoro-N2-[3-(N-methylamino)carbonylmethyleneoxyphenyl]-2,4-pyrimidinediamine in DME-DMF (1:1) was treated with 10 equivalents of MeI and sodium bicarbonate. The mixture was stirred for 1.5 hours at 70° C. and purified by flash chromatography on silica gel to give N4-(3-N-methylaminophenyl)-5-fluoro-N2-[3-(N-methylamino)carbonylmethyleneoxyphenyl]-2,4-pyrimidinediamine as a white solid. LCMS: purity: 92.3%; MS (m/e): 397.02 (MH$^+$, 100).

7.3.929 N4-(3-Carboxy-4-hydroxyphenyl)-5-fluoro-N2-[3-ethoxycarbonylmethyleneoxyphenyl]-2,4-pyrimidinediamine (R950290)

A mixture of equimolar amounts of 2-chloro-N4-(3-carboxy-4-hydroxyphenyl)-5-fluoro-4-aminopyridine and 3-ethoxycarbonylmethyleneoxyaniline in MeOH in a pressure tube at 110° C. for 24 h or in EtOH using microwave at 175° C. for 10-20 min followed by aqueous work up gave N4-(3-carboxy-4-hydroxyphenyl)-5-fluoro-N2-[3-ethoxycarbonylmethyleneoxyphenyl]-2,4-pyrimidinediamine. LCMS: purity: 97.8%; MS (m/e): 443.20 (MH$^+$).

7.3.930 N4-(3-Carboxy-4-hydroxyphenyl)-5-fluoro-N2-[3-carboxymethyleneoxyphenyl]-2,4-pyrimidinediamine (R950291)

The reaction of N4-(3-carboxy-4-hydroxyphenyl)-5-fluoro-N2-[3-ethoxycarbonylmethyleneoxyphenyl]-2,4-pyrimidinediamine (0.1 g) and LiOH (10 equivalents) in MeOH:water (1:1, v/v) for 1 h at room temperature followed by treatment with aqueous HCl gave the solid. The resulting solid was filtered, washed with water and dried to give N4-(3-carboxy-4-hydroxyphenyl)-5-fluoro-N2-[3-carboxymethyleneoxyphenyl]-2,4-pyrimidinediamine. LCMS: purity: 91.5%; MS (m/e): 415.16 (MH$^+$).

7.3.931 N4-(3-Methoxycarbonyl-4-hydroxyphenyl)-5-fluoro-N2-[3-ethoxycarbonylmethyleneoxyphenyl]-2,4-pyrimidinediamine (R950293)

A solution of N4-(3-carboxy-4-hydroxyphenyl)-5-fluoro-N2-[3-ethoxycarbonylmethyleneoxyphenyl]-2,4-pyrimidinediamine in dry MeOH was treated with a 4 M solution of HCl in dioxane. The mixture was stirred for 1 hour at 22° C., concentrated to dryness and purified by flash chromatography on silica gel to give N4-(3-methoxycarbonyl-4-hydroxyphenyl)-5-fluoro-N2-[3-ethoxycarbonylmethyleneoxyphenyl]-2,4-pyrimidinediamine as a white solid. LCMS: purity: 96.8%; MS (m/e): 457.25 (MH$^+$).

7.3.932 N4-(4-Methoxy-3,4-dihydro-2H-1-benzopyran-6-yl)-5-fluoro-N2-[3-ethoxycarbonylmethyleneoxyphenyl]-2,4-pyrimidinediamine (R950294)

A mixture of equimolar amounts of 2-chloro-N4-(4-methoxy-3,4-dihydro-2H-1-benzopyran-6-yl)-5-fluoro-4-aminopyridine and 3-ethoxycarbonylmethyleneoxyaniline in EtOH using microwave at 175° C. for 10-20 min followed by aqueous work up gave N4-(4-methoxy-3,4-dihydro-2H-1-benzopyran-6-yl)-5-fluoro-N2-[3-ethoxycarbonylmethyleneoxyphenyl]-2,4-pyrimidinediamine. LCMS: purity: 92.1%; MS (m/e): 469.26 (MH$^+$).

7.3.933 N4-(4-Methoxy-3,4-dihydro-2H-1-benzopyran-6-yl)-5-fluoro-N2-[3-methoxycarbonylmethyleneoxyphenyl]-2,4-pyrimidinediamine (R950295)

A mixture of equimolar amounts of 2-chloro-N4-(4-methoxy-3,4-dihydro-2H-1-benzopyran-6-yl)-5-fluoro-4-aminopyridine and 3-ethoxycarbonylmethyleneoxyaniline in MeOH in a pressure tube at 110° C. for 24 h followed by aqueous work up gave N4-(4-methoxy-3,4-dihydro-2H-1-benzopyran-6-yl)-5-fluoro-N2-[3-methoxycarbonylmethyleneoxyphenyl]-2,4-pyrimidinediamine. LCMS: purity: 87.6%; MS (m/e): 455.26 (MH$^+$).

7.3.934 N4-(4-Ethoxy-3,4-dihydro-2H-1-benzopyran-6-yl)-5-fluoro-N2-[3-(N-methylamino)carbonylmethyleneoxyphenyl]-2,4-pyrimidinediamine (R950296)

A solution of N4-(4-ethoxy-3,4-dihydro-2H-1-benzopyran-6-yl)-5-fluoro-N2-[3-ethoxycarbonylmethyleneoxyphenyl]-2,4-pyrimidinediamine in EtOH was treated with the HCl salt of methylamine. The mixture was stirred for 4 hours at 100° C., concentrated to dryness and purified by flash

7.3.935 N4-(4-Carboxyethyleneoxyphenyl)-5-fluoro-N2-[3-(N-methylamino)carbonylmethyleneoxyphenyl]-2,4-pyrimidinediamine (R950344)

chromatography on silica gel to give N4-(4-ethoxy-3,4-dihydro-2H-1-benzopyran-6-yl)-5-fluoro-N2-[3-(N-methylamino)carbonylmethyleneoxyphenyl]-2,4-pyrimidinediamine as a white solid. LCMS: purity: 87.4%; MS (m/e): 468.29 (MH$^+$).

A mixture of equimolar amounts of 2-chloro-N4-(4-carboxyethyleneoxyphenyl)-5-fluoro-4-aminopyridine and 3-(N-methylamino)carbonylmethyleneoxyaniline in MeOH in a pressure tube at 110° C. for 24 h or in EtOH using microwave at 175° C. for 10-20 min followed by aqueous work up gave N4-(4-carboxyethyleneoxyphenyl)-5-fluoro-N2-[3-(N-methylamino)carbonylmethyleneoxyphenyl]-2,4-pyrimidinediamine. LCMS: purity: 97.8%; MS (m/e): 456.32 (MH$^+$).

7.3.936 N4-(2,3-Dihydro-4-benzypyranon-6-yl)-5-fluoro-N2-[3-(N-methylamino)carbonylmethyleneoxyphenyl]-2,4-pyrimidinediamine (R950345)

A solution of N4-(4-Methoxycarbonylethyleneoxyphenyl)-5-fluoro-N2-[3-(N-methylamino)carbonylmethyleneoxyphenyl]-2,4-pyrimidinediamine in TfOH was heated for 2 hours at 100° C. Aqueous work up followed by flash chromatography on silica gel gave N4-(2,3-dihydro-4-benzypyranon-6-yl)-5-fluoro-N2-[3-(N-methylamino)carbonylmethyleneoxyphenyl]-2,4-pyrimidinediamine as a white solid. LCMS: purity: 92.2%; MS (m/e): 435.95 (MH$^+$).

7.3.937 N4-(4-Methoxycarbonylethyleneoxyphenyl)-5-fluoro-N2-[3-(N-methylamino)carbonylmethyleneoxyphenyl]-2,4-pyrimidinediamine (R950346)

A solution of N4-(4-carboxyethyleneoxyphenyl)-5-fluoro-N2-[3-(N-methylamino)carbonylmethyleneoxyphenyl]-2,4-pyrimidinediamine in dry MeOH was treated with a 4 M solution of HCl in dioxane. The mixture was stirred for 1 hour at 22° C., concentrated to dryness and purified by flash chromatography on silica gel to give N4-(4-methoxycarbonylethyleneoxyphenyl)-5-fluoro-N2-[3-(N-methylamino)carbonylmethyleneoxyphenyl]-2,4-pyrimidinediamine as a white solid. LCMS: purity: 85.2%; MS (m/e): 468.01 (MH$^+$).

7.3.938 N4-(4-Hydroxyphenyl)-5-fluoro-N2-[3-(N-methylamino)carbonylmethyleneoxyphenyl]-2,4-pyrimidinediamine (R950347)

The reaction of N4-(4-methoxycarbonylethyleneoxyphenyl)-5-fluoro-N2-[3-(N-methylamino)carbonylmethyleneoxyphenyl]-2,4-pyrimidinediamine and LiOH (10 equivalents) in MeOH:water (1:1, v/v) for 1 h at room temperature followed by treatment with aqueous HCl gave a pale yellow solid. The resulting solid was filtered, washed with water and dried to give N4-(4-hydroxyphenyl)-5-fluoro-N2-[3-(N-methylamino)carbonylmethyleneoxyphenyl]-2,4-pyrimidinediamine. LCMS: purity: 94.7%; MS (m/e): 382.03 (MH$^+$).

7.3.939 N4-(2,3-Dihydro-4-oxime-benzypyran-6-yl)-5-fluoro-N2-[3-(N-methylamino)carbonylmethyleneoxyphenyl]-2,4-pyrimidinediamine (R950348)

A mixture N4-(2,3-dihydro-4-benzypyranon-6-yl)-5-fluoro-N2-[3-(N-methylamino)carbonylmethyleneoxyphenyl]-2,4-pyrimidinediamine and hydroxylamine (20 equivalents) in pyridine at 22° C. for 16 hours followed by aqueous work up gave N4-(2,3-dihydro-4-oxime-benzypyran-6-yl)-5-fluoro-N2-[3-(N-methylamino)carbonylmethyleneoxyphenyl]-2,4-pyrimidinediamine as a white solid. LCMS: purity: 89.5%; MS (m/e): 451.00 (MH$^+$).

7.3.940 N4-(4-Hydroxy-3,4-dihydro-2H-1-benzopyran-6-yl)-5-fluoro-N2-[3-(N-methylamino)carbonylmethyleneoxyphenyl]-2,4-pyrimidinediamine (R950349)

A solution of N4-(2,3-dihydro-4-benzypyranon-6-yl)-5-fluoro-N2-[3-(N-methylamino)carbonylmethyleneoxyphenyl]-2,4-pyrimidinediamine in dry MeOH was treated with a sodiumcyanoborohydride. The mixture was stirred for 1 hour at 22° C., concentrated to dryness and purified by flash chromatography on silica gel to give N4-(4-Hydroxy-3,4-dihydro-2H-1-benzopyran-6-yl)-5-fluoro-N2-[3-(N-methylamino)carbonylmethyleneoxyphenyl]-2,4-pyrimidinediamine as a white solid. $^1$H NMR (DMSO): δ 9.19 (s, 1H), 9.09 (s, 1H), 8.03 (d, 1H, J=2.4 Hz), 7.28-7.93 (m, 5H), 7.07 (t, 1H, J=7.2 Hz), 6.71 (d, 1H, J=7.2 Hz), 6.44 (dd, 1H, J=2.6, 7.2 Hz), 5.31 (d, 1H, J=5.1 Hz), 4.14-4.59 (m, 3H), 4.30 (s, 2H), 2.63 (d, 3H, J=4.8 Hz), 1.82-2.03 (m, 2H); LCMS: purity: 93.3%; MS (m/e): 440.15 (MH$^+$).

7.3.941 N4-(2,3-Dihydro-4-O-methyloxime-benzypyran-6-yl)-5-fluoro-N2-[3-(N-methylamino)carbonylmethyleneoxyphenyl]-2,4-pyrimidinediamine (R950356)

A mixture N4-(2,3-dihydro-4-benzypyranon-6-yl)-5-fluoro-N2-[3-(N-methylamino)carbonylmethyleneoxyphenyl]-2,4-pyrimidinediamine and methoxyamine (20 equivalents) in pyridine at 22° C. for 16 hours followed by aqueous work up gave N4-(2,3-dihydro-4-oxime-benzypyran-6-yl)-5-fluoro-N2-[3-(N-methylamino)carbonylmethyleneoxyphenyl]-2,4-pyrimidinediamine as a white solid. LCMS: purity: 85.5%; MS (m/e): 465.10 (MH$^+$).

7.3.942 N4-(4-Amino-3,4-dihydro-2H-1-benzopyran-6-yl)-5-fluoro-N2-[3-(N-methylamino)carbonylmethyleneoxyphenyl]-2,4-pyrimidinediamine (R950368)

A mixture N4-(4-azido-3,4-dihydro-2H-1-benzopyran-6-yl)-5-fluoro-N2-[3-(N-methylamino)carbonylmethyleneoxyphenyl]-2,4-pyrimidinediamine and Pd/C (10%) in MeOH was hydrogenated at 22° C. for 6 hours (40 psi). The mixture was filtered and concentrated to dryness to give N4-(4-amino-3,4-dihydro-2H-1-benzopyran-6-yl)-5-fluoro-N2-[3-(N-methylamino)carbonylmethyleneoxyphenyl]-2,4-pyrimidinediamine as a white solid. $^1$H NMR (DMSO): δ 9.60 (s, 1H), 9.46 (s, 1H), 8.73 (bs, 3H), 8.00-8.10 (m, 3H), 7.47 (s, 1H), 7.42 (m, 1H), 7.29 (d, 1H, J=7.2 Hz), 7.11 (t, 1H, J=7.2 Hz), 6.82 (d, 1H, J 7.0 Hz), 6.46 (m, 1H), 4.23-4.46 (m, 3H), 4.31 (s, 3H), 2.63 (d, 3H, J=4.8 Hz), 2.09-2.29 (m, 2H); LCMS: purity: 97.6%; MS (m/e): 438.98 (MH$^+$).

7.3.943 N4-(3-Methylcarbonylphenyl)-5-fluoro-N2-[3-(N-methylamino)carbonylmethyleneoxyphenyl]-2,4-pyrimidinediamine (R950371)

A mixture of equimolar amounts of 2-chloro-N4-(3-methylcarbonylphenyl)-5-fluoro-4-aminopyridine and 3-(N-methylamino)carbonylmethyleneoxyaniline in MeOH in a pressure tube at 110° C. for 24 h or in EtOH using microwave at 175° C. for 10-20 min followed by aqueous work up gave N4-(3-methylcarbonylphenyl)-5-fluoro-N2-[3-(N-methylamino)carbonylmethyleneoxyphenyl]-2,4-pyrimidinediamine as a white solid. $^1$H NMR (DMSO): δ 10.16 (s, 1H), 9.82 (s, 1H), 8.24 (d, 1H, J=2.4 Hz), 8.15 (s, 1H), 7.91-8.07 (m, 2H), 7.70 (d, 1H, J=7.0 Hz), 7.49 (t, 1H, J=7.2 Hz), 7.08-7.21 (m, 3H), 6.56 (d, 1H, J=7.2 Hz), 4.30 (s, 3H), 2.62 (d, 3H, J=4.8 Hz), 2.48 (s, 3H); LCMS: purity: 93.8%; MS (m/e): 410.50 (MH$^+$).

7.3.944 N4-(3-Phenylcarbonylphenyl)-5-fluoro-N2-[3-(N-methylamino)carbonylmethyleneoxyphenyl]-2,4-pyrimidinediamine (R950372)

A mixture of equimolar amounts of 2-chloro-N4-(3-phenylcarbonylphenyl)-5-fluoro-4-aminopyridine and 3-(N-methylamino)carbonylmethyleneoxyaniline in MeOH in a pressure tube at 110° C. for 24 h or in EtOH using microwave at 175° C. for 10-20 min followed by aqueous work up gave N4-(3-phenylcarbonylphenyl)-5-fluoro-N2-[3-(N-methylamino)carbonylmethyleneoxyphenyl]-2,4-pyrimidinediamine as a white solid. LCMS: purity: 86.0%; MS (m/e): 472.50 (MH$^+$).

7.3.945 N4-(3-Methylcarbonyloximephenyl)-5-fluoro-N2-[3-(N-methylamino)carbonylmethyleneoxyphenyl]-2,4-pyrimidinediamine (R950373)

A mixture N4-(3-methylcarbonylphenyl)-5-fluoro-N2-[3-(N-methylamino)carbonylmethyleneoxyphenyl]-2,4-pyrimidinediamine and hydroxylamine (20 equivalents) in pyridine at 22° C. for 16 hours followed by aqueous work up gave N4-(3-methylcarbonyloximephenyl)-5-fluoro-N2-[3-(N-methylamino)carbonylmethyleneoxyphenyl]-2,4-pyrimidinediamine as a white solid. $^1$H NMR (DMSO): δ 11.21 (s, 1H), 10.11 (s, 1H), 9.85 (s, 1H), 6.54-8.23 (m, 9H), 4.32 (s, 2H), 2.63 (d, J=7.0 Hz, 3H), 2.47 (s, 3H); LCMS: purity: 92.4%; MS (m/e): 425.28 (MH$^+$).

7.3.946 N4-(3-Phenylcarbonyloximephenyl)-5-fluoro-N2-[3-(N-methylamino)carbonylmethyleneoxyphenyl]-2,4-pyrimidinediamine (R950374)

A mixture N4-(3-phenylcarbonylphenyl)-5-fluoro-N2-[3-(N-methylamino)carbonylmethyleneoxyphenyl]-2,4-pyrimidinediamine and hydroxylamine (20 equivalents) in pyridine at 22° C. for 16 hours followed by aqueous work up gave N4-(3-phenylcarbonyloximephenyl)-5-fluoro-N2-[3-(N-methylamino)carbonylmethyleneoxyphenyl]-2,4-pyrimidinediamine as a white solid. $^1$H NMR (DMSO): δ 11.63 (s, 1H), 10.30 (s, 1H), 9.85 (s, 1H), 6.44-8.43 (m, 14H), 4.42 (s, 2H), 2.63 (d, J=7.0 Hz, 3H); LCMS: purity: 92.4%; MS (m/e): 487.31 (MH$^+$).

7.3.947 N2,N4-Bis(3-methylcarbonylphenyl)-5-fluoro-2,4-pyrimidinediamine (R950376)

A mixture of 2,4-dichloro-5-fluoropyridine and three equivalents of 3-acetophenone in MeOH in a pressure tube at 110° C. for 24 h or in EtOH using microwave at 175° C. for 10-20 min followed by aqueous work up gave N2,N4-bis(3-methylcarbonylphenyl)-5-fluoro-2,4-pyrimidinediamine as a white solid. LCMS: purity: 93.1%; MS (m/e): 365.19 (MH$^+$).

7.3.948 N2,N4-Bis(3-phenylcarbonylphenyl)-5-fluoro-2,4-pyrimidinediamine (R950377)

A mixture of 2,4-dichloro-5-fluoropyridine and three equivalents of 3-benzophenone in MeOH in a pressure tube at 110° C. for 24 h or in EtOH using microwave at 175° C. for 10-20 min followed by aqueous work up gave N2,N4-bis(3-phenylcarbonylphenyl)-5-fluoro-2,4-pyrimidinediamine as a white solid. LCMS: purity: 95.7%; MS (m/e): 489.29 (MH$^+$).

7.3.949 N2,N4-Bis(2,3-dihydro-4-benzypyranon-6-yl)-5-fluoro-2,4-pyrimidinediamine (R950378)

A solution of N2,N4-bis(4-methoxycarbonylethyleneoxyphenyl)-5-fluoro-2,4-pyrimidinediamine in TfOH was heated for 2 hours at 100° C. Aqueous work up followed by flash chromatography on silica gel gave N2,N4-bis(2,3-dihydro-4-benzypyranon-6-yl)-5-fluoro-2,4-pyrimidinediamine as a white solid. $^1$H NMR (DMSO): δ 9.36 (s, 1H), 9.14 (s, 1H), 8.06 (d, 1H, J=2.4 Hz), 7.72-7.99 (m, 3H), 6.97 (d, J=7.2 Hz, 1H), 6.87 (d, J=7.2 Hz, 1H), 4.42-4.52 (m, 4H), 2.70-2.78 (m, 4H); LCMS: purity: 94.3%; MS (m/e): 484.50 (MH$^+$).

7.3.950 N2,N4-Bis(3-methylcarbonyloximephenyl)-5-fluoro-2,4-pyrimidinediamine (R950379)

A mixture of N2,N4-bis(3-methylcarbonylphenyl)-5-fluoro-2,4-pyrimidinediamine and hydroxylamine (20 equivalents) in pyridine at 22° C. for 16 hours followed by aqueous work up gave N2,N4-bis(3-methylcarbonyloximephenyl)-5-fluoro-2,4-pyrimidinediamine as a white solid. $^1$H NMR (DMSO): δ 11.21 (s, 1H), 10.11 (s, 1H), 9.85 (s, 1H), 6.54-8.23 (m, 9H), 4.32 (s, 2H), 2.63 (d, J=7.0 Hz, 3H), 2.47 (s, 3H); LCMS: purity: 92.1%; MS (m/e): 393.06 (M-H$^-$).

7.3.951 N2,N4-Bis(3-phenylcarbonyloximephenyl)-5-fluoro-2,4-pyrimidinediamine (R950380)

A mixture of N2,N4-bis(3-phenylcarbonylphenyl)-5-fluoro-2,4-pyrimidinediamine and hydroxylamine (20 equivalents) in pyridine at 22° C. for 16 hours followed by aqueous work up gave N2,N4-bis(3-phenylcarbonyloximephenyl)-5-fluoro-2,4-pyrimidinediamine as a white solid. LCMS: purity: 93.3%; MS (m/e): 486.05 (M-H$^-$).

7.3.952 N2,N4-Bis(2,3-dihydro-4-oxime-benzypyran-6-yl)-5-fluoro-2,4-pyrimidinediamine (R950381)

A mixture of N2,N4-bis(2,3-dihydro-4-benzypyranon-6-yl)-5-fluoro-2,4-pyrimidinediamine and hydroxylamine (20 equivalents) in pyridine at 22° C. for 16 hours followed by aqueous work up gave N2,N4-bis(2,3-dihydro-4-oxime-benzypyran-6-yl)-5-fluoro-2,4-pyrimidinediamine as a white solid. LCMS: purity: 98.1%; MS (m/e): 449.03 (M-H$^-$).

7.3.953 N4-(4-Acetyloxy-3,4-dihydro-2H-1-benzopyran-6-yl)-5-fluoro-N2-[3-(N-methylamino)carbonylmethyleneoxyphenyl]-2,4-pyrimidinediamine (R950382)

A solution of N4-(4-hydroxy-3,4-dihydro-2H-1-benzopyran-6-yl)-5-fluoro-N2-[3-(N-methylamino)carbonylmethyleneoxyphenyl]-2,4-pyrimidinediamine in pyridine was treated with acetic anhydride at 22° C. for 16 hours. Aqueous work up gave N4-(4-acetyloxy-3,4-dihydro-2H-1-benzopyran-6-yl)-5-fluoro-N2-[3-(N-methylamino)carbonylmethylene oxyphenyl]-2,4-pyrimidinediamine as a white solid. $^1$H NMR (DMSO): δ 10.43 (bs, 1H), 9.62 (bs, 1H), 8.03 (d, 1H, J=2.4 Hz), 7.10-7.83 (m, 7H), 6.83 (d, 1H, J=7.4 Hz), 6.52 (d, 1H, J=7.2 Hz), 5.01 (m, 1H), 4.75 (s, 2H), 4.03-4.32 (m, 2H), 2.62 (s, 3H), 2.23 (s, 3H), 1.93-2.13 (m, 2H); LCMS: purity: 92.1%; MS (m/e): 393.06 (M-H$^-$).

7.3.954 N4-(4-Azido-3,4-dihydro-2H-1-benzopyran-6-yl)-5-fluoro-N2-[3-(N-methylamino)carbonylmethyleneoxyphenyl]-2,4-pyrimidinediamine (R950383)

A solution of N4-(4-hydroxy-3,4-dihydro-2H-1-benzopyran-6-yl)-5-fluoro-N2-[3-(N-methylamino)carbonylmethyleneoxyphenyl]-2,4-pyrimidinediamine in dry THF was treated with 2 equivalents of DPPA and DBU. The mixture was stirred for 3 hours at 22° C., concentrated to dryness and purified by flash chromatography on silica gel to give N4-(4-azido-3,4-dihydro-2H-1-benzopyran-6-yl)-5-fluoro-N2-[3-(N-methylamino)carbonylmethyleneoxyphenyl]-2,4-pyrimidinediamine as a white solid. $^1$H NMR (DMSO): δ 10.09 (bs, 1H), 9.83 (bs, 1H), 8.18 (d, 1H, J=2.4 Hz), 7.97 (m, 1H), 7.11-7.61 (m, 6H), 6.82 (d, 1H, J=7.8 Hz), 6.62 (d, 1H, J=7.2 Hz), 4.78 (s, 2H), 4.03-4.33 (m, 3H), 2.62 (s, 3H), 1.93-2.13 (m, 2H); LCMS: purity: 97.9%; MS (m/e): 463.07 (MH$^+$).

7.3.955 N4-(4-Benzypyran-6-yl)-5-fluoro-N2-[3-(N-methylamino)carbonylmethyleneoxyphenyl]-2,4-pyrimidinediamine (R950385)

A solution of N4-(4-hydroxy-3,4-dihydro-2H-1-benzopyran-6-yl)-5-fluoro-N2-[3-(N-methylamino)carbonylmethyleneoxyphenyl]-2,4-pyrimidinediamine in THF was treated with bortrifluoride etherate at 80° C. for 8 hours. Aqueous work up gave N4-(4-benzypyran-6-yl)-5-fluoro-N2-[3-(N-methylamino)carbonylmethyleneoxyphenyl]-2,4-pyrimidinediamine as a white solid. $^1$H NMR (DMSO): δ 9.18 (s, 1H), 9.14 (s, 1H), 8.03 (d, J=2.4 Hz, 1H), 7.93 (bs, 1H), 5.86-7.48 (m, 9H) 4.73-4.74 (m, 2H), 4.33 (s, 2H), 2.62 (s, 3H); LCMS: purity: 96.5%; MS (m/e): 420.07 (M-H$^-$).

7.3.956 N4-(3-Hydroxymethylen-4-methoxyphenyl)-5-fluoro-N2-[3-(N-methylamino)carbonylmethyleneoxyphenyl]-2,4-pyrimidinediamine (R950386)

A mixture of equimolar amounts of 2-chloro-N4-(3-hydroxymethylen-4-methoxyphenyl)-5-fluoro-4-aminopyridine and 3-(N-methylamino)carbonylmethyleneoxyaniline in MeOH in a pressure tube at 110° C. for 24 h or in EtOH using microwave at 175° C. for 10-20 min followed by aqueous work up gave N4-(3-hydroxymethylen-4-methoxyphenyl)-5-fluoro-N2-[3-(N-methylamino)carbonylmethyleneoxyphenyl]-2,4-pyrimidinediamine as a white solid. LCMS: purity: 89.2%; MS (m/e): 410.5 (MH$^+$).

7.3.957 N4-(3-Amino-4-ethoxyphenyl)-5-fluoro-N2-[3-(N-methylamino)carbonylmethyleneoxyphenyl]-2,4-pyrimidinediamine (R950388)

A mixture of 2-chloro-N4-(3-amino-4-ethoxyphenyl)-5-fluoro-4-aminopyridine and 3 equivalents of 3-(N-methylamino)carbonylmethyleneoxyaniline in MeOH in a pressure tube at 110° C. for 24 h or in EtOH using microwave at 175° C. for 10-20 min followed by aqueous work up gave N4-(3-amino-4-ethoxyphenyl)-5-fluoro-N2-[3-(N-methylamino)carbonylmethyleneoxyphenyl]-2,4-pyrimidinediamine as a white solid. LCMS: purity: 95.1%; MS (m/e): 427.18 (MH$^+$).

7.3.958 N4-(4-Ethoxy-3-hydroxysulfonylphenyl)-5-fluoro-N2-[3-(N-methylamino)carbonylmethyleneoxyphenyl]-2,4-pyrimidinediamine (R950389)

A solution of N4-(4-hydroxy-3,4-dihydro-2H-1-benzopyran-6-yl)-5-fluoro-N2-[3-(N-methylamino)carbonylmethyleneoxyphenyl]-2,4-pyrimidinediamine in HOAc was treated with sodium nitrate followed by addition of concentrated aqueous HCl and copper dichloride. The mixture was stirred for 2 hours at 22° C. for 8 hours and purified by aqueous work up followed by column chromatography on silica gel to give N4-(4-ethoxy-3-hydroxysulfonylphenyl)-5-fluoro-N2-[3-(N-methylamino)carbonylmethyleneoxyphenyl]-2,4-pyrimidinediamine. LCMS: purity: 82.3%; MS (m/e): 474.09 (M-H$^-$).

7.3.959 N2,N4-Bis(3-methoxycarbonyl-4-trifluoromethoxyphenyl)-5-fluoro-2,4-pyrimidinediamine (R950391)

A mixture of 2,4-dichloro-5-fluoropyridine and three equivalents of 3-methoxycarbonyl-4-trifluoromethoxyaniline in MeOH in a pressure tube at 110° C. for 24 h or in EtOH using microwave at 175° C. for 10-20 min followed by aqueous work up N2,N4-bis(3-methoxycarbonyl-4-trifluoromethoxyphenyl)-5-fluoro-2,4-pyrimidinediamine as a white solid. $^1$H NMR (DMSO): δ 9.96 (s, 1H), 9.82 (s, 1H), 8.16-8.26 (m, 4H), 7.91 (dd, 1H, J=3.0, 7.2 Hz), 7.42 (d, 1H, J=7.2 Hz), 7.31 (d, 1H, J=7.2 Hz), 3.77 (s, 3H), 3.75 (s, 3H); LCMS: purity: 93.0%; MS (m/e): 565.37 (MH$^+$).

7.3.960 N4-(3-Methoxycarbonyl-4-trifluoromethoxyphenyl)-5-fluoro-N2-[3-(N-methylamino)carbonylmethyleneoxyphenyl]-2,4-pyrimidinediamine (R950392)

A mixture of equimolar amounts of 2-chloro-N4-(3-methoxycarbonyl-4-trifluoromethoxyphenyl)-5-fluoro-4-aminopyridine and 3-(N-methylamino)carbonylmethyleneoxyaniline in MeOH in a pressure tube at 110° C. for 24 h or in EtOH using microwave at 175° C. for 10-20 min followed by aqueous work up gave N4-(3-methoxycarbonyl-4-trifluoromethoxyphenyl)-5-fluoro-N2-[3-(N-methylamino)carbonylmethyleneoxyphenyl]-2,4-pyrimidinediamine as a white solid. LCMS: purity: 95.8%; MS (m/e): 510.41 (MH$^+$).

7.3.961 N4-(4-Acetylamino-3,4-dihydro-2H-1-benzopyran-6-yl)-5-fluoro-N2-[3-(N-methylamino)carbonylmethyleneoxyphenyl]-2,4-pyrimidinediamine (R950393)

A solution of N4-(4-hydroxy-3,4-dihydro-2H-1-benzopyran-6-yl)-5-fluoro-N2-[3-(N-methylamino)carbonylmethyleneoxyphenyl]-2,4-pyrimidinediamine in dry MeCN was treated with concentrated sulfuric acid. The mixture was stirred for 3 hours at 22° C., concentrated to dryness and purified by flash chromatography on silica gel to give N4-(4-acetylamino-3,4-dihydro-2H-1-benzopyran-6-yl)-5-fluoro-N2-[3-(N-methylamino)carbonylmethyleneoxyphenyl]-2,4-pyrimidinediamine as a white solid. $^1$H NMR (DMSO): δ 10.46 (bs, 1H), 9.52 (bs, 1H), 7.98 (d, 1H, J=2.4 Hz), 7.12-7.73 (m, 7H), 6.66 (d, 1H, J=7.2 Hz), 6.49 (d, 1H, J=7.2 Hz), 4.75 (s, 2H), 4.03-4.32 (m, 2H), 3.80 (m, 1H), 2.64 (s, 3H), 2.143 (s, 3H), 1.90-2.11 (m, 2H); LCMS: purity: 92.1%; MS (m/e): 393.06 (M-H$^-$). LCMS: purity: 96.2%; MS (m/e): 479.13 (M-H$^-$).

7.3.962 N4-[2,4-Dihydro-1-oxo-4H-imidazo[2,1-c][1,4]benzoxazin-8-yl]-5-fluoro-N2-(3-hydroxyphenyl)-2,4-pyrimidinediamine (R945236)

N4-[2H-1,4-Benzoxazin-3(4H)-one-6-yl]-5-fluoro-N2-(3-hydroxyphenyl)-2,4-pyrimidinediamine (800 mg, 2.18 mmol) and phosphorus pentasulfide (800 mg, 1.80 mmol) were stirred in pyridine (5 mL) at 70° C. for 2 h. The reaction solution was treated with 1N HCl solution to pH 5. The precipitation was collected with filtration, washed with water, dried to give N4-[2H-1,4-benzoxazin-3(4H)-thione-6-yl]-5-fluoro-N2-(3-hydroxyphenyl)-2,4-pyrimidinediamine.

N4-[2H-1,4-Benzoxazin-3(4H)-thione-6-yl]-5-fluoro-N2-(3-hydroxyphenyl)-2,4-pyrimidinediamine (400 mg, 1.04 mmol), glycine (500 mg) and triethylamine (0.5 mL) were stirred in methanol (10 mL) at 70° C. overnight. The undissolved salt was filtered off, washed with methanol. The filtrate was evaporated and redissolved in THF (5 mL) and DMF (5 mL). To the solution were added EDC (200 mg), HOAt (200 mg) and diisopropylethylamine (0.2 mL). The reaction solution was stirred at 70° C. for 0.5 h. The mixture was diluted with ethyl acetate (60 mL) and washed with water (2×60 mL). The organic layer was separated, dried, evaporated and purified by flash column chromatography (EtOAc/hexanes=1:1, EtOAc) to give N4-[2,4-dihydro-1-oxo-4H-imidazo[2,1-c][1,4]benzoxazin-8-yl]-5-fluoro-N2-(3-hydroxyphenyl)-2,4-pyrimidinediamine as a white solid. $^1$H NMR (CDCl$_3$): δ 4.35 (t, J=2.1 Hz, 2H), 4.92 (t, J=2.1 Hz, 2H), 6.44 (dd, J=1.5 and 8.1 Hz, 1H), 6.81 (m, 2H), 6.99 (s, 1H), 7.11 (m, 2H), 7.39 (m, 2H), 7.97 (d, J=3.0 Hz, 1H), 8.02 (s, 1H), 8.57 (d, J=2.4 Hz, 1H); $^{19}$F NMR (282 MHz, CDCl$_3$): 6-167.46; LCMS: ret. time: 13.71 min.; purity: 93.18%; MS (m/e): 407.10 (MH$^+$).

7.3.963 5-Fluoro-N2-(3-hydroxyphenyl)-N4-[1-oxo-1,2,3,6-tetrahydropyrimido[2,1-c][1,4]benzoxazin-9-yl]-2,4-pyrimidinediamine (R945237)

In a manner analogous to the preparation of N4-[2,4-dihydro-1-oxo-4H-imidazo[2,1-c][1,4]benzoxazin-8-yl]-5-fluoro-N2-(3-hydroxyphenyl)-2,4-pyrimidinediamine, N4-[2H-1,4-benzoxazin-3(4H)-thione-6-yl]-5-fluoro-N2-(3-hydroxyphenyl)-2,4-pyrimidinediamine (400 mg, 1.04 mmol) and β-alanine (500 mg) gave 5-fluoro-N2-(3-hydroxyphenyl)-N4-[1-oxo-1,2,3,6-tetrahydropyrimido[2,1-c][1,4]benzoxazin-9-yl]-2,4-pyrimidinediamine as a white solid. $^1$H NMR (acetone-d$_6$): δ 2.68 (t, J=7.2 Hz, 2H), 3.71 (t, J=7.2 Hz, 2H), 4.62 (t, J=1.2 Hz, 2H), 6.42 (ddd, J=1.2 and 2.4 and 7.5 Hz, 1H), 6.98-7.08 (m, 3H), 7.38 (t, J=2.4 Hz, 1H), 7.62 (dd, J=2.4 and 8.7 Hz, 1H), 7.96 (d, J=3.3 Hz, 1H), 8.12 (s, 1H), 8.16 (s, 1H), 8.52 (d, J=2.7 Hz, 1H), 8.65 (s, 1H); $^{19}$F NMR (282 MHz, acetone-d$_6$): 6-168.04.

7.3.964 5-Fluoro-N2-(3-methylaminocarbonylmethyleneoxyphenyl)-N4-[2H-pyrido[3,2-b]-1,4-oxazin-3(4H)-one-7-yl]-2,4-pyrimidinediamine (R945242)

2H-Pyrido[3,2-b]-1,4-oxazin-3(4H)-one (500 mg) was treated with nitric acid (5 mL) and sulfuric acid (5 mL). The reaction mixture was heated to 70° C. for 30 min and then poured into ice-water. The solution was neutralized with sodium bicarbonate to pH 6. The yellow precipitation was collected by filtration, washed with water and dried to give a mixture of nitrated products (regio-isomers).

The mixture of nitrated compounds was reduced under hydrogenolysis conditions using 10% Pd—C in methanol at 40 psi for 30 min. The catalyst was filtered off. The filtrate was evaporated and treated with 2,4-dichloro-5-fluoropyrimidine (200 mg) in methanol (5 mL), water (5 mL). The reaction mixture was heated at 70° C. overnight, then evaporated. The residue was reacted with 3-methylaminocarbonylmethyleneoxyaniline (300 mg) in methanol (5 mL) and water (1 mL) at 100° C. overnight. The reaction mixture was diluted with 1N HCl solution (60 mL). The brown precipitation was collected by filtration, washed with water and dried to give 5-fluoro-N2-(3-methylaminocarbonylmethyleneoxyphenyl)-N4-[2H-pyrido[3,2-b]-1,4-oxazin-3(4H)-one-7-yl]-2,4-pyrimidinediamine. $^1$H NMR (DMSO-d$_6$): δ 2.62 (d, J=4.8 Hz, 3H), 4.33 (s, 2H), 4.63 (s, 2H), 6.48 (dd, J=2.4 and 7.5 Hz, 1H), 7.11 (t, J=8.1 Hz, 1H), 7.27 (d, J=7.8 Hz, 1H), 7.36 (s, 1H), 7.86 (d, J=2.1 Hz, 1H), 7.97 (m, 1H), 8.12 (d, J=3.6 Hz, 1H), 8.38 (d, J=2.1 Hz, 1H), 9.33 (s, 1H), 9.46 (s, 1H), 11.18 (s, 1H); $^{19}$F NMR (282 MHz, DMSO-d$_6$): 6-164.49; LCMS: ret. time: 13.16 min.; purity: 79.30%; MS (m/e): 440.16 (MH$^+$).

7.3.965 5-Fluoro-N2-(3-methylaminocarbonylmethyleneoxyphenyl)-N4-[2H-pyrido[3,2-b]-1,4-oxazin-7-yl]-2,4-pyrimidinediamine (R945263)

2H-Pyrido[3,2-b]-1,4-oxazin-3(4H)-one (1 g, 6.66 mmol) was refluxed with boron hydride methyl sulfide complex (2 mL) in THF (10 mL) for 30 min to give 2H-pyrido[3,2-b]-1,4-oxazine. In a manner analogous to the preparation of 5-fluoro-N2-(3-methylaminocarbonylmethyleneoxyphenyl)-N4-[2H-pyrido[3,2-b]-1,4-oxazin-3(4H)-one-7-yl]-2,4-pyrimidinediamine, 2H-pyrido[3,2-b]-1,4-oxazine was nitrated, reduced and reacted with 2,4-dichloro-5-fluoropyrimidine (400 mg) and 3-methylaminocarbonylmethyleneoxyaniline (500 mg) to give 5-fluoro-N2-(3-methylaminocarbonylmethyleneoxyphenyl)-N4-[2H-pyrido[3,2-b]-1,4-oxazin-7-yl]-2,4-pyrimidinediamine as a gray solid. $^1$H NMR (CDCl$_3$): δ 2.91 (d, J=4.8 Hz, 3H), 3.55 (t, J=4.2 Hz, 2H), 4.24 (t, J=4.5 Hz, 2H), 4.49 (s, 2H), 4.90 (br, 1H), 6.51 (dd, J=2.7 and 8.1 Hz, 1H), 6.64 (s, 1H), 6.90 (dd, J=2.1 and 8.1 Hz, 1H), 7.08 (s, 1H), 7.14 (br, 1H), 7.18 (t, J=8.1 Hz, 1H), 7.28 (d, J=2.1 Hz, 1H), 7.51 (t, J=2.1 Hz, 1H), 7.93 (d, J=3.0 Hz, 1H), 7.95 (d, J=2.4 Hz, 1H); LCMS: ret. time: 11.91 min.; purity: 100%; MS (m/e): 426.12 (MH$^+$).

7.3.966 5-Fluoro-N2-(3-methylaminocarbonylmethyleneoxyphenyl)-N4-[2H-pyrido[3,2-b]-1,4-oxazin-3(4H)-one-6-yl]-2,4-pyrimidinediamine (R921304)

2H-Pyrido[3,2-b]-1,4-oxazin-3(4H)-one (2.5 g) was dissolved in acetic acid (6 mL) and acetic anhydride (30 mL). Fuming nitric acid (3 mL) was added dropwise to the reaction solution in ice-bath. The reaction solution was stirred in ice-bath overnight. Solution was poured into crashed ice. The light yellow precipitation was collected by filtration, washed with water and dried to give a mixture of nitrated products (regio-isomers). The mixture was crystallized from dichloromethane to give 6-nitro-2H-pyrido[3,2-b]-1,4-oxazin-3(4H)-one (1 g) as a light yellow solid.

6-Nitro-2H-pyrido[3,2-b]-1,4-oxazin-3(4H)-one (1 g) was reduced under hydrogenolysis conditions using 10% Pd—C in methanol (50 mL) and 1N HCl solution (10 mL) at 50 psi for 2 h. The catalyst was filtered off and washed with methanol and 1N HCl solution. The filtrate was evaporated to give 6-amino-2H-pyrido[3,2-b]-1,4-oxazin-3(4H)-one.

In a manner analogous to the preparation of 5-fluoro-N2-(3-methylaminocarbonylmethyleneoxyphenyl)-N4-[2H-pyrido[3,2-b]-1,4-oxazin-3(4H)-one-7-yl]-2,4-pyrimidinediamine, 6-amino-2H-pyrido[3,2-b]-1,4-oxazin-3(4H)-one was reacted with 2,4-dichloro-5-fluoropyrimidine (500 mg) and 3-methylaminocarbonylmethyleneoxyaniline (500 mg) to give 5-fluoro-N2-(3-methylaminocarbonylmethyleneoxyphenyl)-N4-[2H-pyrido[3,2-b]-1,4-oxazin-3(4H)-one-6-yl]-2,4-pyrimidinediamine as a beige solid. $^1$H NMR (DMSO-d$_6$): δ 2.63 (d, J=4.5 Hz, 3H), 4.35 (s, 2H), 4.62 (s, 2H), 6.47 (dd, J=1.8 and 8.1 Hz, 1H), 7.10 (t, J=8.1 Hz, 1H), 7.25 (d, J=8.1 Hz, 1H), 7.37 (m, 2H), 7.59 (d, J=8.4 Hz, 1H), 7.96 (d, J=5.1 Hz, 1H), 8.13 (d, J=3.6 Hz, 1H), 9.26 (s, 1H), 9.29 (s, 1H), 11.13 (s, 1H); $^{19}$F NMR (282 MHz, DMSO-d$_6$): 6-163.20; LCMS: ret. time: 25.22 min.; purity: 97.55%; MS (m/e): 440.25 (MH$^+$).

7.3.967 5-Fluoro-N2-(3-methylaminocarbonylmethyleneoxyphenyl)-N4-[2H-pyrido[3,2-b]-1,4-oxazin-6-yl]-2,4-pyrimidinediamine (R945299)

6-Nitro-2H-pyrido[3,2-b]-1,4-oxazin-3(4H)-one (500 mg) was refluxed with boron hydride methyl sulfide complex (1 mL) in THF (10 mL) for 30 min to give 6-nitro-2H-pyrido[3,2-b]-1,4-oxazine. In a manner analogous to the preparation of 5-fluoro-N2-(3-methylaminocarbonylmethyleneoxyphenyl)-N4-[2H-pyrido[3,2-b]-1,4-oxazin-3(4H)-one-7-yl]-2,4-pyrimidinediamine, 6-nitro-2H-pyrido[3,2-b]-1,4-oxazine was reduced and reacted with 2,4-dichloro-5-fluoropyrimidine (500 mg) and 3-methylaminocarbonylmethyleneoxyaniline (500 mg) to give 5-fluoro-N2-(3-methylaminocarbonylmethyleneoxyphenyl)-N4-[2H-pyrido[3,2-b]-1,4-oxazin-6-yl]-2,4-pyrimidinediamine as a gray solid. $^1$H NMR (CD$_3$OD): δ 2.81 (s, 3H), 3.48 (t, J=4.5 Hz, 2H), 4.14 (t, J=4.5 Hz, 2H), 4.44 (s, 2H), 6.60 (ddd, J=1.5 and 2.7 and 7.5 Hz, 1H), 6.94 (d, J=8.1 Hz, 1H), 7.14 (d, J=3.0 Hz, 1H), 7.17 (t, J=7.8 Hz, 1H), 7.40 (d, J=8.9 Hz, 1H), 7.42 (t, J=2.1 Hz, 1H), 7.92 (d, J=3.3 Hz, 1H); $^{19}$F NMR (282 MHz, CD$_3$OD): 6-168.20; LCMS: ret. time: 25.49 min.; purity: 97.56%; MS (m/e): 426.23 (MH$^+$).

7.3.968 N4-(1,4-Benzoxazin-3-on-7-yl))-5-fluoro-N2-(3-hydroxyphenyl)-2,4-pyrimidinediamine (R908698)

In like manner to N4-(3,4-ethylenedioxyphenyl)-5-fluoro-N2-(3-hydroxyphenyl)-2,4-pyrimidinediamine, 2-chloro-5-fluoro-N4-(1,4-benzoxazin-3-on-7-yl)pyrimidineamine and 3-aminophenol were reacted to yield N4-(1,4-Benzoxazin-3-on-7-yl)-5-fluoro-N2-(3-hydroxyphenyl)-2,4-pyrimidinediamine. 1H (DMSO-d6) 8.2 (d, 1H, J=4 Hz), 7.30 (m, 2H), 7.09 (m, 4H), 6.5 (m, 1H), 4.6 (s, 2H) purity 95%; MS (m/e): 368 (MH+)

7.3.969 N2-(1,4-Benzoxazin-3-on-7-yl)-5-fluoro-N4-(3-hydroxyphenyl)-2,4-pyrimidinediamine (R908699)

In like manner to N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)]pyrimidineamine and 7-amino-1,4-benzoxazine-3-one were reacted to yield N2-(1,4-Benzoxazin-3-on-7-yl)-5-fluoro-N4-(3-hydroxyphenyl)-2,4-pyrimidinediamine. 1H (DMSO-d6) 8.20 (d, 1H, J=4 Hz), 7.10 (m, 5H), 6.65 (m, 1H), 4.54 (s, 2H) purity 95% MS (m/e): 368 (MH+)

7.3.970 N4-(1,4-Benzoxazine-3-on-7-yl)-5-fluoro-N2-((N-methyl acetamido-2)-3-phenoxy)-2,4-pyrimidinediamine (R908700)

In like manner to N4-(3,4-ethylenedioxyphenyl)-5-fluoro-N2-(3-hydroxyphenyl)-2,4-pyrimidinediamine, 2-chloro-5-fluoro-N4-1,4-benzoxazin-3-on-7-yl)phenylpyrimidineamine and 3-(N-methylaminocarbonylmethyleneoxy)aniline were reacted to yield N4-(1,4-Benzoxazine-3-on-7-yl)-5-fluoro-N2-((N-methyl acetamido-2)-3-phenoxy)-2,4-pyrimidinediamine 1H (DMSO-d6) 8.2 (d, 1H, J=4 Hz), 8.00 (m, 1H), 7.19 (m, 1H), 7.09 (m, 3H), 6.55 (m, 1H), 4.64 (s, 2H), 4.27 (s, 2H), 3.18 (s, 3H), 2.63 (m, 3H) purity 95% MS (m/e): 439 (MH+)

7.3.971 N4-(1,4-Benzoxazine-3-on-6-yl)-5-fluoro-N2-[(N-methyl acetamido-2)-3-phenoxy)]-2,4-pyrimidinediamine (R908701)

In like manner to N4-(3,4-ethylenedioxyphenyl)-5-fluoro-N2-(3-hydroxyphenyl)-2,4-pyrimidinediamine, 2-chloro-5-fluoro-N4-[6-(1,4-benzoxazin-3-onyl)]phenylpyrimidineamine and 3-(N-methylaminocarbonylmethyleneoxy)aniline were reacted to yield N4-(1,4-Benzoxazine-3-on-6-yl)-5-fluoro-N2-[(N-methyl acetamido-2)-3-phenoxy]-2,4-pyrimidinediamine 1H (DMSO-d6) 8.2 (d, 1H, J=4 Hz), 8.00 (m, 1H), 7.13 (m, 3H), 6.95 (m, 1H), 6.55 (m, 1H), 4.64 (s, 2H), 4.27 (s, 2H), 3.18 (s, 3H), 2.63 (m, 3H) purity 96% MS (m/e): 439 (MH+)

7.3.972 N4-(1,4-Benzoxazine-3-on-6-yl)-5-fluoro-N2-(3-hydroxyphenyl)-2,4-pyrimidinediamine (R908702)

In like manner to N4-(3,4-ethylenedioxyphenyl)-5-fluoro-N2-(3-hydroxyphenyl)-2,4-pyrimidinediamine, 2-chloro-5-fluoro-N4-(1,4-benzoxazin-3-on-6-yl)phenylpyrimidineamine and 3-aminophenol were reacted to yield N4-(1,4-Benzoxazine-3-on-6-yl)-5-fluoro-N2-(3-hydroxyphenyl)-2,4-pyrimidinediamine 1H (DMSO-d6) 8.20 (d, 1H, J=4 Hz), 7.22 (m, 2H), 7.03 (m, 4H), 6.55 (m, 1H), 4.64 (s, 2H) purity 98% MS (m/e): 368 (MH+)

7.3.973 5-Fluoro-N4-(3-hydroxyphenyl)-N2-(N-methyl-1,4-benzoxazine-3-on-6-yl)-2,4-pyrimidinediamine (R908703)

In like manner to N4-(3,4-ethylenedioxyphenyl)-5-fluoro-N2-(3-hydroxyphenyl)-2,4-pyrimidinediamine, 2-chloro-5-fluoro-N4-(N-methyl-1,4-benzoxazin-3-on-6-yl)]phenylpyrimidineamine and 3-(N-methylaminocarbonylmethyleneoxy)aniline were reacted to yield 5-Fluoro-N2-[3-(N-methylaminocarbonylmethyleneoxy)phenyl]-N4-(N-methyl-1,4-benzoxazin-3-on-6-yl)]pyrimidinediamine 1H (DMSO-d6) 8.20 (d, 1H, J=4 Hz), 7.23 (m, 6H), 6.55 (m, 1H), 4.64 (s, 2H), 3.18 (s, 3H) purity 96%; MS (m/e): 382(MH+)

7.3.974 5-Fluoro-N4-(3-hydroxyphenyl)-N2-(N-methyl-1,4-benzoxazin-7-yl)-2,4-pyrimidinediamine (R908704)

In like manner to N4-(3,4-ethylenedioxyphenyl)-5-fluoro-N2-(3-hydroxyphenyl)-2,4-pyrimidinediamine, 2-chloro-5-fluoro-N4-(N-methyl-1,4-benzoxazin-3-on-7-yl)]phenylpyrimidineamine and 3-(N-methylaminocarbonylmethyleneoxy)aniline were reacted to yield 5-Fluoro-N4-(3-hydroxyphenyl)-N2-(N-methyl-1,4-benzoxazin-7-yl)-2,4-pyrimidinediamine 1H (DMSO-d6) 8.8.13 (d, 1H, J=4 Hz), 7.13 (m, 3H), 6.72 (m, 3H), 6.59 (m, 1H), 4.24 (m, 2H), 4.27 (s, 2H), 3.28 (m, 2H), 2.83 (m, 3H) purity 93%; MS (m/e): 367 (MH+)

7.3.975 5-Fluoro-N2-[(N-methyl acetamido-2)-3-phenoxy]-N4-(N-methyl-1,4-benzoxazin-7-yl)-2,4-pyrimidinediamine (R908705)

In like manner to N4-(3,4-ethylenedioxyphenyl)-5-fluoro-N2-(3-hydroxyphenyl)-2,4-pyrimidinediamine, 2-chloro-5-fluoro-N4-(N-methyl-1,4-benzoxazin-3-on-7-yl)]phenylpyrimidineamine and 3-(N-methylaminocarbonylmethyleneoxy)aniline were reacted to yield 5-Fluoro-N2-[(N-methyl acetamido-2)-3-phenoxy]-N4-(N-methyl-1,4-benzoxazin-7-yl)-2,4-pyrimidinediamine 1H (DMSO-d6) 8.20 (d, 1H, J=4 Hz), 7.13 (m, 5H), 6.75 (m, 2H), 4.44 (s, 2H), 4.27 (m, 2H), 3.22 (m, 2H), 2.83 (s, 3H), 2.63 (m, 3H) purity 96%; MS (m/e): 439 (MH+)

7.3.976 N2-(1,4-Benzoxazin-7-yl)-5-fluoro-N4-(3-hydroxyphenyl)-2,4-pyrimidinediamine (R908706)

In like manner to N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)]pyrimidineamine and 7-amino-1,4-benzoxazine were reacted to yield N2-(1,4-Benzoxazin-7-yl)-5-fluoro-N4-(3-hydroxyphenyl)-2,4-pyrimidinediamine. 1H (DMSO-d6) 7.95 (d, 1H, J=4 Hz), 7.43 (m, 1H), 7.02 (m, 4H), 6.42 (m, 2H), 4.17 (m, 2H), 3.33 (m, 2H) purity 96%; MS (m/e): 353 (MH+)]

7.3.977 5-Fluoro-N2-(3-hydroxyphenyl)-N4-(N-methyl-1,4-benzoxazin-7-yl)-2,4-pyrimidinediamine (R908707)

In like manner to N4-(3,4-ethylenedioxyphenyl)-5-fluoro-N2-(3-hydroxyphenyl)-2,4-pyrimidinediamine, 2-chloro-5-fluoro-N4-(N-methyl-1,4-benzoxazin-7-yl)pyrimidineamine and 3-aminophenol were reacted to yield 5-Fluoro-N2-(3-hydroxyphenyl)-N4-(N-methyl-1,4-benzoxazin-7-yl)-2,4-pyrimidinediamine. 1H (DMSO-d6) 8.20 (d, 1H, J=4 Hz), 7.10 (m, 5H), 6.65 (m, 1H), 4.54 (s, 2H) purity 95% MS (m/e): 368 (MH+)

7.3.978 5-Fluoro-N4-(3-hydroxyphenyl) N2-(N-Methyl-1,4-benzoxazine-3-on-7-yl)-2,4-pyrimidinediamine (R908708)

In like manner to N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)pyrimidineamine and 7-amino-4-N-methyl-1,4-benzoxazine-3-one were reacted to yield 5-Fluoro-N4-(3-hydroxyphenyl) N2-(N-Methyl-1,4-benzoxazine-3-on-7-yl)-2,4-pyrimidinediamine. 1H (DMSO-d6) 8.20 (d, 1H, J=4 Hz), 7.23 (m, 1H), 7.15 (m, 5H), 6.62 (m, IH), 4.64 (s, 2H), 4.27 (s, 2H), 3.18 (s, 3H) purity 95%; MS (m/e): 380 (MH+)]

7.3.979 5-Fluoro-N2-(3-hydroxyphenyl)-N4-(N-methyl-1,4-benzoxazin-3-on-6-yl)-2,4-pyrimidinediamine (R908709)

In like manner to N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)]pyrimidineamine and 6-amino-1,4-benzoxazine were reacted to yield 5-Fluoro-N2-(3-hydroxyphenyl)-N4-(N-methyl-1,4-benzoxazin-3-on-6-yl)-2,4-pyrimidinediamine. 1H (DMSO-d6) 8.20 (d, 1H, J=4 Hz), 7.43 (m, 2H), 7.19 (m, 4H), 6.55 (m, 1H), 4.64 (s, 2H), 3.25 (s, 3H) purity 95%; MS (m/e): 382 (MH+)

7.3.980 5-Fluoro-N2-(3-hydroxyphenyl)-N4-(N-methyl-1,4-benzoxazin-6-yl)-2,4-pyrimidinediamine (R908710)

In like manner to N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)pyrimidineamine and 6-amino-1,4-benzoxazine were reacted to yield 5-Fluoro-N2-(3-hydroxyphenyl)-N4-(N-methyl-1,4-benzoxazin-6-yl)-2,4-pyrimidinediamine. 1H (MeOD-d4) 8.20 (d, 1H, J=4 Hz), 7.43 (m, 3H), 6.90 (m, 2H), 6.75 (m, 1H), 4.25 (m, 2H), 3.25 (m, 2H), 2.85 (bs, 1H) purity 96%; MS (m/e): 382 (MH+)

7.3.981 N4-(1,4-Benzoxazin-7-yl)-5-fluoro-N2-(3-hydroxyphenyl)-pyrimidinediamine (R908711)

In like manner to N4-(3,4-ethylenedioxyphenyl)-5-fluoro-N2-(3-hydroxyphenyl)-2,4-pyrimidinediamine, N4-[6-(1,4-benzoxazinyl)]—N2-chloro-5-fluoropyrimidineamine and 3-ethoxyocarbonylmethyleneoxyaniline were reacted to yield N4-(1,4-Benzoxazin-7-yl)-5-fluoro-N2-(3-hydroxyphenyl)-pyrimidinediamine $^1$H NMR (MeOD-d4): δ 8.2 (d, 1H, J=4 Hz), 7.15 (m, 4H), 6.84 (m, 2H), 6.62 (m, 1H), 4.65 (s, 2H), 4.15 (m, 4H), 3.28 (m, 2H), 1.19 (t, 3H. J=7 Hz) purity 94%; MS (m/e): 439 (MH$^+$).

7.3.982 (+/−)-5-Fluoro-N2-[(N-methyl acetamido-2)-3-phenoxy]-N4-(2-methyl-1,4-benzoxazin-6-yl)-2,4-pyrimidinediamine (R908712)

In like manner to N4-(3,4-ethylenedioxyphenyl)-5-fluoro-N2-(3-hydroxyphenyl)-2,4-pyrimidinediamine, (+/−)-2-chloro-5-fluoro-N4-(2-methyl-1,4-benzoxazin-6-yl)]phenylpyrimidineamine and 3-(N-methylaminocarbonylmethyleneoxy)aniline were reacted to yield (+/−)-5-Fluoro-N2-[(N-methyl acetamido-2)-3-phenoxy]-N4-(2-methyl-1,4-benzoxazin-6-yl)-2,4-pyrimidinediamine 1H (DMSO-d6) 8.20 (d, 1H, J=4 Hz), 8.13 (m, 1H), 7.1 (m, 5H), 6.96 (m, 1H), 6.63 (m, 1H), 4.62 (m, 1H), 4.40 (s, 3H), 2.63 (m, 3H), 1.25 (m, 3H) purity 93%; MS (m/e): 453 (MH+)

7.3.983 N2-(N-Ethylcarbonylmethyleneoxy-1,4-benzoxazin-6-yl)-5-fluoro-N2-[3-hydroxyphenyl) phenyl]pyrimidinediamine (R908734)

In like manner to N4-(3,4-ethylenedioxyphenyl)-5-fluoro-N2-(3-hydroxyphenyl)-2,4-pyrimidinediamine, 2-Chloro-5-fluoro-N4-(3-hydroxyphenyl)pyrimidineamine and 6-Amino-N-carbomethoxy-1,4-benzoxazine were reacted to yield N2-(N-Ethylcarbonylmethyleneoxy-1,4-benzoxazin-6-yl)-5-fluoro-N2-[3-hydroxyphenyl)phenyl]pyrimidinediamine 1H NMR (DMSO-d6): δ 8.23 (m, 1H), 7.20 (m, 1H), 7.14 (m, 4H), 6.95(m, 1H), 6.76 (m, 1H), 4.66 (s, 1H), 4.48 (s, 1H), 4.25 (q, 2H J=6.5 Hz), 1.28 (t, 2H, J=6.5 Hz), purity 95% MS (m/e): 454(MH$^+$).

7.3.984 N4-(1,4-Benzoxazin-6-yl)-N2-(3-chloro-4-hydroxy-5-methylphenyl)-5-fluoropyrimidinediamine (R909255)

In like manner to N4-(3,4-ethylenedioxyphenyl)-5-fluoro-N2-(3-hydroxyphenyl)-2,4-pyrimidinediamine, N4-[6-(1,4-benzoxazinyl)]-N2-chloro-5-fluoropyrimidineamine and 3-chloro-4-hydroxy-5-methylaniline were reacted to yield N4-(1,4-benzoxazin-6-yl)-N2-(3-chloro-4-hydroxy-5-methylphenyl)-5-fluoropyrimidinediamine $^1$H NMR (DMSO-d6): δ7.89 (d, 1H, J=4 Hz), 7.25 (m, 1H), 7.14 (m, 1H), 6.80 (m, 2H), 6.82 (m, 1H), 4.29 (s, 2H), 3.35 (m, 2H), 2.20 (s, 3H) purity 99%; MS (m/e): 402 (MH$^+$).

7.3.985 5-Fluoro-N2-[3-(N-methylaminocarbonylmethyleneoxy)phenyl]-N4-(N-methyl-1,4-benzoxazin-6-yl)pyrimidinediamine (R909259)

In like manner to N4-(3,4-ethylenedioxyphenyl)-5-fluoro-N2-(3-hydroxyphenyl)-2,4-pyrimidinediamine, 2-chloro-5-fluoro-N4-[6-(N-methyl-1,4-benzoxazinyl)]phenyl pyrimidineamine and 3-(N-methylaminocarbonylmethyleneoxy) aniline were reacted to yield 5-Fluoro-N2-[3-(N-methylaminocarbonylmethyleneoxy)phenyl]-N4-(N-methyl-1,4-benzoxazin-6-yl)pyrimidinediamine 1H (DMSO-d6) 8.01 (d, 1H, J=4 Hz), 7.33 (m, 2H), 7.22 (m, 1H), 7.02 (m, 2H), 6.65 (m, 1H), 6.42 (m, 1H), 4.37 (s, 2H), 4.22 (m, 2H), 3.18 (m, 2H), 2.78 (s, 3H) 2.63 (m, 3H) purity 98%; MS (m/e): 439 (MH+)

7.3.986 5-Fluoro-N2-[3-(N-methylaminocarbonylmethyleneoxy) phenyl]-N4-[6-(N-methyl-1,4-benzoxazin-3-onyl)]pyrimidinediamine (R909260)

In like manner to N4-(3,4-ethylenedioxyphenyl)-5-fluoro-N2-(3-hydroxyphenyl)-2,4-pyrimidinediamine, 2-chloro-5-fluoro-N4-[6-(N-methyl-1,4-benzoxazin-3-onyl)]phenylpyrimidineamine and 3-(N-methylaminocarbonylmethyleneoxy)aniline were reacted to yield 5-Fluoro-N2-[3-(N-methylaminocarbonylmethyleneoxy)phenyl]-N4-[6-(N-methyl-1,4-benzoxazin-3-onyl)]pyrimidinediamine 1H (DMSO-d6) 8.01 (d, 1H, J=4 Hz), 7.33 (m, 2H), 7.22 (m, 1H), 7.02 (m, 2H), 6.65 (m, 1H), 6.42 (m, 1H), 4.37 (s, 2H), 4.22 (s, 2H), 3.18 (s, 3H), 2.78 (s, 3H) 2.63 (m, 3H) purity 88%; MS (m/e): 453 (MH+)

7.3.987 5-Fluoro-N2-[3-(N-methylaminocarbonylmethyleneoxy) phenyl]-N4-(N-methyl-1,4-benzoxazin-3-on-7-yl)]-2,4-pyrimidinediamine (R909261)

In like manner to N4-(3,4-ethylenedioxyphenyl)-5-fluoro-N2-(3-hydroxyphenyl)-2,4-pyrimidinediamine, 2-chloro-5-fluoro-N4-(N-methyl-1,4-benzoxazin-3-on-7-yl)phenylpyrimidineamine and 3-(N-methylaminocarbonylmethyleneoxy)aniline were reacted to yield 5-Fluoro-N2-[3-(N-methylaminocarbonylmethyleneoxy)phenyl]-N4-(N-methyl-1,4-benzoxazin-3-on-7-yl)pyrimidinediamine 1H (DMSO-d6) 8.08 (d, 1H, J=4 Hz), 7.43 (m, 2H), 7.19 (m, 1H), 7.09 (m, 3H), 6.55 (m, 1H), 4.64 (s, 2H), 4.27 (s, 2H), 3.18 (s, 3H), 2.63 (m, 3H) MS (m/e): 453 (MH+)

7.3.988 (+/−)-5-Fluoro-N4-(3-hydroxyphenyl]-N2-(2-methyl-1,4-benzothiazin-3-on-6-yl)pyrimidinediamine (R909263)

In like manner to N4-(3,4-ethylenedioxyphenyl)-5-fluoro-N2-(3-hydroxyphenyl)-2,4-pyrimidinediamine, 2-chloro-5-fluoro-N4-(3-hydroxyphenyl)pyrimidineamine and 6-amino-2-methyl-1,4-benzothiazin-3-one were reacted to yield (+/−)-5-Fluoro-N4-(3-hydroxyphenyl]-N2-(2-methyl-1,4-benzothiazin-3-on-6-yl)pyrimidinediamine $^1$H NMR (MeOD-d4): δ8.02 (d, 1H, J=4 Hz), 7.30 (m, 3H), 7.08 (m, 3H), 6.52 (m, 1H), 3.57 (m, 1H), 1.25 (m, 3H) purity 92%; MS (m/e): 398 (MH$^+$).

7.3.989 5-Fluoro-N2-[3-hydroxyphenyl)-N4-(N-methyl-1,4-benzoxazin-3-on-7-yl)-2,4-pyrimidinediamine (R909264)

In like manner to N4-(3,4-ethylenedioxyphenyl)-5-fluoro-N2-(3-hydroxyphenyl)-2,4-pyrimidinediamine, 2-chloro-5-fluoro-N4-(N-methyl-1,4-benzoxazin-3-on-7-yl)]phenylpyrimidineamine and 3-aminophenol were reacted to yield 5-Fluoro-N2-[3-hydroxyphenyl)-N4-(N-methyl-1,4-benzoxazin-3-on-7-yl)]-2,4-pyrimidinediamine 1H (DMSO-d6) 8.08 (d, 1H, J=4 Hz), 7.53 (m, 2H), 7.09 (m, 4H), 6.42 (m, 1H), 4.64 (s, 2H), 3.27 (s, 3H) purity 95% MS (m/e): 382 (MH+)

7.3.990 N4-(3-Ethylcarboxy-4H-imidazo[5,1-c]-1,4-benzoxazin-6-yl)-5-fluoro-N2-[3-(N-methylaminocarbonylmethyleneoxy) phenyl]pyrimidinediamine (R909265)

In like manner to N4-(3,4-ethylenedioxyphenyl)-5-fluoro-N2-(3-hydroxyphenyl)-2,4-pyrimidinediamine, N2-Chloro-N4-(3-ethylcarboxy-4H-imidazo[5,1-c]-1,4-benzoxazin-6-yl)-5-fluoropyrimidineamine and 3-(N-methylaminocarbonylmethyleneoxy)aniline were reacted to yield N4-(3-Ethylcarboxy-4H-imidazo[5,1-c]-1,4-benzoxazin-6-yl)-5-fluoro-N2-[3-(N-methylaminocarbonylmethyleneoxy)phenyl]pyrimidinediamine $^1$H NMR (DMSO-d6): δ 8.23 (m, 2H), 8.08 (d, J=4 Hz, 1H), 7.92 (m, 1H), 7.43 (m, 1H), 7.38(m, 2H), 7.18 (m, 1H), 6.99 (t, 1H), 6.41 (m, 1H), 5.43 (s, 2H) purity 92%; MS (m/e): 534 (MH$^+$).

7.3.991 N4-(1,4-Benzoxazin-7-yl)-N2-[3-ethoxycarbonylmethyleneoxy)phenyl]-5-fluoro-2,4-pyrimidinediamine (R909266)

In like manner to N4-(3,4-ethylenedioxyphenyl)-5-fluoro-N2-(3-hydroxyphenyl)-2,4-pyrimidinediamine, N4-(1,4-Benzoxazin-7-yl)-2-chloro-5-fluoro-pyrimidineamine and 3-(ethoxycarbonylmethyleneoxy)aniline were reacted to yield N4-(1,4-Benzoxazin-7-yl)-N2-[3-ethoxycarbonylmethyleneoxy)phenyl]-5-fluoro-2,4-pyrimidinediamine. 1H (DMSO-d6) 8.2 (d, 1H, J=4 Hz), 7.43 (m, 1H), 7.12 (m, 4H), 6.68 (m, 2H), 4.7 (s, 2H) 4.17 (m, 2H), 3.33 (m, 2H), 3.13 (m, 2H) 1.87 (m, 3H) purity 89%; MS (m/e): 439 (MH+)

7.3.992 N2-(3-Ethylcarboxy-4H-imidazo[5,1-c]-1,4-benzoxazin-6-yl)-5-fluoro-N4-(3-hydroxyphenyl)pyrimidinediamine (R909267)

In like manner to N4-(3,4-ethylenedioxyphenyl)-5-fluoro-N2-(3-hydroxyphenyl)-2,4-pyrimidinediamine, 2-Chloro-5-fluoro-N4-(3-hydroxyphenyl)pyrimidineamine and 3 Ethyl 6-Amino-(3-carboxy-4H-imidazo[5,1-c]-1,4-benzoxazine were reacted to yield N2-(3-Ethylcarboxy-4H-imidazo[5,1-c]-1,4-benzoxazin-6-yl)-5-fluoro-N4-(3-hydroxyphenyl)pyrimidinediamine 1H NMR (DMSO-d6): δ 8.18 (m, 1H), 8.04 (m, 1H), 7.38 (m, 2H), 7.22 (m, 1H), 7.04 (m, 2H), 6.96 (m, 1H), 6.53 (m, 1H), 5.42 (s, 2H), 4.25 (q, 2H J=6.5 Hz), 1.28 (t, 2H, J=6.5 Hz), purity 92% MS (m/e): 409 (MH+).

7.3.993 N2-(1,4-Benzoxazin-3-on-6-yl)-5-fluoro-N4-(3-hydroxyphenyl)-2,4-pyrimidinediamine (R909268)

In like manner to N4-(3,4-ethylenedioxyphenyl)-5-fluoro-N2-(3-hydroxyphenyl)-2,4-pyrimidinediamine N4-[6-(1,4-benzoxazinyl)]-N2-chloro-5-fluoropyrimidineamine and 6-amino-1,4-benzoxazin-3-one were reacted to yield N2-(1,4-benzoxazin-3-on-6-yl)-5-fluoro-N4-(6-(1,4-benzoxazinyl)]-)-2,4-pyrimidinediamine. $^1$H NMR (DMSO-d6): δ 8.18 (d, 1H J=4 Hz), 7.17 (m, 2H), 6.88 (m, 2H), 6.80 (m, 1H), 6.58 (m, 1H) 4.52 (s, 2H), 4.11 (m, 2H), 3.33 (m, 2H) purity: 97%; MS (m/e): 409 (MH+).

7.3.994 N2-[3-(N,N-Dimethylaminocarbonylmethyleneoxy)phenyl]-N4-(1,4-benzoxazin-6-yl)-5-fluoro-2,4-pyrimidinediamine (R909290)

In like manner to N4-(3,4-ethylendioxyphenyl)-5-fluoro-N2-[3-(N-methylamino)carbonylmethyleneoxyphenyl]-2,4-pyrimidinediamine, N4-(1,4-benzoxazin-6-yl)-N2-(3-ethoxyocarbonylmethyleneoxyphenyl)-5-fluoropyrimidinediamine and dimethylamine hydrochloride were reacted to yield N2-[3-(N,N-Dimethylaminocarbonylmethyleneoxy)phenyl]-N4-(1,4-benzoxazin-6-yl)-5-fluoro-2,4-pyrimidinediamine $^1$H NMR (CD$_3$OD): δ 7.8 (d, 1H), 7.4 (m, 1H), 7.05 (m, 2H), 7.0 (s, 1H), 6.8 (dd, 1H), 6.66 (d, 1H), 6.56 (dd, 1H), 4.35 (s, 2H), 4.18 (m, 2H), 3.25 (m, 2H), 2.8 (s, 6H); purity: 95%; MS (m/e): 439 (MH+)

7.3.995 N4-(4N-Carboxamidino-1,4-benzoxazin-6-yl)-5-fluoro-N2-[3-(N-methylamino)carbonylmethyleneoxyphenyl]-2,4-pyrimidinediamine (R909292)

To a solution in 2 mL THF at 0° Celsius containing 250 mg (0.59 mmol) of N4-(1,4-benzoxazin-6-yl)-5-fluoro-N2-[3-(N-methylamino)carbonylmethyleneoxyphenyl]-2,4-pyrimidinediamine, 1.4 eq, 115 uL TEA, and catalytic DMAP was added 0.4 eq, 70 mg of triphosgene. After 30 min 15 mL of aqueous ammonia and stirred for 30 min at RT. The THF was evaporated and the reaction was diluted with water, and the resulting precipitate collection by suction filtration. The crude precipitate was purified by preparative TLC (5% MeOH/EtOAc) to yield N4-(4N-Carboxamidino-1,4-benzoxazin-6-yl)-5-fluoro-N2-[3-(N-methylamino)carbonylmethyleneoxyphenyl]-2,4-pyrimidinediamine. $^1$H NMR (CD$_3$OD): δ 7.83 (m, 1H), 7.42 (m, 1H), 7.12 (m, 2H), 7.08 (s, 1H), 6.84 (m, 1H), 6.66 (m, 1H), 6.48 (m, 1H), 4.30 (s, 2H), 4.15 (m, 2H), 3.22 (m, 2H), 2.82 (s, 3H); purity: 87%; MS (m/e): 468 (MH+)

7.3.996 N4-(3,3-Dimethyl-1,4-benzoxazin-6-yl)-N2-[3-ethoxycarbonylmethyleneoxy)phenyl]-5-fluoro-2,4-pyrimidinediamine (R909308)

In like manner to N4-(3,4-ethylenedioxyphenyl)-5-fluoro-N2-(3-hydroxyphenyl)-2,4-pyrimidinediamine, N2-Chloro-N4-(3,3-dimethyl-1,4-benzoxazin-6-yl)-5-fluoro-pyrimidineamine and 3-(ethoxycarbonylmethyleneoxy)aniline were reacted to yield N4-(3,3-dimethyl-1,4-benzoxazin-6-yl)-N2-[3-ethoxycarbonylmethyleneoxy)phenyl]-5-fluoro-2,4-pyrimidinediamine. 1H (DMSO-d6) 8.00 (m, 1H), 7.43 (m, 2H), 7.05 (m, 1H), 6.82 (m, 2H), 6.68 (m, 1H), 6.41 (m, 1H), 4.80 (s, 2H), 4.18 (q, 2H), 3.74 (s, 2H), 1.03 (t, 3H), 1.00 (s, 6H) purity 99%; MS (m/e): 467 (MH+)

7.3.997 N4-(3,3-Dimethyl-1,4-benzoxazin-6-yl)-5-fluoro-N2-[3-(N-methylaminocarbonylmethyleneoxy)phenyl]-2,4-pyrimidinediamine (R909309)

In like manner to N4-(3,4-ethylendioxyphenyl)-5-fluoro-N2-[3-(N-methylamino)carbonylmethyleneoxyphenyl]-2,4-pyrimidinediamine, N4-(3,3-Dimethyl-1,4-benzoxazin-6-yl)-N2-[3-ethoxycarbonylmethyleneoxy)phenyl]-5-fluoro-2,4-pyrimidinediamine and methylamine hydrochloride were reacted to yield N4-(3,3-Dimethyl-1,4-benzoxazin-6-yl)-5-fluoro-N2-[3-(N-methylaminocarbonyl methyleneoxy)phenyl]-2,4-pyrimidinediamine. 1H (DMSO-d6) 8.04 (d, 1H), 7.93 (m, 1H), 7.45 (m, 2H), 7.09 (m, 1H), 6.93 (m, 2H), 6.62 (m, 1H), 6.43 (m, 1H), 4.37 (s, 2H), 3.74 (s, 2H), 2.62 (d, 3H), 1.07 (s, 6H) purity 99%; MS (m/e): 453 (MH+)

7.3.998 N4-(3,3-Dimethyl-1,4-benzoxazin-6-yl)-5-fluoro-N2-[3-(N-methylaminocarbonylmethyleneoxy)phenyl]-2,4-pyrimidinediamine (R909309)

In like manner to N4-(3,4-ethylendioxyphenyl)-5-fluoro-N2-[3-(N-methylamino)carbonylmethyleneoxyphenyl]-2,4-pyrimidinediamine, N4-(3,3-Dimethyl-1,4-benzoxazin-6-yl)-N2-[3-ethoxycarbonylmethyleneoxy)phenyl]-5-fluoro-2,4-pyrimidinediamine and methylamine hydrochloride were reacted to yield N4-(3,3-Dimethyl-1,4-benzoxazin-6-yl)-5-fluoro-N2-[3-(N-methylaminocarbonyl methyleneoxy)phenyl]-2,4-pyrimidinediamine. 1H (DMSO-d6) 8.04 (d, 1H), 7.93 (m, 1H), 7.45 (m, 2H), 7.09 (m, 1H), 6.93 (m, 2H), 6.62 (m, 1H), 6.43 (m, 1H), 4.37 (s, 2H), 3.74 (s, 2H), 2.62 (d, 3H), 1.07 (s, 6H) purity 99%; MS (m/e): 453 (MH+)

7.3.999 N4-(2,4-Diiodo-3-hydroxypheny)-5-fluoro-N2-(3-iodo-1-methyl-indazoline-5-yl)-2,4-pyrimidinediamine (R935221)

To 5-fluoro-N2-(3-hydroxyphenyl)-N4-(1-methyl-indazoline-5-yl)-2,4-pyrimidinediamine (34.4 mg, 0.098 mmole) in ethanol (2.0 mL) and aq. NH$_4$OH (2.0 mL), 12 (0.126 g, 0.99 mmole atom) was added and stirred at room temperature overnight. Reaction mixture was concentrated, dissolved in EtOAc and treated with aq. hypo solution. Organic layer was separated, dried with anhydrous Na$_2$SO$_4$ and concentrated. The crude material was purified by silica gel column chromatography to provide N4-(2,4-diiodo-3-hydroxypheny)-5-fluoro-N2-[3-iodo-1-methyl-indazoline-5-yl]-2,4-pyrimidinediamine. $^1$H NMR (DMSO-d$_6$): δ 9.86 (s, 1H), 9.51 (s, 1H), 9.12(s, 1H), 8.28 (s, 1H), 8.07 (d, 1H, J=3.5 Hz), 7.79 (s, 1H), 7.63 (s, 1H), 7.32 (d, 1H, J=8.8 Hz), 7.37 (d, 1H, J=8.8 Hz), 3.92 (s, 3H). LCMS: ret. time: 20.88 min.; purity: 91%; MS (m/e): 729 (MH+).

7.3.1000 5-Fluoro-N4-(4-isopropoxyphenyl)-N2-[1-(methoxycarbonyl)methyl-indazoline-5-yl]-2,4-pyrimidinediamine (R935222)

In like manner to the preparation of N4-(3,4-ethylenedioxyphenyl)-5-fluoro-N2-(3-hydroxyphenyl)-2,4-pyrimidinediamine, 2-chloro-5-fluoro-N-(4-isopropoxyphenyl)-4-pyrimidineamine was reacted with 5-amino-1-(methoxycarbonyl)methylindazoline to provide 5-fluoro-N4-(4- isopropoxyphenyl)-N2-[1-(methoxycarbonyl)methyl-indazoline-5-yl]-2,4-pyrimidinediamine. $^1$H NMR (DMSO-d$_6$): δ 9.17 (s, 1H), 9.13 (s, 1H), 8.10 (s, 1H), 8.03 (d, 1H, J=4.1 Hz), 7.85 (s, 1H), 7.58 (d, 2H, J=8.8 Hz), 7.46 (s, 2H), 6.87 (s, 2H, J=8.8 Hz), 5.31 (s, 2H), 4.57 (sep, 1H, J=5.8 Hz), 3.65 (s, 3H), 1.25 (d, 6H, J=5.8 Hz). LCMS: ret. time: 21.33 min.; purity: 96%; MS (m/e): 451 (MH$^+$).

7.3.1001 N4-(3,4-Ethylenedioxyphenyl)-5-fluoro-N2-[1-(methoxycarbonyl)methyl-indazoline-5-yl]-2,4-pyrimidinediamine (R935223)

In like manner to the preparation of N4-(3,4-ethylenedioxyphenyl)-5-fluoro-N2-(3-hydroxyphenyl)-2,4-pyrimidinediamine, 2-chloro-N-(3,4-ethylenedioxyphenyl)-5-fluoro-4-pyrimidineamine was reacted with 5-amino-1-(methoxycarbonyl)methyl-indazoline to provide N4-(3,4-ethylenedioxyphenyl)-5-fluoro-N2-[1-(methoxycarbonyl)methyl-indazoline-5-yl]-2,4-pyrimidinediamine. $^1$H NMR (DMSO-d$_6$): δ 9.16 (s, 1H), 9.14 (s, 1H), 8.13 (s, 1H), 8.04 (d, 1H, J=4.1 Hz), 7.89 (s, 1H), 7.48 (s, 2H), 7.30 (d, 1H, J=2.9 Hz), 7.20 (dd, 1H, J=2.9 and 8.8 Hz), 6.79 (d, 1H, J=8.8 Hz), 5.32 (s, 2H), 4.22 (s, 4H), 3.65 (s, 3H). LCMS: ret. time: 21.33 min.; purity: 96%; MS (m/e): 451 (MH$^+$).

7.3.1002 5-Fluoro-N2-(4-isopropoxyphenyl)-N4-[1-(N-methylaminocarbonyl)methyl-indazoline-6-yl]-2,4-pyrimidinediamine (R935224)

In like manner to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N2-(4-isopropoxyphenyl)-N2-[1-(methoxycarbonyl)methyl-indazoline-6-yl]-2,4-pyrimidinediamine and Me$_2$NH.HCl were reacted to provide 5-fluoro-N2-(4-isopropoxyphenyl)-N4-[1-(N-methylaminocarbonyl)methyl-indazoline-6-yl]-2,4-pyrimidinediamine. $^1$H NMR (DMSO-d$_6$): δ 9.46 (s, 1H), 8.98 (s, 1H), 8.07 (d, 1H, J=4.1 Hz), 8.02 (d, 1H, J=4.7 Hz), 7.98 (s, 2H), 7.66 (d, 1H, J=8.8 Hz), 7.50 (d, 2H, J=8.8 Hz), 7.46 (app s, 1H), 6.74 (d, 2H, J=8.8 Hz), 4.96 (s, 2H), 4.46 (sept, 1H, J=5.8 Hz), 2.58 (d, 3H, J=4.7 Hz), 1.21 (d, 6H, J=5.8 Hz). LCMS: ret. time: 18.22 min.; purity: 93%; MS (m/e): 450 (MH$^+$).

7.3.1003 N2-(3,4-Ethylenedioxyphenyl)-5-fluoro-N4-[1-(N-methylaminocarbonyl)methyl-indazoline-6-yl]-2,4-pyrimidinediamine (R935225)

In like manner to the preparation of N4-(3,4-ethylenedioxyphenyl)-5-fluoro-N2-[3-(N-methylamino)carbonylmethyleneoxyphenyl]-2,4-pyrimidinediamine, N2-(3,4-ethylenedioxyphenyl)-5-fluoro-N2-[1-(methoxycarbonyl)methyl-indazoline-6-yl]-2,4-pyrimidinediamine and Me$_2$NH.HCl were reacted to provide N2-(3,4-ethylenedioxyphenyl)-5-fluoro-N4-[1-(N-methylaminocarbonyl)methyl-indazoline-6-yl]-2,4-pyrimidinediamine. $^1$H NMR (DMSO-d$_6$): δ 9.47 (s, 1H), 8.99 (s, 1H), 8.08 (d, 1H, J=3.5 Hz), 8.06 (s, 1H), 8.01 (d, 1H, J=4.7 Hz), 7.98 (d, 1H, J=1.1 Hz), 7.66 (d, 1H, J=8.8 Hz), 7.45 (dd, 1H, J=1.1 and 8.8 Hz), 7.31 (d, 1H, J=2.3 Hz), 7.01 (dd, 1H, J=2.9 and 8.8 Hz), 6.66 (d, 1H, J=8.8 Hz), 4.95 (s, 2H), 4.14 (s, 4H), 2.57 (d, 3H, J=4.1 Hz). LCMS: ret. time: 15.55 min.; purity: 94%; MS (m/e): 450 (MH$^+$).

7.3.1004 5-Fluoro-N4-(3-hydroxyphenyl)-N2-[1-(methoxycarbonyl)methyl-indazoline-5-yl]-2,4-pyrimidinediamine (R935237)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine was reacted with 5-amino-1-(methoxycarbonyl)methyl-indazoline to produce 5-fluoro-N4-(3-hydroxyphenyl)-N2-[1-(methoxycarbonyl)methyl-indazoline-5-yl]-2,4-pyrimidinediamine. $^1$H NMR (DMSO-d$_6$): δ 9.40 (s, 1H), 9.19 (s, 1H), 9.17 (s, 1H), 8.23 (s, 1H), 8.07 (d, 1H, J=3.5 Hz), 7.90 (s, 1H), 7.47 (s, 2H), 7.25 (d, 1H, J=7.6 Hz), 7.11 (d, 1H, J=7.6 Hz), 7.08 (d, 1H, J=8.2 Hz), 6.53 (d, 1H, J=8.2 Hz), 5.31 (s, 2H), 3.64 (s, 3H). LCMS: ret. time: 15.82 min.; purity: 96%; MS (m/e): 409 (MH$^+$).

7.3.1005 N2, N4-Bis[1-(2-hydroxyethyl)indazoline-6-yl]-5-fluoro-2,4-pyrimidinediamine (R935238)

In like manner to the preparation of N2-(3,4-ethylenedioxyphenyl)-5-fluoro-N4-[4(2-hydroxy-1,1-dimethylethyl)phenyl]-2,4-pyrimidinediamine, N2, N4-bis[1-(methoxycarbonyl)methyl-indazoline-6-yl]-5-fluoro-2,4-pyrimidinediamine was reacted with DIBAL-H to produce N2, N4-bis[1-(2-hydroxyethyl)indazoline-6-yl]-5-fluoro-2,4-pyrimidinediamine. $^1$H NMR (DMSO-d$_6$): δ 9.56 (s, 1H), 9.43 (s, 1H), 8.19 (d, 1H, J=3.5 Hz), 8.06 (s, 1H), 8.03 (s, 1H), 7.98 (s, 1H), 7.86 (s, 1H), 7.66 (d, 1H, J=8.8 Hz), 7.52 (d, 1H, J=8.8 Hz), 7.42 (dd, 1H, J=1.7 and 8.8 Hz), 7.23 (dd, 1H, J=1.7 and 8.8 Hz), 4.75 (t, 1H, J=5.3 Hz), 4.68 (t, 1H, J=5.3 Hz), 4.09-4.02 (m, 2H), 3.81-3.74 (m, 2H), 3.63-3.60 (m, 2H), 3.56-3.52 (m, 2H). LCMS: ret. time: 13.73 min.; purity: 90%; MS (m/e): 449 (MH$^+$).

7.3.1006 5-Fluoro-N4-(4-isopropoxyphenyl)-N2-[1-(N-methylaminocarbonyl)methyl-indazoline-5-yl]-2,4-pyrimidinediamine (R935239)

In like manner to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N4-(4-isopropoxyphenyl)-N2-[1-(methoxycarbonyl)methyl-indazoline-5-yl]-2,4-pyrimidinediamine and Me$_2$NH.HCl were reacted to provide 5-fluoro-N4-(4-isopropoxyphenyl)-N2-[1-(N-methylaminocarbonyl)methyl-indazoline-5-yl]-2,4-pyrimidinediamine. $^1$H NMR (DMSO-d$_6$): δ 9.27 (s, 1H), 9.21 (s, 1H), 8.07 (s, 1H), 8.04 (d, 1H, J=4.1 Hz), 7.90 (qt, 1H, J=4.7 Hz), 7.83 (s, 1H), 7.58 (d, 2H, J=8.8 Hz), 7.44 (s, 2H), 6.87 (d, 2H, J=8.8 Hz), 4.98 (s, 2H), 4.57 (q, 1H, J=5.8 Hz), 2.59 (d, 3H, J=4.1 Hz), 1.21 (d, 6H, J=5.8 Hz). LCMS: ret. time: 17.74 min.; purity: 94%; MS (m/e): 450 (MH$^+$).

7.3.1007 N4-(3,4-Ethylenedioxyphenyl)-5-fluoro-N2-[1-(N-methylaminocarbonyl)methyl-indazoline-5-yl]-2,4-pyrimidinediamine (R935240)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3,4-ethylenedioxyphenyl)-5-fluoro-N2-[1-(methoxycarbonyl)methyl-indazoline-5-yl]-2,4-pyrimidinediamine and Me$_2$NH.HCl were reacted to provide N4-(3,4-ethylenedioxyphenyl)-5-fluoro-N2-[1-(N-methylaminocarbonyl)methyl-indazoline-5-yl]-2,4-pyrimidinediamine. $^1$H NMR (DMSO-d$_6$): δ 9.36 (br s, 2H), 8.06 (d, 1H, J=3.5 Hz), 8.05 (s, 1H), 7.99 (qt, 1H, J=4.7 Hz), 7.87 (s, 1H), 7.46 (s, 2H), 7.30-7.28 (m, 1H), 7.20-7.17 (m, 1H), 6.79 (d, 1H, J=8.8 Hz), 4.99 (s, 2H), 4.22 (s, 4H), 2.59 (d, 3H, J=4.7 Hz). LCMS: ret. time: 15.06 min.; purity: 91%; MS (m/e): 450 (MH$^+$).

7.3.1008 5-Fluoro-N2-(4-isopropoxyphenyl)-N4-[1-(methoxycarbonyl)methyl-indazoline-5-yl]-2,4-pyrimidinediamine (R935242)

In like manner to the preparation of N4-(3,4-ethylenedioxyphenyl)-5-fluoro-N2-(3-hydroxyphenyl)-2,4-pyrimidinediamine, 2-chloro-5-fluoro-N-[1-(methoxycarbonyl)methyl-indazoline-5-yl]-4-pyrimidineamine was reacted with 4-isopropoxyaniline to provide 5-fluoro-N2-(4-isopropoxyphenyl)-N4-[1-(methoxycarbonyl)methyl-indazoline-5-yl]-2,4-pyrimidinediamine. $^1$H NMR (DMSO-d$_6$): δ 10.58 (s, 1H), 10.09 (s, 1H), 8.23 (d, 1H, J=5.3 Hz), 8.04 (s, 1H), 8.02 (s, 1H, J=5.8 Hz), 7.68-7.63 (m 1H), 7.58-7.55 (s, 1H), 7.30 (d, 2H, J=8.8 Hz), 6.82 (d, 2H, J=8.8 Hz), 5.41 (s, 2H), 4.53 (sept, 1H, J=5.8 Hz), 3.66 (s, 3H), 1.21 (d, 6H, J=5.8 Hz). LCMS: ret. time: 19.30 min.; purity: 93%; MS (m/e): 451 (MH$^+$).

7.3.1009 N4-(3,4-Ethylenedioxyphenyl)-5-fluoro-N2-[1-(2-hydroxyethyl)indazoline-6-yl]-2,4-pyrimidinediamine (R935248)

In like manner to the preparation of N2-(3,4-ethylenedioxyphenyl)-5-fluoro-N4-[4(2-hydroxy-1,1-dimethylethyl)phenyl]-2,4-pyrimidinediamine, N4-(3,4-ethylenedioxyphenyl)-5-fluoro-N2-[1-(methoxycarbonyl)methyl-indazoline-6-yl]-2,4-pyrimidinediamine was reacted with DIBAL-H to produce N4-(3,4-ethylenedioxyphenyl)-5-fluoro-N2-[1-(2-hydroxyethyl)indazoline-6-yl]-2,4-pyrimidinediamine. LCMS: ret. time: 19.42 min.; purity: 94%; MS (m/e): 423 (MH$^+$).

7.3.1010 N2-(3,4-Ethylenedioxyphenyl)-5-fluoro-N4-[1-(methoxycarbonyl)methyl-indazoline-5-yl]-2,4-pyrimidinediamine (R935249)

In like manner to the preparation of N4-(3,4-ethylenedioxyphenyl)-5-fluoro-N2-(3-hydroxyphenyl)-2,4-pyrimidinediamine, 2-chloro-5-fluoro-N-[1-(methoxycarbonyl)methyl-indazoline-5-yl]-4-pyridinamine was reacted with 3,4-ethylenedioxyaniline to provide N2-(3,4-ethylenedioxyphenyl)-5-fluoro-N4-[1-(methoxycarbonyl)methyl-indazoline-5-yl]-2,4-pyrimidinediamine. $^1$H NMR (DMSO-d$_6$): δ 9.32 (s, 1H), 8.94 (s, 1H), 8.14 (d, 1H, J=4.7 Hz), 8.03 (d, 1H, J=4.7 Hz), 8.01 (s, 1H), 7.65-7.57 (m, 2H), 7.23 (d, 1H, J=1.7 Hz), 7.02 (dd, 1H, J=1.9 and 8.8 Hz), 6.63 (d, 1H, J=8.8 Hz), 5.38 (s, 2H), 4.14 (s, 4H), 3.66 (s, 3H). LCMS: ret. time: 18.94 min.; purity: 91%; MS (m/e): 451 (MH$^+$).

7.3.1011 5-Fluoro-N2-(3-hydroxyphenyl)-N4-[1-(methoxycarbonyl)methyl-indazoline-5-yl]-2,4-pyrimidinediamine (R935250)

In like manner to the preparation of N4-(3,4-ethylenedioxyphenyl)-5-fluoro-N2-(3-hydroxyphenyl)-2,4-pyrimidinediamine, 2-chloro-5-fluoro-N-[1-(methoxycarbonyl)methyl-indazoline-5-yl]-4-pyrimidineamine was reacted with 3-aminophenol to provide 5-fluoro-N2-(3-hydroxyphenyl)-N4-[1-(methoxycarbonyl)methyl-indazoline-5-yl]-2,4-pyrimidinediamine. $^1$H NMR (DMSO-d$_6$): δ 9.34 (s, 1H), 9.16 (s, 1H), 8.25 (d, 1H, J=4.7 Hz), 8.05 (d, 1H, J=4.7 Hz), 8.02 (s, 1H), 7.65-7.57 (m, 2H), 7.10 (d, 2H, J=5.8 Hz), 6.93 (d, 1H, J=8.8 Hz), 6.90 (d, 1H, J=8.8 Hz), 6.28 (app d, 1H, J=8.8 Hz), 5.37 (s, 2H), 3.66 (s, 3H). LCMS: ret. time: 17.87 min.; purity: 97%; MS (m/e): 409 (MH$^+$)

7.3.1012 5-Fluoro-N4-(4-isopropoxyphenyl)-N2-(1H-pyrrol-1-yl)-2,4-pyrimidinediamine (R935251)

In like manner to the preparation of N4-(3,4-ethylenedioxyphenyl)-5-fluoro-N2-(3-hydroxyphenyl)-2,4-pyrimidinediamine, 2-chloro-5-fluoro-N-(4-isopropoxyphenyl)-4-pyrimidineamine was reacted with 1-aminopyrrole to provide 5-fluoro-N4-(4-isopropoxyphenyl)-N2-(1H-pyrrol-1-yl)-2,4-pyrimidinediamine. $^1$H NMR (DMSO-d$_6$): δ 9.93 (s, 1H), 9.21 (s, 1H), 7.97 (d, 1H, J=4.1 Hz), 7.47 (d, 2H, J=8.8 Hz), 6.70 (dd, 2H, J=2.3 and 4.7 Hz), 6.67 (d, 2H, J=8.8 Hz), 6.02 (dd, 2H, J=2.3 and 4.7 Hz), 4.48 (sept, 1H, J=5.8 Hz), 1.21 (d, 6H, J=5.8 Hz). LCMS: ret. time: 23.44 min.; purity: 90%; MS (m/e): 328 (MH$^+$).

7.3.1013 N4-(3,4-Ethylenedioxyphenyl)-5-fluoro-N2-(1H-pyrrol-1-yl)-2,4-pyrimidinediamine (R935252)

In like manner to the preparation of N4-(3,4-ethylenedioxyphenyl)-5-fluoro-N2-(3-hydroxyphenyl)-2,4-pyrimidinediamine, 2-chloro-N-(3,4-ethylenedioxyphenyl)-5-fluoro-4-pyrimidineamine was reacted with 1-aminopyrrole to provide N4-(3,4-ethylenedioxyphenyl)-5-fluoro-N2-(1H-pyrrol-1-yl)-2,4-pyrimidinediamine. $^1$H NMR (DMSO-d$_6$): δ 9.95 (s, 1H), 9.16 (s, 1H), 7.95 (d, 1H, J=3.5 Hz), 7.16-7.12 (m, 2H), 6.69 (dd, 2H, J=2.3 and 4.7 Hz), 6.61 (d, 1H, J=8.8 Hz), 5.99 (dd, 2H, J=2.3 and 4.7 Hz), 4.12-4.15 (m, 4H). LCMS: ret. time: 19.86 min.; purity: 92%; MS (m/e): 328 (MH$^+$).

7.3.1014 5-Fluoro-N4-(3-hydroxyphenyl)-N2-(1H-pyrrol-1-yl)-2,4-pyrimidinediamine (R935253)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine was reacted with 1-aminopyrrole to provide 5-fluoro-N4-(3-hydroxyphenyl)-N2-(1H-pyrrol-1-yl)-2,4-pyrimidinediamine. $^1$H NMR (DMSO-d$_6$): δ 9.95 (s, 1H), 9.22 (s, 1H), 9.19 (s, 1H), 7.99 (d, 1H, J=3.5 Hz), 7.22 (d, 1H, J=8.2 Hz), 6.94 (br s, 1H), 6.89 (t, 1H, J=8.2 Hz), 6.70 (dd, 2H, J=2.3 and 4.7 Hz), 6.38 (d, 1H, J=8.2 Hz), 5.99 (t, 2H, J=2.3 and 4.7 Hz). LCMS: ret. time: 18.23 min.; purity: 94%; MS (m/e): 286 (MH$^+$).

7.3.1015 5-Fluoro-N2-[1-(2-hydroxyethyl)indazoline-5-yl]-N4-(4-isopropoxyphenyl)-2,4-pyrimidinediamine (R935255)

In like manner to the preparation of N2-(3,4-ethylenedioxyphenyl)-5-fluoro-N4-[4(2-hydroxy-1,1-dimethylethyl)phenyl]-2,4-pyrimidinediamine, 5-fluoro-N4-(4-isopropoxyphenyl)-N2-[1-(methoxycarbonyl)methyl-indazoline-5-yl]-2,4-pyrimidinediamine was reacted with DIBAL-H to produce 5-fluoro-N2-[1-(2-hydroxyethyl)indazoline-5-yl]-N4-(4-isopropoxyphenyl)-2,4-pyrimidinediamine. $^1$H NMR (DMSO-d$_6$): δ 9.16 (s, 1H), 9.10 (s, 1H), 8.09 (s, 1H), 8.02 (s, 1H, J=4.0 Hz), 7.79 (s, 1H), 7.59 (d, 2H, J=8.8 Hz), 7.48 (d, 1H, J=8.8 Hz), 7.42 (dd, 1H, J=1.7 and 8.8 Hz), 6.87 (d, 2H, J=8.8 Hz), 4.83 (t, 1H, J=5.8 Hz), 4.57 (sept, 1H, J=5.8 Hz), 4.35 (t, 2H, J=5.8 Hz), 3.75 (app qt, 2H, J=5.8 Hz), 1.26 (d, 6H, J=5.8 Hz). LCMS: ret. time: 20.90 min.; purity: 94%; MS (m/e): 423 (MH$^+$).

7.3.1016 5-Fluoro-N2-[1-(2-hydroxyethyl)indazoline-5-yl]-N4-(3-hydroxyphenyl)-2,4-pyrimidinediamine (R935256)

In like manner to the preparation of N2-(3,4-ethylenedioxyphenyl)-5-fluoro-N4-[4(2-hydroxy-1,1-dimethylethyl)phenyl]-2,4-pyrimidinediamine, 5-fluoro-N4-(3-hydroxyphenyl)-N2-[1-(methoxycarbonyl)methyl-indazoline-5-yl]-2,4-pyrimidinediamine was reacted with DIBAL-H to produce 5-fluoro-N2-[1-(2-hydroxyethyl)indazoline-5-yl]-N4-(3-hydroxyphenyl)-2,4-pyrimidinediamine. $^1$H NMR (DMSO-$d_6$): δ 9.39 (s, 1H), 9.18 (s, 1H), 9.14 (s, 1H), 8.19 (s, 1H), 8.07 (d, 1H, J=4.1 Hz), 7.84 (s, 1H), 7.50-7.42 (m, 2H), 7.26 (d, 1H, J=8.2 Hz), 7.12-7.06 (m, 2H), 6.52 (d, 1H, J=8.2 Hz), 4.83 (t, 1H, J=5.8 Hz), 4.35 (t, 2H, J=5.8 Hz), 3.75 (app qt, 2H, J=5.8 Hz). LCMS: ret. time: 15.97 min.; purity: 95%; MS (m/e): 381 (MH$^+$).

7.3.1017 N2-(3,4-Ethylenedioxyphenyl)-5-fluoro-N4-[1-(2-hydroxyethyl)indazoline-5-yl]-2,4-pyrimidinediamine (R935258)

In like manner to the preparation of N2-(3,4-ethylenedioxyphenyl)-5-fluoro-N4-[4(2-hydroxy-1,1-dimethylethyl)phenyl]-2,4-pyrimidinediamine, N2-(3,4-ethylenedioxyphenyl)-5-fluoro-N4-[1-(methoxycarbonyl)methyl-indazoline-5-yl]-2,4-pyrimidinediamine was reacted with DIBAL-H to produce N2-(3,4-ethylenedioxyphenyl)-5-fluoro-N4-[1-(2-hydroxyethyl)indazoline-5-yl]-2,4-pyrimidinediamine. $^1$H NMR (DMSO-$d_6$): δ 9.20 (s, 1H), 8.93 (s, 1H), 8.12 (s, 1H), 8.02 (d, 1H, J=3.5 Hz), 7.94 (s, 1H), 7.59 (s, 2H), 7.23 (d, 1H, J=0.9 Hz), 7.02 (dd, 1H, J=1.0 and 8.8 Hz), 6.64 (d, 1H, J=8.8 Hz), 4.86 (t, 1H, J=5.3 Hz), 4.40 (t, 2H, J=5.8 Hz), 4.15 (s, 4H), 3.78 (app qt, 2H, J=5.3 and 5.8 Hz). LCMS: ret. time: 18.07 min.; purity: 93%; MS (m/e): 423 (MH$^+$).

7.3.1018 5-Fluoro-N4-[1-(2-hydroxyethyl)indazoline-5-yl]-N2-(3-hydroxyphenyl)-2,4-pyrimidinediamine (R935259)

In like manner to the preparation of N2-(3,4-ethylenedioxyphenyl)-5-fluoro-N4-[4(2-hydroxy-1,1-dimethylethyl)phenyl]-2,4-pyrimidinediamine, 5-fluoro-N2-(3-hydroxyphenyl)-N4-[1-(methoxycarbonyl)methyl-indazoline-5-yl]-2,4-pyrimidinediamine was reacted with DIBAL-H to produce 5-fluoro-N4-[1-(2-hydroxyethyl)indazoline-5-yl]-N2-(3-hydroxyphenyl)-2,4-pyrimidinediamine. $^1$H NMR (DMSO-$d_6$): δ 9.31 (s, 1H), 9.16 (s, 1H), 9.01 (s, 1H), 8.23 (s, 1H), 8.05 (d, 1H, J=3.5 Hz), 7.96 (s, 1H), 7.60 (s, 2H), 7.10 (app s, 2H), 6.92 (t, 1H, J=8.8 Hz), 6.31 (d, 1H, J=8.8 Hz), 4.86 (t, 1H, J=5.3 Hz), 4.40 (t, 2H, J=5.8 Hz), 3.79 (app qt, 2H, J=5.3 and 5.8 Hz). LCMS: ret. time: 16.09 min.; purity: 89%; MS (m/e): 381 (MH$^+$).

7.3.1019 N2-(3,4-Ethylenedioxyphenyl)-5-fluoro-N4-(indazoline-6-yl)-2,4-pyrimidinediamine (R935261)

In like manner to the preparation of N4-(3,4-ethylenedioxyphenyl)-5-fluoro-N2-(3-hydroxyphenyl)-2,4-pyrimidinediamine, 2-chloro-5-fluoro-N-(indazoline-6-yl)-4-pyrimidineamine was reacted 3,4-ethyelenedioxyaniline to produce N2-(3,4-ethylenedioxyphenyl)-5-fluoro-N4-(indazoline-6-yl)-2,4-pyrimidinediamine. $^1$H NMR (DMSO-$d_6$): δ 12.85 (s, 1H), 9.40 (s, 1H), 9.01 (s, 1H), 8.07 (d, 1H, J=3.5 Hz), 7.97 (s, 1H), 7.86 (s, 1H), 7.65 (d, 1H, J=8.8 Hz), 7.47 (dd, 1H, J=2.3 and 8.8 Hz), 7.27 (d, 1H, J=2.3 Hz), 7.07 (dd, 1H, J=2.3 and 8.8 Hz), 6.64 (dd, 1H, J=1.7 and 8.8 Hz), 4.14 (s, 4H). LCMS: ret. time: 15.90 min.; purity: 100%; MS (m/e): 379 (MH$^+$).

7.3.1020 5-Fluoro-N2-(3-hydroxyphenyl)-N4-(indazoline-6-yl)-2,4-pyrimidinediamine (R935262)

In like manner to the preparation of N4-(3,4-ethylenedioxyphenyl)-5-fluoro-N2-(3-hydroxyphenyl)-2,4-pyrimidinediamine, 2-chloro-5-fluoro-N-(indazoline-6-yl)-4-pyrimidineamine was reacted with 3-aminophenol to produce 5-fluoro-N2-(3-hydroxyphenyl)-N4-(indazoline-6-yl)-2,4-pyrimidinediamine. $^1$H NMR (DMSO-$d_6$): δ 10.80 (s, 1H), 10.49 (s, 1H), 8.35 (d, 1H, J=5.3 Hz), 8.06 (s, 1H), 7.78 (d, 1H), 7.75 (d, 1H, J=8.8 Hz), 7.42 (dd, 1H, J=1.7 and 8.8 Hz), 6.99-6.97 (m, 2H), 6.80 (s, 1H), 6.52-6.48 (m, 1H). LCMS: ret. time: 13.78 min.; purity: 100%; MS (m/e): 379 (MH$^+$).

7.3.1021 N2-(3-Chloro-4-hydroxy-3-methylphenyl)-5-fluoro-N4-[4H-imidazo[2,1-c][1,4]-benzoxazin-8-yl]-2,4-pyrimidinediamine (R935263)

In like manner to the preparation of N4-(3,4-ethylenedioxyphenyl)-5-fluoro-N2-(3-hydroxyphenyl)-2,4-pyrimidinediamine, 2-chloro-5-fluoro-N-[4H-imidazo[2,1-c][1,4]-benzoxazin-8-yl]-4-pyrimidineamine was reacted with 4-amino-2-chloro-6-methylphenol to produce N2-(3-chloro-4-hydroxy-3-methylphenyl)-5-fluoro-N4-[4H-imidazo[2,1-c][1,4]-benzoxazin-8-yl]-2,4-pyrimidinediamine. $^1$H NMR (DMSO-$d_6$): δ 9.40 (s, 1H), 9.04 (s, 1H), 8.51 (s, 1H), 8.07 (d, 1H, J=3.5 Hz), 7.98 (d, 1H, J=2.3 Hz), 7.67 (s, 1H), 7.53 (s, 1H), 7.41-7.36 (m, 1H), 7.20 (s, 1H), 7.10 (d, 1H, J=8.8 Hz), 7.07 (s, 1H), 5.24 (s, 2H), 1.98 (s, 3H). LCMS: ret. time: 13.36 min.; purity: 90%; MS (m/e): 439 (MH$^+$).

7.3.1022 N2-(3-Chloro-4-hydroxy-3-methylphenyl)-5-fluoro-N4-(indazoline-6-yl)-2,4-pyrimidinediamine (R935264)

In like manner to the preparation of N4-(3,4-ethylenedioxyphenyl)-5-fluoro-N2-(3-hydroxyphenyl)-2,4-pyrimidinediamine, 2-chloro-5-fluoro-N-(indazoline-6-yl)-4-pyrimidineamine was reacted with 4-amino-2-chloro-6-methylphenol to produce N2-(3-chloro-4-hydroxy-3-methylphenyl)-5-fluoro-N4-(indazoline-6-yl)-2,4-pyrimidinediamine. $^1$H NMR (DMSO-$d_6$): δ 9.62 (s, 1H), 9.19 (s, 1H), 8.61 (s, 1H), 8.12 (s, 1H), 8.02 (s, 1H), 7.77 (s, 1H), 7.67 (d, 1H, J=8.8 Hz), 7.50-7.45 (m, 2H), 7.26 (s, 1H), 1.98 (s, 3H). LCMS: ret. time: 13.78 min.; purity: 100%; MS (m/e): 385 (MH$^+$).

7.3.1023 5-Fluoro-N4-(indazoline-5-yl)-N2-(4-isopropoxyphenyl)-2,4-pyrimidinediamine (R935266)

In like manner to the preparation of N4-(3,4-ethylenedioxyphenyl)-5-fluoro-N2-(3-hydroxyphenyl)-2,4-pyrimidinediamine, 2-chloro-5-fluoro-N-(indazoline-5-yl)-4-pyrimidineamine was reacted with 4-isoporopoxyaniline to produce 5-fluoro-N4-(indazoline-5-yl)-N2-(4-isopropoxyphenyl)-2,4-pyrimidinediamine. $^1$H NMR (DMSO-$d_6$): δ 10.30 (s, 1H), 9.80 (s, 1H), 8.16 (d, 1H, J=5.3 Hz), 8.06 (s, 1H), 7.98 (s, 1H), 7.51 (s, 2H), 7.32 (d, 2H, J=8.8 Hz), 6.79 (d, 2H, J=8.8 Hz), 4.51 (sept, 1H, J=5.8 Hz), 1.22 (d, 6H, J=5.8 Hz). LCMS: ret. time: 17.65 min.; purity: 98%; MS (m/e): 379 (MH$^+$).

7.3.1024 N2-(3,4-Ethyelenedioxyphenyl)-5-fluoro-N4-(indazoline-5-yl)-2,4-pyrimidinediamine (R935267)

In like manner to the preparation of N4-(3,4-ethylenedioxyphenyl)-5-fluoro-N2-(3-hydroxyphenyl)-2,4-pyrimidinediamine, 2-chloro-5-fluoro-N-(indazoline-5-yl)-4-pyrimidineamine was reacted with 3,4-ethylenedioxyphenylaniline to produce N2-(3,4-ethyelenedioxyphenyl)-5-fluoro-N4-(indazoline-5-yl)-2,4-pyrimidinediamine. $^1$H NMR (DMSO-$d_6$): δ 10.20 (s, 1H), 9.61 (s, 1H), 8.13 (d, 1H, J=5.3 Hz), 8.08 (s, 1H), 7.98 (s, 1H), 7.54-7.48 (m, 2H), 7.06 (d, 1H, J=2.3 Hz), 6.90 (dd, 1H, J=2.3 and 8.8 Hz), 6.72 (d, 1H, J=8.8 Hz), 4.17 (s, 4H). LCMS: ret. time: 15.16 min.; purity: 100%; MS (m/e): 379 (MH$^+$).

7.3.1025 5-Fluoro-N2-(3-hydroxyphenyl)-N4-(indazoline-5-yl)-2,4-pyrimidinediamine (R935268)

In like manner to the preparation of N4-(3,4-ethylenedioxyphenyl)-5-fluoro-N2-(3-hydroxyphenyl)-2,4-pyrimidinediamine, 2-chloro-5-fluoro-N-(indazoline-5-yl)-4-pyrimidineamine was reacted with 3-aminophenol to produce 5-fluoro-N2-(3-hydroxyphenyl)-N4-(indazoline-5-yl)-2,4-pyrimidinediamine. $^1$H NMR (DMSO-$d_6$): δ 10.64 (s, 1H), 10.33 (s, 1H), 8.29 (d, 1H, J=5.3 Hz), 8.12 (s, 1H), 8.03 (s, 1H), 7.55 (dd, 2H, J=1.7 and 8.8 Hz), 7.00 (d, 1H, J=8.8 Hz), 6.90 (d, 1H, J=8.8 Hz), 6.85 (d, 1H, J=1.7 Hz), 6.53 (d, 1H, J=8.8 Hz). LCMS: ret. time: 12.80 min.; purity: 98%; MS (m/e): 337 (MH$^+$)

7.3.1026 5-Fluoro-N4-(indazoline-5-yl)-N2-[3-(methoxycarbonyl methyleneoxy)phenyl]-2,4-pyrimidinediamine (R935269)

In like manner to the preparation of N4-(3,4-ethylenedioxyphenyl)-5-fluoro-N2-(3-hydroxyphenyl)-2,4-pyrimidinediamine, 2-chloro-5-fluoro-N-(indazoline-5-yl)-4-pyrimidineamine was reacted with 3-(methoxycarbonylmethyleneoxy)aniline to produce 5-fluoro-N4-(indazoline-5-yl)-N2-[3-(methoxycarbonylmethyleneoxy)phenyl]-2,4-pyrimidinediamine. $^1$H NMR (DMSO-$d_6$): δ 10.64 (s, 1H), 9.82 (s, 1H), 8.20 (d, 1H, J=4.6 Hz), 8.10 (s, 1H), 8.08 (s, 1H), 7.99 (s, 1H), 7.57 (m, 2H), 7.13-7.6 (m, 3H), 6.56 (d, 1H, J=8.8 Hz), 4.60 (s, 2H), 3.65 (s, 3H). LCMS: ret. time: 15.36 min.; purity: 94%; MS (m/e): 409 (MH$^+$).

7.3.1027 5-Fluoro-N4-(indazoline-5-yl)-N2-(indazoline-6-yl)-2,4-pyrimidinediamine (R935270)

In like manner to the preparation of N4-(3,4-ethylenedioxyphenyl)-5-fluoro-N2-(3-hydroxyphenyl)-2,4-pyrimidinediamine, 2-chloro-5-fluoro-N-(indazoline-5-yl)-4-pyrimidineamine was reacted with 6-aminoindazoline to produce 5-fluoro-N4-(indazoline-5-yl)-N2-(indazoline-6-yl)-2,4-pyrimidinediamine. $^1$H NMR (DMSO-$d_6$): δ 10.35 (s, 1H), 9.19 (s, 1H), 8.25 (d, 1H, J=4.1 Hz), 8.12 (s, 1H), 8.01 (s, 1H), 7.81 (s, 1H), 7.73 (s, 1H), 7.64 (d, 1H, J=8.8 Hz), 7.60 (dd, 2H, J=1.7 and 8.9 Hz), 7.51 (d, 1H, J=8.9 Hz), 7.21 (dd, 1H, J=1.7 and 8.8 Hz). LCMS: ret. time: 13.45 min.; purity: 95%; MS (m/e): 361 (MH$^+$).

7.3.1028 5-Fluoro-N4-[4H-imidazo[2,1-c][1,4]-benzoxazin-8-yl]-N2-[3-(N-methylaminocarbonylmethyleneoxy)phenyl]-2,4-pyrimidinediamine (R935271)

In like manner to the preparation of N4-(3,4-ethylenedioxyphenyl)-5-fluoro-N2-(3-hydroxyphenyl)-2,4-pyrimidinediamine, 2-chloro-5-fluoro-N-[4H-imidazo[2,1-c][1,4]-benzoxazin-8-yl]-4-pyrimidineamine was reacted with 3-(N-methylaminocarbonylmethyleneoxy)aniline to produce 5-fluoro-N4-[4H-imidazo[2,1-c][1,4]-benzoxazin-8-yl]-N2-[3-(N-methylaminocarbonylmethyleneoxy)phenyl]-2,4-pyrimidinediamine. $^1$H NMR (DMSO-$d_6$): δ 9.44 (s, 1H), 9.25 (s, 1H), 8.11 (d, 1H, J=3.5 Hz), 8.03 (d, 1H, J=2.3 Hz), 7.90 (qt, 1H, J=4.6 Hz), 7.69 (d, 1H, J=1.2 Hz), 7.47-7.42 (m, 1H), 7.33 (m, 1H), 7.26 (dd, 1H, J=1.2 and 8.2 Hz), 7.12 (s, 1H), 7.09 (d, 1H, J=1.7 Hz), 6.97 (t, 1H, J=8.2H), 6.40 (dd, 1H, J=2.3 and 8.2 Hz), 5.25 (s, 2H), 4.26 (s, 2H), 2.61 (d, 3H, J=4.6 Hz). LCMS: ret. time: 15.45 min.; purity: 97%; MS (m/e): 462 (MH$^+$).

7.3.1029 5-Fluoro-N2-(4-isopropoxyphenyl)-N4-(1H-pyrrol-1-yl)-2,4-pyrimidinediamine (R935276)

In like manner to the preparation of N4-(3,4-ethylenedioxyphenyl)-5-fluoro-N2-(3-hydroxyphenyl)-2,4-pyrimidinediamine, 2-chloro-5-fluoro-N-(1H-pyrrol-1-yl)-4-pyrimidineamine was reacted with 4-isopropoxyaniline to produce 5-fluoro-N2-(4-isopropoxyphenyl)-N4-(1H-pyrrol-1-yl)-2,4-pyrimidinediamine. $^1$H NMR (DMSO-$d_6$): δ 10.69 (s, 1H), 9.03 (s, 1H), 8.06 (d, 1H, J=3.5 Hz), 7.30 (d, 2H, J=9.3 Hz), 6.82 (t, 2H, J=2.3 Hz), 6.58 (d, 2H, J=9.3 Hz), 6.11 (t, 2H, J=2.3 Hz), 4.41 (sept, 1H, J=5.8 Hz), 1.18 (d, 6H, J=5.8 Hz). LCMS: ret. time: 21.21 min.; purity: 90%; MS (m/e): 328 (MH$^+$).

7.3.1030 N2-(3,4-Ethylenedioxyphenyl)-5-Fluoro-N4-(1H-pyrrol-1-yl)-2,4-pyrimidinediamine (R935277)

In like manner to the preparation of N4-(3,4-ethylenedioxyphenyl)-5-fluoro-N2-(3-hydroxyphenyl)-2,4-pyrimidinediamine, 2-chloro-5-fluoro-N-(1H-pyrrol-1-yl)-4-pyrimidineamine was reacted with 3,4-ethylenedioxyaniline to produce N2-(3,4-ethylenedioxyphenyl)-5-Fluoro-N4-(1H-pyrrol-1-yl)-2,4-pyrimidinediamine. $^1$H NMR (DMSO-$d_6$): δ 11.63 (s, 1H), 9.94 (s, 1H), 8.23 (d, 1H, J=4.7 Hz), 6.86 (m, 4H), 6.58 (d, 1H, J=8.8 Hz), 6.12 (t, 2H, J=2.3 Hz), 4.15 (s, 4H). LCMS: ret. time: 17.36 min.; purity: 96%; MS (m/e): 328 (MH$^+$).

7.3.1031 5-Fluoro-N2-(3-hydroxyphenyl)-N4-(1H-pyrrol-1-yl)-2,4-pyrimidinediamine (R935278)

In like manner to the preparation of N4-(3,4-ethylenedioxyphenyl)-5-fluoro-N2-(3-hydroxyphenyl)-2,4-pyrimidinediamine, 2-chloro-5-fluoro-N-(1H-pyrrol-1-yl)-4-pyrimidineamine was reacted with 3-aminophenol to produce 5-fluoro-N2-(3-hydroxyphenyl)-N4-(1H-pyrrol-1-yl)-2,4-pyrimidinediamine. $^1$H NMR (DMSO-$d_6$): δ 10.68 (s, 1H), 9.04 (s, 1H), 9.00 (s, 1H), 8.08 (d, 1H, J=4.11 Hz), 7.01 (d, 1H, J=8.2 Hz), 6.84-6.75 (m, 4H), 6.22 (dd, 1H, J=1.2 and 8.2 Hz), 6.08 (t, 2H, J=2.3 Hz). LCMS: ret. time: 16.24 min.; purity: 94%; MS (m/e): 286 (MH$^+$).

7.3.1032 5-Fluoro-N4-(indazoline-5-yl)-N2-[3-(N-methylaminocarbonylmethyleneoxy)phenyl]-2,4-pyrimidinediamine (R935279)

In like manner to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N4-(indazoline-5-yl)-N2-[3-(-methoxycarbonylmethyleneoxy)phenyl]-2,4-pyrimidinediamine and Me$_2$NH.HCl were reacted to provide 5-fluoro-N4-(indazoline-5-yl)-N2-[3-(N-methylaminocarbonylmethyleneoxy)phenyl]-2,4-pyrimidinediamine. $^1$H NMR (DMSO-d$_6$): δ 12.98 (s, 1H), 9.35 (s, 1H), 9.16 (s, 1H), 8.21 (s, 1H), 8.07 (d, 1H, J=3.5 Hz), 7.97 (s, 1H), 7.90 (qt, 1H, J=4.7 Hz), 7.59 (dd, 1H, J=8.8 Hz), 7.49 (d, 1H, J=8.8 Hz), 7.32-7.28 (m, 2H), 7.03 (t, 1H, J=8.2 Hz), 6.45 (dd, 1H, J=1.7 and 8.2 Hz), 4.31 (s, 2H), 2.61 (d, 3H, J=4.7 Hz). LCMS: ret. time: 12.92 min.; purity: 90%; MS (m/e): 408 (MH$^+$).

7.3.1033 5-Fluoro-N2-[3-(methoxycarbonylmethyleneoxy)phenyl]-N4-(1H-pyrrol-1-yl)-2,4-pyrimidinediamine (R935280)

In like manner to the preparation of N4-(3,4-ethylenedioxyphenyl)-5-fluoro-N2-(3-hydroxyphenyl)-2,4-pyrimidinediamine, 2-chloro-5-fluoro-N-(1H-pyrrol-1-yl)-4-pyrimidineamine was reacted with 3-(methoxycarbonylmethyleneoxy)aniline to produce 5-fluoro-N2-[3-(methoxycarbonylmethyleneoxy)phenyl]-N4-(1H-pyrrol-1-yl)-2,4-pyrimidinediamine. $^1$H NMR (DMSO-d$_6$): δ 11.45(s, 1H), 9.90 (s, 1H), 8.26 (d, 1H, J=4.7 Hz), 7.07 (d, 1H, J=8.2 Hz), 7.68 (d, 1H, J=8.2 Hz), 6.94 (s, 1H), 6.85 (t, 2H, J=2.3 Hz), 6.47 (dd, 1H, J=2.3 and 8.2 Hz), 6.12 (t, 2H, J=2.3 Hz), 4.64 (s, 2H), 3.68 (s, 3H). LCMS: ret. time: 16.24 min.; purity: 92%; MS (m/e): 358 (MH$^+$).

7.3.1034 5-Fluoro-N2-[3-(N-methylaminocarbonylmethyleneoxy) phenyl]-N4-(1H-pyrrol-1-yl)-2,4-pyrimidinediamine (R935281)

In like manner to the preparation of N4-(3,4-ethylenedioxyphenyl)-5-fluoro-N2-[3-(N-methylamino)carbonylmethyleneoxyphenyl]-2,4-pyrimidinediamine, 5-fluoro-N2-[3-(-methoxycarbonylmethyleneoxy)phenyl]-N4-(1H-pyrrol-1-yl)-2,4-pyrimidinediamine and Me$_2$NH.HCl were reacted to provide 5-fluoro-N2-[3-(N-methylaminocarbonylmethyleneoxy)phenyl]-N4-(1H-pyrrol-1-yl)-2,4-pyrimidinediamine. $^1$H NMR (DMSO-d$_6$): δ 10.73 (s, 1H), 9.21 (s, 1H), 8.11 (d, 1H, J=4.1 Hz), 7.89 (qt, 1H, J=4.7 Hz), 7.14 (d, 1H, J=8.2 Hz), 7.09 (s, 1H), 6.93 (t, 1H, J=8.2 Hz), 6.84 (t, 2H, J=2.3 Hz), 6.40 (dd, 1H, J=2.3 and 8.2 Hz), 6.09 (t, 2H, J=2.3 Hz), 4.29 (s, 2H), 2.63 (s, 3H, J=4.7 Hz). LCMS: ret. time: 16.16 min.; purity: 90%; MS (m/e): 357 (MH$^+$).

7.3.1035 N2-[1-(2-ethoxycarbonylethyl)indazoline-6-yl]-N4-(3,4-ethylenedioxyphenyl)-5-fluoro-2,4-pyrimidinediamine (R935286)

In like manner to the preparation of N4-(3,4-ethylenedioxyphenyl)-5-fluoro-N2-(3-hydroxyphenyl)-2,4-pyrimidinediamine, 2-chloro-N-(3,4-ethylenedioxyphenyl)-5-fluoro-4-pyrimidineamine was reacted with 6-amino-1-(2-ethoxycarbonylethyl)indazoline to provide N2-[1-(2-ethoxycarbonylethyl)indazoline-6-yl]-N4-(3,4-ethylenedioxyphenyl)-5-fluoro-2,4-pyrimidinediamine. $^1$H NMR (DMSO-d$_6$): δ 9.37 (s, 1H), 9.20 (s, 1H), 8.10 (d, 1H, J=3.5 Hz), 8.06 (s, 1H), 7.87 (s, 1H), 7.53 (d, 1H, J=8.8 Hz), 7.33-7.21 (m, 3H), 6.77 (d, 1H, J=8.8 Hz), 4.34 (t, 2H, J=6.4 Hz), 4.19 (s, 4H), 3.93 (qt, 2H, J=7.0 Hz), 2.82 (t, 2H, J=6.4 Hz), 1.04 (t, 3H, J=7.0 Hz). LCMS: ret. time: 24.70 min.; purity: 90%; MS (m/e): 479 (MH$^+$).

7.3.1036 N4-(3,4-Ethylenedioxyphenyl)-5-fluoro-N2-[1-(3-hydroxypropyl)indazoline-6-yl]-2,4-pyrimidinediamine (R935287)

In like manner to the preparation of N2-(3,4-ethylenedioxyphenyl)-5-fluoro-N4-[4(2-hydroxy-1,1-dimethylethyl)phenyl]-2,4-pyrimidinediamine, N2-[1-(2-ethoxycarbonylethyl)indazoline-6-yl]-N4-(3,4-ethylenedioxyphenyl)-5-fluoro-2,4-pyrimidinediamine was reacted with DIBAL-H to produce N4-(3,4-ethylenedioxyphenyl)-5-fluoro-N2-[1-(3-hydroxypropyl)indazoline-6-yl]-2,4-pyrimidinediamine. $^1$H NMR (DMSO-d$_6$): δ 9.35 (s, 1H), 9.19 (s, 1H), 8.09 (d, 1H, J=4.1 Hz), 8.01 (s, 1H), 7.85 (s, 1H), 7.53 (d, 1H, J=8.8 Hz), 7.32-7.20 (m, 3H), 6.77 (d, 1H, J=8.8 Hz), 4.20 (s, 4H), 3.27 (t, 2H, J=6.4 Hz), 3.27 (t, 2H, J=6.4 Hz), 1.84 (q, 2H, J=6.4 Hz). LCMS: ret. time: 24.70 min.; purity: 90%; MS (m/e): 479 (MH$^+$). LCMS: ret. time: 22.09 min.; purity: 90%; MS (m/e): 437 (MH$^+$).

7.3.1037 N2-(3,4-Ethylenedioxyphenyl)-5-fluoro-N4-[1-[2(N-methylaminocarbonyl)ethyl]-indazoline-6-yl]-2,4-pyrimidinediamine (R935288)

In like manner to the preparation of N4-(3,4-ethylenedioxyphenyl)-5-fluoro-N2-[3-(N-methylamino)carbonylmethyleneoxyphenyl]-2,4-pyrimidinediamine, N2-[1-(2-ethoxycarbonylethyl)indazoline-6-yl]-N4-(3,4-ethylenedioxyphenyl)-5-fluoro-2,4-pyrimidinediamine and Me$_2$NH.HCl were reacted to provide N2-(3,4-ethylenedioxyphenyl)-5-fluoro-N4-[1-[2(N-methylaminocarbonyl)ethyl]-indazoline-6-yl]-2,4-pyrimidinediamine. $^1$H NMR (DMSO-d$_6$): δ 9.35 (s, 1H), 9.19 (s, 1H), 8.10 (d, 1H, J=3.5 Hz), 8.02 (s, 1H), 7.86 (s, 1H), 7.81 (qt, 1H, J=4.7 Hz), 7.52 (d, 1H, J=8.2 Hz), 7.34-7.22 (m, 3H), 6.77 (d, 1H, J=8.8 Hz), 4.33 (t, 2H, J=6.4 Hz), 4.19 (s, 4H), 2.57 (t, 2H, J=6.4 Hz), 2.48 (d, 3H, J=4.7 Hz). LCMS: ret. time: 23.10 min.; purity: 93%; MS (m/e): 464 (MH$^+$).

7.3.1038 N4-[1-(2-Ethoxycarbonylethyl)indazoline-6-yl]-5-fluoro-N2-(isopropoxyphenyl)-2,4-pyrimidinediamine (R935289)

In like manner to the preparation of N4-(3,4-ethylenedioxyphenyl)-5-fluoro-N2-(3-hydroxyphenyl)-2,4-pyrimidinediamine, 2-chloro-5-fluoro-N-(4-isopropoxyphenyl)-4-pyrimidineamine was reacted with 6-amino-1-(2-ethoxycarbonylethyl)indazoline to provide N2-[1-(2-ethoxycarbonylethyl)indazoline-6-yl]-5-fluoro-N4-(isopropoxyphenyl)-2,4-pyrimidinediamine. $^1$H NMR (DMSO-d$_6$): δ 10.74 (s, 1H), 10.55 (s, 1H), 8.35 (d, 1H, J=5.8 Hz), 7.98 (s, 1H), 7.77 (s, 1H), 7.66 (d, 1H, J=8.8 Hz), 7.51 (d, 2H, J=8.8 Hz), 7.16 (dd, 1H, J=1.2 and 8.8 Hz), 6.85 (d, 2H, J=8.8 Hz), 4.55 (sept, 1H, J=6.4 Hz), 4.31 (t, 2H, J=6.4 Hz), 3.93 (qt, 2H, J=7.0 Hz), 2.80 (t, 2H, J=6.4 Hz), 1.22 (d, 6H, J=7.0 Hz), 1.02 (t, 3H, J=7.0 Hz). LCMS: ret. time: 26.84 min.; purity: 96%; MS (m/e): 479 (MH$^+$).

7.3.1039 5-Fluoro-N2-[1-(3-hydroxypropyl)indazoline-6-yl]-N4-(4-isopropoxyphenyl)-2,4-pyrimidinediamine (R935290)

In like manner to the preparation of N2-(3,4-ethylenedioxyphenyl)-5-fluoro-N4-[4(2-hydroxy-1,1-dimethylethyl)phenyl]-2,4-pyrimidinediamine, N2-[1-(2-ethoxycarbonylethyl) indazoline-6-yl]-5-fluoro-N4-(isopropoxyphenyl)-2,4-pyrimidinediamine was reacted with DIBAL-H to produce 5-fluoro-N2-[1-(3-hydroxypropyl)indazoline-6-yl]-N4-(4-isopropoxyphenyl)-2,4-pyrimidinediamine $^1$H NMR (DMSO-d$_6$): δ 9.31 (s, 1H), 9.22 (s, 1H), 8.08 (d, 1H, J=4.1 Hz), 7.98 (s, 1H), 7.85 (s, 1H), 7.62 (dd, 2H, J=3.5 and 8.8 Hz), 7.52 (d, 1H, J=8.8 Hz), 7.27 (d, 1H, J=8.8 Hz), 6.86 (d, 2H, J=8.8 Hz), 4.55 (sept, 1H, J=7.0 Hz), 4.49 (t, 1H, J=5.3 Hz), 4.14 (t, 2H, J=6.4 Hz), 3.26 (t, 2H, J=6.4 Hz), 1.84 (q, 2H, J=6.4 Hz), 1.24 (d, 6H, J=7.0 Hz). LCMS: ret. time: 24.13 min.; purity: 97%; MS (m/e): 437 (MH$^+$).

7.3.1040 5-Fluoro-N4-(4-isopropoxyphenyl)-N2-[1-[2(N-methylamino)carbonyl]ethyl-indazoline-6-yl]-2,4-pyrimidinediamine (R935291)

In like manner to the preparation of N4-(3,4-ethylenedioxyphenyl)-5-fluoro-N2-[3-(N-methylamino)carbonylmethyleneoxyphenyl]-2,4-pyrimidinediamine, N2-[1-(2-ethoxycarbonylethyl)indazoline-6-yl]-5-fluoro-N4-(isopropoxyphenyl)-2,4-pyrimidinediamine and Me$_2$NH.HCl were reacted to provide 5-fluoro-N4-(4-isopropoxyphenyl)-N2-[1-[2(N-methylamino)carbonyl]ethyl-indazoline-6-yl]-2,4-pyrimidinediamine. $^1$H NMR (DMSO-d$_6$): δ 9.32(s, 1H), 9.24 (s, 1H), 8.10 (d, 1H, J=3.5 Hz), 7.99 (s, 1H), 7.85 (s, 1H), 7.80 (qt, 1H, J=4.7 Hz), 7.63 (d, 2H, J=8.8 Hz), 7.52 (d, 1H, J=8.8 Hz), 7.28 (d, 1H, J=8.8 Hz), 6.84 (d, 2H, J=8.8 Hz), 4.54 (sept, 1H, J=5.8 Hz), 4.30 (t, 2H, J=6.4 Hz), 2.55 (t, 2H, 7.4 Hz), 2.48 (d, 3H, J=4.7 Hz), 1.24 (d, 6H, J=6H). LCMS: ret. time: 23.68 min.; purity: 95%; MS (m/e): 464 (MH$^+$).

7.3.1041 N4-[1-(2-Ethoxycarbonylethyl)indazoline-6-yl]-5-fluoro-N2-(3-hydroxyphenyl)-2,4-pyrimidinediamine (R935292)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine was reacted with 6-amino-1-(2-ethoxycarbonylethyl)indazoline to provide N4-[1-(2-ethoxycarbonylethyl)indazoline-6-yl]-5-fluoro-N2-(3-hydroxyphenyl)-2,4-pyrimidinediamine. $^1$H NMR (DMSO-d$_6$): δ 10.35 (s, 1H), 10.21 (s, 1H), 8.29 (d, 1H, J=5.3 Hz), 7.96 (s, 1H), 7.90 (s, 1H), 7.63 (d, 1H, J=8.8 Hz), 7.20-7.06 (m, 4H), 6.58 (d, 1H, J=8.2 Hz), 4.33 (t, 2H, J=6.4 Hz), 3.94 (qt, 2H, J=7.0 Hz), 2.82 (t, 2H, J=6.4 Hz), 1.03 (t, 3H, J=7.0 Hz). LCMS: ret. time: 22.73 min.; purity: 94%; MS (m/e): 437 (MH$^+$).

7.3.1042 5-Fluoro-N4-(3-hydroxyphenyl)-N2-[1-(3-hydroxypropyl)indazoline-6-yl]-2,4-pyrimidinediamine (R935293)

In like manner to the preparation of N2-(3,4-ethylenedioxyphenyl)-5-fluoro-N4-[4(2-hydroxy-1,1-dimethylethyl)phenyl]-2,4-pyrimidinediamine, N4-[1-(2-ethoxycarbonylethyl)indazoline-6-yl]-5-fluoro-N2-(3-hydroxyphenyl)-2,4-pyrimidinediamine was reacted with DIBAL-H to produce 5-fluoro-N4-(3-hydroxyphenyl)-N2-[1-(3-hydroxypropyl)indazoline-6-yl]-2,4-pyrimidinediamine. $^1$H NMR (DMSO-d$_6$): δ 9.38 (s, 1H), 9.35 (s, 1H), 9.26 (s, 1H), 8.13 (d, 1H, J=4.1 Hz), 8.05 (s, 1H), 7.85 (s, 1H), 7.52 (d, 1H, J=8.2 Hz), 7.28 (d, 2H, J=8.8 Hz), 7.12 (d, 1H, J=1.7 Hz), 7.08 (t, 1H, J=8.2 Hz), 6.49 (d, 1H, J=8.2 Hz), 4.15 (t, 2H, J=7.0 Hz), 3.26 (t, 2H, J=6.4 Hz), 1.85 (q, 2H, J=6.4 Hz). LCMS: ret. time: 24.70 min.; purity: 90%; MS (m/e): 479 (MH$^+$). LCMS: ret. time: 20.37 min.; purity: 98%; MS (m/e): 395 (MH$^+$).

7.3.1043 5-Fluoro-N4-(3-hydroxyphenyl)-N2-[1-[2-(N-methylaminocarbonyl)ethyl]-indazoline-6-yl]-2,4-pyrimidinediamine (R935294)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-[1-(2-ethoxycarbonylethyl)indazoline-6-yl]-5-fluoro-N2-(3-hydroxyphenyl)-2,4-pyrimidinediamine and Me$_2$NH.HCl were reacted to provide 5-fluoro-N4-(3-hydroxyphenyl)-N2-[1-[2-(N-methylaminocarbonyl)ethyl]-indazoline-6-yl]-2,4-pyrimidinediamine. $^1$H NMR (DMSO-d$_6$): δ 9.36 (s, 1H), 9.33 (s, 1H), 9.25 (s, 1H), 8.14 (d, 1H, J=3.5 Hz), 8.05 (s, 1H), 7.85 (s, 1H), 7.78 (qt, 1H, J=4.7 Hz), 7.52 (d, 1H, J=8.8 Hz), 7.30 (d, 2H, J=8.8 Hz), 7.11 (d, 1H, J=2.3 Hz), 7.07 (t, 1H, J=8.2 Hz), 6.47 (d, 1H, J=8.2 Hz), 4.32 (t, 2H, J=6.4 Hz), 2.57 (t, 2H, J=6.4 Hz), 2.48 (d, 3H, J=4.7 Hz). LCMS: ret. time: 20.18 min.; purity: 93%; MS (m/e): 422 (MH$^+$).

7.3.1044 N4-[1-(2-Ethoxycarbonylethyl)indazoline-6-yl]-5-fluoro-N2-(2-methoxycarbonylbenzofur-5-yl)-2,4-pyrimidinediamine (R935295)

In like manner to the preparation of N4-(3,4-ethylenedioxyphenyl)-5-fluoro-N2-(3-hydroxyphenyl)-2,4-pyrimidinediamine, 2-chloro-5-fluoro-N-(2-methoxycarbonylbenzofur-5-yl)-4-pyrimidineamine was reacted with 6-amino-1-(2-ethoxycarbonylethyl)indazoline to provide N4-[1-(2-ethoxycarbonylethyl)indazoline-6-yl]-5-fluoro-N2-(2-methoxycarbonylbenzofur-5-yl)-2,4-pyrimidinediamine Purification of the crude gave two products.

N4-[1-(2-Ethoxycarbonylethyl)indazoline-6-yl]-5-fluoro-N2-(2-methoxycarbonylbenzofur-5-yl)-2,4-pyrimidinediamine (R935295):
$^1$H NMR (DMSO-d$_6$): δ 9.54 (s, 1H), 9.41 (s, 1H), 8.21 (app d, 1H, J=1.7 Hz), 8.17 (d, 1H, J=3.5 Hz), 8.01 (s, 1H), 7.86 (s, 1H), 7.83-7.80 (m 2H), 7.68 (d, 1H, J=8.8 Hz), 7.59 (s, 1H), 7.52 (d, 1H, J=8.2 Hz), 7.25 (d, 1H, J=8.2 Hz), 4.12 (t, 2H, J=6.4 Hz), 3.91 (qt, 2H, J=7.0 Hz), 3.88 (s, 3H), 2.72 (t, 2H, J=6.4 Hz), 1.02 (t, 3H, J=7.0 Hz). LCMS: ret. time: 25.67 min.; purity: 91%; MS (m/e): 519 (MH$^+$) and N4-[1-(2-carboxyethyl)indazoline-6-yl]-5-fluoro-N2-(2-methoxycarbonylbenzofur-5-yl)-2,4-pyrimidinediamine (R935296)

$^1$H NMR (DMSO-d$_6$): δ 9.54 (s, 1H), 9.39 (s, 1H), 8.23 (app d, 1H, J=1.7 Hz), 8.17 (d, 1H, J=3.5 Hz), 8.00 (s, 1H), 7.86 (s, 1H), 7.83-7.80 (m 2H), 7.68 (d, 1H, J=8.8 Hz), 7.58 (s, 1H), 7.52 (d, 1H, J=8.2 Hz), 7.28 (d, 1H, J=8.2 Hz), 4.13 (t, 2H, J=6.4 Hz), 3.88 (s, 3H), 2.67 (t, 2H, J=6.4 Hz). LCMS: ret. time: 23.28 min.; purity: 91%; MS (m/e): 491 (MH$^+$).

7.3.1045 5-Fluoro-N4-[2-(N-methylaminocarbonyl)benzofuran-5-yl]-N2-[1-[2(N-methylaminocarbonyl)ethyl]-indazoline-6-yl]-2,4-pyrimidinediamine (R935297)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-[1-(2-ethoxycarbonylethyl)indazoline-6-yl]-5-fluoro-N2-(2-methoxycarbonylbenzofur-5-yl)-2,4-pyrimidinediamine and Me$_2$NH.HCl were reacted to provide 5-fluoro-N4-[2-(N-methylaminocarbonyl)benzofuran-5-yl]-N2-[1-[2(N-methylaminocarbonyl)ethyl]-indazoline-6-yl]-2,4-pyrimidinediamine. $^1$H NMR (DMSO-d$_6$): δ 10.00 (s, 1H), 9.90 (s, 1H), 8.70 (qt, 1H, J=4.7 Hz), 8.24 (d, 1H, J=4.1 Hz), 8.12 (d, 1H, J=1.7 Hz), 7.911 (s, 1H), 7.86 (s, 1H), 7.81 (qt, 1H, J=4.7 Hz), 7.71 (d, 2H, J=1.7 and 8.8 Hz), 7.57 (dd, 1H, J=3.5 and 8.8 Hz), 7.35 (s, 1H), 7.26 (dd, 1H, J=3.5 and 8.8 Hz), 4.19 (t, 2H, J=7.0 Hz), 2.53 (t, 2H, J=7.0 Hz), 2.47 (d, 6H, J=4.7 Hz). LCMS: ret. time: 20.18 min.; purity: 89%; MS (m/e): 503 (MH$^+$).

7.3.1046 5-Fluoro-N4-(4-isopropoxyphenyl)-N2-(2-methyl-indazoline-5-yl)-2,4-pyrimidinediamine (R935298)

In like manner to the preparation of N4-(3,4-ethylenedioxyphenyl)-5-fluoro-N2-(3-hydroxyphenyl)-2,4-pyrimidinediamine, 2-chloro-5-fluoro-N-(4-isopropoxyphenyl)-4-pyrimidineamine and 5-amino-2-methylindazoline were reacted to give 5-fluoro-N4-(4-isopropoxyphenyl)-N2-(2-methyl-indazoline-5-yl)-2,4-pyrimidinediamine. $^1$H NMR (DMSO-d$_6$): δ 9.15 (s, 1H), 9.03 (s, 1H), 8.03-8.00 (m, 3H), 7.60 (dd, 2H, J=4.1 and 8.8 Hz), 7.42 (d, 1H, J=9.3 Hz), 7.31 (d, 1H, J=9.3 Hz), 6.86 (d, 2H, J=8.8 Hz), 4.57 (sept, 1H, J=6.4 Hz), 4.08 (s, 3H), 1.26 (d, 6H, J=6.4 Hz), LCMS: ret. time: 23.89 min.; purity: 98%; MS (m/e): 393 (MH$^+$).

7.3.1047 5-Fluoro-N4-(3-hydroxyphenyl)-N2-(2-methy-indazoline-5-yl)-2,4-pyrimidinediamine (R935299)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine was reacted with 5-amino-2-methylindazoline to produce 5-fluoro-N4-(3-hydroxyphenyl)-N2-(2-methy-indazoline-5-yl)-2,4-pyrimidinediamine. $^1$H NMR (DMSO-d$_6$): δ 10.35 (s, 1H), 10.30 (s, 1H), 9.62 (br s, 1H), 8.22 (d, 1H, J=5.3 Hz), 8.13 (s, 1H), 7.85 (s, 1H), 7.49 (d, 1H, J=8.8 Hz), 7.17 (dd, 1H, J=1.7 and 9.3 Hz), 7.08 (d, 2H, J=5.3 Hz), 7.03 (s, 1H), 6.64-6.60 (m, 1H), 4.09 (s, 3H). LCMS: ret. time: 20.01 min.; purity: 97%; MS (m/e): 351 (MH$^+$).

7.3.1048 N4-(3,4-Ethyelenedioxyphenyl)-5-fluoro-N2-(2-methy-indazoline-5-yl)-2,4-pyrimidinediamine (R935300)

In like manner to the preparation of N4-(3,4-ethylenedioxyphenyl)-5-fluoro-N2-(3-hydroxyphenyl)-2,4-pyrimidinediamine, 2-chloro-N-(3,4-ethylenedioxyphenyl)-5-fluoro-4-pyrimidineamine was reacted with 5-amino-2-methylindazoline to produce N4-(3,4-ethyelenedioxyphenyl)-5-fluoro-N2-(2-methy-indazoline-5-yl)-2,4-pyrimidinediamine. $^1$H NMR (DMSO-d$_6$): δ 10.64 (s, 1H), 10.62 (s, 1H), 8.22 (d, 1H, J=5.3 Hz), 8.21 (s, 1H), 7.77 (s, 1H), 7.58 (d, 1H, J=9.3 Hz), 7.23-7.19 (m, 2H), 7.10 (dd, 1H, J=2.3 and 8.8 Hz), 6.78 (d, 1H, J=8.8 Hz), 4.21 (s, 3H), 4.15 (s, 4H). LCMS: ret. time: 21.77 min.; purity: 92%; MS (m/e): 393 (MH$^+$).

7.3.1049 N2-[1-(2-Ethoxycarbonylethyl)indazoline-5-yl]-N4-(3,4-ethylenedioxyphenyl)-5-fluoro-2,4-pyrimidinediamine (R935301)

In like manner to the preparation of N4-(3,4-ethylenedioxyphenyl)-5-fluoro-N2-(3-hydroxyphenyl)-2,4-pyrimidinediamine, 2-chloro-N-(3,4-ethylenedioxyphenyl)-5-fluoro-4-pyrimidineamine was reacted with 5-amino-1-(2-ethoxycarbonylethyl)indazoline to provide N2-[1-(2-ethoxycarbonylethyl)indazoline-5-yl]-N4-(3,4-ethylenedioxyphenyl)-5-fluoro-2,4-pyrimidinediamine. $^1$H NMR (DMSO-d$_6$): δ 9.15 (s, 1H), 9.13 (s, 1H), 8.10, (s, 1H), 8.04 (d, 1H, J=3.5 Hz), 7.83 (s, 1H), 7.50 (s, 2H), 7.30 (d, 1H, J=2.3 and 8.8 Hz), 6.79 (d, 1H, J=8.8 Hz), 4.55 (t, 2H, J=6.4 Hz), 4.22 (s, 4H), 3.97 (qt, 2H, J=7.0 Hz), 2.88 (t, 2H, J=6.4 Hz), 1.06 (t, 3H, J=7.0 Hz). LCMS: ret. time: 25.19 min.; purity: 93%; MS (m/e): 479 (MH$^+$)

7.3.1050 N4-(3,4-Ethylenedioxyphenyl)-5-fluoro-N2-[1-(3-hydroxypropyl)indazoline-5-yl]-2,4-pyrimidinediamine (R935302)

In like manner to the preparation of N2-(3,4-ethylenedioxyphenyl)-5-fluoro-N4-[4(2-hydroxy-1,1-dimethylethyl)phenyl]-2,4-pyrimidinediamine, N2-[1-(2-ethoxycarbonylethyl)indazoline-5-yl]-N4-(3,4-ethylenedioxyphenyl)-5-fluoro-2,4-pyrimidinediamine was reacted with DIBAL-H to produce N4-(3,4-ethylenedioxyphenyl)-5-fluoro-N2-[1-(3-hydroxypropyl)indazoline-5-yl]-2,4-pyrimidinediamine. $^1$H NMR (DMSO-d$_6$): δ 9.14 (s, 1H), 9.13 (s, 1H), 8.09 (s, 1H), 8.03 (d, 1H, J=4.1 Hz), 7.82 (s, 1H), 7.48 (s, 2H), 7.30 (d, 1H, J=2.3 Hz), 7.18 (dd, 1H, J=2.3 and 8.8 Hz), 6.78 (d, 1H, J=8.8 Hz), 4.59 (t, 1H, J=6.4 Hz), 4.37 (t, 2H, J=6.4 Hz), 4.22 (s, 4H), 3.34 (t, 2H, J=6.4 Hz), 1.84 (q, 2H, J=6.4 Hz). LCMS: ret. time: 22.33 min.; purity: 100%; MS (m/e): 437 (MH$^+$).

7.3.1051 N4-[1-(2-Ethoxycarbonylethyl)indazoline-5-yl]-5-fluoro-N2-(3-hydroxyphenyl)-2,4-pyrimidinediamine (R935303)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine was reacted with 5-amino-1-(2-ethoxycarbonylethyl)indazoline to provide N4-[1-(2-ethoxycarbonylethyl)indazoline-5-yl]-5-fluoro-N2-(3-hydroxyphenyl)-2,4-pyrimidinediamine. $^1$H NMR (DMSO-d$_6$): δ 10.50 (s, 1H), 10.46 (s, 1H), 9.62 (br s 1H), 8.28 (d, 1H, J=5.8 Hz), 7.96 (s, 2H), 7.65 (d, 1H, J=8.8 Hz), 7.36 (dd, 1H, J=1.7 and 8.8 Hz), 7.15-7.08 (m, 3H), 6.67-6.64 (m, 1H), 4.59 (t, 2H, J=6.4 Hz), 3.97 (qt, 2H, J=7.0 Hz), 2.89 (t, 2H, J=6.4 Hz), 1.06 (t, 3H, J=7.0 Hz). LCMS: ret. time: 23.68 min.; purity: 97%; MS (m/e): 437 (MH$^+$).

7.3.1052 5-Fluoro-N4-(3-hydroxyphenyl)-N2-[1-(3-hydroxypropyl)indazoline-5-yl]-2,4-pyrimidinediamine (R935304)

In like manner to the preparation of N2-(3,4-ethylenedioxyphenyl)-5-fluoro-N4-[4(2-hydroxy-1,1-dimethylethyl)phenyl]-2,4-pyrimidinediamine, N4-[1-(2-ethoxycarbonylethyl)indazoline-5-yl]-5-fluoro-N2-(3-hydroxyphenyl)-2,4-pyrimidinediamine was reacted with DIBAL-H to produce 5-fluoro-N4-(3-hydroxyphenyl)-N2-[1-(3-hydroxypropyl)indazoline-5-yl]-2,4-pyrimidinediamine. $^1$H NMR (DMSO-d$_6$): δ 9.39 (s, 1H), 9.18 (s, 1H), 9.15 (s, 1H), 8.20 (s, 1H), 8.07 (d, 1H, J=4.1 Hz), 7.84 (s, 1H), 7.46 (s, 2H), 7.24 (d, 1H, J=8.2 Hz), 7.11-7.06 (m, 2H), 6.53 (d, 1H, J=8.8 Hz), 4.56 (t, 1H, J=4.7 Hz), 4.37 (t, 2H, J=6.4 Hz), 3.34 (t, 2H, J=6.4 Hz), 1.92 (q, 2H, J=6.4 Hz). LCMS: ret. time: 24.70 min.; purity: 90%; MS (m/e): 479 (MH$^+$). LCMS: ret. time: 20.89 min.; purity: 98%; MS (m/e): 395 (MH$^+$).

7.3.1053 5-Fluoro-N4-(3-hydroxyphenyl)-N2-[1-[2(N-methylaminocarbonyl)ethyl]-indazoline-5-yl]-2,4-pyrimidinediamine (R935305)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-[1-(2-ethoxycarbonylethyl)indazoline-5-yl]-5-fluoro-N2-(3-hydroxyphenyl)-2,4-pyrimidinediamine and Me$_2$NH.HCl were reacted to provide 5-fluoro-N4-(3-hydroxyphenyl)-N2-[1-[2(N-methylaminocarbonyl)ethyl]-indazoline-5-yl]-2,4-pyrimidinediamine. $^1$H NMR (DMSO-d$_6$): δ 9.39 (s, 1H), 9.18 (s, 1H), 9.15 (s, 1H), 8.19 (s, 1H), 8.06 (d, 1H, J=3.5 Hz), 7.84 (s, 1H), 7.82 (qt, 1H, J=4.7 Hz), 7.46 (t, 2H, J=8.2 Hz), 7.25 (d, 1H, J=8.2 Hz), 7.11 (d, 1H, J=8.2 Hz), 7.10 (d, 1H, J=8.2 Hz), 6.53 (t, 1H, J=8.2 Hz), 4.51 (t, 2H, J=7.0 Hz), 2.61 (t, 2H, J=7.0 Hz), 2.49 (d, 3H, J=4.7 Hz). LCMS: ret. time: 20.66 min.; purity: 95%; MS (m/e): 422 (MH$^+$).

7.3.1054 N4-[1-(2-Ethoxycarbonylethyl)indazoline-5-yl]-5-fluoro-N2-(4-isopropoxyphenyl)-2,4-pyrimidinediamine (R935306)

In like manner to the preparation of N4-(3,4-ethylenedioxyphenyl)-5-fluoro-N2-(3-hydroxyphenyl)-2,4-pyrimidinediamine, 2-chloro-5-fluoro-N-(4-isopropoxyphenyl)-4-pyrimidineamine was reacted with 5-amino-1-(2-ethoxycarbonylethyl)indazoline to provide N2-[1-(2-ethoxycarbonylethyl)indazoline-5-yl]-5-fluoro-N4-(4-isopropoxyphenyl)-2,4-pyrimidinediamine. $^1$H NMR (DMSO-d$_6$): δ 10.48 (s, 1H), 10.41 (s, 1H), 8.25 (d, 1H, J=5.8 Hz), 7.93 (s, 1H), 7.84 (s, 1H), 7.66 (d, 1H, J=8.8 Hz), 7.49 (d, 2H, J=8.8 Hz), 7.36 (dd, 1H, J=2.3 and 8.8 Hz), 6.86 (d, 2H, J=8.8 Hz), 4.59 (t, 2H, J=6.4 Hz), 4.57 (sept, 1H, J=7.0 Hz), 3.96 (qt, 2H, J=7.0 Hz), 2.89 (t, 2H, J=6.4 Hz), 1.23 (d, 6H, J=7.0 Hz), 1.05 (t, 3H, J=7.0 Hz). LCMS: ret. time: 27.39 min.; purity: 98%; MS (m/e): 479 (MH$^+$).

7.3.1055 5-Fluoro-N2-[1-(3-hydroxypropyl)indazoline-5-yl]-N4-(4-isopropoxyphenyl)-2,4-pyrimidinediamine (R935307)

In like manner to the preparation of N2-(3,4-ethylenedioxyphenyl)-5-fluoro-N4-[4(2-hydroxy-1,1-dimethylethyl)phenyl]-2,4-pyrimidinediamine, N2-[1-(2-ethoxycarbonylethyl)indazoline-5-yl]-5-fluoro-N4-(4-isopropoxyphenyl)-2,4-pyrimidinediamine was reacted with DIBAL-H to produce 5-fluoro-N2-[1-(3-hydroxypropyl)indazoline-5-yl]-N4-(4-isopropoxyphenyl)-2,4-pyrimidinediamine. $^1$H NMR (DMSO-d$_6$): δ 9.16 (s, 1H), 9.10 (s, 1H), 8.09 (s, 1H), 8.03 (d, 1H, J=4.1 Hz), 7.79 (s, 1H), 7.57 (d, 2H, J=8.8 Hz), 7.46 (t, 2H), 6.87 (d, 2H, J=8.8 Hz), 4.60-4.52 (m, 2H), 4.37 (t, 2H, J=6.4 Hz), 3.34 (t, 2H, J=6.4 Hz), 1.84 (q, 2H, J=6.4 Hz), 1.24 (d, 6H, J=7.0 Hz). LCMS: ret. time: 23.71 min.; purity: 98%; MS (m/e): 437 (MH$^+$).

7.3.1056 5-Fluoro-N4-(2-hydroxymethylbenzofur-5-yl)-N2-[1-(3-hydroxypropyl)indazoline-6-yl]-2,4-pyrimidinediamine (R935308)

In like manner to the preparation of N2-(3,4-ethylenedioxyphenyl)-5-fluoro-N4-[4(2-hydroxy-1,1-dimethylethyl)phenyl]-2,4-pyrimidinediamine, N4-[1-(2-Ethoxycarbonylethyl)indazoline-6-yl]-5-fluoro-N2-(2-methoxycarbonylbenzofur-5-yl)-2,4-pyrimidinediamine was reacted with DIBAL-H to produce 5-fluoro-N4-(2-hydroxymethylbenzofur-5-yl)-N2-[1-(3-hydroxypropyl)indazoline-6-yl]-2,4-pyrimidinediamine. $^1$H NMR (DMSO-d$_6$): δ 9.35 (s, 1H), 9.33 (s, 1H), 8.12 (d, 1H, J=3.5 Hz), 7.99 (d, 1H, J=1.7 Hz), 7.95 (s, 1H), 7.84 (s, 1H), 7.55-7.49 (m, 3H), 7.28 (d, 1H, J=8.8 Hz), 6.62 (s, 1H), 5.46 (t, 1H, J=5.8 Hz), 4.55 (d, 2H, J=5.8 Hz), 4.45 (t, 1H, J=4.7 Hz), 3.96 (t, 2H, J=6.4 Hz), 3.20 (t, 2H, J=6.4 Hz), 1.76 (q, 2H, J=6.4 Hz). LCMS: ret. time: 20.86 min.; purity: 99%; MS (m/e): 449 (MH$^+$).

7.3.1057 N4-(3,4-Ethylenedioxyphenyl)-5-fluoro-N2-[1-[2(N-methylaminocarbonyl)ethyl]-indazoline-5-yl]-2,4-pyrimidinediamine (R935309)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-[1-(2-ethoxycarbonylethyl)indazoline-5-yl]-N2-(3,4-ethylenedioxyphenyl)-5-fluoro-2,4-pyrimidinediamine and Me$_2$NH.HCl were reacted to provide N4-(3,4-ethylenedioxyphenyl)-5-fluoro-N2-[1-[2(N-methylaminocarbonyl)ethyl]-indazoline-5-yl]-2,4-pyrimidinediamine. $^1$H NMR (DMSO-d$_6$): δ 9.12 (s, 1H), 9.11 (s, 1H), 8.09 (s, 1H), 8.03 (d, 1H, J=3.5 Hz), 7.82 (s, 2H), 7.47 (s, 2H), 7.32-7.30 (m, 1H), 7.22-7.17 (m, 1H), 6.80 (d, 1H, J=8.8 Hz), 4.51 (t, 2H, J=7.0 Hz), 4.22 (s, 4H), 2.62 (t, 2H, J=7.0 Hz), 2.49 (d, 3H, J=4.7 Hz). LCMS: ret. time: 18.67 min.; purity: 100%; MS (m/e): 464 (MH$^+$).

7.3.1058 5-Fluoro-N4-(4-isopropoxyphenyl)-N2-[1-[2(N-methylaminocarbonyl)ethyl]-indazoline-5-yl]-2,4-pyrimidinediamine (R935310)

In like manner to the preparation of N4-(3,4-ethylenedioxyphenyl)-5-fluoro-N2-[3-(N-methylamino)carbonylmethyleneoxyphenyl]-2,4-pyrimidinediamine, N2-[1-(2-ethoxycarbonylethyl)indazoline-5-yl]-5-fluoro-N4-(4-isopropoxyphenyl)-2,4-pyrimidinediamine and Me$_2$NH.HCl were reacted to provide 5-fluoro-N4-(4-isopropoxyphenyl)-N2-[1-[2(N-methylaminocarbonyl)ethyl]indazoline-5-yl]-2,4-pyrimidinediamine. $^1$H NMR (DMSO-d$_6$): δ 9.18 (s, 1H), 9.09 (s, 1H), 8.08 (s, 1H), 8.02 (d, 1H, J=4.1 Hz), 7.82 (qt, 1H, J=4.7 Hz), 7.79 (s, 1H), 7.57 (d, 2H, J=8.8 Hz), 7.45 (d, 2H, J=8.8 Hz), 6.87 (d, 2H, J=8.8 Hz), 4.57 (q, 2H, J=5.8 Hz), 4.51 (t, 2H, J=7.0 Hz), 2.61 (t, 2H, J=7.0 Hz), 2.47 (d, 3H, J=4.7 Hz), 1.26 (d, 6H, J=5.8 Hz). LCMS: ret. time: 17.14 min.; purity: 99%; MS (m/e): 464 (MH$^+$).

7.3.1059 N4-(3,4-Ethylenedioxyphenyl)-5-fluoro-N2-[1-(2-methoxy-4-carbomethoxybenzyl)indazoline-6-yl]-2,4-pyrimidinediamine (R935320)

In like manner to the preparation of N4-(3,4-ethylenedioxyphenyl)-5-fluoro-N2-(3-hydroxyphenyl)-2,4-pyrimidinediamine, 2-chloro-N-(3,4-ethylenedioxyphenyl)-5-fluoro-4-pyrimidineamine was reacted with 6-amino-1-(2-methoxy-3-carbomethoxybenzyl)indazoline to provide N4-(3,4-ethylenedioxyphenyl)-5-fluoro-N2-[1-(2-methoxy-4-carbomethoxybenzyl)indazoline-6-yl]-2,4-pyrimidinediamine. $^1$H NMR (DMSO-d$_6$): δ 9.36 (s, 1H), 9.18 (s, 1H), 8.08 (d, 1H, J=3.5 Hz), 8.04 (s, 1H), 7.56 (d, 1H, J=8.2 Hz), 7.45 (d, 1H, J=1.8 Hz), 7.43-7.38 (m, 1H), 7.36-7.34 (m, 1H), 7.30 (dd, 1H, J=1.7 and 8.8 Hz), 7.20 (dd, 1H, J=2.3 and 8.8 Hz), 6.75 (d, 1H, J=8.8 Hz), 6.68 (d, 1H, J=8.2 Hz), 6.48 (dd, 1H, J=1.7 and 8.2 Hz), 5.39 (s, 2H), 4.16 (s, 4H), 3.83 (s, 3H), 3.79 (s, 3H). LCMS: ret. time: 29.92 min.; purity: 80%; MS (m/e): 557 (MH$^+$).

7.3.1060 5-Fluoro-N4-(3-hydroxyphenyl)-N2-[1-(2-methoxy-4-carbomethoxybenzyl)indazoline-6-yl]-2,4-pyrimidinediamine (R935321)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine was reacted with 6-amino-1-(2-methoxy-3-carbomethoxybenzyl)indazoline to provide 5-fluoro-N4-(3-hydroxyphenyl)-N2-[1-(2-methoxy-4-carbomethoxybenzyl)indazoline-6-yl]-2,4-pyrimidinediamine. $^1$H NMR (DMSO-$d_6$): δ 9.37 (s, 1H), 9.31(s, 1H), 9.23 (s, 1H), 8.11 (d, 1H, J=3.5 Hz), 8.08 (s, 1H), 7.93 (s, 1H), 7.57 (d, 1H, J=8.8 Hz), 7.45 (d, 1H, J=1.7 Hz), 7.40 (dd, 1H, J=1.7 and 8.8 Hz), 7.33-7.27 (, 2H), 7.13 (t, 1H, J=1.7 HZ), 7.03 (t, 2H, J=8.2 Hz), 6.67 (d, 1H, J=8.2 Hz), 6.45 (dd, 1H, J=1.7 and 8.2 Hz), 5.37 (s, 2H), 3.83 (s, 3H), 3.79 (s, 3H). LCMS: ret. time: 28.80 min.; purity: 92%; MS (m/e): 515 (MH$^+$).

7.3.1061 5-Fluoro-N4-(4-isopropoxyphenyl)-N2-[1-[2-methoxy-4-(o-toluylsulfonamidocarboxy)benzyl]indazoline-6-yl]-2,4-pyrimidinediamine (R935322)

In like manner to the preparation of N4-(3,4-ethylenedioxyphenyl)-5-fluoro-N2-(3-hydroxyphenyl)-2,4-pyrimidinediamine, 2-chloro-5-fluoro-N-(4-isopropoxyphenyl)-4-pyrimidineamine was reacted with 6-amino-1-[2-methoxy-4-(o-toluylsulfonamidocarboxy)benzyl]indazoline to provide 5-fluoro-N4-(4-isopropoxyphenyl)-N2-[1-[2-methoxy-4-(o-toluylsulfonamidocarboxy)benzyl]indazoline-6-yl]-2,4-pyrimidinediamine. $^1$H NMR (DMSO-$d_6$): δ 9.60 (s, 2H), 8.11 (d, 1H, J=4.1 Hz), 8.00-7.92 (m, 3H), 7.61-7.53 (m, 4H), 7.47-7.24 (m, 5H), 6.81 (d, 2H, J=8.8 Hz), 6.68 (d, 1H, J=8.2 Hz), 5.34 (s, 2H), 4.48 (sept, 1H, J=5.9 Hz), 3.82 (s, 3H), 2.55 (s, 3H), 1.21 (d, 6H, J=5.9 Hz). LCMS: ret. time: 30.57 min.; purity: 95%; MS (m/e): 696 (MH$^+$).

7.3.1062 N4-(3,4-Ethylenedioxyphenyl)-5-fluoro-N4-[1-[2-methoxy-4-(o-toluylsulfonamidocarboxy)benzyl]indazoline-6-yl]-2,4-pyrimidinediamine (R935323)

In like manner to the preparation of N4-(3,4-ethylenedioxyphenyl)-5-fluoro-N2-(3-hydroxyphenyl)-2,4-pyrimidinediamine, 2-chloro-N-(3,4-ethylenedioxyphenyl)-5-fluoro-4-pyrimidineamine was reacted with 6-amino-1-[2-methoxy-4-(o-toluylsulfonamidocarboxy)benzyl]indazoline to provide N4-(3,4-Ethylenedioxyphenyl)-5-fluoro-N2-[1-[2-methoxy-4-(o-toluylsulfonamidocarboxy)benzyl]indazoline-6-yl]-2,4-pyrimidinediamine. $^1$H NMR (DMSO-$d_6$): δ 9.53 (s, 1H), 9.41 (s, 1H), 8.05 (d, 1H, J=4.1 Hz), 7.96-7.90 (m, 3H), 7.55 (d, 1H, J=8.8 Hz), 7.49 (dd, 1H, J=7.6 Hz), 7.42-7.20 (m, 6H), 7.14-7.10 (m, 1H), 6.69 (d, 1H, J=8.2 Hz), 6.60 (d, 1H, J=8.8 Hz), 5.33 (s, 2H), 4.10 (s, 4H), 3.77 (s, 3H), 2.50 (s, 3H). LCMS: ret. time: 32.11 min.; purity: 93%; MS (m/e): 696 (MH$^+$)

7.3.1063 5-Fluoro-N4-(3-hydroxyphenyl)-N2-[1-[2-methoxy-4-(o-toluylsulfonamidocarboxy)benzyl]indazoline-6-yl]-2,4-pyrimidinediamine (R935324)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine was reacted with 6-amino-1-[2-methoxy-4-(o-toluylsulfonamidocarboxy)benzyl]indazoline to provide 5-fluoro-N4-(3-hydroxyphenyl)-N2-[1-[2-methoxy-4-(o-toluylsulfonamidocarboxy)benzyl]indazoline-6-yl]-2,4-pyrimidinediamine. $^1$H NMR (DMSO-$d_6$): δ 9.64 (s, 1H), 9.56 (s, 1H), 8.15 (d, 1H, J=4.1 Hz), 8.00 (s, 1H), 7.97 (d, 2H, J=8.8 Hz), 7.60 (d, 1H, J=8.8 Hz), 7.53 (d, 1H, J=1.2 and 8.8 Hz), 7.47-7.23 (m, 6H), 7.11 (t, 1H, J=1.7 Hz), 7.03 (t, 1H, J=8.2 Hz), 6.62 (d, 1H, J=8.2 Hz), 6.48 (dd, 1H, J=1.7 and 8.2 Hz), 5.36 (s, 2H), 3.82 (s, 3H), 2.55 (s, 3H). LCMS: ret. time: 29.79 min.; purity: 92%; MS (m/e): 654 (MH$^+$).

7.3.1064 N4-(3,4-Ethylenedioxyphenyl)-5-fluoro-N2-[2-(2-methoxy-4-carbomethoxybenzyl)indazoline-6-yl]-2,4-pyrimidinediamine (R935336)

In like manner to the preparation of N4-(3,4-ethylenedioxyphenyl)-5-fluoro-N2-(3-hydroxyphenyl)-2,4-pyrimidinediamine, 2-chloro-N-(3,4-ethylenedioxyphenyl)-5-fluoro-4-pyrimidineamine was reacted with 6-amino-2-(2-methoxy-3-carbomethoxybenzyl)indazoline to provide N4-(3,4-ethylenedioxyphenyl)-5-fluoro-N2-[2-(2-methoxy-4-carbomethoxybenzyl)indazoline-6-yl]-2,4-pyrimidinediamine. $^1$H NMR (DMSO-$d_6$): δ 9.16 (s, 1H), 9.14 (s, 1H), 8.24 (s, 1H), 8.06 (s, 1h), 8.04 (d, 1H, J=3.5 Hz), 7.51 (d, 2H, J=7.7 Hz), 7.49 (s, 1H), 7.29-7.26 (m, 2H), 7.19 (d, 1H, J=7.7 Hz), 6.92 (d, 1H, J=8.8 Hz), 6.76 (d, 1H, J=8.2 Hz), 5.58 (s, 2H), 4.22 (s, 4H), 3.92 (s, 3H), 3.82 (s, 3H). LCMS: ret. time: 10.91 min.; purity: 91%; MS (m/e): 557 (MH$^+$).

7.3.1065 5-Fluoro-N4-(3-hydroxyphenyl)-N2-[2-(2-methoxy-4-carbomethoxybenzyl)indazoline-6-yl]-2,4-pyrimidinediamine (R935337)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine was reacted with 6-amino-2-(2-methoxy-3-carbomethoxybenzyl)indazoline to provide 5-fluoro-N4-(3-hydroxyphenyl)-N2-[2-(2-methoxy-4-carbomethoxybenzyl)indazoline-6-yl]-2,4-pyrimidinediamine. $^1$H NMR (DMSO-$d_6$): δ 9.31 (s, 1H), 9.17 (s, 1H), 9.15 (s, 1H), 8.26 (s, 1H), 8.09 (d, 1H, J=5.8 Hz), 8.08 (s, 1H), 7.52 (app t, 3H, J=7.6 Hz), 7.42 (d, 1H, J=8.2 Hz), 7.23 (d, 1H, J=8.2 Hz), 7.08 (app s, 1H), 7.03 (d, 1H, J=8.2 Hz), 6.93 (d, 1H, J=7.6 Hz), 6.43 (d, 1H, J=8.2 Hz), 5.57 (s, 2H), 3.90 (s, 3H), 3.82 (s, 3H). LCMS: ret. time: 10.51 min.; purity: 93%; MS (m/e): 515 (MH$^+$).

7.3.1066 5-Fluoro-N4-(4-isopropoxyphenyl)-N2-[2-(2-methoxy-4-carbomethoxybenzyl)indazoline-6-yl]-2,4-pyrimidinediamine (R935338)

In like manner to the preparation of N4-(3,4-ethylenedioxyphenyl)-5-fluoro-N2-(3-hydroxyphenyl)-2,4-pyrimidinediamine, 2-chloro-5-fluoro-N-(4-isopropoxyphenyl)-4-pyrimidineamine was reacted with 6-amino-2-(2-methoxy-4-carbomethoxybenzyl)indazoline to provide 5-fluoro-N4-(4-isopropoxyphenyl)-N2-[2-(2-methoxy-4-carbomethoxybenzyl)indazoline-6-yl]-2,4-pyrimidinediamine. $^1$H NMR (DMSO-$d_6$): δ 9.20 (s, 1H), 9.16 (s, 1H), 8.26 (s, 1H), 8.16 (s, 1H), 8.06 (d, 1H, J=3.5 Hz), 7.66 (d, 2H, J=8.8 Hz), 7.52-7.48 (m, 3H), 7.15 (d, 1H, J=8.2 Hz), 6.86 (d, 2H, J=8.8 Hz), 6.81 (d, 1H, J=8.8 Hz), 5.56 (s, 2H), 4.46 (sept, 1H, J=5.9 Hz), 3.91 (s, 3H), 3.82 (s, 3H), 1.17 (d, 6H, J=5.9 Hz). LCMS: ret. time: 11.94 min.; purity: 90%; MS (m/e): 557 (MH$^+$).

7.3.1067 N4-(3,4-Ethylenedioxyphenyl)-5-fluoro-N2-[1-[2-methoxy-4-(o-toluylsulfonamidocarboxy)benzyl]indazoline-5-yl]-2,4-pyrimidinediamine (R935339)

In like manner to the preparation of N4-(3,4-ethylenedioxyphenyl)-5-fluoro-N2-(3-hydroxyphenyl)-2,4-pyrimidinediamine, 2-chloro-N-(3,4-ethylenedioxyphenyl)-5-fluoro-4-pyrimidineamine was reacted with 5-amino-1-[2-methoxy-4-(o-toluylsulfonamidocarboxy)benzyl]indazoline to provide N4-(3,4-Ethylenedioxyphenyl)-5-fluoro-N2-[1-[2-methoxy-4-(o-toluylsulfonamidocarboxy)benzyl]indazoline-5-yl]-2,4-pyrimidinediamine. $^1$H NMR (DMSO-d$_6$): δ 9.57 (br s, 2H), 8.08 (d, 1H, J=3.5 Hz), 8.01 (s, 1H), 7.99 (d, 1H, J=1.0 Hz), 7.95 (s, 1H), 7.59-7.32 (m, 3H), 7.45-7.32 (m, 4H), 7.27-7.24 (m, 1H), 7.17-7.12 (m, 1H), 6.74 (d, 1H, J=8.7 Hz), 6.65 (d, 1H, J=8.7 Hz), 5.58 (s, 2H), 4.15 (s, 4H), 3.88 (s, 3H), 2.56 (s, 3H). LCMS: ret. time: 11.33 min.; purity: 98%; MS (m/e): 696 (MH$^+$).

7.3.1068 5-Fluoro-N4-(3-hydroxyphenyl)-N2-[1-[2-methoxy-4-(o-toluylsulfonamidocarboxy)benzyl]indazoline-5-yl]-2,4-pyrimidinediamine (R935340)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-hydroxyphenyl)-4-pyrimidineamine was reacted with 5-amino-1-[2-methoxy-4-(o-toluylsulfonamidocarboxy)benzyl]indazoline to provide 5-fluoro-N4-(3-hydroxyphenyl)-N2-[1-[2-methoxy-4-(o-toluylsulfonamidocarboxy)benzyl]indazoline-5-yl]-2,4-pyrimidinediamine. $^1$H NMR (DMSO-d$_6$): δ 9.57 (s, 1H), 9.48 (s, 1H), 8.13 (app s, 2H), 8.00 (d, 1H, J=8.2 Hz), 7.94 (s, 1H), 7.59-7.32 (m, 7H), 7.18 (d, 1H, J=8.2 Hz), 7.06 (app t, 3H, J=8.8 Hz), 6.64 (d, 1H, J=8.2 Hz), 6.55 (d, 1H, J=8.2 Hz), 5.57 (s, 2H), 3.88 (s, 3H), 2.56 (s, 3H). LCMS: ret. time: 10.16 min.; purity: 97%; MS (m/e): 654 (MH$^+$).

7.3.1069 N4-(4-Chlorophenyl)-5-fluoro-N2-(1-methyl-indazoline-5-yl)-2,4-pyrimidinediamine (R935351)

In like manner to the preparation of N4-(3,4-ethylenedioxyphenyl)-5-fluoro-N2-(3-hydroxyphenyl)-2,4-pyrimidinediamine, 2-chloro-N-(4-chlorophenyl)-5-fluoro 4-pyrimidineamine and 1-methyl-5-aminoindazoline were reacted to give N4-(4-chlorophenyl)-5-fluoro-N2-(1-methyl-indazoline-5-yl)-2,4-pyrimidinediamine $^1$H NMR (DMSO-d$_6$): δ 9.86 (s, 1H), 9.61 (s, 1H), 8.17 (d, 1H, J=4.1 Hz), 8.00 (s, 1H), 7.88 (s, 1H), 7.78 (d, 2H, J=8.8 Hz), 7.57 (d, 1H, J=8.8 Hz), 7.43 (d, 1H, J=8.8 Hz), 7.34 (d, 2H, J=8.8 Hz), 4.00 (s, 3H). LCMS: ret. time: 10.64 min.; purity: 94%; MS (m/e): 369 (MH$^+$).

7.3.1070 N4-(4-Chlorophenyl)-5-fluoro-N2-(indazoline-6-yl)-2,4-pyrimidinediamine (R935352)

In like manner to the preparation of N4-(3,4-ethylenedioxyphenyl)-5-fluoro-N2-(3-hydroxyphenyl)-2,4-pyrimidinediamine, 2-chloro-N-(4-chlorophenyl)-5-fluoro 4-pyrimidineamime and 6-aminoindazoline were reacted to give N4-(4-chlorophenyl)-5-fluoro-N2-(indazoline-6-yl)-2,4-pyrimidinediamine. $^1$H NMR (DMSO-d$_6$): δ 10.18 (s, 1H), 10.02 (s, 1H), 8.26 (d, 1H, J=4.1 Hz), 7.98 (s, 1H), 7.84 (d, 1H, J=8.8 Hz), 7.82 (d, 2H, J=8.8 Hz), 7.65 (d, 1H, J=8.8 Hz), 7.35 (d, 2H, J=8.8 Hz), 7.19 (d, 1H, J=8.8 Hz). LCMS: ret. time: 10.80 min.; purity: 90%; MS (m/e): 355 (MH$^+$).

7.3.1071 N4-(4-Chlorophenyl)-N2-[1-(2-ethoxycarbonylethyl)indazoline-5-yl]-5-fluoro-2,4-pyrimidinediamine (R935353)

In like manner to the preparation of N4-(3,4-ethylenedioxyphenyl)-5-fluoro-N2-(3-hydroxyphenyl)-2,4-pyrimidinediamine, 2-chloro-N-(4-chlorophenyl)-5-fluoro-4-pyrimidineamine was reacted with 5-amino-1-(2-ethoxycarbonylethyl)indazoline to provide N4-(4-chlorophenyl)-N2-[1-(2-ethoxycarbonylethyl)indazoline-5-yl]-5-fluoro-2,4-pyrimidinediamine. $^1$H NMR (DMSO-d$_6$): δ 10.37 (s, 1H), 10.17 (s, 1H), 8.26 (d, 1H, J=5.3 Hz), 7.96 (s, 1H), 7.88 (s, 1H), 7.33-7.66 (m, 3H), 7.40 (d, 1H, J=8.8 Hz), 7.35 (d, 2H, J=8.8 Hz), 4.61 (t, 2H, J=6.4 Hz), 3.97 (qt, 2H, J=7.0 Hz), 2.91 (t, 2H, J=6.4 Hz), 1.05 (t, 3H, J=7.0 Hz). LCMS: ret. time: 11.85 min.; purity: 95%; MS (m/e): 455 (MH$^+$).

7.3.1072 N4-(3-Chloro-4-trifluoromethoxy-phenyl)-N2-[1-(2-ethoxycarbonylethyl)indazoline-5-yl]-5-fluoro-2,4-pyrimidinediamine (R935354)

In like manner to the preparation of N4-(3,4-ethylenedioxyphenyl)-5-fluoro-N2-(3-hydroxyphenyl)-2,4-pyrimidinediamine, 2-chloro-N-(3-chloro-trifluoromethoxy-phenyl)-5-fluoro-4-pyrimidineamine was reacted with 5-amino-1-(2-ethoxycarbonylethyl)indazoline to provide N4-(3-chloro-4-trifluoromethoxy-phenyl)-N2-[1-(2-ethoxycarbonylethyl)indazoline-5-yl]-5-fluoro-2,4-pyrimidinediamine. $^1$H NMR (DMSO-d$_6$): δ 9.63 (s, 1H), 9.30 (s, 1H), 8.17 (d, 1H, J=3.5 Hz), 8.10 (t, 1H, J=2.3 Hz), 8.01 (s, 1H), 7.87 (s, 1H), 7.86 (d, 1H, J=8.2 Hz), 7.57 (d, 1H, J=9.4 Hz), 7.47 (t, 2H, J=10.0 Hz), 4.56 (t, 2H, J=6.9 Hz), 3.97 (qt, 2H, J=7.0 Hz), 2.88 (t, 2H, J=6.9 Hz), 1.06 (t, 3H, J=7.0 Hz). LCMS: ret. time: 14.4 min.; purity: 95%; MS (m/e): 539 (MH$^+$).

7.3.1073 N4-(3,4-Dichlorophenyl)-5-fluoro-N2-(1-methylindazoline-5-yl)-2,4-pyrimidinediamine (R935355)

In like manner to the preparation of N4-(3,4-ethylenedioxyphenyl)-5-fluoro-N2-(3-hydroxyphenyl)-2,4-pyrimidinediamine, 2-chloro-N-(3,4-dichlorophenyl)-5-fluoro 4-pyrimidineamime and 1-methyl-5-aminoindazoline were reacted to give N4-(3,4-dichlorophenyl)-5-fluoro-N2-(1-methylindazoline-5-yl)-2,4-pyrimidinediamine. $^1$H NMR (DMSO-d$_6$): δ 9.63 (s, 1H), 9.35 (s, 1H), 8.17 (d, 1H, J=3.5 Hz), 8.08 (s, 1H), 8.01 (s, 1H), 7.86 (s, 1H), 7.79 (d, 1H, J=8.8 Hz), 7.53 (d, 2H, J=8.2 Hz), 7.47 (d, 1H, J=8.2 Hz), 3.99 (s, 3H). LCMS: ret. time: 12.30 min.; purity: 98%; MS (m/e): 404 (MH$^+$).

7.3.1074 5-Fluoro-N2-(1-methylindazoline-5-yl)-N4-(3-trifluoromethoxypheny)-2,4-pyrimidinediamine (R935356)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-trifluoromethoxyphenyl)-4-pyrimidineamime and 1-methyl-5-aminoindazoline were reacted to give 5-fluoro-N2-(1-methylindazoline-5-yl)-N4-(3-trifluoromethoxypheny)-2,4-pyrimidinediamine. $^1$H NMR (DMSO-d$_6$): δ 10.37 (s, 1H), 10.17 (s, 1H), 8.25 (d, 1H, J=4.1 Hz), 7.92 (s, 2H), 7.84 (d, 1H, J=9.4 Hz), 7.75 (s, 1H), 7.59 (d, 1H, J=8.8 Hz), 7.45 (d, 1H, J=9.4 Hz), 7.38 (d, 1H, J=9.4 Hz), 7.08 (d, 1H, J=8.8 Hz), 3.99 (s, 3H). LCMS: ret. time: 12.13 min.; purity: 94%; MS (m/e): 419 (MH$^+$).

7.3.1075 N4-(3,4-Difluoromethylendioxyphenyl)-5-fluoro-N2-(1-methylindazoline-5-yl)-2,4-pyrimidinediamine (R935357)

In like manner to the preparation of N4-(3,4-ethylenedioxyphenyl)-5-fluoro-N2-(3-hydroxyphenyl)-2,4-pyrimidinediamine, 2-chloro-N-(3,4-difluoromethylenedioxyphenyl)-5-fluoro-4-pyrimidineamime and 1-methyl-5-aminoindazoline were reacted to give N4-(3,4-difluoromethylendioxyphenyl)-5-fluoro-N2-(1-methylindazoline-5-yl)-2,4-pyrimidinediamine. $^1$H NMR (DMSO-d$_6$): δ 9.84 (s, 1H), 9.54 (s, 1H), 8.16 (d, 1H, J=4.1 Hz), 8.00 (s, 2H), 7.87 (s, 1H), 7.55-7.32 (m, 4H), 3.99 (s, 3H). LCMS: ret. time: 11.26 min.; purity: 96%; MS (m/e): 415 (MH$^+$).

7.3.1076 N4-(3,4-Difluorophenyl)-5-fluoro-N2-(1-methylindazoline-5-yl)-2,4-pyrimidinediamine (R935358)

In like manner to the preparation of N4-(3,4-ethylenedioxyphenyl)-5-fluoro-N2-(3-hydroxyphenyl)-2,4-pyrimidinediamine, 2-chloro-N-(3,4-difluorophenyl)-5-fluoro-4-pyrimidineamime and 1-methyl-5-aminoindazoline were reacted to give N4-(3,4-difluorophenyl)-5-fluoro-N2-(1-methylindazoline-5-yl)-2,4-pyrimidinediamine. $^1$H NMR (DMSO-d$_6$): δ 9.50 (s, 1H), 9.27 (s, 1H), 8.13 (d, 1H, J=4.1 Hz), 8.08 (app s, 2H), 7.85 (s, 1H), 7.50 (app s, 3H), 7.37 (q, 1H, J=9.4 Hz), 3.99 (s, 3H). LCMS: ret. time: 10.42 min.; purity: 90%; MS (m/e): 371 (MH$^+$).

7.3.1077 N4-(3-chloro-4-trifluoromethoxyphenyl)-5-fluoro-N2-(1-methylindazoline-5-yl)-2,4-pyrimidinediamine (R935359)

In like manner to the preparation of N4-(3,4-ethylenedioxyphenyl)-5-fluoro-N2-(3-hydroxyphenyl)-2,4-pyrimidinediamine, 2-chloro-N-(3-chloro-4-trifluoromethoxyphenyl)-5-fluoro-4-pyrimidineamime and 1-methyl-5-aminoindazoline were reacted to give N4-(3-chloro-4-trifluoromethoxyphenyl)-5-fluoro-N2-(1-methylindazoline-5-yl)-2,4-pyrimidinediamine. $^1$H NMR (DMSO-d$_6$): δ 9.79 (s, 1H), 9.45 (s, 1H), 8.19 (d, 1H, J=4.1 Hz), 8.09 (t, 1H, J=2.8 Hz), 8.00 (s, 1H), 7.85-7.81 (m, 2H), 7.51 (d, 1H, J=8.8 Hz), 7.48-7.44 (m, 2H), 3.99 (s, 3H). LCMS: ret. time: 13.14 min.; purity: 92%; MS (m/e): 453 (MH$^+$).

7.3.1078 N2-[1-(2-Ethoxycarbonylethyl)indazoline-5-yl]-5-fluoro-N4-(3-trifluoromethoxyphenyl)-2,4-pyrimidinediamine (R935360)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-trifluoromethoxyphenyl)-4-pyrimidineamine was reacted with 5-amino-1-(2-ethoxycarbonylethyl)indazoline to provide N2-[1-(2-ethoxycarbonylethyl)indazoline-5-yl]-5-fluoro-N4-(3-trifluoromethoxyphenyl)-2,4-pyrimidinediamine. $^1$H NMR (DMSO-d$_6$): δ 9.55 (s, 1H), 9.26 (s, 1H), 8.15 (d, 1H, J=3.5 Hz), 8.05 (s, 1H), 7.95 (d, 1H, J=8.2 Hz), 7.88 (s, 1H), 7.78 (s, 1H), 7.58 (dd, 1H, J=8.8 and 7.4 Hz), 7.39 (t, 1H, J=8.2 Hz), 7.01 (d, 1H, J=8.8 Hz), 4.56 (t, 2H, J=7.0 Hz), 3.97 (q, 4H, J=7.0 Hz), 2.88 (t, 2H, J=7.0 Hz), 1.06 (t, 3H, J=7.0 Hz). LCMS: ret. time: 13.22 min.; purity: 95%; MS (m/e): 505 (MH$^+$).

7.3.1079 5-Fluoro-N2-[1-[2(N-methylaminocarbonyl)ethyl]indazoline-5-yl]-N4-(3-trifluoromethoxyphenyl)-2,4-pyrimidinediamine (R935361)

In like manner to the preparation of N4-(3,4-ethylenedioxyphenyl)-5-fluoro-N2-[3-(N-methylamino)carbonylmethyleneoxyphenyl]-2,4-pyrimidinediamine, N2-[1-(2-ethoxycarbonylethyl)indazoline-5-yl]-5-fluoro-N4-(3-trifluoromethoxyphenyl)-2,4-pyrimidinediamine and Me$_2$NH.HCl were reacted to provide 5-fluoro-N2-[1-[2(N-methylaminocarbonyl)ethyl]indazoline-5-yl]-N4-(3-trifluoromethoxyphenyl)-2,4-pyrimidinediamine. $^1$H NMR (DMSO-d$_6$): δ 9.55 (s, 1H), 9.25 (s, 1H), 8.15 (d, 1H, J=3.5 Hz), 8.04 (s, 1H), 7.96 (d, 1H, J=8.2 Hz), 7.87 (s, 1H), 7.83 (qt, 1H, J=4.9 Hz), 7.70 (s, 1H), 7.49 (dd, 2H, J=8.2 and 9.4 Hz), 7.40 (d, 1H, J=8.8 Hz), 7.01 (d, 1H, J=8.8 Hz), 4.52 (t, 2H, J=7.0 Hz), 2.63 (t, 2H, J=7.0 Hz), 2.49 (d, 3H, J=4.7 Hz). LCMS: ret. time: 10.00 min.; purity: 100%; MS (m/e): 490 (MH$^+$).

7.3.1080 5-Fluoro-N2-[1-(3-hydroxypropyl)indazoline-5-yl]-N4-(3-trifluoromethoxyphenyl)-2,4-pyrimidinediamine (R935362)

In like manner to the preparation of N2-(3,4-ethylenedioxyphenyl)-5-fluoro-N4-[4(2-hydroxy-1,1-dimethylethyl)phenyl]-2,4-pyrimidinediamine, N2-[1-(2-ethoxycarbonylethyl)indazoline-5-yl]-5-fluoro-N4-(3-trifluoromethoxyphenyl)-2,4-pyrimidinediamine was reacted with DIBAL-H to produce 5-fluoro-N2-[1-(3-hydroxypropyl)indazoline-5-yl]-N4-(3-trifluoromethoxyphenyl)-2,4-pyrimidinediamine. $^1$H NMR (DMSO-d$_6$): δ 9.55 (s, 1H), 9.24 (s, 1H), 8.15 (d, 1H, J=2.9 Hz), 8.05 (s, 1H), 7.92 (d, 1H, J=7.6 Hz), 7.87 (s, 1H), 7.78 (s, 1H), 7.50 (s, 2H), 7.39 (t, 1H, J=8.2 Hz), 7.01 (d, 1H, J=7.6 Hz), 4.56 (t, 1H, J=5.2 Hz), 4.38 (t, 2H, J=7.0 Hz), 3.35 (dd, 2H, J=5.2 and 7.0 Hz), 1.84 (qt, 2H, J=7.0 Hz). LCMS: ret. time: 10.42 min.; purity: 97%; MS (m/e): 463 (MH$^+$)

7.3.1081 5-Fluoro-N2-(indazoline-6-yl)-N4-(3-trifluoromethoxyphenyl)-2,4-pyrimidinediamine (R935363)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-trifluoromethoxyphenyl)-4-pyrimidineamine and 6-aminoindazoline were reacted to give 5-fluoro-N2-(indazoline-6-yl)-N4-(3-trifluoromethoxyphenyl)-2,4-pyrimidinediamine. $^1$H NMR (DMSO-d$_6$): δ 12.72 (s, 1H), 9.60 (s, 1H), 9.42 (s, 1H), 8.21 (d, 1H, J=3.5 Hz), 8.06 (br s, 2H), 7.89 (s, 1H), 7.83 (s, 1H), 7.57 (d, 1H, J=8.8 Hz), 7.42 (t, 1H, J=8.2 Hz), 7.27 (d, 1H, J=8.8 Hz), 7.00 (d, 1H, J=8.2 Hz). LCMS: ret. time: 12.17 min.; purity: 97%; MS (m/e): 405 (MH$^+$).

7.3.1082 5-Fluoro-N2-(indazoline-5-yl)-N4-(3-trifluoro methoxyphenyl)-2,4-pyrimidinediamine (R935364)

In like manner to the preparation of N4-(3,4-ethylenedioxyphenyl)-5-fluoro-N2-(3-hydroxyphenyl)-2,4-pyrimidinediamine, 2-chloro-5-fluoro-N-(3-trifluoromethoxyphenyl)-4-pyrimidineamine and 5-aminoindazoline were reacted to give 5-fluoro-N2-(indazoline-5-yl)-N4-(3-trifluoromethoxyphenyl)-2,4-pyrimidinediamine. $^1$H NMR (DMSO-d$_6$): δ 12.85 (s, 1H), 9.54 (s, 1H), 9.23 (s, 1H), 8.15 (d, 1H, J=3.5 Hz), 8.05 (s, 1H), 7.93 (d, 1H, J=8.2 Hz), 7.89 (s, 1H), 7.78 (s, 1H), 7.48-7.35 (m, 3H), 7.01 (d, 1H, J=8.2 Hz). LCMS: ret. time: 10.44 min.; purity: 98%; MS (m/e): 405 (MH$^+$).

7.3.1083 N4-(4-Chlorophenyl)-5-fluoro-N2-(indazoline-5-yl)-2,4-pyrimidinediamine (R935365)

In like manner to the preparation of N4-(3,4-ethylenedioxyphenyl)-5-fluoro-N2-(3-hydroxyphenyl)-2,4-pyrimidinediamine, 2-chloro-N-(4-chlorophenyl)-5-fluoro 4-pyrimidineamime and 5-aminoindazoline were reacted to give N4-(4-chlorophenyl)-5-fluoro-N2-(indazoline-5-yl)-2,4-pyrimidinediamine. $^1$H NMR (DMSO-d$_6$): δ 12.85 (s, 1H), 9.43 (s, 1H), 9.19 (s, 1H), 8.11 (d, 1H, J=3.5 Hz), 8.08 (s, 1H), 7.87 (s, 1H), 7.82 (dd, 2H, J=3.0 and 8.8 Hz), 7.42 (dd, 2H, J=3.0 and 8.8 Hz), 7.31 (d, 2H, J=8.8 Hz). LCMS: ret. time: 9.07 min.; purity: 91%; MS (m/e): 355 (MH$^+$).

7.3.1084 N4-(3-Chloro-4-trifluoromethoxyphenyl)-5-fluoro-N2-(indazoline-5-yl)-2,4-pyrimidinediamine (R935366)

In like manner to the preparation of N4-(3,4-ethylenedioxyphenyl)-5-fluoro-N2-(3-hydroxyphenyl)-2,4-pyrimidinediamine, 2-chloro-N-(3-chloro-4-trifluoromethoxyphenyl)-5-fluoro-4-pyrimidineamime and 5-aminoindazoline were reacted to give N4-(3-chloro-4-trifluoromethoxyphenyl)-5-fluoro-N2-(indazoline-5-yl)-2,4-pyrimidinediamine. $^1$H NMR (DMSO-d$_6$): δ 12.90 (s, 1H), 9.45 (s, 1H), 9.27 (s, 1H), 8.15 (d, 1H, J=3.5 Hz), 8.11 (t, 1H, J=3.0 Hz), 8.02 (s, 1H), 7.87 (s, 1H), 7.84 (d, 1H, J=8.8 Hz), 7.47 (d, 2H, J=8.8 Hz), 7.44 (d, 1H, J=8.8 Hz). LCMS: ret. time: 11.65 min.; purity: 98%; MS (m/e): 439 (MH$^+$).

7.3.1085 5-Fluoro-N4-[4-(3-phenyl-1,2,4-oxadiazol-5-yl)methyleneoxyphenyl]-N2-(3,4,5-trimethoxyphenyl)-2,4-pyrimidinediamine (R935367)

In like manner to the preparation of N4-(3,4-ethylenedioxyphenyl)-5-fluoro-N2-(3-hydroxyphenyl)-2,4-pyrimidinediamine, 2-chloro-5-fluoro-N4-[4-(3-phenyl-1,2,4-oxadiazol-5-yl)methyleneoxyphenyl]-4-pyrimidineamine and 3,4,5-trimethoxyaniline were reacted by microwave heating at 180° C. Upon concentration of the ethanol and addition of 2N HCl provided 5-fluoro-N4-[4-(3-phenyl-1,2,4-oxadiazol-5-yl)methyleneoxyphenyl]-N2-(3,4,5-trimethoxyphenyl)-2,4-pyrimidinediamine as fine flakes of the solid. $^1$H NMR (DMSO-d$_6$): δ 9.59 (s, 1H), 9.25 (s, 1H), 8.09 (d, 1H, J=3.5 Hz), 8.01 (dd, 2H, J=5.3 and 1.2 Hz), 7.39 (dd, 2H, J=3.1 and 8.8 Hz), 7.60-7.54 (m, 3H), 7.03 (d, 2H, J=8.8 Hz), 6.94 (d, 2H, J=3.1 Hz), 5.57 (s, 2H), 3.59 (s, 6H), 3.57 (s, 3H). LCMS: ret. time: 13.00 min.; purity: 97%; MS (m/e): 547 (MH$^+$).

7.3.1086 N4-(3-Chloro-4-trifluoromethoxyphenyl)-5-fluoro-N2-(indazoline-6-yl)-2,4-pyrimidinediamine (R935368)

In like manner to the preparation of N4-(3,4-ethylenedioxyphenyl)-5-fluoro-N2-(3-hydroxyphenyl)-2,4-pyrimidinediamine, 2-chloro-N-(3-chloro-4-trifluoromethoxyphenyl)-5-fluoro-4-pyrimidineamime and 6-aminoindazoline were reacted to give N4-(3-chloro-4-trifluoromethoxyphenyl)-5-fluoro-N2-(indazoline-6-yl)-2,4-pyrimidinediamine. $^1$H NMR (DMSO-d$_6$): δ 12.73 (s, 1H), 9.67 (s, 1H), 9.46 (s, 1H), 8.21 (d, 1H, J=3.5 Hz), 8.17 (app d, 1H, J=8.8 Hz), 8.04 (br s, 1H), 7.97 (dt, 1H, J=2.4 and 9.3 Hz), 7.89 (s, 1H), 7.58 (d, 1H, J=8.8 Hz), 7.47 (d, 1H, J=9.3 Hz), 7.27 (dd, 1H, J=1.7 and 8.8 Hz). LCMS: ret. time: 13.08 min.; purity: 96%; MS (m/e): 439 (MH$^+$).

7.3.1087 N4-(3-Chloro-4-trifluoromethoxyphenyl)-5-fluoro-N2-[1-[2(N-methylaminocarbonyl)ethyl]indazoline-5-yl]-2,4-pyrimidinediamine (R935369)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(3-chloro-4-trifluoromethoxyphenyl)-N2-[1-(2-ethoxycarbonylethyl)indazoline-5-yl]-5-fluoro-2,4-pyrimidinediamine and Me$_2$NH.HCl were reacted to provide N4-(3-Chloro-4-trifluoromethoxyphenyl)-5-fluoro-N2-[1-[2(N-methylaminocarbonyl)ethyl]indazoline-5-yl]-2,4-pyrimidinediamine. $^1$H NMR (DMSO-d$_6$): δ 9.62 (s, 1H), 9.29 (s, 1H), 8.17 (d, 1H, J=3.5 Hz), 8.11 (t, 1H, J=2.4 Hz), 8.02 (app s, 1H), 7.88-7.82 (m, 3H), 7.53 (d, 1H, J=9.3 Hz), 7.47 (d, 2H, J=8.8 Hz), 4.52 (t, 2H, J=7.0 Hz), 2.48 (t, 2H, J=7.0 Hz), 2.48 (d, 3H, J=4.7 Hz). LCMS: ret. time: 10.51 min.; purity: 99%; MS (m/e): 524 (MH$^+$).

7.3.1088 N4-(3-Chloro-4-trifluoromethoxyphenyl)-5-fluoro-N2-[1-(3-hydroxypropyl)indazoline-5-yl]-2,4-pyrimidinediamine (R935370)

In like manner to the preparation of N2-(3,4-ethylenedioxyphenyl)-5-fluoro-N4-[4(2-hydroxy-1,1-dimethylethyl)phenyl]-2,4-pyrimidinediamine, N4-(3-chloro-4-trifluoromethoxyphenyl)-N2-[1-(2-ethoxycarbonylethyl)indazoline-5-yl]-5-fluoro-2,4-pyrimidinediamine was reacted with DIBAL-H to produce N4-(3-chloro-4-trifluoromethoxyphenyl)-5-fluoro-N2-[1-(3-hydroxypropyl)indazoline-5-yl]-2,4-pyrimidinediamine. $^1$H NMR (DMSO-d$_6$): δ 9.62 (s, 1H), 9.28 (s, 1H), 8.17 (d, 1H, J=3.5 Hz), 8.11 (s, 1H), 8.02 (s, 1H), 7.85 (s, 2H), 7.53 (t, 2H, J=8.8 Hz), 7.46 (t, 1H, J=8.8 Hz), 4.56 (t, 1H, J=5.8 Hz), 4.38 (t, 2H, J=6.4 Hz), 3.35 (dd, 2H, J=5.8 and 6.4 Hz), 1.93 (q, 2H, J=6.4 Hz). LCMS: ret. time: 11.33 min.; purity: 99%; MS (m/e): 497 (MH$^+$).

7.3.1089 N4-(3,4-Dichlorophenyl)-5-fluoro-N2-(indazoline-5-yl)-2,4-pyrimidinediamine (R935371)

In like manner to the preparation of N4-(3,4-ethylenedioxyphenyl)-5-fluoro-N2-(3-hydroxyphenyl)-2,4-pyrimidinediamine, 2-chloro-N-(3,4-dichlorophenyl)-5-fluoro 4-pyrimidineamime and 5-aminoindazoline were reacted to give N4-(3,4-dichlorophenyl)-5-fluoro-N2-(indazoline-5-yl)-2,4-pyrimidinediamine. $^1$H NMR (DMSO-d$_6$): δ 9.90 (s, 1H), 9.60 (s, 1H), 8.20 (d, 1H, J=4.2 Hz), 8.06 (t, 1H, J=2.3 Hz), 7.92 (s, 2H), 7.73 (d, 1H, J=8.8 Hz), 7.51-7.40 (m, 3H). LCMS: ret. time: 9.83 min.; purity: 98%; MS (m/e): 390 (MH$^+$).

7.3.1090 N4-(3,4-Dichlorophenyl)-5-fluoro-N2-(indazoline-6-yl)-2,4-pyrimidinediamine (R935372)

In like manner to the preparation of N4-(3,4-ethylenedioxyphenyl)-5-fluoro-N2-(3-hydroxyphenyl)-2,4-pyrimidinediamine, 2-chloro-N-(3,4-dichlorophenyl)-5-fluoro 4-pyrimidineamime and 6-aminoindazoline were reacted to give N4-(3,4-dichlorophenyl)-5-fluoro-N2-(indazoline-6-yl)-2,4-pyrimidinediamine. $^1$H NMR (DMSO-d$_6$): δ 12.82 (s, 1H), 9.63 (s, 1H), 9.48 (s, 1H), 8.22 (d, 1H, J=4.3 Hz), 8.15 (t, 1H, J=2.3 Hz), 8.02 (s, 1H), 7.92-7.90 (m, 2H), 7.59 (d, 1H, J=8.8 Hz), 7.52 (d, 1H, J=8.8 Hz), 7.26 (dd, 1H, J=1.7 and 8.8 Hz). LCMS: ret. time: 11.73 min.; purity: 99%; MS (m/e): 390 (MH$^+$).

7.3.1091 N4-(3,4-Difluoromethylendioxyphenyl)-5-fluoro-N2-(indazoline-5-yl)-2,4-pyrimidinediamine (R935373)

In like manner to the preparation of N4-(3,4-ethylenedioxyphenyl)-5-fluoro-N2-(3-hydroxyphenyl)-2,4-pyrimidinediamine, 2-chloro-N-(3,4-difluoromethylenedioxyphenyl)-5-fluoro-4-pyrimidineamine and 5-aminoindazoline were reacted to give N4-(3,4-difluoromethylendioxyphenyl)-5-fluoro-N2-(indazoline-5-yl)-2,4-pyrimidinediamine. $^1$H NMR (DMSO-$d_6$): δ 10.40 (s, 1H), 10.11 (s, 1H), 8.25 (d, 1H, J=4.5 Hz), 7.95 (s, 1H), 7.89 (app s, 2H), 7.49 (d, 1H, J=8.8 Hz), 7.37 (app d, 3H, J=8.2 Hz). LCMS: ret. time: 8.56 min.; purity: 99%; MS (m/e): 401 (MH$^+$).

7.3.1092 N4-(3,4-Difluoromethylendioxyphenyl)-5-fluoro-N2-(indazoline-6-yl)-2,4-pyrimidinediamine (R935374)

In like manner to the preparation of N4-(3,4-ethylenedioxyphenyl)-5-fluoro-N2-(3-hydroxyphenyl)-2,4-pyrimidinediamine, 2-chloro-N-(3,4-difluoromethylenedioxyphenyl)-5-fluoro-4-pyrimidineamine and 6-aminoindazoline were reacted to give N4-(3,4-difluoromethylendioxyphenyl)-5-fluoro-N2-(indazoline-6-yl)-2,4-pyrimidinediamine. $^1$H NMR (DMSO-$d_6$): δ 9.53 (s, 1H), 9.52 (s, 1H), 8.21 (d, 1H, J=4.5 Hz), 8.10 (s, 1H), 8.01 (s, 1H), 7.92 (s, 1H), 7.59 (d, 1H, J=8.8 Hz), 7.48 (dt, 1H, J=2.3 and 8.8 Hz), 7.34 (d, 1H, J=8.2 Hz), 7.21 (dd, 1H, J=2.3 and 8.8 Hz). LCMS: ret. time: 11.29 min.; purity: 90%; MS (m/e): 401 (MH$^+$).

7.3.1093 N4-(6-Chloro-3-pyridyl)-5-fluoro-N2-(1-methylindazoline-5-yl)-2,4-pyrimidinediamine (R935375)

In like manner to the preparation of N4-(3,4-ethylenedioxyphenyl)-5-fluoro-N2-(3-hydroxyphenyl)-2,4-pyrimidinediamine, 2-chloro-N-(6-chloro-3-pyridyl)-5-fluoro-4-pyrimidineamine and 5-amino-1-methylindazoline were reacted to give N4-(6-chloro-3-pyridyl)-5-fluoro-N2-(1-methylindazoline-5-yl)-2,4-pyrimidinediamine. $^1$H NMR (DMSO-$d_6$): δ 9.96 (s, 1H), 9.58 (s, 1H), 8.86 (s, 1H), 8.25 (dt, 1H, J=3.9 and 8.8 Hz), 8.20 (d, 1H, J=4.1 Hz), 8.04 (s, 1H), 7.55 (d, 1H, J=8.8 Hz), 7.44 (d, 2H, J=8.8 Hz), 4.00 (s, 3H). LCMS: ret. time: 8.95 min.; purity: 100%; MS (m/e): 370 (MH$^+$).

7.3.1094 N4-(6-Chloro-3-pyridyl)-5-fluoro-N2-(indazoline-5-yl)-2,4-pyrimidinediamine (R935376)

In like manner to the preparation of N4-(3,4-ethylenedioxyphenyl)-5-fluoro-N2-(3-hydroxyphenyl)-2,4-pyrimidinediamine, 2-chloro-N-(6-chloro-3-pyridyl)-5-fluoro-4-pyrimidineamine and 5-aminoindazoline were reacted to give N4-(6-chloro-3-pyridyl)-5-fluoro-N2-(indazoline-5-yl)-2,4-pyrimidinediamine. $^1$H NMR (DMSO-$d_6$): δ 9.78 (s, 1H), 9.41 (s, 1H), 8.88 (s, 1H), 8.24 (d, 1H, J=8.2 Hz), 8.18 (d, 1H, J=3.5 Hz), 8.06 (s, 1H), 7.92 (s, 1H), 7.42 (app s, 3H). LCMS: ret. time: 7.87 min.; purity: 90%; MS (m/e): 356 (MH$^+$).

7.3.1095 N4-(6-Chloro-3-pyridyl)-N2-[1-(2-ethoxycarbonylethyl)indazoline-5-yl]-5-fluoro-2,4-pyrimidinediamine (R935377)

In like manner to the preparation of N4-(3,4-ethylenedioxyphenyl)-5-fluoro-N2-(3-hydroxyphenyl)-2,4-pyrimidinediamine, 2-chloro-N-(6-chloro-3-pyridyl)-5-fluoro-4-pyrimidineamine and 5-amino-1-(2-ethoxycarbonylethyl) indazoline were reacted to give N4-(6-chloro-3-pyridyl-N2-[1-(2-ethoxycarbonylethyl)indazoline-5-yl]-5-fluoro-2,4-pyrimidinediamine. $^1$H NMR (DMSO-$d_6$): δ 10.37 (s, 1H), 10.04 (s, 1H), 8.78 (s, 1H), 8.28 (d, 1H, J=4.8 Hz), 8.20 (dt, 1H, J=2.8 and 8.8 Hz), 7.96 (s, 1H), 7.92 (s, 1H), 7.65 (d, 1H, J=8.8 Hz), 7.45 (d, 1H, J=8.8 Hz), 7.41 (d, 1H, J=8.8 Hz), 4.59 (t, 2H, J=6.0 Hz), 3.97 (qt, 2H, J=7.0 Hz), 2.90 (t, 2H, J=6.4 Hz), 1.06 (t, 3H, J=7.0 Hz). LCMS: ret. time: 10.87 min.; purity: 94%; MS (m/e): 456 (MH$^+$).

7.3.1096 N4-(6-Chloro-3-pyridyl)-5-fluoro-N2-[1-[2(N-methylaminocarbonyl)ethyl]indazoline-5-yl]-2,4-pyrimidinediamine (R935378)

In like manner to the preparation of N4-(3,4-ethylenedioxyphenyl)-5-fluoro-N2-[3-(N-methylamino)carbonylmethyleneoxyphenyl]-2,4-pyrimidinediamine, N4-(6-chloro-3-pyridyl)-N2-[1-(2-ethoxycarbonylethyl)indazoline-5-yl]-5-fluoro-2,4-pyrimidinediamine and Me$_2$NH.HCl were reacted to provide N4-(6-Chloro-3-pyridyl)-5-fluoro-N2-[1-[2(N-methylaminocarbonyl)ethyl]indazoline-5-yl]-2,4-pyrimidinediamine. $^1$H NMR (DMSO-$d_6$): δ 9.67 (s, 1H), 9.31 (s, 1H), 8.88 (s, 1H), 8.27 (dt, 1H, J=3.0 and 8.8 Hz), 8.17 (d, 1H, J=3.5 Hz), 8.08 (s, 1H), 7.88 (s, 1H), 7.83 (q, 1H, J=5.3 Hz), 7.53 (d, 1H, J=8.8 Hz), 7.45 (d, 1H, J=8.8 Hz), 4.53 (t, 2H, J=7.0 Hz), 2.63 (t, 2H, J=7.0 Hz), 2.49 (d, 3H, J=5.3 Hz). LCMS: ret. time: 7.62 min.; purity: 89%; MS (m/e): 441 (MH$^+$).

7.3.1097 N4-(6-Chloro-3-pyridyl)-5-fluoro-N2-[1-(3-hydroxypropyl)indazoline-5-yl]-2,4-pyrimidinediamine (R935379)

In like manner to the preparation of N2-(3,4-ethylenedioxyphenyl)-5-fluoro-N4-[4(2-hydroxy-1,1-dimethylethyl)phenyl]-2,4-pyrimidinediamine, N4-(6-chloro-3-pyridyl)-N2-[1-(2-ethoxycarbonylethyl)indazoline-5-yl]-5-fluoro-2,4-pyrimidinediamine was reacted with DIBAL-H to produce N4-(6-chloro-3-pyridyl)-5-fluoro-N2-[1-(3-hydroxypropyl) indazoline-5-yl]-2,4-pyrimidinediamine. $^1$H NMR (DMSO-$d_6$):. LCMS: ret. time: 8.02 min.; purity: 98%; MS (m/e): 414 (MH$^+$).

7.3.1098 N4-(2,6-Dimethoxy-3-pyridyl)-5-fluoro-N2-[1-methylindazoline-5-yl]-2,4-pyrimidinediamine (R935380)

In like manner to the preparation of N4-(3,4-ethylenedioxyphenyl)-5-fluoro-N2-(3-hydroxyphenyl)-2,4-pyrimidinediamine, 2-chloro-N-(2,6-dimethoxy-3-pyridyl)-6-5-fluoro-4-pyrimidineamine and 1-methyl-5-aminoindazoline were reacted to give N4-(2,6-dimethoxy-3-pyridyl)-5-fluoro-N2-[1-methylindazoline-5-yl]-2,4-pyrimidinediamine. $^1$H NMR (DMSO-$d_6$): δ 9.08 (s, 1H), 8.68 (s, 1H), 8.01 (d, 1H, J=4.1 Hz), 7.96 (s, 1H), 7.76 (dd, 1H, J=4.1 and 8.8 Hz), 7.65 (s, 1H), 7.37 (d, 1H, J=8.8 Hz), 7.34 (d, 1H, J=8.2 Hz), 6.46 (d, 1H, J=8.2 Hz), 3.94 (s, 3H), 3.91 (s, 3H), 3.83 (s, 3H). LCMS: ret. time: 9.57 min.; purity: 92%; MS (m/e): 396 (MH$^+$).

7.3.1099 Additional 2,4-Pyrimidinediamine

Compounds R008951, R008952, R008953, R008955, R008956, R008958, R070153 and R070790 (structures provided below) were purchased from Contact Services. Additional compounds whose structures are provided below were synthesized using methods similar to those described in the previous examples.

| | |
|---|---|
| R008951<br>R067962<br>R926209 | 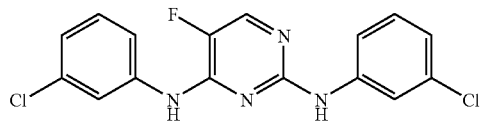 |
| R088814<br>R926017 | 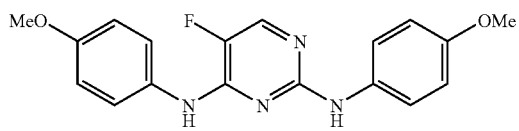 |
| R008952<br>R067963 | 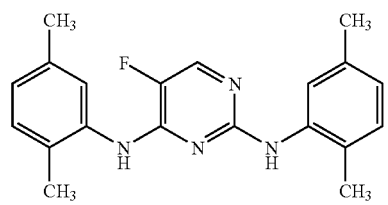 |
| R088815 |  |
| R008953<br>R067964 | 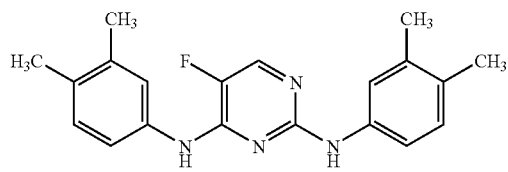 |
| R091880 | 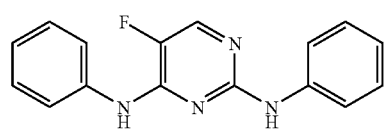 |
| R008955<br>R081166 |  |
| R092788 | 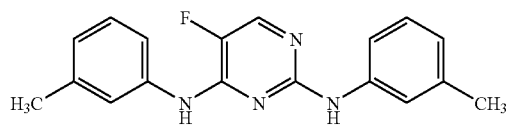 |
| R008956<br>R070791 | 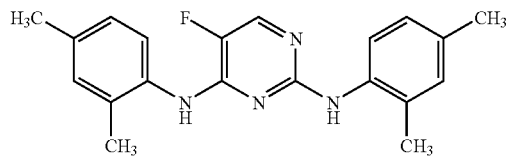 |
| R920846 | 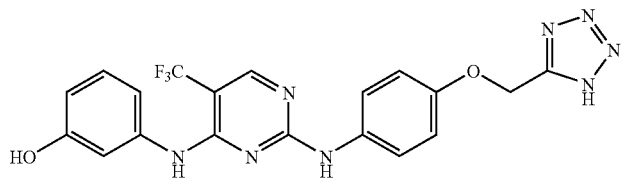 |

-continued
R008958 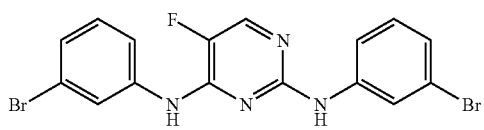
R070153 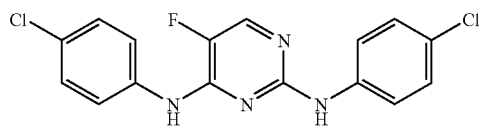
R070790
R926036 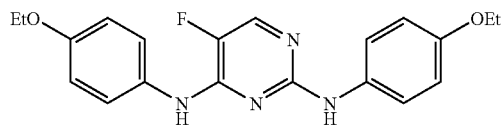
R926593 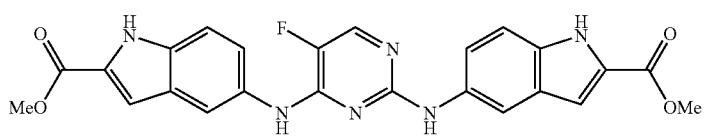
R926736 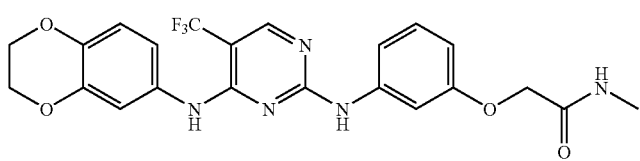
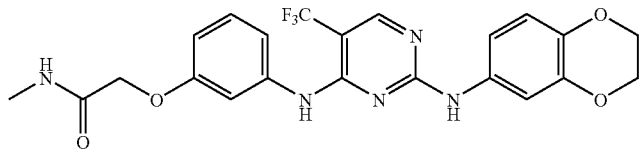
R950189 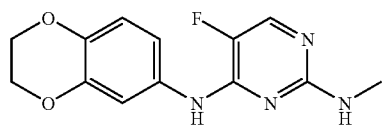
R950216 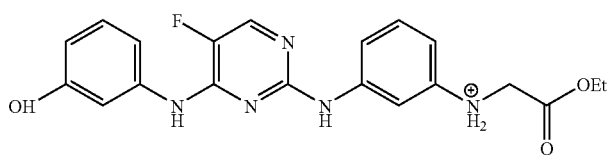
R935117 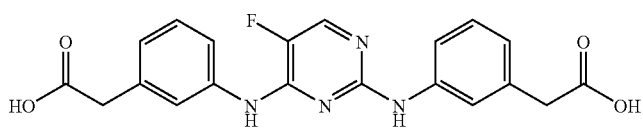
R950218 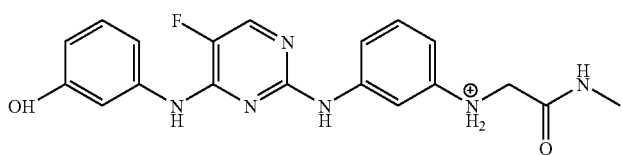

7.3.1100 Synthesis of Intermediates, 2,4-Pyrimidinediamines and 2,4,6-Pyrimidinetriamines According to Schemes VIII and IX A variety of intermediates and 2,4-pyrimidinediamine compounds were synthesized according to Schemes VIII and IX. Scheme VIII is exemplified by the reaction of 2,4,6-trichloropyrimidine with 3-hydroxyaniline to form a mixture of three compounds, which were separated and purified by chromatography. Scheme IX is exemplified by the reaction of 2,4,5,6-tetrachloridepyrimidine with 3,4-ethylenedioxyaniline to form a mixture of three compounds, which were separated and purified by chromatography.

7.3.1101 Reaction of 2,4,6-trichloropyrimidine with 3-hydroxyaniline 4,6-Dichloro-N2-(3-hydroxyphenyl)-2-pyrimidineamine (R926407)

N2,N4-Bis(3-hydroxyphenyl)-6-chloro-2,4-pyrimidinediamine (R926408) and

N2,N4,N6-Tris(3-hydroxyphenyl)-2,4,6-pyrimidinetriamine (R926409)

A mixture of 2,4,6-trichloroaniline (0.183 g, 1 mmol) and 3-hydroxyaniline (0.327 g, 3 mmol) in 5 mL MeOH was heated at 100° C. in a sealed vial for 24 h. The reaction mixture was diluted with $H_2O$, acidified with 2N HCl and extracted with EtOAc (3×50 mL). Upon removal of solvent the residue was purified by chromatography (as well as preparative TLC) to afford three products, mainly the mono-SNAr, 4,6-dichloro-N2-(3-hydroxyphenyl)-2-pyrimidineamine (R926407): $^1$H NMR ($CDCl_3$): δ 7.16 (t, 1H, J=8.1 Hz), 6.78 (m, 2H), 6.64 (dd, 1H, J=1.2 and 8.1 Hz), 6.58 (s, 1H); LCMS: ret. time: 25.08 min.; purity: 99%; MS (m/e): 256 ($M^+$); bis-SNAr product, N2,N4-bis(3-hydroxyphenyl)-6-chloro-2,4-pyrimidinediamine (R926408), $^1$H NMR ($CD_3OD$): δ 7.21 (m, 1H), 7.14-7.03 (m, 5H), 6.50 (m, 1H), 6.44 (m, 1H), 6.16 (s, 1H); LCMS: ret. time: 25.14 min.; purity: 99%; MS (m/e): 329 ($M^+$); and tris-SNAr product, N2,N4,N6-tris(3-hydroxyphenyl)-2,4,6-pyrimidinetriamine (R926409), $^1$H NMR ($CD_3OD$): δ 7.29 (m, 1H), 7.12-7.05 (m, 5H), 7.02 (m, 2H), 6.88 (dd, 2H, J=1.2 and 8.1 Hz), 6.46 (dd, 1H, J=1.5 and 8.1 Hz), 6.41 (dt, 1H); LCMS: ret. time: 20.49 min.; purity: 94%; MS (m/e): 402 ($MH^+$).

7.3.1102 N2,N4-Bis(4-methoxycarbonylmethyleneoxyphenyl)-6-chloro-2,4-pyrimidinediamine (R926411)

In like manner to the reaction of 2,4,6-trichloropyrimidine with 3-hydroxyaniline, the reaction of 2,4,6-trichloropyrimidine with methyl 4-aminophenoxyacetate gave N2,N4-bis(4-methoxycarbonylmethyleneoxyphenyl)-6-chloro-2,4-pyrimidinediamine. $^1$H NMR ($CD_3OD$): δ 7.65 (bs, 1H), 7.40 (bd, 4H), 6.82 (bd, 4H), 6.00 (s, 1H), 6.62 (bs, 4H), 3.78 (bs, 6H); LCMS: ret. time: 29.87 min.; purity: 98%; MS (m/e): 473 ($MH^+$).

7.3.1103 Reaction of 2,4,6-trichloropyrimidine with 3,4-ethylenedioxyaniline 4,6-Dichloro-N2-(3,4-ethylenedioxyphenyl)-2-pyrimidineamine (R926515)

N2,N4-Bis(3,4-ethylenedioxyphenyl)-6-chloro-2,4-pyrimidinediamine (R926245)

N2,N4,N6-Tris(3,4-ethylenedioxyphenyl)-2,4,6-pyrimidinetriamine (R926516)

A mixture of 2,4,6-trichloroaniline (1 mmol) and 3,4-ethylenedioxyaniline (3 mmol) in 5 mL MeOH was heated at 100° C. in a sealed vial for 24 h. The reaction mixture was diluted with $H_2O$, acidified with 2N HCl and extracted with EtOAc (3×50 mL). Upon removal of solvent the residue was purified by chromatography (as well as preparative TLC) to afford three products, mainly the Mono-SNAr product, 4,6-dichloro-N2-(3,4-ethylenedioxyphenyl)-2-pyrimidineamine (R926515). $^1$H NMR ($CD_3OD$): δ 7.05 (s, 1H), 6.83 (m, 2H), 6.45 (bs, 1H), 4.20 (bs, 4H); LCMS: ret. time: 29.75 min.; purity: 96%; MS (m/e): 298 ($M^+$); Bis-SNAr product, N2,N4-bis(3,4-ethylenedioxyphenyl)-6-chloro-2,4-pyrimidinediamine (R926245):
$^1$H NMR ($CDCl_3$): δ 7.23 (d, 1H, J=3 Hz), 6.90-6.70 (m, 6H), 6.02 (s, 1H), 4.26 (bs, 4H), 4.23 (m, 4H); LCMS: ret. time: 31.34 min.; purity: 95%; MS (m/e): 413 ($MH^+$) and Tris-SNAr product, N2,N4,N6-tris(3,4-ethylenedioxyphenyl)-2,4,6-pyrimidinetriamine (R926516)
$^1$H NMR ($CD_3OD$): δ 7.16 (d, 1H, J=3 Hz), 7.05 (bd, 1H), 6.99-6.90 (m, 3H), 6.80-6.70 (m, 4H), 6.03 (s, 1H), 4.22 (s, 4H), 4.20 (s, 8H); LCMS: ret. time: 27.72 min.; purity: 61%; MS (m/e): 528 ($M^+$).

7.3.1104 Reaction of 2,4,6-trichloropyrimidine with ethyl-4-aminophenoxyacetate 4,6-Dichloro-N2-(4-ethoxycarbonylmethyl)-4,6-dichloro-2-pyrimidineamine (R926549)

2,6-Dichloro-N4-(ethoxycarbonylmethyl)-4-pyrimidineamine (R926550)

A mixture of 2,4,6-trichloroaniline (1 mmol) and ethyl 2-aminoacetate (3 mmol) in 5 mL MeOH was heated at 100° C. in a sealed vial for 24 h. The reaction mixture was diluted with $H_2O$, acidified with 2N HCl and extracted with EtOAc (3×50 mL). Upon removal of solvent the residue was purified by chromatography (as well as preparative TLC) to afford three products, mainly the mono-SNAr product, 4,6-dichloro-N2-(4-ethoxycarbonylmethyl)-4,6-dichloro-2-pyrimidineamine (R926549). $^1$H NMR ($CDCl_3$): δ 6.67 (s, 1H), 5.85 (bs, 1H), 4.23 (q, 2H, J=7.2 Hz), 4.19 (s, 2H), 1.29 (t, 3H, J=7.2 Hz); LCMS: ret. time: 26.18 min.; purity: 100%; MS (m/e): 250 ($MH^+$); and Mono-SNAr product, 2,6-dichloro-N4-(ethoxycarbonylmethyl)-4-pyrimidineamine (R926550): $^1$H NMR ($CDCl_3$): d 6.37 (bs, 1H), 4.28 (q, 2H, J=6.9 Hz), 4.19 (bs, 2H), 1.31 (t, 3H, J=7.2 Hz)

7.3.1105 6-Chloro-N2-(4-ethoxycarbonylmethyleneoxyphenyl)-N4-(methoxycarbonylmethyl)-2,4-pyrimidinediamine (R926555)

In like manner to the preparation of 4-[N-(L)-phenylalanine ethyl ester]-N2-(3-hydroxyphenyl)-5-ethoxycarbonyl-2-pyrimidineamine, the reaction of ethyl 4-aminophenoxyacetate with methyl 2-aminoacetate gave 6-chloro-N2-(4-ethoxycarbonylmethyleneoxyphenyl)-N4-(methoxycarbonylmethyl)-2,4-pyrimidinediamine. $^1$H NMR (CD$_3$OD): δ 7.40 (d, 2H, J=8.7 Hz), 6.86 (d, 2H, J=9.3 Hz), 5.97 (s, 1H), 4.64 (s, 2H), 4.26 (q, 2H, J=7.2 Hz), 4.14 (q, 2H, J=6.9 Hz), 4.05 9s, 2H), 1.25 (m, 6H); LCMS: ret. time: 26.21 min.; purity: 93%; MS (m/e): 409 (MH$^+$).

7.3.1106 Reaction of 3,4-ethylenedioxyaniline with 2,4,5,6-tetrachloropyrimidine N4-(3,4-Ethylenedioxyphenyl)-2,5,6-trichloro-4-pyrimidineamine (R926466)

N2,N4-Bis(3,4-ethylenedioxyphenyl)-5,6-dichloro-2,4-pyrimidinediamine (R926467) and N4,N6-Bis(3,4-ethylenedioxyphenyl)-2,5-dichloro-4,6-pyrimidinediamine (R926468)

A mixture of 3,4-ethylenedioxyaniline (0.775 g, 5 mmol) and 2,4,5,6-tetrachloropyrimidine (0.434 g, 2 mmol) in the presence of DIPEA (1.043 mL, 6 mmol) in EtOAc (10 mL) was heated at 80° C. for 3 days. The reaction was diluted with water (50 mL), acidified (2N HCl) and extracted with EtOAc (3×50 mL). The residue obtained after removal of solvent was chromatographed using 5-30% EtOAc/hexanes to obtain three products viz. N4-(3,4-Ethylenedioxyphenyl)-2,5,6-trichloro-4-pyrimidineamine (R926466): $^1$H NMR (CDCl$_3$): δ 7.18 (d, 1H, J=2.7 Hz), 6.92 (dd, 1H, J=2.1 and 8.7 Hz), 6.87 (d, 1H, J=9 Hz); LCMS: ret. time: 33.53 min.; purity: 100%; MS(m/e): 292 (MH$^+$); N2,N4-Bis(3,4-ethylenedioxyphenyl)-5,6-dichloro-2,4-pyrimidinediamine (R926467): $^1$H NMR (CDCl$_3$): δ 7.11 (d, 1H, J=2.4 Hz), 7.06 (d, 1H, J=2.1 Hz), 7.04 (s, IHO, 6.94 (m, 2H), 6.84 (d, 1H, J=8.1 Hz), 6.76 (bd, 2H, J=8.7 Hz), 4.27 (bs, 4H), 4.24 (bs, 1H); LCMS: ret. time: 26.54 min.; purity: 87%; MS(m/e): 364 (MH$^+$); and N4,N6-Bis(3,4-ethylenedioxyphenyl)-2,5-dichloro-4,6-pyrimidinediamine (R926468): $^1$H NMR (CDCl$_3$): δ 7.07 (t, 1H, J=2.4 Hz), 6.99 (s, 2H), 6.83 (dd, 2H, J=2.4 and 8.7 Hz), 6.75 (dd, 2H, J=1.8 and 9 Hz), 4.19 (bs, 4H); LCMS: ret. time: 34.70 min.; purity: 99%; MS(m/e): 365 (MH$^+$).

7.3.1107 Reaction of 2,4,5,6-tetrachloropyrimidine with ethyl-4-aminophenoxyacetate N4-(4-Ethoxycarbonylmethyleneoxyphenyl)-2,5,6-trichloro-4-pyrimidineamine (R926568)

N2,N4-Bis(4-ethoxycarbonylmethyleneoxyphenyl)-5,6-dichloro-2,4-pyrimidinediamine (R926569)

N2,N5-Bis(4-ethoxycarbonylmethyleneoxyphenyl)-2,5-pyrimidinediamine (R926570)

In like manner to the reaction of 2,4,6-trichloropyrimidine with 3,4-ethylenedioxyaniline, the reaction of 2,4,5,6-tetrachloropyrimidine with ethyl 4-aminophenoxyacetate gave a mixture of mono-SNAr product, N4-(4-ethoxycarbonyl methyleneoxyphenyl)-2,5,6-trichloro-4-pyrimidineamine (R926568): $^1$H NMR (CDCl$_3$): δ 7.46 (dd, 2H, J=2.4 and 6.9 Hz), 7.3 (s, 1H), 6.95 (dd, 2H, J=2.4 and 6.9 Hz), 4.63 (s, 2H), 4.28 (q, 2H, J=7.2 Hz), 1.30 (t, 3H, J=7.2 Hz); LCMS: ret. time: 30.62 min.; purity: 99%; MS (m/e): 378 (MH$^+$); Bis-SNAr product, N2,N4-bis((4-ethoxycarbonylmethyleneoxyphenyl)-5,6-dichloro-2,4-pyrimidinediamine (R926569): $^1$H NMR (CDCl$_3$): δ 7.42 (d, 2H, J=9 Hz), 7.35 (d, 2H, J=8.7 Hz), 6.90 (d, 2H, J=9 Hz), 6.83 (d, 2H, J=8.7 Hz), 4.67 (s, 2H), 4.60 (s, 2H), 4.28 (2q, 4H, J=4.8 Hz), 1.31 (2t, 6H, J=6.3 Hz); LCMS: ret. time: 33.09 min.; purity: 85%; MS (m/e): 537 (MH$^+$) and Bis-SNAr product, N2,N5-bis((4-ethoxycarbonylmethyleneoxyphenyl)-2,5-pyrimidinediamine (R926570): $^1$H NMR (CDCl$_3$): δ 7.45 (d, 4H, J=8.7 Hz), 6.92 (d, 4H, J=9 Hz), 6.85 (s, 1H), 4.61 (s, 4H), 4.26 (q, 4H, J=6.9 Hz), 1.30 (t, 6H, J=7.2 Hz); LCMS: ret. time: 31.66 min.; purity: 97%; MS (m/e): 535 (MH$^+$).

7.3.1108 Reaction of 2,4,5,6-tetrachloropyrimidine with tert-Butyl-4-aminophenoxyacetate, N4-(4-tert-Butoxyoxycarbonylmethyleneoxyphenyl)-2,5,6-trichloro-4-pyrimidineamine (R926575), N2,N4-Bis (4-tert-butoxyoxycarbonylmethyleneoxyphenyl)-5,6-dichloro-2,4-pyrimidinediamine (R926576) and N4,N6-Bis(4-tert-butoxyoxycarbonylmethyleneoxyphenyl)-2,5-dichloro-4,6-pyrimidinediamine (R926577)

In like manner to the reaction of 2,4,6-trichloropyrimidine with 3,4-ethylenedioxyaniline, the reaction of 2,4,5,6-tetrachloropyrimidine with tert-butyl-4-aminophenoxyacetate gave a mixture of mono-SNAr product, N4-(4-tert-butoxyoxycarbonylmethyleneoxyphenyl)-2,5,6-trichloro-4-pyrimidineamine (R926575): $^1$H NMR (CDCl$_3$): δ 7.45 (dd, 2H, J=2.4 and 7.2 Hz), 6.93 (dd, 2H, J=2.4 and 7.2 Hz), 4.52 (s, 2H); LCMS: ret. time: 32.56 min.; purity: 100%; MS (m/e): 402 (MH$^+$); Bis-SNAr product, N2,N4-bis(4-tert-butoxyoxycarbonylmethyleneoxyphenyl)-5,6-dichloro-2,4-pyrimidinediamine (R926576): $^1$H NMR (CDCl$_3$): δ 7.42 (d, 2H, J=9 Hz), 7.35 (d, 2H, 9.3 Hz), 7.08 (s, 1H), 6.90 (d, 2H, J=9.3 Hz), 6.82 (d, 2H, J=8.7 Hz), 4.53 (s, 2H), 4.49 (s, 2H), 1.50 (s, 9H), 1.49 (s, 9H); LCMS: ret. time: 36.04 min.; purity: 92%; MS (m/e): 591 (MH$^+$) and Bis-SNAr product, N4,N6-bis(4-tert-butoxyoxycarbonylmethyleneoxyphenyl)-2,5-dichloro-4,6-pyrimidinediamine (R926577): $^1$H NMR (CDCl$_3$): δ 7.43 (d, 4H, J=8.7 Hz), 6.90 (dd, 4H, J=9.3 Hz), 4.50 (s, 2H), 1.49 (s, 18H); LCMS: ret. time: 35.31 min.; purity: 100%; MS (m/e): 591 (MH$^+$).

7.3.1109 Reaction of 2,4,5,6-tetrachloropyrimidine with 3-hydroxyaniline, N4-(3-Hydroxyphenyl)-2,5,6-trichloro-4-pyrimidineamine (R926590), N2,N4-Bis(3-hydroxyphenyl)-5,6-dichloro-2,4-pyrimidinediamine (R926591) and N4,N6-Bis(3-hydroxyphenyl)-2,5-dichloro-4,6-pyrimidinediamine (R926592)

In like manner to the reaction of 2,4,6-trichloropyrimidine with 3,4-ethylenedioxyaniline, the reaction of 2,4,5,6-tetrachloropyrimidine with tert-butyl-4-aminophenoxyacetate gave a mixture of mono-SNAr product, N4-(3-hydroxyphenyl)-2,5,6-trichloro-4-pyrimidineamine (R926590): $^1$H NMR (CDCl$_3$): δ 7.38 (bs, 1H), 7.32 (t, 1H, J=2.4 Hz), 7.22 (s, 1H), 7.01 (dd, 1H, J=1.2 and 8.1 Hz), 6.68 (dd, 1H, J=1.8 and 8.1 Hz); LCMS: ret. time: 26.09 min.; purity: 99%; MS (m/e): 292 (MH$^+$); Bis-SNAr product, N2,N4-bis(3-hydroxyphenyl)-5,6-dichloro-2,4-pyrimidinediamine (R926591): $^1$H NMR (CDCl$_3$): δ 7.45 (s, 1H), 7.30 (t, 1H, J=2.4 Hz), 7.18 (t, 1H, J=2.4 Hz), 7.07 (t, 1H, j=6.6 Hz), 6.98 (t, 1H, J=8.1 Hz), 6.75 (m, 2H), 6.54 (dd, 1H, J=2.4 and 8.1 Hz); LCMS: ret. time: 26.54 min.; purity: 87%; MS (m/e): 364 (MH$^+$); and Bis-SNAr product, N4,N6-bis(3-hydroxyphenyl)-2,5-dichloro-4,6-pyrimidinediamine (R926592): $^1$H NMR (CDCl$_3$): δ 7.34 (t, 2H, j=2.4 Hz), 7.21 (t, 2H, J=7.5 Hz), 6.98 (m, 4H), 6.60 (m, 2H); LCMS: ret. time: 25.38 min.; purity: 73%; MS (m/e): 364 (MH$^+$).

7.3.1110 N2,N4-Bis(3-hydroxyphenyl)-5-chloro-6-thiomethyl-2,4-pyrimidinediamine (R926595)

The reaction of N2 N4-bis(3-hydroxyphenyl)-5,6-dichloro-2,4-pyrimidinediamine (18 mg, 0.05 mmol) with sodium thiomethoxide (10 mg, 0.15 mmol) in absolute EtOH (1 mL) was heated at 80° C. for 3 days, diluted with $H_2O$, extracted with EtOAc (3×10 mL), and solvent was evaporated to obtain the N2 N4-bis(3-hydroxyphenyl)-5-chloro-6-thiomethyl-2,4-pyrimidinediamine (R926595). $^1$H NMR ($CD_3OD$): δ 7.40-7.2 (m, 2H), 7.20-6.80 (m, 3H), 6.67 (m, 1H), 6.45-6.30 (m, 2H), 2.4 (s, 3H); LCMS: ret. time: 27.78 min.; purity: 80%; MS (m/e): 376 ($MH^+$).

7.3.1111 N2,N4-Bis(3,4-ethyelenedioxyphenyl)-5-chloro-6-thiomethyl-2,4-pyrimidinediamine (R926475)

In like manner to the preparation of N2 N4-bis(3-hydroxyphenyl)-5-chloro-6-thiomethyl-2,4-pyrimidinediamine (R926595), the reaction of N2,N4-bis(3,4-ethyelenedioxyphenyl)-5,6-dichloro-2,4-pyrimidinediamine gave N2,N4-bis(3,4-ethyelenedioxyphenyl)-5-chloro-6-thiomethyl-2,4-pyrimidinediamine. $^1$H NMR ($CDCl_3$): δ 7.10 (bd, 2H), 7.00-6.00 (m, 4H), 4.23 (s, 4H), 4.10 (s, 4H), 2.60 (s, 3H); LCMS: ret. time: 36.14 min; purity: 100%; MS (m/e): 459 ($MH^+$).

7.3.1112 6-Chloro N4-(3-hydroxyphenyl)-4-pyrimidineamine (R926530)

The reaction of 4,6-dichloropyrimidine with excess 3-hydroxyaniline in MeOH at 80° C. for 24 h followed by dilution with water and acidification gave the crude product which was purified by silica gel column chromatography to obtain 6-chloro N4-(3-hydroxyphenyl)-4-pyrimidineamine. $^1$H NMR ($CD_3OD$): δ 8.36 (d, 1H, J=1.2 Hz), 7.15 (t, 1H, J=8.4 Hz), 6.93 (dd, 1.2 and 8.1 Hz), 6.74 (d, 1H, J=1.2 Hz), 6.55 (dd, 1.8 and 8.1 Hz); LCMS (m/e): ret. time: 19.75 min.; purity: 99%; MS (m/e): 222 ($MH^+$).

7.3.1113 N2,N4-Bis(3,4-ethylenedioxyphenyl)-5-phenyl-2,4-pyrimidinediamine (R925784)

A mixture of N2,N4-bis(3,4-ethylenedioxyphenyl)-5-bromo-2,4-pyrimidinediamine (20 mg, 0.044 mmol) and phenylboronic acid (6.9 mg, 0.057 mmol) in DME (1 mL) was prepared in a sealed tube and purged with $N_2$. Tetrakis(triphenylphosphine)palladium(O) (0.002 mmol) was added, and the reaction tube sealed and heated at 80° C. overnight. After cooling, the reaction mixture was diluted with EtOAc, washed with IN NaOH and brine, dried ($MgSO_4$), and concentrated. The residue was purified by preparative TLC (40% EtOAc/hexanes) to afford N2,N4-bis(3,4-ethylenedioxyphenyl)-5-phenyl-2,4-pyrimidinediamine. $^1$H NMR ($CD_3OD$): δ 7.77 (s, 1H), 7.52-7.36 (m, 5H), 7.10 (d, 1H, J=2.4 Hz), 7.05 (d, 1H, J=2.4 Hz), 6.93 (dd, 1H, J=2.4 and 8.7 Hz), 6.87 (dd, 1H, J=2.4 and 8.7 Hz), 6.73 (d, 1H, J=8.7 Hz), 6.69 (d, 1H, J=8.7 Hz), 4.23-4.20 (m, 8H); LCMS: ret. time: 25.38 min.; purity: 100%; MS (m/e): 455 ($MH^+$).

7.3.1114 N2,N4-Bis(3,4-ethylenedioxyphenyl)-5-(2-furanyl)-2,4-pyrimidinediamine (R925785)

In a manner similar to the preparation of N2,N4-bis(3,4-ethylenedioxyphenyl)-5-phenyl-2,4-pyrimidinediamine, N2,N4-bis(3,4-ethylenedioxyphenyl)-5-bromo-2,4-pyrimidinediamine and furan-2-boronic acid were reacted to yield N2,N4-bis(3,4-ethylenedioxyphenyl)-5-(2-furanyl)-2,4-pyrimidinediamine. $^1$H NMR ($CD_3OD$): δ 8.13 (s, 1H), 7.61 (d, 1H, J=1.8 Hz), 7.12 (d, 1H, J=2.4 Hz), 7.08 (d, 1H, J=2.4 Hz), 6.93 (td, 2H, J=2.4 and 8.7 Hz), 6.78 (d, 1H, J=8.7 Hz), 6.68 (d, 1H, J=8.7 Hz), 6.58 (d, 1H, J=2.4 Hz), 6.54 (dd, 1H, J=1.8 and 3.6), 4.24 (s, 4H), 4.20 (bs, 4H); LCMS: ret. time: 15.03 min.; purity: 88%; MS (m/e): 445 ($MH^+$).

7.3.1115 N2,N4-Bis(3,4-ethylenedioxyphenyl)-5-(4-chlorophenyl)-2,4-pyrimidinediamine (R925786)

In a manner similar to the preparation of N2,N4-bis(3,4-ethylenedioxyphenyl)-5-phenyl-2,4-pyrimidinediamine, N2,N4-bis(3,4-ethylenedioxyphenyl)-5-bromo-2,4-pyrimidinediamine and 4-chlorophenylboronic acid were reacted to yield N2,N4-bis(3,4-ethylenedioxyphenyl)-5-(4-chlorophenyl)-2,4-pyrimidinediamine. $^1$H NMR (DMSO-d6): δ 8.99 (bs, 1H), 8.05 (bs, 1H), 7.85 (s, 1H), 7.50-7.42 (m, 4H), 7.23 (bs, 1H), 7.10 (dd, 1H, J=2.4 and 8.7 Hz), 7.06 (t, 1H, J=2.4 Hz), 7.00-6.94 (m, 1H), 6.73 (d, 1H, J=8.7 Hz), 6.63 (d, 1H, J=8.7 Hz); LCMS: ret. time: 16.12 min.; purity: 86%; MS (m/e): 490 ($MH^+$).

7.3.1116 N2,N4-Bis(3,4-ethylenedioxyphenyl)-5-(3-chlorophenyl)-2,4-pyrimidinediamine (R925787)

In a manner similar to the preparation of N2,N4-bis(3,4-ethylenedioxyphenyl)-5-phenyl-2,4-pyrimidinediamine, N2,N4-bis(3,4-ethylenedioxyphenyl)-5-bromo-2,4-pyrimidinediamine and 3-chlorophenylboronic acid were reacted to yield N2,N4-bis(3,4-ethylenedioxyphenyl)-5-(3-chlorophenyl)-2,4-pyrimidinediamine. $^1$H NMR ($CD_3OD$): δ 7.77 (s, 1H), 7.45-7.41 (m, 2H), 7.38-7.33 (m, 2H), 7.09 (d, 1H, J=2.4 Hz), 7.01 (d, 1H, J=2.4 Hz), 6.92 (dd, 1H, J=2.4 and 9.0 Hz), 6.86 (dd, 1H, J=2.4 and 8.7 Hz), 6.74 (d, 1H, J=8.7 Hz), 6.67 (d, 1H, J=8.7 Hz), 4.21 (s, 4H), 4.19 (s, 4H); LCMS: ret. time: 27.18 min.; purity: 95%; MS (m/e): 490 ($MH^+$).

7.3.1117 N2,N4-Bis(3,4-ethylenedioxyphenyl)-5-(4-methoxycarbonylphenyl)-2,4-pyrimidinediamine (R925813)

In a manner similar to the preparation of N2,N4-bis(3,4-ethylenedioxyphenyl)-5-phenyl-2,4-pyrimidinediamine, N2,N4-bis(3,4-ethylenedioxyphenyl)-5-bromo-2,4-pyrimidinediamine and (4-methoxycarbonylphenyl)boronic acid were reacted to yield N2,N4-bis(3,4-ethylenedioxyphenyl)-5-(4-methoxycarbonylphenyl)-2,4-pyrimidinediamine. LCMS: ret. time: 26.35 min.; purity: 90%; MS (m/e): 514 ($MH^+$).

7.3.1118 N2,N4-Bis(3,4-ethylenedioxyphenyl)-5-(4-hydroxyphenyl)-2,4-pyrimidinediamine (R925816)

In a manner similar to the preparation of N2,N4-bis(3,4-ethylenedioxyphenyl)-5-phenyl-2,4-pyrimidinediamine, N2,N4-bis(3,4-ethylenedioxyphenyl)-5-bromo-2,4-pyrimidinediamine and 4-hydroxyphenylboronic acid were reacted to yield N2,N4-bis(3,4-ethylenedioxyphenyl)-5-(4-hydroxyphenyl)-2,4-pyrimidinediamine. $^1$H NMR (DMSO-d6): δ 9.53 (s, 1H), 8.92 (s, 1H), 7.78 (s, 1H), 7.74 (bs, 1H), 7.24 (bs, 1H), 7.22 (d, 2H, J=8.7 Hz), 7.12-7.09 (m, 2H), 6.97 (dt, 1H, J=2.4 and 8.7 Hz), 6.83 (d, 2H, J=8.4 Hz), 6.72 (d, 1H, J=8.1 Hz), 6.62 (d, 1H, J=9.0 Hz), 4.19 (s, 4H), 4.17 (s, 4H); LCMS: ret. time: 23.51 min.; purity: 95%; MS (m/e): 471 ($MH^+$).

7.3.1119 N2,N4-Bis(3-hydroxyphenyl)-5-phenyl-2,4-pyrimidinediamine (R925783)

In a manner similar to the preparation of N2,N4-bis(3,4-ethylenedioxyphenyl)-5-phenyl-2,4-pyrimidinediamine, N2,N4-bis(3-hydroxyphenyl)-5-bromo-2,4-pyrimidinediamine and phenylboronic acid were reacted to yield N2,N4-bis(3-hydroxyphenyl)-5-phenyl-2,4-pyrimidinediamine. $^1$H NMR (CD$_3$OD): δ 7.85 (bs, 1H), 7.54-7.38 (m, 5H), 7.13-7.11 (m, 2H), 7.10-7.04 (m, 3H), 6.97 (dt, 1H, J=1.8 and 8.1 Hz), 6.54 (ddd, 1H, J=1.9, 2.4, and 7.2 Hz), 6.44 (dt, 1H, J=1.8 and 6.0 Hz); LCMS: ret. time: 20.66 min.; purity: 96%; MS (m/e): 371 (MH$^+$).

7.3.1120 N2,N4-Bis(3-hydroxyphenyl)-5-(3,4-methylenedioxyphenyl)-2,4-pyrimidinediamine (R925788)

In a manner similar to the preparation of N2,N4-bis(3,4-ethylenedioxyphenyl)-5-phenyl-2,4-pyrimidinediamine, N2,N4-bis(3-hydroxyphenyl)-5-bromo-2,4-pyrimidinediamine and 3,4-methylenedioxyphenylboronic acid were reacted to yield N2,N4-bis(3-hydroxyphenyl)-5-(3,4-methylenedioxyphenyl)-2,4-pyrimidinediamine. $^1$H NMR (CD$_3$OD): δ 7.82 (s, 1H), 7.13-7.06 (m, 3H), 7.04-7.01 (m, 2H), 6.97 (dt, 1H, J=1.2 and 8.7 Hz), 6.94-6.88 (m, 3H), 6.52 (ddd, 1H, J=1.2, 2.4, and 6.9 Hz), 6.42 (dt, 1H, J=2.1 and 7.5 Hz), 6.01 (s, 2H); LCMS: ret. time: 21.11 min.; purity: 99%; MS (m/e): 415 (MH$^+$).

7.3.1121 N2,N4-Bis(3,4-ethylenedioxyphenyl)-6-phenyl-2,4-pyrimidinediamine (R925811)

In a manner similar to the preparation of N2,N4-bis(3,4-ethylenedioxyphenyl)-5-phenyl-2,4-pyrimidinediamine, N2,N4-bis(3,4-ethylenedioxyphenyl)-6-chloro-2,4-pyrimidinediamine and phenylboronic acid were reacted to yield N2,N4-bis(3,4-ethylenedioxyphenyl)-6-phenyl-2,4-pyrimidinediamine. $^1$H NMR (CD$_3$OD): δ 7.97-7.92 (m, 2H), 7.46-7.43 (m, 3H), 7.35 (d, 1H, J=2.7 Hz), 7.19 (d, 1H, J=2.4 Hz), 7.07-7.00 (m, 2H), 6.75 (t, 2H, J=8.7 Hz), 6.50 (s, 1H), 4.24-4.19 (m, 8H); LCMS: ret. time: 26.68 min.; purity: 97%; MS (m/e): 455 (MH$^+$).

7.3.1122 N2,N4-Bis(3-hydroxyphenyl)-6-phenyl-2,4-pyrimidinediamine (R925812)

In a manner similar to the preparation of N2,N4-bis(3,4-ethylenedioxyphenyl)-5-phenyl-2,4-pyrimidinediamine, N2,N4-bis(3-hydroxyphenyl)-6-chloro-2,4-pyrimidinediamine and phenylboronic acid were reacted to yield N2,N4-bis(3-hydroxyphenyl)-6-phenyl-2,4-pyrimidinediamine. LCMS: ret. time: 22.13 min.; purity: 90%; MS (m/e): 371 (MH$^+$)

7.3.1123 N2-(3-Aminocarbonylmethyleneoxyphenyl)-N4-(3,4-ethylenedioxyphenyl)-5-fluoro-2,4-pyrimidinediamine (R926747)

The hydrolysis of N2-(3-cyanomethyleneoxyphenyl)-N4-(3,4-ethylenedioxyphenyl)-5-fluoro-2,4-pyrimidinediamine gave N2-(3-aminocarbonylmethyleneoxyphenyl)-N4-(3,4-ethylenedioxyphenyl)-5-fluoro-2,4-pyrimidinediamine. LCMS: ret. time: 16.76 min.; purity: 93%; MS (m/e): 412 (MH$^+$).

7.3.1124 N2,N4-Bis(3-sodiumphenoxy)-5-fluoro-2,4-pyrimidinediamine (R926461)

The reaction of N2,N4-bis(3-hydroxyphenyl)-5-fluoro-2,4-pyrimidinediamine with 2 equivalents of sodium methoxide in methanol gave the requisite compound, N2,N4-bis(3-sodiumphenoxy)-5-fluoro-2,4-pyrimidinediamine. $^1$H NMR (D$_2$O): δ 7.65 (bd, 1H), 7.00-6.90 (m, 2H), 6.71 (m, 2H), 6.55 (dd, 1H, J=1.2 and 6.3 Hz), 6.31 (bd, 1H, J=8.1 Hz), 6.23 (bd, 1H, J=8.7 Hz); $^{19}$F NMR (D$_2$O): −47016; LCMS: ret. time: 15.68 min.; purity: 99%; MS (m/e): 313 (MH$^+$)

7.3.1125 5-Fluoro-N4-(3-hydroxyphenyl)-N2-[4-(1,4,5,6-tetrahydro-2-pyrimidyl)methyleneoxyphenyl]-2,4-pyrimidinediamine (R945169)

The reaction of N2-(4-cyanomethyleneoxyphenyl)-5-fluoro-N4-(3-hydroxyphenyl)-2,4-pyrimidinediamine and HCl in ethanol, followed by 1,3-diaminopropane in methanol at 100° C. gave 5-fluoro-N4-(3-hydroxyphenyl)-N2-[4-(1,4,5,6-tetrahydro-2-pyrimidyl)methyleneoxyphenyl]-2,4-pyrimidinediamine. $^1$H NMR (CD$_3$OD): δ 2.05 (p, J=5.7 Hz, 2H), 3.49 (t, J=5.7 Hz, 4H), 4.84 (s, 2H), 6.56 (ddd, J=2.1, 3.6 and 5.4 Hz, 1H), 6.93 (d, J=9.0 Hz, 2H), 7.11-7.13 (m, 2H), 7.21 (m, 1H), 7.55 (d, J=9.0 Hz, 2H), 7.87 (d, J=3.9 Hz, 1H); $^{19}$F NMR (282 MHz, CD$_3$OD): 6-168.66; LCMS: ret. time: 12.77 min.; purity: 97.61%; MS (m/e): 409.08 (MH$^+$).

7.3.1126 5-Fluoro-N4-(3-hydroxyphenyl)-N2-[4-[(4,4-dimethyl-3-oxazolin-2-yl)methyleneoxy]phenyl]-2,4-pyrimidinediamine (R926702)

N2-[4-(cyanomethyleneoxy)phenyl]-5-fluoro-N4-(3-hydroxyphenyl)-2,4-pyrimidinediamine and 2-amino-2-methylpropanol were reacted to yield 5-fluoro-N4-(3-hydroxyphenyl)-N2-[4-[(4,4-dimethyl-3-oxazolin-2-yl)methyleneoxy]phenyl]-2,4-pyrimidinediamine. $^1$H NMR (CDCl$_3$): δ 7.87 (d, 1H, J=3.6 Hz), 7.37 (t, 1H, J=2.4 Hz), 7.34 (d, 2H, J=9.0 Hz), 7.14 (t, 1H, J=8.1 Hz), 6.94 (bs, 1H), 6.90 (d, 2H, J=9.0 Hz), 6.78 (dd, 1H, J=2.4 and 8.4 Hz), 6.74 (d, 1H, J=3.0 Hz), 6.62 (ddd, 1H, J=1.2, 2.4, and 8.4 Hz), 4.67 (s, 2H), 4.02 (s, 2H), 1.25 (s, 6H); $^{19}$F NMR (CDCl$_3$): −47399; LCMS: ret. time: 13.82 min.; purity: 98%; MS (m/e): 425 (M+2H).

7.3.1127 N4-(3-Carboxy-4-hydroxyphenyl)-5-fluoro-N2-[3-ethoxycarbonylmethyleneoxyphenyl]-2,4-pyrimidinediamine (R950290)

A mixture of equimolar amounts of 2-chloro-N4-(3-carboxy-4-hydroxyphenyl)-5-fluoro-4-aminopyridine and 3-ethoxycarbonylmethyleneoxyaniline in MeOH in a pressure tube at 110° C. for 24 h or in EtOH using microwave at 175° C. for 10-20 min followed by aqueous work up gave N4-(3-carboxy-4-hydroxyphenyl)-5-fluoro-N2-[3-ethoxycarbonylmethyleneoxyphenyl]-2,4-pyrimidinediamine. LCMS: purity: 97.8%; MS (m/e): 443.20 (MH$^+$).

7.3.1128 N4-(3-Carboxy-4-hydroxyphenyl)-5-fluoro-N2-[3-carboxymethyleneoxyphenyl]-2,4-pyrimidinediamine (R950291)

The reaction of N4-(3-carboxy-4-hydroxyphenyl)-5-fluoro-N2-[3-ethoxycarbonylmethyleneoxyphenyl]-2,4-pyrimidinediamine (0.1 g) and LiOH (10 equivalents) in MeOH:water (1:1, v/v) for 1 h at room temperature followed by treatment with aqueous HCl gave the solid. The resulting solid was filtered, washed with water and dried to give N4-(3-carboxy-4-hydroxyphenyl)-5-fluoro-N2-[3-carboxymethyleneoxyphenyl]-2,4-pyrimidinediamine. LCMS: purity: 91.5%; MS (m/e): 415.16 (MH$^+$).

7.3.1129 N4-(3-Methoxycarbonyl-4-hydroxyphenyl)-5-fluoro-N2-[3-ethoxycarbonyl methyleneoxyphenyl]-2,4-pyrimidinediamine (R950293)

A solution of N4-(3-carboxy-4-hydroxyphenyl)-5-fluoro-N2-[3-ethoxycarbonylmethyleneoxyphenyl]-2,4-pyrimidinediamine in dry MeOH was treated with a 4 M solution of HCl in dioxane. The mixture was stirred for 1 hour at 22° C., concentrated to dryness and purified by flash chromatography on silica gel to give N4-(3-methoxycarbonyl-4-hydroxyphenyl)-5-fluoro-N2-[3-ethoxycarbonylmethyleneoxyphenyl]-2,4-pyrimidinediamine as a white solid. $^1$H NMR (DMSO): δ 10.30 (s, 1H), 10.13 (s, 1H), 8.22 (d, 1H, J=5.3 Hz), 7.96 (d, 1H, J=2.4 Hz), 7.71 (dd, J=2.4, 9.0 Hz, 1H), 6.95-7.11 (m, 4H), 6.51 (m, 1H), 4.56 (s, 2H), 4.09 (q, J=7.2 Hz, 2H), 3.72 (s, 3H), 1.14 (j, J=7.2 Hz, 3H); LCMS: purity: 96.8%; MS (m/e): 457.25 (MH$^+$).

7.3.1130 N4-(4-Methoxy-3,4-dihydro-2H-1-benzopyran-6-yl)-5-fluoro-N2-[3-ethoxycarbonylmethyleneoxyphenyl]-2,4-pyrimidinediamine (R950294)

A mixture of equimolar amounts of 2-chloro-N4-(4-methoxy-3,4-dihydro-2H-1-benzopyran-6-yl)-5-fluoro-4-aminopyridine and 3-ethoxycarbonylmethyleneoxyaniline in EtOH using microwave at 175° C. for 10-20 min followed by aqueous work up gave N4-(4-methoxy-3,4-dihydro-2H-1-benzopyran-6-yl)-5-fluoro-N2-[3-ethoxycarbonylmethyleneoxyphenyl]-2,4-pyrimidinediamine. LCMS: purity: 92.1%; MS (m/e): 469.26 (MH$^+$).

7.3.1131 N4-(4-Methoxy-3,4-dihydro-2H-1-benzopyran-6-yl)-5-fluoro-N2-[3-methoxycarbonylmethyleneoxyphenyl]-2,4-pyrimidinediamine (R950295)

A mixture of equimolar amounts of 2-chloro-N4-(4-methoxy-3,4-dihydro-2H-1-benzopyran-6-yl)-5-fluoro-4-aminopyridine and 3-ethoxycarbonylmethyleneoxyaniline in MeOH in a pressure tube at 110° C. for 24 h followed by aqueous work up gave N4-(4-methoxy-3,4-dihydro-2H-1-benzopyran-6-yl)-5-fluoro-N2-[3-methoxycarbonylmethyleneoxyphenyl]-2,4-pyrimidinediamine. LCMS: purity: 87.6%; MS (m/e): 455.26 (MH$^+$).

7.3.1132 N4-(4-Ethoxy-3,4-dihydro-2H-1-benzopyran-6-yl)-5-fluoro-N2-[3-(N-methylamino) carbonylmethyleneoxyphenyl]-2,4-pyrimidinediamine (R950296)

A solution of N4-(4-ethoxy-3,4-dihydro-2H-1-benzopyran-6-yl)-5-fluoro-N2-[3-ethoxycarbonylmethyleneoxyphenyl]-2,4-pyrimidinediamine in EtOH was treated with the HCl salt of methylamine. The mixture was stirred for 4 hours at 100° C., concentrated to dryness and purified by flash chromatography on silica gel to give N4-(4-ethoxy-3,4-dihydro-2H-1-benzopyran-6-yl)-5-fluoro-N2-[3-(N-methylamino)carbonylmethyleneoxyphenyl]-2,4-pyrimidinediamine as a white solid. LCMS: purity: 87.4%; MS (m/e): 468.29 (MH$^+$).

7.3.1133 N4-(4-Carboxyethyleneoxyphenyl)-5-fluoro-N2-[3-(N-methylamino)carbonyl methyleneoxyphenyl]-2,4-pyrimidinediamine (R950344)

A mixture of equimolar amounts of 2-chloro-N4-(4-carboxyethyleneoxyphenyl)-5-fluoro-4-aminopyridine and 3-(N-methylamino)carbonylmethyleneoxyaniline in MeOH in a pressure tube at 110° C. for 24 h or in EtOH using microwave at 175° C. for 10-20 min followed by aqueous work up gave N4-(4-carboxyethyleneoxyphenyl)-5-fluoro-N2-[3-(N-methylamino)carbonylmethyleneoxyphenyl]-2,4-pyrimidinediamine. LCMS: purity: 97.8%; MS (m/e): 456.32 (MH$^+$).

7.3.1134 N4-(2,3-Dihydro-4-benzypyranon-6-yl)-5-fluoro-N2-[3-(N-methylamino)carbonyl methyleneoxyphenyl]-2,4-pyrimidinediamine (R950345)

A solution of N4-(4-Methoxycarbonylethyleneoxyphenyl)-5-fluoro-N2-[3-(N-methylamino)carbonylmethyleneoxyphenyl]-2,4-pyrimidinediamine in TfOH was heated for 2 hours at 100° C. Aqueous work up followed by flash chromatography on silica gel gave N4-(2,3-dihydro-4-benzypyranon-6-yl)-5-fluoro-N2-[3-(N-methylamino)carbonylmethyleneoxyphenyl]-2,4-pyrimidinediamine as a white solid. LCMS: purity: 92.2%; MS (m/e): 435.95 (MH$^+$).

7.3.1135 N4-(4-Methoxycarbonylethyleneoxyphenyl)-5-fluoro-N2-[3-(N-methylamino)carbonylmethyleneoxyphenyl]-2,4-pyrimidinediamine (R950346)

A solution of N4-(4-carboxyethyleneoxyphenyl)-5-fluoro-N2-[3-(N-methylamino)carbonylmethyleneoxyphenyl]-2,4-pyrimidinediamine in dry MeOH was treated with a 4 M solution of HCl in dioxane. The mixture was stirred for 1 hour at 22° C., concentrated to dryness and purified by flash chromatography on silica gel to give N4-(4-methoxycarbonylethyleneoxyphenyl)-5-fluoro-N2-[3-(N-methylamino)carbonylmethyleneoxyphenyl]-2,4-pyrimidinediamine as a white solid. LCMS: purity: 85.2%; MS (m/e): 468.01 (MH$^+$).

7.3.1136 N4-(4-Hydroxyphenyl)-5-fluoro-N2-[3-(N-methylamino)carbonylmethyleneoxyphenyl]-2,4-pyrimidinediamine (R950347)

The reaction of N4-(4-methoxycarbonylethyleneoxyphenyl)-5-fluoro-N2-[3-(N-methylamino)carbonylmethyleneoxyphenyl]-2,4-pyrimidinediamine and LiOH (10 equivalents) in MeOH:water (1:1, v/v) for 1 h at room temperature followed by treatment with aqueous HCl gave a pale yellow solid. The resulting solid was filtered, washed with water and dried to give N4-(4-hydroxyphenyl)-5-fluoro-N2-[3-(N-methylamino)carbonylmethyleneoxyphenyl]-2,4-pyrimidinediamine. LCMS: purity: 94.7%; MS (m/e): 382.03 (MH$^+$).

7.3.1137 N4-(2,3-Dihydro-4-oxime-benzypyran-6-yl)-5-fluoro-N2-[3-(N-methylamino)carbonylmethyleneoxyphenyl]-2,4-pyrimidinediamine (R950348)

A mixture N4-(2,3-dihydro-4-benzypyranon-6-yl)-5-fluoro-N2-[3-(N-methylamino)carbonylmethyleneoxyphenyl]-2,4-pyrimidinediamine and hydroxylamine (20 equivalents) in pyridine at 22° C. for 16 hours followed by aqueous work up gave N4-(2,3-dihydro-4-oxime-benzypyran-6-yl)-5-fluoro-N2-[3-(N-methylamino)carbonylmethyleneox-

7.3.1138 N4-(4-Hydroxy-3,4-dihydro-2H-1-benzopyran-6-yl)-5-fluoro-N2-[3-(N-methylamino)carbonylmethyleneoxyphenyl]-2,4-pyrimidinediamine (R950349)

A solution of N4-(2,3-dihydro-4-benzypyranon-6-yl)-5-fluoro-N2-[3-(N-methylamino)carbonylmethyleneoxyphenyl]-2,4-pyrimidinediamine in dry MeOH was treated with a sodiumcyanoborohydride. The mixture was stirred for 1 hour at 22° C., concentrated to dryness and purified by flash chromatography on silica gel to give N4-(4-Hydroxy-3,4-dihydro-2H-1-benzopyran-6-yl)-5-fluoro-N2-[3-(N-methylamino)carbonylmethyleneoxyphenyl]-2,4-pyrimidinediamine as a white solid. $^1$H NMR (DMSO): δ 9.19 (s, 1H), 9.09 (s, 1H), 8.03 (d, 1H, J=2.4 Hz), 7.28-7.93 (m, 5H), 7.07 (t, 1H, J=7.2 Hz), 6.71 (d, 1H, J=7.2 Hz), 6.44 (dd, 1H, J=2.6, 7.2 Hz), 5.31 (d, 1H, J=5.1 Hz), 4.14-4.59 (m, 3H), 4.30 (s, 2H), 2.63 (d, 3H, J=4.8 Hz), 1.82-2.03 (m, 2H); LCMS: purity: 93.3%; MS (m/e): 440.15 (MH$^+$).

7.3.1139 N4-(2,3-Dihydro-4-O-methyloxime-benzypyran-6-yl)-5-fluoro-N2-[3-(N-methylamino)carbonylmethyleneoxyphenyl]-2,4-pyrimidinediamine (R950356)

A mixture N4-(2,3-dihydro-4-benzypyranon-6-yl)-5-fluoro-N2-[3-(N-methylamino)carbonylmethyleneoxyphenyl]-2,4-pyrimidinediamine and methoxyamine (20 equivalents) in pyridine at 22° C. for 16 hours followed by aqueous work up gave N4-(2,3-dihydro-4-oxime-benzypyran-6-yl)-5-fluoro-N2-[3-(N-methylamino)carbonylmethyleneoxyphenyl]-2,4-pyrimidinediamine as a white solid. LCMS: purity: 85.5%; MS (m/e): 465.10 (MH$^+$).

7.3.1140 N4-(4-Amino-3,4-dihydro-2H-1-benzopyran-6-yl)-5-fluoro-N2-[3-(N-methylamino)carbonylmethyleneoxyphenyl]-2,4-pyrimidinediamine (R950368)

A mixture N4-(4-azido-3,4-dihydro-2H-1-benzopyran-6-yl)-5-fluoro-N2-[3-(N-methylamino)carbonylmethyleneoxyphenyl]-2,4-pyrimidinediamine and Pd/C (10%) in MeOH was hydrogenated at 22° C. for 6 hours (40 psi). The mixture was filtered and concentrated to dryness to give N4-(4-amino-3,4-dihydro-2H-1-benzopyran-6-yl)-5-fluoro-N2-[3-(N-methylamino)carbonylmethyleneoxyphenyl]-2,4-pyrimidinediamine as a white solid. $^1$H NMR (DMSO): δ 9.60 (s, 1H), 9.46 (s, 1H), 8.73 (bs, 3H), 8.00-8.10 (m, 3H), 7.47 (s, 1H), 7.42 (m, 1H), 7.29 (d, 1H, J=7.2 Hz), 7.11 (t, 1H, J=7.2 Hz), 6.82 (d, 1H, J 7.0 Hz), 6.46 (m, 1H), 4.23-4.46 (m, 3H), 4.31 (s, 3H), 2.63 (d, 3H, J=4.8 Hz), 2.09-2.29 (m, 2H); LCMS: purity: 97.6%; MS (m/e): 438.98 (MH$^+$).

7.3.1141 N4-(3-Methylcarbonylphenyl)-5-fluoro-N2-[3-(N-methylamino)carbonylmethyleneoxyphenyl]-2,4-pyrimidinediamine (R950371)

A mixture of equimolar amounts of 2-chloro-N4-(3-methylcarbonylphenyl)-5-fluoro-4-aminopyridine and 3-(N-methylamino)carbonylmethyleneoxyaniline in MeOH in a pressure tube at 110° C. for 24 h or in EtOH using microwave at 175° C. for 10-20 min followed by aqueous work up gave N4-(3-methylcarbonylphenyl)-5-fluoro-N2-[3-(N-methylamino)carbonylmethyleneoxyphenyl]-2,4-pyrimidinediamine as a white solid. $^1$H NMR (DMSO): δ 10.16 (s, 1H), 9.82 (s, 1H), 8.24 (d, 1H, J=2.4 Hz), 8.15 (s, 1H), 7.91-8.07 (m, 2H), 7.70 (d, 1H, J=7.0 Hz), 7.49 (t, 1H, J=7.2 Hz), 7.08-7.21 (m, 3H), 6.56 (d, 1H, J=7.2 Hz), 4.30 (s, 3H), 2.62 (d, 3H, J=4.8 Hz), 2.48 (s, 3H); LCMS: purity: 93.8%; MS (m/e): 410.50 (MH$^+$).

7.3.1142 N4-(3-Phenylcarbonylphenyl)-5-fluoro-N2-[3-(N-methylamino)carbonylmethyleneoxyphenyl]-2,4-pyrimidinediamine (R950372)

A mixture of equimolar amounts of 2-chloro-N4-(3-phenylcarbonylphenyl)-5-fluoro-4-aminopyridine and 3-(N-methylamino)carbonylmethyleneoxyaniline in MeOH in a pressure tube at 110° C. for 24 h or in EtOH using microwave at 175° C. for 10-20 min followed by aqueous work up gave N4-(3-phenylcarbonylphenyl)-5-fluoro-N2-[3-(N-methylamino)carbonylmethyleneoxyphenyl]-2,4-pyrimidinediamine as a white solid. LCMS: purity: 86.0%; MS (m/e): 472.50 (MH$^+$).

7.3.1143 N4-(3-Methylcarbonyloximephenyl)-5-fluoro-N2-[3-(N-methylamino)carbonylmethyleneoxyphenyl]-2,4-pyrimidinediamine (R950373)

A mixture N4-(3-methylcarbonylphenyl)-5-fluoro-N2-[3-(N-methylamino)carbonylmethyleneoxyphenyl]-2,4-pyrimidinediamine and hydroxylamine (20 equivalents) in pyridine at 22° C. for 16 hours followed by aqueous work up gave N4-(3-methylcarbonyloximephenyl)-5-fluoro-N2-[3-(N-methylamino)carbonylmethyleneoxyphenyl]-2,4-pyrimidinediamine as a white solid. $^1$H NMR (DMSO): δ 11.21 (s, 1H), 10.11 (s, 1H), 9.85 (s, 1H), 6.54-8.23 (m, 9H), 4.32 (s, 2H), 2.63 (d, J=7.0 Hz, 3H), 2.47 (s, 3H); LCMS: purity: 92.4%; MS (m/e): 425.28 (MH$^+$).

7.3.1144 N4-(3-Phenylcarbonyloximephenyl)-5-fluoro-N2-[3-(N-methylamino)carbonylmethyleneoxyphenyl]-2,4-pyrimidinediamine (R950374)

A mixture N4-(3-phenylcarbonylphenyl)-5-fluoro-N2-[3-(N-methylamino)carbonylmethyleneoxyphenyl]-2,4-pyrimidinediamine and hydroxylamine (20 equivalents) in pyridine at 22° C. for 16 hours followed by aqueous work up gave N4-(3-phenylcarbonyloximephenyl)-5-fluoro-N2-[3-(N-methylamino)carbonylmethyleneoxyphenyl]-2,4-pyrimidinediamine as a white solid. $^1$H NMR (DMSO): δ 11.63 (s, 1H), 10.30 (s, 1H), 9.85 (s, 1H), 6.44-8.43 (m, 14H), 4.42 (s, 2H), 2.63 (d, J=7.0 Hz, 3H); LCMS: purity: 92.4%; MS (m/e): 487.31 (MH$^+$).

7.3.1145 N2,N4-Bis(3-methylcarbonylphenyl)-5-fluoro-2,4-pyrimidinediamine (R950376)

A mixture of 2,4-dichloro-5-fluoropyridine and three equivalents of 3-acetophenone in MeOH in a pressure tube at 110° C. for 24 h or in EtOH using microwave at 175° C. for 10-20 min followed by aqueous work up gave N2,N4-bis(3-methylcarbonylphenyl)-5-fluoro-2,4-pyrimidinediamine as a white solid. LCMS: purity: 93.1%; MS (m/e): 365.19 (MH$^+$).

7.3.1146 N2,N4-Bis(3-phenylcarbonylphenyl)-5-fluoro-2,4-pyrimidinediamine (R950377)

A mixture of 2,4-dichloro-5-fluoropyridine and three equivalents of 3-benzophenone in MeOH in a pressure tube at 110° C. for 24 h or in EtOH using microwave at 175° C. for 10-20 min followed by aqueous work up gave N2,N4-bis(3-phenylcarbonylphenyl)-5-fluoro-2,4-pyrimidinediamine as a white solid. LCMS: purity: 95.7%; MS (m/e): 489.29 (MH$^+$).

7.3.1147 N2,N4-Bis(2,3-dihydro-4-benzypyranon-6-yl)-5-fluoro-2,4-pyrimidinediamine (R950378)

A solution of N2,N4-bis(4-methoxycarbonylethyleneoxyphenyl)-5-fluoro-2,4-pyrimidinediamine in TfOH was heated for 2 hours at 100° C. Aqueous work up followed by flash chromatography on silica gel gave N2,N4-bis(2,3-dihydro-4-benzypyranon-6-yl)-5-fluoro-2,4-pyrimidinediamine as a white solid. $^1$H NMR (DMSO): δ 9.36 (s, 1H), 9.14 (s, 1H), 8.06 (d, 1H, J=2.4 Hz), 7.72-7.99 (m, 3H), 6.97 (d, J=7.2 Hz, 1H), 6.87 (d, J=7.2 Hz, 1H), 4.42-4.52 (m, 4H), 2.70-2.78 (m, 4H); LCMS: purity: 94.3%; MS (m/e): 484.50 (MH$^+$).

7.3.1148 N2,N4-Bis(3-methylcarbonyloximephenyl)-5-fluoro-2,4-pyrimidinediamine (R950379)

A mixture of N2,N4-bis(3-methylcarbonylphenyl)-5-fluoro-2,4-pyrimidinediamine and hydroxylamine (20 equivalents) in pyridine at 22° C. for 16 hours followed by aqueous work up gave N2,N4-bis(3-methylcarbonyloximephenyl)-5-fluoro-2,4-pyrimidinediamine as a white solid. $^1$H NMR (DMSO): δ 11.21 (s, 1H), 10.11 (s, 1H), 9.85 (s, 1H), 6.54-8.23 (m, 9H), 4.32 (s, 2H), 2.63 (d, J=7.0 Hz, 3H), 2.47 (s, 3H); LCMS: purity: 92.1%; MS (m/e): 393.06 (M-H$^-$).

7.3.1149 N2,N4-Bis(3-phenylcarbonyloximephenyl)-5-fluoro-2,4-pyrimidinediamine (R950380)

A mixture of N2,N4-bis(3-phenylcarbonylphenyl)-5-fluoro-2,4-pyrimidinediamine and hydroxylamine (20 equivalents) in pyridine at 22° C. for 16 hours followed by aqueous work up gave N2,N4-bis(3-phenylcarbonyloximephenyl)-5-fluoro-2,4-pyrimidinediamine as a white solid. LCMS: purity: 93.3%; MS (m/e): 486.05 (M-H$^-$).

7.3.1150 N2,N4-Bis(2,3-dihydro-4-oxime-benzypyran-6-yl)-5-fluoro-2,4-pyrimidinediamine (R950381)

A mixture of N2,N4-bis(2,3-dihydro-4-benzypyranon-6-yl)-5-fluoro-2,4-pyrimidinediamine and hydroxylamine (20 equivalents) in pyridine at 22° C. for 16 hours followed by aqueous work up gave N2,N4-bis(2,3-dihydro-4-oxime-benzypyran-6-yl)-5-fluoro-2,4-pyrimidinediamine as a white solid. LCMS: purity: 98.1%; MS (m/e): 449.03 (M-H$^-$).

7.3.1151 N4-(4-Acetyloxy-3,4-dihydro-2H-1-benzopyran-6-yl)-5-fluoro-N2-[3-(N-methylamino)carbonyl methyleneoxyphenyl]-2,4-pyrimidinediamine (R950382)

A solution of N4-(4-hydroxy-3,4-dihydro-2H-1-benzopyran-6-yl)-5-fluoro-N2-[3-(N-methylamino)carbonylmethyleneoxyphenyl]-2,4-pyrimidinediamine in pyridine was treated with acetic anhydride at 22° C. for 16 hours. Aqueous work up gave N4-(4-acetyloxy-3,4-dihydro-2H-1-benzopyran-6-yl)-5-fluoro-N2-[3-(N-methylamino)carbonylmethyleneoxyphenyl]-2,4-pyrimidinediamine as a white solid. $^1$H NMR (DMSO): δ 10.43 (bs, 1H), 9.62 (bs, 1H), 8.03 (d, 1H, J=2.4 Hz), 7.10-7.83 (m, 7H), 6.83 (d, 1H, J=7.4 Hz), 6.52 (d, 1H, J=7.2 Hz), 5.01 (m, 1H), 4.75 (s, 2H), 4.03-4.32 (m, 2H), 2.62 (s, 3H), 2.23 (s, 3H), 1.93-2.13 (m, 2H); LCMS: purity: 92.1%; MS (m/e): 393.06 (M-H$^-$).

7.3.1152 N4-(4-Azido-3,4-dihydro-2H-1-benzopyran-6-yl)-5-fluoro-N2-[3-(N-methylamino)carbonyl methyleneoxyphenyl]-2,4-pyrimidinediamine (R950383)

A solution of N4-(4-hydroxy-3,4-dihydro-2H-1-benzopyran-6-yl)-5-fluoro-N2-[3-(N-methylamino)carbonylmethyleneoxyphenyl]-2,4-pyrimidinediamine in dry THF was treated with 2 equivalents of DPPA and DBU. The mixture was stirred for 3 hours at 22° C., concentrated to dryness and purified by flash chromatography on silica gel to give N4-(4-azido-3,4-dihydro-2H-1-benzopyran-6-yl)-5-fluoro-N2-[3-(N-methylamino)carbonylmethyleneoxyphenyl]-2,4-pyrimidinediamine as a white solid. $^1$H NMR (DMSO): δ 10.09 (bs, 1H), 9.83 (bs, 1H), 8.18 (d, 1H, J=2.4 Hz), 7.97 (m, 1H), 7.11-7.61 (m, 6H), 6.82 (d, 1H, J=7.8 Hz), 6.62 (d, 1H, J=7.2 Hz), 4.78 (s, 2H), 4.03-4.33 (m, 3H), 2.62 (s, 3H), 1.93-2.13 (m, 2H); LCMS: purity: 97.9%; MS (m/e): 463.07 (MH$^+$).

7.3.1153 N4-(4-Benzypyran-6-yl)-5-fluoro-N2-[3-(N-methylamino)carbonylmethyleneoxyphenyl]-2,4-pyrimidinediamine (R950385)

A solution of N4-(4-hydroxy-3,4-dihydro-2H-1-benzopyran-6-yl)-5-fluoro-N2-[3-(N-methylamino)carbonylmethyleneoxyphenyl]-2,4-pyrimidinediamine in THF was treated with bortrifluoride etherate at 80° C. for 8 hours. Aqueous work up gave N4-(4-benzypyran-6-yl)-5-fluoro-N2-[3-(N-methylamino)carbonylmethyleneoxyphenyl]-2,4-pyrimidinediamine as a white solid. $^1$H NMR (DMSO): δ 9.18 (s, 1H), 9.14 (s, 1H), 8.03 (d, J=2.4 Hz, 1H), 7.93 (bs, 1H), 5.86-7.48 (m, 9H) 4.73-4.74 (m, 2H), 4.33 (s, 2H), 2.62 (s, 3H); LCMS: purity: 96.5%; MS (m/e): 420.07 (M-H$^-$).

7.3.1154 N4-(3-Hydroxymethylen-4-methoxyphenyl)-5-fluoro-N2-[3-(N-methylamino)carbonylmethyleneoxyphenyl]-2,4-pyrimidinediamine (R950386)

A mixture of equimolar amounts of 2-chloro-N4-(3-hydroxymethylen-4-methoxyphenyl)-5-fluoro-4-aminopyridine and 3-(N-methylamino)carbonylmethyleneoxyaniline in MeOH in a pressure tube at 110° C. for 24 h or in EtOH using microwave at 175° C. for 10-20 min followed by aqueous work up gave N4-(3-hydroxymethylen-4-methoxyphenyl)-5-fluoro-N2-[3-(N-methylamino)carbonylmethyleneoxyphenyl]-2,4-pyrimidinediamine as a white solid. LCMS: purity: 89.2%; MS (m/e): 410.5 (MH$^+$).

7.3.1155 N4-(3-Amino-4-ethoxyphenyl)-5-fluoro-N2-[3-(N-methylamino)carbonylmethyleneoxyphenyl]-2,4-pyrimidinediamine (R950388)

A mixture of 2-chloro-N4-(3-amino-4-ethoxyphenyl)-5-fluoro-4-aminopyridine and 3 equivalents of 3-(N-methylamino)carbonylmethyleneoxyaniline in MeOH in a pressure tube at 110° C. for 24 h or in EtOH using microwave at 175° C. for 10-20 min followed by aqueous work up gave N4-(3-amino-4-ethoxyphenyl)-5-fluoro-N2-[3-(N-methylamino)carbonylmethyleneoxyphenyl]-2,4-pyrimidinediamine as a white solid. LCMS: purity: 95.1%; MS (m/e): 427.18 (MH$^+$).

7.3.1156 N4-(4-Ethoxy-3-hydroxysulfonylphenyl)-5-fluoro-N2-[3-(N-methylamino)carbonylmethyleneoxyphenyl]-2,4-pyrimidinediamine (R950389)

A solution of N4-(4-hydroxy-3,4-dihydro-2H-1-benzopyran-6-yl)-5-fluoro-N2-[3-(N-methylamino)carbonylmethyleneoxyphenyl]-2,4-pyrimidinediamine in HOAc was treated with sodium nitrate followed by addition of concentrated aqueous HCl and copper dichloride. The mixture was stirred for 2 hours at 22° C. for 8 hours and purified by aqueous work up followed by column chromatography on silica gel to give N4-(4-ethoxy-3-hydroxysulfonylphenyl)-5-fluoro-N2-[3-(N-methylamino)carbonylmethyleneoxyphenyl]-2,4-pyrimidinediamine, LCMS: purity: 82.3%; MS (m/e): 474.09 (M-H$^-$).

7.3.1157 N2,N4-Bis(3-methoxycarbonyl-4-trifluoromethoxyphenyl)-5-fluoro-2,4-pyrimidinediamine (R950391)

A mixture of 2,4-dichloro-5-fluoropyridine and three equivalents of 3-methoxycarbonyl-4-trifluoromethoxyaniline in MeOH in a pressure tube at 110° C. for 24 h or in EtOH using microwave at 175° C. for 10-20 min followed by aqueous work up N2,N4-bis(3-methoxycarbonyl-4-trifluoromethoxyphenyl)-5-fluoro-2,4-pyrimidinediamine as a white solid. $^1$H NMR (DMSO): δ 9.96 (s, 1H), 9.82 (s, 1H), 8.16-8.26 (m, 4H), 7.91 (dd, 1H, J=3.0, 7.2 Hz), 7.42 (d, 1H, J=7.2 Hz), 7.31 (d, 1H, J=7.2 Hz), 3.77 (s, 3H), 3.75 (s, 3H); LCMS: purity: 93.0%; MS (m/e): 565.37 (MH$^+$).

7.3.1158 N4-(3-Methoxycarbonyl-4-trifluoro methoxyphenyl)-5-fluoro-N2-[3-(N-methylamino)carbonylmethyleneoxyphenyl]-2,4-pyrimidinediamine (R950392)

A mixture of equimolar amounts of 2-chloro-N4-(3-methoxycarbonyl-4-trifluoromethoxyphenyl)-5-fluoro-4-aminopyridine and 3-(N-methylamino)carbonylmethyleneoxyaniline in MeOH in a pressure tube at 110° C. for 24 h or in EtOH using microwave at 175° C. for 10-20 min followed by aqueous work up gave N4-(3-methoxycarbonyl-4-trifluoromethoxyphenyl)-5-fluoro-N2-[3-(N-methylamino)carbonylmethyleneoxyphenyl]-2,4-pyrimidinediamine as a white solid. LCMS: purity: 95.8%; MS (m/e): 510.41 (MH$^+$).

7.3.1159 N4-(4-Acetylamino-3,4-dihydro-2H-1-benzopyran-6-yl)-5-fluoro-N2-[3-(N-methylamino)carbonyl methyleneoxyphenyl]-2,4-pyrimidinediamine (R950393)

A solution of N4-(4-hydroxy-3,4-dihydro-2H-1-benzopyran-6-yl)-5-fluoro-N2-[3-(N-methylamino)carbonylmethyleneoxyphenyl]-2,4-pyrimidinediamine in dry MeCN was treated with concentrated sulfuric acid. The mixture was stirred for 3 hours at 22° C., concentrated to dryness and purified by flash chromatography on silica gel to give N4-(4-acetylamino-3,4-dihydro-2H-1-benzopyran-6-yl)-5-fluoro-N2-[3-(N-methylamino)carbonylmethyleneoxyphenyl]-2,4-pyrimidinediamine as a white solid. $^1$H NMR (DMSO): δ 10.46 (bs, 1H), 9.52 (bs, 1H), 7.98 (d, 1H, J=2.4 Hz), 7.12-7.73 (m, 7H), 6.66 (d, 1H, J=7.2 Hz), 6.49 (d, 1H, J=7.2 Hz), 4.75 (s, 2H), 4.03-4.32 (m, 2H), 3.80 (m, 1H), 2.64 (s, 3H), 2.143 (s, 3H), 1.90-2.11 (m, 2H); LCMS: purity: 92.1%; MS (m/e): 393.06 (M-H$^-$). LCMS: purity: 96.2%; MS (m/e): 479.13 (M-H$^-$).

7.3.1160 N4-(4-Amino-3,4-dihydro-2H-1-benzopyran-6-yl)-5-fluoro-N2-[3-(N-methylamino)carbonylmethyleneoxyphenyl]-2,4-pyrimidinediamine HCl salt (R950399)

A solution of N4-(4-amino-3,4-dihydro-2H-1-benzopyran-6-yl)-5-fluoro-N2-[3-(N-methylamino)carbonylmethyleneoxyphenyl]-2,4-pyrimidinediamine in MeOH was treated with 1 equivalent of 1 N aqueous HCl. The clear solution was concentrated to dryness and the remaining solid was washed with dry acetone to give the HCl salt of N4-(4-amino-3,4-dihydro-2H-1-benzopyran-6-yl)-5-fluoro-N2-[3-(N-methylamino)carbonylmethyleneoxyphenyl]-2,4-pyrimidinediamine as a white solid. LCMS: purity: 98.2%; MS (m/e): 438.98 (MH$^+$).

7.3.1161 N4-(4-Amino-3,4-dihydro-2H-1-benzopyran-6-yl)-5-fluoro-N2-[3-(N-methylamino)carbonylmethyleneoxyphenyl]-2,4-pyrimidinediamine succinic acid salt (R950400)

A solution of N4-(4-amino-3,4-dihydro-2H-1-benzopyran-6-yl)-5-fluoro-N2-[3-(N-methylamino)carbonylmethyleneoxyphenyl]-2,4-pyrimidinediamine in MeOH was treated with 1 equivalent of succinic acid. The clear solution was concentrated to dryness and the remaining solid was crystallized from dry acetone to give the succinic acid salt of N4-(4-amino-3,4-dihydro-2H-1-benzopyran-6-yl)-5-fluoro-N2-[3-(N-methylamino)carbonylmethyleneoxyphenyl]-2,4-pyrimidinediamine as a white solid. LCMS: purity: 98.1%; MS (m/e): 438.98 (MH$^+$).

7.3.1162 N4-(4-Amino-3,4-dihydro-2H-1-benzopyran-6-yl)-5-fluoro-N2-[3-(N-methylamino)carbonylmethylene oxyphenyl]-2,4-pyrimidinediamine maleic acid salt (R950401)

A solution of N4-(4-amino-3,4-dihydro-2H-1-benzopyran-6-yl)-5-fluoro-N2-[3-(N-methylamino)carbonylmethyleneoxyphenyl]-2,4-pyrimidinediamine in MeOH was treated with 1 equivalent of maleic acid. The clear solution was concentrated to dryness and the remaining solid was crystallized from dry acetone to give the maleic acid salt of N4-(4-amino-3,4-dihydro-2H-1-benzopyran-6-yl)-5-fluoro-N2-[3-(N-methylamino)carbonylmethyleneoxyphenyl]-2,4-pyrimidinediamine as a white solid. LCMS: purity: 97.9%; MS (m/e): 438.98 (MH$^+$).

7.3.1163 N4-(4-Amino-3,4-dihydro-2H-1-benzopyran-6-yl)-5-fluoro-N2-[3-(N-methylamino)carbonylmethyleneoxyphenyl]-2,4-pyrimidinediamine fumaric acid salt (R950402)

A solution of N4-(4-amino-3,4-dihydro-2H-1-benzopyran-6-yl)-5-fluoro-N2-[3-(N-methylamino)carbonylmethyleneoxyphenyl]-2,4-pyrimidinediamine in MeOH was treated with 1 equivalent of fumaric acid. The clear solution was concentrated to dryness and the remaining solid was crystallized from dry acetone to give the fumaric acid salt of N4-(4-amino-3,4-dihydro-2H-1-benzopyran-6-yl)-5-fluoro-N2-[3-(N-methylamino)carbonylmethyleneoxyphenyl]-2,4-pyrimidinediamine as a white solid. LCMS: purity: 97.9%; MS (m/e): 438.98 (MH$^+$).

7.3.1164 N4-(4-Amino-3,4-dihydro-2H-1-benzopyran-6-yl)-5-fluoro-N2-[3-(N-methylamino)carbonylmethyleneoxyphenyl]-2,4-pyrimidinediamine citric acid salt (R950403)

A solution of N4-(4-amino-3,4-dihydro-2H-1-benzopyran-6-yl)-5-fluoro-N2-[3-(N-methylamino)carbonylmethyleneoxyphenyl]-2,4-pyrimidinediamine in MeOH was treated with 1 equivalent of citric acid. The clear solution was concentrated to dryness and the remaining solid was crystallized from dry acetone to give the citric acid salt of N4-(4-amino-3,4-dihydro-2H-1-benzopyran-6-yl)-5-fluoro-N2-[3-(N-methylamino)carbonylmethyleneoxyphenyl]-2,4-pyrimidinediamine as a white solid. LCMS: purity: 97.9%; MS (m/e): 438.98 (MH$^+$).

7.3.1165 N4-(4-Amino-3,4-dihydro-2H-1-benzopyran-6-yl)-5-fluoro-N2-[3-(N-methylamino)carbonylmethyleneoxyphenyl]-2,4-pyrimidinediamine HNO$_3$ salt (R950404)

A solution of N4-(4-amino-3,4-dihydro-2H-1-benzopyran-6-yl)-5-fluoro-N2-[3-(N-methylamino)carbonylmethyleneoxyphenyl]-2,4-pyrimidinediamine in MeOH was treated with 1 equivalent of 1 N aqueous HNO$_3$. The clear solution was concentrated to dryness and the remaining solid was washed with dry acetone to give the nitric acid salt of N4-(4-amino-3,4-dihydro-2H-1-benzopyran-6-yl)-5-fluoro-N2-[3-(N-methylamino)carbonyl methyleneoxyphenyl]-2,4-pyrimidinediamine as a white solid. LCMS: purity: 98.2%; MS (m/e): 438.98 (MH$^+$).

7.4 Synthesis of Prodrugs

Exemplary prodrugs according to structural formula (II) were synthesized as described below.

7.4.1 N-2(4)-Acetyl-N2,N4-bis(3,4-ethylenedioxyphenyl)-5-fluoro-2,4-pyrimidinediamine (R926233)

A mixture of N2,N4-bis(3,4-ethylenedioxyphenyl)-5-fluoro-2,4-pyrimidinediamine, acetyl chloride (4 equivalents), pyridine (4 equivalents) in CH$_2$Cl$_2$ was stirred at room temperature for 48 h. After an aqueous work up the residue was chromatographed on silica gel to give N-2(4)-acetyl-N2,N4-bis(3,4-ethylenedioxyphenyl)-5-fluoro-2,4-pyrimidinediamine. $^1$H NMR (CDCl$_3$): δ 8.23 (d, 1H, J=5.4 Hz), 7.03 (d, 1H, J=2.4 Hz), 7.90-7.80 (m, 3H), 6.76 (m, 2H), 4.28 (bs, 4H), 2.10 (s, 3H); $^{19}$F NMR (CDCl$_3$): −42125; LCMS: ret. time: 27.94 min.; purity: 99%; MS (m/e): 439 (MH$^+$).

7.4.2 N2,N4-Bis(3-N-acetylaminophenyl)-5-fluoro-N2,N4-pyrimidinediacetylamine (R950244)

N2,N4-Bis(3-aminophenyl)-5-fluoro-2,4-pyrimidinediamine, dimethylaminopyridine (DMAP) and acetic anhydride were refluxed in pyridine for 1 hour. The mixture was cooled to room temperature, concentrated, and the residue was subjected to column chromatography on silica gel (CHCl$_3$:Acetone, 2:1) to give N2,N4-bis(3-N-acetylaminophenyl)-5-fluoro-N2,N4-pyrimidinediacetylamine. LCMS: ret. time: 17.03 min.; purity: 87.0%; MS (m/e): 478.89 (MH$^+$).

7.4.3 N4-(3-N,N-Diacetylaminophenyl)-N2-(3-N-acetylaminopheny)-5-fluoro-N2,N4-pyrimidinediacetylamine (R950245)

N2,N4-Bis(3-aminophenyl)-5-fluoro-2,4-pyrimidinediamine, dimethylaminopyridine (DMAP) and acetic anhydride were refluxed in pyridine for 1 hour. The mixture was cooled to room temperature, concentrated, and the residue was subjected to column chromatography on silica gel (CHCl$_3$:Acetone, 2:1) to give N4-(3-N,N-diacetylaminophenyl)-N2-(3-N-acetylaminopheny)-5-fluoro-N2,N4-pyrimidinediacetylamine. LCMS: ret. time: 19.27 min.; purity: 92.6%; MS (m/e): 521.01 (MH$^+$).

7.4.4 N4-(3-N-Acetylaminophenyl)-N2-(3-N,N-diacetylaminopheny)-5-fluoro-N2,N4-pyrimidinediacetylamine (R950246)

N2,N4-Bis(3-aminophenyl)-5-fluoro-2,4-pyrimidinediamine, dimethylaminopyridine (DMAP) and acetic anhydride were refluxed in pyridine for 1 hour. The mixture was cooled to room temperature, concentrated, and the residue was subjected to column chromatography on silica gel (CHCl$_3$:Acetone, 2:1) to give N4-[3-N-acetylaminophenyl]-N2-(3-N,N-diacetylaminopheny)-5-fluoro-N2,N4-pyrimidinediacetylamine. LCMS: ret. time: 18.89 min.; purity: 83.0%; MS (m/e): 520.97 (MH$^+$).

7.4.5 N2,N4-Bis(3-N,N-diacetylaminophenyl)-5-fluoro-N2,N4-pyrimidinediacetylamine (R950247)

N2,N4-Bis(3-aminophenyl)-5-fluoro-2,4-pyrimidinediamine, dimethylaminopyridine (DMAP) and acetic anhydride were refluxed in pyridine for 1 hour. The mixture was cooled to room temperature, concentrated, and the residue was subjected to column chromatography on silica gel (CHCl$_3$:Acetone, 2:1) to give N2,N4-bis(3-N,N-diacetylaminophenyl)-5-fluoro-N2,N4-pyrimidinediacetylamine. LCMS: ret. time: 21.51 min.; purity: 91.8%; MS (m/e): 563.00 (MH$^+$).

7.5 The 2,4-Pyrimidinediamine Compounds of the Invention Inhibit FcεRI Receptor-Mediated Degranulation The ability of the 2,4-pyrimidinediamine compounds of the invention to inhibit IgE-induced degranulation was demonstrated in a variety of cellular assays with cultured human mast cells (CHMC) and/or mouse bone marrow derived cells (BMMC). Inhibition of degranulation was measured at both low and high cell density by quantifying the release of the granule specific factors tryptase, histamine and hexosaminidase. Inhibition of release and/or synthesis of lipid mediators was assessed by measuring the release of leukotriene LTC4 and inhibition of release and/or synthesis of cytokines was monitored by quantifying TNF-α, IL-6 and IL-13. Tryptase and hexosaminidase were quantified using fluorogenic substrates as described in their respective examples. Histamine, TNFα, IL-6, IL-13 and LTC4 were quantified using the following commercial ELISA kits: histamine (Immunotech #2015, Beckman Coulter), TNFα (Biosource #KHC3011), IL-6 (Biosource #KMC0061), IL-13 (Biosource #KHC0132) and LTC4 (Cayman Chemical #520211). The protocols of the various assays are provided below.

7.5.1 Culturing of Human Mast and Basophil Cells

Human mast and basophil cells were cultured from CD34-negative progenitor cells as described below (see also the methods described in copending U.S. application Ser. No. 10/053,355, filed Nov. 8, 2001, the disclosure of which is incorporated herein by reference).

7.5.1.1 Preparation of STEMPRO-34 Complete Medium

To prepare STEMPRO-34 complete medium ("CM"), 250 mL STEMPRO-34 serum free medium ("SFM"; GibcoBRL, Catalog No. 10640) was added to a filter flask. To this was added 13 mL STEMPRO-34 Nutrient Supplement ("NS"; GibcoBRL, Catalog No. 10641) (prepared as described in more detail, below). The NS container was rinsed with approximately 10 mL SFM and the rinse added to the filter flask. Following addition of 5 mL L-glutamine (200 mM; Mediatech, Catalog No. MT 25-005-CI and 5 mL 100× penicillin/streptomycin ("pen-strep"; HyClone, Catalog No. SV30010), the volume was brought to 500 mL with SFM and the solution was filtered.

The most variable aspect of preparing the CM is the method by which the NS is thawed and mixed prior to addition to the SFM. The NS should be thawed in a 37° C. water bath and swirled, not vortexed or shaken, until it is completely in solution. While swirling, take note whether there are any lipids that are not yet in solution. If lipids are present and the NS is not uniform in appearance, return it to the water bath and repeat the swirling process until it is uniform in appearance. Sometimes this component goes into solution immediately, sometimes after a couple of swirling cycles, and sometimes not at all. If, after a couple of hours, the NS is still not in solution, discard it and thaw a fresh unit. NS that appears non-uniform after thaw should not be used.

7.5.1.2 Expansion of CD34+Cells

A starting population of CD34-positive (CD34+) cells of relatively small number ($1\text{-}5 \times 10^6$ cells) was expanded to a relatively large number of CD34-negative progenitor cells (about $2\text{-}4 \times 10^9$ cells) using the culture media and methods described below. The CD34+ cells (from a single donor) were obtained from Allcells (Berkeley, Calif.). Because there is a degree of variation in the quality and number of CD34+ cells that Allcells typically provides, the newly delivered cells were transferred to a 15 mL conical tube and brought up to 10 mL in CM prior to use.

On day 0, a cell count was performed on the viable (phase-bright) cells and the cells were spun at 1200 rpm to pellet. The cells were resuspended to a density of 275,000 cells/mL with CM containing 200 ng/mL recombinant human Stem Cell Factor ("SCF"; Peprotech, Catalog No. 300-07) and 20 ng/mL human flt-3 ligand (Peprotech, Catalog No. 300-19) ("CM/SCF/flt-3 medium"). On about day 4 or 5, the density of the culture was checked by performing a cell count and the culture was diluted to a density of 275,000 cells/mL with fresh CM/SCF/flt-3 medium. On about day 7, the culture was transferred to a sterile tube and a cell count was performed. The cells were spun at 1200 rpm and resuspended to a density of 275,000 cells/mL with fresh CM/SCF/flt-3 medium.

This cycle was repeated, starting from day 0, a total of 3-5 times over the expansion period.

When the culture is large and being maintained in multiple flasks and is to be resuspended, the contents of all of the flasks are combined into a single container prior to performing a cell count. This ensures that an accurate cell count is achieved and provides for a degree of uniformity of treatment for the entire population. Each flask is checked separately for contamination under the microscope prior to combining to prevent contamination of the entire population.

Between days 17-24, the culture can begin to go into decline (i.e., approximately 5-10% of the total number of cells die) and fail to expand as rapidly as before. The cells are then monitored on a daily basis during this time, as complete failure of the culture can take place in as little as 24 hours. Once the decline has begun, the cells are counted, spun down at 850 rpm for 15 minutes, and resuspended at a density of 350,000 cells/mL in CM/SCF/flt-3 medium to induce one or two more divisions out of the culture. The cells are monitored daily to avoid failure of the culture.

When greater than 15% cell death is evident in the progenitor cell culture and some debris is present in the culture, the CD34-negative progenitor cells are ready to be differentiated.

7.5.1.3 Differentiation of CD34-Negative Progenitor Cells into Mucosal Mast Cells A second phase is performed to convert the expanded CD34-negative progenitor cells into differentiated mucosal mast cells. These mucosal cultured human mast cells ("CHMC") are derived from CD34+cells isolated from umbilical cord blood and treated to form a proliferated population of CD34-negative progenitor cells, as described above. To produce the CD43-negative progenitor cells, the resuspension cycle for the culture was the same as that described above, except that the culture was seeded at a density of 425,000 cells/mL and 15% additional media was added on about day four or five without performing a cell count. Also, the cytokine composition of the medium was modified such that it contained SCF (200 ng/mL) and recombinant human IL-6 (200 ng/mL; Peprotech, Catalog No. 200-06 reconstituted to 100 ug/mL in sterile 10 mM acetic acid) ("CM/SCF/IL-6 medium").

Phases I and II together span approximately 5 weeks. Some death and debris in the culture is evident during weeks 1-3 and there is a period during weeks 2-5 during which a small percentage of the culture is no longer in suspension, but is instead attached to the surface of the culture vessel.

As during Phase I, when the culture is to be resuspended on day seven of each cycle, the contents of all flasks are combined into a single container prior to performing a cell count to ensure uniformity of the entire population. Each flask is checked separately for contamination under the microscope prior to combining to prevent contamination of the entire population.

When the flasks are combined, approximately 75% of the volume is transferred to the communal container, leaving behind about 10 mL or so in the flask. The flask containing the remaining volume was rapped sharply and laterally to dislodge the attached cells. The rapping was repeated at a right angle to the first rap to completely dislodge the cells.

The flask was leaned at a 45 degree angle for a couple of minutes before the remaining volume was transferred to the counting vessel. The cells were spun at 950 rpm for 15 min prior to seeding at 35-50 mL per flask (at a density of 425,000 cells/mL).

7.5.1.4 Differentiation of CD34-Negative Progenitor Cells into Connective Tissue-Type Mast Cells A proliferated population of CD34-negative progenitor cells is prepared as above and treated to form a tryptase/chymase positive (connective tissue) phenotype. The methods are performed as described above for mucosal mast cells, but with the substitution of IL-4 for IL-6 in the culture medium. The cells obtained are typical of connective tissue mast cells.

7.5.1.5 Differentiation of CD34-Negative Progenitor Cells into Basophil Cells A proliferated population of CD34-negative progenitor cells is prepared as described in Section 6.4.1.2, above, and used to form a proliferated population of basophil cells. The CD34-negative cells are treated as described for mucosal mast cells, but with the substitution of IL-3 (at 20-50 ng/mL) for IL-6 in the culture medium.

7.5.2 CHMC Low Cell Density IgE Activation: Tryptase and LTC4 Assays

To duplicate 96-well U-bottom plates (Costar 3799) add 65 ul of compound dilutions or control samples that have been prepared in MT [137 mM NaCl, 2.7 mM KCl, 1.8 mM $CaCl_2$, 1.0 mM $MgCl_2$, 5.6 mM Glucose, 20 mM Hepes (pH 7.4), 0.1% Bovine Serum Albumin, (Sigma A4503)] containing 2% MeOH and 1% DMSO. Pellet CHMC cells (980 rpm, 10 min) and resuspend in pre-warmed MT. Add 65 ul of cells to each 96-well plate. Depending on the degranulation activity for each particular CHMC donor, load 1000-1500 cells/well. Mix four times followed by a 1 hr incubation at 37° C. During the 1 hr incubation, prepare 6× anti-IgE solution [rabbit anti-human IgE (1 mg/ml, Bethyl Laboratories A80-109A) diluted 1:167 in MT buffer]. Stimulate cells by adding 25 ul of 6× anti-IgE solution to the appropriate plates. Add 25 ul MT to un-stimulated control wells. Mix twice following addition of the anti-IgE. Incubate at 37° C. for 30 minutes. During the 30 minute incubation, dilute the 20 mM tryptase substrate stock solution [(Z-Ala-Lys-Arg-AMC•2TFA; Enzyme Systems Products, #AMC-246)] 1:2000 in tryptase assay buffer [0.1 M Hepes (pH 7.5), 10% w/v Glycerol, 10 uM Heparin (Sigma H-4898) 0.01% $NaN_3$]. Spin plates at 1000 rpm for 10 min to pellet cells. Transfer 25 ul of supernatant to a 96-well black bottom plate and add 100 ul of freshly diluted tryptase substrate solution to each well. Incubate plates at room temperature for 30 min. Read the optical density of the plates at 355 nm/460 nm on a spectrophotometric plate reader.

Leukotriene C4 (LTC4) is also quantified using an ELISA kit on appropriately diluted supernatant samples (determined empirically for each donor cell population so that the sample measurement falls within the standard curve) following the supplier's instructions.

7.5.3 CHMC High Cell Density IgE Activation: Degranulation (Tryptase, Histamine), Leukotriene (LTC4), and Cytokine (TNFalpha, IL-13) Assays Cultured human mast cells (CHMC) are sensitized for 5 days with IL-4 (20 ng/ml), SCF (200 ng/ml), IL-6 (200 ng/ml), and Human IgE (CP 1035K from Cortx Biochem, 100-500 ng/ml depending on generation) in CM medium. After sensitizing, cells are counted, pelleted (1000 rpm, 5-10 minutes), and resuspended at $1-2\times10^6$ cells/ml in MT buffer. Add 100 ul of cell suspension to each well and 100 ul of compound dilutions. The final vehicle concentration is 0.5% DMSO. Incubate at 37° C. (5% $CO_2$) for 1 hour. After 1 hour of compound treatment, stimulate cells with 6× anti-IgE. Mix wells with the cells and allow plates to incubate at 37° C. (5% $CO_2$) for one hour. After 1 hour incubation, pellet cells (10 minutes, 1000 RPM) and collect 200 ul per well of the supernatant, being careful not to disturb pellet. Place the supernatant plate on ice. During the 7-hour step (see next) perform tryptase assay on supernatant that had been diluted 1:500. Resuspend cell pellet in 240 ul of CM media containing 0.5% DMSO and corresponding concentration of compound. Incubate CHMC cells for 7 hours at 37° C. (5% $CO_2$). After incubation, pellet cells (1000 RPM, 10 minutes) and collect 225 ul per well and place in −80° C. until ready to perform ELISAS. ELISAS are performed on appropriately diluted samples (determined empirically for each donor cell population so that the sample measurement falls within the standard curve) following the supplier's instructions.

7.5.4 BMMC High Cell Density IgE Activation: Degranulation (Hexosiminidase, Histamine), Leukotriene (LTC4), and Cytokine (TNFalpha, IL-6) Assays

7.5.4.1 Preparation of WEHI-Conditioned Medium

WEHI-conditioned medium was obtained by growing murine myelomonocytic WEHI-3B cells (American Type Culture Collection, Rockville, Md.) in Iscove's Modified Eagles Media (Mediatech, Hernandon, Va.) supplemented with 10% heat-inactivated fetal bovine serum (FBS; JRH Biosciences, Kansas City, Mo.), 50 µM 2-mercaptoethanol (Sigma, St. Louis, Mo.) and 100 IU/mL penicillin-streptomycin (Mediatech) in a humidified 37° C., 5% $CO_2$/95% air incubator. An initial cell suspension was seeded at 200,000 cells/mL and then split 1:4 every 3-4 days over a period of two weeks. Cell-free supernatants were harvested, aliquoted and stored at −80° C. until needed.

7.5.4.2 Preparation of BMMC Medium

BMMC media consists of 20% WEHI-conditioned media, 10% heat-inactivated FBS (JHR Biosciences), 25 mM HEPES, pH7.4 (Sigma), 2 mM L-glutamine (Mediatech), 0.1 mM non-essential amino acids (Mediatech), 1 mM sodium pyruvate (Mediatech), 50 µM 2-mercaptoethanol (Sigma) and 100 IU/mL penicillin-streptomycin (Mediatech) in RPMI 1640 media (Mediatech). To prepare the BMMC Media, all components are added to a sterile IL filter unit and filtered through a 0.2 µm filter prior to use.

7.5.4.3 Protocol

Bone marrow derived mast cells (BMMC) are sensitized overnight with murine SCF (20 ng/ml) and monoclonal anti-DNP (10 ng/ml, Clone SPE-7, Sigma # D-8406) in BMMC media at a cell density of $666\times10^3$ cells/ml. After sensitizing, cells are counted, pelleted (1000 rpm, 5-10 minutes), and resuspended at $1-3\times10^6$ cells/ml in MT buffer. Add 100 ul of cell suspension to each well and 100 ul of compound dilutions. The final vehicle concentration is 0.5% DMSO. Incubate at 37° C. (5% $CO_2$) for 1 hour. After 1 hour of compound treatment, stimulate cells with 6× stimulus (60 ng/ml DNP-BSA). Mix wells with the cells and allow plates to incubate at 37° C. (5% $CO_2$) for one hour. After 1 hour incubation, pellet cells (10 minutes, 1000 RPM) and collect 200 ul per well of the supernatant, being careful not to disturb pellet, and transfer to a clean tube or 96-well plate. Place the supernatant plate on ice. During the 4-5 hour step (see next) perform the hexosiminidase assay. Resuspend cell pellet in 240 ul WEI-conditioned media containing 0.5% DMSO and corresponding concentration of compound. Incubate BMMC cells for 4-5 hours at 37° C. (5% $CO_2$). After incubation, pellet cells (1000 RPM, 10 minutes) and collect 225 ul per well and place in −80° C. until ready to perform ELISAS. ELISAS are performed on appropriately diluted samples (determined empirically for each donor cell population so that the sample measurement falls within the standard curve) following the supplier's instructions.

Hexosaminidase assay: In a solid black 96-well assay plate, add 50 uL hexosaminidase substrate (4-methylumbelliferyl-N-acetyl-β-D-glucosaminide; 2 mM) to each well. Add 50 uL of BMMC cell supernatant (see above) to the hexoseaminidase substrate, place at 37° C. for 30 minutes and read the plate at 5, 10, 15, and 30 minutes on a spectrophotometer.

7.5.5 Basophil IgE or Dustmite Activation: Histamine Release Assay

The basophil activation assay was carried out using whole human peripheral blood from donors allergic to dust mites with the majority of the red blood cells removed by dextran sedimentation. Human peripheral blood was mixed 1:1 with 3% dextran T500 and RBCs were allowed to settle for 20-25 min. The upper fraction was diluted with 3 volumes of D-PBS and cells were spun down for 10 min at 1500 rpm, RT. Supernatant was aspirated and cells were washed in an equal volume MT-buffer. Finally, cells were resuspended in MT-buffer containing 0.5% DMSO in the original blood volume. 80 uL cells were mixed with 20 uL compound in the presence of 0.5% DMSO, in triplicate, in a V-bottom 96-well tissue culture plate. A dose range of 8 compound concentrations was tested resulting in a 10-point dose response curve including maximum (stimulated) and minimum (unstimulated) response. Cells were incubated with compound for 1 hour at 37° C., 5% $CO_2$ after which 20 uL of 6× stimulus [1 ug/mL anti-IgE (Bethyl Laboratories) 667 au/mL house dustmite (Antigen Laboratories)] was added. The cells were stimulated for 30 minutes at 37° C., 5% $CO_2$. The plate was spun for 10 min at 1500 rpm at room temperature and 80 uL the supernatant was harvested for histamine content analysis using the histamine ELISA kit supplied by Immunotech. The ELISA was performed according to supplier's instructions.

7.5.6 Results

The results of low density CHMC assays (Section 6.4.3), the high density BMMC assays (Section 6.4.5) and the basophil assays (Section 6.4.6) are provided in TABLE 1. The results of the high density CHMC assays (Section 6.4.4) are provided in TABLE 2. In TABLES 1 and 2, all reported values are $IC_{50}$s (in μM). A value of "9999" indicates an $IC_{50}$>10 μM, with no measurable activity at a 10 μM concentration. Most compounds tested had $IC_{50}$s of less than 10 μM, with many exhibiting $IC_{50}$s in the sub-micromolar range.

7.6 The 2,4-Pyrimidinediamine Compounds Inhibit FcγRI Receptor-Mediated Degranulation The ability of the 2,4-pyrimidinediamine compounds of the invention to inhibit FcγRI-mediated degranulation was demonstrated with Compounds R921218, R921302, R921303, R940347, R920410, R927050, R940350, R935372, R920323, R926971 and R940352 in assays similar to those described in Section 6.4, with the exception that the cells were not primed with IgE and were activated with rabbit anti-human IgG Fab fragment (Bethyl Laboratories, Catalog No. A80-105).

All of the compounds tested exhibited $IC_{50}$s in the sub micromolar range.

TABLE 1

| Test Compound | Low Density | | | | | | |
|---|---|---|---|---|---|---|---|
| | CHMC anti-IgE Tryptase | CHMC Ionomycin Tryptase | CHMC anti-IgE LTC4 | CHMC anti-IgE Hexos. | CHMC Ionomycin Hexos. | Basophils anti-IgE Histamine | Basophils Ionomycin Histamine |
| R008951 | | | | | | | |
| R008952 | | | | | | | |
| R008953 | | | | | | | |
| R008955 | | | | | | | |
| R008956 | | | | | | | |
| R008958 | | | | | | | |
| R067934 | | | | | | | |
| R067963 | | | | | | | |
| R070153 | | | | | | | |
| R070790 | 1.665 | 9999 | | | | | |
| R070791 | | | | | | | |
| R081166 | | | | | | | |
| R088814 | | | | | | | |
| R088815 | | | | | | | |
| R091880 | | | | | | | |
| R092788 | | | | | | | |
| R908696 | 3.553 | | | | | | |
| R908697 | 9999 | 9999 | | | | | |
| R909236 | 0.996 | 9999 | | | | | |
| R909237 | 9999 | 9999 | | | | | |
| R909238 | 0.174 | 9999 | | | | | |
| R909239 | 0.264 | 9999 | | | | | |
| R909240 | 0.262 | 9999 | | | | | |
| R909241 | 0.181 | 9999 | | | | | |
| R909242 | 0.567 | 9999 | | | | | |
| R909243 | 0.263 | >10 | | | | | |
| R909245 | 0.255 | 6.242 | | | | | |
| R909246 | 0.169 | 9999 | | | | | |
| R909247 | 2.393 | 9999 | | | | | |
| R909248 | 3.582 | 9999 | | | | | |

TABLE 1-continued

| | | | | | | | |
|---|---|---|---|---|---|---|---|
| R909249 | 9999 | 9999 | | | | | |
| R909250 | 8.025 | 9999 | | | | | |
| R909251 | 0.138 | 9999 | | | | | |
| R909252 | 0.248 | 9999 | | | | | |
| R909253 | 7.955 | 9999 | | | | | |
| R909254 | 0.136 | 9999 | | | | | |
| R920664 | 9999 | 9999 | | | | | |
| R920665 | 1.1 | 9999 | | | | | |
| R920666 | 2.53 | 9999 | | | | | |
| R920668 | 3.2 | 9999 | | | | | |
| R920669 | 0.42 | 9999 | | | | | |
| R920670 | 2.18 | 9999 | | | | | |
| R920671 | 9999 | 9999 | | | | | |
| R920672 | 9999 | 9999 | | | | | |
| R920818 | 9999 | 9999 | | | | | |
| R920819 | 10 | 9999 | | | | | |
| R920820 | 9999 | 9999 | | | | | |
| R920846 | 9999 | 9999 | | | | | |
| R920860 | 1.009 | 9999 | | | | | |
| R920861 | 0.598 | >10 | | | | | |
| R920893 | 1.239 | 9999 | | | | | |
| R920894 | 0.888 | 5.566 | | | | | |
| R920910 | 0.751 | 7.922 | | | | | |
| R920917 | 1.579 | 9.729 | | | | | |
| R921218 | 0.499 | 9999 | 0.55 | 0.6 | 9999 | 0.24 | 9999 |
| R921219 | 0.059 | 9999 | | | | 0.025 | 9999 |
| R925734 | | | 9.2 | >10 | | | |
| R925747 | 1.021 | 3.1 | | | | | |
| R925755 | 0.898 | 9999 | | | | | |
| R925757 | 2.8 | 9999 | | | | | |
| R925758 | 1.175 | 9999 | | | | | |
| R925760 | 4.85 | 9999 | | | | | |
| R925765 | 6.8 | 9999 | | | | | |
| R925766 | 8.9 | 9999 | | | | | |
| R925767 | 10 | | | | | | |
| R925768 | 9999 | | | | | | |
| R925769 | 9999 | | | | | | |
| R925770 | 9999 | | | | | | |
| R925771 | 0.5 | 2.8 | 0.22 | | | | |
| R925772 | 9999 | 9999 | | | | | |
| R925773 | 0.673 | 9999 | | | | | |
| R925774 | 0.435 | 9999 | | | | | |
| R925775 | 0.225 | 9999 | 0.2 | | | | |
| R925776 | 2.1 | 9999 | | | | | |
| R925778 | 0.225 | 9999 | 0.18 | | | | |
| R925779 | 0.265 | 9999 | 0.19 | | | | |
| R925783 | 2.9 | 9999 | | | | | |
| R925784 | 3.2 | 9999 | | | | | |
| R925785 | 2.5 | 9999 | | | | | |
| R925786 | 1.85 | 9999 | | | | | |
| R925787 | 9 | 9999 | | | | | |
| R925788 | 2.4 | 9999 | | | | | |
| R925790 | 9999 | 9999 | | | | | |
| R925791 | 9999 | 9999 | | | | | |
| R925792 | 6.25 | 9999 | | | | | |
| R925794 | 9999 | 9999 | | | | | |
| R925795 | 9999 | 9999 | | | | | |
| R925796 | 2 | 9999 | | | | | |
| R925797 | 0.85 | 9999 | 0.28 | | | | |
| R925798 | 9999 | 9999 | | | | | |
| R925799 | 9999 | 9999 | | | | | |
| R925800 | 9999 | 9999 | | | | | |
| R925801 | 9999 | 9999 | | | | | |
| R925802 | 9999 | 9999 | | | | | |
| R925803 | 9999 | 9999 | | | | | |
| R925804 | 9999 | 9999 | | | | | |
| R925805 | 9999 | 9999 | | | | | |
| R925806 | 9999 | 9999 | | | | | |
| R925807 | 9999 | 9999 | | | | | |
| R925808 | 9999 | 9999 | | | | | |
| R925810 | 9999 | 9999 | | | | | |
| R925811 | 3.3 | 9999 | | | | | |
| R925812 | 5.8 | 9999 | | | | | |
| R925813 | 9999 | 9999 | | | | | |
| R925814 | 9999 | 9999 | | | | | |
| R925815 | 9999 | 9999 | | | | | |
| R925816 | 6 | 9999 | | | | | |
| R925819 | 9999 | 9999 | | | | | |
| R925820 | 9999 | 9999 | | | | | |

TABLE 1-continued

| | | | | | | | | |
|---|---|---|---|---|---|---|---|---|
| R925821 | 9999 | 9999 | | | | | | |
| R925822 | 9999 | 9999 | | | | | | |
| R925823 | 9999 | 9999 | | | | | | |
| R925824 | 9999 | 9999 | | | | | | |
| R925837 | 9999 | 9999 | | | | | | |
| R925838 | 9999 | 9999 | | | | | | |
| R925839 | 9999 | 9999 | | | | | | |
| R925840 | 9999 | 9999 | | | | | | |
| R925841 | 9999 | 9999 | | | | | | |
| R925842 | 7.3 | 9999 | | | | | | |
| R925843 | 9999 | 9999 | | | | | | |
| R925844 | 5.1 | 9999 | | | | | | |
| R925845 | 2.3 | 9999 | | | | | | |
| R925846 | 9999 | 9999 | | | | | | |
| R925849 | 8.2 | 9999 | | | | | | |
| R925851 | 0.925 | 9999 | | | | | | |
| R925852 | 3 | 9999 | | | | | | |
| R925853 | 9999 | 9999 | | | | | | |
| R925854 | 9999 | 9999 | | | | | | |
| R925855 | 4.2 | 9999 | | | | | | |
| R925856 | 9.85 | 9999 | | | | | | |
| R925857 | 5.95 | 9999 | | | | | | |
| R925858 | 8.05 | 7.3 | | | | | | |
| R925859 | 9999 | 9999 | | | | | | |
| R925860 | 9999 | 9999 | | | | | | |
| R925861 | 9999 | 9999 | | | | | | |
| R925862 | 0.7 | 9999 | | | | | | |
| R925863 | 0.274 | 9999 | | | | | | |
| R925864 | 9999 | 9999 | | | | | | |
| R925865 | 9999 | 9999 | | | | | | |
| R926016 | | | | | | | 9999 | 9999 |
| R926017 | | | | 1.43 | 9999 | | 0.53 | 9999 |
| R926018 | | | | | | | 9999 | 10 |
| R926037 | | | | | | | 9999 | 9999 |
| R926038 | | | | | | | 9999 | 9999 |
| R926039 | | | | | | | 9999 | 9999 |
| R926058 | | | | | | | 9999 | 9999 |
| R926064 | | | | 6.2 | | | | |
| R926065 | | | | 3.5 | | | | |
| R926068 | | | | >10 | | | | |
| R926069 | | | | 9.1 | | | | |
| R926072 | | | | >10 | | | | |
| R926086 | | | | | | | 2.5 | 9999 |
| R926108 | | | 0.76 | 0.787 | 6.4 | | 0.95 | 9999 |
| R926109 | 0.538 | 5.5 | 0.73 | 0.55 | >10 | | 0.15 | 9999 |
| R926110 | 1.071 | 9999 | 1.42 | 1.2 | >10 | | 0.3 | 9999 |
| R926113 | 0.413 | | 0.49 | 0.413 | 9999 | | 0.27 | 9999 |
| R926114 | | | | 3.427 | 8.1 | | 1.7 | 10 |
| R926145 | | | | 4.764 | >10 | | | |
| R926146 | | | 1.59 | 0.761 | 6.7 | | | |
| R926147 | | | | 1.899 | >10 | | | |
| R926206 | | | | | | | >10 | >10 |
| R926209 | | | | | | | >10 | 9999 |
| R926210 | 0.926 | 9999 | 0.8 | 700 | 9999 | | 0.37 | >10 |
| R926211 | 1.299 | 9.8 | | 2.7 | 9999 | | 1.55 | >10 |
| R926212 | 0.654 | 9999 | 0.45 | | | | 0.5 | >10 |
| R926213 | 1.639 | 5.5 | | | | | 1.75 | >10 |
| R926218 | | | | >10 | | | | |
| R926219 | | | | 1.102 | 6.7 | | | |
| R926220 | | | | >10 | | | | |
| R926221 | | | | 8.5 | | | | |
| R926222 | | | | >10 | | | | |
| R926223 | | | | >10 | | | | |
| R926224 | | | | >10 | | | | |
| R926225 | | | | >10 | | | | |
| R926228 | | | | >10 | | | | |
| R926229 | | | | >10 | | | | |
| R926230 | | | | >10 | | | | |
| R926234 | | | | >10 | | | | |
| R926237 | 1.207 | 6.2 | | | | | | |
| R926240 | 0.381 | 1.7 | 0.145 | | | | | |
| R926241 | 7 | 9999 | | | | | | |
| R926242 | 4.2 | 9999 | | | | | | |
| R926243 | 3.1 | 9999 | | | | | | |
| R926245 | 3.1 | 9.4 | | | | | | |
| R926248 | 0.9 | 9999 | 0.76 | | | | | |
| R926249 | 0.5 | 9999 | 0.25 | | | | | |
| R926252 | 2.8 | | | | | | | |
| R926253 | 0.8 | | 0.675 | | | | | |

TABLE 1-continued

| | | | | | |
|---|---|---|---|---|---|
| R926254 | 1.3 | 4 | | | |
| R926255 | 1.4 | 4.5 | | | |
| R926256 | 0.275 | 5.1 | 0.23 | | |
| R926257 | 1.5 | 7.5 | | | |
| R926258 | 0.9 | 9999 | 0.59 | | |
| R926259 | 2.5 | 6.2 | | | |
| R926319 | 9999 | 9999 | | | |
| R926320 | 9999 | 9999 | | | |
| R926321 | 9999 | 9999 | | | |
| R926325 | 9999 | 9999 | | | |
| R926331 | 9999 | 9999 | | | |
| R926339 | 0.66 | 9999 | | | |
| R926340 | 3.23 | 9999 | | | |
| R926341 | 0.875 | 9999 | | | |
| R926342 | 10 | 9999 | | | |
| R926376 | 9999 | | | | |
| R926386 | 9999 | 9999 | | | |
| R926387 | 0.65 | 9999 | 0.7 | | |
| R926394 | 9999 | 9999 | | | |
| R926395 | 0.875 | 6.4 | 0.29 | | |
| R926396 | 0.7 | 2.6 | 0.16 | | |
| R926397 | 9999 | 9999 | | | |
| R926398 | 9999 | 9999 | | | |
| R926399 | 9999 | 9999 | | | |
| R926400 | 9999 | 9999 | | | |
| R926401 | 9999 | 9999 | | | |
| R926402 | 9999 | 9999 | | | |
| R926403 | 9999 | 9999 | | | |
| R926404 | 9999 | 9999 | | | |
| R926405 | 3.4 | 9999 | | | |
| R926406 | 9999 | 9999 | | | |
| R926408 | 9.6 | 9999 | | | |
| R926409 | 3.15 | 9999 | | | |
| R926411 | 0.69 | 2.5 | | | |
| R926412 | 0.62 | 9999 | | | |
| R926461 | 0.725 | 9999 | | | |
| R926467 | 1.175 | 8.8 | | | |
| R926469 | 9999 | | | | |
| R926474 | 2.5 | 9999 | | | |
| R926475 | 2.15 | >10 | | | |
| R926476 | 0.6 | 7.7 | | | |
| R926477 | 0.27 | 9999 | | | |
| R926478 | 9999 | | | | |
| R926479 | 9999 | | | | |
| R926480 | 1.9 | 9999 | | | |
| R926481 | 1.445 | 9999 | | | |
| R926482 | 1.037 | >10 | | | |
| R926483 | 9999 | | | | |
| R926484 | 1.523 | 9999 | | | |
| R926485 | 4.012 | 9999 | | | |
| R926486 | 0.647 | 7.403 | | | |
| R926487 | 0.554 | 8.867 | 1.25 | | |
| R926488 | 0.331 | >10 | 0.752 | | |
| R926489 | 1.414 | >10 | | | |
| R926490 | 1.571 | 9999 | | | |
| R926491 | 1.158 | >10 | | | |
| R926492 | 0.645 | 9999 | | | |
| R926493 | 0.25 | 9.181 | 0.078 | | |
| R926494 | 0.313 | 9999 | 0.078 | | |
| R926495 | 0.121 | >10 | 0.078 | 0.04 | 9999 |
| R926496 | 0.571 | >10 | | | |
| R926497 | 0.138 | 9999 | | 0.27 | 9999 |
| R926498 | 0.209 | >10 | | | |
| R926499 | 0.29 | >10 | | | |
| R926500 | 0.418 | >10 | | | |
| R926501 | 0.298 | >10 | | 0.609 | 9999 |
| R926502 | 0.483 | >10 | | 0.405 | 9999 |
| R926503 | 0.452 | >10 | | | |
| R926504 | 0.569 | >10 | | | |
| R926505 | 0.145 | 9999 | | | |
| R926506 | 0.343 | 9999 | | | |
| R926508 | 0.127 | 9999 | | 0.065 | 9999 |
| R926509 | 1.16 | 9999 | | | |
| R926510 | 0.44 | >10 | | | |
| R926511 | 0.786 | >10 | | | |
| R926514 | 9999 | 9999 | | | |
| R926516 | 1 | 9999 | | | |
| R926526 | 9999 | 9999 | | | |
| R926527 | 9999 | 9999 | | | |

TABLE 1-continued

| | | | |
|---|---|---|---|
| R926528 | 8.75 | 9999 | |
| R926535 | 9999 | 9999 | |
| R926536 | 9999 | 9999 | |
| R926555 | 9999 | 9999 | |
| R926559 | 7.7 | 9999 | |
| R926560 | 9999 | 9999 | |
| R926562 | 9999 | 9999 | |
| R926563 | 9999 | 9999 | |
| R926564 | 3.75 | 9999 | |
| R926565 | 0.625 | 3.3 | |
| R926566 | 2.73 | 9999 | |
| R926567 | 9.3 | 9999 | |
| R926569 | 0.61 | 3.07 | |
| R926571 | 9999 | 9999 | |
| R926572 | 1.8 | 6.08 | |
| R926574 | 1.96 | 2.63 | |
| R926576 | 9999 | 9999 | |
| R926579 | 9999 | 9999 | |
| R926580 | 10 | 9999 | |
| R926582 | 1.3 | 9999 | |
| R926583 | 9999 | 9999 | |
| R926584 | 9999 | 9999 | |
| R926585 | 9999 | 9999 | |
| R926586 | 2.75 | 9999 | |
| R926587 | 9999 | 9999 | |
| R926588 | 7.85 | 9999 | |
| R926589 | 0.325 | 10 | |
| R926591 | 2.62 | 9999 | |
| R926593 | 0.68 | 8.3 | 0.495 |
| R926594 | 9999 | 9999 | |
| R926595 | 4.85 | 9999 | |
| R926604 | 2.85 | 9999 | |
| R926605 | 2.45 | 9999 | |
| R926614 | 0.228 | 9999 | |
| R926615 | 0.445 | 9999 | |
| R926616 | 0.625 | 3.25 | |
| R926617 | 9.45 | 9999 | |
| R926620 | 8.35 | 9999 | |
| R926623 | 9999 | 9999 | |
| R926662 | 9999 | 9999 | |
| R926663 | 9999 | 9999 | |
| R926675 | 0.63 | 9999 | |
| R926676 | 0.76 | 9999 | |
| R926680 | 1.71 | 9999 | |
| R926681 | 0.775 | 9999 | |
| R926682 | 8.41 | 9999 | |
| R926683 | 10 | 9999 | |
| R926688 | 2.25 | >10 | |
| R926690 | 0.146 | >10 | |
| R926696 | 0.309 | >10 | |
| R926698 | 9999 | | |
| R926699 | 0.76 | 9999 | |
| R926700 | 0.157 | >10 | |
| R926701 | 2.2 | 9999 | |
| R926702 | 0.886 | 9999 | |
| R926703 | 0.525 | 9999 | |
| R926704 | 0.564 | 9999 | |
| R926705 | 0.263 | 9999 | 0.533 |
| R926706 | 0.07 | 2.406 | 0.078 |
| R926707 | 0.214 | 9999 | |
| R926708 | 0.472 | 9999 | |
| R926709 | 0.858 | 9999 | |
| R926710 | 1.763 | 9999 | |
| R926711 | 1.245 | 9999 | |
| R926712 | 1.084 | 9999 | |
| R926713 | 0.446 | 8.741 | |
| R926714 | 0.428 | >10 | |
| R926715 | 0.588 | >10 | |
| R926716 | 1.06 | 9999 | |
| R926717 | 7.874 | 9999 | |
| R926718 | 1.826 | 9999 | |
| R926719 | 0.1335 | 4.024 | |
| R926720 | 1.555 | 9999 | |
| R926721 | 4.441 | 9999 | |
| R926722 | 5.96 | 9999 | |
| R926723 | 2.591 | 9999 | |
| R926724 | 2.059 | 9999 | |
| R926725 | 0.431 | 9999 | |
| R926726 | 9999 | 9999 | |

TABLE 1-continued

| | | | | | |
|---|---|---|---|---|---|
| R926727 | 0.387 | 9999 | | | |
| R926728 | 0.482 | >10 | | | |
| R926730 | 0.251 | 9999 | | | |
| R926731 | 9999 | 9999 | | | |
| R926732 | 0.444 | 9999 | | | |
| R926733 | 1.496 | 9999 | | | |
| R926734 | 4.493 | 9999 | | | |
| R926735 | 3.712 | 9999 | | | |
| R926736 | 0.288 | 9999 | | | |
| R926737 | 0.059 | 9999 | | | |
| R926738 | 0.342 | 9999 | | | |
| R926739 | 0.508 | 9999 | | | |
| R926740 | 4.422 | 9999 | | | |
| R926741 | 2.908 | 9999 | | | |
| R926742 | 0.127 | | | 0.043 | 9999 |
| R926743 | 9999 | | | | |
| R926744 | 9999 | | | | |
| R926745 | 0.083 | 9999 | | | |
| R926746 | 0.989 | 9999 | | | |
| R926747 | 0.213 | >10 | | | |
| R926748 | 0.345 | >10 | | | |
| R926749 | 0.472 | 9999 | | | |
| R926750 | 0.361 | >10 | | | |
| R926751 | 0.598 | 9999 | | | |
| R926764 | 0.252 | 5.64 | | | |
| R926765 | 0.324 | 4.39 | | | |
| R926766 | 0.756 | 9999 | | | |
| R926767 | 0.387 | >10 | | | |
| R926768 | 0.443 | >10 | | | |
| R926769 | 1.067 | 9999 | | | |
| R926770 | 0.583 | 9999 | | | |
| R926771 | 2.049 | 9999 | | | |
| R926772 | 0.337 | 7.501 | | | |
| R926773 | 0.548 | 7.849 | | | |
| R926774 | 1.934 | 7.935 | | | |
| R926775 | 3.47 | >10 | | | |
| R926776 | 0.81 | 9999 | | | |
| R926777 | 0.378 | 9999 | | | |
| R926778 | 0.414 | 9999 | | | |
| R926779 | 9999 | 9999 | | | |
| R926780 | 0.152 | >10 | | | |
| R926781 | 0.573 | 9999 | | | |
| R926782 | 0.173 | >10 | | | |
| R926783 | 0.304 | >10 | | | |
| R926784 | 0.252 | 9999 | | | |
| R926785 | 0.222 | >10 | | | |
| R926786 | 0.504 | 9999 | | | |
| R926787 | 5.422 | 9999 | | | |
| R926788 | 0.336 | 6.341 | | | |
| R926789 | 2.315 | 9999 | | | |
| R926790 | 0.462 | 7.412 | | | |
| R926791 | 0.233 | >10 | | | |
| R926792 | 3.197 | 9999 | | | |
| R926793 | 3.073 | 9999 | | | |
| R926795 | 2.041 | >10 | | | |
| R926796 | 0.914 | 9999 | | | |
| R926797 | 2.235 | 9999 | | | |
| R926798 | 2.347 | 5.87 | | | |
| R926799 | 9999 | 9999 | | | |
| R926800 | 4.581 | 9999 | | | |
| R926801 | 10 | 9999 | | | |
| R926802 | 1.251 | >10 | | | |
| R926803 | 1.541 | >10 | | | |
| R926804 | 1.578 | 7.109 | | | |
| R926805 | 0.764 | 9999 | | | |
| R926806 | 0.374 | 9999 | | | |
| R926807 | 0.291 | 9999 | | | |
| R926808 | 0.368 | 9999 | | | |
| R926809 | 0.78 | 3.052 | | | |
| R926810 | 1.221 | 9999 | | | |
| R926811 | 3.662 | 9999 | | | |
| R926812 | 0.185 | >10 | | | |
| R926813 | 0.152 | 9999 | | | |
| R926814 | 1.101 | 9999 | | | |
| R926815 | 1.181 | 9999 | | | |
| R926816 | 0.084 | 9999 | | | |
| R935000 | 9999 | 9999 | | | |
| R935001 | 9999 | 9999 | | | |
| R935002 | 9999 | 9999 | | | |

TABLE 1-continued

| | | |
|---|---|---|
| R935003 | 9999 | 9999 |
| R935004 | 9999 | 9999 |
| R935005 | 9999 | 9999 |
| R935006 | 10 | 9.8 |
| R935016 | 9999 | 9999 |
| R935019 | 8.8 | 9999 |
| R935020 | 9999 | 9999 |
| R935021 | 9999 | 9999 |
| R935023 | 9999 | 9999 |
| R935025 | 1.04 | 9999 |
| R935029 | 2.83 | 9999 |
| R935075 | 0.93 | 9999 |
| R935076 | 4.15 | 9999 |
| R935077 | 9999 | 9999 |
| R935114 | 1.725 | 9999 |
| R935117 | 9999 | |
| R935134 | 0.909 | 1.799 |
| R935135 | 10 | 9999 |
| R935136 | 0.952 | 2.129 |
| R935137 | 10 | 9999 |
| R935138 | 0.096 | 0.552 |
| R935139 | 0.846 | 9999 |
| R935140 | 0.275 | 0.959 |
| R935141 | 0.727 | >10 |
| R935142 | 0.873 | >10 |
| R935143 | 0.573 | >10 |
| R935144 | 0.63 | 9999 |
| R935145 | 0.548 | >10 |
| R935146 | 3.802 | 9999 |
| R935147 | 1.404 | 9999 |
| R935148 | 2.218 | 9.423 |
| R935149 | 0.708 | >10 |
| R935150 | 1.926 | 9.738 |
| R935151 | 0.479 | >10 |
| R935152 | 0.505 | 9.316 |
| R935153 | 0.238 | >10 |
| R935154 | 0.127 | >10 |
| R935155 | 0.401 | 9999 |
| R935156 | 0.149 | >10 |
| R935157 | 0.256 | 4.656 |
| R935158 | 0.551 | >10 |
| R935159 | 0.232 | 4.135 |
| R935160 | 0.202 | >10 |
| R935161 | 0.277 | 9999 |
| R935162 | 0.269 | >10 |
| R935163 | 9999 | 9999 |
| R935164 | 0.204 | 9999 |
| R935165 | 4.988 | 9999 |
| R935166 | 0.568 | 9999 |
| R935167 | 2.132 | >10 |
| R935168 | 0.488 | 9.484 |
| R935169 | 0.999 | 8.007 |
| R935170 | 0.673 | 9999 |
| R935171 | 0.536 | 9999 |
| R935172 | 1.385 | 6.808 |
| R935173 | 0.454 | >10 |
| R935174 | 1.384 | 9999 |
| R935175 | 0.885 | 9999 |
| R935176 | 1.169 | 9999 |
| R935177 | 0.889 | >10 |
| R935178 | 0.515 | 9999 |
| R935179 | 0.557 | 9999 |
| R935180 | 1.22 | 9999 |
| R935181 | 1.76 | 9999 |
| R935182 | 0.124 | 2.469 |
| R935183 | 0.729 | 9999 |
| R935184 | 0.605 | 9999 |
| R935185 | 0.351 | 6.642 |
| R935186 | 0.211 | 9999 |
| R935187 | 9.059 | >10 |
| R935188 | 0.239 | 9999 |
| R935189 | 0.619 | 9999 |
| R935190 | 0.156 | 9999 |
| R935191 | 0.151 | 9999 |
| R935192 | 0.337 | 9999 |
| R935193 | 0.136 | 9999 |
| R935194 | 0.11 | 9999 |
| R935196 | 0.117 | 9999 |
| R935197 | 0.174 | >10 |

TABLE 1-continued

| | | |
|---|---|---|
| R935198 | 0.126 | >10 |
| R935199 | 0.45 | >10 |
| R935202 | 0.181 | 9.765 |
| R935203 | 0.562 | >10 |
| R935204 | 0.554 | 9999 |
| R935205 | 2.959 | 9999 |
| R935206 | 4.711 | 9999 |
| R935207 | 9999 | 9999 |
| R935208 | 1.274 | 9999 |
| R935209 | 0.526 | 1.035 |
| R935211 | 1.238 | 9999 |
| R935212 | 1.427 | 9999 |
| R935213 | 0.619 | 10 |
| R935214 | 0.453 | 5.499 |
| R935218 | 4.712 | 9999 |
| R935219 | 5.409 | 9999 |
| R935220 | 3.789 | 9999 |
| R940089 | 9999 | 9999 |
| R940090 | 9999 | 9999 |
| R940095 | 9999 | 9999 |
| R940100 | 9999 | 9999 |
| R940215 | 0.845 | 9999 |
| R940216 | 0.2675 | 7.3 |
| R940217 | 9999 | 9999 |
| R940222 | 9999 | 9999 |
| R940233 | 0.132 | >10 |
| R940235 | 0.8 | >10 |
| R940250 | | |
| R940251 | | |
| R940253 | 1.006 | >10 |
| R940254 | 0.986 | 9999 |
| R940255 | 1.033 | 9999 |
| R940256 | 1.104 | 9999 |
| R940257 | 0.667 | 9999 |
| R940258 | 0.473 | 5.72 |
| R940260 | 1.126 | 9999 |
| R940261 | 9999 | 9999 |
| R940262 | 9999 | 9999 |
| R940263 | 9999 | 9999 |
| R940264 | 10 | 9999 |
| R940265 | 0.239 | >10 |
| R940266 | 9999 | 9999 |
| R940267 | 3.151 | 9999 |
| R940269 | 1.654 | 9999 |
| R940270 | 2.144 | 8.739 |
| R940271 | 0.401 | 6.821 |
| R940275 | 0.862 | 9999 |
| R940276 | 0.211 | 9999 |
| R940277 | 0.141 | 9999 |
| R940280 | 6.999 | 9999 |
| R940281 | 0.525 | 5.529 |
| R940282 | 0.401 | 3.015 |
| R940283 | 0.553 | 4.982 |
| R940284 | 0.465 | 3.744 |
| R940285 | 3.499 | 9999 |
| R940286 | 0.337 | 7.082 |
| R940287 | 0.288 | 7.684 |
| R940288 | 0.208 | 9999 |
| R940289 | 0.272 | 9999 |
| R940290 | 0.116 | 9999 |
| R940291 | 0.396 | 9999 |
| R940292 | 0.683 | 9999 |
| R940293 | 9999 | 9999 |
| R940294 | 1.366 | 9999 |
| R940295 | 0.126 | 8.812 |
| R940296 | 0.41 | >10 |
| R940297 | 3.465 | 10 |
| R945025 | 9999 | 9999 |
| R945032 | 0.37 | 9999 |
| R945033 | 9999 | 9999 |
| R945034 | 1.85 | 9999 |
| R945035 | 9999 | 9999 |
| R945036 | 9999 | 9999 |
| R945037 | 9999 | 9999 |
| R945038 | 9999 | 9999 |
| R945040 | 9999 | 9999 |
| R945041 | 9999 | 9999 |
| R945042 | 9999 | 9999 |
| R945043 | 9999 | 9999 |

TABLE 1-continued

| | | | | | |
|---|---|---|---|---|---|
| R945045 | 9999 | 9999 | | | |
| R945046 | 0.82 | >10 | | | |
| R945047 | 0.845 | 9999 | | | |
| R945048 | 0.76 | 9999 | | | |
| R945051 | 0.95 | >10 | | | |
| R945052 | 0.425 | 2.48 | | | |
| R945053 | 0.1185 | 1.48 | | | |
| R945056 | 10 | 9999 | | | |
| R945057 | 10 | 9999 | | | |
| R945060 | 0.9375 | >10 | | | |
| R945061 | 10 | 9999 | | | |
| R945062 | 0.625 | >10 | | | |
| R945063 | 1.55 | >10 | | | |
| R945064 | 0.53 | >10 | | | |
| R945065 | 1.425 | >10 | | | |
| R945066 | 5.2 | nd | | | |
| R945067 | 9999 | nd | | | |
| R945068 | 9999 | nd | | | |
| R945070 | 0.45 | >10 | | | |
| R945071 | 0.205 | >10 | | | |
| R945096 | 1.75 | >10 | | | |
| R945097 | 10 | 9999 | | | |
| R945109 | 1.025 | >10 | | | |
| R945110 | 0.602 | 9999 | | | |
| R945117 | 4.077 | 9999 | | | |
| R945118 | 0.668 | 9999 | | | |
| R945124 | 0.69 | 7.852 | | | |
| R945125 | 0.896 | >10 | | | |
| R945126 | 9999 | 9999 | | | |
| R945127 | 0.704 | 8.955 | | | |
| R945128 | 0.685 | 8.8 | | | |
| R945129 | 1.003 | >10 | | | |
| R945130 | 1.874 | 9999 | | | |
| R945131 | 0.77 | 9999 | | | |
| R945132 | 0.571 | 8.77 | | | |
| R945133 | 1.064 | >10 | | | |
| R945134 | 9999 | 9999 | | | |
| R945135 | 0.986 | 8.245 | | | |
| R945137 | 1.649 | >10 | | | |
| R945138 | 1.058 | 6.733 | | | |
| R945139 | 1.016 | >10 | | | |
| R945140 | 0.573 | >10 | | | |
| R945142 | 1.049 | >10 | | | |
| R945144 | 0.244 | 9999 | | | |
| R945145 | 9999 | >10 | | | |
| R945146 | 3.756 | 9999 | | | |
| R945147 | 3.546 | 9999 | | | |
| R945148 | 0.307 | 9999 | | | |
| R945149 | 0.391 | >10 | | | |
| R945150 | 0.467 | >10 | | | |
| R945151 | 4.07 | 9999 | | | |
| R945152 | 6.94 | 9999 | | | |
| R945153 | 0.688 | 6.561 | | | |
| R945155 | 1.878 | >10 | | | |
| R945156 | 0.787 | 9999 | | | |
| R945157 | 1.477 | 9999 | | | |
| R945162 | 9999 | 9999 | | | |
| R945163 | 0.922 | 4.251 | | | |
| R945164 | 10 | 9999 | | | |
| R945165 | 9999 | 9999 | | | |
| R945166 | 9999 | 9999 | | | |
| R945167 | 0.761 | 9999 | | | |
| R945168 | 10 | 9999 | | | |
| R945169 | 10 | 9999 | | | |
| R945170 | 0.661 | >10 | | | |
| R945171 | 1.327 | 9999 | | | |
| R945172 | 1.179 | 9999 | | | |
| R945173 | 1.419 | 9999 | | | |
| R945175 | 1.648 | 9999 | | | |
| R950082 | 9999 | 9999 | | | |
| R950083 | 9999 | 9999 | | | |
| R950090 | 9999 | 9999 | | | |
| R921302 | 0.37 | 9999 | | 0.19 | 9999 |
| R950092 | 9999 | 9999 | | | |
| R950093 | 0.64 | 5.55 | | | |
| R950100 | 0.71 | >10 | | | |
| R950107 | 0.46 | >10 | | | |
| R950108 | 2.075 | >10 | | | |
| R950109 | 7.95 | | | | |

TABLE 1-continued

| | | |
|---|---|---|
| R950120 | 3 | 9999 |
| R950121 | 4.25 | >10 |
| R950122 | 3.025 | 9999 |
| R950123 | 3.25 | 8.45 |
| R950125 | 1.375 | 6.3 |
| R950129 | 0.665 | >10 |
| R950130 | 4.9 | |
| R950131 | 9999 | |
| R950132 | 9 | |
| R950133 | 2.2 | >10 |
| R950134 | 1.875 | 9999 |
| R950135 | 0.85 | >10 |
| R950137 | 2.23 | 9999 |
| R950138 | 9.5 | |
| R950139 | 1.375 | 9999 |
| R950140 | 2.825 | 9999 |
| R950141 | 0.31 | >10 |
| R950142 | 10 | |
| R950143 | 8.23 | |
| R950144 | 10 | |
| R950145 | 9999 | |
| R950146 | 9999 | |
| R950147 | 9999 | |
| R950148 | 2.275 | 9999 |
| R950149 | 10 | 9999 |
| R950150 | 9999 | 9999 |
| R950151 | 9999 | |
| R950152 | 10 | |
| R950153 | 9999 | |
| R950154 | 2.075 | 9999 |
| R950155 | 9999 | |
| R950156 | 9999 | |
| R950157 | 9999 | |
| R950158 | 9.98 | |
| R950159 | 0.61 | 9999 |
| R950160 | 1 | 9999 |
| R950162 | 0.434 | >10 |
| R950163 | 0.874 | 9999 |
| R950164 | 1.893 | 9999 |
| R950165 | 1.288 | 9999 |
| R950166 | 1.889 | 9999 |
| R950167 | 9999 | 9999 |
| R950168 | 6.496 | 8.653 |
| R950169 | 1.273 | 9.518 |
| R950170 | 9999 | 9999 |
| R950171 | 0.585 | >10 |
| R950172 | 0.983 | 9999 |
| R950173 | 2.368 | >10 |
| R950174 | 4.618 | 9999 |
| R950175 | 1.688 | 9999 |
| R950176 | 1.342 | 9999 |
| R950177 | 2.361 | 8.434 |
| R950178 | 0.688 | >10 |
| R950179 | 0.955 | >10 |
| R950180 | 0.278 | 9999 |
| R950181 | 0.254 | 9999 |
| R950182 | 0.627 | 9999 |
| R950183 | 4.797 | 9999 |
| R950184 | 2.222 | 9999 |
| R950185 | 1.03 | 8.81 |
| R950186 | 0.558 | >10 |
| R950187 | 0.724 | >10 |
| R950188 | 2.327 | 9999 |
| R950189 | 10 | 9999 |
| R950190 | 1.573 | 9999 |
| R950191 | 0.178 | 9999 |
| R950192 | 0.244 | 9999 |
| R950193 | 0.61 | 9999 |
| R950194 | 2.04 | 9999 |
| R950195 | 0.473 | 9999 |
| R950196 | 2.2 | 9999 |
| R950197 | 0.531 | 9999 |
| R950198 | 0.406 | >10 |
| R950199 | 0.408 | 9999 |
| R950200 | 0.245 | 9999 |
| R950201 | 0.261 | 9999 |
| R950202 | 3.218 | 9999 |
| R950203 | 9.035 | 9999 |
| R950204 | 6.285 | 9999 |

TABLE 1-continued

| | | |
|---|---:|---:|
| R950205 | 8.997 | 9999 |
| R950206 | 3.66 | >10 |
| R950207 | 0.164 | 9999 |
| R950208 | 0.267 | 9999 |
| R950209 | 0.748 | 9999 |
| R950210 | 10 | 9999 |
| R950211 | 10 | 9999 |
| R950212 | 0.253 | 9999 |
| R950213 | 9999 | 9999 |
| R950214 | 10 | 9999 |
| R950215 | 0.409 | 9999 |
| R950216 | 0.327 | 9999 |
| R950217 | 0.34 | 9999 |
| R950218 | 0.292 | 9999 |
| R950219 | 0.439 | 9999 |
| R950220 | 0.489 | 9999 |
| R950221 | 0.636 | 9999 |
| R950222 | 0.865 | 9999 |
| R950223 | 0.763 | 9999 |
| R950224 | 0.687 | 9999 |
| R950225 | 5.283 | 9999 |
| R950226 | 1.374 | 9999 |
| R950227 | 1.029 | 9999 |
| R950229 | 0.98 | 9999 |
| R950230 | 7.91 | 9999 |
| R950231 | 1.968 | 9999 |
| R950232 | 10 | 9999 |
| R950233 | 0.98 | 9999 |
| R950234 | 10 | 9999 |
| R950235 | 4.095 | 9999 |
| R950236 | 0.955 | 9999 |
| R950237 | 9999 | 9999 |
| R950238 | 10 | 9999 |
| R950239 | 2.063 | 9999 |
| R950240 | 1.766 | 9999 |
| R950241 | 3.275 | 9999 |
| R950251 | 9999 | 9999 |
| R950253 | 0.697 | 9999 |
| R950254 | 0.496 | 9999 |
| R950255 | 10 | 9999 |
| R908698 | 1.67 | 9999 |
| R908699 | 0.217 | 9999 |
| R908700 | 1.273 | 9999 |
| R908701 | 0.099 | 7.643 |
| R908702 | 0.104 | 7.395 |
| R908703 | 0.63 | 9999 |
| R908704 | 0.511 | 9999 |
| R908705 | 0.801 | 9999 |
| R908706 | 0.445 | 9999 |
| R908707 | 1.834 | 9999 |
| R908709 | 2.414 | |
| R908710 | 1.838 | 99 |
| R908711 | 1.761 | |
| R908712 | 0.075 | 99 |
| R908734 | 1.379 | |
| R909255 | 0.244 | 9999 |
| R909259 | 0.43 | 9999 |
| R909260 | 1.041 | 9999 |
| R909261 | 0.93 | 9999 |
| R909263 | 0.289 | 9999 |
| R909264 | | |
| R909265 | 99 | |
| R909266 | 99 | |
| R909267 | 0.589 | 9999 |
| R909268 | 0.071 | 9999 |
| R909290 | 0.226 | |
| R909292 | 1.172 | |
| R909308 | 0.671 | 9999 |
| R909309 | 0.083 | 9999 |
| R920394 | | |
| R920395 | 0.092 | 9999 |
| R920396 | | |
| R920397 | | |
| R920398 | | |
| R920399 | | |
| R920404 | | |
| R920405 | | |
| R920406 | | |
| R920407 | | |

TABLE 1-continued

| | | |
|---|---|---|
| R920408 | | |
| R920410 | 0.125 | 9999 |
| R920411 | 0.564 | 9999 |
| R925745 | 1.766 | 9999 |
| R926238 | 9999 | |
| R926752 | 0.338 | 9999 |
| R926753 | 0.108 | 9999 |
| R926754 | 0.388 | 9999 |
| R926755 | 1.693 | 9999 |
| R926756 | 1.365 | 9999 |
| R926757 | 0.158 | 9999 |
| R926759 | 0.688 | 9999 |
| R926760 | 2.893 | 9999 |
| R926761 | 0.245 | 9999 |
| R926762 | 0.386 | 9999 |
| R926763 | 0.195 | 9999 |
| R926794 | 1.382 | 9999 |
| R926826 | 0.613 | 9999 |
| R926827 | 1.098 | 9999 |
| R926828 | 0.306 | 9999 |
| R926829 | 0.688 | 9999 |
| R926830 | 0.569 | 10 |
| R926831 | 0.133 | 10 |
| R926832 | 0.365 | 9999 |
| R926833 | 1.129 | 9999 |
| R926834 | 0.145 | 9999 |
| R926835 | 0.296 | 9999 |
| R926836 | 10 | 9999 |
| R926837 | 2.994 | 9999 |
| R926838 | 0.583 | 9999 |
| R926839 | 0.161 | 9999 |
| R926840 | 1.1 | 9999 |
| R926841 | 0.551 | 9999 |
| R926842 | 7.733 | 9999 |
| R926843 | 7.371 | 9999 |
| R926844 | 1.1 | 9999 |
| R926845 | 2.558 | 7.812 |
| R926846 | 0.86 | 6.264 |
| R926847 | 1.479 | 6.264 |
| R926848 | 0.254 | 10 |
| R926851 | 0.446 | |
| R926855 | 9999 | 9999 |
| R926856 | 0.734 | 9999 |
| R926857 | 1.209 | 9999 |
| R926859 | | |
| R926860 | 1.949 | 99 |
| R926862 | 0.774 | 9999 |
| R926863 | | |
| R926866 | | |
| R926870 | 3.294 | |
| R926871 | 2.146 | |
| R926874 | 0.638 | 9999 |
| R926879 | 0.397 | 9999 |
| R926880 | | |
| R926881 | | |
| R926883 | | |
| R926885 | | |
| R926886 | | |
| R926887 | 1.747 | |
| R926890 | 0.361 | 9999 |
| R926891 | 0.152 | 9999 |
| R926892 | 0.685 | 9999 |
| R926893 | 10 | 9999 |
| R926894 | 9999 | 9999 |
| R926895 | 0.339 | 9999 |
| R926896 | 1.622 | 9999 |
| R926897 | 1.727 | 9999 |
| R926898 | 1.1 | 9999 |
| R926899 | 1.1 | 9999 |
| R926900 | 9999 | 9999 |
| R926902 | 1.37 | 4.586 |
| R926903 | 0.243 | 9999 |
| R926904 | 0.538 | |
| R926905 | 99 | |
| R926906 | 0.794 | |
| R926907 | 0.764 | |
| R926908 | 0.585 | |
| R926909 | 0.379 | |
| R926913 | 0.548 | 9999 |

TABLE 1-continued

| | | |
|---|---|---|
| R926914 | 1.86 | 9999 |
| R926915 | 1.713 | 9999 |
| R926916 | 1.958 | 9999 |
| R926917 | 1.169 | 9999 |
| R926918 | 2.521 | 9999 |
| R926919 | 1.413 | 9999 |
| R926922 | 0.305 | 9999 |
| R926923 | 0.346 | 9999 |
| R926925 | 0.307 | 99 |
| R926926 | 0.401 | 9999 |
| R926927 | 0.348 | 9999 |
| R926928 | 0.575 | 9999 |
| R926929 | 1.916 | 9999 |
| R926930 | 99 | 9999 |
| R926931 | | |
| R926932 | 0.31 | 9999 |
| R926933 | | |
| R926934 | | |
| R926935 | 4.44 | |
| R926936 | | |
| R926937 | | |
| R926938 | | |
| R926939 | 3.615 | |
| R926940 | 7.754 | |
| R926941 | 4.195 | |
| R926942 | 4.81 | |
| R926943 | | |
| R926944 | 0.225 | 99 |
| R926945 | 0.457 | 9999 |
| R926946 | | |
| R926947 | 0.354 | 9999 |
| R926948 | 0.246 | 9999 |
| R926949 | 0.089 | 9999 |
| R926950 | 99 | 9999 |
| R926951 | 0.183 | 9999 |
| R926953 | 0.049 | 9999 |
| R926954 | 0.284 | 9999 |
| R926955 | 0.36 | 9999 |
| R926956 | 0.211 | 9999 |
| R927016 | 1.408 | |
| R927017 | 2.449 | |
| R927018 | 1.446 | |
| R927019 | 1.179 | |
| R927020 | 1.316 | 9999 |
| R927023 | 0.918 | 9999 |
| R935221 | 9999 | 9999 |
| R935222 | 0.52 | 9999 |
| R935223 | 0.469 | 9999 |
| R935224 | 4.578 | 9999 |
| R935225 | 6.495 | 9999 |
| R935237 | 0.24 | 9999 |
| R935238 | 1.854 | 9999 |
| R935239 | 0.609 | 9999 |
| R935240 | 0.606 | 9999 |
| R935242 | 2.855 | 9999 |
| R935248 | 1.1 | 9999 |
| R935249 | 1.1 | 9999 |
| R935250 | 1.1 | 9999 |
| R935251 | | |
| R935252 | | |
| R935253 | | |
| R935255 | 0.374 | 9999 |
| R935256 | 0.324 | 9999 |
| R935258 | 1.191 | 9999 |
| R935259 | 1.777 | 9999 |
| R935261 | 0.391 | 9999 |
| R935262 | 0.516 | 9999 |
| R935263 | 0.106 | 10 |
| R935264 | 0.135 | 9999 |
| R935266 | 2.97 | |
| R935267 | 2.463 | |
| R935268 | 1.059 | |
| R935269 | 1.715 | |
| R935271 | | |
| R935276 | 2.33 | |
| R935277 | 22.883 | 8.9 |
| R935278 | 4.753 | 9999 |
| R935279 | 0.889 | 9999 |
| R935280 | 99 | |

TABLE 1-continued

| | | |
|---|---|---|
| R935281 | 1.399 | 9999 |
| R935286 | 1.158 | 9999 |
| R935287 | 0.403 | 9999 |
| R935288 | 1.58 | 9999 |
| R935289 | 1.688 | 9999 |
| R935290 | 0.34 | 9999 |
| R935291 | 1.364 | 9999 |
| R935292 | 0.483 | 9999 |
| R935293 | 0.141 | 9999 |
| R935294 | 0.388 | 9999 |
| R935295 | 1.943 | 9999 |
| R935296 | 99 | 9999 |
| R935297 | 7.328 | 9999 |
| R935298 | 0.252 | 99 |
| R935299 | 0.21 | 9999 |
| R935300 | 0.243 | 9999 |
| R935301 | 4.05 | 99 |
| R935302 | 0.189 | 9999 |
| R935303 | 0.244 | 99 |
| R935304 | 0.188 | 9999 |
| R935305 | 0.495 | 9999 |
| R935306 | 0.345 | 99 |
| R935307 | 0.139 | 99 |
| R935308 | 0.275 | 9999 |
| R935309 | | |
| R935310 | | |
| R935320 | 2.769 | |
| R935321 | 2.986 | |
| R935322 | 3.416 | |
| R935323 | 9999 | |
| R935324 | 9999 | |
| R935336 | 0.341 | 9999 |
| R935337 | 9999 | |
| R935338 | 0.411 | 9999 |
| R935339 | 9999 | |
| R935340 | 3.606 | |
| R935351 | 9999 | 9999 |
| R935352 | | |
| R935353 | 9999 | 9999 |
| R935354 | 99 | 9999 |
| R935355 | 9999 | 9999 |
| R935356 | 99 | |
| R935357 | 99 | 9999 |
| R935358 | 9999 | 9999 |
| R935359 | 1.027 | 9999 |
| R935360 | 0.903 | 9999 |
| R935361 | 1.438 | 9999 |
| R935362 | 0.409 | 9999 |
| R935363 | 0.405 | 9999 |
| R935364 | 0.563 | 9999 |
| R935365 | 0.373 | 9999 |
| R935366 | 0.216 | 9999 |
| R935367 | 0.053 | 9999 |
| R940079 | 9999 | |
| R940110 | 9999 | 9999 |
| R940299 | 2.497 | 9999 |
| R940300 | 10 | 9999 |
| R940301 | 1.975 | 9999 |
| R940304 | 9999 | 9999 |
| R940306 | 1.1 | 9999 |
| R940307 | 0.291 | 9999 |
| R940308 | 0.612 | 4.168 |
| R940309 | 1.132 | 9999 |
| R940311 | 1.95 | |
| R940312 | 2.557 | |
| R940314 | 4.197 | |
| R940316 | 1.858 | |
| R940317 | 0.913 | 9999 |
| R940318 | 3.792 | |
| R940319 | 9999 | |
| R940321 | 9999 | |
| R940323 | 0.048 | 9999 |
| R940337 | 1.098 | |
| R940338 | 0.073 | 9999 |
| R921303 | 0.033 | 99 |
| R940345 | 1.712 | |
| R940346 | 0.142 | 99 |
| R940347 | 0.063 | 99 |
| R940348 | 2.189 | |

TABLE 1-continued

| | | |
|---|---|---|
| R940349 | 0.044 | 7.4 |
| R940350 | 0.092 | 4 |
| R940351 | 0.12 | 2.7 |
| R940352 | 0.101 | 9999 |
| R940353 | 0.091 | 9999 |
| R940354 | 0.115 | 99 |
| R945236 | 0.562 | 9999 |
| R945237 | 0.461 | 9999 |
| R945242 | 0.247 | 9999 |
| R945263 | 1.642 | |
| R921304 | 0.085 | 9999 |
| R945299 | | |
| R950244 | 9999 | |
| R950245 | 9999 | |
| R950246 | 9999 | |
| R950247 | 9999 | |
| R950261 | 0.611 | 9999 |
| R950262 | 0.285 | 9999 |
| R950263 | 0.284 | 3.299 |
| R950264 | 0.198 | 9999 |
| R950265 | 0.312 | 9999 |
| R950266 | 0.645 | 9999 |
| R950267 | 0.18 | 9999 |
| R950290 | 9999 | 9999 |
| R950291 | 9999 | 9999 |
| R950293 | 3.689 | 8.155 |
| R950294 | 2.005 | 8.005 |
| R950295 | 2.041 | 8.795 |
| R950296 | 0.495 | 9999 |
| R950344 | 99 | |
| R950345 | 1.962 | 99 |
| R950346 | 0.345 | 9999 |
| R950347 | 0.548 | |
| R950348 | 0.066 | |
| R950349 | 0.078 | 9999 |
| R950356 | | |
| R950368 | 0.038 | 9999 |
| R950371 | | |
| R950372 | 1.348 | 9999 |
| R950373 | | |
| R950374 | 0.599 | 9999 |
| R950376 | 2.539 | |
| R950377 | 99 | |
| R950378 | | |
| R950379 | 0.545 | 9999 |
| R950380 | 3 | 9999 |
| R950381 | 0.11 | 99 |
| R950382 | | |
| R950383 | 0.114 | 9999 |
| R950385 | | |
| R950386 | 0.973 | |
| R950388 | 2.518 | |
| R950389 | 0.612 | 9999 |
| R950391 | 999 | 9999 |
| R950392 | 0.956 | 9999 |
| R950393 | 0.404 | 9999 |
| R945028 | | |
| R935241 | | |
| R940298 | | |
| R940302 | | |
| R940303 | | |
| R940305 | | |
| R935260 | 9999 | |
| R909258 | | |
| R940313 | 9999 | |
| R940315 | 9999 | |
| R935275 | 9999 | |
| R940320 | 9999 | |
| R940322 | 9999 | 9999 |
| R926910 | 9999 | 9999 |
| R926911 | 9999 | 9999 |
| R926912 | 9999 | 9999 |
| R926853 | 9999 | 9999 |
| R926852 | 9999 | 9999 |
| R926854 | 9999 | 9999 |
| R926920 | 9999 | 9999 |
| R926921 | 99 | 9999 |
| R926924 | 99 | 9999 |
| R926858 | | |

TABLE 1-continued

| Test Compound | | |
|---|---|---|
| R926861 | 9999 | 9999 |
| R945298 | 9999 | 9999 |
| R940328 | 9999 | |
| R926869 | | |
| R926873 | 9999 | |
| R926875 | 9999 | |
| R926876 | 9999 | |
| R926877 | 9999 | |
| R940336 | 9999 | |
| R926878 | 9999 | |
| R926882 | 9999 | |
| R926884 | 9999 | |
| R926889 | 9999 | |
| R920400 | 9999 | |
| R920401 | 9999 | |
| R920402 | 9999 | |
| R920403 | 9999 | |
| R940342 | 99 | |
| R920409 | 9999 | |
| R940344 | 9999 | |
| R926888 | 9999 | |
| R926758 | | |
| R927024 | 0.326 | 99 |
| R927025 | 0.326 | |
| R927026 | 9999 | 9999 |
| R927027 | 9999 | 9999 |
| R927028 | 0.208 | 9999 |
| R927029 | | |
| R927030 | 0.26 | 9999 |
| R927031 | 0.215 | 99 |
| R927032 | 0.899 | |
| R927035 | 0.583 | 9999 |
| R927036 | | |
| R927037 | 0.233 | 9999 |
| R927038 | 1.05 | 9999 |
| R927039 | 1.23 | 9999 |
| R927040 | 1.05 | 9999 |
| R927041 | 0.788 | 9999 |
| R927042 | | |
| R935270 | | |
| R935368 | 0.082 | 9999 |
| R935369 | 0.255 | 9999 |
| R935370 | | |
| R935371 | 0.794 | 9999 |
| R935372 | 0.06 | 9999 |
| R935373 | 0.274 | 9999 |
| R935374 | 0.356 | 9999 |
| R935375 | 10 | 9999 |
| R935376 | | |
| R935377 | | |
| R935378 | 0.566 | 9999 |
| R935379 | | |
| R935380 | 1.61 | 99 |

| | | | | High Density | | | |
|---|---|---|---|---|---|---|---|
| Test Compound | Basophils Dust mite Histamine | BMMC anti-IgE hexos | BMMC Ionomycin Hexos. | BMMC anti-IgE histamine | BMMC anti-IgE LTC4 | BMMC anti-IgE TNF-alpha | BMMC anti-IgE IL-6 |
| R008951 | | | | | | | |
| R008952 | | | | | | | |
| R008953 | | | | | | | |
| R008955 | | | | | | | |
| R008956 | | | | | | | |
| R008958 | | | | | | | |
| R067934 | | | | | | | |
| R067963 | | | | | | | |
| R070153 | | | | | | | |
| R070790 | | | | | | | |
| R070791 | | | | | | | |
| R081166 | | | | | | | |
| R088814 | | | | | | | |
| R088815 | | | | | | | |
| R091880 | | | | | | | |
| R092788 | | | | | | | |
| R908696 | | | | | | | |
| R908697 | | | | | | | |
| R909236 | | | | | | | |

TABLE 1-continued

| | | | | | | | |
|---|---|---|---|---|---|---|---|
| R909237 | | | | | | | |
| R909238 | | <0.22 | | <0.22 | 0.521 | 0.432 | <0.22 |
| R909239 | | | | | | | |
| R909240 | | | | | | | |
| R909241 | | <0.22 | | <0.22 | 1.021 | 0.253 | <0.22 |
| R909242 | | | | | | | |
| R909243 | | | | | | | |
| R909245 | | | | | | | |
| R909246 | | | | | | | |
| R909247 | | | | | | | |
| R909248 | | | | | | | |
| R909249 | | | | | | | |
| R909250 | | | | | | | |
| R909251 | | | | | | | |
| R909252 | | | | | | | |
| R909253 | | | | | | | |
| R909254 | | | | | | | |
| R920664 | | | | | | | |
| R920665 | | | | | | | |
| R920666 | | | | | | | |
| R920668 | | | | | | | |
| R920669 | | | | | | | |
| R920670 | | | | | | | |
| R920671 | | | | | | | |
| R920672 | | | | | | | |
| R920818 | | | | | | | |
| R920819 | | | | | | | |
| R920820 | | | | | | | |
| R920846 | | | | | | | |
| R920860 | | | | | | | |
| R920861 | | | | | | | |
| R920893 | | | | | | | |
| R920894 | | | | | | | |
| R920910 | | | | | | | |
| R920917 | | | | | | | |
| R921218 | 0.302 | 0.133 | 9999 | 0.203 | 0.766 | 0.274 | 0.100 |
| R921219 | 0.020 | 0.069 | | 0.058 | 0.040 | 0.039 | 0.009 |
| R925734 | | 9999 | 9999 | | | | |
| R925747 | | 3.1 | | | | | |
| R925755 | | | | | | | |
| R925757 | | | | | | | |
| R925758 | | | | | | | |
| R925760 | | | | | | | |
| R925765 | | | | | | | |
| R925766 | | | | | | | |
| R925767 | | | | | | | |
| R925768 | | | | | | | |
| R925769 | | | | | | | |
| R925770 | | | | | | | |
| R925771 | | | | | | | |
| R925772 | | | | | | | |
| R925773 | | | | | | | |
| R925774 | | | | | | | |
| R925775 | | | | | | | |
| R925776 | | | | | | | |
| R925778 | | | | | | | |
| R925779 | | | | | | | |
| R925783 | | | | | | | |
| R925784 | | | | | | | |
| R925785 | | | | | | | |
| R925786 | | | | | | | |
| R925787 | | | | | | | |
| R925788 | | | | | | | |
| R925790 | | | | | | | |
| R925791 | | | | | | | |
| R925792 | | | | | | | |
| R925794 | | | | | | | |
| R925795 | | | | | | | |
| R925796 | | | | | | | |
| R925797 | | | | | | | |
| R925798 | | | | | | | |
| R925799 | | | | | | | |
| R925800 | | | | | | | |
| R925801 | | | | | | | |
| R925802 | | | | | | | |
| R925803 | | | | | | | |
| R925804 | | | | | | | |
| R925805 | | | | | | | |
| R925806 | | | | | | | |

TABLE 1-continued

| | | |
|---|---|---|
| R925807 | | |
| R925808 | | |
| R925810 | | |
| R925811 | | |
| R925812 | | |
| R925813 | | |
| R925814 | | |
| R925815 | | |
| R925816 | | |
| R925819 | | |
| R925820 | | |
| R925821 | | |
| R925822 | | |
| R925823 | | |
| R925824 | | |
| R925837 | | |
| R925838 | | |
| R925839 | | |
| R925840 | | |
| R925841 | | |
| R925842 | | |
| R925843 | | |
| R925844 | | |
| R925845 | | |
| R925846 | | |
| R925849 | | |
| R925851 | | |
| R925852 | | |
| R925853 | | |
| R925854 | | |
| R925855 | | |
| R925856 | | |
| R925857 | | |
| R925858 | | |
| R925859 | | |
| R925860 | | |
| R925861 | | |
| R925862 | | |
| R925863 | | |
| R925864 | | |
| R925865 | | |
| R926016 | 9999 | 9999 |
| R926017 | 1.4 | 9.6 |
| R926018 | 8.5 | 9999 |
| R926037 | 9999 | 9999 |
| R926038 | 9999 | 9999 |
| R926039 | 9999 | 9999 |
| R926058 | 9999 | 9999 |
| R926064 | 5.9 | 7.3 |
| R926065 | 9999 | 9999 |
| R926068 | 7.4 | 8.2 |
| R926069 | 4.5 | 4.4 |
| R926072 | 9999 | 9999 |
| R926086 | 2.8 | 7.3 |
| R926108 | 0.9 | 9999 |
| R926109 | 0.6 | 3.2 |
| R926110 | 1 | 4.5 |
| R926113 | 0.65 | 9999 |
| R926114 | 9999 | 9999 |
| R926145 | 2.4 | 8.8 |
| R926146 | 1.35 | 5 |
| R926147 | 2 | 7.1 |
| R926206 | 6.6 | 8.6 |
| R926209 | 10 | 9.1 |
| R926210 | 0.6 | >10 |
| R926211 | 3.9 | >10 |
| R926212 | 0.5 | 5 |
| R926213 | | |
| R926218 | 9999 | 9999 |
| R926219 | 2.5 | 3.2 |
| R926220 | 9999 | 9999 |
| R926221 | 9.9 | 9999 |
| R926222 | 9999 | 9999 |
| R926223 | 9999 | 9999 |
| R926224 | 9999 | 9999 |
| R926225 | 9999 | 9999 |
| R926228 | 9999 | |
| R926229 | | |
| R926230 | | |

TABLE 1-continued

| | | | | | | |
|---|---|---|---|---|---|---|
| R926234 | | 9999 | | | | |
| R926237 | | 1.9 | | | | |
| R926240 | | | | | | |
| R926241 | | | | | | |
| R926242 | | | | | | |
| R926243 | | | | | | |
| R926245 | | | | | | |
| R926248 | | | | | | |
| R926249 | | | | | | |
| R926252 | | | | | | |
| R926253 | | | | | | |
| R926254 | | | | | | |
| R926255 | | | | | | |
| R926256 | | | | | | |
| R926257 | | | | | | |
| R926258 | | | | | | |
| R926259 | | | | | | |
| R926319 | | | | | | |
| R926320 | | | | | | |
| R926321 | | | | | | |
| R926325 | | | | | | |
| R926331 | | | | | | |
| R926339 | | | | | | |
| R926340 | | | | | | |
| R926341 | | | | | | |
| R926342 | | | | | | |
| R926376 | | | | | | |
| R926386 | | | | | | |
| R926387 | | | | | | |
| R926394 | | | | | | |
| R926395 | | | | | | |
| R926396 | | | | | | |
| R926397 | | | | | | |
| R926398 | | | | | | |
| R926399 | | | | | | |
| R926400 | | | | | | |
| R926401 | | | | | | |
| R926402 | | | | | | |
| R926403 | | | | | | |
| R926404 | | | | | | |
| R926405 | | | | | | |
| R926406 | | | | | | |
| R926408 | | | | | | |
| R926409 | | | | | | |
| R926411 | | | | | | |
| R926412 | | | | | | |
| R926461 | | | | | | |
| R926467 | | | | | | |
| R926469 | | | | | | |
| R926474 | | | | | | |
| R926475 | | | | | | |
| R926476 | | | | | | |
| R926477 | | | | | | |
| R926478 | | | | | | |
| R926479 | | | | | | |
| R926480 | | | | | | |
| R926481 | | | | | | |
| R926482 | | | | | | |
| R926483 | | | | | | |
| R926484 | | | | | | |
| R926485 | | | | | | |
| R926486 | | | | | | |
| R926487 | | | | | | |
| R926488 | | | | | | |
| R926489 | | | | | | |
| R926490 | | | | | | |
| R926491 | | | | | | |
| R926492 | | | | | | |
| R926493 | | | | | | |
| R926494 | | | | | | |
| R926495 | 0.038 | 0.056 | 0.089 | 0.24 | 0.077 | 0.028 |
| R926496 | | | | | | |
| R926497 | 0.205 | | | | | |
| R926498 | | <0.22 | 0.515 | 0.995 | 0.614 | <0.22 |
| R926499 | | | | | | |
| R926500 | | | | | | |
| R926501 | 0.645 | | | | | |
| R926502 | 0.491 | | | | | |
| R926503 | | | | | | |

TABLE 1-continued

| | | | | | | |
|---|---|---|---|---|---|---|
| R926504 | | | | | | |
| R926505 | | <0.22 | <0.22 | <0.22 | <0.22 | <0.22 |
| R926506 | | | | | | |
| R926508 | 0.054 | 0.086 | 0.107 | 0.162 | 0.054 | 0.026 |
| R926509 | | | | | | |
| R926510 | | | | | | |
| R926511 | | | | | | |
| R926514 | | | | | | |
| R926516 | | | | | | |
| R926526 | | | | | | |
| R926527 | | | | | | |
| R926528 | | | | | | |
| R926535 | | | | | | |
| R926536 | | | | | | |
| R926555 | | | | | | |
| R926559 | | | | | | |
| R926560 | | | | | | |
| R926562 | | | | | | |
| R926563 | | | | | | |
| R926564 | | | | | | |
| R926565 | | | | | | |
| R926566 | | | | | | |
| R926567 | | | | | | |
| R926569 | | | | | | |
| R926571 | | | | | | |
| R926572 | | | | | | |
| R926574 | | | | | | |
| R926576 | | | | | | |
| R926579 | | | | | | |
| R926580 | | | | | | |
| R926582 | | | | | | |
| R926583 | | | | | | |
| R926584 | | | | | | |
| R926585 | | | | | | |
| R926586 | | | | | | |
| R926587 | | | | | | |
| R926588 | | | | | | |
| R926589 | | | | | | |
| R926591 | | | | | | |
| R926593 | | | | | | |
| R926594 | | | | | | |
| R926595 | | | | | | |
| R926604 | | | | | | |
| R926605 | | | | | | |
| R926614 | | | | | | |
| R926615 | | | | | | |
| R926616 | | | | | | |
| R926617 | | | | | | |
| R926620 | | | | | | |
| R926623 | | | | | | |
| R926662 | | | | | | |
| R926663 | | | | | | |
| R926675 | | | | | | |
| R926676 | | | | | | |
| R926680 | | | | | | |
| R926681 | | | | | | |
| R926682 | | | | | | |
| R926683 | | | | | | |
| R926688 | | | | | | |
| R926690 | | | | | | |
| R926696 | | | | | | |
| R926698 | | | | | | |
| R926699 | | | | | | |
| R926700 | | | | | | |
| R926701 | | | | | | |
| R926702 | | | | | | |
| R926703 | | | | | | |
| R926704 | | | | | | |
| R926705 | | | | | | |
| R926706 | | | | | | |
| R926707 | | <0.056 | <0.056 | 0.39 | 0.088 | <0.056 |
| R926708 | | | | | | |
| R926709 | | | | | | |
| R926710 | | | | | | |
| R926711 | | | | | | |
| R926712 | | | | | | |
| R926713 | | | | | | |
| R926714 | | | | | | |
| R926715 | | | | | | |

TABLE 1-continued

| | | | | | | |
|---|---|---|---|---|---|---|
| R926716 | | | | | | |
| R926717 | | | | | | |
| R926718 | | | | | | |
| R926719 | | | | | | |
| R926720 | | | | | | |
| R926721 | | | | | | |
| R926722 | | | | | | |
| R926723 | | | | | | |
| R926724 | | | | | | |
| R926725 | | | | | | |
| R926726 | | | | | | |
| R926727 | | | | | | |
| R926728 | | | | | | |
| R926730 | | | | | | |
| R926731 | | | | | | |
| R926732 | | | | | | |
| R926733 | | | | | | |
| R926734 | | | | | | |
| R926735 | | | | | | |
| R926736 | | | | | | |
| R926737 | | 0.075 | 0.073 | 0.046 | 0.068 | 0.017 |
| R926738 | | | | | | |
| R926739 | | | | | | |
| R926740 | | | | | | |
| R926741 | | 0.961 | 1.025 | 9999 | 0.772 | 0.537 |
| R926742 | 0.055 | 0.041 | 0.055 | 0.105 | 0.053 | 0.022 |
| R926743 | | | | | | |
| R926744 | | | | | | |
| R926745 | | | | | | |
| R926746 | | | | | | |
| R926747 | | | | | | |
| R926748 | | | | | | |
| R926749 | | | | | | |
| R926750 | | | | | | |
| R926751 | | | | | | |
| R926764 | | | | | | |
| R926765 | | | | | | |
| R926766 | | | | | | |
| R926767 | | | | | | |
| R926768 | | | | | | |
| R926769 | | | | | | |
| R926770 | | | | | | |
| R926771 | | | | | | |
| R926772 | | | | | | |
| R926773 | | | | | | |
| R926774 | | | | | | |
| R926775 | | | | | | |
| R926776 | | | | | | |
| R926777 | | | | | | |
| R926778 | | | | | | |
| R926779 | | | | | | |
| R926780 | | <0.22 | <0.22 | 0.461 | <0.22 | <0.22 |
| R926781 | | | | | | |
| R926782 | | <0.22 | <0.22 | 1.461 | 0.276 | <0.22 |
| R926783 | | | | | | |
| R926784 | | | | | | |
| R926785 | | 0.989 | 0.561 | 1.411 | 1.312 | 0.513 |
| R926786 | | | | | | |
| R926787 | | | | | | |
| R926788 | | | | | | |
| R926789 | | | | | | |
| R926790 | | | | | | |
| R926791 | | 0.064 | <0.056 | 0.896 | 0.205 | <0.056 |
| R926792 | | | | | | |
| R926793 | | | | | | |
| R926795 | | | | | | |
| R926796 | | | | | | |
| R926797 | | | | | | |
| R926798 | | | | | | |
| R926799 | | | | | | |
| R926800 | | | | | | |
| R926801 | | | | | | |
| R926802 | | | | | | |
| R926803 | | | | | | |
| R926804 | | | | | | |
| R926805 | | | | | | |
| R926806 | | | | | | |
| R926807 | | | | | | |
| R926808 | | | | | | |

TABLE 1-continued

| | | | | | |
|---|---|---|---|---|---|
| R926809 | | | | | |
| R926810 | | | | | |
| R926811 | | | | | |
| R926812 | | | | | |
| R926813 | | | | | |
| R926814 | | | | | |
| R926815 | | | | | |
| R926816 | | | | | |
| R935000 | | | | | |
| R935001 | | | | | |
| R935002 | | | | | |
| R935003 | | | | | |
| R935004 | | | | | |
| R935005 | | | | | |
| R935006 | | | | | |
| R935016 | | | | | |
| R935019 | | | | | |
| R935020 | | | | | |
| R935021 | | | | | |
| R935023 | | | | | |
| R935025 | | | | | |
| R935029 | | | | | |
| R935075 | | | | | |
| R935076 | | | | | |
| R935077 | | | | | |
| R935114 | | | | | |
| R935117 | | | | | |
| R935134 | | | | | |
| R935135 | | | | | |
| R935136 | | | | | |
| R935137 | | | | | |
| R935138 | <0.22 | <0.22 | 0.373 | 0.409 | <0.22 |
| R935139 | | | | | |
| R935140 | | | | | |
| R935141 | | | | | |
| R935142 | | | | | |
| R935143 | | | | | |
| R935144 | | | | | |
| R935145 | | | | | |
| R935146 | | | | | |
| R935147 | | | | | |
| R935148 | | | | | |
| R935149 | | | | | |
| R935150 | | | | | |
| R935151 | | | | | |
| R935152 | | | | | |
| R935153 | | | | | |
| R935154 | 0.104 | 0.085 | 0.547 | 0.131 | 0.041 |
| R935155 | | | | | |
| R935156 | <0.22 | <0.22 | 0.433 | 0.22 | <0.22 |
| R935157 | | | | | |
| R935158 | | | | | |
| R935159 | | | | | |
| R935160 | <0.22 | 0.317 | 0.876 | 0.484 | <0.22 |
| R935161 | | | | | |
| R935162 | | | | | |
| R935163 | | | | | |
| R935164 | | | | | |
| R935165 | | | | | |
| R935166 | | | | | |
| R935167 | | | | | |
| R935168 | | | | | |
| R935169 | | | | | |
| R935170 | | | | | |
| R935171 | | | | | |
| R935172 | | | | | |
| R935173 | | | | | |
| R935174 | | | | | |
| R935175 | | | | | |
| R935176 | | | | | |
| R935177 | | | | | |
| R935178 | | | | | |
| R935179 | | | | | |
| R935180 | | | | | |
| R935181 | | | | | |
| R935182 | | | | | |
| R935183 | | | | | |
| R935184 | | | | | |
| R935185 | | | | | |

TABLE 1-continued

| | | | | | |
|---|---|---|---|---|---|
| R935186 | | | | | |
| R935187 | | | | | |
| R935188 | | | | | |
| R935189 | | | | | |
| R935190 | | | | | |
| R935191 | 0.068 | 0.043 | 0.213 | 0.071 | 0.027 |
| R935192 | | | | | |
| R935193 | 0.08 | 0.048 | 0.312 | 0.092 | 0.037 |
| R935194 | 0.125 | 0.054 | 0.493 | 0.118 | 0.034 |
| R935196 | | | | | |
| R935197 | | | | | |
| R935198 | | | | | |
| R935199 | | | | | |
| R935202 | | | | | |
| R935203 | | | | | |
| R935204 | | | | | |
| R935205 | | | | | |
| R935206 | | | | | |
| R935207 | | | | | |
| R935208 | | | | | |
| R935209 | | | | | |
| R935211 | | | | | |
| R935212 | | | | | |
| R935213 | | | | | |
| R935214 | | | | | |
| R935218 | | | | | |
| R935219 | | | | | |
| R935220 | | | | | |
| R940089 | | | | | |
| R940090 | | | | | |
| R940095 | | | | | |
| R940100 | | | | | |
| R940215 | | | | | |
| R940216 | | | | | |
| R940217 | | | | | |
| R940222 | | | | | |
| R940233 | | | | | |
| R940235 | | | | | |
| R940250 | | | | | |
| R940251 | | | | | |
| R940253 | | | | | |
| R940254 | | | | | |
| R940255 | | | | | |
| R940256 | | | | | |
| R940257 | | | | | |
| R940258 | | | | | |
| R940260 | | | | | |
| R940261 | | | | | |
| R940262 | | | | | |
| R940263 | | | | | |
| R940264 | | | | | |
| R940265 | 0.981 | 0.306 | 1.211 | 1.131 | 0.486 |
| R940266 | | | | | |
| R940267 | | | | | |
| R940269 | | | | | |
| R940270 | | | | | |
| R940271 | | | | | |
| R940275 | | | | | |
| R940276 | 0.136 | 0.073 | 0.332 | 0.251 | <0.056 |
| R940277 | 0.279 | 0.315 | 0.625 | 0.262 | 0.181 |
| R940280 | | | | | |
| R940281 | | | | | |
| R940282 | | | | | |
| R940283 | | | | | |
| R940284 | | | | | |
| R940285 | | | | | |
| R940286 | | | | | |
| R940287 | | | | | |
| R940288 | | | | | |
| R940289 | | | | | |
| R940290 | 0.255 | 0.545 | 0.59 | 0.246 | 0.1 |
| R940291 | | | | | |
| R940292 | | | | | |
| R940293 | | | | | |
| R940294 | | | | | |
| R940295 | | | | | |
| R940296 | | | | | |
| R940297 | | | | | |
| R945025 | | | | | |

TABLE 1-continued

| | | | | | |
|---|---|---|---|---|---|
| R945032 | | | | | |
| R945033 | | | | | |
| R945034 | | | | | |
| R945035 | | | | | |
| R945036 | | | | | |
| R945037 | | | | | |
| R945038 | | | | | |
| R945040 | | | | | |
| R945041 | | | | | |
| R945042 | | | | | |
| R945043 | | | | | |
| R945045 | | | | | |
| R945046 | | | | | |
| R945047 | | | | | |
| R945048 | | | | | |
| R945051 | | | | | |
| R945052 | | | | | |
| R945053 | | | | | |
| R945056 | | | | | |
| R945057 | | | | | |
| R945060 | | | | | |
| R945061 | | | | | |
| R945062 | | | | | |
| R945063 | | | | | |
| R945064 | | | | | |
| R945065 | | | | | |
| R945066 | | | | | |
| R945067 | | | | | |
| R945068 | | | | | |
| R945070 | | | | | |
| R945071 | | | | | |
| R945096 | | | | | |
| R945097 | | | | | |
| R945109 | | | | | |
| R945110 | | | | | |
| R945117 | | | | | |
| R945118 | | | | | |
| R945124 | | | | | |
| R945125 | | | | | |
| R945126 | | | | | |
| R945127 | | | | | |
| R945128 | | | | | |
| R945129 | | | | | |
| R945130 | | | | | |
| R945131 | | | | | |
| R945132 | | | | | |
| R945133 | | | | | |
| R945134 | | | | | |
| R945135 | | | | | |
| R945137 | | | | | |
| R945138 | | | | | |
| R945139 | | | | | |
| R945140 | | | | | |
| R945142 | | | | | |
| R945144 | | | | | |
| R945145 | | | | | |
| R945146 | | | | | |
| R945147 | | | | | |
| R945148 | | | | | |
| R945149 | | | | | |
| R945150 | >2 | >2 | 9999 | 0.709 | 0.634 |
| R945151 | | | | | |
| R945152 | | | | | |
| R945153 | | | | | |
| R945155 | | | | | |
| R945156 | | | | | |
| R945157 | | | | | |
| R945162 | | | | | |
| R945163 | | | | | |
| R945164 | | | | | |
| R945165 | | | | | |
| R945166 | | | | | |
| R945167 | | | | | |
| R945168 | | | | | |
| R945169 | | | | | |
| R945170 | | | | | |
| R945171 | | | | | |
| R945172 | | | | | |
| R945173 | | | | | |

TABLE 1-continued

| | | | | | | |
|---|---|---|---|---|---|---|
| R945175 | | | | | | |
| R950082 | | | | | | |
| R950083 | | | | | | |
| R950090 | | | | | | |
| R921302 | 0.282 | | | | | |
| R950092 | | | | | | |
| R950093 | | | | | | |
| R950100 | | | | | | |
| R950107 | | | | | | |
| R950108 | | | | | | |
| R950109 | | | | | | |
| R950120 | | | | | | |
| R950121 | | | | | | |
| R950122 | | | | | | |
| R950123 | | | | | | |
| R950125 | | | | | | |
| R950129 | | | | | | |
| R950130 | | | | | | |
| R950131 | | | | | | |
| R950132 | | | | | | |
| R950133 | | | | | | |
| R950134 | | | | | | |
| R950135 | | | | | | |
| R950137 | | | | | | |
| R950138 | | | | | | |
| R950139 | | | | | | |
| R950140 | | | | | | |
| R950141 | | | | | | |
| R950142 | | | | | | |
| R950143 | | | | | | |
| R950144 | | | | | | |
| R950145 | | | | | | |
| R950146 | | | | | | |
| R950147 | | | | | | |
| R950148 | | | | | | |
| R950149 | | | | | | |
| R950150 | | | | | | |
| R950151 | | | | | | |
| R950152 | | | | | | |
| R950153 | | | | | | |
| R950154 | | | | | | |
| R950155 | | | | | | |
| R950156 | | | | | | |
| R950157 | | | | | | |
| R950158 | | | | | | |
| R950159 | | | | | | |
| R950160 | | | | | | |
| R950162 | | | | | | |
| R950163 | | | | | | |
| R950164 | | | | | | |
| R950165 | | | | | | |
| R950166 | | | | | | |
| R950167 | | | | | | |
| R950168 | | | | | | |
| R950169 | | | | | | |
| R950170 | | | | | | |
| R950171 | | | | | | |
| R950172 | | | | | | |
| R950173 | | | | | | |
| R950174 | | | | | | |
| R950175 | | | | | | |
| R950176 | | | | | | |
| R950177 | | | | | | |
| R950178 | | | | | | |
| R950179 | | | | | | |
| R950180 | | | | | | |
| R950181 | | | | | | |
| R950182 | | | | | | |
| R950183 | | | | | | |
| R950184 | | | | | | |
| R950185 | | | | | | |
| R950186 | | | | | | |
| R950187 | | | | | | |
| R950188 | | | | | | |
| R950189 | | | | | | |
| R950190 | | | | | | |
| R950191 | <0.22 | | >2 | 0.401 | <0.22 | <0.22 |
| R950192 | | | | | | |
| R950193 | | | | | | |

TABLE 1-continued

| | | | | | |
|---|---|---|---|---|---|
| R950194 | | | | | |
| R950195 | | | | | |
| R950196 | | | | | |
| R950197 | | | | | |
| R950198 | | | | | |
| R950199 | | | | | |
| R950200 | | | | | |
| R950201 | | | | | |
| R950202 | | | | | |
| R950203 | | | | | |
| R950204 | | | | | |
| R950205 | | | | | |
| R950206 | | | | | |
| R950207 | <0.22 | <0.22 | 0.288 | <0.22 | <0.22 |
| R950208 | | | | | |
| R950209 | | | | | |
| R950210 | | | | | |
| R950211 | | | | | |
| R950212 | | | | | |
| R950213 | | | | | |
| R950214 | | | | | |
| R950215 | | | | | |
| R950216 | | | | | |
| R950217 | | | | | |
| R950218 | | | | | |
| R950219 | | | | | |
| R950220 | | | | | |
| R950221 | | | | | |
| R950222 | | | | | |
| R950223 | | | | | |
| R950224 | | | | | |
| R950225 | | | | | |
| R950226 | | | | | |
| R950227 | | | | | |
| R950229 | | | | | |
| R950230 | | | | | |
| R950231 | | | | | |
| R950232 | | | | | |
| R950233 | | | | | |
| R950234 | | | | | |
| R950235 | | | | | |
| R950236 | | | | | |
| R950237 | | | | | |
| R950238 | | | | | |
| R950239 | | | | | |
| R950240 | | | | | |
| R950241 | | | | | |
| R950251 | | | | | |
| R950253 | | | | | |
| R950254 | | | | | |
| R950255 | | | | | |
| R908698 | | | | | |
| R908699 | | | | | |
| R908700 | | | | | |
| R908701 | | | | | |
| R908702 | | | | | |
| R908703 | | | | | |
| R908704 | | | | | |
| R908705 | | | | | |
| R908706 | | | | | |
| R908707 | | | | | |
| R908709 | | | | | |
| R908710 | | | | | |
| R908711 | | | | | |
| R908712 | | | | | |
| R908734 | | | | | |
| R909255 | | | | | |
| R909259 | | | | | |
| R909260 | | | | | |
| R909261 | | | | | |
| R909263 | | | | | |
| R909264 | | | | | |
| R909265 | | | | | |
| R909266 | | | | | |
| R909267 | | | | | |
| R909268 | | | | | |
| R909290 | | | | | |
| R909292 | | | | | |
| R909308 | | | | | |

TABLE 1-continued

R909309
R920394
R920395
R920396
R920397
R920398
R920399
R920404
R920405
R920406
R920407
R920408
R920410
R920411
R925745
R926238
R926752
R926753
R926754
R926755
R926756
R926757
R926759
R926760
R926761
R926762
R926763
R926794
R926826
R926827
R926828
R926829
R926830
R926831
R926832
R926833
R926834
R926835
R926836
R926837
R926838
R926839
R926840
R926841
R926842
R926843
R926844
R926845
R926846
R926847
R926848
R926851
R926855
R926856
R926857
R926859
R926860
R926862
R926863
R926866
R926870
R926871
R926874
R926879
R926880
R926881
R926883
R926885
R926886
R926887
R926890
R926891
R926892
R926893
R926894
R926895
R926896
R926897
R926898

TABLE 1-continued

R926899
R926900
R926902
R926903
R926904
R926905
R926906
R926907
R926908
R926909
R926913
R926914
R926915
R926916
R926917
R926918
R926919
R926922
R926923
R926925
R926926
R926927
R926928
R926929
R926930
R926931
R926932
R926933
R926934
R926935
R926936
R926937
R926938
R926939
R926940
R926941
R926942
R926943
R926944
R926945
R926946
R926947
R926948
R926949
R926950
R926951
R926953
R926954
R926955
R926956
R927016
R927017
R927018
R927019
R927020
R927023
R935221
R935222
R935223
R935224
R935225
R935237
R935238
R935239
R935240
R935242
R935248
R935249
R935250
R935251
R935252
R935253
R935255
R935256
R935258
R935259
R935261
R935262
R935263

TABLE 1-continued

R935264
R935266
R935267
R935268
R935269
R935271
R935276
R935277
R935278
R935279
R935280
R935281
R935286
R935287
R935288
R935289
R935290
R935291
R935292
R935293
R935294
R935295
R935296
R935297
R935298
R935299
R935300
R935301
R935302
R935303
R935304
R935305
R935306
R935307
R935308
R935309
R935310
R935320
R935321
R935322
R935323
R935324
R935336
R935337
R935338
R935339
R935340
R935351
R935352
R935353
R935354
R935355
R935356
R935357
R935358
R935359
R935360
R935361
R935362
R935363
R935364
R935365
R935366
R935367
R940079
R940110
R940299
R940300
R940301
R940304
R940306
R940307
R940308
R940309
R940311
R940312
R940314
R940316
R940317

TABLE 1-continued

R940318
R940319
R940321
R940323
R940337
R940338
R921303
R940345
R940346
R940347
R940348
R940349
R940350
R940351
R940352
R940353
R940354
R945236
R945237
R945242
R945263
R921304
R945299
R950244
R950245
R950246
R950247
R950261
R950262
R950263
R950264
R950265
R950266
R950267
R950290
R950291
R950293
R950294
R950295
R950296
R950344
R950345
R950346
R950347
R950348
R950349
R950356
R950368
R950371
R950372
R950373
R950374
R950376
R950377
R950378
R950379
R950380
R950381
R950382
R950383
R950385
R950386
R950388
R950389
R950391
R950392
R950393
R945028
R935241
R940298
R940302
R940303
R940305
R935260
R909258
R940313
R940315
R935275
R940320

TABLE 1-continued

R940322
R926910
R926911
R926912
R926853
R926852
R926854
R926920
R926921
R926924
R926858
R926861
R945298
R940328
R926869
R926873
R926875
R926876
R926877
R940336
R926878
R926882
R926884
R926889
R920400
R920401
R920402
R920403
R940342
R920409
R940344
R926888
R926758
R927024
R927025
R927026
R927027
R927028
R927029
R927030
R927031
R927032
R927035
R927036
R927037
R927038
R927039
R927040
R927041
R927042
R935270
R935368
R935369
R935370
R935371
R935372
R935373
R935374
R935375
R935376
R935377
R935378
R935379
R935380

TABLE 2

| | High Density | | | | | | | | | |
|---|---|---|---|---|---|---|---|---|---|---|
| | CHMC high density hexos | CHMC high density tryptase | CHMC high density histamine | CHMC high density LTC4 | CHMC high density TNF-alpha | CHMC high density IL-13 | Toxicity Jurkat Light Scat. | Toxicity Jurkat Cell Titer Glo | Toxicity BJAB Light Scat. | Toxicity BJAB Cell Titer Glo |
| R008951 | | | | | | | | | | |
| R008952 | | | | | | | | | | |
| R008953 | | | | | | | | | | |
| R008955 | | | | | | | | | | |
| R008956 | | | | | | | | | | |
| R008958 | | | | | | | | | | |
| R067934 | | | | | | | | | | |
| R067963 | | | | | | | | | | |
| R070153 | | | | | | | | | | |
| R070791 | | | | | | | | | | |
| R081166 | | | | | | | | | | |
| R088814 | | | | | | | | | | |
| R088815 | | | | | | | | | | |
| R091880 | | | | | | | | | | |
| R092788 | | | | | | | | 9999 | | 9999 |
| R909241 | | | | | | | | 3.736 | | |
| R921219 | 0.124 | 0.121 | 0.162 | 0.034 | 0.190 | 0.175 | | >10 | | >10 |
| R925775 | | | | | | | 9999 | | 9999 | |
| R925778 | | | | | | | 9999 | | 9999 | |
| R925779 | | | | | | | >10 | | 9999 | |
| R925797 | | | | | | | >10 | | 9999 | |
| R926108 | | | | | | | >10 | | >10 | |
| R926109 | 0.783 | 0.906 | 1.827 | 0.808 | 1.504 | 1.664 | >10 | | 9999 | |
| R926110 | | | | | | | >10 | | >10 | |
| R921218 | 0.464 | 0.647 | 0.463 | 0.695 | 1.752 | 2.0776 | >10 | | >10 | |
| R926113 | 1.448 | 1.649 | 1.848 | 0.468 | 5.678 | 3.569 | >10 | | >10 | |
| R926146 | | | | | | | 9999 | | 9999 | |
| R926210 | | | | | | | >10 | | 9999 | |
| R926240 | | | | | | | 10 | | 9999 | |
| R926248 | | | | | | | >10 | | 9999 | |
| R926249 | | | | | | | >10 | | 9999 | |
| R926253 | | | | | | | 9999 | | 9999 | |
| R926256 | | | | | | | >10 | | 9999 | |
| R926258 | | | | | | | 9999 | | 9999 | |
| R926387 | | | | | | | >10 | | 9999 | |
| R926395 | | | | | | | >10 | | 9999 | |
| R926396 | | | | | | | >10 | | 9999 | |
| R926411 | | | | | | | 8.5 | | >10 | |
| R926486 | 1.088 | 1.313 | 1.928 | 0.834 | 0.455 | | | | | |
| R926488 | 0.521 | 0.623 | 0.792 | 0.201 | 2.443 | 1.012 | | | | |
| R926493 | 0.889 | 1.093 | 1.324 | 0.474 | >2 | | | >4.33 | | |
| R926494 | 0.640 | >2 | 9999 | 0.326 | 9999 | | | | | |
| R926495 | 0.100 | 0.235 | 0.066 | 0.241 | 0.362 | 0.449 | | >10 | | >10 |
| R926496 | 0.429 | 0.533 | 0.809 | 0.414 | 0.622 | | | | | |
| R926497 | 1.106 | 1.234 | 1.333 | | 1.876 | 9999 | | | | |
| R926501 | >2 | >2 | 9999 | | 9999 | 9999 | | >4.33 | | >4.33 |
| R926502 | >2 | >2 | >2 | | 1.807 | >2 | | 1.513 | | |
| R926505 | | | | | | | | 4.199 | | |
| R926508 | 0.170 | 0.434 | 0.105 | | 0.505 | 0.763 | | >10 | | >10 |
| R926510 | 0.921 | 1.115 | 1.667 | | 0.417 | 0.686 | | 2.77 | | |
| R926511 | 1.183 | 1.474 | 1.73 | | 1.307 | >2 | | >4.33 | | >4.33 |
| R926614 | >10 | >10 | | | >10 | 6.442 | | | | |
| R926696 | <1.1 | <1.1 | <1.1 | <1.1 | <1.1 | 1.773 | | >5.0 | | |
| R926699 | <1.1 | <1.1 | 1.44 | <1.1 | <1.1 | 1.294 | | | | |
| R926700 | <1.1 | <1.1 | <1.1 | <1.1 | <1.1 | 2.053 | | | | |
| R926703 | 1.512 | 1.947 | >2 | 0.724 | >2 | | | | | |
| R926704 | >2 | 9999 | 9999 | 9999 | 9999 | | | | | |
| R926705 | 1.007 | 1.256 | 0.641 | 0.494 | 9999 | | | | | |
| R926706 | >2 | 9999 | 9999 | 1.491 | 9999 | | | | | |
| R926742 | 0.104 | 0.217 | 0.080 | | 0.385 | 0.667 | | 9 | | >10 |
| R926745 | | | | | | | | >10 | | >10 |
| R926780 | | | | | | | | >5.0 | | |
| R926782 | | | | | | | | >4.33 | | >4.33 |
| R935075 | 0.647 | 1.212 | 0.443 | <0.22 | >2 | | | >4.33 | | >4.33 |
| R935154 | | | | | | | | >4.33 | | |
| R935156 | | | | | | | | 4.054 | | |
| R940216 | <1.1 | <1.1 | 1.176 | <1.1 | 3.188 | 3.006 | | | | |
| R940233 | 0.577 | 0.642 | 0.586 | 0.118 | 2.247 | 1.781 | | >4.33 | | >4.33 |
| R945032 | 0.357 | 0.458 | 0.439 | 0.0929 | 1.082 | 0.291 | | | | |
| R945033 | 8.151 | 8.868 | | | >10 | 5.983 | | | | |
| R945071 | <1.1 | <1.1 | <1.1 | <1.1 | <1.1 | <1.1 | | | | |
| R945128 | 1.279 | 1.749 | 0.547 | 0.729 | >2 | ND | | | | |

TABLE 2-continued

| | High Density | | | | | | | | | |
|---|---|---|---|---|---|---|---|---|---|---|
| | CHMC high density hexos | CHMC high density tryptase | CHMC high density histamine | CHMC high density LTC4 | CHMC high density TNF-alpha | CHMC high density IL-13 | Toxicity Jurkat Light Scat. | Toxicity Jurkat Cell Titer Glo | Toxicity BJAB Light Scat. | Toxicity BJAB Cell Titer Glo |
| R945140 | 0.994 | 1.112 | 1.551 | | 1.714 | 9999 | | | | |
| R945142 | >2 | >2 | 9999 | | >2 | 9999 | | | | |
| R945150 | | | | | | | | >4.33 | | >4.33 |
| R921302 | 0.682 | 0.795 | 1.588 | 0.514 | 1.173 | 1.672 | | | | |
| R950141 | 0.567 | 0.618 | 0.627 | 0.201 | 1.059 | 0.798 | | | | |
| R950207 | | | | | | | | >4.33 | | |

7.7 The 2,4-Pyrimidinediamine Compounds of the Invention Selectively Inhibit the Upstream IgE Receptor Cascade To confirm that many of the 2,4-pyrimidinediamine compounds of the invention exert their inhibitory activity by blocking or inhibiting the early IgE receptor signal transduction cascade, several of the compounds were tested in cellular assays for ionomycin-induced degranulation, as described below.

7.7.1 CHMC Low Cell Density Ionomycin Activation: Tryptase Assay

Assays for ionomycin-induced mast cell degranulation were carried out as described for the CHMC Low Density IgE Activation assays (Section 6.4.3, supra), with the exception that during the 1 hour incubation, 6× ionomycin solution [5 mM ionomycin (Signma 1-0634) in MeOH (stock) diluted 1:416.7 in MT buffer (2 μM final)] was prepared and cells were stimulated by adding 25 μl of the 6× ionomycin solution to the appropriate plates.

7.7.2 Basophil Ionomycin Activation: Histamine Release Assay

Assays for ionomycin-induced basophil cell degranulation were carried out as described for the Basophil IgE or Dust-mite Activation Assay (Section 6.4.6, supra), with the exception that following incubation with compound, cells were stimulated with 20 μl of 2 μM ionomycin.

7.7.3 Results

The results of the ionomycin-induced degranulation assays, reported as $IC_{50}$ values (in μM) are provided in TABLE 1, supra. Of the active compounds tested (i.e., those that inhibit IgE-induced degranulation), the vast majority do not inhibit ionomycin-induced degranulation, confirming that these active compounds selectively inhibit the early (or upstream) IgE receptor signal transduction cascade.

These results were confirmed for certain compounds by measuring anti-IgE-induced and ionomycin-induced calcium ion flux in CHMC cells. In these $Ca^{2+}$ flux tests, 10 μM R921218 and 10 μM R902420 inhibited anti-IgE-induced $Ca^{2+}$ flux, but had no effect on ionomycin-induced $Ca^{2+}$ flux (See FIG. 4).

7.8 The Inhibitory Effect of the 2,4-Pyrimidinediamine Compounds of the Invention is Immediate To test the immediacy of their inhibitory effect, certain 2,4-pyrimidinediamines of the invention were added simultaneously with anti-IgE antibody activator in the cellular assays described above. All compounds tested blocked IgE-induced degranulation of CHMC cells to the same extent as observed when the compounds were pre-incubated with CHMC cells for 10 or 30 min. prior to receptor cross-linking.

7.9 Kinetics of Pharmacological Activity In vitro

Compounds R921218, R921302, R921219, R926240, R940277, R926742, R926495, R909243 and R926782 were tested in washout experiments. In the experiments, CHMC cells were either activated immediately with anti-IgE antibody in the presence of 1.25 μM compound (time zero), or the compound was washed out followed by activation with anti-IgE antibody at 30, 60 or 120 min. The inhibitory activity of these compounds was greatly diminished 30 min. after compound removal, indicating that constant exposure of mast cells to these compounds is required for maximal inhibition of degranulation The other compounds tested yielded similar results.

7.10 Toxicity: T- and B-Cells

The ability of the compounds of the invention to exert their inhibitory activity without being toxic to cells of the immune system was demonstrated in cellular assays with B- and T-cells. The protocols for the assays are provided below.

7.10.1 Jurkat (T-Cell) Toxicity

Dilute Jurkat cells to $2 \times 10^5$ cells/ml in complete RPMI (10% heat-inactivated fetal bovine serum) media and incubate at 37° C., 5% $CO_2$ for 18 hours. Add 65 ul cells at $7.7 \times 10^5$ cells/ml to a 96-well V-bottom plate (TC-treated, Costar) containing 65 ul 2× compound (final vehicle concentration is 0.5% DMSO, 1.5% MeOH). Mix, incubate plates for 18-24 hr at 37° C., 5% $CO_2$. Toxicity was assessed by flow cytometric analysis of cellular light scatter

7.10.2 BJAB (B-Cell) Toxicity

The B-cell line BJAB was cultured in log phase in RPMI1640+10% heat-inactivated fetal bovine serum, 1×L- glutamine, 1× penicillin, 1× streptavidin and 1× beta-mercaptoethanol at 37° C., 5% C02. First, BJABs were harvested, spun and resuspended in culture medium to a concentration of $7.7 \times 10^5$ cells/mL. 65 uL cells were mixed with 65 uL compound, in duplicate and in the presence of 0.1% DMSO in a V-bottomed 96-well tissue culture plate. Cells were incubated with compound at various dilutions at 37° C., 5% $CO_2$. Toxicity was assessed by flow cytometric analysis of cellular light scatter.

7.10.3 Toxicity: Cell Titer Glo Assay

Seed 50 μl cells ($1 \times 10^6$/ml) into each well containing 50 μl compound. The final vehicle concentration is 0.5% DMSO, 1.5% MeOH. Shake plates for 1 minute to mix cells and compound. Incubate plates at 37° C. (5% $CO_2$) for 18 hours. Next day, harvest 50 μl cells from each well, add to 50 μl Cell Titer Glo reagent (Invitrogen). Shake plates for 1 minute. Read on luminometer.

7.10.4 Results

The results of the T- and B-cell toxicity assays, reported as $IC_{50}$ values (in μM), are presented in TABLE 2, supra. With a few exceptions (see TABLE 1), all compounds tested were non-toxic to both B- and T-cells at effective inhibitory concentrations. Assays performed with primary B-cells yielded similar results.

7.11 The 2,4-Pyrimidine Compounds are Tolerated in Animals

The ability of the compounds of the invention to exert their inhibitory activity at doses below those exhibiting toxicity in animals was demonstrated with compounds R921218, R921219 and R921302.

7.11.1 R921218

R921218 was studied in an extensive program of non-clinical safety studies that concluded this agent to be well tolerated in both rodents and non-rodents. To summarize the outcome of toxicology/non-clinical safety testing with R921218; this agent produced no dose limiting toxicity by the intranasal route of administration in non-rodents (rabbits and primates) or by the oral route of administration in rodents (mice and rats) during 14-day repeat-dose toxicity studies at doses many fold above the anticipated dose expected to produce efficacy in man. There were no adverse findings in a core safety pharmacology battery of cardiovascular, respiratory and/or central nervous system function. There was no evidence for mutagenic or clastogenic potential in genetic toxicology testing nor were there untoward effects after exposure to skin and eyes. A short discussion of key toxicology studies is provided.

A 14-day repeat-dose intranasal toxicity study in Cynomolgus monkeys was performed at doses of 2.1, 4.5 or 6.3 mg/kg/day. In life parameters included: clinical observations, body weights, food consumption, ophthalmology, blood pressure, electrocardiography, hematology, clinical chemistry, urinalysis, immunotoxicological assessment, gross necropsy, organ weights, toxicokinetic assessments and histopathology (including the nasal cavity). There were no adverse findings attributed to R921218 in any study parameter and the NOAEL (no observed adverse effect level) was considered 6.3 mg/kg/day.

A 14-day repeat-dose intranasal toxicity study in New Zealand White rabbits was performed at doses of 1.7, 3.4 or 5.0 mg/kg/day. In life parameters included: clinical observations, body weights, food consumption, ophthalmology, hematology, clinical chemistry, gross necropsy, organ weights, toxicokinetic assessments and histopathology (including the nasal cavity). There were no adverse findings attributed to R921218 in any study parameter and the NOAEL (no observed adverse effect level) was considered 5.0 mg/kg/day.

7.11.2 R921219

In pilot dose finding studies a single dose oral dose of 600 mg/kg was considered a NOEL (no observed effect level) while multiple (7-day) doses of 200 mg/kg/day and above were not tolerated.

In the in vitro *Salmonella-Escherichia coli*/Mammalian-Microsome Reverse Mutation Assay (Ames test), R921219 was found to test positive in tester strain TA1537, with and without metabolic activation, confirming the results of an earlier study. R921219 was not found to adversely affect any of the other 4 tester strains. R921219 was not found to possess clastogenic potential when studied in an in vitro chromosomal aberration assay.

7.11.3 R921302

Several non-GLP pilot toxicity studies have been conducted in rodents. In the mouse an oral dose of 1000 mg/kg was tolerated for up to 7-days. In a 14-day oral toxicity study in the mouse was conducted with doses of 100, 300 and 1000 mg/kg. A dose of 1000 mg/kg was not tolerated, while a dose of 300 mg/kg promoted evidence for histopathological changes in the vulva. A dose of 100 mg/kg was considered the NOAEL (no observed adverse effect level) in the study. A 28-day oral toxicity study in the mouse was conducted at doses of 100 mg/kg q.d., 100 mg/kg b.i.d., 300 mg/kg q.d. and 300 mg/kg b.i.d. R921302 was not tolerated at 300 mg/kg q.d. or b.i.d. The lower doses (100 mg/kg q.d. or b.i.d.) appeared to be well tolerated (results of clinical and histopathology are not yet known). In the rat oral doses of 50, 150 and 300 mg/kg given for 32 days appeared to be well tolerated (results of clinical and histopathology are not yet known).

In the in vitro *Salmonella-Escherichia coli*/Mammalian-Microsome Reverse Mutation Assay (Ames test), R921302 was found to test positive in tester strain TA98 with S9 and TA1537, with and without metabolic activation. R921302 was not found to adversely affect any of the other 3 tester strains. R921302 was not clastogenic when assessed in an in vitro chromosomal aberration assay.

7.12 The 2,4-Pyrimidinediamine Compounds are Orally Bioavailable

Over 50 2,4-pyrimidinediamine compounds of the invention were tested for oral bioavailability. For the study, compounds were dissolved in various vehicles (e.g. PEG 400 solution and CMC suspension) for intravenous and oral dosing in the rats. Following administration of the drug, plasma samples were obtained and extracted. The plasma concentrations of the compounds were determined by high performance liquid chromatography/tandem mass spectrometry (LC/MS/MS) methods. Pharmacokinetic analyses were performed based on the plasma concentration data. The pharmacokinetic parameters of interest include Clearance (CL), Volume of distribution at steady-state (Vss), terminal half-life ($t_{1/2}$), and oral bioavailability (% F).

These pharmacokinetic studies indicate that many of the 2,4-pyrimidinediamine compounds are orally available, with % F up to approximately 50% (in the range of 0-50%). The half-lives ranged from 0.5 to 3 hr. In particular, Compounds R940350, R935372, R935193, R927050 and R935391 exhibited good oral bioavailabilities and half-lives in rats. Thus, these studies confirm that these 2,4-pyrimidinediamine compounds are suitable for oral administration.

7.13 The Compounds are Effective for the Treatment of Allergies

The in vivo efficacy of compounds R926109, R921218, R921219, R921302, R926495, R926508, R926742, R926745 and R945150 towards allergies was evaluated in the mouse model of passive cutaneous anaphylaxis (PCA). This model provides a direct measure of IgE-induced degranulation of tissue mast cells. In this model, IgE primed animals are exposed to an allergen challenge, and the change in permeability of dermal vasculature that results from histamine release from mast cells is measured by change in the amount of dye leakage into surrounding tissue. Inhibition of mediator release by compounds that modulate mast cell degranulation is easily measured by extracting the dye from the tissue.

7.13.1 Study Protocol and Results

In the PCA assay mice are passively sensitized by intradermal injection with anti-dinitrophenol (DNP) IgE antibodies (Day −1). At predetermined times animals are treated with the test agent (Day 0). The modulatory effect of the agent on cutaneous mast cell degranulation is measured following intravenous injection of DNP conjugated to human serum albumin (HSA-DNP), together with Evans blue dye. The resulting cross-linking of the IgE receptor and subsequent mast cell degranulation-induced increase in vascular permeability is determined by measuring the amount of dye extravasation into the tissue. Dye is extracted from the tissue by formamide, and the absorbance of this extract is read at 620 nm. The inhibitory effect of drug treatment is reported as the percent inhibition compared to vehicle treatment, that is, the percent reduction in $A_{620}$.

Two compounds have been tested as positive controls: the histamine antagonist diphenhydramine and the serotonin antagonist cyproheptadine. Both mediators (histamine and serotonin) are released upon IgE-mediated degranulation from the mouse mast cell. Both reference compounds inhibit the PCA response; cyproheptadine was used routinely in subsequent experiments. Cyproheptadine reproducibly inhibited the PCA response by 61%+/−4% (8 mg/kg, i.p., 30 minutes pretreatment time, n=23 experiments).

7.13.1.1 Results

A dose-dependent inhibition of the FcεR-mediated vascular leakage was observed with increasing doses of R921218, R926109, R921219 and RR921302. These compounds were administered either in a solution formulation (67% PEG/33% citrate buffer) or an aqueous suspension (1.5% Avicel). These results demonstrate the strong correlation between compound plasma levels, in vivo efficacy, and in vitro potency. The most potent compound, R921219, was active with circulating exposure levels of approximately 10 μg/ml (68% inhibition at a dose level of 100 mg/kg) compared with R921302, a relatively less potent molecule, which reduced plasma extravasation by 42% at a dose level of 100 mg/kg. Further, the length of exposure to circulating compound was reflected in the duration of inhibitory activity. R921302, determined to be the most metabolically stable compound in pharmacokinetics study, inhibited the vascular permeability for 1-2 hours prior to antigen-induced receptor signaling, where after the efficacy began to decrease. These data are summarized in TABLE 3 and TABLE 4.

TABLE 3

Efficacy of R921218, R926109, R921219 and R921302 in the PCA Assay

| Compound | Route | Vehicle | Pretreatment time (min) | Dose (mg/kg) | % Inhibition | Plasma level (μg/ml) |
| --- | --- | --- | --- | --- | --- | --- |
| R921218 | PO | 67% PEG/33% citrate buffer | 10 | 50 | 7 | 3 |
| | | | | 100 | 11 | 4 |
| | | | | 200 | 50 | 18 |
| R926109 | PO | 67% PEG/33% citrate buffer | 15 | 50 | 22 | N.D. |
| | | | | 100 | 32 | |
| | | | | 200 | 48 | |
| R921219 | PO | 1.5% Avicel/water | 15 | 30 | 25 | 0.4 |
| | | | | 100 | 68 | 4 |
| | | | | 300 | 92 | 11 |
| R921302 | PO | 1.5% Avicel/water | 60 | 50 | 35 | 25 |
| | | | | 100 | 42 | 38 |
| | | | | 150 | 56 | 64 |
| | | | | 200 | 93 | 105 |

TABLE 4

Duration of action of R921219 and R921302 in the PCA Assay

| Compound | Route | Vehicle | Dose (mg/kg) | Pretreatment time (min) | % Inhibition | Plasma level (µg/ml) |
|---|---|---|---|---|---|---|
| RR921302 | PO | 1.5% Avicel/water | 200 | 30 | 89 | 88 |
|  |  |  |  | 60 | 83 | 53 |
|  |  |  |  | 120 | 82 | 61 |
|  |  |  |  | 240 | 37 | 8 |

Similar in vivo activity was observed with compounds R926495, R926508, R926742, R926745 and R926150, which were able to inhibit the PCA response after administration by the oral route in a PEG-based formulation (data not shown).

7.14 The Compounds are Effective in the Treatment of Asthma

The efficacy of compounds R921218, R921302, R926495, R926508, R926742 and R921219 in the treatment of asthma was demonstrated in the sheep model of allergic asthma. Sheep develop bronchoconstriction within minutes of exposure to inhaled antigen (*Ascaris suum*), with maximal airflow obstruction during the early allergic response (EAR). Release of preformed mast cell mediators is likely responsible for this early phase of airflow obstruction. In addition to the EAR, the sheep model allows us to evaluate the effect of our compounds on the late asthmatic reaction (LAR) and non-specific airway hyperresponsiveness (AHR), which occur as a result of topical or local administration of allergen to the airway. In the sheep, AHR develops a few hours following antigen challenge, and can persist for up to 2 weeks. The results described below demonstrate the potential of the tested compounds to inhibit a cascade of events that may be a result of release of cytokines from the mast cell.

7.14.1 Study Protocol

In the sheep model of allergic asthma, sheep are administered aerosols of test article via an endotracheal tube, followed by an aerosol challenge with antigen extracted from the roundworm, *Ascaris suum*, to which the sheep are naturally allergic. Allergen challenge leads to direct bronchoconstriction (both EAR and LAR) and a persistent non-specific AHR. These three characteristics are similar to those seen in human allergic asthmatics. The activity of the test agent is determined by changes in the lung resistance ($R_L$), which is calculated from measurements of transpulmonary pressure, flow, and respiratory volume. The historical control data obtained from the same sheep following saline treatment compared with an allergen challenge show that a sharp increase of $R_L$ occurs during the EAR and persists for approximately 2-3 hours following allergen challenge. The LAR is a less pronounced increase in $R_L$, which starts approximately 5-6 hours following allergen challenge and is resolved by 8 hours post-challenge. Twenty-four hours after the challenge, a dose response to carbachol is measured to determine the AHR, which is expressed as the dose of carbachol required to increase $R_L$ by 400% over baseline. (This measurement is referred to as the provocative concentration of carbachol that elicits a 400% increase in $R_L$ over baseline ($PC_{400}$). The data are compared to historical control data for the same individual when administered a saline control aerosol and challenged with Ascaris suum.

7.14.2 Result

All the compounds tested showed inhibitory effects in the LAR and the AHR, and several of these agents inhibited the EAR as well. The optimal response for each compound in a series of studies to evaluate activity at several pretreatment times and using several different solution and suspension formulations are shown in TABLE 5. The efficacy of R921218 on the EAR appeared to be dependent on the formulation, with the greatest effect seen at 30 mg/sheep administered as a solution aerosol in 10% ethanol. R926495, R926742, R926508 and R921219, administered in four different sheep at 45 mg/sheep in an aqueous suspension 60 minutes prior to allergen challenge, demonstrate that the LAR and AHR is blocked. In addition to these late parameters, the EAR was greatly reduced by treatment with R921219, R926508 or R926495. The efficacy of RR921302 was investigated using a 45% PEG400/55% citrate buffer vehicle. Under these conditions, R921302, administered at 30 mg/sheep 60 minutes prior to challenge, blocked the LAR and AHR, and EAR was unaffected.

These data clearly demonstrate that these compounds are able to block the asthmatic responses in allergic sheep. All compounds inhibited the AHR and LAR significantly when compared to the historical control. The EAR was significantly inhibited by R921219, R926508 and R926495 (54%, 21% and 33% respectively). In contrast, R921218, R921302 and R926742 failed to inhibit the EAR when administered in an aqueous suspension.

TABLE 5

Efficacy Of Exemplary Compounds In A Sheep Model Of Allergic Asthma

| Compound | Dose (mg/sheep) | Pretreatment time (min) | Vehicle | EAR (% inhibition) | LAR (% inhibition) | AHR (% inhibition) |
|---|---|---|---|---|---|---|
| R921218 | 30 | 15 | 10% ethanol | 66 | 78 | 101 |
| R926742 | 45 | 60 | Aqueous suspension | −19 | 87 | 94 |

TABLE 5-continued

Efficacy Of Exemplary Compounds In A Sheep Model Of Allergic Asthma

| Compound | Dose (mg/sheep) | Pretreatment time (min) | Vehicle | EAR (% inhibition) | LAR (% inhibition) | AHR (% inhibition) |
|---|---|---|---|---|---|---|
| R926495 | 45 | 60 | | 33 | 85 | 41 |
| R926508 | 45 | 60 | | 21 | 90 | 88 |
| R921219 | 45 | 60 | | 56 | 75 | 90 |
| RR921302 | 30 | 60 | 45% PEG400/55% citrate buffer | −28 | 86 | 82 |

7.15 The Compounds are Effective in the Treatment of Asthma

The efficacy of compounds R921304 and R921219 in the treatment of asthma was also demonstrated in a mouse model of allergic asthma.

7.15.1 Study Protocol

Mice are sensitized to ovalbumin (chicken protein) in the presence of an adjuvant (Alum) by the intraperitoneal route on day 0 and day 7. One week later, mice are challenged intranasally with ovalbumin on Days 14, 15 and 16 (more stringent model) or on Day 14 (less stringent model). This sensitization and challenge regimen leads to airway hyperresponsiveness and inflammation in the lungs, which are two dominant characteristics of human allergic asthma. In the mouse model, the in vivo airway responses are measured using a whole body plethysmograph which determines the PENH (enhanced Pause, Buxco Electronics). The PENH is a dimensionless value comprised of the peak inspiratory flow (PIF), peak expiratory flow (PEF), time of inspiration, time of expiration and relaxation time, and is considered a validated parameter of airway responsiveness. Responses to allergen challenge (OVA) are compared with animals challenged with saline only. Twenty-four hours after challenge, mice are exposed to increasing doses of methacholine (muscarinic receptor agonist) which results in smooth muscle contraction. The ovalbumin-challenged mice demonstrate a significant airway hyperresponsiveness to methacholine when compared to the saline challenged mice. In addition, a cellular infiltrate in the airway is observed in ovalbumin challenged mice when compared with the saline challenged mice. This cellular infiltrate is mainly characterized by eosinophils, but a smaller influx of neutrophils and mononuclear cells is also present.

The use of this model for the evaluation of small molecule inhibitors of mast cell degranulation has been validated is several ways. First, using mast cell deficient mice (W/W$^v$) it has been shown that the ovalbumin-induced responses are dependent upon the presence of mast cells. In the mast cell deficient mice, ovalbumin sensitization and challenge did not result in airway hyperresponsiveness and eosinophil influx. Second, the mast cell stabilizer, Cromolyn, was able to block the ovalbumin-induced airway hyperresponsiveness and inflammation (data not shown). The use of this model to evaluate compounds for the treatment of asthmatic responses that may be mediated by mechanisms other than mast cell stabilization, is further supported by the inhibitory effect of the steroids, dexamethasone and budesonide, on methacoline-induced bronchocontriction.

7.15.2 Results

The efficacy of R921304 was evaluated by intranasal administration on 10 consecutive days, from Day 7 through Day 16, at a dose level of 20 mg/kg, with the last 3 doses administered 30 minutes prior to either saline or ovalbumin challenge. R921304 was able to inhibit the ovalbumin-induced airway hyperresponsiveness to methacholine when compared to the vehicle treated mice.

In a less stringent protocol, in which the mice were challenged with ovalbumin only once on Day 14, R921219 administered subcutaneously at 70 mg/kg in 67% PEG400/33% citrate buffer 30 minutes prior to saline or ovalbumin challenge, demonstrates that R921219 completely blocked the ovalbumin-induced airway hyperresponsiveness and cellular influx.

These results clearly demonstrate that R921219 and R921304 are efficacious in inhibiting the airway responses in a mouse model of allergic asthma.

7.16 2,4-Pyrimidinediamine Compounds Inhibit Phosphorylation of Proteins Downstream of Syk Kinase in Activated Mast Cells The inhibitory effect of the 2,4-pyrimidinediamine compounds on the phosphorylation of proteins downstream of Syk kinase was tested with compounds R921218, R218219 and R921304 in IgE receptor-activated BMMC cells.

For the assay, BMMC cells were incubated in the presence of varying concentrations of test compound (0.08 µM, 0.4 µM, 2 µM and 10 µM) for 1 hr at 37° C. The cells were then stimulated with anti-IgE antibody as previously described. After 10 min, the cells were lysed and the cellular proteins separated by electrophoresis (SDS PAGE).

Following electrophoresis, the phosphorylation of the proteins indicated in FIGS. 7, 10 and 11A-D were assessed by immunoblot. Antibodies were purchased from Cell Signaling Technology, Beverley, Mass.

Referring to FIGS. 7, 10 and 11A-D, the indicated compounds tested inhibited phosphorylation of proteins downstream of Syk, but not upstream of Syk, in the IgE receptor signaling cascade, confirming both that the compounds inhibit upstream IgE induced degranulation, and that the compounds exhert their inhibitory activity by inhibiting Syk kinase.

7.17 2,4-Pyrimidinediamine Compounds Inhibit Syk Kinase in Biochemical Assays Several 2,4-pyrimidinediamine compounds were tested for the ability to inhibit Syk kinase catalyzed phosphorylation of a peptide substrate in a biochemical fluorescenced polarization assay with isolated Syk kinase. In this experiment, Compounds were diluted to 1% DMSO in kinase buffer (20 mM HEPES, pH 7.4, 5 mM MgCl$_2$, 2 mM MnCl$_2$, 1 mM DTT, 0.1 mg/mL acetylated Bovine Gamma Globulin). Compound in 1% DMSO (0.2% DMSO final) was mixed with ATP/substrate solution at room temperature.

Syk kinase (Upstate, Lake Placid N.Y.) was added to a final reaction volume of 20 uL, and the reaction was incubated for 30 minutes at room temperature. Final enzyme reaction conditions were 20 mM HEPES, pH 7.4, 5 mM $MgCl_2$, 2 mM $MnCl_2$, 1 mM DTT, 0.1 mg/mL acetylated Bovine Gamma Globulin, 0.125 ng Syk, 4 uM ATP, 2.5 uM peptide substrate (biotin-EQEDEPEGDYEEVLE-CONH2, SynPep Corporation). EDTA (10 mM final)/anti-phosphotyrosine antibody (1× final)/fluorescent phosphopeptide tracer (0.5× final) was added in FP Dilution Buffer to stop the reaction for a total volume of 40 uL according to manufacturer's instructions (PanVera Corporation) The plate was incubated for 30 minutes in the dark at room temperature. Plates were read on a Polarion fluorescence polarization plate reader (Tecan). Data were converted to amount of phosphopeptide present using a calibration curve generated by competition with the phosphopeptide competitor provided in the Tyrosine Kinase Assay Kit, Green (PanVera Corporation).

The results of the assay are shown in TABLE 6, below:

TABLE 6

| Compound No. | IC50 (in µM) |
|---|---|
| R926505 | 0.0703 |
| R926508 | 0.1315 |
| R926594 | 0.7705 |
| R926715 | 0.534 |
| R926745 | 0.0925 |
| R926782 | 0.1165 |
| R926791 | 0.207 |
| R926813 | 0.4047 |
| R926816 | 0.0615 |
| R935138 | 0.2288 |
| R935190 | 0.0465 |
| R935191 | 0.045 |
| R935193 | 0.075 |
| R935194 | 0.1687 |
| R935196 | 0.2655 |
| R940255 | 0.7705 |
| R940256 | 2.787 |
| R940269 | 0.685 |
| R940275 | 0.7335 |
| R940276 | 0.1265 |
| R940277 | 0.2143 |
| R940290 | 0.187 |
| R945071 | 0.4295 |
| R945140 | 0.611 |
| R945142 | 2.007 |
| R945144 | 0.383 |
| R921302 | 0.2678 |
| R908702 | 0.0378 |
| R908712 | 0.024 |
| R909268 | 0.1253 |
| R920410 | 0.157 |
| R926753 | 0.108 |
| R926757 | 0.5103 |
| R926834 | 0.292 |
| R926839 | 0.055 |
| R926891 | 0.1695 |
| R926931 | 0.2553 |
| R935237 | 0.0455 |
| R935293 | 0.0465 |
| R935302 | 0.0265 |
| R935304 | 0.042 |
| R935307 | 0.057 |
| R935309 | 0.098 |
| R935310 | 0.2003 |
| R940323 | 0.062 |
| R940338 | 0.028 |
| R921303 | 0.00045 |
| R940347 | 0.0345 |
| R921304 | 0.01275 |
| R950368 | 0.0107 |
| R950373 | 0.0665 |

These data demonstrate that all of the compounds tested, except for R945142 and R909236 inhibit Syk kinase phosphorylation with $IC_{50}$s in the submicromolar range. All compounds tested inhibit Syk kinase phosphorylation with $IC_{50}$s in the micromolar range.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated by reference into the application for all purposes.

What is claimed is:

1. A 2,4-pyrimidinediamine compound according to structural formula (II):

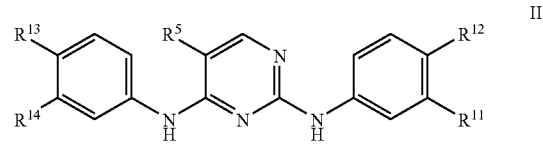

wherein:

$R^5$ is selected from the group consisting of fluoro, (C1-C3) haloalkyl, (C1-C3) perhaloalkyl, (C1-C3) haloalkoxy, (C1-C3) perhaloalkoxy, —C(O)$R^a$, —C(O)O$R^a$, C(O)CF$_3$ and —C(O)OCF$_3$;

each $R^{11}$ $R^{12}$, $R^{13}$ and $R^{14}$, independently of the others, is selected from the group consisting of hydrogen, hydroxy, (C1-C6) perhaloalkyl, (C1-C6) perhaloalkoxy, —NR$^c$R$^c$, (C1-C10) alkyl optionally substituted with one or more of the same or different $R^a$, (C1-C6) alkoxy optionally substituted with one or more of the same or different $R^a$ or $R^b$; —O$R^a$ optionally substituted with one or more of the same or different $R^a$ or $R^b$ groups, —O—(CH$_2$)$_m$—NR$^c$R$^c$, —O—C(O)NR$^c$R$^c$, —O—(CH$_2$)$_m$—C(O)NR$^c$R$^c$, —O—C(O)O$R^a$, —O—(CH$_2$)$_m$—C(O)O$R^a$, —O—C(NH)NR$^c$R$^c$, —O—(CH$_2$)$_m$—C(NH)NR$^c$R$^c$, —NH—(CH$_2$)$_m$—NR$^c$R$^c$, —NH—C(O)NR$^c$R$^c$ and —NH—(CH$_2$)$_m$—C(O)NR$^c$R$^c$, where m is independently an integer from 1 to 3;

each $R^a$ is independently selected from the group consisting of hydrogen, (C1-C6) alkyl, (C3-C8) cycloalkyl, (C4-C11) cycloalkylalkyl, (C5-C10) aryl, (C6-C16) arylalkyl, 2-6 membered heteroalkyl, 3-8 membered cycloheteroalkyl, 4-11 membered cycloheteroalkylalkyl, 5-10 membered heteroaryl and 6-16 membered heteroarylalkyl;

each $R^b$ is a suitable group independently selected from the group consisting of =O, (C1-C3) haloalkyloxy, =S, —S$R^d$, =N$R^d$, =NO$R^d$, halogen, —CF$_3$, —CN, —NC, —OCN, —SCN, —NO, —NO$_2$, =N$_2$, —N$_3$, —S(O)$R^d$, —S(O)$_2$R$^d$, —S(O)$_2$O$R^d$, —S(O)NR$^c$R$^c$, —S(O)$_2$NR$^c$R$^c$, —OS(O)$R^d$, —OS(O)$_2$R$^d$, —OS(O)$_2$O$R^d$, —OS(O)$_2$NR$^c$R$^c$, —C(O)$R^d$, —C(O)O$R^d$, —C(O)NR$^c$R$^c$, —C(NH)NR$^c$R$^c$, —C(NR$^a$)NR$^c$R$^c$, —C(NOH)$R^a$, —C(NOH)NR$^c$R$^c$, —OC(O)$R^d$, —OC(O)O$R^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$O$R^d$, —[NR$^a$C(O)]$_n$, $OR^d$, —$[NHC(O)]_nNR^cR^c$, —$[NR^aC(O)]_nNR^cR^c$, —$[NHC(NH)]_nNR^cR^c$ and —$[NR^aC(NR^a)]_nNR^cR^c$, where n is independently an integer from 0 to 3;

each $R^c$ is independently $R^a$, or, alternatively, two $R^c$ are taken together with the nitrogen atom to which they are bonded to form a 5 to 8-membered cycloheteroalkyl or heteroaryl which may optionally include one or more of the same or different additional heteroatoms and which may optionally be substituted with one or more of the same or different $R^a$ or suitable $R^b$ groups;

each $R^d$ is independently $R^a$;

wherein at least one of $R^{11}$ and $R^{12}$ and one of $R^{13}$ and $R^{14}$ is non-hydrogen;

with the proviso that:
(1) $R^{11}$ and $R^{12}$ are not both methoxy; and
(2) the 2,4-pyrimidinediamine compound is not:
N2,N4-bis(4-ethoxyphenyl)-5-fluoro-2,4-pyrimidinediamine (R070790);
N2,N4-bis(4-methoxyphenyl)-5-fluoro-2,4-pyrimidinediamine (R088814);
N2,N4-bis(3-methylphenyl)-5-fluoro-2,4-pyrimidinediamine (R092788); or
N2,N4-bis(3,4-dimethylphenyl)-5-fluoro-2,4-pyrimidinediamine (R067964).

2. The compound of claim 1, wherein $R^{11}$ and $R^{12}$ are not both optionally substituted alkoxy.

3. The compound of claim 1, wherein $R^{11}$, $R^{12}$, $R^{13}$ and $R^{14}$, independently, are selected from (C1-C10) alkyl optionally substituted with one or more of the same or different $R^a$ or $R^b$, —$OR^a$ optionally substituted with one or more of the same or different $R^a$ or $R^b$ groups, —O—$(CH_2)_m$—$NR^cR^c$, —O—$C(O)NR^cR^c$, —O—$(CH_2)_m$—$C(O)NR^cR^c$, —O—$C(O)OR^a$, —O—$(CH_2)_m$—$C(O)OR^a$, —O—$C(NH)NR^cR^c$, —O—$(CH_2)_m$—$C(NH)NR^cR^c$, —NH—$(CH_2)_m$—$NR^cR^c$, —NH—$C(O)NR^cR^c$ and —NH—$(CH_2)_m$—$C(O)NR^cR^c$, where m is independently an integer from 1 to 3.

4. The compound of claim 1, wherein $R^{11}$, $R^{12}$, $R^{13}$ and $R^{14}$, independently of one another, are selected from the group consisting of hydrogen, hydroxy, (C1-C6) alkoxy and —$NR^cR^c$.

5. The compound of claim 1, wherein $R^{11}$ and $R^{14}$ are the same.

6. The compound of claim 5, wherein $R^{12}$ and $R^{13}$ are the same.

7. The compound of claim 1, wherein $R^{12}$ and $R^{13}$ are the same.

8. The compound of claim 7, wherein $R^{12}$ and $R^{13}$ are hydrogen.

9. The compound of claim 1, wherein one of $R^{11}$ and $R^{12}$ is hydrogen.

10. The compound of claim 1, wherein one of $R^{13}$ and $R^{14}$ is hydrogen.

11. The compound of claim 1, wherein $R^{12}$ is hydrogen and $R^{11}$ is —O—$(CH_2)_m$—$R^b$, wherein m is an integer from 1 to 3.

12. The compound of claim 11, wherein $R^5$ is fluoro or $CF_3$.

13. The compound of claim 11, wherein $R^{11}$ is —O—$CH_2$—$C(O)$—$NHCH_3$.

14. A pharmaceutical composition comprising a compound according to claim 1 and a pharmaceutically acceptable carrier, diluent or excipient.

15. A method of inhibiting cell degranulation, comprising contacting a cell with an amount of a compound according to claim 1 effective to inhibit cell degranulation.

16. The method of claim 15, wherein the cell is a human mast cell, basophil cell, neutrophil cell or eosinophil cell.

17. The method of claim 15, wherein the cell is in a human.

* * * * *